(12) United States Patent
Kurose

(10) Patent No.: US 8,921,373 B2
(45) Date of Patent: Dec. 30, 2014

(54) COMPOUNDS HAVING TRPV1 ANTAGONISTIC ACTIVITY AND USES THEREOF

(75) Inventor: Noriyuki Kurose, Toyonaka (JP)

(73) Assignee: Shionogi & Co., Ltd., Osaka (JP)

( * ) Notice: Subject to any disclaimer, the term of this patent is extended or adjusted under 35 U.S.C. 154(b) by 25 days.

(21) Appl. No.: 13/704,770

(22) PCT Filed: Jun. 22, 2011

(86) PCT No.: PCT/JP2011/064854
§ 371 (c)(1),
(2), (4) Date: Dec. 17, 2012

(87) PCT Pub. No.: WO2011/162409
PCT Pub. Date: Dec. 29, 2011

(65) Prior Publication Data
US 2013/0123239 A1    May 16, 2013

Related U.S. Application Data

(60) Provisional application No. 61/357,327, filed on Jun. 22, 2010, provisional application No. 61/360,721, filed on Jul. 1, 2010, provisional application No. 61/419,737, filed on Dec. 3, 2010.

(51) Int. Cl.
| | | |
|---|---|---|
| A61K 31/496 | (2006.01) | |
| C07D 417/12 | (2006.01) | |
| C07D 513/04 | (2006.01) | |
| C07D 277/82 | (2006.01) | |
| C07D 487/08 | (2006.01) | |
| A61K 31/444 | (2006.01) | |
| A61K 31/4545 | (2006.01) | |
| C07D 401/04 | (2006.01) | |
| C07D 401/14 | (2006.01) | |
| C07D 417/14 | (2006.01) | |

(52) U.S. Cl.
CPC ............ *C07D 401/14* (2013.01); *C07D 277/82* (2013.01); *C07D 401/04* (2013.01); *C07D 417/12* (2013.01); *C07D 417/14* (2013.01); *C07D 487/08* (2013.01)
USPC ........ 514/253.1; 514/318; 514/333; 514/334; 544/364; 544/238; 544/295; 544/333; 544/336; 544/405; 546/194; 546/256

(58) Field of Classification Search
None
See application file for complete search history.

(56) References Cited

U.S. PATENT DOCUMENTS

| | | | |
|---|---|---|---|
| 5,891,889 A | 4/1999 | Anthony et al. | |
| 6,150,129 A | 11/2000 | Cook et al. | |
| 6,248,756 B1 | 6/2001 | Anthony et al. | |
| 6,414,149 B1 | 7/2002 | Chu-Moyer et al. | |
| 6,723,730 B2 | 4/2004 | Bakthavatchalam et al. | |
| 7,091,227 B2 | 8/2006 | Scott et al. | |
| 7,326,705 B2 | 2/2008 | Ahmad et al. | |
| 7,612,075 B2 | 11/2009 | Ewing et al. | |
| 2004/0006091 A1 | 1/2004 | Kyle et al. | |
| 2004/0044003 A1 | 3/2004 | Kyle et al. | |
| 2004/0106625 A1 | 6/2004 | Kyle et al. | |
| 2004/0186111 A1 | 9/2004 | Sun et al. | |
| 2004/0235853 A1 | 11/2004 | Kyle et al. | |
| 2005/0059671 A1 | 3/2005 | Sun et al. | |
| 2006/0128717 A1 | 6/2006 | Sun et al. | |
| 2006/0199824 A1 | 9/2006 | Sun et al. | |
| 2006/0258669 A1 | 11/2006 | Kyle et al. | |

FOREIGN PATENT DOCUMENTS

| | | |
|---|---|---|
| JP | 11-199573 | 7/1999 |
| JP | 2006-528642 | 12/2006 |
| JP | 2006-528643 | 12/2006 |
| JP | 2009-516729 | 4/2009 |
| WO | 97/28140 | 8/1997 |

(Continued)

OTHER PUBLICATIONS

Banker et al. "Modern Pharmaceutics", 3rd Ed. p. 596 (1996).*

(Continued)

*Primary Examiner* — Emily Bernhardt
(74) *Attorney, Agent, or Firm* — Wenderoth, Lind & Ponack, L.L.P.

(57) ABSTRACT

The invention relates to compounds of Formula I and pharmaceutically acceptable derivatives thereof, compositions comprising an effective amount of a compound of Formula I or a pharmaceutically acceptable derivative thereof, and methods for treating or preventing a condition such as pain, UI, an ulcer, IBD and IBS, comprising administering to an animal in need thereof an effective amount of a compound of Formula I or a pharmaceutically acceptable derivative thereof.

32 Claims, 3 Drawing Sheets

(56) References Cited

FOREIGN PATENT DOCUMENTS

| WO | 97/38665 | 10/1997 |
|---|---|---|
| WO | 98/31677 | 7/1998 |
| WO | 03/089410 | 10/2003 |
| WO | 2004/035549 | 4/2004 |
| WO | 2005/004866 | 1/2005 |
| WO | 2005/012287 | 2/2005 |
| WO | 2005/030753 | 4/2005 |
| WO | 2005/030766 | 4/2005 |
| WO | 2005/066130 | 7/2005 |
| WO | 2007/060408 | 5/2007 |
| WO | 2007/069773 | 6/2007 |
| WO | 2008/132600 | 11/2008 |
| WO | 2008/133973 | 11/2008 |

OTHER PUBLICATIONS

Burger's Medicinal Chemistry,, edited by Manfred E.Wolf, 5th Ed. Part 1, pp. 975-977 (1995).*
Vippagunta et al. Advanced Drug Delivery Reviews, vol. 48, p. 3-26 (2001).*
Evans in "Principles of Radiopharmacology", Colombett, L.G. editor, CRC Press, pp. 11-13 and 24 (1979).*
Cocrystal, from Wikipedia, 9 pages, retrieved from the Internet at http://en.wikipedia.org/wiki/Cocrystal on May 19, 2013.*
International Search Report issued Sep. 13, 2011 in International (PCT) Application No. PCT/JP2011/064854.
Written Opinion issued Sep. 13, 2011 in International (PCT) Application No. PCT/JP2011/064854.
International Preliminary Report on Patentability and Written Opinion issued Jan. 10, 2013 in International (PCT) Application No. PCT/JP2011/064854.
Chu-Moyer, Margaret Y., et al., "Orally-Effective, Long-Acting Sorbitol Dehydrogenase Inhibitors: Synthesis, Structure-Activity Relationships, and in Vivo Evaluations of Novel Heterocycle-Substituted Piperazino-Pyrimidines", J. Med. Chem., vol. 45, 2002, pp. 511-528.
Khadse, B. G., et al., "Synthesis and Study of 2-($N^4$-substituted-$N^1$-piperazinyl) pyrido (3,2-d) thiazoles, 5-nitro-2-($N^4$-substituted-$N^1$-piperazinyl) Benzthiazoles and allied compounds as possible anthelmintic agents", Bull. Haff. Inst., vol. 1, No. 3, 1975, pp. 27-32.
Austrian Search Report issued Mar. 9, 2011 in corresponding Austrian Application No. 11-50288.
Supplementary European Search Report issued Nov. 22, 2013 in corresponding European Application No. 11 79 8288.
Martin J. Gunthorpe et al.; "Characterization of SB-705498, a Potent and Selective Vanilloid Receptor-1 (VR1/TRPV1) Antagonist That Inhibits the Capsaicin-, Acid-, and Heat-Mediated Activation of the Receptor"; Journal of Pharmacology and Experimental Therapeutics, American Society for Pharmacology and Experimental Therapeutics; vol. 321, No. 3; 2007; pp. 1183-1192.

* cited by examiner

| Agonist Plate | 1 | 2 | 3 | 4 | 5 | 6 | 7 | 8 | 9 | 10 | 11 | 12 |
|---|---|---|---|---|---|---|---|---|---|---|---|---|
| A | Buffer | | | | | | | | | | | |
| B | $H_2SO_4$ 15.0 mM (final 3.0 mM) | | | | | | | | | | | |
| C | $H_2SO_4$ 15.5 mM (final 3.1 mM) | | | | | | | | | | | |
| D | $H_2SO_4$ 16.0 mM (final 3.2 mM) | | | | | | | | | | | |
| E | $H_2SO_4$ 16.5 mM (final 3.3 mM) | | | | | | | | | | | |
| F | $H_2SO_4$ 17.0 mM (final 3.4 mM) | | | | | | | | | | | |
| G | $H_2SO_4$ 17.5 mM (final 3.5 mM) | | | | | | | | | | | |
| H | $H_2SO_4$ 18.0 mM (final 3.6 mM) | | | | | | | | | | | |

*FIG. 1*

(A) Agonist Plate

| | 1 | 2 | 3 | 4 | 5 | 6 | 7 | 8 | 9 | 10 | 11 | 12 |
|---|---|---|---|---|---|---|---|---|---|---|---|---|
| A | | | | | | | | | | | | |
| B | | | | | | | | | | | | |
| C | | | | $H_2SO_4$ X mM | | | | | $H_2SO_4$ (X + 0.5) mM | | | |
| D | | | | | | | | | | | | |
| E | | | | | | | | | | | | |
| F | | | | | | | | | | | | |
| G | | | | | | | | | | | | |
| H | | | | | | | | | | | | |

(B) Antagonist Plate final antagonist concentration [nM]

| | 1 | 2 | 3 | 4 | 5 | 6 | 7 | 8 | 9 | 10 | 11 | 12 |
|---|---|---|---|---|---|---|---|---|---|---|---|---|
| A | 0.977 | 3.906 | 15.63 | 62.5 | 250 | 1000 | 0.977 | 3.906 | 15.63 | 62.5 | 250 | 1000 |
| B | | | | | | | | | | | | |
| C | | | No Antagonists | | | | | | No Antagonists | | | |
| D | | | | | | | | | | | | |
| E | 0.977 | 3.906 | 15.63 | 62.5 | 250 | 1000 | 0.977 | 3.906 | 15.63 | 62.5 | 250 | 1000 |
| F | | | | | | | | | | | | |
| G | | | | | | | | | | | | |
| H | | | | | | | | | | | | |

FIG. 3

COMPOUNDS HAVING TRPV1 ANTAGONISTIC ACTIVITY AND USES THEREOF

This application is a National Stage of International Application No. PCT/JP2011/064854, filed Jun. 22, 2011 and claims priority to U.S. Provisional Application No. 61/357,327, filed Jun. 22, 2010, U.S. Provisional Application No. 61/360,721, filed Jul. 1, 2010, and U.S. Provisional Application No. 61/419,737, filed Dec. 3, 2010.

TECHNICAL FIELD

The invention relates to compounds of Formula I, and pharmaceutically acceptable derivatives thereof, compositions comprising an effective amount of a compound of Formula I or a pharmaceutically acceptable derivative thereof and methods for treating or preventing a condition such as pain, UI, an ulcer, IBD, and IBS, comprising administering to an animal in need thereof an effective amount of a compound of Formula I or a pharmaceutically acceptable derivative thereof.

BACKGROUND ART

Pain is the most common symptom for which patients seek medical advice and treatment. Pain can be acute or chronic. While acute pain is usually self-limited, chronic pain persists for 3 months or longer and can lead to significant changes in a patient's personality, lifestyle, functional ability and overall quality of life (K. M. Foley, *Pain, in Cecil Textbook of Medicine* pp. 100-107 (J. C. Bennett and F. Plum eds., 20th ed. 1996)).

Moreover, chronic pain can be classified as either nociceptive or neuropathic. Nociceptive pain includes tissue injury-induced pain and inflammatory pain such as that associated with arthritis. Neuropathic pain is caused by damage to the peripheral or central nervous system and is maintained by aberrant somatosensory processing. There is a large body of evidence relating activity at vanilloid receptors (V. Di Marzo et al., *Current Opinion in Neurobiology* 12:372-379 (2002)) to pain processing.

Nociceptive pain has been traditionally managed by administering non-opioid analgesics, such as acetylsalicylic acid, choline magnesium trisalicylate, acetaminophen, ibuprofen, fenoprofen, diflusinal, and naproxen; or opioid analgesics, including morphine, hydromorphone, methadone, levorphanol, fentanyl, oxycodone, and oxymorphone. Id. In addition to the above-listed treatments, neuropathic pain, which can be difficult to treat, has also been treated with anti-epileptics (e.g., gabapentin, carbamazepine, valproic acid, topiramate, phenyloin), NMDA antagonists (e.g., ketamine, dextromethorphan), topical lidocaine (for post-herpetic neuralgia), and tricyclic antidepressants (e.g., fluoxetine, sertraline and amitriptyline).

Urinary incontinence ("UI") is uncontrollable urination, generally caused by bladder-detrusor-muscle instability. UI affects people of all ages and levels of physical health, both in health care settings and in the community at large. Physiologic bladder contraction results in large part from acetylcholine-induced stimulation of post-ganglionic muscarinic-receptor sites on bladder smooth muscle. Treatments for UI include the administration of drugs having bladder-relaxant properties, which help to control bladder-detrusor-muscle overactivity.

None of the existing commercial drug treatments for UI has achieved complete success in all classes of UI patients, nor has treatment occurred without significant adverse side effects.

Treatment of ulcers typically involves reducing or inhibiting the aggressive factors. For example, antacids such as aluminum hydroxide, magnesium hydroxide, sodium bicarbonate, and calcium bicarbonate can be used to neutralize stomach acids. Antacids, however, can cause alkalosis, leading to nausea, headache, and weakness. Antacids can also interfere with the absorption of other drugs into the blood stream and cause diarrhea.

$H_2$ antagonists, such as cimetidine, ranitidine, famotidine, and nizatidine, are also used to treat ulcers. $H_2$ antagonists promote ulcer healing by reducing gastric acid and digestive-enzyme secretion elicited by histamine and other $H_2$ agonists in the stomach and duodenum. $H_2$ antagonists, however, can cause breast enlargement and impotence in men, mental changes (especially in the elderly), headache, dizziness, nausea, myalgia, diarrhea, rash, and fever.

$H^+$, $K^+$-ATPase inhibitors such as omeprazole and lansoprazole are also used to treat ulcers. $H^+$, $K^+$-ATPase inhibitors inhibit the production of enzymes used by the stomach to secrete acid. Side effects associated with $H^+$, $K^+$-ATPase inhibitors include nausea, diarrhea, abdominal colic, headache, dizziness, somnolence, skin rashes, and transient elevations of plasma activities of aminotransferases.

Inflammatory-bowel disease ("IBD") is a chronic disorder in which the bowel becomes inflamed, often causing recurring abdominal cramps and diarrhea. The two types of IBD are Crohn's disease and ulcerative colitis.

Crohn's disease, which can include regional enteritis, granulomatous ileitis, and ileocolitis, is a chronic inflammation of the intestinal wall. Crohn's disease occurs equally in both sexes and is more common in Jews of eastern-European ancestry. Most cases of Crohn's disease begin before age 30 and the majority start between the ages of 14 and 24. The disease typically affects the full thickness of the intestinal wall. Generally the disease affects the lowest portion of the small intestine (ileum) and the large intestine, but can occur in any part of the digestive tract.

Cramps and diarrhea, side effects associated with Crohn's disease, can be relieved by anticholinergic drugs, diphenoxylate, loperamide, deodorized opium tincture, or codeine.

When Crohn's disease causes the intestine to be obstructed or when abscesses or fistulas do not heal, surgery can be necessary to remove diseased sections of the intestine. Surgery, however, does not cure the disease, and inflammation tends to recur where the intestine is rejoined. In almost half of the cases a second operation is needed. Berkow et al., "Crohn's Disease," *The Merck Manual of Medical Information*, pp. 528-530 (1997).

Ulcerative colitis is a chronic disease in which the large intestine becomes inflamed and ulcerated, leading to episodes of bloody diarrhea, abdominal cramps, and fever. Ulcerative colitis usually begins between ages 15 and 30; however, a small group of people have their first attack between ages 50 and 70. Unlike Crohn's disease, ulcerative colitis never affects the small intestine and does not affect the full thickness of the intestine. The disease usually begins in the rectum and the sigmoid colon and eventually spreads partially or completely throughout the large intestine. The cause of ulcerative colitis is unknown.

Treatment of ulcerative colitis is directed to controlling inflammation, reducing symptoms, and replacing lost fluids and nutrients. Anticholinergic drugs and low doses of diphenoxylate or loperamide are administered for treating mild diarrhea. For more intense diarrhea higher doses of diphenoxylate or loperamide, or deodorized opium tincture or codeine are administered.

Irritable-bowel syndrome ("IBS") is a disorder of motility of the entire gastrointestinal tract, causing abdominal pain, constipation, and/or diarrhea. IBS affects three-times more women than men. In IBS, stimuli such as stress, diet, drugs, hormones, or irritants can cause the gastrointestinal tract to contract abnormally. During an episode of IBS, contractions of the gastrointestinal tract become stronger and more frequent, resulting in the rapid transit of food and feces through the small intestine, often leading to diarrhea. Cramps result from the strong contractions of the large intestine and increased sensitivity of pain receptors in the large intestine.

Treatment of IBS typically involves modification of an IBS-patient's diet. Often it is recommended that an IBS patient avoid beans, cabbage, sorbitol, and fructose. A low-fat, high-fiber diet can also help some IBS patients. Regular physical activity can also help keep the gastrointestinal tract functioning properly. Drugs such as propantheline that slow the function of the gastrointestinal tract are generally not effective for treating IBS. Antidiarrheal drugs, such as diphenoxylate and loperamide, help with diarrhea. Berkow et al., "Irritable Bowel Syndrome," *The Merck Manual of Medical Information*, pp. 525-526 (1997).

International publication No. WO 98/31677 describes a class of aromatic amines derived from cyclic amines that are useful as antidepressant drugs.

U.S. Pat. No. 7,326,705 to Ahmad et al. and international publication No. WO 01/27107 describe a class of heterocyclic compounds that are sodium/proton exchange inhibitors.

U.S. Pat. No. 7,612,075 to Ewing et al. and international publication No. WO 99/37304 describe substituted oxoaza-heterocycly compounds useful for inhibiting factor Xa.

U.S. Pat. No. 6,248,756 to Anthony et al. and international publication no. WO 97/38665 describe a class of piperidine-containing compounds that inhibit farnesyl-protein transferase (Ftase).

International publication No. WO 97/28140 describes a class of piperidines derived from 1-(piperazin-1-yl)aryl(oxy/amino)carbonyl-4-aryl-piperidine that are useful as 5-HT$_{1Db}$ receptor antagonists.

U.S. Pat. No. 5,891,889 to Anthony et al. describes a class of substituted piperidine compounds that are useful as inhibitors of farnesyl-protein transferase, and the farnesylation of the oncogene protein Ras.

U.S. Pat. No. 6,150,129 to Cook et al. describes a class of dinitrogen heterocycles useful as antibiotics.

U.S. Pat. No. 7,091,227 to Cusack et al. and international publication No. WO 01/57008 describe a class of 2-benzothiazolyl urea derivatives useful as inhibitors of serine/threonine and tyrosine kinases.

U.S. Pat. No. 6,723,730 to Bakthavatchalam et al. and international publication No. WO 02/08221 describe aryl piperazine compounds useful for treating chronic and acute pain conditions, itch, and urinary incontinence.

U.S. Pat. No. 6,414,149 to Chu-Moyer et al. and international publication No. WO 00/59510 describe aminopyrimidines useful as sorbitol dehydrogenase inhibitors.

Japanese patent application No. 11-199573 to Iwaoka et al. describes benzothiazole derivatives that are neuronal 5HT3 receptor agonists in the intestinal canal nervous system and useful for treating digestive disorders and pancreatic insufficiency.

M. Chu-Moyer et al., *J. Med. Chem.* 45:511-528 (2002) describes heterocycle-substituted piperazino-pyrimidines useful as sorbitol dehydrogenase inhibitors.

B. G. Khadse et al., *Bull. Haff. Inst.* 1(3):27-32 (1975) describes 2-(N$^4$-substituted-N$^1$-piperazinyl)pyrido(3,2-d)thiazoles and 5-nitro-2-(N$^4$-substituted-N$^1$-piperazinyl)benzthiazoles useful as anthelmintic agents.

U.S. Patent Application Publication No. US 2004/0044003, International publication No. WO 2003/066595, U.S. Patent Application Publication No. US 2004/0006091, International publication No. WO 2003/074520, U.S. Patent Application Publication No. US 2004/0106625, International publication No. WO 2004/002983, U.S. Patent Application Publication No. US 2004/0235853, International publication No. WO 2004/011441, U.S. Patent Application Publication No. US 2005/0059671, International publication No. WO 2004/029031, U.S. Patent Application Publication No. US 2004/0186111, International publication No. WO 2004/058754, U.S. Patent Application Publication No. US 2006/0199824, International publication No. WO 2005/009987, U.S. Patent Application Publication Nos. US 2006/0128717 and US 20060258669, International publication Nos. WO 2005/009988, WO 2005/004866, WO 2005/012287, WO 2005/030766, WO 2005/030753, WO 2005/066130, and WO2007/069773, U.S. Patent Application Publication Nos. US 2009/0170868, US 2009/0170867, and US US2009/0176796, International publication Nos. WO 2008/132600, WO2008/133973, and WO 2004/035549 each describe classes of compounds that are useful for treating pain.

There remains, however, a clear need in the art for new drugs useful for treating or preventing pain, UI, an ulcer, IBD, and IBS. Citation of any reference in Section 2 of this application is not to be construed as an admission that such reference is prior art to the present application.

DISCLOSURE OF INVENTION

The invention provides:
1) A compound of Formula I:

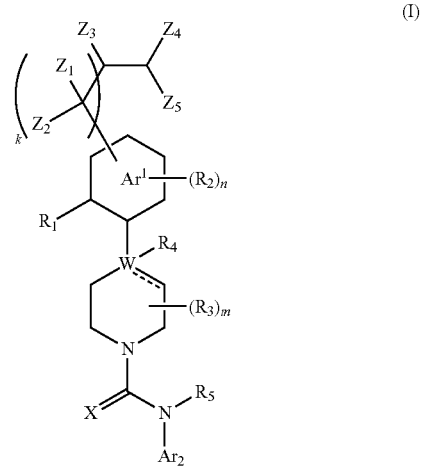

or a pharmaceutically acceptable derivative thereof, wherein
X is O, S, N—CN, or N—OR$_7$;
W is N or C;
the dashed line denotes the presence or absence of a bond, and
when the dashed line is present as a bond to provide one bond of a double bond or W is N then R$_4$ is absent, otherwise R$_4$ is —H, -halo, —(C$_1$-C$_6$)alkyl, —CH$_2$OR$_7$, —CH$_2$(halo), —CH(halo)$_2$, —C(halo)$_3$, —OC(halo)$_3$, —OR$_7$, —SR$_7$, —C(O)OR$_7$, —C(O)R$_7$, —OC(O)R$_7$, —OC(O)N(R$_8$)$_2$, —NR$_7$C(O)R$_{13}$, —C(O)N(R$_8$)$_2$, —S(O)$_2$R$_7$, or —NO$_2$;

R$_1$ is —H, -halo, —NO$_2$, —CN, —OR$_7$, —N(R$_7$)$_2$, —(C$_{1-C4}$)alkyl, —C(halo)$_3$, —CH(halo)$_2$, —CH$_2$(halo), —OC(halo)$_3$, —OCH(halo)$_2$, or —OCH$_2$(halo);

each R$_2$ is independently -halo, —OR$_7$, —CN, —NO$_2$, —N(R$_7$)$_2$, —(C$_1$-C$_{10}$)alkyl, —(C$_2$-C$_{10}$)alkenyl, —(C$_2$-C$_{10}$)alkynyl, or -phenyl, each R$_3$ is independently:

(a) —(C$_1$-C$_6$)alkyl, —(C$_1$-C$_6$)alkyl-OR$_{13}$, —C(O)R$_{13}$, —C(O)OR$_{13}$, —N(R$_{13}$)C(O)R$_{13}$, or —C(O)N(R$_{13}$)$_2$; or (b) two R$_3$ groups together form =O; or (c) two R$_3$ groups together form a (C$_2$-C$_6$)bridge, which is unsubstituted or substituted with 1, 2 or 3 independently selected R$_{13}$ groups, and which bridge optionally contains —HC=CH— within the (C$_2$-C$_6$)bridge; or (d) two R$_3$ groups together form

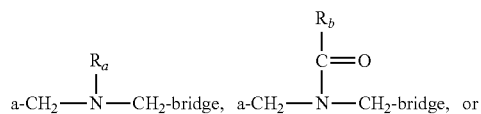

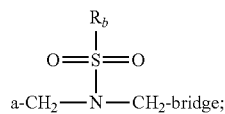

R$_a$ is —H, —(C$_1$-C$_6$)alkyl, —(C$_3$-C$_8$)cycloalkyl, —CH$_2$—C(O)R$_c$, —(CH$_2$)—C(O)OR$_c$, —(CH$_2$)—C(O)N(R$_c$)$_2$, —(CH$_2$)$_2$OR$_c$, —(CH$_2$)$_2$—S(O)$_2$N(R$_c$)$_2$, or –(CH$_2$)$_2$—N(R$_c$)S(O)$_2$R$_c$;

R$_b$ is:

(a) —H, —(C$_1$-C$_6$)alkyl, —(C$_3$-C$_8$)cycloalkyl, -(3- to 7-membered)heterocycle, —N(R$_c$)$_2$, —N(R$_c$)—(C$_3$-C$_8$)cycloalkyl, or —N(R$_c$)-(3- to 7-membered)heterocycle, each of which -(3- to 7-membered)heterocycle or —(C$_3$-C$_8$)cycloalkyl is unsubstituted or substituted with 1, 2 or 3 independently selected R$_{13}$ groups; or (b)-phenyl, -(5- or 6-membered)heteroaryl, —N(R$_a$)-phenyl, or —N(R$_c$)-(5- to 10-membered)heteroaryl, each of which is unsubstituted or substituted with 1, 2 or 3 independently selected R$_{13}$ groups;

each R$_c$ is independently —H or —(C$_1$-C$_4$)alkyl;

R$_5$ is —H, —(C$_1$-C$_6$)alkyl, —(C$_3$-C$_8$)cycloalkyl, —(C$_1$-C$_6$)alkyl-OC(O)R$_7$, —C(O)R$_7$, or —C(O)N(R$_8$)$_2$;

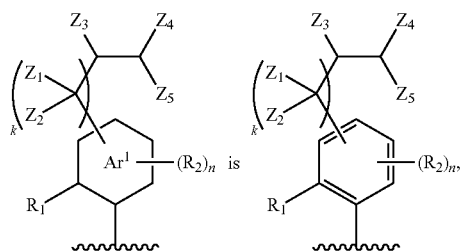

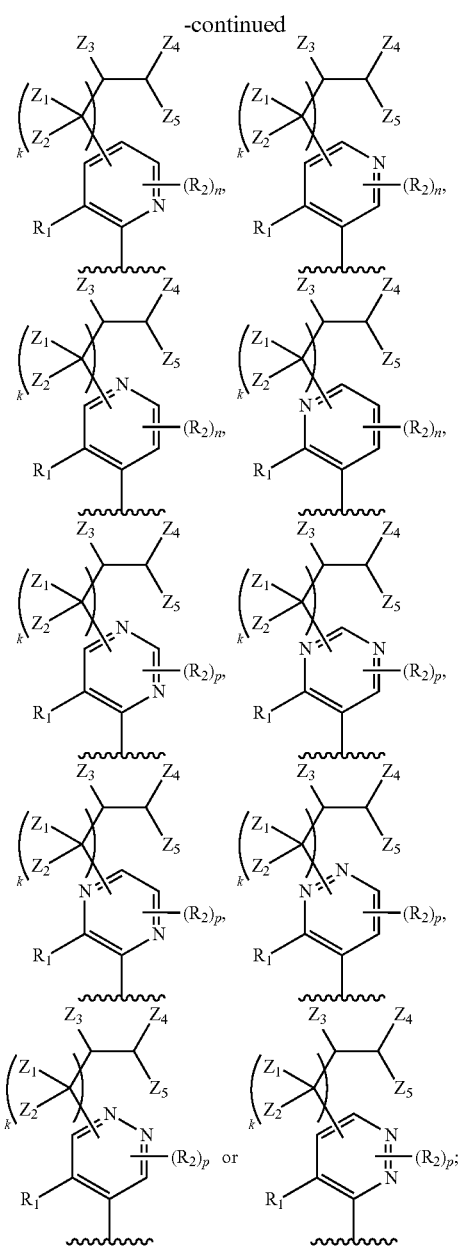

Z$_1$ and Z$_2$ are each independently —H, —(C$_1$-C$_6$)alkyl, —(C$_2$-C$_6$)alkenyl, —(C$_2$-C$_6$)alkynyl, -phenyl, —OR$_{12}$, —N(R$_{12}$)$_2$, -halo, —(C$_3$-C$_8$)cycloalkyl, —C(O)OR$_{13}$, —C(O)R$_{13}$, or —CH=N—OR$_{13}$, or Z$_1$ and Z$_2$ groups together form =O or =N—OR$_{13}$;

Z$_3$ and Z$_4$ are each independently —OR$_{12}$ or —N(R$_{12}$)$_2$;

Z$_5$ is —H, —(C$_1$-C$_6$)alkyl, —(C$_2$-C$_6$)alkenyl, —(C$_2$-C$_6$)alkynyl, or -phenyl;

Ar$_2$ is

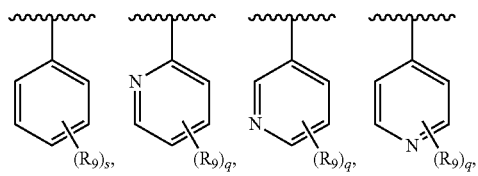

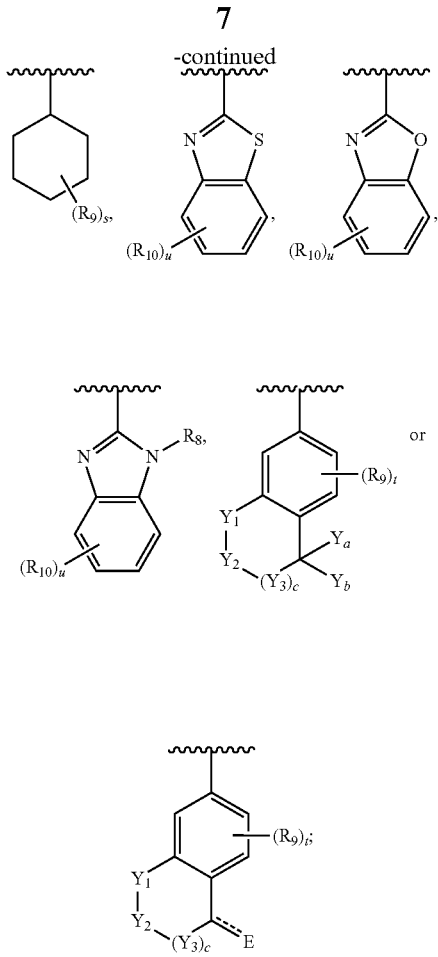

each R$_9$ is independently —(C$_1$-C$_6$)alkyl, —(C$_2$-C$_6$)alkenyl, —(C$_2$-C$_6$)alkynyl, —(C$_3$-C$_8$)cycloalkyl, —(C$_5$-C$_8$)cycloalkenyl, -phenyl, -(3- to 7-membered)heterocycle, —(C$_1$-C$_6$)haloalkyl, —(C$_2$-C$_6$)haloalkenyl, —(C$_2$-C$_6$)haloalkynyl, —(C$_1$-C$_6$)hydroxyalkyl, —(C$_2$-C$_6$)hydroxyalkenyl, —(C$_2$-C$_6$)hydroxyalkynyl, —(C$_1$-C$_6$)alkoxy(C$_1$-C$_6$)alkyl, —(C$_1$-C$_6$)alkoxy(C$_2$-C$_6$)alkenyl, —(C$_1$-C$_6$)alkoxy(C$_2$-C$_6$)alkynyl, —CN, -halo, —N$_3$, —NO$_2$, —CH=NR$_{13}$, —N(R$_{13}$)$_2$, —NR$_{13}$OR$_{13}$, —OR$_{13}$, —SR$_{13}$, —O(CH$_2$)$_b$OR$_{13}$, —O(CH$_2$)$_b$SR$_{13}$, —O(CH$_2$)$_b$N(R$_{13}$)$_2$, —N(R$_{13}$)(CH$_2$)$_b$OR$_{13}$, —N(R$_{13}$)(CH$_2$)$_b$SR$_{13}$, —N(R$_{13}$)(CH$_2$)$_b$N(R$_{13}$)$_2$, —N(R$_{13}$)C(O)R$_{13}$, —C(O)R$_{13}$, —C(O)OR$_{13}$, —OC(O)R$_{13}$, —OC(O)OR$_{13}$, —S(O)R$_{13}$, —S(O)$_2$R$_{13}$, —S(O)$_2$N(R$_{13}$)$_2$, —S(O)$_2$-(3- to 7-membered)heterocycle, —C(O)N(R$_{13}$)$_2$, —(C$_1$-C$_6$)alkyl-C=N—OR$_{13}$, —(C$_1$-C$_6$)alkyl-C(O)N(R$_{13}$)$_2$, —(C$_1$-C$_6$)alkyl-NHS(O)$_2$N(R$_{13}$)$_2$, or —(C$_1$-C$_6$)alkyl-C(=NH)—N(R$_{13}$)$_2$, each of which -phenyl, -(3- to 7-membered)heterocycle, or —(C$_3$-C$_8$)cycloalkyl is unsubstituted or substituted with 1, 2 or 3 independently selected R$_{13}$ groups;

each R$_{10}$ is independently:
(a) —(C$_1$-C$_6$)alkyl, —(C$_2$-C$_6$)alkenyl, —(C$_2$-C$_6$)alkynyl, —(C$_3$-C$_8$)cycloalkyl, —(C$_5$-C$_8$)cycloalkenyl, or -phenyl, each of which is unsubstituted or substituted with 1 or 2 —OH groups;
(b) —CH$_2$CH$_2$(halo), —CH$_2$CH(halo)$_2$, —CH$_2$C(halo)$_3$, —C(halo)$_3$, —CH(halo)$_2$, —CH$_2$(halo), —CN, -halo, —N$_3$, —NO$_2$, —CH=NR$_{13}$, —N(R$_{13}$)$_2$, —NR$_{13}$OR$_{13}$, —OR$_{13}$, —C(O)R$_{13}$, —C(O)OR$_{13}$, —OC(O)R$_{13}$, —OC(O)OR$_{13}$, —SR$_{13}$, —S(O)R$_{13}$, or —S(O)$_2$R$_{13}$; or (c) two R$_{10}$ groups on adjacent carbon atoms together form a (C$_1$-C$_2$)alkylenedioxy bridge, which is unsubstituted or substituted 1, 2 or 3 independently selected R$_{13}$ groups;

Y$_1$, Y$_2$, Y$_3$ are each independently C, N, or O;

wherein no more than one of Y$_1$, Y$_2$, or Y$_3$ can be O, no more than two of Y$_1$, Y$_2$, or Y$_3$ can be N and for each Y$_1$, Y$_2$, and Y$_3$ that is N, the N is bonded to one R$_{14}$ group, and for each Y$_1$, Y$_2$, and Y$_3$ that is C, the C is bonded to two R$_5$ groups, provided that there are no more than a total of two (C$_1$-C$_6$) alkyl groups substituted on all of Y$_1$, Y$_2$, and Y$_3$;

Y$_a$ and Y$_b$ are each independently —H, -halo, or —(C$_1$-C$_6$) alkyl, or Y$_a$ and Y$_b$, together with the carbon to which they are attached, form a 3-8 member carbocyclic ring;

E is =O, =S, =C(R$_7$)$_2$, =CH(C$_2$-C$_6$)alkenyl, —N(R$_7$)$_2$, or =N—OR$_5$;

each R$_7$ is independently —H or —(C$_1$-C$_6$)alkyl;

each R$_8$ is independently —H, —(C$_2$-C$_6$)alkenyl, —(C$_2$-C$_6$)alkynyl, —(C$_3$-C$_8$)cycloalkyl, or phenyl;

each R$_{12}$ is independently —H, —(C$_1$-C$_6$)alkyl, —(C$_3$-C$_8$) cycloalkyl, —C(O)R$_{15}$, —C(O)OR$_{13}$, or —C(O)N(R$_{13}$)$_2$;

each R$_{13}$ is independently —H, —(C$_1$-C$_6$)alkyl, —(C$_2$-C$_6$) alkenyl, —(C$_2$-C$_6$)alkynyl, —(C$_3$-C$_8$)cycloalkyl, —(C$_5$-C$_8$) cycloalkenyl, -phenyl, -benzyl, —(C$_1$-C$_6$)haloalkyl, —(C$_1$-C$_6$)hydroxyalkyl, —(C$_1$-C$_6$)alkoxy(C$_1$-C$_6$)alkyl, —(C$_1$-C$_6$) alkyl-N(R$_8$)$_2$, or —C(O)N(R$_8$)$_2$;

each R$_{14}$ is independently —H, —(C$_1$-C$_6$)alkyl, —C(O)R$_{13}$, —S(O)R$_{13}$, —S(O)$_2$R$_{13}$,

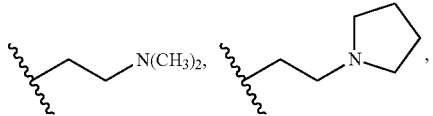

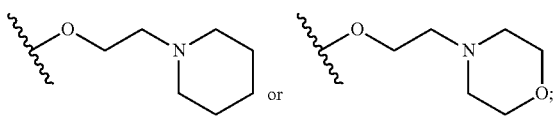

R$_{15}$ is H, 13 (C$_1$-C$_6$)alkyl, —(C$_2$-C$_6$)alkenyl, —(C$_2$-C$_6$) alkynyl, —(C$_1$-C$_6$)haloalkyl, —(C$_1$-C$_6$)hydroxyalkyl, —(C$_1$-C$_6$)alkoxy(C$_1$-C$_6$)alkyl, —(C$_1$-C$_6$)alkyl-N(R$_8$)$_2$, —(C$_3$-C$_8$)cycloalkyl, —(C$_5$-C$_8$)cycloalkenyl, -phenyl, -benzyl, or -(3- to 7-membered)heterocycle;

each halo is independently —F, —Cl, —Br, or —I;

n is the integer 0, 1, or 2;

p is the integer 0 or 1;

m is the integer 0, 1, or 2;

k is the integer 1 or 2;

q is the integer 0, 1, 2, 3, or 4;

s is the integer 0, 1, 2, 3, 4, or 5;

t is the integer 0, 1, 2, or 3;

u is the integer 0, 1, 2 or 3;

each b is independently 1 or 2; and c is the integer 0, 1, or 2.

1') A compound of Formula I':

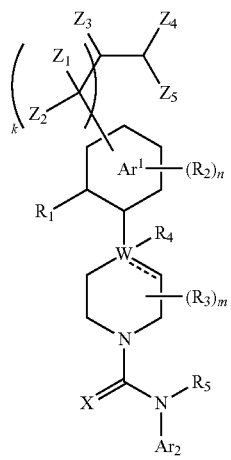

or a pharmaceutically acceptable derivative thereof, wherein
X is O, S, N—CN, or N—OR$_7$;
W is N or C;
the dashed line denotes the presence or absence of a bond, and
when the dashed line is present as a bond to provide one bond of a double bond or W is N then R$_4$ is absent, otherwise R$_4$ is —H, -halo, —(C$_1$-C$_6$)alkyl, —CH$_2$OR$_7$, —CH$_2$(halo), —CH(halo)$_2$, —C(halo)$_3$, —OC(halo)$_3$, —OR$_7$, —SR$_7$, —C(O)OR$_7$, —C(O)R$_7$, —OC(O)R$_7$, —OC(O)N(R$_8$)$_2$, —NR$_7$C(O)R$_{13}$, —C(O)N(R$_8$)$_2$, —S(O)$_2$R$_7$, or —NO$_2$;
R$_1$ is —H, -halo, —NO$_2$, —CN, —OR$_7$, —N(R$_7$)$_2$, —(C$_1$-C$_4$)alkyl, —C(halo)$_3$, —CH(halo)$_2$, —CH$_2$(halo), —OC(halo)$_3$, —OCH(halo)$_2$, or —OCH$_2$(halo);
each R$_2$ is independently -halo, —OR$_7$, —CN, —NO$_2$, —N(R$_7$)$_2$, —(C$_1$-C$_{10}$)alkyl, —(C$_2$-C$_{10}$)alkenyl, —(C$_2$-C$_{10}$)alkynyl, or -phenyl,
each R$_3$ is independently:
(a) —(C$_1$-C$_6$)alkyl, —(C$_1$-C$_6$)alkyl-OR$_{13}$, —C(O)R$_{13}$, —C(O)OR$_{13}$, —N(R$_{13}$)C(O)R$_{13}$, or —C(O)N(R$_{13}$)$_2$; or
(b) two R$_3$ groups together form =O; or
(c) two R$_3$ groups together form a (C$_2$-C$_6$)bridge, which is unsubstituted or substituted with 1, 2 or 3 independently selected R$_{10}$ groups, and which bridge optionally contains —HC=CH— within the (C$_2$-C$_6$)bridge; or
(d) two R$_3$ groups together form

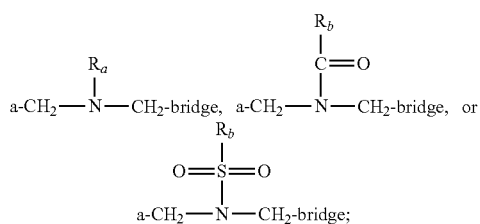

R$_a$ is —H, —(C$_1$-C$_6$)alkyl, —(C$_3$-C$_8$)cycloalkyl, —CH$_2$—C(O)R$_c$, —(CH$_2$)—C(O)OR$_c$, —(CH$_2$)—C(O)N(R$_c$)$_2$, —(CH$_2$)$_2$—OR$_c$, —(CH$_2$)$_2$—S(O)$_2$N(R$_c$)$_2$, or —(CH$_2$)$_2$—N(R$_c$)S(O)$_2$R$_c$;
R$_b$ is:
(a) —H, —(C$_1$-C$_6$)alkyl, —(C$_3$-C$_8$)cycloalkyl, -(3- to 7-membered)heterocycle, —N(R$_c$)$_2$, —N(R$_c$)—(C$_3$-C$_8$)cycloalkyl, or —N(R$_c$)-(3- to 7-membered)heterocycle, each of which -(3- to 7-membered)heterocycle or —(C$_3$-C$_8$)cycloalkyl is unsubstituted or substituted with 1, 2 or 3 independently selected R$_{13}$ groups; or
(b) -phenyl, -(5- or 6-membered)heteroaryl, —N(R$_c$)-phenyl, or —N(R$_c$)-(5- to 10-membered)heteroaryl, each of which is unsubstituted or substituted with 1, 2 or 3 independently selected R$_{13}$ groups;
each R$_c$ is independently —H or —(C$_1$-C$_4$)alkyl;
R$_5$ is —H, —(C$_1$-C$_6$)alkyl, —(C$_3$-C$_8$)cycloalkyl, —(C$_1$-C$_6$)alkyl-OC(O)R$_7$, —C(O)R$_7$, or —C(O)N(R$_8$)$_2$;

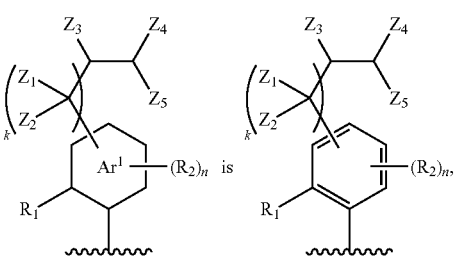

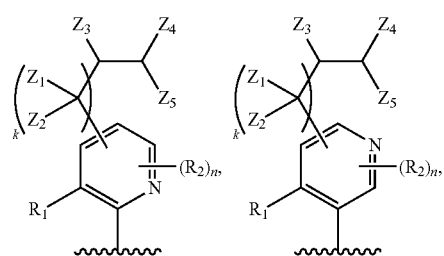

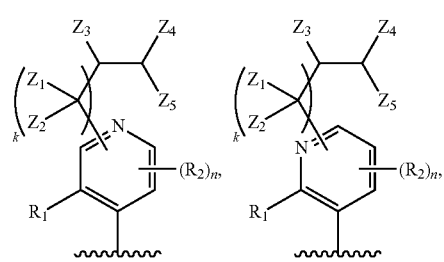

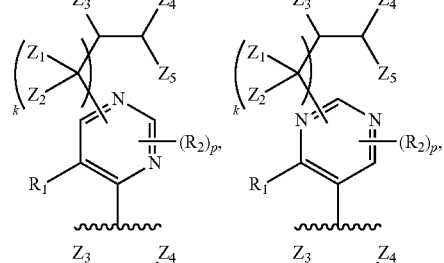

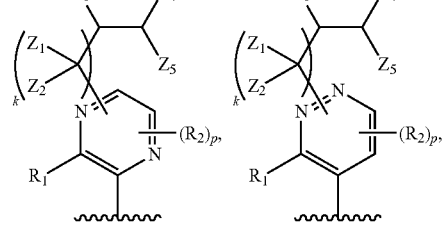

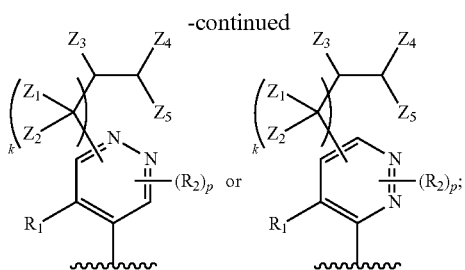

$Z_1$ and $Z_2$ are each independently —H, —($C_1$-$C_6$)alkyl, —($C_2$-$C_6$)alkenyl, —($C_2$-$C_6$)alkynyl, -phenyl, —$OR_{12}$, —$N(R_{12})_2$, -halo, —($C_3$-$C_8$)cycloalkyl, —$C(O)OR_{13}$, —$C(O)R_{13}$, or —CH=N—$OR_{13}$, or $Z_1$ and $Z_2$ groups together form =O or =N—$OR_{13}$;

$Z_3$ and $Z_4$ are each independently —$OR_{12}$ or $NR_{12})_2$;

$Z_5$ is —H, —($C_1$-$C_6$)alkyl, —($C_2$-$C_6$)alkenyl, —($C_2$-$C_6$)alkynyl, or -phenyl;

$Ar_2$ is

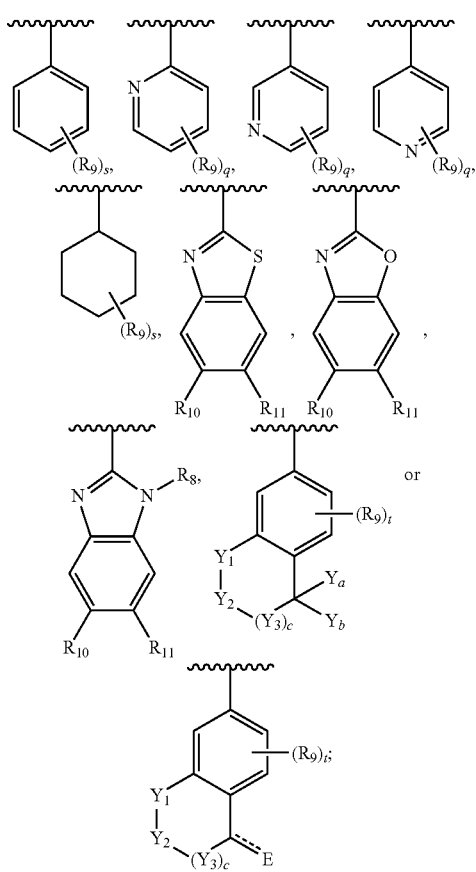

each $R_9$ is independently —($C_1$-$C_6$)alkyl, —($C_2$-$C_6$)alkenyl, —($C_2$-$C_6$)alkynyl, —($C_3$-$C_8$)cycloalkyl, —($C_5$-$C_8$)cycloalkenyl, -phenyl, -(3- to 7-membered)heterocycle, —($C_1$-$C_6$)haloalkyl, —($C_2$-$C_6$)haloalkenyl, —($C_2$-$C_6$)haloalkynyl, —($C_1$-$C_6$)hydroxyalkyl, —($C_2$-$C_6$)hydroxyalkenyl, —($C_2$-$C_6$)hydroxyalkynyl, —($C_1$-$C_6$)alkoxy($C_1$-$C_6$)alkyl, —($C_1$-$C_6$)alkoxy($C_2$-$C_6$)alkenyl, —($C_1$-$C_6$)alkoxy($C_2$-$C_6$)alkynyl, —CN, -halo, —$N_3$, —$NO_2$, —CH=$NR_{13}$, —$N(R_{13})_2$, —$NR_{13}OR_{13}$, —$OR_{13}$, —$SR_{13}$, —$O(CH_2)_bOR_{13}$, —$O(CH_2)_bSR_{13}$, —$O(CH_2)_bN(R_{13})_2$, —$N(R_{13})(CH_2)_bOR_{13}$, —$N(R_{13})(CH_2)_bSR_{13}$, —$N(R_{13})(CH_2)_bN(R_{13})_2$, —$N(R_{13})C(O)R_{13}$, —$C(O)R_{13}$, —$C(O)OR_{13}$, —$OC(O)R_{13}$, —$OC(O)OR_{13}$, —$S(O)R_{13}$, —$S(O)_2R_{13}$, —$S(O)_2N(R_{13})_2$, —$S(O)_2$-(3- to 7-membered)heterocycle, —$C(O)N(R_{13})_2$, —($C_1$-$C_6$)alkyl-C=N—$OR_{13}$, —($C_1$-$C_6$)alkyl-C(O)N($R_{13}$)$_2$, —($C_1$-$C_6$)alkyl-NHS(O)$_2$N($R_{13}$)$_2$, or —($C_1$-$C_6$)alkyl-C(=NH)—N($R_{13}$)$_2$, each of which -phenyl, -(3- to 7-membered) heterocycle, or —($C_3$-$C_8$)cycloalkyl is unsubstituted or substituted with 1, 2 or 3 independently selected $R_{13}$ groups;

$R_{10}$ and $R_{11}$ are each independently:
(a) —($C_1$-$C_6$)alkyl, —($C_2$-$C_6$)alkenyl, —($C_2$-$C_6$)alkynyl, —($C_3$-$C_8$)cycloalkyl, —($C_5$-$C_8$)cycloalkenyl, or -phenyl, each of which is unsubstituted or substituted with 1 or 2 -OH groups;
(b) —H, —$CH_2CH_2$(halo), —$CH_2CH$(halo)$_2$, —$CH_2C$(halo)$_3$, —C(halo)$_3$, —CH(halo)$_2$, —$CH_2$(halo), —CN, -halo, —$N_3$, —$NO_2$, —CH=$NR_{13}$, —$N(R_{13})_2$, —$NR_{13}OR_{13}$, —$OR_{13}$, —$C(O)R_{13}$, —$C(O)OR_{13}$, —$OC(O)R_{13}$, —$OC(O)OR_{13}$, —$SR_{13}$, —$S(O)R_{13}$, or —$S(O)_2R_{13}$; or $Y_1$, $Y_2$, $Y_3$ are each independently C, N, or O;
wherein no more than one of $Y_1$, $Y_2$, or $Y_3$ can be O, no more than two of $Y_1$, $Y_2$, or $Y_3$ can be N and for each $Y_1$, $Y_2$, and $Y_3$ that is N, the N is bonded to one $R_{14}$ group, and for each $Y_1$, $Y_2$, and $Y_3$ that is C, the C is bonded to two $R_5$ groups, provided that there are no more than a total of two ($C_1$-$C_6$) alkyl groups substituted on all of $Y_1$, $Y_2$, and $Y_3$;

$Y_a$ and $Y_b$ are each independently —H, -halo, or —($C_1$-$C_6$) alkyl, or $Y_a$ and $Y_b$, together with the carbon to which they are attached, form a 3-8 member carbocyclic ring;

E is =O, =S, =$C(R_7)_2$, =CH($C_2$-$C_6$)alkenyl, =$N(R_7)_2$, or —N—$OR_5$;

each $R_7$ is independently —H or —($C_1$-$C_6$)alkyl;
each $R_8$ is independently —H, —($C_1$-$C_6$)alkyl, —($C_2$-$C_6$) alkenyl, —($C_2$-$C_6$)alkynyl, —($C_3$-$C_8$)cycloalkyl, or phenyl;
each $R_{12}$ is independently —H, —($C_1$-$C_6$)alkyl, —($C_3$-$C_8$) cycloalkyl, —$C(O)R_{15}$, —$C(O)OR_{13}$, or —$C(O)N(R_{13})_2$;
each $R_{13}$ is independently —H, —($C_1$-$C_6$)alkyl, —($C_2$-$C_6$) alkenyl, —($C_2$-$C_6$)alkynyl, —($C_3$-$C_8$)cycloalkyl, —($C_5$-$C_8$) cycloalkenyl, -phenyl, -benzyl, —($C_1$-$C_6$)haloalkyl, —($C_1$-$C_6$)hydroxyalkyl, —($C_1$-$C_6$)alkoxy($C_1$-$C_6$)alkyl, —($C_1$-$C_6$) alkyl-N($R_8$)$_2$, or —C(O)N($R_8$)$_2$;

each $R_{14}$ is independently —H, —($C_1$-$C_6$)alkyl, —C(O) $R_{13}$, —$S(O)R_{13}$, —$S(O)_2R_{13}$,

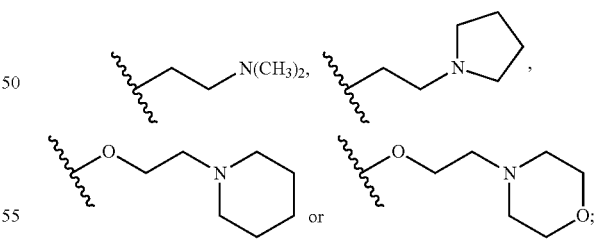

$R_{15}$ is H, —($C_1$-$C_6$)alkyl, —($C_2$-$C_6$)alkenyl, —($C_2$-$C_6$) alkynyl, —($C_1$-$C_6$)haloalkyl, —($C_1$-$C_6$)hydroxyalkyl, —($C_1$-$C_6$)alkoxy($C_1$-$C_6$)alkyl, —($C_1$-$C_6$)alkyl-N($R_8$)$_2$, —($C_3$-$C_8$)cycloalkyl, —($C_5$-$C_8$)cycloalkenyl, -phenyl, -benzyl, or -(3- to 7-membered)heterocycle;

each halo is independently —F, —Cl, —Br, or —I;
n is the integer 0, 1, or 2;
p is the integer 0 or 1;
m is the integer 0, 1, or 2;
k is the integer 1 or 2;

q is the integer 0, 1, 2, 3, or 4;
s is the integer 0, 1, 2, 3, 4, or 5;
t is the integer 0, 1, 2, or 3;
each b is independently 1 or 2; and
c is the integer 0, 1, or 2.

2) The compound according to the above 1) or 1') or a pharmaceutically acceptable derivative thereof, wherein

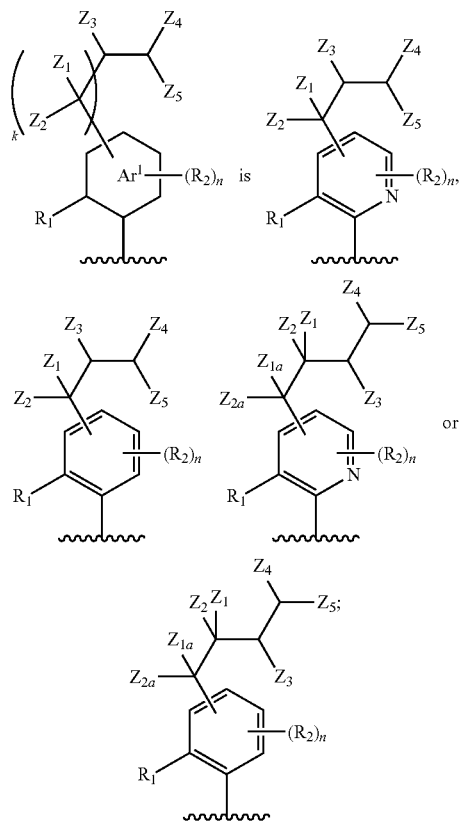

and $Z_{1a}$ and $Z_{2a}$ are each independently —H, —($C_1$-$C_6$)alkyl, —($C_2$-$C_6$)alkenyl, —($C_2$-$C_6$)alkynyl, -phenyl, -halo or —($C_3$-$C_8$)cycloalkyl.

3) The compound according to the above 1), 1') or 2) or a pharmaceutically acceptable derivative thereof, wherein

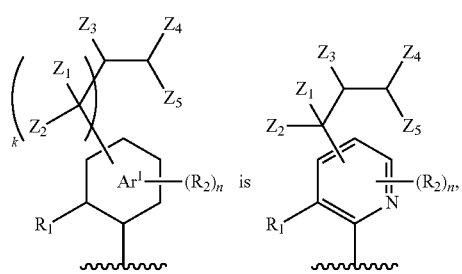

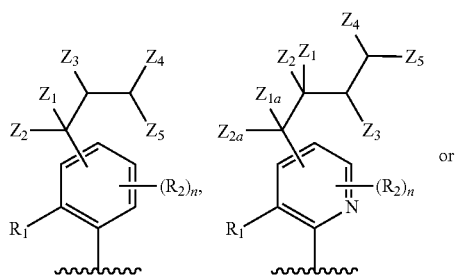

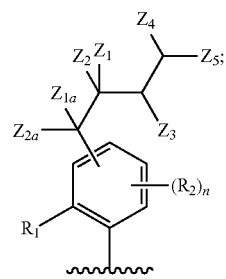

and $Z_{1a}$ and $Z_{2a}$ are each independently —H, —($C_1$-$C_6$)alkyl, —($C_2$-$C_6$)alkenyl, —($C_2$-$C_6$)alkynyl, -phenyl, -halo or —($C_3$-$C_8$)cycloalkyl.

4) The compound according to any one of the above 1), 1') and 2) to 3) or a pharmaceutically acceptable derivative thereof, wherein $Z_1$ is —H, —$OR_{12}$, or -halo, $Z_2$, $Z_{1a}$ and $Z_{2a}$ are each independently —H or -halo, $Z_3$ and $Z_4$ are each independently —$OR_{12}$, and $Z_5$ is —H or —($C_1$-$C_4$)alkyl.

5) The compound according to any one of the above 1), 1') and 2) to 4) or a pharmaceutically acceptable derivative thereof, wherein $Z_1$ is —H, —OH, or -halo, $Z_2$, $Z_{1a}$ and $Z_{2a}$ are each independently —H or -halo, $Z_3$ and $Z_4$ are —OH, and $Z_5$ is —H or —$CH_3$.

6) The compound according to any one of the above 1), 1') and 2) to 5) or a pharmaceutically acceptable derivative thereof, wherein

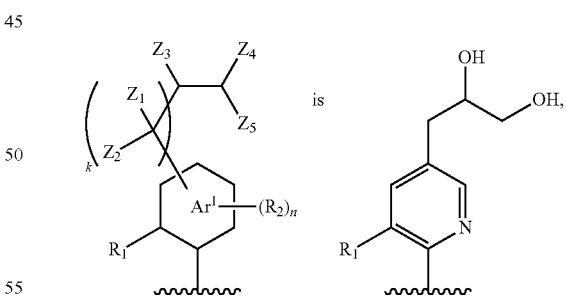

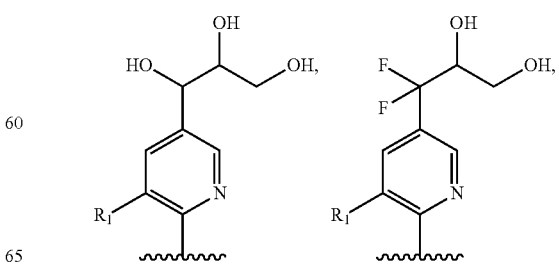

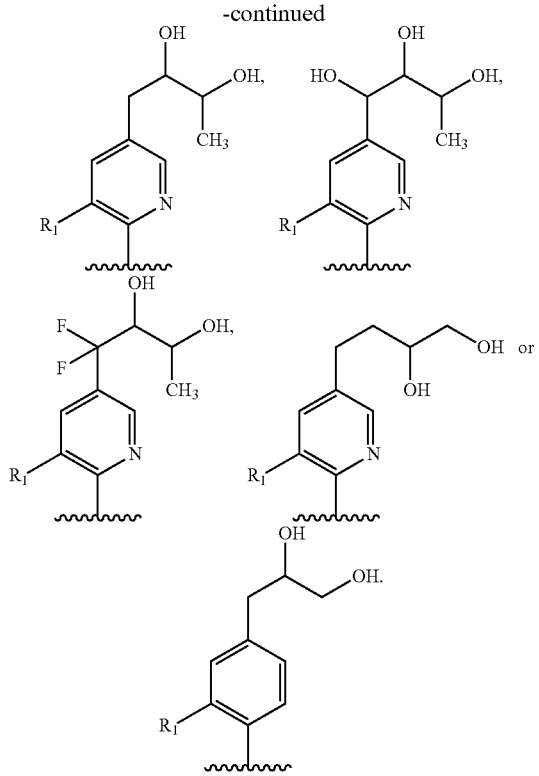

7) The compound according to any one of the above 1), 1') and 2) to 6) or a pharmaceutically acceptable derivative thereof, wherein:

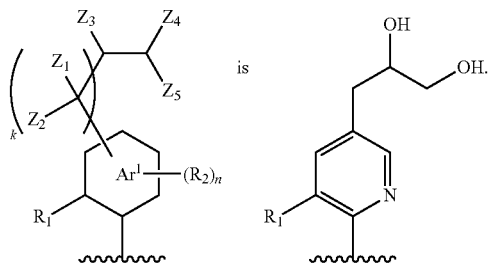

8) The compound according to any one of the above 1), 1') and 2) to 6) or a pharmaceutically acceptable derivative thereof, wherein:

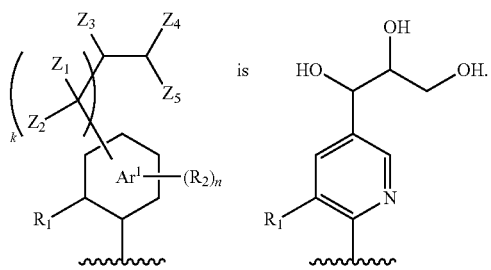

9) The compound according to any one of the above 1), 1') and 2) to 6) or a pharmaceutically acceptable derivative thereof, wherein:

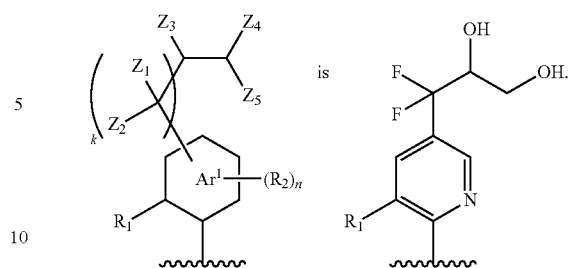

10) The compound according to any one of the above 1), 1') and 2) to 6) or a pharmaceutically acceptable derivative thereof, wherein:

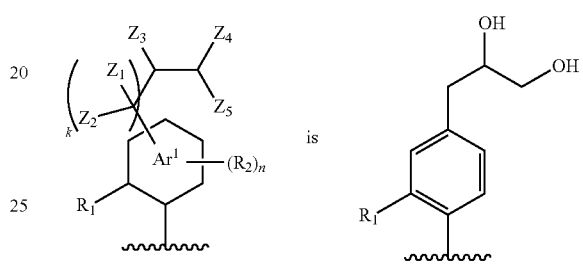

11) The compound according to any one of the above 1), 1') and 2) to 5) or a pharmaceutically acceptable derivative thereof, wherein

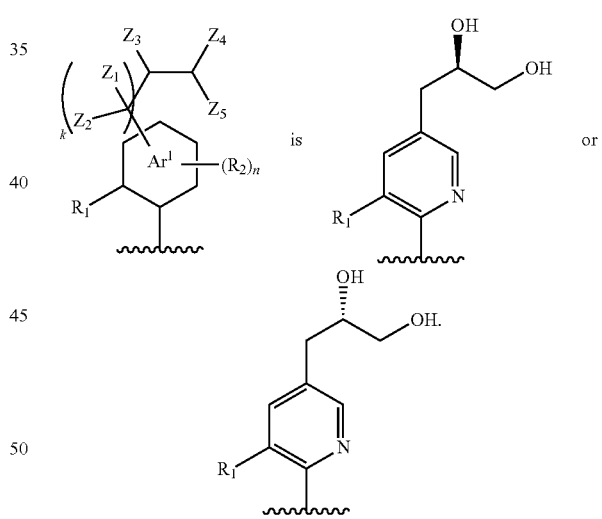

12) The compound according to any one of the above 1), 1') and 2) to 11) or a pharmaceutically acceptable derivative thereof, wherein $R_1$ is —$CH_3$, -halo or —C(halo)$_3$.

13) The compound according to any one of the above 1), 1') and 2) to 12) or a pharmaceutically acceptable derivative thereof, wherein X is O.

14) The compound according to any one of the above 1), 1') and 2) to 13) or a pharmaceutically acceptable derivative thereof, wherein W is C and the dashed line denotes absence of a bond.

15) The compound according to any one of the above 1), 1') and 2) to 14) or a pharmaceutically acceptable derivative thereof, wherein $R_4$ is -halo.

16) The compound according to any one of the above 1), 1') and 2) to 13) or a pharmaceutically acceptable derivative thereof, wherein W is C and the dashed line is present as a bond to provide one bond of a double bond.

17) The compound according to any one of the above 1), 1') and 2) to 13) or a pharmaceutically acceptable derivative thereof, wherein W is N and the dashed line demotes the absence of a bond.

18) The compound according to any one of the above 1), 1') and 2) to 17) or a pharmaceutically acceptable derivative thereof, wherein Ar$_2$ is

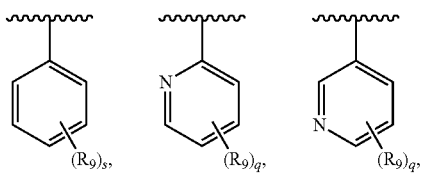

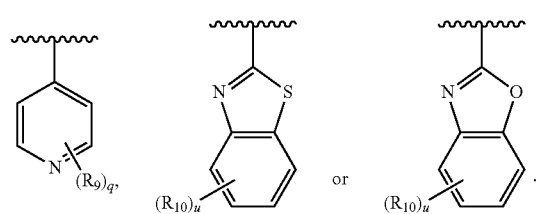

19) The compound according to any one of the above 1), 1') and 2) to 18) or a pharmaceutically acceptable derivative thereof, wherein Ar$_2$ is

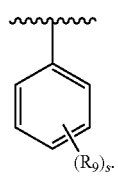

20) The compound according to any one of the above 1), 1'), and 2) to 18) or a pharmaceutically acceptable derivative thereof, wherein Ar$_2$ is

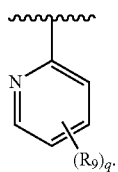

21) The compound according to any one of the above 1), 1'), and 2) to 18) or a pharmaceutically acceptable derivative thereof, wherein Ar$_2$ is

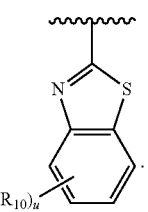

22) The compound according to any one of the above 1), 1') and 2) to 21) or a pharmaceutically acceptable derivative thereof, wherein s, q or u is 1 or 2.

23) The compound according to any one of the above 1), 1') and 2) to 20) and 22) or a pharmaceutically acceptable derivative thereof, wherein each R$_9$ is independently selected from -halo, —C(halo)$_3$, —(C$_1$-C$_6$)alkyl, —(C$_1$-C$_6$)alkoxy, —OC(halo)$_3$, and
—S(O)$_2$C(halo)$_3$.

24) The compound according to any one of the above 1), 1') and 2) to 20), 22) and 23) or a pharmaceutically acceptable derivative thereof, wherein each R$_9$ is independently selected from —CH$_3$, -halo, —C(halo)$_3$, —OCH$_3$, and —OC(halo)$_3$.

25) The compound according to any one of the above 1), 1') and 2) to 18), 21) and 22) or a pharmaceutically acceptable derivative thereof, wherein u is the integer 0, 1 or 2 and each R$_{10}$ is independently selected from -halo, —(C$_1$-C$_6$)alkyl, —C(halo)$_3$, —SC(halo)$_3$ and —S(O)$_2$C(halo)$_3$, or two R$_{10}$ groups on adjacent carbon atoms together form a —O—C(halo)$_2$-O-bridge.

26) The compound according to any one of the above 1), 1') and 2) to 25) or a pharmaceutically acceptable derivative thereof, wherein Ar$_2$ is

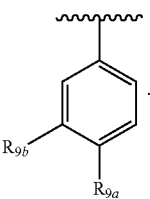

27) The compound according to any one of the above 1), 1') and 2) to 25) or a pharmaceutically acceptable derivative thereof, wherein Ar$_2$ is

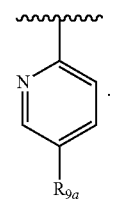

28) The compound according to any one of 1), 1') and 2) to 25) or a pharmaceutically acceptable derivative thereof, wherein Ar$_2$ is

19

[structure: benzothiazole with R10a, R10b substituents]

$R_{9a}$ is —C(halo)$_3$ or —OC(halo)$_3$, $R_{9b}$ is —H, -halo, —CH$_3$, or —OCH$_3$ and $R_{10a}$ and $R_{10b}$ are independently selected from —H, -halo, and —CH$_3$.

29) The compound according to any one of the above 1), 1') and 2) to 28) or a pharmaceutically acceptable derivative thereof, wherein n or p=0.

30) The compound according to any one of the above 1), 1') and 2) to 29) or a pharmaceutically acceptable derivative thereof, wherein m=0, 1 or 2 and $R_3$ is —(C$_1$-C$_6$)alkyl or two $R_3$ groups together form a —CH$_2$CH$_2$— bridge joining positions 2 and 6 of the piperidine, 1,2,3,6-tetrahydropyridine or piperazine ring.

31) The compound according to any one of the above 1), 1') and 2) to 15) and 19) to 30) or a pharmaceutically acceptable derivative thereof, wherein

[structures showing piperidine/tetrahydropyridine with R4 and (R3)m, and piperazine with CH3]

is

[structure: piperazine with CH3]

or

[structure: piperazine with CH3]

32) The compound according to any one of the above 1), 1') and 2) to 31) or a pharmaceutically acceptable derivative thereof, wherein k is 1.

33) The compound according to any one of the above 1), 1') and 2) to 32) or a pharmaceutically acceptable derivative thereof, wherein n is 0.

34) The compound according to any one of the above 1), 1') and 2) to 33) or a pharmaceutically acceptable derivative thereof, wherein s or q is 1 or 2.

35) The compound according to any one of the above 1), 1') and 2) to 33) or a pharmaceutically acceptable derivative thereof, wherein u is 1.

36) A compound of formula II:

(II)

[structure of formula II with Z1, Z2, Z5, R1, (R3)m, Ar2 substituents]

or a pharmaceutically acceptable derivative thereof, wherein $R_1$ is -halo, —(C$_1$-C$_4$)alkyl, —C(halo)$_3$, —CH(halo)$_2$, or —CH$_2$(halo);

each $R_3$ is independently —(C$_1$-C$_6$)alkyl, —CH$_2$OR$_{13}$, —C(O)OR$_{13}$, or —C(O)N(R$_{13}$)$_2$, or two $R_3$ groups together form a —CH$_2$CH$_2$— bridge joining positions 2 and 6 of the piperidine, 1,2,3,6-tetrahydropyridine or piperazine ring;

$Z_1$ is —H, —OH, or -halo;

$Z_2$ is —H or -halo;

or $Z_1$ and $Z_2$ groups together form =O or =N—OR$_{13}$;

$Z_5$ is —H, —CH$_3$, or —CH$_2$CH$_3$;

Ar$_2$ is

[three structures: phenyl with R9a, R9b; pyridine with R9a; benzothiazole with R10a, R10b]

each $R_8$ is independently —H, —(C$_1$-C$_6$)alkyl, —(C$_2$-C$_6$)alkenyl, —(C$_2$-C$_6$)alkynyl, —(C$_3$-C$_8$)cycloalkyl, or phenyl;

$R_{9a}$ is —(C$_1$-C$_6$)haloalkyl, or —(C$_1$-C$_6$)haloalkoxy;

$R_{9b}$ is —H, -halo, —(C$_1$-C$_6$)alkyl, or —(C$_1$-C$_6$)alkoxy;

$R_{10a}$ and $R_{10b}$ are independently selected from —H, -halo, —(C$_1$-C$_6$)alkyl, and —(C$_1$-C$_6$)alkoxy;

each $R_{13}$ is independently —H, —(C$_1$-C$_6$)alkyl, —(C$_2$-C$_6$)alkenyl, —(C$_2$-C$_6$)alkynyl, —(C$_3$-C$_8$)cycloalkyl, —(C$_5$-C$_8$)cycloalkenyl, -phenyl, -benzyl, —(C$_1$-C$_6$)haloalkyl, —(C$_1$-C$_6$)hydroxyalkyl, —(C$_1$-C$_6$)alkoxy(C$_1$-C$_6$)alkyl, —(C$_1$-C$_6$)alkyl-N(R$_8$)$_2$, or —C(O)N(R$_8$)$_2$;

each halo is independently —F, —Cl, —Br, or —I; and m is the integer 0, 1, or 2.

37) A compound of formula III:

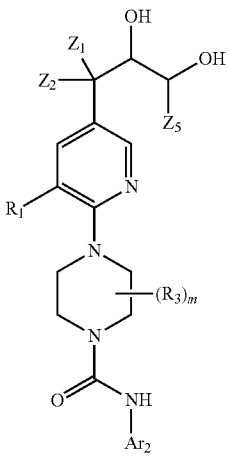

(III)

or a pharmaceutically acceptable derivative thereof, wherein $R_1$ is -halo, —$(C_1-C_4)$alkyl, —C(halo)$_3$, —CH(halo)$_2$, or —CH$_2$(halo);

each $R_3$ is independently —$(C_1-C_6)$alkyl, —CH$_2$OR$_{13}$, —C(O)OR$_{13}$, or —C(O)N(R$_{13}$)$_2$, or two $R_3$ groups together form a —CH$_2$CH$_2$— bridge joining positions 2 and 6 of the piperidine, 1,2,3,6-tetrahydropyridine or piperazine ring;

$Z_1$ is —H, —OH, or -halo;

$Z_2$ is —H or -halo;

or $Z_1$ and $Z_2$ groups together form =O or =N—OR$_{13}$;

$Z_5$ is —H, —CH$_3$, or —CH$_2$CH$_3$;

Ar$_2$ is

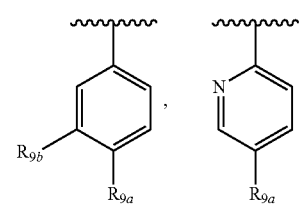, 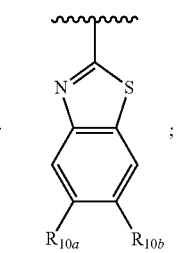 or 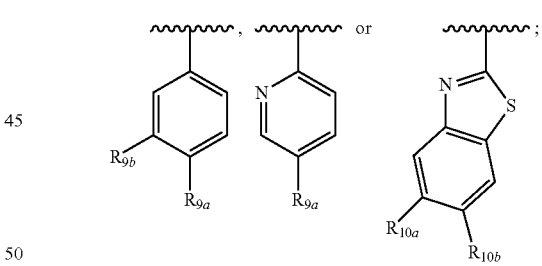;

each $R_8$ is independently —H, —$(C_1-C_6)$alkyl, —$(C_2-C_6)$alkenyl, —$(C_2-C_6)$alkynyl, —$(C_3-C_8)$cycloalkyl, or phenyl;

$R_{9a}$ is —$(C_1-C_6)$haloalkyl, or —$(C_1-C_6)$haloalkoxy;

$R_{9b}$ is —H, -halo, —$(C_1-C_6)$alkyl, or —$(C_1-C_6)$alkoxy;

$R_{10a}$ and $R_{10b}$ are independently selected from —H, -halo, —$(C_1-C_6)$alkyl, and —$(C_1-C_6)$alkoxy;

each $R_{13}$ is independently —H, —$(C_1-C_6)$alkyl, —$(C_2-C_6)$alkenyl, —$(C_2-C_6)$alkynyl, —$(C_3-C_8)$cycloalkyl, —$(C_5-C_8)$cycloalkenyl, -phenyl, -benzyl, —$(C_1-C_6)$haloalkyl, —$(C_1-C_6)$hydroxyalkyl, —$(C_1-C_6)$alkoxy$(C_1-C_6)$alkyl, —$(C_1-C_6)$alkyl-N(R$_8$)$_2$, or —C(O)N(R$_8$)$_2$;

each halo is independently —F, —Cl, —Br, or —I; and m is the integer 0, 1, or 2.

38) A compound of formula IV:

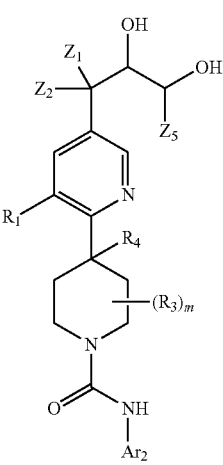

(IV)

or a pharmaceutically acceptable derivative thereof, wherein $R_4$ is -halo;

$R_1$ is -halo, —$(C_1-C_4)$alkyl, —C(halo)$_3$, —CH(halo)$_2$, or —CH$_2$(halo);

each $R_3$ is independently —$(C_1-C_6)$alkyl, —CH$_2$OR$_{13}$, —C(O)OR$_{13}$, or —C(O)N(R$_{13}$)$_2$, or two $R_3$ groups together form a —CH$_2$CH$_2$— bridge joining positions 2 and 6 of the piperidine, 1,2,3,6-tetrahydropyridine or piperazine ring;

$Z_1$ is —H, —OH, or -halo;

$Z_2$ is —H or -halo;

or $Z_1$ and $Z_2$ groups together form =O or =N—OR$_{13}$;

$Z_5$ is —H, —CH$_3$, or —CH$_2$CH$_3$;

Ar$_2$ is each $R_8$ is independently —H, —$(C_1-C_6)$alkyl, —$(C_2-C_6)$alkenyl, —$(C_2-C_6)$alkynyl, —$(C_3-C_8)$cycloalkyl, or phenyl;

$R_{9a}$ is —$(C_1-C_6)$haloalkyl, or —$(C_1-C_6)$haloalkoxy;

$R_{9b}$ is —H, -halo, —$(C_1-C_6)$alkyl, or —$(C_1-C_6)$alkoxy;

$R_{10a}$ and $R_{10b}$ are independently selected from —H, -halo, —$(C_1-C_6)$alkyl, and —$(C_1-C_6)$alkoxy;

each $R_{13}$ is independently —H, —$(C_1-C_6)$alkyl, —$(C_2-C_6)$alkenyl, —$(C_2-C_6)$alkynyl, —$(C_3-C_8)$cycloalkyl, —$(C_5-C_8)$cycloalkenyl, -phenyl, -benzyl, —$(C_1-C_6)$haloalkyl, —$(C_1-C_6)$hydroxyalkyl, —$(C_1-C_6)$alkoxy$(C_1-C_6)$alkyl, —$(C_1-C_6)$alkyl-N(R$_8$)$_2$, or —C(O)N(R$_8$)$_2$;

each halo is independently —F, —Cl, —Br, or —I; and m is the integer 0, 1, or 2.

39) A compound of formula V:

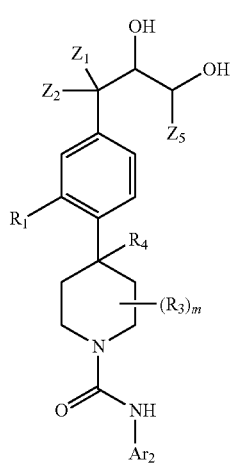

(V)

or a pharmaceutically acceptable derivative thereof, wherein $R_4$ is -halo;

$R_1$ is -halo, —$(C_1$-$C_4)$alkyl, —C(halo)$_3$, —CH(halo)$_2$, or —CH$_2$(halo);

each $R_3$ is independently —$(C_1$-$C_6)$alkyl, —CH$_2$OR$_{13}$, —C(O)OR$_{13}$, or —C(O)N(R$_{13}$)$_2$, or two $R_3$ groups together form a —CH$_2$CH$_2$— bridge joining positions 2 and 6 of the piperidine, 1,2,3,6-tetrahydropyridine or piperazine ring;

$Z_1$ is —H, —OH, or -halo;

$Z_2$ is —H or -halo;

or $Z_1$ and $Z_2$ groups together form =O or =N—OR$_{13}$;

$Z_5$ is —H, —CH$_3$, or —CH$_2$CH$_3$;

$Ar_2$ is

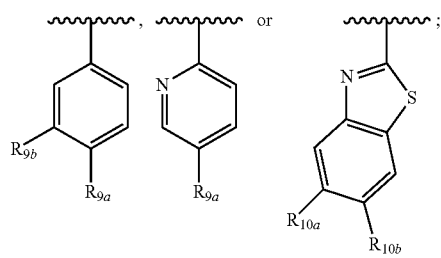

each $R_8$ is independently —H, —$(C_1$-$C_6)$alkyl, —$(C_2$-$C_6)$alkenyl, —$(C_2$-$C_6)$alkynyl, —$(C_3$-$C_8)$cycloalkyl, or phenyl;

$R_{9a}$ is —$(C_1$-$C_6)$haloalkyl, or —$(C_1$-$C_6)$haloalkoxy;

$R_{9b}$ is —H, -halo, —$(C_1$-$C_6)$alkyl, or —$(C_1$-$C_6)$alkoxy;

$R_{10a}$ and $R_{10b}$ are independently selected from —H, -halo, —$(C_1$-$C_6)$alkyl, and —$(C_1$-$C_6)$alkoxy;

each $R_{13}$ is independently —H, —$(C_1$-$C_6)$alkyl, —$(C_2$-$C_6)$alkenyl, —$(C_2$-$C_6)$alkynyl, —$(C_3$-$C_8)$cycloalkyl, —$(C_5$-$C_8)$cycloalkenyl, -phenyl, -benzyl, —$(C_1$-$C_6)$haloalkyl, —$(C_1$-$C_6)$hydroxyalkyl, —$(C_1$-$C_6)$alkoxy$(C_1$-$C_6)$alkyl, —$(C_1$-$C_6)$alkyl-N(R$_8$)$_2$, or —C(O)N(R$_8$)$_2$;

each halo is independently —F, —Cl, —Br, or —I; and m is the integer 0, 1, or 2.

40) A compound of formula VI:

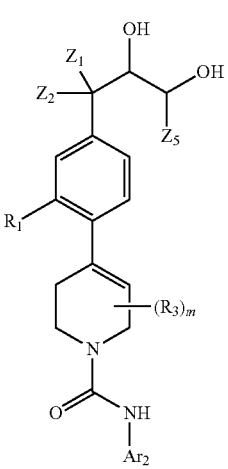

(VI)

or a pharmaceutically acceptable derivative thereof, wherein $R_1$ is -halo, —$(C_1$-$C_4)$alkyl, —C(halo)$_3$, —CH(halo)$_2$, or —CH$_2$(halo);

each $R_3$ is independently —$(C_1$-$C_6)$alkyl, —CH$_2$OR$_{13}$, —C(O)OR$_{13}$, or —C(O)N(R$_{13}$)$_2$, or two $R_3$ groups together form a —CH$_2$CH$_2$— bridge joining positions 2 and 6 of the piperidine, 1,2,3,6-tetrahydropyridine or piperazine ring;

$Z_1$ is —H, —OH, or -halo;

$Z_2$ is —H or -halo;

or $Z_1$ and $Z_2$ groups together form =O or =N—OR$_{13}$;

$Z_5$ is —H, —CH$_3$, or —CH$_2$CH$_3$;

$Ar_2$ is

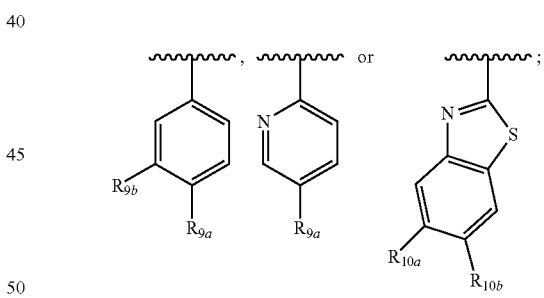

each $R_8$ is independently —H, —$(C_1$-$C_6)$alkyl, —$(C_2$-$C_6)$alkenyl, —$(C_2$-$C_6)$alkynyl, —$(C_3$-$C_8)$cycloalkyl, or phenyl;

$R_{9a}$ is —$(C_1$-$C_6)$haloalkyl, or —$(C_1$-$C_6)$haloalkoxy;

$R_{9b}$ is —H, -halo, —$(C_1$-$C_6)$alkyl, or —$(C_1$-$C_6)$alkoxy;

$R_{10a}$ and $R_{10b}$ are independently selected from —H, -halo, —$(C_1$-$C_6)$alkyl, and —$(C_1$-$C_6)$alkoxy;

each $R_{13}$ is independently —H, —$(C_1$-$C_6)$alkyl, —$(C_2$-$C_6)$alkenyl, —$(C_2$-$C_6)$alkynyl, —$(C_3$-$C_8)$cycloalkyl, —$(C_5$-$C_8)$cycloalkenyl, -phenyl, -benzyl, —$(C_1$-$C_6)$haloalkyl, —$(C_1$-$C_6)$hydroxyalkyl, —$(C_1$-$C_6)$alkoxy$(C_1$-$C_6)$alkyl, —$(C_1$-$C_6)$alkyl-N(R$_8$)$_2$, or —C(O)N(R$_8$)$_2$;

each halo is independently —F, —Cl, —Br, or —I; and m is the integer 0, 1, or 2.

41) A compound of formula VII:

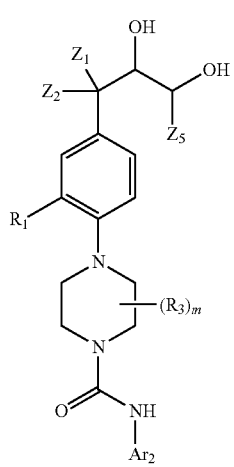

or a pharmaceutically acceptable derivative thereof, wherein $R_1$ is -halo, —$(C_1$-$C_4)$alkyl, —C(halo)$_3$, —CH(halo)$_2$, or —CH$_2$(halo);

each $R_3$ is independently —$(C_1$-$C_6)$alkyl, —CH$_2$OR$_{13}$, —C(O)OR$_{13}$, or —C(O)N(R$_{13}$)$_2$, or two $R_3$ groups together form a —CH$_2$CH$_2$— bridge joining positions 2 and 6 of the piperidine, 1,2,3,6-tetrahydropyridine or piperazine ring;

$Z_1$ is —H, —OH, or -halo;

$Z_2$ is —H or -halo;

or $Z_1$ and $Z_2$ groups together form =O or =N—OR$_{13}$;

$Z_5$ is —H, —CH$_3$, or —CH$_2$CH$_3$;

Ar$_2$ is

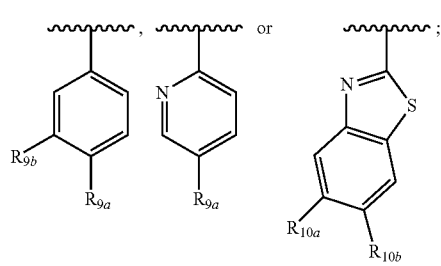

each $R_8$ is independently —H, —$(C_1$-$C_6)$alkyl, —$(C_2$-$C_6)$alkenyl, —$(C_2$-$C_6)$alkynyl, —$(C_3$-$C_8)$cycloalkyl, or phenyl;

$R_{9a}$ is —$(C_1$-$C_6)$haloalkyl, or —$(C_1$-$C_6)$haloalkoxy;

$R_{9b}$ is —H, -halo, —$(C_1$-$C_6)$alkyl, or —$(C_1$-$C_6)$alkoxy;

$R_{10a}$ and $R_{10b}$ are independently selected from —H, -halo, —$(C_1$-$C_6)$alkyl, and —$(C_1$-$C_6)$alkoxy;

each $R_{13}$ is independently —H, —$(C_1$-$C_6)$alkyl, —$(C_2$-$C_6)$alkenyl, —$(C_2$-$C_6)$alkynyl, —$(C_3$-$C_8)$cycloalkyl, —$(C_5$-$C_8)$cycloalkenyl, -phenyl, -benzyl, —$(C_1$-$C_6)$haloalkyl, —$(C_1$-$C_6)$hydroxyalkyl, —$(C_1$-$C_6)$alkoxy$(C_1$-$C_6)$alkyl, —$(C_1$-$C_6)$alkyl-N(R$_8$)$_2$, or —C(O)N(R$_8$)$_2$;

each halo is independently —F, —Cl, —Br, or —I; and m is the integer 0, 1, or 2.

42) A compound of formula VIII:

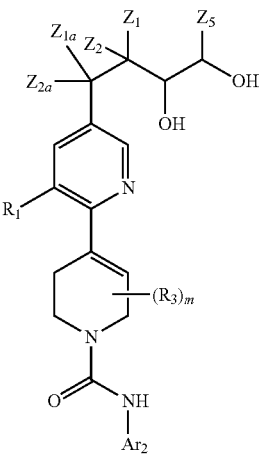

or a pharmaceutically acceptable derivative thereof, wherein $R_1$ is -halo, —$(C_1$-$C_4)$alkyl, —C(halo)$_3$, —CH(halo)$_2$, or —CH$_2$(halo);

each $R_3$ is independently —$(C_1$-$C_6)$alkyl, —CH$_2$OR$_{13}$, —C(O)OR$_{13}$, or —C(O)N(R$_{13}$)$_2$, or two $R_3$ groups together form a —CH$_2$CH$_2$— bridge joining positions 2 and 6 of the piperidine, 1,2,3,6-tetrahydropyridine or piperazine ring;

$Z_1$ is —H, —OH, or -halo;

$Z_2$, $Z_{1a}$ and $Z_{2a}$ are each independently —H or -halo;

or $Z_1$ and $Z_2$ groups together form =O or =N—OR$_{13}$;

$Z_5$ is —H, —CH$_3$, or —CH$_2$CH$_3$;

Ar$_2$ is

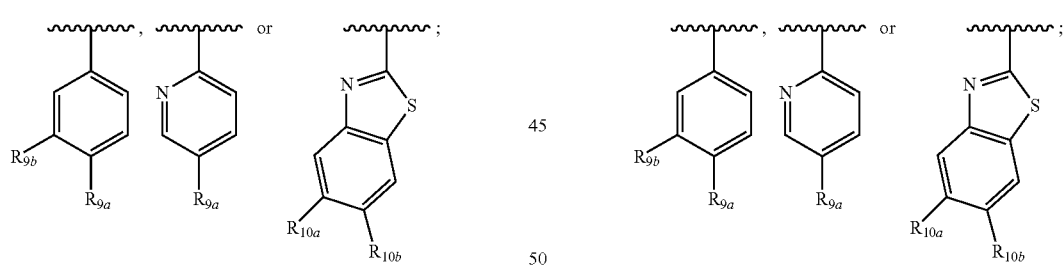

each $R_8$ is independently —H, —$(C_1$-$C_6)$alkyl, —$(C_2$-$C_6)$alkenyl, —$(C_2$-$C_6)$alkynyl, —$(C_3$-$C_8)$cycloalkyl, or phenyl;

$R_{9a}$ is —$(C_1$-$C_6)$haloalkyl, or —$(C_1$-$C_6)$haloalkoxy;

$R_{9b}$ is —H, -halo, —$(C_1$-$C_6)$alkyl, or —$(C_1$-$C_6)$alkoxy;

$R_{10a}$ and $R_{10b}$ are independently selected from —H, -halo, —$(C_1$-$C_6)$alkyl, and —$(C_1$-$C_6)$alkoxy;

each $R_{13}$ is independently —H, —$(C_1$-$C_6)$alkyl, —$(C_2$-$C_6)$alkenyl, —$(C_2$-$C_6)$alkynyl, —$(C_3$-$C_8)$cycloalkyl, —$(C_5$-$C_8)$cycloalkenyl, -phenyl, -benzyl, —$(C_1$-$C_6)$haloalkyl, —$(C_1$-$C_6)$hydroxyalkyl, —$(C_1$-$C_6)$alkoxy$(C_1$-$C_6)$alkyl, —$(C_1$-$C_6)$alkyl-N(R$_8$)$_2$, or —C(O)N(R$_8$)$_2$;

each halo is independently —F, —Cl, —Br, or —I; and m is the integer 0, 1, or 2.

43) A compound of formula IX:

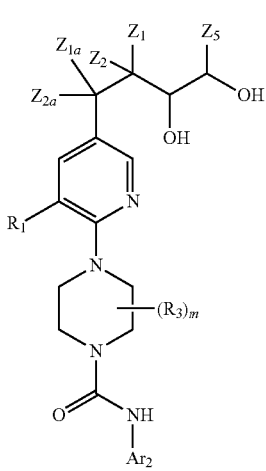

(IX)

or a pharmaceutically acceptable derivative thereof, wherein $R_1$ is -halo, —$(C_1\text{-}C_4)$alkyl, —C(halo)$_3$, —CH(halo)$_2$, or —CH$_2$(halo);

each $R_3$ is independently —$(C_1\text{-}C_6)$alkyl, —CH$_2$OR$_{13}$, —C(O)OR$_{13}$, or —C(O)N(R$_{13}$)$_2$, or two $R_3$ groups together form a —CH$_2$CH$_2$— bridge joining positions 2 and 6 of the piperidine, 1,2,3,6-tetrahydropyridine or piperazine ring;

$Z_1$ is —H, —OH, or -halo;

$Z_2$, $Z_{1a}$ and $Z_{2a}$ are each independently —H or -halo;

or $Z_1$ and $Z_2$ groups together form =O or =N—OR$_{13}$;

$Z_5$ is —H, —CH$_3$, or —CH$_2$CH$_3$;

Ar$_2$ is

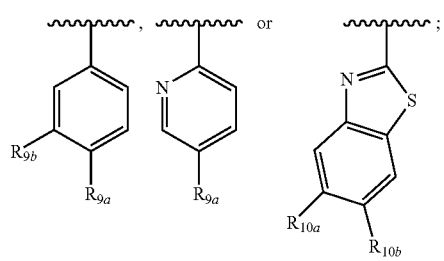

each $R_8$ is independently —H, —$(C_2\text{-}C_6)$alkenyl, —$(C_2\text{-}C_6)$alkynyl, —$(C_3\text{-}C_8)$cycloalkyl, or phenyl;

$R_{9a}$ is —$(C_1\text{-}C_6)$haloalkyl, or —$(C_1\text{-}C_6)$haloalkoxy;

$R_{9b}$ is —H, -halo, —$(C_1\text{-}C_6)$alkyl, or —$(C_1\text{-}C_6)$alkoxy;

$R_{10a}$ and $R_{10b}$ are independently selected from —H, -halo, —$(C_1\text{-}C_6)$alkyl, and —$(C_1\text{-}C_6)$alkoxy;

each $R_{13}$ is independently —H, —$(C_2\text{-}C_6)$alkenyl, —$(C_2\text{-}C_6)$alkynyl, —$(C_3\text{-}C_8)$cycloalkyl, —$(C_5\text{-}C_8)$cycloalkenyl, -phenyl, -benzyl, —$(C_1\text{-}C_6)$haloalkyl, —$(C_1\text{-}C_6)$hydroxyalkyl, —$(C_1\text{-}C_6)$alkoxy$(C_1\text{-}C_6)$alkyl, —$(C_1\text{-}C_6)$alkyl-N(R$_8$)$_2$, or —C(O)N(R$_8$)$_2$;

each halo is independently —F, —Cl, —Br, or —I; and m is the integer 0, 1, or 2.

44) A compound of formula X:

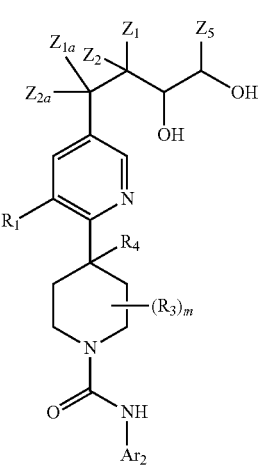

(X)

or a pharmaceutically acceptable derivative thereof, wherein $R_4$ is -halo;

$R_1$ is -halo, —$(C_1\text{-}C_4)$alkyl, —C(halo)$_3$, —CH(halo)$_2$, or —CH$_2$(halo);

each $R_3$ is independently —$(C_1\text{-}C_6)$alkyl, —CH$_2$OR$_{13}$, —C(O)OR$_{13}$, or —C(O)N(R$_{13}$)$_2$, or two $R_3$ groups together form a —CH$_2$CH$_2$— bridge joining positions 2 and 6 of the piperidine, 1,2,3,6-tetrahydropyridine or piperazine ring;

$Z_1$ is —H, —OH, or -halo;

$Z_2$, $Z_{1a}$ and $Z_{2a}$ are each independently —H or -halo;

or $Z_1$ and $Z_2$ groups together form =O or =N—OR$_{13}$;

$Z_5$ is —H, —CH$_3$, or —CH$_2$CH$_3$;

Ar$_2$ is

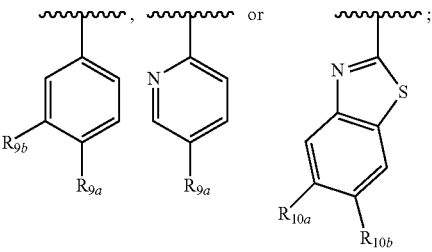

each $R_8$ is independently —H, —$(C_1\text{-}C_6)$alkyl, —$(C_2\text{-}C_6)$alkenyl, —$(C_2\text{-}C_6)$alkynyl, —$(C_3\text{-}C_8)$cycloalkyl, or phenyl;

$R_{9a}$ is —$(C_1\text{-}C_6)$haloalkyl, or —$(C_1\text{-}C_6)$haloalkoxy;

$R_{9b}$ is —H, -halo, —$(C_1\text{-}C_6)$alkyl, or —$(C_1\text{-}C_6)$alkoxy;

$R_{10a}$ and $R_{10b}$ are independently selected from —H, -halo, —$(C_1\text{-}C_6)$alkyl, and —$(C_1\text{-}C_6)$alkoxy;

each $R_{13}$ is independently —H, —$(C_1\text{-}C_6)$alkyl, —$(C_2\text{-}C_6)$alkenyl, —$(C_2\text{-}C_6)$alkynyl, —$(C_3\text{-}C_8)$cycloalkyl, —$(C_5\text{-}C_8)$cycloalkenyl, -phenyl, -benzyl, —$(C_1\text{-}C_6)$haloalkyl, —$(C_1\text{-}C_6)$hydroxyalkyl, —$(C_1\text{-}C_6)$alkoxy$(C_1\text{-}C_6)$alkyl, —$(C_1\text{-}C_6)$alkyl-N(R$_8$)$_2$, or —C(O)N(R$_8$)$_2$;

each halo is independently —F, —Cl, —Br, or —I; and m is the integer 0, 1, or 2.

45) The compound according to any one of the above 1), 1') and 2) to 44) or a pharmaceutically acceptable derivative thereof wherein the pharmaceutically acceptable derivative is a pharmaceutically acceptable salt.

46) A composition comprising a compound of any one of the above 1), 1') and 2) to 45) or a pharmaceutically acceptable derivative thereof and a pharmaceutically acceptable carrier or excipient.

47) A composition for treating or preventing pain, UI, an ulcer, IBD, or IBS (each being a "Condition") in an animal comprising a compound of any one of the above 1), 1') and 2) to 45) or a pharmaceutically acceptable derivative thereof and a pharmaceutically acceptable carrier or excipient.

48) A composition for inhibiting TRPV1 function comprising a compound of any one of the above 1), 1') and 2) to 45) or a pharmaceutically acceptable derivative thereof and a pharmaceutically acceptable carrier or excipient.

49) A method for treating or preventing pain, UI, an ulcer, IBD, or IBS in an animal, comprising administering to an animal in need thereof, an effective amount of a compound of any one of the above 1), 1') and 2) to 45) or a pharmaceutically acceptable derivative thereof.

50) A method of inhibiting TRPV1 function in a cell comprising contacting a cell capable of expressing TRPV1 with an effective amount of a compound of any one of the above 1), 1') and 2) to 45) or a pharmaceutically acceptable derivative thereof.

51) A compound according to any one of the above 1), 1') and 2) to 45) or a pharmaceutically acceptable derivative thereof for use in the treatment or prevention of pain, UI, an ulcer, IBD, or IBS in an animal.

52) A compound according to any one of the above 1), 1') and 2) to 45) or a pharmaceutically acceptable derivative thereof for use in inhibiting TRPV1 function.

The invention further relates to use of a compound of Formula I or a pharmaceutically acceptable derivative thereof in the manufacture of a medicament for treating and/or preventing a Condition.

The invention still further relates to a method for preparing a composition comprising the step of admixing a compound of Formula I or a pharmaceutically acceptable derivative thereof, and a pharmaceutically acceptable carrier or excipient.

The invention still further relates to a kit comprising a container containing an effective amount of a compound of Formula I or a pharmaceutically acceptable derivative thereof.

Compounds of Formula I or a pharmaceutically acceptable derivative thereof are highly soluble in aqueous solutions at either pH 6.8 or pH 1.2, are exceptionally potent at TRPV1 receptors, have excellent bioavailability, have a high therapeutic index, and are believed to be highly efficacious in animals for the treatment of pain.

The invention can be understood more fully by reference to the following detailed description and illustrative examples, which are intended to exemplify non-limiting embodiments of the invention.

BRIEF DESCRIPTION OF DRAWINGS

FIG. 1. 96-well plate with different agonist solutions (Agonist Plate). Seven different sulfuric acid solutions, or agonist solutions, with different sulfuric acid ($H_2SO_4$) concentrations (of from 15.0 mM to 18 mM as indicated) were used for the pH assay as indicated. For the wells in row A, measuring buffer alone was used. The final concentration of sulfuric acid in the wells for each row, after a 1:4 dilution of the agonist solution, is also indicated in each row in parenthesis.

FIG. 3. (A) A 96-well plate with two different sulfuric acid concentrations. Wells in columns 1 to 6 had one final sulfuric acid concentration; wells in columns 7 to 12 had a different final sulfuric acid concentration. The final sulfuric acid concentration was reached by 1:4 dilution of two different agonist solutions with sulfuric acid concentrations of X mM and (X+0.5) mM, respectively. In the experiment described in Section 2 of Protocol 2, X was determined to be 16 mM. (B) A 96-well plate with different test compound, or antagonist, concentrations indicated in nM. Only one kind of test compound was applied per 96-well plate. Since two different sulfuric acid concentrations were used (columns 1-6 vs. columns 7-12), seven wells were tested for each combination of test compound concentration and agonist solution (e.g., wells A1, B1, C1, E1, F1, G1, and H1 were tested for test compound concentration 0.977 nM and agonist solution with sulfuric acid solution X mM). The wells in row D did not include an antagonist in order to measure the maximal $Ca^{2+}$ response.

BEST MODE FOR CARRYING OUT THE INVENTION

Figure 2:
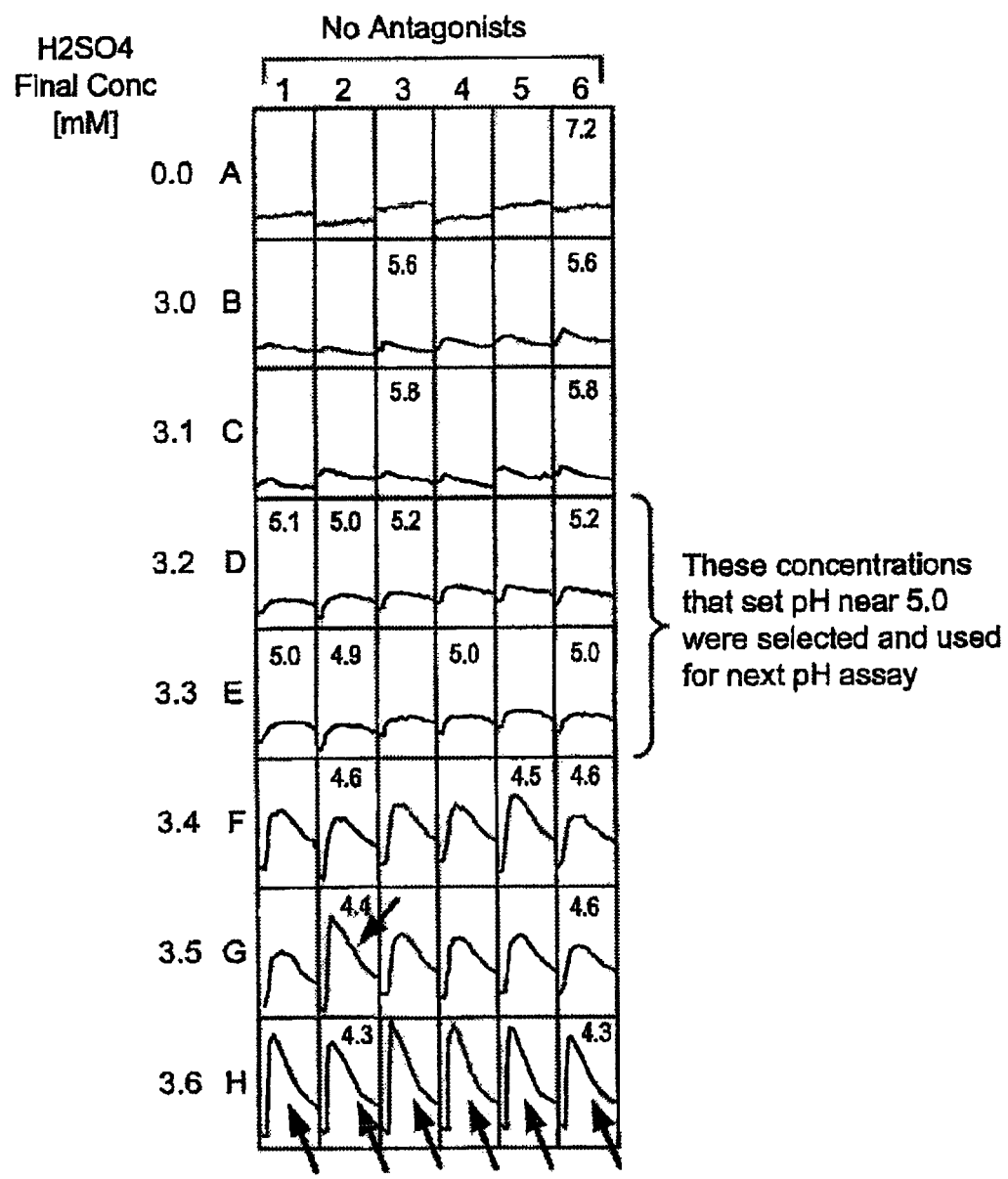
FIG. 2. pH dependent $Ca^{2+}$ responses in TRPV1/CHO cells. $Ca^{2+}$ influx into TRPV1/CHO cells as measured by Fura-2 AM fluorescence is indicated by the graph within each rectangular field. The graph presents the fluorescence intensity over time starting from the addition of agonist solution. Each rectangular field presents one experiment performed in one well of a 96-well plate. Each row presents six experiments performed at the same final sulfuric acid concentration; the final sulfuric acid concentration is indicated at the left. Actual pH values were measured after the experiment and are indicated above the graph. No antagonists were added to the cell culture. Final sulfuric acid concentrations of 3.2 and 3.3 mM produced an appropriate $Ca^{2+}$ response and were selected for subsequent assays. These final sulfuric acid concentrations can be obtained by 1:4 dilutions of agonist solution with sulfuric acid concentrations of 16.0 mM or 16.5 mM, respectively (see FIG. 1).

The invention encompasses compounds of Formula I:

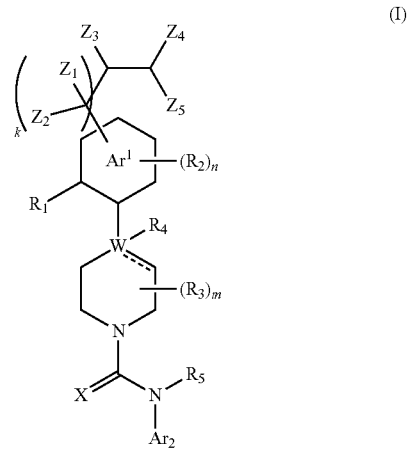

(I)

or a pharmaceutically acceptable derivative thereof, wherein the dashed line, $Ar^1$, $Ar^2$, W, X, $Z_1$, $Z_2$, $Z_3$, $Z_4$, $Z_5$, $R_1$, $R_2$, $R_3$, $R_4$, $R_5$, k, m, and n are as defined above for compounds of Formula I.

Certain embodiments of Formula I are presented below.

In one embodiment, a compound of Formula I is a pharmaceutically acceptable derivative of a compound of Formula I.

In another embodiment, a compound of Formula I is a pharmaceutically acceptable salt of a compound of Formula I.

In another embodiment, $Ar_1$ is a pyridyl group.
In another embodiment, $Ar_1$ is a pyrimidinyl group.
In another embodiment, $Ar_1$ is a pyrazinyl group.
In another embodiment, $Ar_1$ is a pyridazinyl group.
In another embodiment, $Ar_1$ is a phenyl group.
In another embodiment, W is N and $R_4$ is absent.
In another embodiment, W is C, the dashed line is present as a bond to provide one bond of a double bond and $R_4$ is absent.
In another embodiment, W is C, the dashed line denotes the absence of a bond and $R_4$ is present.
In another embodiment, $R_4$ is —OH.
In another embodiment, $R_4$ is —$OCF_3$.
In another embodiment, $R_4$ is -halo.
In another embodiment, $R_4$ is —F.
In another embodiment, $R_4$ is —Cl.
In another embodiment, $R_4$ is —$(C_1$-$C_6)$alkyl.
In another embodiment, $R_4$ is —$CH_3$.
In another embodiment, $R_4$ is —$CH_2OH$.
In another embodiment, $R_4$ is —$CH_2Cl$.
In another embodiment, $R_4$ is —$CH_2Br$.
In another embodiment, $R_4$ is —$CH_2I$.
In another embodiment, $R_4$ is —$CH_2F$.
In another embodiment, $R_4$ is —$CH(halo)_2$.
In another embodiment, $R_4$ is —$CF_3$.
In another embodiment, $R_4$ is —$NO_2$.
In another embodiment, $R_4$ is —$OR_7$.
In another embodiment, $R_4$ is —$SR_7$.
In another embodiment, $R_4$ is —$C(O)R_7$.
In another embodiment, $R_4$ is —$C(O)OR_7$.
In another embodiment, $R_4$ is —$C(O)OH$.
In another embodiment, $R_4$ is —$C(O)H$.
In another embodiment, $R_4$ is —$OC(O)R_7$.
In another embodiment, $R_4$ is —$S(O)_2R_7$.
In another embodiment, $R_4$ is —$OC(O)NHR_7$.
In another embodiment, $R_4$ is —$NHC(O)R_8$.
In another embodiment, $R_4$ is —$C(O)N(R_8)_2$.
In another embodiment, X is O.
In another embodiment, X is S.
In another embodiment, X is N—CN.
In another embodiment, X is N—$OR_7$.
In another embodiment, X is N—OH.
In another embodiment, $Ar_2$ is

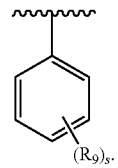

In another embodiment, $Ar_2$ is

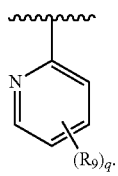

In another embodiment, $Ar_2$ is

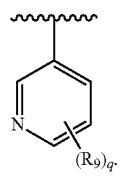

In another embodiment, $Ar_2$ is

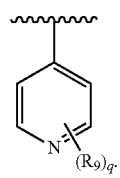

In another embodiment, $Ar_2$ is

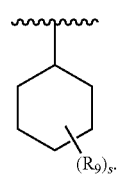

In another embodiment, $Ar_2$ is

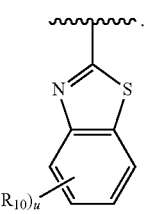

In another embodiment, $Ar_2$ is

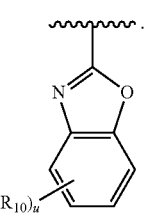

In another embodiment, $Ar_2$ is

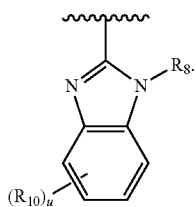

In another embodiment, $Ar_2$ is

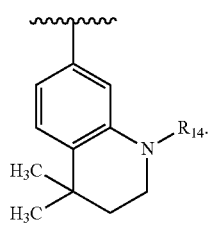

In another embodiment, $Ar_2$ is

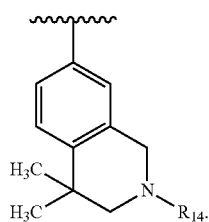

In another embodiment, $Ar_2$ is

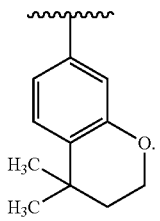

In another embodiment, n is 2.
In another embodiment, n is 1.
In another embodiment, n is 0.
In another embodiment, m is 2.
In another embodiment, m is 1.
In another embodiment, m is 0.
In another embodiment, m is 1 and $R_3$ is —$(C_1-C_6)$alkyl.
In another embodiment, m is 1 and $R_3$ is —$CH_3$.

In another embodiment,

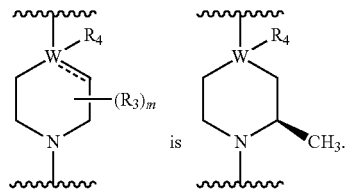

In another embodiment,

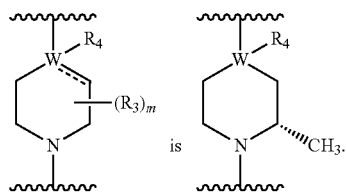

In another embodiment,

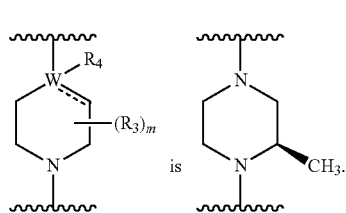

In another embodiment,

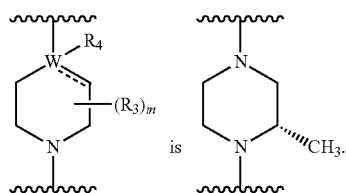

In another embodiment, m is 2 and two $R_3$ groups together form =O.

In another embodiment, two $R_3$ groups together form a $(C_2-C_6)$bridge, which is unsubstituted or substituted with 1, 2 or 3 independently selected $R_{10}$ groups, and which bridge optionally contains —HC=CH— within the $(C_2-C_6)$bridge.

In another embodiment, two $R_3$ groups together form a $(C_2-C_6)$bridge, which is unsubstituted or substituted with an $R_{10}$ group, and which bridge optionally contains —HC=CH— within the $(C_2-C_6)$bridge.

In another embodiment, two $R_3$ groups together form a $(C_2-C_3)$bridge, which is unsubstituted or substituted with an $R_{10}$ group, and which bridge optionally contains —HC=CH— within the $(C_2-C_3)$bridge.

In another embodiment, two $R_3$ groups together form a $(C_2-C_3)$bridge, which is unsubstituted and which bridge optionally contains —HC=CH— within the $(C_2-C_3)$bridge.

In another embodiment, two $R_3$ groups together form a $(C_2)$bridge, a —HC=CH— bridge, or a $(C_3)$bridge each of which is unsubstituted.

In another embodiment, two $R_3$ groups together form a $(C_2-C_6)$bridge, which is unsubstituted or substituted with 1, 2 or 3 independently selected $R_{10}$ groups, which bridge optionally contains —HC═CH— within the $(C_2$-$C_6)$bridge, and which bridge joins positions 2 and 6 of the piperidine, 1,2,3,6-tetrahydropyridine or piperazine ring.

In another embodiment, two $R_3$ groups together form a $(C_2$-$C_6)$bridge, which is unsubstituted or substituted with an $R_{10}$ group, which bridge optionally contains —HC═CH— within the $(C_2$-$C_6)$bridge, and which bridge joins positions 2 and 6 of the piperidine, 1,2,3,6-tetrahydropyridine or piperazine ring.

In another embodiment, two $R_3$ groups together form a $(C_2$-$C_3)$bridge, which is unsubstituted or substituted with an $R_{10}$ group, which bridge optionally contains —HC═CH— within the $(C_2$-$C_3)$bridge, and which bridge joins positions 2 and 6 of the piperidine, 1,2,3,6-tetrahydropyridine or piperazine ring.

In another embodiment, two $R_3$ groups together form a $(C_2$-$C_3)$bridge, which is unsubstituted, which bridge optionally contains —HC═CH— within the $(C_2$-$C_3)$bridge, and which bridge joins positions 2 and 6 of the piperidine, 1,2,3,6-tetrahydropyridine or piperazine ring.

In another embodiment, two $R_3$ groups together form a —CH$_2$CH$_2$— bridge, a —HC═CH-bridge, or a —CH$_2$CH$_2$CH$_2$-bridge, and which bridge joins positions 2 and 6 of the piperidine, 1,2,3,6-tetrahydropyridine or piperazine ring.

In another embodiment, two $R_3$ groups together form

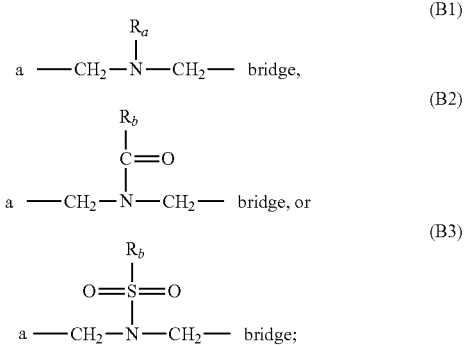

wherein $R_a$ is —H, —$(C_1$-$C_6)$alkyl, —$(C_3$-$C_8)$cycloalkyl, —CH$_2$—C(O)—R$_c$, —(CH$_2$)—C(O)—OR$_c$, —(CH$_2$)—C(O)—N(R$_c$)$_2$, —(CH$_2$)$_2$—O—R$_c$, —(CH$_2$)$_2$—S(O)$_2$N(R$_c$)$_2$, or —(CH$_2$)$_2$—N(R$_c$)S(O)$_2$—R$_c$;

$R_b$ is:
(a) —H, —$(C_1$-$C_6)$alkyl, —$(C_3$-$C_8)$cycloalkyl, -(3- to 7-membered)heterocycle, —N(R$_c$)$_2$, —N(R$_c$)—(C$_3$-C$_8$)cycloalkyl, or —N(R$_c$)-(3- to 7-membered)heterocycle; or
(b) -phenyl, -(5- or 6-membered)heteroaryl, —N(R$_c$)-phenyl, or —N(R$_c$)-(5- to 10-membered)heteroaryl, each of which is unsubstituted or substituted with 1, 2 or 3 independently selected $R_{13}$ groups; and each $R_c$ is independently —H or —$(C_1$-$C_4)$alkyl;

In another embodiment, the B1, B2, or B3 bridge joins positions 2 and 6 of the piperidine, 1,2,3,6-tetrahydropyridine or piperazine ring.

In another embodiment, s or q is 0.
In another embodiment, s or q is 1.
In another embodiment, s or q is 2.
In another embodiment, $R_1$ is —H.
In another embodiment, $R_1$ is -halo.
In another embodiment, $R_1$ is —Cl.
In another embodiment, $R_1$ is —F.
In another embodiment, $R_1$ is —CH$_3$.

In another embodiment, $R_1$ is —NO$_2$.
In another embodiment, $R_1$ is —CN.
In another embodiment, $R_1$ is —OH.
In another embodiment, $R_1$ is —OCH$_3$.
In another embodiment, $R_1$ is —NH$_2$.
In another embodiment, $R_1$ is —C(halo)$_3$.
In another embodiment, $R_1$ is —CF$_3$.
In another embodiment, $R_1$ is —CH(halo)$_2$.
In another embodiment, $R_1$ is —CH$_2$(halo).
In another embodiment, $Ar_1$ is a pyridyl group, $R_1$ is -halo or —$(C_1$-$C_4)$alkyl, and n is 0.
In another embodiment, $Ar_1$ is a pyrazinyl group, $R_1$ is -halo or —$(C_1$-$C_4)$alkyl, and n is 0.
In another embodiment, $Ar_1$ is a pyrimidinyl group, $R_1$ is -halo or —$(C_1$-$C_4)$alkyl, and n is 0.
In another embodiment, $Ar_1$ is a pyridazinyl group, $R_1$ is -halo or —$(C_1$-$C_4)$alkyl, and n is 0.
In another embodiment, $Ar_1$ is a phenyl group, $R_1$ is -halo or —$(C_1$-$C_4)$alkyl, and n is 0.
In another embodiment, $Z_1$ and $Z_2$ are each independently —H, —$(C_1$-$C_6)$alkyl, —$(C_2$-$C_6)$alkenyl, —OR$_{12}$, —N(R$_{12})_2$, or -halo, or $Z_1$ and $Z_2$ groups together form ═O or ═N—OR$_{13}$;

In another embodiment, $Z_1$ and $Z_2$ are each independently —H, —$(C_1$-$C_6)$alkyl, —OR$_{12}$, —N(R$_{12})_2$, or -halo, or $Z_1$ and $Z_2$ groups together form ═O.

In another embodiment, $Z_1$ and $Z_2$ are each independently —H, —OR$_{12}$, —N(R$_{12})_2$, or -halo, or $Z_1$ and $Z_2$ groups together form ═O.

In another embodiment, $Z_1$ and $Z_2$ are each independently —H, —OR$_{12}$, —N(R$_{12})_2$, or -halo.

In another embodiment, $Z_1$ and $Z_2$ are each independently —H—OR$_{12}$, —N(R$_{12})_2$, or -halo.

In another embodiment, $Z_1$ and $Z_2$ are each —H.
In another embodiment, $Z_1$ and $Z_2$ are each -halo.
In another embodiment, $Z_1$ is —OR$_{12}$ and $Z_2$ is —H.
In another embodiment, $Z_1$ is —N(R$_{12})_2$ and $Z_2$ is —H.
In another embodiment, $Z_1$ is —halo and $Z_2$ is —H.
In another embodiment, $Z_1$ and $Z_2$ groups together form ═O.

In another embodiment, $Z_1$ is —OR$_{12}$, $Z_2$, $Z_{1a}$ and $Z_{2a}$ are —H

In another embodiment, $Z_3$ and $Z_4$ are each independently —OR$_{12}$.
In another embodiment, $Z_3$ and $Z_4$ are each independently —N(R$_{12})_2$.
In another embodiment, $Z_3$ is —OR$_{12}$ and $Z_4$ is —N(R$_{12})_2$.
In another embodiment, $Z_3$ is —N(R$_{12})_2$ and $Z_4$ is —OR$_{12}$.
In another embodiment, $Z_3$ is —OH and $Z_4$ is —N(R$_{12})_2$.
In another embodiment, $Z_3$ is —N(R$_{12})_2$ and $Z_4$ is —OH.
In another embodiment, $Z_3$ is —OR$_{12}$ and $Z_4$ is N(R$_{12})_2$.
In another embodiment, $Z_3$ is —NH$_2$ and $Z_4$ is —OR$_{12}$.
In another embodiment, $Z_3$ is —OR$_{12}$ and $Z_4$ is —NHCH$_3$.
In another embodiment, $Z_3$ is —NHCH$_3$ and $Z_4$ is —OR$_{12}$.
In another embodiment, $Z_3$ is —OCH$_3$ and $Z_4$ is —N(R$_{12})_2$.
In another embodiment, $Z_3$ is —N(R$_{12})_2$ and $Z_4$ is —OCH$_3$.
In another embodiment, $Z_3$ and $Z_4$ are each —OH.
In another embodiment, $Z_3$ and $Z_4$ are each —NH$_2$.
In another embodiment, $Z_5$ is —H, —$(C_1$-$C_6)$alkyl or —$(C_2$-$C_6)$alkenyl.
In another embodiment, $Z_5$ is —H or —$(C_1$-$C_6)$alkyl.
In another embodiment, $Z_5$ is —H or —$(C_1$-$C_4)$alkyl.
In another embodiment, $Z_5$ is —H, —CH$_3$, or —CH$_2$CH$_3$.
In another embodiment, $Z_5$ is —H or —CH$_3$.
In another embodiment, $Z_5$ is —H.
In another embodiment, $Z_5$ is —CH$_3$.

In another embodiment,
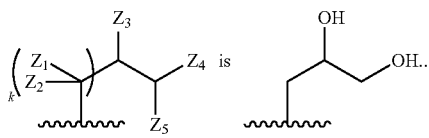
In another embodiment,
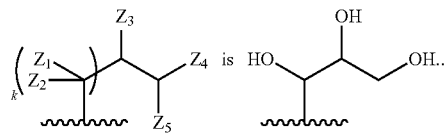
In another embodiment,
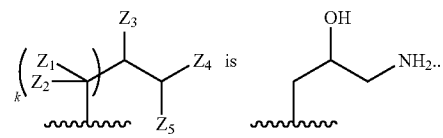
In another embodiment,
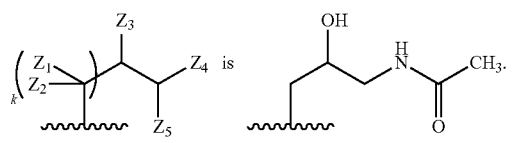
In another embodiment,
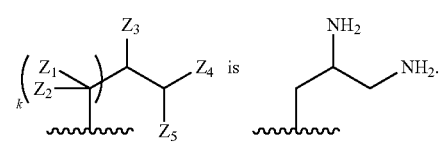
In another embodiment,
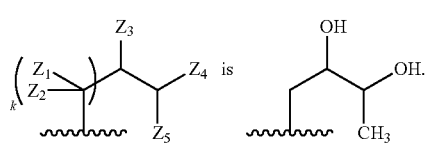
In another embodiment,
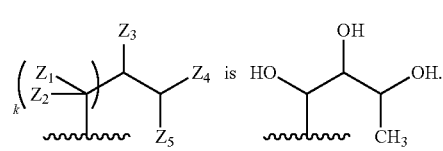
In another embodiment,
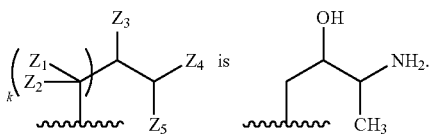
In another embodiment,
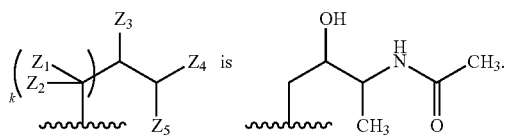
In another embodiment,
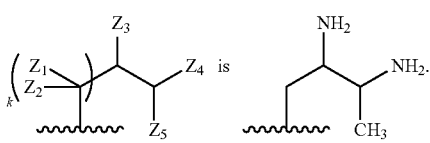
In another embodiment,
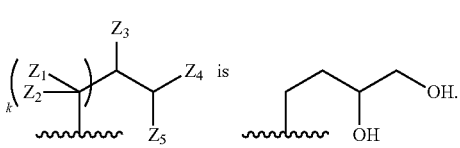
In another embodiment,
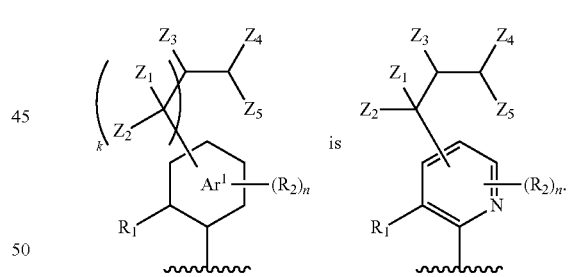
In another embodiment,
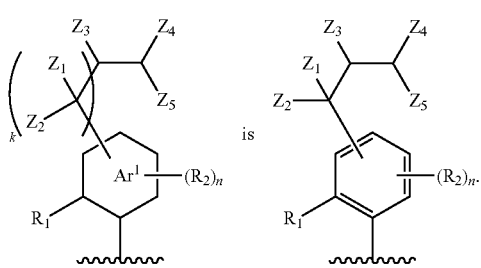

In another embodiment,
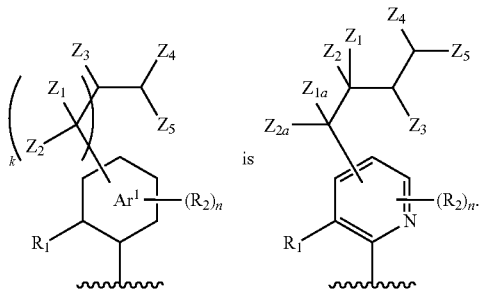 is 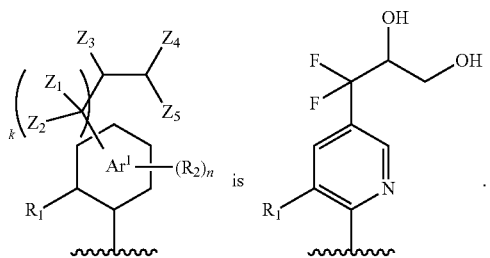
In another embodiment,
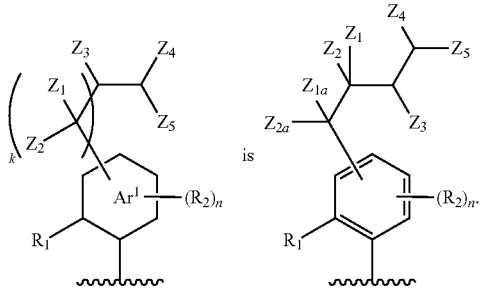 is 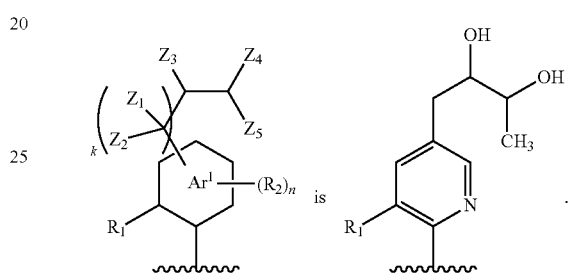
In another embodiment,
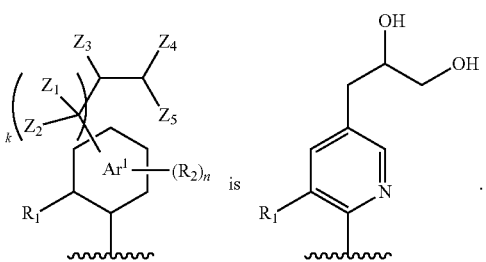 is 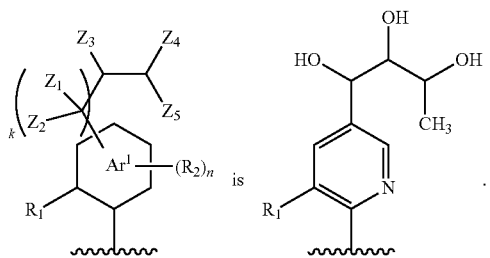
In another embodiment,
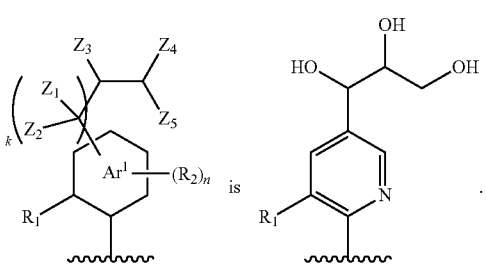 is 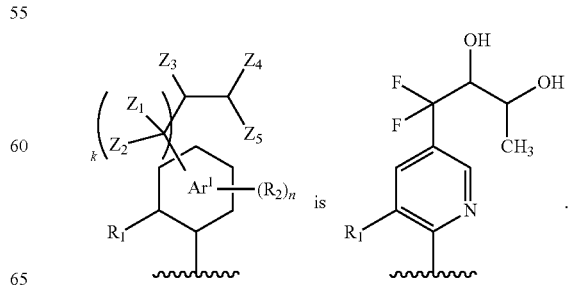
In another embodiment,
In another embodiment,
In another embodiment,
In another embodiment, In another embodiment,

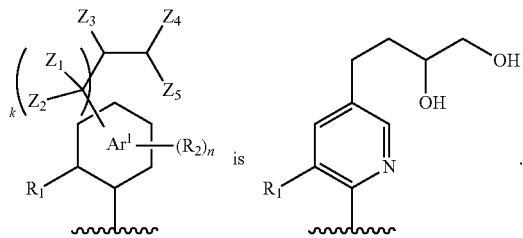 is 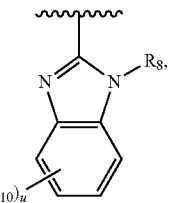.

In another embodiment,

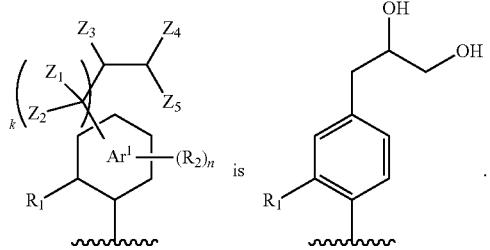 is 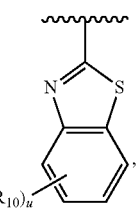.

In another embodiment, each $R_{12}$ is independently —H, —($C_1$-$C_6$)alkyl, —C(O)$R_{15}$, —C(O)O$R_{13}$, or —C(O)N($R_{13}$)$_2$.

In another embodiment, each $R_{12}$ is —H.
In another embodiment, each $R_{12}$ is —($C_1$-$C_6$)alkyl.
In another embodiment, each $R_{12}$ is -acetyl.
In another embodiment, each $R_{12}$ is —C(O)OH.
In another embodiment, each $R_{12}$ is —C(O)NH$_2$.
In another embodiment, $Ar_2$ is

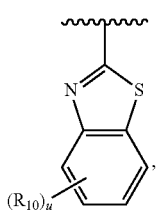

u is 1 and $R_{10}$ is -halo.
In another embodiment, $Ar_2$ is

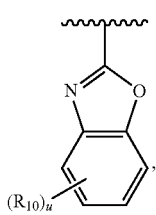

u is 1 and $R_{10}$ is -halo.

In another embodiment, $Ar_2$ is

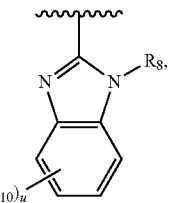

u is 1 and $R_{10}$ is -halo.
In another embodiment, $Ar_2$ is

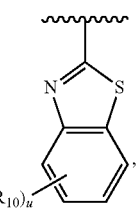

u is 1 and $R_{10}$ is —($C_1$-$C_4$)alkyl.
In another embodiment, $Ar_2$ is

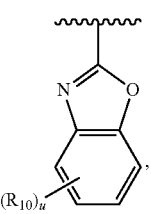

u is 1 and $R_{10}$ is —($C_1$-$C_4$)alkyl.
In another embodiment, $Ar_2$ is

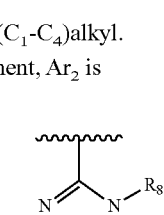

u is 1 and $R_{10}$ is —($C_1$-$C_4$)alkyl.
In another embodiment, $Ar_2$ is

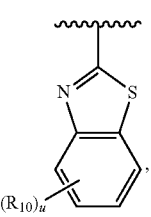

u is 2 and $R_{10}$ are each independently —($C_1$-$C_4$)alkyl.

In another embodiment, $Ar_2$ is

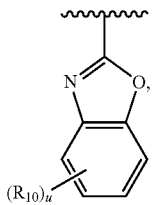

u is 2 and $R_{10}$ are each independently —$(C_1-C_4)$alkyl.
In another embodiment, $Ar_2$ is

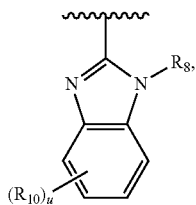

u is 2 and $R_{10}$ are each independently —$(C_1-C_4)$alkyl.
In another embodiment, $Ar_2$ is

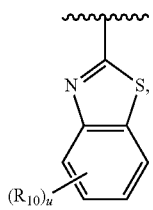

and u is 0.
In another embodiment, $Ar_2$ is

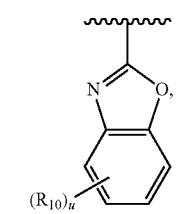

and u is 0.
In another embodiment, $Ar_2$ is

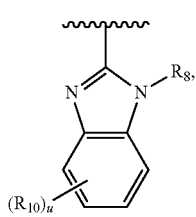

and u is 0.

In another embodiment, $Ar_2$ is

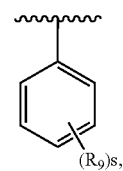

s is 1 and $R_9$ is —$(C_1-C_6)$alkyl, -halo, —C(halo)$_3$, —OC(halo)$_3$, —OR$_{13}$, —N(R$_{13}$)$_2$, —S(O)$_2$R$_{13}$, or —S(O)$_2$C(halo)$_3$.

In another embodiment, $Ar_2$ is

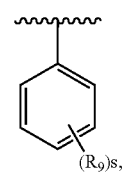

s is 1 and $R_9$ is —$(C_1-C_6)$alkyl, -halo, —C(halo)$_3$, —OC(halo)$_3$, or —$(C_1-C_6)$alkoxy.

In another embodiment, $Ar_2$ is

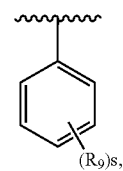

s is 1 and $R_9$ is —$(C_1-C_6)$alkyl, -halo, —CF$_3$, or —OCF$_3$.

In another embodiment, $Ar_2$ is

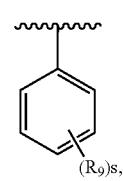

s is 1 and $R_9$ is —CF$_3$.

In another embodiment, $Ar_2$ is

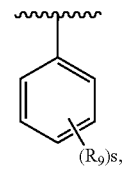

s is 2, and each $R_9$ group independently is —$(C_1-C_6)$alkyl, -halo, —C(halo)$_3$, —OC(halo)$_3$, —OR$_{13}$, —N(R$_{13}$)$_2$, —S(O)$_2$R$_{13}$, or —S(O)$_2$C(halo)$_3$.

In another embodiment, Ar$_2$ is

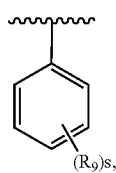

s is 2, and each R$_9$ group independently is —(C$_1$-C$_6$)alkyl, -halo, —CF$_3$, —OCF$_3$, —(C$_1$-C$_6$)alkoxy.

In another embodiment, Ar$_2$ is

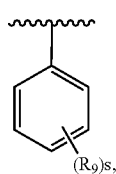

s is 2, and each R$_9$ group independently is —CH$_3$, —Cl, —F, —CF$_3$, —OCF$_3$, or —OCH$_3$.

In another embodiment, Ar$_2$ is

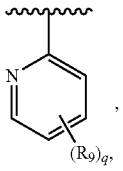

q is 1 and R$_9$ is —(C$_1$-C$_6$)alkyl, -halo, —C(halo)$_3$, —OC(halo)$_3$, —OR$_{13}$, —N(R$_{13}$)$_2$, —S(O)$_2$R$_{13}$, or —S(O)$_2$C(halo)$_3$.

In another embodiment, Ar$_2$ is

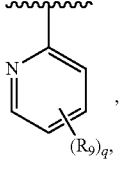

q is 1 and R$_9$ is —(C$_1$-C$_6$)alkyl, -halo, —C(halo)$_3$, —OC(halo)$_3$, or —(C$_1$-C$_6$)alkoxy.

In another embodiment, Ar$_2$ is

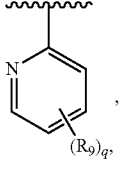

q is 1 and R$_9$ is —(C$_1$-C$_6$)alkyl, -halo, —CF$_3$, or —OCF$_3$.

In another embodiment, Ar$_2$ is

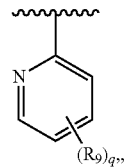

q is 1 and R$_9$ is —CF$_3$.

In another embodiment,

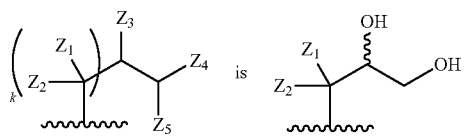

wherein the compound of Formula I is racemic.

In another embodiment.

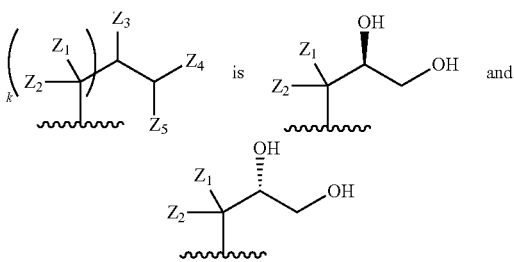

wherein the % ee of the R enantiomer is greater than 60%, 70%, 80%, 90% or 99%.

In another embodiment

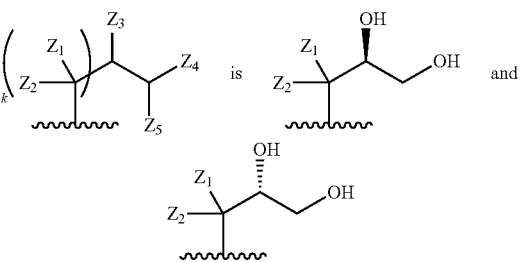

wherein the % ee of the S enantiomer is greater than 60%, 70%, 80%, 90% or 99%.

In another embodiment,

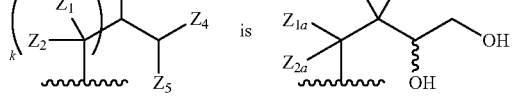

wherein the compound of Formula I is racemic.

In another embodiment,

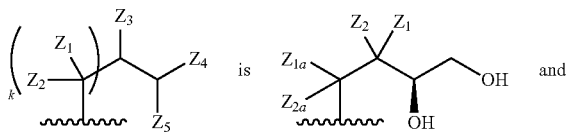

wherein the % ee of the R enantiomer is greater than 60%, 70%, 80%, 90% or 99%.

In another embodiment,

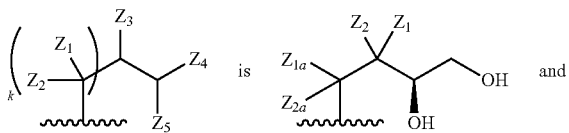

wherein the % ee of the S enantiomer is greater than 60%, 70%, 80%, 90% or 99%.

In another embodiment,

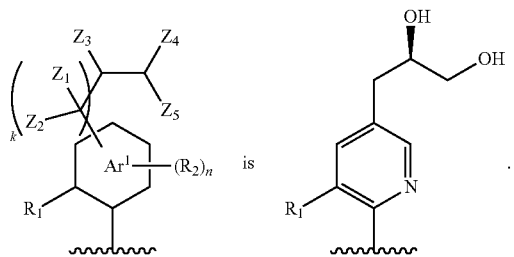

In another embodiment,

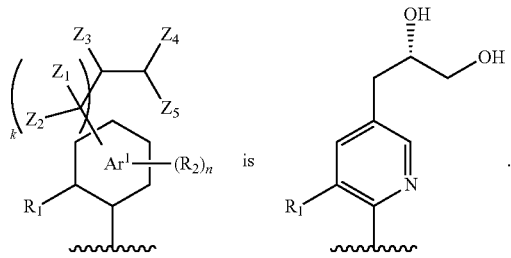

Aqueous solubility of compounds is often a desirable feature. For example, aqueous solubility of a compound permits that compound to be more easily formulated into a variety of dosage forms that may be administered to an animal. When a compound is not fully soluble in the blood, it may precipitate in the blood, and the animal's exposure to the drug will accordingly not correspond to the administered dose. Aqueous solubility increases the likelihood that a compound will not precipitate in an animal's blood, and increases the ability to predict exposure at the target sight of the compound.

Compounds of Formula I are highly soluble in aqueous solution. For example, the aqueous solubility at pH 6.8, in compounds of Formula I are >3.0, >10.0, >20.0, 30.0 or >50.0. The aqueous solubility at pH 1.2, in of compounds of Formula I are >3.0, >10.0, >20.0, 30.0 or >50.0. Additionally, the aqueous solubility at either pH 6.8 or pH 1.2 of each of compounds of Formula I is >50 μM.

In addition to being highly soluble in aqueous solution, compounds of Formula I are desirable because side effects are less severe (e.g., attenuation or removal of central nervous system side effects) in animals administered a compound of Formula I. For example, muscle relaxation is attenuated or absent in animals administered a compound of Formula I. Sedation is attenuated or absent in animals administered a compound of Formula I. Ataxia is attenuated or absent in animals administered a compound of Formula I. Flat body posture is attenuated or absent in animals administered a compound of Formula I. Tremor is attenuated or absent in animals administered a compound of Formula I. Hyperthermia is attenuated or absent in animals administered a compound of Formula I. When a compound induces less severe side effects, the therapeutic index, which is the difference between an effective dose and a dose that causes adverse effects, is increased. Therapeutic index is a measure of the safety of a compound when administered to an animal. The greater the therapeutic index, the safer the compound.

Compounds of Formula I also have excellent pharmacokinetic properties. Specifically, the plasma level of a compound of Formula I in an animal is dose proportionate. Therefore, the amount of compound in the plasma of an animal can be more readily controlled according to the dose of the compound administered to the animal. Moreover, compounds of Formula I may have one or more of the following characteristics:

high selectivity to TRPV1 receptor,
high stability
high oral absorbability,
high bioavailability,
low clearance,
easily transfers to brain
long half-life,
long efficacy of a medicine
less side effect and/or
high protein-unbound fraction.

Therefore se compounds of Formula I are considered useful as inhibitors of TRPV1 receptor.
Compounds of Formula II, III, IV, V, VI, VII, VIII, IX or X
Compounds of Formula I of interest are compounds of Formula II, III, IV, V, VI, VII, VIII, IX or X:
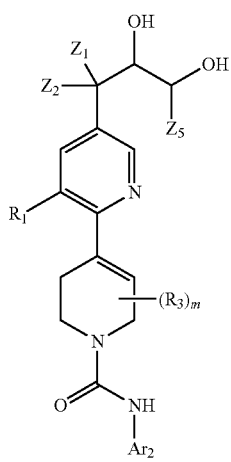
(II)
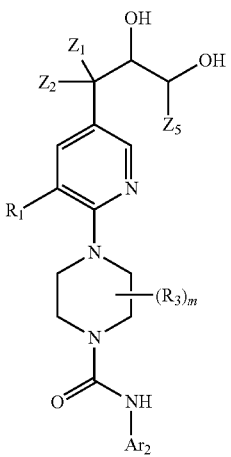
(III)
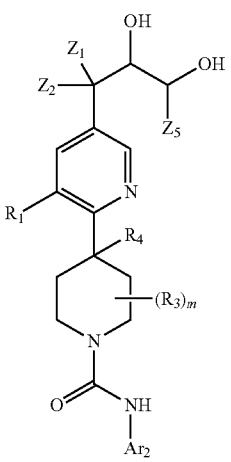
(IV)
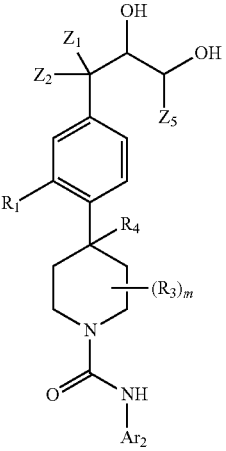
(V)
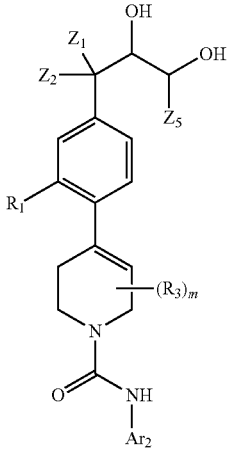
(VI)
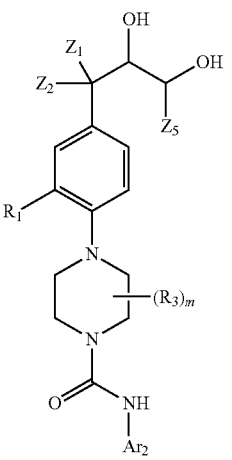
(VII)

-continued

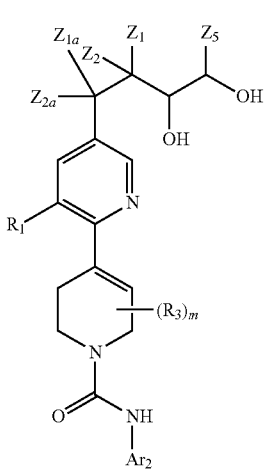
(VIII)

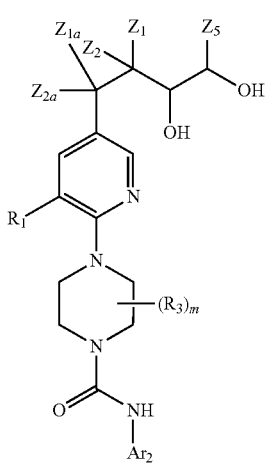
(IX)

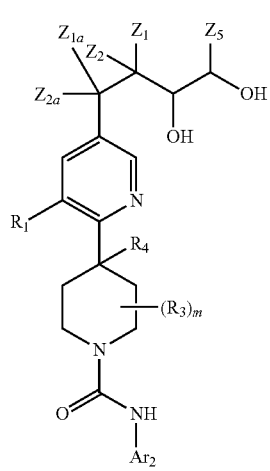
(X)

or a pharmaceutically acceptable derivative thereof, wherein $Ar^2$, $Z_1$, $Z_2$, $Z_{1a}$, $Z_{2a}$, $Z_5$, $R_1$, $R_3$, $R_4$, and m are as defined above for compounds of Formula I or I'.

In one embodiment, a compound of Formula II, III, IV, V, VI, VII, VIII, IX or X is a pharmaceutically acceptable derivative of a compound of Formula II, III, IV, V, VI, VII, VIII, IX or X, respectively.

In another embodiment, a compound of Formula II, III, IV, V, VI, VII, VIII, IX or X is a compound of Formula II, III, IV, V, VI, VII, VIII, IX or X wherein the derivative is a pharmaceutically acceptable salt, respectively.

In another embodiment, a compound of Formula II, III, IV, V, VI, VII, VIII, IX or X is a pharmaceutically acceptable salt of a compound of Formula II, III, IV, V, VI, VII, VIII, IX or X, respectively.

In another embodiment,

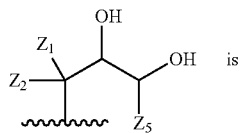 is (Za)

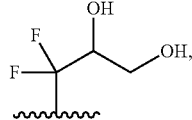

(Zb)

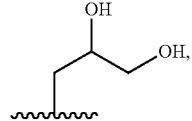

(Zc)

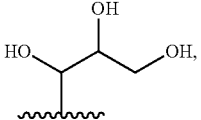

(Zd)

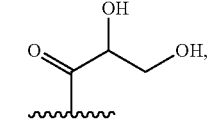

(Ze)

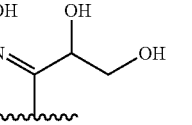

(Zf)

In another embodiment,

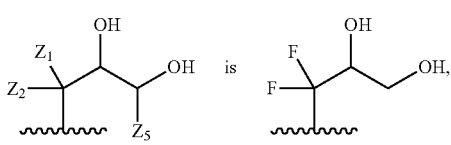

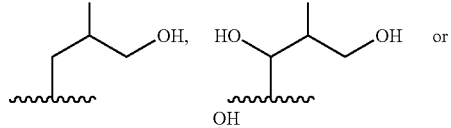

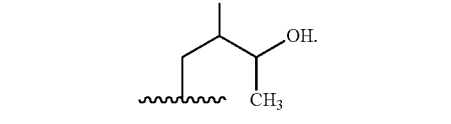

In another embodiment,
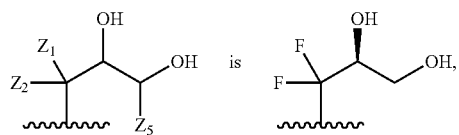 is 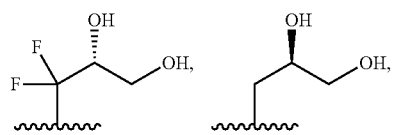,
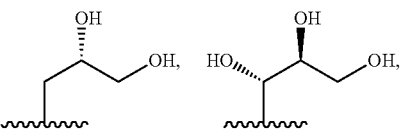
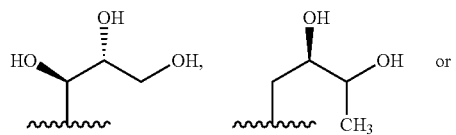
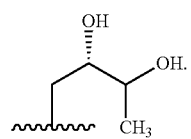
In another embodiment,
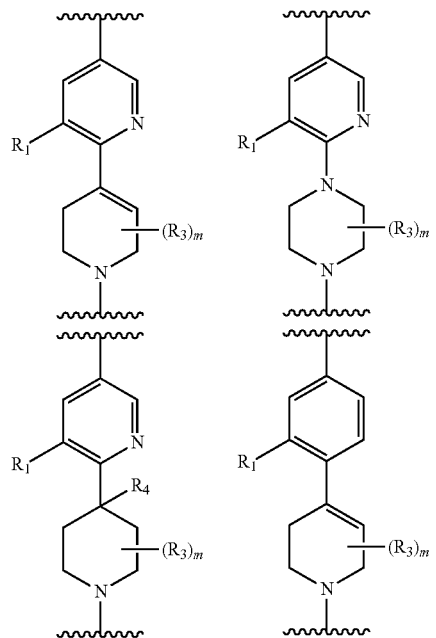
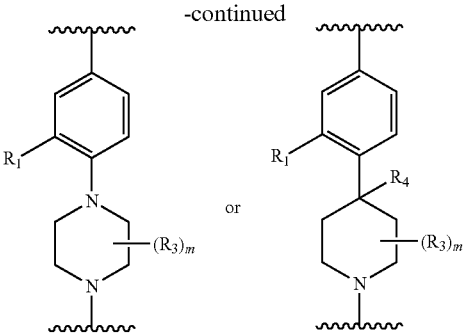
(hereinafter referred to as "Ring") is
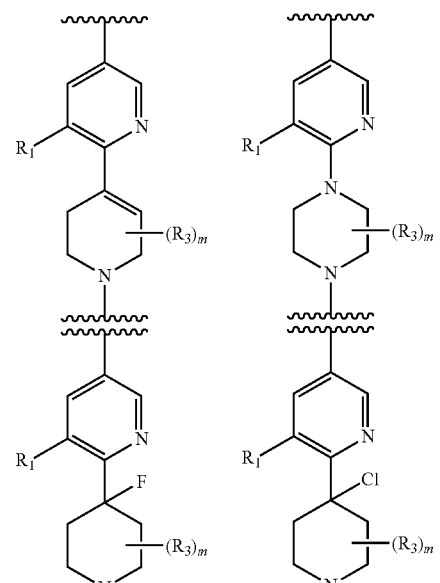
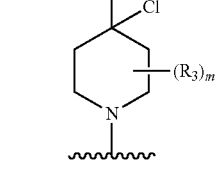

In another embodiment, Ring is
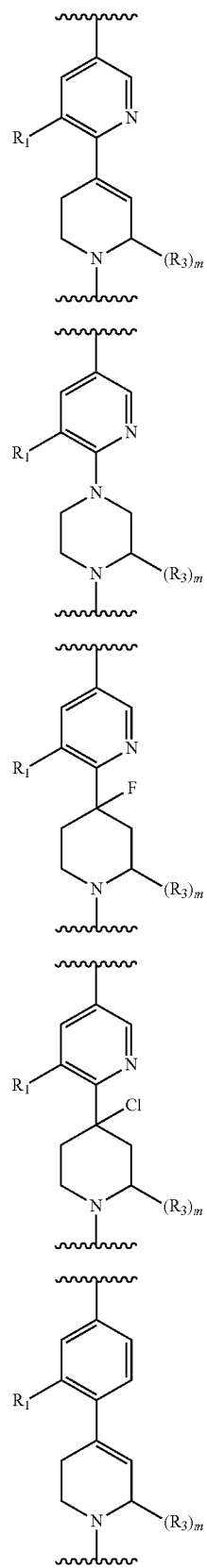
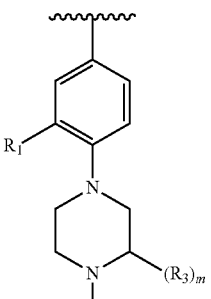
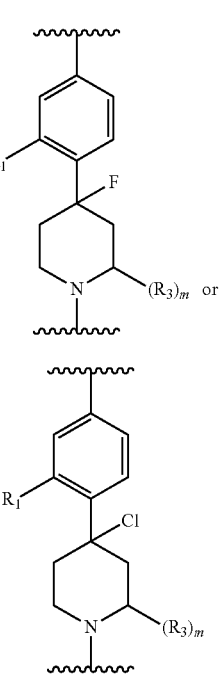
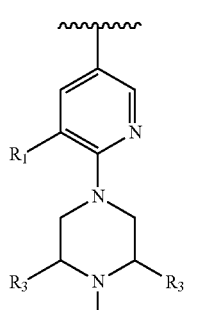
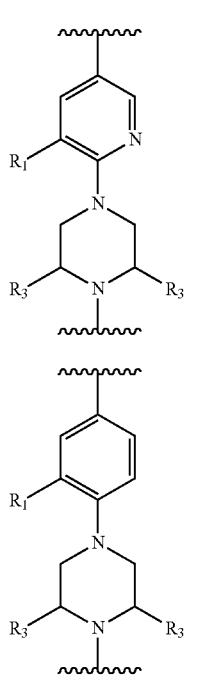
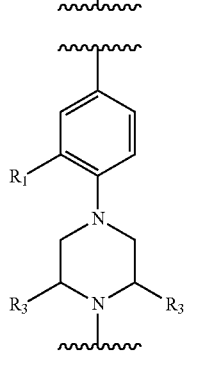

In another embodiment, $R_1$ is -halo.
In another embodiment, $R_1$ is —Cl (hereinafter referred to as $R_1$ is R1a).
In another embodiment, $R_1$ is —F (hereinafter referred to as $R_1$ is R1b).
In another embodiment, $R_1$ is —$(C_1$-$C_4)$alkyl.
In another embodiment, $R_1$ is -Me (hereinafter referred to as $R_1$ is R1c).
In another embodiment, $R_1$ is —$CF_3$ (hereinafter referred to as $R_1$ is R1d).
In another embodiment, m is 0 (hereinafter referred to as $R_3$ is R3a).
In another embodiment, m is 1 and $R_3$ is —$(C_1$-$C_6)$alkyl.
In another embodiment, m is 1 and $R_3$ is -Me (hereinafter referred to as $R_3$ is R3b).
In another embodiment, m is 1 and $R_3$ is —$CH_2OH$ (hereinafter referred to as $R_3$ is R3c).
In another embodiment, m is 1 and $R_3$ is —C(O)OH (hereinafter referred to as $R_3$ is R3d).
In another embodiment, m is 1 and $R_3$ is —$C(O)NH_2$ (hereinafter referred to as $R_3$ is R3e).
In another embodiment, m is 2 and two $R_3$ groups together form =O (hereinafter referred to as $R_3$ is R3f).
In another embodiment, m is two $R_3$ groups are both Me (hereinafter referred to as $R_3$ is R3g).
In another embodiment, m is two $R_3$ groups together form —$CH_2CH_2$— bridge (hereinafter referred to as $R_3$ is R3h).
In another embodiment, $Ar_2$ is

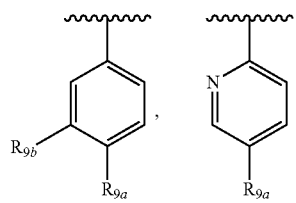 , 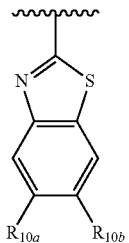 or 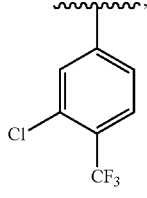

where $R_{9a}$ is —$CH_2$(halo), —CH(halo)$_2$, —C(halo)$_3$, —$OCH_2$(halo), —OCH(halo)$_2$, —OC(halo)$_3$;
$R_{9b}$ is —H, -halo, -methyl, or -methoxy;
$R_{10a}$ and $R_{10b}$ are independently selected from —H, -halo, -methyl, and -methoxy.
In another embodiment, $Ar_2$ is

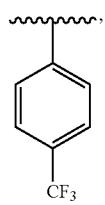 (Ara)

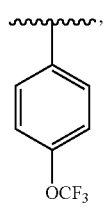 (Arb)

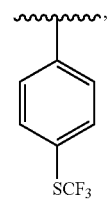 (Arc)

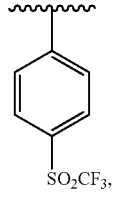 (Ard)

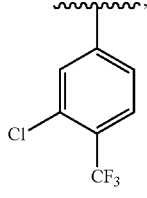 (Are)

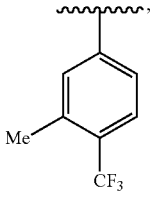 (Arf)

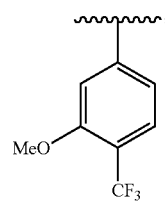 (Arg)

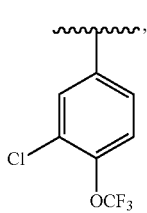 (Arh)

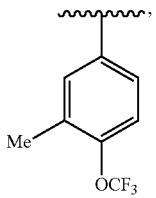 (Ari)

-continued (Arj) 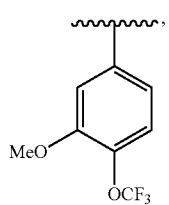

(Ark) 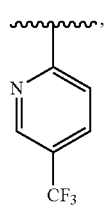

(Arl) 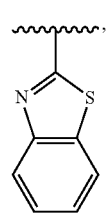

(Arm) 

(Arn) 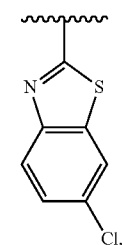

(Aro) 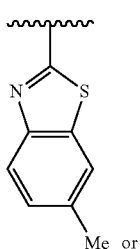

-continued (Arp) 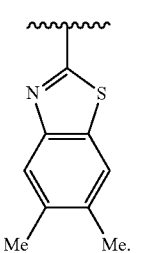

In addition to being highly soluble in aqueous solution at both pH 6.8 and pH 1.2, having a very high therapeutic index, and having excellent pharmacokinetic parameters as described for Formulae II, III, IV, V, VI, VII, VIII, IX and X compounds of Formulae II, III, IV, V, VI, VII, VIII, IX and X are of interest because they are also very bioavailable, and are believed to be highly efficacious in animals for the treatment of pain. Bioavailability is a measure of how much of the dose administered reaches systemic circulation after oral administration.

In another embodiment,

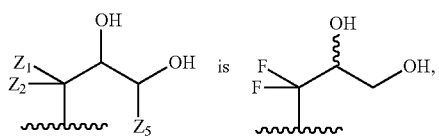

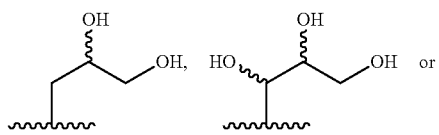

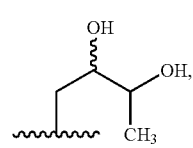

wherein the compound of Formula II, III, IV, V, VI or VII is racemic.

In another embodiment,

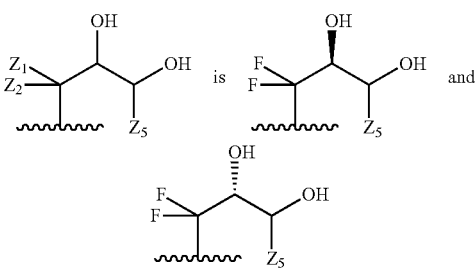

wherein the % ee of the R enantiomer is greater than 60%, 70%, 80%, 90% or 99%.

In another embodiment,

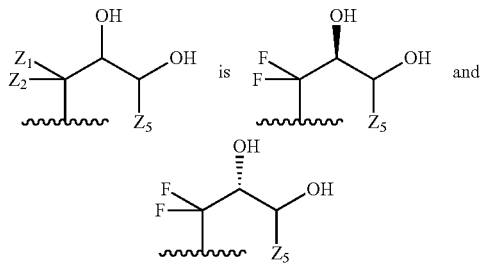

wherein the % ee of the S enantiomer is greater than 60%, 70%, 80%, 90% or 99%.

In another embodiment,

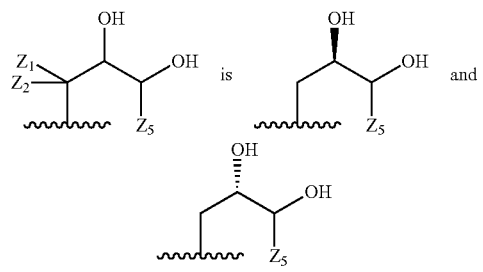

wherein the % ee of the R enantiomer is greater than 60%, 70%, 80%, 90% or 99%.

In another embodiment,

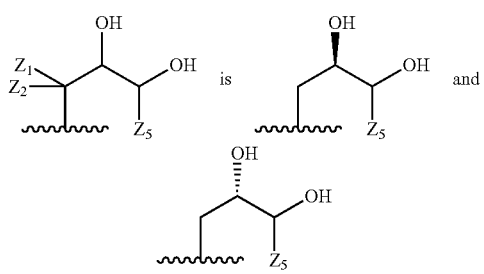

wherein the % ee of the S enantiomer is greater than 60%, 70%, 80%, 90% or 99%.

In another embodiment,

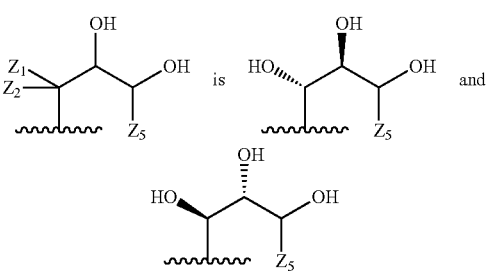

wherein the % ee of the R enantiomer is greater than 60%, 70%, 80%, 90% or 99%.

In another embodiment,

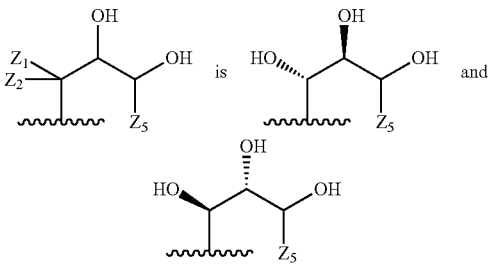

wherein the % ee of the S enantiomer is greater than 60%, 70%, 80%, 90% or 99%.

Compounds of Formula II, III, IV, V, VI, VII, VIII, IX or X are also of interest because they have a high therapeutic index. Therapeutic index is the difference between the amount of a compound that is effective for treating a Condition and the amount of that same compound that induces adverse effects, for example, body temperature increase.

Illustrative compounds of Formula II, III, IV, V, VI or VII are the compound wherein the combination of

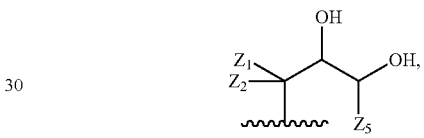

Ring, $R_1$, m and $R_3$, and $Ar_2$ (Z, Ring, $R_1$, m+$R_3$, $Ar_2$) are one of the listed below.

(Z, Ring, $R_1$, m+$R_3$, $Ar_2$)=(Za,Ra,R1a,R3a,Ara), (Za,Ra,R1a,R3a,Arb), (Za,Ra,R1a,R3a,Arc), (Za,Ra,R1a,R3a,Ard), (Za,Ra,R1a,R3a,Are), (Za,Ra,R1a,R3a,Arf), (Za,Ra,R1a,R3a,Arg), (Za,Ra,R1a,R3a,Arh), (Za,Ra,R1a,R3a,Ari), (Za,Ra,R1a,R3a,Arj), (Za,Ra,R1a,R3a,Ark), (Za,Ra,R1a,R3a,Arl), (Za,Ra,R1a,R3a,Arm), (Za,Ra,R1a,R3a,Arn), (Za,Ra,R1a,R3a,Aro), (Za,Ra,R1a,R3a,Arp), (Za,Ra,R1a,R3b,Ara), (Za,Ra,R1a,R3b,Arb), (Za,Ra,R1a,R3b,Arc), (Za,Ra,R1a,R3b,Ard), (Za,Ra,R1a,R3b,Are), (Za,Ra,R1a,R3b,Arf), (Za,Ra,R1a,R3b,Arg), (Za,Ra,R1a,R3b,Arh), (Za,Ra,R1a,R3b,Ari), (Za,Ra,R1a,R3b,Arj), (Za,Ra,R1a,R3b,Ark), (Za,Ra,R1a,R3b,Arl), (Za,Ra,R1a,R3b,Arm), (Za,Ra,R1a,R3b,Arn), (Za,Ra,R1a,R3b,Aro), (Za,Ra,R1a,R3b,Arp), (Za,Ra,R1a,R3c,Ara), (Za,Ra,R1a,R3c,Arb), (Za,Ra,R1a,R3c,Arc), (Za,Ra,R1a,R3c,Ard), (Za,Ra,R1a,R3c,Are), (Za,Ra,R1a,R3c,Arf), (Za,Ra,R1a,R3c,Arg), (Za,Ra,R1a,R3c,Arh), (Za,Ra,R1a,R3c,Ari), (Za,Ra,R1a,R3c,Arj), (Za,Ra,R1a,R3c,Ark), (Za,Ra,R1a,R3c,Arl), (Za,Ra,R1a,R3c,Arm), (Za,Ra,R1a,R3c,Arn), (Za,Ra,R1a,R3c,Aro), (Za,Ra,R1a,R3c,Arp), (Za,Ra,R1a,R3d,Ara), (Za,Ra,R1a,R3d,Arb), (Za,Ra,R1a,R3d,Arc), (Za,Ra,R1a,R3d,Ard), (Za,Ra,R1a,R3d,Are), (Za,Ra,R1a,R3d,Arf), (Za,Ra,R1a,R3d,Arg), (Za,Ra,R1a,R3d,Arh), (Za,Ra,R1a,R3d,Ari), (Za,Ra,R1a,R3d,Arj), (Za,Ra,R1a,R3d,Ark), (Za,Ra,R1a,R3d,Arl), (Za,Ra,R1a,R3d,Arm), (Za,Ra,R1a,R3d,Arn), (Za,Ra,R1a,R3d,Aro), (Za,Ra,R1a,R3d,Arp), (Za,Ra,R1a,R3e,Ara), (Za,Ra,R1a,R3e,Arb), (Za,Ra,R1a,R3e,Arc), (Za,Ra,R1a,R3e,Ard), (Za,Ra,R1a,R3e,Are), (Za,Ra,R1a,R3e,Arf), (Za,Ra,R1a,R3e,Arg), (Za,Ra,R1a,R3e,Arh), (Za,Ra,R1a,R3e,Ari), (Za,Ra,R1a,R3e,Arj), (Za,Ra,R1a,R3e,Ark), (Za,Ra,R1a,R3e,Arl), (Za,Ra,R1a,R3e,Arm), (Za,Ra,R1a,R3e,Arn), (Za,Ra,R1a,R3e,Aro), (Za,Ra,R1a,R3e,Arp), (Za,Ra,R1a,R3f,Ara), (Za,Ra, (Za,Ra,R1a,R3f,Arb), (Za,Ra,R1a,R3f,Arc), (Za,Ra,R1a,R3f,Ard), (Za,Ra,R1a,R3f,Are), (Za,Ra,R1a,R3f,Arf), (Za,Ra,R1a,R3f,Arg), (Za,Ra,R1a,R3f,Arh), (Za,Ra,R1a,R3f,Ari), (Za,Ra,R1a,R3f,Arj), (Za,Ra,R1a,R3f,Ark), (Za,Ra,R1a,R3f,Arl), (Za,Ra,R1a,R3f,Arm), (Za,Ra,R1a,R3f,Arn), (Za,Ra,R1a,R3f,Aro), (Za,Ra,R1a,R3f,Arp), (Za,Ra,R1a,R3g,Ara), (Za,Ra,R1a,R3g,Arb), (Za,Ra,R1a,R3g,Arc), (Za,Ra,R1a,R3g,Ard), (Za,Ra,R1a,R3g,Are), (Za,Ra,R1a,R3g,Arf), (Za,Ra,R1a,R3g,Arg), (Za,Ra,R1a,R3g,Arh), (Za,Ra,R1a,R3g,Ari), (Za,Ra,R1a,R3g,Arj), (Za,Ra,R1a,R3g,Ark), (Za,Ra,R1a,R3g,Arl), (Za,Ra,R1a,R3g,Arm), (Za,Ra,R1a,R3g,Arn), (Za,Ra,R1a,R3g,Aro), (Za,Ra,R1a,R3g,Arp), (Za,Ra,R1a,R3h,Ara), (Za,Ra,R1a,R3h,Arb), (Za,Ra,R1a,R3h,Arc), (Za,Ra,R1a,R3h,Ard), (Za,Ra,R1a,R3h,Are), (Za,Ra,R1a,R3h,Arf), (Za,Ra,R1a,R3h,Arg), (Za,Ra,R1a,R3h,Arh), (Za,Ra,R1a,R3h,Ari), (Za,Ra,R1a,R3h,Arj), (Za,Ra,R1a,R3h,Ark), (Za,Ra,R1a,R3h,Arl), (Za,Ra,R1a,R3h,Arm), (Za,Ra,R1a,R3h,Arn), (Za,Ra,R1a,R3h,Aro), (Za,Ra,R1a,R3h,Arp), (Za,Ra,R1b,R3a,Ara), (Za,Ra,R1b,R3a,Arb), (Za,Ra,R1b,R3a,Arc), (Za,Ra,R1b,R3a,Ard), (Za,Ra,R1b,R3a,Are), (Za,Ra,R1b,R3a,Arf), (Za,Ra,R1b,R3a,Arg), (Za,Ra,R1b,R3a,Arh), (Za,Ra,R1b,R3a,Ari), (Za,Ra,R1b,R3a,Arj), (Za,Ra,R1b,R3a,Ark), (Za,Ra,R1b,R3a,Arl), (Za,Ra,R1b,R3a,Arm), (Za,Ra,R1b,R3a,Arn), (Za,Ra,R1b,R3a,Aro), (Za,Ra,R1b,R3a,Arp), (Za,Ra,R1b,R3b,Ara), (Za,Ra,R1b,R3b,Arb), (Za,Ra,R1b,R3b,Arc), (Za,Ra,R1b,R3b,Ard), (Za,Ra,R1b,R3b,Are), (Za,Ra,R1b,R3b,Arf), (Za,Ra,R1b,R3b,Arg), (Za,Ra,R1b,R3b,Arh), (Za,Ra,R1b,R3b,Ari), (Za,Ra,R1b,R3b,Arj), (Za,Ra,R1b,R3b,Ark), (Za,Ra,R1b,R3b,Arl), (Za,Ra,R1b,R3b,Arm), (Za,Ra,R1b,R3b,Arn), (Za,Ra,R1b,R3b,Aro), (Za,Ra,R1b,R3b,Arp), (Za,Ra,R1b,R3c,Ara), (Za,Ra,R1b,R3c,Arb), (Za,Ra,R1b,R3c,Arc), (Za,Ra,R1b,R3c,Ard), (Za,Ra,R1b,R3c,Are), (Za,Ra,R1b,R3c,Arf), (Za,Ra,R1b,R3c,Arg), (Za,Ra,R1b,R3c,Arh), (Za,Ra,R1b,R3c,Ari), (Za,Ra,R1b,R3c,Arj), (Za,Ra,R1b,R3c,Ark), (Za,Ra,R1b,R3c,Arl), (Za,Ra,R1b,R3c,Arm), (Za,Ra,R1b,R3c,Arn), (Za,Ra,R1b,R3c,Aro), (Za,Ra,R1b,R3c,Arp), (Za,Ra,R1b,R3d,Ara), (Za,Ra,R1b,R3d,Arb), (Za,Ra,R1b,R 3d,Arc), (Za,Ra,R1b,R3d,Ard), (Za,Ra,R1b,R3d,Are), (Za,Ra,R1b,R3d,Arf), (Za,Ra,R1b,R3d,Arg), (Za,Ra,R1b,R3d,Arh), (Za,Ra,R1b,R3d,Ari), (Za,Ra,R1b,R3d,Arj), (Za,Ra,R1b,R3d,Ark), (Za,Ra,R1b,R3d,Arl), (Za,Ra,R1b,R3d,Arm), (Za,Ra,R1b,R3d,Arn), (Za,Ra,R1b,R3d,Aro), (Za,Ra,R1b,R3d,Arp), (Za,Ra,R1b,R3e,Ara), (Za,Ra,R1b,R3e,Arb), (Za,Ra,R1b,R3e,Arc), (Za,Ra,R1b,R3e,Ard), (Za,Ra,R1b,R3e,Are), (Za,Ra,R1b,R3e,Arf), (Za,Ra,R1b,R3e,Arg), (Za,Ra,R1b,R3e,Arh), (Za,Ra,R1b,R3e,Ari), (Za,Ra,R1b,R3e,Arj), (Za,Ra,R1b,R3e,Ark), (Za,Ra,R1b,R3e,Arl), (Za,Ra,R1b,R3e,Arm), (Za,Ra,R1b,R3e,Arn), (Za,Ra,R1b,R3e,Aro), (Za,Ra,R1b,R3e,Arp), (Za,Ra,R1b,R3f,Ara), (Za,Ra,R1b,R3f,Arb), (Za,Ra,R1b,R3f,Arc), (Za,Ra,R1b,R3f,Ard), (Za,Ra,R1b,R3f,Are), (Za,Ra,R1b,R3f,Arf), (Za,Ra,R1b,R3f,Arg), (Za,Ra,R1b,R3f,Arh), (Za,Ra,R1b,R3f,Ari), (Za,Ra,R1b,R3f,Arj), (Za,Ra,R1b,R3f,Ark), (Za,Ra,R1b,R3f,Arl), (Za,Ra,R1b,R3f,Arm), (Za,Ra,R1b,R3f,Arn), (Za,Ra,R1b,R3f,Aro), (Za,Ra,R1b,R3f,Arp), (Za,Ra,R1b,R3g,Ara), (Za,Ra,R1b,R3g,Arb), (Za,Ra,R1b,R3g,Arc), (Za,Ra,R1b,R3g,Ard), (Za,Ra,R1b,R3g,Are), (Za,Ra,R1b,R3g,Arf), (Za,Ra,R1b,R3g,Arg), (Za,Ra,R1b,R3g,Arh), (Za,Ra,R1b,R3g,Ari), (Za,Ra,R1b,R3g,Arj), (Za,Ra,R1b,R3g,Ark), (Za,Ra,R1b,R3g,Arl), (Za,Ra,R1b,R3g,Arm), (Za,Ra,R1b,R3g,Arn), (Za,Ra,R1b,R3g,Aro), (Za,Ra,R1b,R3g,Arp), (Za,Ra,R1b,R3h,Ara), (Za,Ra,R1b,R3h,Arb), (Za,Ra,R1b,R3h,Arc), (Za,Ra,R1b,R3h,Ard), (Za,Ra,R1b,R3h,Are), (Za,Ra,R1b,R3h,Arf), (Za,Ra,R1b,R3h,Arg), (Za,Ra,R1b,R3h,Arh), (Za,Ra,R1b,R3h,Ari), (Za,Ra,R1b,R3h,Arj), (Za,Ra,R1b,R3h,Ark), (Za,Ra,R1b,R3h,Arl), (Za,Ra,R1b,R3h,Arm), (Za,Ra,R1b,R3h,Arn), (Za,Ra,R1b,R3h,Aro), (Za,Ra,R1b,R3h,Arp), (Za,Ra,R1c,R3a,Ara), (Za,Ra,R1c,R3a,Arb), (Za,Ra,R1c,R3a,Arc), (Za,Ra,R1c,R3a,Ard), (Za,Ra,R1c,R3a,Are), (Za,Ra,R1c,R3a,Arf), (Za,Ra,R1c,R3a,Arg), (Za,Ra,R1c,R3a,Arh), (Za,Ra,R1c,R3a,Ari), (Za,Ra,R1c,R3a,Arj), (Za,Ra,R1c,R3a,Ark), (Za,Ra,R1c,R3a,Arl), (Za,Ra,R1c,R3a,Arm), (Za,Ra,R1c,R3a,Arn), (Za,Ra,R1c,R3a,Aro), (Za,Ra,R1c,R3a,Arp), (Za,Ra,R1c,R3b,Ara), (Za,Ra,R1c,R3b,Arb), (Za,Ra,R1c,R3b,Arc), (Za,Ra,R1c,R3b,Ard), (Za,Ra,R1c,R3b,Are), (Za,Ra,R1c,R3b,Arf), (Za,Ra,R1c,R3b,Arg), (Za,Ra,R1c,R3b,Arh), (Za,Ra,R1c,R3b,Ari), (Za,Ra,R1c,R3b,Arj), (Za,Ra,R1c,R3b,Ark), (Za,Ra,R1c,R3b,Arl), (Za,Ra,R1c,R3b,Arm), (Za,Ra,R1c,R3b,Arn), (Za,Ra,R1c,R3b,Aro), (Za,Ra,R1c,R3b,Arp), (Za,Ra,R1c,R3c,Ara), (Za,Ra,R1c,R3c,Arb), (Za,Ra,R1c,R3c,Arc), (Za,Ra,R1c,R3c,Ard), (Za,Ra,R1c,R3c,Are), (Za,Ra,R1c,R3c,Arf), (Za,Ra,R1c,R3c,Arg), (Za,Ra,R1c,R3c,Arh), (Za,Ra,R1c,R3c,Ari), (Za,Ra,R1c,R3c,Arj), (Za,Ra,R1c,R3c,Ark), (Za,Ra,R1c,R3c,Arl), (Za,Ra,R1c,R3c,Arm), (Za,Ra,R1c,R3c,Arn), (Za,Ra,R1c,R3c,Aro), (Za,Ra,R1c,R3c,Arp), (Za,Ra,R1c,R3d,Ara), (Za,Ra,R1c,R3d,Arb), (Za,Ra,R1c,R3d,Arc), (Za,Ra,R1c,R3d,Ard), (Za,Ra,R1c,R3d,Are), (Za,Ra,R1c,R3d,Arf), (Za,Ra,R1c,R3d,Arg), (Za,Ra,R1c,R3d,Arh), (Za,Ra,R1c,R3d,Ari), (Za,Ra,R1c,R3d,Arj), (Za,Ra,R1c,R3d,Ark), (Za,Ra,R1c,R3d,Arl), (Za,Ra,R1c,R3d,Arm), (Za,Ra,R1c,R3d,Arn), (Za,Ra,R1c,R3d,Aro), (Za,Ra,R1c,R3d,Arp), (Za,Ra,R1c,R3e,Ara), (Za,Ra,R1c,R3e,Arb), (Za,Ra,R1c,R3e,Arc), (Za,Ra,R1c,R3e,Ard), (Za,Ra,R1c,R3e,Are), (Za,Ra,R1c,R3e,Arf), (Za,Ra,R1c,R3e,Arg), (Za,Ra,R1c,R3e,Arh), (Za,Ra,R1c,R3e,Ari), (Za,Ra,R1c,R3e,Arj), (Za,Ra,R1c,R3e,Ark), (Za,Ra,R1c,R3e,Arl), (Za,Ra,R1c,R3e,Arm), (Za,Ra,R1c,R3e,Arn), (Za,Ra,R1c,R3e,Aro), (Za,Ra,R1c,R3e,Arp), (Za,Ra,R1c,R3f,Ara), (Za,Ra,R1c,R3f,Arb), (Za,Ra,R1c,R3f,Arc), (Za,Ra,R1c,R3f,Ard), (Za,Ra,R1c,R3f,Are), (Za,Ra,R1c,R3f,Arf), (Za,Ra,R1c,R3f,Arg), (Za,Ra,R1c,R3f,Arh), (Za,Ra,R1c,R3f,Ari), (Za,Ra,R1c,R3f,Arj), (Za,Ra,R1c,R3f,Ark), (Za,Ra,R1c,R3f,Arl), (Za,Ra,R1c,R3f,Arm), (Za,Ra,R1c,R3f,Arn), (Za,Ra,R1c,R3f,Aro), (Za,Ra,R1c,R3f,Arp), (Za,Ra,R1c,R3g,Ara), (Za,Ra,R1c,R3g,Arb), (Za,Ra,R1c,R3g,Arc), (Za,Ra,R1c,R3g,Ard), (Za,Ra,R1c,R3g,Are), (Za,Ra,R1c,R3g,Arf), (Za,Ra,R1c,R3g,Arg), (Za,Ra,R1c,R3g,Arh), (Za,Ra,R1c,R3g,Ari), (Za,Ra,R1c,R3g,Arj), (Za,Ra,R1c,R3g,Ark), (Za,Ra,R1c,R3g,Arl), (Za,Ra,R1c,R3g,Arm), (Za,Ra,R1c,R3g,Arn), (Za,Ra,R1c,R3g,Aro), (Za,Ra,R1c,R3g,Arp), (Za,Ra,R1c,R3h,Ara), (Za,Ra,R1c,R3h,Arb), (Za,Ra,R1c,R3h,Arc), (Za,Ra,R1c,R3h,Ard), (Za,Ra,R1c,R3h,Are), (Za,Ra,R1c,R3h,Arf), (Za,Ra,R1c,R3h,Arg), (Za,Ra,R1c,R3h,Arh), (Za,Ra,R1c,R3h,Ari), (Za,Ra,R1c,R3h,Arj), (Za,Ra,R1c,R3h,Ark), (Za,Ra,R1c,R3h,Arl), (Za,Ra,R1c,R3h,Arm), (Za,Ra,R1c,R3h,Arn), (Za,Ra,R1c,R3h,Aro), (Za,Ra,R1c,R3h,Arp), (Za,Ra,R1d,R3a,Ara), (Za,Ra,R1d,R3a,Arb), (Za,Ra,R1d,R3a,Arc), (Za,Ra,R1d,R3a,Ard), (Za,Ra,R1d,R3a,Are), (Za,Ra,R1d,R3a,Arf), (Za,Ra,R1d,R3a,Arg), (Za,Ra,R1d,R3a,Arh), (Za,Ra,R1d,R3a,Ari), (Za,Ra,R1d,R3a,Arj), (Za,Ra,R1d,R3a,Ark), (Za,Ra,R1d,R3a,Arl), (Za,Ra,R1d,R3a,Arm), (Za,Ra,R1d,R3a,Arn), (Za,Ra,R1d,R3a,Aro), (Za,Ra,R1d,R3a,Arp), (Za,Ra,R1d,R3b,Ara), (Za,Ra,R1d,R3b,Arb), (Za,Ra,R1d,R3b,Arc), (Za,Ra,R1d,R3b,Ard), (Za,Ra,R1d,R3b,Are), (Za,Ra,R1d,R3b,Arf), (Za,Ra,R1d,R3b,Arg), (Za,Ra,R1d,R3b,Arh), (Za,Ra,R1d,R3b,Ari), (Za,Ra,R1d,R3b,Arj), (Za,Ra,R1d,R3b,Ark), (Za,Ra,R1d,R3b,Arl), (Za,Ra,R1d,R3b,Arm), (Za,Ra,R1d,R3b,Arn), (Za,Ra,R1d,R3b,Aro), (Za,Ra,R1d,R3b,Arp), (Za,Ra,R1d,R3c,Ara), (Za,Ra,R1d,R3c,Arb), (Za,Ra,R1d,R3c,Arc), (Za,Ra,R1d,R3c,Ard), (Za,Ra,R1d,R3c,Are), (Za,Ra,R1d,R3c,Arf), (Za,Ra,R1d,R3c,Arg), (Za,Ra,R1d,R3c,Arh), (Za,Ra,R1d,R3c,Ari), (Za,Ra,R1d,R3c,Arj), (Za,Ra,R1d,R3c,Ark), (Za,Ra,R1d,R3c,Arl), (Za,Ra,R1d,R3c,Arm), (Za,Ra,R1d, R3c,Arn), (Za,Ra,R1d,R3c,Aro), (Za,Ra,R1d,R3c,Arp), (Za, Ra,R1d,R3d,Ara), (Za,Ra,R1d,R3d,Arb), (Za,Ra,R1d,R3d, Arc), (Za,Ra,R1d,R3d,Ard), (Za,Ra,R1d,R3d,Are), (Za,Ra, R1d,R3d,Arf), (Za,Ra,R1d,R3d,Arg), (Za,Ra,R1d,R3d, Arh), (Za,Ra,R1d,R3d,Ari), (Za,Ra,R1d,R3d,Arj), (Za,Ra, R1d,R3d,Ark), (Za,Ra,R1d,R3d,Arl), (Za,Ra,R1d,R3d, Arm), (Za,Ra,R1d,R3d,Arn), (Za,Ra,R1d,R3d,Aro), (Za,Ra, R1d,R3d,Arp), (Za,Ra,R1d,R3e,Ara), (Za,Ra,R1d,R3e, Arb), (Za,Ra,R1d,R3e,Arc), (Za,Ra,R1d,R3e,Ard), (Za,Ra, R1d,R3e,Are), (Za,Ra,R1d,R3e,Arf), (Za,Ra,R1d,R3e,Arg), (Za,Ra,R1d,R3e,Arh), (Za,Ra,R1d,R3e,Ari), (Za,Ra,R1d, R3e,Arj), (Za,Ra,R1d,R3e,Ark), (Za,Ra,R1d,R3e,Arl), (Za, Ra,R1d,R3e,Arm), (Za,Ra,R1d,R3e,Arn), (Za,Ra,R1d,R3e, Aro), (Za,Ra,R1d,R3e,Arp), (Za,Ra,R1d,R3f,Ara), (Za,Ra, R1d,R3f,Arb), (Za,Ra,R1d,R3f,Arc), (Za,Ra,R1d,R3f,Ard), (Za,Ra,R1d,R3f,Are), (Za,Ra,R1d,R3f,Arf), (Za,Ra,R1d, R3f,Arg), (Za,Ra,R1d,R3f,Arh), (Za,Ra,R1d,R3f,Ari), (Za, Ra,R1d,R3f,Arj), (Za,Ra,R1d,R3f,Ark), (Za,Ra,R1d,R3f, Arl), (Za,Ra,R1d,R3f,Arm), (Za,Ra,R1d,R3f,Arn), (Za,Ra, R1d,R3f,Aro), (Za,Ra,R1d,R3f,Arp), (Za,Ra,R1d,R3g,Ara), (Za,Ra,R1d,R3g,Arb), (Za,Ra,R1d,R3g,Arc), (Za,Ra,R1d, R3g,Ard), (Za,Ra,R1d,R3g,Are), (Za,Ra,R1d,R3g,Arf), (Za, Ra,R1d,R3g,Arg), (Za,Ra,R1d,R3g,Arh), (Za,Ra,R1d,R3g, Ari), (Za,Ra,R1d,R3g,Arj), (Za,Ra,R1d,R3g,Ark), (Za,Ra, R1d,R3g,Arl), (Za,Ra,R1d,R3g,Arm), (Za,Ra,R1d,R3g, Arn), (Za,Ra,R1d,R3g,Aro), (Za,Ra,R1d,R3g,Arp), (Za,Ra, R1d,R3h,Ara), (Za,Ra,R1d,R3h,Arb), (Za,Ra,R1d,R3h, Arc), (Za,Ra,R1d,R3h,Ard), (Za,Ra,R1d,R3h,Are), (Za,Ra, R1d,R3h,Arf), (Za,Ra,R1d,R3h,Arg), (Za,Ra,R1d,R3h, Arh), (Za,Ra,R1d,R3h,Ari), (Za,Ra,R1d,R3h,Arj), (Za,Ra, R1d,R3h,Ark), (Za,Ra,R1d,R3h,Arl), (Za,Ra,R1d,R3h, Arm), (Za,Ra,R1d,R3h,Arn), (Za,Ra,R1d,R3h,Aro), (Za,Ra, R1d,R3h,Arp), (Za,Rb,R1a,R3a,Ara), (Za,Rb,R1a,R3a, Arb), (Za,Rb,R1a,R3a,Arc), (Za,Rb,R1a,R3a,Ard), (Za,Rb, R1a,R3a,Are), (Za,Rb,R1a,R3a,Arf), (Za,Rb,R1a,R3a,Arg), (Za,Rb,R1a,R3a,Arh), (Za,Rb,R1a,R3a,Ari), (Za,Rb,R1a, R3a,Arj), (Za,Rb,R1a,R3a,Ark), (Za,Rb,R1a,R3a,Arl), (Za, Rb,R1a,R3a,Arm), (Za,Rb,R1a,R3a,Arn), (Za,Rb,R1a,R3a, Aro), (Za,Rb,R1a,R3a,Arp), (Za,Rb,R1a,R3b,Ara), (Za,Rb, R1a,R3b,Arb), (Za,Rb,R1a,R3b,Arc), (Za,Rb,R1a,R3b, Ard), (Za,Rb,R1a,R3b,Are), (Za,Rb,R1a,R3b,Arf), (Za,Rb, R1a,R3b,Arg), (Za,Rb,R1a,R3b,Arh), (Za,Rb,R1a,R3b,Ari), (Za,Rb,R1a,R3b,Arj), (Za,Rb,R1a,R3b,Ark), (Za,Rb,R1a, R3b,Arl), (Za,Rb,R1a,R3b,Arm), (Za,Rb,R1a,R3b,Arn), (Za,Rb,R1a,R3b,Aro), (Za,Rb,R1a,R3b,Arp), (Za,Rb,R1a, R3c,Ara), (Za,Rb,R1a,R3c,Arb), (Za,Rb,R1a,R3c,Arc), (Za, Rb,R1a,R3c,Ard), (Za,Rb,R1a,R3c,Are), (Za,Rb,R1a,R3c, Arf), (Za,Rb,R1a,R3c,Arg), (Za,Rb,R1a,R3c,Arh), (Za,Rb, R1a,R3c,Ari), (Za,Rb,R1a,R3c,Arj), (Za,Rb,R1a,R3c,Ark), (Za,Rb,R1a,R3c,Arl), (Za,Rb,R1a,R3c,Arm), (Za,Rb,R1a, R3c,Arn), (Za,Rb,R1a,R3c,Aro), (Za,Rb,R1a,R3c,Arp), (Za, Rb,R1a,R3d,Ara), (Za,Rb,R1a,R3d,Arb), (Za,Rb,R1a,R3d, Arc), (Za,Rb,R1a,R3d,Ard), (Za,Rb,R1a,R3d,Are), (Za,Rb, R1a,R3d,Arf), (Za,Rb,R1a,R3d,Arg), (Za,Rb,R1a,R3d,Arh), (Za,Rb,R1a,R3d,Ari), (Za,Rb,R1a,R3d,Arj), (Za,Rb,R1a, R3d,Ark), (Za,Rb,R1a,R3d,Arl), (Za,Rb,R1a,R3d,Arm), (Za,Rb,R1a,R3d,Arn), (Za,Rb,R1a,R3d,Aro), (Za,Rb,R1a, R3d,Arp), (Za,Rb,R1a,R3e,Ara), (Za,Rb,R1a,R3e,Arb), (Za, Rb,R1a,R3e,Arc), (Za,Rb,R1a,R3e,Ard), (Za,Rb,R1a,R3e, Are), (Za,Rb,R1a,R3e,Arf), (Za,Rb,R1a,R3e,Arg), (Za,Rb, R1a,R3e,Arh), (Za,Rb,R1a,R3e,Ari), (Za,Rb,R1a,R3e,Arj), (Za,Rb,R1a,R3e,Ark), (Za,Rb,R1a,R3e,Arl), (Za,Rb,R1a, R3e,Arm), (Za,Rb,R1a,R3e,Arn), (Za,Rb,R1a,R3e,Aro), (Za,Rb,R1a,R3e,Arp), (Za,Rb,R1a,R3f,Ara), (Za,Rb,R1a, R3f,Arb), (Za,Rb,R1a,R3f,Arc), (Za,Rb,R1a,R3f,Ard), (Za, Rb,R1a,R3f,Are), (Za,Rb,R1a,R3f,Arf), (Za,Rb,R1a,R3f, Arg), (Za,Rb,R1a,R3f,Arh), (Za,Rb,R1a,R3f,Ari), (Za,Rb, R1a,R3f,Arj), (Za,Rb,R1a,R3f,Ark), (Za,Rb,R1a,R3f,Arl), (Za,Rb,R1a,R3f,Arm), (Za,Rb,R1a,R3f,Arn), (Za,Rb,R1a, R3f,Aro), (Za,Rb,R1a,R3f,Arp), (Za,Rb,R1a,R3g,Ara), (Za, Rb,R1a,R3g,Arb), (Za,Rb,R1a,R3g,Arc), (Za,Rb,R1a,R3g, Ard), (Za,Rb,R1a,R3g,Are), (Za,Rb,R1a,R3g,Arf), (Za,Rb, R1a,R3g,Arg), (Za,Rb,R1a,R3g,Arh), (Za,Rb,R1a,R3g,Ari), (Za,Rb,R1a,R3g,Arj), (Za,Rb,R1a,R3g,Ark), (Za,Rb,R1a, R3g,Arl), (Za,Rb,R1a,R3g,Arm), (Za,Rb,R1a,R3g,Arn), (Za,Rb,R1a,R3g,Aro), (Za,Rb,R1a,R3g,Arp), (Za,Rb,R1a, R3h,Ara), (Za,Rb,R1a,R3h,Arb), (Za,Rb,R1a,R3h,Arc), (Za, Rb,R1a,R3h,Ard), (Za,Rb,R1a,R3h,Are), (Za,Rb,R1a,R3h, Arf), (Za,Rb,R1a,R3h,Arg), (Za,Rb,R1a,R3h,Arh), (Za,Rb, R1a,R3h,Ari), (Za,Rb,R1a,R3h,Arj), (Za,Rb,R1a,R3h,Ark), (Za,Rb,R1a,R3h,Arl), (Za,Rb,R1a,R3h,Arm), (Za,Rb,R1a, R3h,Arn), (Za,Rb,R1a,R3h,Aro), (Za,Rb,R1a,R3h,Arp), (Za,Rb,R1b,R3a,Ara), (Za,Rb,R1b,R3a,Arb), (Za,Rb,R1b, R3a,Arc), (Za,Rb,R1b,R3a,Ard), (Za,Rb,R1b,R3a,Are), (Za, Rb,R1b,R3a,Arf), (Za,Rb,R1b,R3a,Arg), (Za,Rb,R1b,R3a, Arh), (Za,Rb,R1b,R3a,Ari), (Za,Rb,R1b,R3a,Arj), (Za,Rb, R1b,R3a,Ark), (Za,Rb,R1b,R3a,Arl), (Za,Rb,R1b,R3a, Arm), (Za,Rb,R1b,R3a,Arn), (Za,Rb,R1b,R3a,Aro), (Za,Rb, R1b,R3a,Arp), (Za,Rb,R1b,R3b,Ara), (Za,Rb,R1b,R3b, Arb), (Za,Rb,R1b,R3b,Arc), (Za,Rb,R1b,R3b,Ard), (Za,Rb, R1b,R3b,Are), (Za,Rb,R1b,R3b,Arf), (Za,Rb,R1b,R3b, Arg), (Za,Rb,R1b,R3b,Arh), (Za,Rb,R1b,R3b,Ari), (Za,Rb, R1b,R3b,Arj), (Za,Rb,R1b,R3b,Ark), (Za,Rb,R1b,R3b,Arl), (Za,Rb,R1b,R3b,Arm), (Za,Rb,R1b,R3b,Arn), (Za,Rb,R1b, R3b,Aro), (Za,Rb,R1b,R3b,Arp), (Za,Rb,R1b,R3c,Ara), (Za,Rb,R1b,R3c,Arb), (Za,Rb,R1b,R3c,Arc), (Za,Rb,R1b, R3c,Ard), (Za,Rb,R1b,R3c,Are), (Za,Rb,R1b,R3c,Arf), (Za, Rb,R1b,R3c,Arg), (Za,Rb,R1b,R3c,Arh), (Za,Rb,R1b,R3c, Ari), (Za,Rb,R1b,R3c,Arj), (Za,Rb,R1b,R3c,Ark), (Za,Rb, R1b,R3c,Arl), (Za,Rb,R1b,R3c,Arm), (Za,Rb,R1b,R3c, Arn), (Za,Rb,R1b,R3c,Aro), (Za,Rb,R1b,R3c,Arp), (Za,Rb, R1b,R3d,Ara), (Za,Rb,R1b,R3d,Arb), (Za,Rb,R1b,R3d, Arc), (Za,Rb,R1b,R3d,Ard), (Za,Rb,R1b,R3d,Are), (Za,Rb, R1b,R3d,Arf), (Za,Rb,R1b,R3d,Arg), (Za,Rb,R1b,R3d, Arh), (Za,Rb,R1b,R3d,Ari), (Za,Rb,R1b,R3d,Arj), (Za,Rb, R1b,R3d,Ark), (Za,Rb,R1b,R3d,Arl), (Za,Rb,R1b,R3d, Arm), (Za,Rb,R1b,R3d,Arn), (Za,Rb,R1b,R3d,Aro), (Za,Rb, R1b,R3d,Arp), (Za,Rb,R1b,R3e,Ara), (Za,Rb,R1b,R3e, Arb), (Za,Rb,R1b,R3e,Arc), (Za,Rb,R1b,R3e,Ard), (Za,Rb, R1b,R3e,Are), (Za,Rb,R1b,R3e,Arf), (Za,Rb,R1b,R3e,Arg), (Za,Rb,R1b,R3e,Arh), (Za,Rb,R1b,R3e,Ari), (Za,Rb,R1b, R3e,Arj), (Za,Rb,R1b,R3e,Ark), (Za,Rb,R1b,R3e, Arl), (Za, Rb,R1b,R3e,Arm), (Za,Rb,R1b,R3e,Arn), (Za,Rb,R1b,R3e, Aro), (Za,Rb,R1b,R3e,Arp), (Za,Rb,R1b,R3f,Ara), (Za,Rb, R1b,R3f,Arb), (Za,Rb,R1b,R3f,Arc), (Za,Rb,R1b,R3f,Ard), (Za,Rb,R1b,R3f,Are), (Za,Rb,R1b,R3f,Arf), (Za,Rb,R1b, R3f,Arg), (Za,Rb,R1b,R3f,Arh), (Za,Rb,R1b,R3f,Ari), (Za, Rb,R1b,R3f,Arj), (Za,Rb,R1b,R3f,Ark), (Za,Rb,R1b,R3f, Arl), (Za,Rb,R1b,R3f,Arm), (Za,Rb,R1b,R3f,Arn), (Za,Rb, R1b,R3f,Aro), (Za,Rb,R1b,R3f,Arp), (Za,Rb,R1b,R3g,Ara), (Za,Rb,R1b,R3g,Arb), (Za,Rb,R1b,R3g,Arc), (Za,Rb,R1b, R3g,Ard), (Za,Rb,R1b,R3g,Are), (Za, Rb,R1b,R3g,Arf), (Za,Rb,R1b,R3g,Arg), (Za,Rb,R1b,R3g,Arh), (Za,Rb,R1b, R3g,Ari), (Za,Rb,R1b,R3g,Arj), (Za,Rb,R1b,R3g,Ark), (Za, Rb,R1b,R3g,Arl), (Za,Rb,R1b,R3g,Arm), (Za,Rb,R1b,R3g, Arn), (Za,Rb,R1b,R3g,Aro), (Za,Rb,R1b,R3g,Arp), (Za,Rb, R1b,R3h,Ara), (Za,Rb,R1b,R3h,Arb), (Za,Rb,R1b,R3h, Arc), (Za,Rb,R1b,R3h,Ard), (Za,Rb,R1b,R3h,Are), (Za,Rb, R1b,R3h,Arf), (Za,Rb,R1b,R3h,Arg), (Za,Rb,R1b,R3h, Arh), (Za,Rb,R1b,R3h,Ari), (Za,Rb,R1b,R3h,Arj), (Za,Rb, R1b,R3h,Ark), (Za,Rb,R1b,R3h,Arl), (Za,Rb,R1b,R3h, Arm), (Za,Rb,R1b,R3h,Arn), (Za,Rb,R1b,R3h,Aro), (Za,Rb, R1b,R3h,Arp), (Za,Rb,R1c,R3a,Ara), (Za,Rb,R1c,R3a, Arb), (Za,Rb,R1c,R3a,Arc), (Za,Rb,R1c,R3a,Ard), (Za,Rb,R1c,R3a,Are), (Za,Rb,R1c,R3a,Arf), (Za,Rb,R1c,R3a,Arg), (Za,Rb,R1c,R3a,Arh), (Za,Rb,R1c,R3a,Ari), (Za,Rb,R1c,R3a,Arj), (Za,Rb,R1c,R3a,Ark), (Za,Rb,R1c,R3a,Arl), (Za,Rb,R1c,R3a,Arm), (Za,Rb,R1c,R3a,Arn), (Za,Rb,R1c,R3a,Aro), (Za,Rb,R1c,R3a,Arp), (Za,Rb,R1c,R3b,Ara), (Za,Rb,R1c,R3b,Arb), (Za,Rb,R1c,R3b,Arc), (Za,Rb,R1c,R3b,Ard), (Za,Rb,R1c,R3b,Are), (Za,Rb,R1c,R3b,Arf), (Za,Rb,R1c,R3b,Arg), (Za,Rb,R1c,R3b,Arh), (Za,Rb,R1c,R3b,Ari), (Za,Rb,R1c,R3b,Arj), (Za,Rb,R1c,R3b,Ark), (Za,Rb,R1c,R3b,Arl), (Za,Rb,R1c,R3b,Arm), (Za,Rb,R1c,R3b,Arn), (Za,Rb,R1c,R3b,Aro), (Za,Rb,R1c,R3b,Arp), (Za,Rb,R1c,R3c,Ara), (Za,Rb,R1c,R3c,Arb), (Za,Rb,R1c,R3c,Arc), (Za,Rb,R1c,R3c,Ard), (Za,Rb,R1c,R3c,Are), (Za,Rb,R1c,R3c,Arf), (Za,Rb,R1c,R3c,Arg), (Za,Rb,R1c,R3c,Arh), (Za,Rb,R1c,R3c,Ari), (Za,Rb,R1c,R3c,Arj), (Za,Rb,R1c,R3c,Ark), (Za,Rb,R1c,R3c,Arl), (Za,Rb,R1c,R3c,Arm), (Za,Rb,R1c,R3c,Arn), (Za,Rb,R1c,R3c,Aro), (Za,Rb,R1c,R3c,Arp), (Za,Rb,R1c,R3d,Ara), (Za,Rb,R1c,R3d,Arb), (Za,Rb,R1c,R3d,Arc), (Za,Rb,R1c,R3d,Ard), (Za,Rb,R1c,R3d,Are), (Za,Rb,R1c,R3d,Arf), (Za,Rb,R1c,R3d,Arg), (Za,Rb,R1c,R3d,Arh), (Za,Rb,R1c,R3d,Ari), (Za,Rb,R1c,R3d,Arj), (Za,Rb,R1c,R3d,Ark), (Za,Rb,R1c,R3d,Arl), (Za,Rb,R1c,R3d,Arm), (Za,Rb,R1c,R3d,Arn), (Za,Rb,R1c,R3d,Aro), (Za,Rb,R1c,R3d,Arp), (Za,Rb,R1c,R3e,Ara), (Za,Rb,R1c,R3e,Arb), (Za,Rb,R1c,R3e,Arc), (Za,Rb,R1c,R3e,Ard), (Za,Rb,R1c,R3e,Are), (Za,Rb,R1c,R3e,Arf), (Za,Rb,R1c,R3e,Arg), (Za,Rb,R1c,R3e,Arh), (Za,Rb,R1c,R3e,Ari), (Za,Rb,R1c,R3e,Arj), (Za,Rb,R1c,R3e,Ark), (Za,Rb,R1c,R3e,Arl), (Za,Rb,R1c,R3e,Arm), (Za,Rb,R1c,R3e,Arn), (Za,Rb,R1c,R3e,Aro), (Za,Rb,R1c,R3e,Arp), (Za,Rb,R1c,R3f,Ara), (Za,Rb,R1c,R3f,Arb), (Za,Rb,R1c,R3f,Arc), (Za,Rb,R1c,R3f,Ard), (Za,Rb,R1c,R3f,Are), (Za,Rb,R1c,R3f,Arf), (Za,Rb,R1c,R3f,Arg), (Za,Rb,R1c,R3f,Arh), (Za,Rb,R1c,R3f,Ari), (Za,Rb,R1c,R3f,Arj), (Za,Rb,R1c,R3f,Ark), (Za,Rb,R1c,R3f,Arl), (Za,Rb,R1c,R3f,Arm), (Za,Rb,R1c,R3f,Arn), (Za,Rb,R1c,R3f,Aro), (Za,Rb,R1c,R3f,Arp), (Za,Rb,R1c,R3g,Ara), (Za,Rb,R1c,R3g,Arb), (Za,Rb,R1c,R3g,Arc), (Za,Rb,R1c,R3g,Ard), (Za,Rb,R1c,R3g,Are), (Za,Rb,R1c,R3g,Arf), (Za,Rb,R1c,R3g,Arg), (Za,Rb,R1c,R3g,Arh), (Za,Rb,R1c,R3g,Ari), (Za,Rb,R1c,R3g,Arj), (Za,Rb,R1c,R3g,Ark), (Za,Rb,R1c,R3g,Arl), (Za,Rb,R1c,R3g,Arm), (Za,Rb,R1c,R3g,Arn), (Za,Rb,R1c,R3g,Aro), (Za,Rb,R1c,R3g,Arp), (Za,Rb,R1c,R3h,Ara), (Za,Rb,R1c,R3h,Arb), (Za,Rb,R1c,R3h,Arc), (Za,Rb,R1c,R3h,Ard), (Za,Rb,R1c,R3h,Are), (Za,Rb,R1c,R3h,Arf), (Za,Rb,R1c,R3h,Arg), (Za,Rb,R1c,R3h,Arh), (Za,Rb,R1c,R3h,Ari), (Za,Rb,R1c,R3h,Arj), (Za,Rb,R1c,R3h,Ark), (Za,Rb,R1c,R3h,Arl), (Za,Rb,R1c,R3h,Arm), (Za,Rb,R1c,R3h,Arn), (Za,Rb,R1c,R3h,Aro), (Za,Rb,R1c,R3h,Arp), (Za,Rb,R1d,R3a,Ara), (Za,Rb,R1d,R3a,Arb), (Za,Rb,R1d,R3a,Arc), (Za,Rb,R1d,R3a,Ard), (Za,Rb,R1d,R3a,Are), (Za,Rb,R1d,R3a,Arf), (Za,Rb,R1d,R3a,Arg), (Za,Rb,R1d,R3a,Arh), (Za,Rb,R1d,R3a,Ari), (Za,Rb,R1d,R3a,Arj), (Za,Rb,R1d,R3a,Ark), (Za,Rb,R1d,R3a,Arl), (Za,Rb,R1d,R3a,Arm), (Za,Rb,R1d,R3a,Arn), (Za,Rb,R1d,R3a,Aro), (Za,Rb,R1d,R3a,Arp), (Za,Rb,R1d,R3b,Ara), (Za,Rb,R1d,R3b,Arb), (Za,Rb,R1d,R3b,Arc), (Za,Rb,R1d,R3b,Ard), (Za,Rb,R1d,R3b,Are), (Za,Rb,R1d,R3b,Arf), (Za,Rb,R1d,R3b,Arg), (Za,Rb,R1d,R3b,Arh), (Za,Rb,R1d,R3b,Ari), (Za,Rb,R1d,R3b,Arj), (Za,Rb,R1d,R3b,Ark), (Za,Rb,R1d,R3b,Arl), (Za,Rb,R1d,R3b,Arm), (Za,Rb,R1d,R3b,Arn), (Za,Rb,R1d,R3b,Aro), (Za,Rb,R1d,R3b,Arp), (Za,Rb,R1d,R3c,Ara), (Za,Rb,R1d,R3c,Arb), (Za,Rb,R1d,R3c,Arc), (Za,Rb,R1d,R3c,Ard), (Za,Rb,R1d,R3c,Are), (Za,Rb,R1d,R3c,Arf), (Za,Rb,R1d,R3c,Arg), (Za,Rb,R1d,R3c,Arh), (Za,Rb,R1d,R3c,Ari), (Za,Rb,R1d,R3c,Arj), (Za,Rb,R1d,R3c,Ark), (Za,Rb,R1d,R3c,Arl), (Za,Rb,R1d,R3c,Arm), (Za,Rb,R1d,R3c,Arn), (Za,Rb,R1d,R3c,Aro), (Za,Rb,R1d,R3c,Arp), (Za,Rb,R1d,R3d,Ara), (Za,Rb,R1d,R3d,Arb), (Za,Rb,R1d,R3d,Arc), (Za,Rb,R1d,R3d,Ard), (Za,Rb,R1d,R3d,Are), (Za,Rb,R1d,R3d,Arf), (Za,Rb,R1d,R3d,Arg), (Za,Rb,R1d,R3d,Arh), (Za,Rb,R1d,R3d,Ari), (Za,Rb,R1d,R3d,Arj), (Za,Rb,R1d,R3d,Ark), (Za,Rb,R1d,R3d,Arl), (Za,Rb,R1d,R3d,Arm), (Za,Rb,R1d,R3d,Arn), (Za,Rb,R1d,R3d,Aro), (Za,Rb,R1d,R3d,Arp), (Za,Rb,R1d,R3e,Ara), (Za,Rb,R1d,R3e,Arb), (Za,Rb,R1d,R3e,Arc), (Za,Rb,R1d,R3e,Ard), (Za,Rb,R1d,R3e,Are), (Za,Rb,R1d,R3e,Arf), (Za,Rb,R1d,R3e,Arg), (Za,Rb,R1d,R3e,Arh), (Za,Rb,R1d,R3e,Ari), (Za,Rb,R1d,R3e,Arj), (Za,Rb,R1d,R3e,Ark), (Za,Rb,R1d,R3e,Arl), (Za,Rb,R1d,R3e,Arm), (Za,Rb,R1d,R3e,Arn), (Za,Rb,R1d,R3e,Aro), (Za,Rb,R1d,R3e,Arp), (Za,Rb,R1d,R3f,Ara), (Za,Rb,R1d,R3f,Arb), (Za,Rb,R1d,R3f,Arc), (Za,Rb,R1d,R3f,Ard), (Za,Rb,R1d,R3f,Are), (Za,Rb,R1d,R3f,Arf), (Za,Rb,R1d,R3f,Arg), (Za,Rb,R1d,R3f,Arh), (Za,Rb,R1d,R3f,Ari), (Za,Rb,R1d,R3f,Arj), (Za,Rb,R1d,R3f,Ark), (Za,Rb,R1d,R3f,Arl), (Za,Rb,R1d,R3f,Arm), (Za,Rb,R1d,R3f,Arn), (Za,Rb,R1d,R3f,Aro), (Za,Rb,R1d,R3f,Arp), (Za,Rb,R1d,R3g,Ara), (Za,Rb,R1d,R3g,Arb), (Za,Rb,R1d,R3g,Arc), (Za,Rb,R1d,R3g,Ard), (Za,Rb,R1d,R3g,Are), (Za,Rb,R1d,R3g,Arf), (Za,Rb,R1d,R3g,Arg), (Za,Rb,R1d,R3g,Arh), (Za,Rb,R1d,R3g,Ari), (Za,Rb,R1d,R3g,Arj), (Za,Rb,R1d,R3g,Ark), (Za,Rb,R1d,R3g,Arl), (Za,Rb,R1d,R3g,Arm), (Za,Rb,R1d,R3g,Arn), (Za,Rb,R1d,R3g,Aro), (Za,Rb,R1d,R3g,Arp), (Za,Rb,R1d,R3h,Ara), (Za,Rb,R1d,R3h,Arb), (Za,Rb,R1d,R3h,Arc), (Za,Rb,R1d,R3h,Ard), (Za,Rb,R1d,R3h,Are), (Za,Rb,R1d,R3h,Arf), (Za,Rb,R1d,R3h,Arg), (Za,Rb,R1d,R3h,Arh), (Za,Rb,R1d,R3h,Ari), (Za,Rb,R1d,R3h,Arj), (Za,Rb,R1d,R3h,Ark), (Za,Rb,R1d,R3h,Arl), (Za,Rb,R1d,R3h,Arm), (Za,Rb,R1d,R3h,Arn), (Za,Rb,R1d,R3h,Aro), (Za,Rb,R1d,R3h,Arp), (Za,Rc,R1a,R3a,Ara), (Za,Rc,R1a,R3a,Arb), (Za,Rc,R1a,R3a,Arc), (Za,Rc,R1a,R3a,Ard), (Za,Rc,R1a,R3a,Are), (Za,Rc,R1a,R3a,Arf), (Za,Rc,R1a,R3a,Arg), (Za,Rc,R1a,R3a,Arh), (Za,Rc,R1a,R3a,Ari), (Za,Rc,R1a,R3a,Arj), (Za,Rc,R1a,R3a,Ark), (Za,Rc,R1a,R3a,Arl), (Za,Rc,R1a,R3a,Arm), (Za,Rc,R1a,R3a,Arn), (Za,Rc,R1a,R3a,Aro), (Za,Rc,R1a,R3a,Arp), (Za,Rc,R1a,R3b,Ara), (Za,Rc,R1a,R3b,Arb), (Za,Rc,R1a,R3b,Arc), (Za,Rc,R1a,R3b,Ard), (Za,Rc,R1a,R3b,Are), (Za,Rc,R1a,R3b,Arf), (Za,Rc,R1a,R3b,Arg), (Za,Rc,R1a,R3b,Arh), (Za,Rc,R1a,R3b,Ari), (Za,Rc,R1a,R3b,Arj), (Za,Rc,R1a,R3b,Ark), (Za,Rc,R1a,R3b,Arl), (Za,Rc,R1a,R3b,Arm), (Za,Rc,R1a,R3b,Arn), (Za,Rc,R1a,R3b,Aro), (Za,Rc,R1a,R3b,Arp), (Za,Rc,R1a,R3c,Ara), (Za,Rc,R1a,R3c,Arb), (Za,Rc,R1a,R3c,Arc), (Za,Rc,R1a,R3c,Ard), (Za,Rc,R1a,R3c,Are), (Za,Rc,R1a,R3c,Arf), (Za,Rc,R1a,R3c,Arg), (Za,Rc,R1a,R3c,Arh), (Za,Rc,R1a,R3c,Ari), (Za,Rc,R1a,R3c,Arj), (Za,Rc,R1a,R3c,Ark), (Za,Rc,R1a,R3c,Arl), (Za,Rc,R1a,R3c,Arm), (Za,Rc,R1a,R3c,Arn), (Za,Rc,R1a,R3c,Aro), (Za,Rc,R1a,R3c,Arp), (Za,Rc,R1a,R3d,Ara), (Za,Rc,R1a,R3d,Arb), (Za,Rc,R1a,R3d,Arc), (Za,Rc,R1a,R3d,Ard), (Za,Rc,R1a,R3d,Are), (Za,Rc,R1a,R3d,Arf), (Za,Rc,R1a,R3d,Arg), (Za,Rc,R1a,R3d,Arh), (Za,Rc,R1a,R3d,Ari), (Za,Rc,R1a,R3d,Arj), (Za,Rc,R1a,R3d,Ark), (Za,Rc,R1a,R3d,Arl), (Za,Rc,R1a,R3d,Arm), (Za,Rc,R1a,R3d,Arn), (Za,Rc,R1a,R3d,Aro), (Za,Rc,R1a,R3d,Arp), (Za,Rc,R1a,R3e,Ara), (Za,Rc,R1a,R3e,Arb), (Za,Rc,R1a,R3e,Arc), (Za,Rc,R1a,R3e,Ard), (Za,Rc,R1a,R3e,Are), (Za,Rc,R1a,R3e,Arf), (Za,Rc,R1a,R3e,Arg), (Za,Rc,R1a,R3e,Arh), (Za,Rc,R1a,R3e,Ari), (Za,Rc,R1a,R3e,Arj), (Za,Rc,R1a,R3e,Ark), (Za,Rc,R1a,R3e,Arl), (Za,Rc,R1a,R3e,Arm), (Za,Rc,R1a,R3e,Arn), (Za,Rc,R1a,R3e,Aro), (Za,Rc,R1a,R3e,Arp), (Za,Rc,R1a,R3f,Ara), (Za,Rc,R1a,R3f,Arb), (Za,Rc,R1a,R3f,Arc), (Za,Rc,R1a,R3f,Ard), (Za,Rc,R1a,R3f,Are), (Za,Rc,R1a,R3f,Arf), (Za,Rc,R1a,R3f,Arg), (Za,Rc,R1a,R3f,Arh), (Za,Rc,R1a,R3f,Ari), (Za,Rc,R1a,R3f,Arj), (Za, Rc,R1a,R3f,Ark), (Za,Rc,R1a,R3f,Arl), (Za,Rc,R1a,R3f, Arm), (Za,Rc,R1a,R3f,Arn), (Za,Rc,R1a,R3f,Aro), (Za,Rc, R1a,R3f,Arp), (Za,Rc,R1a,R3g,Ara), (Za,Rc,R1a,R3g,Arb), (Za,Rc,R1a,R3g,Arc), (Za,Rc,R1a,R3g,Ard), (Za,Rc,R1a, R3g,Are), (Za,Rc,R1a,R3g,Arf), (Za,Rc,R1a,R3g,Arg), (Za, Rc,R1a,R3g,Arh), (Za,Rc,R1a,R3g,Ari), (Za,Rc,R1a,R3g, Arj), (Za,Rc,R1a,R3g,Ark), (Za,Rc,R1a,R3g,Arl), (Za,Rc, R1a,R3g,Arm), (Za,Rc,R1a,R3g,Arn), (Za,Rc,R1a,R3g, Aro), (Za,Rc,R1a,R3g,Arp), (Za,Rc,R1a,R3h,Ara), (Za,Rc, R1a,R3h,Arb), (Za,Rc,R1a,R3h,Arc), (Za,Rc,R1a,R3h,Ard), (Za,Rc,R1a,R3h,Are), (Za,Rc,R1a,R3h,Arf), (Za,Rc,R1a, R3h,Arg), (Za,Rc,R1a,R3h,Arh), (Za,Rc,R1a,R3h,Ari), (Za, Rc,R1a,R3h,Arj), (Za,Rc,R1a,R3h,Ark), (Za,Rc,R1a,R3h, Arl), (Za,Rc,R1a,R3h,Arm), (Za,Rc,R1a,R3h,Arn), (Za,Rc, R1a,R3h,Aro), (Za,Rc,R1a,R3h,Arp), (Za,Rc,R1b,R3a,Ara), (Za,Rc,R1b,R3a,Arb), (Za,Rc,R1b,R3a,Arc), (Za,Rc,R1b, R3a,Ard), (Za,Rc,R1b,R3a,Are), (Za,Rc,R1b,R3a,Arf), (Za, Rc,R1b,R3a,Arg), (Za,Rc,R1b,R3a,Arh), (Za,Rc,R1b,R3a, Ari), (Za,Rc,R1b,R3a,Arj), (Za,Rc,R1b,R3a,Ark), (Za,Rc, R1b,R3a,Arl), (Za,Rc,R1b,R3a,Arm), (Za,Rc,R1b,R3a, Arn), (Za,Rc,R1b,R3a,Aro), (Za,Rc,R1b,R3a,Arp), (Za,Rc, R1b,R3b,Ara), (Za,Rc,R1b,R3b,Arb), (Za,Rc,R1b,R3b, Arc), (Za,Rc,R1b,R3b,Ard), (Za,Rc,R1b,R3b,Are), (Za,Rc, R1b,R3b,Arf), (Za,Rc,R1b,R3b,Arg), (Za,Rc,R1b,R3b, Arh), (Za,Rc,R1b,R3b,Ari), (Za,Rc,R1b,R3b,Arj), (Za,Rc, R1b,R3b,Ark), (Za,Rc,R1b,R3b,Arl), (Za,Rc,R1b,R3b, Arm), (Za,Rc,R1b,R3b,Arn), (Za,Rc,R1b,R3b,Aro), (Za,Rc, R1b,R3b,Arp), (Za,Rc,R1b,R3c,Ara), (Za,Rc,R1b,R3c, Arb), (Za,Rc,R1b,R3c,Arc), (Za,Rc,R1b,R3c,Ard), (Za,Rc, R1b,R3c,Are), (Za,Rc,R1b,R3c,Arf), (Za,Rc,R1b,R3c,Arg), (Za,Rc,R1b,R3c,Arh), (Za,Rc,R1b,R3c,Ari), (Za,Rc,R1b, R3c,Arj), (Za,Rc,R1b,R3c,Ark), (Za,Rc,R1b,R3c,Arl), (Za, Rc,R1b,R3c,Arm), (Za,Rc,R1b,R3c,Arn), (Za,Rc,R1b,R3c, Aro), (Za,Rc,R1b,R3c,Arp), (Za,Rc,R1b,R3d,Ara), (Za,Rc, R1b,R3d,Arb), (Za,Rc,R1b,R3d,Arc), (Za,Rc,R1b,R3d, Ard), (Za,Rc,R1b,R3d,Are), (Za,Rc,R1b,R3d,Arf), (Za,Rc, R1b,R3d,Arg), (Za,Rc,R1b,R3d,Arh), (Za,Rc,R1b,R3d,Ari), (Za,Rc,R1b,R3d,Arj), (Za,Rc,R1b,R3d,Ark), (Za,Rc,R1b, R3d,Arl), (Za,Rc,R1b,R3d,Arm), (Za,Rc,R1b,R3d,Arn), (Za,Rc,R1b,R3d,Aro), (Za,Rc,R1b,R3d,Arp), (Za,Rc,R1b, R3e,Ara), (Za,Rc,R1b,R3e,Arb), (Za,Rc,R1b,R3e,Arc), (Za, Rc,R1b,R3e,Ard), (Za,Rc,R1b,R3e,Are), (Za,Rc,R1b,R3e, Arf), (Za,Rc,R1b,R3e,Arg), (Za,Rc,R1b,R3e,Arh), (Za,Rc, R1b,R3e,Ari), (Za,Rc,R1b,R3e,Arj), (Za,Rc,R1b,R3e,Ark), (Za,Rc,R1b,R3e,Arl), (Za,Rc,R1b,R3e,Arm), (Za,Rc,R1b, R3e,Arn), (Za,Rc,R1b,R3e,Aro), (Za,Rc,R1b,R3e,Arp), (Za, Rc,R1b,R3f,Ara), (Za,Rc,R1b,R3f,Arb), (Za,Rc,R1b,R3f, Arc), (Za,Rc,R1b,R3f,Ard), (Za,Rc,R1b,R3f,Are), (Za,Rc, R1b,R3f,Arf), (Za,Rc,R1b,R3f,Arg), (Za,Rc,R1b,R3f,Arh), (Za,Rc,R1b,R3f,Ari), (Za,Rc,R1b,R3f,Arj), (Za,Rc,R1b, R3f,Ark), (Za,Rc,R1b,R3f,Arl), (Za,Rc,R1b,R3f,Arm), (Za, Rc,R1b,R3f,Arn), (Za,Rc,R1b,R3f,Aro), (Za,Rc,R1b,R3f, Arp), (Za,Rc,R1b,R3g,Ara), (Za,Rc,R1b,R3g,Arb), (Za,Rc, R1b,R3g,Arc), (Za,Rc,R1b,R3g,Ard), (Za,Rc,R1b,R3g, Are), (Za,Rc,R1b,R3g,Arf), (Za,Rc,R1b,R3g,Arg), (Za,Rc, R1b,R3g,Arh), (Za,Rc,R1b,R3g,Ari), (Za,Rc,R1b,R3g,Arj), (Za,Rc,R1b,R3g,Ark), (Za,Rc,R1b,R3g,Arl), (Za,Rc,R1b, R3g,Arm), (Za,Rc,R1b,R3g,Arn), (Za,Rc,R1b,R3g,Aro), (Za,Rc,R1b,R3g,Arp), (Za,Rc,R1b,R3h,Ara), (Za,Rc,R1b, R3h,Arb), (Za,Rc,R1b,R3h,Arc), (Za,Rc,R1b,R3h,Ard), (Za,Rc,R1b,R3h,Are), (Za,Rc,R1b,R3h,Arf), (Za,Rc,R1b, R3h,Arg), (Za,Rc,R1b,R3h,Arh), (Za,Rc,R1b,R3h,Ari), (Za, Rc,R1b,R3h,Arj), (Za,Rc,R1b,R3h,Ark), (Za,Rc,R1b,R3h, Arl), (Za,Rc,R1b,R3h,Arm), (Za,Rc,R1b,R3h,Arn), (Za,Rc, R1b,R3h,Aro), (Za,Rc,R1b,R3h,Arp), (Za,Rc,R1c,R3a, Ara), (Za,Rc,R1c,R3a,Arb), (Za,Rc,R1c,R3a,Arc), (Za,Rc, R1c,R3a,Ard), (Za,Rc,R1c,R3a,Are), (Za,Rc,R1c,R3a,Arf), (Za,Rc,R1c,R3a,Arg), (Za,Rc,R1c,R3a,Arh), (Za,Rc,R1c, R3a,Ari), (Za,Rc,R1c,R3a,Arj), (Za,Rc,R1c,R3a,Ark), (Za, Rc,R1c,R3a,Arl), (Za,Rc,R1c,R3a,Arm), (Za,Rc,R1c,R3a, Arn), (Za,Rc,R1c,R3a,Aro), (Za,Rc,R1c,R3a,Arp), (Za,Rc, R1c,R3b,Ara), (Za,Rc,R1c,R3b,Arb), (Za,Rc,R1c,R3b,Arc), (Za,Rc,R1c,R3b,Ard), (Za,Rc,R1c,R3b,Are), (Za,Rc,R1c, R3b,Arf), (Za,Rc,R1c,R3b,Arg), (Za,Rc,R1c,R3b,Arh), (Za, Rc,R1c,R3b,Ari), (Za,Rc,R1c,R3b,Arj), (Za,Rc,R1c,R3b, Ark), (Za,Rc,R1c,R3b,Arl), (Za,Rc,R1c,R3b,Arm), (Za,Rc, R1c,R3b,Arn), (Za,Rc,R1c,R3b,Aro), (Za,Rc,R1c,R3b, Arp), (Za,Rc,R1c,R3c,Ara), (Za,Rc,R1c,R3c,Arb), (Za,Rc, R1c,R3c,Arc), (Za,Rc,R1c,R3c,Ard), (Za,Rc,R1c,R3c,Are), (Za,Rc,R1c,R3c,Arf), (Za,Rc,R1c,R3c,Arg), (Za,Rc,R1c, R3c,Arh), (Za,Rc,R1c,R3c,Ari), (Za,Rc,R1c,R3c,Arj), (Za, Rc,R1c,R3c,Ark), (Za,Rc,R1c,R3c,Arl), (Za,Rc,R1c,R3c, Arm), (Za,Rc,R1c,R3c,Arn), (Za,Rc,R1c,R3c,Aro), (Za,Rc, R1c,R3c,Arp), (Za,Rc,R1c,R3d,Ara), (Za,Rc,R1c,R3d,Arb), (Za,Rc,R1c,R3d,Arc), (Za,Rc,R1c,R3d,Ard), (Za,Rc,R1c, R3d,Are), (Za,Rc,R1c,R3d,Arf), (Za,Rc,R1c,R3d,Arg), (Za, Rc,R1c,R3d,Arh), (Za,Rc,R1c,R3d,Ari), (Za,Rc,R1c,R3d, Arj), (Za,Rc,R1c,R3d,Ark), (Za,Rc,R1c,R3d,Arl), (Za,Rc, R1c,R3d,Arm), (Za,Rc,R1c,R3d,Arn), (Za,Rc,R1c,R3d, Aro), (Za,Rc,R1c,R3d,Arp), (Za,Rc,R1c,R3e,Ara), (Za,Rc, R1c,R3e,Arb), (Za,Rc,R1c,R3e,Arc), (Za,Rc,R1c,R3e,Ard), (Za,Rc,R1c,R3e,Are), (Za,Rc,R1c,R3e,Arf), (Za,Rc,R1c, R3e,Arg), (Za,Rc,R1c,R3e,Arh), (Za,Rc,R1c,R3e,Ari), (Za, Rc,R1c,R3e,Arj), (Za,Rc,R1c,R3e,Ark), (Za,Rc,R1c,R3e, Arl), (Za,Rc,R1c,R3e,Arm), (Za,Rc,R1c,R3e,Arn), (Za,Rc, R1c,R3e,Aro), (Za,Rc,R1c,R3e,Arp), (Za,Rc,R1c,R3f,Ara), (Za,Rc,R1c,R3f,Arb), (Za,Rc,R1c,R3f,Arc), (Za,Rc,R1c, R3f,Ard), (Za,Rc,R1c,R3f,Are), (Za,Rc,R1c,R3f,Arf), (Za, Rc,R1c,R3f,Arg), (Za,Rc,R1c,R3f,Arh), (Za,Rc,R1c,R3f, Ari), (Za,Rc,R1c,R3f,Arj), (Za,Rc,R1c,R3f,Ark), (Za,Rc, R1c,R3f,Arl), (Za,Rc,R1c,R3f,Arm), (Za,Rc,R1c,R3f,Arn), (Za,Rc,R1c,R3f,Aro), (Za,Rc,R1c,R3f,Arp), (Za,Rc,R1c, R3g,Ara), (Za,Rc,R1c,R3g,Arb), (Za,Rc,R1c,R3g,Arc), (Za, Rc,R1c,R3g,Ard), (Za,Rc,R1c,R3g,Are), (Za,Rc,R1c,R3g, Arf), (Za,Rc,R1c,R3g,Arg), (Za,Rc,R1c,R3g,Arh), (Za,Rc, R1c,R3g,Ari), (Za,Rc,R1c,R3g,Arj), (Za,Rc,R1c,R3g,Ark), (Za,Rc,R1c,R3g,Arl), (Za,Rc,R1c,R3g,Arm), (Za,Rc,R1c, R3g,Arn), (Za,Rc,R1c,R3g,Aro), (Za,Rc,R1c,R3g,Arp), (Za, Rc,R1c,R3h,Ara), (Za,Rc,R1c,R3h,Arb), (Za,Rc,R1c,R3h, Arc), (Za,Rc,R1c,R3h,Ard), (Za,Rc,R1c,R3h,Are), (Za,Rc, R1c,R3h,Arf), (Za,Rc,R1c,R3h,Arg), (Za,Rc,R1c,R3h,Arh), (Za,Rc,R1c,R3h,Ari), (Za,Rc,R1c,R3h,Arj), (Za,Rc,R1c, R3h,Ark), (Za,Rc,R1c,R3h,Arl), (Za,Rc,R1c,R3h,Arm), (Za,Rc,R1c,R3h,Arn), (Za,Rc,R1c,R3h,Aro), (Za,Rc,R1c, R3h,Arp), (Za,Rc,R1d,R3a,Ara), (Za,Rc,R1d,R3a,Arb), (Za, Rc,R1d,R3a,Arc), (Za,Rc,R1d,R3a,Ard), (Za,Rc,R1d,R3a, Are), (Za,Rc,R1d,R3a,Arf), (Za,Rc,R1d,R3a,Arg), (Za,Rc, R1d,R3a,Arh), (Za,Rc,R1d,R3a,Ari), (Za,Rc,R1d,R3a, Arj), (Za,Rc,R1d,R3a,Ark), (Za,Rc,R1d,R3a,Arl), (Za,Rc,R1d, R3a,Arm), (Za,Rc,R1d,R3a,Arn), (Za,Rc,R1d,R3a,Aro), (Za,Rc,R1d,R3a,Arp), (Za,Rc,R1d,R3b,Ara), (Za,Rc,R1d, R3b,Arb), (Za,Rc,R1d,R3b,Arc), (Za,Rc,R1d,R3b,Ard), (Za,Rc,R1d,R3b,Are), (Za,Rc,R1d,R3b,Arf), (Za,Rc,R1d, R3b,Arg), (Za,Rc,R1d,R3b,Arh), (Za,Rc,R1d,R3b,Ari), (Za, Rc,R1d,R3b,Arj), (Za,Rc,R1d,R3b,Ark), (Za,Rc,R1d,R3b, Arl), (Za,Rc,R1d,R3b,Arm), (Za,Rc,R1d,R3b,Arn), (Za,Rc, R1d,R3b,Aro), (Za,Rc,R1d,R3b,Arp), (Za,Rc,R1d,R3c, Ara), (Za,Rc,R1d,R3c,Arb), (Za,Rc,R1d,R3c,Arc), (Za,Rc, R1d,R3c,Ard), (Za,Rc,R1d,R3c,Are), (Za,Rc,R1d,R3c,Arf), (Za,Rc,R1d,R3c,Arg), (Za,Rc,R1d,R3c,Arh), (Za,Rc,R1d, R3c,Ari), (Za,Rc,R1d,R3c,Arj), (Za,Rc,R1d,R3c,Ark), (Za, Rc,R1d,R3c,Arl), (Za,Rc,R1d,R3c,Arm), (Za,Rc,R1d,R3c, Arn), (Za,Rc,R1d,R3c,Aro), (Za,Rc,R1d,R3c,Arp), (Za,Rc, R1d,R3d,Ara), (Za,Rc,R1d,R3d,Arb), (Za,Rc,R1d,R3d, Arc), (Za,Rc,R1d,R3d,Ard), (Za,Rc,R1d,R3d,Are), (Za,Rc,R1d,R3d,Arf), (Za,Rc,R1d,R3d,Arg), (Za,Rc,R1d,R3d,Arh), (Za,Rc,R1d,R3d,Ari), (Za,Rc,R1d,R3d,Arj), (Za,Rc,R1d,R3d,Ark), (Za,Rc,R1d,R3d,Arl), (Za,Rc,R1d,R3d,Arm), (Za,Rc,R1d,R3d,Arn), (Za,Rc,R1d,R3d,Aro), (Za,Rc,R1d,R3d,Arp), (Za,Rc,R1d,R3e,Ara), (Za,Rc,R1d,R3e,Arb), (Za,Rc,R1d,R3e,Arc), (Za,Rc,R1d,R3e,Ard), (Za,Rc,R1d,R3e,Are), (Za,Rc,R1d,R3e,Arf), (Za,Rc,R1d,R3e,Arg), (Za,Rc,R1d,R3e,Arh), (Za,Rc,R1d,R3e,Ari), (Za,Rc,R1d,R3e,Arj), (Za,Rc,R1d,R3e,Ark), (Za,Rc,R1d,R3e,Arl), (Za,Rc,R1d,R3e,Arm), (Za,Rc,R1d,R3e,Arn), (Za,Rc,R1d,R3e,Aro), (Za,Rc,R1d,R3e,Arp), (Za,Rc,R1d,R3f,Ara), (Za,Rc,R1d,R3f,Arb), (Za,Rc,R1d,R3f,Arc), (Za,Rc,R1d,R3f,Ard), (Za,Rc,R1d,R3f,Are), (Za,Rc,R1d,R3f,Arf), (Za,Rc,R1d,R3f,Arg), (Za,Rc,R1d,R3f,Arh), (Za,Rc,R1d,R3f,Ari), (Za,Rc,R1d,R3f,Arj), (Za,Rc,R1d,R3f,Ark), (Za,Rc,R1d,R3f,Arl), (Za,Rc,R1d,R3f,Arm), (Za,Rc,R1d,R3f,Arn), (Za,Rc,R1d,R3f,Aro), (Za,Rc,R1d,R3f,Arp), (Za,Rc,R1d,R3g,Ara), (Za,Rc,R1d,R3g,Arb), (Za,Rc,R1d,R3g,Arc), (Za,Rc,R1d,R3g,Ard), (Za,Rc,R1d,R3g,Are), (Za,Rc,R1d,R3g,Arf), (Za,Rc,R1d,R3g,Arg), (Za,Rc,R1d,R3g,Arh), (Za,Rc,R1d,R3g,Ari), (Za,Rc,R1d,R3g,Arj), (Za,Rc,R1d,R3g,Ark), (Za,Rc,R1d,R3g,Arl), (Za,Rc,R1d,R3g,Arm), (Za,Rc,R1d,R3g,Arn), (Za,Rc,R1d,R3g,Aro), (Za,Rc,R1d,R3g,Arp), (Za,Rc,R1d,R3h,Ara), (Za,Rc,R1d,R3h,Arb), (Za,Rc,R1d,R3h,Arc), (Za,Rc,R1d,R3h,Ard), (Za,Rc,R1d,R3h,Are), (Za,Rc,R1d,R3h,Arf), (Za,Rc,R1d,R3h,Arg), (Za,Rc,R1d,R3h,Arh), (Za,Rc,R1d,R3h,Ari), (Za,Rc,R1d,R3h,Arj), (Za,Rc,R1d,R3h,Ark), (Za,Rc,R1d,R3h,Arl), (Za,Rc,R1d,R3h,Arm), (Za,Rc,R1d,R3h,Arn), (Za,Rc,R1d,R3h,Aro), (Za,Rc,R1d,R3h,Arp), (Za,Rd,R1a,R3a,Ara), (Za,Rd,R1a,R3a,Arb), (Za,Rd,R1a,R3a,Arc), (Za,Rd,R1a,R3a,Ard), (Za,Rd,R1a,R3a,Are), (Za,Rd,R1a,R3a,Arf), (Za,Rd,R1a,R3a,Arg), (Za,Rd,R1a,R3a,Arh), (Za,Rd,R1a,R3a,Ari), (Za,Rd,R1a,R3a,Arj), (Za,Rd,R1a,R3a,Ark), (Za,Rd,R1a,R3a,Arl), (Za,Rd,R1a,R3a,Arm), (Za,Rd,R1a,R3a,Arn), (Za,Rd,R1a,R3a,Aro), (Za,Rd,R1a,R3a,Arp), (Za,Rd,R1a,R3b,Ara), (Za,Rd,R1a,R3b,Arb), (Za,Rd,R1a,R3b,Arc), (Za,Rd,R1a,R3b,Ard), (Za,Rd,R1a,R3b,Are), (Za,Rd,R1a,R3b,Arf), (Za,Rd,R1a,R3b,Arg), (Za,Rd,R1a,R3b,Arh), (Za,Rd,R1a,R3b,Ari), (Za,Rd,R1a,R3b,Arj), (Za,Rd,R1a,R3b,Ark), (Za,Rd,R1a,R3b,Arl), (Za,Rd,R1a,R3b,Arm), (Za,Rd,R1a,R3b,Arn), (Za,Rd,R1a,R3b,Aro), (Za,Rd,R1a,R3b,Arp), (Za,Rd,R1a,R3c,Ara), (Za,Rd,R1a,R3c,Arb), (Za,Rd,R1a,R3c,Arc), (Za,Rd,R1a,R3c,Ard), (Za,Rd,R1a,R3c,Are), (Za,Rd,R1a,R3c,Arf), (Za,Rd,R1a,R3c,Arg), (Za,Rd,R1a,R3c,Arh), (Za,Rd,R1a,R3c,Ari), (Za,Rd,R1a,R3c,Arj), (Za,Rd,R1a,R3c,Ark), (Za,Rd,R1a,R3c,Arl), (Za,Rd,R1a,R3c,Arm), (Za,Rd,R1a,R3c,Arn), (Za,Rd,R1a,R3c,Aro), (Za,Rd,R1a,R3c,Arp), (Za,Rd,R1a,R3d,Ara), (Za,Rd,R1a,R3d,Arb), (Za,Rd,R1a,R3d,Arc), (Za,Rd,R1a,R3d,Ard), (Za,Rd,R1a,R3d,Are), (Za,Rd,R1a,R3d,Arf), (Za,Rd,R1a,R3d,Arg), (Za,Rd,R1a,R3d,Arh), (Za,Rd,R1a,R3d,Ari), (Za,Rd,R1a,R3d,Arj), (Za,Rd,R1a,R3d,Ark), (Za,Rd,R1a,R3d,Arl), (Za,Rd,R1a,R3d,Arm), (Za,Rd,R1a,R3d,Arn), (Za,Rd,R1a,R3d,Aro), (Za,Rd,R1a,R3d,Arp), (Za,Rd,R1a,R3e,Ara), (Za,Rd,R1a,R3e,Arb), (Za,Rd,R1a,R3e,Arc), (Za,Rd,R1a,R3e,Ard), (Za,Rd,R1a,R3e,Are), (Za,Rd,R1a,R3e,Arf), (Za,Rd,R1a,R3e,Arg), (Za,Rd,R1a,R3e,Arh), (Za,Rd,R1a,R3e,Ari), (Za,Rd,R1a,R3e,Arj), (Za,Rd,R1a,R3e,Ark), (Za,Rd,R1a,R3e,Arl), (Za,Rd,R1a,R3e,Arm), (Za,Rd,R1a,R3e,Arn), (Za,Rd,R1a,R3e,Aro), (Za,Rd,R1a,R3e,Arp), (Za,Rd,R1a,R3f,Ara), (Za,Rd,R1a,R3f,Arb), (Za,Rd,R1a,R3f,Arc), (Za,Rd,R1a,R3f,Ard), (Za,Rd,R1a,R3f,Are), (Za,Rd,R1a,R3f,Arf), (Za,Rd,R1a,R3f,Arg), (Za,Rd,R1a,R3f,Arh), (Za,Rd,R1a,R3f,Ari), (Za,Rd,R1a,R3f,Arj), (Za,Rd,R1a,R3f,Ark), (Za,Rd,R1a,R3f,Arl), (Za,Rd,R1a,R3f,Arm), (Za,Rd,R1a,R3f,Arn), (Za,Rd,R1a,R3f,Aro), (Za,Rd,R1a,R3f,Arp), (Za,Rd,R1a,R3g,Ara), (Za,Rd,R1a,R3g,Arb), (Za,Rd,R1a,R3g,Arc), (Za,Rd,R1a,R3g,Ard), (Za,Rd,R1a,R3g,Are), (Za,Rd,R1a,R3g,Arf), (Za,Rd,R1a,R3g,Arg), (Za,Rd,R1a,R3g,Arh), (Za,Rd,R1a,R3g,Ari), (Za,Rd,R1a,R3g,Arj), (Za,Rd,R1a,R3g,Ark), (Za,Rd,R1a,R3g,Arl), (Za,Rd,R1a,R3g,Arm), (Za,Rd,R1a,R3g,Arn), (Za,Rd,R1a,R3g,Aro), (Za,Rd,R1a,R3g,Arp), (Za,Rd,R1a,R3h,Ara), (Za,Rd,R1a,R3h,Arb), (Za,Rd,R1a,R3h,Arc), (Za,Rd,R1a,R3h,Ard), (Za,Rd,R1a,R3h,Are), (Za,Rd,R1a,R3h,Arf), (Za,Rd,R1a,R3h,Arg), (Za,Rd,R1a,R3h,Arh), (Za,Rd,R1a,R3h,Ari), (Za,Rd,R1a,R3h,Arj), (Za,Rd,R1a,R3h,Ark), (Za,Rd,R1a,R3h,Arl), (Za,Rd,R1a,R3h,Arm), (Za,Rd,R1a,R3h,Arn), (Za,Rd,R1a,R3h,Aro), (Za,Rd,R1a,R3h,Arp), (Za,Rd,R1b,R3a,Ara), (Za,Rd,R1b,R3a,Arb), (Za,Rd,R1b,R3a,Arc), (Za,Rd,R1b,R3a,Ard), (Za,Rd,R1b,R3a,Are), (Za,Rd,R1b,R3a,Arf), (Za,Rd,R1b,R3a,Arg), (Za,Rd,R1b,R3a,Arh), (Za,Rd,R1b,R3a,Ari), (Za,Rd,R1b,R3a,Arj), (Za,Rd,R1b,R3a,Ark), (Za,Rd,R1b,R3a,Arl), (Za,Rd,R1b,R3a,Arm), (Za,Rd,R1b,R3a,Arn), (Za,Rd,R1b,R3a,Aro), (Za,Rd,R1b,R3a,Arp), (Za,Rd,R1b,R3b,Ara), (Za,Rd,R1b,R3b,Arb), (Za,Rd,R1b,R3b,Arc), (Za,Rd,R1b,R3b,Ard), (Za,Rd,R1b,R3b,Are), (Za,Rd,R1b,R3b,Arf), (Za,Rd,R1b,R3b,Arg), (Za,Rd,R1b,R3b,Arh), (Za,Rd,R1b,R3b,Ari), (Za,Rd,R1b,R3b,Arj), (Za,Rd,R1b,R3b,Ark), (Za,Rd,R1b,R3b,Arl), (Za,Rd,R1b,R3b,Arm), (Za,Rd,R1b,R3b,Arn), (Za,Rd,R1b,R3b,Aro), (Za,Rd,R1b,R3b,Arp), (Za,Rd,R1b,R3c,Ara), (Za,Rd,R1b,R3c,Arb), (Za,Rd,R1b,R3c,Arc), (Za,Rd,R1b,R3c,Ard), (Za,Rd,R1b,R3c,Are), (Za,Rd,R1b,R3c,Arf), (Za,Rd,R1b,R3c,Arg), (Za,Rd,R1b,R3c,Arh), (Za,Rd,R1b,R3c,Ari), (Za,Rd,R1b,R3c,Arj), (Za,Rd,R1b,R3c,Ark), (Za,Rd,R1b,R3c,Arl), (Za,Rd,R1b,R3c,Arm), (Za,Rd,R1b,R3c,Arn), (Za,Rd,R1b,R3c,Aro), (Za,Rd,R1b,R3c,Arp), (Za,Rd,R1b,R3d,Ara), (Za,Rd,R1b,R3d,Arb), (Za,Rd,R1b,R3d,Arc), (Za,Rd,R1b,R3d,Ard), (Za,Rd,R1b,R3d,Are), (Za,Rd,R1b,R3d,Arf), (Za,Rd,R1b,R3d,Arg), (Za,Rd,R1b,R3d,Arh), (Za,Rd,R1b,R3d,Ari), (Za,Rd,R1b,R3d,Arj), (Za,Rd,R1b,R3d,Ark), (Za,Rd,R1b,R3d,Arl), (Za,Rd,R1b,R3d,Arm), (Za,Rd,R1b,R3d,Arn), (Za,Rd,R1b,R3d,Aro), (Za,Rd,R1b,R3d,Arp), (Za,Rd,R1b,R3e,Ara), (Za,Rd,R1b,R3e,Arb), (Za,Rd,R1b,R3e,Arc), (Za,Rd,R1b,R3e,Ard), (Za,Rd,R1b,R3e,Are), (Za,Rd,R1b,R3e,Arf), (Za,Rd,R1b,R3e,Arg), (Za,Rd,R1b,R3e,Arh), (Za,Rd,R1b,R3e,Ari), (Za,Rd,R1b,R3e,Arj), (Za,Rd,R1b,R3e,Ark), (Za,Rd,R1b,R3e,Arl), (Za,Rd,R1b,R3e,Arm), (Za,Rd,R1b,R3e,Arn), (Za,Rd,R1b,R3e,Aro), (Za,Rd,R1b,R3e,Arp), (Za,Rd,R1b,R3f,Ara), (Za,Rd,R1b,R3f,Arb), (Za,Rd,R1b,R3f,Arc), (Za,Rd,R1b,R3f,Ard), (Za,Rd,R1b,R3f,Are), (Za,Rd,R1b,R3f,Arf), (Za,Rd,R1b,R3f,Arg), (Za,Rd,R1b,R3f,Arh), (Za,Rd,R1b,R3f,Ari), (Za,Rd,R1b,R3f,Arj), (Za,Rd,R1b,R3f,Ark), (Za,Rd,R1b,R3f,Arl), (Za,Rd,R1b,R3f,Arm), (Za,Rd,R1b,R3f,Arn), (Za,Rd,R1b,R3f,Aro), (Za,Rd,R1b,R3f,Arp), (Za,Rd,R1b,R3g,Ara), (Za,Rd,R1b,R3g,Arb), (Za,Rd,R1b,R3g,Arc), (Za,Rd,R1b,R3g,Ard), (Za,Rd,R1b,R3g,Are), (Za,Rd,R1b,R3g,Arf), (Za,Rd,R1b,R3g,Arg), (Za,Rd,R1b,R3g,Arh), (Za,Rd,R1b,R3g,Ari), (Za,Rd,R1b,R3g,Arj), (Za,Rd,R1b,R3g,Ark), (Za,Rd,R1b,R3g,Arl), (Za,Rd,R1b,R3g,Arm), (Za,Rd,R1b,R3g,Arn), (Za,Rd,R1b,R3g,Aro), (Za,Rd,R1b,R3g,Arp), (Za,Rd,R1b,R3h,Ara), (Za,Rd,R1b,R3h,Arb), (Za,Rd,R1b,R3h,Arc), (Za,Rd,R1b,R3h,Ard), (Za,Rd,R1b,R3h,Are), (Za,Rd,R1b,R3h,Arf), (Za,Rd,R1b,R3h,Arg), (Za,Rd,R1b,R3h,Arh), (Za,Rd,R1b,R3h,Ari), (Za,Rd,R1b,R3h,Arj), (Za,Rd,R1b,R3h,Ark), (Za,Rd,R1b,R3h,Arl), (Za,Rd,R1b,R3h,Arm), (Za,Rd,R1b,R3h,Arn), (Za,Rd,R1b,R3h,Aro), (Za,Rd,R1b,R3h,Arp), (Za,Rd,R1c,R3a,Ara), (Za,Rd,R1c,R3a,Arb), (Za,Rd,R1c,R3a,Arc), (Za,Rd,R1c,R3a,Ard), (Za,Rd,R1c,R3a,Are), (Za,Rd,R1c,R3a,Arf), (Za,Rd,R1c,R3a,Arg), (Za,Rd,R1c,R3a,Arh), (Za,Rd,R1c,R3a,Ari), (Za,Rd,R1c, R3a,Arj), (Za,Rd,R1c,R3a,Ark), (Za,Rd,R1c,R3a,Arl), (Za,Rd,R1c,R3a,Arm), (Za,Rd,R1c,R3a,Arn), (Za,Rd,R1c,R3a,Aro), (Za,Rd,R1c,R3a,Arp), (Za,Rd,R1c,R3b,Ara), (Za,Rd,R1c,R3b,Arb), (Za,Rd,R1c,R3b,Arc), (Za,Rd,R1c,R3b,Ard), (Za,Rd,R1c,R3b,Are), (Za,Rd,R1c,R3b,Arf), (Za,Rd,R1c,R3b,Arg), (Za,Rd,R1c,R3b,Arh), (Za,Rd,R1c,R3b,Ari), (Za,Rd,R1c,R3b,Arj), (Za,Rd,R1c,R3b,Ark), (Za,Rd,R1c,R3b,Arl), (Za,Rd,R1c,R3b,Arm), (Za,Rd,R1c,R3b,Arn), (Za,Rd,R1c,R3b,Aro), (Za,Rd,R1c,R3b,Arp), (Za,Rd,R1c,R3c,Ara), (Za,Rd,R1c,R3c,Arb), (Za,Rd,R1c,R3c,Arc), (Za,Rd,R1c,R3c,Ard), (Za,Rd,R1c,R3c,Are), (Za,Rd,R1c,R3c,Arf), (Za,Rd,R1c,R3c,Arg), (Za,Rd,R1c,R3c,Arh), (Za,Rd,R1c,R3c,Ari), (Za,Rd,R1c,R3c,Arj), (Za,Rd,R1c,R3c,Ark), (Za,Rd,R1c,R3c,Arl), (Za,Rd,R1c,R3c,Arm), (Za,Rd,R1c,R3c,Arn), (Za,Rd,R1c,R3c,Aro), (Za,Rd,R1c,R3c,Arp), (Za,Rd,R1c,R3d,Ara), (Za,Rd,R1c,R3d,Arb), (Za,Rd,R1c,R3d,Arc), (Za,Rd,R1c,R3d,Ard), (Za,Rd,R1c,R3d,Are), (Za,Rd,R1c,R3d,Arf), (Za,Rd,R1c,R3d,Arg), (Za,Rd,R1c,R3d,Arh), (Za,Rd,R1c,R3d,Ari), (Za,Rd,R1c,R3d,Arj), (Za,Rd,R1c,R3d,Ark), (Za,Rd,R1c,R3d,Arl), (Za,Rd,R1c,R3d,Arm), (Za,Rd,R1c,R3d,Arn), (Za,Rd,R1c,R3d,Aro), (Za,Rd,R1c,R3d,Arp), (Za,Rd,R1c,R3e,Ara), (Za,Rd,R1c,R3e,Arb), (Za,Rd,R1c,R3e,Arc), (Za,Rd,R1c,R3e,Ard), (Za,Rd,R1c,R3e,Are), (Za,Rd,R1c,R3e,Arf), (Za,Rd,R1c,R3e,Arg), (Za,Rd,R1c,R3e,Arh), (Za,Rd,R1c,R3e,Ari), (Za,Rd,R1c,R3e,Arj), (Za,Rd,R1c,R3e,Ark), (Za,Rd,R1c,R3e,Arl), (Za,Rd,R1c,R3e,Arm), (Za,Rd,R1c,R3e,Arn), (Za,Rd,R1c,R3e,Aro), (Za,Rd,R1c,R3e,Arp), (Za,Rd,R1c,R3f,Ara), (Za,Rd,R1c,R3f,Arb), (Za,Rd,R1c,R3f,Arc), (Za,Rd,R1c,R3f,Ard), (Za,Rd,R1c,R3f,Are), (Za,Rd,R1c,R3f,Arf), (Za,Rd,R1c,R3f,Arg), (Za,Rd,R1c,R3f,Arh), (Za,Rd,R1c,R3f,Ari), (Za,Rd,R1c,R3f,Arj), (Za,Rd,R1c,R3f,Ark), (Za,Rd,R1c,R3f,Arl), (Za,Rd,R1c,R3f,Arm), (Za,Rd,R1c,R3f,Arn), (Za,Rd,R1c,R3f,Aro), (Za,Rd,R1c,R3f,Arp), (Za,Rd,R1c,R3g,Ara), (Za,Rd,R1c,R3g,Arb), (Za,Rd,R1c,R3g,Arc), (Za,Rd,R1c,R3g,Ard), (Za,Rd,R1c,R3g,Are), (Za,Rd,R1c,R3g,Arf), (Za,Rd,R1c,R3g,Arg), (Za,Rd,R1c,R3g,Arh), (Za,Rd,R1c,R3g,Ari), (Za,Rd,R1c,R3g,Arj), (Za,Rd,R1c,R3g,Ark), (Za,Rd,R1c,R3g,Arl), (Za,Rd,R1c,R3g,Arm), (Za,Rd,R1c,R3g,Arn), (Za,Rd,R1c,R3g,Aro), (Za,Rd,R1c,R3g,Arp), (Za,Rd,R1c,R3h,Ara), (Za,Rd,R1c,R3h,Arb), (Za,Rd,R1c,R3h,Arc), (Za,Rd,R1c,R3h,Ard), (Za,Rd,R1c,R3h,Are), (Za,Rd,R1c,R3h,Arf), (Za,Rd,R1c,R3h,Arg), (Za,Rd,R1c,R3h,Arh), (Za,Rd,R1c,R3h,Ari), (Za,Rd,R1c,R3h,Arj), (Za,Rd,R1c,R3h,Ark), (Za,Rd,R1c,R3h,Arl), (Za,Rd,R1c,R3h,Arm), (Za,Rd,R1c,R3h,Arn), (Za,Rd,R1c,R3h,Aro), (Za,Rd,R1c,R3h,Arp), (Za,Rd,R1d,R3a,Ara), (Za,Rd,R1d,R3a,Arb), (Za,Rd,R1d,R3a,Arc), (Za,Rd,R1d,R3a,Ard), (Za,Rd,R1d,R3a,Are), (Za,Rd,R1d,R3a,Arf), (Za,Rd,R1d,R3a,Arg), (Za,Rd,R1d,R3a,Arh), (Za,Rd,R1d,R3a,Ari), (Za,Rd,R1d,R3a,Arj), (Za,Rd,R1d,R3a,Ark), (Za,Rd,R1d,R3a,Arl), (Za,Rd,R1d,R3a,Arm), (Za,Rd,R1d,R3a,Arn), (Za,Rd,R1d,R3a,Aro), (Za,Rd,R1d,R3a,Arp), (Za,Rd,R1d,R3b,Ara), (Za,Rd,R1d,R3b,Arb), (Za,Rd,R1d,R3b,Arc), (Za,Rd,R1d,R3b,Ard), (Za,Rd,R1d,R3b,Are), (Za,Rd,R1d,R3b,Arf), (Za,Rd,R1d,R3b,Arg), (Za,Rd,R1d,R3b,Arh), (Za,Rd,R1d,R3b,Ari), (Za,Rd,R1d,R3b,Arj), (Za,Rd,R1d,R3b,Ark), (Za,Rd,R1d,R3b,Arl), (Za,Rd,R1d,R3b,Arm), (Za,Rd,R1d,R3b,Arn), (Za,Rd,R1d,R3b,Aro), (Za,Rd,R1d,R3b,Arp), (Za,Rd,R1d,R3c,Ara), (Za,Rd,R1d,R3c,Arb), (Za,Rd,R1d,R3c,Arc), (Za,Rd,R1d,R3c,Ard), (Za,Rd,R1d,R3c,Are), (Za,Rd,R1d,R3c,Arf), (Za,Rd,R1d,R3c,Arg), (Za,Rd,R1d,R3c,Arh), (Za,Rd,R1d,R3c,Ari), (Za,Rd,R1d,R3c,Arj), (Za,Rd,R1d,R3c,Ark), (Za,Rd,R1d,R3c,Arl), (Za,Rd,R1d,R3c,Arm), (Za,Rd,R1d,R3c,Arn), (Za,Rd,R1d,R3c,Aro), (Za,Rd,R1d,R3c,Arp), (Za,Rd,R1d,R3d,Ara), (Za,Rd,R1d,R3d,Arb), (Za,Rd,R1d,R3d,Arc), (Za,Rd,R1d,R3d,Ard), (Za,Rd,R1d,R3d,Are), (Za,Rd,R1d,R3d,Arf), (Za,Rd,R1d,R3d,Arg), (Za,Rd,R1d,R3d,Arh), (Za,Rd,R1d,R3d,Ari), (Za,Rd,R1d,R3d,Arj), (Za,Rd,R1d,R3d,Ark), (Za,Rd,R1d,R3d,Arl), (Za,Rd,R1d,R3d,Arm), (Za,Rd,R1d,R3d,Arn), (Za,Rd,R1d,R3d,Aro), (Za,Rd,R1d,R3d,Arp), (Za,Rd,R1d,R3e,Ara), (Za,Rd,R1d,R3e,Arb), (Za,Rd,R1d,R3e,Arc), (Za,Rd,R1d,R3e,Ard), (Za,Rd,R1d,R3e,Are), (Za,Rd,R1d,R3e,Arf), (Za,Rd,R1d,R3e,Arg), (Za,Rd,R1d,R3e,Arh), (Za,Rd,R1d,R3e,Ari), (Za,Rd,R1d,R3e,Arj), (Za,Rd,R1d,R3e,Ark), (Za,Rd,R1d,R3e,Arl), (Za,Rd,R1d,R3e,Arm), (Za,Rd,R1d,R3e,Arn), (Za,Rd,R1d,R3e,Aro), (Za,Rd,R1d,R3e,Arp), (Za,Rd,R1d,R3f,Ara), (Za,Rd,R1d,R3f,Arb), (Za,Rd,R1d,R3f,Arc), (Za,Rd,R1d,R3f,Ard), (Za,Rd,R1d,R3f,Are), (Za,Rd,R1d,R3f,Arf), (Za,Rd,R1d,R3f,Arg), (Za,Rd,R1d,R3f,Arh), (Za,Rd,R1d,R3f,Ari), (Za,Rd,R1d,R3f,Arj), (Za,Rd,R1d,R3f,Ark), (Za,Rd,R1d,R3f,Arl), (Za,Rd,R1d,R3f,Arm), (Za,Rd,R1d,R3f,Arn), (Za,Rd,R1d,R3f,Aro), (Za,Rd,R1d,R3f,Arp), (Za,Rd,R1d,R3g,Ara), (Za,Rd,R1d,R3g,Arb), (Za,Rd,R1d,R3g,Arc), (Za,Rd,R1d,R3g,Ard), (Za,Rd,R1d,R3g,Are), (Za,Rd,R1d,R3g,Arf), (Za,Rd,R1d,R3g,Arg), (Za,Rd,R1d,R3g,Arh), (Za,Rd,R1d,R3g,Ari), (Za,Rd,R1d,R3g,Arj), (Za,Rd,R1d,R3g,Ark), (Za,Rd,R1d,R3g,Arl), (Za,Rd,R1d,R3g,Arm), (Za,Rd,R1d,R3g,Arn), (Za,Rd,R1d,R3g,Aro), (Za,Rd,R1d,R3g,Arp), (Za,Rd,R1d,R3h,Ara), (Za,Rd,R1d,R3h,Arb), (Za,Rd,R1d,R3h,Arc), (Za,Rd,R1d,R3h,Ard), (Za,Rd,R1d,R3h,Are), (Za,Rd,R1d,R3h,Arf), (Za,Rd,R1d,R3h,Arg), (Za,Rd,R1d,R3h,Arh), (Za,Rd,R1d,R3h,Ari), (Za,Rd,R1d,R3h,Arj), (Za,Rd,R1d,R3h,Ark), (Za,Rd,R1d,R3h,Arl), (Za,Rd,R1d,R3h,Arm), (Za,Rd,R1d,R3h,Arn), (Za,Rd,R1d,R3h,Aro), (Za,Rd,R1d,R3h,Arp), (Za,Re,R1a,R3a,Ara), (Za,Re,R1a,R3a,Arb), (Za,Re,R1a,R3a,Arc), (Za,Re,R1a,R3a,Ard), (Za,Re,R1a,R3a,Are), (Za,Re,R1a,R3a,Arf), (Za,Re,R1a,R3a,Arg), (Za,Re,R1a,R3a,Arh), (Za,Re,R1a,R3a,Ari), (Za,Re,R1a,R3a,Arj), (Za,Re,R1a,R3a,Ark), (Za,Re,R1a,R3a,Arl), (Za,Re,R1a,R3a,Arm), (Za,Re,R1a,R3a,Arn), (Za,Re,R1a,R3a,Aro), (Za,Re,R1a,R3a,Arp), (Za,Re,R1a,R3b,Ara), (Za,Re,R1a,R3b,Arb), (Za,Re,R1a,R3b,Arc), (Za,Re,R1a,R3b,Ard), (Za,Re,R1a,R3b,Are), (Za,Re,R1a,R3b,Arf), (Za,Re,R1a,R3b,Arg), (Za,Re,R1a,R3b,Arh), (Za,Re,R1a,R3b,Ari), (Za,Re,R1a,R3b,Arj), (Za,Re,R1a,R3b,Ark), (Za,Re,R1a,R3b,Arl), (Za,Re,R1a,R3b,Arm), (Za,Re,R1a,R3b,Arn), (Za,Re,R1a,R3b,Aro), (Za,Re,R1a,R3b,Arp), (Za,Re,R1a,R3c,Ara), (Za,Re,R1a,R3c,Arb), (Za,Re,R1a,R3c,Arc), (Za,Re,R1a,R3c,Ard), (Za,Re,R1a,R3c,Are), (Za,Re,R1a,R3c,Arf), (Za,Re,R1a,R3c,Arg), (Za,Re,R1a,R3c,Arh), (Za,Re,R1a,R3c,Ari), (Za,Re,R1a,R3c,Arj), (Za,Re,R1a,R3c,Ark), (Za,Re,R1a,R3c,Arl), (Za,Re,R1a,R3c,Arm), (Za,Re,R1a,R3c,Arn), (Za,Re,R1a,R3c,Aro), (Za,Re,R1a,R3c,Arp), (Za,Re,R1a,R3d,Ara), (Za,Re,R1a,R3d,Arb), (Za,Re,R1a,R3d,Arc), (Za,Re,R1a,R3d,Ard), (Za,Re,R1a,R3d,Are), (Za,Re,R1a,R3d,Arf), (Za,Re,R1a,R3d,Arg), (Za,Re,R1a,R3d,Arh), (Za,Re,R1a,R3d,Ari), (Za,Re,R1a,R3d,Arj), (Za,Re,R1a,R3d,Ark), (Za,Re,R1a,R3d,Arl), (Za,Re,R1a,R3d,Arm), (Za,Re,R1a,R3d,Arn), (Za,Re,R1a,R3d,Aro), (Za,Re,R1a,R3d,Arp), (Za,Re,R1a,R3e,Ara), (Za,Re,R1a,R3e,Arb), (Za,Re,R1a,R3e,Arc), (Za,Re,R1a,R3e,Ard), (Za,Re,R1a,R3e,Are), (Za,Re,R1a,R3e,Arf), (Za,Re,R1a,R3e,Arg), (Za,Re,R1a,R3e,Arh), (Za,Re,R1a,R3e,Ari), (Za,Re,R1a,R3e,Arj), (Za,Re,R1a,R3e,Ark), (Za,Re,R1a,R3e,Arl), (Za,Re,R1a,R3e,Arm), (Za,Re,R1a,R3e,Arn), (Za,Re,R1a,R3e,Aro), (Za,Re,R1a,R3e,Arp), (Za,Re,R1a,R3f,Ara), (Za,Re,R1a,R3f,Arb), (Za,Re,R1a,R3f,Arc), (Za,Re,R1a,R3f,Ard), (Za,Re,R1a,R3f,Are), (Za,Re,R1a,R3f,Arf), (Za,Re,R1a,R3f,Arg), (Za,Re,R1a,R3f,Arh), (Za,Re,R1a,R3f,Ari), (Za,Re,R1a,R3f,Arj), (Za,Re,R1a,R3f,Ark), (Za,Re,R1a,R3f,Arl), (Za,Re,R1a,R3f,Arm), (Za,Re,R1a,R3f,Arn), (Za,Re,R1a,R3f,Aro), (Za,Re,R1a,R3f,Arp), (Za,Re,R1a,R3g,Ara), (Za,Re,R1a,R3g,Arb), (Za,Re,R1a,R3g,Arc), (Za,Re,R1a,R3g,Ard), (Za,Re,R1a, R3g,Are), (Za,Re,R1a,R3g,Arf), (Za,Re,R1a,R3g,Arg), (Za, Re,R1a,R3g,Arh), (Za,Re,R1a,R3g,Ari), (Za,Re,R1a,R3g, Arj), (Za,Re,R1a,R3g,Ark), (Za,Re,R1a,R3g,Arl), (Za,Re, R1a,R3g,Arm), (Za,Re,R1a,R3g,Arn), (Za,Re,R1a,R3g, Aro), (Za,Re,R1a,R3g,Arp), (Za,Re,R1a,R3h,Ara), (Za,Re, R1a,R3h,Arb), (Za,Re,R1a,R3h,Arc), (Za,Re,R1a,R3h,Ard), (Za,Re,R1a,R3h,Are), (Za,Re,R1a,R3h,Arf), (Za,Re,R1a, R3h,Arg), (Za,Re,R1a,R3h,Arh), (Za,Re,R1a,R3h,Ari), (Za, Re,R1a,R3h,Arj), (Za,Re,R1a,R3h,Ark), (Za,Re,R1a,R3h, Arl), (Za,Re,R1a,R3h,Arm), (Za,Re,R1a,R3h,Arn), (Za,Re, R1a,R3h,Aro), (Za,Re,R1a,R3h,Arp), (Za,Re,R1b,R3a,Ara), (Za,Re,R1b,R3a,Arb), (Za,Re,R1b,R3a,Arc), (Za,Re,R1b, R3a,Ard), (Za,Re,R1b,R3a,Are), (Za,Re,R1b,R3a,Arf), (Za, Re,R1b,R3a,Arg), (Za,Re,R1b,R3a,Arh), (Za,Re,R1b,R3a, Ari), (Za,Re,R1b,R3a,Arj), (Za,Re,R1b,R3a,Ark), (Za,Re, R1b,R3a,Arl), (Za,Re,R1b,R3a,Arm), (Za,Re,R1b,R3a, Arn), (Za,Re,R1b,R3a,Aro), (Za,Re,R1b,R3a,Arp), (Za,Re, R1b,R3b,Ara), (Za,Re,R1b,R3b,Arb), (Za,Re,R1b,R3b, Arc), (Za,Re,R1b,R3b,Ard), (Za,Re,R1b,R3b,Are), (Za,Re, R1b,R3b,Arf), (Za,Re,R1b,R3b,Arg), (Za,Re,R1b,R3b, Arh), (Za,Re,R1b,R3b,Ari), (Za,Re,R1b,R3b,Arj), (Za,Re, R1b,R3b,Ark), (Za,Re,R1b,R3b,Arl), (Za,Re,R1b,R3b, Arm), (Za,Re,R1b,R3b,Arn), (Za,Re,R1b,R3b,Aro), (Za,Re, R1b,R3b,Arp), (Za,Re,R1b,R3c,Ara), (Za,Re,R1b,R3c, Arb), (Za,Re,R1b,R3c,Arc), (Za,Re,R1b,R3c,Ard), (Za,Re, R1b,R3c,Are), (Za,Re,R1b,R3c,Arf), (Za,Re,R1b,R3c,Arg), (Za,Re,R1b,R3c,Arh), (Za,Re,R1b,R3c,Ari), (Za,Re,R1b, R3c,Arj), (Za,Re,R1b,R3c,Ark), (Za,Re,R1b,R3c,Arl), (Za, Re,R1b,R3c,Arm), (Za,Re,R1b,R3c,Arn), (Za,Re,R1b,R3c, Aro), (Za,Re,R1b,R3c,Arp), (Za,Re,R1b,R3d,Ara), (Za,Re, R1b,R3d,Arb), (Za,Re,R1b,R3d,Arc), (Za,Re,R1b,R3d, Ard), (Za,Re,R1b,R3d,Are), (Za,Re,R1b,R3d,Arf), (Za,Re, R1b,R3d,Arg), (Za,Re,R1b,R3d,Arh), (Za,Re,R1b,R3d,Ari), (Za,Re,R1b,R3d,Arj), (Za,Re,R1b,R3d,Ark), (Za,Re,R1b, R3d,Arl), (Za,Re,R1b,R3d,Arm), (Za,Re,R1b,R3d,Arn), (Za,Re,R1b,R3d,Aro), (Za,Re,R1b,R3d,Arp), (Za,Re,R1b, R3e,Ara), (Za,Re,R1b,R3e,Arb), (Za,Re,R1b,R3e,Arc), (Za, Re,R1b,R3e,Ard), (Za,Re,R1b,R3e,Are), (Za,Re,R1b,R3e, Arf), (Za,Re,R1b,R3e,Arg), (Za,Re,R1b,R3e,Arh), (Za,Re, R1b,R3e,Ari), (Za,Re,R1b,R3e,Arj), (Za,Re,R1b,R3e,Ark), (Za,Re,R1b,R3e,Arl), (Za,Re,R1b,R3e,Arm), (Za,Re,R1b, R3e,Arn), (Za,Re,R1b,R3e,Aro), (Za,Re,R1b,R3e,Arp), (Za, Re,R1b,R3f,Ara), (Za,Re,R1b,R3f,Arb), (Za,Re,R1b,R3f, Arc), (Za,Re,R1b,R3f,Ard), (Za,Re,R1b,R3f,Are), (Za,Re, R1b,R3f,Arf), (Za,Re,R1b,R3f,Arg), (Za,Re,R1b,R3f,Arh), (Za,Re,R1b,R3f,Ari), (Za,Re,R1b,R3f,Arj), (Za,Re,R1b, R3f,Ark), (Za,Re,R1b,R3f,Arl), (Za,Re,R1b,R3f,Arm), (Za, Re,R1b,R3f,Arn), (Za,Re,R1b,R3f,Aro), (Za,Re,R1b,R3f, Arp), (Za,Re,R1b,R3g,Ara), (Za,Re,R1b,R3g,Arb), (Za,Re, R1b,R3g,Arc), (Za,Re,R1b,R3g,Ard), (Za,Re,R1b,R3g, Are), (Za,Re,R1b,R3g,Arf), (Za,Re,R1b,R3g,Arg), (Za,Re, R1b,R3g,Arh), (Za,Re,R1b,R3g,Ari), (Za,Re,R1b,R3g,Arj), (Za,Re,R1b,R3g,Ark), (Za,Re,R1b,R3g,Arl), (Za,Re,R1b, R3g,Arm), (Za,Re,R1b,R3g,Arn), (Za,Re,R1b,R3g,Aro), (Za,Re,R1b,R3g,Arp), (Za,Re,R1b,R3h,Ara), (Za,Re,R1b, R3h,Arb), (Za,Re,R1b,R3h,Arc), (Za,Re,R1b,R3h,Ard), (Za,Re,R1b,R3h,Are), (Za,Re,R1b,R3h,Arf), (Za,Re,R1b, R3h,Arg), (Za,Re,R1b,R3h,Arh), (Za,Re,R1b,R3h,Ari), (Za, Re,R1b,R3h,Arj), (Za,Re,R1b,R3h,Ark), (Za,Re,R1b,R3h, Arl), (Za,Re,R1b,R3h,Arm), (Za,Re,R1b,R3h,Arn), (Za,Re, R1b,R3h,Aro), (Za,Re,R1b,R3h,Arp), (Za,Re,R1c,R3a, Ara), (Za,Re,R1c,R3a,Arb), (Za,Re,R1c,R3a,Arc), (Za,Re, R1c,R3a,Ard), (Za,Re,R1c,R3a,Are), (Za,Re,R1c,R3a,Arf), (Za,Re,R1c,R3a,Arg), (Za,Re,R1c,R3a,Arh), (Za,Re,R1c, R3a,Ari), (Za,Re,R1c,R3a,Arj), (Za,Re,R1c,R3a,Ark), (Za, Re,R1c,R3a,Arl), (Za,Re,R1c,R3a,Arm), (Za,Re,R1c,R3a, Arn), (Za,Re,R1c,R3a,Aro), (Za,Re,R1c,R3a,Arp), (Za,Re, R1c,R3b,Ara), (Za,Re,R1c,R3b,Arb), (Za,Re,R1c,R3b,Arc), (Za,Re,R1c,R3b,Ard), (Za,Re,R1c,R3b,Are), (Za,Re,R1c, R3b,Arf), (Za,Re,R1c,R3b,Arg), (Za,Re,R1c,R3b,Arh), (Za, Re,R1c,R3b,Ari), (Za,Re,R1c,R3b,Arj), (Za,Re,R1c,R3b, Ark), (Za,Re,R1c,R3b,Arl), (Za,Re,R1c,R3b,Arm), (Za,Re, R1c,R3b,Arn), (Za,Re,R1c,R3b,Aro), (Za,Re,R1c,R3b, Arp), (Za,Re,R1c,R3c,Ara), (Za,Re,R1c,R3c,Arb), (Za,Re, R1c,R3c,Arc), (Za,Re,R1c,R3c,Ard), (Za,Re,R1c,R3c,Are), (Za,Re,R1c,R3c,Arf), (Za,Re,R1c,R3c,Arg), (Za,Re,R1c, R3c,Arh), (Za,Re,R1c,R3c,Ari), (Za,Re,R1c,R3c,Arj), (Za, Re,R1c,R3c,Ark), (Za,Re,R1c,R3c,Arl), (Za,Re,R1c,R3c, Arm), (Za,Re,R1c,R3c,Arn), (Za,Re,R1c,R3c,Aro), (Za,Re, R1c,R3c,Arp), (Za,Re,R1c,R3d,Ara), (Za,Re,R1c,R3d,Arb), (Za,Re,R1c,R3d,Arc), (Za,Re,R1c,R3d,Ard), (Za,Re,R1c, R3d,Are), (Za,Re,R1c,R3d,Arf), (Za,Re,R1c,R3d,Arg), (Za, Re,R1c,R3d,Arh), (Za,Re,R1c,R3d,Ari), (Za,Re,R1c,R3d, Arj), (Za,Re,R1c,R3d,Ark), (Za,Re,R1c,R3d,Arl), (Za,Re, R1c,R3d,Arm), (Za,Re,R1c,R3d,Arn), (Za,Re,R1c,R3d, Aro), (Za,Re,R1c,R3d,Arp), (Za,Re,R1c,R3e,Ara), (Za,Re, R1c,R3e,Arb), (Za,Re,R1c,R3e,Arc), (Za,Re,R1c,R3e,Ard), (Za,Re,R1c,R3e,Are), (Za,Re,R1c,R3e,Arf), (Za,Re,R1c, R3e,Arg), (Za,Re,R1c,R3e,Arh), (Za,Re,R1c,R3e,Ari), (Za, Re,R1c,R3e,Arj), (Za,Re,R1c,R3e,Ark), (Za,Re,R1c,R3e, Arl), (Za,Re,R1c,R3e,Arm), (Za,Re,R1c,R3e,Arn), (Za,Re, R1c,R3e,Aro), (Za,Re,R1c,R3e,Arp), (Za,Re,R1c,R3f,Ara), (Za,Re,R1c,R3f,Arb), (Za,Re,R1c,R3f,Arc), (Za,Re,R1c, R3f,Ard), (Za,Re,R1c,R3f,Are), (Za,Re,R1c,R3f,Arf), (Za, Re,R1c,R3f,Arg), (Za,Re,R1c,R3f,Arh), (Za,Re,R1c,R3f, Ari), (Za,Re,R1c,R3f,Arj), (Za,Re,R1c,R3f,Ark), (Za,Re, R1c,R3f,Arl), (Za,Re,R1c,R3f,Arm), (Za,Re,R1c,R3f,Arn), (Za,Re,R1c,R3f,Aro), (Za,Re,R1c,R3f,Arp), (Za,Re,R1c, R3g,Ara), (Za,Re,R1c,R3g,Arb), (Za,Re,R1c,R3g,Arc), (Za, Re,R1c,R3g,Ard), (Za,Re,R1c,R3g,Are), (Za,Re,R1c,R3g, Arf), (Za,Re,R1c,R3g,Arg), (Za,Re,R1c,R3g,Arh), (Za,Re, R1c,R3g,Ari), (Za,Re,R1c,R3g,Arj), (Za,Re,R1c,R3g,Ark), (Za,Re,R1c,R3g,Arl), (Za,Re,R1c,R3g,Arm), (Za,Re,R1c, R3g,Arn), (Za,Re,R1c,R3g,Aro), (Za,Re,R1c,R3g,Arp), (Za, Re,R1c,R3h,Ara), (Za,Re,R1c,R3h,Arb), (Za,Re,R1c,R3h, Arc), (Za,Re,R1c,R3h,Ard), (Za,Re,R1c,R3h,Are), (Za,Re, R1c,R3h,Arf), (Za,Re,R1c,R3h,Arg), (Za,Re,R1c,R3h,Arh), (Za,Re,R1c,R3h,Ari), (Za,Re,R1c,R3h,Arj), (Za,Re,R1c, R3h,Ark), (Za,Re,R1c,R3h,Arl), (Za,Re,R1c,R3h,Arm), (Za,Re,R1c,R3h,Arn), (Za,Re,R1c,R3h,Aro), (Za,Re,R1c, R3h,Arp), (Za,Re,R1d,R3a,Ara), (Za,Re,R1d,R3a,Arb), (Za, Re,R1d,R3a,Arc), (Za,Re,R1d,R3a,Ard), (Za,Re,R1d,R3a, Are), (Za,Re,R1d,R3a,Arf), (Za,Re,R1d,R3a,Arg), (Za,Re, R1d,R3a,Arh), (Za,Re,R1d,R3a,Ari), (Za,Re,R1d,R3a,Arj), (Za,Re,R1d,R3a,Ark), (Za,Re,R1d,R3a,Arl), (Za,Re,R1d, R3a,Arm), (Za,Re,R1d,R3a,Arn), (Za,Re,R1d,R3a,Aro), (Za,Re,R1d,R3a,Arp), (Za,Re,R1d,R3b,Ara), (Za,Re,R1d, R3b,Arb), (Za,Re,R1d,R3b,Arc), (Za,Re,R1d,R3b,Ard), (Za,Re,R1d,R3b,Are), (Za,Re,R1d,R3b,Arf), (Za,Re,R1d, R3b,Arg), (Za,Re,R1d,R3b,Arh), (Za,Re,R1d,R3b,Ari), (Za, Re,R1d,R3b,Arj), (Za,Re,R1d,R3b,Ark), (Za,Re,R1d,R3b, Arl), (Za,Re,R1d,R3b,Arm), (Za,Re,R1d,R3b,Arn), (Za,Re, R1d,R3b,Aro), (Za,Re,R1d,R3b,Arp), (Za,Re,R1d,R3c, Ara), (Za,Re,R1d,R3c,Arb), (Za,Re,R1d,R3c,Arc), (Za,Re, R1d,R3c,Ard), (Za,Re,R1d,R3c,Are), (Za,Re,R1d,R3c,Arf), (Za,Re,R1d,R3c,Arg), (Za,Re,R1d,R3c,Arh), (Za,Re,R1d, R3c,Ari), (Za,Re,R1d,R3c,Arj), (Za,Re,R1d,R3c,Ark), (Za, Re,R1d,R3c,Arl), (Za,Re,R1d,R3c,Arm), (Za,Re,R1d,R3c, Arn), (Za,Re,R1d,R3c,Aro), (Za,Re,R1d,R3c,Arp), (Za,Re, R1d,R3d,Ara), (Za,Re,R1d,R3d,Arb), (Za,Re,R1d,R3d, Arc), (Za,Re,R1d,R3d,Ard), (Za,Re,R1d,R3d,Are), (Za,Re, R1d,R3d,Arf), (Za,Re,R1d,R3d,Arg), (Za,Re,R1d,R3d, Arh), (Za,Re,R1d,R3d,Ari), (Za,Re,R1d,R3d,Arj), (Za,Re, R1d,R3d,Ark), (Za,Re,R1d,R3d,Arl), (Za,Re,R1d,R3d, Arm), (Za,Re,R1d,R3d,Arn), (Za,Re,R1d,R3d,Aro), (Za,Re, R1d,R3d,Arp), (Za,Re,R1d,R3e,Ara), (Za,Re,R1d,R3e, Arb), (Za,Re,R1d,R3e,Arc), (Za,Re,R1d,R3e,Ard), (Za,Re, R1d,R3e,Are), (Za,Re,R1d,R3e,Arf), (Za,Re,R1d,R3e,Arg), (Za,Re,R1d,R3e,Arh), (Za,Re,R1d,R3e,Ari), (Za,Re,R1d, R3e,Arj), (Za,Re,R1d,R3e,Ark), (Za,Re,R1d,R3e,Arl), (Za, Re,R1d,R3e,Arm), (Za,Re,R1d,R3e,Arn), (Za,Re,R1d,R3e, Aro), (Za,Re,R1d,R3e,Arp), (Za,Re,R1d,R3f,Ara), (Za,Re, R1d,R3f,Arb), (Za,Re,R1d,R3f,Arc), (Za,Re,R1d,R3f,Ard), (Za,Re,R1d,R3f,Are), (Za,Re,R1d,R3f,Arf), (Za,Re,R1d, R3f,Arg), (Za,Re,R1d,R3f,Arh), (Za,Re,R1d,R3f,Ari), (Za, Re,R1d,R3f,Arj), (Za,Re,R1d,R3f,Ark), (Za,Re,R1d,R3f, Arl), (Za,Re,R1d,R3f,Arm), (Za,Re,R1d,R3f,Arn), (Za,Re, R1d,R3f,Aro), (Za,Re,R1d,R3f,Arp), (Za,Re,R1d,R3g,Ara), (Za,Re,R1d,R3g,Arb), (Za,Re,R1d,R3g,Arc), (Za,Re,R1d, R3g,Ard), (Za,Re,R1d,R3g,Are), (Za,Re,R1d,R3g,Arf), (Za, Re,R1d,R3g,Arg), (Za,Re,R1d,R3g,Arh), (Za,Re,R1d,R3g, Ari), (Za,Re,R1d,R3g,Arj), (Za,Re,R1d,R3g,Ark), (Za,Re, R1d,R3g,Arl), (Za,Re,R1d,R3g,Arm), (Za,Re,R1d,R3g, Arn), (Za,Re,R1d,R3g,Aro), (Za,Re,R1d,R3g,Arp), (Za,Re, R1d,R3h,Ara), (Za,Re,R1d,R3h,Arb), (Za,Re,R1d,R3h, Arc), (Za,Re,R1d,R3h,Ard), (Za,Re,R1d,R3h,Are), (Za,Re, R1d,R3h,Arf), (Za,Re,R1d,R3h,Arg), (Za,Re,R1d,R3h, Arh), (Za,Re,R1d,R3h,Ari), (Za,Re,R1d,R3h,Arj), (Za,Re, R1d,R3h,Ark), (Za,Re,R1d,R3h,Arl), (Za,Re,R1d,R3h, Arm), (Za,Re,R1d,R3h,Arn), (Za,Re,R1d,R3h,Aro), (Za,Re, R1d,R3h,Arp), (Za,Rf,R1a,R3a,Ara), (Za,Rf,R1a,R3a,Arb), (Za,Rf,R1a,R3a,Arc), (Za,Rf,R1a,R3a,Ard), (Za,Rf,R1a, R3a,Are), (Za,Rf,R1a,R3a,Arf), (Za,Rf,R1a,R3a,Arg), (Za, Rf,R1a,R3a,Arh), (Za,Rf,R1a,R3a,Ari), (Za,Rf,R1a,R3a, Arj), (Za,Rf,R1a,R3a,Ark), (Za,Rf,R1a,R3a,Arl), (Za,Rf, R1a,R3a,Arm), (Za,Rf,R1a,R3a,Arn), (Za,Rf,R1a,R3a,Aro), (Za,Rf,R1a,R3a,Arp), (Za,Rf,R1a,R3b,Ara), (Za,Rf,R1a, R3b,Arb), (Za,Rf,R1a,R3b,Arc), (Za,Rf,R1a,R3b,Ard), (Za, Rf,R1a,R3b,Are), (Za,Rf,R1a,R3b,Arf), (Za,Rf,R1a,R3b, Arg), (Za,Rf,R1a,R3b,Arh), (Za,Rf,R1a,R3b,Ari), (Za,Rf, R1a,R3b,Arj), (Za,Rf,R1a,R3b,Ark), (Za,Rf,R1a,R3b,Arl), (Za,Rf,R1a,R3b,Arm), (Za,Rf,R1a,R3b,Arn), (Za,Rf,R1a, R3b,Aro), (Za,Rf,R1a,R3b,Arp), (Za,Rf,R1a,R3c,Ara), (Za, Rf,R1a,R3c,Arb), (Za,Rf,R1a,R3c,Arc), (Za,Rf,R1a,R3c, Ard), (Za,Rf,R1a,R3c,Are), (Za,Rf,R1a,R3c,Arf), (Za,Rf, R1a,R3c,Arg), (Za,Rf,R1a,R3c,Arh), (Za,Rf,R1a,R3c,Ari), (Za,Rf,R1a,R3c,Arj), (Za,Rf,R1a,R3c,Ark), (Za,Rf,R1a, R3c,Arl), (Za,Rf,R1a,R3c,Arm), (Za,Rf,R1a,R3c,Arn), (Za, Rf,R1a,R3c,Aro), (Za,Rf,R1a,R3c,Arp), (Za,Rf,R1a,R3d, Ara), (Za,Rf,R1a,R3d,Arb), (Za,Rf,R1a,R3d,Arc), (Za,Rf, R1a,R3d,Ard), (Za,Rf,R1a,R3d,Are), (Za,Rf,R1a,R3d,Arf), (Za,Rf,R1a,R3d,Arg), (Za,Rf,R1a,R3d,Arh), (Za,Rf,R1a, R3d,Ari), (Za,Rf,R1a,R3d,Arj), (Za,Rf,R1a,R3d,Ark), (Za, Rf,R1a,R3d,Arl), (Za,Rf,R1a,R3d,Arm), (Za,Rf,R1a,R3d, Arn), (Za,Rf,R1a,R3d,Aro), (Za,Rf,R1a,R3d,Arp), (Za,Rf, R1a,R3e,Ara), (Za,Rf,R1a,R3e,Arb), (Za,Rf,R1a,R3e,Arc), (Za,Rf,R1a,R3e,Ard), (Za,Rf,R1a,R3e,Are), (Za,Rf,R1a, R3e,Arf), (Za,Rf,R1a,R3e,Arg), (Za,Rf,R1a,R3e,Arh), (Za, Rf,R1a,R3e,Ari), (Za,Rf,R1a,R3e,Arj), (Za,Rf,R1a,R3e, Ark), (Za,Rf,R1a,R3e,Arl), (Za,Rf,R1a,R3e,Arm), (Za,Rf, R1a,R3e,Arn), (Za,Rf,R1a,R3e,Aro), (Za,Rf,R1a,R3e,Arp), (Za,Rf,R1a,R3f,Ara), (Za,Rf,R1a,R3f,Arb), (Za,Rf,R1a, R3f,Arc), (Za,Rf,R1a,R3f,Ard), (Za,Rf,R1a,R3f,Are), (Za, Rf,R1a,R3f,Arf), (Za,Rf,R1a,R3f,Arg), (Za,Rf,R1a,R3f, Arh), (Za,Rf,R1a,R3f,Ari), (Za,Rf,R1a,R3f,Arj), (Za,Rf, R1a,R3f,Ark), (Za,Rf,R1a,R3f,Arl), (Za,Rf,R1a,R3f,Arm), (Za,Rf,R1a,R3f,Arn), (Za,Rf,R1a,R3f,Aro), (Za,Rf,R1a, R3f,Arp), (Za,Rf,R1a,R3g,Ara), (Za,Rf,R1a,R3g,Arb), (Za, Rf,R1a,R3g,Arc), (Za,Rf,R1a,R3g,Ard), (Za,Rf,R1a,R3g, Are), (Za,Rf,R1a,R3g,Arf), (Za,Rf,R1a,R3g,Arg), (Za,Rf, R1a,R3g,Arh), (Za,Rf,R1a,R3g,Ari), (Za,Rf,R1a,R3g,Arj), (Za,Rf,R1a,R3g,Ark), (Za,Rf,R1a,R3g,Arl), (Za,Rf,R1a, R3g,Arm), (Za,Rf,R1a,R3g,Arn), (Za,Rf,R1a,R3g,Aro), (Za,Rf,R1a,R3g,Arp), (Za,Rf,R1a,R3h,Ara), (Za,Rf,R1a, R3h,Arb), (Za,Rf,R1a,R3h,Arc), (Za,Rf,R1a,R3h,Ard), (Za, Rf,R1a,R3h,Are), (Za,Rf,R1a,R3h,Arf), (Za,Rf,R1a,R3h, Arg), (Za,Rf,R1a,R3h,Arh), (Za,Rf,R1a,R3h,Ari), (Za,Rf, R1a,R3h,Arj), (Za,Rf,R1a,R3h,Ark), (Za,Rf,R1a,R3h,Arl), (Za,Rf,R1a,R3h,Arm), (Za,Rf,R1a,R3h,Arn), (Za,Rf,R1a, R3h,Aro), (Za,Rf,R1a,R3h,Arp), (Za,Rf,R1b,R3a,Ara), (Za, Rf,R1b,R3a,Arb), (Za,Rf,R1b,R3a,Arc), (Za,Rf,R1b,R3a, Ard), (Za,Rf,R1b,R3a,Are), (Za,Rf,R1b,R3a,Arf), (Za,Rf, R1b,R3a,Arg), (Za,Rf,R1b,R3a,Arh), (Za,Rf,R1b,R3a,Ari), (Za,Rf,R1b,R3a,Arj), (Za,Rf,R1b,R3a,Ark), (Za,Rf,R1b, R3a,Arl), (Za,Rf,R1b,R3a,Arm), (Za,Rf,R1b,R3a,Arn), (Za, Rf,R1b,R3a,Aro), (Za,Rf,R1b,R3a,Arp), (Za,Rf,R1b,R3b, Ara), (Za,Rf,R1b,R3b,Arb), (Za,Rf,R1b,R3b,Arc), (Za,Rf, R1b,R3b,Ard), (Za,Rf,R1b,R3b,Are), (Za,Rf,R1b,R3b,Arf), (Za,Rf,R1b,R3b,Arg), (Za,Rf,R1b,R3b,Arh), (Za,Rf,R1b, R3b,Ari), (Za,Rf,R1b,R3b,Arj), (Za,Rf,R1b,R3b,Ark), (Za, Rf,R1b,R3b,Arl), (Za,Rf,R1b,R3b,Arm), (Za,Rf,R1b,R3b, Arn), (Za,Rf,R1b,R3b,Aro), (Za,Rf,R1b,R3b,Arp), (Za,Rf, R1b,R3c,Ara), (Za,Rf,R1b,R3c,Arb), (Za,Rf,R1b,R3c,Arc), (Za,Rf,R1b,R3c,Ard), (Za,Rf,R1b,R3c,Are), (Za,Rf,R1b, R3c,Arf), (Za,Rf,R1b,R3c,Arg), (Za,Rf,R1b,R3c,Arh), (Za, Rf,R1b,R3c,Ari), (Za,Rf,R1b,R3c,Arj), (Za,Rf,R1b,R3c, Ark), (Za,Rf,R1b,R3c,Arl), (Za,Rf,R1b,R3c,Arm), (Za,Rf, R1b,R3c,Arn), (Za,Rf,R1b,R3c,Aro), (Za,Rf,R1b,R3c,Arp), (Za,Rf,R1b,R3d,Ara), (Za,Rf,R1b,R3d,Arb), (Za,Rf,R1b, R3d,Arc), (Za,Rf,R1b,R3d,Ard), (Za,Rf,R1b,R3d,Are), (Za, Rf,R1b,R3d,Arf), (Za,Rf,R1b,R3d,Arg), (Za,Rf,R1b,R3d, Arh), (Za,Rf,R1b,R3d,Ari), (Za,Rf,R1b,R3d,Arj), (Za,Rf, R1b,R3d,Ark), (Za,Rf,R1b,R3d,Arl), (Za,Rf,R1b,R3d, Arm), (Za,Rf,R1b,R3d,Arn), (Za,Rf,R1b,R3d,Aro), (Za,Rf, R1b,R3d,Arp), (Za,Rf,R1b,R3e,Ara), (Za,Rf,R1b,R3e,Arb), (Za,Rf,R1b,R3e,Arc), (Za,Rf,R1b,R3e,Ard), (Za,Rf,R1b, R3e,Are), (Za,Rf,R1b,R3e,Arf), (Za,Rf,R1b,R3e,Arg), (Za, Rf,R1b,R3e,Arh), (Za,Rf,R1b,R3e,Ari), (Za,Rf,R1b,R3e, Arj), (Za,Rf,R1b,R3e,Ark), (Za,Rf,R1b,R3e,Arl), (Za,Rf, R1b,R3e,Arm), (Za,Rf,R1b,R3e,Arn), (Za,Rf,R1b,R3e, Aro), (Za,Rf,R1b,R3e,Arp), (Za,Rf,R1b,R3f,Ara), (Za,Rf, R1b,R3f,Arb), (Za,Rf,R1b,R3f,Arc), (Za,Rf,R1b,R3f,Ard), (Za,Rf,R1b,R3f,Are), (Za,Rf,R1b,R3f,Arf), (Za,Rf,R1b, R3f,Arg), (Za,Rf,R1b,R3f,Arh), (Za,Rf,R1b,R3f,Ari), (Za, Rf,R1b,R3f,Arj), (Za,Rf,R1b,R3f,Ark), (Za,Rf,R1b,R3f, Arl), (Za,Rf,R1b,R3f,Arm), (Za,Rf,R1b,R3f,Arn), (Za,Rf, R1b,R3f,Aro), (Za,Rf,R1b,R3f,Arp), (Za,Rf,R1b,R3g,Ara), (Za,Rf,R1b,R3g,Arb), (Za,Rf,R1b,R3g,Arc), (Za,Rf,R1b, R3g,Ard), (Za,Rf,R1b,R3g,Are), (Za,Rf,R1b,R3g,Arf), (Za, Rf,R1b,R3g,Arg), (Za,Rf,R1b,R3g,Arh), (Za,Rf,R1b,R3g, Ari), (Za,Rf,R1b,R3g,Arj), (Za,Rf,R1b,R3g,Ark), (Za,Rf, R1b,R3g,Arl), (Za,Rf,R1b,R3g,Arm), (Za,Rf,R1b,R3g, Arn), (Za,Rf,R1b,R3g,Aro), (Za,Rf,R1b,R3g,Arp), (Za,Rf, R1b,R3h,Ara), (Za,Rf,R1b,R3h,Arb), (Za,Rf,R1b,R3h,Arc), (Za,Rf,R1b,R3h,Ard), (Za,Rf,R1b,R3h,Are), (Za,Rf,R1b, R3h,Arf), (Za,Rf,R1b,R3h,Arg), (Za,Rf,R1b,R3h,Arh), (Za, Rf,R1b,R3h,Ari), (Za,Rf,R1b,R3h,Arj), (Za,Rf,R1b,R3h, Ark), (Za,Rf,R1b,R3h,Arl), (Za,Rf,R1b,R3h,Arm), (Za,Rf, R1b,R3h,Arn), (Za,Rf,R1b,R3h,Aro), (Za,Rf,R1b,R3h,Arp), (Za,Rf,R1c,R3a,Ara), (Za,Rf,R1c,R3a,Arb), (Za,Rf,R1c, R3a,Arc), (Za,Rf,R1c,R3a,Ard), (Za,Rf,R1c,R3a,Are), (Za, Rf,R1c,R3a,Arf), (Za,Rf,R1c,R3a,Arg), (Za,Rf,R1c,R3a, Arh), (Za,Rf,R1c,R3a,Ari), (Za,Rf,R1c,R3a,Arj), (Za,Rf, R1c,R3a,Ark), (Za,Rf,R1c,R3a,Arl), (Za,Rf,R1c,R3a,Arm), (Za,Rf,R1c,R3a,Arn), (Za,Rf,R1c,R3a,Aro), (Za,Rf,R1c, R3a,Arp), (Za,Rf,R1c,R3b,Ara), (Za,Rf,R1c,R3b,Arb), (Za, Rf,R1c,R3b,Arc), (Za,Rf,R1c,R3b,Ard), (Za,Rf,R1c,R3b, Are), (Za,Rf,R1c,R3b,Arf), (Za,Rf,R1c,R3b,Arg), (Za,Rf,R1c,R3b,Arh), (Za,Rf,R1c,R3b,Ari), (Za,Rf,R1c,R3b,Arj), (Za,Rf,R1c,R3b,Ark), (Za,Rf,R1c,R3b,Arl), (Za,Rf,R1c,R3b,Arm), (Za,Rf,R1c,R3b,Arn), (Za,Rf,R1c,R3b,Aro), (Za,Rf,R1c,R3b,Arp), (Za,Rf,R1c,R3c,Ara), (Za,Rf,R1c,R3c,Arb), (Za,Rf,R1c,R3c,Arc), (Za,Rf,R1c,R3c,Ard), (Za,Rf,R1c,R3c,Are), (Za,Rf,R1c,R3c,Arf), (Za,Rf,R1c,R3c,Arg), (Za,Rf,R1c,R3c,Arh), (Za,Rf,R1c,R3c,Ari), (Za,Rf,R1c,R3c,Arj), (Za,Rf,R1c,R3c,Ark), (Za,Rf,R1c,R3c,Arl), (Za,Rf,R1c,R3c,Arm), (Za,Rf,R1c,R3c,Arn), (Za,Rf,R1c,R3c,Aro), (Za,Rf,R1c,R3c,Arp), (Za,Rf,R1c,R3d,Ara), (Za,Rf,R1c,R3d,Arb), (Za,Rf,R1c,R3d,Arc), (Za,Rf,R1c,R3d,Ard), (Za,Rf,R1c,R3d,Are), (Za,Rf,R1c,R3d,Arf), (Za,Rf,R1c,R3d,Arg), (Za,Rf,R1c,R3d,Arh), (Za,Rf,R1c,R3d,Ari), (Za,Rf,R1c,R3d,Arj), (Za,Rf,R1c,R3d,Ark), (Za,Rf,R1c,R3d,Arl), (Za,Rf,R1c,R3d,Arm), (Za,Rf,R1c,R3d,Arn), (Za,Rf,R1c,R3d,Aro), (Za,Rf,R1c,R3d,Arp), (Za,Rf,R1c,R3e,Ara), (Za,Rf,R1c,R3e,Arb), (Za,Rf,R1c,R3e,Arc), (Za,Rf,R1c,R3e,Ard), (Za,Rf,R1c,R3e,Are), (Za,Rf,R1c,R3e,Arf), (Za,Rf,R1c,R3e,Arg), (Za,Rf,R1c,R3e,Arh), (Za,Rf,R1c,R3e,Ari), (Za,Rf,R1c,R3e,Arj), (Za,Rf,R1c,R3e,Ark), (Za,Rf,R1c,R3e,Arl), (Za,Rf,R1c,R3e,Arm), (Za,Rf,R1c,R3e,Arn), (Za,Rf,R1c,R3e,Aro), (Za,Rf,R1c,R3e,Arp), (Za,Rf,R1c,R3f,Ara), (Za,Rf,R1c,R3f,Arb), (Za,Rf,R1c,R3f,Arc), (Za,Rf,R1c,R3f,Ard), (Za,Rf,R1c,R3f,Are), (Za,Rf,R1c,R3f,Arf), (Za,Rf,R1c,R3f,Arg), (Za,Rf,R1c,R3f,Arh), (Za,Rf,R1c,R3f,Ari), (Za,Rf,R1c,R3f,Arj), (Za,Rf,R1c,R3f,Ark), (Za,Rf,R1c,R3f,Arl), (Za,Rf,R1c,R3f,Arm), (Za,Rf,R1c,R3f,Arn), (Za,Rf,R1c,R3f,Aro), (Za,Rf,R1c,R3f,Arp), (Za,Rf,R1c,R3g,Ara), (Za,Rf,R1c,R3g,Arb), (Za,Rf,R1c,R3g,Arc), (Za,Rf,R1c,R3g,Ard), (Za,Rf,R1c,R3g,Are), (Za,Rf,R1c,R3g,Arf), (Za,Rf,R1c,R3g,Arg), (Za,Rf,R1c,R3g,Arh), (Za,Rf,R1c,R3g,Ari), (Za,Rf,R1c,R3g,Arj), (Za,Rf,R1c,R3g,Ark), (Za,Rf,R1c,R3g,Arl), (Za,Rf,R1c,R3g,Arm), (Za,Rf,R1c,R3g,Arn), (Za,Rf,R1c,R3g,Aro), (Za,Rf,R1c,R3g,Arp), (Za,Rf,R1c,R3h,Ara), (Za,Rf,R1c,R3h,Arb), (Za,Rf,R1c,R3h,Arc), (Za,Rf,R1c,R3h,Ard), (Za,Rf,R1c,R3h,Are), (Za,Rf,R1c,R3h,Arf), (Za,Rf,R1c,R3h,Arg), (Za,Rf,R1c,R3h,Arh), (Za,Rf,R1c,R3h,Ari), (Za,Rf,R1c,R3h,Arj), (Za,Rf,R1c,R3h,Ark), (Za,Rf,R1c,R3h,Arl), (Za,Rf,R1c,R3h,Arm), (Za,Rf,R1c,R3h,Arn), (Za,Rf,R1c,R3h,Aro), (Za,Rf,R1c,R3h,Arp), (Za,Rf,R1d,R3a,Ara), (Za,Rf,R1d,R3a,Arb), (Za,Rf,R1d,R3a,Arc), (Za,Rf,R1d,R3a,Ard), (Za,Rf,R1d,R3a,Are), (Za,Rf,R1d,R3a,Arf), (Za,Rf,R1d,R3a,Arg), (Za,Rf,R1d,R3a,Arh), (Za,Rf,R1d,R3a,Ari), (Za,Rf,R1d,R3a,Arj), (Za,Rf,R1d,R3a,Ark), (Za,Rf,R1d,R3a,Arl), (Za,Rf,R1d,R3a,Arm), (Za,Rf,R1d,R3a,Arn), (Za,Rf,R1d,R3a,Aro), (Za,Rf,R1d,R3a,Arp), (Za,Rf,R1d,R3b,Ara), (Za,Rf,R1d,R3b,Arb), (Za,Rf,R1d,R3b,Arc), (Za,Rf,R1d,R3b,Ard), (Za,Rf,R1d,R3b,Are), (Za,Rf,R1d,R3b,Arf), (Za,Rf,R1d,R3b,Arg), (Za,Rf,R1d,R3b,Arh), (Za,Rf,R1d,R3b,Ari), (Za,Rf,R1d,R3b,Arj), (Za,Rf,R1d,R3b,Ark), (Za,Rf,R1d,R3b,Arl), (Za,Rf,R1d,R3b,Arm), (Za,Rf,R1d,R3b,Arn), (Za,Rf,R1d,R3b,Aro), (Za,Rf,R1d,R3b,Arp), (Za,Rf,R1d,R3c,Ara), (Za,Rf,R1d,R3c,Arb), (Za,Rf,R1d,R3c,Arc), (Za,Rf,R1d,R3c,Ard), (Za,Rf,R1d,R3c,Are), (Za,Rf,R1d,R3c,Arf), (Za,Rf,R1d,R3c,Arg), (Za,Rf,R1d,R3c,Arh), (Za,Rf,R1d,R3c,Ari), (Za,Rf,R1d,R3c,Arj), (Za,Rf,R1d,R3c,Ark), (Za,Rf,R1d,R3c,Arl), (Za,Rf,R1d,R3c,Arm), (Za,Rf,R1d,R3c,Arn), (Za,Rf,R1d,R3c,Aro), (Za,Rf,R1d,R3c,Arp), (Za,Rf,R1d,R3d,Ara), (Za,Rf,R1d,R3d,Arb), (Za,Rf,R1d,R3d,Arc), (Za,Rf,R1d,R3d,Ard), (Za,Rf,R1d,R3d,Are), (Za,Rf,R1d,R3d,Arf), (Za,Rf,R1d,R3d,Arg), (Za,Rf,R1d,R3d,Arh), (Za,Rf,R1d,R3d,Ari), (Za,Rf,R1d,R3d,Arj), (Za,Rf,R1d,R3d,Ark), (Za,Rf,R1d,R3d,Arl), (Za,Rf,R1d,R3d,Arm), (Za,Rf,R1d,R3d,Arn), (Za,Rf,R1d,R3d,Aro), (Za,Rf,R1d,R3d,Arp), (Za,Rf,R1d,R3e,Ara), (Za,Rf,R1d,R3e,Arb), (Za,Rf,R1d,R3e,Arc), (Za,Rf,R1d,R3e,Ard), (Za,Rf,R1d,R3e,Are), (Za,Rf,R1d,R3e,Arf), (Za,Rf,R1d,R3e,Arg), (Za,Rf,R1d,R3e,Arh), (Za,Rf,R1d,R3e,Ari), (Za,Rf,R1d,R3e,Arj), (Za,Rf,R1d,R3e,Ark), (Za,Rf,R1d,R3e,Arl), (Za,Rf,R1d,R3e,Arm), (Za,Rf,R1d,R3e,Arn), (Za,Rf,R1d,R3e,Aro), (Za,Rf,R1d,R3e,Arp), (Za,Rf,R1d,R3f,Ara), (Za,Rf,R1d,R3f,Arb), (Za,Rf,R1d,R3f,Arc), (Za,Rf,R1d,R3f,Ard), (Za,Rf,R1d,R3f,Are), (Za,Rf,R1d,R3f,Arf), (Za,Rf,R1d,R3f,Arg), (Za,Rf,R1d,R3f,Arh), (Za,Rf,R1d,R3f,Ari), (Za,Rf,R1d,R3f,Arj), (Za,Rf,R1d,R3f,Ark), (Za,Rf,R1d,R3f,Arl), (Za,Rf,R1d,R3f,Arm), (Za,Rf,R1d,R3f,Arn), (Za,Rf,R1d,R3f,Aro), (Za,Rf,R1d,R3f,Arp), (Za,Rf,R1d,R3g,Ara), (Za,Rf,R1d,R3g,Arb), (Za,Rf,R1d,R3g,Arc), (Za,Rf,R1d,R3g,Ard), (Za,Rf,R1d,R3g,Are), (Za,Rf,R1d,R3g,Arf), (Za,Rf,R1d,R3g,Arg), (Za,Rf,R1d,R3g,Arh), (Za,Rf,R1d,R3g,Ari), (Za,Rf,R1d,R3g,Arj), (Za,Rf,R1d,R3g,Ark), (Za,Rf,R1d,R3g,Arl), (Za,Rf,R1d,R3g,Arm), (Za,Rf,R1d,R3g,Arn), (Za,Rf,R1d,R3g,Aro), (Za,Rf,R1d,R3g,Arp), (Za,Rf,R1d,R3h,Ara), (Za,Rf,R1d,R3h,Arb), (Za,Rf,R1d,R3h,Arc), (Za,Rf,R1d,R3h,Ard), (Za,Rf,R1d,R3h,Are), (Za,Rf,R1d,R3h,Arf), (Za,Rf,R1d,R3h,Arg), (Za,Rf,R1d,R3h,Arh), (Za,Rf,R1d,R3h,Ari), (Za,Rf,R1d,R3h,Arj), (Za,Rf,R1d,R3h,Ark), (Za,Rf,R1d,R3h,Arl), (Za,Rf,R1d,R3h,Arm), (Za,Rf,R1d,R3h,Arn), (Za,Rf,R1d,R3h,Aro), (Za,Rf,R1d,R3h,Arp), (Za,R9,R1a,R3a,Ara), (Za,Rg,R1a,R3a,Arb), (Za,Rg,R1a,R3a,Arc), (Za,Rg,R1a,R3a,Ard), (Za,Rg,R1a,R3a,Are), (Za,Rg,R1a,R3a,Arf), (Za,Rg,R1a,R3a,Arg), (Za,Rg,R1a,R3a,Arh), (Za,Rg,R1a,R3a,Ari), (Za,Rg,R1a,R3a,Arj), (Za,Rg,R1a,R3a,Ark), (Za,Rg,R1a,R3a,Arl), (Za,Rg,R1a,R3a,Arm), (Za,Rg,R1a,R3a,Arn), (Za,Rg,R1a,R3a,Aro), (Za,Rg,R1a,R3a,Arp), (Za,Rg,R1a,R3b,Ara), (Za,Rg,R1a,R3b,Arb), (Za,Rg,R1a,R3b,Arc), (Za,Rg,R1a,R3b,Ard), (Za,Rg,R1a,R3b,Are), (Za,Rg,R1a,R3b,Arf), (Za,Rg,R1a,R3b,Arg), (Za,Rg,R1a,R3b,Arh), (Za,Rg,R1a,R3b,Ari), (Za,Rg,R1a,R3b,Arj), (Za,Rg,R1a,R3b,Ark), (Za,Rg,R1a,R3b,Arl), (Za,Rg,R1a,R3b,Arm), (Za,Rg,R1a,R3b,Arn), (Za,Rg,R1a,R3b,Aro), (Za,Rg,R1a,R3b,Arp), (Za,Rg,R1a,R3c,Ara), (Za,Rg,R1a,R3c,Arb), (Za,Rg,R1a,R3c,Arc), (Za,Rg,R1a,R3c,Ard), (Za,Rg,R1a,R3c,Are), (Za,Rg,R1a,R3c,Arf), (Za,Rg,R1a,R3c,Arg), (Za,Rg,R1a,R3c,Arh), (Za,Rg,R1a,R3c,Ari), (Za,Rg,R1a,R3c,Ad), (Za,Rg,R1a,R3c,Ark), (Za,Rg,R1a,R3c,Arl), (Za,Rg,R1a,R3c,Arm), (Za,Rg,R1a,R3c,Arn), (Za,Rg,R1a,R3c,Aro), (Za,Rg,R1a,R3c,Arp), (Za,Rg,R1a,R3d,Ara), (Za,Rg,R1a,R3d,Arb), (Za,Rg,R1a,R3d,Arc), (Za,Rg,R1a,R3d,Ard), (Za,Rg,R1a,R3d,Are), (Za,Rg,R1a,R3d,Arf), (Za,Rg,R1a,R3d,Arg), (Za,Rg,R1a,R3d,Arh), (Za,Rg,R1a,R3d,Ari), (Za,Rg,R1a,R3d,Arj), (Za,Rg,R1a,R3d,Ark), (Za,Rg,R1a,R3d,Arl), (Za,Rg,R1a,R3d,Arm), (Za,Rg,R1a,R3d,Arn), (Za,Rg,R1a,R3d,Aro), (Za,Rg,R1a,R3d,Arp), (Za,Rg,R1a,R3e,Ara), (Za,Rg,R1a,R3e,Arb), (Za,Rg,R1a,R3e,Arc), (Za,Rg,R1a,R3e,Ard), (Za,Rg,R1a,R3e,Are), (Za,Rg,R1a,R3e,Arf), (Za,Rg,R1a,R3e,Arg), (Za,Rg,R1a,R3e,Arh), (Za,Rg,R1a,R3e,Ari), (Za,Rg,R1a,R3e,Arj), (Za,Rg,R1a,R3e,Ark), (Za,Rg,R1a,R3e,Arl), (Za,Rg,R1a,R3e,Arm), (Za,Rg,R1a,R3e,Arn), (Za,Rg,R1a,R3e,Aro), (Za,Rg,R1a,R3e,Arp), (Za,Rg,R1a,R3f,Ara), (Za,Rg,R1a,R3f,Arb), (Za,Rg,R1a,R3f,Arc), (Za,Rg,R1a,R3f,Ard), (Za,Rg,R1a,R3f,Are), (Za,Rg,R1a,R3f,Arf), (Za,Rg,R1a,R3f,Arg), (Za,Rg,R1a,R3f,Arh), (Za,Rg,R1a,R3f,Ari), (Za,Rg,R1a,R3f,Arj), (Za,Rg,R1a,R3f,Ark), (Za,Rg,R1a,R3f,Arl), (Za,Rg,R1a,R3f,Arm), (Za,Rg,R1a,R3f,Arn), (Za,Rg,R1a,R3f,Aro), (Za,Rg,R1a,R3f,Arp), (Za,Rg,R1a,R3g,Ara), (Za,Rg,R1a,R3g,Arb), (Za,Rg,R1a,R3g,Arc), (Za,Rg,R1a,R3g,Ard), (Za,Rg,R1a,R3g,Are), (Za,Rg,R1a,R3g,Arf), (Za,Rg,R1a,R3g,Arg), (Za,Rg,R1a,R3g,Arh), (Za,Rg,R1a,R3g,Ari), (Za,Rg,R1a,R3g,Arj), (Za,Rg,R1a,R3g,Ark), (Za,Rg,R1a,R3g,Arl), (Za,Rg,R1a,R3g,Arm), (Za,Rg,R1a,R3g,Arn), (Za,Rg,R1a,R3g,Aro), (Za,Rg, R1a,R3g,Arp), (Za,Rg,R1a,R3h,Ara), (Za,Rg,R1a,R3h, Arb), (Za,Rg,R1a,R3h,Arc), (Za,Rg,R1a,R3h,Ard), (Za,Rg, R1a,R3h,Are), (Za,Rg,R1a,R3h,Arf), (Za,Rg,R1a,R3h,Arg), (Za,Rg,R1a,R3h,Arh), (Za,Rg,R1a,R3h,Ari), (Za,Rg,R1a, R3h,Arj), (Za,Rg,R1a,R3h,Ark), (Za,Rg,R1a,R3h,Arl), (Za, Rg,R1a,R3h,Arm), (Za,Rg,R1a,R3h,Arn), (Za,Rg,R1a,R3h, Aro), (Za,Rg,R1a,R3h,Arp), (Za,Rg,R1b,R3a,Ara), (Za,Rg, R1b,R3a,Arb), (Za,Rg,R1b,R3a,Arc), (Za,Rg,R1b,R3a, Ard), (Za,Rg,R1b,R3a,Are), (Za,Rg,R1b,R3a,Arf), (Za,Rg, R1b,R3a,Arg), (Za,Rg,R1b,R3a,Arh), (Za,Rg,R1b,R3a,Ari), (Za,Rg,R1b,R3a,Arj), (Za,Rg,R1b,R3a,Ark), (Za,Rg,R1b, R3a,Arl), (Za,Rg,R1b,R3a,Arm), (Za,Rg,R1b,R3a,Arn), (Za,Rg,R1b,R3a,Aro), (Za,Rg,R1b,R3a,Arp), (Za,Rg,R1b, R3b,Ara), (Za,Rg,R1b,R3b,Arb), (Za,Rg,R1b,R3b,Arc), (Za,Rg,R1b,R3b,Ard), (Za,Rg,R1b,R3b,Are), (Za,Rg,R1b, R3b,Arf), (Za,Rg,R1b,R3b,Arg), (Za,Rg,R1b,R3b,Arh), (Za,Rg,R1b,R3b,Ari), (Za,Rg,R1b,R3b,Arj), (Za,Rg,R1b, R3b,Ark), (Za,Rg,R1b,R3b,Arl), (Za,Rg,R1b,R3b,Arm), (Za,Rg,R1b,R3b,Arn), (Za,Rg,R1b,R3b,Aro), (Za,Rg,R1b, R3b,Arp), (Za,Rg,R1b,R3c,Ara), (Za,Rg,R1b,R3c,Arb), (Za,Rg,R1b,R3c,Arc), (Za,Rg,R1b,R3c,Ard), (Za,Rg,R1b, R3c,Are), (Za,Rg,R1b,R3c,Arf), (Za,Rg,R1b,R3c,Arg), (Za, Rg,R1b,R3c,Arh), (Za,Rg,R1b,R3c,Ari), (Za,Rg,R1b,R3c, Arj), (Za,Rg,R1b,R3c,Ark), (Za,Rg,R1b,R3c,Arl), (Za,Rg, R1b,R3c,Arm), (Za,Rg,R1b,R3c,Arn), (Za,Rg,R1b,R3c, Aro), (Za,Rg,R1b,R3c,Arp), (Za,Rg,R1b,R3d,Ara), (Za,Rg, R1b,R3d,Arb), (Za,Rg,R1b,R3d,Arc), (Za,Rg,R1b,R3d, Ard), (Za,Rg,R1b,R3d,Are), (Za,Rg,R1b,R3d,Arf), (Za,Rg, R1b,R3d,Arg), (Za,Rg,R1b,R3d,Arh), (Za,Rg,R1b,R3d, Ari), (Za,Rg,R1b,R3d,Arj), (Za,Rg,R1b,R3d,Ark), (Za,Rg, R1b,R3d,Arl), (Za,Rg,R1b,R3d,Arm), (Za,Rg,R1b,R3d, Arn), (Za,Rg,R1b,R3d,Aro), (Za,Rg,R1b,R3d,Arp), (Za,Rg, R1b,R3e,Ara), (Za,Rg,R1b,R3e,Arb), (Za,Rg,R1b,R3e, Arc), (Za,Rg,R1b,R3e,Ard), (Za,Rg,R1b,R3e,Are), (Za,Rg, R1b,R3e,Arf), (Za,Rg,R1b,R3e,Arg), (Za,Rg,R1b,R3e,Arh), (Za,Rg,R1b,R3e,Ari), (Za,Rg,R1b,R3e,Arj), (Za,Rg,R1b, R3e,Ark), (Za,Rg,R1b,R3e,Arl), (Za,Rg,R1b,R3e,Arm), (Za,Rg,R1b,R3e,Arn), (Za,Rg,R1b,R3e,Aro), (Za,Rg,R1b, R3e,Arp), (Za,Rg,R1b,R3f,Ara), (Za,Rg,R1b,R3f,Arb), (Za, Rg,R1b,R3f,Arc), (Za,Rg,R1b,R3f,Ard), (Za,Rg,R1b,R3f, Are), (Za,Rg,R1b,R3f,Arf), (Za,Rg,R1b,R3f,Arg), (Za,Rg, R1b,R3f,Arh), (Za,Rg,R1b,R3f,Ari), (Za,Rg,R1b,R3f,Arj), (Za,Rg,R1b,R3f,Ark), (Za,Rg,R1b,R3f,Arl), (Za,Rg,R1b, R3f,Arm), (Za,Rg,R1b,R3f,Arn), (Za,Rg,R1b,R3f,Aro), (Za, Rg,R1b,R3f,Arp), (Za,Rg,R1b,R3g,Ara), (Za,Rg,R1b,R3g, Arb), (Za,Rg,R1b,R3g,Arc), (Za,Rg,R1b,R3g,Ard), (Za,Rg, R1b,R3g,Are), (Za,Rg,R1b,R3g,Arf), (Za,Rg,R1b,R3g, Arg), (Za,Rg,R1b,R3g,Arh), (Za,Rg,R1b,R3g,Ari), (Za,Rg, R1b,R3g,Arj), (Za,Rg,R1b,R3g,Ark), (Za,Rg,R1b,R3g,Arl), (Za,Rg,R1b,R3g,Arm), (Za,Rg,R1b,R3g,Arn), (Za,Rg,R1b, R3g,Aro), (Za,Rg,R1b,R3g,Arp), (Za,Rg,R1b,R3h,Ara), (Za,Rg,R1b,R3h,Arb), (Za,Rg,R1b,R3h,Arc), (Za,Rg,R1b, R3h,Ard), (Za,Rg,R1b,R3h,Are), (Za,Rg,R1b,R3h,Arf), (Za, Rg,R1b,R3h,Arg), (Za,Rg,R1b,R3h,Arh), (Za,Rg,R1b,R3h, Ari), (Za,Rg,R1b,R3h,Arj), (Za,Rg,R1b,R3h,Ark), (Za,Rg, R1b,R3h,Arl), (Za,Rg,R1b,R3h,Arm), (Za,Rg,R1b,R3h, Arn), (Za,Rg,R1b,R3h,Aro), (Za,Rg,R1b,R3h,Arp), (Za,Rg, R1c,R3a,Ara), (Za,Rg,R1c,R3a,Arb), (Za,Rg,R1c,R3a,Arc), (Za,Rg,R1c,R3a,Ard), (Za,Rg,R1c,R3a,Are), (Za,Rg,R1c, R3a,Arf), (Za,Rg,R1c,R3a,Arg), (Za,Rg,R1c,R3a,Arh), (Za, Rg,R1c,R3a,Ari), (Za,Rg,R1c,R3a,Arj), (Za,Rg,R1c,R3a, Ark), (Za,Rg,R1c,R3a,Arl), (Za,Rg,R1c,R3a,Arm), (Za,Rg, R1c,R3a,Arn), (Za,Rg,R1c,R3a,Aro), (Za,Rg,R1c,R3a,Arp), (Za,Rg,R1c,R3b,Ara), (Za,Rg,R1c,R3b,Arb), (Za,Rg,R1c, R3b,Arc), (Za,Rg,R1c,R3b,Ard), (Za,Rg,R1c,R3b,Are), (Za, Rg,R1c,R3b,Arf), (Za,Rg,R1c,R3b,Arg), (Za,Rg,R1c,R3b, Arh), (Za,Rg,R1c,R3b,Ari), (Za,Rg,R1c,R3b,Arj), (Za,Rg, R1c,R3b,Ark), (Za,Rg,R1c,R3b,Arl), (Za,Rg,R1c,R3b, Arm), (Za,Rg,R1c,R3b,Arn), (Za,Rg,R1c,R3b,Aro), (Za,Rg, R1c,R3b,Arp), (Za,Rg,R1c,R3c,Ara), (Za,Rg,R1c,R3c,Arb), (Za,Rg,R1c,R3c,Arc), (Za,Rg,R1c,R3c,Ard), (Za,Rg,R1c, R3c,Are), (Za,Rg,R1c,R3c,Arf), (Za,Rg,R1c,R3c,Arg), (Za, Rg,R1c,R3c,Arh), (Za,Rg,R1c,R3c,Ari), (Za,Rg,R1c,R3c, Arj), (Za,Rg,R1c,R3c,Ark), (Za,Rg,R1c,R3c,Arl), (Za,Rg, R1c,R3c,Arm), (Za,Rg,R1c,R3c,Arn), (Za,Rg,R1c,R3c, Aro), (Za,Rg,R1c,R3c,Arp), (Za,Rg,R1c,R3d,Ara), (Za,Rg, R1c,R3d,Arb), (Za,Rg,R1c,R3d,Arc), (Za,Rg,R1c,R3d, Ard), (Za,Rg,R1c,R3d,Are), (Za,Rg,R1c,R3d,Arf), (Za,Rg, R1c,R3d,Arg), (Za,Rg,R1c,R3d,Arh), (Za,Rg,R1c,R3d,Ari), (Za,Rg,R1c,R3d,Arj), (Za,Rg,R1c,R3d,Ark), (Za,Rg,R1c, R3d,Arl), (Za,Rg,R1c,R3d,Arm), (Za,Rg,R1c,R3d,Arn), (Za,Rg,R1c,R3d,Aro), (Za,Rg,R1c,R3d,Arp), (Za,Rg,R1c, R3e,Ara), (Za,Rg,R1c,R3e,Arb), (Za,Rg,R1c,R3e,Arc), (Za, Rg,R1c,R3e,Ard), (Za,Rg,R1c,R3e,Are), (Za,Rg,R1c,R3e, Arf), (Za,Rg,R1c,R3e,Arg), (Za,Rg,R1c,R3e,Arh), (Za,Rg, R1c,R3e,Ari), (Za,Rg,R1c,R3e,Arj), (Za,Rg,R1c,R3e,Ark), (Za,Rg,R1c,R3e,Arl), (Za,Rg,R1c,R3e,Arm), (Za,Rg,R1c, R3e,Arn), (Za,Rg,R1c,R3e,Aro), (Za,Rg,R1c,R3e,Arp), (Za, Rg,R1c,R3f,Ara), (Za,Rg,R1c,R3f,Arb), (Za,Rg,R1c,R3f, Arc), (Za,Rg,R1c,R3f,Ard), (Za,Rg,R1c,R3f,Are), (Za,Rg, R1c,R3f,Arf), (Za,Rg,R1c,R3f,Arg), (Za,Rg,R1c,R3f,Arh), (Za,Rg,R1c,R3f,Ari), (Za,Rg,R1c,R3f,Arj), (Za,Rg,R1c, R3f,Ark), (Za,Rg,R1c,R3f,Arl), (Za,Rg,R1c,R3f,Arm), (Za, Rg,R1c,R3f,Arn), (Za,Rg,R1c,R3f,Aro), (Za,Rg,R1c,R3f, Arp), (Za,Rg,R1c,R3g,Ara), (Za,Rg,R1c,R3g,Arb), (Za,Rg, R1c,R3g,Arc), (Za,Rg,R1c,R3g,Ard), (Za,Rg,R1c,R3g, Are), (Za,Rg,R1c,R3g,Arf), (Za,Rg,R1c,R3g,Arg), (Za,Rg, R1c,R3g,Arh), (Za,Rg,R1c,R3g,Ari), (Za,Rg,R1c,R3g,Arj), (Za,Rg,R1c,R3g,Ark), (Za,Rg,R1c,R3g,Arl), (Za,Rg,R1c, R3g,Arm), (Za,Rg,R1c,R3g,Arn), (Za,Rg,R1c,R3g,Aro), (Za,Rg,R1c,R3g,Arp), (Za,Rg,R1c,R3h,Ara), (Za,Rg,R1c, R3h,Arb), (Za,Rg,R1c,R3h,Arc), (Za,Rg,R1c,R3h,Ard), (Za,Rg,R1c,R3h,Are), (Za,Rg,R1c,R3h,Arf), (Za,Rg,R1c, R3h,Arg), (Za,Rg,R1c,R3h,Arh), (Za,Rg,R1c,R3h,Ari), (Za, Rg,R1c,R3h,Arj), (Za,Rg,R1c,R3h,Ark), (Za,Rg,R1c,R3h, Arl), (Za,Rg,R1c,R3h,Arm), (Za,Rg,R1c,R3h,Arn), (Za,Rg, R1c,R3h,Aro), (Za,Rg,R1c,R3h,Arp), (Za,Rg,R1d,R3a, Ara), (Za,Rg,R1d,R3a,Arb), (Za,Rg,R1d,R3a,Arc), (Za,Rg, R1d,R3a,Ard), (Za,Rg,R1d,R3a,Are), (Za,Rg,R1d,R3a,Arf), (Za,Rg,R1d,R3a,Arg), (Za,Rg,R1d,R3a,Arh), (Za,Rg,R1d, R3a,Ari), (Za,Rg,R1d,R3a,Arj), (Za,Rg,R1d,R3a,Ark), (Za, Rg,R1d,R3a,Arl), (Za,Rg,R1d,R3a,Arm), (Za,Rg,R1d,R3a, Arn), (Za,Rg,R1d,R3a,Aro), (Za,Rg,R1d,R3a,Arp), (Za,Rg, R1d,R3b,Ara), (Za,Rg,R1d,R3b,Arb), (Za,Rg,R1d,R3b, Arc), (Za,Rg,R1d,R3b,Ard), (Za,Rg,R1d,R3b,Are), (Za,Rg, R1d,R3b,Arf), (Za,Rg,R1d,R3b,Arg), (Za,Rg,R1d,R3b, Arh), (Za,Rg,R1d,R3b,Ari), (Za,Rg,R1d,R3b,Arj), (Za,Rg, R1d,R3b,Ark), (Za,Rg,R1d,R3b,Arl), (Za,Rg,R1d,R3b, Arm), (Za,Rg,R1d,R3b,Arn), (Za,Rg,R1d,R3b,Aro), (Za,Rg, R1d,R3b,Arp), (Za,Rg,R1d,R3c,Ara), (Za,Rg,R1d,R3c, Arb), (Za,Rg,R1d,R3c,Arc), (Za,Rg,R1d,R3c,Ard), (Za,Rg, R1d,R3c,Are), (Za,Rg,R1d,R3c,Arf), (Za,Rg,R1d,R3c,Arg), (Za,Rg,R1d,R3c,Arh), (Za,Rg,R1d,R3c,Ari), (Za,Rg,R1d, R3c,Arj), (Za,Rg,R1d,R3c,Ark), (Za,Rg,R1d,R3c,Arl), (Za, Rg,R1d,R3c,Arm), (Za,Rg,R1d,R3c,Arn), (Za,Rg,R1d,R3c, Aro), (Za,Rg,R1d,R3c,Arp), (Za,Rg,R1d,R3d,Ara), (Za,Rg, R1d,R3d,Arb), (Za,Rg,R1d,R3d,Arc), (Za,Rg,R1d,R3d, Ard), (Za,Rg,R1d,R3d,Are), (Za,Rg,R1d,R3d,Arf), (Za,Rg, R1d,R3d,Arg), (Za,Rg,R1d,R3d,Arh), (Za,Rg,R1d,R3d, Ari), (Za,Rg,R1d,R3d,Arj), (Za,Rg,R1d,R3d,Ark), (Za,Rg, R1d,R3d,Arl), (Za,Rg,R1d,R3d,Arm), (Za,Rg,R1d,R3d, Arn), (Za,Rg,R1d,R3d,Aro), (Za,Rg,R1d,R3d,Arp), (Za,Rg, R1d,R3e,Ara), (Za,Rg,R1d,R3e,Arb), (Za,Rg,R1d,R3e, Arc), (Za,Rg,R1d,R3e,Ard), (Za,Rg,R1d,R3e,Are), (Za,Rg, R1d,R3e,Arf), (Za,Rg,R1d,R3e,Arg), (Za,Rg,R1d,R3e,Arh), (Za,Rg,R1d,R3e,Ari), (Za,Rg,R1d,R3e,Arj), (Za,Rg,R1d,R3e,Ark), (Za,Rg,R1d,R3e,Arl), (Za,Rg,R1d,R3e,Arm), (Za,Rg,R1d,R3e,Arn), (Za,Rg,R1d,R3e,Aro), (Za,Rg,R1d,R3e,Arp), (Za,Rg,R1d,R3f,Ara), (Za,Rg,R1d,R3f,Arb), (Za,Rg,R1d,R3f,Arc), (Za,Rg,R1d,R3f,Ard), (Za,Rg,R1d,R3f,Are), (Za,Rg,R1d,R3f,Arf), (Za,Rg,R1d,R3f,Arg), (Za,Rg,R1d,R3f,Arh), (Za,Rg,R1d,R3f,Ari), (Za,Rg,R1d,R3f,Arj), (Za,Rg,R1d,R3f,Ark), (Za,Rg,R1d,R3f,Arl), (Za,Rg,R1d,R3f,Arm), (Za,Rg,R1d,R3f,Arn), (Za,Rg,R1d,R3f,Aro), (Za,Rg,R1d,R3f,Arp), (Za,Rg,R1d,R3g,Ara), (Za,Rg,R1d,R3g,Arb), (Za,Rg,R1d,R3g,Arc), (Za,Rg,R1d,R3g,Ard), (Za,Rg,R1d,R3g,Are), (Za,Rg,R1d,R3g,Arf), (Za,Rg,R1d,R3g,Arg), (Za,Rg,R1d,R3g,Arh), (Za,Rg,R1d,R3g,Ari), (Za,Rg,R1d,R3g,Arj), (Za,Rg,R1d,R3g,Ark), (Za,Rg,R1d,R3g,Arl), (Za,Rg,R1d,R3g,Arm), (Za,Rg,R1d,R3g,Arn), (Za,Rg,R1d,R3g,Aro), (Za,Rg,R1d,R3g,Arp), (Za,Rg,R1d,R3h,Ara), (Za,Rg,R1d,R3h,Arb), (Za,Rg,R1d,R3h,Arc), (Za,Rg,R1d,R3h,Ard), (Za,Rg,R1d,R3h,Are), (Za,Rg,R1d,R3h,Arf), (Za,Rg,R1d,R3h,Arg), (Za,Rg,R1d,R3h,Arh), (Za,Rg,R1d,R3h,Ari), (Za,Rg,R1d,R3h,Arj), (Za,Rg,R1d,R3h,Ark), (Za,Rg,R1d,R3h,Arl), (Za,Rg,R1d,R3h,Arm), (Za,Rg,R1d,R3h,Arn), (Za,Rg,R1d,R3h,Aro), (Za,Rg,R1d,R3h,Arp), (Za,Rh,R1a,R3a,Ara), (Za,Rh,R1a,R3a,Arb), (Za,Rh,R1a,R3a,Arc), (Za,Rh,R1a,R3a,Ard), (Za,Rh,R1a,R3a,Are), (Za,Rh,R1a,R3a,Arf), (Za,Rh,R1a,R3a,Arg), (Za,Rh,R1a,R3a,Arh), (Za,Rh,R1a,R3a,Ari), (Za,Rh,R1a,R3a,Arj), (Za,Rh,R1a,R3a,Ark), (Za,Rh,R1a,R3a,Arl), (Za,Rh,R1a,R3a,Arm), (Za,Rh,R1a,R3a,Arn), (Za,Rh,R1a,R3a,Aro), (Za,Rh,R1a,R3a,Arp), (Za,Rh,R1a,R3b,Ara), (Za,Rh,R1a,R3b,Arb), (Za,Rh,R1a,R3b,Arc), (Za,Rh,R1a,R3b,Ard), (Za,Rh,R1a,R3b,Are), (Za,Rh,R1a,R3b,Arf), (Za,Rh,R1a,R3b,Arg), (Za,Rh,R1a,R3b,Arh), (Za,Rh,R1a,R3b,Ari), (Za,Rh,R1a,R3b,Arj), (Za,Rh,R1a,R3b,Ark), (Za,Rh,R1a,R3b,Arl), (Za,Rh,R1a,R3b,Arm), (Za,Rh,R1a,R3b,Arn), (Za,Rh,R1a,R3b,Aro), (Za,Rh,R1a,R3b,Arp), (Za,Rh,R1a,R3c,Ara), (Za,Rh,R1a,R3c,Arb), (Za,Rh,R1a,R3c,Arc), (Za,Rh,R1a,R3c,Ard), (Za,Rh,R1a,R3c,Are), (Za,Rh,R1a,R3c,Arf), (Za,Rh,R1a,R3c,Arg), (Za,Rh,R1a,R3c,Arh), (Za,Rh,R1a,R3c,Ari), (Za,Rh,R1a,R3c,Arj), (Za,Rh,R1a,R3c,Ark), (Za,Rh,R1a,R3c,Arl), (Za,Rh,R1a,R3c,Arm), (Za,Rh,R1a,R3c,Arn), (Za,Rh,R1a,R3c,Aro), (Za,Rh,R1a,R3c,Arp), (Za,Rh,R1a,R3d,Ara), (Za,Rh,R1a,R3d,Arb), (Za,Rh,R1a,R3d,Arc), (Za,Rh,R1a,R3d,Ard), (Za,Rh,R1a,R3d,Are), (Za,Rh,R1a,R3d,Arf), (Za,Rh,R1a,R3d,Arg), (Za,Rh,R1a,R3d,Arh), (Za,Rh,R1a,R3d,Ari), (Za,Rh,R1a,R3d,Arj), (Za,Rh,R1a,R3d,Ark), (Za,Rh,R1a,R3d,Arl), (Za,Rh,R1a,R3d,Arm), (Za,Rh,R1a,R3d,Arn), (Za,Rh,R1a,R3d,Aro), (Za,Rh,R1a,R3d,Arp), (Za,Rh,R1a,R3e,Ara), (Za,Rh,R1a,R3e,Arb), (Za,Rh,R1a,R3e,Arc), (Za,Rh,R1a,R3e,Ard), (Za,Rh,R1a,R3e,Are), (Za,Rh,R1a,R3e,Arf), (Za,Rh,R1a,R3e,Arg), (Za,Rh,R1a,R3e,Arh), (Za,Rh,R1a,R3e,Ari), (Za,Rh,R1a,R3e,Arj), (Za,Rh,R1a,R3e,Ark), (Za,Rh,R1a,R3e,Arl), (Za,Rh,R1a,R3e,Arm), (Za,Rh,R1a,R3e,Arn), (Za,Rh,R1a,R3e,Aro), (Za,Rh,R1a,R3e,Arp), (Za,Rh,R1a,R3f,Ara), (Za,Rh,R1a,R3f,Arb), (Za,Rh,R1a,R3f,Arc), (Za,Rh,R1a,R3f,Ard), (Za,Rh,R1a,R3f,Are), (Za,Rh,R1a,R3f,Arf), (Za,Rh,R1a,R3f,Arg), (Za,Rh,R1a,R3f,Arh), (Za,Rh,R1a,R3f,Ari), (Za,Rh,R1a,R3f,Arj), (Za,Rh,R1a,R3f,Ark), (Za,Rh,R1a,R3f,Arl), (Za,Rh,R1a,R3f,Arm), (Za,Rh,R1a,R3f,Arn), (Za,Rh,R1a,R3f,Aro), (Za,Rh,R1a,R3f,Arp), (Za,Rh,R1a,R3g,Ara), (Za,Rh,R1a,R3g,Arb), (Za,Rh,R1a,R3g,Arc), (Za,Rh,R1a,R3g,Ard), (Za,Rh,R1a,R3g,Are), (Za,Rh,R1a,R3g,Arf), (Za,Rh,R1a,R3g,Arg), (Za,Rh,R1a,R3g,Arh), (Za,Rh,R1a,R3g,Ari), (Za,Rh,R1a,R3g,Arj), (Za,Rh,R1a,R3g,Ark), (Za,Rh,R1a,R3g,Arl), (Za,Rh,R1a,R3g,Arm), (Za,Rh,R1a,R3g,Arn), (Za,Rh,R1a,R3g,Aro), (Za,Rh,R1a,R3g,Arp), (Za,Rh,R1a,R3h,Ara), (Za,Rh,R1a,R3h,Arb), (Za,Rh,R1a,R3h,Arc), (Za,Rh,R1a,R3h,Ard), (Za,Rh,R1a,R3h,Are), (Za,Rh,R1a,R3h,Arf), (Za,Rh,R1a,R3h,Arg), (Za,Rh,R1a,R3h,Arh), (Za,Rh,R1a,R3h,Ari), (Za,Rh,R1a,R3h,Arj), (Za,Rh,R1a,R3h,Ark), (Za,Rh,R1a,R3h,Arl), (Za,Rh,R1a,R3h,Arm), (Za,Rh,R1a,R3h,Arn), (Za,Rh,R1a,R3h,Aro), (Za,Rh,R1a,R3h,Arp), (Za,Rh,R1b,R3a,Ara), (Za,Rh,R1b,R3a,Arb), (Za,Rh,R1b,R3a,Arc), (Za,Rh,R1b,R3a,Ard), (Za,Rh,R1b,R3a,Are), (Za,Rh,R1b,R3a,Arf), (Za,Rh,R1b,R3a,Arg), (Za,Rh,R1b,R3a,Arh), (Za,Rh,R1b,R3a,Ari), (Za,Rh,R1b,R3a,Arj), (Za,Rh,R1b,R3a,Ark), (Za,Rh,R1b,R3a,Arl), (Za,Rh,R1b,R3a,Arm), (Za,Rh,R1b,R3a,Arn), (Za,Rh,R1b,R3a,Aro), (Za,Rh,R1b,R3a,Arp), (Za,Rh,R1b,R3b,Ara), (Za,Rh,R1b,R3b,Arb), (Za,Rh,R1b,R3b,Arc), (Za,Rh,R1b,R3b,Ard), (Za,Rh,R1b,R3b,Are), (Za,Rh,R1b,R3b,Arf), (Za,Rh,R1b,R3b,Arg), (Za,Rh,R1b,R3b,Arh), (Za,Rh,R1b,R3b,Ari), (Za,Rh,R1b,R3b,Arj), (Za,Rh,R1b,R3b,Ark), (Za,Rh,R1b,R3b,Arl), (Za,Rh,R1b,R3b,Arm), (Za,Rh,R1b,R3b,Arn), (Za,Rh,R1b,R3b,Aro), (Za,Rh,R1b,R3b,Arp), (Za,Rh,R1b,R3c,Ara), (Za,Rh,R1b,R3c,Arb), (Za,Rh,R1b,R3c,Arc), (Za,Rh,R1b,R3c,Ard), (Za,Rh,R1b,R3c,Are), (Za,Rh,R1b,R3c,Arf), (Za,Rh,R1b,R3c,Arg), (Za,Rh,R1b,R3c,Arh), (Za,Rh,R1b,R3c,Ari), (Za,Rh,R1b,R3c,Arj), (Za,Rh,R1b,R3c,Ark), (Za,Rh,R1b,R3c,Arl), (Za,Rh,R1b,R3c,Arm), (Za,Rh,R1b,R3c,Arn), (Za,Rh,R1b,R3c,Aro), (Za,Rh,R1b,R3c,Arp), (Za,Rh,R1b,R3d,Ara), (Za,Rh,R1b,R3d,Arb), (Za,Rh,R1b,R3d,Arc), (Za,Rh,R1b,R3d,Ard), (Za,Rh,R1b,R3d,Are), (Za,Rh,R1b,R3d,Arf), (Za,Rh,R1b,R3d,Arg), (Za,Rh,R1b,R3d,Arh), (Za,Rh,R1b,R3d,Ari), (Za,Rh,R1b,R3d,Arj), (Za,Rh,R1b,R3d,Ark), (Za,Rh,R1b,R3d,Arl), (Za,Rh,R1b,R3d,Arm), (Za,Rh,R1b,R3d,Arn), (Za,Rh,R1b,R3d,Aro), (Za,Rh,R1b,R3d,Arp), (Za,Rh,R1b,R3e,Ara), (Za,Rh,R1b,R3e,Arb), (Za,Rh,R1b,R3e,Arc), (Za,Rh,R1b,R3e,Ard), (Za,Rh,R1b,R3e,Are), (Za,Rh,R1b,R3e,Arf), (Za,Rh,R1b,R3e,Arg), (Za,Rh,R1b,R3e,Arh), (Za,Rh,R1b,R3e,Ari), (Za,Rh,R1b,R3e,Arj), (Za,Rh,R1b,R3e,Ark), (Za,Rh,R1b,R3e,Arl), (Za,Rh,R1b,R3e,Arm), (Za,Rh,R1b,R3e,Arn), (Za,Rh,R1b,R3e,Aro), (Za,Rh,R1b,R3e,Arp), (Za,Rh,R1b,R3f,Ara), (Za,Rh,R1b,R3f,Arb), (Za,Rh,R1b,R3f,Arc), (Za,Rh,R1b,R3f,Ard), (Za,Rh,R1b,R3f,Are), (Za,Rh,R1b,R3f,Arf), (Za,Rh,R1b,R3f,Arg), (Za,Rh,R1b,R3f,Arh), (Za,Rh,R1b,R3f,Ari), (Za,Rh,R1b,R3f,Arj), (Za,Rh,R1b,R3f,Ark), (Za,Rh,R1b,R3f,Arl), (Za,Rh,R1b,R3f,Arm), (Za,Rh,R1b,R3f,Arn), (Za,Rh,R1b,R3f,Aro), (Za,Rh,R1b,R3f,Arp), (Za,Rh,R1b,R3g,Ara), (Za,Rh,R1b,R3g,Arb), (Za,Rh,R1b,R3g,Arc), (Za,Rh,R1b,R3g,Ard), (Za,Rh,R1b,R3g,Are), (Za,Rh,R1b,R3g,Arf), (Za,Rh,R1b,R3g,Arg), (Za,Rh,R1b,R3g,Arh), (Za,Rh,R1b,R3g,Ari), (Za,Rh,R1b,R3g,Arj), (Za,Rh,R1b,R3g,Ark), (Za,Rh,R1b,R3g,Arl), (Za,Rh,R1b,R3g,Arm), (Za,Rh,R1b,R3g,Arn), (Za,Rh,R1b,R3g,Aro), (Za,Rh,R1b,R3g,Arp), (Za,Rh,R1b,R3h,Ara), (Za,Rh,R1b,R3h,Arb), (Za,Rh,R1b,R3h,Arc), (Za,Rh,R1b,R3h,Ard), (Za,Rh,R1b,R3h,Are), (Za,Rh,R1b,R3h,Arf), (Za,Rh,R1b,R3h,Arg), (Za,Rh,R1b,R3h,Arh), (Za,Rh,R1b,R3h,Ari), (Za,Rh,R1b,R3h,Arj), (Za,Rh,R1b,R3h,Ark), (Za,Rh,R1b,R3h,Arl), (Za,Rh,R1b,R3h,Arm), (Za,Rh,R1b,R3h,Arn), (Za,Rh,R1b,R3h,Aro), (Za,Rh,R1b,R3h,Arp), (Za,Rh,R1c,R3a,Ara), (Za,Rh,R1c,R3a,Arb), (Za,Rh,R1c,R3a,Arc), (Za,Rh,R1c,R3a,Ard), (Za,Rh,R1c,R3a,Are), (Za,Rh,R1c,R3a,Arf), (Za,Rh,R1c,R3a,Arg), (Za,Rh,R1c,R3a,Arh), (Za,Rh,R1c,R3a,Ari), (Za,Rh,R1c,R3a,Arj), (Za,Rh,R1c,R3a,Ark), (Za,Rh,R1c,R3a,Arl), (Za,Rh,R1c,R3a,Arm), (Za,Rh,R1c,R3a,Arn), (Za,Rh,R1c,R3a,Aro), (Za,Rh,R1c,R3a,Arp), (Za,Rh,R1c,R3b,Ara), (Za,Rh,R1c,R3b,Arb), (Za,Rh,R1c,R3b,Arc), (Za,Rh,R1c,R3b,Ard), (Za,Rh,R1c,R3b,Are), (Za,Rh,R1c,R3b,Arf), (Za,Rh,R1c,R3b,Arg), (Za,Rh,R1c,R3b,Arh), (Za,Rh,R1c,R3b,Ari), (Za,Rh,R1c,R3b,Arj), (Za,Rh,R1c,R3b,Ark), (Za,Rh,R1c,R3b,Arl), (Za,Rh,R1c,R3b, Arm), (Za,Rh,R1c,R3b,Arn), (Za,Rh,R1c,R3b,Aro), (Za,Rh,R1c,R3b,Arp), (Za,Rh,R1c,R3c,Ara), (Za,Rh,R1c,R3c,Arb), (Za,Rh,R1c,R3c,Arc), (Za,Rh,R1c,R3c,Ard), (Za,Rh,R1c,R3c,Are), (Za,Rh,R1c,R3c,Arf), (Za,Rh,R1c,R3c,Arg), (Za,Rh,R1c,R3c,Arh), (Za,Rh,R1c,R3c,Ari), (Za,Rh,R1c,R3c,Arj), (Za,Rh,R1c,R3c,Ark), (Za,Rh,R1c,R3c,Arl), (Za,Rh,R1c,R3c,Arm), (Za,Rh,R1c,R3c,Arn), (Za,Rh,R1c,R3c,Aro), (Za,Rh,R1c,R3c,Arp), (Za,Rh,R1c,R3d,Ara), (Za,Rh,R1c,R3d,Arb), (Za,Rh,R1c,R3d,Arc), (Za,Rh,R1c,R3d,Ard), (Za,Rh,R1c,R3d,Are), (Za,Rh,R1c,R3d,Arf), (Za,Rh,R1c,R3d,Arg), (Za,Rh,R1c,R3d,Arh), (Za,Rh,R1c,R3d,Ari), (Za,Rh,R1c,R3d,Arj), (Za,Rh,R1c,R3d,Ark), (Za,Rh,R1c,R3d,Arl), (Za,Rh,R1c,R3d,Arm), (Za,Rh,R1c,R3d,Arn), (Za,Rh,R1c,R3d,Aro), (Za,Rh,R1c,R3d,Arp), (Za,Rh,R1c,R3e,Ara), (Za,Rh,R1c,R3e,Arb), (Za,Rh,R1c,R3e,Arc), (Za,Rh,R1c,R3e,Ard), (Za,Rh,R1c,R3e,Are), (Za,Rh,R1c,R3e,Arf), (Za,Rh,R1c,R3e,Arg), (Za,Rh,R1c,R3e,Arh), (Za,Rh,R1c,R3e,Ari), (Za,Rh,R1c,R3e,Arj), (Za,Rh,R1c,R3e,Ark), (Za,Rh,R1c,R3e,Arl), (Za,Rh,R1c,R3e,Arm), (Za,Rh,R1c,R3e,Arn), (Za,Rh,R1c,R3e,Aro), (Za,Rh,R1c,R3e,Arp), (Za,Rh,R1c,R3f,Ara), (Za,Rh,R1c,R3f,Arb), (Za,Rh,R1c,R3f,Arc), (Za,Rh,R1c,R3f,Ard), (Za,Rh,R1c,R3f,Are), (Za,Rh,R1c,R3f,Arf), (Za,Rh,R1c,R3f,Arg), (Za,Rh,R1c,R3f,Arh), (Za,Rh,R1c,R3f,Ari), (Za,Rh,R1c,R3f,Arj), (Za,Rh,R1c,R3f,Ark), (Za,Rh,R1c,R3f,Arl), (Za,Rh,R1c,R3f,Arm), (Za,Rh,R1c,R3f,Arn), (Za,Rh,R1c,R3f,Aro), (Za,Rh,R1c,R3f,Arp), (Za,Rh,R1c,R3g,Ara), (Za,Rh,R1c,R3g,Arb), (Za,Rh,R1c,R3g,Arc), (Za,Rh,R1c,R3g,Ard), (Za,Rh,R1c,R3g,Are), (Za,Rh,R1c,R3g,Arf), (Za,Rh,R1c,R3g,Arg), (Za,Rh,R1c,R3g,Arh), (Za,Rh,R1c,R3g,Ari), (Za,Rh,R1c,R3g,Arj), (Za,Rh,R1c,R3g,Ark), (Za,Rh,R1c,R3g,Arl), (Za,Rh,R1c,R3g,Arm), (Za,Rh,R1c,R3g,Arn), (Za,Rh,R1c,R3g,Aro), (Za,Rh,R1c,R3g,Arp), (Za,Rh,R1c,R3h,Ara), (Za,Rh,R1c,R3h,Arb), (Za,Rh,R1c,R3h,Arc), (Za,Rh,R1c,R3h,Ard), (Za,Rh,R1c,R3h,Are), (Za,Rh,R1c,R3h,Arf), (Za,Rh,R1c,R3h,Arg), (Za,Rh,R1c,R3h,Arh), (Za,Rh,R1c,R3h,Ari), (Za,Rh,R1c,R3h,Arj), (Za,Rh,R1c,R3h,Ark), (Za,Rh,R1c,R3h,Arl), (Za,Rh,R1c,R3h,Arm), (Za,Rh,R1c,R3h,Arn), (Za,Rh,R1c,R3h,Aro), (Za,Rh,R1c,R3h,Arp), (Za,Rh,R1d,R3a,Ara), (Za,Rh,R1d,R3a,Arb), (Za,Rh,R1d,R3a,Arc), (Za,Rh,R1d,R3a,Ard), (Za,Rh,R1d,R3a,Are), (Za,Rh,R1d,R3a,Arf), (Za,Rh,R1d,R3a,Arg), (Za,Rh,R1d,R3a,Arh), (Za,Rh,R1d,R3a,Ari), (Za,Rh,R1d,R3a,Arj), (Za,Rh,R1d,R3a,Ark), (Za,Rh,R1d,R3a,Arl), (Za,Rh,R1d,R3a,Arm), (Za,Rh,R1d,R3a,Arn), (Za,Rh,R1d,R3a,Aro), (Za,Rh,R1d,R3a,Arp), (Za,Rh,R1d,R3b,Ara), (Za,Rh,R1d,R3b,Arb), (Za,Rh,R1d,R3b,Arc), (Za,Rh,R1d,R3b,Ard), (Za,Rh,R1d,R3b,Are), (Za,Rh,R1d,R3b,Arf), (Za,Rh,R1d,R3b,Arg), (Za,Rh,R1d,R3b,Arh), (Za,Rh,R1d,R3b,Ari), (Za,Rh,R1d,R3b,Arj), (Za,Rh,R1d,R3b,Ark), (Za,Rh,R1d,R3b,Arl), (Za,Rh,R1d,R3b,Arm), (Za,Rh,R1d,R3b,Arn), (Za,Rh,R1d,R3b,Aro), (Za,Rh,R1d,R3b,Arp), (Za,Rh,R1d,R3c,Ara), (Za,Rh,R1d,R3c,Arb), (Za,Rh,R1d,R3c,Arc), (Za,Rh,R1d,R3c,Ard), (Za,Rh,R1d,R3c,Are), (Za,Rh,R1d,R3c,Arf), (Za,Rh,R1d,R3c,Arg), (Za,Rh,R1d,R3c,Arh), (Za,Rh,R1d,R3c,Ari), (Za,Rh,R1d,R3c,Arj), (Za,Rh,R1d,R3c,Ark), (Za,Rh,R1d,R3c,Arl), (Za,Rh,R1d,R3c,Arm), (Za,Rh,R1d,R3c,Arn), (Za,Rh,R1d,R3c,Aro), (Za,Rh,R1d,R3c,Arp), (Za,Rh,R1d,R3d,Ara), (Za,Rh,R1d,R3d,Arb), (Za,Rh,R1d,R3d,Arc), (Za,Rh,R1d,R3d,Ard), (Za,Rh,R1d,R3d,Are), (Za,Rh,R1d,R3d,Arf), (Za,Rh,R1d,R3d,Arg), (Za,Rh,R1d,R3d,Arh), (Za,Rh,R1d,R3d,Ari), (Za,Rh,R1d,R3d,Arj), (Za,Rh,R1d,R3d,Ark), (Za,Rh,R1d,R3d,Arl), (Za,Rh,R1d,R3d,Arm), (Za,Rh,R1d,R3d,Arn), (Za,Rh,R1d,R3d,Aro), (Za,Rh,R1d,R3d,Arp), (Za,Rh,R1d,R3e,Ara), (Za,Rh,R1d,R3e,Arb), (Za,Rh,R1d,R3e,Arc), (Za,Rh,R1d,R3e,Ard), (Za,Rh,R1d,R3e,Are), (Za,Rh,R1d,R3e,Arf), (Za,Rh,R1d,R3e,Arg), (Za,Rh,R1d,R3e,Arh), (Za,Rh,R1d,R3e,Ari), (Za,Rh,R1d,R3e,Arj), (Za,Rh,R1d,R3e,Ark), (Za,Rh,R1d,R3e,Arl), (Za,Rh,R1d,R3e,Arm), (Za,Rh,R1d,R3e,Arn), (Za,Rh,R1d,R3e,Aro), (Za,Rh,R1d,R3e,Arp), (Za,Rh,R1d,R3f,Ara), (Za,Rh,R1d,R3f,Arb), (Za,Rh,R1d,R3f,Arc), (Za,Rh,R1d,R3f,Ard), (Za,Rh,R1d,R3f,Are), (Za,Rh,R1d,R3f,Arf), (Za,Rh,R1d,R3f,Arg), (Za,Rh,R1d,R3f,Arh), (Za,Rh,R1d,R3f,Ari), (Za,Rh,R1d,R3f,Arj), (Za,Rh,R1d,R3f,Ark), (Za,Rh,R1d,R3f,Arl), (Za,Rh,R1d,R3f,Arm), (Za,Rh,R1d,R3f,Arn), (Za,Rh,R1d,R3f,Aro), (Za,Rh,R1d,R3f,Arp), (Za,Rh,R1d,R3g,Ara), (Za,Rh,R1d,R3g,Arb), (Za,Rh,R1d,R3g,Arc), (Za,Rh,R1d,R3g,Ard), (Za,Rh,R1d,R3g,Are), (Za,Rh,R1d,R3g,Arf), (Za,Rh,R1d,R3g,Arg), (Za,Rh,R1d,R3g,Arh), (Za,Rh,R1d,R3g,Ari), (Za,Rh,R1d,R3g,Arj), (Za,Rh,R1d,R3g,Ark), (Za,Rh,R1d,R3g,Arl), (Za,Rh,R1d,R3g,Arm), (Za,Rh,R1d,R3g,Arn), (Za,Rh,R1d,R3g,Aro), (Za,Rh,R1d,R3g,Arp), (Za,Rh,R1d,R3h,Ara), (Za,Rh,R1d,R3h,Arb), (Za,Rh,R1d,R3h,Arc), (Za,Rh,R1d,R3h,Ard), (Za,Rh,R1d,R3h,Are), (Za,Rh,R1d,R3h,Arf), (Za,Rh,R1d,R3h,Arg), (Za,Rh,R1d,R3h,Arh), (Za,Rh,R1d,R3h,Ari), (Za,Rh,R1d,R3h,Arj), (Za,Rh,R1d,R3h,Ark), (Za,Rh,R1d,R3h,Arl), (Za,Rh,R1d,R3h,Arm), (Za,Rh,R1d,R3h,Arn), (Za,Rh,R1d,R3h,Aro), (Za,Rh,R1d,R3h,Arp), (Za,Ri,R1a,R3a,Ara), (Za,Ri,R1a,R3a,Arb), (Za,Ri,R1a,R3a,Arc), (Za,Ri,R1a,R3a,Ard), (Za,Ri,R1a,R3a,Are), (Za,Ri,R1a,R3a,Arf), (Za,Ri,R1a,R3a,Arg), (Za,Ri,R1a,R3a,Arh), (Za,Ri,R1a,R3a,Ari), (Za,Ri,R1a,R3a,Arj), (Za,Ri,R1a,R3a,Ark), (Za,Ri,R1a,R3a,Arl), (Za,Ri,R1a,R3a,Arm), (Za,Ri,R1a,R3a,Arn), (Za,Ri,R1a,R3a,Aro), (Za,Ri,R1a,R3a,Arp), (Za,Ri,R1a,R3b,Ara), (Za,Ri,R1a,R3b,Arb), (Za,Ri,R1a,R3b,Arc), (Za,Ri,R1a,R3b,Ard), (Za,Ri,R1a,R3b,Are), (Za,Ri,R1a,R3b,Arf), (Za,Ri,R1a,R3b,Arg), (Za,Ri,R1a,R3b,Arh), (Za,Ri,R1a,R3b,Ari), (Za,Ri,R1a,R3b,Arj), (Za,Ri,R1a,R3b,Ark), (Za,Ri,R1a,R3b,Arl), (Za,Ri,R1a,R3b,Arm), (Za,Ri,R1a,R3b,Arn), (Za,Ri,R1a,R3b,Aro), (Za,Ri,R1a,R3b,Arp), (Za,Ri,R1a,R3c,Ara), (Za,Ri,R1a,R3c,Arb), (Za,Ri,R1a,R3c,Arc), (Za,Ri,R1a,R3c,Ard), (Za,Ri,R1a,R3c,Are), (Za,Ri,R1a,R3c,Arf), (Za,Ri,R1a,R3c,Arg), (Za,Ri,R1a,R3c,Arh), (Za,Ri,R1a,R3c,Ari), (Za,Ri,R1a,R3c,Arj), (Za,Ri,R1a,R3c,Ark), (Za,Ri,R1a,R3c,Arl), (Za,Ri,R1a,R3c,Arm), (Za,Ri,R1a,R3c,Arn), (Za,Ri,R1a,R3c,Aro), (Za,Ri,R1a,R3c,Arp), (Za,Ri,R1a,R3d,Ara), (Za,Ri,R1a,R3d,Arb), (Za,Ri,R1a,R3d,Arc), (Za,Ri,R1a,R3d,Ard), (Za,Ri,R1a,R3d,Are), (Za,R1,R1a,R3d,Arf), (Za,Ri,R1a,R3d,Arg), (Za,Ri,R1a,R3d,Arh), (Za,Ri,R1a,R3d,Ari), (Za,Ri,R1a,R3d,Arj), (Za,Ri,R1a,R3d,Ark), (Za,Ri,R1a,R3d,Arl), (Za,Ri,R1a,R3d,Arm), (Za,Ri,R1a,R3d,Arn), (Za,Ri,R1a,R3d,Aro), (Za,Ri,R1a,R3d,Arp), (Za,Ri,R1a,R3e,Ara), (Za,Ri,R1a,R3e,Arb), (Za,R1,R1a,R3e,Arc), (Za,Ri,R1a,R3e,Ard), (Za,Ri,R1a,R3e,Are), (Za,Ri,R1a,R3e,Arf), (Za,Ri,R1a,R3e,Arg), (Za,Ri,R1a,R3e,Arh), (Za,Ri,R1a,R3e,Ari), (Za,Ri,R1a,R3e,Arj), (Za,Ri,R1a,R3e,Ark), (Za,Ri,R1a,R3e,Arl), (Za,Ri,R1a,R3e,Arm), (Za,Ri,R1a,R3e,Arn), (Za,Ri,R1a,R3e,Aro), (Za,Ri,R1a,R3e,Arp), (Za,Ri,R1a,R3f,Ara), (Za,Ri,R1a,R3f,Arb), (Za,Ri,R1a,R3f,Arc), (Za,Ri,R1a,R3f,Ard), (Za,Ri,R1a,R3f,Are), (Za,Ri,R1a,R3f,Arf), (Za,Ri,R1a,R3f,Arg), (Za,Ri,R1a,R3f,Arh), (Za,Ri,R1a,R3f,Ari), (Za,Ri,R1a,R3f,Arj), (Za,Ri,R1a,R3f,Ark), (Za,Ri,R1a,R3f,Arl), (Za,Ri,R1a,R3f,Arm), (Za,Ri,R1a,R3f,Arn), (Za,Ri,R1a,R3f,Aro), (Za,Ri,R1a,R3f,Arp), (Za,Ri,R1a,R3g,Ara), (Za,Ri,R1a,R3g,Arb), (Za,Ri,R1a,R3g,Arc), (Za,Ri,R1a,R3g,Ard), (Za,Ri,R1a,R3g,Are), (Za,Ri,R1a,R3g,Arf), (Za,Ri,R1a,R3g,Arg), (Za,Ri,R1a,R3g,Arh), (Za,Ri,R1a,R3g,Ari), (Za,R1,R1a,R3g,Arj), (Za,Ri,R1a,R3g,Ark), (Za,Ri,R1a,R3g,Arl), (Za,Ri,R1a,R3g,Arm), (Za,Ri,R1a,R3g,Arn), (Za,Ri,R1a,R3g,Aro), (Za,Ri,R1a,R3g,Arp), (Za,Ri,R1a,R3h,Ara), (Za,Ri,R1a,R3h,Arb), (Za,Ri,R1a,R3h,Arc), (Za,Ri,R1a,R3h,Ard), (Za,Ri,R1a,R3h,Are), (Za,Ri,R1a,R3h, Arf), (Za,Ri,R1a,R3h,Arg), (Za,Ri,R1a,R3h,Arh), (Za,Ri,R1a,R3h,Ari), (Za,Ri,R1a,R3h,Arj), (Za,Ri,R1a,R3h,Ark), (Za,Ri,R1a,R3h,Arl), (Za,Ri,R1a,R3h,Arm), (Za,Ri,R1a,R3h,Arn), (Za,Ri,R1a,R3h,Aro), (Za,Ri,R1a,R3h,Arp), (Za,Ri,R1b,R3a,Ara), (Za,Ri,R1b,R3a,Arb), (Za,Ri,R1b,R3a,Arc), (Za,Ri,R1b,R3a,Ard), (Za,Ri,R1b,R3a,Are), (Za,Ri,R1b,R3a,Arf), (Za,Ri,R1b,R3a,Arg), (Za,Ri,R1b,R3a,Arh), (Za,Ri,R1b,R3a,Ari), (Za,Ri,R1b,R3a,Arj), (Za,Ri,R1b,R3a,Ark), (Za,Ri,R1b,R3a,Arl), (Za,Ri,R1b,R3a,Arm), (Za,Ri,R1b,R3a,Arn), (Za,Ri,R1b,R3a,Aro), (Za,Ri,R1b,R3a,Arp), (Za,Ri,R1b,R3b,Ara), (Za,Ri,R1b,R3b,Arb), (Za,Ri,R1b,R3b,Arc), (Za,Ri,R1b,R3b,Ard), (Za,Ri,R1b,R3b,Are), (Za,Ri,R1b,R3b,Arf), (Za,Ri,R1b,R3b,Arg), (Za,Ri,R1b,R3b,Arh), (Za,Ri,R1b,R3b,Ari), (Za,Ri,R1b,R3b,Arj), (Za,Ri,R1b,R3b,Ark), (Za,Ri,R1b,R3b,Arl), (Za,Ri,R1b,R3b,Arm), (Za,R1,R1b,R3b,Arn), (Za,Ri,R1b,R3b,Aro), (Za,Ri,R1b,R3b,Arp), (Za,Ri,R1b,R3c,Ara), (Za,Ri,R1b,R3c,Arb), (Za,Ri,R1b,R3c,Arc), (Za,Ri,R1b,R3c,Ard), (Za,Ri,R1b,R3c,Are), (Za,Ri,R1b,R3c,Arf), (Za,Ri,R1b,R3c,Arg), (Za,Ri,R1b,R3c,Arh), (Za,Ri,R1b,R3c,Ari), (Za,Ri,R1b,R3c,Arj), (Za,Ri,R1b,R3c,Ark), (Za,Ri,R1b,R3c,Arl), (Za,Ri,R1b,R3c,Arm), (Za,Ri,R1b,R3c,Arn), (Za,Ri,R1b,R3c,Aro), (Za,Ri,R1b,R3c,Arp), (Za,Ri,R1b,R3d,Ara), (Za,Ri,R1b,R3d,Arb), (Za,Ri,R1b,R3d,Arc), (Za,Ri,R1b,R3d,Ard), (Za,Ri,R1b,R3d,Are), (Za,Ri,R1b,R3d,Arf), (Za,Ri,R1b,R3d,Arg), (Za,Ri,R1b,R3d,Arh), (Za,Ri,R1b,R3d,Ari), (Za,Ri,R1b,R3d,Arj), (Za,Ri,R1b,R3d,Ark), (Za,Ri,R1b,R3d,Arl), (Za,Ri,R1b,R3d,Arm), (Za,Ri,R1b,R3d,Arn), (Za,Ri,R1b,R3d,Aro), (Za,Ri,R1b,R3d,Arp), (Za,Ri,R1b,R3e,Ara), (Za,Ri,R1b,R3e,Arb), (Za,Ri,R1b,R3e,Arc), (Za,Ri,R1b,R3e,Ard), (Za,Ri,R1b,R3e,Are), (Za,Ri,R1b,R3e,Arf), (Za,Ri,R1b,R3e,Arg), (Za,Ri,R1b,R3e,Arh), (Za,Ri,R1b,R3e,Ari), (Za,Ri,R1b,R3e,Arj), (Za,Ri,R1b,R3e,Ark), (Za,Ri,R1b,R3e,Arl), (Za,Ri,R1b,R3e,Arm), (Za,Ri,R1b,R3e,Arn), (Za,Ri,R1b,R3e,Aro), (Za,Ri,R1b,R3e,Arp), (Za,Ri,R1b,R3f,Ara), (Za,Ri,R1b,R3f,Arb), (Za,Ri,R1b,R3f,Arc), (Za,Ri,R1b,R3f,Ard), (Za,Ri,R1b,R3f,Are), (Za,Ri,R1b,R3f,Arf), (Za,Ri,R1b,R3f,Arg), (Za,Ri,R1b,R3f,Arh), (Za,Ri,R1b,R3f,Ari), (Za,Ri,R1b,R3f,Arj), (Za,Ri,R1b,R3f,Ark), (Za,Ri,R1b,R3f,Arl), (Za,Ri,R1b,R3f,Arm), (Za,Ri,R1b,R3f,Arn), (Za,Ri,R1b,R3f,Aro), (Za,Ri,R1b,R3f,Arp), (Za,Ri,R1b,R3g,Ara), (Za,Ri,R1b,R3g,Arb), (Za,Ri,R1b,R3g,Arc), (Za,Ri,R1b,R3g,Ard), (Za,Ri,R1b,R3g,Are), (Za,Ri,R1b,R3g,Arf), (Za,Ri,R1b,R3g,Arg), (Za,Ri,R1b,R3g,Arh), (Za,Ri,R1b,R3g,Ari), (Za,Ri,R1b,R3g,Arj), (Za,Ri,R1b,R3g,Ark), (Za,Ri,R1b,R3g,Arl), (Za,Ri,R1b,R3g,Arm), (Za,Ri,R1b,R3g,Arn), (Za,Ri,R1b,R3g,Aro), (Za,Ri,R1b,R3g,Arp), (Za,Ri,R1b,R3h,Ara), (Za,Ri,R1b,R3h,Arb), (Za,Ri,R1b,R3h,Arc), (Za,Ri,R1b,R3h,Ard), (Za,Ri,R1b,R3h,Are), (Za,Ri,R1b,R3h,Arf), (Za,Ri,R1b,R3h,Arg), (Za,Ri,R1b,R3h,Arh), (Za,Ri,R1b,R3h,Ari), (Za,Ri,R1b,R3h,Arj), (Za,Ri,R1b,R3h,Ark), (Za,Ri,R1b,R3h,Arl), (Za,Ri,R1b,R3h,Arm), (Za,Ri,R1b,R3h,Arn), (Za,Ri,R1b,R3h,Aro), (Za,Ri,R1b,R3h,Arp), (Za,Ri,R1c,R3a,Ara), (Za,Ri,R1c,R3a,Arb), (Za,Ri,R1c,R3a,Arc), (Za,Ri,R1c,R3a,Ard), (Za,Ri,R1c,R3a,Are), (Za,Ri,R1c,R3a,Arf), (Za,Ri,R1c,R3a,Arg), (Za,Ri,R1c,R3a,Arh), (Za,Ri,R1c,R3a,Ari), (Za,Ri,R1c,R3a,Arj), (Za,Ri,R1c,R3a,Ark), (Za,Ri,R1c,R3a,Arl), (Za,Ri,R1c,R3a,Arm), (Za,Ri,R1c,R3a,Arn), (Za,Ri,R1c,R3a,Aro), (Za,Ri,R1c,R3a,Arp), (Za,Ri,R1c,R3b,Ara), (Za,Ri,R1c,R3b,Arb), (Za,Ri,R1c,R3b,Arc), (Za,Ri,R1c,R3b,Ard), (Za,Ri,R1c,R3b,Are), (Za,Ri,R1c,R3b,Arf), (Za,Ri,R1c,R3b,Arg), (Za,Ri,R1c,R3b,Arh), (Za,Ri,R1c,R3b,Ari), (Za,Ri,R1c,R3b,Arj), (Za,Ri,R1c,R3b,Ark), (Za,Ri,R1c,R3b,Arl), (Za,Ri,R1c,R3b,Arm), (Za,Ri,R1c,R3b,Arn), (Za,Ri,R1c,R3b,Aro), (Za,Ri,R1c,R3b,Arp), (Za,Ri,R1c,R3c,Ara), (Za,Ri,R1c,R3c,Arb), (Za,Ri,R1c,R3c,Arc), (Za,Ri,R1c,R3c,Ard), (Za,Ri,R1c,R3c,Are), (Za,Ri,R1c,R3c,Arf), (Za,Ri,R1c,R3c,Arg), (Za,Ri,R1c,R3c,Arh), (Za,Ri,R1c,R3c,Ari), (Za,Ri,R1c,R3c,Arj), (Za,Ri,R1c,R3c,Ark), (Za,Ri,R1c,R3c,Arl), (Za,Ri,R1c,R3c,Arm), (Za,Ri,R1c,R3c,Arn), (Za,Ri,R1c,R3c,Aro), (Za,Ri,R1c,R3c,Arp), (Za,Ri,R1c,R3d,Ara), (Za,Ri,R1c,R3d,Arb), (Za,Ri,R1c,R3d,Arc), (Za,Ri,R1c,R3d,Ard), (Za,Ri,R1c,R3d,Are), (Za,Ri,R1c,R3d,Arf), (Za,Ri,R1c,R3d,Arg), (Za,Ri,R1c,R3d,Arh), (Za,Ri,R1c,R3d,Ari), (Za,Ri,R1c,R3d,Arj), (Za,Ri,R1c,R3d,Ark), (Za,Ri,R1c,R3d,Arl), (Za,Ri,R1c,R3d,Arm), (Za,Ri,R1c,R3d,Arn), (Za,Ri,R1c,R3d,Aro), (Za,Ri,R1c,R3d,Arp), (Za,Ri,R1c,R3e,Ara), (Za,Ri,R1c,R3e,Arb), (Za,Ri,R1c,R3e,Arc), (Za,Ri,R1c,R3e,Ard), (Za,Ri,R1c,R3e,Are), (Za,Ri,R1c,R3e,Arf), (Za,Ri,R1c,R3e,Arg), (Za,Ri,R1c,R3e,Arh), (Za,Ri,R1c,R3e,Ari), (Za,Ri,R1c, R3e,Arj), (Za,Ri,R1c,R3e,Ark), (Za,Ri,R1c,R3e,Arl), (Za,Ri,R1c,R3e,Arm), (Za,Ri,R1c,R3e,Arn), (Za,Ri,R1c,R3e,Aro), (Za,Ri,R1c,R3e,Arp), (Za,Ri,R1c,R3f,Ara), (Za,Ri,R1c,R3f,Arb), (Za,Ri,R1c,R3f,Arc), (Za,Ri,R1c,R3f,Ard), (Za,Ri,R1c,R3f,Are), (Za,Ri,R1c,R3f,Arf), (Za,Ri,R1c,R3f,Arg), (Za,Ri,R1c,R3f,Arh), (Za,Ri,R1c,R3f,Ari), (Za,Ri,R1c,R3f,Arj), (Za,Ri,R1c,R3f,Ark), (Za,R1,R1c,R3f,Arl), (Za,Ri,R1c,R3f,Arm), (Za,Ri,R1c,R3f,Arn), (Za,Ri,R1c,R3f,Aro), (Za,Ri,R1c,R3f,Arp), (Za,Ri,R1c,R3g,Ara), (Za,Ri,R1c,R3g,Arb), (Za,Ri,R1c,R3g,Arc), (Za,Ri,R1c,R3g,Ard), (Za,Ri,R1c,R3g,Are), (Za,Ri,R1c,R3g,Arf), (Za,Ri,R1c,R3g,Arg), (Za,Ri,R1c,R3g,Arh), (Za,R1,R1c,R3g,Ari), (Za,Ri,R1c,R3g,Arj), (Za,Ri,R1c,R3g,Ark), (Za,Ri,R1c,R3g,Arl), (Za,Ri,R1c,R3g,Arm), (Za,Ri,R1c,R3g,Arn), (Za,Ri,R1c,R3g,Aro), (Za,Ri,R1c,R3g,Arp), (Za,Ri,R1c,R3h,Ara), (Za,Ri,R1c,R3h,Arb), (Za,Ri,R1c,R3h,Arc), (Za,Ri,R1c,R3h,Ard), (Za,Ri,R1c,R3h,Are), (Za,Ri,R1c,R3h,Arf), (Za,Ri,R1c,R3h,Arg), (Za,Ri,R1c,R3h,Arh), (Za,Ri,R1c,R3h,Ari), (Za,Ri,R1c,R3h,Arj), (Za,Ri,R1c,R3h,Ark), (Za,Ri,R1c,R3h,Arl), (Za,Ri,R1c,R3h,Arm), (Za,Ri,R1c,R3h,Arn), (Za,Ri,R1c,R3h,Aro), (Za,Ri,R1c,R3h,Arp), (Za,Ri,R1d,R3a,Ara), (Za,Ri,R1d,R3a,Arb), (Za,Ri,R1d,R3a,Arc), (Za,Ri,R1d,R3a,Ard), (Za,Ri,R1d,R3a,Are), (Za,Ri,R1d,R3a,Arf), (Za,Ri,R1d,R3a,Arg), (Za,Ri,R1d,R3a,Arh), (Za,Ri,R1d,R3a,Ari), (Za,Ri,R1d,R3a,Arj), (Za,Ri,R1d,R3a,Ark), (Za,Ri,R1d,R3a,Arl), (Za,Ri,R1d,R3a,Arm), (Za,Ri,R1d,R3a,Arn), (Za,Ri,R1d,R3a,Aro), (Za,Ri,R1d,R3a,Arp), (Za,Ri,R1d,R3b,Ara), (Za,Ri,R1d,R3b,Arb), (Za,Ri,R1d,R3b,Arc), (Za,Ri,R1d,R3b,Ard), (Za,Ri,R1d,R3b,Are), (Za,Ri,R1d,R3b,Arf), (Za,Ri,R1d,R3b,Arg), (Za,Ri,R1d,R3b,Arh), (Za,Ri,R1d,R3b,Ari), (Za,Ri,R1d,R3b,Arj), (Za,Ri,R1d,R3b,Ark), (Za,Ri,R1d,R3b,Arl), (Za,Ri,R1d,R3b,Arm), (Za,Ri,R1d,R3b,Arn), (Za,Ri,R1d,R3b,Aro), (Za,Ri,R1d,R3b,Arp), (Za,R1,R1d,R3c,Ara), (Za,Ri,R1d,R3c,Arb), (Za,Ri,R1d,R3c,Arc), (Za,Ri,R1d,R3c,Ard), (Za,Ri,R1d,R3c,Are), (Za,Ri,R1d,R3c,Arf), (Za,Ri,R1d,R3c,Arg), (Za,Ri,R1d,R3c,Arh), (Za,Ri,R1d,R3c,Ari), (Za,Ri,R1d,R3c,Arj), (Za,Ri,R1d,R3c,Ark), (Za,Ri,R1d,R3c,Arl), (Za,Ri,R1d,R3c,Arm), (Za,Ri,R1d,R3c,Arn), (Za,Ri,R1d,R3c,Aro), (Za,Ri,R1d,R3c,Arp), (Za,Ri,R1d,R3d,Ara), (Za,Ri,R1d,R3d,Arb), (Za,Ri,R1d,R3d,Arc), (Za,Ri,R1d,R3d,Ard), (Za,Ri,R1d,R3d,Are), (Za,Ri,R1d,R3d,Arf), (Za,Ri,R1d,R3d,Arg), (Za,Ri,R1d,R3d,Arh), (Za,Ri,R1d,R3d,Ari), (Za,Ri,R1d,R3d,Arj), (Za,Ri,R1d,R3d,Ark), (Za,Ri,R1d,R3d,Arl), (Za,Ri,R1d,R3d,Arm), (Za,Ri,R1d,R3d,Arn), (Za,Ri,R1d,R3d,Aro), (Za,Ri,R1d,R3d,Arp), (Za,Ri,R1d,R3e,Ara), (Za,Ri,R1d,R3e,Arb), (Za,Ri,R1d,R3e,Arc), (Za,Ri,R1d,R3e,Ard), (Za,Ri,R1d,R3e,Are), (Za,Ri,R1d,R3e,Arf), (Za,Ri,R1d,R3e,Arg), (Za,Ri,R1d,R3e,Arh), (Za,Ri,R1d,R3e,Ari), (Za,Ri,R1d,R3e,Arj), (Za,Ri,R1d,R3e,Ark), (Za,Ri,R1d,R3e,Arl), (Za,Ri,R1d,R3e,Arm), (Za,Ri,R1d,R3e,Arn), (Za,Ri,R1d,R3e,Aro), (Za,Ri,R1d,R3e,Arp), (Za,Ri,R1d,R3f,Ara), (Za,Ri,R1d,R3f,Arb), (Za,Ri,R1d, R3f,Arc), (Za,Ri,R1d,R3f,Ard), (Za,Ri,R1d,R3f,Are), (Za,Ri,R1d,R3f,Arf), (Za,Ri,R1d,R3f,Arg), (Za,Ri,R1d,R3f,Arh), (Za,Ri,R1d,R3f,Ari), (Za,Ri,R1d,R3f,Arj), (Za,Ri,R1d,R3f,Ark), (Za,Ri,R1d,R3f,Arl), (Za,Ri,R1d,R3f,Arm), (Za,Ri,R1d,R3f,Arn), (Za,Ri,R1d,R3f,Aro), (Za,Ri,R1d,R3f,Arp), (Za,Ri,R1d,R3g,Ara), (Za,Ri,R1d,R3g,Arb), (Za,Ri,R1d,R3g,Arc), (Za,Ri,R1d,R3g,Ard), (Za,Ri,R1d,R3g,Are), (Za,Ri,R1d,R3g,Arf), (Za,Ri,R1d,R3g,Arg), (Za,Ri,R1d,R3g,Arh), (Za,Ri,R1d,R3g,Ari), (Za,Ri,R1d,R3g,Arj), (Za,Ri,R1d,R3g,Ark), (Za,Ri,R1d,R3g,Arl), (Za,Ri,R1d,R3g,Arm), (Za,Ri,R1d,R3g,Arn), (Za,Ri,R1d,R3g,Aro), (Za,Ri,R1d,R3g,Arp), (Za,Ri,R1d,R3h,Ara), (Za,Ri,R1d,R3h,Arb), (Za,Ri,R1d,R3h,Arc), (Za,Ri,R1d,R3h,Ard), (Za,Ri,R1d,R3h,Are), (Za,Ri,R1d,R3h,Arf), (Za,Ri,R1d,R3h,Arg), (Za,Ri,R1d,R3h,Arh), (Za,Ri,R1d,R3h,Ari), (Za,Ri,R1d,R3h,Arj), (Za,Ri,R1d,R3h,Ark), (Za,Ri,R1d,R3h,Arl), (Za,Ri,R1d,R3h,Arm), (Za,Ri,R1d,R3h,Arn), (Za,Ri,R1d,R3h,Aro), (Za,Ri,R1d,R3h,Arp), (Za,Rj,R1a,R3a,Ara), (Za,Rj,R1a,R3a,Arb), (Za,Rj,R1a,R3a,Arc), (Za,Rj,R1a,R3a,Ard), (Za,Rj,R1a,R3a,Are), (Za,Rj,R1a,R3a,Arf), (Za,Rj,R1a,R3a,Arg), (Za,Rj,R1a,R3a,Arh), (Za,Rj,R1a,R3a,Ari), (Za,Rj,R1a,R3a,Arj), (Za,Rj,R1a,R3a,Ark), (Za,Rj,R1a,R3a,Arl), (Za,Rj,R1a,R3a,Arm), (Za,Rj,R1a,R3a,Arn), (Za,Rj,R1a,R3a,Aro), (Za,Rj,R1a,R3a,Arp), (Za,Rj,R1a,R3b,Ara), (Za,Rj,R1a,R3b,Arb), (Za,Rj,R1a,R3b,Arc), (Za,Rj,R1a,R3b,Ard), (Za,Rj,R1a,R3b,Are), (Za,Rj,R1a,R3b,Arf), (Za,Rj,R1a,R3b,Arg), (Za,Rj,R1a,R3b,Arh), (Za,Rj,R1a,R3b,Ari), (Za,Rj,R1a,R3b,Arj), (Za,Rj,R1a,R3b,Ark), (Za,Rj,R1a,R3b,Arl), (Za,Rj,R1a,R3b,Arm), (Za,Rj,R1a,R3b,Arn), (Za,Rj,R1a,R3b,Aro), (Za,Rj,R1a,R3b,Arp), (Za,Rj,R1a,R3c,Ara), (Za,Rj,R1a,R3c,Arb), (Za,Rj,R1a,R3c,Arc), (Za,Rj,R1a,R3c,Ard), (Za,Rj,R1a,R3c,Are), (Za,Rj,R1a,R3c,Arf), (Za,Rj,R1a,R3c,Arg), (Za,Rj,R1a,R3c,Arh), (Za,Rj,R1a,R3c,Ari), (Za,Rj,R1a,R3c,Arj), (Za,Rj,R1a,R3c,Ark), (Za,Rj,R1a,R3c,Arl), (Za,Rj,R1a,R3c,Arm), (Za,Rj,R1a,R3c,Arn), (Za,Rj,R1a,R3c,Aro), (Za,Rj,R1a,R3c,Arp), (Za,Rj,R1a,R3d,Ara), (Za,Rj,R1a,R3d,Arb), (Za,Rj,R1a,R3d,Arc), (Za,Rj,R1a,R3d,Ard), (Za,Rj,R1a,R3d,Are), (Za,Rj,R1a,R3d,Arf), (Za,Rj,R1a,R3d,Arg), (Za,Rj,R1a,R3d,Arh), (Za,Rj,R1a,R3d,Ari), (Za,Rj,R1a,R3d,Arj), (Za,Rj,R1a,R3d,Ark), (Za,Rj,R1a,R3d,Arl), (Za,Rj,R1a,R3d,Arm), (Za,Rj,R1a,R3d,Arn), (Za,Rj,R1a,R3d,Aro), (Za,Rj,R1a,R3d,Arp), (Za,Rj,R1a,R3e,Ara), (Za,Rj,R1a,R3e,Arb), (Za,Rj,R1a,R3e,Arc), (Za,Rj,R1a,R3e,Ard), (Za,Rj,R1a,R3e,Are), (Za,Rj,R1a,R3e,Arf), (Za,Rj,R1a,R3e,Arg), (Za,Rj,R1a,R3e,Arh), (Za,Rj,R1a,R3e,Ari), (Za,Rj,R1a,R3e,Arj), (Za,Rj,R1a,R3e,Ark), (Za,Rj,R1a,R3e,Arl), (Za,Rj,R1a,R3e,Arm), (Za,Rj,R1a,R3e,Arn), (Za,Rj,R1a,R3e,Aro), (Za,Rj,R1a,R3e,Arp), (Za,Rj,R1a,R3f,Ara), (Za,Rj,R1a,R3f,Arb), (Za,Rj,R1a,R3f,Arc), (Za,Rj,R1a,R3f,Ard), (Za,Rj,R1a,R3f,Are), (Za,Rj,R1a,R3f,Arf), (Za,Rj,R1a,R3f,Arg), (Za,Rj,R1a,R3f,Arh), (Za,Rj,R1a,R3f,Ari), (Za,Rj,R1a,R3f,Arj), (Za,Rj,R1a,R3f,Ark), (Za,Rj,R1a,R3f,Arl), (Za,Rj,R1a,R3f,Arm), (Za,Rj,R1a,R3f,Arn), (Za,Rj,R1a,R3f,Aro), (Za,Rj,R1a,R3f,Arp), (Za,Rj,R1a,R3g,Ara), (Za,Rj,R1a,R3g,Arb), (Za,Rj,R1a,R3g,Arc), (Za,Rj,R1a,R3g,Ard), (Za,Rj,R1a,R3g,Are), (Za,Rj,R1a,R3g,Arf), (Za,Rj,R1a,R3g,Arg), (Za,Rj,R1a,R3g,Arh), (Za,Rj,R1a,R3g,Ari), (Za,Rj,R1a,R3g,Arj), (Za,Rj,R1a,R3g,Ark), (Za,Rj,R1a,R3g,Arl), (Za,Rj,R1a,R3g,Arm), (Za,Rj,R1a,R3g,Arn), (Za,Rj,R1a,R3g,Aro), (Za,Rj,R1a,R3g,Arp), (Za,Rj,R1a,R3h,Ara), (Za,Rj,R1a,R3h,Arb), (Za,Rj,R1a,R3h,Arc), (Za,Rj,R1a,R3h,Ard), (Za,Rj,R1a,R3h,Are), (Za,Rj,R1a,R3h,Arf), (Za,Rj,R1a,R3h,Arg), (Za,Rj,R1a,R3h,Arh), (Za,Rj,R1a,R3h,Ari), (Za,Rj,R1a,R3h,Arj), (Za,Rj,R1a,R3h,Ark), (Za,Rj,R1a,R3h,Arl), (Za,Rj,R1a,R3h,Arm), (Za,Rj,R1a,R3h,Arn), (Za,Rj,R1a,R3h,Aro), (Za,Rj,R1a,R3h,Arp), (Za,Rj,R1b,R3a,Ara), (Za,Rj,R1b,R3a,Arb), (Za,Rj,R1b,R3a,Arc), (Za,Rj,R1b,R3a,Ard), (Za,Rj,R1b,R3a,Are), (Za,Rj,R1b,R3a,Arf), (Za,Rj,R1b,R3a,Arg), (Za,Rj,R1b,R3a,Arh), (Za,Rj,R1b,R3a,Ari), (Za,Rj,R1b,R3a,Arj), (Za,Rj,R1b,R3a,Ark), (Za,Rj,R1b,R3a,Arl), (Za,Rj,R1b,R3a,Arm), (Za,Rj,R1b,R3a,Arn), (Za,Rj,R1b,R3a,Aro), (Za,Rj,R1b,R3a,Arp), (Za,Rj,R1b,R3b,Ara), (Za,Rj,R1b,R3b,Arb), (Za,Rj,R1b,R3b,Arc), (Za,Rj,R1b,R3b,Ard), (Za,Rj,R1b,R3b,Are), (Za,Rj,R1b,R3b,Arf), (Za,Rj,R1b,R3b,Arg), (Za,Rj,R1b,R3b,Arh), (Za,Rj,R1b,R3b,Ari), (Za,Rj,R1b,R3b,Arj), (Za,Rj,R1b,R3b,Ark), (Za,Rj,R1b,R3b,Arl), (Za,Rj,R1b,R3b,Arm), (Za,Rj,R1b,R3b,Arn), (Za,Rj,R1b,R3b,Aro), (Za,Rj,R1b,R3b,Arp), (Za,Rj,R1b,R3c,Ara), (Za,Rj,R1b,R3c,Arb), (Za,Rj,R1b,R3c,Arc), (Za,Rj,R1b,R3c,Ard), (Za,Rj,R1b,R3c,Are), (Za,Rj,R1b,R3c,Arf), (Za,Rj,R1b,R3c,Arg), (Za,Rj,R1b,R3c,Arh), (Za,Rj,R1b,R3c,Ari), (Za,Rj,R1b,R3c,Arj), (Za,Rj,R1b,R3c,Ark), (Za,Rj,R1b,R3c,Arl), (Za,Rj,R1b,R3c,Arm), (Za,Rj,R1b,R3c,Arn), (Za,Rj,R1b,R3c,Aro), (Za,Rj,R1b,R3c,Arp), (Za,Rj,R1b,R3d,Ara), (Za,Rj,R1b,R3d,Arb), (Za,Rj,R1b,R3d,Arc), (Za,Rj,R1b,R3d,Ard), (Za,Rj,R1b,R3d,Are), (Za,Rj,R1b,R3d,Arf), (Za,Rj,R1b,R3d,Arg), (Za,Rj,R1b,R3d,Arh), (Za,Rj,R1b,R3d,Ari), (Za,Rj,R1b,R3d,Arj), (Za,Rj,R1b,R3d,Ark), (Za,Rj,R1b,R3d,Arl), (Za,Rj,R1b,R3d,Arm), (Za,Rj,R1b,R3d,Arn), (Za,Rj,R1b,R3d,Aro), (Za,Rj,R1b,R3d,Arp), (Za,Rj,R1b,R3e,Ara), (Za,Rj,R1b,R3e,Arb), (Za,Rj,R1b,R3e,Arc), (Za,Rj,R1b,R3e,Ard), (Za,Rj,R1b,R3e,Are), (Za,Rj,R1b,R3e,Arf), (Za,Rj,R1b,R3e,Arg), (Za,Rj,R1b,R3e,Arh), (Za,Rj,R1b,R3e,Ari), (Za,Rj,R1b,R3e,Arj), (Za,Rj,R1b,R3e,Ark), (Za,Rj,R1b,R3e,Arl), (Za,Rj,R1b,R3e,Arm), (Za,Rj,R1b,R3e,Arn), (Za,Rj,R1b,R3e,Aro), (Za,Rj,R1b,R3e,Arp), (Za,Rj,R1b,R3f,Ara), (Za,Rj,R1b,R3f,Arb), (Za,Rj,R1b,R3f,Arc), (Za,Rj,R1b,R3f,Ard), (Za,Rj,R1b,R3f,Are), (Za,Rj,R1b,R3f,Arf), (Za,Rj,R1b,R3f,Arg), (Za,Rj,R1b,R3f,Arh), (Za,Rj,R1b,R3f,Ari), (Za,Rj,R1b,R3f,Arj), (Za,Rj,R1b,R3f,Ark), (Za,Rj,R1b,R3f,Arl), (Za,Rj,R1b,R3f,Arm), (Za,Rj,R1b,R3f,Arn), (Za,Rj,R1b,R3f,Aro), (Za,Rj,R1b,R3f,Arp), (Za,Rj,R1b,R3g,Ara), (Za,Rj,R1b,R3g,Arb), (Za,Rj,R1b,R3g,Arc), (Za,Rj,R1b,R3g,Ard), (Za,Rj,R1b,R3g,Are), (Za,Rj,R1b,R3g,Arf), (Za,Rj,R1b,R3g,Arg), (Za,Rj,R1b,R3g,Arh), (Za,Rj,R1b,R3g,Ari), (Za,Rj,R1b,R3g,Arj), (Za,Rj,R1b,R3g,Ark), (Za,Rj,R1b,R3g,Arl), (Za,Rj,R1b,R3g,Arm), (Za,Rj,R1b,R3g,Arn), (Za,Rj,R1b,R3g,Aro), (Za,Rj,R1b,R3g,Arp), (Za,Rj,R1b,R3h,Ara), (Za,Rj,R1b,R3h,Arb), (Za,Rj,R1b,R3h,Arc), (Za,Rj,R1b,R3h,Ard), (Za,Rj,R1b,R3h,Are), (Za,Rj,R1b,R3h,Arf), (Za,Rj,R1b,R3h,Arg), (Za,Rj,R1b,R3h,Arh), (Za,Rj,R1b,R3h,Ari), (Za,Rj,R1b,R3h,Arj), (Za,Rj,R1b,R3h,Ark), (Za,Rj,R1b,R3h,Arl), (Za,Rj,R1b,R3h,Arm), (Za,Rj,R1b,R3h,Arn), (Za,Rj,R1b,R3h,Aro), (Za,Rj,R1b,R3h,Arp), (Za,Rj,R1c,R3a,Ara), (Za,Rj,R1c,R3a,Arb), (Za,Rj,R1c,R3a,Arc), (Za,Rj,R1c,R3a,Ard), (Za,Rj,R1c,R3a,Are), (Za,Rj,R1c,R3a,Arf), (Za,Rj,R1c,R3a,Arg), (Za,Rj,R1c,R3a,Arh), (Za,Rj,R1c,R3a,Ari), (Za,Rj,R1c,R3a,Arj), (Za,Rj,R1c,R3a,Ark), (Za,Rj,R1c,R3a,Arl), (Za,Rj,R1c,R3a,Arm), (Za,Rj,R1c,R3a,Arn), (Za,Rj,R1c,R3a,Aro), (Za,Rj,R1c,R3a,Arp), (Za,Rj,R1c,R3b,Ara), (Za,Rj,R1c,R3b,Arb), (Za,Rj,R1c,R3b,Arc), (Za,Rj,R1c,R3b,Ard), (Za,Rj,R1c,R3b,Are), (Za,Rj,R1c,R3b,Arf), (Za,Rj,R1c,R3b,Arg), (Za,Rj,R1c,R3b,Arh), (Za,Rj,R1c,R3b,Ari), (Za,Rj,R1c,R3b,Arj), (Za,Rj,R1c,R3b,Ark), (Za,Rj,R1c,R3b,Arl), (Za,Rj,R1c,R3b,Arm), (Za,Rj,R1c,R3b,Arn), (Za,Rj,R1c,R3b,Aro), (Za,Rj,R1c,R3b,Arp), (Za,Rj,R1c,R3c,Ara), (Za,Rj,R1c,R3c,Arb), (Za,Rj,R1c,R3c,Arc), (Za,Rj,R1c,R3c,Ard), (Za,Rj,R1c,R3c,Are), (Za,Rj,R1c,R3c,Arf), (Za,Rj,R1c,R3c,Arg), (Za,Rj,R1c,R3c,Arh), (Za,Rj,R1c,R3c,Ari), (Za,Rj,R1c,R3c,Arj), (Za,Rj,R1c,R3c,Ark), (Za,Rj,R1c,R3c,Arl), (Za,Rj,R1c,R3c,Arm), (Za,Rj,R1c,R3c,Arn), (Za,Rj,R1c,R3c,Aro), (Za,Rj,R1c, R3c,Arp), (Za,Rj,R1c,R3d,Ara), (Za,Rj,R1c,R3d,Arb), (Za, Rj,R1c,R3d,Arc), (Za,Rj,R1c,R3d,Ard), (Za,Rj,R1c,R3d, Are), (Za,Rj,R1c,R3d,Arf), (Za,Rj,R1c,R3d,Arg), (Za,Rj, R1c,R3d,Arh), (Za,Rj,R1c,R3d,Ari), (Za,Rj,R1c,R3d,Arj), (Za,Rj,R1c,R3d,Ark), (Za,Rj,R1c,R3d,Arl), (Za,Rj,R1c, R3d,Arm), (Za,Rj,R1c,R3d,Arn), (Za,Rj,R1c,R3d,Aro), (Za, Rj,R1c,R3d,Arp), (Za,Rj,R1c,R3e,Ara), (Za,Rj,R1c,R3e, Arb), (Za,Rj,R1c,R3e,Arc), (Za,Rj,R1c,R3e,Ard), (Za,Rj, R1c,R3e,Are), (Za,Rj,R1c,R3e,Arf), (Za,Rj,R1c,R3e,Arg), (Za,Rj,R1c,R3e,Arh), (Za,Rj,R1c,R3e,Ari), (Za,Rj,R1c, R3e,Arj), (Za,Rj,R1c,R3e,Ark), (Za,Rj,R1c,R3e,Arl), (Za, Rj,R1c,R3e,Arm), (Za,Rj,R1c,R3e,Arn), (Za,Rj,R1c,R3e, Aro), (Za,Rj,R1c,R3e,Arp), (Za,Rj,R1c,R3f,Ara), (Za,Rj, R1c,R3f,Arb), (Za,Rj,R1c,R3f,Arc), (Za,Rj,R1c,R3f,Ard), (Za,Rj,R1c,R3f,Are), (Za,Rj,R1c,R3f,Arf), (Za,Rj,R1c,R3f, Arg), (Za,Rj,R1c,R3f,Arh), (Za,Rj,R1c,R3f,Ari), (Za,Rj, R1c,R3f,Arj), (Za,Rj,R1c,R3f,Ark), (Za,Rj,R1c,R3f,Arl), (Za,Rj,R1c,R3f,Arm), (Za,Rj,R1c,R3f,Arn), (Za,Rj,R1c, R3f,Aro), (Za,Rj,R1c,R3f,Arp), (Za,Rj,R1c,R3g,Ara), (Za, Rj,R1c,R3g,Arb), (Za,Rj,R1c,R3g,Arc), (Za,Rj,R1c,R3g, Ard), (Za,Rj,R1c,R3g,Are), (Za,Rj,R1c,R3g,Arf), (Za,Rj, R1c,R3g,Arg), (Za,Rj,R1c,R3g,Arh), (Za,Rj,R1c,R3g,Ari), (Za,Rj,R1c,R3g,Arj), (Za,Rj,R1c,R3g,Ark), (Za,Rj,R1c, R3g,Arl), (Za,Rj,R1c,R3g,Arm), (Za,Rj,R1c,R3g,Arn), (Za, Rj,R1c,R3g,Aro), (Za,Rj,R1c,R3g,Arp), (Za,Rj,R1c,R3h, Ara), (Za,Rj,R1c,R3h,Arb), (Za,Rj,R1c,R3h,Arc), (Za,Rj, R1c,R3h,Ard), (Za,Rj,R1c,R3h,Are), (Za,Rj,R1c,R3h,Arf), (Za,Rj,R1c,R3h,Arg), (Za,Rj,R1c,R3h,Arh), (Za,Rj,R1c, R3h,Ari), (Za,Rj,R1c,R3h,Arj), (Za,Rj,R1c,R3h,Ark), (Za, Rj,R1c,R3h,Arl), (Za,Rj,R1c,R3h,Arm), (Za,Rj,R1c,R3h, Arn), (Za,Rj,R1c,R3h,Aro), (Za,Rj,R1c,R3h,Arp), (Za,Rj, R1d,R3a,Ara), (Za,Rj,R1d,R3a,Arb), (Za,Rj,R1d,R3a,Arc), (Za,Rj,R1d,R3a,Ard), (Za,Rj,R1d,R3a,Are), (Za,Rj,R1d, R3a,Arf), (Za,Rj,R1d,R3a,Arg), (Za,Rj,R1d,R3a,Arh), (Za, Rj,R1d,R3a,Ari), (Za,Rj,R1d,R3a,Arj), (Za,Rj,R1d,R3a, Ark), (Za,Rj,R1d,R3a,Arl), (Za,Rj,R1d,R3a,Arm), (Za,Rj, R1d,R3a,Arn), (Za,Rj,R1d,R3a,Aro), (Za,Rj,R1d,R3a,Arp), (Za,Rj,R1d,R3b,Ara), (Za,Rj,R1d,R3b,Arb), (Za,Rj,R1d, R3b,Arc), (Za,Rj,R1d,R3b,Ard), (Za,Rj,R1d,R3b,Are), (Za, Rj,R1d,R3b,Arf), (Za,Rj,R1d,R3b,Arg), (Za,Rj,R1d,R3b, Arh), (Za,Rj,R1d,R3b,Ari), (Za,Rj,R1d,R3b,Arj), (Za,Rj, R1d,R3b,Ark), (Za,Rj,R1d,R3b,Arl), (Za,Rj,R1d,R3b,Arm), (Za,Rj,R1d,R3b,Arn), (Za,Rj,R1d,R3b,Aro), (Za,Rj,R1d, R3b,Arp), (Za,Rj,R1d,R3c,Ara), (Za,Rj,R1d,R3c,Arb), (Za, Rj,R1d,R3c,Arc), (Za,Rj,R1d,R3c,Ard), (Za,Rj,R1d,R3c, Are), (Za,Rj,R1d,R3c,Arf), (Za,Rj,R1d,R3c,Arg), (Za,Rj, R1d,R3c,Arh), (Za,Rj,R1d,R3c,Ari), (Za,Rj,R1d,R3c,Arj), (Za,Rj,R1d, R3c,Ark), (Za,Rj,R1d,R3c,Arl), (Za,Rj,R1d, R3c,Arm), (Za,Rj,R1d,R3c,Arn), (Za,Rj,R1d,R3c,Aro), (Za, Rj,R1d,R3c,Arp), (Za,Rj,R1d,R3d,Ara), (Za,Rj,R1d,R3d, Arb), (Za,Rj,R1d,R3d,Arc), (Za,Rj,R1d,R3d,Ard), (Za,Rj, R1d,R3d,Are), (Za,Rj,R1d,R3d,Arf), (Za,Rj,R1d,R3d,Arg), (Za,Rj,R1d,R3d,Arh), (Za,Rj,R1d,R3d,Ari), (Za,Rj,R1d, R3d,Arj), (Za,Rj,R1d,R3d,Ark), (Za,Rj,R1d,R3d,Arl), (Za, Rj,R1d,R3d,Arm), (Za,Rj,R1d,R3d,Arn), (Za,Rj,R1d,R3d, Aro), (Za,Rj,R1d,R3d,Arp), (Za,Rj,R1d,R3e,Ara), (Za,Rj, R1d,R3e,Arb), (Za,Rj,R1d,R3e,Arc), (Za,Rj,R1d,R3e,Ard), (Za,Rj,R1d,R3e,Are), (Za,Rj,R1d,R3e,Arf), (Za,Rj,R1d, R3e,Arg), (Za,Rj,R1d,R3e,Arh), (Za,Rj,R1d,R3e,Ari), (Za, Rj,R1d,R3e,Arj), (Za,Rj,R1d,R3e,Ark), (Za,Rj,R1d,R3e, Arl), (Za,Rj,R1d,R3e,Arm), (Za,Rj,R1d,R3e,Arn), (Za,Rj, R1d,R3e,Aro), (Za,Rj,R1d,R3e,Arp), (Za,Rj,R1d,R3f,Ara), (Za,Rj,R1d,R3f,Arb), (Za,Rj,R1d,R3f,Arc), (Za,Rj,R1d, R3f,Ard), (Za,Rj,R1d,R3f,Are), (Za,Rj,R1d,R3f,Arf), (Za, Rj,R1d,R3f,Arg), (Za,Rj,R1d,R3f,Arh), (Za,Rj,R1d,R3f, Ari), (Za,Rj,R1d,R3f,Arj), (Za,Rj,R1d,R3f,Ark), (Za,Rj, R1d,R3f,Arl), (Za,Rj,R1d,R3f,Arm), (Za,Rj,R1d,R3f,Arn), (Za,Rj,R1d,R3f,Aro), (Za,Rj,R1d,R3f,Arp), (Za,Rj,R1d, R3g,Ara), (Za,Rj,R1d,R3g,Arb), (Za,Rj,R1d,R3g,Arc), (Za, Rj,R1d,R3g,Ard), (Za,Rj,R1d,R3g,Are), (Za,Rj,R1d,R3g, Arf), (Za,Rj,R1d,R3g,Arg), (Za,Rj,R1d,R3g,Arh), (Za,Rj, R1d,R3g,Ari), (Za,Rj,R1d,R3g,Atj), (Za,Rj,R1d,R3g,Ark), (Za,Rj,R1d,R3g,Arl), (Za,Rj,R1d,R3g,Arm), (Za,Rj,R1d, R3g,Arn), (Za,Rj,R1d,R3g,Aro), (Za,Rj,R1d,R3g,Arp), (Za, Rj,R1d,R3h,Ara), (Za,Rj,R1d,R3h,Arb), (Za,Rj,R1d,R3h, Arc), (Za,Rj,R1d,R3h,Ard), (Za,Rj,R1d,R3h,Are), (Za,Rj, R1d,R3h,Arf), (Za,Rj,R1d,R3h,Arg), (Za,Rj,R1d,R3h,Arh), (Za,Rj,R1d,R3h,Ari), (Za,Rj,R1d,R3h,Arj), (Za,Rj,R1d, R3h,Ark), (Za,Rj,R1d,R3h,Arl), (Za,Rj,R1d,R3h,Arm), (Za, Rj,R1d,R3h,Arn), (Za,Rj,R1d,R3h,Aro), (Za,Rj,R1d,R3h, Arp), (Zb,Ra,R1a,R3a,Ara), (Zb,Ra,R1a,R3a,Arb), (Zb,Ra, R1a,R3a,Arc), (Zb,Ra,R1a,R3a,Ard), (Zb,Ra,R1a,R3a,Are), (Zb,Ra,R1a,R3a,Arf), (Zb,Ra,R1a,R3a,Arg), (Zb,Ra,R1a, R3a,Arh), (Zb,Ra,R1a,R3a,Ari), (Zb,Ra,R1a,R3a,Arj), (Zb, Ra,R1a,R3a,Ark), (Zb,Ra,R1a,R3a,Arl), (Zb,Ra,R1a,R3a, Arm), (Zb,Ra,R1a,R3a,Arn), (Zb,Ra,R1a,R3a,Aro), (Zb,Ra, R1a,R3a,Arp), (Zb,Ra,R1a,R3b,Ara), (Zb,Ra,R1a,R3b, Arb), (Zb,Ra,R1a,R3b,Arc), (Zb,Ra,R1a,R3b,Ard), (Zb,Ra, R1a,R3b,Are), (Zb,Ra,R1a,R3b,Arf), (Zb,Ra,R1a,R3b,Arg), (Zb,Ra,R1a,R3b,Arh), (Zb,Ra,R1a,R3b,Ari), (Zb,Ra,R1a, R3b,Arj), (Zb,Ra,R1a,R3b,Ark), (Zb,Ra,R1a,R3b,Arl), (Zb, Ra,R1a,R3b,Arm), (Zb,Ra,R1a,R3b,Arn), (Zb,Ra,R1a,R3b, Aro), (Zb,Ra,R1a,R3b,Arp), (Zb,Ra,R1a,R3c,Ara), (Zb,Ra, R1a,R3c,Arb), (Zb,Ra,R1a,R3c,Arc), (Zb,Ra,R1a,R3c,Ard), (Zb,Ra,R1a,R3c,Are), (Zb,Ra,R1a,R3c,Arf), (Zb,Ra,R1a, R3c,Arg), (Zb,Ra,R1a,R3c,Arh), (Zb,Ra,R1a,R3c,Ari), (Zb, Ra,R1a,R3c,Arj), (Zb,Ra,R1a,R3c,Ark), (Zb,Ra,R1a,R3c, Arl), (Zb,Ra,R1a,R3c,Arm), (Zb,Ra,R1a,R3c,Arn), (Zb,Ra, R1a,R3c,Aro), (Zb,Ra,R1a,R3c,Arp), (Zb,Ra,R1a,R3d,Ara), (Zb,Ra,R1a,R3d,Arb), (Zb,Ra,R1a,R3d,Arc), (Zb,Ra,R1a, R3d,Ard), (Zb,Ra,R1a,R3d,Are), (Zb,Ra,R1a,R3d,Arf), (Zb, Ra,R1a,R3d,Arg), (Zb,Ra,R1a,R3d,Arh), (Zb,Ra,R1a,R3d, Ari), (Zb,Ra,R1a,R3d,Arj), (Zb,Ra,R1a,R3d,Ark), (Zb,Ra, R1a,R3d,Arl), (Zb,Ra,R1a,R3d,Arm), (Zb,Ra,R1a,R3d, Arn), (Zb,Ra,R1a,R3d,Aro), (Zb,Ra,R1a,R3d,Arp), (Zb,Ra, R1a,R3e,Ara), (Zb,Ra,R1a,R3e,Arb), (Zb,Ra,R1a,R3e,Arc), (Zb,Ra,R1a,R3e,Ard), (Zb,Ra,R1a,R3e,Are), (Zb,Ra,R1a, R3e,Arf), (Zb,Ra,R1a,R3e,Arg), (Zb,Ra,R1a,R3e,Arh), (Zb, Ra,R1a,R3e,Ari), (Zb,Ra,R1a,R3e,Arj), (Zb,Ra,R1a,R3e, Ark), (Zb,Ra,R1a,R3e,Arl), (Zb,Ra,R1a,R3e,Arm), (Zb,Ra, R1a,R3e,Arn), (Zb,Ra,R1a,R3e,Aro), (Zb,Ra,R1a,R3e,Arp), (Zb,Ra,R1a,R3f,Ara), (Zb,Ra,R1a,R3f,Arb), (Zb,Ra,R1a, R3f,Arc), (Zb,Ra,R1a,R3f,Ard), (Zb,Ra,R1a,R3f,Are), (Zb, Ra,R1a,R3f,Arf), (Zb,Ra,R1a,R3f,Arg), (Zb,Ra,R1a,R3f, Arh), (Zb,Ra,R1a,R3f,Ari), (Zb,Ra,R1a,R3f,Arj), (Zb,Ra, R1a,R3f,Ark), (Zb,Ra,R1a,R3f,Arl), (Zb,Ra,R1a,R3f,Arm), (Zb,Ra,R1a,R3f,Arn), (Zb,Ra,R1a,R3f,Aro), (Zb,Ra,R1a, R3f,Arp), (Zb,Ra,R1a,R3g,Ara), (Zb,Ra,R1a,R3g,Arb), (Zb, Ra,R1a,R3g,Arc), (Zb,Ra,R1a,R3g,Ard), (Zb,Ra,R1a,R3g, Are), (Zb,Ra,R1a,R3g,Arf), (Zb,Ra,R1a,R3g,Arg), (Zb,Ra, R1a,R3g,Arh), (Zb,Ra,R1a,R3g,Ari), (Zb,Ra,R1a,R3g,Arj), (Zb,Ra,R1a,R3g,Ark), (Zb,Ra,R1a,R3g,Arl), (Zb,Ra,R1a, R3g,Arm), (Zb,Ra,R1a,R3g,Arn), (Zb,Ra,R1a,R3g,Aro), (Zb,Ra,R1a,R3g,Arp), (Zb,Ra,R1a,R3h,Ara), (Zb,Ra,R1a, R3h,Arb), (Zb,Ra,R1a,R3h,Arc), (Zb,Ra,R1a,R3h,Ard), (Zb,Ra,R1a,R3h,Are), (Zb,Ra,R1a,R3h,Arf), (Zb,Ra,R1a, R3h,Arg), (Zb,Ra,R1a,R3h,Arh), (Zb,Ra,R1a,R3h,Ari), (Zb, Ra,R1a,R3h,Arj), (Zb,Ra,R1a,R3h,Ark), (Zb,Ra,R1a,R3h, Arl), (Zb,Ra,R1a,R3h,Arm), (Zb,Ra,R1a,R3h,Arn), (Zb,Ra, R1a,R3h,Aro), (Zb,Ra,R1a,R3h,Arp), (Zb,Ra,R1b,R3a, Ara), (Zb,Ra,R1b,R3a,Arb), (Zb,Ra,R1b,R3a,Arc), (Zb,Ra, R1b,R3a,Ard), (Zb,Ra,R1b,R3a,Are), (Zb,Ra,R1b,R3a,Arf), (Zb,Ra,R1b,R3a,Arg), (Zb,Ra,R1b,R3a,Arh), (Zb,Ra,R1b, R3a,Ari), (Zb,Ra,R1b,R3a,Arj), (Zb,Ra,R1b,R3a,Ark), (Zb, Ra,R1b,R3a,Arl), (Zb,Ra,R1b,R3a,Arm), (Zb,Ra,R1b,R3a, Arn), (Zb,Ra,R1b,R3a,Aro), (Zb,Ra,R1b,R3a,Arp), (Zb,Ra, R1b,R3b,Ara), (Zb,Ra,R1b,R3b,Arb), (Zb,Ra,R1b,R3b, Arc), (Zb,Ra,R1b,R3b,Ard), (Zb,Ra,R1b,R3b,Are), (Zb,Ra, R1b,R3b,Arf), (Zb,Ra,R1b,R3b,Arg), (Zb,Ra,R1b,R3b, Arh), (Zb,Ra,R1b,R3b,Ari), (Zb,Ra,R1b,R3b,Arj), (Zb,Ra, R1b,R3b,Ark), (Zb,Ra,R1b,R3b,Arl), (Zb,Ra,R1b,R3b, Arm), (Zb,Ra,R1b,R3b,Arn), (Zb,Ra,R1b,R3b,Aro), (Zb,Ra, R1b,R3b,Arp), (Zb,Ra,R1b,R3c,Ara), (Zb,Ra,R1b,R3c, Arb), (Zb,Ra,R1b,R3c,Arc), (Zb,Ra,R1b,R3c,Ard), (Zb,Ra, R1b,R3c,Are), (Zb,Ra,R1b,R3c,Arf), (Zb,Ra,R1b,R3c,Arg), (Zb,Ra,R1b,R3c,Arh), (Zb,Ra,R1b,R3c,Ari), (Zb,Ra,R1b, R3c,Arj), (Zb,Ra,R1b,R3c,Ark), (Zb,Ra,R1b,R3c,Arl), (Zb, Ra,R1b,R3c,Arm), (Zb,Ra,R1b,R3c,Arn), (Zb,Ra,R1b,R3c, Aro), (Zb,Ra,R1b,R3c,Arp), (Zb,Ra,R1b,R3d,Ara), (Zb,Ra, R1b,R3d,Arb), (Zb,Ra,R1b,R3d,Arc), (Zb,Ra,R1b,R3d, Ard), (Zb,Ra,R1b,R3d,Are), (Zb,Ra,R1b,R3d,Arf), (Zb,Ra, R1b,R3d,Arg), (Zb,Ra,R1b,R3d,Arh), (Zb,Ra,R1b,R3d, Ari), (Zb,Ra,R1b,R3d,Arj), (Zb,Ra,R1b,R3d,Ark), (Zb,Ra, R1b,R3d,Arl), (Zb,Ra,R1b,R3d,Arm), (Zb,Ra,R1b,R3d, Arn), (Zb,Ra,R1b,R3d,Aro), (Zb,Ra,R1b,R3d,Arp), (Zb,Ra, R1b,R3e,Ara), (Zb,Ra,R1b,R3e,Arb), (Zb,Ra,R1b,R3e, Arc), (Zb,Ra,R1b,R3e,Ard), (Zb,Ra,R1b,R3e,Are), (Zb,Ra, R1b,R3e,Arf), (Zb,Ra,R1b,R3e,Arg), (Zb,Ra,R1b,R3e,Arh), (Zb,Ra,R1b,R3e,Ari), (Zb,Ra,R1b,R3e,Arj), (Zb,Ra,R1b, R3e,Ark), (Zb,Ra,R1b,R3e,Arl), (Zb,Ra,R1b,R3e,Arm), (Zb,Ra,R1b,R3e,Arn), (Zb,Ra,R1b,R3e,Aro), (Zb,Ra,R1b, R3e,Arp), (Zb,Ra,R1b,R3f,Ara), (Zb,Ra,R1b,R3f,Arb), (Zb, Ra,R1b,R3f,Arc), (Zb,Ra,R1b,R3f,Ard), (Zb,Ra,R1b,R3f, Are), (Zb,Ra,R1b,R3f,Arf), (Zb,Ra,R1b,R3f,Arg), (Zb,Ra, R1b,R3f,Arh), (Zb,Ra,R1b,R3f,Ari), (Zb,Ra,R1b,R3f,Arj), (Zb,Ra,R1b,R3f,Ark), (Zb,Ra,R1b,R3f,Arl), (Zb,Ra,R1b, R3f,Arm), (Zb,Ra,R1b,R3f,Arn), (Zb,Ra,R1b,R3f,Aro), (Zb,Ra,R1b,R3f,Arp), (Zb,Ra,R1b,R3g,Ara), (Zb,Ra,R1b, R3g,Arb), (Zb,Ra,R1b,R3g,Arc), (Zb,Ra,R1b,R3g,Ard), (Zb,Ra,R1b,R3g,Are), (Zb,Ra,R1b,R3g,Arf), (Zb,Ra,R1b, R3g,Arg), (Zb,Ra,R1b,R3g,Arh), (Zb,Ra,R1b,R3g,Ari), (Zb,Ra,R1b,R3g,Arj), (Zb,Ra,R1b,R3g,Ark), (Zb,Ra,R1b, R3g,Arl), (Zb,Ra,R1b,R3g,Arm), (Zb,Ra,R1b,R3g,Arn), (Zb,Ra,R1b,R3g,Aro), (Zb,Ra,R1b,R3g,Arp), (Zb,Ra,R1b, R3h,Ara), (Zb,Ra,R1b,R3h,Arb), (Zb,Ra,R1b,R3h,Arc), (Zb,Ra,R1b,R3h,Ard), (Zb,Ra,R1b,R3h,Are), (Zb,Ra,R1b, R3h,Arf), (Zb,Ra,R1b,R3h,Arg), (Zb,Ra,R1b,R3h,Arh), (Zb,Ra,R1b,R3h,Ari), (Zb,Ra,R1b,R3h,Arj), (Zb,Ra,R1b, R3h,Ark), (Zb,Ra,R1b,R3h,Arl), (Zb,Ra,R1b,R3h,Arm), (Zb,Ra,R1b,R3h,Arn), (Zb,Ra,R1b,R3h,Aro), (Zb,Ra,R1b, R3h,Arp), (Zb,Ra,R1c,R3a,Ara), (Zb,Ra,R1c,R3a,Arb), (Zb, Ra,R1c,R3a,Arc), (Zb,Ra,R1c,R3a,Ard), (Zb,Ra,R1c,R3a, Are), (Zb,Ra,R1c,R3a,Arf), (Zb,Ra,R1c,R3a,Arg), (Zb,Ra, R1c,R3a,Arh), (Zb,Ra,R1c,R3a,Ari), (Zb,Ra,R1c,R3a,Arj), (Zb,Ra,R1c,R3a,Ark), (Zb,Ra,R1c,R3a,Arl), (Zb,Ra,R1c, R3a,Arm), (Zb,Ra,R1c,R3a,Arn), (Zb,Ra,R1c,R3a,Aro), (Zb,Ra,R1c,R3a,Arp), (Zb,Ra,R1c,R3b,Ara), (Zb,Ra,R1c, R3b,Arb), (Zb,Ra,R1c,R3b,Arc), (Zb,Ra,R1c,R3b,Ard), (Zb,Ra,R1c,R3b,Are), (Zb,Ra,R1c,R3b,Arf), (Zb,Ra,R1c, R3b,Arg), (Zb,Ra,R1c,R3b,Arh), (Zb,Ra,R1c,R3b,Ari), (Zb, Ra,R1c,R3b,Arj), (Zb,Ra,R1c,R3b,Ark), (Zb,Ra,R1c,R3b, Arl), (Zb,Ra,R1c,R3b,Arm), (Zb,Ra,R1c,R3b,Arn), (Zb,Ra, R1c,R3b,Aro), (Zb,Ra,R1c,R3b,Arp), (Zb,Ra,R1c,R3c, Ara), (Zb,Ra,R1c,R3c,Arb), (Zb,Ra,R1c,R3c,Arc), (Zb,Ra, R1c,R3c,Ard), (Zb,Ra,R1c,R3c,Are), (Zb,Ra,R1c,R3c,Arf), (Zb,Ra,R1c,R3c,Arg), (Zb,Ra,R1c,R3c,Arh), (Zb,Ra,R1c, R3c,Ari), (Zb,Ra,R1c,R3c,Arj), (Zb,Ra,R1c,R3c,Ark), (Zb, Ra,R1c,R3c,Arl), (Zb,Ra,R1c,R3c,Arm), (Zb,Ra,R1c,R3c, Arn), (Zb,Ra,R1c,R3c,Aro), (Zb,Ra,R1c,R3c,Arp), (Zb,Ra, R1c,R3d,Ara), (Zb,Ra,R1c,R3d,Arb), (Zb,Ra,R1c,R3d, Arc), (Zb,Ra,R1c,R3d,Ard), (Zb,Ra,R1c,R3d,Are), (Zb,Ra, R1c,R3d,Arf), (Zb,Ra,R1c,R3d,Arg), (Zb,Ra,R1c,R3d,Arh), (Zb,Ra,R1c,R3d,Ari), (Zb,Ra,R1c,R3d,Arj), (Zb,Ra,R1c, R3d,Ark), (Zb,Ra,R1c,R3d,Arl), (Zb,Ra,R1c,R3d,Arm), (Zb,Ra,R1c,R3d,Arn), (Zb,Ra,R1c,R3d,Aro), (Zb,Ra,R1c, R3d,Arp), (Zb,Ra,R1c,R3e,Ara), (Zb,Ra,R1c,R3e,Arb), (Zb, Ra,R1c,R3e,Arc), (Zb,Ra,R1c,R3e,Ard), (Zb,Ra,R1c,R3e, Are), (Zb,Ra,R1c,R3e,Arf), (Zb,Ra,R1c,R3e,Arg), (Zb,Ra, R1c,R3e,Arh), (Zb,Ra,R1c,R3e,Ari), (Zb,Ra,R1c,R3e,Arj), (Zb,Ra,R1c,R3e,Ark), (Zb,Ra,R1c,R3e,Arl), (Zb,Ra,R1c, R3e,Arm), (Zb,Ra,R1c,R3e,Arn), (Zb,Ra,R1c,R3e,Aro), (Zb,Ra,R1c,R3e,Arp), (Zb,Ra,R1c,R3f,Ara), (Zb,Ra,R1c, R3f,Arb), (Zb,Ra,R1c,R3f,Arc), (Zb,Ra,R1c,R3f,Ard), (Zb, Ra,R1c,R3f,Are), (Zb,Ra,R1c,R3f,Arf), (Zb,Ra,R1c,R3f, Arg), (Zb,Ra,R1c,R3f,Arh), (Zb,Ra,R1c,R3f,Ari), (Zb,Ra, R1c,R3f,Arj), (Zb,Ra,R1c,R3f,Ark), (Zb,Ra,R1c,R3f,Arl), (Zb,Ra,R1c,R3f,Arm), (Zb,Ra,R1c,R3f,Arn), (Zb,Ra,R1c, R3f,Aro), (Zb,Ra,R1c,R3f,Arp), (Zb,Ra,R1c,R3g,Ara), (Zb, Ra,R1c,R3g,Arb), (Zb,Ra,R1c,R3g,Arc), (Zb,Ra,R1c,R3g, Ard), (Zb,Ra,R1c,R3g,Are), (Zb,Ra,R1c,R3g,Arf), (Zb,Ra, R1c,R3g,Arg), (Zb,Ra,R1c,R3g,Arh), (Zb,Ra,R1c,R3g,Ari), (Zb,Ra,R1c,R3g,Arj), (Zb,Ra,R1c,R3g,Ark), (Zb,Ra,R1c, R3g,Arl), (Zb,Ra,R1c,R3g,Arm), (Zb,Ra,R1c,R3g,Arn), (Zb,Ra,R1c,R3g,Aro), (Zb,Ra,R1c,R3g,Arp), (Zb,Ra,R1c, R3h,Ara), (Zb,Ra,R1c,R3h,Arb), (Zb,Ra,R1c,R3h,Arc), (Zb,Ra,R1c,R3h,Ard), (Zb,Ra,R1c,R3h,Are), (Zb,Ra,R1c, R3h,Arf), (Zb,Ra,R1c,R3h,Arg), (Zb,Ra,R1c,R3h,Arh), (Zb, Ra,R1c,R3h,Ari), (Zb,Ra,R1c,R3h,Arj), (Zb,Ra,R1c,R3h, Ark), (Zb,Ra,R1c,R3h,Arl), (Zb,Ra,R1c,R3h,Arm), (Zb,Ra, R1c,R3h,Arn), (Zb,Ra,R1c,R3h,Aro), (Zb,Ra,R1c,R3h, Arp), (Zb,Ra,R1d,R3a,Ara), (Zb,Ra,R1d,R3a,Arb), (Zb,Ra, R1d,R3a,Arc), (Zb,Ra,R1d,R3a,Ard), (Zb,Ra,R1d,R3a, Are), (Zb,Ra,R1d,R3a,Arf), (Zb,Ra,R1d,R3a,Arg), (Zb,Ra, R1d,R3a,Arh), (Zb,Ra,R1d,R3a,Ari), (Zb,Ra,R1d,R3a,Arj), (Zb,Ra,R1d,R3a,Ark), (Zb,Ra,R1d,R3a,Arl), (Zb,Ra,R1d, R3a,Arm), (Zb,Ra,R1d,R3a,Arn), (Zb,Ra,R1d,R3a,Aro), (Zb,Ra,R1d,R3a,Arp), (Zb,Ra,R1d,R3b,Ara), (Zb,Ra,R1d, R3b,Arb), (Zb,Ra,R1d,R3b,Arc), (Zb,Ra,R1d,R3b,Ard), (Zb,Ra,R1d,R3b,Are), (Zb,Ra,R1d,R3b,Arf), (Zb,Ra,R1d, R3b,Arg), (Zb,Ra,R1d,R3b,Arh), (Zb,Ra,R1d,R3b,Ari), (Zb,Ra,R1d,R3b,Arj), (Zb,Ra,R1d,R3b,Ark), (Zb,Ra,R1d, R3b,Arl), (Zb,Ra,R1d,R3b,Arm), (Zb,Ra,R1d,R3b,Arn), (Zb,Ra,R1d,R3b,Aro), (Zb,Ra,R1d,R3b,Arp), (Zb,Ra,R1d, R3c,Ara), (Zb,Ra,R1d,R3c,Arb), (Zb,Ra,R1d,R3c,Arc), (Zb, Ra,R1d,R3c,Ard), (Zb,Ra,R1d,R3c,Are), (Zb,Ra,R1d,R3c, Arp,(Zb,Ra,R1d,R3c,Arg), (Zb,Ra,R1d,R3c,Arh), (Zb,Ra, R1d,R3c,Ari), (Zb,Ra,R1d,R3c,Arj), (Zb,Ra,R1d,R3c,Ark), (Zb,Ra,R1d,R3c,Arl), (Zb,Ra,R1d,R3c,Arm), (Zb,Ra,R1d, R3c,Arn), (Zb,Ra,R1d,R3c,Aro), (Zb,Ra,R1d,R3c,Arp), (Zb,Ra,R1d,R3d,Ara), (Zb,Ra,R1d,R3d,Arb), (Zb,Ra,R1d, R3d,Arc), (Zb,Ra,R1d,R3d,Ard), (Zb,Ra,R1d,R3d,Are), (Zb,Ra,R1d,R3d,Arf), (Zb,Ra,R1d,R3d,Arg), (Zb,Ra,R1d, R3d,Arh), (Zb,Ra,R1d,R3d,Ari), (Zb,Ra,R1d,R3d,Arj), (Zb, Ra,R1d,R3d,Ark), (Zb,Ra,R1d,R3d,Arl), (Zb,Ra,R1d,R3d, Arm), (Zb,Ra,R1d,R3d,Arn), (Zb,Ra,R1d,R3d,Aro), (Zb,Ra, R1d,R3d,Arp), (Zb,Ra,R1d,R3e,Ara), (Zb,Ra,R1d,R3e, Arb), (Zb,Ra,R1d,R3e,Arc), (Zb,Ra,R1d,R3e,Ard), (Zb,Ra, R1d,R3e,Are), (Zb,Ra,R1d,R3e,Arf), (Zb,Ra,R1d,R3e,Arg), (Zb,Ra,R1d,R3e,Arh), (Zb,Ra,R1d,R3e,Ari), (Zb,Ra,R1d, R3e,Arj), (Zb,Ra,R1d,R3e,Ark), (Zb,Ra,R1d,R3e,Arl), (Zb, Ra,R1d,R3e,Arm), (Zb,Ra,R1d,R3e,Arn), (Zb,Ra,R1d,R3e, Aro), (Zb,Ra,R1d,R3e,Arp), (Zb,Ra,R1d,R3f,Ara), (Zb,Ra, R1d,R3f,Arb), (Zb,Ra,R1d,R3f,Arc), (Zb,Ra,R1d,R3f,Ard), (Zb,Ra,R1d,R3f,Are), (Zb,Ra,R1d,R3f,Arf), (Zb,Ra,R1d, R3f,Arg), (Zb,Ra,R1d,R3f,Arh), (Zb,Ra,R1d,R3f,Ari), (Zb, Ra,R1d,R3f,Arj), (Zb,Ra,R1d,R3f,Ark), (Zb,Ra,R1d,R3f, Arl), (Zb,Ra,R1d,R3f,Arm), (Zb,Ra,R1d,R3f,Arn), (Zb,Ra, R1d,R3f,Aro), (Zb,Ra,R1d,R3f,Arp), (Zb,Ra,R1d,R3g,Ara), (Zb,Ra,R1d,R3g,Arb), (Zb,Ra,R1d,R3g,Arc), (Zb,Ra,R1d,R3g,Ard), (Zb,Ra,R1d,R3g,Are), (Zb,Ra,R1d,R3g,Arf), (Zb,Ra,R1d,R3g,Arg), (Zb,Ra,R1d,R3g,Arh), (Zb,Ra,R1d,R3g,Ari), (Zb,Ra,R1d,R3g,Arj), (Zb,Ra,R1d,R3g,Ark), (Zb,Ra,R1d,R3g,Arl), (Zb,Ra,R1d,R3g,Arm), (Zb,Ra,R1d,R3g,Arn), (Zb,Ra,R1d,R3g,Aro), (Zb,Ra,R1d,R3g,Arp), (Zb,Ra,R1d,R3h,Ara), (Zb,Ra,R1d,R3h,Arb), (Zb,Ra,R1d,R3h,Arc), (Zb,Ra,R1d,R3h,Ard), (Zb,Ra,R1d,R3h,Are), (Zb,Ra,R1d,R3h,Arf), (Zb,Ra,R1d,R3h,Arg), (Zb,Ra,R1d,R3h,Arh), (Zb,Ra,R1d,R3h,Ari), (Zb,Ra,R1d,R3h,Arj), (Zb,Ra,R1d,R3h,Ark), (Zb,Ra,R1d,R3h,Arl), (Zb,Ra,R1d,R3h,Arm), (Zb,Ra,R1d,R3h,Arn), (Zb,Ra,R1d,R3h,Aro), (Zb,Ra,R1d,R3h,Arp), (Zb,Rb,R1a,R3a,Ara), (Zb,Rb,R1a,R3a,Arb), (Zb,Rb,R1a,R3a,Arc), (Zb,Rb,R1a,R3a,Ard), (Zb,Rb,R1a,R3a,Are), (Zb,Rb,R1a,R3a,Arf), (Zb,Rb,R1a,R3a,Arg), (Zb,Rb,R1a,R3a,Arh), (Zb,Rb,R1a,R3a,Ari), (Zb,Rb,R1a,R3a,Arj), (Zb,Rb,R1a,R3a,Ark), (Zb,Rb,R1a,R3a,Arl), (Zb,Rb,R1a,R3a,Arm), (Zb,Rb,R1a,R3a,Arn), (Zb,Rb,R1a,R3a,Aro), (Zb,Rb,R1a,R3a,Arp), (Zb,Rb,R1a,R3b,Ara), (Zb,Rb,R1a,R3b,Arb), (Zb,Rb,R1a,R3b,Arc), (Zb,Rb,R1a,R3b,Ard), (Zb,Rb,R1a,R3b,Are), (Zb,Rb,R1a,R3b,Arf), (Zb,Rb,R1a,R3b,Arg), (Zb,Rb,R1a,R3b,Arh), (Zb,Rb,R1a,R3b,Ari), (Zb,Rb,R1a,R3b,Arj), (Zb,Rb,R1a,R3b,Ark), (Zb,Rb,R1a,R3b,Arl), (Zb,Rb,R1a,R3b,Arm), (Zb,Rb,R1a,R3b,Arn), (Zb,Rb,R1a,R3b,Aro), (Zb,Rb,R1a,R3b,Arp), (Zb,Rb,R1a,R3c,Ara), (Zb,Rb,R1a,R3c,Arb), (Zb,Rb,R1a,R3c,Arc), (Zb,Rb,R1a,R3c,Ard), (Zb,Rb,R1a,R3c,Are), (Zb,Rb,R1a,R3c,Arf), (Zb,Rb,R1a,R3c,Arg), (Zb,Rb,R1a,R3c,Arh), (Zb,Rb,R1a,R3c,Ari), (Zb,Rb,R1a,R3c,Arj), (Zb,Rb,R1a,R3c,Ark), (Zb,Rb,R1a,R3c,Arl), (Zb,Rb,R1a,R3c,Arm), (Zb,Rb,R1a,R3c,Arn), (Zb,Rb,R1a,R3c,Aro), (Zb,Rb,R1a,R3c,Arp), (Zb,Rb,R1a,R3d,Ara), (Zb,Rb,R1a,R3d,Arb), (Zb,Rb,R1a,R3d,Arc), (Zb,Rb,R1a,R3d,Ard), (Zb,Rb,R1a,R3d,Are), (Zb,Rb,R1a,R3d,Arf), (Zb,Rb,R1a,R3d,Arg), (Zb,Rb,R1a,R3d,Arh), (Zb,Rb,R1a,R3d,Ari), (Zb,Rb,R1a,R3d,Arj), (Zb,Rb,R1a,R3d,Ark), (Zb,Rb,R1a,R3d,Arl), (Zb,Rb,R1a,R3d,Arm), (Zb,Rb,R1a,R3d,Arn), (Zb,Rb,R1a,R3d,Aro), (Zb,Rb,R1a,R3d,Arp), (Zb,Rb,R1a,R3e,Ara), (Zb,Rb,R1a,R3e,Arb), (Zb,Rb,R1a,R3e,Arc), (Zb,Rb,R1a,R3e,Ard), (Zb,Rb,R1a,R3e,Are), (Zb,Rb,R1a,R3e,Arf), (Zb,Rb,R1a,R3e,Arg), (Zb,Rb,R1a,R3e,Arh), (Zb,Rb,R1a,R3e,Ari), (Zb,Rb,R1a,R3e,Arj), (Zb,Rb,R1a,R3e,Ark), (Zb,Rb,R1a,R3e,Arl), (Zb,Rb,R1a,R3e,Arm), (Zb,Rb,R1a,R3e,Arn), (Zb,Rb,R1a,R3e,Aro), (Zb,Rb,R1a,R3e,Arp), (Zb,Rb,R1a,R3f,Ara), (Zb,Rb,R1a,R3f,Arb), (Zb,Rb,R1a,R3f,Arc), (Zb,Rb,R1a,R3f,Ard), (Zb,Rb,R1a,R3f,Are), (Zb,Rb,R1a,R3f,Arf), (Zb,Rb,R1a,R3f,Arg), (Zb,Rb,R1a,R3f,Arh), (Zb,Rb,R1a,R3f,Ari), (Zb,Rb,R1a,R3f,Arj), (Zb,Rb,R1a,R3f,Ark), (Zb,Rb,R1a,R3f,Arl), (Zb,Rb,R1a,R3f,Arm), (Zb,Rb,R1a,R3f,Arn), (Zb,Rb,R1a,R3f,Aro), (Zb,Rb,R1a,R3f,Arp), (Zb,Rb,R1a,R3g,Ara), (Zb,Rb,R1a,R3g,Arb), (Zb,Rb,R1a,R3g,Arc), (Zb,Rb,R1a,R3g,Ard), (Zb,Rb,R1a,R3g,Are), (Zb,Rb,R1a,R3g,Arf), (Zb,Rb,R1a,R3g,Arg), (Zb,Rb,R1a,R3g,Arh), (Zb,Rb,R1a,R3g,Ari), (Zb,Rb,R1a,R3g,Arj), (Zb,Rb,R1a,R3g,Ark), (Zb,Rb,R1a,R3g,Arl), (Zb,Rb,R1a,R3g,Arm), (Zb,Rb,R1a,R3g,Arn), (Zb,Rb,R1a,R3g,Aro), (Zb,Rb,R1a,R3g,Arp), (Zb,Rb,R1a,R3h,Ara), (Zb,Rb,R1a,R3h,Arb), (Zb,Rb,R1a,R3h,Arc), (Zb,Rb,R1a,R3h,Ard), (Zb,Rb,R1a,R3h,Are), (Zb,Rb,R1a,R3h,Arf), (Zb,Rb,R1a,R3h,Arg), (Zb,Rb,R1a,R3h,Arh), (Zb,Rb,R1a,R3h,Ari), (Zb,Rb,R1a,R3h,Arj), (Zb,Rb,R1a,R3h,Ark), (Zb,Rb,R1a,R3h,Arl), (Zb,Rb,R1a,R3h,Arm), (Zb,Rb,R1a,R3h,Arn), (Zb,Rb,R1a,R3h,Aro), (Zb,Rb,R1a,R3h,Arp), (Zb,Rb,R1b,R3a,Ara), (Zb,Rb,R1b,R3a,Arb), (Zb,Rb,R1b,R3a,Arc), (Zb,Rb,R1b,R3a,Ard), (Zb,Rb,R1b,R3a,Are), (Zb,Rb,R1b,R3a,Arf), (Zb,Rb,R1b,R3a,Arg), (Zb,Rb,R1b,R3a,Arh), (Zb,Rb,R1b,R3a,Ari), (Zb,Rb,R1b,R3a,Arj), (Zb,Rb,R1b,R3a,Ark), (Zb,Rb,R1b,R3a,Arl), (Zb,Rb,R1b,R3a,Arm), (Zb,Rb,R1b,R3a,Arn), (Zb,Rb,R1b,R3a,Aro), (Zb,Rb,R1b,R3a,Arp), (Zb,Rb,R1b,R3b,Ara), (Zb,Rb,R1b,R3b,Arb), (Zb,Rb,R1b,R3b,Arc), (Zb,Rb,R1b,R3b,Ard), (Zb,Rb,R1b,R3b,Are), (Zb,Rb,R1b,R3b,Arf), (Zb,Rb,R1b,R3b,Arg), (Zb,Rb,R1b,R3b,Arh), (Zb,Rb,R1b,R3b,Ari), (Zb,Rb,R1b,R3b,Arj), (Zb,Rb,R1b,R3b,Ark), (Zb,Rb,R1b,R3b,Arl), (Zb,Rb,R1b,R3b,Arm), (Zb,Rb,R1b,R3b,Arn), (Zb,Rb,R1b,R3b,Aro), (Zb,Rb,R1b,R3b,Arp), (Zb,Rb,R1b,R3c,Ara), (Zb,Rb,R1b,R3c,Arb), (Zb,Rb,R1b,R3c,Arc), (Zb,Rb,R1b,R3c,Ard), (Zb,Rb,R1b,R3c,Are), (Zb,Rb,R1b,R3c,Arf), (Zb,Rb,R1b,R3c,Arg), (Zb,Rb,R1b,R3c,Arh), (Zb,Rb,R1b,R3c,Ari), (Zb,Rb,R1b,R3c,Arj), (Zb,Rb,R1b,R3c,Ark), (Zb,Rb,R1b,R3c,Arl), (Zb,Rb,R1b,R3c,Arm), (Zb,Rb,R1b,R3c,Arn), (Zb,Rb,R1b,R3c,Aro), (Zb,Rb,R1b,R3c,Arp), (Zb,Rb,R1b,R3d,Ara), (Zb,Rb,R1b,R3d,Arb), (Zb,Rb,R1b,R3d,Arc), (Zb,Rb,R1b,R3d,Ard), (Zb,Rb,R1b,R3d,Are), (Zb,Rb,R1b,R3d,Arf), (Zb,Rb,R1b,R3d,Arg), (Zb,Rb,R1b,R3d,Arh), (Zb,Rb,R1b,R3d,Ari), (Zb,Rb,R1b,R3d,Arj), (Zb,Rb,R1b,R3d,Ark), (Zb,Rb,R1b,R3d,Arl), (Zb,Rb,R1b,R3d,Arm), (Zb,Rb,R1b,R3d,Arn), (Zb,Rb,R1b,R3d,Aro), (Zb,Rb,R1b,R3d,Arp), (Zb,Rb,R1b,R3e,Ara), (Zb,Rb,R1b,R3e,Arb), (Zb,Rb,R1b,R3e,Arc), (Zb,Rb,R1b,R3e,Ard), (Zb,Rb,R1b,R3e,Are), (Zb,Rb,R1b,R3e,Arf), (Zb,Rb,R1b,R3e,Arg), (Zb,Rb,R1b,R3e,Arh), (Zb,Rb,R1b,R3e,Ari), (Zb,Rb,R1b,R3e,Arj), (Zb,Rb,R1b,R3e,Ark), (Zb,Rb,R1b,R3e,Arl), (Zb,Rb,R1b,R3e,Arm), (Zb,Rb,R1b,R3e,Arn), (Zb,Rb,R1b,R3e,Aro), (Zb,Rb,R1b,R3e,Arp), (Zb,Rb,R1b,R3f,Ara), (Zb,Rb,R1b,R3f,Arb), (Zb,Rb,R1b,R3f,Arc), (Zb,Rb,R1b,R3f,Ard), (Zb,Rb,R1b,R3f,Are), (Zb,Rb,R1b,R3f,Arf), (Zb,Rb,R1b,R3f,Arg), (Zb,Rb,R1b,R3f,Arh), (Zb,Rb,R1b,R3f,Ari), (Zb,Rb,R1b,R3f,Arj), (Zb,Rb,R1b,R3f,Ark), (Zb,Rb,R1b,R3f,Arl), (Zb,Rb,R1b,R3f,Arm), (Zb,Rb,R1b,R3f,Arn), (Zb,Rb,R1b,R3f,Aro), (Zb,Rb,R1b,R3f,Arp), (Zb,Rb,R1b,R3g,Ara), (Zb,Rb,R1b,R3g,Arb), (Zb,Rb,R1b,R3g,Arc), (Zb,Rb,R1b,R3g,Ard), (Zb,Rb,R1b,R3g,Are), (Zb,Rb,R1b,R3g,Arf), (Zb,Rb,R1b,R3g,Arg), (Zb,Rb,R1b,R3g,Arh), (Zb,Rb,R1b,R3g,Ari), (Zb,Rb,R1b,R3g,Arj), (Zb,Rb,R1b,R3g,Ark), (Zb,Rb,R1b,R3g,Arl), (Zb,Rb,R1b,R3g,Arm), (Zb,Rb,R1b,R3g,Arn), (Zb,Rb,R1b,R3g,Aro), (Zb,Rb,R1b,R3g,Arp), (Zb,Rb,R1b,R3h,Ara), (Zb,Rb,R1b,R3h,Arb), (Zb,Rb,R1b,R3h,Arc), (Zb,Rb,R1b,R3h,Ard), (Zb,Rb,R1b,R3h,Are), (Zb,Rb,R1b,R3h,Arf), (Zb,Rb,R1b,R3h,Arg), (Zb,Rb,R1b,R3h,Arh), (Zb,Rb,R1b,R3h,Ari), (Zb,Rb,R1b,R3h,Arj), (Zb,Rb,R1b,R3h,Ark), (Zb,Rb,R1b,R3h,Arl), (Zb,Rb,R1b,R3h,Arm), (Zb,Rb,R1b,R3h,Arn), (Zb,Rb,R1b,R3h,Aro), (Zb,Rb,R1b,R3h,Arp), (Zb,Rb,R1c,R3a,Ara), (Zb,Rb,R1c,R3a,Arb), (Zb,Rb,R1c,R3a,Arc), (Zb,Rb,R1c,R3a,Ard), (Zb,Rb,R1c,R3a,Are), (Zb,Rb,R1c,R3a,Arf), (Zb,Rb,R1c,R3a,Arg), (Zb,Rb,R1c,R3a,Arh), (Zb,Rb,R1c,R3a,Ari), (Zb,Rb,R1c,R3a,Arj), (Zb,Rb,R1c,R3a,Ark), (Zb,Rb,R1c,R3a,Arl), (Zb,Rb,R1c,R3a,Arm), (Zb,Rb,R1c,R3a,Arn), (Zb,Rb,R1c,R3a,Aro), (Zb,Rb,R1c,R3a,Arp), (Zb,Rb,R1c,R3b,Ara), (Zb,Rb,R1c,R3b,Arb), (Zb,Rb,R1c,R3b,Arc), (Zb,Rb,R1c,R3b,Ard), (Zb,Rb,R1c,R3b,Are), (Zb,Rb,R1c,R3b,Arf), (Zb,Rb,R1c,R3b,Arg), (Zb,Rb,R1c,R3b,Arh), (Zb,Rb,R1c,R3b,Ari), (Zb,Rb,R1c,R3b,Arj), (Zb,Rb,R1c,R3b,Ark), (Zb,Rb,R1c,R3b,Arl), (Zb,Rb,R1c,R3b,Arm), (Zb,Rb,R1c,R3b,Arn), (Zb,Rb,R1c,R3b,Aro), (Zb,Rb,R1c,R3b,Arp), (Zb,Rb,R1c,R3c,Ara), (Zb,Rb,R1c,R3c,Arb), (Zb,Rb,R1c,R3c,Arc), (Zb,Rb,R1c,R3c,Ard), (Zb,Rb,R1c,R3c,Are), (Zb,Rb,R1c,R3c,Arf), (Zb,Rb,R1c,R3c,Arg), (Zb,Rb,R1c,R3c,Arh), (Zb,Rb,R1c,R3c,Ari), (Zb,Rb,R1c,R3c,Arj), (Zb,Rb,R1c,R3c,Ark), (Zb,Rb,R1c,R3c,Arl), (Zb,Rb,R1c,R3c,Arm), (Zb,Rb,R1c,R3c,Arn), (Zb,Rb,R1c,R3c,Aro), (Zb,Rb,R1c,R3c,Arp), (Zb,Rb,R1c,R3d,Ara), (Zb,Rb,R1c,R3d,Arb), (Zb,Rb,R1c,R3d,Arc), (Zb,Rb,R1c,R3d,Ard), (Zb,Rb,R1c,R3d, Are), (Zb,Rb,R1c,R3d,Arf), (Zb,Rb,R1c,R3d,Arg), (Zb,Rb, R1c,R3d,Arh), (Zb,Rb,R1c,R3d,Ari), (Zb,Rb,R1c,R3d,Arj), (Zb,Rb,R1c,R3d,Ark), (Zb,Rb,R1c,R3d,Arl), (Zb,Rb,R1c, R3d,Arm), (Zb,Rb,R1c,R3d,Arn), (Zb,Rb,R1c,R3d,Aro), (Zb,Rb,R1c,R3d,Arp), (Zb,Rb,R1c,R3e,Ara), (Zb,Rb,R1c, R3e,Arb), (Zb,Rb,R1c,R3e,Arc), (Zb,Rb,R1c,R3e,Ard), (Zb,Rb,R1c,R3e,Are), (Zb,Rb,R1c,R3e,Arf), (Zb,Rb,R1c, R3e,Arg), (Zb,Rb,R1c,R3e,Arh), (Zb,Rb,R1c,R3e,Ari), (Zb, Rb,R1c,R3e,Arj), (Zb,Rb,R1c,R3e,Ark), (Zb,Rb,R1c,R3e, Arl), (Zb,Rb,R1c,R3e,Arm), (Zb,Rb,R1c,R3e,Arn), (Zb,Rb, R1c,R3e,Aro), (Zb,Rb,R1c,R3e,Arp), (Zb,Rb,R1c,R3f,Ara), (Zb,Rb,R1c,R3f,Arb), (Zb,Rb,R1c,R3f,Arc), (Zb,Rb,R1c, R3f,Ard), (Zb,Rb,R1c,R3f,Are), (Zb,Rb,R1c,R3f,Arf), (Zb, Rb,R1c,R3f,Arg), (Zb,Rb,R1c,R3f,Arh), (Zb,Rb,R1c,R3f, Ari), (Zb,Rb,R1c,R3f,Arj), (Zb,Rb,R1c,R3f,Ark), (Zb,Rb, R1c,R3f,Arl), (Zb,Rb,R1c,R3f,Arm), (Zb,Rb,R1c,R3f,Arn), (Zb,Rb,R1c,R3f,Aro), (Zb,Rb,R1c,R3f,Arp), (Zb,Rb,R1c, R3g,Ara), (Zb,Rb,R1c,R3g,Arb), (Zb,Rb,R1c,R3g,Arc), (Zb,Rb,R1c,R3g,Ard), (Zb,Rb,R1c,R3g,Are), (Zb,Rb,R1c, R3g,Arf), (Zb,Rb,R1c,R3g,Arg), (Zb,Rb,R1c,R3g,Arh), (Zb,Rb,R1c,R3g,Ari), (Zb,Rb,R1c,R3g,Arj), (Zb,Rb,R1c, R3g,Ark), (Zb,Rb,R1c,R3g,Arl), (Zb,Rb,R1c,R3g,Arm), (Zb,Rb,R1c,R3g,Arn), (Zb,Rb,R1c,R3g,Aro), (Zb,Rb,R1c, R3g,Arp), (Zb,Rb,R1c,R3h,Ara), (Zb,Rb,R1c,R3h,Arb), (Zb,Rb,R1c,R3h,Arc), (Zb,Rb,R1c,R3h,Ard), (Zb,Rb,R1c, R3h,Are), (Zb,Rb,R1c,R3h,Arf), (Zb,Rb,R1c,R3h,Arg), (Zb,Rb,R1c,R3h,Arh), (Zb,Rb,R1c,R3h,Ari), (Zb,Rb,R1c, R3h,Arj), (Zb,Rb,R1c,R3h,Ark), (Zb,Rb,R1c,R3h,Arl), (Zb, Rb,R1c,R3h,Arm), (Zb,Rb,R1c,R3h,Arn), (Zb,Rb,R1c,R3h, Aro), (Zb,Rb,R1c,R3h,Arp), (Zb,Rb,R1d,R3a,Ara), (Zb,Rb, R1d,R3a,Arb), (Zb,Rb,R1d,R3a,Arc), (Zb,Rb,R1d,R3a, Ard), (Zb,Rb,R1d,R3a,Are), (Zb,Rb,R1d,R3a,Arf), (Zb,Rb, R1d,R3a,Arg), (Zb,Rb,R1d,R3a,Arh), (Zb,Rb,R1d,R3a, Ari), (Zb,Rb,R1d,R3a,Arj), (Zb,Rb,R1d,R3a,Ark), (Zb,Rb, R1d,R3a,Arl), (Zb,Rb,R1d,R3a,Arm), (Zb,Rb,R1d,R3a, Arn), (Zb,Rb,R1d,R3a,Aro), (Zb,Rb,R1d,R3a,Arp), (Zb,Rb, R1d,R3b,Ara), (Zb,Rb,R1d,R3b,Arb), (Zb,Rb,R1d,R3b, Arc), (Zb,Rb,R1d,R3b,Ard), (Zb,Rb,R1d,R3b,Are), (Zb,Rb, R1d,R3b,Arf), (Zb,Rb,R1d,R3b,Arg), (Zb,Rb,R1d,R3b, Arh), (Zb,Rb,R1d,R3b,Ari), (Zb,Rb,R1d,R3b,Arj), (Zb,Rb, R1d,R3b,Ark), (Zb,Rb,R1d,R3b,Arl), (Zb,Rb,R1d,R3b, Arm), (Zb,Rb,R1d,R3b,Arn), (Zb,Rb,R1d,R3b,Aro), (Zb, Rb,R1d,R3b,Arp), (Zb,Rb,R1d,R3c,Ara), (Zb,Rb,R1d,R3c, Arb), (Zb,Rb,R1d,R3c,Arc), (Zb,Rb,R1d,R3c,Ard), (Zb,Rb, R1d,R3c,Are), (Zb,Rb,R1d,R3c,Arf), (Zb,Rb,R1d,R3c, Arg), (Zb,Rb,R1d,R3c,Arh), (Zb,Rb,R1d,R3c,Ari), (Zb,Rb, R1d,R3c,Arj), (Zb,Rb,R1d,R3c,Ark), (Zb,Rb,R1d,R3c,Arl), (Zb,Rb,R1d,R3c,Arm), (Zb,Rb,R1d,R3c,Arn), (Zb,Rb,R1d, R3c,Aro), (Zb,Rb,R1d,R3c,Arp), (Zb,Rb,R1d,R3d,Ara), (Zb,Rb,R1d,R3d,Arb), (Zb,Rb,R1d,R3d,Arc), (Zb,Rb,R1d, R3d,Ard), (Zb,Rb,R1d,R3d,Are), (Zb,Rb,R1d,R3d,Arf), (Zb,Rb,R1d,R3d,Arg), (Zb,Rb,R1d,R3d,Arh), (Zb,Rb,R1d, R3d,Ari), (Zb,Rb,R1d,R3d,Arj), (Zb,Rb,R1d,R3d,Ark), (Zb, Rb,R1d,R3d,Arl), (Zb,Rb,R1d,R3d,Arm), (Zb,Rb,R1d,R3d, Arn), (Zb,Rb,R1d,R3d,Aro), (Zb,Rb,R1d,R3d,Arp), (Zb,Rb, R1d,R3e,Ara), (Zb,Rb,R1d,R3e,Arb), (Zb,Rb,R1d,R3e, Arc), (Zb,Rb,R1d,R3e,Ard), (Zb,Rb,R1d,R3e,Are), (Zb,Rb, R1d,R3e,Arf), (Zb,Rb,R1d,R3e,Arg), (Zb,Rb,R1d,R3e, Arh), (Zb,Rb,R1d,R3e,Ari), (Zb,Rb,R1d,R3e,Arj), (Zb,Rb, R1d,R3e,Ark), (Zb,Rb,R1d,R3e,Arl), (Zb,Rb,R1d,R3e, Arm), (Zb,Rb,R1d,R3e,Arn), (Zb,Rb,R1d,R3e,Aro), (Zb, Rb,R1d,R3e,Arp), (Zb,Rb,R1d,R3f,Ara), (Zb,Rb,R1d,R3f, Arb), (Zb,Rb,R1d,R3f,Arc), (Zb,Rb,R1d,R3f,Ard), (Zb,Rb, R1d,R3f,Are), (Zb,Rb,R1d,R3f,Arf), (Zb,Rb,R1d,R3f,Arg), (Zb,Rb,R1d,R3f,Arh), (Zb,Rb,R1d,R3f,Ari), (Zb,Rb,R1d, R3f,Arj), (Zb,Rb,R1d,R3f,Ark), (Zb,Rb,R1d,R3f,Arl), (Zb, Rb,R1d,R3f,Arm), (Zb,Rb,R1d,R3f,Arn), (Zb,Rb,R1d,R3f, Aro), (Zb,Rb,R1d,R3f,Arp), (Zb,Rb,R1d,R3g,Ara), (Zb,Rb, R1d,R3g,Arb), (Zb,Rb,R1d,R3g,Arc), (Zb,Rb,R1d,R3g, Ard), (Zb,Rb,R1d,R3g,Are), (Zb,Rb,R1d,R3g,Arf), (Zb,Rb, R1d,R3g,Arg), (Zb,Rb,R1d,R3g,Arh), (Zb,Rb,R1d,R3g, Ari), (Zb,Rb,R1d,R3g,Arj), (Zb,Rb,R1d,R3g,Ark), (Zb,Rb, R1d,R3g,Arl), (Zb,Rb,R1d,R3g,Arm), (Zb,Rb,R1d,R3g, Arn), (Zb,Rb,R1d,R3g,Aro), (Zb,Rb,R1d,R3g,Arp), (Zb,Rb, R1d,R3h,Ara), (Zb,Rb,R1d,R3h,Arb), (Zb,Rb,R1d,R3h, Arc), (Zb,Rb,R1d,R3h,Ard), (Zb,Rb,R1d,R3h,Are), (Zb,Rb, R1d,R3h,Arf), (Zb,Rb,R1d,R3h,Arg), (Zb,Rb,R1d,R3h, Arh), (Zb,Rb,R1d,R3h,Ari), (Zb,Rb,R1d,R3h,Arj), (Zb,Rb, R1d,R3h,Ark), (Zb,Rb,R1d,R3h,Arl), (Zb,Rb,R1d,R3h, Arm), (Zb,Rb,R1d,R3h,Arn), (Zb,Rb,R1d,R3h,Aro), (Zb, Rb,R1d,R3h,Arp), (Zb,Rc,R1a,R3a,Ara), (Zb,Rc,R1a,R3a, Arb), (Zb,Rc,R1a,R3a,Arc), (Zb,Rc,R1a,R3a,Ard), (Zb,Rc, R1a,R3a,Are), (Zb,Rc,R1a,R3a,Arf), (Zb,Rc,R1a,R3a,Arg), (Zb,Rc,R1a,R3a,Arh), (Zb,Rc,R1a,R3a,Ari), (Zb,Rc,R1a, R3a,Arj), (Zb,Rc,R1a,R3a,Ark), (Zb,Rc,R1a,R3a,Arl), (Zb, Rc,R1a,R3a,Arm), (Zb,Rc,R1a,R3a,Arn), (Zb,Rc,R1a,R3a, Aro), (Zb,Rc,R1a,R3a,Arp), (Zb,Rc,R1a,R3b,Ara), (Zb,Rc, R1a,R3b,Arb), (Zb,Rc,R1a,R3b,Arc), (Zb,Rc,R1a,R3b, Ard), (Zb,Rc,R1a,R3b,Are), (Zb,Rc,R1a,R3b,Arf), (Zb,Rc, R1a,R3b,Arg), (Zb,Rc,R1a,R3b,Arh), (Zb,Rc,R1a,R3b,Ari), (Zb,Rc,R1a,R3b,Arj), (Zb,Rc,R1a,R3b,Ark), (Zb,Rc,R1a, R3b,Arl), (Zb,Rc,R1a,R3b,Arm), (Zb,Rc,R1a,R3b,Arn), (Zb,Rc,R1a,R3b,Aro), (Zb,Rc,R1a,R3b,Arp), (Zb,Rc,R1a, R3c,Ara), (Zb,Rc,R1a,R3c,Arb), (Zb,Rc,R1a,R3c,Arc), (Zb, Rc,R1a,R3c,Ard), (Zb,Rc,R1a,R3c,Are), (Zb,Rc,R1a,R3c, Arf), (Zb,Rc,R1a,R3c,Arg), (Zb,Rc,R1a,R3c,Arh), (Zb,Rc, R1a,R3c,Ari), (Zb,Rc,R1a,R3c,Arj), (Zb,Rc,R1a,R3c,Ark), (Zb,Rc,R1a,R3c,Arl), (Zb,Rc,R1a,R3c,Arm), (Zb,Rc,R1a, R3c,Arm), (Zb,Rc,R1a,R3c,Aro), (Zb,Rc,R1a,R3c,Arp), (Zb,Rc,R1a,R3d,Ara), (Zb,Rc,R1a,R3d,Arb), (Zb,Rc,R1a, R3d,Arc), (Zb,Rc,R1a,R3d,Ard), (Zb,Rc,R1a,R3d,Are), (Zb,Rc,R1a,R3d,Arf), (Zb,Rc,R1a,R3d,Arg), (Zb,Rc,R1a, R3d,Arh), (Zb,Rc,R1a,R3d,Ari), (Zb,Rc,R1a,R3d,Arj), (Zb, Rc,R1a,R3d,Ark), (Zb,Rc,R1a,R3d,Arl), (Zb,Rc,R1a,R3d, Arm), (Zb,Rc,R1a,R3d,Arn), (Zb,Rc,R1a,R3d,Aro), (Zb,Rc, R1a,R3d,Arp), (Zb,Rc,R1a,R3e,Ara), (Zb,Rc,R1a,R3e,Arb), (Zb,Rc,R1a,R3e,Arc), (Zb,Rc,R1a,R3e,Ard), (Zb,Rc,R1a, R3e,Are), (Zb,Rc,R1a,R3e,Arf), (Zb,Rc,R1a,R3e,Arg), (Zb, Rc,R1a,R3e,Arh), (Zb,Rc,R1a,R3e,Ari), (Zb,Rc,R1a,R3e, Arj), (Zb,Rc,R1a,R3e,Ark), (Zb,Rc,R1a,R3e,Arl), (Zb,Rc, R1a,R3e,Arm), (Zb,Rc,R1a,R3e,Arn), (Zb,Rc,R1a,R3e, Aro), (Zb,Rc,R1a,R3e,Arp), (Zb,Rc,R1a,R3f,Ara), (Zb,Rc, R1a,R3f,Arb), (Zb,Rc,R1a,R3f,Arc), (Zb,Rc,R1a,R3f,Ard), (Zb,Rc,R1a,R3f,Are), (Zb,Rc,R1a,R3f,Arf), (Zb,Rc,R1a, R3f,Arg), (Zb,Rc,R1a,R3f,Arh), (Zb,Rc,R1a,R3f,Ari), (Zb, Rc,R1a,R3f,Arj), (Zb,Rc,R1a,R3f,Ark), (Zb,Rc,R1a,R3f, Arl), (Zb,Rc,R1a,R3f,Arm), (Zb,Rc,R1a,R3f,Arn), (Zb,Rc, R1a,R3f,Aro), (Zb,Rc,R1a,R3f,Arp), (Zb,Rc,R1a,R3g,Ara), (Zb,Rc,R1a,R3g,Arb), (Zb,Rc,R1a,R3g,Arc), (Zb,Rc,R1a, R3g,Ard), (Zb,Rc,R1a,R3g,Are), (Zb,Rc,R1a,R3g,Arf), (Zb, Rc,R1a,R3g,Arg), (Zb,Rc,R1a,R3g,Arh), (Zb,Rc,R1a,R3g, Ari), (Zb,Rc,R1a,R3g,Arj), (Zb,Rc,R1a,R3g,Ark), (Zb,Rc, R1a,R3g,Arl), (Zb,Rc,R1a,R3g,Arm), (Zb,Rc,R1a,R3g, Arn), (Zb,Rc,R1a,R3g,Aro), (Zb,Rc,R1a,R3g,Arp), (Zb,Rc, R1a,R3h,Ara), (Zb,Rc,R1a,R3h,Arb), (Zb,Rc,R1a,R3h, Arc), (Zb,Rc,R1a,R3h,Ard), (Zb,Rc,R1a,R3h,Are), (Zb,Rc, R1a,R3h,Arf), (Zb,Rc,R1a,R3h,Arg), (Zb,Rc,R1a,R3h,Arh), (Zb,Rc,R1a,R3h,Ari), (Zb,Rc,R1a,R3h,Arj), (Zb,Rc,R1a, R3h,Ark), (Zb,Rc,R1a,R3h,Arl), (Zb,Rc,R1a,R3h,Arm), (Zb,Rc,R1a,R3h,Arn), (Zb,Rc,R1a,R3h,Aro), (Zb,Rc,R1a, R3h,Arp), (Zb,Rc,R1b,R3a,Ara), (Zb,Rc,R1b,R3a,Arb), (Zb,Rc,R1b,R3a,Arc), (Zb,Rc,R1b,R3a,Ard), (Zb,Rc,R1b, R3a,Are), (Zb,Rc,R1b,R3a,Arf), (Zb,Rc,R1b,R3a,Arg), (Zb, Rc,R1b,R3a,Arh), (Zb,Rc,R1b,R3a,Ari), (Zb,Rc,R1b,R3a, Arj), (Zb,Rc,R1b,R3a,Ark), (Zb,Rc,R1b,R3a,Arl), (Zb,Rc,R1b,R3a,Arm), (Zb,Rc,R1b,R3a,Arn), (Zb,Rc,R1b,R3a,Aro), (Zb,Rc,R1b,R3a,Arp), (Zb,Rc,R1b,R3b,Ara), (Zb,Rc,R1b,R3b,Arb), (Zb,Rc,R1b,R3b,Arc), (Zb,Rc,R1b,R3b,Ard), (Zb,Rc,R1b,R3b,Are), (Zb,Rc,R1b,R3b,Arf), (Zb,Rc,R1b,R3b,Arg), (Zb,Rc,R1b,R3b,Arh), (Zb,Rc,R1b,R3b,Ari), (Zb,Rc,R1b,R3b,Arj), (Zb,Rc,R1b,R3b,Ark), (Zb,Rc,R1b,R3b,Arl), (Zb,Rc,R1b,R3b,Arm), (Zb,Rc,R1b,R3b,Arn), (Zb,Rc,R1b,R3b,Aro), (Zb,Rc,R1b,R3b,Arp), (Zb,Rc,R1b,R3c,Ara), (Zb,Rc,R1b,R3c,Arb), (Zb,Rc,R1b,R3c,Arc), (Zb,Rc,R1b,R3c,Ard), (Zb,Rc,R1b,R3c,Are), (Zb,Rc,R1b,R3c,Arf), (Zb,Rc,R1b,R3c,Arg), (Zb,Rc,R1b,R3c,Arh), (Zb,Rc,R1b,R3c,Ari), (Zb,Rc,R1b,R3c,Arj), (Zb,Rc,R1b,R3c,Ark), (Zb,Rc,R1b,R3c,Arl), (Zb,Rc,R1b,R3c,Arm), (Zb,Rc,R1b,R3c,Arn), (Zb,Rc,R1b,R3c,Aro), (Zb,Rc,R1b,R3c,Arp), (Zb,Rc,R1b,R3d,Ara), (Zb,Rc,R1b,R3d,Arb), (Zb,Rc,R1b,R3d,Arc), (Zb,Rc,R1b,R3d,Ard), (Zb,Rc,R1b,R3d,Are), (Zb,Rc,R1b,R3d,Arf), (Zb,Rc,R1b,R3d,Arg), (Zb,Rc,R1b,R3d,Arh), (Zb,Rc,R1b,R3d,Ari), (Zb,Rc,R1b,R3d,Arj), (Zb,Rc,R1b,R3d,Ark), (Zb,Rc,R1b,R3d,Arl), (Zb,Rc,R1b,R3d,Arm), (Zb,Rc,R1b,R3d,Arn), (Zb,Rc,R1b,R3d,Aro), (Zb,Rc,R1b,R3d,Arp), (Zb,Rc,R1b,R3e,Ara), (Zb,Rc,R1b,R3e,Arb), (Zb,Rc,R1b,R3e,Arc), (Zb,Rc,R1b,R3e,Ard), (Zb,Rc,R1b,R3e,Are), (Zb,Rc,R1b,R3e,Arf), (Zb,Rc,R1b,R3e,Arg), (Zb,Rc,R1b,R3e,Arh), (Zb,Rc,R1b,R3e,Ari), (Zb,Rc,R1b,R3e,Arj), (Zb,Rc,R1b,R3e,Ark), (Zb,Rc,R1b,R3e,Arl), (Zb,Rc,R1b,R3e,Arm), (Zb,Rc,R1b,R3e,Arn), (Zb,Rc,R1b,R3e,Aro), (Zb,Rc,R1b,R3e,Arp), (Zb,Rc,R1b,R3f,Ara), (Zb,Rc,R1b,R3f,Arb), (Zb,Rc,R1b,R3f,Arc), (Zb,Rc,R1b,R3f,Ard), (Zb,Rc,R1b,R3f,Are), (Zb,Rc,R1b,R3f,Arf), (Zb,Rc,R1b,R3f,Arg), (Zb,Rc,R1b,R3f,Arh), (Zb,Rc,R1b,R3f,Ari), (Zb,Rc,R1b,R3f,Arj), (Zb,Rc,R1b,R3f,Ark), (Zb,Rc,R1b,R3f,Arl), (Zb,Rc,R1b,R3f,Arm), (Zb,Rc,R1b,R3f,Arn), (Zb,Rc,R1b,R3f,Aro), (Zb,Rc,R1b,R3f,Arp), (Zb,Rc,R1b,R3g,Ara), (Zb,Rc,R1b,R3g,Arb), (Zb,Rc,R1b,R3g,Arc), (Zb,Rc,R1b,R3g,Ard), (Zb,Rc,R1b,R3g,Are), (Zb,Rc,R1b,R3g,Arf), (Zb,Rc,R1b,R3g,Arg), (Zb,Rc,R1b,R3g,Arh), (Zb,Rc,R1b,R3g,Ari), (Zb,Rc,R1b,R3g,Arj), (Zb,Rc,R1b,R3g,Ark), (Zb,Rc,R1b,R3g,Arl), (Zb,Rc,R1b,R3g,Arm), (Zb,Rc,R1b,R3g,Arn), (Zb,Rc,R1b,R3g,Aro), (Zb,Rc,R1b,R3g,Arp), (Zb,Rc,R1b,R3h,Ara), (Zb,Rc,R1b,R3h,Arb), (Zb,Rc,R1b,R3h,Arc), (Zb,Rc,R1b,R3h,Ard), (Zb,Rc,R1b,R3h,Are), (Zb,Rc,R1b,R3h,Arf), (Zb,Rc,R1b,R3h,Arg), (Zb,Rc,R1b,R3h,Arh), (Zb,Rc,R1b,R3h,Ari), (Zb,Rc,R1b,R3h,Arj), (Zb,Rc,R1b,R3h,Ark), (Zb,Rc,R1b,R3h,Arl), (Zb,Rc,R1b,R3h,Arm), (Zb,Rc,R1b,R3h,Arn), (Zb,Rc,R1b,R3h,Aro), (Zb,Rc,R1b,R3h,Arp), (Zb,Rc,R1c,R3a,Ara), (Zb,Rc,R1c,R3a,Arb), (Zb,Rc,R1c,R3a,Arc), (Zb,Rc,R1c,R3a,Ard), (Zb,Rc,R1c,R3a,Are), (Zb,Rc,R1c,R3a,Arf), (Zb,Rc,R1c,R3a,Arg), (Zb,Rc,R1c,R3a,Arh), (Zb,Rc,R1c,R3a,Ari), (Zb,Rc,R1c,R3a,Arj), (Zb,Rc,R1c,R3a,Ark), (Zb,Rc,R1c,R3a,Arl), (Zb,Rc,R1c,R3a,Arm), (Zb,Rc,R1c,R3a,Arn), (Zb,Rc,R1c,R3a,Aro), (Zb,Rc,R1c,R3a,Arp), (Zb,Rc,R1c,R3b,Ara), (Zb,Rc,R1c,R3b,Arb), (Zb,Rc,R1c,R3b,Arc), (Zb,Rc,R1c,R3b,Ard), (Zb,Rc,R1c,R3b,Are), (Zb,Rc,R1c,R3b,Arf), (Zb,Rc,R1c,R3b,Arg), (Zb,Rc,R1c,R3b,Arh), (Zb,Rc,R1c,R3b,Ari), (Zb,Rc,R1c,R3b,Arj), (Zb,Rc,R1c,R3b,Ark), (Zb,Rc,R1c,R3b,Arl), (Zb,Rc,R1c,R3b,Arm), (Zb,Rc,R1c,R3b,Arn), (Zb,Rc,R1c,R3b,Aro), (Zb,Rc,R1c,R3b,Arp), (Zb,Rc,R1c,R3c,Ara), (Zb,Rc,R1c,R3c,Arb), (Zb,Rc,R1c,R3c,Arc), (Zb,Rc,R1c,R3c,Ard), (Zb,Rc,R1c,R3c,Are), (Zb,Rc,R1c,R3c,Arf), (Zb,Rc,R1c,R3c,Arg), (Zb,Rc,R1c,R3c,Arh), (Zb,Rc,R1c,R3c,Ari), (Zb,Rc,R1c,R3c,Arj), (Zb,Rc,R1c,R3c,Ark), (Zb,Rc,R1c,R3c,Arl), (Zb,Rc,R1c,R3c,Arm), (Zb,Rc,R1c,R3c,Arn), (Zb,Rc,R1c,R3c,Aro), (Zb,Rc,R1c,R3c,Arp), (Zb,Rc,R1c,R3d,Ara), (Zb,Rc,R1c,R3d,Arb), (Zb,Rc,R1c,R3d,Arc), (Zb,Rc,R1c,R3d,Ard), (Zb,Rc,R1c,R3d,Are), (Zb,Rc,R1c,R3d,Arf), (Zb,Rc,R1c,R3d,Arg), (Zb,Rc,R1c,R3d,Arh), (Zb,Rc,R1c,R3d,Ari), (Zb,Rc,R1c,R3d,Arj), (Zb,Rc,R1c,R3d,Ark), (Zb,Rc,R1c,R3d,Arl), (Zb,Rc,R1c,R3d,Arm), (Zb,Rc,R1c,R3d,Arn), (Zb,Rc,R1c,R3d,Aro), (Zb,Rc,R1c,R3d,Arp), (Zb,Rc,R1c,R3e,Ara), (Zb,Rc,R1c,R3e,Arb), (Zb,Rc,R1c,R3e,Arc), (Zb,Rc,R1c,R3e,Ard), (Zb,Rc,R1c,R3e,Are), (Zb,Rc,R1c,R3e,Arf), (Zb,Rc,R1c,R3e,Arg), (Zb,Rc,R1c,R3e,Arh), (Zb,Rc,R1c,R3e,Ari), (Zb,Rc,R1c,R3e,Arj), (Zb,Rc,R1c,R3e,Ark), (Zb,Rc,R1c,R3e,Arl), (Zb,Rc,R1c,R3e,Arm), (Zb,Rc,R1c,R3e,Arn), (Zb,Rc,R1c,R3e,Aro), (Zb,Rc,R1c,R3e,Arp), (Zb,Rc,R1c,R3f,Ara), (Zb,Rc,R1c,R3f,Arb), (Zb,Rc,R1c,R3f,Arc), (Zb,Rc,R1c,R3f,Ard), (Zb,Rc,R1c,R3f,Are), (Zb,Rc,R1c,R3f,Arf), (Zb,Rc,R1c,R3f,Arg), (Zb,Rc,R1c,R3f,Arh), (Zb,Rc,R1c,R3f,Ari), (Zb,Rc,R1c,R3f,Arj), (Zb,Rc,R1c,R3f,Ark), (Zb,Rc,R1c,R3f,Arl), (Zb,Rc,R1c,R3f,Arm), (Zb,Rc,R1c,R3f,Arn), (Zb,Rc,R1c,R3f,Aro), (Zb,Rc,R1c,R3f,Arp), (Zb,Rc,R1c,R3g,Ara), (Zb,Rc,R1c,R3g,Arb), (Zb,Rc,R1c,R3g,Arc), (Zb,Rc,R1c,R3g,Ard), (Zb,Rc,R1c,R3g,Are), (Zb,Rc,R1c,R3g,Arf), (Zb,Rc,R1c,R3g,Arg), (Zb,Rc,R1c,R3g,Arh), (Zb,Rc,R1c,R3g,Ari), (Zb,Rc,R1c,R3g,Arj), (Zb,Rc,R1c,R3g,Ark), (Zb,Rc,R1c,R3g,Arl), (Zb,Rc,R1c,R3g,Arm), (Zb,Rc,R1c,R3g,Arn), (Zb,Rc,R1c,R3g,Aro), (Zb,Rc,R1c,R3g,Arp), (Zb,Rc,R1c,R3h,Ara), (Zb,Rc,R1c,R3h,Arb), (Zb,Rc,R1c,R3h,Arc), (Zb,Rc,R1c,R3h,Ard), (Zb,Rc,R1c,R3h,Are), (Zb,Rc,R1c,R3h,Arf), (Zb,Rc,R1c,R3h,Arg), (Zb,Rc,R1c,R3h,Arh), (Zb,Rc,R1c,R3h,Ari), (Zb,Rc,R1c,R3h,Arj), (Zb,Rc,R1c,R3h,Ark), (Zb,Rc,R1c,R3h,Arl), (Zb,Rc,R1c,R3h,Arm), (Zb,Rc,R1c,R3h,Arn), (Zb,Rc,R1c,R3h,Aro), (Zb,Rc,R1c,R3h,Arp), (Zb,Rc,R1d,R3a,Ara), (Zb,Rc,R1d,R3a,Arb), (Zb,Rc,R1d,R3a,Arc), (Zb,Rc,R1d,R3a,Ard), (Zb,Rc,R1d,R3a,Are), (Zb,Rc,R1d,R3a,Arf), (Zb,Rc,R1d,R3a,Arg), (Zb,Rc,R1d,R3a,Arh), (Zb,Rc,R1d,R3a,Ari), (Zb,Rc,R1d,R3a,Arj), (Zb,Rc,R1d,R3a,Ark), (Zb,Rc,R1d,R3a,Arl), (Zb,Rc,R1d,R3a,Arm), (Zb,Rc,R1d,R3a,Arn), (Zb,Rc,R1d,R3a,Aro), (Zb,Rc,R1d,R3a,Arp), (Zb,Rc,R1d,R3b,Ara), (Zb,Rc,R1d,R3b,Arb), (Zb,Rc,R1d,R3b,Arc), (Zb,Rc,R1d,R3b,Ard), (Zb,Rc,R1d,R3b,Are), (Zb,Rc,R1d,R3b,Arf), (Zb,Rc,R1d,R3b,Arg), (Zb,Rc,R1d,R3b,Arh), (Zb,Rc,R1d,R3b,Ari), (Zb,Rc,R1d,R3b,Arj), (Zb,Rc,R1d,R3b,Ark), (Zb,Rc,R1d,R3b,Arl), (Zb,Rc,R1d,R3b,Arm), (Zb,Rc,R1d,R3b,Arn), (Zb,Rc,R1d,R3b,Aro), (Zb,Rc,R1d,R3b,Arp), (Zb,Rc,R1d,R3c,Ara), (Zb,Rc,R1d,R3c,Arb), (Zb,Rc,R1d,R3c,Arc), (Zb,Rc,R1d,R3c,Ard), (Zb,Rc,R1d,R3c,Are), (Zb,Rc,R1d,R3c,Arf), (Zb,Rc,R1d,R3c,Arg), (Zb,Rc,R1d,R3c,Arh), (Zb,Rc,R1d,R3c,Ari), (Zb,Rc,R1d,R3c,Arj), (Zb,Rc,R1d,R3c,Ark), (Zb,Rc,R1d,R3c,Arl), (Zb,Rc,R1d,R3c,Arm), (Zb,Rc,R1d,R3c,Arn), (Zb,Rc,R1d,R3c,Aro), (Zb,Rc,R1d,R3c,Arp), (Zb,Rc,R1d,R3d,Ara), (Zb,Rc,R1d,R3d,Arb), (Zb,Rc,R1d,R3d,Arc), (Zb,Rc,R1d,R3d,Ard), (Zb,Rc,R1d,R3d,Are), (Zb,Rc,R1d,R3d,Arf), (Zb,Rc,R1d,R3d,Arg), (Zb,Rc,R1d,R3d,Arh), (Zb,Rc,R1d,R3d,Ari), (Zb,Rc,R1d,R3d,Arj), (Zb,Rc,R1d,R3d,Ark), (Zb,Rc,R1d,R3d,Arl), (Zb,Rc,R1d,R3d,Arm), (Zb,Rc,R1d,R3d,Arn), (Zb,Rc,R1d,R3d,Aro), (Zb,Rc,R1d,R3d,Arp), (Zb,Rc,R1d,R3e,Ara), (Zb,Rc,R1d,R3e,Arb), (Zb,Rc,R1d,R3e,Arc), (Zb,Rc,R1d,R3e,Ard), (Zb,Rc,R1d,R3e,Are), (Zb,Rc,R1d,R3e,Arf), (Zb,Rc,R1d,R3e,Arg), (Zb,Rc,R1d,R3e,Arh), (Zb,Rc,R1d,R3e,Ari), (Zb,Rc,R1d,R3e,Arj), (Zb,Rc,R1d,R3e,Ark), (Zb,Rc,R1d,R3e,Arl), (Zb,Rc,R1d,R3e,Arm), (Zb,Rc,R1d,R3e,Arn), (Zb,Rc,R1d,R3e,Aro), (Zb,Rc,R1d,R3e,Arp), (Zb,Rc,R1d,R3f,Ara), (Zb,Rc,R1d,R3f,Arb), (Zb,Rc,R1d,R3f,Arc), (Zb,Rc,R1d,R3f,Ard), (Zb,Rc,R1d,R3f,Are), (Zb,Rc,R1d,R3f,Arf), (Zb,Rc,R1d,R3f,Arg), (Zb,Rc,R1d,R3f,Arh), (Zb,Rc,R1d,R3f,Ari), (Zb,Rc,R1d,R3f,Arj), (Zb,Rc,R1d,R3f,Ark), (Zb,Rc,R1d,R3f,Arl), (Zb,Rc,R1d,R3f,Arm), (Zb,Rc,R1d,R3f,Arn), (Zb,Rc,R1d,R3f,Aro), (Zb,Rc,R1d,R3f,Arp), (Zb,Rc,R1d,R3g,Ara), (Zb,Rc,R1d, R3g,Arb), (Zb,Rc,R1d,R3g,Arc), (Zb,Rc,R1d,R3g,Ard), (Zb,Rc,R1d,R3g,Are), (Zb,Rc,R1d,R3g,Arf), (Zb,Rc,R1d, R3g,Arg), (Zb,Rc,R1d,R3g,Arh), (Zb,Rc,R1d,R3g,Ari), (Zb,Rc,R1d,R3g,Arj), (Zb,Rc,R1d,R3g,Ark), (Zb,Rc,R1d, R3g,Arl), (Zb,Rc,R1d,R3g,Arm), (Zb,Rc,R1d,R3g,Arn), (Zb,Rc,R1d,R3g,Aro), (Zb,Rc,R1d,R3g,Arp), (Zb,Rc,R1d, R3h,Ara), (Zb,Rc,R1d,R3h,Arb), (Zb,Rc,R1d,R3h,Arc), (Zb,Rc,R1d,R3h,Ard), (Zb,Rc,R1d,R3h,Are), (Zb,Rc,R1d, R3h,Arf), (Zb,Rc,R1d,R3h,Arg), (Zb,Rc,R1d,R3h,Arh), (Zb,Rc,R1d,R3h,Ari), (Zb,Rc,R1d,R3h,Arj), (Zb,Rc,R1d, R3h,Ark), (Zb,Rc,R1d,R3h,Arl), (Zb,Rc,R1d,R3h,Arm), (Zb,Rc,R1d,R3h,Arn), (Zb,Rc,R1d,R3h,Aro), (Zb,Rc,R1d, R3h,Arp), (Zb,Rd,R1a,R3a,Ara), (Zb,Rd,R1a,R3a,Arb), (Zb,Rd,R1a,R3a,Arc), (Zb,Rd,R1a,R3a,Ard), (Zb,Rd,R1a, R3a,Are), (Zb,Rd,R1a,R3a,Arf), (Zb,Rd,R1a,R3a,Arg), (Zb, Rd,R1a,R3a,Arh), (Zb,Rd,R1a,R3a,Ari), (Zb,Rd,R1a,R3a, Arj), (Zb,Rd,R1a,R3a,Ark), (Zb,Rd,R1a,R3a,Arl), (Zb,Rd, R1a,R3a,Arm), (Zb,Rd,R1a,R3a,Arn), (Zb,Rd,R1a,R3a, Aro), (Zb,Rd,R1a,R3a,Arp), (Zb,Rd,R1a,R3b,Ara), (Zb,Rd, R1a,R3b,Arb), (Zb,Rd,R1a,R3b,Arc), (Zb,Rd,R1a,R3b, Ard), (Zb,Rd,R1a,R3b,Are), (Zb,Rd,R1a,R3b,Arf), (Zb,Rd, R1a,R3b,Arg), (Zb,Rd,R1a,R3b,Arh), (Zb,Rd,R1a,R3b, Ari), (Zb,Rd,R1a,R3b,Arj), (Zb,Rd,R1a,R3b,Ark), (Zb,Rd, R1a,R3b,Arl), (Zb,Rd,R1a,R3b,Arm), (Zb,Rd,R1a,R3b, Arn), (Zb,Rd,R1a,R3b,Aro), (Zb,Rd,R1a,R3b,Arp), (Zb,Rd, R1a,R3c,Ara), (Zb,Rd,R1a,R3c,Arb), (Zb,Rd,R1a,R3c,Arc), (Zb,Rd,R1a,R3c,Ard), (Zb,Rd,R1a,R3c,Are), (Zb,Rd,R1a, R3c,Arf), (Zb,Rd,R1a,R3c,Arg), (Zb,Rd,R1a,R3c,Arh), (Zb, Rd,R1a,R3c,Ari), (Zb,Rd,R1a,R3c,Arj), (Zb,Rd,R1a,R3c, Ark), (Zb,Rd,R1a,R3c,Arl), (Zb,Rd,R1a,R3c,Arm), (Zb,Rd, R1a,R3c,Arn), (Zb,Rd,R1a,R3c,Aro), (Zb,Rd,R1a,R3c, Arp), (Zb,Rd,R1a,R3d,Ara), (Zb,Rd,R1a,R3d,Arb), (Zb,Rd, R1a,R3d,Arc), (Zb,Rd,R1a,R3d,Ard), (Zb,Rd,R1a,R3d, Are), (Zb,Rd,R1a,R3d,Arf), (Zb,Rd,R1a,R3d,Arg), (Zb,Rd, R1a,R3d,Arh), (Zb,Rd,R1a,R3d,Ari), (Zb,Rd,R1a,R3d,Arj), (Zb,Rd,R1a,R3d,Ark), (Zb,Rd,R1a,R3d,Arl), (Zb,Rd,R1a, R3d,Arm), (Zb,Rd,R1a,R3d,Arn), (Zb,Rd,R1a,R3d,Aro), (Zb,Rd,R1a,R3d,Arp), (Zb,Rd,R1a,R3e,Ara), (Zb,Rd,R1a, R3e,Arb), (Zb,Rd,R1a,R3e,Arc), (Zb,Rd,R1a,R3e,Ard), (Zb,Rd,R1a,R3e,Are), (Zb,Rd,R1a,R3e,Arf), (Zb,Rd,R1a, R3e,Arg), (Zb,Rd,R1a,R3e,Arh), (Zb,Rd,R1a,R3e,Ari), (Zb, Rd,R1a,R3e,Atj), (Zb,Rd,R 1a,R3e,Ark), (Zb,Rd,R1a,R3e, Arl), (Zb,Rd,R1a,R3e,Arm), (Zb,Rd,R1a,R3e,Arn), (Zb,Rd, R1a,R3e,Aro), (Zb,Rd,R1a,R3e,Arp), (Zb,Rd,R1a,R3f,Ara), (Zb,Rd,R1a,R3f,Arb), (Zb,Rd,R1a,R3f,Arc), (Zb,Rd,R1a, R3f,Ard), (Zb,Rd,R1a,R3f,Are), (Zb,Rd,R1a,R3f,Arf), (Zb, Rd,R1a,R3f,Arg), (Zb,Rd,R1a,R3f,Arh), (Zb,Rd,R1a,R3f, Ari), (Zb,Rd,R1a,R3f,Arj), (Zb,Rd,R1a,R3f,Ark), (Zb,Rd, R1a,R3f,Arl), (Zb,Rd,R1a,R3f,Arm), (Zb,Rd,R1a,R3f,Arn), (Zb,Rd,R1a,R3f,Aro), (Zb,Rd,R1a,R3f,Arp), (Zb,Rd,R1a, R3g,Ara), (Zb,Rd,R1a,R3g,Arb), (Zb,Rd,R1a,R3g,Arc), (Zb,Rd,R1a,R3g,Ard), (Zb,Rd,R1a,R3g,Are), (Zb,Rd,R1a, R3g,Arf), (Zb,Rd,R1a,R3g,Arg), (Zb,Rd,R1a,R3g,Arh), (Zb,Rd,R1a,R3g,Ari), (Zb,Rd,R1a,R3g,Arj), (Zb,Rd,R1a, R3g,Ark), (Zb,Rd,R1a,R3g,Arl), (Zb,Rd,R1a,R3g,Arm), (Zb,Rd,R1a,R3g,Arn), (Zb,Rd,R1a,R3g,Aro), (Zb,Rd,R1a, R3g,Arp), (Zb,Rd,R1a,R3h,Ara), (Zb,Rd,R1a,R3h,Arb), (Zb,Rd,R1a,R3h,Arc), (Zb,Rd,R1a,R3h,Ard), (Zb,Rd,R1a, R3h,Are), (Zb,Rd,R1a,R3h,Arf), (Zb,Rd,R1a,R3h,Arg), (Zb,Rd,R1a,R3h,Arh), (Zb,Rd,R1a,R3h,Ari), (Zb,Rd,R1a, R3h,Arj), (Zb,Rd,R1a,R3h,Ark), (Zb,Rd,R1a,R3h,Arl), (Zb, Rd,R1a,R3h,Arm), (Zb,Rd,R1a,R3h,Arn), (Zb,Rd,R1a,R3h, Aro), (Zb,Rd,R1a,R3h,Arp), (Zb,Rd,R1b,R3a,Ara), (Zb,Rd, R1b,R3a,Arb), (Zb,Rd,R1b,R3a,Arc), (Zb,Rd,R1b,R3a, Ard), (Zb,Rd,R1b,R3a,Are), (Zb,Rd,R1b,R3a,Arf), (Zb,Rd, R1b,R3a,Arg), (Zb,Rd,R1b,R3a,Arh), (Zb,Rd,R1b,R3a, Ari), (Zb,Rd,R1b,R3a,Arj), (Zb,Rd,R1b,R3a,Ark), (Zb,Rd, R1b,R3a,Arl), (Zb,Rd,R1b,R3a,Arm), (Zb,Rd,R1b,R3a, Arn), (Zb,Rd,R1b,R3a,Aro), (Zb,Rd,R1b,R3a,Arp), (Zb,Rd, R1b,R3b,Ara), (Zb,Rd,R1b,R3b,Arb), (Zb,Rd,R1b,R3b, Arc), (Zb,Rd,R1b,R3b,Ard), (Zb,Rd,R1b,R3b,Are), (Zb,Rd, R1b,R3b,Arf), (Zb,Rd,R1b,R3b,Arg), (Zb,Rd,R1b,R3b, Arh), (Zb,Rd,R1b,R3b,Ari), (Zb,Rd,R1b,R3b,Arj), (Zb,Rd, R1b,R3b,Ark), (Zb,Rd,R1b,R3b,Arl), (Zb,Rd,R1b,R3b, Arm), (Zb,Rd,R1b,R3b,Arn), (Zb,Rd,R1b,R3b,Aro), (Zb, Rd,R1b,R3b,Arp), (Zb,Rd,R1b,R3c,Ara), (Zb,Rd,R1b,R3c, Arb), (Zb,Rd,R1b,R3c,Arc), (Zb,Rd,R1b,R3c,Ard), (Zb,Rd, R1b,R3c,Are), (Zb,Rd,R1b,R3c,Arf), (Zb,Rd,R1b,R3c, Arg), (Zb,Rd,R1b,R3c,Arh), (Zb,Rd,R1b,R3c,Ari), (Zb,Rd, R1b,R3c,Arj), (Zb,Rd,R1b,R3c,Ark), (Zb,Rd,R1b,R3c,Arl), (Zb,Rd,R1b,R3c,Arm), (Zb,Rd,R1b,R3c,Arn), (Zb,Rd,R1b, R3c,Aro), (Zb,Rd,R1b,R3c,Arp), (Zb,Rd,R1b,R3d,Ara), (Zb,Rd,R1b,R3d,Arb), (Zb,Rd,R1b,R3d,Arc), (Zb,Rd,R1b, R3d,Ard), (Zb,Rd,R1b,R3d,Are), (Zb,Rd,R1b,R3d,Arf), (Zb,Rd,R1b,R3d,Arg), (Zb,Rd,R1b,R3d,Arh), (Zb,Rd,R1b, R3d,Ari), (Zb,Rd,R1b,R3d,Arj), (Zb,Rd,R1b,R3d,Ark), (Zb, Rd,R1b,R3d,Arl), (Zb,Rd,R1b,R3d,Arm), (Zb,Rd,R1b,R3d, Arn), (Zb,Rd,R1b,R3d,Aro), (Zb,Rd,R1b,R3d,Arp), (Zb,Rd, R1b,R3e,Ara), (Zb,Rd,R1b,R3e,Arb), (Zb,Rd,R1b,R3e, Arc), (Zb,Rd,R1b,R3e,Ard), (Zb,Rd,R1b,R3e,Are), (Zb,Rd, R1b,R3e,Arf), (Zb,Rd,R1b,R3e,Arg), (Zb,Rd,R1b,R3e, Arh), (Zb,Rd,R1b,R3e,Ari), (Zb,Rd,R1b,R3e,Arj), (Zb,Rd, R1b,R3e,Ark), (Zb,Rd,R1b,R3e,Arl), (Zb,Rd,R1b,R3e, Arm), (Zb,Rd,R1b,R3e,Arn), (Zb,Rd,R1b,R3e,Aro), (Zb, Rd,R1b,R3e,Arp), (Zb,Rd,R1b,R3f,Ara), (Zb,Rd,R1b,R3f, Arb), (Zb,Rd,R1b,R3f,Arc), (Zb,Rd,R1b,R3f,Ard), (Zb,Rd, R1b,R3f,Are), (Zb,Rd,R1b,R3f,Arf), (Zb,Rd,R1b,R3f,Arg), (Zb,Rd,R1b,R3f,Arh), (Zb,Rd,R1b,R3f,Ari), (Zb,Rd,R1b, R3f,Arj), (Zb,Rd,R1b,R3f,Ark), (Zb,Rd,R1b,R3f,Arl), (Zb, Rd,R1b,R3f,Arm), (Zb,Rd,R1b,R3f,Arn), (Zb,Rd,R1b,R3f, Aro), (Zb,Rd,R1b,R3f,Arp), (Zb,Rd,R1b,R3g,Ara), (Zb,Rd, R1b,R3g,Arb), (Zb,Rd,R1b,R3g,Arc), (Zb,Rd,R1b,R3g, Ard), (Zb,Rd,R1b,R3g,Are), (Zb,Rd,R1b,R3g,Arf), (Zb,Rd, R1b,R3g,Arg), (Zb,Rd,R1b,R3g,Arh), (Zb,Rd,R1b,R3g, Ari), (Zb,Rd,R1b,R3g,Arj), (Zb,Rd,R1b,R3g,Ark), (Zb,Rd, R1b,R3g,Arl), (Zb,Rd,R1b,R3g,Arm), (Zb,Rd,R1b,R3g, Arn), (Zb,Rd,R1b,R3g,Aro), (Zb,Rd,R1b,R3g,Arp), (Zb,Rd, R1b,R3h,Ara), (Zb,Rd,R1b,R3h,Arb), (Zb,Rd,R1b,R3h, Arc), (Zb,Rd,R1b,R3h,Ard), (Zb,Rd,R1b,R3h,Are), (Zb,Rd, R1b,R3h,Arf), (Zb,Rd,R1b,R3h,Arg), (Zb,Rd,R1b,R3h, Arh), (Zb,Rd,R1b,R3h,Ari), (Zb,Rd,R1b,R3h,Arj), (Zb,Rd, R1b,R3h,Ark), (Zb,Rd,R1b,R3h,Arl), (Zb,Rd,R1b,R3h, Arm), (Zb,Rd,R1b,R3h,Arn), (Zb,Rd,R1b,R3h,Aro), (Zb, Rd,R1b,R3h,Arp), (Zb,Rd,R1c,R3a,Ara), (Zb,Rd,R1c,R3a, Arb), (Zb,Rd,R1c,R3a,Arc), (Zb,Rd,R1c,R3a,Ard), (Zb,Rd, R1c,R3a,Are), (Zb,Rd,R1c,R3a,Arf), (Zb,Rd,R1c,R3a,Arg), (Zb,Rd,R1c,R3a,Arh), (Zb,Rd,R1c,R3a,Ari), (Zb,Rd,R1c, R3a,Arj), (Zb,Rd,R1c,R3a,Ark), (Zb,Rd,R1c,R3a,Arl), (Zb, Rd,R1c,R3a,Arm), (Zb,Rd,R1c,R3a,Arn), (Zb,Rd,R1c,R3a, Aro), (Zb,Rd,R1c,R3a,Arp), (Zb,Rd,R1c,R3b,Ara), (Zb,Rd, R1c,R3b,Arb), (Zb,Rd,R1c,R3b,Arc), (Zb,Rd,R1c,R3b, Ard), (Zb,Rd,R1c,R3b,Are), (Zb,Rd,R1c,R3b,Arf), (Zb,Rd, R1c,R3b,Arg), (Zb,Rd,R1c,R3b,Arh), (Zb,Rd,R1c,R3b, Ari), (Zb,Rd,R1c,R3b,Arj), (Zb,Rd,R1c,R3b,Ark), (Zb,Rd, R1c,R3b,Arl), (Zb,Rd,R1c,R3b,Arm), (Zb,Rd,R1c,R3b, Arn), (Zb,Rd,R1c,R3b,Aro), (Zb,Rd,R1c,R3b,Arp), (Zb,Rd, R1c,R3c,Ara), (Zb,Rd,R1c,R3c,Arb), (Zb,Rd,R1c,R3c,Arc), (Zb,Rd,R1c,R3c,Ard), (Zb,Rd,R1c,R3c,Are), (Zb,Rd,R1c, R3c,Arf), (Zb,Rd,R1c,R3c,Arg), (Zb,Rd,R1c,R3c,Arh), (Zb, Rd,R1c,R3c,Ari), (Zb,Rd,R1c,R3c,Arj), (Zb,Rd,R1c,R3c, Ark), (Zb,Rd,R1c,R3c,Arl), (Zb,Rd,R1c,R3c,Arm), (Zb,Rd, R1c,R3c,Arn), (Zb,Rd,R1c,R3c,Aro), (Zb,Rd,R1c,R3c, Arp), (Zb,Rd,R1c,R3d,Ara), (Zb,Rd,R1c,R3d,Arb), (Zb,Rd, R1c,R3d,Arc), (Zb,Rd,R1c,R3d,Ard), (Zb,Rd,R1c,R3d,Are), (Zb,Rd,R1c,R3d,Arf), (Zb,Rd,R1c,R3d,Arg), (Zb,Rd,R1c,R3d,Arh), (Zb,Rd,R1c,R3d,Ari), (Zb,Rd,R1c,R3d,Arj), (Zb,Rd,R1c,R3d,Ark), (Zb,Rd,R1c,R3d,Arl), (Zb,Rd,R1c,R3d,Arm), (Zb,Rd,R1c,R3d,Arn), (Zb,Rd,R1c,R3d,Aro), (Zb,Rd,R1c,R3d,Arp), (Zb,Rd,R1c,R3e,Ara), (Zb,Rd,R1c,R3e,Arb), (Zb,Rd,R1c,R3e,Arc), (Zb,Rd,R1c,R3e,Ard), (Zb,Rd,R1c,R3e,Are), (Zb,Rd,R1c,R3e,Arf), (Zb,Rd,R1c,R3e,Arg), (Zb,Rd,R1c,R3e,Arh), (Zb,Rd,R1c,R3e,Ari), (Zb,Rd,R1c,R3e,Arj), (Zb,Rd,R1c,R3e,Ark), (Zb,Rd,R1c,R3e,Arl), (Zb,Rd,R1c,R3e,Arm), (Zb,Rd,R1c,R3e,Arn), (Zb,Rd,R1c,R3e,Aro), (Zb,Rd,R1c,R3e,Arp), (Zb,Rd,R1c,R3f,Ara), (Zb,Rd,R1c,R3f,Arb), (Zb,Rd,R1c,R3f,Arc), (Zb,Rd,R1c,R3f,Ard), (Zb,Rd,R1c,R3f,Are), (Zb,Rd,R1c,R3f,Arf), (Zb,Rd,R1c,R3f,Arg), (Zb,Rd,R1c,R3f,Arh), (Zb,Rd,R1c,R3f,Ari), (Zb,Rd,R1c,R3f,Arj), (Zb,Rd,R1c,R3f,Ark), (Zb,Rd,R1c,R3f,Arl), (Zb,Rd,R1c,R3f,Arm), (Zb,Rd,R1c,R3f,Arn), (Zb,Rd,R1c,R3f,Aro), (Zb,Rd,R1c,R3f,Arp), (Zb,Rd,R1c,R3g,Ara), (Zb,Rd,R1c,R3g,Arb), (Zb,Rd,R1c,R3g,Arc), (Zb,Rd,R1c,R3g,Ard), (Zb,Rd,R1c,R3g,Are), (Zb,Rd,R1c,R3g,Arf), (Zb,Rd,R1c,R3g,Arg), (Zb,Rd,R1c,R3g,Arh), (Zb,Rd,R1c,R3g,Ari), (Zb,Rd,R1c,R3g,Arj), (Zb,Rd,R1c,R3g,Ark), (Zb,Rd,R1c,R3g,Arl), (Zb,Rd,R1c,R3g,Arm), (Zb,Rd,R1c,R3g,Arn), (Zb,Rd,R1c,R3g,Aro), (Zb,Rd,R1c,R3g,Arp), (Zb,Rd,R1c,R3h,Ara), (Zb,Rd,R1c,R3h,Arb), (Zb,Rd,R1c,R3h,Arc), (Zb,Rd,R1c,R3h,Ard), (Zb,Rd,R1c,R3h,Are), (Zb,Rd,R1c,R3h,Arf), (Zb,Rd,R1c,R3h,Arg), (Zb,Rd,R1c,R3h,Arh), (Zb,Rd,R1c,R3h,Ari), (Zb,Rd,R1c,R3h,Arj), (Zb,Rd,R1c,R3h,Ark), (Zb,Rd,R1c,R3h,Arl), (Zb,Rd,R1c,R3h,Arm), (Zb,Rd,R1c,R3h,Arn), (Zb,Rd,R1c,R3h,Aro), (Zb,Rd,R1c,R3h,Arp), (Zb,Rd,R1d,R3a,Ara), (Zb,Rd,R1d,R3a,Arb), (Zb,Rd,R1d,R3a,Arc), (Zb,Rd,R1d,R3a,Ard), (Zb,Rd,R1d,R3a,Are), (Zb,Rd,R1d,R3a,Arf), (Zb,Rd,R1d,R3a,Arg), (Zb,Rd,R1d,R3a,Arh), (Zb,Rd,R1d,R3a,Ari), (Zb,Rd,R1d,R3a,Arj), (Zb,Rd,R1d,R3a,Ark), (Zb,Rd,R1d,R3a,Arl), (Zb,Rd,R1d,R3a,Arm), (Zb,Rd,R1d,R3a,Arn), (Zb,Rd,R1d,R3a,Aro), (Zb,Rd,R1d,R3a,Arp), (Zb,Rd,R1d,R3b,Ara), (Zb,Rd,R1d,R3b,Arb), (Zb,Rd,R1d,R3b,Arc), (Zb,Rd,R1d,R3b,Ard), (Zb,Rd,R1d,R3b,Are), (Zb,Rd,R1d,R3b,Arf), (Zb,Rd,R1d,R3b,Arg), (Zb,Rd,R1d,R3b,Arh), (Zb,Rd,R1d,R3b,Ari), (Zb,Rd,R1d,R3b,Arj), (Zb,Rd,R1d,R3b,Ark), (Zb,Rd,R1d,R3b,Arl), (Zb,Rd,R1d,R3b,Arm), (Zb,Rd,R1d,R3b,Arn), (Zb,Rd,R1d,R3b,Aro), (Zb,Rd,R1d,R3b,Arp), (Zb,Rd,R1d,R3c,Ara), (Zb,Rd,R1d,R3c,Arb), (Zb,Rd,R1d,R3c,Arc), (Zb,Rd,R1d,R3c,Ard), (Zb,Rd,R1d,R3c,Are), (Zb,Rd,R1d,R3c,Arf), (Zb,Rd,R1d,R3c,Arg), (Zb,Rd,R1d,R3c,Arh), (Zb,Rd,R1d,R3c,Ari), (Zb,Rd,R1d,R3c,Arj), (Zb,Rd,R1d,R3c,Ark), (Zb,Rd,R1d,R3c,Arl), (Zb,Rd,R1d,R3c,Arm), (Zb,Rd,R1d,R3c,Arn), (Zb,Rd,R1d,R3c,Aro), (Zb,Rd,R1d,R3c,Arp), (Zb,Rd,R1d,R3d,Ara), (Zb,Rd,R1d,R3d,Arb), (Zb,Rd,R1d,R3d,Arc), (Zb,Rd,R1d,R3d,Ard), (Zb,Rd,R1d,R3d,Are), (Zb,Rd,R1d,R3d,Arf), (Zb,Rd,R1d,R3d,Arg), (Zb,Rd,R1d,R3d,Arh), (Zb,Rd,R1d,R3d,Ari), (Zb,Rd,R1d,R3d,Arj), (Zb,Rd,R1d,R3d,Ark), (Zb,Rd,R1d,R3d,Arl), (Zb,Rd,R1d,R3d,Arm), (Zb,Rd,R1d,R3d,Arn), (Zb,Rd,R1d,R3d,Aro), (Zb,Rd,R1d,R3d,Arp), (Zb,Rd,R1d,R3e,Ara), (Zb,Rd,R1d,R3e,Arb), (Zb,Rd,R1d,R3e,Arc), (Zb,Rd,R1d,R3e,Ard), (Zb,Rd,R1d,R3e,Are), (Zb,Rd,R1d,R3e,Arf), (Zb,Rd,R1d,R3e,Arg), (Zb,Rd,R1d,R3e,Arh), (Zb,Rd,R1d,R3e,Ari), (Zb,Rd,R1d,R3e,Arj), (Zb,Rd,R1d,R3e,Ark), (Zb,Rd,R1d,R3e,Arl), (Zb,Rd,R1d,R3e,Arm), (Zb,Rd,R1d,R3e,Arn), (Zb,Rd,R1d,R3e,Aro), (Zb,Rd,R1d,R3e,Arp), (Zb,Rd,R1d,R3f,Ara), (Zb,Rd,R1d,R3f,Arb), (Zb,Rd,R1d,R3f,Arc), (Zb,Rd,R1d,R3f,Ard), (Zb,Rd,R1d,R3f,Are), (Zb,Rd,R1d,R3f,Arf), (Zb,Rd,R1d,R3f,Arg), (Zb,Rd,R1d,R3f,Arh), (Zb,Rd,R1d,R3f,Ari), (Zb,Rd,R1d,R3f,Arj), (Zb,Rd,R1d,R3f,Ark), (Zb,Rd,R1d,R3f,Arl), (Zb,Rd,R1d,R3f,Arm), (Zb,Rd,R1d,R3f,Arn), (Zb,Rd,R1d,R3f,Aro), (Zb,Rd,R1d,R3f,Arp), (Zb,Rd,R1d,R3g,Ara), (Zb,Rd,R1d,R3g,Arb), (Zb,Rd,R1d,R3g,Arc), (Zb,Rd,R1d,R3g,Ard), (Zb,Rd,R1d,R3g,Are), (Zb,Rd,R1d,R3g,Arf), (Zb,Rd,R1d,R3g,Arg), (Zb,Rd,R1d,R3g,Arh), (Zb,Rd,R1d,R3g,Ari), (Zb,Rd,R1d,R3g,Arj), (Zb,Rd,R1d,R3g,Ark), (Zb,Rd,R1d,R3g,Arl), (Zb,Rd,R1d,R3g,Arm), (Zb,Rd,R1d,R3g,Arn), (Zb,Rd,R1d,R3g,Aro), (Zb,Rd,R1d,R3g,Arp), (Zb,Rd,R1d,R3h,Ara), (Zb,Rd,R1d,R3h,Arb), (Zb,Rd,R1d,R3h,Arc), (Zb,Rd,R1d,R3h,Ard), (Zb,Rd,R1d,R3h,Are), (Zb,Rd,R1d,R3h,Arf), (Zb,Rd,R1d,R3h,Arg), (Zb,Rd,R1d,R3h,Arh), (Zb,Rd,R1d,R3h,Ari), (Zb,Rd,R1d,R3h,Arj), (Zb,Rd,R1d,R3h,Ark), (Zb,Rd,R1d,R3h,Arl), (Zb,Rd,R1d,R3h,Arm), (Zb,Rd,R1d,R3h,Arn), (Zb,Rd,R1d,R3h,Aro), (Zb,Rd,R1d,R3h,Arp), (Zb,Re,R1a,R3a,Ara), (Zb,Re,R1a,R3a,Arb), (Zb,Re,R1a,R3a,Arc), (Zb,Re,R1a,R3a,Ard), (Zb,Re,R1a,R3a,Are), (Zb,Re,R1a,R3a,Arf), (Zb,Re,R1a,R3a,Arg), (Zb,Re,R1a,R3a,Arh), (Zb,Re,R1a,R3a,Ari), (Zb,Re,R1a,R3a,Arj), (Zb,Re,R1a,R3a,Ark), (Zb,Re,R1a,R3a,Arl), (Zb,Re,R1a,R3a,Arm), (Zb,Re,R1a,R3a,Arn), (Zb,Re,R1a,R3a,Aro), (Zb,Re,R1a,R3a,Arp), (Zb,Re,R1a,R3b,Ara), (Zb,Re,R1a,R3b,Arb), (Zb,Re,R1a,R3b,Arc), (Zb,Re,R1a,R3b,Ard), (Zb,Re,R1a,R3b,Are), (Zb,Re,R1a,R3b,Arf), (Zb,Re,R1a,R3b,Arg), (Zb,Re,R1a,R3b,Arh), (Zb,Re,R1a,R3b,Ari), (Zb,Re,R1a,R3b,Arj), (Zb,Re,R1a,R3b,Ark), (Zb,Re,R1a,R3b,Arl), (Zb,Re,R1a,R3b,Arm), (Zb,Re,R1a,R3b,Arn), (Zb,Re,R1a,R3b,Aro), (Zb,Re,R1a,R3b,Arp), (Zb,Re,R1a,R3c,Ara), (Zb,Re,R1a,R3c,Arb), (Zb,Re,R1a,R3c,Arc), (Zb,Re,R1a,R3c,Ard), (Zb,Re,R1a,R3c,Are), (Zb,Re,R1a,R3c,Arf), (Zb,Re,R1a,R3c,Arg), (Zb,Re,R1a,R3c,Arh), (Zb,Re,R1a,R3c,Ari), (Zb,Re,R1a,R3c,Arj), (Zb,Re,R1a,R3c,Ark), (Zb,Re,R1a,R3c,Arl), (Zb,Re,R1a,R3c,Arm), (Zb,Re,R1a,R3c,Arn), (Zb,Re,R1a,R3c,Aro), (Zb,Re,R1a,R3c,Arp), (Zb,Re,R1a,R3d,Ara), (Zb,Re,R1a,R3d,Arb), (Zb,Re,R1a,R3d,Arc), (Zb,Re,R1a,R3d,Ard), (Zb,Re,R1a,R3d,Are), (Zb,Re,R1a,R3d,Arf), (Zb,Re,R1a,R3d,Arg), (Zb,Re,R1a,R3d,Arh), (Zb,Re,R1a,R3d,Ari), (Zb,Re,R1a,R3d,Arj), (Zb,Re,R1a,R3d,Ark), (Zb,Re,R1a,R3d,Arl), (Zb,Re,R1a,R3d,Arm), (Zb,Re,R1a,R3d,Arn), (Zb,Re,R1a,R3d,Aro), (Zb,Re,R1a,R3d,Arp), (Zb,Re,R1a,R3e,Ara), (Zb,Re,R1a,R3e,Arb), (Zb,Re,R1a,R3e,Arc), (Zb,Re,R1a,R3e,Ard), (Zb,Re,R1a,R3e,Are), (Zb,Re,R1a,R3e,Arf), (Zb,Re,R1a,R3e,Arg), (Zb,Re,R1a,R3e,Arh), (Zb,Re,R1a,R3e,Ari), (Zb,Re,R1a,R3e,Arj), (Zb,Re,R1a,R3e,Ark), (Zb,Re,R1a,R3e,Arl), (Zb,Re,R1a,R3e,Arm), (Zb,Re,R1a,R3e,Arn), (Zb,Re,R1a,R3e,Aro), (Zb,Re,R1a,R3e,Arp), (Zb,Re,R1a,R3f,Ara), (Zb,Re,R1a,R3f,Arb), (Zb,Re,R1a,R3f,Arc), (Zb,Re,R1a,R3f,Ard), (Zb,Re,R1a,R3f,Are), (Zb,Re,R1a,R3f,Arf), (Zb,Re,R1a,R3f,Arg), (Zb,Re,R1a,R3f,Arh), (Zb,Re,R1a,R3f,Ari), (Zb,Re,R1a,R3f,Arj), (Zb,Re,R1a,R3f,Ark), (Zb,Re,R1a,R3f,Arl), (Zb,Re,R1a,R3f,Arm), (Zb,Re,R1a,R3f,Arn), (Zb,Re,R1a,R3f,Aro), (Zb,Re,R1a,R3f,Arp), (Zb,Re,R1a,R3g,Ara), (Zb,Re,R1a,R3g,Arb), (Zb,Re,R1a,R3g,Arc), (Zb,Re,R1a,R3g,Ard), (Zb,Re,R1a,R3g,Are), (Zb,Re,R1a,R3g,Arf), (Zb,Re,R1a,R3g,Arg), (Zb,Re,R1a,R3g,Arh), (Zb,Re,R1a,R3g,Ari), (Zb,Re,R1a,R3g,Arj), (Zb,Re,R1a,R3g,Ark), (Zb,Re,R1a,R3g,Arl), (Zb,Re,R1a,R3g,Arm), (Zb,Re,R1a,R3g,Arn), (Zb,Re,R1a,R3g,Aro), (Zb,Re,R1a,R3g,Arp), (Zb,Re,R1a,R3h,Ara), (Zb,Re,R1a,R3h,Arb), (Zb,Re,R1a,R3h,Arc), (Zb,Re,R1a,R3h,Ard), (Zb,Re,R1a,R3h,Are), (Zb,Re,R1a,R3h,Arf), (Zb,Re,R1a,R3h,Arg), (Zb,Re,R1a,R3h,Arh), (Zb,Re,R1a,R3h,Ari), (Zb,Re,R1a,R3h,Arj), (Zb,Re,R1a,R3h,Ark), (Zb,Re,R1a,R3h,Arl), (Zb,Re,R1a,R3h,Arm), (Zb,Re,R1a,R3h,Arn), (Zb,Re,R1a,R3h,Aro), (Zb,Re,R1a,R3h,Arp), (Zb,Re,R1b,R3a,Ara), (Zb,Re,R1b,R3a,Arb), (Zb,Re,R1b,R3a,Arc), (Zb,Re,R1b,R3a,Ard), (Zb,Re,R1b,R3a,Are), (Zb,Re,R1b,R3a,Arf), (Zb,Re,R1b,R3a,Arg), (Zb,Re, R1b,R3a,Arh), (Zb,Re,R1b,R3a,Ari), (Zb,Re,R1b,R3a,Arj), (Zb,Re,R1b,R3a,Ark), (Zb,Re,R1b,R3a,Arl), (Zb,Re,R1b,R3a,Arm), (Zb,Re,R1b,R3a,Arn), (Zb,Re,R1b,R3a,Aro), (Zb,Re,R1b,R3a,Arp), (Zb,Re,R1b,R3b,Ara), (Zb,Re,R1b,R3b,Arb), (Zb,Re,R1b,R3b,Arc), (Zb,Re,R1b,R3b,Ard), (Zb,Re,R1b,R3b,Are), (Zb,Re,R1b,R3b,Arf), (Zb,Re,R1b,R3b,Arg), (Zb,Re,R1b,R3b,Arh), (Zb,Re,R1b,R3b,Ari), (Zb,Re,R1b,R3b,Arj), (Zb,Re,R1b,R3b,Ark), (Zb,Re,R1b,R3b,Arl), (Zb,Re,R1b,R3b,Arm), (Zb,Re,R1b,R3b,Arn), (Zb,Re,R1b,R3b,Aro), (Zb,Re,R1b,R3b,Arp), (Zb,Re,R1b,R3c,Ara), (Zb,Re,R1b,R3c,Arb), (Zb,Re,R1b,R3c,Arc), (Zb,Re,R1b,R3c,Ard), (Zb,Re,R1b,R3c,Are), (Zb,Re,R1b,R3c,Arf), (Zb,Re,R1b,R3c,Arg), (Zb,Re,R1b,R3c,Arh), (Zb,Re,R1b,R3c,Ari), (Zb,Re,R1b,R3c,Arj), (Zb,Re,R1b,R3c,Ark), (Zb,Re,R1b,R3c,Arl), (Zb,Re,R1b,R3c,Arm), (Zb,Re,R1b,R3c,Arn), (Zb,Re,R1b, R3c,Aro), (Zb,Re,R1b,R3c,Arp), (Zb,Re,R1b,R3d,Ara), (Zb,Re,R1b,R3d,Arb), (Zb,Re,R1b,R3d,Arc), (Zb,Re,R1b,R3d,Ard), (Zb,Re,R1b,R3d,Are), (Zb,Re,R1b,R3d,Arf), (Zb,Re,R1b,R3d,Arg), (Zb,Re,R1b,R3d,Arh), (Zb,Re,R1b,R3d,Ari), (Zb,Re,R1b,R3d,Arj), (Zb,Re,R1b,R3d,Ark), (Zb,Re,R1b,R3d,Arl), (Zb,Re,R1b,R3d,Arm), (Zb,Re,R1b,R3d,Arn), (Zb,Re,R1b,R3d,Aro), (Zb,Re,R1b,R3d,Arp), (Zb,Re,R1b,R3e,Ara), (Zb,Re,R1b,R3e,Arb), (Zb,Re,R1b,R3e,Arc), (Zb,Re,R1b,R3e,Ard), (Zb,Re,R1b,R3e,Are), (Zb,Re,R1b,R3e,Arf), (Zb,Re,R1b,R3e,Arg), (Zb,Re,R1b,R3e,Arh), (Zb,Re,R1b,R3e,Ari), (Zb,Re,R1b,R3e,Arj), (Zb,Re,R1b,R3e,Ark), (Zb,Re,R1b,R3e,Arl), (Zb,Re,R1b,R3e,Arm), (Zb,Re,R1b,R3e,Arn), (Zb,Re,R1b,R3e,Aro), (Zb,Re,R1b,R3e,Arp), (Zb,Re,R1b,R3f,Ara), (Zb,Re,R1b,R3f,Arb), (Zb,Re,R1b,R3f,Arc), (Zb,Re,R1b,R3f,Ard), (Zb,Re,R1b,R3f,Are), (Zb,Re,R1b,R3f,Arf), (Zb,Re,R1b,R3f,Arg), (Zb,Re,R1b,R3f,Arh), (Zb,Re,R1b,R3f,Ari), (Zb,Re,R1b,R3f,Arj), (Zb,Re,R1b,R3f,Ark), (Zb,Re,R1b,R3f,Arl), (Zb,Re,R1b,R3f,Arm), (Zb,Re,R1b,R3f,Arn), (Zb,Re,R1b,R3f,Aro), (Zb,Re,R1b,R3f,Arp), (Zb,Re,R1b,R3g,Ara), (Zb,Re,R1b,R3g,Arb), (Zb,Re,R1b,R3g,Arc), (Zb,Re,R1b,R3g,Ard), (Zb,Re,R1b,R3g,Are), (Zb,Re,R1b,R3g,Arf), (Zb,Re,R1b,R3g,Arg), (Zb,Re,R1b,R3g,Arh), (Zb,Re,R1b,R3g,Ari), (Zb,Re,R1b,R3g,Arj), (Zb,Re,R1b,R3g,Ark), (Zb,Re,R1b,R3g,Arl), (Zb,Re,R1b,R3g,Arm), (Zb,Re,R1b,R3g,Arn), (Zb,Re,R1b,R3g,Aro), (Zb,Re,R1b,R3g,Arp), (Zb,Re,R1b,R3h,Ara), (Zb,Re,R1b,R3h,Arb), (Zb,Re,R1b,R3h,Arc), (Zb,Re,R1b,R3h,Ard), (Zb,Re,R1b,R3h,Are), (Zb,Re,R1b,R3h,Arf), (Zb,Re,R1b,R3h,Arg), (Zb,Re,R1b,R3h,Arh), (Zb,Re,R1b,R3h,Ari), (Zb,Re,R1b,R3h,Arj), (Zb,Re,R1b,R3h,Ark), (Zb,Re,R1b,R3h,Arl), (Zb,Re,R1b,R3h,Arm), (Zb,Re,R1b,R3h,Arn), (Zb,Re,R1b,R3h,Aro), (Zb,Re,R1b,R3h,Arp), (Zb,Re,R1c,R3a,Ara), (Zb,Re,R1c,R3a,Arb), (Zb,Re,R1c,R3a,Arc), (Zb,Re,R1c,R3a,Ard), (Zb,Re,R1c,R3a,Are), (Zb,Re,R1c,R3a,Arf), (Zb,Re,R1c,R3a,Arg), (Zb,Re,R1c,R3a,Arh), (Zb,Re,R1c,R3a,Ari), (Zb,Re,R1c,R3a,Arj), (Zb,Re,R1c,R3a,Ark), (Zb,Re,R1c,R3a,Arl), (Zb,Re,R1c,R3a,Arm), (Zb,Re,R1c,R3a,Arn), (Zb,Re,R1c,R3a,Aro), (Zb,Re,R1c,R3a,Arp), (Zb,Re,R1c,R3b,Ara), (Zb,Re,R1c,R3b,Arb), (Zb,Re,R1c,R3b,Arc), (Zb,Re,R1c,R3b,Ard), (Zb,Re,R1c,R3b,Are), (Zb,Re,R1c,R3b,Arf), (Zb,Re,R1c,R3b,Arg), (Zb,Re,R1c,R3b,Arh), (Zb,Re,R1c,R3b,Ari), (Zb,Re,R1c,R3b,Arj), (Zb,Re,R1c,R3b,Ark), (Zb,Re,R1c,R3b,Arl), (Zb,Re,R1c,R3b,Arm), (Zb,Re,R1c,R3b,Arn), (Zb,Re,R1c,R3b,Aro), (Zb,Re,R1c,R3b,Arp), (Zb,Re,R1c,R3c,Ara), (Zb,Re,R1c,R3c,Arb), (Zb,Re,R1c,R3c,Arc), (Zb,Re,R1c,R3c,Ard), (Zb,Re,R1c,R3c,Are), (Zb,Re,R1c,R3c,Arf), (Zb,Re,R1c,R3c,Arg), (Zb,Re,R1c,R3c,Arh), (Zb,Re,R1c,R3c,Ari), (Zb,Re,R1c,R3c,Arj), (Zb,Re,R1c,R3c,Ark), (Zb,Re,R1c,R3c,Arl), (Zb,Re,R1c,R3c,Arm), (Zb,Re,R1c,R3c,Arn), (Zb,Re,R1c,R3c,Aro), (Zb,Re,R1c,R3c,Arp), (Zb,Re,R1c,R3d,Ara), (Zb,Re,R1c,R3d,Arb), (Zb,Re,R1c,R3d,Arc), (Zb,Re,R1c,R3d,Ard), (Zb,Re,R1c,R3d,Are), (Zb,Re,R1c,R3d,Arf), (Zb,Re,R1c,R3d,Arg), (Zb,Re,R1c,R3d,Arh), (Zb,Re,R1c,R3d,Ari), (Zb,Re,R1c,R3d,Arj), (Zb,Re,R1c,R3d,Ark), (Zb,Re,R1c,R3d,Arl), (Zb,Re,R1c,R3d,Arm), (Zb,Re,R1c,R3d,Arn), (Zb,Re,R1c,R3d,Aro), (Zb,Re,R1c,R3d,Arp), (Zb,Re,R1c,R3e,Ara), (Zb,Re,R1c,R3e,Arb), (Zb,Re,R1c,R3e,Arc), (Zb,Re,R1c,R3e,Ard), (Zb,Re,R1c,R3e,Are), (Zb,Re,R1c,R3e,Arf), (Zb,Re,R1c,R3e,Arg), (Zb,Re,R1c,R3e,Arh), (Zb,Re,R1c,R3e,Ari), (Zb,Re,R1c,R3e,Arj), (Zb,Re,R1c,R3e,Ark), (Zb,Re,R1c,R3e,Arl), (Zb,Re,R1c,R3e,Arm), (Zb,Re,R1c,R3e,Arn), (Zb,Re,R1c,R3e,Aro), (Zb,Re,R1c,R3e,Arp), (Zb,Re,R1c,R3f,Ara), (Zb,Re,R1c,R3f,Arb), (Zb,Re,R1c,R3f,Arc), (Zb,Re,R1c,R3f,Ard), (Zb,Re,R1c,R3f,Are), (Zb,Re,R1c,R3f,Arf), (Zb,Re,R1c,R3f,Arg), (Zb,Re,R1c,R3f,Arh), (Zb,Re,R1c,R3f,Ari), (Zb,Re,R1c,R3f,Arj), (Zb,Re,R1c,R3f,Ark), (Zb,Re,R1c,R3f,Arl), (Zb,Re,R1c,R3f,Arm), (Zb,Re,R1c,R3f,Arn), (Zb,Re,R1c,R3f,Aro), (Zb,Re,R1c,R3f,Arp), (Zb,Re,R1c,R3g,Ara), (Zb,Re,R1c,R3g,Arb), (Zb,Re,R1c,R3g,Arc), (Zb,Re,R1c,R3g,Ard), (Zb,Re,R1c,R3g,Are), (Zb,Re,R1c,R3g,Arf), (Zb,Re,R1c,R3g,Arg), (Zb,Re,R1c,R3g,Arh), (Zb,Re,R1c,R3g,Ari), (Zb,Re,R1c,R3g,Arj), (Zb,Re,R1c,R3g,Ark), (Zb,Re,R1c,R3g,Arl), (Zb,Re,R1c,R3g,Arm), (Zb,Re,R1c,R3g,Arn), (Zb,Re,R1c,R3g,Aro), (Zb,Re,R1c,R3g,Arp), (Zb,Re,R1c,R3h,Ara), (Zb,Re,R1c,R3h,Arb), (Zb,Re,R1c,R3h,Arc), (Zb,Re,R1c,R3h,Ard), (Zb,Re,R1c,R3h,Are), (Zb,Re,R1c,R3h,Arf), (Zb,Re,R1c,R3h,Arg), (Zb,Re,R1c,R3h,Arh), (Zb,Re,R1c,R3h,Ari), (Zb,Re,R1c,R3h,Arj), (Zb,Re,R1c,R3h,Ark), (Zb,Re,R1c,R3h,Arl), (Zb,Re,R1c,R3h,Arm), (Zb,Re,R1c,R3h,Arn), (Zb,Re,R1c,R3h,Aro), (Zb,Re,R1c,R3h,Arp), (Zb,Re,R1d,R3a,Ara), (Zb,Re,R1d,R3a,Arb), (Zb,Re,R1d,R3a,Arc), (Zb,Re,R1d,R3a,Ard), (Zb,Re,R1d,R3a,Are), (Zb,Re,R1d,R3a,Arf), (Zb,Re,R1d,R3a,Arg), (Zb,Re,R1d,R3a,Arh), (Zb,Re,R1d,R3a,Ari), (Zb,Re,R1d,R3a,Arj), (Zb,Re,R1d,R3a,Ark), (Zb,Re,R1d,R3a,Arl), (Zb,Re,R1d,R3a,Arm), (Zb,Re,R1d,R3a,Arn), (Zb,Re,R1d,R3a,Aro), (Zb,Re,R1d,R3a,Arp), (Zb,Re,R1d,R3b,Ara), (Zb,Re,R1d,R3b,Arb), (Zb,Re,R1d,R3b,Arc), (Zb,Re,R1d,R3b,Ard), (Zb,Re,R1d,R3b,Are), (Zb,Re,R1d,R3b,Arf), (Zb,Re,R1d,R3b,Arg), (Zb,Re,R1d,R3b,Arh), (Zb,Re,R1d,R3b,Ari), (Zb,Re,R1d,R3b,Arj), (Zb,Re,R1d,R3b,Ark), (Zb,Re,R1d,R3b,Arl), (Zb,Re,R1d,R3b,Arm), (Zb,Re,R1d,R3b,Arn), (Zb,Re,R1d,R3b,Aro), (Zb,Re,R1d,R3b,Arp), (Zb,Re,R1d,R3c,Ara), (Zb,Re,R1d,R3c,Arb), (Zb,Re,R1d,R3c,Arc), (Zb,Re,R1d,R3c,Ard), (Zb,Re,R1d,R3c,Are), (Zb,Re,R1d,R3c,Arf), (Zb,Re,R1d,R3c,Arg), (Zb,Re,R1d,R3c,Arh), (Zb,Re,R1d,R3c,Ari), (Zb,Re,R1d,R3c,Arj), (Zb,Re,R1d,R3c,Ark), (Zb,Re,R1d,R3c,Arl), (Zb,Re,R1d,R3c,Arm), (Zb,Re,R1d,R3c,Arn), (Zb,Re,R1d,R3c,Aro), (Zb,Re,R1d,R3c,Arp), (Zb,Re,R1d,R3d,Ara), (Zb,Re,R1d,R3d,Arb), (Zb,Re,R1d,R3d,Arc), (Zb,Re,R1d,R3d,Ard), (Zb,Re,R1d,R3d,Are), (Zb,Re,R1d,R3d,Arf), (Zb,Re,R1d,R3d,Arg), (Zb,Re,R1d,R3d,Arh), (Zb,Re,R1d,R3d,Ari), (Zb,Re,R1d,R3d,Arj), (Zb,Re,R1d,R3d,Ark), (Zb,Re,R1d,R3d,Arl), (Zb,Re,R1d,R3d,Arm), (Zb,Re,R1d,R3d,Arn), (Zb,Re,R1d,R3d,Aro), (Zb,Re,R1d,R3d,Arp), (Zb,Re,R1d,R3e,Ara), (Zb,Re,R1d,R3e,Arb), (Zb,Re,R1d,R3e,Arc), (Zb,Re,R1d,R3e,Ard), (Zb,Re,R1d,R3e,Are), (Zb,Re,R1d,R3e,Arf), (Zb,Re,R1d,R3e,Arg), (Zb,Re,R1d,R3e,Arh), (Zb,Re,R1d,R3e,Ari), (Zb,Re,R1d,R3e,Arj), (Zb,Re,R1d,R3e,Ark), (Zb,Re,R1d,R3e,Arl), (Zb,Re,R1d,R3e,Arm), (Zb,Re,R1d,R3e,Arn), (Zb,Re,R1d,R3e,Aro), (Zb,Re,R1d,R3e,Arp), (Zb,Re,R1d,R3f,Ara), (Zb,Re,R1d,R3f,Arb), (Zb,Re,R1d,R3f,Arc), (Zb,Re,R1d,R3f,Ard), (Zb,Re,R1d,R3f,Are), (Zb,Re,R1d,R3f,Arf), (Zb,Re,R1d,R3f,Arg), (Zb,Re,R1d,R3f,Arh), (Zb,Re,R1d,R3f,Ari), (Zb,Re,R1d,R3f,Arj), (Zb,Re,R1d,R3f,Ark), (Zb,Re,R1d,R3f,Arl), (Zb,Re,R1d,R3f,Arm), (Zb,Re,R1d,R3f,Arn), (Zb,Re, R1d,R3f,Aro), (Zb,Re,R1d,R3f,Arp), (Zb,Re,R1d,R3g,Ara), (Zb,Re,R1d,R3g,Arb), (Zb,Re,R1d,R3g,Arc), (Zb,Re,R1d, R3g,Ard), (Zb,Re,R1d,R3g,Are), (Zb,Re,R1d,R3g,Arf), (Zb,Re,R1d,R3g,Arg), (Zb,Re,R1d,R3g,Arh), (Zb,Re,R1d, R3g,Ari), (Zb,Re,R1d,R3g,Arj), (Zb,Re,R1d,R3g,Ark), (Zb, Re,R1d,R3g,Arl), (Zb,Re,R1d,R3g,Arm), (Zb,Re,R1d,R3g, Arn), (Zb,Re,R1d,R3g,Aro), (Zb,Re,R1d,R3g,Arp), (Zb,Re, R1d,R3h,Ara), (Zb,Re,R1d,R3h,Arb), (Zb,Re,R1d,R3h, Arc), (Zb,Re,R1d,R3h,Ard), (Zb,Re,R1d,R3h,Are), (Zb,Re, R1d,R3h,Arf), (Zb,Re,R1d,R3h,Arg), (Zb,Re,R1d,R3h, Arh), (Zb,Re,R1d,R3h,Ari), (Zb,Re,R1d,R3h,Arj), (Zb,Re, R1d,R3h,Ark), (Zb,Re,R1d,R3h,Arl), (Zb,Re,R1d,R3h, Arm), (Zb,Re,R1d,R3h,Arn), (Zb,Re,R1d,R3h,Aro), (Zb,Re, R1d,R3h,Arp), (Zb,Rf,R1a,R3a,Ara), (Zb,Rf,R1a,R3a,Arb), (Zb,Rf,R1a,R3a,Arc), (Zb,Rf,R1a,R3a,Ard), (Zb,Rf,R1a, R3a,Are), (Zb,Rf,R1a,R3a,Arf), (Zb,Rf,R1a,R3a,Arg), (Zb, Rf,R1a,R3a,Arh), (Zb,Rf,R1a,R3a,Ari), (Zb,Rf,R1a,R3a, Arj), (Zb,Rf,R1a,R3a,Ark), (Zb,Rf,R1a,R3a,Arl), (Zb,Rf, R1a,R3a,Arm), (Zb,Rf,R1a,R3a,Arn), (Zb,Rf,R1a,R3a, Aro), (Zb,Rf,R1a,R3a,Arp), (Zb,Rf,R1a,R3b,Ara), (Zb,Rf, R1a,R3b,Arb), (Zb,Rf,R1a,R3b,Arc), (Zb,Rf,R1a,R3b,Ard), (Zb,Rf,R1a,R3b,Are), (Zb,Rf,R1a,R3b,Arf), (Zb,Rf,R1a, R3b,Arg), (Zb,Rf,R1a,R3b,Arh), (Zb,Rf,R1a,R3b,Ari), (Zb, Rf,R1a,R3b,Arj), (Zb,Rf,R1a,R3b,Ark), (Zb,Rf,R1a,R3b, Arl), (Zb,Rf,R1a,R3b,Arm), (Zb,Rf,R1a,R3b,Arn), (Zb,Rf, R1a,R3b,Aro), (Zb,Rf,R1a,R3b,Arp), (Zb,Rf,R1a,R3c,Ara), (Zb,Rf,R1a,R3c,Arb), (Zb,Rf,R1a,R3c,Arc), (Zb,Rf,R1a, R3c,Ard), (Zb,Rf,R1a,R3c,Are), (Zb,Rf,R1a,R3c,Arf), (Zb, Rf,R1a,R3c,Arg), (Zb,Rf,R1a,R3c,Arh), (Zb,Rf,R1a,R3c, Ari), (Zb,Rf,R1a,R3c,Arj), (Zb,Rf,R1a,R3c,Ark), (Zb,Rf, R1a,R3c,Arl), (Zb,Rf,R1a,R3c,Arm), (Zb,Rf,R1a,R3c,Arn), (Zb,Rf,R1a,R3c,Aro), (Zb,Rf,R1a,R3c,Arp), (Zb,Rf,R1a, R3d,Ara), (Zb,Rf,R1a,R3d,Arb), (Zb,Rf,R1a,R3d,Arc), (Zb, Rf,R1a,R3d,Ard), (Zb,Rf,R1a,R3d,Are), (Zb,Rf,R1a,R3d, Arf), (Zb,Rf,R1a,R3d,Arg), (Zb,Rf,R1a,R3d,Arh), (Zb,Rf, R1a,R3d,Ari), (Zb,Rf,R1a,R3d,Arj), (Zb,Rf,R1a,R3d,Ark), (Zb,Rf,R1a,R3d,Arl), (Zb,Rf,R1a,R3d,Arm), (Zb,Rf,R1a, R3d,Arn), (Zb,Rf,R1a,R3d,Aro), (Zb,Rf,R1a,R3d,Arp), (Zb, Rf,R1a,R3e,Ara), (Zb,Rf,R1a,R3e,Arb), (Zb,Rf,R1a,R3e, Arc), (Zb,Rf,R1a,R3e,Ard), (Zb,Rf,R1a,R3e,Are), (Zb,Rf, R1a,R3e,Arf), (Zb,Rf,R1a,R3e,Arg), (Zb,Rf,R1a,R3e,Arh), (Zb,Rf,R1a,R3e,Ari), (Zb,Rf,R1a,R3e,Arj), (Zb,Rf,R1a, R3e,Ark), (Zb,Rf,R1a,R3e,Arl), (Zb,Rf,R1a,R3e,Arm), (Zb, Rf,R1a,R3e,Arn), (Zb,Rf,R1a,R3e,Aro), (Zb,Rf,R1a,R3e, Arp), (Zb,Rf,R1a,R3f,Ara), (Zb,Rf,R1a,R3f,Arb), (Zb,Rf, R1a,R3f,Arc), (Zb,Rf,R1a,R3f,Ard), (Zb,Rf,R1a,R3f,Are), (Zb,Rf,R1a,R3f,Arf), (Zb,Rf,R1a,R3f,Arg), (Zb,Rf,R1a, R3f,Arh), (Zb,Rf,R1a,R3f,Ari), (Zb,Rf,R1a,R3f,Arj), (Zb, Rf,R1a,R3f,Ark), (Zb,Rf,R1a,R3f,Arl), (Zb,Rf,R1a,R3f, Arm), (Zb,Rf,R1a,R3f,Arn), (Zb,Rf,R1a,R3f,Aro), (Zb,Rf, R1a,R3f,Arp), (Zb,Rf,R1a,R3g,Ara), (Zb,Rf,R1a,R3g,Arb), (Zb,Rf,R1a,R3g,Arc), (Zb,Rf,R1a,R3g,Ard), (Zb,Rf,R1a, R3g,Are), (Zb,Rf,R1a,R3g,Arf), (Zb,Rf,R1a,R3g,Arg), (Zb, Rf,R1a,R3g,Arh), (Zb,Rf,R1a,R3g,Ari), (Zb,Rf,R1a,R3g, Arj), (Zb,Rf,R1a,R3g,Ark), (Zb,Rf,R1a,R3g,Arl), (Zb,Rf, R1a,R3g,Arm), (Zb,Rf,R1a,R3g,Arn), (Zb,Rf,R1a,R3g, Aro), (Zb,Rf,R1a,R3g,Arp), (Zb,Rf,R1a,R3h,Ara), (Zb,Rf, R1a,R3h,Arb), (Zb,Rf,R1a,R3h,Arc), (Zb,Rf,R1a,R3h,Ard), (Zb,Rf,R1a,R3h,Are), (Zb,Rf,R1a,R3h,Arf), (Zb,Rf,R1a, R3h,Arg), (Zb,Rf,R1a,R3h,Arh), (Zb,Rf,R1a,R3h,Ari), (Zb, Rf,R1a,R3h,Arj), (Zb,Rf,R1a,R3h,Ark), (Zb,Rf,R1a,R3h, Arl), (Zb,Rf,R1a,R3h,Arm), (Zb,Rf,R1a,R3h,Arn), (Zb,Rf, R1a,R3h,Aro), (Zb,Rf,R1a,R3h,Arp), (Zb,Rf,R1b,R3a,Ara), (Zb,Rf,R1b,R3a,Arb), (Zb,Rf,R1b,R3a,Arc), (Zb,Rf,R1b, R3a,Ard), (Zb,Rf,R1b,R3a,Are), (Zb,Rf,R1b,R3a,Arf), (Zb, Rf,R1b,R3a,Arg), (Zb,Rf,R1b,R3a,Arh), (Zb,Rf,R1b,R3a, Ari), (Zb,Rf,R1b,R3a,Arj), (Zb,Rf,R1b,R3a,Ark), (Zb,Rf, R1b,R3a,Arl), (Zb,Rf,R1b,R3a,Arm), (Zb,Rf,R1b,R3a,Arn), (Zb,Rf,R1b,R3a,Aro), (Zb,Rf,R1b,R3a,Arp), (Zb,Rf,R1b, R3b,Ara), (Zb,Rf,R1b,R3b,Arb), (Zb,Rf,R1b,R3b,Arc), (Zb, Rf,R1b,R3b,Ard), (Zb,Rf,R1b,R3b,Are), (Zb,Rf,R1b,R3b, Arf), (Zb,Rf,R1b,R3b,Arg), (Zb,Rf,R1b,R3b,Arh), (Zb,Rf, R1b,R3b,Ari), (Zb,Rf,R1b,R3b,Arj), (Zb,Rf,R1b,R3b,Ark), (Zb,Rf,R1b,R3b,Arl), (Zb,Rf,R1b,R3b,Arm), (Zb,Rf,R1b, R3b,Arn), (Zb,Rf,R1b,R3b,Aro), (Zb,Rf,R1b,R3b,Arp), (Zb,Rf,R1b,R3c,Ara), (Zb,Rf,R1b,R3c,Arb), (Zb,Rf,R1b, R3c,Arc), (Zb,Rf,R1b,R3c,Ard), (Zb,Rf,R1b,R3c,Are), (Zb, Rf,R1b,R3c,Arf), (Zb,Rf,R1b,R3c,Arg), (Zb,Rf,R1b,R3c, Arh), (Zb,Rf,R1b,R3c,Ari), (Zb,Rf,R1b,R3c,Arj), (Zb,Rf, R1b,R3c,Ark), (Zb,Rf,R1b,R3c,Arl), (Zb,Rf,R1b,R3c,Arm), (Zb,Rf,R1b,R3c,Arn), (Zb,Rf,R1b,R3c,Aro), (Zb,Rf,R1b, R3c,Arp), (Zb,Rf,R1b,R3d,Ara), (Zb,Rf,R1b,R3d,Arb), (Zb, Rf,R1b,R3d,Arc), (Zb,Rf,R1b,R3d,Ard), (Zb,Rf,R1b,R3d, Are), (Zb,Rf,R1b,R3d,Arf), (Zb,Rf,R1b,R3d,Arg), (Zb,Rf, R1b,R3d,Arh), (Zb,Rf,R1b,R3d,Ari), (Zb,Rf,R1b,R3d,Arj), (Zb,Rf,R1b,R3d,Ark), (Zb,Rf,R1b,R3d,Arl), (Zb,Rf,R1b, R3d,Arm), (Zb,Rf,R1b,R3d,Arn), (Zb,Rf,R1b,R3d,Aro), (Zb,Rf,R1b,R3d,Arp), (Zb,Rf,R1b,R3e,Ara), (Zb,Rf,R1b, R3e,Arb), (Zb,Rf,R1b,R3e,Arc), (Zb,Rf,R1b,R3e,Ard), (Zb, Rf,R1b,R3e,Are), (Zb,Rf,R1b,R3e,Arf), (Zb,Rf,R1b,R3e, Arg), (Zb,Rf,R1b,R3e,Arh), (Zb,Rf,R1b,R3e,Ari), (Zb,Rf, R1b,R3e,Arj), (Zb,Rf,R1b,R3e,Ark), (Zb,Rf,R1b,R3e,Arl), (Zb,Rf,R1b,R3e,Arm), (Zb,Rf,R1b,R3e,Arn), (Zb,Rf,R1b, R3e,Aro), (Zb,Rf,R1b,R3e,Arp), (Zb,Rf,R1b,R3f,Ara), (Zb, Rf,R1b,R3f,Arb), (Zb,Rf,R1b,R3f,Arc), (Zb,Rf,R1b,R3f, Ard), (Zb,Rf,R1b,R3f,Are), (Zb,Rf,R1b,R3f,Arf), (Zb,Rf, R1b,R3f,Arg), (Zb,Rf,R1b,R3f,Arh), (Zb,Rf,R1b,R3f,Ari), (Zb,Rf,R1b,R3f,Arj), (Zb,Rf,R1b,R3f,Ark), (Zb,Rf,R1b, R3f,Arl), (Zb,Rf,R1b,R3f,Arm), (Zb,Rf,R1b,R3f,Arn), (Zb, Rf,R1b,R3f,Aro), (Zb,Rf,R1b,R3f,Arp), (Zb,Rf,R1b,R3g, Ara), (Zb,Rf,R1b,R3g,Arb), (Zb,Rf,R1b,R3g,Arc), (Zb,Rf, R1b,R3g,Ard), (Zb,Rf,R1b,R3g,Are), (Zb,Rf,R1b,R3g,Arf), (Zb,Rf,R1b,R3g,Arg), (Zb,Rf,R1b,R3g,Arh), (Zb,Rf,R1b, R3g,Ari), (Zb,Rf,R1b,R3g,Arj), (Zb,Rf,R1b,R3g,Ark), (Zb, Rf,R1b,R3g,Arl), (Zb,Rf,R1b,R3g,Arm), (Zb,Rf,R1b,R3g, Arn), (Zb,Rf,R1b,R3g,Aro), (Zb,Rf,R1b,R3g,Arp), (Zb,Rf, R1b,R3h,Ara), (Zb,Rf,R1b,R3h,Arb), (Zb,Rf,R1b,R3h,Arc), (Zb,Rf,R1b,R3h,Ard), (Zb,Rf,R1b,R3h,Are), (Zb,Rf,R1b, R3h,Arf), (Zb,Rf,R1b,R3h,Arg), (Zb,Rf,R1b,R3h,Arh), (Zb, Rf,R1b,R3h,Ari), (Zb,Rf,R1b,R3h,Arj), (Zb,Rf,R1b,R3h, Ark), (Zb,Rf,R1b,R3h,Arl), (Zb,Rf,R1b,R3h,Arm), (Zb,Rf, R1b,R3h,Arn), (Zb,Rf,R1b,R3h,Aro), (Zb,Rf,R1b,R3h, Arp), (Zb,Rf,R1c,R3a,Ara), (Zb,Rf,R1c,R3a,Arb), (Zb,Rf, R1c,R3a,Arc), (Zb,Rf,R1c,R3a,Ard), (Zb,Rf,R1c,R3a,Are), (Zb,Rf,R1c,R3a,Arf), (Zb,Rf,R1c,R3a,Arg), (Zb,Rf,R1c, R3a,Arh), (Zb,Rf,R1c,R3a,Ari), (Zb,Rf,R1c,R3a,Arj), (Zb, Rf,R1c,R3a,Ark), (Zb,Rf,R1c,R3a,Arl), (Zb,Rf,R1c,R3a, Arm), (Zb,Rf,R1c,R3a,Arn), (Zb,Rf,R1c,R3a,Aro), (Zb,Rf, R1c,R3a,Arp), (Zb,Rf,R1c,R3b,Ara), (Zb,Rf,R1c,R3b,Arb), (Zb,Rf,R1c,R3b,Arc), (Zb,Rf,R1c,R3b,Ard), (Zb,Rf,R1c, R3b,Are), (Zb,Rf,R1c,R3b,Arf), (Zb,Rf,R1c,R3b,Arg), (Zb, Rf,R1c,R3b,Arh), (Zb,Rf,R1c,R3b,Ari), (Zb,Rf,R1c,R3b, Arj), (Zb,Rf,R1c,R3b,Ark), (Zb,Rf,R1c,R3b,Arl), (Zb,Rf, R1c,R3b,Arm), (Zb,Rf,R1c,R3b,Arn), (Zb,Rf,R1c,R3b, Aro), (Zb,Rf,R1c,R3b,Arp), (Zb,Rf,R1c,R3c,Ara), (Zb,Rf, R1c,R3c,Arb), (Zb,Rf,R1c,R3c,Arc), (Zb,Rf,R1c,R3c,Ard), (Zb,Rf,R1c,R3c,Are), (Zb,Rf,R1c,R3c,Arf), (Zb,Rf,R1c, R3c,Arg), (Zb,Rf,R1c,R3c,Arh), (Zb,Rf,R1c,R3c,Ari), (Zb, Rf,R1c,R3c,Arj), (Zb,Rf,R1c,R3c,Ark), (Zb,Rf,R1c,R3c, Arl), (Zb,Rf,R1c,R3c,Arm), (Zb,Rf,R1c,R3c,Arn), (Zb,Rf, R1c,R3c,Aro), (Zb,Rf,R1c,R3c,Arp), (Zb,Rf,R1c,R3d,Ara), (Zb,Rf,R1c,R3d,Arb), (Zb,Rf,R1c,R3d,Arc), (Zb,Rf,R1c, R3d,Ard), (Zb,Rf,R1c,R3d,Are), (Zb,Rf,R1c,R3d,Arf), (Zb, Rf,R1c,R3d,Arg), (Zb,Rf,R1c,R3d,Arh), (Zb,Rf,R1c,R3d, Ari), (Zb,Rf,R1c,R3d,Arj), (Zb,Rf,R1c,R3d,Ark), (Zb,Rf,R1c,R3d,Arl), (Zb,Rf,R1c,R3d,Arm), (Zb,Rf,R1c,R3d,Arn), (Zb,Rf,R1c,R3d,Aro), (Zb,Rf,R1c,R3d,Arp), (Zb,Rf,R1c,R3e,Ara), (Zb,Rf,R1c,R3e,Arb), (Zb,Rf,R1c,R3e,Arc), (Zb,Rf,R1c,R3e,Ard), (Zb,Rf,R1c,R3e,Are), (Zb,Rf,R1c,R3e,Arf), (Zb,Rf,R1c,R3e,Arg), (Zb,Rf,R1c,R3e,Arh), (Zb,Rf,R1c,R3e,Ari), (Zb,Rf,R1c,R3e,Arj), (Zb,Rf,R1c,R3e,Ark), (Zb,Rf,R1c,R3e,Arl), (Zb,Rf,R1c,R3e,Arm), (Zb,Rf,R1c,R3e,Arn), (Zb,Rf,R1c,R3e,Aro), (Zb,Rf,R1c,R3e,Arp), (Zb,Rf,R1c,R3f,Ara), (Zb,Rf,R1c,R3f,Arb), (Zb,Rf,R1c,R3f,Arc), (Zb,Rf,R1c,R3f,Ard), (Zb,Rf,R1c,R3f,Are), (Zb,Rf,R1c,R3f,Arf), (Zb,Rf,R1c,R3f,Arg), (Zb,Rf,R1c,R3f,Arh), (Zb,Rf,R1c,R3f,Ari), (Zb,Rf,R1c,R3f,Arj), (Zb,Rf,R1c,R3f,Ark), (Zb,Rf,R1c,R3f,Arl), (Zb,Rf,R1c,R3f,Arm), (Zb,Rf,R1c,R3f,Arn), (Zb,Rf,R1c,R3f,Aro), (Zb,Rf,R1c,R3f,Arp), (Zb,Rf,R1c,R3g,Ara), (Zb,Rf,R1c,R3g,Arb), (Zb,Rf,R1c,R3g,Arc), (Zb,Rf,R1c,R3g,Ard), (Zb,Rf,R1c,R3g,Are), (Zb,Rf,R1c,R3g,Arf), (Zb,Rf,R1c,R3g,Arg), (Zb,Rf,R1c,R3g,Arh), (Zb,Rf,R1c,R3g,Ari), (Zb,Rf,R1c,R3g,Arj), (Zb,Rf,R1c,R3g,Ark), (Zb,Rf,R1c,R3g,Arl), (Zb,Rf,R1c,R3g,Arm), (Zb,Rf,R1c,R3g,Arn), (Zb,Rf,R1c,R3g,Aro), (Zb,Rf,R1c,R3g,Arp), (Zb,Rf,R1c,R3h,Ara), (Zb,Rf,R1c,R3h,Arb), (Zb,Rf,R1c,R3h,Arc), (Zb,Rf,R1c,R3h,Ard), (Zb,Rf,R1c,R3h,Are), (Zb,Rf,R1c,R3h,Arf), (Zb,Rf,R1c,R3h,Arg), (Zb,Rf,R1c,R3h,Arh), (Zb,Rf,R1c,R3h,Ari), (Zb,Rf,R1c,R3h,Arj), (Zb,Rf,R1c,R3h,Ark), (Zb,Rf,R1c,R3h,Arl), (Zb,Rf,R1c,R3h,Arm), (Zb,Rf,R1c,R3h,Arn), (Zb,Rf,R1c,R3h,Aro), (Zb,Rf,R1c,R3h,Arp), (Zb,Rf,R1d,R3a,Ara), (Zb,Rf,R1d,R3a,Arb), (Zb,Rf,R1d,R3a,Arc), (Zb,Rf,R1d,R3a,Ard), (Zb,Rf,R1d,R3a,Are), (Zb,Rf,R1d,R3a,Arf), (Zb,Rf,R1d,R3a,Arg), (Zb,Rf,R1d,R3a,Arh), (Zb,Rf,R1d,R3a,Ari), (Zb,Rf,R1d,R3a,Arj), (Zb,Rf,R1d,R3a,Ark), (Zb,Rf,R1d,R3a,Arl), (Zb,Rf,R1d,R3a,Arm), (Zb,Rf,R1d,R3a,Arn), (Zb,Rf,R1d,R3a,Aro), (Zb,Rf,R1d,R3a,Arp), (Zb,Rf,R1d,R3b,Ara), (Zb,Rf,R1d,R3b,Arb), (Zb,Rf,R1d,R3b,Arc), (Zb,Rf,R1d,R3b,Ard), (Zb,Rf,R1d,R3b,Are), (Zb,Rf,R1d,R3b,Arf), (Zb,Rf,R1d,R3b,Arg), (Zb,Rf,R1d,R3b,Arh), (Zb,Rf,R1d,R3b,Ari), (Zb,Rf,R1d,R3b,Arj), (Zb,Rf,R1d,R3b,Ark), (Zb,Rf,R1d,R3b,Arl), (Zb,Rf,R1d,R3b,Arm), (Zb,Rf,R1d,R3b,Arn), (Zb,Rf,R1d,R3b,Aro), (Zb,Rf,R1d,R3b,Arp), (Zb,Rf,R1d,R3c,Ara), (Zb,Rf,R1d,R3c,Arb), (Zb,Rf,R1d,R3c,Arc), (Zb,Rf,R1d,R3c,Ard), (Zb,Rf,R1d,R3c,Are), (Zb,Rf,R1d,R3c,Arf), (Zb,Rf,R1d,R3c,Arg), (Zb,Rf,R1d,R3c,Arh), (Zb,Rf,R1d,R3c,Ari), (Zb,Rf,R1d,R3c,Arj), (Zb,Rf,R1d,R3c,Ark), (Zb,Rf,R1d,R3c,Arl), (Zb,Rf,R1d,R3c,Arm), (Zb,Rf,R1d,R3c,Arn), (Zb,Rf,R1d,R3c,Aro), (Zb,Rf,R1d,R3c,Arp), (Zb,Rf,R1d,R3d,Ara), (Zb,Rf,R1d,R3d,Arb), (Zb,Rf,R1d,R3d,Arc), (Zb,Rf,R1d,R3d,Ard), (Zb,Rf,R1d,R3d,Are), (Zb,Rf,R1d,R3d,Arf), (Zb,Rf,R1d,R3d,Arg), (Zb,Rf,R1d,R3d,Arh), (Zb,Rf,R1d,R3d,Ari), (Zb,Rf,R1d,R3d,Arj), (Zb,Rf,R1d,R3d,Ark), (Zb,Rf,R1d,R3d,Arl), (Zb,Rf,R1d,R3d,Arm), (Zb,Rf,R1d,R3d,Arn), (Zb,Rf,R1d,R3d,Aro), (Zb,Rf,R1d,R3d,Arp), (Zb,Rf,R1d,R3e,Ara), (Zb,Rf,R1d,R3e,Arb), (Zb,Rf,R1d,R3e,Arc), (Zb,Rf,R1d,R3e,Ard), (Zb,Rf,R1d,R3e,Are), (Zb,Rf,R1d,R3e,Arf), (Zb,Rf,R1d,R3e,Arg), (Zb,Rf,R1d,R3e,Arh), (Zb,Rf,R1d,R3e,Ari), (Zb,Rf,R1d,R3e,Arj), (Zb,Rf,R1d,R3e,Ark), (Zb,Rf,R1d,R3e,Arl), (Zb,Rf,R1d,R3e,Arm), (Zb,Rf,R1d,R3e,Arn), (Zb,Rf,R1d,R3e,Aro), (Zb,Rf,R1d,R3e,Arp), (Zb,Rf,R1d,R3f,Ara), (Zb,Rf,R1d,R3f,Arb), (Zb,Rf,R1d,R3f,Arc), (Zb,Rf,R1d,R3f,Ard), (Zb,Rf,R1d,R3f,Are), (Zb,Rf,R1d,R3f,Arf), (Zb,Rf,R1d,R3f,Arg), (Zb,Rf,R1d,R3f,Arh), (Zb,Rf,R1d,R3f,Ari), (Zb,Rf,R1d,R3f,Arj), (Zb,Rf,R1d,R3f,Ark), (Zb,Rf,R1d,R3f,Arl), (Zb,Rf,R1d,R3f,Arm), (Zb,Rf,R1d,R3f,Arn), (Zb,Rf,R1d,R3f,Aro), (Zb,Rf,R1d,R3f,Arp), (Zb,Rf,R1d,R3g,Ara), (Zb,Rf,R1d,R3g,Arb), (Zb,Rf,R1d,R3g,Arc), (Zb,Rf,R1d,R3g,Ard), (Zb,Rf,R1d,R3g,Are), (Zb,Rf,R1d,R3g,Arf), (Zb,Rf,R1d,R3g,Arg), (Zb,Rf,R1d,R3g,Arh), (Zb,Rf,R1d,R3g,Ari), (Zb,Rf,R1d,R3g,Arj), (Zb,Rf,R1d,R3g,Ark), (Zb,Rf,R1d,R3g,Arl), (Zb,Rf,R1d,R3g,Arm), (Zb,Rf,R1d,R3g,Arn), (Zb,Rf,R1d,R3g,Aro), (Zb,Rf,R1d,R3g,Arp), (Zb,Rf,R1d,R3h,Ara), (Zb,Rf,R1d,R3h,Arb), (Zb,Rf,R1d,R3h,Arc), (Zb,Rf,R1d,R3h,Ard), (Zb,Rf,R1d,R3h,Are), (Zb,Rf,R1d,R3h,Arf), (Zb,Rf,R1d,R3h,Arg), (Zb,Rf,R1d,R3h,Arh), (Zb,Rf,R1d,R3h,Ari), (Zb,Rf,R1d,R3h,Arj), (Zb,Rf,R1d,R3h,Ark), (Zb,Rf,R1d,R3h,Arl), (Zb,Rf,R1d,R3h,Arm), (Zb,Rf,R1d,R3h,Arn), (Zb,Rf,R1d,R3h,Aro), (Zb,Rf,R1d,R3h,Arp), (Zb,Rg,R1a,R3a,Ara), (Zb,Rg,R1a,R3a,Arb), (Zb,Rg,R1a,R3a,Arc), (Zb,Rg,R1a,R3a,Ard), (Zb,Rg,R1a,R3a,Are), (Zb,Rg,R1a,R3a,Arf), (Zb,Rg,R1a,R3a,Arg), (Zb,Rg,R1a,R3a,Arh), (Zb,Rg,R1a,R3a,Ari), (Zb,Rg,R1a,R3a,Arj), (Zb,Rg,R1a,R3a,Ark), (Zb,Rg,R1a,R3a,Arl), (Zb,Rg,R1a,R3a,Arm), (Zb,Rg,R1a,R3a,Arn), (Zb,Rg,R1a,R3a,Aro), (Zb,Rg,R1a,R3a,Arp), (Zb,Rg,R1a,R3b,Ara), (Zb,Rg,R1a,R3b,Arb), (Zb,Rg,R1a,R3b,Arc), (Zb,Rg,R1a,R3b,Ard), (Zb,Rg,R1a,R3b,Are), (Zb,Rg,R1a,R3b,Arf), (Zb,Rg,R1a,R3b,Arg), (Zb,Rg,R1a,R3b,Arh), (Zb,Rg,R1a,R3b,Ari), (Zb,Rg,R1a,R3b,Arj), (Zb,Rg,R1a,R3b,Ark), (Zb,Rg,R1a,R3b,Arl), (Zb,Rg,R1a,R3b,Arm), (Zb,Rg,R1a,R3b,Arn), (Zb,Rg,R1a,R3b,Aro), (Zb,Rg,R1a,R3b,Arp), (Zb,Rg,R1a,R3c,Ara), (Zb,Rg,R1a,R3c,Arb), (Zb,Rg,R1a,R3c,Arc), (Zb,Rg,R1a,R3c,Ard), (Zb,Rg,R1a,R3c,Are), (Zb,Rg,R1a,R3c,Arf), (Zb,Rg,R1a,R3c,Arg), (Zb,Rg,R1a,R3c,Arh), (Zb,Rg,R1a,R3c,Ari), (Zb,Rg,R1a,R3c,Arj), (Zb,Rg,R1a,R3c,Ark), (Zb,Rg,R1a,R3c,Arl), (Zb,Rg,R1a,R3c,Arm), (Zb,Rg,R1a,R3c,Arn), (Zb,Rg,R1a,R3c,Aro), (Zb,Rg,R1a,R3c,Arp), (Zb,Rg,R1a,R3d,Ara), (Zb,Rg,R1a,R3d,Arb), (Zb,Rg,R1a,R3d,Arc), (Zb,Rg,R1a,R3d,Ard), (Zb,Rg,R1a,R3d,Are), (Zb,Rg,R1a,R3d,Arf), (Zb,Rg,R1a,R3d,Arg), (Zb,Rg,R1a,R3d,Arh), (Zb,Rg,R1a,R3d,Ari), (Zb,Rg,R1a,R3d,Arj), (Zb,Rg,R1a,R3d,Ark), (Zb,Rg,R1a,R3d,Arl), (Zb,Rg,R1a,R3d,Arm), (Zb,Rg,R1a,R3d,Arn), (Zb,Rg,R1a,R3d,Aro), (Zb,Rg,R1a,R3d,Arp), (Zb,Rg,R1a,R3e,Ara), (Zb,Rg,R1a,R3e,Arb), (Zb,Rg,R1a,R3e,Arc), (Zb,Rg,R1a,R3e,Ard), (Zb,Rg,R1a,R3e,Are), (Zb,Rg,R1a,R3e,Arf), (Zb,Rg,R1a,R3e,Arg), (Zb,Rg,R1a,R3e,Arh), (Zb,Rg,R1a,R3e,Ari), (Zb,Rg,R1a,R3e,Arj), (Zb,Rg,R1a,R3e,Ark), (Zb,Rg,R1a,R3e,Arl), (Zb,Rg,R1a,R3e,Arm), (Zb,Rg,R1a,R3e,Arn), (Zb,Rg,R1a,R3e,Aro), (Zb,Rg,R1a,R3e,Arp), (Zb,Rg,R1a,R3f,Ara), (Zb,Rg,R1a,R3f,Arb), (Zb,Rg,R1a,R3f,Arc), (Zb,Rg,R1a,R3f,Ard), (Zb,Rg,R1a,R3f,Are), (Zb,Rg,R1a,R3f,Arf), (Zb,Rg,R1a,R3f,Arg), (Zb,Rg,R1a,R3f,Arh), (Zb,Rg,R1a,R3f,Ari), (Zb,Rg,R1a,R3f,Arj), (Zb,Rg,R1a,R3f,Ark), (Zb,Rg,R1a,R3f,Arl), (Zb,Rg,R1a,R3f,Arm), (Zb,Rg,R1a,R3f,Arn), (Zb,Rg,R1a,R3f,Aro), (Zb,Rg,R1a,R3f,Arp), (Zb,Rg,R1a,R3g,Ara), (Zb,Rg,R1a,R3g,Arb), (Zb,Rg,R1a,R3g,Arc), (Zb,Rg,R1a,R3g,Ard), (Zb,Rg,R1a,R3g,Are), (Zb,Rg,R1a,R3g,Arf), (Zb,Rg,R1a,R3g,Arg), (Zb,Rg,R1a,R3g,Arh), (Zb,Rg,R1a,R3g,Ari), (Zb,Rg,R1a,R3g,Arj), (Zb,Rg,R1a,R3g,Ark), (Zb,Rg,R1a,R3g,Arl), (Zb,Rg,R1a,R3g,Arm), (Zb,Rg,R1a,R3g,Arn), (Zb,Rg,R1a,R3g,Aro), (Zb,Rg,R1a,R3g,Arp), (Zb,Rg,R1a,R3h,Ara), (Zb,Rg,R1a,R3h,Arb), (Zb,Rg,R1a,R3h,Arc), (Zb,Rg,R1a,R3h,Ard), (Zb,Rg,R1a,R3h,Are), (Zb,Rg,R1a,R3h,Arf), (Zb,Rg,R1a,R3h,Arg), (Zb,Rg,R1a,R3h,Arh), (Zb,Rg,R1a,R3h,Ari), (Zb,Rg,R1a,R3h,Arj), (Zb,Rg,R1a,R3h,Ark), (Zb,Rg,R1a,R3h,Arl), (Zb,Rg,R1a,R3h,Arm), (Zb,Rg,R1a,R3h,Arn), (Zb,Rg,R1a,R3h,Aro), (Zb,Rg,R1a,R3h,Arp), (Zb,Rg,R1b,R3a,Ara), (Zb,Rg,R1b,R3a,Arb), (Zb,Rg,R1b,R3a,Arc), (Zb,Rg,R1b,R3a,Ard), (Zb,Rg,R1b,R3a,Are), (Zb,Rg,R1b,R3a,Arf), (Zb,Rg,R1b,R3a,Arg), (Zb,Rg,R1b,R3a,Arh), (Zb,Rg,R1b,R3a,Ari), (Zb,Rg,R1b,R3a,Arj), (Zb,Rg,R1b,R3a,Ark), (Zb,Rg,R1b,R3a,Arl), (Zb,Rg,R1b,R3a,Arm), (Zb,Rg,R1b,R3a,Arn), (Zb,Rg,R1b,R3a,Aro), (Zb,Rg,R1b,R3a,Arp), (Zb,Rg,R1b,R3b,Ara), (Zb,Rg,R1b,R3b,Arb), (Zb,Rg,R1b,R3b,Arc), (Zb,Rg,R1b,R3b,Ard), (Zb,Rg,R1b,R3b,Are), (Zb,Rg,R1b,R3b,Arf), (Zb,Rg,R1b,R3b,Arg), (Zb,Rg,R1b,R3b,Arh), (Zb,Rg,R1b,R3b,Ari), (Zb,Rg,R1b,R3b,Arj), (Zb,Rg,R1b,R3b,Ark), (Zb,Rg,R1b,R3b,Arl), (Zb,Rg,R1b,R3b,Arm), (Zb,Rg,R1b,R3b,Arn), (Zb,Rg,R1b,R3b,Aro), (Zb,Rg,R1b,R3b,Arp), (Zb,Rg,R1b,R3c,Ara), (Zb,Rg,R1b,R3c,Arb), (Zb,Rg,R1b,R3c,Arc), (Zb,Rg,R1b,R3c,Ard), (Zb,Rg,R1b,R3c,Are), (Zb,Rg,R1b,R3c,Arf), (Zb,Rg,R1b,R3c,Arg), (Zb,Rg,R1b,R3c,Arh), (Zb,Rg,R1b,R3c,Ari), (Zb,Rg,R1b,R3c,Arj), (Zb,Rg,R1b,R3c,Ark), (Zb,Rg,R1b,R3c,Arl), (Zb,Rg,R1b,R3c,Arm), (Zb,Rg,R1b,R3c,Arn), (Zb,Rg,R1b,R3c,Aro), (Zb,Rg,R1b,R3c,Arp), (Zb,Rg,R1b,R3d,Ara), (Zb,Rg,R1b,R3d,Arb), (Zb,Rg,R1b,R3d,Arc), (Zb,Rg,R1b,R3d,Ard), (Zb,Rg,R1b,R3d,Are), (Zb,Rg,R1b,R3d,Arf), (Zb,Rg,R1b,R3d,Arg), (Zb,Rg,R1b,R3d,Arh), (Zb,Rg,R1b,R3d,Ari), (Zb,Rg,R1b,R3d,Arj), (Zb,Rg,R1b,R3d,Ark), (Zb,Rg,R1b,R3d,Arl), (Zb,Rg,R1b,R3d,Arm), (Zb,Rg,R1b,R3d,Arn), (Zb,Rg,R1b,R3d,Aro), (Zb,Rg,R1b,R3d,Arp), (Zb,Rg,R1b,R3e,Ara), (Zb,Rg,R1b,R3e,Arb), (Zb,Rg,R1b,R3e,Arc), (Zb,Rg,R1b,R3e,Ard), (Zb,Rg,R1b,R3e,Are), (Zb,Rg,R1b,R3e,Arf), (Zb,Rg,R1b,R3e,Arg), (Zb,Rg,R1b,R3e,Arh), (Zb,Rg,R1b,R3e,Ari), (Zb,Rg,R1b,R3e,Arj), (Zb,Rg,R1b,R3e,Ark), (Zb,Rg,R1b,R3e,Arl), (Zb,Rg,R1b,R3e,Arm), (Zb,Rg,R1b,R3e,Arn), (Zb,Rg,R1b,R3e,Aro), (Zb,Rg,R1b,R3e,Arp), (Zb,Rg,R1b,R3f,Ara), (Zb,Rg,R1b,R3f,Arb), (Zb,Rg,R1b,R3f,Arc), (Zb,Rg,R1b,R3f,Ard), (Zb,Rg,R1b,R3f,Are), (Zb,Rg,R1b,R3f,Arf), (Zb,Rg,R1b,R3f,Arg), (Zb,Rg,R1b,R3f,Arh), (Zb,Rg,R1b,R3f,Ari), (Zb,Rg,R1b,R3f,Arj), (Zb,Rg,R1b,R3f,Ark), (Zb,Rg,R1b,R3f,Arl), (Zb,Rg,R1b,R3f,Arm), (Zb,Rg,R1b,R3f,Arn), (Zb,Rg,R1b,R3f,Aro), (Zb,Rg,R1b,R3f,Arp), (Zb,Rg,R1b,R3g,Ara), (Zb,Rg,R1b,R3g,Arb), (Zb,Rg,R1b,R3g,Arc), (Zb,Rg,R1b,R3g,Ard), (Zb,Rg,R1b,R3g,Are), (Zb,Rg,R1b,R3g,Arf), (Zb,Rg,R1b,R3g,Arg), (Zb,Rg,R1b,R3g,Arh), (Zb,Rg,R1b,R3g,Ari), (Zb,Rg,R1b,R3g,Arj), (Zb,Rg,R1b,R3g,Ark), (Zb,Rg,R1b,R3g,Arl), (Zb,Rg,R1b,R3g,Arm), (Zb,Rg,R1b,R3g,Arn), (Zb,Rg,R1b,R3g,Aro), (Zb,Rg,R1b,R3g,Arp), (Zb,Rg,R1b,R3h,Ara), (Zb,Rg,R1b,R3h,Arb), (Zb,Rg,R1b,R3h,Arc), (Zb,Rg,R1b,R3h,Ard), (Zb,Rg,R1b,R3h,Are), (Zb,Rg,R1b,R3h,Arf), (Zb,Rg,R1b,R3h,Arg), (Zb,Rg,R1b,R3h,Arh), (Zb,Rg,R1b,R3h,Ari), (Zb,Rg,R1b,R3h,Arj), (Zb,Rg,R1b,R3h,Ark), (Zb,Rg,R1b,R3h,Arl), (Zb,Rg,R1b,R3h,Arm), (Zb,Rg,R1b,R3h,Arn), (Zb,Rg,R1b,R3h,Aro), (Zb,Rg,R1b,R3h,Arp), (Zb,Rg,R1c,R3a,Ara), (Zb,Rg,R1c,R3a,Arb), (Zb,Rg,R1c,R3a,Arc), (Zb,Rg,R1c,R3a,Ard), (Zb,Rg,R1c,R3a,Are), (Zb,Rg,R1c,R3a,Arf), (Zb,Rg,R1c,R3a,Arg), (Zb,Rg,R1c,R3a,Arh), (Zb,Rg,R1c,R3a,Ari), (Zb,Rg,R1c,R3a,Arj), (Zb,Rg,R1c,R3a,Ark), (Zb,Rg,R1c,R3a,Arl), (Zb,Rg,R1c,R3a,Arm), (Zb,Rg,R1c,R3a,Arn), (Zb,Rg,R1c,R3a,Aro), (Zb,Rg,R1c,R3a,Arp), (Zb,Rg,R1c,R3b,Ara), (Zb,Rg,R1c,R3b,Arb), (Zb,Rg,R1c,R3b,Arc), (Zb,Rg,R1c,R3b,Ard), (Zb,Rg,R1c,R3b,Are), (Zb,Rg,R1c,R3b,Arf), (Zb,Rg,R1c,R3b,Arg), (Zb,Rg,R1c,R3b,Arh), (Zb,Rg,R1c,R3b,Ari), (Zb,Rg,R1c,R3b,Arj), (Zb,Rg,R1c,R3b,Ark), (Zb,Rg,R1c,R3b,Arl), (Zb,Rg,R1c,R3b,Arm), (Zb,Rg,R1c,R3b,Arn), (Zb,Rg,R1c,R3b,Aro), (Zb,Rg,R1c,R3b,Arp), (Zb,Rg,R1c,R3c,Ara), (Zb,Rg,R1c,R3c,Arb), (Zb,Rg,R1c,R3c,Arc), (Zb,Rg,R1c,R3c,Ard), (Zb,Rg,R1c,R3c,Are), (Zb,Rg,R1c,R3c,Arf), (Zb,Rg,R1c,R3c,Arg), (Zb,Rg,R1c,R3c,Arh), (Zb,Rg,R1c,R3c,Ari), (Zb,Rg,R1c,R3c,Arj), (Zb,Rg,R1c,R3c,Ark), (Zb,Rg,R1c,R3c,Arl), (Zb,Rg,R1c,R3c,Arm), (Zb,Rg,R1c,R3c,Arn), (Zb,Rg,R1c,R3c,Aro), (Zb,Rg,R1c,R3c,Arp), (Zb,Rg,R1c,R3d,Ara), (Zb,Rg,R1c,R3d,Arb), (Zb,Rg,R1c,R3d,Arc), (Zb,Rg,R1c,R3d,Ard), (Zb,Rg,R1c,R3d,Are), (Zb,Rg,R1c,R3d,Arf), (Zb,Rg,R1c,R3d,Arg), (Zb,Rg,R1c,R3d,Arh), (Zb,Rg,R1c,R3d,Ari), (Zb,Rg,R1c,R3d,Arj), (Zb,Rg,R1c,R3d,Ark), (Zb,Rg,R1c,R3d,Arl), (Zb,Rg,R1c,R3d,Arm), (Zb,Rg,R1c,R3d,Arn), (Zb,Rg,R1c,R3d,Aro), (Zb,Rg,R1c,R3d,Arp), (Zb,Rg,R1c,R3e,Ara), (Zb,Rg,R1c,R3e,Arb), (Zb,Rg,R1c,R3e,Arc), (Zb,Rg,R1c,R3e,Ard), (Zb,Rg,R1c,R3e,Are), (Zb,Rg,R1c,R3e,Arf), (Zb,Rg,R1c,R3e,Arg), (Zb,Rg,R1c,R3e,Arh), (Zb,Rg,R1c,R3e,Ari), (Zb,Rg,R1c,R3e,Arj), (Zb,Rg,R1c,R3e,Ark), (Zb,Rg,R1c,R3e,Arl), (Zb,Rg,R1c,R3e,Arm), (Zb,Rg,R1c,R3e,Arn), (Zb,Rg,R1c,R3e,Aro), (Zb,Rg,R1c,R3e,Arp), (Zb,Rg,R1c,R3f,Ara), (Zb,Rg,R1c,R3f,Arb), (Zb,Rg,R1c,R3f,Arc), (Zb,Rg,R1c,R3f,Ard), (Zb,Rg,R1c,R3f,Are), (Zb,Rg,R1c,R3f,Arf), (Zb,Rg,R1c,R3f,Arg), (Zb,Rg,R1c,R3f,Arh), (Zb,Rg,R1c,R3f,Ari), (Zb,Rg,R1c,R3f,Arj), (Zb,Rg,R1c,R3f,Ark), (Zb,Rg,R1c,R3f,Arl), (Zb,Rg,R1c,R3f,Arm), (Zb,Rg,R1c,R3f,Arn), (Zb,Rg,R1c,R3f,Aro), (Zb,Rg,R1c,R3f,Arp), (Zb,Rg,R1c,R3g,Ara), (Zb,Rg,R1c,R3g,Arb), (Zb,Rg,R1c,R3g,Arc), (Zb,Rg,R1c,R3g,Ard), (Zb,Rg,R1c,R3g,Are), (Zb,Rg,R1c,R3g,Arf), (Zb,Rg,R1c,R3g,Arg), (Zb,Rg,R1c,R3g,Arh), (Zb,Rg,R1c,R3g,Ari), (Zb,Rg,R1c,R3g,Arj), (Zb,Rg,R1c,R3g,Ark), (Zb,Rg,R1c,R3g,Arl), (Zb,Rg,R1c,R3g,Arm), (Zb,Rg,R1c,R3g,Arn), (Zb,Rg,R1c,R3g,Aro), (Zb,Rg,R1c,R3g,Arp), (Zb,Rg,R1c,R3h,Ara), (Zb,Rg,R1c,R3h,Arb), (Zb,Rg,R1c,R3h,Arc), (Zb,Rg,R1c,R3h,Ard), (Zb,Rg,R1c,R3h,Are), (Zb,Rg,R1c,R3h,Arf), (Zb,Rg,R1c,R3h,Arg), (Zb,Rg,R1c,R3h,Arh), (Zb,Rg,R1c,R3h,Ari), (Zb,Rg,R1c,R3h,Arj), (Zb,Rg,R1c,R3h,Ark), (Zb,Rg,R1c,R3h,Arl), (Zb,Rg,R1c,R3h,Arm), (Zb,Rg,R1c,R3h,Arn), (Zb,Rg,R1c,R3h,Aro), (Zb,Rg,R1c,R3h,Arp), (Zb,Rg,R1d,R3a,Ara), (Zb,Rg,R1d,R3a,Arb), (Zb,Rg,R1d,R3a,Arc), (Zb,Rg,R1d,R3a,Ard), (Zb,Rg,R1d,R3a,Are), (Zb,Rg,R1d,R3a,Arf), (Zb,Rg,R1d,R3a,Arg), (Zb,Rg,R1d,R3a,Arh), (Zb,Rg,R1d,R3a,Ari), (Zb,Rg,R1d,R3a,Arj), (Zb,Rg,R1d,R3a,Ark), (Zb,Rg,R1d,R3a,Arl), (Zb,Rg,R1d,R3a,Arm), (Zb,Rg,R1d,R3a,Arn), (Zb,Rg,R1d,R3a,Aro), (Zb,Rg,R1d,R3a,Arp), (Zb,Rg,R1d,R3b,Ara), (Zb,Rg,R1d,R3b,Arb), (Zb,Rg,R1d,R3b,Arc), (Zb,Rg,R1d,R3b,Ard), (Zb,Rg,R1d,R3b,Are), (Zb,Rg,R1d,R3b,Arf), (Zb,Rg,R1d,R3b,Arg), (Zb,Rg,R1d,R3b,Arh), (Zb,Rg,R1d,R3b,Ari), (Zb,Rg,R1d,R3b,Arj), (Zb,Rg,R1d,R3b,Ark), (Zb,Rg,R1d,R3b,Arl), (Zb,Rg,R1d,R3b,Arm), (Zb,Rg,R1d,R3b,Arn), (Zb,Rg,R1d,R3b,Aro), (Zb,Rg,R1d,R3b,Arp), (Zb,Rg,R1d,R3c,Ara), (Zb,Rg,R1d,R3c,Arb), (Zb,Rg,R1d,R3c,Arc), (Zb,Rg,R1d,R3c,Ard), (Zb,Rg,R1d,R3c,Are), (Zb,Rg,R1d,R3c,Arf), (Zb,Rg,R1d,R3c,Arg), (Zb,Rg,R1d,R3c,Arh), (Zb,Rg,R1d,R3c,Ari), (Zb,Rg,R1d,R3c,Arj), (Zb,Rg,R1d,R3c,Ark), (Zb,Rg,R1d,R3c,Arl), (Zb,Rg,R1d,R3c,Arm), (Zb,Rg,R1d,R3c,Arn), (Zb,Rg,R1d,R3c,Aro), (Zb,Rg,R1d,R3c,Arp), (Zb,Rg,R1d,R3d,Ara), (Zb,Rg,R1d,R3d,Arb), (Zb,Rg,R1d,R3d,Arc), (Zb,Rg,R1d,R3d,Ard), (Zb,Rg,R1d,R3d,Are), (Zb,Rg,R1d,R3d,Arf), (Zb,Rg,R1d,R3d,Arg), (Zb,Rg,R1d,R3d,Arh), (Zb,Rg,R1d,R3d,Ari), (Zb,Rg,R1d,R3d,Arj), (Zb,Rg,R1d,R3d,Ark), (Zb,Rg,R1d,R3d,Arl), (Zb,Rg,R1d,R3d,Arm), (Zb,Rg,R1d,R3d,Arn), (Zb,Rg,R1d,R3d,Aro), (Zb,Rg,R1d,R3d,Arp), (Zb,Rg,R1d,R3e,Ara), (Zb,Rg,R1d,R3e,Arb), (Zb,Rg,R1d,R3e,Arc), (Zb,Rg,R1d,R3e,Ard), (Zb,Rg,R1d,R3e,Are), (Zb,Rg,R1d,R3e,Arf), (Zb,Rg,R1d,R3e,Arg), (Zb,Rg,R1d,R3e,Arh), (Zb,Rg,R1d,R3e,Ari), (Zb,Rg,R1d,R3e,Arj), (Zb,Rg,R1d,R3e,Ark), (Zb,Rg,R1d,R3e,Arl), (Zb,Rg,R1d,R3e,Arm), (Zb,Rg,R1d,R3e,Arn), (Zb,Rg,R1d,R3e,Aro), (Zb,Rg,R1d,R3e,Arp), (Zb,Rg,R1d,R3f,Ara), (Zb,Rg,R1d,R3f,Arb), (Zb,Rg,R1d,R3f,Arc), (Zb,Rg,R1d,R3f,Ard), (Zb,Rg,R1d,R3f,Are), (Zb,Rg,R1d,R3f,Arf), (Zb,Rg,R1d,R3f,Arg), (Zb,Rg,R1d,R3f,Arh), (Zb,Rg,R1d,R3f,Ari), (Zb,Rg,R1d,R3f,Arj), (Zb,Rg,R1d,R3f,Ark), (Zb,Rg,R1d,R3f,Arl), (Zb,Rg,R1d,R3f,Arm), (Zb,Rg,R1d,R3f,Arn), (Zb,Rg,R1d,R3f,Aro), (Zb,Rg,R1d,R3f,Arp), (Zb,Rg,R1d,R3g,Ara), (Zb,Rg,R1d,R3g,Arb), (Zb,Rg,R1d,R3g,Arc), (Zb,Rg,R1d,R3g,Ard), (Zb,Rg,R1d,R3g,Are), (Zb,Rg,R1d, R3g,Arf), (Zb,Rg,R1d,R3g,Arg), (Zb,Rg,R1d,R3g,Arh), (Zb,Rg,R1d,R3g,Ari), (Zb,Rg,R1d,R3g,Arj), (Zb,Rg,R1d, R3g,Ark), (Zb,Rg,R1d,R3g,Arl), (Zb,Rg,R1d,R3g,Arm), (Zb,Rg,R1d,R3g,Arn), (Zb,Rg,R1d,R3g,Aro), (Zb,Rg,R1d, R3g,Arp), (Zb,Rg,R1d,R3h,Ara), (Zb,Rg,R1d,R3h,Arb), (Zb,Rg,R1d,R3h,Arc), (Zb,Rg,R1d,R3h,Ard), (Zb,Rg,R1d, R3h,Are), (Zb,Rg,R1d,R3h,Arf), (Zb,Rg,R1d,R3h,Arg), (Zb,Rg,R1d,R3h,Arh), (Zb,Rg,R1d,R3h,Ari), (Zb,Rg,R1d, R3h,Arj), (Zb,Rg,R1d,R3h,Ark), (Zb,Rg,R1d,R3h,Arl), (Zb, Rg,R1d,R3h,Arm), (Zb,Rg,R1d,R3h,Arn), (Zb,Rg,R1d,R3h, Aro), (Zb,Rg,R1d,R3h,Arp), (Zb,Rh,R1a,R3a,Ara), (Zb,Rh, R1a,R3a,Arb), (Zb,Rh,R1a,R3a,Arc), (Zb,Rh,R1a,R3a, Ard), (Zb,Rh,R1a,R3a,Are), (Zb,Rh,R1a,R3a,Arf), (Zb,Rh, R1a,R3a,Arg), (Zb,Rh,R1a,R3a,Arh), (Zb,Rh,R1a,R3a,Ari), (Zb,Rh,R1a,R3a,Arj), (Zb,Rh,R1a,R3a,Ark), (Zb,Rh,R1a, R3a,Arl), (Zb,Rh,R1a,R3a,Arm), (Zb,Rh,R1a,R3a,Arn), (Zb,Rh,R1a,R3a,Aro), (Zb,Rh,R1a,R3a,Arp), (Zb,Rh,R1a, R3b,Ara), (Zb,Rh,R1a,R3b,Arb), (Zb,Rh,R1a,R3b,Arc), (Zb,Rh,R1a,R3b,Ard), (Zb,Rh,R1a,R3b,Are), (Zb,Rh,R1a, R3b,Arf), (Zb,Rh,R1a,R3b,Arg), (Zb,Rh,R1a,R3b,Arh), (Zb,Rh,R1a,R3b,Ari), (Zb,Rh,R1a,R3b,Arj), (Zb,Rh,R1a, R3b,Ark), (Zb,Rh,R1a,R3b,Arl), (Zb,Rh,R1a,R3b,Arm), (Zb,Rh,R1a,R3b,Arn), (Zb,Rh,R1a,R3b,Aro), (Zb,Rh,R1a, R3b,Arp), (Zb,Rh,R1a,R3c,Ara), (Zb,Rh,R1a,R3c,Arb), (Zb,Rh,R1a,R3c,Arc), (Zb,Rh,R1a,R3c,Ard), (Zb,Rh,R1a, R3c,Are), (Zb,Rh,R1a,R3c,Arf), (Zb,Rh,R1a,R3c,Arg), (Zb, Rh,R1a,R3c,Arh), (Zb,Rh,R1a,R3c,Ari), (Zb,Rh,R1a,R3c, Arj), (Zb,Rh,R1a,R3c,Ark), (Zb,Rh,R1a,R3c,Arl), (Zb,Rh, R1a,R3c,Arm), (Zb,Rh,R1a,R3c,Arn), (Zb,Rh,R1a,R3c, Aro), (Zb,Rh,R1a,R3c,Arp), (Zb,Rh,R1a,R3d,Ara), (Zb,Rh, R1a,R3d,Arb), (Zb,Rh,R1a,R3d,Arc), (Zb,Rh,R1a,R3d, Ard), (Zb,Rh,R1a,R3d,Are), (Zb,Rh,R1a,R3d,Arf), (Zb,Rh, R1a,R3d,Arg), (Zb,Rh,R1a,R3d,Arh), (Zb,Rh,R1a,R3d, Ari), (Zb,Rh,R1a,R3d,Arj), (Zb,Rh,R1a,R3d,Ark), (Zb,Rh, R1a,R3d,Arl), (Zb,Rh,R1a,R3d,Arm), (Zb,Rh,R1a,R3d, Arn), (Zb,Rh,R1a,R3d,Aro), (Zb,Rh,R1a,R3d,Arp), (Zb,Rh, R1a,R3e,Ara), (Zb,Rh,R1a,R3e,Arb), (Zb,Rh,R1a,R3e,Arc), (Zb,Rh,R1a,R3e,Ard), (Zb,Rh,R1a,R3e,Are), (Zb,Rh,R1a, R3e,Arf), (Zb,Rh,R1a,R3e,Arg), (Zb,Rh,R1a,R3e,Arh), (Zb, Rh,R1a,R3e,Ari), (Zb,Rh,R1a,R3e, Arj), (Zb,Rh,R1a,R3e, Ark), (Zb,Rh,R1a,R3e,Arl), (Zb,Rh,R1a,R3e,Arm), (Zb,Rh, R1a,R3e,Arn), (Zb,Rh,R1a,R3e,Aro), (Zb,Rh,R1a,R3e, Arp), (Zb,Rh,R1a,R3f,Ara), (Zb,Rh,R1a,R3f,Arb), (Zb,Rh, R1a,R3f,Arc), (Zb,Rh,R1a,R3f,Ard), (Zb,Rh,R1a,R3f,Are), (Zb,Rh,R1a,R3f,Arf), (Zb,Rh,R1a,R3f,Arg), (Zb,Rh,R1a, R3f,Arh), (Zb,Rh,R1a,R3f,Ari), (Zb,Rh,R1a,R3f,Arj), (Zb, Rh,R1a,R3f,Ark), (Zb,Rh,R1a,R3f,Arl), (Zb,Rh,R1a,R3f, Arm), (Zb,Rh,R1a,R3f,Arn), (Zb,Rh,R1a,R3f,Aro), (Zb,Rh, R1a,R3f,Arp), (Zb,Rh,R1a,R3g,Ara), (Zb,Rh,R1a,R3g, Arb), (Zb,Rh,R1a,R3g,Arc), (Zb,Rh,R1a,R3g,Ard), (Zb,Rh, R1a,R3g,Are), (Zb,Rh,R1a,R3g,Arf), (Zb,Rh,R1a,R3g, Arg), (Zb,Rh,R1a,R3g,Arh), (Zb,Rh,R1a,R3g,Ari), (Zb,Rh, R1a,R3g,Arj), (Zb,Rh,R1a,R3g,Ark), (Zb,Rh,R1a,R3g,Arl), (Zb,Rh,R1a,R3g,Arm), (Zb,Rh,R1a,R3g,Arn), (Zb,Rh,R1a, R3g,Aro), (Zb,Rh,R1a,R3g,Arp), (Zb,Rh,R1a,R3h,Ara), (Zb,Rh,R1a,R3h,Arb), (Zb,Rh,R1a,R3h,Arc), (Zb,Rh,R1a, R3h,Ard), (Zb,Rh,R1a,R3h,Are), (Zb,Rh,R1a,R3h,Arf), (Zb,Rh,R1a,R3h,Arg), (Zb,Rh,R1a,R3h,Arh), (Zb,Rh,R1a, R3h,Ari), (Zb,Rh,R1a,R3h,Arj), (Zb,Rh,R1a,R3h,Ark), (Zb, Rh,R1a,R3h,Arl), (Zb,Rh,R1a,R3h,Arm), (Zb,Rh,R1a,R3h, Arn), (Zb,Rh,R1a,R3h,Aro), (Zb,Rh,R1a,R3h,Arp), (Zb,Rh, R1b,R3a,Ara), (Zb,Rh,R1b,R3a,Arb), (Zb,Rh,R1b,R3a, Arc), (Zb,Rh,R1b,R3a,Ard), (Zb,Rh,R1b,R3a,Are), (Zb,Rh, R1b,R3a,Arf), (Zb,Rh,R1b,R3a,Arg), (Zb,Rh,R1b,R3a, Arh), (Zb,Rh,R1b,R3a,Ari), (Zb,Rh,R1b,R3a,Arj), (Zb,Rh, R1b,R3a,Ark), (Zb,Rh,R1b,R3a,Arl), (Zb,Rh,R1b,R3a, Arm), (Zb,Rh,R1b,R3a,Arn), (Zb,Rh,R1b,R3a,Aro), (Zb, Rh,R1b,R3a,Arp), (Zb,Rh,R1b,R3b,Ara), (Zb,Rh,R1b,R3b, Arb), (Zb,Rh,R1b,R3b,Arc), (Zb,Rh,R1b,R3b,Ard), (Zb,Rh, R1b,R3b,Are), (Zb,Rh,R1b,R3b,Arf), (Zb,Rh,R1b,R3b, Arg), (Zb,Rh,R1b,R3b,Arh), (Zb,Rh,R1b,R3b,Ari), (Zb,Rh, R1b,R3b,Arj), (Zb,Rh,R1b,R3b,Ark), (Zb,Rh,R1b,R3b,Arl), (Zb,Rh,R1b,R3b,Arm), (Zb,Rh,R1b,R3b,Arn), (Zb,Rh,R1b, R3b,Aro), (Zb,Rh,R1b,R3b,Arp), (Zb,Rh,R1b,R3c,Ara), (Zb,Rh,R1b,R3c,Arb), (Zb,Rh,R1b,R3c,Arc), (Zb,Rh,R1b, R3c,Ard), (Zb,Rh,R1b,R3c,Are), (Zb,Rh,R1b,R3c,Arf), (Zb, Rh,R1b,R3c,Arg), (Zb,Rh,R1b,R3c,Arh), (Zb,Rh,R1b,R3c, Ari), (Zb,Rh,R1b,R3c,Arj), (Zb,Rh,R1b,R3c,Ark), (Zb,Rh, R1b,R3c,Arl), (Zb,Rh,R1b,R3c,Arm), (Zb,Rh,R1b,R3c, Arn), (Zb,Rh,R1b,R3c,Aro), (Zb,Rh,R1b,R3c,Arp), (Zb,Rh, R1b,R3d,Ara), (Zb,Rh,R1b,R3d,Arb), (Zb,Rh,R1b,R3d, Arc), (Zb,Rh,R1b,R3d,Ard), (Zb,Rh,R1b,R3d,Are), (Zb,Rh, R1b,R3d,Arf), (Zb,Rh,R1b,R3d,Arg), (Zb,Rh,R1b,R3d, Arh), (Zb,Rh,R1b,R3d,Ari), (Zb,Rh,R1b,R3d,Arj), (Zb,Rh, R1b,R3d,Ark), (Zb,Rh,R1b,R3d,Arl), (Zb,Rh,R1b,R3d, Arm), (Zb,Rh,R1b,R3d,Arn), (Zb,Rh,R1b,R3d,Aro), (Zb, Rh,R1b,R3d,Arp), (Zb,Rh,R1b,R3e,Ara), (Zb,Rh,R1b,R3e, Arb), (Zb,Rh,R1b,R3e,Arc), (Zb,Rh,R1b,R3e,Ard), (Zb,Rh, R1b,R3e,Are), (Zb,Rh,R1b,R3e,Arf), (Zb,Rh,R1b,R3e, Arg), (Zb,Rh,R1b,R3e,Arh), (Zb,Rh,R1b,R3e,Ari), (Zb,Rh, R1b,R3e,Arj), (Zb,Rh,R1b,R3e,Ark), (Zb,Rh,R1b,R3e,Arl), (Zb,Rh,R1b,R3e,Arm), (Zb,Rh,R1b,R3e,Arn), (Zb,Rh,R1b, R3e,Aro), (Zb,Rh,R1b,R3e,Arp), (Zb,Rh,R1b,R3f,Ara), (Zb,Rh,R1b,R3f,Arb), (Zb,Rh,R1b,R3f,Arc), (Zb,Rh,R1b, R3f,Ard), (Zb,Rh,R1b,R3f,Are), (Zb,Rh,R1b,R3f,Arf), (Zb, Rh,R1b,R3f,Arg), (Zb,Rh,R1b,R3f,Arh), (Zb,Rh,R1b,R3f, Ari), (Zb,Rh,R1b,R3f,Arj), (Zb,Rh,R1b,R3f,Ark), (Zb,Rh, R1b,R3f,Arl), (Zb,Rh,R1b,R3f,Arm), (Zb,Rh,R1b,R3f,Arn), (Zb,Rh,R1b,R3f,Aro), (Zb,Rh,R1b,R3f,Arp), (Zb,Rh,R1b, R3g,Ara), (Zb,Rh,R1b,R3g,Arb), (Zb,Rh,R1b,R3g,Arc), (Zb,Rh,R1b,R3g,Ard), (Zb,Rh,R1b,R3g,Are), (Zb,Rh,R1b, R3g,Arf), (Zb,Rh,R1b,R3g,Arg), (Zb,Rh,R1b,R3g,Arh), (Zb,Rh,R1b,R3g,Ari), (Zb,Rh,R1b,R3g,Arj), (Zb,Rh,R1b, R3g,Ark), (Zb,Rh,R1b,R3g,Arl), (Zb,Rh,R1b,R3g,Arm), (Zb,Rh,R1b,R3g,Arn), (Zb,Rh,R1b,R3g,Aro), (Zb,Rh,R1b, R3g,Arp), (Zb,Rh,R1b,R3h,Ara), (Zb,Rh,R1b,R3h,Arb), (Zb,Rh,R1b,R3h,Arc), (Zb,Rh,R1b,R3h,Ard), (Zb,Rh,R1b, R3h,Are), (Zb,Rh,R1b,R3h,Arf), (Zb,Rh,R1b,R3h,Arg), (Zb,Rh,R1b,R3h,Arh), (Zb,Rh,R1b,R3h,Ari), (Zb,Rh,R1b, R3h,Arj), (Zb,Rh,R1b,R3h,Ark), (Zb,Rh,R1b,R3h,Arl), (Zb, Rh,R1b,R3h,Arm), (Zb,Rh,R1b,R3h,Arn), (Zb,Rh,R1b,R3h, Aro), (Zb,Rh,R1b,R3h,Arp), (Zb,Rh,R1c,R3a,Ara), (Zb,Rh, R1c,R3a,Arb), (Zb,Rh,R1c,R3a,Arc), (Zb,Rh,R1c,R3a, Ard), (Zb,Rh,R1c,R3a,Are), (Zb,Rh,R1c,R3a,Arf), (Zb,Rh, R1c,R3a,Arg), (Zb,Rh,R1c,R3a,Arh), (Zb,Rh,R1c,R3a,Ari), (Zb,Rh,R1c,R3a,Arj), (Zb,Rh,R1c,R3a,Ark), (Zb,Rh,R1c, R3a,Arl), (Zb,Rh,R1c,R3a,Arm), (Zb,Rh,R1c,R3a,Arn), (Zb,Rh,R1c,R3a,Aro), (Zb,Rh,R1c,R3a,Arp), (Zb,Rh,R1c, R3b,Ara), (Zb,Rh,R1c,R3b,Arb), (Zb,Rh,R1c,R3b,Arc), (Zb,Rh,R1c,R3b,Ard), (Zb,Rh,R1c,R3b,Are), (Zb,Rh,R1c, R3b,Arf), (Zb,Rh,R1c,R3b,Arg), (Zb,Rh,R1c,R3b,Arh), (Zb,Rh,R1c,R3b,Ari), (Zb,Rh,R1c,R3b,Arj), (Zb,Rh,R1c, R3b,Ark), (Zb,Rh,R1c,R3b,Arl), (Zb,Rh,R1c,R3b,Arm), (Zb,Rh,R1c,R3b,Arn), (Zb,Rh,R1c,R3b,Aro), (Zb,Rh,R1c, R3b,Arp), (Zb,Rh,R1c,R3c,Ara), (Zb,Rh,R1c,R3c,Arb), (Zb,Rh,R1c,R3c,Arc), (Zb,Rh,R1c,R3c,Ard), (Zb,Rh,R1c, R3c,Are), (Zb,Rh,R1c,R3c,Arf), (Zb,Rh,R1c,R3c,Arg), (Zb, Rh,R1c,R3c,Arh), (Zb,Rh,R1c,R3c,Ari), (Zb,Rh,R1c,R3c, Arj), (Zb,Rh,R1c,R3c,Ark), (Zb,Rh,R1c,R3c,Arl), (Zb,Rh, R1c,R3c,Arm), (Zb,Rh,R1c,R3c,Arn), (Zb,Rh,R1c,R3c, Aro), (Zb,Rh,R1c,R3c,Arp), (Zb,Rh,R1c,R3d,Ara), (Zb,Rh, R1c,R3d,Arb), (Zb,Rh,R1c,R3d,Arc), (Zb,Rh,R1c,R3d, Ard), (Zb,Rh,R1c,R3d,Are), (Zb,Rh,R1c,R3d,Arf), (Zb,Rh, R1c,R3d,Arg), (Zb,Rh,R1c,R3d,Arh), (Zb,Rh,R1c,R3d, Ari), (Zb,Rh,R1c,R3d,Arj), (Zb,Rh,R1c,R3d,Ark), (Zb,Rh, R1c,R3d,Arl), (Zb,Rh,R1c,R3d,Arm), (Zb,Rh,R1c,R3d, Arn), (Zb,Rh,R1c,R3d,Aro), (Zb,Rh,R1c,R3d,Arp), (Zb,Rh, R1c,R3e,Ara), (Zb,Rh,R1c,R3e,Arb), (Zb,Rh,R1c,R3e,Arc), (Zb,Rh,R1c,R3e,Ard), (Zb,Rh,R1c,R3e,Are), (Zb,Rh,R1c, R3e,Arf), (Zb,Rh,R1c,R3e,Arg), (Zb,Rh,R1c,R3e,Arh), (Zb, Rh,R1c,R3e,Ari), (Zb,Rh,R1c,R3e,Arj), (Zb,Rh,R1c,R3e, Ark), (Zb,Rh,R1c,R3e,Arl), (Zb,Rh,R1c,R3e,Arm), (Zb,Rh, R1c,R3e,Arn), (Zb,Rh,R1c,R3e,Aro), (Zb,Rh,R1c,R3e, Arp), (Zb,Rh,R1c,R3f,Ara), (Zb,Rh,R1c,R3f,Arb), (Zb,Rh, R1c,R3f,Arc), (Zb,Rh,R1c,R3f,Ard), (Zb,Rh,R1c,R3f,Are), (Zb,Rh,R1c,R3f,Arf), (Zb,Rh,R1c,R3f,Arg), (Zb,Rh,R1c, R3f,Arh), (Zb,Rh,R1c,R3f,Ari), (Zb,Rh,R1c,R3f,Arj), (Zb, Rh,R1c,R3f,Ark), (Zb,Rh,R1c,R3f,Arl), (Zb,Rh,R1c,R3f, Arm), (Zb,Rh,R1c,R3f,Arn), (Zb,Rh,R1c,R3f,Aro), (Zb,Rh, R1c,R3f,Arp), (Zb,Rh,R1c,R3g,Ara), (Zb,Rh,R1c,R3g, Arb), (Zb,Rh,R1c,R3g,Arc), (Zb,Rh,R1c,R3g,Ard), (Zb,Rh, R1c,R3g,Are), (Zb,Rh,R1c,R3g,Arf), (Zb,Rh,R1c, R3g, Arg), (Zb,Rh,R1c,R3g,Arh), (Zb,Rh,R1c,R3g,Ari), (Zb,Rh, R1c,R3g,Arj), (Zb,Rh,R1c,R3g,Ark), (Zb,Rh,R1c,R3g,Arl), (Zb,Rh,R1c,R3g,Arm), (Zb,Rh,R1c,R3g,Arn), (Zb,Rh,R1c, R3g,Aro), (Zb,Rh,R1c,R3g,Arp), (Zb,Rh,R1c,R3h,Ara), (Zb,Rh,R1c,R3h,Arb), (Zb,Rh,R1c,R3h,Arc), (Zb,Rh,R1c, R3h,Ard), (Zb,Rh,R1c,R3h,Are), (Zb,Rh,R1c,R3h,Arf), (Zb,Rh,R1c,R3h,Arg), (Zb,Rh,R1c,R3h,Arh), (Zb,Rh,R1c, R3h,Ari), (Zb,Rh,R1c,R3h,Arj), (Zb,Rh,R1c,R3h,Ark), (Zb, Rh,R1c,R3h,Arl), (Zb,Rh,R1c,R3h,Arm), (Zb,Rh,R1c,R3h, Arn), (Zb,Rh,R1c,R3h,Aro), (Zb,Rh,R1c,R3h,Arp), (Zb,Rh, R1d,R3a,Ara), (Zb,Rh,R1d,R3a,Arb), (Zb,Rh,R1d,R3a, Arc), (Zb,Rh,R1d,R3a,Ard), (Zb,Rh,R1d,R3a,Are), (Zb,Rh, R1d,R3a,Arf), (Zb,Rh,R1d,R3a,Arg), (Zb,Rh,R1d,R3a, Arh), (Zb,Rh,R1d,R3a,Ari), (Zb,Rh,R1d,R3a,Arj), (Zb,Rh, R1d,R3a,Ark), (Zb,Rh,R1d,R3a,Arl), (Zb,Rh,R1d,R3a, Arm), (Zb,Rh,R1d,R3a,Arn), (Zb,Rh,R1d,R3a,Aro), (Zb, Rh,R1d,R3a,Arp), (Zb,Rh,R1d,R3b,Ara), (Zb,Rh,R1d,R3b, Arb), (Zb,Rh,R1d,R3b,Arc), (Zb,Rh,R1d,R3b,Ard), (Zb,Rh, R1d,R3b,Are), (Zb,Rh,R1d,R3b,Arf), (Zb,Rh,R1d,R3b, Arg), (Zb,Rh,R1d,R3b,Arh), (Zb,Rh,R1d,R3b,Ari), (Zb,Rh, R1d,R3b,Arj), (Zb,Rh,R1d,R3b,Ark), (Zb,Rh,R1d,R3b,Arl), (Zb,Rh,R1d,R3b,Arm), (Zb,Rh,R1d,R3b,Arn), (Zb,Rh,R1d, R3b,Aro), (Zb,Rh,R1d,R3b,Arp), (Zb,Rh,R1d,R3c,Ara), (Zb,Rh,R1d,R3c,Arb), (Zb,Rh,R1d,R3c,Arc), (Zb,Rh,R1d, R3c,Ard), (Zb,Rh,R1d,R3c,Are), (Zb,Rh,R1d,R3c,Arf), (Zb, Rh,R1d,R3c,Arg), (Zb,Rh,R1d,R3c,Arh), (Zb,Rh,R1d,R3c, Ari), (Zb,Rh,R1d,R3c,Arj), (Zb,Rh,R1d,R3c,Ark), (Zb,Rh, R1d,R3c,Arl), (Zb,Rh,R1d,R3c,Arm), (Zb,Rh,R1d,R3c, Arn), (Zb,Rh,R1d,R3c,Aro), (Zb,Rh,R1d,R3c,Arp), (Zb,Rh, R1d,R3d,Ara), (Zb,Rh,R1d,R3d,Arb), (Zb,Rh,R1d,R3d, Arc), (Zb,Rh,R1d,R3d,Ard), (Zb,Rh,R1d,R3d,Are), (Zb,Rh, R1d,R3d,Arf), (Zb,Rh,R1d,R3d,Arg), (Zb,Rh,R1d,R3d, Arh), (Zb,Rh,R1d,R3d,Ari), (Zb,Rh,R1d,R3d,Arj), (Zb,Rh, R1d,R3d,Ark), (Zb,Rh,R1d,R3d,Arl), (Zb,Rh,R1d,R3d, Arm), (Zb,Rh,R1d,R3d,Arn), (Zb,Rh,R1d,R3d,Aro), (Zb, Rh,R1d,R3d,Arp), (Zb,Rh,R1d,R3e,Ara), (Zb,Rh,R1d,R3e, Arb), (Zb,Rh,R1d,R3e,Arc), (Zb,Rh,R1d,R3e,Ard), (Zb,Rh, R1d,R3e,Are), (Zb,Rh,R1d,R3e,Arf), (Zb,Rh,R1d,R3e, Arg), (Zb,Rh,R1d,R3e,Arh), (Zb,Rh,R1d,R3e,Ari), (Zb,Rh, R1d,R3e,Arj), (Zb,Rh,R1d,R3e,Ark), (Zb,Rh,R1d,R3e,Arl), (Zb,Rh,R1d,R3e,Arm), (Zb,Rh,R1d,R3e,Arn), (Zb,Rh,R1d, R3e,Aro), (Zb,Rh,R1d,R3e,Arp), (Zb,Rh,R1d,R3f,Ara), (Zb,Rh,R1d,R3f,Arb), (Zb,Rh,R1d,R3f,Arc), (Zb,Rh,R1d, R3f,Ard), (Zb,Rh,R1d,R3f,Are), (Zb,Rh,R1d,R3f,Arf), (Zb, Rh,R1d,R3f,Arg), (Zb,Rh,R1d,R3f,Arh), (Zb,Rh,R1d,R3f, Ari), (Zb,Rh,R1d,R3f,Arj), (Zb,Rh,R1d,R3f,Ark), (Zb,Rh, R1d,R3f,Arl), (Zb,Rh,R1d,R3f,Arm), (Zb,Rh,R1d,R3f,Arn), (Zb,Rh,R1d,R3f,Aro), (Zb,Rh,R1d,R3f,Arp), (Zb,Rh,R1d, R3g,Ara), (Zb,Rh,R1d,R3g,Arb), (Zb,Rh,R1d,R3g,Arc), (Zb,Rh,R1d,R3g,Ard), (Zb,Rh,R1d,R3g,Are), (Zb,Rh,R1d, R3g,Arf), (Zb,Rh,R1d,R3g,Arg), (Zb,Rh,R1d,R3g,Arh), (Zb,Rh,R1d,R3g,Ari), (Zb,Rh,R1d,R3g,Arj), (Zb,Rh,R1d, R3g,Ark), (Zb,Rh,R1d,R3g,Arl), (Zb,Rh,R1d,R3g,Arm), (Zb,Rh,R1d,R3g,Arn), (Zb,Rh,R1d,R3g,Aro), (Zb,Rh,R1d, R3g,Arp), (Zb,Rh,R1d,R3h,Ara), (Zb,Rh,R1d,R3h,Arb), (Zb,Rh,R1d,R3h,Arc), (Zb,Rh,R1d,R3h,Ard), (Zb,Rh,R1d, R3h,Are), (Zb,Rh,R1d,R3h,Arf), (Zb,Rh,R1d,R3h,Arg), (Zb,Rh,R1d,R3h,Arh), (Zb,Rh,R1d,R3h,Ari), (Zb,Rh,R1d, R3h,Arj), (Zb,Rh,R1d,R3h,Ark), (Zb,Rh,R1d,R3h,Arl), (Zb, Rh,R1d,R3h,Arm), (Zb,Rh,R1d,R3h,Arn), (Zb,Rh,R1d,R3h, Aro), (Zb,Rh,R1d,R3h,Arp), (Zb,Ri,R1a,R3a,Ara), (Zb,Ri, R1a,R3a,Arb), (Zb,Ri,R1a,R3a,Arc), (Zb,Ri,R1a,R3a,Ard), (Zb,Ri,R1a,R3a,Are), (Zb,Ri,R1a,R3a,Arf), (Zb,Ri,R1a, R3a,Arg), (Zb,Ri,R1a,R3a,Arh), (Zb,Ri,R1a,R3a,Ari), (Zb, Ri,R1a,R3a,Arj), (Zb,Ri,R1a,R3a,Ark), (Zb,Ri,R1a,R3a, Arl), (Zb,Ri,R1a,R3a,Arm), (Zb,Ri,R1a,R3a,Arn), (Zb,Ri, R1a,R3a,Aro), (Zb,Ri,R1a,R3a,Arp), (Zb,Ri,R1a,R3b,Ara), (Zb,Ri,R1a,R3b,Arb), (Zb,Ri,R1a,R3b,Arc), (Zb,Ri,R1a, R3b,Ard), (Zb,Ri,R1a,R3b,Are), (Zb,Ri,R1a,R3b,Arf), (Zb, Ri,R1a,R3b,Arg), (Zb,Ri,R1a,R3b,Arh), (Zb,Ri,R1a,R3b, Ari), (Zb,Ri,R1a,R3b,Arj), (Zb,Ri,R1a,R3b,Ark), (Zb,Ri, R1a,R3b,Arl), (Zb,Ri,R1a,R3b,Arm), (Zb,Ri,R1a,R3b,Arn), (Zb,Ri,R1a,R3b,Aro), (Zb,Ri,R1a,R3b,Arp), (Zb,Ri,R1a, R3c,Ara), (Zb,Ri,R1a,R3c,Arb), (Zb,Ri,R1a,R3c,Arc), (Zb, Ri,R1a,R3c,Ard), (Zb,Ri,R1a,R3c,Are), (Zb,Ri,R1a,R3c, Arf), (Zb,Ri,R1a,R3c,Arg), (Zb,Ri,R1a,R3c,Arh), (Zb,Ri, R1a,R3c,Ari), (Zb,Ri,R1a,R3c,Arj), (Zb,Ri,R1a,R3c,Ark), (Zb,Ri,R1a,R3c,Arl), (Zb,Ri,R1a,R3c,Arm), (Zb,Ri,R1a, R3c,Arn), (Zb,Ri,R1a,R3c,Aro), (Zb,Ri,R1a,R3c,Arp), (Zb, Ri,R1a,R3d,Ara), (Zb,Ri,R1a,R3d,Arb), (Zb,Ri,R1a,R3d, Arc), (Zb,Ri,R1a,R3d,Ard), (Zb,Ri,R1a,R3d,Are), (Zb,Ri, R1a,R3d,Arf), (Zb,Ri,R1a,R3d,Arg), (Zb,Ri,R1a,R3d,Arh), (Zb,Ri,R1a,R3d,Ari), (Zb,Ri,R1a,R3d,Arj), (Zb,Ri,R1a, R3d,Ark), (Zb,Ri,R1a,R3d,Arl), (Zb,Ri,R1a,R3d,Arm), (Zb, Ri,R1a,R3d,Arn), (Zb,Ri,R1a,R3d,Aro), (Zb,Ri,R1a,R3d, Arp), (Zb,Ri,R1a,R3e,Ara), (Zb,Ri,R1a,R3e,Arb), (Zb,Ri, R1a,R3e,Arc), (Zb,Ri,R1a,R3e,Ard), (Zb,Ri,R1a,R3e,Are), (Zb,Ri,R1a,R3e,Arf), (Zb,Ri,R1a,R3e,Arg), (Zb,Ri,R1a, R3e,Arh), (Zb,Ri,R1a,R3e,Ari), (Zb,Ri,R1a,R3e,Arj), (Zb, Ri,R1a,R3e,Ark), (Zb,Ri,R1a,R3e,Arl), (Zb,Ri,R1a,R3e, Arm), (Zb,Ri,R1a,R3e,Arn), (Zb,Ri,R1a,R3e,Aro), (Zb,Ri, R1a,R3e,Arp), (Zb,Ri,R1a,R3f,Ara), (Zb,Ri,R1a,R3f,Arb), (Zb,Ri,R1a,R3f,Arc), (Zb,Ri,R1a,R3f,Ard), (Zb,Ri,R1a, R3f,Are), (Zb,Ri,R1a,R3f,Arf), (Zb,Ri,R1a,R3f,Arg), (Zb, Ri,R1a,R3f,Arh), (Zb,Ri,R1a,R3f,Ari), (Zb,Ri,R1a,R3f, Arj), (Zb,Ri,R1a,R3f,Ark), (Zb,Ri,R1a,R3f,Arl), (Zb,Ri, R1a,R3f,Arm), (Zb,Ri,R1a,R3f,Arn), (Zb,Ri,R1a,R3f,Aro), (Zb,Ri,R1a,R3f,Arp), (Zb,Ri,R1a,R3g,Ara), (Zb,Ri,R1a, R3g,Arb), (Zb,Ri,R1a,R3g,Arc), (Zb,Ri,R1a,R3g,Ard), (Zb, Ri,R1a,R3g,Are), (Zb,Ri,R1a,R3g,Arf), (Zb,Ri,R1a,R3g, Arg), (Zb,Ri,R1a,R3g,Arh), (Zb,Ri,R1a,R3g,Ari), (Zb,Ri, R1a,R3g,Arj), (Zb,Ri,R1a,R3g,Ark), (Zb,Ri,R1a,R3g,Arl), (Zb,Ri,R1a,R3g,Arm), (Zb,Ri,R1a,R3g,Arn), (Zb,Ri,R1a, R3g,Aro), (Zb,Ri,R1a,R3g,Arp), (Zb,Ri,R1a,R3h,Ara), (Zb, Ri,R1a,R3h,Arb), (Zb,Ri,R1a,R3h,Arc), (Zb,Ri,R1a,R3h, Ard), (Zb,Ri,R1a,R3h,Are), (Zb,Ri,R1a,R3h,Arf), (Zb,Ri, R1a,R3h,Arg), (Zb,Ri,R1a,R3h,Arh), (Zb,Ri,R1a,R3h,Ari), (Zb,Ri,R1a,R3h,Arj), (Zb,Ri,R1a,R3h,Ark), (Zb,Ri,R1a, R3h,Arl), (Zb,Ri,R1a,R3h,Arm), (Zb,Ri,R1a,R3h,Arn), (Zb, Ri,R1a,R3h,Aro), (Zb,Ri,R1a,R3h,Arp), (Zb,Ri,R1b,R3a, Ara), (Zb,Ri,R1b,R3a,Arb), (Zb,Ri,R1b,R3a,Arc), (Zb,Ri, R1b,R3a,Ard), (Zb,Ri,R1b,R3a,Are), (Zb,Ri,R1b,R3a,Arf), (Zb,Ri,R1b,R3a,Arg), (Zb,Ri,R1b,R3a,Arh), (Zb,Ri,R1b, R3a,Ari), (Zb,Ri,R1b,R3a,Arj), (Zb,Ri,R1b,R3a,Ark), (Zb, Ri,R1b,R3a,Arl), (Zb,Ri,R1b,R3a,Arm), (Zb,Ri,R1b,R3a, Arn), (Zb,Ri,R1b,R3a,Aro), (Zb,Ri,R1b,R3a,Arp), (Zb,Ri, R1b,R3b,Ara), (Zb,Ri,R1b,R3b,Arb), (Zb,Ri,R1b,R3b,Arc), (Zb,Ri,R1b,R3b,Ard), (Zb,Ri,R1b,R3b,Are), (Zb,Ri,R1b,R3b,Arf), (Zb,Ri,R1b,R3b,Arg), (Zb,Ri,R1b,R3b,Arh), (Zb,Ri,R1b,R3b,Ari), (Zb,Ri,R1b,R3b,Arj), (Zb,Ri,R1b,R3b,Ark), (Zb,Ri,R1b,R3b,Arl), (Zb,Ri,R1b,R3b,Arm), (Zb,Ri,R1b,R3b,Arn), (Zb,Ri,R1b,R3b,Aro), (Zb,Ri,R1b,R3b,Arp), (Zb,Ri,R1b,R3c,Ara), (Zb,Ri,R1b,R3c,Arb), (Zb,Ri,R1b,R3c,Arc), (Zb,Ri,R1b,R3c,Ard), (Zb,Ri,R1b,R3c,Are), (Zb,Ri,R1b,R3c,Arf), (Zb,Ri,R1b,R3c,Arg), (Zb,Ri,R1b,R3c,Arh), (Zb,Ri,R1b,R3c,Ari), (Zb,Ri,R1b,R3c,Arj), (Zb,Ri,R1b,R3c,Ark), (Zb,Ri,R1b,R3c,Arl), (Zb,Ri,R1b,R3c,Arm), (Zb,Ri,R1b,R3c,Arn), (Zb,Ri,R1b,R3c,Aro), (Zb,Ri,R1b,R3c,Arp), (Zb,Ri,R1b,R3d,Ara), (Zb,Ri,R1b,R3d,Arb), (Zb,Ri,R1b,R3d,Arc), (Zb,Ri,R1b,R3d,Ard), (Zb,Ri,R1b,R3d,Are), (Zb,Ri,R1b,R3d,Arf), (Zb,Ri,R1b,R3d,Arg), (Zb,Ri,R1b,R3d,Arh), (Zb,Ri,R1b,R3d,Ari), (Zb,Ri,R1b,R3d,Arj), (Zb,Ri,R1b,R3d,Ark), (Zb,Ri,R1b,R3d,Arl), (Zb,Ri,R1b,R3d,Arm), (Zb,Ri,R1b,R3d,Arn), (Zb,Ri,R1b,R3d,Aro), (Zb,Ri,R1b,R3d,Arp), (Zb,Ri,R1b,R3e,Ara), (Zb,Ri,R1b,R3e,Arb), (Zb,Ri,R1b,R3e,Arc), (Zb,Ri,R1b,R3e,Ard), (Zb,Ri,R1b,R3e,Are), (Zb,Ri,R1b,R3e,Arf), (Zb,Ri,R1b,R3e,Arg), (Zb,Ri,R1b,R3e,Arh), (Zb,Ri,R1b,R3e,Ari), (Zb,Ri,R1b,R3e,Arj), (Zb,Ri,R1b,R3e,Ark), (Zb,Ri,R1b,R3e,Arl), (Zb,Ri,R1b,R3e,Arm), (Zb,Ri,R1b,R3e,Arn), (Zb,Ri,R1b,R3e,Aro), (Zb,Ri,R1b,R3e,Arp), (Zb,Ri,R1b,R3f,Ara), (Zb,Ri,R1b,R3f,Arb), (Zb,Ri,R1b,R3f,Arc), (Zb,Ri,R1b,R3f,Ard), (Zb,Ri,R1b,R3f,Are), (Zb,Ri,R1b,R3f,Arf), (Zb,Ri,R1b,R3f,Arg), (Zb,Ri,R1b,R3f,Arh), (Zb,Ri,R1b,R3f,Ari), (Zb,Ri,R1b,R3f,Arj), (Zb,Ri,R1b,R3f,Ark), (Zb,Ri,R1b,R3f,Arl), (Zb,Ri,R1b,R3f,Arm), (Zb,Ri,R1b,R3f,Arn), (Zb,Ri,R1b,R3f,Aro), (Zb,Ri,R1b,R3f,Arp), (Zb,Ri,R1b,R3g,Ara), (Zb,Ri,R1b,R3g,Arb), (Zb,Ri,R1b,R3g,Arc), (Zb,Ri,R1b,R3g,Ard), (Zb,Ri,R1b,R3g,Are), (Zb,Ri,R1b,R3g,Arf), (Zb,Ri,R1b,R3g,Arg), (Zb,Ri,R1b,R3g,Arh), (Zb,Ri,R1b,R3g,Ari), (Zb,Ri,R1b,R3g,Arj), (Zb,Ri,R1b,R3g,Ark), (Zb,Ri,R1b,R3g,Arl), (Zb,Ri,R1b,R3g,Arm), (Zb,Ri,R1b,R3g,Arn), (Zb,Ri,R1b,R3g,Aro), (Zb,Ri,R1b,R3g,Arp), (Zb,Ri,R1b,R3h,Ara), (Zb,Ri,R1b,R3h,Arb), (Zb,Ri,R1b,R3h,Arc), (Zb,Ri,R1b,R3h,Ard), (Zb,Ri,R1b,R3h,Are), (Zb,Ri,R1b,R3h,Arf), (Zb,Ri,R1b,R3h,Arg), (Zb,Ri,R1b,R3h,Arh), (Zb,Ri,R1b,R3h,Ari), (Zb,Ri,R1b,R3h,Arj), (Zb,Ri,R1b,R3h,Ark), (Zb,Ri,R1b,R3h,Arl), (Zb,Ri,R1b,R3h,Arm), (Zb,Ri,R1b,R3h,Arn), (Zb,Ri,R1b,R3h,Aro), (Zb,Ri,R1b,R3h,Arp), (Zb,Ri,R1c,R3a,Ara), (Zb,Ri,R1c,R3a,Arb), (Zb,Ri,R1c,R3a,Arc), (Zb,Ri,R1c,R3a,Ard), (Zb,Ri,R1c,R3a,Are), (Zb,Ri,R1c,R3a,Arf), (Zb,Ri,R1c,R3a,Arg), (Zb,Ri,R1c,R3a,Arh), (Zb,Ri,R1c,R3a,Ari), (Zb,Ri,R1c,R3a,Arj), (Zb,Ri,R1c,R3a,Ark), (Zb,Ri,R1c,R3a,Arl), (Zb,Ri,R1c,R3a,Arm), (Zb,Ri,R1c,R3a,Arn), (Zb,Ri,R1c,R3a,Aro), (Zb,Ri,R1c,R3a,Arp), (Zb,Ri,R1c,R3b,Ara), (Zb,Ri,R1c,R3b,Arb), (Zb,Ri,R1c,R3b,Arc), (Zb,Ri,R1c,R3b,Ard), (Zb,Ri,R1c,R3b,Are), (Zb,Ri,R1c,R3b,Arf), (Zb,Ri,R1c,R3b,Arg), (Zb,Ri,R1c,R3b,Arh), (Zb,Ri,R1c,R3b,Ari), (Zb,Ri,R1c,R3b,Arj), (Zb,Ri,R1c,R3b,Ark), (Zb,Ri,R1c,R3b,Arl), (Zb,Ri,R1c,R3b,Arm), (Zb,Ri,R1c,R3b,Arn), (Zb,Ri,R1c,R3b,Aro), (Zb,Ri,R1c,R3b,Arp), (Zb,Ri,R1c,R3c,Ara), (Zb,Ri,R1c,R3c,Arb), (Zb,Ri,R1c,R3c,Arc), (Zb,Ri,R1c,R3c,Ard), (Zb,Ri,R1c,R3c,Are), (Zb,Ri,R1c,R3c,Arf), (Zb,Ri,R1c,R3c,Arg), (Zb,Ri,R1c,R3c,Arh), (Zb,Ri,R1c,R3c,Ari), (Zb,Ri,R1c,R3c,Arj), (Zb,Ri,R1c,R3c,Ark), (Zb,Ri,R1c,R3c,Arl), (Zb,Ri,R1c,R3c,Arm), (Zb,Ri,R1c,R3c,Arn), (Zb,Ri,R1c,R3c,Aro), (Zb,Ri,R1c,R3c,Arp), (Zb,Ri,R1c,R3d,Ara), (Zb,Ri,R1c,R3d,Arb), (Zb,Ri,R1c,R3d,Arc), (Zb,Ri,R1c,R3d,Ard), (Zb,Ri,R1c,R3d,Are), (Zb,Ri,R1c,R3d,Arf), (Zb,Ri,R1c,R3d,Arg), (Zb,Ri,R1c,R3d,Arh), (Zb,Ri,R1c,R3d,Ari), (Zb,Ri,R1c,R3d,Arj), (Zb,Ri,R1c,R3d,Ark), (Zb,Ri,R1c,R3d,Arl), (Zb,Ri,R1c,R3d,Arm), (Zb,Ri,R1c,R3d,Arn), (Zb,Ri,R1c,R3d,Aro), (Zb,Ri,R1c,R3d,Arp), (Zb,Ri,R1c,R3e,Ara), (Zb,Ri,R1c,R3e,Arb), (Zb,Ri,R1c,R3e,Arc), (Zb,Ri,R1c,R3e,Ard), (Zb,Ri,R1c,R3e,Are), (Zb,Ri,R1c,R3e,Arf), (Zb,Ri,R1c,R3e,Arg), (Zb,Ri,R1c,R3e,Arh), (Zb,Ri,R1c,R3e,Ari), (Zb,Ri,R1c,R3e,Arj), (Zb,Ri,R1c,R3e,Ark), (Zb,Ri,R1c,R3e,Arl), (Zb,Ri,R1c,R3e,Arm), (Zb,Ri,R1c,R3e,Arn), (Zb,Ri,R1c,R3e,Aro), (Zb,Ri,R1c,R3e,Arp), (Zb,Ri,R1c,R3f,Ara), (Zb,Ri,R1c,R3f,Arb), (Zb,Ri,R1c,R3f,Arc), (Zb,Ri,R1c,R3f,Ard), (Zb,Ri,R1c,R3f,Are), (Zb,Ri,R1c,R3f,Arf), (Zb,Ri,R1c,R3f,Arg), (Zb,Ri,R1c,R3f,Arh), (Zb,Ri,R1c,R3f,Ari), (Zb,Ri,R1c,R3f,Arj), (Zb,Ri,R1c,R3f,Ark), (Zb,Ri,R1c,R3f,Arl), (Zb,Ri,R1c,R3f,Arm), (Zb,Ri,R1c,R3f,Arn), (Zb,Ri,R1c,R3f,Aro), (Zb,Ri,R1c,R3f,Arp), (Zb,Ri,R1c,R3g,Ara), (Zb,Ri,R1c,R3g,Arb), (Zb,Ri,R1c,R3g,Arc), (Zb,Ri,R1c,R3g,Ard), (Zb,Ri,R1c,R3g,Are), (Zb,Ri,R1c,R3g,Arf), (Zb,Ri,R1c,R3g,Arg), (Zb,Ri,R1c,R3g,Arh), (Zb,Ri,R1c,R3g,Ari), (Zb,Ri,R1c,R3g,Arj), (Zb,Ri,R1c,R3g,Ark), (Zb,Ri,R1c,R3g,Arl), (Zb,Ri,R1c,R3g,Arm), (Zb,Ri,R1c,R3g,Arn), (Zb,Ri,R1c,R3g,Aro), (Zb,Ri,R1c,R3g,Arp), (Zb,Ri,R1c,R3h,Ara), (Zb,Ri,R1c,R3h,Arb), (Zb,Ri,R1c,R3h,Arc), (Zb,Ri,R1c,R3h,Ard), (Zb,Ri,R1c,R3h,Are), (Zb,Ri,R1c,R3h,Arf), (Zb,Ri,R1c,R3h,Arg), (Zb,Ri,R1c,R3h,Arh), (Zb,Ri,R1c,R3h,Ari), (Zb,Ri,R1c,R3h,Arj), (Zb,Ri,R1c,R3h,Ark), (Zb,Ri,R1c,R3h,Arl), (Zb,Ri,R1c,R3h,Arm), (Zb,Ri,R1c,R3h,Arn), (Zb,Ri,R1c,R3h,Aro), (Zb,Ri,R1c,R3h,Arp), (Zb,Ri,R1d,R3a,Ara), (Zb,Ri,R1d,R3a,Arb), (Zb,Ri,R1d,R3a,Arc), (Zb,Ri,R1d,R3a,Ard), (Zb,Ri,R1d,R3a,Are), (Zb,Ri,R1d,R3a,Arf), (Zb,Ri,R1d,R3a,Arg), (Zb,Ri,R1d,R3a,Arh), (Zb,Ri,R1d,R3a,Ari), (Zb,Ri,R1d,R3a,Arj), (Zb,Ri,R1d,R3a,Ark), (Zb,Ri,R1d,R3a,Arl), (Zb,Ri,R1d,R3a,Arm), (Zb,Ri,R1d,R3a,Arn), (Zb,Ri,R1d,R3a,Aro), (Zb,Ri,R1d,R3a,Arp), (Zb,Ri,R1d,R3b,Ara), (Zb,Ri,R1d,R3b,Arb), (Zb,Ri,R1d,R3b,Arc), (Zb,Ri,R1d,R3b,Ard), (Zb,Ri,R1d,R3b,Are), (Zb,Ri,R1d,R3b,Arf), (Zb,Ri,R1d,R3b,Arg), (Zb,Ri,R1d,R3b,Arh), (Zb,Ri,R1d,R3b,Ari), (Zb,Ri,R1d,R3b,Arj), (Zb,Ri,R1d,R3b,Ark), (Zb,Ri,R1d,R3b,Arl), (Zb,Ri,R1d,R3b,Arm), (Zb,Ri,R1d,R3b,Arn), (Zb,Ri,R1d,R3b,Aro), (Zb,Ri,R1d,R3b,Arp), (Zb,Ri,R1d,R3c,Ara), (Zb,Ri,R1d,R3c,Arb), (Zb,Ri,R1d,R3c,Arc), (Zb,Ri,R1d,R3c,Ard), (Zb,Ri,R1d,R3c,Are), (Zb,Ri,R1d,R3c,Arf), (Zb,Ri,R1d,R3c,Arg), (Zb,Ri,R1d,R3c,Arh), (Zb,Ri,R1d,R3c,Ari), (Zb,Ri,R1d,R3c,Arj), (Zb,Ri,R1d,R3c,Ark), (Zb,Ri,R1d,R3c,Arl), (Zb,Ri,R1d,R3c,Arm), (Zb,Ri,R1d,R3c,Arn), (Zb,Ri,R1d,R3c,Aro), (Zb,Ri,R1d,R3c,Arp), (Zb,Ri,R1d,R3d,Ara), (Zb,Ri,R1d,R3d,Arb), (Zb,Ri,R1d,R3d,Arc), (Zb,Ri,R1d,R3d,Ard), (Zb,Ri,R1d,R3d,Are), (Zb,Ri,R1d,R3d,Arf), (Zb,Ri,R1d,R3d,Arg), (Zb,Ri,R1d,R3d,Arh), (Zb,Ri,R1d,R3d,Ari), (Zb,Ri,R1d,R3d,Arj), (Zb,Ri,R1d,R3d,Ark), (Zb,Ri,R1d,R3d,Arl), (Zb,Ri,R1d,R3d,Arm), (Zb,Ri,R1d,R3d,Arn), (Zb,Ri,R1d,R3d,Aro), (Zb,Ri,R1d,R3d,Arp), (Zb,Ri,R1d,R3e,Ara), (Zb,Ri,R1d,R3e,Arb), (Zb,Ri,R1d,R3e,Arc), (Zb,Ri,R1d,R3e,Ard), (Zb,Ri,R1d,R3e,Are), (Zb,Ri,R1d,R3e,Arf), (Zb,Ri,R1d,R3e,Arg), (Zb,Ri,R1d,R3e,Arh), (Zb,Ri,R1d,R3e,Ari), (Zb,Ri,R1d,R3e,Arj), (Zb,Ri,R1d,R3e,Ark), (Zb,Ri,R1d,R3e,Arl), (Zb,Ri,R1d,R3e,Arm), (Zb,Ri,R1d,R3e,Arn), (Zb,Ri,R1d,R3e,Aro), (Zb,Ri,R1d,R3e,Arp), (Zb,Ri,R1d,R3f,Ara), (Zb,Ri,R1d,R3f,Arb), (Zb,Ri,R1d,R3f,Arc), (Zb,Ri,R1d,R3f,Ard), (Zb,Ri,R1d,R3f,Are), (Zb,Ri,R1d,R3f,Arf), (Zb,Ri,R1d,R3f,Arg), (Zb,Ri,R1d,R3f,Arh), (Zb,Ri,R1d,R3f,Ari), (Zb,Ri,R1d,R3f,Arj), (Zb,Ri,R1d,R3f,Ark), (Zb,Ri,R1d,R3f,Arl), (Zb,Ri,R1d,R3f,Arm), (Zb,Ri,R1d,R3f,Arn), (Zb,Ri,R1d,R3f,Aro), (Zb,Ri,R1d,R3f,Arp), (Zb,Ri,R1d,R3g,Ara), (Zb,Ri,R1d,R3g,Arb), (Zb,Ri,R1d,R3g,Arc), (Zb,Ri,R1d,R3g,Ard), (Zb,Ri,R1d,R3g,Are), (Zb,Ri,R1d,R3g,Arf), (Zb,Ri,R1d,R3g,Arg), (Zb,Ri,R1d,R3g,Arh), (Zb,Ri,R1d,R3g,Ari), (Zb,Ri,R1d,R3g,Arj), (Zb,Ri,R1d,R3g,Ark), (Zb,Ri,R1d,R3g,Arl), (Zb, Ri,R1d,R3g,Arm), (Zb,Ri,R1d,R3g,Arn), (Zb,Ri,R1d,R3g, Aro), (Zb,Ri,R1d,R3g,Arp), (Zb,Ri,R1d,R3h,Ara), (Zb,Ri, R1d,R3h,Arb), (Zb,Ri,R1d,R3h,Arc), (Zb,Ri,R1d,R3h,Ard), (Zb,Ri,R1d,R3h,Are), (Zb,Ri,R1d,R3h,Arf), (Zb,Ri,R1d, R3h,Arg), (Zb,Ri,R1d,R3h,Arh), (Zb,Ri,R1d,R3h,Ari), (Zb, Ri,R1d,R3h,Arj), (Zb,Ri,R1d,R3h,Ark), (Zb,Ri,R1d,R3h, Arl), (Zb,Ri,R1d,R3h,Arm), (Zb,Ri,R1d,R3h,Arn), (Zb,Ri, R1d,R3h,Aro), (Zb,Ri,R1d,R3h,Arp), (Zb,Rj,R1a,R3a,Ara), (Zb,Rj,R1a,R3a,Arb), (Zb,Rj,R1a,R3a,Arc), (Zb,Rj,R1a, R3a,Ard), (Zb,Rj,R1a,R3a,Are), (Zb,Rj,R1a,R3a,Arf), (Zb, Rj,R1a,R3a,Arg), (Zb,Rj,R1a,R3a,Arh), (Zb,Rj,R1a,R3a, Ari), (Zb,Rj,R1a,R3a,Arj), (Zb,Rj,R1a,R3a,Ark), (Zb,Rj, R1a,R3a,Arl), (Zb,Rj,R1a,R3a,Arm), (Zb,Rj,R1a,R3a,Arn), (Zb,Rj,R1a,R3a,Aro), (Zb,Rj,R1a,R3a,Arp), (Zb,Rj,R1a, R3b,Ara), (Zb,Rj,R1a,R3b,Arb), (Zb,Rj,R1a,R3b,Arc), (Zb, Rj,R1a,R3b,Ard), (Zb,Rj,R1a,R3b,Are), (Zb,Rj,R1a,R3b, Arf), (Zb,Rj,R1a,R3b,Arg), (Zb,Rj,R1a,R3b,Arh), (Zb,Rj, R1a,R3b,Ari), (Zb,Rj,R1a,R3b,Arj), (Zb,Rj,R1a,R3b,Ark), (Zb,Rj,R1a,R3b,Arl), (Zb,Rj,R1a,R3b,Arm), (Zb,Rj,R1a, R3b,Arn), (Zb,Rj,R1a,R3b,Aro), (Zb,Rj,R1a,R3b,Arp), (Zb, Rj,R1a,R3c,Ara), (Zb,Rj,R1a,R3c,Arb), (Zb,Rj,R1a,R3c, Arc), (Zb,Rj,R1a,R3c,Ard), (Zb,Rj,R1a,R3c,Are), (Zb,Rj, R1a,R3c,Arf), (Zb,Rj,R1a,R3c,Arg), (Zb,Rj,R1a,R3c,Arh), (Zb,Rj,R1a,R3c,Ari), (Zb,Rj,R1a,R3c,Arj), (Zb,Rj,R1a,R3c, Ark), (Zb,Rj,R1a,R3c,Arl), (Zb,Rj,R1a,R3c,Arm), (Zb,Rj, R1a,R3c,Arn), (Zb,Rj,R1a,R3c,Aro), (Zb,Rj,R1a,R3c,Arp), (Zb,Rj,R1a,R3d,Ara), (Zb,Rj,R1a,R3d,Arb), (Zb,Rj,R1a, R3d,Arc), (Zb,Rj,R1a,R3d,Ard), (Zb,Rj,R1a,R3d,Are), (Zb, Rj,R1a,R3d,Arf), (Zb,Rj,R1a,R3d,Arg), (Zb,Rj,R1a,R3d, Arh), (Zb,Rj,R1a,R3d,Ari), (Zb,Rj,R1a,R3d,Arj), (Zb,Rj, R1a,R3d,Ark), (Zb,Rj,R1a,R3d,Arl), (Zb,Rj,R1a,R3d,Arm), (Zb,Rj,R1a,R3d,Arn), (Zb,Rj,R1a,R3d,Aro), (Zb,Rj,R1a, R3d,Arp), (Zb,Rj,R1a,R3e,Ara), (Zb,Rj,R1a,R3e,Arb), (Zb, Rj,R1a,R3e,Arc), (Zb,Rj,R1a,R3e,Ard), (Zb,Rj,R1a,R3e, Are), (Zb,Rj,R1a,R3e,Arf), (Zb,Rj,R1a,R3e,Arg), (Zb,Rj, R1a,R3e,Arh), (Zb,Rj,R1a,R3e,Ari), (Zb,Rj,R1a,R3e,Arj), (Zb,Rj,R1a,R3e,Ark), (Zb,Rj,R1a,R3e,Arl), (Zb,Rj,R1a, R3e,Arm), (Zb,Rj,R1a,R3e,Arn), (Zb,Rj,R1a,R3e,Aro), (Zb, Rj,R1a,R3e,Arp), (Zb,Rj,R1a,R3f,Ara), (Zb,Rj,R1a,R3f, Arb), (Zb,Rj,R1a,R3f,Arc), (Zb,Rj,R1a,R3f,Ard), (Zb,Rj, R1a,R3f,Are), (Zb,Rj,R1a,R3f,Arf), (Zb,Rj,R1a,R3f,Arg), (Zb,Rj,R1a,R3f,Arh), (Zb,Rj,R1a,R3f,Ari), (Zb,Rj,R1a,R3f, Arj), (Zb,Rj,R1a,R3f,Ark), (Zb,Rj,R1a,R3f,Arl), (Zb,Rj, R1a,R3f,Arm), (Zb,Rj,R1a,R3f,Arn), (Zb,Rj,R1a,R3f,Aro), (Zb,Rj,R1a,R3f,Arp), (Zb,Rj,R1a,R3g,Ara), (Zb,Rj,R1a, R3g,Arb), (Zb,Rj,R1a,R3g,Arc), (Zb,Rj,R1a,R3g,Ard), (Zb, Rj,R1a,R3g,Are), (Zb,Rj,R1a,R3g,Arf), (Zb,Rj,R1a,R3g, Arg), (Zb,Rj,R1a,R3g,Arh), (Zb,Rj,R1a,R3g,Ari), (Zb,Rj, R1a,R3g,Arj), (Zb,Rj,R1a,R3g,Ark), (Zb,Rj,R1a,R3g,Arl), (Zb,Rj,R1a,R3g,Arm), (Zb,Rj,R1a,R3g,Arn), (Zb,Rj,R1a, R3g,Aro), (Zb,Rj,R1a,R3g,Arp), (Zb,Rj,R1a,R3h,Ara), (Zb, Rj,R1a,R3h,Arb), (Zb,Rj,R1a,R3h,Arc), (Zb,Rj,R1a,R3h, Ard), (Zb,Rj,R1a,R3h,Are), (Zb,Rj,R1a,R3h,Arf), (Zb,Rj, R1a,R3h,Arg), (Zb,Rj,R1a,R3h,Arh), (Zb,Rj,R1a,R3h,Ari), (Zb,Rj,R1a,R3h,Arj), (Zb,Rj,R1a,R3h,Ark), (Zb,Rj,R1a, R3h,Arl), (Zb,Rj,R1a,R3h,Arm), (Zb,Rj,R1a,R3h,Arn), (Zb, Rj,R1a,R3h,Aro), (Zb,Rj,R1a,R3h,Arp), (Zb,Rj,R1b,R3a, Ara), (Zb,Rj,R1b,R3a,Arb), (Zb,Rj,R1b,R3a,Arc), (Zb,Rj, R1b,R3a,Ard), (Zb,Rj,R1b,R3a,Are), (Zb,Rj,R1b,R3a,Arf), (Zb,Rj,R1b,R3a,Arg), (Zb,Rj,R1b,R3a,Arh), (Zb,Rj,R1b, R3a,Ari), (Zb,Rj,R1b,R3a,Arj), (Zb,Rj,R1b,R3a,Ark), (Zb, Rj,R1b,R3a,Arl), (Zb,Rj,R1b,R3a,Arm), (Zb,Rj,R1b,R3a, Arn), (Zb,Rj,R1b,R3a,Aro), (Zb,Rj,R1b,R3a,Arp), (Zb,Rj, R1b,R3b,Ara), (Zb,Rj,R1b,R3b,Arb), (Zb,Rj,R1b,R3b,Arc), (Zb,Rj,R1b,R3b,Ard), (Zb,Rj,R1b,R3b,Are), (Zb,Rj,R1b, R3b,Arf), (Zb,Rj,R1b,R3b,Arg), (Zb,Rj,R1b,R3b,Arh), (Zb, Rj,R1b,R3b,Ari), (Zb,Rj,R1b,R3b,Arj), (Zb,Rj,R1b,R3b, Ark), (Zb,Rj,R1b,R3b,Arl), (Zb,Rj,R1b,R3b,Arm), (Zb,Rj, R1b,R3b,Arn), (Zb,Rj,R1b,R3b,Aro), (Zb,Rj,R1b,R3b,Arp), (Zb,Rj,R1b,R3c,Ara), (Zb,Rj,R1b,R3c,Arb), (Zb,Rj,R1b, R3c,Arc), (Zb,Rj,R1b,R3c,Ard), (Zb,Rj,R1b,R3c,Are), (Zb, Rj,R1b,R3c,Arf), (Zb,Rj,R1b,R3c,Arg), (Zb,Rj,R1b,R3c, Arh), (Zb,Rj,R1b,R3c,Ari), (Zb,Rj,R1b,R3c,Arj), (Zb,Rj, R1b,R3c,Ark), (Zb,Rj,R1b,R3c,Arl), (Zb,Rj,R1b,R3c,Arm), (Zb,Rj,R1b,R3c,Arn), (Zb,Rj,R1b,R3c,Aro), (Zb,Rj,R1b, R3c,Arp), (Zb,Rj,R1b,R3d,Ara), (Zb,Rj,R1b,R3d,Arb), (Zb, Rj,R1b,R3d,Arc), (Zb,Rj,R1b,R3d,Ard), (Zb,Rj,R1b,R3d, Are), (Zb,Rj,R1b,R3d,Arf), (Zb,Rj,R1b,R3d,Arg), (Zb,Rj, R1b,R3d,Arh), (Zb,Rj,R1b,R3d,Ari), (Zb,Rj,R1b,R3d,Arj), (Zb,Rj,R1b,R3d,Ark), (Zb,Rj,R1b,R3d,Arl), (Zb,Rj,R1b, R3d,Arm), (Zb,Rj,R1b,R3d,Arn), (Zb,Rj,R1b,R3d,Aro), (Zb,Rj,R1b,R3d,Arp), (Zb,Rj,R1b,R3e,Ara), (Zb,Rj,R1b, R3e,Arb), (Zb,Rj,R1b,R3e,Arc), (Zb,Rj,R1b,R3e,Ard), (Zb, Rj,R1b,R3e,Are), (Zb,Rj,R1b,R3e,Arf), (Zb,Rj,R1b,R3e, Arg), (Zb,Rj,R1b,R3e,Arh), (Zb,Rj,R1b,R3e,Ari), (Zb,Rj, R1b,R3e,Arj), (Zb,Rj,R1b,R3e,Ark), (Zb,Rj,R1b,R3e,Arl), (Zb,Rj,R1b,R3e,Arm), (Zb,Rj,R1b,R3e,Arn), (Zb,Rj,R1b, R3e,Aro), (Zb,Rj,R1b,R3e,Arp), (Zb,Rj,R1b,R3f,Ara), (Zb, Rj,R1b,R3f,Arb), (Zb,Rj,R1b,R3f,Arc), (Zb,Rj,R1b,R3f, Ard), (Zb,Rj,R1b,R3f,Are), (Zb,Rj,R1b,R3f,Arf), (Zb,Rj, R1b,R3f,Arg), (Zb,Rj,R1b,R3f,Arh), (Zb,Rj,R1b,R3f,Ari), (Zb,Rj,R1b,R3f,Arj), (Zb,Rj,R1b,R3f,Ark), (Zb,Rj,R1b, R3f,Arl), (Zb,Rj,R1b,R3f,Arm), (Zb,Rj,R1b,R3f,Arn), (Zb, Rj,R1b,R3f,Aro), (Zb,Rj,R1b,R3f,Arp), (Zb,Rj,R1b,R3g, Ara), (Zb,Rj,R1b,R3g,Arb), (Zb,Rj,R1b,R3g,Arc), (Zb,Rj, R1b,R3g,Ard), (Zb,Rj,R1b,R3g,Are), (Zb,Rj,R1b,R3g,Arf), (Zb,Rj,R1b,R3g,Arg), (Zb,Rj,R1b,R3g,Arh), (Zb,Rj,R1b, R3g,Ari), (Zb,Rj,R1b,R3g,Arj), (Zb,Rj,R1b,R3g,Ark), (Zb, Rj,R1b,R3g,Arl), (Zb,Rj,R1b,R3g,Arm), (Zb,Rj,R1b,R3g, Arn), (Zb,Rj,R1b,R3g,Aro), (Zb,Rj,R1b,R3g,Arp), (Zb,Rj, R1b,R3h,Ara), (Zb,Rj,R1b,R3h,Arb), (Zb,Rj,R1b,R3h,Arc), (Zb,Rj,R1b,R3h,Ard), (Zb,Rj,R1b,R3h,Are), (Zb,Rj,R1b, R3h,Arf), (Zb,Rj,R1b,R3h,Arg), (Zb,Rj,R1b,R3h,Arh), (Zb, Rj,R1b,R3h,Ari), (Zb,Rj,R1b,R3h,Arj), (Zb,Rj,R1b,R3h, Ark), (Zb,Rj,R1b,R3h,Arl), (Zb,Rj,R1b,R3h,Arm), (Zb,Rj, R1b,R3h,Arn), (Zb,Rj,R1b,R3h,Aro), (Zb,Rj,R1b,R3h,Arp), (Zb,Rj,R1c,R3a,Ara), (Zb,Rj,R1c,R3a,Arb), (Zb,Rj,R1c, R3a,Arc), (Zb,Rj,R1c,R3a,Ard), (Zb,Rj,R1c,R3a,Are), (Zb, Rj,R1c,R3a,Arf), (Zb,Rj,R1c,R3a,Arg), (Zb,Rj,R1c,R3a, Arh), (Zb,Rj,R1c,R3a,Ari), (Zb,Rj,R1c,R3a,Arj), (Zb,Rj, R1c,R3a,Ark), (Zb,Rj,R1c,R3a,Arl), (Zb,Rj,R1c,R3a,Arm), (Zb,Rj,R1c,R3a,Arn), (Zb,Rj,R1c,R3a,Aro), (Zb,Rj,R1c, R3a,Arp), (Zb,Rj,R1c,R3b,Ara), (Zb,Rj,R1c,R3b,Arb), (Zb, Rj,R1c,R3b,Arc), (Zb,Rj,R1c,R3b,Ard), (Zb,Rj,R1c,R3b, Are), (Zb,Rj,R1c,R3b,Arf), (Zb,Rj,R1c,R3b,Arg), (Zb,Rj, R1c,R3b,Arh), (Zb,Rj,R1c,R3b,Ari), (Zb,Rj,R1c,R3b,Arj), (Zb,Rj,R1c,R3b,Ark), (Zb,Rj,R1c,R3b,Arl), (Zb,Rj,R1c, R3b,Arm), (Zb,Rj,R1c,R3b,Arn), (Zb,Rj,R1c,R3b,Aro), (Zb,Rj,R1c,R3b,Arp), (Zb,Rj,R1c,R3c,Ara), (Zb,Rj,R1c, R3c,Arb), (Zb,Rj,R1c,R3c,Arc), (Zb,Rj,R1c,R3c,Ard), (Zb, Rj,R1c,R3c,Are), (Zb,Rj,R1c,R3c,Arf), (Zb,Rj,R1c,R3c, Arg), (Zb,Rj,R1c,R3c,Arh), (Zb,Rj,R1c,R3c,Ari), (Zb,Rj, R1c,R3c,Arj), (Zb,Rj,R1c,R3c,Ark), (Zb,Rj,R1c,R3c,Arl), (Zb,Rj,R1c,R3c,Arm), (Zb,Rj,R1c,R3c,Arn), (Zb,Rj,R1c, R3c,Aro), (Zb,Rj,R1c,R3c,Arp), (Zb,Rj,R1c,R3d,Ara), (Zb, Rj,R1c,R3d,Arb), (Zb,Rj,R1c,R3d,Arc), (Zb,Rj,R1c,R3d, Ard), (Zb,Rj,R1c,R3d,Are), (Zb,Rj,R1c,R3d,Arf), (Zb,Rj, R1c,R3d,Arg), (Zb,Rj,R1c,R3d,Arh), (Zb,Rj,R1c,R3d,Ari), (Zb,Rj,R1c,R3d,Arj), (Zb,Rj,R1c,R3d,Ark), (Zb,Rj,R1c, R3d,Arl), (Zb,Rj,R1c,R3d,Arm), (Zb,Rj,R1c,R3d,Arn), (Zb, Rj,R1c,R3d,Aro), (Zb,Rj,R1c,R3d,Arp), (Zb,Rj,R1c,R3e, Ara), (Zb,Rj,R1c,R3e,Arb), (Zb,Rj,R1c,R3e,Arc), (Zb,Rj, R1c,R3e,Ard), (Zb,Rj,R1c,R3e,Are), (Zb,Rj,R1c,R3e,Arf), (Zb,Rj,R1c,R3e,Arg), (Zb,Rj,R1c,R3e,Arh), (Zb,Rj,R1c, R3e,Ari), (Zb,Rj,R1c,R3e,Arj), (Zb,Rj,R1c,R3e,Ark), (Zb, Rj,R1c,R3e,Arl), (Zb,Rj,R1c,R3e,Arm), (Zb,Rj,R1c,R3e, Arn), (Zb,Rj,R1c,R3e,Aro), (Zb,Rj,R1c,R3e,Arp), (Zb,Rj, R1c,R3f,Ara), (Zb,Rj,R1c,R3f,Arb), (Zb,Rj,R1c,R3f,Arc), (Zb,Rj,R1c,R3f,Ard), (Zb,Rj,R1c,R3f,Are), (Zb,Rj,R1c, R3f,Arf), (Zb,Rj,R1c,R3f,Arg), (Zb,Rj,R1c,R3f,Arh), (Zb, Rj,R1c,R3f,Ari), (Zb,Rj,R1c,R3f,Arj), (Zb,Rj,R1c,R3f, Ark), (Zb,Rj,R1c,R3f,Arl), (Zb,Rj,R1c,R3f,Arm), (Zb,Rj, R1c,R3f,Arn), (Zb,Rj,R1c,R3f,Aro), (Zb,Rj,R1c,R3f,Arp), (Zb,Rj,R1c,R3g,Ara), (Zb,Rj,R1c,R3g,Arb), (Zb,Rj,R1c, R3g,Arc), (Zb,Rj,R1c,R3g,Ard), (Zb,Rj,R1c,R3g,Are), (Zb, Rj,R1c,R3g,Arf), (Zb,Rj,R1c,R3g,Arg), (Zb,Rj,R1c,R3g, Arh), (Zb,Rj,R1c,R3g,Ari), (Zb,Rj,R1c,R3g,Arj), (Zb,Rj, R1c,R3g,Ark), (Zb,Rj,R1c,R3g,Arl), (Zb,Rj,R1c,R3g,Arm), (Zb,Rj,R1c,R3g,Arn), (Zb,Rj,R1c,R3g,Aro), (Zb,Rj,R1c, R3g,Arp), (Zb,Rj,R1c,R3h,Ara), (Zb,Rj,R1c,R3h,Arb), (Zb, Rj,R1c,R3h,Arc), (Zb,Rj,R1c,R3h,Ard), (Zb,Rj,R1c,R3h, Are), (Zb,Rj,R1c,R3h,Arf), (Zb,Rj,R1c,R3h,Arg), (Zb,Rj, R1c,R3h,Arh), (Zb,Rj,R1c,R3h,Ari), (Zb,Rj,R1c,R3h,Arj), (Zb,Rj,R1c,R3h,Ark), (Zb,Rj,R1c,R3h,Arl), (Zb,Rj,R1c, R3h,Arm), (Zb,Rj,R1c,R3h,Arn), (Zb,Rj,R1c,R3h,Aro), (Zb,Rj,R1c,R3h,Arp), (Zb,Rj,R1d,R3a,Ara), (Zb,Rj,R1d, R3a,Arb), (Zb,Rj,R1d,R3a,Arc), (Zb,Rj,R1d,R3a,Ard), (Zb, Rj,R1d,R3a,Are), (Zb,Rj,R1d,R3a,Arf), (Zb,Rj,R1d,R3a, Arg), (Zb,Rj,R1d,R3a,Arh), (Zb,Rj,R1d,R3a,Ari), (Zb,Rj, R1d,R3a,Arj), (Zb,Rj,R1d,R3a,Ark), (Zb,Rj,R1d,R3a,Arl), (Zb,Rj,R1d,R3a,Arm), (Zb,Rj,R1d,R3a,Arn), (Zb,Rj,R1d, R3a,Aro), (Zb,Rj,R1d,R3a,Arp), (Zb,Rj,R1d,R3b,Ara), (Zb, Rj,R1d,R3b,Arb), (Zb,Rj,R1d,R3b,Arc), (Zb,Rj,R1d,R3b, Ard), (Zb,Rj,R1d,R3b,Are), (Zb,Rj,R1d,R3b,Arf), (Zb,Rj, R1d,R3b,Arg), (Zb,Rj,R1d,R3b,Arh), (Zb,Rj,R1d,R3b,Ari), (Zb,Rj,R1d,R3b,Arj), (Zb,Rj,R1d,R3b,Ark), (Zb,Rj,R1d, R3b,Arl), (Zb,Rj,R1d,R3b,Arm), (Zb,Rj,R1d,R3b,Arn), (Zb, Rj,R1d,R3b,Aro), (Zb,Rj,R1d,R3b,Arp), (Zb,Rj,R1d,R3c, Ara), (Zb,Rj,R1d,R3c,Arb), (Zb,Rj,R1d,R3c,Arc), (Zb,Rj, R1d,R3c,Ard), (Zb,Rj,R1d,R3c,Are), (Zb,Rj,R1d,R3c,Arf), (Zb,Rj,R1d,R3c,Arg), (Zb,Rj,R1d,R3c,Arh), (Zb,Rj,R1d, R3c,Ari), (Zb,Rj,R1d,R3c,Arj), (Zb,Rj,R1d,R3c,Ark), (Zb, Rj,R1d,R3c,Arl), (Zb,Rj,R1d,R3c,Arm), (Zb,Rj,R1d,R3c, Arn), (Zb,Rj,R1d,R3c,Aro), (Zb,Rj,R1d,R3c,Arp), (Zb,Rj, R1d,R3d,Ara), (Zb,Rj,R1d,R3d,Arb), (Zb,Rj,R1d,R3d,Arc), (Zb,Rj,R1d,R3d,Ard), (Zb,Rj,R1d,R3d,Are), (Zb,Rj,R1d, R3d,Arf), (Zb,Rj,R1d,R3d,Arg), (Zb,Rj,R1d,R3d,Arh), (Zb, Rj,R1d,R3d,Ari), (Zb,Rj,R1d,R3d,Arj), (Zb,Rj,R1d,R3d, Ark), (Zb,Rj,R1d,R3d,Arl), (Zb,Rj,R1d,R3d,Arm), (Zb,Rj, R1d,R3d,Arn), (Zb,Rj,R1d,R3d,Aro), (Zb,Rj,R1d,R3d,Arp), (Zb,Rj,R1d,R3e,Ara), (Zb,Rj,R1d,R3e,Arb), (Zb,Rj,R1d, R3e,Arc), (Zb,Rj,R1d,R3e,Ard), (Zb,Rj,R1d,R3e,Are), (Zb, Rj,R1d,R3e,Arf), (Zb,Rj,R1d,R3e,Arg), (Zb,Rj,R1d,R3e, Arh), (Zb,Rj,R1d,R3e,Ari), (Zb,Rj,R1d,R3e,Arj), (Zb,Rj, R1d,R3e,Ark), (Zb,Rj,R1d,R3e,Arl), (Zb,Rj,R1d,R3e,Arm), (Zb,Rj,R1d,R3e,Arn), (Zb,Rj,R1d,R3e,Aro), (Zb,Rj,R1d, R3e,Arp), (Zb,Rj,R1d,R3f,Ara), (Zb,Rj,R1d,R3f,Arb), (Zb, Rj,R1d,R3f,Arc), (Zb,Rj,R1d,R3f,Ard), (Zb,Rj,R1d,R3f, Are), (Zb,Rj,R1d,R3f,Arf), (Zb,Rj,R1d,R3f,Arg), (Zb,Rj, R1d,R3f,Arh), (Zb,Rj,R1d,R3f,Ari), (Zb,Rj,R1d,R3f,Arj), (Zb,Rj,R1d,R3f,Ark), (Zb,Rj,R1d,R3f,Arl), (Zb,Rj,R1d, R3f,Arm), (Zb,Rj,R1d,R3f,Arn), (Zb,Rj,R1d,R3f,Aro), (Zb, Rj,R1d,R3f,Arp), (Zb,Rj,R1d,R3g,Ara), (Zb,Rj,R1d,R3g, Arb), (Zb,Rj,R1d,R3g,Arc), (Zb,Rj,R1d,R3g,Ard), (Zb,Rj, R1d,R3g,Are), (Zb,Rj,R1d,R3g,Arf), (Zb,Rj,R1d,R3g,Arg), (Zb,Rj,R1d,R3g,Arh), (Zb,Rj,R1d,R3g,Ari), (Zb,Rj,R1d, R3g,Arj), (Zb,Rj,R1d,R3g,Ark), (Zb,Rj,R1d,R3g,Arl), (Zb, Rj,R1d,R3g,Arm), (Zb,Rj,R1d,R3g,Arn), (Zb,Rj,R1d,R3g, Aro), (Zb,Rj,R1d,R3g,Arp), (Zb,Rj,R1d,R3h,Ara), (Zb,Rj, R1d,R3h,Arb), (Zb,Rj,R1d,R3h,Arc), (Zb,Rj,R1d,R3h,Ard), (Zb,Rj,R1d,R3h,Are), (Zb,Rj,R1d,R3h,Arf), (Zb,Rj,R1d, R3h,Arg), (Zb,Rj,R1d,R3h,Arh), (Zb,Rj,R1d,R3h,Ari), (Zb, Rj,R1d,R3h,Arj), (Zb,Rj,R1d,R3h,Ark), (Zb,Rj,R1d,R3h, Arl), (Zb,Rj,R1d,R3h,Arm), (Zb,Rj,R1d,R3h,Arn), (Zb,Rj, R1d,R3h,Aro), (Zb,Rj,R1d,R3h,Arp), (Zc,Ra,R1a,R3a,Ara), (Zc,Ra,R1a,R3a,Arb), (Zc,Ra,R1a,R3a,Arc), (Zc,Ra,R1a, R3a,Ard), (Zc,Ra,R1a,R3a,Are), (Zc,Ra,R1a,R3a,Arf), (Zc, Ra,R1a,R3a,Arg), (Zc,Ra,R1a,R3a,Arh), (Zc,Ra,R1a,R3a, Ari), (Zc,Ra,R1a,R3a,Arj), (Zc,Ra,R1a,R3a,Ark), (Zc,Ra, R1a,R3a,Arl), (Zc,Ra,R1a,R3a,Arm), (Zc,Ra,R1a,R3a,Arn), (Zc,Ra,R1a,R3a,Aro), (Zc,Ra,R1a,R3a,Arp), (Zc,Ra,R1a, R3b,Ara), (Zc,Ra,R1a,R3b,Arb), (Zc,Ra,R1a,R3b,Arc), (Zc, Ra,R1a,R3b,Ard), (Zc,Ra,R1a,R3b,Are), (Zc,Ra,R1a,R3b, Arf), (Zc,Ra,R1a,R3b,Arg), (Zc,Ra,R1a,R3b,Arh), (Zc,Ra, R1a,R3b,Ari), (Zc,Ra,R1a,R3b,Arj), (Zc,Ra,R1a,R3b,Ark), (Zc,Ra,R1a,R3b,Arl), (Zc,Ra,R1a,R3b,Arm), (Zc,Ra,R1a, R3b,Arn), (Zc,Ra,R1a,R3b,Aro), (Zc,Ra,R1a,R3b,Arp), (Zc, Ra,R1a,R3c,Ara), (Zc,Ra,R1a,R3c,Arb), (Zc,Ra,R1a,R3c, Arc), (Zc,Ra,R1a,R3c,Ard), (Zc,Ra,R1a,R3c,Are), (Zc,Ra, R1a,R3c,Arf), (Zc,Ra,R1a,R3c,Arg), (Zc,Ra,R1a,R3c,Arh), (Zc,Ra,R1a,R3c,Ari), (Zc,Ra,R1a,R3c,Arj), (Zc,Ra,R1a, R3c,Ark), (Zc,Ra,R1a,R3c,Arl), (Zc,Ra,R1a,R3c,Arm), (Zc, Ra,R1a,R3c,Arn), (Zc,Ra,R1a,R3c,Aro), (Zc,Ra,R1a,R3c, Arp), (Zc,Ra,R1a,R3d,Ara), (Zc,Ra,R1a,R3d,Arb), (Zc,Ra, R1a,R3d,Arc), (Zc,Ra,R1a,R3d,Ard), (Zc,Ra,R1a,R3d,Are), (Zc,Ra,R1a,R3d,Arf), (Zc,Ra,R1a,R3d,Arg), (Zc,Ra,R1a, R3d,Arh), (Zc,Ra,R1a,R3d,Ari), (Zc,Ra,R1a,R3d,Arj), (Zc, Ra,R1a,R3d,Ark), (Zc,Ra,R1a,R3d,Arl), (Zc,Ra,R1a,R3d, Arm), (Zc,Ra,R1a,R3d,Arn), (Zc,Ra,R1a,R3d,Aro), (Zc,Ra, R1a,R3d,Arp), (Zc,Ra,R1a,R3e,Ara), (Zc,Ra,R1a,R3e,Arb), (Zc,Ra,R1a,R3e,Arc), (Zc,Ra,R1a,R3e,Ard), (Zc,Ra,R1a, R3e,Are), (Zc,Ra,R1a,R3e,Arf), (Zc,Ra,R1a,R3e,Arg), (Zc, Ra,R1a,R3e,Arh), (Zc,Ra,R1a,R3e,Ari), (Zc,Ra,R1a,R3e, Arj), (Zc,Ra,R1a,R3e,Ark), (Zc,Ra,R1a,R3e,Arl), (Zc,Ra, R1a,R3e,Arm), (Zc,Ra,R1a,R3e,Arn), (Zc,Ra,R1a,R3e, Aro), (Zc,Ra,R1a,R3e,Arp), (Zc,Ra,R1a,R3f,Ara), (Zc,Ra, R1a,R3f,Arb), (Zc,Ra,R1a,R3f,Arc), (Zc,Ra,R1a,R3f,Ard), (Zc,Ra,R1a,R3f,Are), (Zc,Ra,R1a,R3f,Arf), (Zc,Ra,R1a, R3f,Arg), (Zc,Ra,R1a,R3f,Arh), (Zc,Ra,R1a,R3f,Ari), (Zc, Ra,R1a,R3f,Arj), (Zc,Ra,R1a,R3f,Ark), (Zc,Ra,R1a,R3f, Arl), (Zc,Ra,R1a,R3f,Arm), (Zc,Ra,R1a,R3f,Arn), (Zc,Ra, R1a,R3f,Aro), (Zc,Ra,R1a,R3f,Arp), (Zc,Ra,R1a,R3g,Ara), (Zc,Ra,R1a,R3g,Arb), (Zc,Ra,R1a,R3g,Arc), (Zc,Ra,R1a, R3g,Ard), (Zc,Ra,R1a,R3g,Are), (Zc,Ra,R1a,R3g,Arf), (Zc, Ra,R1a,R3g,Arg), (Zc,Ra,R1a,R3g,Arh), (Zc,Ra,R1a,R3g, Ari), (Zc,Ra,R1a,R3g,Arj), (Zc,Ra,R1a,R3g,Ark), (Zc,Ra, R1a,R3g,Arl), (Zc,Ra,R1a,R3g,Arm), (Zc,Ra,R1a,R3g, Arn), (Zc,Ra,R1a,R3g,Aro), (Zc,Ra,R1a,R3g,Arp), (Zc,Ra, R1a,R3h,Ara), (Zc,Ra,R1a,R3h,Arb), (Zc,Ra,R1a,R3h,Arc), (Zc,Ra,R1a,R3h,Ard), (Zc,Ra,R1a,R3h,Are), (Zc,Ra,R1a, R3h,Arf), (Zc,Ra,R1a,R3h,Arg), (Zc,Ra,R1a,R3h,Arh), (Zc, Ra,R1a,R3h,Ari), (Zc,Ra,R1a,R3h,Arj), (Zc,Ra,R1a,R3h, Ark), (Zc,Ra,R1a,R3h,Arl), (Zc,Ra,R1a,R3h,Arm), (Zc,Ra, R1a,R3h,Arn), (Zc,Ra,R1a,R3h,Aro), (Zc,Ra,R1a,R3h, Arp), (Zc,Ra,R1b,R3a,Ara), (Zc,Ra,R1b,R3a,Arb), (Zc,Ra, R1b,R3a,Arc), (Zc,Ra,R1b,R3a,Ard), (Zc,Ra,R1b,R3a,Are), (Zc,Ra,R1b,R3a,Arf), (Zc,Ra,R1b,R3a,Arg), (Zc,Ra,R1b, R3a,Arh), (Zc,Ra,R1b,R3a,Ari), (Zc,Ra,R1b,R3a,Arj), (Zc, Ra,R1b,R3a,Ark), (Zc,Ra,R1b,R3a,Arl), (Zc,Ra,R1b,R3a, Arm), (Zc,Ra,R1b,R3a,Arn), (Zc,Ra,R1b,R3a,Aro), (Zc,Ra, R1b,R3a,Arp), (Zc,Ra,R1b,R3b,Ara), (Zc,Ra,R1b,R3b, Arb), (Zc,Ra,R1b,R3b,Arc), (Zc,Ra,R1b,R3b,Ard), (Zc,Ra, R1b,R3b,Are), (Zc,Ra,R1b,R3b,Arf), (Zc,Ra,R1b,R3b,Arg), (Zc,Ra,R1b,R3b,Arh), (Zc,Ra,R1b,R3b,Ari), (Zc,Ra,R1b, R3b,Arj), (Zc,Ra,R1b,R3b,Ark), (Zc,Ra,R1b,R3b,Arl), (Zc, Ra,R1b,R3b,Arm), (Zc,Ra,R1b,R3b,Arn), (Zc,Ra,R1b,R3b, Aro), (Zc,Ra,R1b,R3b,Arp), (Zc,Ra,R1b,R3c,Ara), (Zc,Ra, R1b,R3c,Arb), (Zc,Ra,R1b,R3c,Arc), (Zc,Ra,R1b,R3c,Ard), (Zc,Ra,R1b,R3c,Are), (Zc,Ra,R1b,R3c,Arf), (Zc,Ra,R1b,R3c,Arg), (Zc,Ra,R1b,R3c,Arh), (Zc,Ra,R1b,R3c,Ari), (Zc,Ra,R1b,R3c,Arj), (Zc,Ra,R1b,R3c,Ark), (Zc,Ra,R1b,R3c,Arl), (Zc,Ra,R1b,R3c,Arm), (Zc,Ra,R1b,R3c,Arn), (Zc,Ra,R1b,R3c,Aro), (Zc,Ra,R1b,R3c,Arp), (Zc,Ra,R1b,R3d,Ara), (Zc,Ra,R1b,R3d,Arb), (Zc,Ra,R1b,R3d,Arc), (Zc,Ra,R1b,R3d,Ard), (Zc,Ra,R1b,R3d,Are), (Zc,Ra,R1b,R3d,Arf), (Zc,Ra,R1b,R3d,Arg), (Zc,Ra,R1b,R3d,Arh), (Zc,Ra,R1b,R3d,Ari), (Zc,Ra,R1b,R3d,Arj), (Zc,Ra,R1b,R3d,Ark), (Zc,Ra,R1b,R3d,Arl), (Zc,Ra,R1b,R3d,Arm), (Zc,Ra,R1b,R3d,Arn), (Zc,Ra,R1b,R3d,Aro), (Zc,Ra,R1b,R3d,Arp), (Zc,Ra,R1b,R3e,Ara), (Zc,Ra,R1b,R3e,Arb), (Zc,Ra,R1b,R3e,Arc), (Zc,Ra,R1b,R3e,Ard), (Zc,Ra,R1b,R3e,Are), (Zc,Ra,R1b,R3e,Arf), (Zc,Ra,R1b,R3e,Arg), (Zc,Ra,R1b,R3e,Arh), (Zc,Ra,R1b,R3e,Ari), (Zc,Ra,R1b,R3e,Arj), (Zc,Ra,R1b,R3e,Ark), (Zc,Ra,R1b,R3e,Arl), (Zc,Ra,R1b,R3e,Arm), (Zc,Ra,R1b,R3e,Arn), (Zc,Ra,R1b,R3e,Aro), (Zc,Ra,R1b,R3e,Arp), (Zc,Ra,R1b,R3f,Ara), (Zc,Ra,R1b,R3f,Arb), (Zc,Ra,R1b,R3f,Arc), (Zc,Ra,R1b,R3f,Ard), (Zc,Ra,R1b,R3f,Are), (Zc,Ra,R1b,R3f,Arf), (Zc,Ra,R1b,R3f,Arg), (Zc,Ra,R1b,R3f,Arh), (Zc,Ra,R1b,R3f,Ari), (Zc,Ra,R1b,R3f,Arj), (Zc,Ra,R1b,R3f,Ark), (Zc,Ra,R1b,R3f,Arl), (Zc,Ra,R1b,R3f,Arm), (Zc,Ra,R1b,R3f,Arn), (Zc,Ra,R1b,R3f,Aro), (Zc,Ra,R1b,R3f,Arp), (Zc,Ra,R1b,R3g,Ara), (Zc,Ra,R1b,R3g,Arb), (Zc,Ra,R1b,R3g,Arc), (Zc,Ra,R1b,R3g,Ard), (Zc,Ra,R1b,R3g,Are), (Zc,Ra,R1b,R3g,Arf), (Zc,Ra,R1b,R3g,Arg), (Zc,Ra,R1b,R3g,Arh), (Zc,Ra,R1b,R3g,Ari), (Zc,Ra,R1b,R3g,Arj), (Zc,Ra,R1b,R3g,Ark), (Zc,Ra,R1b,R3g,Arl), (Zc,Ra,R1b,R3g,Arm), (Zc,Ra,R1b,R3g,Arn), (Zc,Ra,R1b,R3g,Aro), (Zc,Ra,R1b,R3g,Arp), (Zc,Ra,R1b,R3h,Ara), (Zc,Ra,R1b,R3h,Arb), (Zc,Ra,R1b,R3h,Arc), (Zc,Ra,R1b,R3h,Ard), (Zc,Ra,R1b,R3h,Are), (Zc,Ra,R1b,R3h,Arf), (Zc,Ra,R1b,R3h,Arg), (Zc,Ra,R1b,R3h,Arh), (Zc,Ra,R1b,R3h,Ari), (Zc,Ra,R1b,R3h,Arj), (Zc,Ra,R1b,R3h,Ark), (Zc,Ra,R1b,R3h,Arl), (Zc,Ra,R1b,R3h,Arm), (Zc,Ra,R1b,R3h,Arn), (Zc,Ra,R1b,R3h,Aro), (Zc,Ra,R1b,R3h,Arp), (Zc,Ra,R1c,R3a,Ara), (Zc,Ra,R1c,R3a,Arb), (Zc,Ra,R1c,R3a,Arc), (Zc,Ra,R1c,R3a,Ard), (Zc,Ra,R1c,R3a,Are), (Zc,Ra,R1c,R3a,Arf), (Zc,Ra,R1c,R3a,Arg), (Zc,Ra,R1c,R3a,Arh), (Zc,Ra,R1c,R3a,Ari), (Zc,Ra,R1c,R3a,Arj), (Zc,Ra,R1c,R3a,Ark), (Zc,Ra,R1c,R3a,Arl), (Zc,Ra,R1c,R3a,Arm), (Zc,Ra,R1c,R3a,Arn), (Zc,Ra,R1c,R3a,Aro), (Zc,Ra,R1c,R3a,Arp), (Zc,Ra,R1c,R3b,Ara), (Ze,Ra,R1c,R3b,Arb), (Zc,Ra,R1c,R3b,Arc), (Zc,Ra,R1c,R3b,Ard), (Zc,Ra,R1c,R3b,Are), (Zc,Ra,R1c,R3b,Arf), (Zc,Ra,R1c,R3b,Arg), (Zc,Ra,R1c,R3b,Arh), (Zc,Ra,R1c,R3b,Ari), (Zc,Ra,R1c,R3b,Arj), (Zc,Ra,R1c,R3b,Ark), (Zc,Ra,R1c,R3b,Arl), (Zc,Ra,R1c,R3b,Arm), (Zc,Ra,R1c,R3b,Arn), (Zc,Ra,R1c,R3b,Aro), (Zc,Ra,R1c,R3b,Arp), (Zc,Ra,R1c,R3c,Ara), (Zc,Ra,R1c,R3c,Arb), (Zc,Ra,R1c,R3c,Arc), (Zc,Ra,R1c,R3c,Ard), (Zc,Ra,R1c,R3c,Are), (Zc,Ra,R1c,R3c,Arf), (Zc,Ra,R1c,R3c,Arg), (Zc,Ra,R1c,R3c,Arh), (Zc,Ra,R1c,R3c,Ari), (Zc,Ra,R1c,R3c,Arj), (Zc,Ra,R1c,R3c,Ark), (Zc,Ra,R1c,R3c,Arl), (Zc,Ra,R1c,R3c,Arm), (Zc,Ra,R1c,R3c,Arn), (Zc,Ra,R1c,R3c,Aro), (Zc,Ra,R1c,R3c,Arp), (Zc,Ra,R1c,R3d,Ara), (Zc,Ra,R1c,R3d,Arb), (Zc,Ra,R1c,R3d,Arc), (Zc,Ra,R1c,R3d,Ard), (Zc,Ra,R1c,R3d,Are), (Zc,Ra,R1c,R3d,Arf), (Zc,Ra,R1c,R3d,Arg), (Zc,Ra,R1c,R3d,Arh), (Zc,Ra,R1c,R3d,Ari), (Zc,Ra,R1c,R3d,Arj), (Zc,Ra,R1c,R3d,Ark), (Zc,Ra,R1c,R3d,Arl), (Zc,Ra,R1c,R3d,Arm), (Zc,Ra,R1c,R3d,Arn), (Zc,Ra,R1c,R3d,Aro), (Zc,Ra,R1c,R3d,Arp), (Zc,Ra,R1c,R3e,Ara), (Zc,Ra,R1c,R3e,Arb), (Zc,Ra,R1c,R3e,Arc), (Zc,Ra,R1c,R3e,Ard), (Zc,Ra,R1c,R3e,Are), (Zc,Ra,R1c,R3e,Arf), (Zc,Ra,R1c,R3e,Arg), (Zc,Ra,R1c,R3e,Arh), (Zc,Ra,R1c,R3e,Ari), (Zc,Ra,R1c,R3e,Arj), (Zc,Ra,R1c,R3e,Ark), (Zc,Ra,R1c,R3e,Arl), (Zc,Ra,R1c,R3e,Arm), (Zc,Ra,R1c,R3e,Arn), (Zc,Ra,R1c,R3e,Aro), (Zc,Ra,R1c,R3e,Arp), (Zc,Ra,R1c,R3f,Ara), (Zc,Ra,R1c,R3f,Arb), (Zc,Ra,R1c,R3f,Arc), (Zc,Ra,R1c,R3f,Ard), (Zc,Ra,R1c,R3f,Are), (Zc,Ra,R1c,R3f,Arf), (Zc,Ra,R1c,R3f,Arg), (Zc,Ra,R1c,R3f,Arh), (Zc,Ra,R1c,R3f,Ari), (Zc,Ra,R1c,R3f,Arj), (Zc,Ra,R1c,R3f,Ark), (Zc,Ra,R1c,R3f,Arl), (Zc,Ra,R1c,R3f,Arm), (Zc,Ra,R1c,R3f,Arn), (Zc,Ra,R1c,R3f,Aro), (Zc,Ra,R1c,R3f,Arp), (Zc,Ra,R1c,R3g,Ara), (Zc,Ra,R1c,R3g,Arb), (Zc,Ra,R1c,R3g,Arc), (Zc,Ra,R1c,R3g,Ard), (Zc,Ra,R1c,R3g,Are), (Zc,Ra,R1c,R3g,Arf), (Zc,Ra,R1c,R3g,Arg), (Zc,Ra,R1c,R3g,Arh), (Zc,Ra,R1c,R3g,Ari), (Zc,Ra,R1c,R3g,Arj), (Zc,Ra,R1c,R3g,Ark), (Zc,Ra,R1c,R3g,Arl), (Zc,Ra,R1c,R3g,Arm), (Zc,Ra,R1c,R3g,Arn), (Zc,Ra,R1c,R3g,Aro), (Zc,Ra,R1c,R3g,Arp), (Zc,Ra,R1c,R3h,Ara), (Zc,Ra,R1c,R3h,Arb), (Zc,Ra,R1c,R3h,Arc), (Zc,Ra,R1c,R3h,Ard), (Zc,Ra,R1c,R3h,Are), (Zc,Ra,R1c,R3h,Arf), (Zc,Ra,R1c,R3h,Arg), (Zc,Ra,R1c,R3h,Arh), (Zc,Ra,R1c,R3h,Ari), (Zc,Ra,R1c,R3h,Arj), (Zc,Ra,R1c,R3h,Ark), (Zc,Ra,R1c,R3h,Arl), (Zc,Ra,R1c,R3h,Arm), (Zc,Ra,R1c,R3h,Arn), (Zc,Ra,R1c,R3h,Aro), (Zc,Ra,R1c,R3h,Arp), (Zc,Ra,R1d,R3a,Ara), (Zc,Ra,R1d,R3a,Arb), (Zc,Ra,R1d,R3a,Arc), (Zc,Ra,R1d,R3a,Ard), (Zc,Ra,R1d,R3a,Are), (Zc,Ra,R1d,R3a,Arf), (Zc,Ra,R1d,R3a,Arg), (Zc,Ra,R1d,R3a,Arh), (Zc,Ra,R1d,R3a,Ari), (Zc,Ra,R1d,R3a,Arj), (Zc,Ra,R1d,R3a,Ark), (Zc,Ra,R1d,R3a,Arl), (Zc,Ra,R1d,R3a,Arm), (Zc,Ra,R1d,R3a,Arn), (Zc,Ra,R1d,R3a,Aro), (Zc,Ra,R1d,R3a,Arp), (Zc,Ra,R1d,R3b,Ara), (Zc,Ra,R1d,R3b,Arb), (Zc,Ra,R1d,R3b,Arc), (Zc,Ra,R1d,R3b,Ard), (Zc,Ra,R1d,R3b,Are), (Zc,Ra,R1d,R3b,Arf), (Zc,Ra,R1d,R3b,Arg), (Zc,Ra,R1d,R3b,Arh), (Zc,Ra,R1d,R3b,Ari), (Zc,Ra,R1d,R3b,Arj), (Zc,Ra,R1d,R3b,Ark), (Zc,Ra,R1d,R3b,Arl), (Zc,Ra,R1d,R3b,Arm), (Zc,Ra,R1d,R3b,Arn), (Zc,Ra,R1d,R3b,Aro), (Zc,Ra,R1d,R3b,Arp), (Zc,Ra,R1d,R3c,Ara), (Zc,Ra,R1d,R3c,Arb), (Zc,Ra,R1d,R3c,Arc), (Zc,Ra,R1d,R3c,Ard), (Zc,Ra,R1d,R3c,Are), (Zc,Ra,R1d,R3c,Arf), (Zc,Ra,R1d,R3c,Arg), (Zc,Ra,R1d,R3c,Arh), (Zc,Ra,R1d,R3c,Ari), (Zc,Ra,R1d,R3c,Arj), (Zc,Ra,R1d,R3c,Ark), (Zc,Ra,R1d,R3c,Arl), (Zc,Ra,R1d,R3c,Arm), (Zc,Ra,R1d,R3c,Arn), (Zc,Ra,R1d,R3c,Aro), (Zc,Ra,R1d,R3c,Arp), (Zc,Ra,R1d,R3d,Ara), (Zc,Ra,R1d,R3d,Arb), (Zc,Ra,R1d,R3d,Arc), (Zc,Ra,R1d,R3d,Ard), (Zc,Ra,R1d,R3d,Are), (Zc,Ra,R1d,R3d,Arf), (Zc,Ra,R1d,R3d,Arg), (Zc,Ra,R1d,R3d,Arh), (Zc,Ra,R1d,R3d,Ari), (Zc,Ra,R1d,R3d,Aij), (Zc,Ra,R1d,R3d,Ark), (Zc,Ra,R1d,R3d,Arl), (Zc,Ra,R1d,R3d,Arm), (Zc,Ra,R1d,R3d,Arn), (Zc,Ra,R1d,R3d,Aro), (Zc,Ra,R1d,R3d,Arp), (Zc,Ra,R1d,R3e,Ara), (Zc,Ra,R1d,R3e,Arb), (Zc,Ra,R1d,R3e,Arc), (Zc,Ra,R1d,R3e,Ard), (Zc,Ra,R1d,R3e,Are), (Zc,Ra,R1d,R3e,Arf), (Zc,Ra,R1d,R3e,Arg), (Zc,Ra,R1d,R3e,Arh), (Zc,Ra,R1d,R3e,Ari), (Zc,Ra,R1d,R3e,Arj), (Zc,Ra,R1d,R3e,Ark), (Zc,Ra,R1d,R3e,Arl), (Zc,Ra,R1d,R3e,Arm), (Zc,Ra,R1d,R3e,Arn), (Zc,Ra,R1d,R3e,Aro), (Zc,Ra,R1d,R3e,Arp), (Zc,Ra,R1d,R3f,Ara), (Zc,Ra,R1d,R3f,Arb), (Zc,Ra,R1d,R3f,Arc), (Zc,Ra,R1d,R3f,Ard), (Zc,Ra,R1d,R3f,Are), (Zc,Ra,R1d,R3f,Arf), (Zc,Ra,R1d,R3f,Arg), (Zc,Ra,R1d,R3f,Arh), (Zc,Ra,R1d,R3f,Ari), (Zc,Ra,R1d,R3f,Arj), (Zc,Ra,R1d,R3f,Ark), (Zc,Ra,R1d,R3f,Arl), (Zc,Ra,R1d,R3f,Arm), (Zc,Ra,R1d,R3f,Arn), (Zc,Ra,R1d,R3f,Aro), (Zc,Ra,R1d,R3f,Arp), (Zc,Ra,R1d,R3g,Ara), (Zc,Ra,R1d,R3g,Arb), (Zc,Ra,R1d,R3g,Arc), (Zc,Ra,R1d,R3g,Ard), (Zc,Ra,R1d,R3g,Are), (Zc,Ra,R1d,R3g,Arf), (Zc,Ra,R1d,R3g,Arg), (Zc,Ra,R1d,R3g,Arh), (Zc,Ra,R1d,R3g,Ari), (Zc,Ra,R1d,R3g,Arj), (Zc,Ra,R1d,R3g,Ark), (Zc,Ra,R1d,R3g,Arl), (Zc,Ra,R1d,R3g,Arm), (Zc,Ra,R1d,R3g,Arn), (Zc,Ra,R1d,R3g,Aro), (Zc,Ra,R1d,R3g,Arp), (Zc,Ra,R1d,R3h,Ara), (Zc,Ra,R1d,R3h,Arb), (Zc,Ra,R1d,R3h,Arc), (Zc,Ra,R1d,R3h,Ard), (Zc,Ra,R1d,R3h,Are), (Zc,Ra,R1d,R3h,Arf), (Zc,Ra,R1d,R3h,Arg), (Zc,Ra,R1d,R3h,Arh), (Zc,Ra,R1d,R3h,Ari), (Zc,Ra,R1d,R3h,Arj), (Zc,Ra,R1d,R3h,Ark), (Zc,Ra,R1d,R3h,Arl), (Zc,Ra,R1d,R3h, Arm), (Zc,Ra,R1d,R3h,Arn), (Zc,Ra,R1d,R3h,Aro), (Zc,Ra,R1d,R3h,Arp), (Zc,Rb,R1a,R3a,Ara), (Zc,Rb,R1a,R3a,Arb), (Zc,Rb,R1a,R3a,Arc), (Zc,Rb,R1a,R3a,Ard), (Zc,Rb,R1a,R3a,Are), (Zc,Rb,R1a,R3a,Arf), (Zc,Rb,R1a,R3a,Arg), (Zc,Rb,R1a,R3a,Arh), (Zc,Rb,R1a,R3a,Ari), (Zc,Rb,R1a,R3a,Arj), (Zc,Rb,R1a,R3a,Ark), (Zc,Rb,R1a,R3a,Arl), (Zc,Rb,R1a,R3a,Arm), (Zc,Rb,R1a,R3a,Arn), (Zc,Rb,R1a,R3a,Aro), (Zc,Rb,R1a,R3a,Arp), (Zc,Rb,R1a,R3b,Ara), (Zc,Rb,R1a,R3b,Arb), (Zc,Rb,R1a,R3b,Arc), (Zc,Rb,R1a,R3b,Ard), (Zc,Rb,R1a,R3b,Are), (Zc,Rb,R1a,R3b,Arf), (Zc,Rb,R1a,R3b,Arg), (Zc,Rb,R1a,R3b,Arh), (Zc,Rb,R1a,R3b,Ari), (Zc,Rb,R1a,R3b,Arj), (Zc,Rb,R1a,R3b,Ark), (Zc,Rb,R1a,R3b,Arl), (Zc,Rb,R1a,R3b,Arm), (Zc,Rb,R1a,R3b,Arn), (Zc,Rb,R1a,R3b,Aro), (Zc,Rb,R1a,R3b,Arp), (Zc,Rb,R1a,R3c,Ara), (Zc,Rb,R1a,R3c,Arb), (Zc,Rb,R1a,R3c,Arc), (Zc,Rb,R1a,R3c,Ard), (Zc,Rb,R1a,R3c,Are), (Zc,Rb,R1a,R3c,Arf), (Zc,Rb,R1a,R3c,Arg), (Zc,Rb,R1a,R3c,Arh), (Zc,Rb,R1a,R3c,Ari), (Zc,Rb,R1a,R3c,Arj), (Zc,Rb,R1a,R3c,Ark), (Zc,Rb,R1a,R3c,Arl), (Zc,Rb,R1a,R3c,Arm), (Zc,Rb,R1a,R3c,Arn), (Zc,Rb,R1a,R3c,Aro), (Zc,Rb,R1a,R3c,Arp), (Zc,Rb,R1a,R3d,Ara), (Zc,Rb,R1a,R3d,Arb), (Zc,Rb,R1a,R3d,Arc), (Zc,Rb,R1a,R3d,Ard), (Zc,Rb,R1a,R3d,Are), (Zc,Rb,R1a,R3d,Arf), (Zc,Rb,R1a,R3d,Arg), (Zc,Rb,R1a,R3d,Arh), (Zc,Rb,R1a,R3d,Ari), (Zc,Rb,R1a,R3d,Arj), (Zc,Rb,R1a,R3d,Ark), (Zc,Rb,R1a,R3d,Arl), (Zc,Rb,R1a,R3d,Arm), (Zc,Rb,R1a,R3d,Arn), (Zc,Rb,R1a,R3d,Aro), (Zc,Rb,R1a,R3d,Arp), (Zc,Rb,R1a,R3e,Ara), (Zc,Rb,R1a,R3e,Arb), (Zc,Rb,R1a,R3e,Arc), (Zc,Rb,R1a,R3e,Ard), (Zc,Rb,R1a,R3e,Are), (Zc,Rb,R1a,R3e,Arf), (Zc,Rb,R1a,R3e,Arg), (Zc,Rb,R1a,R3e,Arh), (Zc,Rb,R1a,R3e,Ari), (Zc,Rb,R1a,R3e,Arj), (Zc,Rb,R1a,R3e,Ark), (Zc,Rb,R1a,R3e,Arl), (Zc,Rb,R1a,R3e,Arm), (Zc,Rb,R1a,R3e,Arn), (Zc,Rb,R1a,R3e,Aro), (Zc,Rb,R1a,R3e,Arp), (Zc,Rb,R1a,R3f,Ara), (Zc,Rb,R1a,R3f,Arb), (Zc,Rb,R1a,R3f,Arc), (Zc,Rb,R1a,R3f,Ard), (Zc,Rb,R1a,R3f,Are), (Zc,Rb,R1a,R3f,Arf), (Zc,Rb,R1a,R3f,Arg), (Zc,Rb,R1a,R3f,Arh), (Zc,Rb,R1a,R3f,Ari), (Zc,Rb,R1a,R3f,Arj), (Zc,Rb,R1a,R3f,Ark), (Zc,Rb,R1a,R3f,Arl), (Zc,Rb,R1a,R3f,Arm), (Zc,Rb,R1a,R3f,Arn), (Zc,Rb,R1a,R3f,Aro), (Zc,Rb,R1a,R3f,Arp), (Zc,Rb,R1a,R3g,Ara), (Zc,Rb,R1a,R3g,Arb), (Zc,Rb,R1a,R3g,Arc), (Zc,Rb,R1a,R3g,Ard), (Zc,Rb,R1a,R3g,Are), (Zc,Rb,R1a,R3g,Arf), (Zc,Rb,R1a,R3g,Arg), (Zc,Rb,R1a,R3g,Arh), (Zc,Rb,R1a,R3g,Ari), (Zc,Rb,R1a,R3g,Arj), (Zc,Rb,R1a,R3g,Ark), (Zc,Rb,R1a,R3g,Arl), (Zc,Rb,R1a,R3g,Arm), (Zc,Rb,R1a,R3g,Arn), (Zc,Rb,R1a,R3g,Aro), (Zc,Rb,R1a,R3g,Arp), (Zc,Rb,R1a,R3h,Ara), (Zc,Rb,R1a,R3h,Arb), (Zc,Rb,R1a,R3h,Arc), (Zc,Rb,R1a,R3h,Ard), (Zc,Rb,R1a,R3h,Are), (Zc,Rb,R1a,R3h,Arf), (Zc,Rb,R1a,R3h,Arg), (Zc,Rb,R1a,R3h,Arh), (Zc,Rb,R1a,R3h,Ari), (Zc,Rb,R1a,R3h,Arj), (Zc,Rb,R1a,R3h,Ark), (Zc,Rb,R1a,R3h,Arl), (Zc,Rb,R1a,R3h,Arm), (Zc,Rb,R1a,R3h,Arn), (Zc,Rb,R1a,R3h,Aro), (Zc,Rb,R1a,R3h,Arp), (Zc,Rb,R1b,R3a,Ara), (Zc,Rb,R1b,R3a,Arb), (Zc,Rb,R1b,R3a,Arc), (Zc,Rb,R1b,R3a,Ard), (Zc,Rb,R1b,R3a,Are), (Zc,Rb,R1b,R3a,Arf), (Zc,Rb,R1b,R3a,Arg), (Zc,Rb,R1b,R3a,Arh), (Zc,Rb,R1b,R3a,Ari), (Zc,Rb,R1b,R3a,Arj), (Zc,Rb,R1b,R3a,Ark), (Zc,Rb,R1b,R3a,Arl), (Zc,Rb,R1b,R3a,Arm), (Zc,Rb,R1b,R3a,Arn), (Zc,Rb,R1b,R3a,Aro), (Zc,Rb,R1b,R3a,Arp), (Zc,Rb,R1b,R3b,Ara), (Zc,Rb,R1b,R3b,Arb), (Zc,Rb,R1b,R3b,Arc), (Zc,Rb,R1b,R3b,Ard), (Zc,Rb,R1b,R3b,Are), (Zc,Rb,R1b,R3b,Arf), (Zc,Rb,R1b,R3b,Arg), (Zc,Rb,R1b,R3b,Arh), (Zc,Rb,R1b,R3b,Ari), (Zc,Rb,R1b,R3b,Arj), (Zc,Rb,R1b,R3b,Ark), (Zc,Rb,R1b,R3b,Arl), (Zc,Rb,R1b,R3b,Arm), (Zc,Rb,R1b,R3b,Arn), (Zc,Rb,R1b,R3b,Aro), (Zc,Rb,R1b,R3b,Arp), (Zc,Rb,R1b,R3c,Ara), (Zc,Rb,R1b,R3c,Arb), (Zc,Rb,R1b,R3c,Arc), (Zc,Rb,R1b,R3c,Ard), (Zc,Rb,R1b,R3c,Are), (Zc,Rb,R1b,R3c,Arf), (Zc,Rb,R1b,R3c,Arg), (Zc,Rb,R1b,R3c,Arh), (Zc,Rb,R1b,R3c,Ari), (Zc,Rb,R1b,R3c,Arj), (Zc,Rb,R1b,R3c,Ark), (Zc,Rb,R1b,R3c,Arl), (Zc,Rb,R1b,R3c,Arm), (Zc,Rb,R1b,R3c,Arn), (Zc,Rb,R1b,R3c,Aro), (Zc,Rb,R1b,R3c,Arp), (Zc,Rb,R1b,R3d,Ara), (Zc,Rb,R1b,R3d,Arb), (Zc,Rb,R1b,R3d,Arc), (Zc,Rb,R1b,R3d,Ard), (Zc,Rb,R1b,R3d,Are), (Zc,Rb,R1b,R3d,Arf), (Zc,Rb,R1b,R3d,Arg), (Zc,Rb,R1b,R3d,Arh), (Zc,Rb,R1b,R3d,Ari), (Zc,Rb,R1b,R3d,Arj), (Zc,Rb,R1b,R3d,Ark), (Zc,Rb,R1b,R3d,Arl), (Zc,Rb,R1b,R3d,Arm), (Zc,Rb,R1b,R3d,Arn), (Zc,Rb,R1b,R3d,Aro), (Zc,Rb,R1b,R3d,Arp), (Zc,Rb,R1b,R3e,Ara), (Zc,Rb,R1b,R3e,Arb), (Zc,Rb,R1b,R3e,Arc), (Zc,Rb,R1b,R3e,Ard), (Zc,Rb,R1b,R3e,Are), (Zc,Rb,R1b,R3e,Arf), (Zc,Rb,R1b,R3e,Arg), (Zc,Rb,R1b,R3e,Arh), (Zc,Rb,R1b,R3e,Ari), (Zc,Rb,R1b,R3e,Arj), (Zc,Rb,R1b,R3e,Ark), (Zc,Rb,R1b,R3e,Arl), (Zc,Rb,R1b,R3e,Arm), (Zc,Rb,R1b,R3e,Arn), (Zc,Rb,R1b,R3e,Aro), (Zc,Rb,R1b,R3e,Arp), (Zc,Rb,R1b,R3f,Ara), (Zc,Rb,R1b,R3f,Arb), (Zc,Rb,R1b,R3f,Arc), (Zc,Rb,R1b,R3f,Ard), (Zc,Rb,R1b,R3f,Are), (Zc,Rb,R1b,R3f,Arf), (Zc,Rb,R1b,R3f,Arg), (Zc,Rb,R1b,R3f,Arh), (Zc,Rb,R1b,R3f,Ari), (Zc,Rb,R1b,R3f,Arj), (Zc,Rb,R1b,R3f,Ark), (Zc,Rb,R1b,R3f,Arl), (Zc,Rb,R1b,R3f,Arm), (Zc,Rb,R1b,R3f,Arn), (Zc,Rb,R1b,R3f,Aro), (Zc,Rb,R1b,R3f,Arp), (Zc,Rb,R1b,R3g,Ara), (Zc,Rb,R1b,R3g,Arb), (Zc,Rb,R1b,R3g,Arc), (Zc,Rb,R1b,R3g,Ard), (Zc,Rb,R1b,R3g,Are), (Zc,Rb,R1b,R3g,Arf), (Zc,Rb,R1b,R3g,Arg), (Zc,Rb,R1b,R3g,Arh), (Zc,Rb,R1b,R3g,Ari), (Zc,Rb,R1b,R3g,Arj), (Zc,Rb,R1b,R3g,Ark), (Zc,Rb,R1b,R3g,Arl), (Zc,Rb,R1b,R3g,Arm), (Zc,Rb,R1b,R3g,Arn), (Zc,Rb,R1b,R3g,Aro), (Zc,Rb,R1b,R3g,Arp), (Zc,Rb,R1b,R3h,Ara), (Zc,Rb,R1b,R3h,Arb), (Zc,Rb,R1b,R3h,Arc), (Zc,Rb,R1b,R3h,Ard), (Zc,Rb,R1b,R3h,Are), (Zc,Rb,R1b,R3h,Arf), (Zc,Rb,R1b,R3h,Arg), (Zc,Rb,R1b,R3h,Arh), (Zc,Rb,R1b,R3h,Ari), (Zc,Rb,R1b,R3h,Arj), (Zc,Rb,R1b,R3h,Ark), (Zc,Rb,R1b,R3h,Arl), (Zc,Rb,R1b,R3h,Arm), (Zc,Rb,R1b,R3h,Arn), (Zc,Rb,R1b,R3h,Aro), (Zc,Rb,R1b,R3h,Arp), (Zc,Rb,R1c,R3a,Ara), (Zc,Rb,R1c,R3a,Arb), (Zc,Rb,R1c,R3a,Arc), (Zc,Rb,R1c,R3a,Ard), (Zc,Rb,R1c,R3a,Are), (Zc,Rb,R1c,R3a,Arf), (Zc,Rb,R1c,R3a,Arg), (Zc,Rb,R1c,R3a,Arh), (Zc,Rb,R1c,R3a,Ari), (Zc,Rb,R1c,R3a,Arj), (Zc,Rb,R1c,R3a,Ark), (Zc,Rb,R1c,R3a,Arl), (Zc,Rb,R1c,R3a,Arm), (Zc,Rb,R1c,R3a,Arn), (Zc,Rb,R1c,R3a,Aro), (Zc,Rb,R1c,R3a,Arp), (Zc,Rb,R1c,R3b,Ara), (Zc,Rb,R1c,R3b,Arb), (Zc,Rb,R1c,R3b,Arc), (Zc,Rb,R1c,R3b,Ard), (Zc,Rb,R1c,R3b,Are), (Zc,Rb,R1c,R3b,Arf), (Zc,Rb,R1c,R3b,Arh), (Zc,Rb,R1c,R3b,Ari), (Zc,Rb,R1c,R3b,Arj), (Zc,Rb,R1c,R3b,Ark), (Zc,Rb,R1c,R3b,Arl), (Zc,Rb,R1c,R3b,Arm), (Zc,Rb,R1c,R3b,Arn), (Zc,Rb,R1c,R3b,Aro), (Zc,Rb,R1c,R3b,Arp), (Zc,Rb,R1c,R3c,Ara), (Zc,Rb,R1c,R3c,Arb), (Zc,Rb,R1c,R3c,Arc), (Zc,Rb,R1c,R3c,Ard), (Zc,Rb,R1c,R3c,Are), (Zc,Rb,R1c,R3c,Arf), (Zc,Rb,R1c,R3c,Arg), (Zc,Rb,R1c,R3c,Arh), (Zc,Rb,R1c,R3c,Ari), (Zc,Rb,R1c,R3c,Arj), (Zc,Rb,R1c,R3c,Ark), (Zc,Rb,R1c,R3c,Arl), (Zc,Rb,R1c,R3c,Arm), (Zc,Rb,R1c,R3c,Arn), (Zc,Rb,R1c,R3c,Aro), (Zc,Rb,R1c,R3c,Arp), (Zc,Rb,R1c,R3d,Ara), (Zc,Rb,R1c,R3d,Arb), (Zc,Rb,R1c,R3d,Arc), (Zc,Rb,R1c,R3d,Ard), (Zc,Rb,R1c,R3d,Are), (Zc,Rb,R1c,R3d,Arf), (Zc,Rb,R1c,R3d,Arg), (Zc,Rb,R1c,R3d,Arh), (Zc,Rb,R1c,R3d,Ari), (Zc,Rb,R1c,R3d,Arj), (Zc,Rb,R1c,R3d,Ark), (Zc,Rb,R1c,R3d,Arl), (Zc,Rb,R1c,R3d,Arm), (Zc,Rb,R1c,R3d,Arn), (Zc,Rb,R1c,R3d,Aro), (Zc,Rb,R1c,R3d,Arp), (Zc,Rb,R1c,R3e,Ara), (Zc,Rb,R1c,R3e,Arb), (Zc,Rb,R1c,R3e,Arc), (Zc,Rb,R1c,R3e,Ard), (Zc,Rb,R1c,R3e,Are), (Zc,Rb,R1c,R3e,Arf), (Zc,Rb,R1c,R3e,Arg), (Zc,Rb,R1c,R3e,Arh), (Zc,Rb,R1c,R3e,Ari), (Zc,Rb,R1c,R3e,Arj), (Zc,Rb,R1c,R3e,Ark), (Zc,Rb,R1c,R3e,Arl), (Zc,Rb,R1c,R3e,Arm), (Zc,Rb,R1c,R3e,Arn), (Zc,Rb,R1c,R3e,Aro), (Zc,Rb,R1c,R3e,Arp), (Zc,Rb,R1c,R3f,Ara), (Zc,Rb,R1c,R3f,Arb), (Zc,Rb,R1c,R3f,Arc), (Zc,Rb,R1c,R3f,Ard), (Zc, Rb,R1c,R3f,Are), (Zc,Rb,R1c,R3f,Arf), (Zc,Rb,R1c,R3f,Arg), (Zc,Rb,R1c,R3f,Arh), (Zc,Rb,R1c,R3f,Ari), (Zc,Rb,R1c,R3f,Arj), (Zc,Rb,R1c,R3f,Ark), (Zc,Rb,R1c,R3f,Arl), (Zc,Rb,R1c,R3f,Arm), (Zc,Rb,R1c,R3f,Arn), (Zc,Rb,R1c,R3f,Aro), (Zc,Rb,R1c,R3f,Arp), (Zc,Rb,R1c,R3g,Ara), (Zc,Rb,R1c,R3g,Arb), (Zc,Rb,R1c,R3g,Arc), (Zc,Rb,R1c,R3g,Ard), (Zc,Rb,R1c,R3g,Are), (Zc,Rb,R1c,R3g,Arf), (Zc,Rb,R1c,R3g,Arg), (Zc,Rb,R1c,R3g,Arh), (Zc,Rb,R1c,R3g,Ari), (Zc,Rb,R1c,R3g,Arj), (Zc,Rb,R1c,R3g,Ark), (Zc,Rb,R1c,R3g,Arl), (Zc,Rb,R1c,R3g,Arm), (Zc,Rb,R1c,R3g,Arn), (Zc,Rb,R1c,R3g,Aro), (Zc,Rb,R1c,R3g,Arp), (Zc,Rb,R1c,R3h,Ara), (Zc,Rb,R1c,R3h,Arb), (Zc,Rb,R1c,R3h,Arc), (Zc,Rb,R1c,R3h,Ard), (Zc,Rb,R1c,R3h,Are), (Zc,Rb,R1c,R3h,Arf), (Zc,Rb,R1c,R3h,Arg), (Zc,Rb,R1c,R3h,Arh), (Zc,Rb,R1c,R3h,Ari), (Zc,Rb,R1c,R3h,Arj), (Zc,Rb,R1c,R3h,Ark), (Zc,Rb,R1c,R3h,Arl), (Zc,Rb,R1c,R3h,Arm), (Zc,Rb,R1c,R3h,Arn), (Zc,Rb,R1c,R3h,Aro), (Zc,Rb,R1c,R3h,Arp), (Zc,Rb,R1d,R3a,Ara), (Zc,Rb,R1d,R3a,Arb), (Zc,Rb,R1d,R3a,Arc), (Zc,Rb,R1d,R3a,Ard), (Zc,Rb,R1d,R3a,Are), (Zc,Rb,R1d,R3a,Arf), (Zc,Rb,R1d,R3a,Arg), (Zc,Rb,R1d,R3a,Arh), (Zc,Rb,R1d,R3a,Ari), (Zc,Rb,R1d,R3a,Arj), (Zc,Rb,R1d,R3a,Ark), (Zc,Rb,R1d,R3a,Arl), (Zc,Rb,R1d,R3a,Arm), (Zc,Rb,R1d,R3a,Arn), (Zc,Rb,R1d,R3a,Aro), (Zc,Rb,R1d,R3a,Arp), (Zc,Rb,R1d,R3b,Ara), (Zc,Rb,R1d,R3b,Arb), (Zc,Rb,R1d,R3b,Arc), (Zc,Rb,R1d,R3b,Ard), (Zc,Rb,R1d,R3b,Are), (Zc,Rb,R1d,R3b,Arf), (Zc,Rb,R1d,R3b,Arg), (Zc,Rb,R1d,R3b,Arh), (Zc,Rb,R1d,R3b,Ari), (Zc,Rb,R1d,R3b,Arj), (Zc,Rb,R1d,R3b,Ark), (Zc,Rb,R1d,R3b,Arl), (Zc,Rb,R1d,R3b,Arm), (Zc,Rb,R1d,R3b,Arn), (Zc,Rb,R1d,R3b,Aro), (Zc,Rb,R1d,R3b,Arp), (Zc,Rb,R1d,R3c,Ara), (Zc,Rb,R1d,R3c,Arb), (Zc,Rb,R1d,R3c,Arc), (Zc,Rb,R1d,R3c,Ard), (Zc,Rb,R1d,R3c,Are), (Zc,Rb,R1d,R3c,Arf), (Zc,Rb,R1d,R3c,Arg), (Zc,Rb,R1d,R3c,Arh), (Zc,Rb,R1d,R3c,Ari), (Zc,Rb,R1d,R3c,Arj), (Zc,Rb,R1d,R3c,Ark), (Zc,Rb,R1d,R3c,Arl), (Zc,Rb,R1d,R3c,Arm), (Zc,Rb,R1d,R3c,Arn), (Zc,Rb,R1d,R3c,Aro), (Zc,Rb,R1d,R3c,Arp), (Zc,Rb,R1d,R3d,Ara), (Zc,Rb,R1d,R3d,Arb), (Zc,Rb,R1d,R3d,Arc), (Zc,Rb,R1d,R3d,Ard), (Zc,Rb,R1d,R3d,Are), (Zc,Rb,R1d,R3d,Arf), (Zc,Rb,R1d,R3d,Arg), (Zc,Rb,R1d,R3d,Arh), (Zc,Rb,R1d,R3d,Ari), (Zc,Rb,R1d,R3d,Arj), (Zc,Rb,R1d,R3d,Ark), (Zc,Rb,R1d,R3d,Arl), (Zc,Rb,R1d,R3d,Arm), (Zc,Rb,R1d,R3d,Arn), (Zc,Rb,R1d,R3d,Aro), (Zc,Rb,R1d,R3d,Arp), (Zc,Rb,R1d,R3e,Ara), (Zc,Rb,R1d,R3e,Arb), (Zc,Rb,R1d,R3e,Arc), (Zc,Rb,R1d,R3e,Ard), (Zc,Rb,R1d,R3e,Are), (Zc,Rb,R1d,R3e,Arf), (Zc,Rb,R1d,R3e,Arg), (Zc,Rb,R1d,R3e,Arh), (Zc,Rb,R1d,R3e,Ari), (Zc,Rb,R1d,R3e,Arj), (Zc,Rb,R1d,R3e,Ark), (Zc,Rb,R1d,R3e,Arl), (Zc,Rb,R1d,R3e,Arm), (Zc,Rb,R1d,R3e,Arn), (Zc,Rb,R1d,R3e,Aro), (Zc,Rb,R1d,R3e,Arp), (Zc,Rb,R1d,R3f,Ara), (Zc,Rb,R1d,R3f,Arb), (Zc,Rb,R1d,R3f,Arc), (Zc,Rb,R1d,R3f,Ard), (Zc,Rb,R1d,R3f,Are), (Zc,Rb,R1d,R3f,Arf), (Zc,Rb,R1d,R3f,Arg), (Zc,Rb,R1d,R3f,Arh), (Zc,Rb,R1d,R3f,Ari), (Zc,Rb,R1d,R3f,Arj), (Zc,Rb,R1d,R3f,Ark), (Zc,Rb,R1d,R3f,Arl), (Zc,Rb,R1d,R3f,Arm), (Zc,Rb,R1d,R3f,Arn), (Zc,Rb,R1d,R3f,Aro), (Zc,Rb,R1d,R3f,Arp), (Zc,Rb,R1d,R3g,Ara), (Zc,Rb,R1d,R3g,Arb), (Zc,Rb,R1d,R3g,Arc), (Zc,Rb,R1d,R3g,Ard), (Zc,Rb,R1d,R3g,Are), (Zc,Rb,R1d,R3g,Arf), (Zc,Rb,R1d,R3g,Arg), (Zc,Rb,R1d,R3g,Arh), (Zc,Rb,R1d,R3g,Ari), (Zc,Rb,R1d,R3g,Arj), (Zc,Rb,R1d,R3g,Ark), (Zc,Rb,R1d,R3g,Arl), (Zc,Rb,R1d,R3g,Arm), (Zc,Rb,R1d,R3g,Arn), (Zc,Rb,R1d,R3g,Aro), (Zc,Rb,R1d,R3g,Arp), (Zc,Rb,R1d,R3h,Ara), (Zc,Rb,R1d,R3h,Arb), (Zc,Rb,R1d,R3h,Arc), (Zc,Rb,R1d,R3h,Ard), (Zc,Rb,R1d,R3h,Are), (Zc,Rb,R1d,R3h,Arf), (Zc,Rb,R1d,R3h,Arg), (Zc,Rb,R1d,R3h,Arh), (Zc,Rb,R1d,R3h,Ari), (Zc,Rb,R1d,R3h,Arj), (Zc,Rb,R1d,R3h,Ark), (Zc,Rb,R1d,R3h,Arl), (Zc,Rb,R1d,R3h,Arm), (Zc,Rb,R1d,R3h,Arn), (Zc,Rb,R1d,R3h,Aro), (Zc,Rb,R1d,R3h,Arp), (Zc,Rc,R1a,R3a,Ara), (Zc,Rc,R1a,R3a,Arb), (Zc,Rc,R1a,R3a,Arc), (Zc,Rc,R1a,R3a,Ard), (Zc,Rc,R1a,R3a,Are), (Zc,Rc,R1a,R3a,Arf), (Zc,Rc,R1a,R3a,Arg), (Zc,Rc,R1a,R3a,Arh), (Zc,Rc,R1a,R3a,Ari), (Zc,Rc,R1a,R3a,Arj), (Zc,Rc,R1a,R3a,Ark), (Zc,Rc,R1a,R3a,Arl), (Zc,Rc,R1a,R3a,Arm), (Zc,Rc,R1a,R3a,Arn), (Zc,Rc,R1a,R3a,Aro), (Zc,Rc,R1a,R3a,Arp), (Zc,Rc,R1a,R3b,Ara), (Zc,Rc,R1a,R3b,Arb), (Zc,Rc,R1a,R3b,Arc), (Zc,Rc,R1a,R3b,Ard), (Zc,Rc,R1a,R3b,Are), (Zc,Rc,R1a,R3b,Arf), (Zc,Rc,R1a,R3b,Arg), (Zc,Rc,R1a,R3b,Arh), (Zc,Rc,R1a,R3b,Ari), (Zc,Rc,R1a,R3b,Arj), (Zc,Rc,R1a,R3b,Ark), (Zc,Rc,R1a,R3b,Arl), (Zc,Rc,R1a,R3b,Arm), (Zc,Rc,R1a,R3b,Arn), (Zc,Rc,R1a,R3b,Aro), (Zc,Rc,R1a,R3b,Arp), (Zc,Rc,R1a,R3c,Ara), (Zc,Rc,R1a,R3c,Arb), (Zc,Rc,R1a,R3c,Arc), (Zc,Rc,R1a,R3c,Ard), (Zc,Rc,R1a,R3c,Are), (Zc,Rc,R1a,R3c,Arf), (Zc,Rc,R1a,R3c,Arg), (Zc,Rc,R1a,R3c,Arh), (Zc,Rc,R1a,R3c,Ari), (Zc,Rc,R1a,R3c,Arj), (Zc,Rc,R1a,R3c,Ark), (Zc,Rc,R1a,R3c,Arl), (Zc,Rc,R1a,R3c,Arm), (Zc,Rc,R1a,R3c,Arn), (Zc,Rc,R1a,R3c,Aro), (Zc,Rc,R1a,R3c,Arp), (Zc,Rc,R1a,R3d,Ara), (Zc,Rc,R1a,R3d,Arb), (Zc,Rc,R1a,R3d,Arc), (Zc,Rc,R1a,R3d,Ard), (Zc,Rc,R1a,R3d,Are), (Zc,Rc,R1a,R3d,Arf), (Zc,Rc,R1a,R3d,Arg), (Zc,Rc,R1a,R3d,Arh), (Zc,Rc,R1a,R3d,Ari), (Zc,Rc,R1a,R3d,Arj), (Zc,Rc,R1a,R3d,Ark), (Zc,Rc,R1a,R3d,Arl), (Zc,Rc,R1a,R3d,Arm), (Zc,Rc,R1a,R3d,Arn), (Zc,Rc,R1a,R3d,Aro), (Zc,Rc,R1a,R3d,Arp), (Zc,Rc,R1a,R3e,Ara), (Zc,Rc,R1a,R3e,Arb), (Zc,Rc,R1a,R3e,Arc), (Zc,Rc,R1a,R3e,Ard), (Zc,Rc,R1a,R3e,Are), (Zc,Rc,R1a,R3e,Arf), (Zc,Rc,R1a,R3e,Arg), (Zc,Rc,R1a,R3e,Arh), (Zc,Rc,R1a,R3e,Ari), (Zc,Rc,R1a,R3e,Arj), (Zc,Rc,R1a,R3e,Ark), (Zc,Rc,R1a,R3e,Arl), (Zc,Rc,R1a,R3e,Arm), (Zc,Rc,R1a,R3e,Arn), (Zc,Rc,R1a,R3e,Aro), (Zc,Rc,R1a,R3e,Arp), (Zc,Rc,R1a,R3f,Ara), (Zc,Rc,R1a,R3f,Arb), (Zc,Rc,R1a,R3f,Arc), (Zc,Rc,R1a,R3f,Ard), (Zc,Rc,R1a,R3f,Are), (Zc,Rc,R1a,R3f,Arf), (Zc,Rc,R1a,R3f,Arg), (Zc,Rc,R1a,R3f,Arh), (Zc,Rc,R1a,R3f,Ari), (Zc,Rc,R1a,R3f,Arj), (Zc,Rc,R1a,R3f,Ark), (Zc,Rc,R1a,R3f,Arl), (Zc,Rc,R1a,R3f,Arm), (Zc,Rc,R1a,R3f,Arn), (Zc,Rc,R1a,R3f,Aro), (Zc,Rc,R1a,R3f,Arp), (Zc,Rc,R1a,R3g,Ara), (Zc,Rc,R1a,R3g,Arb), (Zc,Rc,R1a,R3g,Arc), (Zc,Rc,R1a,R3g,Ard), (Zc,Rc,R1a,R3g,Are), (Zc,Rc,R1a,R3g,Arf), (Zc,Rc,R1a,R3g,Arg), (Zc,Rc,R1a,R3g,Arh), (Zc,Rc,R1a,R3g,Ari), (Zc,Rc,R1a,R3g,Arj), (Zc,Rc,R1a,R3g,Ark), (Zc,Rc,R1a,R3g,Arl), (Zc,Rc,R1a,R3g,Arm), (Zc,Rc,R1a,R3g,Arn), (Zc,Rc,R1a,R3g,Aro), (Zc,Rc,R1a,R3g,Arp), (Zc,Rc,R1a,R3h,Ara), (Zc,Rc,R1a,R3h,Arb), (Zc,Rc,R1a,R3h,Arc), (Zc,Rc,R1a,R3h,Ard), (Zc,Rc,R1a,R3h,Are), (Zc,Rc,R1a,R3h,Arf), (Zc,Rc,R1a,R3h,Arg), (Zc,Rc,R1a,R3h,Arh), (Zc,Rc,R1a,R3h,Ari), (Zc,Rc,R1a,R3h,Arj), (Zc,Rc,R1a,R3h,Ark), (Zc,Rc,R1a,R3h,Arl), (Zc,Rc,R1a,R3h,Arm), (Zc,Rc,R1a,R3h,Arn), (Zc,Rc,R1a,R3h,Aro), (Zc,Rc,R1a,R3h,Arp), (Zc,Rc,R1b,R3a,Ara), (Zc,Rc,R1b,R3a,Arb), (Zc,Rc,R1b,R3a,Arc), (Zc,Rc,R1b,R3a,Ard), (Zc,Rc,R1b,R3a,Are), (Zc,Rc,R1b,R3a,Arf), (Zc,Rc,R1b,R3a,Arg), (Zc,Rc,R1b,R3a,Arh), (Zc,Rc,R1b,R3a,Ari), (Zc,Rc,R1b,R3a,Arj), (Zc,Rc,R1b,R3a,Ark), (Zc,Rc,R1b,R3a,Arl), (Zc,Rc,R1b,R3a,Arm), (Zc,Rc,R1b,R3a,Arn), (Zc,Rc,R1b,R3a,Aro), (Zc,Rc,R1b,R3a,Arp), (Zc,Rc,R1b,R3b,Ara), (Zc,Rc,R1b,R3b,Arb), (Zc,Rc,R1b,R3b,Arc), (Zc,Rc,R1b,R3b,Ard), (Zc,Rc,R1b,R3b,Are), (Zc,Rc,R1b,R3b,Arf), (Zc,Rc,R1b,R3b,Arg), (Zc,Rc,R1b,R3b,Arh), (Zc,Rc,R1b,R3b,Ari), (Zc,Rc,R1b,R3b,Arj), (Zc,Rc,R1b,R3b,Ark), (Zc,Rc,R1b,R3b,Arl), (Zc,Rc,R1b,R3b,Arm), (Zc,Rc,R1b,R3b,Arn), (Zc,Rc,R1b,R3b,Aro), (Zc,Rc,R1b,R3b,Arp), (Zc,Rc,R1b,R3c,Ara), (Zc,Rc,R1b,R3c,Arb), (Zc,Rc,R1b,R3c,Arc), (Zc,Rc,R1b,R3c,Ard), (Zc,Rc,R1b,R3c,Are), (Zc,Rc,R1b,R3c,Arf), (Zc,Rc,R1b,R3c,Arg), (Zc,Rc,R1b,R3c,Arh), (Zc,Rc,R1b,R3c,Ari), (Zc,Rc,R1b,R3c,Arj), (Zc,Rc,R1b,R3c,Ark), (Zc,Rc,R1b,R3c,Arl), (Zc, Rc,R1b,R3c,Arm), (Zc,Rc,R1b,R3c,Arn), (Zc,Rc,R1b,R3c, Aro), (Zc,Rc,R1b,R3c,Arp), (Zc,Rc,R1b,R3d,Ara), (Zc,Rc, R1b,R3d,Arb), (Zc,Rc,R1b,R3d,Arc), (Zc,Rc,R1b,R3d, Ard), (Zc,Rc,R1b,R3d,Are), (Zc,Rc,R1b,R3d,Arf), (Zc,Rc, R1b,R3d,Arg),(Zc,Rc,R1b,R3d,Arh), (Zc,Rc,R1b,R3d,Ari), (Zc,Rc,R1b,R3d,Arj), (Zc,Rc,R1b,R3d,Ark), (Zc,Rc,R1b, R3d,Arl), (Zc,Rc,R1b,R3d,Arm), (Zc,Rc,R1b,R3d,Arn), (Zc,Rc,R1b,R3d,Aro), (Zc,Rc,R1b,R3d,Arp), (Zc,Rc,R1b, R3e,Ara), (Zc,Rc,R1b,R3e,Arb), (Zc,Rc,R1b,R3e,Arc), (Zc, Rc,R1b,R3e,Ard), (Zc,Rc,R1b,R3e,Are), (Zc,Rc,R1b,R3e, Arf), (Zc,Rc,R1b,R3e,Arg), (Zc,Rc,R1b,R3e,Arh), (Zc,Rc, R1b,R3e,Ari), (Zc,Rc,R1b,R3e,Arj), (Zc,Rc,R1b,R3e,Ark), (Zc,Rc,R1b,R3e,Arl), (Zc,Rc,R1b,R3e,Arm), (Zc,Rc,R1b, R3e,Arn),(Zc,Rc,R1b,R3e,Aro), (Zc,Rc,R1b,R3e,Arp), (Zc, Rc,R1b,R3f,Ara), (Zc,Rc,R1b,R3f,Arb), (Zc,Rc,R1b,R3f, Arc), (Zc,Rc,R1b,R3f,Ard), (Zc,Rc,R1b,R3f,Are), (Zc,Rc, R1b,R3f,Arf), (Zc,Rc,R1b,R3f,Arg), (Zc,Rc,R1b,R3f,Arh), (Zc,Rc,R1b,R3f,Ari), (Zc,Rc,R1b,R3f,Arj), (Zc,Rc,R1b, R3f,Ark),(Zc,Rc,R1b,R3f,Arl), (Zc,Rc,R1b,R3f,Arm), (Zc, Rc,R1b,R3f,Arn), (Zc,Rc,R1b,R3f,Aro), (Zc,Rc,R1b,R3f, Arp), (Zc,Rc,R1b,R3g,Ara), (Zc,Rc,R1b,R3g,Arb), (Zc,Rc, R1b,R3g,Arc), (Zc,Rc,R1b,R3g,Ard), (Zc,Rc,R1b,R3g, Are), (Zc,Rc,R1b,R3g,Arf), (Zc,Rc,R1b,R3g,Arg), (Zc,Rc, R1b,R3g,Arh), (Zc,Rc,R1b,R3g,Ari), (Zc,Rc,R1b,R3g,Arj), (Zc,Rc,R1b,R3g,Ark), (Zc,Rc,R1b,R3g,Arl), (Zc,Rc,R1b, R3g,Arm), (Zc,Rc,R1b,R3g,Arn), (Zc,Rc,R1b,R3g,Aro), (Zc,Rc,R1b,R3g,Arp), (Zc,Rc,R1b,R3h,Ara), (Zc,Rc,R1b, R3h,Arb), (Zc,Rc,R1b,R3h,Arc), (Zc,Rc,R1b,R3h,Ard), (Zc,Rc,R1b,R3h,Are), (Zc,Rc,R1b,R3h,Arf), (Zc,Rc,R1b, R3h,Arg),(Zc,Rc,R1b,R3h,Arh),(Zc,Rc,R1b,R3h,Ari), (Zc, Rc,R1b,R3h,Arj), (Zc,Rc,R1b,R3h,Ark), (Zc,Rc,R1b,R3h, Arl), (Zc,Rc,R1b,R3h,Arm), (Zc,Rc,R1b,R3h,Arn), (Zc,Rc, R1b,R3h,Aro), (Zc,Rc,R1b,R3h,Arp), (Zc,Rc,R1c,R3a, Ara), (Zc,Rc,R1c,R3a,Arb), (Zc,Rc,R1c,R3a,Arc), (Zc,Rc, R1c,R3a,Ard), (Zc,Rc,R1c,R3a,Are), (Zc,Rc,R1c,R3a,Arf), (Zc,Rc,R1c,R3a,Arg), (Zc,Rc,R1c,R3a,Arh), (Zc,Rc,R1c, R3a,Ari), (Zc,Rc,R1c,R3a,Arj), (Zc,Rc,R1c,R3a,Ark), (Zc, Rc,R1c,R3a,Arl), (Zc,Rc,R1c,R3a,Arm), (Zc,Rc,R1c,R3a, Arn), (Zc,Rc,R1c,R3a,Aro), (Zc,Rc,R1c,R3a,Arp), (Zc,Rc, R1c,R3b,Ara), (Zc,Rc,R1c,R3b,Arb), (Zc,Rc,R1c,R3b,Arc), (Zc,Rc,R1c,R3b,Ard), (Zc,Rc,R1c,R3b,Are), (Zc,Rc,R1c, R3b,Arf), (Zc,Rc,R1c,R3b,Arg), (Zc,Rc,R1c,R3b,Arh), (Zc, Rc,R1c,R3b,Ari), (Zc,Rc,R1c,R3b,Arj), (Zc,Rc,R1c,R3b, Ark), (Zc,Rc,R1c,R3b,Arl), (Zc,Rc,R1c,R3b,Arm), (Zc,Rc, R1c,R3b,Arn), (Zc,Rc,R1c,R3b,Aro), (Zc,Rc,R1c,R3b, Arp), (Zc,Rc,R1c,R3c,Ara), (Zc,Rc,R1c,R3c,Arb), (Zc,Rc, R1c,R3c,Arc), (Zc,Rc,R1c,R3c,Ard), (Zc,Rc,R1c,R3c,Are), (Zc,Rc,R1c,R3c,Arf), (Zc,Rc,R1c,R3c,Arg), (Zc,Rc,R1c, R3c,Arh), (Zc,Rc,R1c,R3c,Ari), (Zc,Rc,R1c,R3c,Arj), (Zc, Rc,R1c,R3c,Ark), (Zc,Rc,R1c,R3c,Arl), (Zc,Rc,R1c,R3c, Arm), (Zc,Rc,R1c,R3c,Arn), (Zc,Rc,R1c,R3c,Aro), (Zc,Rc, R1c,R3c,Arp), (Zc,Rc,R1c,R3d,Ara), (Zc,Rc,R1c,R3d,Arb), (Zc,Rc,R1c,R3d,Arc), (Zc,Rc,R1c,R3d,Ard), (Zc,Rc,R1c, R3d,Are), (Zc,Rc,R1c,R3d,Arf), (Zc,Rc,R1c,R3d,Arg), (Zc, Rc,R1c,R3d,Arh), (Zc,Rc,R1c,R3d,Ari), (Zc,Rc,R1c,R3d, Arj), (Zc,Rc,R1c,R3d,Ark), (Zc,Rc,R1c,R3d,Arl), (Zc,Rc, R1c,R3d,Arm), (Zc,Rc,R1c,R3d,Arn), (Zc,Rc,R1c,R3d, Aro), (Zc,Rc,R1c,R3d,Arp), (Zc,Rc,R1c,R3e,Ara), (Zc,Rc, R1c,R3e,Arb), (Zc,Rc,R1c,R3e,Arc), (Zc,Rc,R1c,R3e,Ard), (Zc,Rc,R1c,R3e,Are), (Zc,Rc,R1c,R3e,Arf), (Zc,Rc,R1c, R3e,Arg), (Zc,Rc,R1c,R3e,Arh), (Zc,Rc,R1c,R3e,Ari), (Zc, Rc,R1c,R3e,Arj), (Zc,Rc,R1c,R3e,Ark), (Zc,Rc,R1c,R3e, Arl), (Zc,Rc,R1c,R3e,Arm), (Zc,Rc,R1c,R3e,Arn), (Zc,Rc, R1c,R3e,Aro), (Zc,Rc,R1c,R3e,Arp), (Zc,Rc,R1c,R3f,Ara), (Zc,Rc,R1c,R3f,Arb), (Zc,Rc,R1c,R3f,Arc), (Zc,Rc,R1c, R3f,Ard), (Zc,Rc,R1c,R3f,Are), (Zc,Rc,R1c,R3f,Arf), (Zc, Rc,R1c,R3f,Arg), (Zc,Rc,R1c,R3f,Arh), (Zc,Rc,R1c,R3f, Ari), (Zc,Rc,R1c,R3f,Arj), (Zc,Rc,R1c,R3f,Ark), (Zc,Rc, R1c,R3f,Arl), (Zc,Rc,R1c,R3f,Arm), (Zc,Rc,R1c,R3f,Arn), (Zc,Rc,R1c,R3f,Aro), (Zc,Rc,R1c,R3f,Arp), (Zc,Rc,R1c, R3g,Ara), (Zc,Rc,R1c,R3g,Arb), (Zc,Rc,R1c,R3g,Arc), (Zc, Rc,R1c,R3g,Ard), (Zc,Rc,R1c,R3g,Are), (Zc,Rc,R1c,R3g, Arf), (Zc,Rc,R1c,R3g,Arg), (Zc,Rc,R1c,R3g,Arh), (Zc,Rc, R1c,R3g,Ari), (Zc,Rc,R1c,R3g,Arj), (Zc,Rc,R1c,R3g,Ark), (Zc,Rc,R1c,R3g,Arl), (Zc,Rc,R1c,R3g,Arm), (Zc,Rc,R1c, R3g,Arn),(Zc,Rc,R1c,R3g,Aro),(Zc,Rc,R1c,R3g,Arp), (Zc, Rc,R1c,R3h,Ara), (Zc,Rc,R1c,R3h,Arb), (Zc,Rc,R1c,R3h, Arc), (Zc,Rc,R1c,R3h,Ard), (Zc,Rc,R1c,R3h,Are), (Zc,Rc, R1c,R3h,Arf), (Zc,Rc,R1c,R3h,Arg), (Zc,Rc,R1c,R3h,Arh), (Zc,Rc,R1c,R3h,Ari), (Zc,Rc,R1c,R3h,Arj), (Zc,Rc,R1c, R3h,Ark), (Zc,Rc,R1c,R3h,Arl), (Zc,Rc,R1c,R3h,Arm), (Zc,Rc,R1c,R3h,Arn), (Zc,Rc,R1c,R3h,Aro), (Zc,Rc,R1c, R3h,Arp),(Zc,Rc,R1d,R3a,Ara), (Zc,Rc,R1d,R3a,Arb), (Zc, Rc,R1d,R3a,Arc), (Zc,Rc,R1d,R3a,Ard), (Zc,Rc,R1d,R3a, Are), (Zc,Rc,R1d,R3a,Arf), (Zc,Rc,R1d,R3a,Arg), (Zc,Rc, R1d,R3a,Arh), (Zc,Rc,R1d,R3a,Ari), (Zc,Rc,R1d,R3a,Arj), (Zc,Rc,R1d,R3a,Ark), (Zc,Rc,R1d,R3a,Arl), (Zc,Rc,R1d, R3a,Arm), (Zc,Rc,R1d,R3a,Arn), (Zc,Rc,R1d,R3a,Aro), (Zc,Rc,R1d,R3a,Arp), (Zc,Rc,R1d,R3b,Ara), (Zc,Rc,R1d, R3b,Arb), (Zc,Rc,R1d,R3b,Arc), (Zc,Rc,R1d,R3b,Ard), (Zc,Rc,R1d,R3b,Are), (Zc,Rc,R1d,R3b,Arf), (Zc,Rc,R1d, R3b,Arg),(Zc,Rc,R1d,R3b,Arh), (Zc,Rc,R1d,R3b,Ari), (Zc, Rc,R1d,R3b,Arj), (Zc,Rc,R1d,R3b,Ark), (Zc,Rc,R1d,R3b, Arl), (Zc,Rc,R1d,R3b,Arm), (Zc,Rc,R1d,R3b,Arn), (Zc,Rc, R1d,R3b,Aro), (Zc,Rc,R1d,R3b,Arp), (Zc,Rc,R1d,R3c, Ara), (Zc,Rc,R1d,R3c,Arb), (Zc,Rc,R1d,R3c,Arc), (Zc,Rc, R1d,R3c,Ard), (Zc,Rc,R1d,R3c,Are), (Zc,Rc,R1d,R3c,Arf), (Zc,Rc,R1d,R3c,Arg), (Zc,Rc,R1d,R3c,Arh), (Zc,Rc,R1d, R3c,Ari), (Zc,Rc,R1d,R3c,Arj), (Zc,Rc,R1d,R3c,Ark), (Zc, Rc,R1d,R3c,Arl), (Zc,Rc,R1d,R3c,Arm), (Zc,Rc,R1d,R3c, Arn), (Zc,Rc,R1d,R3c,Aro), (Zc,Rc,R1d,R3c,Arp), (Zc,Rc, R1d,R3d,Ara), (Zc,Rc,R1d,R3d,Arb), (Zc,Rc,R1d,R3d, Arc), (Zc,Rc,R1d,R3d,Ard), (Zc,Rc,R1d,R3d,Are), (Zc,Rc, R1d,R3d,Arf), (Zc,Rc,R1d,R3d,Arg), (Zc,Rc,R1d,R3d, Arh), (Zc,Rc,R1d,R3d,Ari), (Zc,Rc,R1d,R3d,Arj), (Zc,Rc, R1d,R3d,Ark), (Zc,Rc,R1d,R3d,Arl), (Zc,Rc,R1d,R3d, Arm),(Zc,Rc,R1d,R3d,Arn),(Zc,Rc,R1d,R3d,Aro), (Zc,Rc, R1d,R3d,Arp), (Zc,Rc,R1d,R3e,Ara), (Zc,Rc,R1d,R3e, Arb), (Zc,Rc,R1d,R3e,Arc), (Zc,Rc,R1d,R3e,Ard), (Zc,Rc, R1d,R3e,Are), (Zc,Rc,R1d,R3e,Arf), (Zc,Rc,R1d,R3e,Arg), (Zc,Rc,R1d,R3e,Arh), (Zc,Rc,R1d,R3e,Ari), (Zc,Rc,R1d, R3e,Arj), (Zc,Rc,R1d,R3e,Ark), (Zc,Rc,R1d,R3e,Arl), (Zc, Rc,R1d,R3e,Arm), (Zc,Rc,R1d,R3e,Arn), (Zc,Rc,R1d,R3e, Aro), (Zc,Rc,R1d,R3e,Arp), (Zc,Rc,R1d,R3f,Ara), (Zc,Rc, R1d,R3f,Arb), (Zc,Rc,R1d,R3f,Arc), (Zc,Rc,R1d,R3f,Ard), (Zc,Rc,R1d,R3f,Are), (Zc,Rc,R1d,R3f,Arf), (Zc,Rc,R1d, R3f,Arg), (Zc,Rc,R1d,R3f,Arh), (Zc,Rc,R1d,R3f,Ari), (Zc, Rc,R1d,R3f,Arj), (Zc,Rc,R1d,R3f,Ark), (Zc,Rc,R1d,R3f, Arl), (Zc,Rc,R1d,R3f,Arm), (Zc,Rc,R1d,R3f,Arn), (Zc,Rc, R1d,R3f,Aro), (Zc,Rc,R1d,R3f,Arp), (Zc,Rc,R1d,R3g,Ara), (Zc,Rc,R1d,R3g,Arb), (Zc,Rc,R1d,R3g,Arc), (Zc,Rc,R1d, R3g,Ard), (Zc,Rc,R1d,R3g,Are), (Zc,Rc,R1d,R3g,Arf), (Zc, Rc,R1d,R3g,Arg), (Zc,Rc,R1d,R3g,Arh), (Zc,Rc,R1d,R3g, Ari), (Zc,Rc,R1d,R3g,Arj), (Zc,Rc,R1d,R3g,Ark), (Zc,Rc, R1d,R3g,Arl), (Zc,Rc,R1d,R3g,Arm), (Zc,Rc,R1d,R3g, Arn), (Zc,Rc,R1d,R3g,Aro), (Zc,Rc,R1d,R3g,Arp), (Zc,Rc, R1d,R3h,Ara), (Zc,Rc,R1d,R3h,Arb), (Zc,Rc,R1d,R3h, Arc), (Zc,Rc,R1d,R3h,Ard), (Zc,Rc,R1d,R3h,Are), (Zc,Rc, R1d,R3h,Arf), (Zc,Rc,R1d,R3h,Arg), (Zc,Rc,R1d,R3h, Arh), (Zc,Rc,R1d,R3h,Ari), (Zc,Rc,R1d,R3h,Arj), (Zc,Rc, R1d,R3h,Ark), (Zc,Rc,R1d,R3h,Arl), (Zc,Rc,R1d,R3h, Arm),(Zc,Rc,R1d,R3h,Arn), (Zc,Rc,R1d,R3h,Aro), (Zc,Rc, R1d,R3h,Arp), (Zc,Rd,R1a,R3a,Ara), (Zc,Rd,R1a,R3a, Arb), (Zc,Rd,R1a,R3a,Arc), (Zc,Rd,R1a,R3a,Ard), (Zc,Rd, R1a,R3a,Are), (Zc,Rd,R1a,R3a,Arf), (Zc,Rd,R1a,R3a,Arg), (Zc,Rd,R1a,R3a,Arh), (Zc,Rd,R1a,R3a,Ari), (Zc,Rd,R1a,R3a,Arj), (Zc,Rd,R1a,R3a,Ark), (Zc,Rd,R1a,R3a,Arl), (Zc,Rd,R1a,R3a,Arm), (Zc,Rd,R1a,R3a,Arn), (Zc,Rd,R1a,R3a,Aro), (Zc,Rd,R1a,R3a,Arp), (Zc,Rd,R1a,R3b,Ara), (Zc,Rd,R1a,R3b,Arb), (Zc,Rd,R1a,R3b,Arc), (Zc,Rd,R1a,R3b,Ard), (Zc,Rd,R1a,R3b,Are), (Zc,Rd,R1a,R3b,Arf), (Zc,Rd,R1a,R3b,Arg), (Zc,Rd,R1a,R3b,Arh), (Zc,Rd,R1a,R3b,Ari), (Zc,Rd,R1a,R3b,Arj), (Zc,Rd,R1a,R3b,Ark), (Zc,Rd,R1a,R3b,Arl), (Zc,Rd,R1a,R3b,Arm), (Zc,Rd,R1a,R3b,Arn), (Zc,Rd,R1a,R3b,Aro), (Zc,Rd,R1a,R3b,Arp), (Zc,Rd,R1a,R3c,Ara), (Zc,Rd,R1a,R3c,Arb), (Zc,Rd,R1a,R3c,Arc), (Zc,Rd,R1a,R3c,Ard), (Zc,Rd,R1a,R3c,Are), (Zc,Rd,R1a,R3c,Arf), (Zc,Rd,R1a,R3c,Arg), (Zc,Rd,R1a,R3c,Arh), (Zc,Rd,R1a,R3c,Ari), (Zc,Rd,R1a,R3c,Arj), (Zc,Rd,R1a,R3c,Ark), (Zc,Rd,R1a,R3c,Arl), (Zc,Rd,R1a,R3c,Arm), (Zc,Rd,R1a,R3c,Arn), (Zc,Rd,R1a,R3c,Aro), (Zc,Rd,R1a,R3c,Arp), (Zc,Rd,R1a,R3d,Ara), (Zc,Rd,R1a,R3d,Arb), (Zc,Rd,R1a,R3d,Arc), (Zc,Rd,R1a,R3d,Ard), (Zc,Rd,R1a,R3d,Are), (Zc,Rd,R1a,R3d,Arf), (Zc,Rd,R1a,R3d,Arg), (Zc,Rd,R1a,R3d,Arh), (Zc,Rd,R1a,R3d,Ari), (Zc,Rd,R1a,R3d,Arj), (Zc,Rd,R1a,R3d,Ark), (Zc,Rd,R1a,R3d,Arl), (Zc,Rd,R1a,R3d,Arm), (Zc,Rd,R1a,R3d,Arn), (Zc,Rd,R1a,R3d,Aro), (Zc,Rd,R1a,R3d,Arp), (Zc,Rd,R1a,R3e,Ara), (Zc,Rd,R1a,R3e,Arb), (Zc,Rd,R1a,R3e,Arc), (Zc,Rd,R1a,R3e,Ard), (Zc,Rd,R1a,R3e,Are), (Zc,Rd,R1a,R3e,Arf), (Zc,Rd,R1a,R3e,Arg), (Zc,Rd,R1a,R3e,Arh), (Zc,Rd,R1a,R3e,Ari), (Zc,Rd,R1a,R3e,Arj), (Zc,Rd,R1a,R3e,Ark), (Zc,Rd,R1a,R3e,Arl), (Zc,Rd,R1a,R3e,Arm), (Zc,Rd,R1a,R3e,Arn), (Zc,Rd,R1a,R3e,Aro), (Zc,Rd,R1a,R3e,Arp), (Zc,Rd,R1a,R3f,Ara), (Zc,Rd,R1a,R3f,Arb), (Zc,Rd,R1a,R3f,Arc), (Zc,Rd,R1a,R3f,Ard), (Zc,Rd,R1a,R3f,Are), (Zc,Rd,R1a,R3f,Arf), (Zc,Rd,R1a,R3f,Arg), (Zc,Rd,R1a,R3f,Arh), (Zc,Rd,R1a,R3f,Ari), (Zc,Rd,R1a,R3f,Arj), (Zc,Rd,R1a,R3f,Ark), (Zc,Rd,R1a,R3f,Arl), (Zc,Rd,R1a,R3f,Arm), (Zc,Rd,R1a,R3f,Arn), (Zc,Rd,R1a,R3f,Aro), (Zc,Rd,R1a,R3f,Arp), (Zc,Rd,R1a,R3g,Ara), (Zc,Rd,R1a,R3g,Arb), (Zc,Rd,R1a,R3g,Arc), (Zc,Rd,R1a,R3g,Ard), (Zc,Rd,R1a,R3g,Are), (Zc,Rd,R1a,R3g,Arf), (Zc,Rd,R1a,R3g,Arg), (Zc,Rd,R1a,R3g,Arh), (Zc,Rd,R1a,R3g,Ari), (Zc,Rd,R1a,R3g,Arj), (Zc,Rd,R1a,R3g,Ark), (Zc,Rd,R1a,R3g,Arl), (Zc,Rd,R1a,R3g,Arm), (Zc,Rd,R1a,R3g,Arn), (Zc,Rd,R1a,R3g,Aro), (Zc,Rd,R1a,R3g,Arp), (Zc,Rd,R1a,R3h,Ara), (Zc,Rd,R1a,R3h,Arb), (Zc,Rd,R1a,R3h,Arc), (Zc,Rd,R1a,R3h,Ard), (Zc,Rd,R1a,R3h,Are), (Zc,Rd,R1a,R3h,Arf), (Zc,Rd,R1a,R3h,Arg), (Zc,Rd,R1a,R3h,Arh), (Zc,Rd,R1a,R3h,Ari), (Zc,Rd,R1a,R3h,Arj), (Zc,Rd,R1a,R3h,Ark), (Zc,Rd,R1a,R3h,Arl), (Zc,Rd,R1a,R3h,Arm), (Zc,Rd,R1a,R3h,Arn), (Zc,Rd,R1a,R3h,Aro), (Zc,Rd,R1a,R3h,Arp), (Zc,Rd,R1b,R3a,Ara), (Zc,Rd,R1b,R3a,Arb), (Zc,Rd,R1b,R3a,Arc), (Zc,Rd,R1b,R3a,Ard), (Zc,Rd,R1b,R3a,Are), (Zc,Rd,R1b,R3a,Arf), (Zc,Rd,R1b,R3a,Arg), (Zc,Rd,R1b,R3a,Arh), (Zc,Rd,R1b,R3a,Ari), (Zc,Rd,R1b,R3a,Arj), (Zc,Rd,R1b,R3a,Ark), (Zc,Rd,R1b,R3a,Arl), (Zc,Rd,R1b,R3a,Arm), (Zc,Rd,R1b,R3a,Arn), (Zc,Rd,R1b,R3a,Aro), (Zc,Rd,R1b,R3a,Arp), (Zc,Rd,R1b,R3b,Ara), (Zc,Rd,R1b,R3b,Arb), (Zc,Rd,R1b,R3b,Arc), (Zc,Rd,R1b,R3b,Ard), (Zc,Rd,R1b,R3b,Are), (Zc,Rd,R1b,R3b,Arf), (Zc,Rd,R1b,R3b,Arg), (Zc,Rd,R1b,R3b,Arh), (Zc,Rd,R1b,R3b,Ari), (Zc,Rd,R1b,R3b,Arj), (Zc,Rd,R1b,R3b,Ark), (Zc,Rd,R1b,R3b,Arl), (Zc,Rd,R1b,R3b,Arm), (Zc,Rd,R1b,R3b,Arn), (Zc,Rd,R1b,R3b,Aro), (Zc,Rd,R1b,R3b,Arp), (Zc,Rd,R1b,R3c,Ara), (Zc,Rd,R1b,R3c,Arb), (Zc,Rd,R1b,R3c,Arc), (Zc,Rd,R1b,R3c,Ard), (Zc,Rd,R1b,R3c,Are), (Zc,Rd,R1b,R3c,Arf), (Zc,Rd,R1b,R3c,Arg), (Zc,Rd,R1b,R3c,Arh), (Zc,Rd,R1b,R3c,Ari), (Zc,Rd,R1b,R3c,Arj), (Zc,Rd,R1b,R3c,Ark), (Zc,Rd,R1b,R3c,Arl), (Zc,Rd,R1b,R3c,Arm), (Zc,Rd,R1b,R3c,Arn), (Zc,Rd,R1b,R3c,Aro), (Zc,Rd,R1b,R3c,Arp), (Zc,Rd,R1b,R3d,Ara), (Zc,Rd,R1b,R3d,Arb), (Zc,Rd,R1b,R3d,Arc), (Zc,Rd,R1b,R3d,Ard), (Zc,Rd,R1b,R3d,Are), (Zc,Rd,R1b,R3d,Arf), (Zc,Rd,R1b,R3d,Arg), (Zc,Rd,R1b,R3d,Arh), (Zc,Rd,R1b,R3d,Ari), (Zc,Rd,R1b,R3d,Arj), (Zc,Rd,R1b,R3d,Ark), (Zc,Rd,R1b,R3d,Arl), (Zc,Rd,R1b,R3d,Arm), (Zc,Rd,R1b,R3d,Arn), (Zc,Rd,R1b,R3d,Aro), (Zc,Rd,R1b,R3d,Arp), (Zc,Rd,R1b,R3e,Ara), (Zc,Rd,R1b,R3e,Arb), (Zc,Rd,R1b,R3e,Arc), (Zc,Rd,R1b,R3e,Ard), (Zc,Rd,R1b,R3e,Are), (Zc,Rd,R1b,R3e,Arf), (Zc,Rd,R1b,R3e,Arg), (Zc,Rd,R1b,R3e,Arh), (Zc,Rd,R1b,R3e,Ari), (Zc,Rd,R1b,R3e,Arj), (Zc,Rd,R1b,R3e,Ark), (Zc,Rd,R1b,R3e,Arl), (Zc,Rd,R1b,R3e,Arm), (Zc,Rd,R1b,R3e,Arn), (Zc,Rd,R1b,R3e,Aro), (Zc,Rd,R1b,R3e,Arp), (Zc,Rd,R1b,R3f,Ara), (Zc,Rd,R1b,R3f,Arb), (Zc,Rd,R1b,R3f,Arc), (Zc,Rd,R1b,R3f,Ard), (Zc,Rd,R1b,R3f,Are), (Zc,Rd,R1b,R3f,Arf), (Zc,Rd,R1b,R3f,Arg), (Zc,Rd,R1b,R3f,Arh), (Zc,Rd,R1b,R3f,Ari), (Zc,Rd,R1b,R3f,Arj), (Zc,Rd,R1b,R3f,Ark), (Zc,Rd,R1b,R3f,Arl), (Zc,Rd,R1b,R3f,Arm), (Zc,Rd,R1b,R3f,Arn), (Zc,Rd,R1b,R3f,Aro), (Zc,Rd,R1b,R3f,Arp), (Zc,Rd,R1b,R3g,Ara), (Zc,Rd,R1b,R3g,Arb), (Zc,Rd,R1b,R3g,Arc), (Zc,Rd,R1b,R3g,Ard), (Zc,Rd,R1b,R3g,Are), (Zc,Rd,R1b,R3g,Arf), (Zc,Rd,R1b,R3g,Arg), (Zc,Rd,R1b,R3g,Arh), (Zc,Rd,R1b,R3g,Ari), (Zc,Rd,R1b,R3g,Arj), (Zc,Rd,R1b,R3g,Ark), (Zc,Rd,R1b,R3g,Arl), (Zc,Rd,R1b,R3g,Arm), (Zc,Rd,R1b,R3g,Arn), (Zc,Rd,R1b,R3g,Aro), (Zc,Rd,R1b,R3g,Arp), (Zc,Rd,R1b,R3h,Ara), (Zc,Rd,R1b,R3h,Arb), (Zc,Rd,R1b,R3h,Arc), (Zc,Rd,R1b,R3h,Ard), (Zc,Rd,R1b,R3h,Are), (Zc,Rd,R1b,R3h,Arf), (Zc,Rd,R1b,R3h,Arg), (Zc,Rd,R1b,R3h,Arh), (Zc,Rd,R1b,R3h,Ari), (Zc,Rd,R1b,R3h,Arj), (Zc,Rd,R1b,R3h,Ark), (Zc,Rd,R1b,R3h,Arl), (Zc,Rd,R1b,R3h,Arm), (Zc,Rd,R1b,R3h,Arn), (Zc,Rd,R1b,R3h,Aro), (Zc,Rd,R1b,R3h,Arp), (Zc,Rd,R1c,R3a,Ara), (Zc,Rd,R1c,R3a,Arb), (Zc,Rd,R1c,R3a,Arc), (Zc,Rd,R1c,R3a,Ard), (Zc,Rd,R1c,R3a,Are), (Zc,Rd,R1c,R3a,Arf), (Zc,Rd,R1c,R3a,Arg), (Zc,Rd,R1c,R3a,Arh), (Zc,Rd,R1c,R3a,Ari), (Zc,Rd,R1c,R3a,Arj), (Zc,Rd,R1c,R3a,Ark), (Zc,Rd,R1c,R3a,Arl), (Zc,Rd,R1c,R3a,Arm), (Zc,Rd,R1c,R3a,Arn), (Zc,Rd,R1c,R3a,Aro), (Zc,Rd,R1c,R3a,Arp), (Zc,Rd,R1c,R3b,Ara), (Zc,Rd,R1c,R3b,Arb), (Zc,Rd,R1c,R3b,Arc), (Zc,Rd,R1c,R3b,Ard), (Zc,Rd,R1c,R3b,Are), (Zc,Rd,R1c,R3b,Arf), (Zc,Rd,R1c,R3b,Arg), (Zc,Rd,R1c,R3b,Arh), (Zc,Rd,R1c,R3b,Ari), (Zc,Rd,R1c,R3b,Arj), (Zc,Rd,R1c,R3b,Ark), (Zc,Rd,R1c,R3b,Arl), (Zc,Rd,R1c,R3b,Arm), (Zc,Rd,R1c,R3b,Arn), (Zc,Rd,R1c,R3b,Aro), (Zc,Rd,R1c,R3b,Arp), (Zc,Rd,R1c,R3c,Ara), (Zc,Rd,R1c,R3c,Arb), (Zc,Rd,R1c,R3c,Arc), (Zc,Rd,R1c,R3c,Ard), (Zc,Rd,R1c,R3c,Are), (Zc,Rd,R1c,R3c,Arf), (Zc,Rd,R1c,R3c,Arg), (Zc,Rd,R1c,R3c,Arh), (Zc,Rd,R1c,R3c,Ari), (Zc,Rd,R1c,R3c,Arj), (Zc,Rd,R1c,R3c,Ark), (Zc,Rd,R1c,R3c,Arl), (Zc,Rd,R1c,R3c,Arm), (Zc,Rd,R1c,R3c,Arn), (Zc,Rd,R1c,R3c,Aro), (Zc,Rd,R1c,R3c,Arp), (Zc,Rd,R1c,R3d,Ara), (Zc,Rd,R1c,R3d,Arb), (Zc,Rd,R1c,R3d,Arc), (Zc,Rd,R1c,R3d,Ard), (Zc,Rd,R1c,R3d,Are), (Zc,Rd,R1c,R3d,Arf), (Zc,Rd,R1c,R3d,Arg), (Zc,Rd,R1c,R3d,Arh), (Zc,Rd,R1c,R3d,Ari), (Zc,Rd,R1c,R3d,Aij), (Zc,Rd,R1c,R3d,Ark), (Zc,Rd,R1c,R3d,Arl), (Zc,Rd,R1c,R3d,Arm), (Zc,Rd,R1c,R3d,Arn), (Zc,Rd,R1c,R3d,Aro), (Zc,Rd,R1c,R3d,Arp), (Zc,Rd,R1c,R3e,Ara), (Zc,Rd,R1c,R3e,Arb), (Zc,Rd,R1c,R3e,Arc), (Zc,Rd,R1c,R3e,Ard), (Zc,Rd,R1c,R3e,Are), (Zc,Rd,R1c,R3e,Arf), (Zc,Rd,R1c,R3e,Arg), (Zc,Rd,R1c,R3e,Arh), (Zc,Rd,R1c,R3e,Ari), (Zc,Rd,R1c,R3e,Arj), (Zc,Rd,R1c,R3e,Ark), (Zc,Rd,R1c,R3e,Arl), (Zc,Rd,R1c,R3e,Arm), (Zc,Rd,R1c,R3e,Arn), (Zc,Rd,R1c,R3e,Aro), (Zc,Rd,R1c,R3e,Arp), (Zc,Rd,R1c,R3f,Ara), (Zc,Rd,R1c,R3f,Arb), (Zc,Rd,R1c,R3f,Arc), (Zc,Rd,R1c,R3f,Ard), (Zc,Rd,R1c,R3f,Are), (Zc,Rd,R1c,R3f,Arf), (Zc,Rd,R1c,R3f,Arg), (Zc,Rd,R1c,R3f,Arh), (Zc,Rd,R1c,R3f,Ari), (Zc,Rd,R1c,R3f,Arj), (Zc,Rd,R1c,R3f,Ark), (Zc,Rd,R1c,R3f,Arl), (Zc,Rd,R1c,R3f,Arm), (Zc,Rd,R1c,R3f,Arn), (Zc,Rd,R1c,R3f,Aro), (Zc,Rd,R1c,R3f,Arp), (Zc,Rd,R1c,R3g,Ara), (Zc,Rd,R1c,R3g,Arb), (Zc,Rd,R1c,R3g,Arc), (Zc,Rd,R1c,R3g,Ard), (Zc,Rd,R1c,R3g,Are), (Zc,Rd,R1c,R3g,Arf), (Zc,Rd,R1c,R3g,Arg), (Zc,Rd,R1c,R3g,Arh), (Zc,Rd,R1c,R3g,Ari), (Zc,Rd,R1c,R3g,Arj), (Zc,Rd,R1c,R3g,Ark), (Zc,Rd,R1c,R3g,Arl), (Zc,Rd,R1c,R3g,Arm), (Zc,Rd,R1c,R3g,Arn), (Zc,Rd,R1c,R3g,Aro), (Zc,Rd,R1c,R3g,Arp), (Zc,Rd,R1c,R3h,Ara), (Zc,Rd,R1c,R3h,Arb), (Zc,Rd,R1c,R3h,Arc), (Zc,Rd,R1c,R3h,Ard), (Zc,Rd,R1c,R3h,Are), (Zc,Rd,R1c,R3h,Arf), (Zc,Rd,R1c,R3h,Arg), (Zc,Rd,R1c,R3h,Arh), (Zc,Rd,R1c,R3h,Ari), (Zc,Rd,R1c,R3h,Arj), (Zc,Rd,R1c,R3h,Ark), (Zc,Rd,R1c,R3h,Arl), (Zc,Rd,R1c,R3h,Arm), (Zc,Rd,R1c,R3h,Arn), (Zc,Rd,R1c,R3h,Aro), (Zc,Rd,R1c,R3h,Arp), (Zc,Rd,R1d,R3a,Ara), (Zc,Rd,R1d,R3a,Arb), (Zc,Rd,R1d,R3a,Arc), (Zc,Rd,R1d,R3a,Ard), (Zc,Rd,R1d,R3a,Are), (Zc,Rd,R1d,R3a,Arf), (Zc,Rd,R1d,R3a,Arg), (Zc,Rd,R1d,R3a,Arh), (Zc,Rd,R1d,R3a,Ari), (Zc,Rd,R1d,R3a,Arj), (Zc,Rd,R1d,R3a,Ark), (Zc,Rd,R1d,R3a,Arl), (Zc,Rd,R1d,R3a,Arm), (Zc,Rd,R1d,R3a,Arn), (Zc,Rd,R1d,R3a,Aro), (Zc,Rd,R1d,R3a,Arp), (Zc,Rd,R1d,R3b,Ara), (Zc,Rd,R1d,R3b,Arb), (Zc,Rd,R1d,R3b,Arc), (Zc,Rd,R1d,R3b,Ard), (Zc,Rd,R1d,R3b,Are), (Zc,Rd,R1d,R3b,Arf), (Zc,Rd,R1d,R3b,Arg), (Zc,Rd,R1d,R3b,Arh), (Zc,Rd,R1d,R3b,Ari), (Zc,Rd,R1d,R3b,Arj), (Zc,Rd,R1d,R3b,Ark), (Zc,Rd,R1d,R3b,Arl), (Zc,Rd,R1d,R3b,Arm), (Zc,Rd,R1d,R3b,Arn), (Zc,Rd,R1d,R3b,Aro), (Zc,Rd,R1d,R3b,Arp), (Zc,Rd,R1d,R3c,Ara), (Zc,Rd,R1d,R3c,Arb), (Zc,Rd,R1d,R3c,Arc), (Zc,Rd,R1d,R3c,Ard), (Zc,Rd,R1d,R3c,Are), (Zc,Rd,R1d,R3c,Arf), (Zc,Rd,R1d,R3c,Arg), (Zc,Rd,R1d,R3c,Arh), (Zc,Rd,R1d,R3c,Ari), (Zc,Rd,R1d,R3c,Arj), (Zc,Rd,R1d,R3c,Ark), (Zc,Rd,R1d,R3c,Arl), (Zc,Rd,R1d,R3c,Arm), (Zc,Rd,R1d,R3c,Arn), (Zc,Rd,R1d,R3c,Aro), (Zc,Rd,R1d,R3c,Arp), (Zc,Rd,R1d,R3d,Ara), (Zc,Rd,R1d,R3d,Arb), (Zc,Rd,R1d,R3d,Arc), (Zc,Rd,R1d,R3d,Ard), (Zc,Rd,R1d,R3d,Are), (Zc,Rd,R1d,R3d,Arf), (Zc,Rd,R1d,R3d,Arg), (Zc,Rd,R1d,R3d,Arh), (Zc,Rd,R1d,R3d,Ari), (Zc,Rd,R1d,R3d,Arj), (Zc,Rd,R1d,R3d,Ark), (Zc,Rd,R1d,R3d,Arl), (Zc,Rd,R1d,R3d,Arm), (Zc,Rd,R1d,R3d,Arn), (Zc,Rd,R1d,R3d,Aro), (Zc,Rd,R1d,R3d,Arp), (Zc,Rd,R1d,R3e,Ara), (Zc,Rd,R1d,R3e,Arb), (Zc,Rd,R1d,R3e,Arc), (Zc,Rd,R1d,R3e,Ard), (Zc,Rd,R1d,R3e,Are), (Zc,Rd,R1d,R3e,Arf), (Zc,Rd,R1d,R3e,Arg), (Zc,Rd,R1d,R3e,Arh), (Zc,Rd,R1d,R3e,Ari), (Zc,Rd,R1d,R3e,Arj), (Zc,Rd,R1d,R3e,Ark), (Zc,Rd,R1d,R3e,Arl), (Zc,Rd,R1d,R3e,Arm), (Zc,Rd,R1d,R3e,Arn), (Zc,Rd,R1d,R3e,Aro), (Zc,Rd,R1d,R3e,Arp), (Zc,Rd,R1d,R3f,Ara), (Zc,Rd,R1d,R3f,Arb), (Zc,Rd,R1d,R3f,Arc), (Zc,Rd,R1d,R3f,Ard), (Zc,Rd,R1d,R3f,Are), (Zc,Rd,R1d,R3f,Arf), (Zc,Rd,R1d,R3f,Arg), (Zc,Rd,R1d,R3f,Arh), (Zc,Rd,R1d,R3f,Ari), (Zc,Rd,R1d,R3f,Arj), (Zc,Rd,R1d,R3f,Ark), (Zc,Rd,R1d,R3f,Arl), (Zc,Rd,R1d,R3f,Arm), (Zc,Rd,R1d,R3f,Arn), (Zc,Rd,R1d,R3f,Aro), (Zc,Rd,R1d,R3f,Arp), (Zc,Rd,R1d,R3g,Ara), (Zc,Rd,R1d,R3g,Arb), (Zc,Rd,R1d,R3g,Arc), (Zc,Rd,R1d,R3g,Ard), (Zc,Rd,R1d,R3g,Are), (Zc,Rd,R1d,R3g,Arf), (Zc,Rd,R1d,R3g,Arg), (Zc,Rd,R1d,R3g,Arh), (Zc,Rd,R1d,R3g,Ari), (Zc,Rd,R1d,R3g,Arj), (Zc,Rd,R1d,R3g,Ark), (Zc,Rd,R1d,R3g,Arl), (Zc,Rd,R1d,R3g,Arm), (Zc,Rd,R1d,R3g,Arn), (Zc,Rd,R1d,R3g,Aro), (Zc,Rd,R1d,R3g,Arp), (Zc,Rd,R1d,R3h,Ara), (Zc,Rd,R1d,R3h,Arb), (Zc,Rd,R1d,R3h,Arc), (Zc,Rd,R1d,R3h,Ard), (Zc,Rd,R1d,R3h,Are), (Zc,Rd,R1d,R3h,Arf), (Zc,Rd,R1d,R3h,Arg), (Zc,Rd,R1d,R3h,Arh), (Zc,Rd,R1d,R3h,Ari), (Zc,Rd,R1d,R3h,Atj), (Zc,Rd,R1d,R3h,Ark), (Zc,Rd,R1d,R3h,Arl), (Zc,Rd,R1d,R3h,Arm), (Zc,Rd,R1d,R3h,Arn), (Zc,Rd,R1d,R3h,Aro), (Zc,Rd,R1d,R3h,Arp), (Zc,Re,R1a,R3a,Ara), (Zc,Re,R1a,R3a,Arb), (Zc,Re,R1a,R3a,Arc), (Zc,Re,R1a,R3a,Ard), (Zc,Re,R1a,R3a,Are), (Zc,Re,R1a,R3a,Arf), (Zc,Re,R1a,R3a,Arg), (Zc,Re,R1a,R3a,Arh), (Zc,Re,R1a,R3a,Ari), (Zc,Re,R1a,R3a,Arj), (Zc,Re,R1a,R3a,Ark), (Zc,Re,R1a,R3a,Arl), (Zc,Re,R1a,R3a,Arm), (Zc,Re,R1a,R3a,Arn), (Zc,Re,R1a,R3a,Aro), (Zc,Re,R1a,R3a,Arp), (Zc,Re,R1a,R3b,Ara), (Zc,Re,R1a,R3b,Arb), (Zc,Re,R1a,R3b,Arc), (Zc,Re,R1a,R3b,Ard), (Zc,Re,R1a,R3b,Are), (Zc,Re,R1a,R3b,Arf), (Zc,Re,R1a,R3b,Arg), (Zc,Re,R1a,R3b,Arh), (Zc,Re,R1a,R3b,Ari), (Zc,Re,R1a,R3b,Arj), (Zc,Re,R1a,R3b,Ark), (Zc,Re,R1a,R3b,Arl), (Zc,Re,R1a,R3b,Arm), (Zc,Re,R1a,R3b,Arn), (Zc,Re,R1a,R3b,Aro), (Zc,Re,R1a,R3b,Arp), (Zc,Re,R1a,R3c,Ara), (Zc,Re,R1a,R3c,Arb), (Zc,Re,R1a,R3c,Arc), (Zc,Re,R1a,R3c,Ard), (Zc,Re,R1a,R3c,Are), (Zc,Re,R1a,R3c,Arf), (Zc,Re,R1a,R3c,Arg), (Zc,Re,R1a,R3c,Arh), (Zc,Re,R1a,R3c,Ari), (Zc,Re,R1a,R3c,Arj), (Zc,Re,R1a,R3c,Ark), (Zc,Re,R1a,R3c,Arl), (Zc,Re,R1a,R3c,Arm), (Zc,Re,R1a,R3c,Arn), (Zc,Re,R1a,R3c,Aro), (Zc,Re,R1a,R3c,Arp), (Zc,Re,R1a,R3d,Ara), (Zc,Re,R1a,R3d,Arb), (Zc,Re,R1a,R3d,Arc), (Zc,Re,R1a,R3d,Ard), (Zc,Re,R1a,R3d,Are), (Zc,Re,R1a,R3d,Arf), (Zc,Re,R1a,R3d,Arg), (Zc,Re,R1a,R3d,Arh), (Zc,Re,R1a,R3d,Ari), (Zc,Re,R1a,R3d,Arj), (Zc,Re,R1a,R3d,Ark), (Zc,Re,R1a,R3d,Arl), (Zc,Re,R1a,R3d,Arm), (Zc,Re,R1a,R3d,Arn), (Zc,Re,R1a,R3d,Aro), (Zc,Re,R1a,R3d,Arp), (Zc,Re,R1a,R3e,Ara), (Zc,Re,R1a,R3e,Arb), (Zc,Re,R1a,R3e,Arc), (Zc,Re,R1a,R3e,Ard), (Zc,Re,R1a,R3e,Are), (Zc,Re,R1a,R3e,Arf), (Zc,Re,R1a,R3e,Arg), (Zc,Re,R1a,R3e,Arh), (Zc,Re,R1a,R3e,Ari), (Zc,Re,R1a,R3e,Arj), (Zc,Re,R1a,R3e,Ark), (Zc,Re,R1a,R3e,Arl), (Zc,Re,R1a,R3e,Arm), (Zc,Re,R1a,R3e,Arn), (Zc,Re,R1a,R3e,Aro), (Zc,Re,R1a,R3e,Arp), (Zc,Re,R1a,R3f,Ara), (Zc,Re,R1a,R3f,Arb), (Zc,Re,R1a,R3f,Arc), (Zc,Re,R1a,R3f,Ard), (Zc,Re,R1a,R3f,Are), (Zc,Re,R1a,R3f,Arf), (Zc,Re,R1a,R3f,Arg), (Zc,Re,R1a,R3f,Arh), (Zc,Re,R1a,R3f,Ari), (Zc,Re,R1a,R3f,Arj), (Zc,Re,R1a,R3f,Ark), (Zc,Re,R1a,R3f,Arl), (Zc,Re,R1a,R3f,Arm), (Zc,Re,R1a,R3f,Arn), (Zc,Re,R1a,R3f,Aro), (Zc,Re,R1a,R3f,Arp), (Zc,Re,R1a,R3g,Ara), (Zc,Re,R1a,R3g,Arb), (Zc,Re,R1a,R3g,Arc), (Zc,Re,R1a,R3g,Ard), (Zc,Re,R1a,R3g,Are), (Zc,Re,R1a,R3g,Arf), (Zc,Re,R1a,R3g,Arg), (Zc,Re,R1a,R3g,Arh), (Zc,Re,R1a,R3g,Ari), (Zc,Re,R1a,R3g,Arj), (Zc,Re,R1a,R3g,Ark), (Zc,Re,R1a,R3g,Arl), (Zc,Re,R1a,R3g,Arm), (Zc,Re,R1a,R3g,Arn), (Zc,Re,R1a,R3g,Aro), (Zc,Re,R1a,R3g,Arp), (Zc,Re,R1a,R3h,Ara), (Zc,Re,R1a,R3h,Arb), (Zc,Re,R1a,R3h,Arc), (Zc,Re,R1a,R3h,Ard), (Zc,Re,R1a,R3h,Are), (Zc,Re,R1a,R3h,Arf), (Zc,Re,R1a,R3h,Arg), (Zc,Re,R1a,R3h,Arh), (Zc,Re,R1a,R3h,Ari), (Zc,Re,R1a,R3h,Arj), (Zc,Re,R1a,R3h,Ark), (Zc,Re,R1a,R3h,Arl), (Zc,Re,R1a,R3h,Arm), (Zc,Re,R1a,R3h,Arn), (Zc,Re,R1a,R3h,Aro), (Zc,Re,R1a,R3h,Arp), (Zc,Re,R1b,R3a,Ara), (Zc,Re,R1b,R3a,Arb), (Zc,Re,R1b,R3a,Arc), (Zc,Re,R1b,R3a,Ard), (Zc,Re,R1b,R3a,Are), (Zc,Re,R1b,R3a,Arf), (Zc,Re,R1b,R3a,Arg), (Zc,Re,R1b,R3a,Arh), (Zc,Re,R1b,R3a,Ari), (Zc,Re,R1b,R3a,Arj), (Zc,Re,R1b,R3a,Ark), (Zc,Re,R1b,R3a,Arl), (Zc,Re,R1b,R3a,Arm), (Zc,Re,R1b,R3a,Arn), (Zc,Re,R1b,R3a,Aro), (Zc,Re,R1b,R3a,Arp), (Zc,Re,R1b,R3b,Ara), (Zc,Re,R1b,R3b,Arb), (Zc,Re,R1b,R3b,Arc), (Zc,Re,R1b,R3b,Ard), (Zc,Re,R1b,R3b,Are), (Zc,Re,R1b,R3b,Arf), (Zc,Re,R1b,R3b,Arg), (Zc,Re,R1b,R3b,Arh), (Zc,Re,R1b,R3b,Ari), (Zc,Re,R1b,R3b,Arj), (Zc,Re,R1b,R3b,Ark), (Zc,Re,R1b,R3b,Arl), (Zc,Re,R1b,R3b,Arm), (Zc,Re,R1b,R3b,Arn), (Zc,Re,R1b,R3b,Aro), (Zc,Re,R1b,R3b,Arp), (Zc,Re,R1b,R3c,Ara), (Zc,Re,R1b,R3c,Arb), (Zc,Re,R1b,R3c,Arc), (Zc,Re,R1b,R3c,Ard), (Zc,Re,R1b,R3c,Are), (Zc,Re,R1b,R3c,Arf), (Zc,Re,R1b,R3c,Arg), (Zc,Re,R1b,R3c,Arh), (Zc,Re,R1b,R3c,Ari), (Zc,Re,R1b,R3c,Arj), (Zc,Re,R1b,R3c,Ark), (Zc,Re,R1b,R3c,Arl), (Zc,Re,R1b,R3c,Arm), (Zc,Re,R1b,R3c,Arn), (Zc,Re,R1b,R3c,Aro), (Zc,Re,R1b,R3c,Arp), (Zc,Re,R1b,R3d,Ara), (Zc,Re,R1b,R3d,Arb), (Zc,Re,R1b,R3d,Arc), (Zc,Re,R1b,R3d, Ard), (Zc,Re,R1b,R3d,Are), (Zc,Re,R1b,R3d,Arf), (Zc,Re,R1b,R3d,Arg), (Zc,Re,R1b,R3d,Arh), (Zc,Re,R1b,R3d,Ari), (Zc,Re,R1b,R3d,Arj), (Zc,Re,R1b,R3d,Ark), (Zc,Re,R1b,R3d,Arl), (Zc,Re,R1b,R3d,Arm), (Zc,Re,R1b,R3d,Arn), (Zc,Re,R1b,R3d,Aro), (Zc,Re,R1b,R3d,Arp), (Zc,Re,R1b,R3e,Ara), (Zc,Re,R1b,R3e,Arb), (Zc,Re,R1b,R3e,Arc), (Zc,Re,R1b,R3e,Ard), (Zc,Re,R1b,R3e,Are), (Zc,Re,R1b,R3e,Arf), (Zc,Re,R1b,R3e,Arg), (Zc,Re,R1b,R3e,Arh), (Zc,Re,R1b,R3e,Ari), (Zc,Re,R1b,R3e,Arj), (Zc,Re,R1b,R3e,Ark), (Zc,Re,R1b,R3e,Arl), (Zc,Re,R1b,R3e,Arm), (Zc,Re,R1b,R3e,Arn), (Zc,Re,R1b,R3e,Aro), (Zc,Re,R1b,R3e,Arp), (Zc,Re,R1b,R3f,Ara), (Zc,Re,R1b,R3f,Arb), (Zc,Re,R1b,R3f,Arc), (Zc,Re,R1b,R3f,Ard), (Zc,Re,R1b,R3f,Are), (Zc,Re,R1b,R3f,Arf), (Zc,Re,R1b,R3f,Arg), (Zc,Re,R1b,R3f,Arh), (Zc,Re,R1b,R3f,Ari), (Zc,Re,R1b,R3f,Arj), (Zc,Re,R1b,R3f,Ark), (Zc,Re,R1b,R3f,Arl), (Zc,Re,R1b,R3f,Arm), (Zc,Re,R1b,R3f,Arn), (Zc,Re,R1b,R3f,Aro), (Zc,Re,R1b,R3f,Arp), (Zc,Re,R1b,R3g,Ara), (Zc,Re,R1b,R3g,Arb), (Zc,Re,R1b,R3g,Arc), (Zc,Re,R1b,R3g,Ard), (Zc,Re,R1b,R3g,Are), (Zc,Re,R1b,R3g,Arf), (Zc,Re,R1b,R3g,Arg), (Zc,Re,R1b,R3g,Arh), (Zc,Re,R1b,R3g,Ari), (Zc,Re,R1b,R3g,Arj), (Zc,Re,R1b,R3g,Ark), (Zc,Re,R1b,R3g,Arl), (Zc,Re,R1b,R3g,Arm), (Zc,Re,R1b,R3g,Arn), (Zc,Re,R1b,R3g,Aro), (Zc,Re,R1b,R3g,Arp), (Zc,Re,R1b,R3h,Ara), (Zc,Re,R1b,R3h,Arb), (Zc,Re,R1b,R3h,Arc), (Zc,Re,R1b,R3h,Ard), (Zc,Re,R1b,R3h,Are), (Zc,Re,R1b,R3h,Arf), (Zc,Re,R1b,R3h,Arg), (Zc,Re,R1b,R3h,Arh), (Zc,Re,R1b,R3h,Ari), (Zc,Re,R1b,R3h,Arj), (Zc,Re,R1b,R3h,Ark), (Zc,Re,R1b,R3h,Arl), (Zc,Re,R1b,R3h,Arm), (Zc,Re,R1b,R3h,Arn), (Zc,Re,R1b,R3h,Aro), (Zc,Re,R1b,R3h,Arp), (Zc,Re,R1c,R3a,Ara), (Zc,Re,R1c,R3a,Arb), (Zc,Re,R1c,R3a,Arc), (Zc,Re,R1c,R3a,Ard), (Zc,Re,R1c,R3a,Are), (Zc,Re,R1c,R3a,Arf), (Zc,Re,R1c,R3a,Arg), (Zc,Re,R1c,R3a,Arh), (Zc,Re,R1c,R3a,Ari), (Zc,Re,R1c,R3a,Arj), (Zc,Re,R1c,R3a,Ark), (Zc,Re,R1c,R3a,Arl), (Zc,Re,R1c,R3a,Arm), (Zc,Re,R1c,R3a,Arn), (Zc,Re,R1c,R3a,Aro), (Zc,Re,R1c,R3a,Arp), (Zc,Re,R1c,R3b,Ara), (Zc,Re,R1c,R3b,Arb), (Zc,Re,R1c,R3b,Arc), (Zc,Re,R1c,R3b,Ard), (Zc,Re,R1c,R3b,Are), (Zc,Re,R1c,R3b,Arf), (Zc,Re,R1c,R3b,Arg), (Zc,Re,R1c,R3b,Arh), (Zc,Re,R1c,R3b,Ari), (Zc,Re,R1c,R3b,Arj), (Zc,Re,R1c,R3b,Ark), (Zc,Re,R1c,R3b,Arl), (Zc,Re,R1c,R3b,Arm), (Zc,Re,R1c,R3b,Arn), (Zc,Re,R1c,R3b,Aro), (Zc,Re,R1c,R3b,Arp), (Zc,Re,R1c,R3c,Ara), (Zc,Re,R1c,R3c,Arb), (Zc,Re,R1c,R3c,Arc), (Zc,Re,R1c,R3c,Ard), (Zc,Re,R1c,R3c,Are), (Zc,Re,R1c,R3c,Arf), (Zc,Re,R1c,R3c,Arg), (Zc,Re,R1c,R3c,Arh), (Zc,Re,R1c,R3c,Ari), (Zc,Re,R1c,R3c,Arj), (Zc,Re,R1c,R3c,Ark), (Zc,Re,R1c,R3c,Arl), (Zc,Re,R1c,R3c,Arm), (Zc,Re,R1c,R3c,Arn), (Zc,Re,R1c,R3c,Aro), (Zc,Re,R1c,R3c,Arp), (Zc,Re,R1c,R3d,Ara), (Zc,Re,R1c,R3d,Arb), (Zc,Re,R1c,R3d,Arc), (Zc,Re,R1c,R3d,Ard), (Zc,Re,R1c,R3d,Are), (Zc,Re,R1c,R3d,Arf), (Zc,Re,R1c,R3d,Arg), (Zc,Re,R1c,R3d,Arh), (Zc,Re,R1c,R3d,Ari), (Zc,Re,R1c,R3d,Arj), (Zc,Re,R1c,R3d,Ark), (Zc,Re,R1c,R3d,Arl), (Zc,Re,R1c,R3d,Arm), (Zc,Re,R1c,R3d,Arn), (Zc,Re,R1c,R3d,Aro), (Zc,Re,R1c,R3d,Arp), (Zc,Re,R1c,R3e,Ara), (Zc,Re,R1c,R3e,Arb), (Zc,Re,R1c,R3e,Arc), (Zc,Re,R1c,R3e,Ard), (Zc,Re,R1c,R3e,Are), (Zc,Re,R1c,R3e,Arf), (Zc,Re,R1c,R3e,Arg), (Zc,Re,R1c,R3e,Arh), (Zc,Re,R1c,R3e,Ari), (Zc,Re,R1c,R3e,Arj), (Zc,Re,R1c,R3e,Ark), (Zc,Re,R1c,R3e,Arl), (Zc,Re,R1c,R3e,Arm), (Zc,Re,R1c,R3e,Arn), (Zc,Re,R1c,R3e,Aro), (Zc,Re,R1c,R3e,Arp), (Zc,Re,R1c,R3f,Ara), (Zc,Re,R1c,R3f,Arb), (Zc,Re,R1c,R3f,Arc), (Zc,Re,R1c,R3f,Ard), (Zc,Re,R1c,R3f,Are), (Zc,Re,R1c,R3f,Arf), (Zc,Re,R1c,R3f,Arg), (Zc,Re,R1c,R3f,Arh), (Zc,Re,R1c,R3f,Ari), (Zc,Re,R1c,R3f,Arj), (Zc,Re,R1c,R3f,Ark), (Zc,Re,R1c,R3f,Arl), (Zc,Re,R1c,R3f,Arm), (Zc,Re,R1c,R3f,Arn), (Zc,Re,R1c,R3f,Aro), (Zc,Re,R1c,R3f,Arp), (Zc,Re,R1c,R3g,Ara), (Zc,Re,R1c,R3g,Arb), (Zc,Re,R1c,R3g,Arc), (Zc,Re,R1c,R3g,Ard), (Zc,Re,R1c,R3g,Are), (Zc,Re,R1c,R3g,Arf), (Zc,Re,R1c,R3g,Arg), (Zc,Re,R1c,R3g,Arh), (Zc,Re,R1c,R3g,Ari), (Zc,Re,R1c,R3g,Arj), (Zc,Re,R1c,R3g,Ark), (Zc,Re,R1c,R3g,Arl), (Zc,Re,R1c,R3g,Arm), (Zc,Re,R1c,R3g,Arn), (Zc,Re,R1c,R3g,Aro), (Zc,Re,R1c,R3g,Arp), (Zc,Re,R1c,R3h,Ara), (Zc,Re,R1c,R3h,Arb), (Zc,Re,R1c,R3h,Arc), (Zc,Re,R1c,R3h,Ard), (Zc,Re,R1c,R3h,Are), (Zc,Re,R1c,R3h,Arf), (Zc,Re,R1c,R3h,Arg), (Zc,Re,R1c,R3h,Arh), (Zc,Re,R1c,R3h,Ari), (Zc,Re,R1c,R3h,Arj), (Zc,Re,R1c,R3h,Ark), (Zc,Re,R1c,R3h,Arl), (Zc,Re,R1c,R3h,Arm), (Zc,Re,R1c,R3h,Arn), (Zc,Re,R1c,R3h,Aro), (Zc,Re,R1c,R3h,Arp), (Zc,Re,R1d,R3a,Ara), (Zc,Re,R1d,R3a,Arb), (Zc,Re,R1d,R3a,Arc), (Zc,Re,R1d,R3a,Ard), (Zc,Re,R1d,R3a,Are), (Zc,Re,R1d,R3a,Arf), (Zc,Re,R1d,R3a,Arg), (Zc,Re,R1d,R3a,Arh), (Zc,Re,R1d,R3a,Ari), (Zc,Re,R1d,R3a,Arj), (Zc,Re,R1d,R3a,Ark), (Zc,Re,R1d,R3a,Arl), (Zc,Re,R1d,R3a,Arm), (Zc,Re,R1d,R3a,Arn), (Zc,Re,R1d,R3a,Aro), (Zc,Re,R1d,R3a,Arp), (Zc,Re,R1d,R3b,Ara), (Zc,Re,R1d,R3b,Arb), (Zc,Re,R1d,R3b,Arc), (Zc,Re,R1d,R3b,Ard), (Zc,Re,R1d,R3b,Are), (Zc,Re,R1d,R3b,Arf), (Zc,Re,R1d,R3b,Arg), (Zc,Re,R1d,R3b,Arh), (Zc,Re,R1d,R3b,Ari), (Zc,Re,R1d,R3b,Arj), (Zc,Re,R1d,R3b,Ark), (Zc,Re,R1d,R3b,Arl), (Zc,Re,R1d,R3b,Arm), (Zc,Re,R1d,R3b,Arn), (Zc,Re,R1d,R3b,Aro), (Zc,Re,R1d,R3b,Arp), (Zc,Re,R1d,R3c,Ara), (Zc,Re,R1d,R3c,Arb), (Zc,Re,R1d,R3c,Arc), (Zc,Re,R1d,R3c,Ard), (Zc,Re,R1d,R3c,Are), (Zc,Re,R1d,R3c,Arf), (Zc,Re,R1d,R3c,Arg), (Zc,Re,R1d,R3c,Arh), (Zc,Re,R1d,R3c,Ari), (Zc,Re,R1d,R3c,Arj), (Zc,Re,R1d,R3c,Ark), (Zc,Re,R1d,R3c,Arl), (Zc,Re,R1d,R3c,Arm), (Zc,Re,R1d,R3c,Arn), (Zc,Re,R1d,R3c,Aro), (Zc,Re,R1d,R3c,Arp), (Zc,Re,R1d,R3d,Ara), (Zc,Re,R1d,R3d,Arb), (Zc,Re,R1d,R3d,Arc), (Zc,Re,R1d,R3d,Ard), (Zc,Re,R1d,R3d,Are), (Zc,Re,R1d,R3d,Arf), (Zc,Re,R1d,R3d,Arg), (Zc,Re,R1d,R3d,Arh), (Zc,Re,R1d,R3d,Ari), (Zc,Re,R1d,R3d,Arj), (Zc,Re,R1d,R3d,Ark), (Zc,Re,R1d,R3d,Arl), (Zc,Re,R1d,R3d,Arm), (Zc,Re,R1d,R3d,Arn), (Zc,Re,R1d,R3d,Aro), (Zc,Re,R1d,R3d,Arp), (Zc,Re,R1d,R3e,Ara), (Zc,Re,R1d,R3e,Arb), (Zc,Re,R1d,R3e,Arc), (Zc,Re,R1d,R3e,Ard), (Zc,Re,R1d,R3e,Are), (Zc,Re,R1d,R3e,Arf), (Zc,Re,R1d,R3e,Arg), (Zc,Re,R1d,R3e,Arh), (Zc,Re,R1d,R3e,Ari), (Zc,Re,R1d,R3e,Arj), (Zc,Re,R1d,R3e,Ark), (Zc,Re,R1d,R3e,Arl), (Zc,Re,R1d,R3e,Arm), (Zc,Re,R1d,R3e,Arn), (Zc,Re,R1d,R3e,Aro), (Zc,Re,R1d,R3e,Arp), (Zc,Re,R1d,R3f,Ara), (Zc,Re,R1d,R3f,Arb), (Zc,Re,R1d,R3f,Arc), (Zc,Re,R1d,R3f,Ard), (Zc,Re,R1d,R3f,Are), (Zc,Re,R1d,R3f,Arf), (Zc,Re,R1d,R3f,Arg), (Zc,Re,R1d,R3f,Arh), (Zc,Re,R1d,R3f,Ari), (Zc,Re,R1d,R3f,Arj), (Zc,Re,R1d,R3f,Ark), (Zc,Re,R1d,R3f,Arl), (Zc,Re,R1d,R3f,Arm), (Zc,Re,R1d,R3f,Arn), (Zc,Re,R1d,R3f,Aro), (Zc,Re,R1d,R3f,Arp), (Zc,Re,R1d,R3g,Ara), (Zc,Re,R1d,R3g,Arb), (Zc,Re,R1d,R3g,Arc), (Zc,Re,R1d,R3g,Ard), (Zc,Re,R1d,R3g,Are), (Zc,Re,R1d,R3g,Arf), (Zc,Re,R1d,R3g,Arg), (Zc,Re,R1d,R3g,Arh), (Zc,Re,R1d,R3g,Ari), (Zc,Re,R1d,R3g,Arj), (Zc,Re,R1d,R3g,Ark), (Zc,Re,R1d,R3g,Arl), (Zc,Re,R1d,R3g,Arm), (Zc,Re,R1d,R3g,Arn), (Zc,Re,R1d,R3g,Aro), (Zc,Re,R1d,R3g,Arp), (Zc,Re,R1d,R3h,Ara), (Zc,Re,R1d,R3h,Arb), (Zc,Re,R1d,R3h,Arc), (Zc,Re,R1d,R3h,Ard), (Zc,Re,R1d,R3h,Are), (Zc,Re,R1d,R3h,Arf), (Zc,Re,R1d,R3h,Arg), (Zc,Re,R1d,R3h,Arh), (Zc,Re,R1d,R3h,Ari), (Zc,Re,R1d,R3h,Arj), (Zc,Re,R1d,R3h,Ark), (Zc,Re,R1d,R3h,Arl), (Zc,Re,R1d,R3h,Arm), (Zc,Re,R1d,R3h,Arn), (Zc,Re,R1d,R3h,Aro), (Zc,Re,R1d,R3h,Arp), (Zc,Rf,R1a,R3a,Ara), (Zc,Rf,R1a,R3a,Arb), (Zc,Rf,R1a,R3a,Arc), (Zc,Rf,R1a,R3a,Ard), (Zc,Rf,R1a,R3a,Are), (Zc,Rf,R1a,R3a,Arf), (Zc,Rf,R1a,R3a,Arg), (Zc,Rf,R1a,R3a,Arh), (Zc,Rf,R1a,R3a,Ari), (Zc,Rf,R1a,R3a,Arj), (Zc,Rf,R1a,R3a,Ark), (Zc,Rf,R1a,R3a,Arl), (Zc,Rf, R1a,R3a,Arm), (Zc,Rf,R1a,R3a,Arn), (Zc,Rf,R1a,R3a,Aro), (Zc,Rf,R1a,R3a,Arp), (Zc,Rf,R1a,R3b,Ara), (Zc,Rf,R1a,R3b,Arb), (Zc,Rf,R1a,R3b,Arc), (Zc,Rf,R1a,R3b,Ard), (Zc,Rf,R1a,R3b,Are), (Zc,Rf,R1a,R3b,Arf), (Zc,Rf,R1a,R3b,Arg), (Zc,Rf,R1a,R3b,Arh), (Zc,Rf,R1a,R3b,Ari), (Zc,Rf,R1a,R3b,Arj), (Zc,Rf,R1a,R3b,Ark), (Zc,Rf,R1a,R3b,Arl), (Zc,Rf,R1a,R3b,Arm), (Zc,Rf,R1a,R3b,Arn), (Zc,Rf,R1a,R3b,Aro), (Zc,Rf,R1a,R3b,Arp), (Zc,Rf,R1a,R3c,Ara), (Zc,Rf,R1a,R3c,Arb), (Zc,Rf,R1a,R3c,Arc), (Zc,Rf,R1a,R3c,Ard), (Zc,Rf,R1a,R3c,Are), (Zc,Rf,R1a,R3c,Arf), (Zc,Rf,R1a,R3c,Arg), (Zc,Rf,R1a,R3c,Arh), (Zc,Rf,R1a,R3c,Ari), (Zc,Rf,R1a,R3c,Arj), (Zc,Rf,R1a,R3c,Ark), (Zc,Rf,R1a,R3c,Arl), (Zc,Rf,R1a,R3c,Arm), (Zc,Rf,R1a,R3c,Arn), (Zc,Rf,R1a,R3c,Aro), (Zc,Rf,R1a,R3c,Arp), (Zc,Rf,R1a,R3d,Ara), (Zc,Rf,R1a,R3d,Arb), (Zc,Rf,R1a,R3d,Arc), (Zc,Rf,R1a,R3d,Ard), (Zc,Rf,R1a,R3d,Are), (Zc,Rf,R1a,R3d,Arf), (Zc,Rf,R1a,R3d,Arg), (Zc,Rf,R1a,R3d,Arh), (Zc,Rf,R1a,R3d,Ari), (Zc,Rf,R1a,R3d,Arj), (Zc,Rf,R1a,R3d,Ark), (Zc,Rf,R1a,R3d,Arl), (Zc,Rf,R1a,R3d,Arm), (Zc,Rf,R1a,R3d,Arn), (Zc,Rf,R1a,R3d,Aro), (Zc,Rf,R1a,R3d,Arp), (Zc,Rf,R1a,R3e,Ara), (Zc,Rf,R1a,R3e,Arb), (Zc,Rf,R1a,R3e,Arc), (Zc,Rf,R1a,R3e,Ard), (Zc,Rf,R1a,R3e,Are), (Zc,Rf,R1a,R3e,Arf), (Zc,Rf,R1a,R3e,Arg), (Zc,Rf,R1a,R3e,Arh), (Zc,Rf,R1a,R3e,Ari), (Zc,Rf,R1a,R3e,Arj), (Zc,Rf,R1a,R3e,Ark), (Zc,Rf,R1a,R3e,Arl), (Zc,Rf,R1a,R3e,Arm), (Zc,Rf,R1a,R3e,Arn), (Zc,Rf,R1a,R3e,Aro), (Zc,Rf,R1a,R3e,Arp), (Zc,Rf,R1a,R3f,Ara), (Zc,Rf,R1a,R3f,Arb), (Zc,Rf,R1a,R3f,Arc), (Zc,Rf,R1a,R3f,Ard), (Zc,Rf,R1a,R3f,Are), (Zc,Rf,R1a,R3f,Arf), (Zc,Rf,R1a,R3f,Arg), (Zc,Rf,R1a,R3f,Arh), (Zc,Rf,R1a,R3f,Ari), (Zc,Rf,R1a,R3f,Arj), (Zc,Rf,R1a,R3f,Ark), (Zc,Rf,R1a,R3f,Arl), (Zc,Rf,R1a,R3f,Arm), (Zc,Rf,R1a,R3f,Arn), (Zc,Rf,R1a,R3f,Aro), (Zc,Rf,R1a,R3f,Arp), (Zc,Rf,R1a,R3g,Ara), (Zc,Rf,R1a,R3g,Arb), (Zc,Rf,R1a,R3g,Arc), (Zc,Rf,R1a,R3g,Ard), (Zc,Rf,R1a,R3g,Are), (Zc,Rf,R1a,R3g,Arf), (Zc,Rf,R1a,R3g,Arg), (Zc,Rf,R1a,R3g,Arh), (Zc,Rf,R1a,R3g,Ari), (Zc,Rf,R1a,R3g,Arj), (Zc,Rf,R1a,R3g,Ark), (Zc,Rf,R1a,R3g,Arl), (Zc,Rf,R1a,R3g,Arm), (Zc,Rf,R1a,R3g,Arn), (Zc,Rf,R1a,R3g,Aro), (Zc,Rf,R1a,R3g,Arp), (Zc,Rf,R1a,R3h,Ara), (Zc,Rf,R1a,R3h,Arb), (Zc,Rf,R1a,R3h,Arc), (Zc,Rf,R1a,R3h,Ard), (Zc,Rf,R1a,R3h,Are), (Zc,Rf,R1a,R3h,Arf), (Zc,Rf,R1a,R3h,Arg), (Zc,Rf,R1a,R3h,Arh), (Zc,Rf,R1a,R3h,Ari), (Zc,Rf,R1a,R3h,Arj), (Zc,Rf,R1a,R3h,Ark), (Zc,Rf,R1a,R3h,Arl), (Zc,Rf,R1a,R3h,Arm), (Zc,Rf,R1a,R3h,Arn), (Zc,Rf,R1a,R3h,Aro), (Zc,Rf,R1a,R3h,Arp), (Zc,Rf,R1b,R3a,Ara), (Zc,Rf,R1b,R3a,Arb), (Zc,Rf,R1b,R3a,Arc), (Zc,Rf,R1b,R3a,Ard), (Zc,Rf,R1b,R3a,Are), (Zc,Rf,R1b,R3a,Arf), (Zc,Rf,R1b,R3a,Arg), (Zc,Rf,R1b,R3a,Arh), (Zc,Rf,R1b,R3a,Ari), (Zc,Rf,R1b,R3a,Arj), (Zc,Rf,R1b,R3a,Ark), (Zc,Rf,R1b,R3a,Arl), (Zc,Rf,R1b,R3a,Arm), (Zc,Rf,R1b,R3a,Arn), (Zc,Rf,R1b,R3a,Aro), (Zc,Rf,R1b,R3a,Arp), (Zc,Rf,R1b,R3b,Ara), (Zc,Rf,R1b,R3b,Arb), (Zc,Rf,R1b,R3b,Arc), (Zc,Rf,R1b,R3b,Ard), (Zc,Rf,R1b,R3b,Are), (Zc,Rf,R1b,R3b,Arf), (Zc,Rf,R1b,R3b,Arg), (Zc,Rf,R1b,R3b,Arh), (Zc,Rf,R1b,R3b,Ari), (Zc,Rf,R1b,R3b,Arj), (Zc,Rf,R1b,R3b,Ark), (Zc,Rf,R1b,R3b,Arl), (Zc,Rf,R1b,R3b,Arm), (Zc,Rf,R1b,R3b,Arn), (Zc,Rf,R1b,R3b,Aro), (Zc,Rf,R1b,R3b,Arp), (Zc,Rf,R1b,R3c,Ara), (Zc,Rf,R1b,R3c,Arb), (Zc,Rf,R1b,R3c,Arc), (Zc,Rf,R1b,R3c,Ard), (Zc,Rf,R1b,R3c,Are), (Zc,Rf,R1b,R3c,Arf), (Zc,Rf,R1b,R3c,Arg), (Zc,Rf,R1b,R3c,Arh), (Zc,Rf,R1b,R3c,Ari), (Zc,Rf,R1b,R3c,Arj), (Zc,Rf,R1b,R3c,Ark), (Zc,Rf,R1b,R3c,Arl), (Zc,Rf,R1b,R3c,Arm), (Zc,Rf,R1b,R3c,Arn), (Zc,Rf,R1b,R3c,Aro), (Zc,Rf,R1b,R3c,Arp), (Zc,Rf,R1b,R3d,Ara), (Zc,Rf,R1b,R3d,Arb), (Zc,Rf,R1b,R3d,Arc), (Zc,Rf,R1b,R3d,Ard), (Zc,Rf,R1b,R3d,Are), (Zc,Rf,R1b,R3d,Arf), (Zc,Rf,R1b,R3d,Arg), (Zc,Rf,R1b,R3d,Arh), (Zc,Rf,R1b,R3d,Ari), (Zc,Rf,R1b,R3d,Atj), (Zc,Rf,R1b,R3d,Ark), (Zc,Rf,R1b,R3d,Arl), (Zc,Rf,R1b,R3d,Arm), (Zc,Rf,R1b,R3d,Arn), (Zc,Rf,R1b,R3d,Aro), (Zc,Rf,R1b,R3d,Arp), (Zc,Rf,R1b,R3e,Ara), (Zc,Rf,R1b,R3e,Arb), (Zc,Rf,R1b,R3e,Arc), (Zc,Rf,R1b,R3e,Ard), (Zc,Rf,R1b,R3e,Are), (Zc,Rf,R1b,R3e,Arf), (Zc,Rf,R1b,R3e,Arg), (Zc,Rf,R1b,R3e,Arh), (Zc,Rf,R1b,R3e,Ari), (Zc,Rf,R1b,R3e,Arj), (Zc,Rf,R1b,R3e,Ark), (Zc,Rf,R1b,R3e,Arl), (Zc,Rf,R1b,R3e,Arm), (Zc,Rf,R1b,R3e,Arn), (Zc,Rf,R1b,R3e,Aro), (Zc,Rf,R1b,R3e,Arp), (Zc,Rf,R1b,R3f,Ara), (Zc,Rf,R1b,R3f,Arb), (Zc,Rf,R1b,R3f,Arc), (Zc,Rf,R1b,R3f,Ard), (Zc,Rf,R1b,R3f,Are), (Zc,Rf,R1b,R3f,Arf), (Zc,Rf,R1b,R3f,Arg), (Zc,Rf,R1b,R3f,Arh), (Zc,Rf,R1b,R3f,Ari), (Zc,Rf,R1b,R3f,Arj), (Zc,Rf,R1b,R3f,Ark), (Zc,Rf,R1b,R3f,Arl), (Zc,Rf,R1b,R3f,Arm), (Zc,Rf,R1b,R3f,Arn), (Zc,Rf,R1b,R3f,Aro), (Zc,Rf,R1b,R3f,Arp), (Zc,Rf,R1b,R3g,Ara), (Zc,Rf,R1b,R3g,Arb), (Zc,Rf,R1b,R3g,Arc), (Zc,Rf,R1b,R3g,Ard), (Zc,Rf,R1b,R3g,Are), (Zc,Rf,R1b,R3g,Arf), (Zc,Rf,R1b,R3g,Arg), (Zc,Rf,R1b,R3g,Arh), (Zc,Rf,R1b,R3g,Ari), (Zc,Rf,R1b,R3g,Arj), (Zc,Rf,R1b,R3g,Ark), (Zc,Rf,R1b,R3g,Arl), (Zc,Rf,R1b,R3g,Arm), (Zc,Rf,R1b,R3g,Arn), (Zc,Rf,R1b,R3g,Aro), (Zc,Rf,R1b,R3g,Arp), (Zc,Rf,R1b,R3h,Ara), (Zc,Rf,R1b,R3h,Arb), (Zc,Rf,R1b,R3h,Arc), (Zc,Rf,R1b,R3h,Ard), (Zc,Rf,R1b,R3h,Are), (Zc,Rf,R1b,R3h,Arf), (Zc,Rf,R1b,R3h,Arg), (Zc,Rf,R1b,R3h,Arh), (Zc,Rf,R1b,R3h,Ari), (Zc,Rf,R1b,R3h,Arj), (Zc,Rf,R1b,R3h,Ark), (Zc,Rf,R1b,R3h,Arl), (Zc,Rf,R1b,R3h,Arm), (Zc,Rf,R1b,R3h,Arn), (Zc,Rf,R1b,R3h,Aro), (Zc,Rf,R1b,R3h,Arp), (Zc,Rf,R1c,R3a,Ara), (Zc,Rf,R1c,R3a,Arb), (Zc,Rf,R1c,R3a,Arc), (Zc,Rf,R1c,R3a,Ard), (Zc,Rf,R1c,R3a,Are), (Zc,Rf,R1c,R3a,Arf), (Zc,Rf,R1c,R3a,Arg), (Zc,Rf,R1c,R3a,Arh), (Zc,Rf,R1c,R3a,Ari), (Zc,Rf,R1c,R3a,Arj), (Zc,Rf,R1c,R3a,Ark), (Zc,Rf,R1c,R3a,Arl), (Zc,Rf,R1c,R3a,Arm), (Zc,Rf,R1c,R3a,Arn), (Zc,Rf,R1c,R3a,Aro), (Zc,Rf,R1c,R3a,Arp), (Zc,Rf,R1c,R3b,Ara), (Zc,Rf,R1c,R3b,Arb), (Zc,Rf,R1c,R3b,Arc), (Zc,Rf,R1c,R3b,Ard), (Zc,Rf,R1c,R3b,Are), (Zc,Rf,R1c,R3b,Arf), (Zc,Rf,R1c,R3b,Arg), (Zc,Rf,R1c,R3b,Arh), (Zc,Rf,R1c,R3b,Ari), (Zc,Rf,R1c,R3b,Arj), (Zc,Rf,R1c,R3b,Ark), (Zc,Rf,R1c,R3b,Arl), (Zc,Rf,R1c,R3b,Arm), (Zc,Rf,R1c,R3b,Arn), (Zc,Rf,R1c,R3b,Aro), (Zc,Rf,R1c,R3b,Arp), (Zc,Rf,R1c,R3c,Ara), (Zc,Rf,R1c,R3c,Arb), (Zc,Rf,R1c,R3c,Arc), (Zc,Rf,R1c,R3c,Ard), (Zc,Rf,R1c,R3c,Are), (Zc,Rf,R1c,R3c,Arf), (Zc,Rf,R1c,R3c,Arg), (Zc,Rf,R1c,R3c,Arh), (Zc,Rf,R1c,R3c,Ari), (Zc,Rf,R1c,R3c,Arj), (Zc,Rf,R1c,R3c,Ark), (Zc,Rf,R1c,R3c,Arl), (Zc,Rf,R1c,R3c,Arm), (Zc,Rf,R1c,R3c,Arn), (Zc,Rf,R1c,R3c,Aro), (Zc,Rf,R1c,R3c,Arp), (Zc,Rf,R1c,R3d,Ara), (Zc,Rf,R1c,R3d,Arb), (Zc,Rf,R1c,R3d,Arc), (Zc,Rf,R1c,R3d,Ard), (Zc,Rf,R1c,R3d,Are), (Zc,Rf,R1c,R3d,Arf), (Zc,Rf,R1c,R3d,Arg), (Zc,Rf,R1c,R3d,Arh), (Zc,Rf,R1c,R3d,Ari), (Zc,Rf,R1c,R3d,Arj), (Zc,Rf,R1c,R3d,Ark), (Zc,Rf,R1c,R3d,Arl), (Zc,Rf,R1c,R3d,Arm), (Zc,Rf,R1c,R3d,Arn), (Zc,Rf,R1c,R3d,Aro), (Zc,Rf,R1c,R3d,Arp), (Zc,Rf,R1c,R3e,Ara), (Zc,Rf,R1c,R3e,Arb), (Zc,Rf,R1c,R3e,Arc), (Zc,Rf,R1c,R3e,Ard), (Zc,Rf,R1c,R3e,Are), (Zc,Rf,R1c,R3e,Arf), (Zc,Rf,R1c,R3e,Arg), (Zc,Rf,R1c,R3e,Arh), (Zc,Rf,R1c,R3e,Ari), (Zc,Rf,R1c,R3e,Arj), (Zc,Rf,R1c,R3e,Ark), (Zc,Rf,R1c,R3e,Arl), (Zc,Rf,R1c,R3e,Arm), (Zc,Rf,R1c,R3e,Arn), (Zc,Rf,R1c,R3e,Aro), (Zc,Rf,R1c,R3e,Arp), (Zc,Rf,R1c,R3f,Ara), (Zc,Rf,R1c,R3f,Arb), (Zc,Rf,R1c,R3f,Arc), (Zc,Rf,R1c,R3f,Ard), (Zc,Rf,R1c,R3f,Are), (Zc,Rf,R1c,R3f,Arf), (Zc,Rf,R1c,R3f,Arg), (Zc,Rf,R1c,R3f,Arh), (Zc,Rf,R1c,R3f,Ari), (Zc,Rf,R1c,R3f,Arj), (Zc,Rf,R1c,R3f,Ark), (Zc,Rf,R1c,R3f,Arl), (Zc,Rf,R1c,R3f,Arm), (Zc,Rf,R1c,R3f,Arn), (Zc,Rf,R1c,R3f,Aro), (Zc,Rf,R1c,R3f,Arp), (Zc,Rf,R1c,R3g,Ara), (Zc,Rf,R1c,R3g,Arb), (Zc,Rf,R1c,R3g,Arc), (Zc,Rf,R1c,R3g,Ard), (Zc,Rf,R1c,R3g,Are), (Zc,Rf,R1c,R3g,Arf), (Zc,Rf,R1c,R3g,Arg), (Zc,Rf,R1c,R3g, Arh), (Zc,Rf,R1c,R3g,Ari), (Zc,Rf,R1c,R3g,Arj), (Zc,Rf,R1c,R3g,Ark), (Zc,Rf,R1c,R3g,Arl), (Zc,Rf,R1c,R3g,Arm), (Zc,Rf,R1c,R3g,Arn), (Zc,Rf,R1c,R3g,Aro), (Zc,Rf,R1c,R3g,Arp), (Zc,Rf,R1c,R3h,Ara), (Zc,Rf,R1c,R3h,Arb), (Zc,Rf,R1c,R3h,Arc), (Zc,Rf,R1c,R3h,Ard), (Zc,Rf,R1c,R3h,Are), (Zc,Rf,R1c,R3h,Arf), (Zc,Rf,R1c,R3h,Arg), (Zc,Rf,R1c,R3h,Arh), (Zc,Rf,R1c,R3h,Ari), (Zc,Rf,R1c,R3h,Arj), (Zc,Rf,R1c,R3h,Ark), (Zc,Rf,R1c,R3h,Arl), (Zc,Rf,R1c,R3h,Arm), (Zc,Rf,R1c,R3h,Arn), (Zc,Rf,R1c,R3h,Aro), (Zc,Rf,R1c,R3h,Arp), (Zc,Rf,R1d,R3a,Ara), (Zc,Rf,R1d,R3a,Arb), (Zc,Rf,R1d,R3a,Arc), (Zc,Rf,R1d,R3a,Ard), (Zc,Rf,R1d,R3a,Are), (Zc,Rf,R1d,R3a,Arf), (Zc,Rf,R1d,R3a,Arg), (Zc,Rf,R1d,R3a,Arh), (Zc,Rf,R1d,R3a,Ari), (Zc,Rf,R1d,R3a,Arj), (Zc,Rf,R1d,R3a,Ark), (Zc,Rf,R1d,R3a,Arl), (Zc,Rf,R1d,R3a,Arm), (Zc,Rf,R1d,R3a,Arn), (Zc,Rf,R1d,R3a,Aro), (Zc,Rf,R1d,R3a,Arp), (Zc,Rf,R1d,R3b,Ara), (Zc,Rf,R1d,R3b,Arb), (Zc,Rf,R1d,R3b,Arc), (Zc,Rf,R1d,R3b,Ard), (Zc,Rf,R1d,R3b,Are), (Zc,Rf,R1d,R3b,Arf), (Zc,Rf,R1d,R3b,Arg), (Zc,Rf,R1d,R3b,Arh), (Zc,Rf,R1d,R3b,Ari), (Zc,Rf,R1d,R3b,Arj), (Zc,Rf,R1d,R3b,Ark), (Zc,Rf,R1d,R3b,Arl), (Zc,Rf,R1d,R3b,Arm), (Zc,Rf,R1d,R3b,Arn), (Zc,Rf,R1d,R3b,Aro), (Zc,Rf,R1d,R3b,Arp), (Zc,Rf,R1d,R3c,Ara), (Zc,Rf,R1d,R3c,Arb), (Zc,Rf,R1d,R3c,Arc), (Zc,Rf,R1d,R3c,Ard), (Zc,Rf,R1d,R3c,Are), (Zc,Rf,R1d,R3c,Arf), (Zc,Rf,R1d,R3c,Arg), (Zc,Rf,R1d,R3c,Arh), (Zc,Rf,R1d,R3c,Ari), (Zc,Rf,R1d,R3c,Arj), (Zc,Rf,R1d,R3c,Ark), (Zc,Rf,R1d,R3c,Arl), (Zc,Rf,R1d,R3c,Arm), (Zc,Rf,R1d,R3c,Arn), (Zc,Rf,R1d,R3c,Aro), (Zc,Rf,R1d,R3c,Arp), (Zc,Rf,R1d,R3d,Ara), (Zc,Rf,R1d,R3d,Arb), (Zc,Rf,R1d,R3d,Arc), (Zc,Rf,R1d,R3d,Ard), (Zc,Rf,R1d,R3d,Are), (Zc,Rf,R1d,R3d,Arf), (Zc,Rf,R1d,R3d,Arg), (Zc,Rf,R1d,R3d,Arh), (Zc,Rf,R1d,R3d,Ari), (Zc,Rf,R1d,R3d,Arj), (Zc,Rf,R1d,R3d,Ark), (Zc,Rf,R1d,R3d,Arl), (Zc,Rf,R1d,R3d,Arm), (Zc,Rf,R1d,R3d,Arn), (Zc,Rf,R1d,R3d,Aro), (Zc,Rf,R1d,R3d,Arp), (Zc,Rf,R1d,R3e,Ara), (Zc,Rf,R1d,R3e,Arb), (Zc,Rf,R1d,R3e,Arc), (Zc,Rf,R1d,R3e,Ard), (Zc,Rf,R1d,R3e,Are), (Zc,Rf,R1d,R3e,Arf), (Zc,Rf,R1d,R3e,Arg), (Zc,Rf,R1d,R3e,Arh), (Zc,Rf,R1d,R3e,Ari), (Zc,Rf,R1d,R3e,Arj), (Zc,Rf,R1d,R3e,Ark), (Zc,Rf,R1d,R3e,Arl), (Zc,Rf,R1d,R3e,Arm), (Zc,Rf,R1d,R3e,Arn), (Zc,Rf,R1d,R3e,Aro), (Zc,Rf,R1d,R3e,Arp), (Zc,Rf,R1d,R3f,Ara), (Zc,Rf,R1d,R3f,Arb), (Zc,Rf,R1d,R3f,Arc), (Zc,Rf,R1d,R3f,Ard), (Zc,Rf,R1d,R3f,Are), (Zc,Rf,R1d,R3f,Arf), (Zc,Rf,R1d,R3f,Arg), (Zc,Rf,R1d,R3f,Arh), (Zc,Rf,R1d,R3f,Ari), (Zc,Rf,R1d,R3f,Arj), (Zc,Rf,R1d,R3f,Ark), (Zc,Rf,R1d,R3f,Arl), (Zc,Rf,R1d,R3f,Arm), (Zc,Rf,R1d,R3f,Arn), (Zc,Rf,R1d,R3f,Aro), (Zc,Rf,R1d,R3f,Arp), (Zc,Rf,R1d,R3g,Ara), (Zc,Rf,R1d,R3g,Arb), (Zc,Rf,R1d,R3g,Arc), (Zc,Rf,R1d,R3g,Ard), (Zc,Rf,R1d,R3g,Are), (Zc,Rf,R1d,R3g,Arf), (Zc,Rf,R1d,R3g,Arg), (Zc,Rf,R1d,R3g,Arh), (Zc,Rf,R1d,R3g,Ari), (Zc,Rf,R1d,R3g,Arj), (Zc,Rf,R1d,R3g,Ark), (Zc,Rf,R1d,R3g,Arl), (Zc,Rf,R1d,R3g,Arm), (Zc,Rf,R1d,R3g,Arn), (Zc,Rf,R1d,R3g,Aro), (Zc,Rf,R1d,R3g,Arp), (Zc,Rf,R1d,R3h,Ara), (Zc,Rf,R1d,R3h,Arb), (Zc,Rf,R1d,R3h,Arc), (Zc,Rf,R1d,R3h,Ard), (Zc,Rf,R1d,R3h,Are), (Zc,Rf,R1d,R3h,Arf), (Zc,Rf,R1d,R3h,Arg), (Zc,Rf,R1d,R3h,Arh), (Zc,Rf,R1d,R3h,Ari), (Zc,Rf,R1d,R3h,Arj), (Zc,Rf,R1d,R3h,Ark), (Zc,Rf,R1d,R3h,Arl), (Zc,Rf,R1d,R3h,Arm), (Zc,Rf,R1d,R3h,Arn), (Zc,Rf,R1d,R3h,Aro), (Zc,Rf,R1d,R3h,Arp), (Zc,Rg,R1a,R3a,Ara), (Zc,Rg,R1a,R3a,Arb), (Zc,Rg,R1a,R3a,Arc), (Zc,Rg,R1a,R3a,Ard), (Zc,Rg,R1a,R3a,Are), (Zc,Rg,R1a,R3a,Arf), (Zc,Rg,R1a,R3a,Arg), (Zc,Rg,R1a,R3a,Arh), (Zc,Rg,R1a,R3a,Ari), (Zc,Rg,R1a,R3a,Arj), (Zc,Rg,R1a,R3a,Ark), (Zc,Rg,R1a,R3a,Arl), (Zc,Rg,R1a,R3a,Arm), (Zc,Rg,R1a,R3a,Arn), (Zc,Rg,R1a,R3a,Aro), (Zc,Rg,R1a,R3a,Arp), (Zc,Rg,R1a,R3b,Ara), (Zc,Rg,R1a,R3b,Arb), (Zc,Rg,R1a,R3b,Arc), (Zc,Rg,R1a,R3b,Ard), (Zc,Rg,R1a,R3b,Are), (Zc,Rg,R1a,R3b,Arf), (Zc,Rg,R1a,R3b,Arg), (Zc,Rg,R1a,R3b,Arh), (Zc,Rg,R1a,R3b,Ari), (Zc,Rg,R1a,R3b,Arj), (Zc,Rg,R1a,R3b,Ark), (Zc,Rg,R1a,R3b,Arl), (Zc,Rg,R1a,R3b,Arm), (Zc,Rg,R1a,R3b,Arn), (Zc,Rg,R1a,R3b,Aro), (Zc,Rg,R1a,R3b,Arp), (Zc,Rg,R1a,R3c,Ara), (Zc,Rg,R1a,R3c,Arb), (Zc,Rg,R1a,R3c,Arc), (Zc,Rg,R1a,R3c,Ard), (Zc,Rg,R1a,R3c,Are), (Zc,Rg,R1a,R3c,Arf), (Zc,Rg,R1a,R3c,Arg), (Zc,Rg,R1a,R3c,Arh), (Zc,Rg,R1a,R3c,Ari), (Zc,Rg,R1a,R3c,Arj), (Zc,Rg,R1a,R3c,Ark), (Zc,Rg,R1a,R3c,Arl), (Zc,Rg,R1a,R3c,Arm), (Zc,Rg,R1a,R3c,Arn), (Zc,Rg,R1a,R3c,Aro), (Zc,Rg,R1a,R3c,Arp), (Zc,Rg,R1a,R3d,Ara), (Zc,Rg,R1a,R3d,Arb), (Zc,Rg,R1a,R3d,Arc), (Zc,Rg,R1a,R3d,Ard), (Zc,Rg,R1a,R3d,Are), (Zc,Rg,R1a,R3d,Arf), (Zc,Rg,R1a,R3d,Arg), (Zc,Rg,R1a,R3d,Arh), (Zc,Rg,R1a,R3d,Ari), (Zc,Rg,R1a,R3d,Arj), (Zc,Rg,R1a,R3d,Ark), (Zc,Rg,R1a,R3d,Arl), (Zc,Rg,R1a,R3d,Arm), (Zc,Rg,R1a,R3d,Arn), (Zc,Rg,R1a,R3d,Aro), (Zc,Rg,R1a,R3d,Arp), (Zc,Rg,R1a,R3e,Ara), (Zc,Rg,R1a,R3e,Arb), (Zc,Rg,R1a,R3e,Arc), (Zc,Rg,R1a,R3e,Ard), (Zc,Rg,R1a,R3e,Are), (Zc,Rg,R1a,R3e,Arf), (Zc,Rg,R1a,R3e,Arg), (Zc,Rg,R1a,R3e,Arh), (Zc,Rg,R1a,R3e,Ari), (Zc,Rg,R1a,R3e,Arj), (Zc,Rg,R1a,R3e,Ark), (Zc,Rg,R1a,R3e,Arl), (Zc,Rg,R1a,R3e,Arm), (Zc,Rg,R1a,R3e,Arn), (Zc,Rg,R1a,R3e,Aro), (Zc,Rg,R1a,R3e,Arp), (Zc,Rg,R1a,R3f,Ara), (Zc,Rg,R1a,R3f,Arb), (Zc,Rg,R1a,R3f,Arc), (Zc,Rg,R1a,R3f,Ard), (Zc,Rg,R1a,R3f,Are), (Zc,Rg,R1a,R3f,Arf), (Zc,Rg,R1a,R3f,Arg), (Zc,Rg,R1a,R3f,Arh), (Zc,Rg,R1a,R3f,Ari), (Zc,Rg,R1a,R3f,Arj), (Zc,Rg,R1a,R3f,Ark), (Zc,Rg,R1a,R3f,Arl), (Zc,Rg,R1a,R3f,Arm), (Zc,Rg,R1a,R3f,Arn), (Zc,Rg,R1a,R3f,Aro), (Zc,Rg,R1a,R3f,Arp), (Zc,Rg,R1a,R3g,Ara), (Zc,Rg,R1a,R3g,Arb), (Zc,Rg,R1a,R3g,Arc), (Zc,Rg,R1a,R3g,Ard), (Zc,Rg,R1a,R3g,Are), (Zc,Rg,R1a,R3g,Arf), (Zc,Rg,R1a,R3g,Arg), (Zc,Rg,R1a,R3g,Arh), (Zc,Rg,R1a,R3g,Ari), (Zc,Rg,R1a,R3g,Arj), (Zc,Rg,R1a,R3g,Ark), (Zc,Rg,R1a,R3g,Arl), (Zc,Rg,R1a,R3g,Arm), (Zc,Rg,R1a,R3g,Arn), (Zc,Rg,R1a,R3g,Aro), (Zc,Rg,R1a,R3g,Arp), (Zc,Rg,R1a,R3h,Ara), (Zc,Rg,R1a,R3h,Arb), (Zc,Rg,R1a,R3h,Arc), (Zc,Rg,R1a,R3h,Ard), (Zc,Rg,R1a,R3h,Are), (Zc,Rg,R1a,R3h,Arf), (Zc,Rg,R1a,R3h,Arg), (Zc,Rg,R1a,R3h,Arh), (Zc,Rg,R1a,R3h,Ari), (Zc,Rg,R1a,R3h,Arj), (Zc,Rg,R1a,R3h,Ark), (Zc,Rg,R1a,R3h,Arl), (Zc,Rg,R1a,R3h,Arm), (Zc,Rg,R1a,R3h,Arn), (Zc,Rg,R1a,R3h,Aro), (Zc,Rg,R1a,R3h,Arp), (Zc,Rg,R1b,R3a,Ara), (Zc,Rg,R1b,R3a,Arb), (Zc,Rg,R1b,R3a,Arc), (Zc,Rg,R1b,R3a,Ard), (Zc,Rg,R1b,R3a,Are), (Zc,Rg,R1b,R3a,Arf), (Zc,Rg,R1b,R3a,Arg), (Zc,Rg,R1b,R3a,Arh), (Zc,Rg,R1b,R3a,Ari), (Zc,Rg,R1b,R3a,Arj), (Zc,Rg,R1b,R3a,Ark), (Zc,Rg,R1b,R3a,Arl), (Zc,Rg,R1b,R3a,Arm), (Zc,Rg,R1b,R3a,Arn), (Zc,Rg,R1b,R3a,Aro), (Zc,Rg,R1b,R3a,Arp), (Zc,Rg,R1b,R3b,Ara), (Zc,Rg,R1b,R3b,Arb), (Zc,Rg,R1b,R3b,Arc), (Zc,Rg,R1b,R3b,Ard), (Zc,Rg,R1b,R3b,Are), (Zc,Rg,R1b,R3b,Arf), (Zc,Rg,R1b,R3b,Arg), (Zc,Rg,R1b,R3b,Arh), (Zc,Rg,R1b,R3b,Ari), (Zc,Rg,R1b,R3b,Arj), (Zc,Rg,R1b,R3b,Ark), (Zc,Rg,R1b,R3b,Arl), (Zc,Rg,R1b,R3b,Arm), (Zc,Rg,R1b,R3b,Arn), (Zc,Rg,R1b,R3b,Aro), (Zc,Rg,R1b,R3b,Arp), (Zc,Rg,R1b,R3c,Ara), (Zc,Rg,R1b,R3c,Arb), (Zc,Rg,R1b,R3c,Arc), (Zc,Rg,R1b,R3c,Ard), (Zc,Rg,R1b,R3c,Are), (Zc,Rg,R1b,R3c,Arf), (Zc,Rg,R1b,R3c,Arg), (Zc,Rg,R1b,R3c,Arh), (Zc,Rg,R1b,R3c,Ari), (Zc,Rg,R1b,R3c,Arj), (Zc,Rg,R1b,R3c,Ark), (Zc,Rg,R1b,R3c,Arl), (Zc,Rg,R1b,R3c,Arm), (Zc,Rg,R1b,R3c,Arn), (Zc,Rg,R1b,R3c,Aro), (Zc,Rg,R1b,R3c,Arp), (Zc,Rg,R1b,R3d,Ara), (Zc,Rg,R1b,R3d,Arb), (Zc,Rg,R1b,R3d,Arc), (Zc,Rg,R1b,R3d,Ard), (Zc,Rg,R1b,R3d,Are), (Zc,Rg,R1b,R3d,Arf), (Zc,Rg,R1b,R3d,Arg), (Zc,Rg,R1b,R3d,Arh), (Zc,Rg,R1b,R3d,Ari), (Zc,Rg,R1b,R3d,Arj), (Zc,Rg,R1b,R3d,Ark), (Zc,Rg,R1b,R3d,Arl), (Zc,Rg,R1b,R3d,Arm), (Zc,Rg,R1b,R3d,Arn), (Zc,Rg,R1b,R3d,Aro), (Zc,Rg,R1b,R3d,Arp), (Zc,Rg, R1b,R3e,Ara), (Zc,Rg,R1b,R3e,Arb), (Zc,Rg,R1b,R3e, Arc), (Zc,Rg,R1b,R3e,Ard), (Zc,Rg,R1b,R3e,Are), (Zc,Rg, R1b,R3e,Arf), (Zc,Rg,R1b,R3e,Arg), (Zc,Rg,R1b,R3e,Arh), (Zc,Rg,R1b,R3e,Ari), (Zc,Rg,R1b,R3e,Arj), (Zc,Rg,R1b, R3e,Ark), (Zc,Rg,R1b,R3e,Arl), (Zc,Rg,R1b,R3e,Arm), (Zc,Rg,R1b,R3e,Arn), (Zc,Rg,R1b,R3e,Aro), (Zc,Rg,R1b, R3e,Arp), (Zc,Rg,R1b,R3f,Ara), (Zc,Rg,R1b,R3f,Arb), (Zc, Rg,R1b,R3f,Arc), (Zc,Rg,R1b,R3f,Ard), (Zc,Rg,R1b,R3f, Are), (Zc,Rg,R1b,R3f,Arf), (Zc,Rg,R1b,R3f,Arg), (Zc,Rg, R1b,R3f,Arh), (Zc,Rg,R1b,R3f,Ari), (Zc,Rg,R1b,R3f,Arj), (Zc,Rg,R1b,R3f,Ark), (Zc,Rg,R1b,R3f,Arl), (Zc,Rg,R1b, R3f,Arm), (Zc,Rg,R1b,R3f,Arn), (Zc,Rg,R1b,R3f,Aro), (Zc, Rg,R1b,R3f,Arp), (Zc,Rg,R1b,R3g,Ara), (Zc,Rg,R1b,R3g, Arb), (Zc,Rg,R1b,R3g,Arc), (Zc,Rg,R1b,R3g,Ard), (Zc,Rg, R1b,R3g,Are), (Zc,Rg,R1b,R3g,Arf), (Zc,Rg,R1b,R3g, Arg), (Zc,Rg,R1b,R3g,Arh), (Zc,Rg,R1b,R3g,Ari), (Zc,Rg, R1b,R3g,Arj), (Zc,Rg,R1b,R3g,Ark), (Zc,Rg,R1b,R3g,Arl), (Zc,Rg,R1b,R3g,Arm), (Zc,Rg,R1b,R3g,Arn), (Zc,Rg,R1b, R3g,Aro), (Zc,Rg,R1b,R3g,Arp), (Zc,Rg,R1b,R3h,Ara), (Zc,Rg,R1b,R3h,Arb), (Zc,Rg,R1b,R3h,Arc), (Zc,Rg,R1b, R3h,Ard), (Zc,Rg,R1b,R3h,Are), (Zc,Rg,R1b,R3h,Arf), (Zc, Rg,R1b,R3h,Arg), (Zc,Rg,R1b,R3h,Arh), (Zc,Rg,R1b,R3h, Ari), (Zc,Rg,R1b,R3h,Arj), (Zc,Rg,R1b,R3h,Ark), (Zc,Rg, R1b,R3h,Arl), (Zc,Rg,R1b,R3h,Arm), (Zc,Rg,R1b,R3h, Arn), (Zc,Rg,R1b,R3h,Aro), (Zc,Rg,R1b,R3h,Arp), (Zc,Rg, R1c,R3a,Ara), (Zc,Rg,R1c,R3a,Arb), (Zc,Rg,R1c,R3a,Arc), (Zc,Rg,R1c,R3a,Ard), (Zc,Rg,R1c,R3a,Are), (Zc,Rg,R1c, R3a,Arf), (Zc,Rg,R1c,R3a,Arg), (Zc,Rg,R1c,R3a,Arh), (Zc, Rg,R1c,R3a,Ari), (Zc,Rg,R1c,R3a,Arj), (Zc,Rg,R1c,R3a, Ark), (Zc,Rg,R1c,R3a,Arl), (Zc,Rg,R1c,R3a,Arm), (Zc,Rg, R1c,R3a,Arn), (Zc,Rg,R1c,R3a,Aro), (Zc,Rg,R1c,R3a,Arp), (Zc,Rg,R1c,R3b,Ara), (Zc,Rg,R1c,R3b,Arb), (Zc,Rg,R1c, R3b,Arc), (Zc,Rg,R1c,R3b,Ard), (Zc,Rg,R1c,R3b,Are), (Zc, Rg,R1c,R3b,Arf), (Zc,Rg,R1c,R3b,Arg), (Zc,Rg,R1c,R3b, Arh), (Zc,Rg,R1c,R3b,Ari), (Zc,Rg,R1c,R3b,Arj), (Zc,Rg, R1c,R3b,Ark), (Zc,Rg,R1c,R3b,Arl), (Zc,Rg,R1c,R3b, Arm), (Zc,Rg,R1c,R3b,Arn), (Zc,Rg,R1c,R3b,Aro), (Zc,Rg, R1c,R3b,Arp), (Zc,Rg,R1c,R3c,Ara), (Zc,Rg,R1c,R3c,Arb), (Zc,Rg,R1c,R3c,Arc), (Zc,Rg,R1c,R3c,Ard), (Zc,Rg,R1c, R3c,Are), (Zc,Rg,R1c,R3c,Arf), (Zc,Rg,R1c,R3c,Arg), (Zc, Rg,R1c,R3c,Arh), (Zc,Rg,R1c,R3c,Ari), (Zc,Rg,R1c,R3c, Arj), (Zc,Rg,R1c,R3c,Ark), (Zc,Rg,R1c,R3c,Arl), (Zc,Rg, R1c,R3c,Arm), (Zc,Rg,R1c,R3c,Arn), (Zc,Rg,R1c,R3c, Aro), (Zc,Rg,R1c,R3c,Arp), (Zc,Rg,R1c,R3d,Ara), (Zc,Rg, R1c,R3d,Arb), (Zc,Rg,R1c,R3d,Arc), (Zc,Rg,R1c,R3d, Ard), (Zc,Rg,R1c,R3d,Are), (Zc,Rg,R1c,R3d,Arf), (Zc,Rg, R1c,R3d,Arg), (Zc,Rg,R1c,R3d,Arh), (Zc,Rg,R1c,R3d,Ari), (Zc,Rg,R1c,R3d,Arj), (Zc,Rg,R1c,R3d,Ark), (Zc,Rg,R1c, R3d,Arl), (Zc,Rg,R1c,R3d,Arm), (Zc,Rg,R1c,R3d,Arn), (Zc,Rg,R1c,R3d,Aro), (Zc,Rg,R1c,R3d,Arp), (Zc,Rg,R1c, R3e,Ara), (Zc,Rg,R1c,R3e,Arb), (Zc,Rg,R1c,R3e,Arc), (Zc, Rg,R1c,R3e,Ard), (Zc,Rg,R1c,R3e,Are), (Zc,Rg,R1c,R3e, Arf), (Zc,Rg,R1c,R3e,Arg), (Zc,Rg,R1c,R3e,Arh), (Zc,Rg, R1c,R3e,Ari), (Zc,Rg,R1c,R3e,Arj), (Zc,Rg,R1c,R3e,Ark), (Zc,Rg,R1c,R3e,Arl), (Zc,Rg,R1c,R3e,Arm), (Zc,Rg,R1c, R3e,Arn), (Zc,Rg,R1c,R3e,Aro), (Zc,Rg,R1c,R3e,Arp), (Zc, Rg,R1c,R3f,Ara), (Zc,Rg,R1c,R3f,Arb), (Zc,Rg,R1c,R3f, Arc), (Zc,Rg,R1c,R3f,Ard), (Zc,Rg,R1c,R3f,Are), (Zc,Rg, R1c,R3f,Arf), (Zc,Rg,R1c,R3f,Arg), (Zc,Rg,R1c,R3f,Arh), (Zc,Rg,R1c,R3f,Ari), (Zc,Rg,R1c,R3f,Arj), (Zc,Rg,R1c, R3f,Ark), (Zc,Rg,R1c,R3f,Arl), (Zc,Rg,R1c,R3f,Arm), (Zc, Rg,R1c,R3f,Arn), (Zc,Rg,R1c,R3f,Aro), (Zc,Rg,R1c,R3f, Arp), (Zc,Rg,R1c,R3g,Ara), (Zc,Rg,R1c,R3g,Arb), (Zc,Rg, R1c,R3g,Arc), (Zc,Rg,R1c,R3g,Ard), (Zc,Rg,R1c,R3g, Are), (Zc,Rg,R1c,R3g,Arf), (Zc,Rg,R1c,R3g,Arg), (Zc,Rg, R1c,R3g,Arh), (Zc,Rg,R1c,R3g,Ari), (Zc,Rg,R1c,R3g,Arj), (Zc,Rg,R1c,R3g,Ark), (Zc,Rg,R1c,R3g,Arl), (Zc,Rg,R1c, R3g,Arm), (Zc,Rg,R1c,R3g,Arn), (Zc,Rg,R1c,R3g,Aro), (Zc,Rg,R1c,R3g,Arp), (Zc,Rg,R1c,R3h,Ara), (Zc,Rg,R1c, R3h,Arb), (Zc,Rg,R1c,R3h,Arc), (Zc,Rg,R1c,R3h,Ard), (Zc,Rg,R1c,R3h,Are), (Zc,Rg,R1c,R3h,Arf), (Zc,Rg,R1c, R3h,Arg), (Zc,Rg,R1c,R3h,Arh), (Zc,Rg,R1c,R3h,Ari), (Zc, Rg,R1c,R3h,Arj), (Zc,Rg,R1c,R3h,Ark), (Zc,Rg,R1c,R3h, Arl), (Zc,Rg,R1c,R3h,Arm), (Zc,Rg,R1c,R3h,Arn), (Zc,Rg, R1c,R3h,Aro), (Zc,Rg,R1c,R3h,Arp), (Zc,Rg,R1d,R3a, Ara), (Zc,Rg,R1d,R3a,Arb), (Zc,Rg,R1d,R3a,Arc), (Zc,Rg, R1d,R3a,Ard), (Zc,Rg,R1d,R3a,Are), (Zc,Rg,R1d,R3a,Arf), (Zc,Rg,R1d,R3a,Arg), (Zc,Rg,R1d,R3a,Arh), (Zc,Rg,R1d, R3a,Ari), (Zc,Rg,R1d,R3a,Arj), (Zc,Rg,R1d,R3a,Ark), (Zc, Rg,R1d,R3a,Arl), (Zc,Rg,R1d,R3a,Arm), (Zc,Rg,R1d,R3a, Arn), (Zc,Rg,R1d,R3a,Aro), (Zc,Rg,R1d,R3a,Arp), (Zc,Rg, R1d,R3b,Ara), (Zc,Rg,R1d,R3b,Arb), (Zc,Rg,R1d,R3b, Arc), (Zc,Rg,R1d,R3b,Ard), (Zc,Rg,R1d,R3b,Are), (Zc,Rg, R1d,R3b,Arf), (Zc,Rg,R1d,R3b,Arg), (Zc,Rg,R1d,R3b, Arh), (Zc,Rg,R1d,R3b,Ari), (Zc,Rg,R1d,R3b,Arj), (Zc,Rg, R1d,R3b,Ark), (Zc,Rg,R1d,R3b,Arl), (Zc,Rg,R1d,R3b, Arm), (Zc,Rg,R1d,R3b,Arn), (Zc,Rg,R1d,R3b,Aro), (Zc,Rg, R1d,R3b,Arp), (Zc,Rg,R1d,R3c,Ara), (Zc,Rg,R1d,R3c, Arb), (Zc,Rg,R1d,R3c,Arc), (Zc,Rg,R1d,R3c,Ard), (Zc,Rg, R1d,R3c,Are), (Zc,Rg,R1d,R3c,Arf), (Zc,Rg,R1d,R3c,Arg), (Zc,Rg,R1d,R3c,Arh), (Zc,Rg,R1d,R3c,Ari), (Zc,Rg,R1d, R3c,Arj), (Zc,Rg,R1d,R3c,Ark), (Zc,Rg,R1d,R3c,Arl), (Zc, Rg,R1d,R3c,Arm), (Zc,Rg,R1d,R3c,Arn), (Zc,Rg,R1d,R3c, Aro), (Zc,Rg,R1d,R3c,Arp), (Zc,Rg,R1d,R3d,Ara), (Zc,Rg, R1d,R3d,Arb), (Zc,Rg,R1d,R3d,Arc), (Zc,Rg,R1d,R3d, Ard), (Zc,Rg,R1d,R3d,Are), (Zc,Rg,R1d,R3d,Arf), (Zc,Rg, R1d,R3d,Arg), (Zc,Rg,R1d,R3d,Arh), (Zc,Rg,R1d,R3d, Ari), (Zc,Rg,R1d,R3d,Arj), (Zc,Rg,R1d,R3d,Ark), (Zc,Rg, R1d,R3d,Arl), (Zc,Rg,R1d,R3d,Arm), (Zc,Rg,R1d,R3d, Arn), (Zc,Rg,R1d,R3d,Aro), (Zc,Rg,R1d,R3d,Arp), (Zc,Rg, R1d,R3e,Ara), (Zc,Rg,R1d,R3e,Arb), (Zc,Rg,R1d,R3e, Arc), (Zc,Rg,R1d,R3e,Ard), (Zc,Rg,R1d,R3e,Are), (Zc,Rg, R1d,R3e,Arf), (Zc,Rg,R1d,R3e,Arg), (Zc,Rg,R1d,R3e,Arh), (Zc,Rg,R1d,R3e,Ari), (Zc,Rg,R1d,R3e,Arj), (Zc,Rg,R1d, R3e,Ark), (Zc,Rg,R1d,R3e,Arl), (Zc,Rg,R1d,R3e,Arm), (Zc,Rg,R1d,R3e,Arn), (Zc,Rg,R1d,R3e,Aro), (Zc,Rg,R1d, R3e,Arp), (Zc,Rg,R1d,R3f,Ara), (Zc,Rg,R1d,R3f,Arb), (Zc, Rg,R1d,R3f,Arc), (Zc,Rg,R1d,R3f,Ard), (Zc,Rg,R1d,R3f, Are), (Zc,Rg,R1d,R3f,Arf), (Zc,Rg,R1d,R3f,Arg), (Zc,Rg, R1d,R3f,Arh), (Zc,Rg,R1d,R3f,Ari), (Zc,Rg,R1d,R3f,Arj), (Zc,Rg,R1d,R3f,Ark), (Zc,Rg,R1d,R3f,Arl), (Zc,Rg,R1d, R3f,Arm), (Zc,Rg,R1d,R3f,Arn), (Zc,Rg,R1d,R3f,Aro), (Zc, Rg,R1d,R3f,Arp), (Zc,Rg,R1d,R3g,Ara), (Zc,Rg,R1d,R3g, Arb), (Zc,Rg,R1d,R3g,Arc), (Zc,Rg,R1d,R3g,Ard), (Zc,Rg, R1d,R3g,Are), (Zc,Rg,R1d,R3g,Arf), (Zc,Rg,R1d,R3g, Arg), (Zc,Rg,R1d,R3g,Arh), (Zc,Rg,R1d,R3g,Ari), (Zc,Rg, R1d,R3g,Arj), (Zc,Rg,R1d,R3g,Ark), (Zc,Rg,R1d,R3g,Arl), (Zc,Rg,R1d,R3g,Arm), (Zc,Rg,R1d,R3g,Arn), (Zc,Rg,R1d, R3g,Aro), (Zc,Rg,R1d,R3g,Arp), (Zc,Rg,R1d,R3h,Ara), (Zc,Rg,R1d,R3h,Arb), (Zc,Rg,R1d,R3h,Arc), (Zc,Rg,R1d, R3h,Ard), (Zc,Rg,R1d,R3h,Are), (Zc,Rg,R1d,R3h,Arf), (Zc, Rg,R1d,R3h,Arg), (Zc,Rg,R1d,R3h,Arh), (Zc,Rg,R1d,R3h, Ari), (Zc,Rg,R1d,R3h,Arj), (Zc,Rg,R1d,R3h,Ark), (Zc,Rg, R1d,R3h,Arl), (Zc,Rg,R1d,R3h,Arm), (Zc,Rg,R1d,R3h, Arn), (Zc,Rg,R1d,R3h,Aro), (Zc,Rg,R1d,R3h,Arp), (Zc,Rh, R1a,R3a,Ara), (Zc,Rh,R1a,R3a,Arb), (Zc,Rh,R1a,R3a,Arc), (Zc,Rh,R1a,R3a,Ard), (Zc,Rh,R1a,R3a,Are), (Zc,Rh,R1a, R3a,Arf), (Zc,Rh,R1a,R3a,Arg), (Zc,Rh,R1a,R3a,Arh), (Zc, Rh,R1a,R3a,Ari), (Zc,Rh,R1a,R3a,Arj), (Zc,Rh,R1a,R3a, Ark), (Zc,Rh,R1a,R3a,Arl), (Zc,Rh,R1a,R3a,Arm), (Zc,Rh, R1a,R3a,Arn), (Zc,Rh,R1a,R3a,Aro), (Zc,Rh,R1a,R3a,Arp), (Zc,Rh,R1a,R3b,Ara), (Zc,Rh,R1a,R3b,Arb), (Zc,Rh,R1a, R3b,Arc), (Zc,Rh,R1a,R3b,Ard), (Zc,Rh,R1a,R3b,Are), (Zc, Rh,R1a,R3b,Arf), (Zc,Rh,R1a,R3b,Arg), (Zc,Rh,R1a,R3b, Arh), (Zc,Rh,R1a,R3b,Ari), (Zc,Rh,R1a,R3b,Arj), (Zc,Rh,R1a,R3b,Ark), (Zc,Rh,R1a,R3b,Arl), (Zc,Rh,R1a,R3b,Arm), (Zc,Rh,R1a,R3b,Arn), (Zc,Rh,R1a,R3b,Aro), (Zc,Rh,R1a,R3b,Arp), (Zc,Rh,R1a,R3c,Ara), (Zc,Rh,R1a,R3c,Arb), (Zc,Rh,R1a,R3c,Arc), (Zc,Rh,R1a,R3c,Ard), (Zc,Rh,R1a,R3c,Are), (Zc,Rh,R1a,R3c,Arf), (Zc,Rh,R1a,R3c,Arg), (Zc,Rh,R1a,R3c,Arh), (Zc,Rh,R1a,R3c,Ari), (Zc,Rh,R1a,R3c,Arj), (Zc,Rh,R1a,R3c,Ark), (Zc,Rh,R1a,R3c,Arl), (Zc,Rh,R1a,R3c,Arm), (Zc,Rh,R1a,R3c,Arn), (Zc,Rh,R1a,R3c,Aro), (Zc,Rh,R1a,R3c,Arp), (Zc,Rh,R1a,R3d,Ara), (Zc,Rh,R1a,R3d,Arb), (Zc,Rh,R1a,R3d,Arc), (Zc,Rh,R1a,R3d,Ard), (Zc,Rh,R1a,R3d,Are), (Zc,Rh,R1a,R3d,Arf), (Zc,Rh,R1a,R3d,Arg), (Zc,Rh,R1a,R3d,Arh), (Zc,Rh,R1a,R3d,Ari), (Zc,Rh,R1a,R3d,Arj), (Zc,Rh,R1a,R3d,Ark), (Zc,Rh,R1a,R3d,Arl), (Zc,Rh,R1a,R3d,Arm), (Zc,Rh,R1a,R3d,Arn), (Zc,Rh,R1a,R3d,Aro), (Zc,Rh,R1a,R3d,Arp), (Zc,Rh,R1a,R3e,Ara), (Zc,Rh,R1a,R3e,Arb), (Zc,Rh,R1a,R3e,Arc), (Zc,Rh,R1a,R3e,Ard), (Zc,Rh,R1a,R3e,Are), (Zc,Rh,R1a,R3e,Arf), (Zc,Rh,R1a,R3e,Arg), (Zc,Rh,R1a,R3e,Arh), (Zc,Rh,R1a,R3e,Ari), (Zc,Rh,R1a,R3e,Arj), (Zc,Rh,R1a,R3e,Ark), (Zc,Rh,R1a,R3e,Arl), (Zc,Rh,R1a,R3e,Arm), (Zc,Rh,R1a,R3e,Arn), (Zc,Rh,R1a,R3e,Aro), (Zc,Rh,R1a,R3e,Arp), (Zc,Rh,R1a,R3f,Ara), (Zc,Rh,R1a,R3f,Arb), (Zc,Rh,R1a,R3f,Arc), (Zc,Rh,R1a,R3f,Ard), (Zc,Rh,R1a,R3f,Are), (Zc,Rh,R1a,R3f,Arf), (Zc,Rh,R1a,R3f,Arg), (Zc,Rh,R1a,R3f,Arh), (Zc,Rh,R1a,R3f,Ari), (Zc,Rh,R1a,R3f,Arj), (Zc,Rh,R1a,R3f,Ark), (Zc,Rh,R1a,R3f,Arl), (Zc,Rh,R1a,R3f,Arm), (Zc,Rh,R1a,R3f,Arn), (Zc,Rh,R1a,R3f,Aro), (Zc,Rh,R1a,R3f,Arp), (Zc,Rh,R1a,R3g,Ara), (Zc,Rh,R1a,R3g,Arb), (Zc,Rh,R1a,R3g,Arc), (Zc,Rh,R1a,R3g,Ard), (Zc,Rh,R1a,R3g,Are), (Zc,Rh,R1a,R3g,Arf), (Zc,Rh,R1a,R3g,Arg), (Zc,Rh,R1a,R3g,Arh), (Zc,Rh,R1a,R3g,Ari), (Zc,Rh,R1a,R3g,Arj), (Zc,Rh,R1a,R3g,Ark), (Zc,Rh,R1a,R3g,Arl), (Zc,Rh,R1a,R3g,Arm), (Zc,Rh,R1a,R3g,Arn), (Zc,Rh,R1a,R3g,Aro), (Zc,Rh,R1a,R3g,Arp), (Zc,Rh,R1a,R3h,Ara), (Zc,Rh,R1a,R3h,Arb), (Zc,Rh,R1a,R3h,Arc), (Zc,Rh,R1a,R3h,Ard), (Zc,Rh,R1a,R3h,Are), (Zc,Rh,R1a,R3h,Arf), (Zc,Rh,R1a,R3h,Arg), (Zc,Rh,R1a,R3h,Arh), (Zc,Rh,R1a,R3h,Ari), (Zc,Rh,R1a,R3h,Arj), (Zc,Rh,R1a,R3h,Ark), (Zc,Rh,R1a,R3h,Arl), (Zc,Rh,R1a,R3h,Arm), (Zc,Rh,R1a,R3h,Arn), (Zc,Rh,R1a,R3h,Aro), (Zc,Rh,R1a,R3h,Arp), (Zc,Rh,R1b,R3a,Ara), (Zc,Rh,R1b,R3a,Arb), (Zc,Rh,R1b,R3a,Arc), (Zc,Rh,R1b,R3a,Ard), (Zc,Rh,R1b,R3a,Are), (Zc,Rh,R1b,R3a,Arf), (Zc,Rh,R1b,R3a,Arg), (Zc,Rh,R1b,R3a,Arh), (Zc,Rh,R1b,R3a,Ari), (Zc,Rh,R1b,R3a,Arj), (Zc,Rh,R1b,R3a,Ark), (Zc,Rh,R1b,R3a,Arl), (Zc,Rh,R1b,R3a,Arm), (Zc,Rh,R1b,R3a,Arn), (Zc,Rh,R1b,R3a,Aro), (Zc,Rh,R1b,R3a,Arp), (Zc,Rh,R1b,R3b,Ara), (Zc,Rh,R1b,R3b,Arb), (Zc,Rh,R1b,R3b,Arc), (Zc,Rh,R1b,R3b,Ard), (Zc,Rh,R1b,R3b,Are), (Zc,Rh,R1b,R3b,Arf), (Zc,Rh,R1b,R3b,Arg), (Zc,Rh,R1b,R3b,Arh), (Zc,Rh,R1b,R3b,Ari), (Zc,Rh,R1b,R3b,Arj), (Zc,Rh,R1b,R3b,Ark), (Zc,Rh,R1b,R3b,Arl), (Zc,Rh,R1b,R3b,Arm), (Zc,Rh,R1b,R3b,Arn), (Zc,Rh,R1b,R3b,Aro), (Zc,Rh,R1b,R3b,Arp), (Zc,Rh,R1b,R3c,Ara), (Zc,Rh,R1b,R3c,Arb), (Zc,Rh,R1b,R3c,Arc), (Zc,Rh,R1b,R3c,Ard), (Zc,Rh,R1b,R3c,Are), (Zc,Rh,R1b,R3c,Arf), (Zc,Rh,R1b,R3c,Arg), (Zc,Rh,R1b,R3c,Arh), (Zc,Rh,R1b,R3c,Ari), (Zc,Rh,R1b,R3c,Arj), (Zc,Rh,R1b,R3c,Ark), (Zc,Rh,R1b,R3c,Arl), (Zc,Rh,R1b,R3c,Arm), (Zc,Rh,R1b,R3c,Arn), (Zc,Rh,R1b,R3c,Aro), (Zc,Rh,R1b,R3c,Arp), (Zc,Rh,R1b,R3d,Ara), (Zc,Rh,R1b,R3d,Arb), (Zc,Rh,R1b,R3d,Arc), (Zc,Rh,R1b,R3d,Ard), (Zc,Rh,R1b,R3d,Are), (Zc,Rh,R1b,R3d,Arf), (Zc,Rh,R1b,R3d,Arg), (Zc,Rh,R1b,R3d,Arh), (Zc,Rh,R1b,R3d,Ari), (Zc,Rh,R1b,R3d,Arj), (Zc,Rh,R1b,R3d,Ark), (Zc,Rh,R1b,R3d,Arl), (Zc,Rh,R1b,R3d,Arm), (Zc,Rh,R1b,R3d,Arn), (Zc,Rh,R1b,R3d,Aro), (Zc,Rh,R1b,R3d,Arp), (Zc,Rh,R1b,R3e,Ara), (Zc,Rh,R1b,R3e,Arb), (Zc,Rh,R1b,R3e,Arc), (Zc,Rh,R1b,R3e,Ard), (Zc,Rh,R1b,R3e,Are), (Zc,Rh,R1b,R3e,Arf), (Zc,Rh,R1b,R3e,Arg), (Zc,Rh,R1b,R3e,Arh), (Zc,Rh,R1b,R3e,Ari), (Zc,Rh,R1b,R3e,Arj), (Zc,Rh,R1b,R3e,Ark), (Zc,Rh,R1b,R3e,Arl), (Zc,Rh,R1b,R3e,Arm), (Zc,Rh,R1b,R3e,Arn), (Zc,Rh,R1b,R3e,Aro), (Zc,Rh,R1b,R3e,Arp), (Zc,Rh,R1b,R3f,Ara), (Zc,Rh,R1b,R3f,Arb), (Zc,Rh,R1b,R3f,Arc), (Zc,Rh,R1b,R3f,Ard), (Zc,Rh,R1b,R3f,Are), (Zc,Rh,R1b,R3f,Arf), (Zc,Rh,R1b,R3f,Arg), (Zc,Rh,R1b,R3f,Arh), (Zc,Rh,R1b,R3f,Ari), (Zc,Rh,R1b,R3f,Arj), (Zc,Rh,R1b,R3f,Ark), (Zc,Rh,R1b,R3f,Arl), (Zc,Rh,R1b,R3f,Arm), (Zc,Rh,R1b,R3f,Arn), (Zc,Rh,R1b,R3f,Aro), (Zc,Rh,R1b,R3f,Arp), (Zc,Rh,R1b,R3g,Ara), (Zc,Rh,R1b,R3g,Arb), (Zc,Rh,R1b,R3g,Arc), (Zc,Rh,R1b,R3g,Ard), (Zc,Rh,R1b,R3g,Are), (Zc,Rh,R1b,R3g,Arf), (Zc,Rh,R1b,R3g,Arg), (Zc,Rh,R1b,R3g,Arh), (Zc,Rh,R1b,R3g,Ari), (Zc,Rh,R1b,R3g,Arj), (Zc,Rh,R1b,R3g,Ark), (Zc,Rh,R1b,R3g,Arl), (Zc,Rh,R1b,R3g,Arm), (Zc,Rh,R1b,R3g,Arn), (Zc,Rh,R1b,R3g,Aro), (Zc,Rh,R1b,R3g,Arp), (Zc,Rh,R1b,R3h,Ara), (Zc,Rh,R1b,R3h,Arb), (Zc,Rh,R1b,R3h,Arc), (Zc,Rh,R1b,R3h,Ard), (Zc,Rh,R1b,R3h,Are), (Zc,Rh,R1b,R3h,Arf), (Zc,Rh,R1b,R3h,Arg), (Zc,Rh,R1b,R3h,Arh), (Zc,Rh,R1b,R3h,Ari), (Zc,Rh,R1b,R3h,Arj), (Zc,Rh,R1b,R3h,Ark), (Zc,Rh,R1b,R3h,Arl), (Zc,Rh,R1b,R3h,Arm), (Zc,Rh,R1b,R3h,Arn), (Zc,Rh,R1b,R3h,Aro), (Zc,Rh,R1b,R3h,Arp), (Zc,Rh,R1c,R3a,Ara), (Zc,Rh,R1c,R3a,Arb), (Zc,Rh,R1c,R3a,Arc), (Zc,Rh,R1c,R3a,Ard), (Zc,Rh,R1c,R3a,Are), (Zc,Rh,R1c,R3a,Arf), (Zc,Rh,R1c,R3a,Arg), (Zc,Rh,R1c,R3a,Arh), (Zc,Rh,R1c,R3a,Ari), (Zc,Rh,R1c,R3a,Arj), (Zc,Rh,R1c,R3a,Ark), (Zc,Rh,R1c,R3a,Arl), (Zc,Rh,R1c,R3a,Arm), (Zc,Rh,R1c,R3a,Arn), (Zc,Rh,R1c,R3a,Aro), (Zc,Rh,R1c,R3a,Arp), (Zc,Rh,R1c,R3b,Ara), (Zc,Rh,R1c,R3b,Arb), (Zc,Rh,R1c,R3b,Arc), (Zc,Rh,R1c,R3b,Ard), (Zc,Rh,R1c,R3b,Are), (Zc,Rh,R1c,R3b,Arf), (Zc,Rh,R1c,R3b,Arg), (Zc,Rh,R1c,R3b,Arh), (Zc,Rh,R1c,R3b,Ari), (Zc,Rh,R1c,R3b,Arj), (Zc,Rh,R1c,R3b,Ark), (Zc,Rh,R1c,R3b,Arl), (Zc,Rh,R1c,R3b,Arm), (Zc,Rh,R1c,R3b,Arn), (Zc,Rh,R1c,R3b,Aro), (Zc,Rh,R1c,R3b,Arp), (Zc,Rh,R1c,R3c,Ara), (Zc,Rh,R1c,R3c,Arb), (Zc,Rh,R1c,R3c,Arc), (Zc,Rh,R1c,R3c,Ard), (Zc,Rh,R1c,R3c,Are), (Zc,Rh,R1c,R3c,Arf), (Zc,Rh,R1c,R3c,Arg), (Zc,Rh,R1c,R3c,Arh), (Zc,Rh,R1c,R3c,Ari), (Zc,Rh,R1c,R3c,Arj), (Zc,Rh,R1c,R3c,Ark), (Zc,Rh,R1c,R3c,Arl), (Zc,Rh,R1c,R3c,Arm), (Zc,Rh,R1c,R3c,Arn), (Zc,Rh,R1c,R3c,Aro), (Zc,Rh,R1c,R3c,Arp), (Zc,Rh,R1c,R3d,Ara), (Zc,Rh,R1c,R3d,Arb), (Zc,Rh,R1c,R3d,Arc), (Zc,Rh,R1c,R3d,Ard), (Zc,Rh,R1c,R3d,Are), (Zc,Rh,R1c,R3d,Arf), (Zc,Rh,R1c,R3d,Arg), (Zc,Rh,R1c,R3d,Arh), (Zc,Rh,R1c,R3d,Ari), (Zc,Rh,R1c,R3d,Arj), (Zc,Rh,R1c,R3d,Ark), (Zc,Rh,R1c,R3d,Arl), (Zc,Rh,R1c,R3d,Arm), (Zc,Rh,R1c,R3d,Arn), (Zc,Rh,R1c,R3d,Aro), (Zc,Rh,R1c,R3d,Arp), (Zc,Rh,R1c,R3e,Ara), (Zc,Rh,R1c,R3e,Arb), (Zc,Rh,R1c,R3e,Arc), (Zc,Rh,R1c,R3e,Ard), (Zc,Rh,R1c,R3e,Are), (Zc,Rh,R1c,R3e,Arf), (Zc,Rh,R1c,R3e,Arg), (Zc,Rh,R1c,R3e,Arh), (Zc,Rh,R1c,R3e,Ari), (Zc,Rh,R1c,R3e,Arj), (Zc,Rh,R1c,R3e,Ark), (Zc,Rh,R1c,R3e,Arl), (Zc,Rh,R1c,R3e,Arm), (Zc,Rh,R1c,R3e,Arn), (Zc,Rh,R1c,R3e,Aro), (Zc,Rh,R1c,R3e,Arp), (Zc,Rh,R1c,R3f,Ara), (Zc,Rh,R1c,R3f,Arb), (Zc,Rh,R1c,R3f,Arc), (Zc,Rh,R1c,R3f,Ard), (Zc,Rh,R1c,R3f,Are), (Zc,Rh,R1c,R3f,Arf), (Zc,Rh,R1c,R3f,Arg), (Zc,Rh,R1c,R3f,Arh), (Zc,Rh,R1c,R3f,Ari), (Zc,Rh,R1c,R3f,Arj), (Zc,Rh,R1c,R3f,Ark), (Zc,Rh,R1c,R3f,Arl), (Zc,Rh,R1c,R3f,Arm), (Zc,Rh,R1c,R3f,Arn), (Zc,Rh,R1c,R3f,Aro), (Zc,Rh,R1c,R3f,Arp), (Zc,Rh,R1c,R3g,Ara), (Zc,Rh,R1c,R3g,Arb), (Zc,Rh,R1c,R3g,Arc), (Zc,Rh,R1c,R3g,Ard), (Zc,Rh,R1c,R3g,Are), (Zc,Rh,R1c,R3g,Arf), (Zc,Rh,R1c,R3g,Arg), (Zc,Rh,R1c,R3g,Arh), (Zc,Rh,R1c,R3g,Ari), (Zc,Rh,R1c,R3g,Arj), (Zc,Rh,R1c,R3g,Ark), (Zc,Rh,R1c,R3g,Arl), (Zc,Rh,R1c,R3g,Arm), (Zc,Rh,R1c,R3g,Arn), (Zc,Rh,R1c,R3g,Aro), (Zc,Rh,R1c,R3g,Arp), (Zc,Rh,R1c,R3h,Ara), (Zc,Rh,R1c, R3h,Arb), (Zc,Rh,R1c,R3h,Arc), (Zc,Rh,R1c,R3h,Ard), (Zc,Rh,R1c,R3h,Are), (Zc,Rh,R1c,R3h,Arf), (Zc,Rh,R1c, R3h,Arg), (Zc,Rh,R1c,R3h,Arh), (Zc,Rh,R1c,R3h,Ari), (Zc, Rh,R1c,R3h,Arj), (Zc,Rh,R1c,R3h,Ark), (Zc,Rh,R1c,R3h, Arl), (Zc,Rh,R1c,R3h,Arm), (Zc,Rh,R1c,R3h,Arn), (Zc,Rh, R1c,R3h,Aro), (Zc,Rh,R1c,R3h,Arp), (Zc,Rh,R1d,R3a, Ara), (Zc,Rh,R1d,R3a,Arb), (Zc,Rh,R1d,R3a,Arc), (Zc,Rh, R1d,R3a,Ard), (Zc,Rh,R1d,R3a,Are), (Zc,Rh,R1d,R3a,Arf), (Zc,Rh,R1d,R3a,Arg), (Zc,Rh,R1d,R3a,Arh), (Zc,Rh,R1d, R3a,Ari), (Zc,Rh,R1d,R3a,Arj), (Zc,Rh,R1d,R3a,Ark), (Zc, Rh,R1d,R3a,Arl), (Zc,Rh,R1d,R3a,Arm), (Zc,Rh,R1d,R3a, Arn), (Zc,Rh,R1d,R3a,Aro), (Zc,Rh,R1d,R3a,Arp), (Zc,Rh, R1d,R3b,Ara), (Zc,Rh,R1d,R3b,Arb), (Zc,Rh,R1d,R3b, Arc), (Zc,Rh,R1d,R3b,Ard), (Zc,Rh,R1d,R3b,Are), (Zc,Rh, R1d,R3b,Arf), (Zc,Rh,R1d,R3b,Arg), (Zc,Rh,R1d,R3b, Arh), (Zc,Rh,R1d,R3b,Ari), (Zc,Rh,R1d,R3b,Arj), (Zc,Rh, R1d,R3b,Ark), (Zc,Rh,R1d,R3b,Arl), (Zc,Rh,R1d,R3b, Arm), (Zc,Rh,R1d,R3b,Arn), (Zc,Rh,R1d,R3b,Aro), (Zc,Rh, R1d,R3b,Arp), (Zc,Rh,R1d,R3c,Ara), (Zc,Rh,R1d,R3c, Arb), (Zc,Rh,R1d,R3c,Arc), (Zc,Rh,R1d,R3c,Ard), (Zc,Rh, R1d,R3c,Are), (Zc,Rh,R1d,R3c,Arf), (Zc,Rh,R1d,R3c,Arg), (Zc,Rh,R1d,R3c,Arh), (Zc,Rh,R1d,R3c,Ari), (Zc,Rh,R1d, R3c,Arj), (Zc,Rh,R1d,R3c,Ark), (Zc,Rh,R1d,R3c,Arl), (Zc, Rh,R1d,R3c,Arm), (Zc,Rh,R1d,R3c,Arn), (Zc,Rh,R1d,R3c, Aro), (Zc,Rh,R1d,R3c,Arp), (Zc,Rh,R1d,R3d,Ara), (Zc,Rh, R1d,R3d,Arb), (Zc,Rh,R1d,R3d,Arc), (Zc,Rh,R1d,R3d, Ard), (Zc,Rh,R1d,R3d,Are), (Zc,Rh,R1d,R3d,Arf), (Zc,Rh, R1d,R3d,Arg), (Zc,Rh,R1d,R3d,Arh), (Zc,Rh,R1d,R3d, Ari), (Zc,Rh,R1d,R3d,Arj), (Zc,Rh,R1d,R3d,Ark), (Zc,Rh, R1d,R3d,Arl), (Zc,Rh,R1d,R3d,Arm), (Zc,Rh,R1d,R3d, Arn), (Zc,Rh,R1d,R3d,Aro), (Zc,Rh,R1d,R3d,Arp), (Zc,Rh, R1d,R3e,Ara), (Zc,Rh,R1d,R3e,Arb), (Zc,Rh,R1d,R3e, Arc), (Zc,Rh,R1d,R3e,Ard), (Zc,Rh,R1d,R3e,Are), (Zc,Rh, R1d,R3e,Arf), (Zc,Rh,R1d,R3e,Arg), (Zc,Rh,R1d,R3e,Arh), (Zc,Rh,R1d,R3e,Ari), (Zc,Rh,R1d,R3e,Arj), (Zc,Rh,R1d, R3e,Ark), (Zc,Rh,R1d,R3e,Arl), (Zc,Rh,R1d,R3e,Arm), (Zc,Rh,R1d,R3e,Arn), (Zc,Rh,R1d,R3e,Aro), (Zc,Rh,R1d, R3e,Arp), (Zc,Rh,R1d,R3f,Ara), (Zc,Rh,R1d,R3f,Arb), (Zc, Rh,R1d,R3f,Arc), (Zc,Rh,R1d,R3f,Ard), (Zc,Rh,R1d,R3f, Are), (Zc,Rh,R1d,R3f,Arf), (Zc,Rh,R1d,R3f,Arg), (Zc,Rh, R1d,R3f,Arh), (Zc,Rh,R1d,R3f,Ari), (Zc,Rh,R1d,R3f,Arj), (Zc,Rh,R1d,R3f,Ark), (Zc,Rh,R1d,R3f,Arl), (Zc,Rh,R1d, R3f,Arm), (Zc,Rh,R1d,R3f,Arn), (Zc,Rh,R1d,R3f,Aro), (Zc, Rh,R1d,R3f,Arp), (Zc,Rh,R1d,R3g,Ara), (Zc,Rh,R1d,R3g, Arb), (Zc,Rh,R1d,R3g,Arc), (Zc,Rh,R1d,R3g,Ard), (Zc,Rh, R1d,R3g,Are), (Zc,Rh,R1d,R3g,Arf), (Zc,Rh,R1d,R3g, Arg), (Zc,Rh,R1d,R3g,Arh), (Zc,Rh,R1d,R3g,Ari), (Zc,Rh, R1d,R3g,Arj), (Zc,Rh,R1d,R3g,Ark), (Zc,Rh,R1d,R3g,Arl), (Zc,Rh,R1d,R3g,Arm), (Zc,Rh,R1d,R3g,Arm), (Zc,Rh,R1d, R3g,Aro), (Zc,Rh,R1d,R3g,Arp), (Zc,Rh,R1d,R3h,Ara), (Zc,Rh,R1d,R3h,Arb), (Zc,Rh,R1d,R3h,Arc), (Zc,Rh,R1d, R3h,Ard), (Zc,Rh,R1d,R3h,Are), (Zc,Rh,R1d,R3h,Arf), (Zc, Rh,R1d,R3h,Arg), (Zc,Rh,R1d,R3h,Arh), (Zc,Rh,R1d,R3h, Ari), (Zc,Rh,R1d,R3h,Arj), (Zc,Rh,R1d,R3h,Ark), (Zc,Rh, R1d,R3h,Arl), (Zc,Rh,R1d,R3h,Arm), (Zc,Rh,R1d,R3h, Arn), (Zc,Rh,R1d,R3h,Aro), (Zc,Rh,R1d,R3h,Arp), (Zc,Ri, R1a,R3a,Ara), (Zc,Ri,R1a,R3a,Arb), (Zc,Ri,R1a,R3a,Arc), (Zc,Ri,R1a,R3a,Ard), (Zc,Ri,R1a,R3a,Are), (Zc,Ri,R1a, R3a,Arf), (Zc,Ri,R1a,R3a,Arg), (Zc,Ri,R1a,R3a,Arh), (Zc, Ri,R1a,R3a,Ari), (Zc,Ri,R1a,R3a,Arj), (Zc,Ri,R1a,R3a, Ark), (Zc,Ri,R1a,R3a,Arl), (Zc,Ri,R1a,R3a,Arm), (Zc,Ri, R1a,R3a,Arn), (Zc,Ri,R1a,R3a,Aro), (Zc,Ri,R1a,R3a,Arp), (Zc,Ri,R1a,R3b,Ara), (Zc,Ri,R1a,R3b,Arb), (Zc,Ri,R1a, R3b,Arc), (Zc,Ri,R1a,R3b,Ard), (Zc,Ri,R1a,R3b,Are), (Zc, Ri,R1a,R3b,Arf), (Zc,Ri,R1a,R3b,Arg), (Zc,Ri,R1a,R3b, Arh), (Zc,Ri,R1a,R3b,Ari), (Zc,Ri,R1a,R3b,Arj), (Zc,Ri, R1a,R3b,Ark), (Zc,Ri,R1a,R3b,Arl), (Zc,Ri,R1a,R3b,Arm), (Zc,Ri,R1a,R3b,Arn), (Zc,Ri,R1a,R3b,Aro), (Zc,Ri,R1a, R3b,Arp), (Zc,Ri,R1a,R3c,Ara), (Zc,Ri,R1a,R3c,Arb), (Zc, Ri,R1a,R3c,Arc), (Zc,Ri,R1a,R3c,Ard), (Zc,Ri,R1a,R3c, Are), (Zc,Ri,R1a,R3c,Arf), (Zc,Ri,R1a,R3c,Arg), (Zc,Ri, R1a,R3c,Arh), (Zc,Ri,R1a,R3c,Ari), (Zc,Ri,R1a,R3c,Arj), (Zc,Ri,R1a,R3c,Ark), (Zc,Ri,R1a,R3c,Arl), (Zc,Ri,R1a, R3c,Arm), (Zc,Ri,R1a,R3c,Arn), (Zc,Ri,R1a,R3c,Aro), (Zc, Ri,R1a,R3c,Arp), (Zc,Ri,R1a,R3d,Ara), (Zc,Ri,R1a,R3d, Arb), (Zc,Ri,R1a,R3d,Arc), (Zc,Ri,R1a,R3d,Ard), (Zc,Ri, R1a,R3d,Are), (Zc,Ri,R1a,R3d,Arf), (Zc,Ri,R1a,R3d,Arg), (Zc,Ri,R1a,R3d,Arh), (Zc,Ri,R1a,R3d,Ari), (Zc,Ri,R1a, R3d,Arj), (Zc,Ri,R1a,R3d,Ark), (Zc,Ri,R1a,R3d,Arl), (Zc, Ri,R1a,R3d,Arm), (Zc,Ri,R1a,R3d,Arn), (Zc,Ri,R1a,R3d, Aro), (Zc,Ri,R1a,R3d,Arp), (Zc,R1,R1a,R3e,Ara), (Zc,Ri, R1a,R3e,Arb), (Zc,Ri,R1a,R3e,Arc), (Zc,Ri,R1a,R3e,Ard), (Zc,Ri,R1a,R3e,Are), (Zc,Ri,R1a,R3e,Arf), (Zc,R1,R1a, R3e,Arg), (Zc,Ri,R1a,R3e,Arh), (Zc,Ri,R1a,R3e,Ari), (Zc, Ri,R1a,R3e,Arj), (Zc,Ri,R1a,R3e,Ark), (Zc,Ri,R1a,R3e, Arl), (Zc,Ri,R1a,R3e,Arm), (Zc,Ri,R1a,R3e,Arn), (Zc,Ri, R1a,R3e,Aro), (Zc,Ri,R1a,R3e,Arp), (Zc,Ri,R1a,R3f,Ara), (Zc,Ri,R1a,R3f,Arb), (Zc,Ri,R1a,R3f,Arc), (Zc,Ri,R1a,R3f, Ard), (Zc,Ri,R1a,R3f,Are), (Zc,Ri,R1a,R3f,Arf), (Zc,Ri, R1a,R3f,Arg), (Zc,Ri,R1a,R3f,Arh), (Zc,Ri,R1a,R3f,Ari), (Zc,Ri,R1a,R3f,Arj), (Zc,Ri,R1a,R3f,Ark), (Zc,Ri,R1a,R3f, Arl), (Zc,Ri,R1a,R3f,Arm), (Zc,Ri,R1a,R3f,Arn), (Zc,Ri, R1a,R3f,Aro), (Zc,Ri,R1a,R3f,Arp), (Zc,Ri,R1a,R3g,Ara), (Zc,Ri,R1a,R3g,Arb), (Zc,Ri,R1a,R3g,Arc), (Zc,Ri,R1a, R3g,Ard), (Zc,Ri,R1a,R3g,Are), (Zc,Ri,R1a,R3g,Arf), (Zc, Ri,R1a,R3g,Arg), (Zc,Ri,R1a,R3g,Arh), (Zc,Ri,R1a,R3g, Ari), (Zc,Ri,R1a,R3g,Arj), (Zc,Ri,R1a,R3g,Ark), (Zc,Ri, R1a,R3g,Arl), (Zc,Ri,R1a,R3g,Arm), (Zc,R1,R1a,R3g,Arn), (Zc,Ri,R1a,R3g,Aro), (Zc,Ri,R1a,R3g,Arp), (Zc,Ri,R1a, R3h,Ara), (Zc,Ri,R1a,R3h,Arb), (Zc,Ri,R1a,R3h,Arc), (Zc, Ri,R1a,R3h,Ard), (Zc,Ri,R1a,R3h,Are), (Zc,Ri,R1a,R3h, Arf), (Zc,Ri,R1a,R3h,Arg), (Zc,Ri,R1a,R3h,Arh), (Zc,Ri, R1a,R3h,Ari), (Zc,Ri,R1a,R3h,Arj), (Zc,Ri,R1a,R3h,Ark), (Zc,R1,R1a,R3h,Arl), (Zc,Ri,R1a,R3h,Arm), (Zc,Ri,R1a, R3h,Arn), (Zc,Ri,R1a,R3h,Aro), (Zc,Ri,R1a,R3h,Arp), (Zc, Ri,R1b,R3a,Ara), (Zc,Ri,R1b,R3a,Arb), (Zc,Ri,R1b,R3a, Arc), (Zc,Ri,R1b,R3a,Ard), (Zc,Ri,R1b,R3a,Are), (Zc,Ri, R1b,R3a,Arf), (Zc,Ri,R1b,R3a,Arg), (Zc,Ri,R1b,R3a,Arh), (Zc,Ri,R1b,R3a,Ari), (Zc,Ri,R1b,R3a,Arj), (Zc,Ri,R1b,R3a, Ark), (Zc,Ri,R1b,R3a,Arl), (Zc,Ri,R1b,R3a,Arm), (Zc,Ri, R1b,R3a,Arn), (Zc,Ri,R1b,R3a,Aro), (Zc,Ri,R1b,R3a,Arp), (Zc,Ri,R1b,R3b,Ara), (Zc,Ri,R1b,R3b,Arb), (Zc,Ri,R1b, R3b,Arc), (Zc,Ri,R1b,R3b,Ard), (Zc,Ri,R1b,R3b,Are), (Zc, Ri,R1b,R3b,Arf), (Zc,Ri,R1b,R3b,Arg), (Zc,Ri,R1b,R3b, Arh), (Zc,Ri,R1b,R3b,Ari), (Zc,Ri,R1b,R3b,Arj), (Zc,Ri, R1b,R3b,Ark), (Zc,Ri,R1b,R3b,Arl), (Zc,R1,R1b,R3b, Arm), (Zc,R1,R1b,R3b,Arn), (Zc,Ri,R1b,R3b,Aro), (Zc,Ri, R1b,R3b,Arp), (Zc,Ri,R1b,R3c,Ara), (Zc,Ri,R1b,R3c,Arb), (Zc,Ri,R1b,R3c,Arc), (Zc,Ri,R1b,R3c,Ard), (Zc,Ri,R1b, R3c,Are), (Zc,Ri,R1b,R3c,Arf), (Zc,Ri,R1b,R3c,Arg), (Zc, Ri,R1b,R3c,Arh), (Zc,Ri,R1b,R3c,Ari), (Zc,Ri,R1b,R3c, Arj), (Zc,Ri,R1b,R3c,Ark), (Zc,Ri,R1b,R3c,Arl), (Zc,Ri, R1b,R3c,Arm), (Zc,Ri,R1b,R3c,Arn), (Zc,Ri,R1b,R3c,Aro), (Zc,Ri,R1b,R3c,Arp), (Zc,Ri,R1b,R3d,Ara), (Zc,Ri,R1b, R3d,Arb), (Zc,Ri,R1b,R3d,Arc), (Zc,Ri,R1b,R3d,Ard), (Zc, Ri,R1b,R3d,Are), (Zc,Ri,R1b,R3d,Arf), (Zc,Ri,R1b,R3d, Arg), (Zc,Ri,R1b,R3d,Arh), (Zc,Ri,R1b,R3d,Ari), (Zc,Ri, R1b,R3d,Arj), (Zc,Ri,R1b,R3d,Ark), (Zc,Ri,R1b,R3d,Arl), (Zc,R1,R1b,R3d,Arm), (Zc,Ri,R1b,R3d,Arn), (Zc,Ri,R1b, R3d,Aro), (Zc,Ri,R1b,R3d,Arp), (Zc,Ri,R1b,R3e,Ara), (Zc, Ri,R1b,R3e,Arb), (Zc,Ri,R1b,R3e,Arc), (Zc,Ri,R1b,R3e, Ard), (Zc,Ri,R1b,R3e,Are), (Zc,Ri,R1b,R3e,Arf), (Zc,Ri, R1b,R3e,Arg), (Zc,Ri,R1b,R3e,Arh), (Zc,Ri,R1b,R3e,Ari), (Zc,Ri,R1b,R3e,Arj), (Zc,Ri,R1b,R3e,Ark), (Zc,Ri,R1b,R3e,Arl), (Zc,Ri,R1b,R3e,Arm), (Zc,Ri,R1b,R3e,Arn), (Zc,Ri,R1b,R3e,Aro), (Zc,Ri,R1b,R3e,Arp), (Zc,Ri,R1b,R3f,Ara), (Zc,Ri,R1b,R3f,Arb), (Zc,Ri,R1b,R3f,Arc), (Zc,Ri,R1b,R3f,Ard), (Zc,Ri,R1b,R3f,Are), (Zc,Ri,R1b,R3f,Arf), (Zc,Ri,R1b,R3f,Arg), (Zc,Ri,R1b,R3f,Arh), (Zc,Ri,R1b,R3f,Ari), (Zc,Ri,R1b,R3f,Arj), (Zc,Ri,R1b,R3f,Ark), (Zc,Ri,R1b,R3f,Arl), (Zc,Ri,R1b,R3f,Arm), (Zc,Ri,R1b,R3f,Arn), (Zc,Ri,R1b,R3f,Aro), (Zc,Ri,R1b,R3f,Arp), (Zc,Ri,R1b,R3g,Ara), (Zc,Ri,R1b,R3g,Arb), (Zc,Ri,R1b,R3g,Arc), (Zc,Ri,R1b,R3g,Ard), (Zc,Ri,R1b,R3g,Are), (Zc,Ri,R1b,R3g,Arf), (Zc,Ri,R1b,R3g,Arg), (Zc,Ri,R1b,R3g,Arh), (Zc,Ri,R1b,R3g,Ari), (Zc,Ri,R1b,R3g,Arj), (Zc,Ri,R1b,R3g,Ark), (Zc,Ri,R1b,R3g,Arl), (Zc,Ri,R1b,R3g,Arm), (Zc,Ri,R1b,R3g,Arn), (Zc,Ri,R1b,R3g,Aro), (Zc,Ri,R1b,R3g,Arp), (Zc,Ri,R1b,R3h,Ara), (Zc,Ri,R1b,R3h,Arb), (Zc,Ri,R1b,R3h,Arc), (Zc,Ri,R1b,R3h,Ard), (Zc,Ri,R1b,R3h,Are), (Zc,Ri,R1b,R3h,Arf), (Zc,Ri,R1b,R3h,Arg), (Zc,Ri,R1b,R3h,Arh), (Zc,Ri,R1b,R3h,Ari), (Zc,Ri,R1b,R3h,Arj), (Zc,Ri,R1b,R3h,Ark), (Zc,Ri,R1b,R3h,Arl), (Zc,Ri,R1b,R3h,Arm), (Zc,Ri,R1b,R3h,Arn), (Zc,Ri,R1b,R3h,Aro), (Zc,Ri,R1b,R3h,Arp), (Zc,Ri,R1c,R3a,Ara), (Zc,Ri,R1c,R3a,Arb), (Zc,Ri,R1c,R3a,Arc), (Zc,Ri,R1c,R3a,Ard), (Zc,Ri,R1c,R3a,Are), (Zc,Ri,R1c,R3a,Arf), (Zc,Ri,R1c,R3a,Arg), (Zc,Ri,R1c,R3a,Arh), (Zc,Ri,R1c,R3a,Ari), (Zc,Ri,R1c,R3a,Arj), (Zc,Ri,R1c,R3a,Ark), (Zc,Ri,R1c,R3a,Arl), (Zc,Ri,R1c,R3a,Arm), (Zc,Ri,R1c,R3a,Arn), (Zc,Ri,R1c,R3a,Aro), (Zc,Ri,R1c,R3a,Arp), (Zc,Ri,R1c,R3b,Ara), (Zc,Ri,R1c,R3b,Arb), (Zc,Ri,R1c,R3b,Arc), (Zc,Ri,R1c,R3b,Ard), (Zc,Ri,R1c,R3b,Are), (Zc,Ri,R1c,R3b,Arf), (Zc,Ri,R1c,R3b,Arg), (Zc,Ri,R1c,R3b,Arh), (Zc,Ri,R1c,R3b,Ari), (Zc,Ri,R1c,R3b,Arj), (Zc,Ri,R1c,R3b,Ark), (Zc,Ri,R1c,R3b,Arl), (Zc,Ri,R1c,R3b,Arm), (Zc,Ri,R1c,R3b,Arn), (Zc,Ri,R1c,R3b,Aro), (Zc,Ri,R1c,R3b,Arp), (Zc,Ri,R1c,R3c,Ara), (Zc,Ri,R1c,R3c,Arb), (Zc,Ri,R1c,R3c,Arc), (Zc,Ri,R1c,R3c,Ard), (Zc,Ri,R1c,R3c,Are), (Zc,Ri,R1c,R3c,Arf), (Zc,Ri,R1c,R3c,Arg), (Zc,Ri,R1c,R3c,Arh), (Zc,Ri,R1c,R3c,Ari), (Zc,Ri,R1c,R3c,Arj), (Zc,Ri,R1c,R3c,Ark), (Zc,Ri,R1c,R3c,Arl), (Zc,Ri,R1c,R3c,Arm), (Zc,Ri,R1c,R3c,Arn), (Zc,Ri,R1c,R3c,Aro), (Zc,Ri,R1c,R3c,Arp), (Zc,Ri,R1c,R3d,Ara), (Zc,Ri,R1c,R3d,Arb), (Zc,Ri,R1c,R3d,Arc), (Zc,Ri,R1c,R3d,Ard), (Zc,Ri,R1c,R3d,Are), (Zc,Ri,R1c,R3d,Arf), (Zc,Ri,R1c,R3d,Arg), (Zc,Ri,R1c,R3d,Arh), (Zc,Ri,R1c,R3d,Ari), (Zc,Ri,R1c,R3d,Arj), (Zc,Ri,R1c,R3d,Ark), (Zc,Ri,R1c,R3d,Arl), (Zc,Ri,R1c,R3d,Arm), (Zc,Ri,R1c,R3d,Arn), (Zc,Ri,R1c,R3d,Aro), (Zc,Ri,R1c,R3d,Arp), (Zc,Ri,R1c,R3e,Ara), (Zc,Ri,R1c,R3e,Arb), (Zc,Ri,R1c,R3e,Arc), (Zc,Ri,R1c,R3e,Ard), (Zc,Ri,R1c,R3e,Are), (Zc,Ri,R1c,R3e,Arf), (Zc,Ri,R1c,R3e,Arg), (Zc,Ri,R1c,R3e,Arh), (Zc,Ri,R1c,R3e,Ari), (Zc,Ri,R1c,R3e,Arj), (Zc,Ri,R1c,R3e,Ark), (Zc,Ri,R1c,R3e,Arl), (Zc,Ri,R1c,R3e,Arm), (Zc,Ri,R1c,R3e,Arn), (Zc,Ri,R1c,R3e,Aro), (Zc,Ri,R1c,R3e,Arp), (Zc,Ri,R1c,R3f,Ara), (Zc,Ri,R1c,R3f,Arb), (Zc,Ri,R1c,R3f,Arc), (Zc,Ri,R1c,R3f,Ard), (Zc,Ri,R1c,R3f,Are), (Zc,Ri,R1c,R3f,Arf), (Zc,Ri,R1c,R3f,Arg), (Zc,Ri,R1c,R3f,Arh), (Zc,Ri,R1c,R3f,Ari), (Zc,Ri,R1c,R3f,Arj), (Zc,Ri,R1c,R3f,Ark), (Zc,Ri,R1c,R3f,Arl), (Zc,Ri,R1c,R3f,Arm), (Zc,Ri,R1c,R3f,Arn), (Zc,Ri,R1c,R3f,Aro), (Zc,Ri,R1c,R3f,Arp), (Zc,Ri,R1c,R3g,Ara), (Zc,Ri,R1c,R3g,Arb), (Zc,Ri,R1c,R3g,Arc), (Zc,Ri,R1c,R3g,Ard), (Zc,Ri,R1c,R3g,Are), (Zc,Ri,R1c,R3g,Arf), (Zc,Ri,R1c,R3g,Arg), (Zc,Ri,R1c,R3g,Arh), (Zc,Ri,R1c,R3g,Ari), (Zc,Ri,R1c,R3g,Arj), (Zc,Ri,R1c,R3g,Ark), (Zc,Ri,R1c,R3g,Arl), (Zc,Ri,R1c,R3g,Arm), (Zc,Ri,R1c,R3g,Arn), (Zc,Ri,R1c,R3g,Aro), (Zc,Ri,R1c,R3g,Arp), (Zc,Ri,R1c,R3h,Ara), (Zc,Ri,R1c,R3h,Arb), (Zc,Ri,R1c,R3h,Arc), (Zc,Ri,R1c,R3h,Ard), (Zc,Ri,R1c,R3h,Are), (Zc,Ri,R1c,R3h,Arf), (Zc,Ri,R1c,R3h,Arg), (Zc,Ri,R1c,R3h,Arh), (Zc,Ri,R1c,R3h,Ari), (Zc,Ri,R1c,R3h,Arj), (Zc,Ri,R1c,R3h,Ark), (Zc,Ri,R1c,R3h,Arl), (Zc,Ri,R1c,R3h,Arm), (Zc,Ri,R1c,R3h,Arn), (Zc,Ri,R1c,R3h,Aro), (Zc,Ri,R1c,R3h,Arp), (Zc,Ri,R1d,R3a,Ara), (Zc,Ri,R1d,R3a,Arb), (Zc,Ri,R1d,R3a,Arc), (Zc,Ri,R1d,R3a,Ard), (Zc,Ri,R1d,R3a,Are), (Zc,Ri,R1d,R3a,Arf), (Zc,Ri,R1d,R3a,Arg), (Zc,Ri,R1d,R3a,Arh), (Zc,Ri,R1d,R3a,Ari), (Zc,Ri,R1d,R3a,Arj), (Zc,Ri,R1d,R3a,Ark), (Zc,Ri,R1d,R3a,Arl), (Zc,Ri,R1d,R3a,Arm), (Zc,Ri,R1d,R3a,Arn), (Zc,Ri,R1d,R3a,Aro), (Zc,Ri,R1d,R3a,Arp), (Zc,Ri,R1d,R3b,Ara), (Zc,Ri,R1d,R3b,Arb), (Zc,Ri,R1d,R3b,Arc), (Zc,Ri,R1d,R3b,Ard), (Zc,Ri,R1d,R3b,Are), (Zc,Ri,R1d,R3b,Arf), (Zc,Ri,R1d,R3b,Arg), (Zc,Ri,R1d,R3b,Arh), (Zc,Ri,R1d,R3b,Ari), (Zc,Ri,R1d,R3b,Arj), (Zc,Ri,R1d,R3b,Ark), (Zc,Ri,R1d,R3b,Arl), (Zc,Ri,R1d,R3b,Arm), (Zc,Ri,R1d,R3b,Arn), (Zc,Ri,R1d,R3b,Aro), (Zc,Ri,R1d,R3b,Arp), (Zc,Ri,R1d,R3c,Ara), (Zc,Ri,R1d,R3c,Arb), (Zc,Ri,R1d,R3c,Arc), (Zc,Ri,R1d,R3c,Ard), (Zc,Ri,R1d,R3c,Are), (Zc,Ri,R1d,R3c,Arf), (Zc,Ri,R1d,R3c,Arg), (Zc,Ri,R1d,R3c,Arh), (Zc,Ri,R1d,R3c,Ari), (Zc,Ri,R1d,R3c,Arj), (Zc,Ri,R1d,R3c,Ark), (Zc,Ri,R1d,R3c,Arl), (Zc,Ri,R1d,R3c,Arm), (Zc,Ri,R1d,R3c,Arn), (Zc,Ri,R1d,R3c,Aro), (Zc,Ri,R1d,R3c,Arp), (Zc,Ri,R1d,R3d,Ara), (Zc,Ri,R1d,R3d,Arb), (Zc,Ri,R1d,R3d,Arc), (Zc,Ri,R1d,R3d,Ard), (Zc,Ri,R1d,R3d,Are), (Zc,Ri,R1d,R3d,Arf), (Zc,Ri,R1d,R3d,Arg), (Zc,Ri,R1d,R3d,Arh), (Zc,Ri,R1d,R3d,Ari), (Zc,Ri,R1d,R3d,Arj), (Zc,Ri,R1d,R3d,Ark), (Zc,Ri,R1d,R3d,Arl), (Zc,Ri,R1d,R3d,Arm), (Zc,Ri,R1d,R3d,Arn), (Zc,Ri,R1d,R3d,Aro), (Zc,Ri,R1d,R3d,Arp), (Zc,Ri,R1d,R3e,Ara), (Zc,Ri,R1d,R3e,Arb), (Zc,Ri,R1d,R3e,Arc), (Zc,Ri,R1d,R3e,Ard), (Zc,Ri,R1d,R3e,Are), (Zc,Ri,R1d,R3e,Arf), (Zc,Ri,R1d,R3e,Arg), (Zc,Ri,R1d,R3e,Arh), (Zc,Ri,R1d,R3e,Ari), (Zc,Ri,R1d,R3e,Arj), (Zc,Ri,R1d,R3e,Ark), (Zc,Ri,R1d,R3e,Arl), (Zc,Ri,R1d,R3e,Arm), (Zc,Ri,R1d,R3e,Arn), (Zc,Ri,R1d,R3e,Aro), (Zc,Ri,R1d,R3e,Arp), (Zc,Ri,R1d,R3f,Ara), (Zc,Ri,R1d,R3f,Arb), (Zc,Ri,R1d,R3f,Arc), (Zc,Ri,R1d,R3f,Ard), (Zc,Ri,R1d,R3f,Are), (Zc,Ri,R1d,R3f,Arf), (Zc,Ri,R1d,R3f,Arg), (Zc,Ri,R1d,R3f,Arh), (Zc,Ri,R1d,R3f,Ari), (Zc,Ri,R1d,R3f,Arj), (Zc,Ri,R1d,R3f,Ark), (Zc,Ri,R1d,R3f,Arl), (Zc,Ri,R1d,R3f,Arm), (Zc,Ri,R1d,R3f,Arn), (Zc,Ri,R1d,R3f,Aro), (Zc,Ri,R1d,R3f,Arp), (Zc,Ri,R1d,R3g,Ara), (Zc,Ri,R1d,R3g,Arb), (Zc,Ri,R1d,R3g,Arc), (Zc,Ri,R1d,R3g,Ard), (Zc,Ri,R1d,R3g,Are), (Zc,Ri,R1d,R3g,Arf), (Zc,Ri,R1d,R3g,Arg), (Zc,Ri,R1d,R3g,Arh), (Zc,Ri,R1d,R3g,Ari), (Zc,Ri,R1d,R3g,Arj), (Zc,Ri,R1d,R3g,Ark), (Zc,Ri,R1d,R3g,Arl), (Zc,Ri,R1d,R3g,Arm), (Zc,Ri,R1d,R3g,Arn), (Zc,Ri,R1d,R3g,Aro), (Zc,Ri,R1d,R3g,Arp), (Zc,Ri,R1d,R3h,Ara), (Zc,Ri,R1d,R3h,Arb), (Zc,Ri,R1d,R3h,Arc), (Zc,Ri,R1d,R3h,Ard), (Zc,Ri,R1d,R3h,Are), (Zc,Ri,R1d,R3h,Arf), (Zc,Ri,R1d,R3h,Arg), (Zc,Ri,R1d,R3h,Arh), (Zc,Ri,R1d,R3h,Ari), (Zc,Ri,R1d,R3h,Arj), (Zc,Ri,R1d,R3h,Ark), (Zc,Ri,R1d,R3h,Arl), (Zc,Ri,R1d,R3h,Arm), (Zc,Ri,R1d,R3h,Arn), (Zc,Ri,R1d,R3h,Aro), (Zc,Ri,R1d,R3h,Arp), (Zc,Rj,R1a,R3a,Ara), (Zc,Rj,R1a,R3a,Arb), (Zc,Rj,R1a,R3a,Arc), (Zc,Rj,R1a,R3a,Ard), (Zc,Rj,R1a,R3a,Are), (Zc,Rj,R1a,R3a,Arf), (Zc,Rj,R1a,R3a,Arg), (Zc,Rj,R1a,R3a,Arh), (Zc,Rj,R1a,R3a,Ari), (Zc,Rj,R1a,R3a,Arj), (Zc,Rj,R1a,R3a,Ark), (Zc,Rj,R1a,R3a,Arl), (Zc,Rj,R1a,R3a,Arm), (Zc,Rj,R1a,R3a,Arn), (Zc,Rj,R1a,R3a,Aro), (Zc,Rj,R1a,R3a,Arp), (Zc,Rj,R1a,R3b,Ara), (Zc,Rj,R1a,R3b,Arb), (Zc,Rj,R1a,R3b,Arc), (Zc,Rj,R1a,R3b,Ard), (Zc,Rj,R1a,R3b,Are), (Zc,Rj,R1a,R3b,Arf), (Zc,Rj,R1a,R3b,Arg), (Zc,Rj,R1a,R3b,Arh), (Zc,Rj,R1a,R3b,Ari), (Zc,Rj,R1a,R3b,Arj), (Zc,Rj,R1a,R3b,Ark), (Zc,Rj,R1a,R3b,Arl), (Zc,Rj,R1a,R3b,Arm), (Zc,Rj,R1a,R3b,Arn), (Zc,Rj,R1a,R3b,Aro), (Zc,Rj,R1a,R3b,Arp), (Zc,Rj,R1a,R3c,Ara), (Zc,Rj,R1a,R3c,Arb), (Zc,Rj,R1a,R3c,Arc), (Zc,Rj,R1a,R3c,Ard), (Zc,Rj,R1a,R3c,Are), (Zc,Rj,R1a,R3c,Arf), (Zc,Rj,R1a,R3c,Arg), (Zc,Rj,R1a,R3c,Arh), (Zc,Rj,R1a,R3c,Ari), (Zc,Rj,R1a,R3c,Arj), (Zc,Rj,R1a,R3c,Ark), (Zc,Rj,R1a,R3c,Arl), (Zc,Rj,R1a,R3c,Arm), (Zc,Rj,R1a,R3c,Arn), (Zc,Rj,R1a,R3c,Aro), (Zc,Rj,R1a,R3c,Arp), (Zc,Rj,R1a,R3d,Ara), (Zc,Rj,R1a,R3d,Arb), (Zc,Rj,R1a,R3d,Arc), (Zc,Rj,R1a,R3d,Ard), (Zc,Rj,R1a,R3d,Are), (Zc,Rj,R1a,R3d,Arf), (Zc,Rj,R1a,R3d,Arg), (Zc,Rj,R1a,R3d,Arh), (Zc,Rj,R1a,R3d,Ari), (Zc,Rj,R1a,R3d,Arj), (Zc,Rj,R1a,R3d,Ark), (Zc,Rj,R1a,R3d,Arl), (Zc,Rj,R1a,R3d,Arm), (Zc,Rj,R1a,R3d,Arn), (Zc,Rj,R1a,R3d,Aro), (Zc,Rj,R1a,R3d,Arp), (Zc,Rj,R1a,R3e,Ara), (Zc,Rj,R1a,R3e,Arb), (Zc,Rj,R1a,R3e,Arc), (Zc,Rj,R1a,R3e,Ard), (Zc,Rj,R1a,R3e,Are), (Zc,Rj,R1a,R3e,Arf), (Zc,Rj,R1a,R3e,Arg), (Zc,Rj,R1a,R3e,Arh), (Zc,Rj,R1a,R3e,Ari), (Zc,Rj,R1a,R3e,Arj), (Zc,Rj,R1a,R3e,Ark), (Zc,Rj,R1a,R3e,Arl), (Zc,Rj,R1a,R3e,Arm), (Zc,Rj,R1a,R3e,Arn), (Zc,Rj,R1a,R3e,Aro), (Zc,Rj,R1a,R3e,Arp), (Zc,Rj,R1a,R3f,Ara), (Zc,Rj,R1a,R3f,Arb), (Zc,Rj,R1a,R3f,Arc), (Zc,Rj,R1a,R3f,Ard), (Zc,Rj,R1a,R3f,Are), (Zc,Rj,R1a,R3f,Arf), (Zc,Rj,R1a,R3f,Arg), (Zc,Rj,R1a,R3f,Arh), (Zc,Rj,R1a,R3f,Ari), (Zc,Rj,R1a,R3f,Arj), (Zc,Rj,R1a,R3f,Ark), (Zc,Rj,R1a,R3f,Arl), (Zc,Rj,R1a,R3f,Arm), (Zc,Rj,R1a,R3f,Arn), (Zc,Rj,R1a,R3f,Aro), (Zc,Rj,R1a,R3f,Arp), (Zc,Rj,R1a,R3g,Ara), (Zc,Rj,R1a,R3g,Arb), (Zc,Rj,R1a,R3g,Arc), (Zc,Rj,R1a,R3g,Ard), (Zc,Rj,R1a,R3g,Are), (Zc,Rj,R1a,R3g,Arf), (Zc,Rj,R1a,R3g,Arg), (Zc,Rj,R1a,R3g,Arh), (Zc,Rj,R1a,R3g,Ari), (Zc,Rj,R1a,R3g,Arj), (Zc,Rj,R1a,R3g,Ark), (Zc,Rj,R1a,R3g,Arl), (Zc,Rj,R1a,R3g,Arm), (Zc,Rj,R1a,R3g,Arn), (Zc,Rj,R1a,R3g,Aro), (Zc,Rj,R1a,R3g,Arp), (Zc,Rj,R1a,R3h,Ara), (Zc,Rj,R1a,R3h,Arb), (Zc,Rj,R1a,R3h,Arc), (Zc,Rj,R1a,R3h,Ard), (Zc,Rj,R1a,R3h,Are), (Zc,Rj,R1a,R3h,Arf), (Zc,Rj,R1a,R3h,Arg), (Zc,Rj,R1a,R3h,Arh), (Zc,Rj,R1a,R3h,Ari), (Zc,Rj,R1a,R3h,Arj), (Zc,Rj,R1a,R3h,Ark), (Zc,Rj,R1a,R3h,Arl), (Zc,Rj,R1a,R3h,Arm), (Zc,Rj,R1a,R3h,Arn), (Zc,Rj,R1a,R3h,Aro), (Zc,Rj,R1a,R3h,Arp), (Zc,Rj,R1b,R3a,Ara), (Zc,Rj,R1b,R3a,Arb), (Zc,Rj,R1b,R3a,Arc), (Zc,Rj,R1b,R3a,Ard), (Zc,Rj,R1b,R3a,Are), (Zc,Rj,R1b,R3a,Arf), (Zc,Rj,R1b,R3a,Arg), (Zc,Rj,R1b,R3a,Arh), (Zc,Rj,R1b,R3a,Ari), (Zc,Rj,R1b,R3a,Arj), (Zc,Rj,R1b,R3a,Ark), (Zc,Rj,R1b,R3a,Arl), (Zc,Rj,R1b,R3a,Arm), (Zc,Rj,R1b,R3a,Arn), (Zc,Rj,R1b,R3a,Aro), (Zc,Rj,R1b,R3a,Arp), (Zc,Rj,R1b,R3b,Ara), (Zc,Rj,R1b,R3b,Arb), (Zc,Rj,R1b,R3b,Arc), (Zc,Rj,R1b,R3b,Ard), (Zc,Rj,R1b,R3b,Are), (Zc,Rj,R1b,R3b,Arf), (Zc,Rj,R1b,R3b,Arg), (Zc,Rj,R1b,R3b,Arh), (Zc,Rj,R1b,R3b,Ari), (Zc,Rj,R1b,R3b,Arj), (Zc,Rj,R1b,R3b,Ark), (Zc,Rj,R1b,R3b,Arl), (Zc,Rj,R1b,R3b,Arm), (Zc,Rj,R1b,R3b,Arn), (Zc,Rj,R1b,R3b,Aro), (Zc,Rj,R1b,R3b,Arp), (Zc,Rj,R1b,R3c,Ara), (Zc,Rj,R1b,R3c,Arb), (Zc,Rj,R1b,R3c,Arc), (Zc,Rj,R1b,R3c,Ard), (Zc,Rj,R1b,R3c,Are), (Zc,Rj,R1b,R3c,Arf), (Zc,Rj,R1b,R3c,Arg), (Zc,Rj,R1b,R3c,Arh), (Zc,Rj,R1b,R3c,Ari), (Zc,Rj,R1b,R3c,Arj), (Zc,Rj,R1b,R3c,Ark), (Zc,Rj,R1b,R3c,Arl), (Zc,Rj,R1b,R3c,Arm), (Zc,Rj,R1b,R3c,Arn), (Zc,Rj,R1b,R3c,Aro), (Zc,Rj,R1b,R3c,Arp), (Zc,Rj,R1b,R3d,Ara), (Zc,Rj,R1b,R3d,Arb), (Zc,Rj,R1b,R3d,Arc), (Zc,Rj,R1b,R3d,Ard), (Zc,Rj,R1b,R3d,Are), (Zc,Rj,R1b,R3d,Arf), (Zc,Rj,R1b,R3d,Arg), (Zc,Rj,R1b,R3d,Arh), (Zc,Rj,R1b,R3d,Ari), (Zc,Rj,R1b,R3d,Arj), (Zc,Rj,R1b,R3d,Ark), (Zc,Rj,R1b,R3d,Arl), (Zc,Rj,R1b,R3d,Arm), (Zc,Rj,R1b,R3d,Arn), (Zc,Rj,R1b,R3d,Aro), (Zc,Rj,R1b,R3d,Arp), (Zc,Rj,R1b,R3e,Ara), (Zc,Rj,R1b,R3e,Arb), (Zc,Rj,R1b,R3e,Arc), (Zc,Rj,R1b,R3e,Ard), (Zc,Rj,R1b,R3e,Are), (Zc,Rj,R1b,R3e,Arf), (Zc,Rj,R1b,R3e,Arg), (Zc,Rj,R1b,R3e,Arh), (Zc,Rj,R1b,R3e,Ari), (Zc,Rj,R1b,R3e,Arj), (Zc,Rj,R1b,R3e,Ark), (Zc,Rj,R1b,R3e,Arl), (Zc,Rj,R1b,R3e,Arm), (Zc,Rj,R1b,R3e,Arn), (Zc,Rj,R1b,R3e,Aro), (Zc,Rj,R1b,R3e,Arp), (Zc,Rj,R1b,R3f,Ara), (Zc,Rj,R1b,R3f,Arb), (Zc,Rj,R1b,R3f,Arc), (Zc,Rj,R1b,R3f,Ard), (Zc,Rj,R1b,R3f,Are), (Zc,Rj,R1b,R3f,Arf), (Zc,Rj,R1b,R3f,Arg), (Zc,Rj,R1b,R3f,Arh), (Zc,Rj,R1b,R3f,Ari), (Zc,Rj,R1b,R3f,Arj), (Zc,Rj,R1b,R3f,Ark), (Zc,Rj,R1b,R3f,Arl), (Zc,Rj,R1b,R3f,Arm), (Zc,Rj,R1b,R3f,Arn), (Zc,Rj,R1b,R3f,Aro), (Zc,Rj,R1b,R3f,Arp), (Zc,Rj,R1b,R3g,Ara), (Zc,Rj,R1b,R3g,Arb), (Zc,Rj,R1b,R3g,Arc), (Zc,Rj,R1b,R3g,Ard), (Zc,Rj,R1b,R3g,Are), (Zc,Rj,R1b,R3g,Arf), (Zc,Rj,R1b,R3g,Arg), (Zc,Rj,R1b,R3g,Arh), (Zc,Rj,R1b,R3g,Ari), (Zc,Rj,R1b,R3g,Arj), (Zc,Rj,R1b,R3g,Ark), (Zc,Rj,R1b,R3g,Arl), (Zc,Rj,R1b,R3g,Arm), (Zc,Rj,R1b,R3g,Arn), (Zc,Rj,R1b,R3g,Aro), (Zc,Rj,R1b,R3g,Arp), (Zc,Rj,R1b,R3h,Ara), (Zc,Rj,R1b,R3h,Arb), (Zc,Rj,R1b,R3h,Arc), (Zc,Rj,R1b,R3h,Ard), (Zc,Rj,R1b,R3h,Are), (Zc,Rj,R1b,R3h,Arf), (Zc,Rj,R1b,R3h,Arg), (Zc,Rj,R1b,R3h,Arh), (Zc,Rj,R1b,R3h,Ari), (Zc,Rj,R1b,R3h,Arj), (Zc,Rj,R1b,R3h,Ark), (Zc,Rj,R1b,R3h,Arl), (Zc,Rj,R1b,R3h,Arm), (Zc,Rj,R1b,R3h,Arn), (Zc,Rj,R1b,R3h,Aro), (Zc,Rj,R1b,R3h,Arp), (Zc,Rj,R1c,R3a,Ara), (Zc,Rj,R1c,R3a,Arb), (Zc,Rj,R1c,R3a,Arc), (Zc,Rj,R1c,R3a,Ard), (Zc,Rj,R1c,R3a,Are), (Zc,Rj,R1c,R3a,Arf), (Zc,Rj,R1c,R3a,Arg), (Zc,Rj,R1c,R3a,Arh), (Zc,Rj,R1c,R3a,Ari), (Zc,Rj,R1c,R3a,Arj), (Zc,Rj,R1c,R3a,Ark), (Zc,Rj,R1c,R3a,Arl), (Zc,Rj,R1c,R3a,Arm), (Zc,Rj,R1c,R3a,Arn), (Zc,Rj,R1c,R3a,Aro), (Zc,Rj,R1c,R3a,Arp), (Zc,Rj,R1c,R3b,Ara), (Zc,Rj,R1c,R3b,Arb), (Zc,Rj,R1c,R3b,Arc), (Zc,Rj,R1c,R3b,Ard), (Zc,Rj,R1c,R3b,Are), (Zc,Rj,R1c,R3b,Arf), (Zc,Rj,R1c,R3b,Arg), (Zc,Rj,R1c,R3b,Arh), (Zc,Rj,R1c,R3b,Ari), (Zc,Rj,R1c,R3b,Arj), (Zc,Rj,R1c,R3b,Ark), (Zc,Rj,R1c,R3b,Arl), (Zc,Rj,R1c,R3b,Arm), (Zc,Rj,R1c,R3b,Arn), (Zc,Rj,R1c,R3b,Aro), (Zc,Rj,R1c,R3b,Arp), (Zc,Rj,R1c,R3c,Ara), (Zc,Rj,R1c,R3c,Arb), (Zc,Rj,R1c,R3c,Arc), (Zc,Rj,R1c,R3c,Ard), (Zc,Rj,R1c,R3c,Are), (Zc,Rj,R1c,R3c,Arf), (Zc,Rj,R1c,R3c,Arg), (Zc,Rj,R1c,R3c,Arh), (Zc,Rj,R1c,R3c,Ari), (Zc,Rj,R1c,R3c,Arj), (Zc,Rj,R1c,R3c,Ark), (Zc,Rj,R1c,R3c,Arl), (Zc,Rj,R1c,R3c,Arm), (Zc,Rj,R1c,R3c,Arn), (Zc,Rj,R1c,R3c,Aro), (Zc,Rj,R1c,R3c,Arp), (Zc,Rj,R1c,R3d,Ara), (Zc,Rj,R1c,R3d,Arb), (Zc,Rj,R1c,R3d,Arc), (Zc,Rj,R1c,R3d,Ard), (Zc,Rj,R1c,R3d,Are), (Zc,Rj,R1c,R3d,Arf), (Zc,Rj,R1c,R3d,Arg), (Zc,Rj,R1c,R3d,Arh), (Zc,Rj,R1c,R3d,Ari), (Zc,Rj,R1c,R3d,Arj), (Zc,Rj,R1c,R3d,Ark), (Zc,Rj,R1c,R3d,Arl), (Zc,Rj,R1c,R3d,Arm), (Zc,Rj,R1c,R3d,Arn), (Zc,Rj,R1c,R3d,Aro), (Zc,Rj,R1c,R3d,Arp), (Zc,Rj,R1c,R3e,Ara), (Zc,Rj,R1c,R3e,Arb), (Zc,Rj,R1c,R3e,Arc), (Zc,Rj,R1c,R3e,Ard), (Zc,Rj,R1c,R3e,Are), (Zc,Rj,R1c,R3e,Arf), (Zc,Rj,R1c,R3e,Arg), (Zc,Rj,R1c,R3e,Arh), (Zc,Rj,R1c,R3e,Ari), (Zc,Rj,R1c,R3e,Arj), (Zc,Rj,R1c,R3e,Ark), (Zc,Rj,R1c,R3e,Arl), (Zc,Rj,R1c,R3e,Arm), (Zc,Rj,R1c,R3e,Arn), (Zc,Rj,R1c,R3e,Aro), (Zc,Rj,R1c,R3e,Arp), (Zc,Rj,R1c,R3f,Ara), (Zc,Rj,R1c,R3f,Arb), (Zc,Rj,R1c,R3f,Arc), (Zc,Rj,R1c,R3f,Ard), (Zc,Rj,R1c,R3f,Are), (Zc,Rj,R1c,R3f,Arf), (Zc,Rj,R1c,R3f,Arg), (Zc,Rj,R1c,R3f,Arh), (Zc,Rj,R1c,R3f,Ari), (Zc,Rj,R1c,R3f,Arj), (Zc,Rj,R1c,R3f,Ark), (Zc,Rj,R1c,R3f,Arl), (Zc,Rj,R1c,R3f,Arm), (Zc,Rj,R1c,R3f,Arn), (Zc,Rj,R1c,R3f,Aro), (Zc,Rj,R1c,R3f,Arp), (Zc,Rj,R1c,R3g,Ara), (Zc,Rj,R1c,R3g,Arb), (Zc,Rj,R1c,R3g,Arc), (Zc,Rj,R1c,R3g,Ard), (Zc,Rj,R1c,R3g,Are), (Zc,Rj,R1c,R3g,Arf), (Zc,Rj,R1c,R3g,Arg), (Zc,Rj,R1c,R3g,Arh), (Zc,Rj,R1c,R3g,Ari), (Zc,Rj,R1c,R3g,Arj), (Zc,Rj,R1c,R3g,Ark), (Zc,Rj,R1c,R3g,Arl), (Zc,Rj,R1c,R3g,Arm), (Zc,Rj,R1c,R3g,Arn), (Zc,Rj,R1c,R3g,Aro), (Zc,Rj,R1c,R3g,Arp), (Zc,Rj,R1c,R3h,Ara), (Zc,Rj,R1c,R3h,Arb), (Zc,Rj,R1c,R3h,Arc), (Zc,Rj,R1c,R3h,Ard), (Zc,Rj,R1c,R3h,Are), (Zc,Rj,R1c,R3h,Arf), (Zc,Rj,R1c,R3h,Arg), (Zc,Rj,R1c,R3h,Arh), (Zc,Rj,R1c,R3h,Ari), (Zc,Rj,R1c,R3h,Arj), (Zc,Rj,R1c,R3h,Ark), (Zc,Rj,R1c,R3h,Arl), (Zc,Rj,R1c,R3h,Arm), (Zc,Rj,R1c,R3h,Arn), (Zc,Rj,R1c,R3h,Aro), (Zc,Rj,R1c,R3h,Arp), (Zc,Rj,R1d,R3a,Ara), (Zc,Rj,R1d,R3a,Arb), (Zc,Rj,R1d,R3a,Arc), (Zc,Rj,R1d,R3a,Ard), (Zc,Rj,R1d,R3a,Are), (Zc,Rj,R1d,R3a,Arf), (Zc,Rj,R1d,R3a,Arg), (Zc,Rj,R1d,R3a,Arh), (Zc,Rj,R1d,R3a,Ari), (Zc,Rj,R1d,R3a,Arj), (Zc,Rj,R1d,R3a,Ark), (Zc,Rj,R1d,R3a,Arl), (Zc,Rj,R1d,R3a,Arm), (Zc,Rj,R1d,R3a,Arn), (Zc,Rj,R1d,R3a,Aro), (Zc,Rj,R1d,R3a,Arp), (Zc,Rj,R1d,R3b,Ara), (Zc,Rj,R1d,R3b,Arb), (Zc,Rj,R1d,R3b,Arc), (Zc,Rj,R1d,R3b,Ard), (Zc,Rj,R1d,R3b,Are), (Zc,Rj,R1d,R3b,Arf), (Zc,Rj,R1d,R3b,Arg), (Zc,Rj,R1d,R3b,Arh), (Zc,Rj,R1d,R3b,Ari), (Zc,Rj,R1d,R3b,Arj), (Zc,Rj,R1d,R3b,Ark), (Zc,Rj,R1d,R3b,Arl), (Zc,Rj,R1d,R3b,Arm), (Zc,Rj,R1d,R3b,Arn), (Zc,Rj,R1d,R3b,Aro), (Zc,Rj,R1d,R3b,Arp), (Zc,Rj,R1d,R3c,Ara), (Zc,Rj,R1d,R3c,Arb), (Zc,Rj,R1d,R3c,Arc), (Zc,Rj,R1d,R3c,Ard), (Zc,Rj,R1d,R3c,Are), (Zc,Rj,R1d,R3c,Arf), (Zc,Rj,R1d,R3c,Arg), (Zc,Rj,R1d,R3c,Arh), (Zc,Rj,R1d,R3c,Ari), (Zc,Rj,R1d,R3c,Arj), (Zc,Rj,R1d,R3c,Ark), (Zc,Rj,R1d,R3c,Arl), (Zc,Rj,R1d,R3c,Arm), (Zc,Rj,R1d,R3c,Arn), (Zc,Rj,R1d,R3c,Aro), (Zc,Rj,R1d,R3c,Arp), (Zc,Rj,R1d,R3d,Ara), (Zc,Rj,R1d,R3d,Arb), (Zc,Rj,R1d,R3d,Arc), (Zc,Rj,R1d,R3d,Ard), (Zc,Rj,R1d,R3d,Are), (Zc,Rj,R1d,R3d,Arf), (Zc,Rj,R1d,R3d,Arg), (Zc,Rj,R1d,R3d,Arh), (Zc,Rj,R1d,R3d,Ari), (Zc,Rj,R1d,R3d,Arj), (Zc,Rj,R1d,R3d,Ark), (Zc,Rj,R1d,R3d,Arl), (Zc,Rj,R1d,R3d,Arm), (Zc,Rj,R1d,R3d,Arn), (Zc,Rj,R1d,R3d,Aro), (Zc,Rj,R1d,R3d,Arp), (Zc,Rj,R1d,R3e,Ara), (Zc,Rj,R1d,R3e,Arb), (Zc,Rj,R1d,R3e,Arc), (Zc,Rj,R1d,R3e,Ard), (Zc,Rj,R1d,R3e,Are), (Zc,Rj,R1d,R3e,Arf), (Zc,Rj,R1d,R3e,Arg), (Zc,Rj,R1d,R3e,Arh), (Zc,Rj,R1d,R3e,Ari), (Zc,Rj,R1d,R3e,Arj), (Zc,Rj,R1d,R3e,Ark), (Zc,Rj,R1d,R3e,Arl), (Zc,Rj,R1d,R3e,Arm), (Zc,Rj,R1d,R3e,Arn), (Zc,Rj,R1d,R3e,Aro), (Zc,Rj,R1d,R3e,Arp), (Zc,Rj,R1d,R3f,Ara), (Zc,Rj,R1d,R3f,Arb), (Zc,Rj,R1d,R3f,Arc), (Zc,Rj,R1d,R3f,Ard), (Zc,Rj,R1d,R3f,Are), (Zc,Rj,R1d,R3f,Arf), (Zc,Rj,R1d,R3f,Arg), (Zc,Rj,R1d,R3f,Arh), (Zc,Rj,R1d,R3f,Ari), (Zc,Rj,R1d,R3f,Arj), (Zc,Rj,R1d,R3f,Ark), (Zc,Rj,R1d,R3f,Arl), (Zc,Rj,R1d,R3f,Arm), (Zc,Rj,R1d,R3f,Arn), (Zc,Rj,R1d,R3f,Aro), (Zc,Rj,R1d,R3f,Arp), (Zc,Rj,R1d,R3g,Ara), (Zc,Rj,R1d,R3g,Arb), (Zc,Rj,R1d,R3g,Arc), (Zc,Rj,R1d,R3g,Ard), (Zc,Rj,R1d,R3g,Are), (Zc,Rj,R1d,R3g,Arf), (Zc,Rj,R1d,R3g,Arg), (Zc,Rj,R1d,R3g,Arh), (Zc,Rj,R1d,R3g,Ari), (Zc,Rj,R1d,R3g,Arj), (Zc,Rj,R1d,R3g,Ark), (Zc,Rj,R1d,R3g,Arl), (Zc,Rj,R1d,R3g,Arm), (Zc,Rj,R1d,R3g,Arn), (Zc,Rj,R1d,R3g,Aro), (Zc,Rj,R1d,R3g,Arp), (Zc,Rj,R1d,R3h,Ara), (Zc,Rj,R1d,R3h,Arb), (Zc,Rj,R1d,R3h,Arc), (Zc,Rj,R1d,R3h,Ard), (Zc,Rj,R1d,R3h,Are), (Zc,Rj,R1d,R3h,Arf), (Zc,Rj,R1d,R3h,Arg), (Zc,Rj,R1d,R3h,Arh), (Zc,Rj,R1d,R3h,Ari), (Zc,Rj,R1d,R3h,Arj), (Zc,Rj,R1d,R3h,Ark), (Zc,Rj,R1d,R3h,Arl), (Zc,Rj,R1d,R3h,Arm), (Zc,Rj,R1d,R3h,Arn), (Zc,Rj,R1d,R3h,Aro), (Zc,Rj,R1d,R3h,Arp), (Zd,Ra,R1a,R3a,Ara), (Zd,Ra,R1a,R3a,Arb), (Zd,Ra,R1a,R3a,Arc), (Zd,Ra,R1a,R3a,Ard), (Zd,Ra,R1a,R3a,Are), (Zd,Ra,R1a,R3a,Arf), (Zd,Ra,R1a,R3a,Arg), (Zd,Ra,R1a,R3a,Arh), (Zd,Ra,R1a,R3a,Ari), (Zd,Ra,R1a,R3a,Arj), (Zd,Ra,R1a,R3a,Ark), (Zd,Ra,R1a,R3a,Arl), (Zd,Ra,R1a,R3a,Arm), (Zd,Ra,R1a,R3a,Arn), (Zd,Ra,R1a,R3a,Aro), (Zd,Ra,R1a,R3a,Arp), (Zd,Ra,R1a,R3b,Ara), (Zd,Ra,R1a,R3b,Arb), (Zd,Ra,R1a,R3b,Arc), (Zd,Ra,R1a,R3b,Ard), (Zd,Ra,R1a,R3b,Are), (Zd,Ra,R1a,R3b,Arf), (Zd,Ra,R1a,R3b,Arg), (Zd,Ra,R1a,R3b,Arh), (Zd,Ra,R1a,R3b,Ari), (Zd,Ra,R1a,R3b,Arj), (Zd,Ra,R1a,R3b,Ark), (Zd,Ra,R1a,R3b,Arl), (Zd,Ra,R1a,R3b,Arm), (Zd,Ra,R1a,R3b,Arn), (Zd,Ra,R1a,R3b,Aro), (Zd,Ra,R1a,R3b,Arp), (Zd,Ra,R1a,R3c,Ara), (Zd,Ra,R1a,R3c,Arb), (Zd,Ra,R1a,R3c,Arc), (Zd,Ra,R1a,R3c,Ard), (Zd,Ra,R1a,R3c,Are), (Zd,Ra,R1a,R3c,Arf), (Zd,Ra,R1a,R3c,Arg), (Zd,Ra,R1a,R3c,Arh), (Zd,Ra,R1a,R3c,Ari), (Zd,Ra,R1a,R3c,Arj), (Zd,Ra,R1a,R3c,Ark), (Zd,Ra,R1a,R3c,Arl), (Zd,Ra,R1a,R3c,Arm), (Zd,Ra,R1a,R3c,Arn), (Zd,Ra,R1a,R3c,Aro), (Zd,Ra,R1a,R3c,Arp), (Zd,Ra,R1a,R3d,Ara), (Zd,Ra,R1a,R3d,Arb), (Zd,Ra,R1a,R3d,Arc), (Zd,Ra,R1a,R3d,Ard), (Zd,Ra,R1a,R3d,Are), (Zd,Ra,R1a,R3d,Arf), (Zd,Ra,R1a,R3d,Arg), (Zd,Ra,R1a,R3d,Arh), (Zd,Ra,R1a,R3d,Ari), (Zd,Ra,R1a,R3d,Arj), (Zd,Ra,R1a,R3d,Ark), (Zd,Ra,R1a,R3d,Arl), (Zd,Ra,R1a,R3d,Arm), (Zd,Ra,R1a,R3d,Arn), (Zd,Ra,R1a,R3d,Aro), (Zd,Ra,R1a,R3d,Arp), (Zd,Ra,R1a,R3e,Ara), (Zd,Ra,R1a,R3e,Arb), (Zd,Ra,R1a,R3e,Arc), (Zd,Ra,R1a,R3e,Ard), (Zd,Ra,R1a,R3e,Are), (Zd,Ra,R1a,R3e,Arf), (Zd,Ra,R1a,R3e,Arg), (Zd,Ra,R1a,R3e,Arh), (Zd,Ra,R1a,R3e,Ari), (Zd,Ra,R1a,R3e,Arj), (Zd,Ra,R1a,R3e,Ark), (Zd,Ra,R1a,R3e,Arl), (Zd,Ra,R1a,R3e,Arm), (Zd,Ra,R1a,R3e,Arn), (Zd,Ra,R1a,R3e,Aro), (Zd,Ra,R1a,R3e,Arp), (Zd,Ra,R1a,R3f,Ara), (Zd,Ra,R1a,R3f,Arb), (Zd,Ra,R1a,R3f,Arc), (Zd,Ra,R1a,R3f,Ard), (Zd,Ra,R1a,R3f,Are), (Zd,Ra,R1a,R3f,Arf), (Zd,Ra,R1a,R3f,Arg), (Zd,Ra,R1a,R3f,Arh), (Zd,Ra,R1a,R3f,Ari), (Zd,Ra,R1a,R3f,Arj), (Zd,Ra,R1a,R3f,Ark), (Zd,Ra,R1a,R3f,Arl), (Zd,Ra,R1a,R3f,Arm), (Zd,Ra,R1a,R3f,Arn), (Zd,Ra,R1a,R3f,Aro), (Zd,Ra,R1a,R3f,Arp), (Zd,Ra,R1a,R3g,Ara), (Zd,Ra,R1a,R3g,Arb), (Zd,Ra,R1a,R3g,Arc), (Zd,Ra,R1a,R3g,Ard), (Zd,Ra,R1a,R3g,Are), (Zd,Ra,R1a,R3g,Arf), (Zd,Ra,R1a,R3g,Arg), (Zd,Ra,R1a,R3g,Arh), (Zd,Ra,R1a,R3g,Ari), (Zd,Ra,R1a,R3g,Arj), (Zd,Ra,R1a,R3g,Ark), (Zd,Ra,R1a,R3g,Arl), (Zd,Ra,R1a,R3g,Arm), (Zd,Ra,R1a,R3g,Arn), (Zd,Ra,R1a,R3g,Aro), (Zd,Ra,R1a,R3h,Ara), (Zd,Ra,R1a,R3h,Arb), (Zd,Ra,R1a,R3h,Arc), (Zd,Ra,R1a,R3h,Ard), (Zd,Ra,R1a,R3h,Are), (Zd,Ra,R1a,R3h,Arf), (Zd,Ra,R1a,R3h,Arg), (Zd,Ra,R1a,R3h,Arh), (Zd,Ra,R1a,R3h,Ari), (Zd,Ra,R1a,R3h,Arj), (Zd,Ra,R1a,R3h,Ark), (Zd,Ra,R1a,R3h,Arl), (Zd,Ra,R1a,R3h,Arm), (Zd,Ra,R1a,R3h,Arn), (Zd,Ra,R1a,R3h,Aro), (Zd,Ra,R1a,R3h,Arp), (Zd,Ra,R1b,R3a,Ara), (Zd,Ra,R1b,R3a,Arb), (Zd,Ra,R1b,R3a,Arc), (Zd,Ra,R1b,R3a,Ard), (Zd,Ra,R1b,R3a,Are), (Zd,Ra,R1b,R3a,Arf), (Zd,Ra,R1b,R3a,Arg), (Zd,Ra,R1b,R3a,Arh), (Zd,Ra,R1b,R3a,Ari), (Zd,Ra,R1b,R3a,Arj), (Zd,Ra,R1b,R3a,Ark), (Zd,Ra,R1b,R3a,Arl), (Zd,Ra,R1b,R3a,Arm), (Zd,Ra,R1b,R3a,Arn), (Zd,Ra,R1b,R3a,Aro), (Zd,Ra,R1b,R3a,Arp), (Zd,Ra,R1b,R3b,Ara), (Zd,Ra,R1b,R3b,Arb), (Zd,Ra,R1b,R3b,Arc), (Zd,Ra,R1b,R3b,Ard), (Zd,Ra,R1b,R3b,Are), (Zd,Ra,R1b,R3b,Arf), (Zd,Ra,R1b,R3b,Arg), (Zd,Ra,R1b,R3b,Arh), (Zd,Ra,R1b,R3b,Ari), (Zd,Ra,R1b,R3b,Arj), (Zd,Ra,R1b,R3b,Ark), (Zd,Ra,R1b,R3b,Arl), (Zd,Ra,R1b,R3b,Arm), (Zd,Ra,R1b,R3b,Arn), (Zd,Ra,R1b,R3b,Aro), (Zd,Ra,R1b,R3b,Arp), (Zd,Ra,R1b,R3c,Ara), (Zd,Ra,R1b,R3c,Arb), (Zd,Ra,R1b,R3c,Arc), (Zd,Ra,R1b,R3c,Ard), (Zd,Ra,R1b,R3c,Are), (Zd,Ra,R1b,R3c,Arf), (Zd,Ra,R1b,R3c,Arg), (Zd,Ra,R1b,R3c,Arh), (Zd,Ra,R1b,R3c,Ari), (Zd,Ra,R1b,R3c,Arj), (Zd,Ra,R1b,R3c,Ark), (Zd,Ra,R1b,R3c,Arl), (Zd,Ra,R1b,R3c,Arm), (Zd,Ra,R1b,R3c,Arn), (Zd,Ra,R1b,R3c,Aro), (Zd,Ra,R1b,R3c,Arp), (Zd,Ra,R1b,R3d,Ara), (Zd,Ra,R1b,R3d,Arb), (Zd,Ra,R1b,R3d,Arc), (Zd,Ra,R1b,R3d,Ard), (Zd,Ra,R1b,R3d,Are), (Zd,Ra,R1b,R3d,Arf), (Zd,Ra,R1b,R3d,Arg), (Zd,Ra,R1b,R3d,Arh), (Zd,Ra,R1b,R3d,Ari), (Zd,Ra,R1b,R3d,Arj), (Zd,Ra,R1b,R3d,Ark), (Zd,Ra,R1b,R3d,Arl), (Zd,Ra,R1b,R3d,Arm), (Zd,Ra,R1b,R3d,Arn), (Zd,Ra,R1b,R3d,Aro), (Zd,Ra,R1b,R3d,Arp), (Zd,Ra,R1b,R3e,Ara), (Zd,Ra,R1b,R3e,Arb), (Zd,Ra,R1b,R3e,Arc), (Zd,Ra,R1b,R3e,Ard), (Zd,Ra,R1b,R3e,Are), (Zd,Ra,R1b,R3e,Arf), (Zd,Ra,R1b,R3e,Arg), (Zd,Ra,R1b,R3e,Arh), (Zd,Ra,R1b,R3e,Ari), (Zd,Ra,R1b,R3e,Arj), (Zd,Ra,R1b,R3e,Ark), (Zd,Ra,R1b,R3e,Arl), (Zd,Ra,R1b,R3e,Arm), (Zd,Ra,R1b,R3e,Arn), (Zd,Ra,R1b,R3e,Aro), (Zd,Ra,R1b,R3e,Arp), (Zd,Ra,R1b,R3f,Ara), (Zd,Ra,R1b,R3f,Arb), (Zd,Ra,R1b,R3f,Arc), (Zd,Ra,R1b,R3f,Ard), (Zd,Ra,R1b,R3f,Are), (Zd,Ra,R1b,R3f,Arf), (Zd,Ra,R1b,R3f,Arg), (Zd,Ra,R1b,R3f,Arh), (Zd,Ra,R1b,R3f,Ari), (Zd,Ra,R1b,R3f,Arj), (Zd,Ra,R1b,R3f,Ark), (Zd,Ra,R1b,R3f,Arl), (Zd,Ra,R1b, R3f,Arm), (Zd,Ra,R1b,R3f,Arn), (Zd,Ra,R1b,R3f,Aro), (Zd,Ra,R1b,R3f,Arp), (Zd,Ra,R1b,R3g,Ara), (Zd,Ra,R1b,R3g,Arb), (Zd,Ra,R1b,R3g,Arc), (Zd,Ra,R1b,R3g,Ard), (Zd,Ra,R1b,R3g,Are), (Zd,Ra,R1b,R3g,Arf), (Zd,Ra,R1b,R3g,Arg), (Zd,Ra,R1b,R3g,Arh), (Zd,Ra,R1b,R3g,Ari), (Zd,Ra,R1b,R3g,Arj), (Zd,Ra,R1b,R3g,Ark), (Zd,Ra,R1b,R3g,Arl), (Zd,Ra,R1b,R3g,Arm), (Zd,Ra,R1b,R3g,Arn), (Zd,Ra,R1b,R3g,Aro), (Zd,Ra,R1b,R3g,Arp), (Zd,Ra,R1b,R3h,Ara), (Zd,Ra,R1b,R3h,Arb), (Zd,Ra,R1b,R3h,Arc), (Zd,Ra,R1b,R3h,Ard), (Zd,Ra,R1b,R3h,Are), (Zd,Ra,R1b,R3h,Arf), (Zd,Ra,R1b,R3h,Arg), (Zd,Ra,R1b,R3h,Arh), (Zd,Ra,R1b,R3h,Ari), (Zd,Ra,R1b,R3h,Arj), (Zd,Ra,R1b,R3h,Ark), (Zd,Ra,R1b,R3h,Arl), (Zd,Ra,R1b,R3h,Arm), (Zd,Ra,R1b,R3h,Arn), (Zd,Ra,R1b,R3h,Aro), (Zd,Ra,R1b,R3h,Arp),(Zd,Ra,R1c,R3a,Ara),(Zd,Ra,R1c,R3a,Arb),(Zd,Ra,R1c,R3a,Arc), (Zd,Ra,R1c,R3a,Ard), (Zd,Ra,R1c,R3a,Are), (Zd,Ra,R1c,R3a,Arf), (Zd,Ra,R1c,R3a,Arg), (Zd,Ra,R1c,R3a,Arh), (Zd,Ra,R1c,R3a,Ari), (Zd,Ra,R1c,R3a,Arj), (Zd,Ra,R1c,R3a,Ark), (Zd,Ra,R1c,R3a,Arl), (Zd,Ra,R1c,R3a,Arm), (Zd,Ra,R1c,R3a,Arn), (Zd,Ra,R1c,R3a,Aro), (Zd,Ra,R1c,R3a,Arp), (Zd,Ra,R1c,R3b,Ara), (Zd,Ra,R1c,R3b,Arb), (Zd,Ra,R1c,R3b,Arc), (Zd,Ra,R1c,R3b,Ard), (Zd,Ra,R1c,R3b,Are), (Zd,Ra,R1c,R3b,Arf), (Zd,Ra,R1c,R3b,Arg),(Zd,Ra,R1c,R3b,Arh),(Zd,Ra,R1c,R3b,Ari),(Zd,Ra,R1c,R3b,Arj),(Zd,Ra,R1c,R3b,Ark), (Zd,Ra,R1c,R3b,Arl), (Zd,Ra,R1c,R3b,Arm), (Zd,Ra,R1c,R3b,Arn), (Zd,Ra,R1c,R3b,Aro), (Zd,Ra,R1c,R3b,Arp), (Zd,Ra,R1c,R3c,Ara), (Zd,Ra,R1c,R3c,Arb), (Zd,Ra,R1c,R3c,Arc), (Zd,Ra,R1c,R3c,Ard), (Zd,Ra,R1c,R3c,Are), (Zd,Ra,R1c,R3c,Arf), (Zd,Ra,R1c,R3c,Arg), (Zd,Ra,R1c,R3c,Arh), (Zd,Ra,R1c,R3c,Ari), (Zd,Ra,R1c,R3c,Arj), (Zd,Ra,R1c,R3c,Ark), (Zd,Ra,R1c,R3c,Arl), (Zd,Ra,R1c,R3c,Arm), (Zd,Ra,R1c,R3c,Arn), (Zd,Ra,R1c,R3c,Aro), (Zd,Ra,R1c,R3c,Arp), (Zd,Ra,R1c,R3d,Ara), (Zd,Ra,R1c,R3d,Arb), (Zd,Ra,R1c,R3d,Arc), (Zd,Ra,R1c,R3d,Ard), (Zd,Ra,R1c,R3d,Are), (Zd,Ra,R1c,R3d,Arf),(Zd,Ra,R1c,R3d,Arg),(Zd,Ra,R1c,R3d,Arh), (Zd,Ra,R1c,R3d,Ari), (Zd,Ra,R1c,R3d,Arj), (Zd,Ra,R1c,R3d,Ark), (Zd,Ra,R1c,R3d,Arl), (Zd,Ra,R1c,R3d,Arm), (Zd,Ra,R1c,R3d,Arn), (Zd,Ra,R1c,R3d,Aro), (Zd,Ra,R1c,R3d,Arp),(Zd,Ra,R1c,R3e,Ara),(Zd,Ra,R1c,R3e,Arb),(Zd,Ra,R1c,R3e,Arc), (Zd,Ra,R1c,R3e,Ard), (Zd,Ra,R1c,R3e,Are), (Zd,Ra,R1c,R3e,Arf), (Zd,Ra,R1c,R3e,Arg), (Zd,Ra,R1c,R3e,Arh), (Zd,Ra,R1c,R3e,Ari), (Zd,Ra,R1c,R3e,Arj), (Zd,Ra,R1c,R3e,Ark), (Zd,Ra,R1c,R3e,Arl), (Zd,Ra,R1c,R3e,Arm), (Zd,Ra,R1c,R3e,Arn), (Zd,Ra,R1c,R3e,Aro), (Zd,Ra,R1c,R3e,Arp), (Zd,Ra,R1c,R3f,Ara), (Zd,Ra,R1c,R3f,Arb), (Zd,Ra,R1c,R3f,Arc), (Zd,Ra,R1c,R3f,Ard), (Zd,Ra,R1c,R3f,Are), (Zd,Ra,R1c,R3f,Arf), (Zd,Ra,R1c,R3f,Arg), (Zd,Ra,R1c,R3f,Arh), (Zd,Ra,R1c,R3f,Ari), (Zd,Ra,R1c,R3f,Arj), (Zd,Ra,R1c,R3f,Ark), (Zd,Ra,R1c,R3f,Arl), (Zd,Ra,R1c,R3f,Arm), (Zd,Ra,R1c,R3f,Arn), (Zd,Ra,R1c,R3f,Aro), (Zd,Ra,R1c,R3f,Arp), (Zd,Ra,R1c,R3g,Ara), (Zd,Ra,R1c,R3g,Arb), (Zd,Ra,R1c,R3g,Arc), (Zd,Ra,R1c,R3g,Ard), (Zd,Ra,R1c,R3g,Are), (Zd,Ra,R1c,R3g,Arf), (Zd,Ra,R1c,R3g,Arg), (Zd,Ra,R1c,R3g,Arh), (Zd,Ra,R1c,R3g,Ari), (Zd,Ra,R1c,R3g,Arj), (Zd,Ra,R1c,R3g,Ark), (Zd,Ra,R1c,R3g,Arl), (Zd,Ra,R1c,R3g,Arm), (Zd,Ra,R1c,R3g,Arn), (Zd,Ra,R1c,R3g,Aro), (Zd,Ra,R1c,R3g,Arp), (Zd,Ra,R1c,R3h,Ara), (Zd,Ra,R1c,R3h,Arb), (Zd,Ra,R1c,R3h,Arc), (Zd,Ra,R1c,R3h,Ard), (Zd,Ra,R1c,R3h,Are), (Zd,Ra,R1c,R3h,Arf),(Zd,Ra,R1c,R3h,Arg),(Zd,Ra,R1c,R3h,Arh),(Zd,Ra,R1c,R3h,Ari), (Zd,Ra,R1c,R3h,Arj), (Zd,Ra,R1c,R3h,Ark), (Zd,Ra,R1c,R3h,Arl), (Zd,Ra,R1c,R3h,Arm), (Zd,Ra,R1c,R3h,Arn), (Zd,Ra,R1c,R3h,Aro), (Zd,Ra,R1c,R3h,Arp), (Zd,Ra,R1d,R3a,Ara), (Zd,Ra,R1d,R3a,Arb), (Zd,Ra,R1d,R3a,Arc), (Zd,Ra,R1d,R3a,Ard), (Zd,Ra,R1d,R3a,Are), (Zd,Ra,R1d,R3a,Arf), (Zd,Ra,R1d,R3a,Arg), (Zd,Ra,R1d,R3a,Arh), (Zd,Ra,R1d,R3a,Ari), (Zd,Ra,R1d,R3a,Arj), (Zd,Ra,R1d,R3a,Ark), (Zd,Ra,R1d,R3a,Arl), (Zd,Ra,R1d,R3a,Arm), (Zd,Ra,R1d,R3a,Arn), (Zd,Ra,R1d,R3a,Aro), (Zd,Ra,R1d,R3a,Arp), (Zd,Ra,R1d,R3b,Ara), (Zd,Ra,R1d,R3b,Arb), (Zd,Ra,R1d,R3b,Arc), (Zd,Ra,R1d,R3b,Ard), (Zd,Ra,R1d,R3b,Are), (Zd,Ra,R1d,R3b,Arf), (Zd,Ra,R1d,R3b,Arg), (Zd,Ra,R1d,R3b,Arh), (Zd,Ra,R1d,R3b,Ari), (Zd,Ra,R1d,R3b,Arj), (Zd,Ra,R1d,R3b,Ark), (Zd,Ra,R1d,R3b,Arl), (Zd,Ra,R1d,R3b,Arm), (Zd,Ra,R1d,R3b,Arn), (Zd,Ra,R1d,R3b,Aro), (Zd,Ra,R1d,R3b,Arp), (Zd,Ra,R1d,R3c,Ara),(Zd,Ra,R1d,R3c,Arb),(Zd,Ra,R1d,R3c,Arc),(Zd,Ra,R1d,R3c,Ard), (Zd,Ra,R1d,R3c,Are), (Zd,Ra,R1d,R3c,Arf), (Zd,Ra,R1d,R3c,Arg), (Zd,Ra,R1d,R3c,Arh), (Zd,Ra,R1d,R3c,Ari), (Zd,Ra,R1d,R3c,Arj), (Zd,Ra,R1d,R3c,Ark), (Zd,Ra,R1d,R3c,Arl), (Zd,Ra,R1d,R3c,Arm), (Zd,Ra,R1d,R3c,Arn), (Zd,Ra,R1d,R3c,Aro), (Zd,Ra,R1d,R3c,Arp), (Zd,Ra,R1d,R3d,Ara), (Zd,Ra,R1d,R3d,Arb), (Zd,Ra,R1d,R3d,Arc), (Zd,Ra,R1d,R3d,Ard), (Zd,Ra,R1d,R3d,Are), (Zd,Ra,R1d,R3d,Arf), (Zd,Ra,R1d,R3d,Arg), (Zd,Ra,R1d,R3d,Arh), (Zd,Ra,R1d,R3d,Ari), (Zd,Ra,R1d,R3d,Arj), (Zd,Ra,R1d,R3d,Ark), (Zd,Ra,R1d,R3d,Arl), (Zd,Ra,R1d,R3d,Arm),(Zd,Ra,R1d,R3d,Arn),(Zd,Ra,R1d,R3d,Aro), (Zd,Ra,R1d,R3d,Arp), (Zd,Ra,R1d,R3e,Ara), (Zd,Ra,R1d,R3e,Arb), (Zd,Ra,R1d,R3e,Arc), (Zd,Ra,R1d,R3e,Ard), (Zd,Ra,R1d,R3e,Are), (Zd,Ra,R1d,R3e,Arf), (Zd,Ra,R1d,R3e,Arg), (Zd,Ra,R1d,R3e,Arh), (Zd,Ra,R1d,R3e,Ari), (Zd,Ra,R1d,R3e,Arj), (Zd,Ra,R1d,R3e,Ark), (Zd,Ra,R1d,R3e,Arl), (Zd,Ra,R1d,R3e,Arm), (Zd,Ra,R1d,R3e,Arn), (Zd,Ra,R1d,R3e,Aro), (Zd,Ra,R1d,R3e,Arp), (Zd,Ra,R1d,R3f,Ara), (Zd,Ra,R1d,R3f,Arb), (Zd,Ra,R1d,R3f,Arc), (Zd,Ra,R1d,R3f,Ard), (Zd,Ra,R1d,R3f,Are), (Zd,Ra,R1d,R3f,Arf), (Zd,Ra,R1d,R3f,Arg), (Zd,Ra,R1d,R3f,Arh), (Zd,Ra,R1d,R3f,Ari), (Zd,Ra,R1d,R3f,Arj), (Zd,Ra,R1d,R3f,Ark), (Zd,Ra,R1d,R3f,Arl), (Zd,Ra,R1d,R3f,Arm), (Zd,Ra,R1d,R3f,Arn), (Zd,Ra,R1d,R3f,Aro), (Zd,Ra,R1d,R3f,Arp), (Zd,Ra,R1d,R3g,Ara), (Zd,Ra,R1d,R3g,Arb), (Zd,Ra,R1d,R3g,Arc), (Zd,Ra,R1d,R3g,Ard), (Zd,Ra,R1d,R3g,Are), (Zd,Ra,R1d,R3g,Arf), (Zd,Ra,R1d,R3g,Arg), (Zd,Ra,R1d,R3g,Arh), (Zd,Ra,R1d,R3g,Ari), (Zd,Ra,R1d,R3g,Arj), (Zd,Ra,R1d,R3g,Ark), (Zd,Ra,R1d,R3g,Arl), (Zd,Ra,R1d,R3g,Arm), (Zd,Ra,R1d,R3g,Arn), (Zd,Ra,R1d,R3g,Aro), (Zd,Ra,R1d,R3g,Arp), (Zd,Ra,R1d,R3h,Ara), (Zd,Ra,R1d,R3h,Arb), (Zd,Ra,R1d,R3h,Arc), (Zd,Ra,R1d,R3h,Ard), (Zd,Ra,R1d,R3h,Are), (Zd,Ra,R1d,R3h,Arf), (Zd,Ra,R1d,R3h,Arg), (Zd,Ra,R1d,R3h,Arh), (Zd,Ra,R1d,R3h,Ari), (Zd,Ra,R1d,R3h,Arj), (Zd,Ra,R1d,R3h,Ark), (Zd,Ra,R1d,R3h,Arl), (Zd,Ra,R1d,R3h,Arm),(Zd,Ra,R1d,R3h,Arn),(Zd,Ra,R1d,R3h,Aro), (Zd,Ra,R1d,R3h,Arp), (Zd,Rb,R1a,R3a,Ara), (Zd,Rb,R1a,R3a,Arb), (Zd,Rb,R1a,R3a,Arc), (Zd,Rb,R1a,R3a,Ard), (Zd,Rb,R1a,R3a,Are), (Zd,Rb,R1a,R3a,Arf), (Zd,Rb,R1a,R3a,Arg), (Zd,Rb,R1a,R3a,Arh), (Zd,Rb,R1a,R3a,Ari), (Zd,Rb,R1a,R3a,Arj), (Zd,Rb,R1a,R3a,Ark), (Zd,Rb,R1a,R3a,Arl), (Zd,Rb,R1a,R3a,Arm), (Zd,Rb,R1a,R3a,Arn), (Zd,Rb,R1a,R3a,Aro), (Zd,Rb,R1a,R3a,Arp), (Zd,Rb,R1a,R3b,Ara), (Zd,Rb,R1a,R3b,Arb), (Zd,Rb,R1a,R3b,Arc), (Zd,Rb,R1a,R3b,Ard), (Zd,Rb,R1a,R3b,Are), (Zd,Rb,R1a,R3b,Arf), (Zd,Rb,R1a,R3b,Arg), (Zd,Rb,R1a,R3b,Arh), (Zd,Rb,R1a,R3b,Ari), (Zd,Rb,R1a,R3b,Arj), (Zd,Rb,R1a,R3b,Ark), (Zd,Rb,R1a,R3b,Arl), (Zd,Rb,R1a,R3b,Arm), (Zd,Rb,R1a,R3b,Arn), (Zd,Rb,R1a,R3b,Aro), (Zd,Rb,R1a,R3b,Arp), (Zd,Rb,R1a,R3c,Ara),(Zd,Rb,R1a,R3c,Arb),(Zd,Rb,R1a,R3c,Arc), (Zd,Rb,R1a,R3c,Ard), (Zd,Rb,R1a,R3c,Are), (Zd,Rb,R1a,R3c,Arf), (Zd,Rb,R1a,R3c,Arg), (Zd,Rb,R1a,R3c,Arh), (Zd,Rb,R1a,R3c,Ari), (Zd,Rb,R1a,R3c,Arj), (Zd,Rb,R1a,R3c,Ark), (Zd,Rb,R1a,R3c,Arl), (Zd,Rb,R1a,R3c,Arm), (Zd,Rb,R1a,R3c,Arn), (Zd,Rb,R1a,R3c,Aro), (Zd,Rb,R1a,R3c,Arp), (Zd,Rb,R1a,R3d,Ara), (Zd,Rb,R1a,R3d,Arb), (Zd,Rb, R1a,R3d,Arc), (Zd,Rb,R1a,R3d,Ard), (Zd,Rb,R1a,R3d,Are), (Zd,Rb,R1a,R3d,Arf), (Zd,Rb,R1a,R3d,Arg), (Zd,Rb,R1a,R3d,Arh), (Zd,Rb,R1a,R3d,Ari), (Zd,Rb,R1a,R3d,Arj), (Zd,Rb,R1a,R3d,Ark), (Zd,Rb,R1a,R3d,Arl), (Zd,Rb,R1a,R3d,Arm), (Zd,Rb,R1a,R3d,Arn), (Zd,Rb,R1a,R3d,Aro), (Zd,Rb,R1a,R3d,Arp), (Zd,Rb,R1a,R3e,Ara), (Zd,Rb,R1a,R3e,Arb), (Zd,Rb,R1a,R3e,Arc), (Zd,Rb,R1a,R3e,Ard), (Zd,Rb,R1a,R3e,Are), (Zd,Rb,R1a,R3e,Arf), (Zd,Rb,R1a,R3e,Arg), (Zd,Rb,R1a,R3e,Arh), (Zd,Rb,R1a,R3e,Ari), (Zd,Rb,R1a,R3e,Arj), (Zd,Rb,R1a,R3e,Ark), (Zd,Rb,R1a,R3e,Arl), (Zd,Rb,R1a,R3e,Arm), (Zd,Rb,R1a,R3e,Arn), (Zd,Rb,R1a,R3e,Aro), (Zd,Rb,R1a,R3e,Arp), (Zd,Rb,R1a,R3f,Ara), (Zd,Rb,R1a,R3f,Arb), (Zd,Rb,R1a,R3f,Arc), (Zd,Rb,R1a,R3f,Ard), (Zd,Rb,R1a,R3f,Are), (Zd,Rb,R1a,R3f,Arf), (Zd,Rb,R1a,R3f,Arg), (Zd,Rb,R1a,R3f,Arh), (Zd,Rb,R1a,R3f,Ari), (Zd,Rb,R1a,R3f,Arj), (Zd,Rb,R1a,R3f,Ark), (Zd,Rb,R1a,R3f,Arl), (Zd,Rb,R1a,R3f,Arm), (Zd,Rb,R1a,R3f,Arn), (Zd,Rb,R1a,R3f,Aro), (Zd,Rb,R1a,R3f,Arp), (Zd,Rb,R1a,R3g,Ara), (Zd,Rb,R1a,R3g,Arb), (Zd,Rb,R1a,R3g,Arc), (Zd,Rb,R1a,R3g,Ard), (Zd,Rb,R1a,R3g,Are), (Zd,Rb,R1a,R3g,Arf), (Zd,Rb,R1a,R3g,Arg), (Zd,Rb,R1a,R3g,Arh), (Zd,Rb,R1a,R3g,Ari), (Zd,Rb,R1a,R3g,Arj), (Zd,Rb,R1a,R3g,Ark), (Zd,Rb,R1a,R3g,Arl), (Zd,Rb,R1a,R3g,Arm), (Zd,Rb,R1a,R3g,Arn), (Zd,Rb,R1a,R3g,Aro), (Zd,Rb,R1a,R3g,Arp), (Zd,Rb,R1a,R3h,Ara), (Zd,Rb,R1a,R3h,Arb), (Zd,Rb,R1a,R3h,Arc), (Zd,Rb,R1a,R3h,Ard), (Zd,Rb,R1a,R3h,Are), (Zd,Rb,R1a,R3h,Arf), (Zd,Rb,R1a,R3h,Arg), (Zd,Rb,R1a,R3h,Arh), (Zd,Rb,R1a,R3h,Ari), (Zd,Rb,R1a,R3h,Arj), (Zd,Rb,R1a,R3h,Ark), (Zd,Rb,R1a,R3h,Arl), (Zd,Rb,R1a,R3h,Arm), (Zd,Rb,R1a,R3h,Arn), (Zd,Rb,R1a,R3h,Aro), (Zd,Rb,R1a,R3h,Arp), (Zd,Rb,R1b,R3a,Ara), (Zd,Rb,R1b,R3a,Arb), (Zd,Rb,R1b,R3a,Arc), (Zd,Rb,R1b,R3a,Ard), (Zd,Rb,R1b,R3a,Are), (Zd,Rb,R1b,R3a,Arf), (Zd,Rb,R1b,R3a,Arg), (Zd,Rb,R1b,R3a,Arh), (Zd,Rb,R1b,R3a,Ari), (Zd,Rb,R1b,R3a,Arj), (Zd,Rb,R1b,R3a,Ark), (Zd,Rb,R1b,R3a,Arl), (Zd,Rb,R1b,R3a,Arm), (Zd,Rb,R1b,R3a,Arn), (Zd,Rb,R1b,R3a,Aro), (Zd,Rb,R1b,R3a,Arp), (Zd,Rb,R1b,R3b,Ara), (Zd,Rb,R1b,R3b,Arb), (Zd,Rb,R1b,R3b,Arc), (Zd,Rb,R1b,R3b,Ard), (Zd,Rb,R1b,R3b,Are), (Zd,Rb,R1b,R3b,Arf), (Zd,Rb,R1b,R3b,Arg), (Zd,Rb,R1b,R3b,Arh), (Zd,Rb,R1b,R3b,Ari), (Zd,Rb,R1b,R3b,Arj), (Zd,Rb,R1b,R3b,Ark), (Zd,Rb,R1b,R3b,Arl), (Zd,Rb,R1b,R3b,Arm), (Zd,Rb,R1b,R3b,Arn), (Zd,Rb,R1b,R3b,Aro), (Zd,Rb,R1b,R3b,Arp), (Zd,Rb,R1b,R3c,Ara), (Zd,Rb,R1b,R3c,Arb), (Zd,Rb,R1b,R3c,Arc), (Zd,Rb,R1b,R3c,Ard), (Zd,Rb,R1b,R3c,Are), (Zd,Rb,R1b,R3c,Arf), (Zd,Rb,R1b,R3c,Arg), (Zd,Rb,R1b,R3c,Arh), (Zd,Rb,R1b,R3c,Ari), (Zd,Rb,R1b,R3c,Arj), (Zd,Rb,R1b,R3c,Ark), (Zd,Rb,R1b,R3c,Arl), (Zd,Rb,R1b,R3c,Arm), (Zd,Rb,R1b,R3c,Arn), (Zd,Rb,R1b,R3c,Aro), (Zd,Rb,R1b,R3c,Arp), (Zd,Rb,R1b,R3d,Ara), (Zd,Rb,R1b,R3d,Arb), (Zd,Rb,R1b,R3d,Arc), (Zd,Rb,R1b,R3d,Ard), (Zd,Rb,R1b,R3d,Are), (Zd,Rb,R1b,R3d,Arf), (Zd,Rb,R1b,R3d,Arg), (Zd,Rb,R1b,R3d,Arh), (Zd,Rb,R1b,R3d,Ari), (Zd,Rb,R1b,R3d,Arj), (Zd,Rb,R1b,R3d,Ark), (Zd,Rb,R1b,R3d,Arl), (Zd,Rb,R1b,R3d,Arm), (Zd,Rb,R1b,R3d,Arn), (Zd,Rb,R1b,R3d,Aro), (Zd,Rb,R1b,R3d,Arp), (Zd,Rb,R1b,R3e,Ara), (Zd,Rb,R1b,R3e,Arb), (Zd,Rb,R1b,R3e,Arc), (Zd,Rb,R1b,R3e,Ard), (Zd,Rb,R1b,R3e,Are), (Zd,Rb,R1b,R3e,Arf), (Zd,Rb,R1b,R3e,Arg), (Zd,Rb,R1b,R3e,Arh), (Zd,Rb,R1b,R3e,Ari), (Zd,Rb,R1b,R3e,Arj), (Zd,Rb,R1b,R3e,Ark), (Zd,Rb,R1b,R3e,Arl), (Zd,Rb,R1b,R3e,Arm), (Zd,Rb,R1b,R3e,Arn), (Zd,Rb,R1b,R3e,Aro), (Zd,Rb,R1b,R3e,Arp), (Zd,Rb,R1b,R3f,Ara), (Zd,Rb,R1b,R3f,Arb), (Zd,Rb,R1b,R3f,Arc), (Zd,Rb,R1b,R3f,Ard), (Zd,Rb,R1b,R3f,Are), (Zd,Rb,R1b,R3f,Arf), (Zd,Rb,R1b,R3f,Arg), (Zd,Rb,R1b,R3f,Arh), (Zd,Rb,R1b,R3f,Ari), (Zd,Rb,R1b,R3f,Arj), (Zd,Rb,R1b,R3f,Ark), (Zd,Rb,R1b,R3f,Arl), (Zd,Rb,R1b,R3f,Arm), (Zd,Rb,R1b,R3f,Arn), (Zd,Rb,R1b,R3f,Aro), (Zd,Rb,R1b,R3f,Arp), (Zd,Rb,R1b,R3g,Ara), (Zd,Rb,R1b,R3g,Arb), (Zd,Rb,R1b,R3g,Arc), (Zd,Rb,R1b,R3g,Ard), (Zd,Rb,R1b,R3g,Are), (Zd,Rb,R1b,R3g,Arf), (Zd,Rb,R1b,R3g,Arg), (Zd,Rb,R1b,R3g,Arh), (Zd,Rb,R1b,R3g,Ari), (Zd,Rb,R1b,R3g,Arj), (Zd,Rb,R1b,R3g,Ark), (Zd,Rb,R1b,R3g,Arl), (Zd,Rb,R1b,R3g,Arm), (Zd,Rb,R1b,R3g,Arn), (Zd,Rb,R1b,R3g,Aro), (Zd,Rb,R1b,R3g,Arp), (Zd,Rb,R1b,R3h,Ara), (Zd,Rb,R1b,R3h,Arb), (Zd,Rb,R1b,R3h,Arc), (Zd,Rb,R1b,R3h,Ard), (Zd,Rb,R1b,R3h,Are), (Zd,Rb,R1b,R3h,Arf), (Zd,Rb,R1b,R3h,Arg), (Zd,Rb,R1b,R3h,Arh), (Zd,Rb,R1b,R3h,Ari), (Zd,Rb,R1b,R3h,Arj), (Zd,Rb,R1b,R3h,Ark), (Zd,Rb,R1b,R3h,Arl), (Zd,Rb,R1b,R3h,Arm), (Zd,Rb,R1b,R3h,Arn), (Zd,Rb,R1b,R3h,Aro), (Zd,Rb,R1b,R3h,Arp), (Zd,Rb,R1c,R3a,Ara), (Zd,Rb,R1c,R3a,Arb), (Zd,Rb,R1c,R3a,Arc), (Zd,Rb,R1c,R3a,Ard), (Zd,Rb,R1c,R3a,Are), (Zd,Rb,R1c,R3a,Arf), (Zd,Rb,R1c,R3a,Arg), (Zd,Rb,R1c,R3a,Arh), (Zd,Rb,R1c,R3a,Ari), (Zd,Rb,R1c,R3a,Arj), (Zd,Rb,R1c,R3a,Ark), (Zd,Rb,R1c,R3a,Arl), (Zd,Rb,R1c,R3a,Arm), (Zd,Rb,R1c,R3a,Arn), (Zd,Rb,R1c,R3a,Aro), (Zd,Rb,R1c,R3a,Arp), (Zd,Rb,R1c,R3b,Ara), (Zd,Rb,R1c,R3b,Arb), (Zd,Rb,R1c,R3b,Arc), (Zd,Rb,R1c,R3b,Ard), (Zd,Rb,R1c,R3b,Are), (Zd,Rb,R1c,R3b,Arf), (Zd,Rb,R1c,R3b,Arg), (Zd,Rb,R1c,R3b,Arh), (Zd,Rb,R1c,R3b,Ari), (Zd,Rb,R1c,R3b,Arj), (Zd,Rb,R1c,R3b,Ark), (Zd,Rb,R1c,R3b,Arl), (Zd,Rb,R1c,R3b,Arm), (Zd,Rb,R1c,R3b,Arn), (Zd,Rb,R1c,R3b,Aro), (Zd,Rb,R1c,R3b,Arp), (Zd,Rb,R1c,R3c,Ara), (Zd,Rb,R1c,R3c,Arb), (Zd,Rb,R1c,R3c,Arc), (Zd,Rb,R1c,R3c,Ard), (Zd,Rb,R1c,R3c,Are), (Zd,Rb,R1c,R3c,Arf), (Zd,Rb,R1c,R3c,Arg), (Zd,Rb,R1c,R3c,Arh), (Zd,Rb,R1c,R3c,Ari), (Zd,Rb,R1c,R3c,Arj), (Zd,Rb,R1c,R3c,Ark), (Zd,Rb,R1c,R3c,Arl), (Zd,Rb,R1c,R3c,Arm), (Zd,Rb,R1c,R3c,Arn), (Zd,Rb,R1c,R3c,Aro), (Zd,Rb,R1c,R3c,Arp), (Zd,Rb,R1c,R3d,Ara), (Zd,Rb,R1c,R3d,Arb), (Zd,Rb,R1c,R3d,Arc), (Zd,Rb,R1c,R3d,Ard), (Zd,Rb,R1c,R3d,Are), (Zd,Rb,R1c,R3d,Arf), (Zd,Rb,R1c,R3d,Arg), (Zd,Rb,R1c,R3d,Arh), (Zd,Rb,R1c,R3d,Ari), (Zd,Rb,R1c,R3d,Arj), (Zd,Rb,R1c,R3d,Ark), (Zd,Rb,R1c,R3d,Arl), (Zd,Rb,R1c,R3d,Arm), (Zd,Rb,R1c,R3d,Arn), (Zd,Rb,R1c,R3d,Aro), (Zd,Rb,R1c,R3d,Arp), (Zd,Rb,R1c,R3e,Ara), (Zd,Rb,R1c,R3e,Arb), (Zd,Rb,R1c,R3e,Arc), (Zd,Rb,R1c,R3e,Ard), (Zd,Rb,R1c,R3e,Are), (Zd,Rb,R1c,R3e,Arf), (Zd,Rb,R1c,R3e,Arg), (Zd,Rb,R1c,R3e,Arh), (Zd,Rb,R1c,R3e,Ari), (Zd,Rb,R1c,R3e,Arj), (Zd,Rb,R1c,R3e,Ark), (Zd,Rb,R1c,R3e,Arl), (Zd,Rb,R1c,R3e,Arm), (Zd,Rb,R1c,R3e,Arn), (Zd,Rb,R1c,R3e,Aro), (Zd,Rb,R1c,R3e,Arp), (Zd,Rb,R1c,R3f,Ara), (Zd,Rb,R1c,R3f,Arb), (Zd,Rb,R1c,R3f,Arc), (Zd,Rb,R1c,R3f,Ard), (Zd,Rb,R1c,R3f,Are), (Zd,Rb,R1c,R3f,Arf), (Zd,Rb,R1c,R3f,Arg), (Zd,Rb,R1c,R3f,Arh), (Zd,Rb,R1c,R3f,Ari), (Zd,Rb,R1c,R3f,Arj), (Zd,Rb,R1c,R3f,Ark), (Zd,Rb,R1c,R3f,Arl), (Zd,Rb,R1c,R3f,Arm), (Zd,Rb,R1c,R3f,Arn), (Zd,Rb,R1c,R3f,Aro), (Zd,Rb,R1c,R3f,Arp), (Zd,Rb,R1c,R3g,Ara), (Zd,Rb,R1c,R3g,Arb), (Zd,Rb,R1c,R3g,Arc), (Zd,Rb,R1c,R3g,Ard), (Zd,Rb,R1c,R3g,Are), (Zd,Rb,R1c,R3g,Arf), (Zd,Rb,R1c,R3g,Arg), (Zd,Rb,R1c,R3g,Arh), (Zd,Rb,R1c,R3g,Ari), (Zd,Rb,R1c,R3g,Arj), (Zd,Rb,R1c,R3g,Ark), (Zd,Rb,R1c,R3g,Arl), (Zd,Rb,R1c,R3g,Arm), (Zd,Rb,R1c,R3g,Arn), (Zd,Rb,R1c,R3g,Aro), (Zd,Rb,R1c,R3g,Arp), (Zd,Rb,R1c,R3h,Ara), (Zd,Rb,R1c,R3h,Arb), (Zd,Rb,R1c,R3h,Arc), (Zd,Rb,R1c,R3h,Ard), (Zd,Rb,R1c,R3h,Are), (Zd,Rb,R1c,R3h,Arf), (Zd,Rb,R1c,R3h,Arg), (Zd,Rb,R1c,R3h,Arh), (Zd,Rb,R1c,R3h,Ari), (Zd,Rb,R1c,R3h,Arj), (Zd,Rb,R1c,R3h,Ark), (Zd,Rb,R1c,R3h,Arl), (Zd,Rb,R1c,R3h,Arm), (Zd,Rb,R1c,R3h,Arn), (Zd,Rb,R1c,R3h,Aro), (Zd,Rb,R1c,R3h,Arp), (Zd,Rb,R1d,R3a,Ara), (Zd,Rb,R1d,R3a,Arb), (Zd,Rb,R1d,R3a,Arc), (Zd,Rb,R1d,R3a,Ard), (Zd,Rb,R1d,R3a,Are), (Zd,Rb,R1d,R3a,Arf), (Zd,Rb, R1d,R3a,Arg), (Zd,Rb,R1d,R3a,Arh), (Zd,Rb,R1d,R3a, Ari), (Zd,Rb,R1d,R3a,Arj), (Zd,Rb,R1d,R3a,Ark), (Zd,Rb, R1d,R3a,Arl), (Zd,Rb,R1d,R3a,Arm), (Zd,Rb,R1d,R3a, Arn), (Zd,Rb,R1d,R3a,Aro), (Zd,Rb,R1d,R3a,Arp), (Zd,Rb, R1d,R3b,Ara), (Zd,Rb,R1d,R3b,Arb), (Zd,Rb,R1d,R3b, Arc), (Zd,Rb,R1d,R3b,Ard), (Zd,Rb,R1d,R3b,Are), (Zd,Rb, R1d,R3b,Arf), (Zd,Rb,R1d,R3b,Arg), (Zd,Rb,R1d,R3b, Arh), (Zd,Rb,R1d,R3b,Ari), (Zd,Rb,R1d,R3b,Arj), (Zd,Rb, R1d,R3b,Ark), (Zd,Rb,R1d,R3b,Arl), (Zd,Rb,R1d,R3b, Arm), (Zd,Rb,R1d,R3b,Arn), (Zd,Rb,R1d,R3b,Aro), (Zd, Rb,R1d,R3b,Arp), (Zd,Rb,R1d,R3c,Ara), (Zd,Rb,R1d,R3c, Arb), (Zd,Rb,R1d,R3c,Arc), (Zd,Rb,R1d,R3c,Ard), (Zd,Rb, R1d,R3c,Are), (Zd,Rb,R1d,R3c,Arf), (Zd,Rb,R1d,R3c, Arg), (Zd,Rb,R1d,R3c,Arh), (Zd,Rb,R1d,R3c,Ari), (Zd,Rb, R1d,R3c,Arj), (Zd,Rb,R1d,R3c,Ark), (Zd,Rb,R1d,R3c,Arl) (Zd,Rb,R1d,R3c,Arm), (Zd,Rb,R1d,R3c,Arn), (Zd,Rb,R1d, R3c,Aro), (Zd,Rb,R1d,R3c,Arp), (Zd,Rb,R1d,R3d,Ara), (Zd,Rb,R1d,R3d,Arb), (Zd,Rb,R1d,R3d,Arc), (Zd,Rb,R1d, R3d,Ard), (Zd,Rb,R1d,R3d,Are), (Zd,Rb,R1d,R3d,Arf), (Zd,Rb,R1d,R3d,Arg), (Zd,Rb,R1d,R3d,Arh), (Zd,Rb,R1d, R3d,Ari), (Zd,Rb,R1d,R3d,Arj), (Zd,Rb,R1d,R3d,Ark), (Zd, Rb,R1d,R3d,Arl), (Zd,Rb,R1d,R3d,Arm), (Zd,Rb,R1d,R3d, Arn), (Zd,Rb,R1d,R3d,Aro), (Zd,Rb,R1d,R3d,Arp), (Zd,Rb, R1d,R3e,Ara), (Zd,Rb,R1d,R3e,Arb), (Zd,Rb,R1d,R3e, Arc), (Zd,Rb,R1d,R3e,Ard), (Zd,Rb,R1d,R3e,Are), (Zd,Rb, R1d,R3e,Arf), (Zd,Rb,R1d,R3e,Arg), (Zd,Rb,R1d,R3e, Arh), (Zd,Rb,R1d,R3e,Ari), (Zd,Rb,R1d,R3e,Arj), (Zd,Rb, R1d,R3e,Ark), (Zd,Rb,R1d,R3e,Arl), (Zd,Rb,R1d,R3e, Arm), (Zd,Rb,R1d,R3e,Arn), (Zd,Rb,R1d,R3e,Aro), (Zd, Rb,R1d,R3e,Arp), (Zd,Rb,R1d,R3f,Ara), (Zd,Rb,R1d,R3f, Arb), (Zd,Rb,R1d,R3f,Arc), (Zd,Rb,R1d,R3f,Ard), (Zd,Rb, R1d,R3f,Are), (Zd,Rb,R1d,R3f,Arf), (Zd,Rb,R1d,R3f,Arg), (Zd,Rb,R1d,R3f,Arh), (Zd,Rb,R1d,R3f,Ari), (Zd,Rb,R1d, R3f,Arj), (Zd,Rb,R1d,R3f,Ark), (Zd,Rb,R1d,R3f,Arl), (Zd, Rb,R1d,R3f,Arm), (Zd,Rb,R1d,R3f,Arn), (Zd,Rb,R1d,R3f, Aro), (Zd,Rb,R1d,R3f,Arp), (Zd,Rb,R1d,R3g,Ara), (Zd,Rb, R1d,R3g,Arb), (Zd,Rb,R1d,R3g,Arc), (Zd,Rb,R1d,R3g, Ard), (Zd,Rb,R1d,R3g,Are), (Zd,Rb,R1d,R3g,Arf), (Zd,Rb, R1d,R3g,Arg), (Zd,Rb,R1d,R3g,Arh), (Zd,Rb,R1d,R3g, Ari), (Zd,Rb,R1d,R3g,Arj), (Zd,Rb,R1d,R3g,Ark), (Zd,Rb, R1d,R3g,Arl), (Zd,Rb,R1d,R3g,Arm), (Zd,Rb,R1d,R3g, Arn), (Zd,Rb,R1d,R3g,Aro), (Zd,Rb,R1d,R3g,Arp), (Zd,Rb, R1d,R3h,Ara), (Zd,Rb,R1d,R3h,Arb), (Zd,Rb,R1d,R3h, Arc), (Zd,Rb,R1d,R3h,Ard), (Zd,Rb,R1d,R3h,Are), (Zd,Rb, R1d,R3h,Arf), (Zd,Rb,R1d,R3h,Arg), (Zd,Rb,R1d,R3h, Arh), (Zd,Rb,R1d,R3h,Ari), (Zd,Rb,R1d,R3h,Arj), (Zd,Rb, R1d,R3h,Ark), (Zd,Rb,R1d,R3h,Arl), (Zd,Rb,R1d,R3h, Arm), (Zd,Rb,R1d,R3h,Arn), (Zd,Rb,R1d,R3h,Aro), (Zd, Rb,R1d,R3h,Arp), (Zd,Rc,R1a,R3a,Ara), (Zd,Rc,R1a,R3a, Arb), (Zd,Rc,R1a,R3a,Arc), (Zd,Rc,R1a,R3a,Ard), (Zd,Rc, R1a,R3a,Are), (Zd,Rc,R1a,R3a,Arf), (Zd,Rc,R1a,R3a,Arg), (Zd,Rc,R1a,R3a,Arh), (Zd,Rc,R1a,R3a,Ari), (Zd,Rc,R1a, R3a,Arj), (Zd,Rc,R1a,R3a,Ark), (Zd,Rc,R1a,R3a,Arl), (Zd, Rc,R1a,R3a,Arm), (Zd,Rc,R1a,R3a,Arn), (Zd,Rc,R1a,R3a, Aro), (Zd,Rc,R1a,R3a,Arp), (Zd,Rc,R1a,R3b,Ara), (Zd,Rc, R1a,R3b,Arb), (Zd,Rc,R1a,R3b,Arc), (Zd,Rc,R1a,R3b, Ard), (Zd,Rc,R1a,R3b,Are), (Zd,Rc,R1a,R3b,Arf), (Zd,Rc, R1a,R3b,Arg), (Zd,Rc,R1a,R3b,Arh), (Zd,Rc,R1a,R3b,Ari), (Zd,Rc,R1a,R3b,Arj), (Zd,Rc,R1a,R3b,Ark), (Zd,Rc,R1a, R3b,Arl), (Zd,Rc,R1a,R3b,Arm), (Zd,Rc,R1a,R3b,Arn), (Zd,Rc,R1a,R3b,Aro), (Zd,Rc,R1a,R3b,Arp), (Zd,Rc,R1a, R3c,Ara), (Zd,Rc,R1a,R3c,Arb), (Zd,Rc,R1a,R3c,Arc), (Zd, Rc,R1a,R3c,Ard), (Zd,Rc,R1a,R3c,Are), (Zd,Rc,R1a,R3c, Arf), (Zd,Rc,R1a,R3c,Arg), (Zd,Rc,R1a,R3c,Arh), (Zd,Rc, R1a,R3c,Ari), (Zd,Rc,R1a,R3c,Arj), (Zd,Rc,R1a,R3c,Ark), (Zd,Rc,R1a,R3c,Arl), (Zd,Rc,R1a,R3c,Arm), (Zd,Rc,R1a, R3c,Arn), (Zd,Rc,R1a,R3c,Aro), (Zd,Rc,R1a,R3c,Arp), (Zd, Rc,R1a,R3d,Ara), (Zd,Rc,R1a,R3d,Arb), (Zd,Rc,R1a,R3d, Arc), (Zd,Rc,R1a,R3d,Ard), (Zd,Rc,R1a,R3d,Are), (Zd,Rc, R1a,R3d,Arf), (Zd,Rc,R1a,R3d,Arg), (Zd,Rc,R1a,R3d,Arh), (Zd,Rc,R1a,R3d,Ari), (Zd,Rc,R1a,R3d,Arj), (Zd,Rc,R1a, R3d,Ark), (Zd,Rc,R1a,R3d,Arl), (Zd,Rc,R1a,R3d,Arm), (Zd,Rc,R1a,R3d,Arn), (Zd,Rc,R1a,R3d,Aro), (Zd,Rc,R1a, R3d,Arp), (Zd,Rc,R1a,R3e,Ara), (Zd,Rc,R1a,R3e,Arb), (Zd, Rc,R1a,R3e,Arc), (Zd,Rc,R1a,R3e,Ard), (Zd,Rc,R1a,R3e, Are), (Zd,Rc,R1a,R3e,Arf), (Zd,Rc,R1a,R3e,Arg), (Zd,Rc, R1a,R3e,Arh), (Zd,Rc,R1a,R3e,Ari), (Zd,Rc,R1a,R3e,Arj), (Zd,Rc,R1a,R3e,Ark), (Zd,Rc,R1a,R3e,Arl), (Zd,Rc,R1a, R3e,Arm), (Zd,Rc,R1a,R3e,Arn), (Zd,Rc,R1a,R3e,Aro), (Zd,Rc,R1a,R3e,Arp), (Zd,Rc,R1a,R3f,Ara), (Zd,Rc,R1a, R3f,Arb), (Zd,Rc,R1a,R3f,Arc), (Zd,Rc,R1a,R3f,Ard), (Zd, Rc,R1a,R3f,Are), (Zd,Rc,R1a,R3f,Arf), (Zd,Rc,R1a,R3f, Arg), (Zd,Rc,R1a,R3f,Arh), (Zd,Rc,R1a,R3f,Ari), (Zd,Rc, R1a,R3f,Arj), (Zd,Rc,R1a,R3f,Ark), (Zd,Rc,R1a,R3f,Arl), (Zd,Rc,R1a,R3f,Arm), (Zd,Rc,R1a,R3f,Arn), (Zd,Rc,R1a, R3f,Aro), (Zd,Rc,R1a,R3f,Arp), (Zd,Rc,R1a,R3g,Ara), (Zd, Rc,R1a,R3g,Arb), (Zd,Rc,R1a,R3g,Arc), (Zd,Rc,R1a,R3g, Ard), (Zd,Rc,R1a,R3g,Are), (Zd,Rc,R1a,R3g,Arf), (Zd,Rc, R1a,R3g,Arg), (Zd,Rc,R1a,R3g,Arh), (Zd,Rc,R1a,R3g,Ari), (Zd,Rc,R1a,R3g,Arj), (Zd,Rc,R1a,R3g,Ark), (Zd,Rc,R1a, R3g,Arl), (Zd,Rc,R1a,R3g,Arm), (Zd,Rc,R1a,R3g,Arn), (Zd,Rc,R1a,R3g,Aro), (Zd,Rc,R1a,R3g,Arp), (Zd,Rc,R1a, R3h,Ara), (Zd,Rc,R1a,R3h,Arb), (Zd,Rc,R1a,R3h,Arc), (Zd,Rc,R1a,R3h,Ard), (Zd,Rc,R1a,R3h,Are), (Zd,Rc,R1a, R3h,Arf), (Zd,Rc,R1a,R3h,Arg), (Zd,Rc,R1a,R3h,Arh), (Zd, Rc,R1a,R3h,Ari), (Zd,Rc,R1a,R3h,Arj), (Zd,Rc,R1a,R3h, Ark), (Zd,Rc,R1a,R3h,Arl), (Zd,Rc,R1a,R3h,Arm), (Zd,Rc, R1a,R3h,Arn), (Zd,Rc,R1a,R3h,Aro), (Zd,Rc,R1a,R3h, Arp), (Zd,Rc,R1b,R3a,Ara), (Zd,Rc,R1b,R3a,Arb), (Zd,Rc, R1b,R3a,Arc), (Zd,Rc,R1b,R3a,Ard), (Zd,Rc,R1b,R3a, Are), (Zd,Rc,R1b,R3a,Arf), (Zd,Rc,R1b,R3a,Arg), (Zd,Rc, R1b,R3a,Arh), (Zd,Rc,R1b,R3a,Ari), (Zd,Rc,R1b,R3a,Arj), (Zd,Rc,R1b,R3a,Ark), (Zd,Rc,R1b,R3a,Arl), (Zd,Rc,R1b, R3a,Arm), (Zd,Rc,R1b,R3a,Arn), (Zd,Rc,R1b,R3a,Aro), (Zd,Rc,R1b,R3a,Arp), (Zd,Rc,R1b,R3b,Ara), (Zd,Rc,R1b, R3b,Arb), (Zd,Rc,R1b,R3b,Arc), (Zd,Rc,R1b,R3b,Ard), (Zd,Rc,R1b,R3b,Are), (Zd,Rc,R1b,R3b,Arf), (Zd,Rc,R1b, R3b,Arg), (Zd,Rc,R1b,R3b,Arh), (Zd,Rc,R1b,R3b,Ari), (Zd,Rc,R1b,R3b,Arj), (Zd,Rc,R1b,R3b,Ark), (Zd,Rc,R1b, R3b,Arl), (Zd,Rc,R1b,R3b,Arm), (Zd,Rc,R1b,R3b,Arn), (Zd,Rc,R1b,R3b,Aro), (Zd,Rc,R1b,R3b,Arp), (Zd,Rc,R1b, R3c,Ara), (Zd,Rc,R1b,R3c,Arb), (Zd,Rc,R1b,R3c,Arc), (Zd, Rc,R1b,R3c,Ard), (Zd,Rc,R1b,R3c,Are), (Zd,Rc,R1b,R3c, Arf), (Zd,Rc,R1b,R3c,Arg), (Zd,Rc,R1b,R3c,Arh), (Zd,Rc, R1b,R3c,Ari), (Zd,Rc,R1b,R3c,Arj), (Zd,Rc,R1b,R3c,Ark), (Zd,Rc,R1b,R3c,Arl), (Zd,Rc,R1b,R3c,Arm), (Zd,Rc,R1b, R3c,Arn), (Zd,Rc,R1b,R3c,Aro), (Zd,Rc,R1b,R3c,Arp), (Zd,Rc,R1b,R3d,Ara), (Zd,Rc,R1b,R3d,Arb), (Zd,Rc,R1b, R3d,Arc), (Zd,Rc,R1b,R3d,Ard), (Zd,Rc,R1b,R3d,Are), (Zd,Rc,R1b,R3d,Arf), (Zd,Rc,R1b,R3d,Arg), (Zd,Rc,R1b, R3d,Arh), (Zd,Rc,R1b,R3d,Ari), (Zd,Rc,R1b,R3d,Arj), (Zd, Rc,R1b,R3d,Ark), (Zd,Rc,R1b,R3d,Arl), (Zd,Rc,R1b,R3d, Arm), (Zd,Rc,R1b,R3d,Arn), (Zd,Rc,R1b,R3d,Aro), (Zd,Rc, R1b,R3d,Arp), (Zd,Rc,R1b,R3e,Ara), (Zd,Rc,R1b,R3e, Arb), (Zd,Rc,R1b,R3e,Arc), (Zd,Rc,R1b,R3e,Ard), (Zd,Rc, R1b,R3e,Are), (Zd,Rc,R1b,R3e,Arf), (Zd,Rc,R1b,R3e,Arg), (Zd,Rc,R1b,R3e,Arh), (Zd,Rc,R1b,R3e,Ari), (Zd,Rc,R1b, R3e,Arj), (Zd,Rc,R1b,R3e,Ark), (Zd,Rc,R1b,R3e,Arl), (Zd, Rc,R1b,R3e,Arm), (Zd,Rc,R1b,R3e,Arn), (Zd,Rc,R1b,R3e, Aro), (Zd,Rc,R1b,R3e,Arp), (Zd,Rc,R1b,R3f,Ara), (Zd,Rc, R1b,R3f,Arb), (Zd,Rc,R1b,R3f,Arc), (Zd,Rc,R1b,R3f,Ard), (Zd,Rc,R1b,R3f,Are), (Zd,Rc,R1b,R3f,Arf), (Zd,Rc,R1b, R3f,Arg), (Zd,Rc,R1b,R3f,Arh), (Zd,Rc,R1b,R3f,Ari), (Zd, Rc,R1b,R3f,Arj), (Zd,Rc,R1b,R3f,Ark), (Zd,Rc,R1b,R3f, Arl), (Zd,Rc,R1b,R3f,Arm), (Zd,Rc,R1b,R3f,Arn), (Zd,Rc, R1b,R3f,Aro), (Zd,Rc,R1b,R3f,Arp), (Zd,Rc,R1b,R3g,Ara), (Zd,Rc,R1b,R3g,Arb), (Zd,Rc,R1b,R3g,Arc), (Zd,Rc,R1b, R3g,Ard), (Zd,Rc,R1b,R3g,Are), (Zd,Rc,R1b,R3g,Arf), (Zd,Rc,R1b,R3g,Arg), (Zd,Rc,R1b,R3g,Arh), (Zd,Rc,R1b, R3g,Ari), (Zd,Rc,R1b,R3g,Arj), (Zd,Rc,R1b,R3g,Ark), (Zd, Rc,R1b,R3g,Arl), (Zd,Rc,R1b,R3g,Arm), (Zd,Rc,R1b,R3g, Arn), (Zd,Rc,R1b,R3g,Aro), (Zd,Rc,R1b,R3g,Arp), (Zd,Rc, R1b,R3h,Ara), (Zd,Rc,R1b,R3h,Arb), (Zd,Rc,R1b,R3h, Arc), (Zd,Rc,R1b,R3h,Ard), (Zd,Rc,R1b,R3h,Are), (Zd,Rc, R1b,R3h,Arf), (Zd,Rc,R1b,R3h,Arg), (Zd,Rc,R1b,R3h, Arh), (Zd,Rc,R1b,R3h,Ari), (Zd,Rc,R1b,R3h,Arj), (Zd,Rc, R1b,R3h,Ark), (Zd,Rc,R1b,R3h,Arl), (Zd,Rc,R1b,R3h, Arm), (Zd,Rc,R1b,R3h,Arn), (Zd,Rc,R1b,R3h,Aro), (Zd,Rc, R1b,R3h,Arp), (Zd,Rc,R1c,R3a,Ara), (Zd,Rc,R1c,R3a, Arb), (Zd,Rc,R1c,R3a,Arc), (Zd,Rc,R1c,R3a,Ard), (Zd,Rc, R1c,R3a,Are), (Zd,Rc,R1c,R3a,Arf), (Zd,Rc,R1c,R3a,Arg), (Zd,Rc,R1c,R3a,Arh), (Zd,Rc,R1c,R3a,Ari), (Zd,Rc,R1c, R3a,Arj), (Zd,Rc,R1c,R3a,Ark), (Zd,Rc,R1c,R3a,Arl), (Zd, Rc,R1c,R3a,Arm), (Zd,Rc,R1c,R3a,Arn), (Zd,Rc,R1c,R3a, Aro), (Zd,Rc,R1c,R3a,Arp), (Zd,Rc,R1c,R3b,Ara), (Zd,Rc, R1c,R3b,Arb), (Zd,Rc,R1c,R3b,Arc), (Zd,Rc,R1c,R3b, Ard), (Zd,Rc,R1c,R3b,Are), (Zd,Rc,R1c,R3b,Arf), (Zd,Rc, R1c,R3b,Arg), (Zd,Rc,R1c,R3b,Arh), (Zd,Rc,R1c,R3b,Ari), (Zd,Rc,R1c,R3b,Arj), (Zd,Rc,R1c,R3b,Ark), (Zd,Rc,R1c, R3b,Arl), (Zd,Rc,R1c,R3b,Arm), (Zd,Rc,R1c,R3b,Arn), (Zd,Rc,R1c,R3b,Aro), (Zd,Rc,R1c,R3b,Arp), (Zd,Rc,R1c, R3c,Ara), (Zd,Rc,R1c,R3c,Arb), (Zd,Rc,R1c,R3c,Arc), (Zd, Rc,R1c,R3c,Ard), (Zd,Rc,R1c,R3c,Are), (Zd,Rc,R1c,R3c, Arf), (Zd,Rc,R1c,R3c,Arg), (Zd,Rc,R1c,R3c,Arh), (Zd,Rc, R1c,R3c,Ari), (Zd,Rc,R1c,R3c,Arj), (Zd,Rc,R1c,R3c,Ark), (Zd,Rc,R1c,R3c,Arl), (Zd,Rc,R1c,R3c,Arm), (Zd,Rc,R1c, R3c,Arn), (Zd,Rc,R1c,R3c,Aro), (Zd,Rc,R1c,R3c,Arp), (Zd, Rc,R1c,R3d,Ara), (Zd,Rc,R1c,R3d,Arb), (Zd,Rc,R1c,R3d, Arc), (Zd,Rc,R1c,R3d,Ard), (Zd,Rc,R1c,R3d,Are), (Zd,Rc, R1c,R3d,Arf), (Zd,Rc,R1c,R3d,Arg), (Zd,Rc,R1c,R3d,Arh), (Zd,Rc,R1c,R3d,Ari), (Zd,Rc,R1c,R3d,Arj), (Zd,Rc,R1c, R3d,Ark), (Zd,Rc,R1c,R3d,Arl), (Zd,Rc,R1c,R3d,Arm), (Zd,Rc,R1c,R3d,Arn), (Zd,Rc,R1c,R3d,Aro), (Zd,Rc,R1c, R3d,Arp), (Zd,Rc,R1c,R3e,Ara), (Zd,Rc,R1c,R3e,Arb), (Zd, Rc,R1c,R3e,Arc), (Zd,Rc,R1c,R3e,Ard), (Zd,Rc,R1c,R3e, Are), (Zd,Rc,R1c,R3e,Arf), (Zd,Rc,R1c,R3e,Arg), (Zd,Rc, R1c,R3e,Arh), (Zd,Rc,R1c,R3e,Ari), (Zd,Rc,R1c,R3e,Arj), (Zd,Rc,R1c,R3e,Ark), (Zd,Rc,R1c,R3e,Arl), (Zd,Rc,R1c, R3e,Arm), (Zd,Rc,R1c,R3e,Arn), (Zd,Rc,R1c,R3e,Aro), (Zd,Rc,R1c,R3e,Arp), (Zd,Rc,R1c,R3f,Ara), (Zd,Rc,R1c, R3f,Arb), (Zd,Rc,R1c,R3f,Arc), (Zd,Rc,R1c,R3f,Ard), (Zd, Rc,R1c,R3f,Are), (Zd,Rc,R1c,R3f,Arf), (Zd,Rc,R1c,R3f, Arg), (Zd,Rc,R1c,R3f,Arh), (Zd,Rc,R1c,R3f,Ari), (Zd,Rc, R1c,R3f,Arj), (Zd,Rc,R1c,R3f,Ark), (Zd,Rc,R1c,R3f,Arl), (Zd,Rc,R1c,R3f,Arm), (Zd,Rc,R1c,R3f,Arn), (Zd,Rc,R1c, R3f,Aro), (Zd,Rc,R1c,R3f,Arp), (Zd,Rc,R1c,R3g,Ara), (Zd, Rc,R1c,R3g,Arb), (Zd,Rc,R1c,R3g,Arc), (Zd,Rc,R1c,R3g, Ard), (Zd,Rc,R1c,R3g,Are), (Zd,Rc,R1c,R3g,Arf), (Zd,Rc, R1c,R3g,Arg), (Zd,Rc,R1c,R3g,Arh), (Zd,Rc,R1c,R3g,Ari), (Zd,Rc,R1c,R3g,Arj), (Zd,Rc,R1c,R3g,Ark), (Zd,Rc,R1c, R3g,Arl), (Zd,Rc,R1c,R3g,Arm), (Zd,Rc,R1c,R3g,Arn), (Zd,Rc,R1c,R3g,Aro), (Zd,Rc,R1c,R3g,Arp), (Zd,Rc,R1c, R3h,Ara), (Zd,Rc,R1c,R3h,Arb), (Zd,Rc,R1c,R3h,Arc), (Zd,Rc,R1c,R3h,Ard), (Zd,Rc,R1c,R3h,Are), (Zd,Rc,R1c, R3h,Arf), (Zd,Rc,R1c,R3h,Arg), (Zd,Rc,R1c,R3h,Arh), (Zd, Rc,R1c,R3h,Ari), (Zd,Rc,R1c,R3h,Arj), (Zd,Rc,R1c,R3h, Ark), (Zd,Rc,R1c,R3h,Arl), (Zd,Rc,R1c,R3h,Arm), (Zd,Rc, R1c,R3h,Arn), (Zd,Rc,R1c,R3h,Aro), (Zd,Rc,R1c,R3h, Arp), (Zd,Rc,R1d,R3a,Ara), (Zd,Rc,R1d,R3a,Arb), (Zd,Rc, R1d,R3a,Arc), (Zd,Rc,R1d,R3a,Ard), (Zd,Rc,R1d,R3a, Are), (Zd,Rc,R1d,R3a,Arf), (Zd,Rc,R1d,R3a,Arg), (Zd,Rc, R1d,R3a,Arh), (Zd,Rc,R1d,R3a,Ari), (Zd,Rc,R1d,R3a,Arj), (Zd,Rc,R1d,R3a,Ark), (Zd,Rc,R1d,R3a,Arl), (Zd,Rc,R1d, R3a,Arm), (Zd,Rc,R1d,R3a,Arn), (Zd,Rc,R1d,R3a,Aro), (Zd,Rc,R1d,R3a,Arp), (Zd,Rc,R1d,R3b,Ara), (Zd,Rc,R1d, R3b,Arb), (Zd,Rc,R1d,R3b,Arc), (Zd,Rc,R1d,R3b,Ard), (Zd,Rc,R1d,R3b,Are), (Zd,Rc,R1d,R3b,Arf), (Zd,Rc,R1d, R3b,Arg), (Zd,Rc,R1d,R3b,Arh), (Zd,Rc,R1d,R3b,Ari), (Zd,Rc,R1d,R3b,Arj), (Zd,Rc,R1d,R3b,Ark), (Zd,Rc,R1d, R3b,Arl), (Zd,Rc,R1d,R3b,Arm), (Zd,Rc,R1d,R3b,Arn), (Zd,Rc,R1d,R3b,Aro), (Zd,Rc,R1d,R3b,Arp), (Zd,Rc,R1d, R3c,Ara), (Zd,Rc,R1d,R3c,Arb), (Zd,Rc,R1d,R3c,Arc), (Zd, Rc,R1d,R3c,Ard), (Zd,Rc,R1d,R3c,Are), (Zd,Rc,R1d,R3c, Arf), (Zd,Rc,R1d,R3c,Arg), (Zd,Rc,R1d,R3c,Arh), (Zd,Rc, R1d,R3c,Ari), (Zd,Rc,R1d,R3c,Arj), (Zd,Rc,R1d,R3c,Ark), (Zd,Rc,R1d,R3c,Arl), (Zd,Rc,R1d,R3c,Arm), (Zd,Rc,R1d, R3c,Arn), (Zd,Rc,R1d,R3c,Aro), (Zd,Rc,R1d,R3c,Arp), (Zd,Rc,R1d,R3d,Ara), (Zd,Rc,R1d,R3d,Arb), (Zd,Rc,R1d, R3d,Arc), (Zd,Rc,R1d,R3d,Ard), (Zd,Rc,R1d,R3d,Are), (Zd,Rc,R1d,R3d,Arf), (Zd,Rc,R1d,R3d,Arg), (Zd,Rc,R1d, R3d,Arh), (Zd,Rc,R1d,R3d,Ari), (Zd,Rc,R1d,R3d,Arj), (Zd, Rc,R1d,R3d,Ark), (Zd,Rc,R1d,R3d,Arl), (Zd,Rc,R1d,R3d, Arm), (Zd,Rc,R1d,R3d,Arn), (Zd,Rc,R1d,R3d,Aro), (Zd,Rc, R1d,R3d,Arp), (Zd,Rc,R1d,R3e,Ara), (Zd,Rc,R1d,R3e, Arb), (Zd,Rc,R1d,R3e,Arc), (Zd,Rc,R1d,R3e,Ard), (Zd,Rc, R1d,R3e,Are), (Zd,Rc,R1d,R3e,Arf), (Zd,Rc,R1d,R3e,Arg), (Zd,Rc,R1d,R3e,Arh), (Zd,Rc,R1d,R3e,Ari), (Zd,Rc,R1d, R3e,Arj), (Zd,Rc,R1d,R3e,Ark), (Zd,Rc,R1d,R3e,Arl), (Zd, Rc,R1d,R3e,Arm), (Zd,Rc,R1d,R3e,Arn), (Zd,Rc,R1d,R3e, Aro), (Zd,Rc,R1d,R3e,Arp), (Zd,Rc,R1d,R3f,Ara), (Zd,Rc, R1d,R3f,Arb), (Zd,Rc,R1d,R3f,Arc), (Zd,Rc,R1d,R3f,Ard), (Zd,Rc,R1d,R3f,Are), (Zd,Rc,R1d,R3f,Arf), (Zd,Rc,R1d, R3f,Arg), (Zd,Rc,R1d,R3f,Arh), (Zd,Rc,R1d,R3f,Ari), (Zd, Rc,R1d,R3f,Arj), (Zd,Rc,R1d,R3f,Ark), (Zd,Rc,R1d,R3f, Arl), (Zd,Rc,R1d,R3f,Arm), (Zd,Rc,R1d,R3f,Arn), (Zd,Rc, R1d,R3f,Aro), (Zd,Rc,R1d,R3f,Arp), (Zd,Rc,R1d,R3g,Ara), (Zd,Rc,R1d,R3g,Arb), (Zd,Rc,R1d,R3g,Arc), (Zd,Rc,R1d, R3g,Ard), (Zd,Rc,R1d,R3g,Are), (Zd,Rc,R1d,R3g,Arf), (Zd,Rc,R1d,R3g,Arg), (Zd,Rc,R1d,R3g,Arh), (Zd,Rc,R1d, R3g,Ari), (Zd,Rc,R1d,R3g,Arj), (Zd,Rc,R1d,R3g,Ark), (Zd, Rc,R1d,R3g,Arl), (Zd,Rc,R1d,R3g,Arm), (Zd,Rc,R1d,R3g, Arn), (Zd,Rc,R1d,R3g,Aro), (Zd,Rc,R1d,R3g,Arp), (Zd,Rc, R1d,R3h,Ara), (Zd,Rc,R1d,R3h,Arb), (Zd,Rc,R1d,R3h, Arc), (Zd,Rc,R1d,R3h,Ard), (Zd,Rc,R1d,R3h,Are), (Zd,Rc, R1d,R3h,Arf), (Zd,Rc,R1d,R3h,Arg), (Zd,Rc,R1d,R3h, Arh), (Zd,Rc,R1d,R3h,Ari), (Zd,Rc,R1d,R3h,Arj), (Zd,Rc, R1d,R3h,Ark), (Zd,Rc,R1d,R3h,Arl), (Zd,Rc,R1d,R3h, Arm), (Zd,Rc,R1d,R3h,Arn), (Zd,Rc,R1d,R3h,Aro), (Zd,Rc, R1d,R3h,Arp), (Zd,Rd,R1a,R3a,Ara), (Zd,Rd,R1a,R3a, Arb), (Zd,Rd,R1a,R3a,Arc), (Zd,Rd,R1a,R3a,Ard), (Zd,Rd, R1a,R3a,Are), (Zd,Rd,R1a,R3a,Arf), (Zd,Rd,R1a,R3a,Arg), (Zd,Rd,R1a,R3a,Arh), (Zd,Rd,R1a,R3a,Ari), (Zd,Rd,R1a, R3a,Arj), (Zd,Rd,R1a,R3a,Ark), (Zd,Rd,R1a,R3a,Arl), (Zd, Rd,R1a,R3a,Arm), (Zd,Rd,R1a,R3a,Arn), (Zd,Rd,R1a,R3a, Aro), (Zd,Rd,R1a,R3a,Arp), (Zd,Rd,R1a,R3b,Ara), (Zd,Rd, R1a,R3b,Arb), (Zd,Rd,R1a,R3b,Arc), (Zd,Rd,R1a,R3b, Ard), (Zd,Rd,R1a,R3b,Are), (Zd,Rd,R1a,R3b,Arf), (Zd,Rd, R1a,R3b,Arg), (Zd,Rd,R1a,R3b,Arh), (Zd,Rd,R1a,R3b, Ari), (Zd,Rd,R1a,R3b,Arj), (Zd,Rd,R1a,R3b,Ark), (Zd,Rd, R1a,R3b,Arl), (Zd,Rd,R1a,R3b,Arm), (Zd,Rd,R1a,R3b, Arn), (Zd,Rd,R1a,R3b,Aro), (Zd,Rd,R1a,R3b,Arp), (Zd,Rd, R1a,R3c,Ara), (Zd,Rd,R1a,R3c,Arb), (Zd,Rd,R1a,R3c,Arc), (Zd,Rd,R1a,R3c,Ard), (Zd,Rd,R1a,R3c,Are), (Zd,Rd,R1a, R3c,Arf), (Zd,Rd,R1a,R3c,Arg), (Zd,Rd,R1a,R3c,Arh), (Zd, Rd,R1a,R3c,Ari), (Zd,Rd,R1a,R3c,Arj), (Zd,Rd,R1a,R3c, Ark), (Zd,Rd,R1a,R3c,Arl), (Zd,Rd,R1a,R3c,Arm), (Zd,Rd, R1a,R3c,Arn), (Zd,Rd,R1a,R3c,Aro), (Zd,Rd,R1a,R3c, Arp), (Zd,Rd,R1a,R3d,Ara), (Zd,Rd,R1a,R3d,Arb), (Zd,Rd, R1a,R3d,Arc), (Zd,Rd,R1a,R3d,Ard), (Zd,Rd,R1a,R3d,Are), (Zd,Rd,R1a,R3d,Arf), (Zd,Rd,R1a,R3d,Arg), (Zd,Rd,R1a,R3d,Arh), (Zd,Rd,R1a,R3d,Ari), (Zd,Rd,R1a,R3d,Arj), (Zd,Rd,R1a,R3d,Ark), (Zd,Rd,R1a,R3d,Arl), (Zd,Rd,R1a,R3d,Arm), (Zd,Rd,R1a,R3d,Arn), (Zd,Rd,R1a,R3d,Aro), (Zd,Rd,R1a,R3d,Arp), (Zd,Rd,R1a,R3e,Ara), (Zd,Rd,R1a,R3e,Arb), (Zd,Rd,R1a,R3e,Arc), (Zd,Rd,R1a,R3e,Ard), (Zd,Rd,R1a,R3e,Are), (Zd,Rd,R1a,R3e,Arf), (Zd,Rd,R1a,R3e,Arg), (Zd,Rd,R1a,R3e,Arh), (Zd,Rd,R1a,R3e,Ari), (Zd,Rd,R1a,R3e,Arj), (Zd,Rd,R1a,R3e,Ark), (Zd,Rd,R1a,R3e,Arl), (Zd,Rd,R1a,R3e,Arm), (Zd,Rd,R1a,R3e,Arn), (Zd,Rd,R1a,R3e,Aro), (Zd,Rd,R1a,R3e,Arp), (Zd,Rd,R1a,R3f,Ara), (Zd,Rd,R1a,R3f,Arb), (Zd,Rd,R1a,R3f,Arc), (Zd,Rd,R1a,R3f,Ard), (Zd,Rd,R1a,R3f,Are), (Zd,Rd,R1a,R3f,Arf), (Zd,Rd,R1a,R3f,Arg), (Zd,Rd,R1a,R3f,Arh), (Zd,Rd,R1a,R3f,Ari), (Zd,Rd,R1a,R3f,Arj), (Zd,Rd,R1a,R3f,Ark), (Zd,Rd,R1a,R3f,Arl), (Zd,Rd,R1a,R3f,Arm), (Zd,Rd,R1a,R3f,Arn), (Zd,Rd,R1a,R3f,Aro), (Zd,Rd,R1a,R3f,Arp), (Zd,Rd,R1a,R3g,Ara), (Zd,Rd,R1a,R3g,Arb), (Zd,Rd,R1a,R3g,Arc), (Zd,Rd,R1a,R3g,Ard), (Zd,Rd,R1a,R3g,Are), (Zd,Rd,R1a,R3g,Arf), (Zd,Rd,R1a,R3g,Arg), (Zd,Rd,R1a,R3g,Arh), (Zd,Rd,R1a,R3g,Ari), (Zd,Rd,R1a,R3g,Arj), (Zd,Rd,R1a,R3g,Ark), (Zd,Rd,R1a,R3g,Arl), (Zd,Rd,R1a,R3g,Arm), (Zd,Rd,R1a,R3g,Arn), (Zd,Rd,R1a,R3g,Aro), (Zd,Rd,R1a,R3g,Arp), (Zd,Rd,R1a,R3h,Ara), (Zd,Rd,R1a,R3h,Arb), (Zd,Rd,R1a,R3h,Arc), (Zd,Rd,R1a,R3h,Ard), (Zd,Rd,R1a,R3h,Are), (Zd,Rd,R1a,R3h,Arf), (Zd,Rd,R1a,R3h,Arg), (Zd,Rd,R1a,R3h,Arh), (Zd,Rd,R1a,R3h,Ari), (Zd,Rd,R1a,R3h,Arj), (Zd,Rd,R1a,R3h,Ark), (Zd,Rd,R1a,R3h,Arl), (Zd,Rd,R1a,R3h,Arm), (Zd,Rd,R1a,R3h,Arn), (Zd,Rd,R1a,R3h,Aro), (Zd,Rd,R1a,R3h,Arp), (Zd,Rd,R1b,R3a,Ara), (Zd,Rd,R1b,R3a,Arb), (Zd,Rd,R1b,R3a,Arc), (Zd,Rd,R1b,R3a,Ard), (Zd,Rd,R1b,R3a,Are), (Zd,Rd,R1b,R3a,Arf), (Zd,Rd,R1b,R3a,Arg), (Zd,Rd,R1b,R3a,Arh), (Zd,Rd,R1b,R3a,Ari), (Zd,Rd,R1b,R3a,Arj), (Zd,Rd,R1b,R3a,Ark), (Zd,Rd,R1b,R3a,Arl), (Zd,Rd,R1b,R3a,Arm), (Zd,Rd,R1b,R3a,Arn), (Zd,Rd,R1b,R3a,Aro), (Zd,Rd,R1b,R3a,Arp), (Zd,Rd,R1b,R3b,Ara), (Zd,Rd,R1b,R3b,Arb), (Zd,Rd,R1b,R3b,Arc), (Zd,Rd,R1b,R3b,Ard), (Zd,Rd,R1b,R3b,Are), (Zd,Rd,R1b,R3b,Arf), (Zd,Rd,R1b,R3b,Arg), (Zd,Rd,R1b,R3b,Arh), (Zd,Rd,R1b,R3b,Ari), (Zd,Rd,R1b,R3b,Arj), (Zd,Rd,R1b,R3b,Ark), (Zd,Rd,R1b,R3b,Arl), (Zd,Rd,R1b,R3b,Arm), (Zd,Rd,R1b,R3b,Arn), (Zd,Rd,R1b,R3b,Aro), (Zd,Rd,R1b,R3b,Arp), (Zd,Rd,R1b,R3c,Ara), (Zd,Rd,R1b,R3c,Arb), (Zd,Rd,R1b,R3c,Arc), (Zd,Rd,R1b,R3c,Ard), (Zd,Rd,R1b,R3c,Are), (Zd,Rd,R1b,R3c,Arf), (Zd,Rd,R1b,R3c,Arg), (Zd,Rd,R1b,R3c,Arh), (Zd,Rd,R1b,R3c,Ari), (Zd,Rd,R1b,R3c,Arj), (Zd,Rd,R1b,R3c,Ark), (Zd,Rd,R1b,R3c,Arl), (Zd,Rd,R1b,R3c,Arm), (Zd,Rd,R1b,R3c,Arn), (Zd,Rd,R1b,R3c,Aro), (Zd,Rd,R1b,R3c,Arp), (Zd,Rd,R1b,R3d,Ara), (Zd,Rd,R1b,R3d,Arb), (Zd,Rd,R1b,R3d,Arc), (Zd,Rd,R1b,R3d,Ard), (Zd,Rd,R1b,R3d,Are), (Zd,Rd,R1b,R3d,Arf), (Zd,Rd,R1b,R3d,Arg), (Zd,Rd,R1b,R3d,Arh), (Zd,Rd,R1b,R3d,Ari), (Zd,Rd,R1b,R3d,Arj), (Zd,Rd,R1b,R3d,Ark), (Zd,Rd,R1b,R3d,Arl), (Zd,Rd,R1b,R3d,Arm), (Zd,Rd,R1b,R3d,Arn), (Zd,Rd,R1b,R3d,Aro), (Zd,Rd,R1b,R3d,Arp), (Zd,Rd,R1b,R3e,Ara), (Zd,Rd,R1b,R3e,Arb), (Zd,Rd,R1b,R3e,Arc), (Zd,Rd,R1b,R3e,Ard), (Zd,Rd,R1b,R3e,Are), (Zd,Rd,R1b,R3e,Arf), (Zd,Rd,R1b,R3e,Arg), (Zd,Rd,R1b,R3e,Arh), (Zd,Rd,R1b,R3e,Ari), (Zd,Rd,R1b,R3e,Arj), (Zd,Rd,R1b,R3e,Ark), (Zd,Rd,R1b,R3e,Arl), (Zd,Rd,R1b,R3e,Arm), (Zd,Rd,R1b,R3e,Arn), (Zd,Rd,R1b,R3e,Aro), (Zd,Rd,R1b,R3e,Arp), (Zd,Rd,R1b,R3f,Ara), (Zd,Rd,R1b,R3f,Arb), (Zd,Rd,R1b,R3f,Arc), (Zd,Rd,R1b,R3f,Ard), (Zd,Rd,R1b,R3f,Are), (Zd,Rd,R1b,R3f,Arf), (Zd,Rd,R1b,R3f,Arg), (Zd,Rd,R1b,R3f,Arh), (Zd,Rd,R1b,R3f,Ari), (Zd,Rd,R1b,R3f,Arj), (Zd,Rd,R1b,R3f,Ark), (Zd,Rd,R1b,R3f,Arl), (Zd,Rd,R1b,R3f,Arm), (Zd,Rd,R1b,R3f,Arn), (Zd,Rd,R1b,R3f,Aro), (Zd,Rd,R1b,R3f,Arp), (Zd,Rd,R1b,R3g,Ara), (Zd,Rd,R1b,R3g,Arb), (Zd,Rd,R1b,R3g,Arc), (Zd,Rd,R1b,R3g,Ard), (Zd,Rd,R1b,R3g,Are), (Zd,Rd,R1b,R3g,Arf), (Zd,Rd,R1b,R3g,Arg), (Zd,Rd,R1b,R3g,Arh), (Zd,Rd,R1b,R3g,Ari), (Zd,Rd,R1b,R3g,Arj), (Zd,Rd,R1b,R3g,Ark), (Zd,Rd,R1b,R3g,Arl), (Zd,Rd,R1b,R3g,Arm), (Zd,Rd,R1b,R3g,Arn), (Zd,Rd,R1b,R3g,Aro), (Zd,Rd,R1b,R3g,Arp), (Zd,Rd,R1b,R3h,Ara), (Zd,Rd,R1b,R3h,Arb), (Zd,Rd,R1b,R3h,Arc), (Zd,Rd,R1b,R3h,Ard), (Zd,Rd,R1b,R3h,Are), (Zd,Rd,R1b,R3h,Arf), (Zd,Rd,R1b,R3h,Arg), (Zd,Rd,R1b,R3h,Arh), (Zd,Rd,R1b,R3h,Ari), (Zd,Rd,R1b,R3h,Arj), (Zd,Rd,R1b,R3h,Ark), (Zd,Rd,R1b,R3h,Arl), (Zd,Rd,R1b,R3h,Arm), (Zd,Rd,R1b,R3h,Arn), (Zd,Rd,R1b,R3h,Aro), (Zd,Rd,R1b,R3h,Arp), (Zd,Rd,R1c,R3a,Ara), (Zd,Rd,R1c,R3a,Arb), (Zd,Rd,R1c,R3a,Arc), (Zd,Rd,R1c,R3a,Ard), (Zd,Rd,R1c,R3a,Are), (Zd,Rd,R1c,R3a,Arf), (Zd,Rd,R1c,R3a,Arg), (Zd,Rd,R1c,R3a,Arh), (Zd,Rd,R1c,R3a,Ari), (Zd,Rd,R1c,R3a,Arj), (Zd,Rd,R1c,R3a,Ark), (Zd,Rd,R1c,R3a,Arl), (Zd,Rd,R1c,R3a,Arm), (Zd,Rd,R1c,R3a,Arn), (Zd,Rd,R1c,R3a,Aro), (Zd,Rd,R1c,R3a,Arp), (Zd,Rd,R1c,R3b,Ara), (Zd,Rd,R1c,R3b,Arb), (Zd,Rd,R1c,R3b,Arc), (Zd,Rd,R1c,R3b,Ard), (Zd,Rd,R1c,R3b,Are), (Zd,Rd,R1c,R3b,Arf), (Zd,Rd,R1c,R3b,Arg), (Zd,Rd,R1c,R3b,Arh), (Zd,Rd,R1c,R3b,Ari), (Zd,Rd,R1c,R3b,Arj), (Zd,Rd,R1c,R3b,Ark), (Zd,Rd,R1c,R3b,Arl), (Zd,Rd,R1c,R3b,Arm), (Zd,Rd,R1c,R3b,Arn), (Zd,Rd,R1c,R3b,Aro), (Zd,Rd,R1c,R3b,Arp), (Zd,Rd,R1c,R3c,Ara), (Zd,Rd,R1c,R3c,Arb), (Zd,Rd,R1c,R3c,Arc), (Zd,Rd,R1c,R3c,Ard), (Zd,Rd,R1c,R3c,Are), (Zd,Rd,R1c,R3c,Arf), (Zd,Rd,R1c,R3c,Arg), (Zd,Rd,R1c,R3c,Arh), (Zd,Rd,R1c,R3c,Ari), (Zd,Rd,R1c,R3c,Arj), (Zd,Rd,R1c,R3c,Ark), (Zd,Rd,R1c,R3c,Arl), (Zd,Rd,R1c,R3c,Arm), (Zd,Rd,R1c,R3c,Arn), (Zd,Rd,R1c,R3c,Aro), (Zd,Rd,R1c,R3c,Arp), (Zd,Rd,R1c,R3d,Ara), (Zd,Rd,R1c,R3d,Arb), (Zd,Rd,R1c,R3d,Arc), (Zd,Rd,R1c,R3d,Ard), (Zd,Rd,R1c,R3d,Are), (Zd,Rd,R1c,R3d,Arf), (Zd,Rd,R1c,R3d,Arg), (Zd,Rd,R1c,R3d,Arh), (Zd,Rd,R1c,R3d,Ari), (Zd,Rd,R1c,R3d,Arj), (Zd,Rd,R1c,R3d,Ark), (Zd,Rd,R1c,R3d,Arl), (Zd,Rd,R1c,R3d,Arm), (Zd,Rd,R1c,R3d,Arn), (Zd,Rd,R1c,R3d,Aro), (Zd,Rd,R1c,R3d,Arp), (Zd,Rd,R1c,R3e,Ara), (Zd,Rd,R1c,R3e,Arb), (Zd,Rd,R1c,R3e,Arc), (Zd,Rd,R1c,R3e,Ard), (Zd,Rd,R1c,R3e,Are), (Zd,Rd,R1c,R3e,Arf), (Zd,Rd,R1c,R3e,Arg), (Zd,Rd,R1c,R3e,Arh), (Zd,Rd,R1c,R3e,Ari), (Zd,Rd,R1c,R3e,Arj), (Zd,Rd,R1c,R3e,Ark), (Zd,Rd,R1c,R3e,Arl), (Zd,Rd,R1c,R3e,Arm), (Zd,Rd,R1c,R3e,Arn), (Zd,Rd,R1c,R3e,Aro), (Zd,Rd,R1c,R3e,Arp), (Zd,Rd,R1c,R3f,Ara), (Zd,Rd,R1c,R3f,Arb), (Zd,Rd,R1c,R3f,Arc), (Zd,Rd,R1c,R3f,Ard), (Zd,Rd,R1c,R3f,Are), (Zd,Rd,R1c,R3f,Arf), (Zd,Rd,R1c,R3f,Arg), (Zd,Rd,R1c,R3f,Arh), (Zd,Rd,R1c,R3f,Ari), (Zd,Rd,R1c,R3f,Arj), (Zd,Rd,R1c,R3f,Ark), (Zd,Rd,R1c,R3f,Arl), (Zd,Rd,R1c,R3f,Arm), (Zd,Rd,R1c,R3f,Arn), (Zd,Rd,R1c,R3f,Aro), (Zd,Rd,R1c,R3f,Arp), (Zd,Rd,R1c,R3g,Ara), (Zd,Rd,R1c,R3g,Arb), (Zd,Rd,R1c,R3g,Arc), (Zd,Rd,R1c,R3g,Ard), (Zd,Rd,R1c,R3g,Are), (Zd,Rd,R1c,R3g,Arf), (Zd,Rd,R1c,R3g,Arg), (Zd,Rd,R1c,R3g,Arh), (Zd,Rd,R1c,R3g,Ari), (Zd,Rd,R1c,R3g,Arj), (Zd,Rd,R1c,R3g,Ark), (Zd,Rd,R1c,R3g,Arl), (Zd,Rd,R1c,R3g,Arm), (Zd,Rd,R1c,R3g,Arn), (Zd,Rd,R1c,R3g,Aro), (Zd,Rd,R1c,R3g,Arp), (Zd,Rd,R1c,R3h,Ara), (Zd,Rd,R1c,R3h,Arb), (Zd,Rd,R1c,R3h,Arc), (Zd,Rd,R1c,R3h,Ard), (Zd,Rd,R1c,R3h,Are), (Zd,Rd,R1c,R3h,Arf), (Zd,Rd,R1c,R3h,Arg), (Zd,Rd,R1c,R3h,Arh), (Zd,Rd,R1c,R3h,Ari), (Zd,Rd,R1c,R3h,Arj), (Zd,Rd,R1c,R3h,Ark), (Zd,Rd,R1c,R3h,Arl), (Zd,Rd,R1c,R3h,Arm), (Zd,Rd,R1c,R3h,Arn), (Zd,Rd,R1c,R3h,Aro), (Zd,Rd,R1c,R3h,Arp), (Zd,Rd,R1d,R3a,Ara), (Zd,Rd,R1d,R3a,Arb), (Zd,Rd,R1d,R3a,Arc), (Zd,Rd,R1d,R3a,Ard), (Zd,Rd,R1d,R3a,Are), (Zd,Rd,R1d,R3a,Arf), (Zd,Rd, R1d,R3a,Arg), (Zd,Rd,R1d,R3a,Arh), (Zd,Rd,R1d,R3a, Ari), (Zd,Rd,R1d,R3a,Arj), (Zd,Rd,R1d,R3a,Ark), (Zd,Rd, R1d,R3a,Arl), (Zd,Rd,R1d,R3a,Arm), (Zd,Rd,R1d,R3a, Arn), (Zd,Rd,R1d,R3a,Aro), (Zd,Rd,R1d,R3a,Arp), (Zd,Rd, R1d,R3b,Ara), (Zd,Rd,R1d,R3b,Arb), (Zd,Rd,R1d,R3b, Arc), (Zd,Rd,R1d,R3b,Ard), (Zd,Rd,R1d,R3b,Are), (Zd,Rd, R1d,R3b,Arf), (Zd,Rd,R1d,R3b,Arg), (Zd,Rd,R1d,R3b, Arh), (Zd,Rd,R1d,R3b,Ari), (Zd,Rd,R1d,R3b,Arj), (Zd,Rd, R1d,R3b,Ark), (Zd,Rd,R1d,R3b,Arl), (Zd,Rd,R1d,R3b, Arm), (Zd,Rd,R1d,R3b,Arn), (Zd,Rd,R1d,R3b,Aro), (Zd, Rd,R1d,R3b,Arp), (Zd,Rd,R1d,R3c,Ara), (Zd,Rd,R1d,R3c, Arb), (Zd,Rd,R1d,R3c,Arc), (Zd,Rd,R1d,R3c,Ard), (Zd,Rd, R1d,R3c,Are), (Zd,Rd,R1d,R3c,Arf), (Zd,Rd,R1d,R3c, Arg), (Zd,Rd,R1d,R3c,Arh), (Zd,Rd,R1d,R3c,Ari), (Zd,Rd, R1d,R3c,Arj), (Zd,Rd,R1d,R3c,Ark), (Zd,Rd,R1d,R3c,Arl), (Zd,Rd,R1d,R3c,Arm), (Zd,Rd,R1d,R3c,Arn), (Zd,Rd,R1d, R3c,Aro), (Zd,Rd,R1d,R3c,Arp), (Zd,Rd,R1d,R3d,Ara), (Zd,Rd,R1d,R3d,Arb), (Zd,Rd,R1d,R3d,Arc), (Zd,Rd,R1d, R3d,Ard), (Zd,Rd,R1d,R3d,Are), (Zd,Rd,R1d,R3d,Arf), (Zd,Rd,R1d,R3d,Arg), (Zd,Rd,R1d,R3d,Arh), (Zd,Rd,R1d, R3d,Ari), (Zd,Rd,R1d,R3d,Arj), (Zd,Rd,R1d,R3d,Ark), (Zd, Rd,R1d,R3d,Arl), (Zd,Rd,R1d,R3d,Arm), (Zd,Rd,R1d,R3d, Arn), (Zd,Rd,R1d,R3d,Aro), (Zd,Rd,R1d,R3d,Arp), (Zd,Rd, R1d,R3e,Ara), (Zd,Rd,R1d,R3e,Arb), (Zd,Rd,R1d,R3e, Arc), (Zd,Rd,R1d,R3e,Ard), (Zd,Rd,R1d,R3e,Are), (Zd,Rd, R1d,R3e,Arf), (Zd,Rd,R1d,R3e,Arg), (Zd,Rd,R1d,R3e, Arh), (Zd,Rd,R1d,R3e,Ari), (Zd,Rd,R1d,R3e,Arj), (Zd,Rd, R1d,R3e,Ark), (Zd,Rd,R1d,R3e,Arl), (Zd,Rd,R1d,R3e, Arm), (Zd,Rd,R1d,R3e,Arn), (Zd,Rd,R1d,R3e,Aro), (Zd, Rd,R1d,R3e,Arp), (Zd,Rd,R1d,R3f,Ara), (Zd,Rd,R1d,R3f, Arb), (Zd,Rd,R1d,R3f,Arc), (Zd,Rd,R1d,R3f,Ard), (Zd,Rd, R1d,R3f,Are), (Zd,Rd,R1d,R3f,Arf), (Zd,Rd,R1d,R3f,Arg), (Zd,Rd,R1d,R3f,Arh), (Zd,Rd,R1d,R3f,Ari), (Zd,Rd,R1d, R3f,Arj), (Zd,Rd,R1d,R3f,Ark), (Zd,Rd,R1d,R3f,Arl), (Zd, Rd,R1d,R3f,Arm), (Zd,Rd,R1d,R3f,Arn), (Zd,Rd,R1d,R3f, Aro), (Zd,Rd,R1d,R3f,Arp), (Zd,Rd,R1d,R3g,Ara), (Zd,Rd, R1d,R3g,Arb), (Zd,Rd,R1d,R3g,Arc), (Zd,Rd,R1d,R3g, Ard), (Zd,Rd,R1d,R3g,Are), (Zd,Rd,R1d,R3g,Arf), (Zd,Rd, R1d,R3g,Arg), (Zd,Rd,R1d,R3g,Arh), (Zd,Rd,R1d,R3g, Ari), (Zd,Rd,R1d,R3g,Arj), (Zd,Rd,R1d,R3g,Ark), (Zd,Rd, R1d,R3g,Arl), (Zd,Rd,R1d,R3g,Arm), (Zd,Rd,R1d,R3g, Arn), (Zd,Rd,R1d,R3g,Aro), (Zd,Rd,R1d,R3g,Arp), (Zd,Rd, R1d,R3h,Ara), (Zd,Rd,R1d,R3h,Arb), (Zd,Rd,R1d,R3h, Arc), (Zd,Rd,R1d,R3h,Ard), (Zd,Rd,R1d,R3h,Are), (Zd,Rd, R1d,R3h,Arf), (Zd,Rd,R1d,R3h,Arg), (Zd,Rd,R1d,R3h, Arh), (Zd,Rd,R1d,R3h,Ari), (Zd,Rd,R1d,R3h,Arj), (Zd,Rd, R1d,R3h,Ark), (Zd,Rd,R1d,R3h,Arl), (Zd,Rd,R1d,R3h, Arm), (Zd,Rd,R1d,R3h,Arn), (Zd,Rd,R1d,R3h,Aro), (Zd, Rd,R1d,R3h,Arp), (Zd,Re,R1a,R3a,Ara), (Zd,Re,R1a,R3a, Arb), (Zd,Re,R1a,R3a,Arc), (Zd,Re,R1a,R3a,Ard), (Zd,Re, R1a,R3a,Are), (Zd,Re,R1a,R3a,Arf), (Zd,Re,R1a,R3a,Arg), (Zd,Re,R1a,R3a,Arh), (Zd,Re,R1a,R3a,Ari), (Zd,Re,R1a, R3a,Arj), (Zd,Re,R1a,R3a,Ark), (Zd,Re,R1a,R3a,Arl), (Zd, Re,R1a,R3a,Arm), (Zd,Re,R1a,R3a,Arn), (Zd,Re,R1a,R3a, Aro), (Zd,Re,R1a,R3a,Arp), (Zd,Re,R1a,R3b,Ara), (Zd,Re, R1a,R3b,Arb), (Zd,Re,R1a,R3b,Arc), (Zd,Re,R1a,R3b, Ard), (Zd,Re,R1a,R3b,Are), (Zd,Re,R1a,R3b,Arf), (Zd,Re, R1a,R3b,Arg), (Zd,Re,R1a,R3b,Arh), (Zd,Re,R1a,R3b,Ari), (Zd,Re,R1a,R3b,Arj), (Zd,Re,R1a,R3b,Ark), (Zd,Re,R1a, R3b,Arl), (Zd,Re,R1a,R3b,Arm), (Zd,Re,R1a,R3b,Arn), (Zd,Re,R1a,R3b,Aro), (Zd,Re,R1a,R3b,Arp), (Zd,Re,R1a, R3c,Ara), (Zd,Re,R1a,R3c,Arb), (Zd,Re,R1a,R3c,Arc), (Zd, Re,R1a,R3c,Ard), (Zd,Re,R1a,R3c,Are), (Zd,Re,R1a,R3c, Arf), (Zd,Re,R1a,R3c,Arg), (Zd,Re,R1a,R3c,Arh), (Zd,Re, R1a,R3c,Ari), (Zd,Re,R1a,R3c,Arj), (Zd,Re,R1a,R3c,Ark), (Zd,Re,R1a,R3c,Arl), (Zd,Re,R1a,R3c,Arm), (Zd,Re,R1a, R3c,Arn), (Zd,Re,R1a,R3c,Aro), (Zd,Re,R1a,R3c,Arp), (Zd, Re,R1a,R3d,Ara), (Zd,Re,R1a,R3d,Arb), (Zd,Re,R1a,R3d, Arc), (Zd,Re,R1a,R3d,Ard), (Zd,Re,R1a,R3d,Are), (Zd,Re, R1a,R3d,Arf), (Zd,Re,R1a,R3d,Arg), (Zd,Re,R1a,R3d,Arh), (Zd,Re,R1a,R3d,Ari), (Zd,Re,R1a,R3d,Arj), (Zd,Re,R1a, R3d,Ark), (Zd,Re,R1a,R3d,Arl), (Zd,Re,R1a,R3d,Arm), (Zd,Re,R1a,R3d,Arn), (Zd,Re,R1a,R3d,Aro), (Zd,Re,R1a, R3d,Arp), (Zd,Re,R1a,R3e,Ara), (Zd,Re,R1a,R3e,Arb), (Zd, Re,R1a,R3e,Arc), (Zd,Re,R1a,R3e,Ard), (Zd,Re,R1a,R3e, Are), (Zd,Re,R1a,R3e,Arf), (Zd,Re,R1a,R3e,Arg), (Zd,Re, R1a,R3e,Arh), (Zd,Re,R1a,R3e,Ari), (Zd,Re,R1a,R3e,Arj), (Zd,Re,R1a,R3e,Ark), (Zd,Re,R1a,R3e,Arl), (Zd,Re,R1a, R3e,Arm), (Zd,Re,R1a,R3e,Arn), (Zd,Re,R1a,R3e,Aro), (Zd,Re,R1a,R3e,Arp), (Zd,Re,R1a,R3f,Ara), (Zd,Re,R1a, R3f,Arb), (Zd,Re,R1a,R3f,Arc), (Zd,Re,R1a,R3f,Ard), (Zd, Re,R1a,R3f,Are), (Zd,Re,R1a,R3f,Arf), (Zd,Re,R1a,R3f, Arg), (Zd,Re,R1a,R3f,Arh), (Zd,Re,R1a,R3f,Ari), (Zd,Re, R1a,R3f,Arj), (Zd,Re,R1a,R3f,Ark), (Zd,Re,R1a,R3f,Arl), (Zd,Re,R1a,R3f,Arm), (Zd,Re,R1a,R3f,Arn), (Zd,Re,R1a, R3f,Aro), (Zd,Re,R1a,R3f,Arp), (Zd,Re,R1a,R3g,Ara), (Zd, Re,R1a,R3g,Arb), (Zd,Re,R1a,R3g,Arc), (Zd,Re,R1a,R3g, Ard), (Zd,Re,R1a,R3g,Are), (Zd,Re,R1a,R3g,Arf), (Zd,Re, R1a,R3g,Arg), (Zd,Re,R1a,R3g,Arh), (Zd,Re,R1a,R3g,Ari), (Zd,Re,R1a,R3g,Arj), (Zd,Re,R1a,R3g,Ark), (Zd,Re,R1a, R3g,Arl), (Zd,Re,R1a,R3g,Arm), (Zd,Re,R1a,R3g,Arn), (Zd,Re,R1a,R3g,Aro), (Zd,Re,R1a,R3g,Arp), (Zd,Re,R1a, R3h,Ara), (Zd,Re,R1a,R3h,Arb), (Zd,Re,R1a,R3h,Arc), (Zd,Re,R1a,R3h,Ard), (Zd,Re,R1a,R3h,Are), (Zd,Re,R1a, R3h,Arf), (Zd,Re,R1a,R3h,Arg), (Zd,Re,R1a,R3h,Arh), (Zd, Re,R1a,R3h,Ari), (Zd,Re,R1a,R3h,Arj), (Zd,Re,R1a,R3h, Ark), (Zd,Re,R1a,R3h,Arl), (Zd,Re,R1a,R3h,Arm), (Zd,Re, R1a,R3h,Arn), (Zd,Re,R1a,R3h,Aro), (Zd,Re,R1a,R3h, Arp), (Zd,Re,R1b,R3a,Ara), (Zd,Re,R1b,R3a,Arb), (Zd,Re, R1b,R3a,Arc), (Zd,Re,R1b,R3a,Ard), (Zd,Re,R1b,R3a, Are), (Zd,Re,R1b,R3a,Arf), (Zd,Re,R1b,R3a,Arg), (Zd,Re, R1b,R3a,Arh), (Zd,Re,R1b,R3a,Ari), (Zd,Re,R1b,R3a,Arj), (Zd,Re,R1b,R3a,Ark), (Zd,Re,R1b,R3a,Arl), (Zd,Re,R1b, R3a,Arm), (Zd,Re,R1b,R3a,Arn), (Zd,Re,R1b,R3a,Aro), (Zd,Re,R1b,R3a,Arp), (Zd,Re,R1b,R3b,Ara), (Zd,Re,R1b, R3b,Arb), (Zd,Re,R1b,R3b,Arc), (Zd,Re,R1b,R3b,Ard), (Zd,Re,R1b,R3b,Are), (Zd,Re,R1b,R3b,Arf), (Zd,Re,R1b, R3b,Arg), (Zd,Re,R1b,R3b,Arh), (Zd,Re,R1b,R3b,Ari), (Zd,Re,R1b,R3b,Arj), (Zd,Re,R1b,R3b,Ark), (Zd,Re,R1b, R3b,Arl), (Zd,Re,R1b,R3b,Arm), (Zd,Re,R1b,R3b,Arn), (Zd,Re,R1b,R3b,Aro), (Zd,Re,R1b,R3b,Arp), (Zd,Re,R1b, R3c,Ara), (Zd,Re,R1b,R3c,Arb), (Zd,Re,R1b,R3c,Arc), (Zd, Re,R1b,R3c,Ard), (Zd,Re,R1b,R3c,Are), (Zd,Re,R1b,R3c, Arf), (Zd,Re,R1b,R3c,Arg), (Zd,Re,R1b,R3c,Arh), (Zd,Re, R1b,R3c,Ari), (Zd,Re,R1b,R3c,Arj), (Zd,Re,R1b,R3c,Ark), (Zd,Re,R1b,R3c,Arl), (Zd,Re,R1b,R3c,Arm), (Zd,Re,R1b, R3c,Arn), (Zd,Re,R1b,R3c,Aro), (Zd,Re,R1b,R3c,Arp), (Zd,Re,R1b,R3d,Ara), (Zd,Re,R1b,R3d,Arb), (Zd,Re,R1b, R3d,Arc), (Zd,Re,R1b,R3d,Ard), (Zd,Re,R1b,R3d,Are), (Zd,Re,R1b,R3d,Arf), (Zd,Re,R1b,R3d,Arg), (Zd,Re,R1b, R3d,Arh), (Zd,Re,R1b,R3d,Ari), (Zd,Re,R1b,R3d,Arj), (Zd, Re,R1b,R3d,Ark), (Zd,Re,R1b,R3d,Arl), (Zd,Re,R1b,R3d, Arm), (Zd,Re,R1b,R3d,Arn), (Zd,Re,R1b,R3d,Aro), (Zd,Re, R1b,R3d,Arp), (Zd,Re,R1b,R3e,Ara), (Zd,Re,R1b,R3e, Arb), (Zd,Re,R1b,R3e,Arc), (Zd,Re,R1b,R3e,Ard), (Zd,Re, R1b,R3e,Are), (Zd,Re,R1b,R3e,Arf), (Zd,Re,R1b,R3e,Arg), (Zd,Re,R1b,R3e,Arh), (Zd,Re,R1b,R3e,Ari), (Zd,Re,R1b, R3e,Arj), (Zd,Re,R1b,R3e,Ark), (Zd,Re,R1b,R3e,Arl), (Zd, Re,R1b,R3e,Arm), (Zd,Re,R1b,R3e,Arn), (Zd,Re,R1b,R3e, Aro), (Zd,Re,R1b,R3e,Arp), (Zd,Re,R1b,R3f,Ara), (Zd,Re, R1b,R3f,Arb), (Zd,Re,R1b,R3f,Arc), (Zd,Re,R1b,R3f,Ard), (Zd,Re,R1b,R3f,Are), (Zd,Re,R1b,R3f,Arf), (Zd,Re,R1b, R3f,Arg), (Zd,Re,R1b,R3f,Arh), (Zd,Re,R1b,R3f,Ari), (Zd, Re,R1b,R3f,Arj), (Zd,Re,R1b,R3f,Ark), (Zd,Re,R1b,R3f, Arl), (Zd,Re,R1b,R3f,Arm), (Zd,Re,R1b,R3f,Arn), (Zd,Re,R1b,R3f,Aro), (Zd,Re,R1b,R3f,Arp), (Zd,Re,R1b,R3g,Ara), (Zd,Re,R1b,R3g,Arb), (Zd,Re,R1b,R3g,Arc), (Zd,Re,R1b,R3g,Ard), (Zd,Re,R1b,R3g,Are), (Zd,Re,R1b,R3g,Arf), (Zd,Re,R1b,R3g,Arg), (Zd,Re,R1b,R3g,Arh), (Zd,Re,R1b,R3g,Ari), (Zd,Re,R1b,R3g,Arj), (Zd,Re,R1b,R3g,Ark), (Zd,Re,R1b,R3g,Arl), (Zd,Re,R1b,R3g,Arm), (Zd,Re,R1b,R3g,Arn), (Zd,Re,R1b,R3g,Aro), (Zd,Re,R1b,R3g,Arp), (Zd,Re,R1b,R3h,Ara), (Zd,Re,R1b,R3h,Arb), (Zd,Re,R1b,R3h,Arc), (Zd,Re,R1b,R3h,Ard), (Zd,Re,R1b,R3h,Are), (Zd,Re,R1b,R3h,Arf), (Zd,Re,R1b,R3h,Arg), (Zd,Re,R1b,R3h,Arh), (Zd,Re,R1b,R3h,Ari), (Zd,Re,R1b,R3h,Arj), (Zd,Re,R1b,R3h,Ark), (Zd,Re,R1b,R3h,Arl), (Zd,Re,R1b,R3h,Arm), (Zd,Re,R1b,R3h,Arn), (Zd,Re,R1b,R3h,Aro), (Zd,Re,R1b,R3h,Arp), (Zd,Re,R1c,R3a,Ara), (Zd,Re,R1c,R3a,Arb), (Zd,Re,R1c,R3a,Arc), (Zd,Re,R1c,R3a,Ard), (Zd,Re,R1c,R3a,Are), (Zd,Re,R1c,R3a,Arf), (Zd,Re,R1c,R3a,Arg), (Zd,Re,R1c,R3a,Arh), (Zd,Re,R1c,R3a,Ari), (Zd,Re,R1c,R3a,Arj), (Zd,Re,R1c,R3a,Ark), (Zd,Re,R1c,R3a,Arl), (Zd,Re,R1c,R3a,Arm), (Zd,Re,R1c,R3a,Arn), (Zd,Re,R1c,R3a,Aro), (Zd,Re,R1c,R3a,Arp), (Zd,Re,R1c,R3b,Ara), (Zd,Re,R1c,R3b,Arb), (Zd,Re,R1c,R3b,Arc), (Zd,Re,R1c,R3b,Ard), (Zd,Re,R1c,R3b,Are), (Zd,Re,R1c,R3b,Arf), (Zd,Re,R1c,R3b,Arg), (Zd,Re,R1c,R3b,Arh), (Zd,Re,R1c,R3b,Ari), (Zd,Re,R1c,R3b,Arj), (Zd,Re,R1c,R3b,Ark), (Zd,Re,R1c,R3b,Arl), (Zd,Re,R1c,R3b,Arm), (Zd,Re,R1c,R3b,Arn), (Zd,Re,R1c,R3b,Aro), (Zd,Re,R1c,R3b,Arp), (Zd,Re,R1c,R3c,Ara), (Zd,Re,R1c,R3c,Arb), (Zd,Re,R1c,R3c,Arc), (Zd,Re,R1c,R3c,Ard), (Zd,Re,R1c,R3c,Are), (Zd,Re,R1c,R3c,Arf), (Zd,Re,R1c,R3c,Arg), (Zd,Re,R1c,R3c,Arh), (Zd,Re,R1c,R3c,Ari), (Zd,Re,R1c,R3c,Arj), (Zd,Re,R1c,R3c,Ark), (Zd,Re,R1c,R3c,Arl), (Zd,Re,R1c,R3c,Arm), (Zd,Re,R1c,R3c,Arn), (Zd,Re,R1c,R3c,Aro), (Zd,Re,R1c,R3c,Arp), (Zd,Re,R1c,R3d,Ara), (Zd,Re,R1c,R3d,Arb), (Zd,Re,R1c,R3d,Arc), (Zd,Re,R1c,R3d,Ard), (Zd,Re,R1c,R3d,Are), (Zd,Re,R1c,R3d,Arf), (Zd,Re,R1c,R3d,Arg), (Zd,Re,R1c,R3d,Arh), (Zd,Re,R1c,R3d,Ari), (Zd,Re,R1c,R3d,Arj), (Zd,Re,R1c,R3d,Ark), (Zd,Re,R1c,R3d,Arl), (Zd,Re,R1c,R3d,Arm), (Zd,Re,R1c,R3d,Arn), (Zd,Re,R1c,R3d,Aro), (Zd,Re,R1c,R3d,Arp), (Zd,Re,R1c,R3e,Ara), (Zd,Re,R1c,R3e,Arb), (Zd,Re,R1c,R3e,Arc), (Zd,Re,R1c,R3e,Ard), (Zd,Re,R1c,R3e,Are), (Zd,Re,R1c,R3e,Arf), (Zd,Re,R1c,R3e,Arg), (Zd,Re,R1c,R3e,Arh), (Zd,Re,R1c,R3e,Ari), (Zd,Re,R1c,R3e,Arj), (Zd,Re,R1c,R3e,Ark), (Zd,Re,R1c,R3e,Arl), (Zd,Re,R1c,R3e,Arm), (Zd,Re,R1c,R3e,Arn), (Zd,Re,R1c,R3e,Aro), (Zd,Re,R1c,R3e,Arp), (Zd,Re,R1c,R3f,Ara), (Zd,Re,R1c,R3f,Arb), (Zd,Re,R1c,R3f,Arc), (Zd,Re,R1c,R3f,Ard), (Zd,Re,R1c,R3f,Are), (Zd,Re,R1c,R3f,Arf), (Zd,Re,R1c,R3f,Arg), (Zd,Re,R1c,R3f,Arh), (Zd,Re,R1c,R3f,Ari), (Zd,Re,R1c,R3f,Arj), (Zd,Re,R1c,R3f,Ark), (Zd,Re,R1c,R3f,Arl), (Zd,Re,R1c,R3f,Arm), (Zd,Re,R1c,R3f,Arn), (Zd,Re,R1c,R3f,Aro), (Zd,Re,R1c,R3f,Arp), (Zd,Re,R1c,R3g,Ara), (Zd,Re,R1c,R3g,Arb), (Zd,Re,R1c,R3g,Arc), (Zd,Re,R1c,R3g,Ard), (Zd,Re,R1c,R3g,Are), (Zd,Re,R1c,R3g,Arf), (Zd,Re,R1c,R3g,Arg), (Zd,Re,R1c,R3g,Arh), (Zd,Re,R1c,R3g,Ari), (Zd,Re,R1c,R3g,Arj), (Zd,Re,R1c,R3g,Ark), (Zd,Re,R1c,R3g,Arl), (Zd,Re,R1c,R3g,Arm), (Zd,Re,R1c,R3g,Arn), (Zd,Re,R1c,R3g,Aro), (Zd,Re,R1c,R3g,Arp), (Zd,Re,R1c,R3h,Ara), (Zd,Re,R1c,R3h,Arb), (Zd,Re,R1c,R3h,Arc), (Zd,Re,R1c,R3h,Ard), (Zd,Re,R1c,R3h,Are), (Zd,Re,R1c,R3h,Arf), (Zd,Re,R1c,R3h,Arg), (Zd,Re,R1c,R3h,Arh), (Zd,Re,R1c,R3h,Ari), (Zd,Re,R1c,R3h,Arj), (Zd,Re,R1c,R3h,Ark), (Zd,Re,R1c,R3h,Arl), (Zd,Re,R1c,R3h,Arm), (Zd,Re,R1c,R3h,Arn), (Zd,Re,R1c,R3h,Aro), (Zd,Re,R1c,R3h,Arp), (Zd,Re,R1d,R3a,Ara), (Zd,Re,R1d,R3a,Arb), (Zd,Re,R1d,R3a,Arc), (Zd,Re,R1d,R3a,Ard), (Zd,Re,R1d,R3a,Are), (Zd,Re,R1d,R3a,Arf), (Zd,Re,R1d,R3a,Arg), (Zd,Re,R1d,R3a,Arh), (Zd,Re,R1d,R3a,Ari), (Zd,Re,R1d,R3a,Arj), (Zd,Re,R1d,R3a,Ark), (Zd,Re,R1d,R3a,Arl), (Zd,Re,R1d,R3a,Arm), (Zd,Re,R1d,R3a,Arn), (Zd,Re,R1d,R3a,Aro), (Zd,Re,R1d,R3a,Arp), (Zd,Re,R1d,R3b,Ara), (Zd,Re,R1d,R3b,Arb), (Zd,Re,R1d,R3b,Arc), (Zd,Re,R1d,R3b,Ard), (Zd,Re,R1d,R3b,Are), (Zd,Re,R1d,R3b,Arf), (Zd,Re,R1d,R3b,Arg), (Zd,Re,R1d,R3b,Arh), (Zd,Re,R1d,R3b,Ari), (Zd,Re,R1d,R3b,Arj), (Zd,Re,R1d,R3b,Ark), (Zd,Re,R1d,R3b,Arl), (Zd,Re,R1d,R3b,Arm), (Zd,Re,R1d,R3b,Arn), (Zd,Re,R1d,R3b,Aro), (Zd,Re,R1d,R3b,Arp), (Zd,Re,R1d,R3c,Ara), (Zd,Re,R1d,R3c,Arb), (Zd,Re,R1d,R3c,Arc), (Zd,Re,R1d,R3c,Ard), (Zd,Re,R1d,R3c,Are), (Zd,Re,R1d,R3c,Arf), (Zd,Re,R1d,R3c,Arg), (Zd,Re,R1d,R3c,Arh), (Zd,Re,R1d,R3c,Ari), (Zd,Re,R1d,R3c,Arj), (Zd,Re,R1d,R3c,Ark), (Zd,Re,R1d,R3c,Arl), (Zd,Re,R1d,R3c,Arm), (Zd,Re,R1d,R3c,Arn), (Zd,Re,R1d,R3c,Aro), (Zd,Re,R1d,R3c,Arp), (Zd,Re,R1d,R3d,Ara), (Zd,Re,R1d,R3d,Arb), (Zd,Re,R1d,R3d,Arc), (Zd,Re,R1d,R3d,Ard), (Zd,Re,R1d,R3d,Are), (Zd,Re,R1d,R3d,Arf), (Zd,Re,R1d,R3d,Arg), (Zd,Re,R1d,R3d,Arh), (Zd,Re,R1d,R3d,Ari), (Zd,Re,R1d,R3d,Arj), (Zd,Re,R1d,R3d,Ark), (Zd,Re,R1d,R3d,Arl), (Zd,Re,R1d,R3d,Arm), (Zd,Re,R1d,R3d,Arn), (Zd,Re,R1d,R3d,Aro), (Zd,Re,R1d,R3d,Arp), (Zd,Re,R1d,R3e,Ara), (Zd,Re,R1d,R3e,Arb), (Zd,Re,R1d,R3e,Arc), (Zd,Re,R1d,R3e,Ard), (Zd,Re,R1d,R3e,Are), (Zd,Re,R1d,R3e,Arf), (Zd,Re,R1d,R3e,Arg), (Zd,Re,R1d,R3e,Arh), (Zd,Re,R1d,R3e,Ari), (Zd,Re,R1d,R3e,Arj), (Zd,Re,R1d,R3e,Ark), (Zd,Re,R1d,R3e,Arl), (Zd,Re,R1d,R3e,Arm), (Zd,Re,R1d,R3e,Arn), (Zd,Re,R1d,R3e,Aro), (Zd,Re,R1d,R3e,Arp), (Zd,Re,R1d,R3f,Ara), (Zd,Re,R1d,R3f,Arb), (Zd,Re,R1d,R3f,Arc), (Zd,Re,R1d,R3f,Ard), (Zd,Re,R1d,R3f,Are), (Zd,Re,R1d,R3f,Arf), (Zd,Re,R1d,R3f,Arg), (Zd,Re,R1d,R3f,Arh), (Zd,Re,R1d,R3f,Ari), (Zd,Re,R1d,R3f,Arj), (Zd,Re,R1d,R3f,Ark), (Zd,Re,R1d,R3f,Arl), (Zd,Re,R1d,R3f,Arm), (Zd,Re,R1d,R3f,Arn), (Zd,Re,R1d,R3f,Aro), (Zd,Re,R1d,R3f,Arp), (Zd,Re,R1d,R3g,Ara), (Zd,Re,R1d,R3g,Arb), (Zd,Re,R1d,R3g,Arc), (Zd,Re,R1d,R3g,Ard), (Zd,Re,R1d,R3g,Are), (Zd,Re,R1d,R3g,Arf), (Zd,Re,R1d,R3g,Arg), (Zd,Re,R1d,R3g,Arh), (Zd,Re,R1d,R3g,Ari), (Zd,Re,R1d,R3g,Arj), (Zd,Re,R1d,R3g,Ark), (Zd,Re,R1d,R3g,Arl), (Zd,Re,R1d,R3g,Arm), (Zd,Re,R1d,R3g,Arn), (Zd,Re,R1d,R3g,Aro), (Zd,Re,R1d,R3g,Arp), (Zd,Re,R1d,R3h,Ara), (Zd,Re,R1d,R3h,Arb), (Zd,Re,R1d,R3h,Arc), (Zd,Re,R1d,R3h,Ard), (Zd,Re,R1d,R3h,Are), (Zd,Re,R1d,R3h,Arf), (Zd,Re,R1d,R3h,Arg), (Zd,Re,R1d,R3h,Arh), (Zd,Re,R1d,R3h,Ari), (Zd,Re,R1d,R3h,Arj), (Zd,Re,R1d,R3h,Ark), (Zd,Re,R1d,R3h,Arl), (Zd,Re,R1d,R3h,Arm), (Zd,Re,R1d,R3h,Arn), (Zd,Re,R1d,R3h,Aro), (Zd,Re,R1d,R3h,Arp), (Zd,Rf,R1a,R3a,Ara), (Zd,Rf,R1a,R3a,Arb), (Zd,Rf,R1a,R3a,Arc), (Zd,Rf,R1a,R3a,Ard), (Zd,Rf,R1a,R3a,Are), (Zd,Rf,R1a,R3a,Arf), (Zd,Rf,R1a,R3a,Arg), (Zd,Rf,R1a,R3a,Arh), (Zd,Rf,R1a,R3a,Ari), (Zd,Rf,R1a,R3a,Arj), (Zd,Rf,R1a,R3a,Ark), (Zd,Rf,R1a,R3a,Arl), (Zd,Rf,R1a,R3a,Arm), (Zd,Rf,R1a,R3a,Arn), (Zd,Rf,R1a,R3a,Aro), (Zd,Rf,R1a,R3a,Arp), (Zd,Rf,R1a,R3b,Ara), (Zd,Rf,R1a,R3b,Arb), (Zd,Rf,R1a,R3b,Arc), (Zd,Rf,R1a,R3b,Ard), (Zd,Rf,R1a,R3b,Are), (Zd,Rf,R1a,R3b,Arf), (Zd,Rf,R1a,R3b,Arg), (Zd,Rf,R1a,R3b,Arh), (Zd,Rf,R1a,R3b,Ari), (Zd,Rf,R1a,R3b,Arj), (Zd,Rf,R1a,R3b,Ark), (Zd,Rf,R1a,R3b,Arl), (Zd,Rf,R1a,R3b,Arm), (Zd,Rf,R1a,R3b,Arn), (Zd,Rf,R1a,R3b,Aro), (Zd,Rf,R1a,R3b,Arp), (Zd,Rf,R1a,R3c,Ara), (Zd,Rf,R1a,R3c,Arb), (Zd,Rf,R1a,R3c,Arc), (Zd,Rf,R1a,R3c,Ard), (Zd,Rf,R1a,R3c,Are), (Zd,Rf,R1a,R3c,Arf), (Zd,Rf,R1a,R3c,Arg), (Zd,Rf,R1a,R3c,Arh), (Zd,Rf,R1a,R3c,Ari), (Zd,Rf,R1a,R3c,Arj), (Zd,Rf,R1a,R3c,Ark), (Zd,Rf,R1a,R3c,Arl), (Zd,Rf,R1a,R3c,Arm), (Zd,Rf,R1a,R3c,Arn), (Zd,Rf,R1a,R3c,Aro), (Zd,Rf,R1a,R3c,Arp), (Zd,Rf,R1a,R3d,Ara), (Zd,Rf,R1a,R3d,Arb), (Zd,Rf,R1a,R3d,Arc), (Zd, Rf,R1a,R3d,Ard), (Zd,Rf,R1a,R3d,Are), (Zd,Rf,R1a,R3d,Arf), (Zd,Rf,R1a,R3d,Arg), (Zd,Rf,R1a,R3d,Arh), (Zd,Rf,R1a,R3d,Ari), (Zd,Rf,R1a,R3d,Arj), (Zd,Rf,R1a,R3d,Ark), (Zd,Rf,R1a,R3d,Arl), (Zd,Rf,R1a,R3d,Arm), (Zd,Rf,R1a,R3d,Arn), (Zd,Rf,R1a,R3d,Aro), (Zd,Rf,R1a,R3d,Arp), (Zd,Rf,R1a,R3e,Ara), (Zd,Rf,R1a,R3e,Arb), (Zd,Rf,R1a,R3e,Arc), (Zd,Rf,R1a,R3e,Ard), (Zd,Rf,R1a,R3e,Are), (Zd,Rf,R1a,R3e,Arf), (Zd,Rf,R1a,R3e,Arg), (Zd,Rf,R1a,R3e,Arh), (Zd,Rf,R1a,R3e,Ari), (Zd,Rf,R1a,R3e,Arj), (Zd,Rf,R1a,R3e,Ark), (Zd,Rf,R1a,R3e,Arl), (Zd,Rf,R1a,R3e,Arm), (Zd,Rf,R1a,R3e,Arn), (Zd,Rf,R1a,R3e,Aro), (Zd,Rf,R1a,R3e,Arp), (Zd,Rf,R1a,R3f,Ara), (Zd,Rf,R1a,R3f,Arb), (Zd,Rf,R1a,R3f,Arc), (Zd,Rf,R1a,R3f,Ard), (Zd,Rf,R1a,R3f,Are), (Zd,Rf,R1a,R3f,Arf), (Zd,Rf,R1a,R3f,Arg), (Zd,Rf,R1a,R3f,Arh), (Zd,Rf,R1a,R3f,Ari), (Zd,Rf,R1a,R3f,Arj), (Zd,Rf,R1a,R3f,Ark), (Zd,Rf,R1a,R3f,Arl), (Zd,Rf,R1a,R3f,Arm), (Zd,Rf,R1a,R3f,Arn), (Zd,Rf,R1a,R3f,Aro), (Zd,Rf,R1a,R3f,Arp), (Zd,Rf,R1a,R3g,Ara), (Zd,Rf,R1a,R3g,Arb), (Zd,Rf,R1a,R3g,Arc), (Zd,Rf,R1a,R3g,Ard), (Zd,Rf,R1a,R3g,Are), (Zd,Rf,R1a,R3g,Arf), (Zd,Rf,R1a,R3g,Arg), (Zd,Rf,R1a,R3g,Arh), (Zd,Rf,R1a,R3g,Ari), (Zd,Rf,R1a,R3g,Arj), (Zd,Rf,R1a,R3g,Ark), (Zd,Rf,R1a,R3g,Arl), (Zd,Rf,R1a,R3g,Arm), (Zd,Rf,R1a,R3g,Arn), (Zd,Rf,R1a,R3g,Aro), (Zd,Rf,R1a,R3g,Arp), (Zd,Rf,R1a,R3h,Ara), (Zd,Rf,R1a,R3h,Arb), (Zd,Rf,R1a,R3h,Arc), (Zd,Rf,R1a,R3h,Ard), (Zd,Rf,R1a,R3h,Are), (Zd,Rf,R1a,R3h,Arf), (Zd,Rf,R1a,R3h,Arg), (Zd,Rf,R1a,R3h,Arh), (Zd,Rf,R1a,R3h,Ari), (Zd,Rf,R1a,R3h,Arj), (Zd,Rf,R1a,R3h,Ark), (Zd,Rf,R1a,R3h,Arl), (Zd,Rf,R1a,R3h,Arm), (Zd,Rf,R1a,R3h,Arn), (Zd,Rf,R1a,R3h,Aro), (Zd,Rf,R1a,R3h,Arp), (Zd,Rf,R1b,R3a,Ara), (Zd,Rf,R1b,R3a,Arb), (Zd,Rf,R1b,R3a,Arc), (Zd,Rf,R1b,R3a,Ard), (Zd,Rf,R1b,R3a,Are), (Zd,Rf,R1b,R3a,Arf), (Zd,Rf,R1b,R3a,Arg), (Zd,Rf,R1b,R3a,Arh), (Zd,Rf,R1b,R3a,Ari), (Zd,Rf,R1b,R3a,Arj), (Zd,Rf,R1b,R3a,Ark), (Zd,Rf,R1b,R3a,Arl), (Zd,Rf,R1b,R3a,Arm), (Zd,Rf,R1b,R3a,Arn), (Zd,Rf,R1b,R3a,Aro), (Zd,Rf,R1b,R3a,Arp), (Zd,Rf,R1b,R3b,Ara), (Zd,Rf,R1b,R3b,Arb), (Zd,Rf,R1b,R3b,Arc), (Zd,Rf,R1b,R3b,Ard), (Zd,Rf,R1b,R3b,Are), (Zd,Rf,R1b,R3b,Arf), (Zd,Rf,R1b,R3b,Arg), (Zd,Rf,R1b,R3b,Arh), (Zd,Rf,R1b,R3b,Ari), (Zd,Rf,R1b,R3b,Arj), (Zd,Rf,R1b,R3b,Ark), (Zd,Rf,R1b,R3b,Arl), (Zd,Rf,R1b,R3b,Arm), (Zd,Rf,R1b,R3b,Arn), (Zd,Rf,R1b,R3b,Aro), (Zd,Rf,R1b,R3b,Arp), (Zd,Rf,R1b,R3c,Ara), (Zd,Rf,R1b,R3c,Arb), (Zd,Rf,R1b,R3c,Arc), (Zd,Rf,R1b,R3c,Ard), (Zd,Rf,R1b,R3c,Are), (Zd,Rf,R1b,R3c,Arf), (Zd,Rf,R1b,R3c,Arg), (Zd,Rf,R1b,R3c,Arh), (Zd,Rf,R1b,R3c,Ari), (Zd,Rf,R1b,R3c,Arj), (Zd,Rf,R1b,R3c,Ark), (Zd,Rf,R1b,R3c,Arl), (Zd,Rf,R1b,R3c,Arm), (Zd,Rf,R1b,R3c,Arn), (Zd,Rf,R1b,R3c,Aro), (Zd,Rf,R1b,R3c,Arp), (Zd,Rf,R1b,R3d,Ara), (Zd,Rf,R1b,R3d,Arb), (Zd,Rf,R1b,R3d,Arc), (Zd,Rf,R1b,R3d,Ard), (Zd,Rf,R1b,R3d,Are), (Zd,Rf,R1b,R3d,Arf), (Zd,Rf,R1b,R3d,Arg), (Zd,Rf,R1b,R3d,Arh), (Zd,Rf,R1b,R3d,Ari), (Zd,Rf,R1b,R3d,Arj), (Zd,Rf,R1b,R3d,Ark), (Zd,Rf,R1b,R3d,Arl), (Zd,Rf,R1b,R3d,Arm), (Zd,Rf,R1b,R3d,Arn), (Zd,Rf,R1b,R3d,Aro), (Zd,Rf,R1b,R3d,Arp), (Zd,Rf,R1b,R3e,Ara), (Zd,Rf,R1b,R3e,Arb), (Zd,Rf,R1b,R3e,Arc), (Zd,Rf,R1b,R3e,Ard), (Zd,Rf,R1b,R3e,Are), (Zd,Rf,R1b,R3e,Arf), (Zd,Rf,R1b,R3e,Arg), (Zd,Rf,R1b,R3e,Arh), (Zd,Rf,R1b,R3e,Ari), (Zd,Rf,R1b,R3e,Arj), (Zd,Rf,R1b,R3e,Ark), (Zd,Rf,R1b,R3e,Arl), (Zd,Rf,R1b,R3e,Arm), (Zd,Rf,R1b,R3e,Arn), (Zd,Rf,R1b,R3e,Aro), (Zd,Rf,R1b,R3e,Arp), (Zd,Rf,R1b,R3f,Ara), (Zd,Rf,R1b,R3f,Arb), (Zd,Rf,R1b,R3f,Arc), (Zd,Rf,R1b,R3f,Ard), (Zd,Rf,R1b,R3f,Are), (Zd,Rf,R1b,R3f,Arf), (Zd,Rf,R1b,R3f,Arg), (Zd,Rf,R1b,R3f,Arh), (Zd,Rf,R1b,R3f,Ari), (Zd,Rf,R1b,R3f,Arj), (Zd,Rf,R1b,R3f,Ark), (Zd,Rf,R1b,R3f,Arl), (Zd,Rf,R1b,R3f,Arm), (Zd,Rf,R1b,R3f,Arn), (Zd,Rf,R1b,R3f,Aro), (Zd,Rf,R1b,R3f,Arp), (Zd,Rf,R1b,R3g,Ara), (Zd,Rf,R1b,R3g,Arb), (Zd,Rf,R1b,R3g,Arc), (Zd,Rf,R1b,R3g,Ard), (Zd,Rf,R1b,R3g,Are), (Zd,Rf,R1b,R3g,Arf), (Zd,Rf,R1b,R3g,Arg), (Zd,Rf,R1b,R3g,Arh), (Zd,Rf,R1b,R3g,Ari), (Zd,Rf,R1b,R3g,Arj), (Zd,Rf,R1b,R3g,Ark), (Zd,Rf,R1b,R3g,Arl), (Zd,Rf,R1b,R3g,Arm), (Zd,Rf,R1b,R3g,Arn), (Zd,Rf,R1b,R3g,Aro), (Zd,Rf,R1b,R3g,Arp), (Zd,Rf,R1b,R3h,Ara), (Zd,Rf,R1b,R3h,Arb), (Zd,Rf,R1b,R3h,Arc), (Zd,Rf,R1b,R3h,Ard), (Zd,Rf,R1b,R3h,Are), (Zd,Rf,R1b,R3h,Arf), (Zd,Rf,R1b,R3h,Arg), (Zd,Rf,R1b,R3h,Arh), (Zd,Rf,R1b,R3h,Ari), (Zd,Rf,R1b,R3h,Arj), (Zd,Rf,R1b,R3h,Ark), (Zd,Rf,R1b,R3h,Arl), (Zd,Rf,R1b,R3h,Arm), (Zd,Rf,R1b,R3h,Arn), (Zd,Rf,R1b,R3h,Aro), (Zd,Rf,R1b,R3h,Arp), (Zd,Rf,R1c,R3a,Ara), (Zd,Rf,R1c,R3a,Arb), (Zd,Rf,R1c,R3a,Arc), (Zd,Rf,R1c,R3a,Ard), (Zd,Rf,R1c,R3a,Are), (Zd,Rf,R1c,R3a,Arf), (Zd,Rf,R1c,R3a,Arg), (Zd,Rf,R1c,R3a,Arh), (Zd,Rf,R1c,R3a,Ari), (Zd,Rf,R1c,R3a,Arj), (Zd,Rf,R1c,R3a,Ark), (Zd,Rf,R1c,R3a,Arl), (Zd,Rf,R1c,R3a,Arm), (Zd,Rf,R1c,R3a,Arn), (Zd,Rf,R1c,R3a,Aro), (Zd,Rf,R1c,R3a,Arp), (Zd,Rf,R1c,R3b,Ara), (Zd,Rf,R1c,R3b,Arb), (Zd,Rf,R1c,R3b,Arc), (Zd,Rf,R1c,R3b,Ard), (Zd,Rf,R1c,R3b,Are), (Zd,Rf,R1c,R3b,Arf), (Zd,Rf,R1c,R3b,Arg), (Zd,Rf,R1c,R3b,Arh), (Zd,Rf,R1c,R3b,Ari), (Zd,Rf,R1c,R3b,Arj), (Zd,Rf,R1c,R3b,Ark), (Zd,Rf,R1c,R3b,Arl), (Zd,Rf,R1c,R3b,Arm), (Zd,Rf,R1c,R3b,Arn), (Zd,Rf,R1c,R3b,Aro), (Zd,Rf,R1c,R3b,Arp), (Zd,Rf,R1c,R3c,Ara), (Zd,Rf,R1c,R3c,Arb), (Zd,Rf,R1c,R3c,Arc), (Zd,Rf,R1c,R3c,Ard), (Zd,Rf,R1c,R3c,Are), (Zd,Rf,R1c,R3c,Arf), (Zd,Rf,R1c,R3c,Arg), (Zd,Rf,R1c,R3c,Arh), (Zd,Rf,R1c,R3c,Ari), (Zd,Rf,R1c,R3c,Atj), (Zd,Rf,R1c,R3c,Ark), (Zd,Rf,R1c,R3c,Arl), (Zd,Rf,R1c,R3c,Arm), (Zd,Rf,R1c,R3c,Arn), (Zd,Rf,R1c,R3c,Aro), (Zd,Rf,R1c,R3c,Arp), (Zd,Rf,R1c,R3d,Ara), (Zd,Rf,R1c,R3d,Arb), (Zd,Rf,R1c,R3d,Arc), (Zd,Rf,R1c,R3d,Ard), (Zd,Rf,R1c,R3d,Are), (Zd,Rf,R1c,R3d,Arf), (Zd,Rf,R1c,R3d,Arg), (Zd,Rf,R1c,R3d,Arh), (Zd,Rf,R1c,R3d,Ari), (Zd,Rf,R1c,R3d,Arj), (Zd,Rf,R1c,R3d,Ark), (Zd,Rf,R1c,R3d,Arl), (Zd,Rf,R1c,R3d,Arm), (Zd,Rf,R1c,R3d,Arn), (Zd,Rf,R1c,R3d,Aro), (Zd,Rf,R1c,R3d,Arp), (Zd,Rf,R1c,R3e,Ara), (Zd,Rf,R1c,R3e,Arb), (Zd,Rf,R1c,R3e,Arc), (Zd,Rf,R1c,R3e,Ard), (Zd,Rf,R1c,R3e,Are), (Zd,Rf,R1c,R3e,Arf), (Zd,Rf,R1c,R3e,Arg), (Zd,Rf,R1c,R3e,Arh), (Zd,Rf,R1c,R3e,Ari), (Zd,Rf,R1c,R3e,Arj), (Zd,Rf,R1c,R3e,Ark), (Zd,Rf,R1c,R3e,Arl), (Zd,Rf,R1c,R3e,Arm), (Zd,Rf,R1c,R3e,Arn), (Zd,Rf,R1c,R3e,Aro), (Zd,Rf,R1c,R3e,Arp), (Zd,Rf,R1c,R3f,Ara), (Zd,Rf,R1c,R3f,Arb), (Zd,Rf,R1c,R3f,Arc), (Zd,Rf,R1c,R3f,Ard), (Zd,Rf,R1c,R3f,Are), (Zd,Rf,R1c,R3f,Arf), (Zd,Rf,R1c,R3f,Arg), (Zd,Rf,R1c,R3f,Arh), (Zd,Rf,R1c,R3f,Ari), (Zd,Rf,R1c,R3f,Arj), (Zd,Rf,R1c,R3f,Ark), (Zd,Rf,R1c,R3f,Arl), (Zd,Rf,R1c,R3f,Arm), (Zd,Rf,R1c,R3f,Arn), (Zd,Rf,R1c,R3f,Aro), (Zd,Rf,R1c,R3f,Arp), (Zd,Rf,R1c,R3g,Ara), (Zd,Rf,R1c,R3g,Arb), (Zd,Rf,R1c,R3g,Arc), (Zd,Rf,R1c,R3g,Ard), (Zd,Rf,R1c,R3g,Are), (Zd,Rf,R1c,R3g,Arf), (Zd,Rf,R1c,R3g,Arg), (Zd,Rf,R1c,R3g,Arh), (Zd,Rf,R1c,R3g,Ari), (Zd,Rf,R1c,R3g,Arj), (Zd,Rf,R1c,R3g,Ark), (Zd,Rf,R1c,R3g,Arl), (Zd,Rf,R1c,R3g,Arm), (Zd,Rf,R1c,R3g,Arn), (Zd,Rf,R1c,R3g,Aro), (Zd,Rf,R1c,R3g,Arp), (Zd,Rf,R1c,R3h,Ara), (Zd,Rf,R1c,R3h,Arb), (Zd,Rf,R1c,R3h,Arc), (Zd,Rf,R1c,R3h,Ard), (Zd,Rf,R1c,R3h,Are), (Zd,Rf,R1c,R3h,Arf), (Zd,Rf,R1c,R3h,Arg), (Zd,Rf,R1c,R3h,Arh), (Zd,Rf,R1c,R3h,Ari), (Zd,Rf,R1c,R3h,Arj), (Zd,Rf,R1c,R3h,Ark), (Zd,Rf,R1c,R3h,Arl), (Zd,Rf,R1c,R3h,Arm), (Zd,Rf,R1c,R3h,Arn), (Zd,Rf,R1c,R3h,Aro), (Zd,Rf,R1c,R3h,Arp), (Zd,Rf,R1d,R3a,Ara), (Zd,Rf,R1d,R3a,Arb), (Zd,Rf,R1d,R3a,Arc), (Zd,Rf,R1d,R3a,Ard), (Zd,Rf,R1d,R3a,Are), (Zd,Rf,R1d,R3a,Arf), (Zd,Rf,R1d,R3a,Arg), (Zd,Rf,R1d,R3a,Arh), (Zd,Rf,R1d,R3a,Ari), (Zd,Rf,R1d,R3a,Arj), (Zd,Rf,R1d,R3a,Ark), (Zd,Rf,R1d,R3a,Arl), (Zd,Rf,R1d,R3a,Arm), (Zd,Rf,R1d,R3a,Arn), (Zd,Rf,R1d, R3a,Aro), (Zd,Rf,R1d,R3a,Arp), (Zd,Rf,R1d,R3b,Ara), (Zd,Rf,R1d,R3b,Arb), (Zd,Rf,R1d,R3b,Arc), (Zd,Rf,R1d,R3b,Ard), (Zd,Rf,R1d,R3b,Are), (Zd,Rf,R1d,R3b,Arf), (Zd,Rf,R1d,R3b,Arg), (Zd,Rf,R1d,R3b,Arh), (Zd,Rf,R1d,R3b,Ari), (Zd,Rf,R1d,R3b,Arj), (Zd,Rf,R1d,R3b,Ark), (Zd,Rf,R1d,R3b,Arl), (Zd,Rf,R1d,R3b,Arm), (Zd,Rf,R1d,R3b,Arn), (Zd,Rf,R1d,R3b,Aro), (Zd,Rf,R1d,R3b,Arp), (Zd,Rf,R1d,R3c,Ara), (Zd,Rf,R1d,R3c,Arb), (Zd,Rf,R1d,R3c,Arc), (Zd,Rf,R1d,R3c,Ard), (Zd,Rf,R1d,R3c,Are), (Zd,Rf,R1d,R3c,Arf), (Zd,Rf,R1d,R3c,Arg), (Zd,Rf,R1d,R3c,Arh), (Zd,Rf,R1d,R3c,Ari), (Zd,Rf,R1d,R3c,Arj), (Zd,Rf,R1d,R3c,Ark), (Zd,Rf,R1d,R3c,Arl), (Zd,Rf,R1d,R3c,Arm), (Zd,Rf,R1d,R3c,Arn), (Zd,Rf,R1d,R3c,Aro), (Zd,Rf,R1d,R3c,Arp), (Zd,Rf,R1d,R3d,Ara), (Zd,Rf,R1d,R3d,Arb), (Zd,Rf,R1d,R3d,Arc), (Zd,Rf,R1d,R3d,Ard), (Zd,Rf,R1d,R3d,Are), (Zd,Rf,R1d,R3d,Arf), (Zd,Rf,R1d,R3d,Arg), (Zd,Rf,R1d,R3d,Arh), (Zd,Rf,R1d,R3d,Ari), (Zd,Rf,R1d,R3d,Arj), (Zd,Rf,R1d,R3d,Ark), (Zd,Rf,R1d,R3d,Arl), (Zd,Rf,R1d,R3d,Arm), (Zd,Rf,R1d,R3d,Arn), (Zd,Rf,R1d,R3d,Aro), (Zd,Rf,R1d,R3d,Arp), (Zd,Rf,R1d,R3e,Ara), (Zd,Rf,R1d,R3e,Arb), (Zd,Rf,R1d,R3e,Arc), (Zd,Rf,R1d,R3e,Ard), (Zd,Rf,R1d,R3e,Are), (Zd,Rf,R1d,R3e,Arf), (Zd,Rf,R1d,R3e,Arg), (Zd,Rf,R1d,R3e,Arh), (Zd,Rf,R1d,R3e,Ari), (Zd,Rf,R1d,R3e,Arj), (Zd,Rf,R1d,R3e,Ark), (Zd,Rf,R1d,R3e,Arl), (Zd,Rf,R1d,R3e,Arm), (Zd,Rf,R1d,R3e,Arn), (Zd,Rf,R1d,R3e,Aro), (Zd,Rf,R1d,R3e,Arp), (Zd,Rf,R1d,R3f,Ara), (Zd,Rf,R1d,R3f,Arb), (Zd,Rf,R1d,R3f,Arc), (Zd,Rf,R1d,R3f,Ard), (Zd,Rf,R1d,R3f,Are), (Zd,Rf,R1d,R3f,Arf), (Zd,Rf,R1d,R3f,Arg), (Zd,Rf,R1d,R3f,Arh), (Zd,Rf,R1d,R3f,Ari), (Zd,Rf,R1d,R3f,Arj), (Zd,Rf,R1d,R3f,Ark), (Zd,Rf,R1d,R3f,Arl), (Zd,Rf,R1d,R3f,Arm), (Zd,Rf,R1d,R3f,Arn), (Zd,Rf,R1d,R3f,Aro), (Zd,Rf,R1d,R3f,Arp), (Zd,Rf,R1d,R3g,Ara), (Zd,Rf,R1d,R3g,Arb), (Zd,Rf,R1d,R3g,Arc), (Zd,Rf,R1d,R3g,Ard), (Zd,Rf,R1d,R3g,Are), (Zd,Rf,R1d,R3g,Arf), (Zd,Rf,R1d,R3g,Arg), (Zd,Rf,R1d,R3g,Arh), (Zd,Rf,R1d,R3g,Ari), (Zd,Rf,R1d,R3g,Arj), (Zd,Rf,R1d,R3g,Ark), (Zd,Rf,R1d,R3g,Arl), (Zd,Rf,R1d,R3g,Arm), (Zd,Rf,R1d,R3g,Arn), (Zd,Rf,R1d,R3g,Aro), (Zd,Rf,R1d,R3g,Arp), (Zd,Rf,R1d,R3h,Ara), (Zd,Rf,R1d,R3h,Arb), (Zd,Rf,R1d,R3h,Arc), (Zd,Rf,R1d,R3h,Ard), (Zd,Rf,R1d,R3h,Are), (Zd,Rf,R1d,R3h,Arf), (Zd,Rf,R1d,R3h,Arg), (Zd,Rf,R1d,R3h,Arh), (Zd,Rf,R1d,R3h,Ari), (Zd,Rf,R1d,R3h,Arj), (Zd,Rf,R1d,R3h,Ark), (Zd,Rf,R1d,R3h,Arl), (Zd,Rf,R1d,R3h,Arm), (Zd,Rf,R1d,R3h,Arn), (Zd,Rf,R1d,R3h,Aro), (Zd,Rf,R1d,R3h,Arp), (Zd,Rg,R1a,R3a,Ara), (Zd,Rg,R1a,R3a,Arb), (Zd,Rg,R1a,R3a,Arc), (Zd,Rg,R1a,R3a,Ard), (Zd,Rg,R1a,R3a,Are), (Zd,Rg,R1a,R3a,Arf), (Zd,Rg,R1a,R3a,Arg), (Zd,Rg,R1a,R3a,Arh), (Zd,Rg,R1a,R3a,Ari), (Zd,Rg,R1a,R3a,Arj), (Zd,Rg,R1a,R3a,Ark), (Zd,Rg,R1a,R3a,Arl), (Zd,Rg,R1a,R3a,Arm), (Zd,Rg,R1a,R3a,Arn), (Zd,Rg,R1a,R3a,Aro), (Zd,Rg,R1a,R3a,Arp), (Zd,Rg,R1a,R3b,Ara), (Zd,Rg,R1a,R3b,Arb), (Zd,Rg,R1a,R3b,Arc), (Zd,Rg,R1a,R3b,Ard), (Zd,Rg,R1a,R3b,Are), (Zd,Rg,R1a,R3b,Arf), (Zd,Rg,R1a,R3b,Arg), (Zd,Rg,R1a,R3b,Arh), (Zd,Rg,R1a,R3b,Ari), (Zd,Rg,R1a,R3b,Arj), (Zd,Rg,R1a,R3b,Ark), (Zd,Rg,R1a,R3b,Arl), (Zd,Rg,R1a,R3b,Arm), (Zd,Rg,R1a,R3b,Arn), (Zd,Rg,R1a,R3b,Aro), (Zd,Rg,R1a,R3b,Arp), (Zd,Rg,R1a,R3c,Ara), (Zd,Rg,R1a,R3c,Arb), (Zd,Rg,R1a,R3c,Arc), (Zd,Rg,R1a,R3c,Ard), (Zd,Rg,R1a,R3c,Are), (Zd,Rg,R1a,R3c,Arf), (Zd,Rg,R1a,R3c,Arg), (Zd,Rg,R1a,R3c,Arh), (Zd,Rg,R1a,R3c,Ari), (Zd,Rg,R1a,R3c,Arj), (Zd,Rg,R1a,R3c,Ark), (Zd,Rg,R1a,R3c,Arl), (Zd,Rg,R1a,R3c,Arm), (Zd,Rg,R1a,R3c,Arn), (Zd,Rg,R1a,R3c,Aro), (Zd,Rg,R1a,R3c,Arp), (Zd,Rg,R1a,R3d,Ara), (Zd,Rg,R1a,R3d,Arb), (Zd,Rg,R1a,R3d,Arc), (Zd,Rg,R1a,R3d,Ard), (Zd,Rg,R1a,R3d,Are), (Zd,Rg,R1a,R3d,Arf), (Zd,Rg,R1a,R3d,Arg), (Zd,Rg,R1a,R3d,Arh), (Zd,Rg,R1a,R3d,Ari), (Zd,Rg,R1a,R3d,Arj), (Zd,Rg,R1a,R3d,Ark), (Zd,Rg,R1a,R3d,Arl), (Zd,Rg,R1a,R3d,Arm), (Zd,Rg,R1a,R3d,Arn), (Zd,Rg,R1a,R3d,Aro), (Zd,Rg,R1a,R3d,Arp), (Zd,Rg,R1a,R3e,Ara), (Zd,Rg,R1a,R3e,Arb), (Zd,Rg,R1a,R3e,Arc), (Zd,Rg,R1a,R3e,Ard), (Zd,Rg,R1a,R3e,Are), (Zd,Rg,R1a,R3e,Arf), (Zd,Rg,R1a,R3e,Arg), (Zd,Rg,R1a,R3e,Arh), (Zd,Rg,R1a,R3e,Ari), (Zd,Rg,R1a,R3e,Arj), (Zd,Rg,R1a,R3e,Ark), (Zd,Rg,R1a,R3e,Arl), (Zd,Rg,R1a,R3e,Arm), (Zd,Rg,R1a,R3e,Arn), (Zd,Rg,R1a,R3e,Aro), (Zd,Rg,R1a,R3e,Arp), (Zd,Rg,R1a,R3f,Ara), (Zd,Rg,R1a,R3f,Arb), (Zd,Rg,R1a,R3f,Arc), (Zd,Rg,R1a,R3f,Ard), (Zd,Rg,R1a,R3f,Are), (Zd,Rg,R1a,R3f,Arf), (Zd,Rg,R1a,R3f,Arg), (Zd,Rg,R1a,R3f,Arh), (Zd,Rg,R1a,R3f,Ari), (Zd,Rg,R1a,R3f,Arj), (Zd,Rg,R1a,R3f,Ark), (Zd,Rg,R1a,R3f,Arl), (Zd,Rg,R1a,R3f,Arm), (Zd,Rg,R1a,R3f,Arn), (Zd,Rg,R1a,R3f,Aro), (Zd,Rg,R1a,R3f,Arp), (Zd,Rg,R1a,R3g,Ara), (Zd,Rg,R1a,R3g,Arb), (Zd,Rg,R1a,R3g,Arc), (Zd,Rg,R1a,R3g,Ard), (Zd,Rg,R1a,R3g,Are), (Zd,Rg,R1a,R3g,Arf), (Zd,Rg,R1a,R3g,Arg), (Zd,Rg,R1a,R3g,Arh), (Zd,Rg,R1a,R3g,Ari), (Zd,Rg,R1a,R3g,Arj), (Zd,Rg,R1a,R3g,Ark), (Zd,Rg,R1a,R3g,Arl), (Zd,Rg,R1a,R3g,Arm), (Zd,Rg,R1a,R3g,Arn), (Zd,Rg,R1a,R3g,Aro), (Zd,Rg,R1a,R3g,Arp), (Zd,Rg,R1a,R3h,Ara), (Zd,Rg,R1a,R3h,Arb), (Zd,Rg,R1a,R3h,Arc), (Zd,Rg,R1a,R3h,Ard), (Zd,Rg,R1a,R3h,Are), (Zd,Rg,R1a,R3h,Arf), (Zd,Rg,R1a,R3h,Arg), (Zd,Rg,R1a,R3h,Arh), (Zd,Rg,R1a,R3h,Ari), (Zd,Rg,R1a,R3h,Arj), (Zd,Rg,R1a,R3h,Ark), (Zd,Rg,R1a,R3h,Arl), (Zd,Rg,R1a,R3h,Arm), (Zd,Rg,R1a,R3h,Arn), (Zd,Rg,R1a,R3h,Aro), (Zd,Rg,R1a,R3h,Arp), (Zd,Rg,R1b,R3a,Ara), (Zd,Rg,R1b,R3a,Arb), (Zd,Rg,R1b,R3a,Arc), (Zd,Rg,R1b,R3a,Ard), (Zd,Rg,R1b,R3a,Are), (Zd,Rg,R1b,R3a,Arf), (Zd,Rg,R1b,R3a,Arg), (Zd,Rg,R1b,R3a,Arh), (Zd,Rg,R1b,R3a,Ari), (Zd,Rg,R1b,R3a,Arj), (Zd,Rg,R1b,R3a,Ark), (Zd,Rg,R1b,R3a,Arl), (Zd,Rg,R1b,R3a,Arm), (Zd,Rg,R1b,R3a,Arn), (Zd,Rg,R1b,R3a,Aro), (Zd,Rg,R1b,R3a,Arp), (Zd,Rg,R1b,R3b,Ara), (Zd,Rg,R1b,R3b,Arb), (Zd,Rg,R1b,R3b,Arc), (Zd,Rg,R1b,R3b,Ard), (Zd,Rg,R1b,R3b,Are), (Zd,Rg,R1b,R3b,Arf), (Zd,Rg,R1b,R3b,Arg), (Zd,Rg,R1b,R3b,Arh), (Zd,Rg,R1b,R3b,Ari), (Zd,Rg,R1b,R3b,Arj), (Zd,Rg,R1b,R3b,Ark), (Zd,Rg,R1b,R3b,Arl), (Zd,Rg,R1b,R3b,Arm), (Zd,Rg,R1b,R3b,Arn), (Zd,Rg,R1b,R3b,Aro), (Zd,Rg,R1b,R3b,Arp), (Zd,Rg,R1b,R3c,Ara), (Zd,Rg,R1b,R3c,Arb), (Zd,Rg,R1b,R3c,Arc), (Zd,Rg,R1b,R3c,Ard), (Zd,Rg,R1b,R3c,Are), (Zd,Rg,R1b,R3c,Arf), (Zd,Rg,R1b,R3c,Arg), (Zd,Rg,R1b,R3c,Arh), (Zd,Rg,R1b,R3c,Ari), (Zd,Rg,R1b,R3c,Arj), (Zd,Rg,R1b,R3c,Ark), (Zd,Rg,R1b,R3c,Arl), (Zd,Rg,R1b,R3c,Arm), (Zd,Rg,R1b,R3c,Arn), (Zd,Rg,R1b,R3c,Aro), (Zd,Rg,R1b,R3c,Arp), (Zd,Rg,R1b,R3d,Ara), (Zd,Rg,R1b,R3d,Arb), (Zd,Rg,R1b,R3d,Arc), (Zd,Rg,R1b,R3d,Ard), (Zd,Rg,R1b,R3d,Are), (Zd,Rg,R1b,R3d,Arf), (Zd,Rg,R1b,R3d,Arg), (Zd,Rg,R1b,R3d,Arh), (Zd,Rg,R1b,R3d,Ari), (Zd,Rg,R1b,R3d,Arj), (Zd,Rg,R1b,R3d,Ark), (Zd,Rg,R1b,R3d,Arl), (Zd,Rg,R1b,R3d,Arm), (Zd,Rg,R1b,R3d,Arn), (Zd,Rg,R1b,R3d,Aro), (Zd,Rg,R1b,R3d,Arp), (Zd,Rg,R1b,R3e,Ara), (Zd,Rg,R1b,R3e,Arb), (Zd,Rg,R1b,R3e,Arc), (Zd,Rg,R1b,R3e,Ard), (Zd,Rg,R1b,R3e,Are), (Zd,Rg,R1b,R3e,Arf), (Zd,Rg,R1b,R3e,Arg), (Zd,Rg,R1b,R3e,Arh), (Zd,Rg,R1b,R3e,Ari), (Zd,Rg,R1b,R3e,Arj), (Zd,Rg,R1b,R3e,Ark), (Zd,Rg,R1b,R3e,Arl), (Zd,Rg,R1b,R3e,Arm), (Zd,Rg,R1b,R3e,Arn), (Zd,Rg,R1b,R3e,Aro), (Zd,Rg,R1b,R3e,Arp), (Zd,Rg,R1b,R3f,Ara), (Zd,Rg,R1b,R3f,Arb), (Zd,Rg,R1b,R3f,Arc), (Zd,Rg,R1b,R3f,Ard), (Zd,Rg,R1b,R3f,Are), (Zd,Rg,R1b,R3f,Arf), (Zd,Rg,R1b,R3f,Arg), (Zd,Rg,R1b,R3f,Arh), (Zd,Rg,R1b,R3f,Ari), (Zd,Rg,R1b,R3f,Arj), (Zd,Rg,R1b,R3f,Ark), (Zd,Rg,R1b,R3f,Arl), (Zd,Rg,R1b,R3f,Arm), (Zd,Rg,R1b,R3f,Arn), (Zd,Rg,R1b,R3f,Aro), (Zd,Rg,R1b,R3f,Arp), (Zd,Rg,R1b,R3g,Ara), (Zd,Rg,R1b,R3g,Arb), (Zd,Rg,R1b,R3g,Arc), (Zd,Rg,R1b,R3g,Ard), (Zd,Rg,R1b,R3g,Are), (Zd,Rg,R1b,R3g,Arf), (Zd,Rg,R1b,R3g,Arg), (Zd,Rg,R1b,R3g,Arh), (Zd,Rg,R1b,R3g,Ari), (Zd,Rg,R1b,R3g,Arj), (Zd,Rg,R1b,R3g,Ark), (Zd,Rg,R1b,R3g,Arl), (Zd,Rg,R1b,R3g,Arm), (Zd,Rg,R1b,R3g,Arn), (Zd,Rg,R1b,R3g,Aro), (Zd,Rg,R1b,R3g,Arp), (Zd,Rg,R1b,R3h,Ara), (Zd,Rg,R1b,R3h,Arb), (Zd,Rg,R1b,R3h,Arc), (Zd,Rg,R1b,R3h,Ard), (Zd,Rg,R1b,R3h,Are), (Zd,Rg,R1b,R3h,Arf), (Zd,Rg,R1b,R3h,Arg), (Zd,Rg,R1b,R3h,Arh), (Zd,Rg,R1b,R3h,Ari), (Zd,Rg,R1b,R3h,Arj), (Zd,Rg,R1b,R3h,Ark), (Zd,Rg,R1b,R3h,Arl), (Zd,Rg,R1b,R3h,Arm), (Zd,Rg,R1b,R3h,Arn), (Zd,Rg,R1b,R3h,Aro), (Zd,Rg,R1b,R3h,Arp), (Zd,Rg,R1c,R3a,Ara), (Zd,Rg,R1c,R3a,Arb), (Zd,Rg,R1c,R3a,Arc), (Zd,Rg,R1c,R3a,Ard), (Zd,Rg,R1c,R3a,Are), (Zd,Rg,R1c,R3a,Arf), (Zd,Rg,R1c,R3a,Arg), (Zd,Rg,R1c,R3a,Arh), (Zd,Rg,R1c,R3a,Ari), (Zd,Rg,R1c,R3a,Arj), (Zd,Rg,R1c,R3a,Ark), (Zd,Rg,R1c,R3a,Arl), (Zd,Rg,R1c,R3a,Arm), (Zd,Rg,R1c,R3a,Arn), (Zd,Rg,R1c,R3a,Aro), (Zd,Rg,R1c,R3a,Arp), (Zd,Rg,R1c,R3b,Ara), (Zd,Rg,R1c,R3b,Arb), (Zd,Rg,R1c,R3b,Arc), (Zd,Rg,R1c,R3b,Ard), (Zd,Rg,R1c,R3b,Are), (Zd,Rg,R1c,R3b,Arf), (Zd,Rg,R1c,R3b,Arg), (Zd,Rg,R1c,R3b,Arh), (Zd,Rg,R1c,R3b,Ari), (Zd,Rg,R1c,R3b,Arj), (Zd,Rg,R1c,R3b,Ark), (Zd,Rg,R1c,R3b,Arl), (Zd,Rg,R1c,R3b,Arm), (Zd,Rg,R1c,R3b,Arn), (Zd,Rg,R1c,R3b,Aro), (Zd,Rg,R1c,R3b,Arp), (Zd,Rg,R1c,R3c,Ara), (Zd,Rg,R1c,R3c,Arb), (Zd,Rg,R1c,R3c,Arc), (Zd,Rg,R1c,R3c,Ard), (Zd,Rg,R1c,R3c,Are), (Zd,Rg,R1c,R3c,Arf), (Zd,Rg,R1c,R3c,Arg), (Zd,Rg,R1c,R3c,Arh), (Zd,Rg,R1c,R3c,Ari), (Zd,Rg,R1c,R3c,Arj), (Zd,Rg,R1c,R3c,Ark), (Zd,Rg,R1c,R3c,Arl), (Zd,Rg,R1c,R3c,Arm), (Zd,Rg,R1c,R3c,Arn), (Zd,Rg,R1c,R3c,Aro), (Zd,Rg,R1c,R3c,Arp), (Zd,Rg,R1c,R3d,Ara), (Zd,Rg,R1c,R3d,Arb), (Zd,Rg,R1c,R3d,Arc), (Zd,Rg,R1c,R3d,Ard), (Zd,Rg,R1c,R3d,Are), (Zd,Rg,R1c,R3d,Arf), (Zd,Rg,R1c,R3d,Arg), (Zd,Rg,R1c,R3d,Arh), (Zd,Rg,R1c,R3d,Ari), (Zd,Rg,R1c,R3d,Arj), (Zd,Rg,R1c,R3d,Ark), (Zd,Rg,R1c,R3d,Arl), (Zd,Rg,R1c,R3d,Arm), (Zd,Rg,R1c,R3d,Arn), (Zd,Rg,R1c,R3d,Aro), (Zd,Rg,R1c,R3d,Arp), (Zd,Rg,R1c,R3e,Ara), (Zd,Rg,R1c,R3e,Arb), (Zd,Rg,R1c,R3e,Arc), (Zd,Rg,R1c,R3e,Ard), (Zd,Rg,R1c,R3e,Are), (Zd,Rg,R1c,R3e,Arf), (Zd,Rg,R1c,R3e,Arg), (Zd,Rg,R1c,R3e,Arh), (Zd,Rg,R1c,R3e,Ari), (Zd,Rg,R1c,R3e,Arj), (Zd,Rg,R1c,R3e,Ark), (Zd,Rg,R1c,R3e,Arl), (Zd,Rg,R1c,R3e,Arm), (Zd,Rg,R1c,R3e,Arn), (Zd,Rg,R1c,R3e,Aro), (Zd,Rg,R1c,R3e,Arp), (Zd,Rg,R1c,R3f,Ara), (Zd,Rg,R1c,R3f,Arb), (Zd,Rg,R1c,R3f,Arc), (Zd,Rg,R1c,R3f,Ard), (Zd,Rg,R1c,R3f,Are), (Zd,Rg,R1c,R3f,Arf), (Zd,Rg,R1c,R3f,Arg), (Zd,Rg,R1c,R3f,Arh), (Zd,Rg,R1c,R3f,Ari), (Zd,Rg,R1c,R3f,Arj), (Zd,Rg,R1c,R3f,Ark), (Zd,Rg,R1c,R3f,Arl), (Zd,Rg,R1c,R3f,Arm), (Zd,Rg,R1c,R3f,Arn), (Zd,Rg,R1c,R3f,Aro), (Zd,Rg,R1c,R3f,Arp), (Zd,Rg,R1c,R3g,Ara), (Zd,Rg,R1c,R3g,Arb), (Zd,Rg,R1c,R3g,Arc), (Zd,Rg,R1c,R3g,Ard), (Zd,Rg,R1c,R3g,Are), (Zd,Rg,R1c,R3g,Arf), (Zd,Rg,R1c,R3g,Arg), (Zd,Rg,R1c,R3g,Arh), (Zd,Rg,R1c,R3g,Ari), (Zd,Rg,R1c,R3g,Arj), (Zd,Rg,R1c,R3g,Ark), (Zd,Rg,R1c,R3g,Arl), (Zd,Rg,R1c,R3g,Arm), (Zd,Rg,R1c,R3g,Arn), (Zd,Rg,R1c,R3g,Aro), (Zd,Rg,R1c,R3g,Arp), (Zd,Rg,R1c,R3h,Ara), (Zd,Rg,R1c,R3h,Arb), (Zd,Rg,R1c,R3h,Arc), (Zd,Rg,R1c,R3h,Ard), (Zd,Rg,R1c,R3h,Are), (Zd,Rg,R1c,R3h,Arf), (Zd,Rg,R1c,R3h,Arg), (Zd,Rg,R1c,R3h,Arh), (Zd,Rg,R1c,R3h,Ari), (Zd,Rg,R1c,R3h,Arj), (Zd,Rg,R1c,R3h,Ark), (Zd,Rg,R1c,R3h,Arl), (Zd,Rg,R1c,R3h,Arm), (Zd,Rg,R1c,R3h,Arn), (Zd,Rg,R1c,R3h,Aro), (Zd,Rg,R1c,R3h,Arp), (Zd,Rg,R1d,R3a,Ara), (Zd,Rg,R1d,R3a,Arb), (Zd,Rg,R1d,R3a,Arc), (Zd,Rg,R1d,R3a,Ard), (Zd,Rg,R1d,R3a,Are), (Zd,Rg,R1d,R3a,Arf), (Zd,Rg,R1d,R3a,Arg), (Zd,Rg,R1d,R3a,Arh), (Zd,Rg,R1d,R3a,Ari), (Zd,Rg,R1d,R3a,Arj), (Zd,Rg,R1d,R3a,Ark), (Zd,Rg,R1d,R3a,Arl), (Zd,Rg,R1d,R3a,Arm), (Zd,Rg,R1d,R3a,Arn), (Zd,Rg,R1d,R3a,Aro), (Zd,Rg,R1d,R3a,Arp), (Zd,Rg,R1d,R3b,Ara), (Zd,Rg,R1d,R3b,Arb), (Zd,Rg,R1d,R3b,Arc), (Zd,Rg,R1d,R3b,Ard), (Zd,Rg,R1d,R3b,Are), (Zd,Rg,R1d,R3b,Arf), (Zd,Rg,R1d,R3b,Arg), (Zd,Rg,R1d,R3b,Arh), (Zd,Rg,R1d,R3b,Ari), (Zd,Rg,R1d,R3b,Arj), (Zd,Rg,R1d,R3b,Ark), (Zd,Rg,R1d,R3b,Arl), (Zd,Rg,R1d,R3b,Arm), (Zd,Rg,R1d,R3b,Arn), (Zd,Rg,R1d,R3b,Aro), (Zd,Rg,R1d,R3b,Arp), (Zd,Rg,R1d,R3c,Ara), (Zd,Rg,R1d,R3c,Arb), (Zd,Rg,R1d,R3c,Arc), (Zd,Rg,R1d,R3c,Ard), (Zd,Rg,R1d,R3c,Are), (Zd,Rg,R1d,R3c,Arf), (Zd,Rg,R1d,R3c,Arg), (Zd,Rg,R1d,R3c,Arh), (Zd,Rg,R1d,R3c,Ari), (Zd,Rg,R1d,R3c,Arj), (Zd,Rg,R1d,R3c,Ark), (Zd,Rg,R1d,R3c,Arl), (Zd,Rg,R1d,R3c,Arm), (Zd,Rg,R1d,R3c,Arn), (Zd,Rg,R1d,R3c,Aro), (Zd,Rg,R1d,R3c,Arp), (Zd,Rg,R1d,R3d,Ara), (Zd,Rg,R1d,R3d,Arb), (Zd,Rg,R1d,R3d,Arc), (Zd,Rg,R1d,R3d,Ard), (Zd,Rg,R1d,R3d,Are), (Zd,Rg,R1d,R3d,Arf), (Zd,Rg,R1d,R3d,Arg), (Zd,Rg,R1d,R3d,Arh), (Zd,Rg,R1d,R3d,Ari), (Zd,Rg,R1d,R3d,Arj), (Zd,Rg,R1d,R3d,Ark), (Zd,Rg,R1d,R3d,Arl), (Zd,Rg,R1d,R3d,Arm), (Zd,Rg,R1d,R3d,Arn), (Zd,Rg,R1d,R3d,Aro), (Zd,Rg,R1d,R3d,Arp), (Zd,Rg,R1d,R3e,Ara), (Zd,Rg,R1d,R3e,Arb), (Zd,Rg,R1d,R3e,Arc), (Zd,Rg,R1d,R3e,Ard), (Zd,Rg,R1d,R3e,Are), (Zd,Rg,R1d,R3e,Arf), (Zd,Rg,R1d,R3e,Arg), (Zd,Rg,R1d,R3e,Arh), (Zd,Rg,R1d,R3e,Ari), (Zd,Rg,R1d,R3e,Arj), (Zd,Rg,R1d,R3e,Ark), (Zd,Rg,R1d,R3e,Arl), (Zd,Rg,R1d,R3e,Arm), (Zd,Rg,R1d,R3e,Arn), (Zd,Rg,R1d,R3e,Aro), (Zd,Rg,R1d,R3e,Arp), (Zd,Rg,R1d,R3f,Ara), (Zd,Rg,R1d,R3f,Arb), (Zd,Rg,R1d,R3f,Arc), (Zd,Rg,R1d,R3f,Ard), (Zd,Rg,R1d,R3f,Are), (Zd,Rg,R1d,R3f,Arf), (Zd,Rg,R1d,R3f,Arg), (Zd,Rg,R1d,R3f,Arh), (Zd,Rg,R1d,R3f,Ari), (Zd,Rg,R1d,R3f,Arj), (Zd,Rg,R1d,R3f,Ark), (Zd,Rg,R1d,R3f,Arl), (Zd,Rg,R1d,R3f,Arm), (Zd,Rg,R1d,R3f,Arn), (Zd,Rg,R1d,R3f,Aro), (Zd,Rg,R1d,R3f,Arp), (Zd,Rg,R1d,R3g,Ara), (Zd,Rg,R1d,R3g,Arb), (Zd,Rg,R1d,R3g,Arc), (Zd,Rg,R1d,R3g,Ard), (Zd,Rg,R1d,R3g,Are), (Zd,Rg,R1d,R3g,Arf), (Zd,Rg,R1d,R3g,Arg), (Zd,Rg,R1d,R3g,Arh), (Zd,Rg,R1d,R3g,Ari), (Zd,Rg,R1d,R3g,Arj), (Zd,Rg,R1d,R3g,Ark), (Zd,Rg,R1d,R3g,Arl), (Zd,Rg,R1d,R3g,Arm), (Zd,Rg,R1d,R3g,Arn), (Zd,Rg,R1d,R3g,Aro), (Zd,Rg,R1d,R3g,Arp), (Zd,Rg,R1d,R3h,Ara), (Zd,Rg,R1d,R3h,Arb), (Zd,Rg,R1d,R3h,Arc), (Zd,Rg,R1d,R3h,Ard), (Zd,Rg,R1d,R3h,Are), (Zd,Rg,R1d,R3h,Arf), (Zd,Rg,R1d,R3h,Arg), (Zd,Rg,R1d,R3h,Arh), (Zd,Rg,R1d,R3h,Ari), (Zd,Rg,R1d,R3h,Arj), (Zd,Rg,R1d,R3h,Ark), (Zd,Rg,R1d,R3h,Arl), (Zd,Rg,R1d,R3h,Arm), (Zd,Rg,R1d,R3h,Arn), (Zd,Rg,R1d,R3h,Aro), (Zd,Rg,R1d,R3h,Arp), (Zd,Rh,R1a,R3a,Ara), (Zd,Rh,R1a,R3a,Arb), (Zd,Rh,R1a,R3a,Arc), (Zd,Rh,R1a,R3a,Ard), (Zd,Rh,R1a,R3a,Are), (Zd,Rh,R1a,R3a,Arf), (Zd,Rh,R1a,R3a,Arg), (Zd,Rh,R1a,R3a,Arh), (Zd,Rh,R1a,R3a,Ari), (Zd,Rh,R1a,R3a,Arj), (Zd,Rh,R1a,R3a,Ark), (Zd,Rh,R1a,R3a,Arl), (Zd,Rh,R1a,R3a,Arm), (Zd,Rh,R1a,R3a,Arn), (Zd,Rh,R1a,R3a,Aro), (Zd,Rh,R1a,R3a,Arp), (Zd,Rh,R1a,R3b,Ara), (Zd,Rh,R1a,R3b,Arb), (Zd,Rh,R1a,R3b,Arc), (Zd,Rh,R1a,R3b,Ard), (Zd,Rh,R1a,R3b,Are), (Zd,Rh,R1a,R3b,Arf), (Zd,Rh,R1a,R3b,Arg), (Zd,Rh,R1a,R3b,Arh), (Zd,Rh,R1a,R3b,Ari), (Zd,Rh,R1a,R3b,Arj), (Zd,Rh,R1a,R3b,Ark), (Zd,Rh,R1a,R3b,Arl), (Zd,Rh,R1a,R3b,Arm), (Zd,Rh,R1a,R3b,Arn), (Zd,Rh,R1a,R3b,Aro), (Zd,Rh,R1a,R3b,Arp), (Zd,Rh,R1a,R3c,Ara), (Zd,Rh,R1a,R3c,Arb), (Zd,Rh,R1a,R3c,Arc), (Zd,Rh,R1a,R3c,Ard), (Zd,Rh,R1a,R3c,Are), (Zd,Rh,R1a,R3c,Arf), (Zd,Rh,R1a,R3c,Arg), (Zd,Rh,R1a,R3c,Arh), (Zd,Rh,R1a,R3c,Ari), (Zd,Rh,R1a,R3c,Arj), (Zd,Rh,R1a,R3c,Ark), (Zd,Rh,R1a,R3c,Arl), (Zd,Rh,R1a,R3c,Arm), (Zd,Rh,R1a,R3c,Arn), (Zd,Rh,R1a,R3c,Aro), (Zd,Rh,R1a,R3c,Arp), (Zd,Rh,R1a,R3d,Ara), (Zd,Rh,R1a,R3d,Arb), (Zd,Rh,R1a,R3d,Arc), (Zd,Rh,R1a,R3d,Ard), (Zd,Rh,R1a,R3d,Are), (Zd,Rh,R1a,R3d,Arf), (Zd,Rh,R1a,R3d,Arg), (Zd,Rh,R1a,R3d,Arh), (Zd,Rh,R1a,R3d, Ari), (Zd,Rh,R1a,R3d,Arj), (Zd,Rh,R1a,R3d,Ark), (Zd,Rh,R1a,R3d,Arl), (Zd,Rh,R1a,R3d,Arm), (Zd,Rh,R1a,R3d,Arn), (Zd,Rh,R1a,R3d,Aro), (Zd,Rh,R1a,R3d,Arp), (Zd,Rh,R1a,R3e,Ara), (Zd,Rh,R1a,R3e,Arb), (Zd,Rh,R1a,R3e,Arc), (Zd,Rh,R1a,R3e,Ard), (Zd,Rh,R1a,R3e,Are), (Zd,Rh,R1a,R3e,Arf), (Zd,Rh,R1a,R3e,Arg), (Zd,Rh,R1a,R3e,Arh), (Zd,Rh,R1a,R3e,Ari), (Zd,Rh,R1a,R3e,Arj), (Zd,Rh,R1a,R3e,Ark), (Zd,Rh,R1a,R3e,Arl), (Zd,Rh,R1a,R3e,Arm), (Zd,Rh,R1a,R3e,Arn), (Zd,Rh,R1a,R3e,Aro), (Zd,Rh,R1a,R3e,Arp), (Zd,Rh,R1a,R3f,Ara), (Zd,Rh,R1a,R3f,Arb), (Zd,Rh,R1a,R3f,Arc), (Zd,Rh,R1a,R3f,Ard), (Zd,Rh,R1a,R3f,Are), (Zd,Rh,R1a,R3f,Arf), (Zd,Rh,R1a,R3f,Arg), (Zd,Rh,R1a,R3f,Arh), (Zd,Rh,R1a,R3f,Ari), (Zd,Rh,R1a,R3f,Arj), (Zd,Rh,R1a,R3f,Ark), (Zd,Rh,R1a,R3f,Arl), (Zd,Rh,R1a,R3f,Arm), (Zd,Rh,R1a,R3f,Arn), (Zd,Rh,R1a,R3f,Aro), (Zd,Rh,R1a,R3f,Arp), (Zd,Rh,R1a,R3g,Ara), (Zd,Rh,R1a,R3g,Arb), (Zd,Rh,R1a,R3g,Arc), (Zd,Rh,R1a,R3g,Ard), (Zd,Rh,R1a,R3g,Are), (Zd,Rh,R1a,R3g,Arf), (Zd,Rh,R1a,R3g,Arg), (Zd,Rh,R1a,R3g,Arh), (Zd,Rh,R1a,R3g,Ari), (Zd,Rh,R1a,R3g,Arj), (Zd,Rh,R1a,R3g,Ark), (Zd,Rh,R1a,R3g,Arl), (Zd,Rh,R1a,R3g,Arm), (Zd,Rh,R1a,R3g,Arn), (Zd,Rh,R1a,R3g,Aro), (Zd,Rh,R1a,R3g,Arp), (Zd,Rh,R1a,R3h,Ara), (Zd,Rh,R1a,R3h,Arb), (Zd,Rh,R1a,R3h,Arc), (Zd,Rh,R1a,R3h,Ard), (Zd,Rh,R1a,R3h,Are), (Zd,Rh,R1a,R3h,Arf), (Zd,Rh,R1a,R3h,Arg), (Zd,Rh,R1a,R3h,Arh), (Zd,Rh,R1a,R3h,Ari), (Zd,Rh,R1a,R3h,Arj), (Zd,Rh,R1a,R3h,Ark), (Zd,Rh,R1a,R3h,Arl), (Zd,Rh,R1a,R3h,Arm), (Zd,Rh,R1a,R3h,Arn), (Zd,Rh,R1a,R3h,Aro), (Zd,Rh,R1a,R3h,Arp), (Zd,Rh,R1b,R3a,Ara), (Zd,Rh,R1b,R3a,Arb), (Zd,Rh,R1b,R3a,Arc), (Zd,Rh,R1b,R3a,Ard), (Zd,Rh,R1b,R3a,Are), (Zd,Rh,R1b,R3a,Arf), (Zd,Rh,R1b,R3a,Arg), (Zd,Rh,R1b,R3a,Arh), (Zd,Rh,R1b,R3a,Ari), (Zd,Rh,R1b,R3a,Arj), (Zd,Rh,R1b,R3a,Ark), (Zd,Rh,R1b,R3a,Arl), (Zd,Rh,R1b,R3a,Arm), (Zd,Rh,R1b,R3a,Arn), (Zd,Rh,R1b,R3a,Aro), (Zd,Rh,R1b,R3a,Arp), (Zd,Rh,R1b,R3b,Ara), (Zd,Rh,R1b,R3b,Arb), (Zd,Rh,R1b,R3b,Arc), (Zd,Rh,R1b,R3b,Ard), (Zd,Rh,R1b,R3b,Are), (Zd,Rh,R1b,R3b,Arf), (Zd,Rh,R1b,R3b,Arg), (Zd,Rh,R1b,R3b,Arh), (Zd,Rh,R1b,R3b,Ari), (Zd,Rh,R1b,R3b,Arj), (Zd,Rh,R1b,R3b,Ark), (Zd,Rh,R1b,R3b,Arl), (Zd,Rh,R1b,R3b,Arm), (Zd,Rh,R1b,R3b,Arn), (Zd,Rh,R1b,R3b,Aro), (Zd,Rh,R1b,R3b,Arp), (Zd,Rh,R1b,R3c,Ara), (Zd,Rh,R1b,R3c,Arb), (Zd,Rh,R1b,R3c,Arc), (Zd,Rh,R1b,R3c,Ard), (Zd,Rh,R1b,R3c,Are), (Zd,Rh,R1b,R3c,Arf), (Zd,Rh,R1b,R3c,Arg), (Zd,Rh,R1b,R3c,Arh), (Zd,Rh,R1b,R3c,Ari), (Zd,Rh,R1b,R3c,Arj), (Zd,Rh,R1b,R3c,Ark), (Zd,Rh,R1b,R3c,Arl), (Zd,Rh,R1b,R3c,Arm), (Zd,Rh,R1b,R3c,Arn), (Zd,Rh,R1b,R3c,Aro), (Zd,Rh,R1b,R3c,Arp), (Zd,Rh,R1b,R3d,Ara), (Zd,Rh,R1b,R3d,Arb), (Zd,Rh,R1b,R3d,Arc), (Zd,Rh,R1b,R3d,Ard), (Zd,Rh,R1b,R3d,Are), (Zd,Rh,R1b,R3d,Arf), (Zd,Rh,R1b,R3d,Arg), (Zd,Rh,R1b,R3d,Arh), (Zd,Rh,R1b,R3d,Ari), (Zd,Rh,R1b,R3d,Arj), (Zd,Rh,R1b,R3d,Ark), (Zd,Rh,R1b,R3d,Arl), (Zd,Rh,R1b,R3d,Arm), (Zd,Rh,R1b,R3d,Arn), (Zd,Rh,R1b,R3d,Aro), (Zd,Rh,R1b,R3d,Arp), (Zd,Rh,R1b,R3e,Ara), (Zd,Rh,R1b,R3e,Arb), (Zd,Rh,R1b,R3e,Arc), (Zd,Rh,R1b,R3e,Ard), (Zd,Rh,R1b,R3e,Are), (Zd,Rh,R1b,R3e,Arf), (Zd,Rh,R1b,R3e,Arg), (Zd,Rh,R1b,R3e,Arh), (Zd,Rh,R1b,R3e,Ari), (Zd,Rh,R1b,R3e,Arj), (Zd,Rh,R1b,R3e,Ark), (Zd,Rh,R1b,R3e,Arl), (Zd,Rh,R1b,R3e,Arm), (Zd,Rh,R1b,R3e,Arn), (Zd,Rh,R1b,R3e,Aro), (Zd,Rh,R1b,R3e,Arp), (Zd,Rh,R1b,R3f,Ara), (Zd,Rh,R1b,R3f,Arb), (Zd,Rh,R1b,R3f,Arc), (Zd,Rh,R1b,R3f,Ard), (Zd,Rh,R1b,R3f,Are), (Zd,Rh,R1b,R3f,Arf), (Zd,Rh,R1b,R3f,Arg), (Zd,Rh,R1b,R3f,Arh), (Zd,Rh,R1b,R3f,Ari), (Zd,Rh,R1b,R3f,Arj), (Zd,Rh,R1b,R3f,Ark), (Zd,Rh,R1b,R3f,Arl), (Zd,Rh,R1b,R3f,Arm), (Zd,Rh,R1b,R3f,Arn), (Zd,Rh,R1b,R3f,Aro), (Zd,Rh,R1b,R3f,Arp), (Zd,Rh,R1b,R3g,Ara), (Zd,Rh,R1b,R3g,Arb), (Zd,Rh,R1b,R3g,Arc), (Zd,Rh,R1b,R3g,Ard), (Zd,Rh,R1b,R3g,Are), (Zd,Rh,R1b,R3g,Arf), (Zd,Rh,R1b,R3g,Arg), (Zd,Rh,R1b,R3g,Arh), (Zd,Rh,R1b,R3g,Ari), (Zd,Rh,R1b,R3g,Arj), (Zd,Rh,R1b,R3g,Ark), (Zd,Rh,R1b,R3g,Arl), (Zd,Rh,R1b,R3g,Arm), (Zd,Rh,R1b,R3g,Arn), (Zd,Rh,R1b,R3g,Aro), (Zd,Rh,R1b,R3g,Arp), (Zd,Rh,R1b,R3h,Ara), (Zd,Rh,R1b,R3h,Arb), (Zd,Rh,R1b,R3h,Arc), (Zd,Rh,R1b,R3h,Ard), (Zd,Rh,R1b,R3h,Are), (Zd,Rh,R1b,R3h,Arf), (Zd,Rh,R1b,R3h,Arg), (Zd,Rh,R1b,R3h,Arh), (Zd,Rh,R1b,R3h,Ari), (Zd,Rh,R1b,R3h,Arj), (Zd,Rh,R1b,R3h,Ark), (Zd,Rh,R1b,R3h,Arl), (Zd,Rh,R1b,R3h,Arm), (Zd,Rh,R1b,R3h,Arn), (Zd,Rh,R1b,R3h,Aro), (Zd,Rh,R1b,R3h,Arp), (Zd,Rh,R1c,R3a,Ara), (Zd,Rh,R1c,R3a,Arb), (Zd,Rh,R1c,R3a,Arc), (Zd,Rh,R1c,R3a,Ard), (Zd,Rh,R1c,R3a,Are), (Zd,Rh,R1c,R3a,Arf), (Zd,Rh,R1c,R3a,Arg), (Zd,Rh,R1c,R3a,Arh), (Zd,Rh,R1c,R3a,Ari), (Zd,Rh,R1c,R3a,Arj), (Zd,Rh,R1c,R3a,Ark), (Zd,Rh,R1c,R3a,Arl), (Zd,Rh,R1c,R3a,Arm), (Zd,Rh,R1c,R3a,Arn), (Zd,Rh,R1c,R3a,Aro), (Zd,Rh,R1c,R3a,Arp), (Zd,Rh,R1c,R3b,Ara), (Zd,Rh,R1c,R3b,Arb), (Zd,Rh,R1c,R3b,Arc), (Zd,Rh,R1c,R3b,Ard), (Zd,Rh,R1c,R3b,Are), (Zd,Rh,R1c,R3b,Arf), (Zd,Rh,R1c,R3b,Arg), (Zd,Rh,R1c,R3b,Arh), (Zd,Rh,R1c,R3b,Ari), (Zd,Rh,R1c,R3b,Arj), (Zd,Rh,R1c,R3b,Ark), (Zd,Rh,R1c,R3b,Arl), (Zd,Rh,R1c,R3b,Arm), (Zd,Rh,R1c,R3b,Arn), (Zd,Rh,R1c,R3b,Aro), (Zd,Rh,R1c,R3b,Arp), (Zd,Rh,R1c,R3c,Ara), (Zd,Rh,R1c,R3c,Arb), (Zd,Rh,R1c,R3c,Arc), (Zd,Rh,R1c,R3c,Ard), (Zd,Rh,R1c,R3c,Are), (Zd,Rh,R1c,R3c,Arf), (Zd,Rh,R1c,R3c,Arg), (Zd,Rh,R1c,R3c,Arh), (Zd,Rh,R1c,R3c,Ari), (Zd,Rh,R1c,R3c,Arj), (Zd,Rh,R1c,R3c,Ark), (Zd,Rh,R1c,R3c,Arl), (Zd,Rh,R1c,R3c,Arm), (Zd,Rh,R1c,R3c,Arn), (Zd,Rh,R1c,R3c,Aro), (Zd,Rh,R1c,R3c,Arp), (Zd,Rh,R1c,R3d,Ara), (Zd,Rh,R1c,R3d,Arb), (Zd,Rh,R1c,R3d,Arc), (Zd,Rh,R1c,R3d,Ard), (Zd,Rh,R1c,R3d,Are), (Zd,Rh,R1c,R3d,Arf), (Zd,Rh,R1c,R3d,Arg), (Zd,Rh,R1c,R3d,Arh), (Zd,Rh,R1c,R3d,Ari), (Zd,Rh,R1c,R3d,Arj), (Zd,Rh,R1c,R3d,Ark), (Zd,Rh,R1c,R3d,Arl), (Zd,Rh,R1c,R3d,Arm), (Zd,Rh,R1c,R3d,Arn), (Zd,Rh,R1c,R3d,Aro), (Zd,Rh,R1c,R3d,Arp), (Zd,Rh,R1c,R3e,Ara), (Zd,Rh,R1c,R3e,Arb), (Zd,Rh,R1c,R3e,Arc), (Zd,Rh,R1c,R3e,Ard), (Zd,Rh,R1c,R3e,Are), (Zd,Rh,R1c,R3e,Arf), (Zd,Rh,R1c,R3e,Arg), (Zd,Rh,R1c,R3e,Arh), (Zd,Rh,R1c,R3e,Ari), (Zd,Rh,R1c,R3e,Arj), (Zd,Rh,R1c,R3e,Ark), (Zd,Rh,R1c,R3e,Arl), (Zd,Rh,R1c,R3e,Arm), (Zd,Rh,R1c,R3e,Arn), (Zd,Rh,R1c,R3e,Aro), (Zd,Rh,R1c,R3e,Arp), (Zd,Rh,R1c,R3f,Ara), (Zd,Rh,R1c,R3f,Arb), (Zd,Rh,R1c,R3f,Arc), (Zd,Rh,R1c,R3f,Ard), (Zd,Rh,R1c,R3f,Are), (Zd,Rh,R1c,R3f,Arf), (Zd,Rh,R1c,R3f,Arg), (Zd,Rh,R1c,R3f,Arh), (Zd,Rh,R1c,R3f,Ari), (Zd,Rh,R1c,R3f,Arj), (Zd,Rh,R1c,R3f,Ark), (Zd,Rh,R1c,R3f,Arl), (Zd,Rh,R1c,R3f,Arm), (Zd,Rh,R1c,R3f,Arn), (Zd,Rh,R1c,R3f,Aro), (Zd,Rh,R1c,R3f,Arp), (Zd,Rh,R1c,R3g,Ara), (Zd,Rh,R1c,R3g,Arb), (Zd,Rh,R1c,R3g,Arc), (Zd,Rh,R1c,R3g,Ard), (Zd,Rh,R1c,R3g,Are), (Zd,Rh,R1c,R3g,Arf), (Zd,Rh,R1c,R3g,Arg), (Zd,Rh,R1c,R3g,Arh), (Zd,Rh,R1c,R3g,Ari), (Zd,Rh,R1c,R3g,Arj), (Zd,Rh,R1c,R3g,Ark), (Zd,Rh,R1c,R3g,Arl), (Zd,Rh,R1c,R3g,Arm), (Zd,Rh,R1c,R3g,Arn), (Zd,Rh,R1c,R3g,Aro), (Zd,Rh,R1c,R3g,Arp), (Zd,Rh,R1c,R3h,Ara), (Zd,Rh,R1c,R3h,Arb), (Zd,Rh,R1c,R3h,Arc), (Zd,Rh,R1c,R3h,Ard), (Zd,Rh,R1c,R3h,Are), (Zd,Rh,R1c,R3h,Arf), (Zd,Rh,R1c,R3h,Arg), (Zd,Rh,R1c,R3h,Arh), (Zd,Rh,R1c,R3h,Ari), (Zd,Rh,R1c,R3h,Arj), (Zd,Rh,R1c,R3h,Ark), (Zd,Rh,R1c,R3h,Arl), (Zd,Rh,R1c,R3h,Arm), (Zd,Rh,R1c,R3h,Arn), (Zd,Rh,R1c,R3h,Aro), (Zd,Rh,R1c,R3h,Arp), (Zd,Rh,R1d,R3a,Ara), (Zd,Rh,R1d,R3a,Arb), (Zd,Rh,R1d,R3a,Arc), (Zd,Rh,R1d,R3a,Ard), (Zd,Rh,R1d,R3a,Are), (Zd,Rh,R1d,R3a,Arf), (Zd,Rh,R1d,R3a,Arg), (Zd,Rh,R1d,R3a,Arh), (Zd,Rh,R1d,R3a,Ari), (Zd,Rh,R1d,R3a,Arj), (Zd,Rh,R1d,R3a,Ark), (Zd,Rh,R1d,R3a,Arl), (Zd,Rh,R1d,R3a, Arm), (Zd,Rh,R1d,R3a,Arn), (Zd,Rh,R1d,R3a,Aro), (Zd,Rh,R1d,R3a,Arp), (Zd,Rh,R1d,R3b,Ara), (Zd,Rh,R1d,R3b,Arb), (Zd,Rh,R1d,R3b,Arc), (Zd,Rh,R1d,R3b,Ard), (Zd,Rh,R1d,R3b,Are), (Zd,Rh,R1d,R3b,Arf), (Zd,Rh,R1d,R3b,Arg), (Zd,Rh,R1d,R3b,Arh), (Zd,Rh,R1d,R3b,Ari), (Zd,Rh,R1d,R3b,Arj), (Zd,Rh,R1d,R3b,Ark), (Zd,Rh,R1d,R3b,Arl), (Zd,Rh,R1d,R3b,Arm), (Zd,Rh,R1d,R3b,Arn), (Zd,Rh,R1d,R3b,Aro), (Zd,Rh,R1d,R3b,Arp), (Zd,Rh,R1d,R3c,Ara), (Zd,Rh,R1d,R3c,Arb), (Zd,Rh,R1d,R3c,Arc), (Zd,Rh,R1d,R3c,Ard), (Zd,Rh,R1d,R3c,Are), (Zd,Rh,R1d,R3c,Arf), (Zd,Rh,R1d,R3c,Arg), (Zd,Rh,R1d,R3c,Arh), (Zd,Rh,R1d,R3c,Ari), (Zd,Rh,R1d,R3c,Arj), (Zd,Rh,R1d,R3c,Ark), (Zd,Rh,R1d,R3c,Arl), (Zd,Rh,R1d,R3c,Arm), (Zd,Rh,R1d,R3c,Arn), (Zd,Rh,R1d,R3c,Aro), (Zd,Rh,R1d,R3c,Arp), (Zd,Rh,R1d,R3d,Ara), (Zd,Rh,R1d,R3d,Arb), (Zd,Rh,R1d,R3d,Arc), (Zd,Rh,R1d,R3d,Ard), (Zd,Rh,R1d,R3d,Are), (Zd,Rh,R1d,R3d,Arf), (Zd,Rh,R1d,R3d,Arg), (Zd,Rh,R1d,R3d,Arh), (Zd,Rh,R1d,R3d,Ari), (Zd,Rh,R1d,R3d,Arj), (Zd,Rh,R1d,R3d,Ark), (Zd,Rh,R1d,R3d,Arl), (Zd,Rh,R1d,R3d,Arm), (Zd,Rh,R1d,R3d,Arn), (Zd,Rh,R1d,R3d,Aro), (Zd,Rh,R1d,R3d,Arp), (Zd,Rh,R1d,R3e,Ara), (Zd,Rh,R1d,R3e,Arb), (Zd,Rh,R1d,R3e,Arc), (Zd,Rh,R1d,R3e,Ard), (Zd,Rh,R1d,R3e,Are), (Zd,Rh,R1d,R3e,Arf), (Zd,Rh,R1d,R3e,Arg), (Zd,Rh,R1d,R3e,Arh), (Zd,Rh,R1d,R3e,Ari), (Zd,Rh,R1d,R3e,Arj), (Zd,Rh,R1d,R3e,Ark), (Zd,Rh,R1d,R3e,Arl), (Zd,Rh,R1d,R3e,Arm), (Zd,Rh,R1d,R3e,Arn), (Zd,Rh,R1d,R3e,Aro), (Zd,Rh,R1d,R3e,Arp), (Zd,Rh,R1d,R3f,Ara), (Zd,Rh,R1d,R3f,Arb), (Zd,Rh,R1d,R3f,Arc), (Zd,Rh,R1d,R3f,Ard), (Zd,Rh,R1d,R3f,Are), (Zd,Rh,R1d,R3f,Arf), (Zd,Rh,R1d,R3f,Arg), (Zd,Rh,R1d,R3f,Arh), (Zd,Rh,R1d,R3f,Ari), (Zd,Rh,R1d,R3f,Arj), (Zd,Rh,R1d,R3f,Ark), (Zd,Rh,R1d,R3f,Arl), (Zd,Rh,R1d,R3f,Arm), (Zd,Rh,R1d,R3f,Arn), (Zd,Rh,R1d,R3f,Aro), (Zd,Rh,R1d,R3f,Arp), (Zd,Rh,R1d,R3g,Ara), (Zd,Rh,R1d,R3g,Arb), (Zd,Rh,R1d,R3g,Arc), (Zd,Rh,R1d,R3g,Ard), (Zd,Rh,R1d,R3g,Are), (Zd,Rh,R1d,R3g,Arf), (Zd,Rh,R1d,R3g,Arg), (Zd,Rh,R1d,R3g,Arh), (Zd,Rh,R1d,R3g,Ari), (Zd,Rh,R1d,R3g,Arj), (Zd,Rh,R1d,R3g,Ark), (Zd,Rh,R1d,R3g,Arl), (Zd,Rh,R1d,R3g,Arm), (Zd,Rh,R1d,R3g,Arn), (Zd,Rh,R1d,R3g,Aro), (Zd,Rh,R1d,R3g,Arp), (Zd,Rh,R1d,R3h,Ara), (Zd,Rh,R1d,R3h,Arb), (Zd,Rh,R1d,R3h,Arc), (Zd,Rh,R1d,R3h,Ard), (Zd,Rh,R1d,R3h,Are), (Zd,Rh,R1d,R3h,Arf), (Zd,Rh,R1d,R3h,Arg), (Zd,Rh,R1d,R3h,Arh), (Zd,Rh,R1d,R3h,Ari), (Zd,Rh,R1d,R3h,Arj), (Zd,Rh,R1d,R3h,Ark), (Zd,Rh,R1d,R3h,Arl), (Zd,Rh,R1d,R3h,Arm), (Zd,Rh,R1d,R3h,Arn), (Zd,Rh,R1d,R3h,Aro), (Zd,Rh,R1d,R3h,Arp), (Zd,Ri,R1a,R3a,Ara), (Zd,Ri,R1a,R3a,Arb), (Zd,Ri,R1a,R3a,Arc), (Zd,Ri,R1a,R3a,Ard), (Zd,Ri,R1a,R3a,Are), (Zd,Ri,R1a,R3a,Arf), (Zd,Ri,R1a,R3a,Arg), (Zd,Ri,R1a,R3a,Arh), (Zd,Ri,R1a,R3a,Ari), (Zd,Ri,R1a,R3a,Arj), (Zd,Ri,R1a,R3a,Ark), (Zd,Ri,R1a,R3a,Arl), (Zd,Ri,R1a,R3a,Arm), (Zd,Ri,R1a,R3a,Arn), (Zd,Ri,R1a,R3a,Aro), (Zd,Ri,R1a,R3a,Arp), (Zd,Ri,R1a,R3b,Ara), (Zd,Ri,R1a,R3b,Arb), (Zd,Ri,R1a,R3b,Arc), (Zd,Ri,R1a,R3b,Ard), (Zd,Ri,R1a,R3b,Are), (Zd,Ri,R1a,R3b,Arf), (Zd,Ri,R1a,R3b,Arg), (Zd,Ri,R1a,R3b,Arh), (Zd,Ri,R1a,R3b,Ari), (Zd,Ri,R1a,R3b,Arj), (Zd,Ri,R1a,R3b,Ark), (Zd,Ri,R1a,R3b,Arl), (Zd,Ri,R1a,R3b,Arm), (Zd,Ri,R1a,R3b,Arn), (Zd,Ri,R1a,R3b,Aro), (Zd,Ri,R1a,R3b,Arp), (Zd,Ri,R1a,R3c,Ara), (Zd,Ri,R1a,R3c,Arb), (Zd,Ri,R1a,R3c,Arc), (Zd,Ri,R1a,R3c,Ard), (Zd,Ri,R1a,R3c,Are), (Zd,Ri,R1a,R3c,Arf), (Zd,Ri,R1a,R3c,Arg), (Zd,Ri,R1a,R3c,Arh), (Zd,Ri,R1a,R3c,Ari), (Zd,Ri,R1a,R3c,Arj), (Zd,Ri,R1a,R3c,Ark), (Zd,Ri,R1a,R3c,Arl), (Zd,Ri,R1a,R3c,Arm), (Zd,Ri,R1a,R3c,Arn), (Zd,Ri,R1a,R3c,Aro), (Zd,Ri,R1a,R3c,Arp), (Zd,Ri,R1a,R3d,Ara), (Zd,Ri,R1a,R3d,Arb), (Zd,Ri,R1a,R3d,Arc), (Zd,Ri,R1a,R3d,Ard), (Zd,Ri,R1a,R3d,Are), (Zd,Ri,R1a,R3d,Arf), (Zd,Ri,R1a,R3d,Arg), (Zd,Ri,R1a,R3d,Arh), (Zd,Ri,R1a,R3d,Ari), (Zd,Ri,R1a,R3d,Arj), (Zd,Ri,R1a,R3d,Ark), (Zd,Ri,R1a,R3d,Arl), (Zd,Ri,R1a,R3d,Arm), (Zd,Ri,R1a,R3d,Arn), (Zd,Ri,R1a,R3d,Aro), (Zd,Ri,R1a,R3d,Arp), (Zd,Ri,R1a,R3e,Ara), (Zd,Ri,R1a,R3e,Arb), (Zd,Ri,R1a,R3e,Arc), (Zd,Ri,R1a,R3e,Ard), (Zd,Ri,R1a,R3e,Are), (Zd,Ri,R1a,R3e,Arf), (Zd,Ri,R1a,R3e,Arg), (Zd,Ri,R1a,R3e,Arh), (Zd,Ri,R1a,R3e,Ari), (Zd,Ri,R1a,R3e,Arj), (Zd,Ri,R1a,R3e,Ark), (Zd,Ri,R1a,R3e,Arl), (Zd,Ri,R1a,R3e,Arm), (Zd,Ri,R1a,R3e,Arn), (Zd,Ri,R1a,R3e,Aro), (Zd,Ri,R1a,R3e,Arp), (Zd,Ri,R1a,R3f,Ara), (Zd,Ri,R1a,R3f,Arb), (Zd,Ri,R1a,R3f,Arc), (Zd,Ri,R1a,R3f,Ard), (Zd,Ri,R1a,R3f,Are), (Zd,Ri,R1a,R3f,Arf), (Zd,Ri,R1a,R3f,Arg), (Zd,Ri,R1a,R3f,Arh), (Zd,Ri,R1a,R3f,Ari), (Zd,Ri,R1a,R3f,Arj), (Zd,Ri,R1a,R3f,Ark), (Zd,Ri,R1a,R3f,Arl), (Zd,Ri,R1a,R3f,Arm), (Zd,Ri,R1a,R3f,Arn), (Zd,Ri,R1a,R3f,Aro), (Zd,Ri,R1a,R3f,Arp), (Zd,Ri,R1a,R3g,Ara), (Zd,Ri,R1a,R3g,Arb), (Zd,Ri,R1a,R3g,Arc), (Zd,Ri,R1a,R3g,Ard), (Zd,Ri,R1a,R3g,Are), (Zd,Ri,R1a,R3g,Arf), (Zd,Ri,R1a,R3g,Arg), (Zd,Ri,R1a,R3g,Arh), (Zd,Ri,R1a,R3g,Ari), (Zd,Ri,R1a,R3g,Arj), (Zd,Ri,R1a,R3g,Ark), (Zd,Ri,R1a,R3g,Arl), (Zd,Ri,R1a,R3g,Arm), (Zd,Ri,R1a,R3g,Arn), (Zd,Ri,R1a,R3g,Aro), (Zd,Ri,R1a,R3g,Arp), (Zd,Ri,R1a,R3h,Ara), (Zd,Ri,R1a,R3h,Arb), (Zd,Ri,R1a,R3h,Arc), (Zd,Ri,R1a,R3h,Ard), (Zd,Ri,R1a,R3h,Are), (Zd,Ri,R1a,R3h,Arf), (Zd,Ri,R1a,R3h,Arg), (Zd,Ri,R1a,R3h,Arh), (Zd,Ri,R1a,R3h,Ari), (Zd,Ri,R1a,R3h,Arj), (Zd,Ri,R1a,R3h,Ark), (Zd,Ri,R1a,R3h,Arl), (Zd,Ri,R1a,R3h,Arm), (Zd,Ri,R1a,R3h,Arn), (Zd,Ri,R1a,R3h,Aro), (Zd,Ri,R1a,R3h,Arp), (Zd,Ri,R1b,R3a,Ara), (Zd,Ri,R1b,R3a,Arb), (Zd,Ri,R1b,R3a,Arc), (Zd,Ri,R1b,R3a,Ard), (Zd,Ri,R1b,R3a,Are), (Zd,Ri,R1b,R3a,Arf), (Zd,R1,R1b,R3a,Arg), (Zd,Ri,R1b,R3a,Arh), (Zd,Ri,R1b,R3a,Ari), (Zd,Ri,R1b,R3a,Arj), (Zd,Ri,R1b,R3a,Ark), (Zd,Ri,R1b,R3a,Arl), (Zd,Ri,R1b,R3a,Arm), (Zd,Ri,R1b,R3a,Arn), (Zd,Ri,R1b,R3a,Aro), (Zd,Ri,R1b,R3a,Arp), (Zd,Ri,R1b,R3b,Ara), (Zd,Ri,R1b,R3b,Arb), (Zd,Ri,R1b,R3b,Arc), (Zd,Ri,R1b,R3b,Ard), (Zd,Ri,R1b,R3b,Are), (Zd,Ri,R1b,R3b,Arf), (Zd,Ri,R1b,R3b,Arg), (Zd,R1,R1b,R3b,Arh), (Zd,Ri,R1b,R3b,Ari), (Zd,Ri,R1b,R3b,Arj), (Zd,Ri,R1b,R3b,Ark), (Zd,R1, R1b,R3b,Arl), (Zd,Ri,R1b,R3b,Arm), (Zd,Ri,R1b,R3b,Arn), (Zd,Ri,R1b,R3b,Aro), (Zd,Ri,R1b,R3b,Arp), (Zd,Ri,R1b,R3c,Ara), (Zd,Ri,R1b,R3c,Arb), (Zd,Ri,R1b,R3c,Arc), (Zd,Ri,R1b,R3c,Ard), (Zd,Ri,R1b,R3c,Are), (Zd,Ri,R1b,R3c,Arf), (Zd,Ri,R1b,R3c,Arg), (Zd,Ri,R1b,R3c,Arh), (Zd,Ri,R1b,R3c,Ari), (Zd,Ri,R1b,R3c,Arj), (Zd,Ri,R1b,R3c,Ark), (Zd,Ri,R1b,R3c,Arl), (Zd,Ri,R1b,R3c,Arm), (Zd,Ri,R1b,R3c,Arn), (Zd,Ri,R1b,R3c,Aro), (Zd,Ri,R1b,R3c,Arp), (Zd,Ri,R1b,R3d,Ara), (Zd,Ri,R1b,R3d,Arb), (Zd,Ri,R1b,R3d,Arc), (Zd,Ri,R1b,R3d,Ard), (Zd,Ri,R1b,R3d,Are), (Zd,Ri,R1b,R3d,Arf), (Zd,Ri,R1b,R3d,Arg), (Zd,Ri,R1b,R3d,Arh), (Zd,Ri,R1b,R3d,Ari), (Zd,Ri,R1b,R3d,Arj), (Zd,Ri,R1b,R3d,Ark), (Zd,Ri,R1b,R3d,Arl), (Zd,Ri,R1b,R3d,Arm), (Zd,Ri,R1b,R3d,Arn), (Zd,Ri,R1b,R3d,Aro), (Zd,Ri,R1b,R3d,Arp), (Zd,Ri,R1b,R3e,Ara), (Zd,Ri,R1b,R3e,Arb), (Zd,Ri,R1b,R3e,Arc), (Zd,Ri,R1b,R3e,Ard), (Zd,Ri,R1b,R3e,Are), (Zd,Ri,R1b,R3e,Arf), (Zd,Ri,R1b,R3e,Arg), (Zd,Ri,R1b,R3e,Arh), (Zd,Ri,R1b,R3e,Ari), (Zd,Ri,R1b,R3e,Arj), (Zd,Ri,R1b,R3e,Ark), (Zd,Ri,R1b,R3e,Arl), (Zd,Ri,R1b,R3e,Arm), (Zd,Ri,R1b,R3e,Arn), (Zd,Ri,R1b,R3e,Aro), (Zd,Ri,R1b,R3e,Arp), (Zd,Ri,R1b,R3f,Ara), (Zd,Ri,R1b,R3f,Arb), (Zd,Ri,R1b,R3f,Arc), (Zd,Ri,R1b,R3f,Ard), (Zd,Ri,R1b,R3f,Are), (Zd,Ri,R1b,R3f,Arf), (Zd,Ri,R1b,R3f,Arg), (Zd,Ri,R1b,R3f,Arh), (Zd,Ri,R1b,R3f,Ari), (Zd,Ri,R1b,R3f,Arj), (Zd,Ri,R1b,R3f,Ark), (Zd,Ri,R1b,R3f,Arl), (Zd,Ri,R1b,R3f,Arm), (Zd,Ri,R1b,R3f,Arn), (Zd,Ri,R1b,R3f,Aro), (Zd,Ri,R1b,R3f,Arp), (Zd,Ri,R1b,R3g,Ara), (Zd,Ri,R1b,R3g,Arb), (Zd,Ri,R1b,R3g,Arc), (Zd,Ri,R1b,R3g,Ard), (Zd,Ri,R1b,R3g,Are), (Zd,Ri,R1b,R3g,Arf), (Zd,Ri,R1b,R3g,Arg), (Zd,Ri,R1b,R3g,Arh), (Zd,Ri,R1b,R3g,Ari), (Zd,Ri,R1b,R3g,Arj), (Zd,Ri,R1b,R3g,Ark), (Zd,Ri,R1b,R3g,Arl), (Zd,Ri,R1b,R3g,Arm), (Zd,Ri,R1b,R3g,Arn), (Zd,Ri,R1b,R3g,Aro), (Zd,Ri,R1b,R3g,Arp), (Zd,Ri,R1b,R3h,Ara), (Zd,Ri,R1b,R3h,Arb), (Zd,Ri,R1b,R3h,Arc), (Zd,Ri,R1b,R3h,Ard), (Zd,Ri,R1b,R3h,Are), (Zd,Ri,R1b,R3h,Arf), (Zd,Ri,R1b,R3h,Arg), (Zd,Ri,R1b,R3h,Arh), (Zd,Ri,R1b,R3h,Ari), (Zd,Ri,R1b,R3h,Arj), (Zd,Ri,R1b,R3h,Ark), (Zd,Ri,R1b,R3h,Arl), (Zd,Ri,R1b,R3h,Arm), (Zd,Ri,R1b,R3h,Arn), (Zd,Ri,R1b,R3h,Aro), (Zd,Ri,R1b,R3h,Arp), (Zd,Ri,R1c,R3a,Ara), (Zd,Ri,R1c,R3a,Arb), (Zd,Ri,R1c,R3a,Arc), (Zd,Ri,R1c,R3a,Ard), (Zd,Ri,R1c,R3a,Are), (Zd,Ri,R1c,R3a,Arf), (Zd,Ri,R1c,R3a,Arg), (Zd,Ri,R1c,R3a,Arh), (Zd,Ri,R1c,R3a,Ari), (Zd,Ri,R1c,R3a,Arj), (Zd,Ri,R1c,R3a,Ark), (Zd,Ri,R1c,R3a,Arl), (Zd,Ri,R1c,R3a,Arm), (Zd,Ri,R1c,R3a,Arn), (Zd,Ri,R1c,R3a,Aro), (Zd,Ri,R1c,R3a,Arp), (Zd,Ri,R1c,R3b,Ara), (Zd,Ri,R1c,R3b,Arb), (Zd,Ri,R1c,R3b,Arc), (Zd,Ri,R1c,R3b,Ard), (Zd,Ri,R1c,R3b,Are), (Zd,Ri,R1c,R3b,Arf), (Zd,Ri,R1c,R3b,Arg), (Zd,Ri,R1c,R3b,Arh), (Zd,Ri,R1c,R3b,Ari), (Zd,Ri,R1c,R3b,Arj), (Zd,Ri,R1c,R3b,Ark), (Zd,Ri,R1c,R3b,Arl), (Zd,Ri,R1c,R3b,Arm), (Zd,Ri,R1c,R3b,Arn), (Zd,Ri,R1c,R3b,Aro), (Zd,Ri,R1c,R3b,Arp), (Zd,Ri,R1c,R3c,Ara), (Zd,Ri,R1c,R3c,Arb), (Zd,Ri,R1c,R3c,Arc), (Zd,Ri,R1c,R3c,Ard), (Zd,Ri,R1c,R3c,Are), (Zd,Ri,R1c,R3c,Arf), (Zd,Ri,R1c,R3c,Arg), (Zd,Ri,R1c,R3c,Arh), (Zd,Ri,R1c,R3c,Ari), (Zd,Ri,R1c,R3c,Arj), (Zd,Ri,R1c,R3c,Ark), (Zd,Ri,R1c,R3c,Arl), (Zd,Ri,R1c,R3c,Arm), (Zd,R1,R1c,R3c,Arn), (Zd,Ri,R1c,R3c,Aro), (Zd,Ri,R1c,R3c,Arp), (Zd,Ri,R1c,R3d,Ara), (Zd,Ri,R1c,R3d,Arb), (Zd,Ri,R1c,R3d,Arc), (Zd,Ri,R1c,R3d,Ard), (Zd,Ri,R1c,R3d,Are), (Zd,Ri,R1c,R3d,Arf), (Zd,Ri,R1c,R3d,Arg), (Zd,Ri,R1c,R3d,Arh), (Zd,Ri,R1c,R3d,Ari), (Zd,Ri,R1c,R3d,Arj), (Zd,Ri,R1c,R3d,Ark), (Zd,Ri,R1c,R3d,Arl), (Zd,Ri,R1c,R3d,Arm), (Zd,Ri,R1c,R3d,Arn), (Zd,Ri,R1c,R3d,Aro), (Zd,Ri,R1c,R3d,Arp), (Zd,Ri,R1c,R3e,Ara), (Zd,Ri,R1c,R3e,Arb), (Zd,Ri,R1c,R3e,Arc), (Zd,Ri,R1c,R3e,Ard), (Zd,Ri,R1c,R3e,Are), (Zd,Ri,R1c,R3e,Arf), (Zd,Ri,R1c,R3e,Arg), (Zd,Ri,R1c,R3e,Arh), (Zd,Ri,R1c,R3e,Ari), (Zd,Ri,R1c,R3e,Arj), (Zd,Ri,R1c,R3e,Ark), (Zd,Ri,R1c,R3e,Arl), (Zd,Ri,R1c,R3e,Arm), (Zd,Ri,R1c,R3e,Arn), (Zd,Ri,R1c,R3e,Aro), (Zd,Ri,R1c,R3e,Arp), (Zd,Ri,R1c,R3f,Ara), (Zd,Ri,R1c,R3f,Arb), (Zd,Ri,R1c,R3f,Arc), (Zd,Ri,R1c,R3f,Ard), (Zd,Ri,R1c,R3f,Are), (Zd,Ri,R1c,R3f,Arf), (Zd,Ri,R1c,R3f,Arg), (Zd,Ri,R1c,R3f,Arh), (Zd,Ri,R1c,R3f,Ari), (Zd,Ri,R1c,R3f,Arj), (Zd,Ri,R1c,R3f,Ark), (Zd,Ri,R1c,R3f,Arl), (Zd,Ri,R1c,R3f,Arm), (Zd,Ri,R1c,R3f,Arn), (Zd,Ri,R1c,R3f,Aro), (Zd,Ri,R1c,R3f,Arp), (Zd,Ri,R1c,R3g,Ara), (Zd,Ri,R1c,R3g,Arb), (Zd,Ri,R1c,R3g,Arc), (Zd,Ri,R1c,R3g,Ard), (Zd,Ri,R1c,R3g,Are), (Zd,Ri,R1c,R3g,Arf), (Zd,Ri,R1c,R3g,Arg), (Zd,Ri,R1c,R3g,Arh), (Zd,Ri,R1c,R3g,Ari), (Zd,Ri,R1c,R3g,Arj), (Zd,Ri,R1c,R3g,Ark), (Zd,Ri,R1c,R3g,Arl), (Zd,Ri,R1c,R3g,Arm), (Zd,Ri,R1c,R3g,Arn), (Zd,Ri,R1c,R3g,Aro), (Zd,Ri,R1c,R3g,Arp), (Zd,Ri,R1c,R3h,Ara), (Zd,Ri,R1c,R3h,Arb), (Zd,Ri,R1c,R3h,Arc), (Zd,Ri,R1c,R3h,Ard), (Zd,Ri,R1c,R3h,Are), (Zd,Ri,R1c,R3h,Arf), (Zd,Ri,R1c,R3h,Arg), (Zd,Ri,R1c,R3h,Arh), (Zd,Ri,R1c,R3h,Ari), (Zd,Ri,R1c,R3h,Arj), (Zd,Ri,R1c,R3h,Ark), (Zd,Ri,R1c,R3h,Arl), (Zd,Ri,R1c,R3h,Arm), (Zd,Ri,R1c,R3h,Arn), (Zd,Ri,R1c,R3h,Aro), (Zd,Ri,R1c,R3h,Arp), (Zd,Ri,R1d,R3a,Ara), (Zd,Ri,R1d,R3a,Arb), (Zd,Ri,R1d,R3a,Arc), (Zd,Ri,R1d,R3a,Ard), (Zd,Ri,R1d,R3a,Are), (Zd,Ri,R1d,R3a,Arf), (Zd,Ri,R1d,R3a,Arg), (Zd,Ri,R1d,R3a,Arh), (Zd,Ri,R1d,R3a,Ari), (Zd,Ri,R1d,R3a,Arj), (Zd,Ri,R1d,R3a,Ark), (Zd,Ri,R1d,R3a,Arl), (Zd,Ri,R1d,R3a,Arm), (Zd,Ri,R1d,R3a,Arn), (Zd,Ri,R1d,R3a,Aro), (Zd,Ri,R1d,R3a,Arp), (Zd,Ri,R1d,R3b,Ara), (Zd,Ri,R1d,R3b,Arb), (Zd,Ri,R1d,R3b,Arc), (Zd,Ri,R1d,R3b,Ard), (Zd,Ri,R1d,R3b,Are), (Zd,Ri,R1d,R3b,Arf), (Zd,Ri,R1d,R3b,Arg), (Zd,Ri,R1d,R3b,Arh), (Zd,Ri,R1d,R3b,Ari), (Zd,Ri,R1d,R3b,Arj), (Zd,Ri,R1d,R3b,Ark), (Zd,Ri,R1d,R3b,Arl), (Zd,Ri,R1d,R3b,Arm), (Zd,Ri,R1d,R3b,Arn), (Zd,Ri,R1d,R3b,Aro), (Zd,Ri,R1d,R3b,Arp), (Zd,Ri,R1d,R3c,Ara), (Zd,Ri,R1d,R3c,Arb), (Zd,Ri,R1d,R3c,Arc), (Zd,Ri,R1d,R3c,Ard), (Zd,Ri,R1d,R3c,Are), (Zd,Ri,R1d,R3c,Arf), (Zd,Ri,R1d,R3c,Arg), (Zd,Ri,R1d,R3c,Arh), (Zd,Ri,R1d,R3c,Ari), (Zd,Ri,R1d,R3c,Arj), (Zd,Ri,R1d,R3c,Ark), (Zd,Ri,R1d,R3c,Arl), (Zd,Ri,R1d,R3c,Arm), (Zd,Ri,R1d,R3c,Arn), (Zd,Ri,R1d,R3c,Aro), (Zd,Ri,R1d,R3c,Arp), (Zd,Ri,R1d,R3d,Ara), (Zd,Ri,R1d,R3d,Arb), (Zd,Ri,R1d,R3d,Arc), (Zd,Ri,R1d,R3d,Ard), (Zd,Ri,R1d,R3d,Are), (Zd,Ri,R1d,R3d,Arf), (Zd,Ri,R1d,R3d,Arg), (Zd,Ri,R1d,R3d,Arh), (Zd,Ri,R1d,R3d,Ari), (Zd,Ri,R1d,R3d,Arj), (Zd,Ri,R1d,R3d,Ark), (Zd,Ri,R1d,R3d,Arl), (Zd,Ri,R1d,R3d,Arm), (Zd,Ri,R1d,R3d,Arn), (Zd,Ri,R1d,R3d,Aro), (Zd,Ri,R1d,R3d,Arp), (Zd,Ri,R1d,R3e,Ara), (Zd,Ri,R1d,R3e,Arb), (Zd,Ri,R1d,R3e,Arc), (Zd,Ri,R1d,R3e,Ard), (Zd,Ri,R1d,R3e,Are), (Zd,Ri,R1d,R3e,Arf), (Zd,Ri,R1d,R3e,Arg), (Zd,Ri,R1d,R3e,Arh), (Zd,Ri,R1d,R3e,Ari), (Zd,Ri,R1d,R3e,Arj), (Zd,Ri,R1d,R3e,Ark), (Zd,Ri,R1d,R3e,Arl), (Zd,Ri,R1d,R3e,Arm), (Zd,Ri,R1d,R3e,Arn), (Zd,Ri,R1d,R3e,Aro), (Zd,Ri,R1d,R3e,Arp), (Zd,Ri,R1d,R3f,Ara), (Zd,Ri,R1d,R3f,Arb), (Zd,Ri,R1d,R3f,Arc), (Zd,Ri,R1d,R3f,Ard), (Zd,Ri,R1d,R3f,Are), (Zd,Ri,R1d,R3f,Arf), (Zd,Ri,R1d,R3f,Arg), (Zd,Ri,R1d,R3f,Arh), (Zd,Ri,R1d,R3f,Ari), (Zd,Ri,R1d,R3f,Arj), (Zd,Ri,R1d,R3f,Ark), (Zd,Ri,R1d,R3f,Arl), (Zd,Ri,R1d,R3f,Arm), (Zd,Ri,R1d,R3f,Arn), (Zd,Ri,R1d,R3f,Aro), (Zd,Ri,R1d,R3f,Arp), (Zd,Ri,R1d,R3g,Ara), (Zd,Ri,R1d,R3g,Arb), (Zd,Ri,R1d,R3g,Arc), (Zd,Ri,R1d,R3g,Ard), (Zd,Ri,R1d,R3g,Are), (Zd,Ri,R1d,R3g,Arf), (Zd,Ri,R1d,R3g,Arg), (Zd,Ri,R1d,R3g,Arh), (Zd,Ri,R1d,R3g,Ari), (Zd,Ri,R1d,R3g,Arj), (Zd,Ri,R1d,R3g,Ark), (Zd,Ri,R1d,R3g,Arl), (Zd,Ri,R1d,R3g,Arm), (Zd,Ri,R1d,R3g,Arn), (Zd,Ri,R1d,R3g,Aro), (Zd,Ri,R1d,R3g,Arp), (Zd,Ri,R1d,R3h,Ara), (Zd,Ri,R1d,R3h,Arb), (Zd,Ri,R1d,R3h,Arc), (Zd,Ri,R1d,R3h,Ard), (Zd,Ri,R1d,R3h,Are), (Zd,Ri,R1d,R3h,Arf), (Zd,Ri,R1d,R3h,Arg), (Zd,Ri,R1d,R3h,Arh), (Zd,Ri,R1d,R3h,Ari), (Zd,Ri,R1d,R3h,Arj), (Zd,Ri,R1d,R3h,Ark), (Zd,Ri,R1d,R3h,Arl), (Zd,Ri,R1d,R3h,Arm), (Zd,Ri,R1d,R3h,Arn), (Zd,Ri,R1d,R3h,Aro), (Zd,Ri,R1d,R3h,Arp), (Zd,Rj,R1a,R3a,Ara), (Zd,Rj,R1a,R3a,Arb), (Zd,Rj,R1a,R3a,Arc), (Zd,Rj,R1a,R3a,Ard), (Zd,Rj,R1a,R3a,Are), (Zd,Rj,R1a,R3a,Arf), (Zd,Rj,R1a,R3a,Arg), (Zd,Rj,R1a,R3a,Arh), (Zd,Rj,R1a,R3a,Ari), (Zd,Rj,R1a,R3a,Arj), (Zd,Rj,R1a,R3a,Ark), (Zd,Rj,R1a,R3a,Arl), (Zd,Rj,R1a,R3a,Arm), (Zd,Rj,R1a,R3a,Arn), (Zd,Rj,R1a,R3a,Aro), (Zd,Rj,R1a,R3a,Arp), (Zd,Rj,R1a,R3b,Ara), (Zd,Rj,R1a,R3b,Arb), (Zd,Rj,R1a,R3b,Arc), (Zd,Rj,R1a,R3b,Ard), (Zd,Rj,R1a,R3b,Are), (Zd,Rj,R1a,R3b,Arf), (Zd,Rj,R1a,R3b,Arg), (Zd,Rj,R1a,R3b,Arh), (Zd,Rj,R1a,R3b,Ari), (Zd,Rj,R1a,R3b,Arj), (Zd,Rj,R1a,R3b,Ark), (Zd,Rj,R1a,R3b,Arl), (Zd,Rj,R1a,R3b,Arm), (Zd,Rj,R1a,R3b,Arn), (Zd,Rj,R1a,R3b,Aro), (Zd,Rj,R1a,R3b,Arp), (Zd,Rj,R1a,R3c,Ara), (Zd,Rj,R1a,R3c,Arb), (Zd,Rj,R1a,R3c,Arc), (Zd,Rj,R1a,R3c,Ard), (Zd,Rj,R1a,R3c,Are), (Zd,Rj,R1a,R3c,Arf), (Zd,Rj,R1a,R3c,Arg), (Zd,Rj,R1a,R3c,Arh), (Zd,Rj,R1a,R3c,Ari), (Zd,Rj,R1a,R3c,Arj), (Zd,Rj,R1a,R3c,Ark), (Zd,Rj,R1a,R3c,Arl), (Zd,Rj,R1a,R3c,Arm), (Zd,Rj,R1a,R3c,Arn), (Zd,Rj,R1a,R3c,Aro), (Zd,Rj,R1a,R3c,Arp), (Zd,Rj,R1a,R3d,Ara), (Zd,Rj,R1a,R3d,Arb), (Zd,Rj,R1a,R3d,Arc), (Zd,Rj,R1a,R3d,Ard), (Zd,Rj,R1a,R3d,Are), (Zd,Rj,R1a,R3d,Arf), (Zd,Rj,R1a,R3d,Arg), (Zd,Rj,R1a,R3d,Arh), (Zd,Rj,R1a,R3d,Ari), (Zd,Rj,R1a,R3d,Arj), (Zd,Rj,R1a,R3d,Ark), (Zd,Rj,R1a,R3d,Arl), (Zd,Rj,R1a,R3d,Arm), (Zd,Rj,R1a,R3d,Arn), (Zd,Rj,R1a,R3d,Aro), (Zd,Rj,R1a,R3d,Arp), (Zd,Rj,R1a,R3e,Ara), (Zd,Rj,R1a,R3e,Arb), (Zd, Rj,R1a,R3e,Arc), (Zd,Rj,R1a,R3e,Ard), (Zd,Rj,R1a,R3e, Are), (Zd,Rj,R1a,R3e,Arf), (Zd,Rj,R1a,R3e,Arg), (Zd,Rj, R1a,R3e,Arh), (Zd,Rj,R1a,R3e,Ari), (Zd,Rj,R1a,R3e,Arj), (Zd,Rj,R1a,R3e,Ark), (Zd,Rj,R1a,R3e,Arl), (Zd,Rj,R1a, R3e,Arm),(Zd,Rj,R1a,R3e,Arn),(Zd,Rj,R1a,R3e,Aro),(Zd, Rj,R1a,R3e,Arp), (Zd,Rj,R1a,R3f,Ara), (Zd,Rj,R1a,R3f, Arb), (Zd,Rj,R1a,R3f,Arc), (Zd,Rj,R1a,R3f,Ard), (Zd,Rj, R1a,R3f,Are), (Zd,Rj,R1a,R3f,Arf), (Zd,Rj,R1a,R3f,Arg), (Zd,Rj,R1a,R3f,Arh),(Zd,Rj,R1a,R3f,Ari), (Zd,Rj,R1a,R3f, Arj), (Zd,Rj,R1a,R3f,Ark), (Zd,Rj,R1a,R3f,Arl), (Zd,Rj, R1a,R3f,Arm), (Zd,Rj,R1a,R3f,Arn), (Zd,Rj,R1a,R3f,Aro), (Zd,Rj,R1a,R3f,Arp), (Zd,Rj,R1a,R3g,Ara), (Zd,Rj,R1a, R3g,Arb),(Zd,Rj,R1a,R3g,Arc),(Zd,Rj,R1a,R3g,Ard), (Zd, Rj,R1a,R3g,Are), (Zd,Rj,R1a,R3g,Arf), (Zd,Rj,R1a,R3g, Arg), (Zd,Rj,R1a,R3g,Arh), (Zd,Rj,R1a,R3g,Ari), (Zd,Rj, R1a,R3g,Arj), (Zd,Rj,R1a,R3g,Ark), (Zd,Rj,R1a,R3g,Arl), (Zd,Rj,R1a,R3g,Arm), (Zd,Rj,R1a,R3g,Arn), (Zd,Rj,R1a, R3g,Aro), (Zd,Rj,R1a,R3g,Arp), (Zd,Rj,R1a,R3h,Ara), (Zd, Rj,R1a,R3h,Arb), (Zd,Rj,R1a,R3h,Arc), (Zd,Rj,R1a,R3h, Ard), (Zd,Rj,R1a,R3h,Are), (Zd,Rj,R1a,R3h,Arf), (Zd,Rj, R1a,R3h,Arg),(Zd,Rj,R1a,R3h,Arh), (Zd,Rj,R1a,R3h,Ari), (Zd,Rj,R1a,R3h,Arj), (Zd,Rj,R1a,R3h,Ark), (Zd,Rj,R1a, R3h,Arl), (Zd,Rj,R1a,R3h,Arm), (Zd,Rj,R1a,R3h,Arn), (Zd, Rj,R1a,R3h,Aro), (Zd,Rj,R1a,R3h,Arp), (Zd,Rj,R1b,R3a, Ara), (Zd,Rj,R1b,R3a,Arb), (Zd,Rj,R1b,R3a,Arc), (Zd,Rj, R1b,R3a,Ard),(Zd,Rj,R1b,R3a,Are), (Zd,Rj,R1b,R3a,Arf), (Zd,Rj,R1b,R3a,Arg), (Zd,Rj,R1b,R3a,Arh), (Zd,Rj,R1b, R3a,Ari), (Zd,Rj,R1b,R3a,Arj), (Zd,Rj,R1b,R3a,Ark), (Zd, Rj,R1b,R3a,Arl), (Zd,Rj,R1b,R3a,Arm), (Zd,Rj,R1b,R3a, Arn), (Zd,Rj,R1b,R3a,Aro), (Zd,Rj,R1b,R3a,Arp), (Zd,Rj, R1b,R3b,Ara),(Zd,Rj,R1b,R3b,Arb), (Zd,Rj,R1b,R3b,Arc), (Zd,Rj,R1b,R3b,Ard), (Zd,Rj,R1b,R3b,Are), (Zd,Rj,R1b, R3b,Arf), (Zd,Rj,R1b,R3b,Arg), (Zd,Rj,R1b,R3b,Arh), (Zd, Rj,R1b,R3b,Ari), (Zd,Rj,R1b,R3b,Arj), (Zd,Rj,R1b,R3b, Ark), (Zd,Rj,R1b,R3b,Arl), (Zd,Rj,R1b,R3b,Arm), (Zd,Rj, R1b,R3b,Arn),(Zd,Rj,R1b,R3b,Aro),(Zd,Rj,R1b,R3b,Arp), (Zd,Rj,R1b,R3c,Ara), (Zd,Rj,R1b,R3c,Arb), (Zd,Rj,R1b, R3c,Arc), (Zd,Rj,R1b,R3c,Ard), (Zd,Rj,R1b,R3c,Are), (Zd, Rj,R1b,R3c,Arf), (Zd,Rj,R1b,R3c,Arg), (Zd,Rj,R1b,R3c, Arh), (Zd,Rj,R1b,R3c,Ari), (Zd,Rj,R1b,R3c,Arj), (Zd,Rj, R1b,R3c,Ark),(Zd,Rj,R1b,R3c,Arl), (Zd,Rj,R1b,R3c,Arm), (Zd,Rj,R1b,R3c,Arn), (Zd,Rj,R1b,R3c,Aro), (Zd,Rj,R1b, R3c,Arp), (Zd,Rj,R1b,R3d,Ara), (Zd,Rj,R1b,R3d,Arb), (Zd, Rj,R1b,R3d,Arc), (Zd,Rj,R1b,R3d,Ard), (Zd,Rj,R1b,R3d, Are), (Zd,Rj,R1b,R3d,Arf), (Zd,Rj,R1b,R3d,Arg), (Zd,Rj, R1b,R3d,Arh), (Zd,Rj,R1b,R3d,Ari), (Zd,Rj,R1b,R3d,Arj), (Zd,Rj,R1b,R3d,Ark), (Zd,Rj,R1b,R3d,Arl), (Zd,Rj,R1b, R3d,Arm), (Zd,Rj,R1b,R3d,Arn), (Zd,Rj,R1b,R3d,Aro), (Zd,Rj,R1b,R3d,Arp), (Zd,Rj,R1b,R3e,Ara), (Zd,Rj,R1b, R3e,Arb), (Zd,Rj,R1b,R3e,Arc), (Zd,Rj,R1b,R3e,Ard), (Zd, Rj,R1b,R3e,Are), (Zd,Rj,R1b,R3e,Arf), (Zd,Rj,R1b,R3e, Arg), (Zd,Rj,R1b,R3e,Arh), (Zd,Rj,R1b,R3e,Ari), (Zd,Rj, R1b,R3e,Arj), (Zd,Rj,R1b,R3e,Ark), (Zd,Rj,R1b,R3e,Arl), (Zd,Rj,R1b,R3e,Arm), (Zd,Rj,R1b,R3e,Arn), (Zd,Rj,R1b, R3e,Aro), (Zd,Rj,R1b,R3e,Arp), (Zd,Rj,R1b,R3f,Ara), (Zd, Rj,R1b,R3f,Arb), (Zd,Rj,R1b,R3f,Arc), (Zd,Rj,R1b,R3f, Ard), (Zd,Rj,R1b,R3f,Are), (Zd,Rj,R1b,R3f,Arf), (Zd,Rj, R1b,R3f,Arg), (Zd,Rj,R1b,R3f,Arh), (Zd,Rj,R1b,R3f,Ari), (Zd,Rj,R1b,R3f,Arj), (Zd,Rj,R1b,R3f,Ark), (Zd,Rj,R1b, R3f,Arl), (Zd,Rj,R1b,R3f,Arm), (Zd,Rj,R1b,R3f,Arn), (Zd, Rj,R1b,R3f,Aro), (Zd,Rj,R1b,R3f,Arp), (Zd,Rj,R1b,R3g, Ara), (Zd,Rj,R1b,R3g,Arb), (Zd,Rj,R1b,R3g,Arc), (Zd,Rj, R1b,R3g,Ard),(Zd,Rj,R1b,R3g,Are), (Zd,Rj,R1b,R3g,Arf), (Zd,Rj,R1b,R3g,Arg), (Zd,Rj,R1b,R3g,Arh), (Zd,Rj,R1b, R3g,Ari), (Zd,Rj,R1b,R3g,Arj), (Zd,Rj,R1b,R3g,Ark), (Zd, Rj,R1b,R3g,Arl), (Zd,Rj,R1b,R3g,Arm), (Zd,Rj,R1b,R3g, Arn), (Zd,Rj,R1b,R3g,Aro), (Zd,Rj,R1b,R3g,Arp), (Zd,Rj, R1b,R3h,Ara), (Zd,Rj,R1b,R3h,Arb), (Zd,Rj,R1b,R3h,Arc), (Zd,Rj,R1b,R3h,Ard), (Zd,Rj,R1b,R3h,Are), (Zd,Rj,R1b, R3h,Arf), (Zd,Rj,R1b,R3h,Arg), (Zd,Rj,R1b,R3h,Arh), (Zd, Rj,R1b,R3h,Ari), (Zd,Rj,R1b,R3h,Arj), (Zd,Rj,R1b,R3h, Ark), (Zd,Rj,R1b,R3h,Arl), (Zd,Rj,R1b,R3h,Arm), (Zd,Rj, R1b,R3h,Arn),(Zd,Rj,R1b,R3h,Aro),(Zd,Rj,R1b,R3h,Arp), (Zd,Rj,R1c,R3a,Ara), (Zd,Rj,R1c,R3a,Arb), (Zd,Rj,R1c, R3a,Arc), (Zd,Rj,R1c,R3a,Ard), (Zd,Rj,R1c,R3a,Are), (Zd, Rj,R1c,R3a,Arf), (Zd,Rj,R1c,R3a,Arg), (Zd,Rj,R1c,R3a, Arh), (Zd,Rj,R1c,R3a,Ari), (Zd,Rj,R1c,R3a,Arj), (Zd,Rj, R1c,R3a,Ark), (Zd,Rj,R1c,R3a,Arl), (Zd,Rj,R1c,R3a,Arm), (Zd,Rj,R1c,R3a,Arn), (Zd,Rj,R1c,R3a,Aro), (Zd,Rj,R1c, R3a,Arp), (Zd,Rj,R1c,R3b,Ara), (Zd,Rj,R1c,R3b,Arb), (Zd, Rj,R1c,R3b,Arc), (Zd,Rj,R1c,R3b,Ard), (Zd,Rj,R1c,R3b, Are), (Zd,Rj,R1c,R3b,Arf), (Zd,Rj,R1c,R3b,Arg), (Zd,Rj, R1c,R3b,Arh), (Zd,Rj,R1c,R3b,Ari), (Zd,Rj,R1c,R3b,Arj), (Zd,Rj,R1c,R3b,Ark), (Zd,Rj,R1c,R3b,Arl), (Zd,Rj,R1c, R3b,Arm), (Zd,Rj,R1c,R3b,Arn), (Zd,Rj,R1c,R3b,Aro), (Zd,Rj,R1c,R3b,Arp), (Zd,Rj,R1c,R3c,Ara), (Zd,Rj,R1c, R3c,Arb), (Zd,Rj,R1c,R3c,Arc), (Zd,Rj,R1c,R3c,Ard), (Zd, Rj,R1c,R3c,Are), (Zd,Rj,R1c,R3c,Arf), (Zd,Rj,R1c,R3c, Arg), (Zd,Rj,R1c,R3c,Arh), (Zd,Rj,R1c,R3c,Ari), (Zd,Rj, R1c,R3c,Arj), (Zd,Rj,R1c,R3c,Ark), (Zd,Rj,R1c,R3c,Arl), (Zd,Rj,R1c,R3c,Arm), (Zd,Rj,R1c,R3c,Arn), (Zd,Rj,R1c, R3c,Aro), (Zd,Rj,R1c,R3c,Arp), (Zd,Rj,R1c,R3d,Ara), (Zd, Rj,R1c,R3d,Arb), (Zd,Rj,R1c,R3d,Arc), (Zd,Rj,R1c,R3d, Ard), (Zd,Rj,R1c,R3d,Are), (Zd,Rj,R1c,R3d,Arf), (Zd,Rj, R1c,R3d,Arg), (Zd,Rj,R1c,R3d,Arh), (Zd,Rj,R1c,R3d,Ari), (Zd,Rj,R1c,R3d,Arj), (Zd,Rj,R1c,R3d,Ark), (Zd,Rj,R1c, R3d,Arl), (Zd,Rj,R1c,R3d,Arm), (Zd,Rj,R1c,R3d,Arn), (Zd, Rj,R1c,R3d,Aro), (Zd,Rj,R1c,R3d,Arp), (Zd,Rj,R1c,R3e, Ara), (Zd,Rj,R1c,R3e,Arb), (Zd,Rj,R1c,R3e,Arc), (Zd,Rj, R1c,R3e,Ard), (Zd,Rj,R1c,R3e,Are), (Zd,Rj,R1c,R3e,Arf), (Zd,Rj,R1c,R3e,Arg), (Zd,Rj,R1c,R3e,Arh), (Zd,Rj,R1c, R3e,Ari), (Zd,Rj,R1c,R3e,Arj), (Zd,Rj,R1c,R3e,Ark), (Zd, Rj,R1c,R3e,Arl), (Zd,Rj,R1c,R3e,Arm), (Zd,Rj,R1c,R3e, Arn), (Zd,Rj,R1c,R3e,Aro), (Zd,Rj,R1c,R3e,Arp), (Zd,Rj, R1c,R3f,Ara), (Zd,Rj,R1c,R3f,Arb), (Zd,Rj,R1c,R3f,Arc), (Zd,Rj,R1c,R3f,Ard), (Zd,Rj,R1c,R3f,Are), (Zd,Rj,R1c, R3f,Arf), (Zd,Rj,R1c,R3f,Arg), (Zd,Rj,R1c,R3f,Arh), (Zd, Rj,R1c,R3f,Ari), (Zd,Rj,R1c,R3f,Arj), (Zd,Rj,R1c,R3f, Ark), (Zd,Rj,R1c,R3f,Arl), (Zd,Rj,R1c,R3f,Arm), (Zd,Rj, R1c,R3f,Arn), (Zd,Rj,R1c,R3f,Aro), (Zd,Rj,R1c,R3f,Arp), (Zd,Rj,R1c,R3g,Ara), (Zd,Rj,R1c,R3g,Arb), (Zd,Rj,R1c, R3g,Arc), (Zd,Rj,R1c,R3g,Ard), (Zd,Rj,R1c,R3g,Are), (Zd, Rj,R1c,R3g,Arf), (Zd,Rj,R1c,R3g,Arg), (Zd,Rj,R1c,R3g, Arh), (Zd,Rj,R1c,R3g,Ari), (Zd,Rj,R1c,R3g,Arj), (Zd,Rj, R1c,R3g,Ark),(Zd,Rj,R1c,R3g,Arl), (Zd,Rj,R1c,R3g,Arm), (Zd,Rj,R1c,R3g,Arn), (Zd,Rj,R1c,R3g,Aro), (Zd,Rj,R1c, R3g,Arp), (Zd,Rj,R1c,R3h,Ara), (Zd,Rj,R1c,R3h,Arb), (Zd, Rj,R1c,R3h,Arc), (Zd,Rj,R1c,R3h,Ard), (Zd,Rj,R1c,R3h, Are), (Zd,Rj,R1c,R3h,Arf), (Zd,Rj,R1c,R3h,Arg), (Zd,Rj, R1c,R3h,Arh), (Zd,Rj,R1c,R3h,Ari), (Zd,Rj,R1c,R3h,Arj), (Zd,Rj,R1c,R3h,Ark), (Zd,Rj,R1c,R3h,Arl), (Zd,Rj,R1c, R3h,Arm), (Zd,Rj,R1c,R3h,Arn), (Zd,Rj,R1c,R3h,Aro), (Zd,Rj,R1c,R3h,Arp), (Zd,Rj,R1d,R3a,Ara), (Zd,Rj,R1d, R3a,Arb), (Zd,Rj,R1d,R3a,Arc), (Zd,Rj,R1d,R3a,Ard), (Zd, Rj,R1d,R3a,Are), (Zd,Rj,R1d,R3a,Arf), (Zd,Rj,R1d,R3a, Arg), (Zd,Rj,R1d,R3a,Arh), (Zd,Rj,R1d,R3a,Ari), (Zd,Rj, R1d,R3a,Arj), (Zd,Rj,R1d,R3a,Ark), (Zd,Rj,R1d,R3a,Arl), (Zd,Rj,R1d,R3a,Arm), (Zd,Rj,R1d,R3a,Arn), (Zd,Rj,R1d, R3a,Aro), (Zd,Rj,R1d,R3a,Arp), (Zd,Rj,R1d,R3b,Ara), (Zd, Rj,R1d,R3b,Arb), (Zd,Rj,R1d,R3b,Arc), (Zd,Rj,R1d,R3b, Ard), (Zd,Rj,R1d,R3b,Are), (Zd,Rj,R1d,R3b,Arf), (Zd,Rj, R1d,R3b,Arg), (Zd,Rj,R1d,R3b,Arh), (Zd,Rj,R1d,R3b,Ari), (Zd,Rj,R1d,R3b,Arj), (Zd,Rj,R1d,R3b,Ark), (Zd,Rj,R1d, R3b,Arl), (Zd,Rj,R1d,R3b,Arm), (Zd,Rj,R1d,R3b,Arn), (Zd, Rj,R1d,R3b,Aro), (Zd,Rj,R1d,R3b,Arp), (Zd,Rj,R1d,R3c, Ara), (Zd,Rj,R1d,R3c,Arb), (Zd,Rj,R1d,R3c,Arc), (Zd,Rj, R1d,R3c,Ard), (Zd,Rj,R1d,R3c,Are), (Zd,Rj,R1d,R3c,Arf), (Zd,Rj,R1d,R3c,Arg), (Zd,Rj,R1d,R3c,Arh), (Zd,Rj,R1d, R3c,Ari), (Zd,Rj,R1d,R3c,Arj), (Zd,Rj,R1d,R3c,Ark), (Zd, Rj,R1d,R3c,Arl), (Zd,Rj,R1d,R3c,Arm), (Zd,Rj,R1d,R3c, Arn), (Zd,Rj,R1d,R3c,Aro), (Zd,Rj,R1d,R3c,Arp), (Zd,Rj, R1d,R3d,Ara), (Zd,Rj,R1d,R3d,Arb), (Zd,Rj,R1d,R3d,Arc), (Zd,Rj,R1d,R3d,Ard), (Zd,Rj,R1d,R3d,Are), (Zd,Rj,R1d, R3d,Arf), (Zd,Rj,R1d,R3d,Arg), (Zd,Rj,R1d,R3d,Arh), (Zd, Rj,R1d,R3d,Ari), (Zd,Rj,R1d,R3d,Arj), (Zd,Rj,R1d,R3d, Ark), (Zd,Rj,R1d,R3d,Arl), (Zd,Rj,R1d,R3d,Arm), (Zd,Rj, R1d,R3d,Arn),(Zd,Rj,R1d,R3d,Aro),(Zd,Rj,R1d,R3d,Arp), (Zd,Rj,R1d,R3e,Ara), (Zd,Rj,R1d,R3e,Arb), (Zd,Rj,R1d, R3e,Arc), (Zd,Rj,R1d,R3e,Ard), (Zd,Rj,R1d,R3e,Are), (Zd, Rj,R1d,R3e,Arf), (Zd,Rj,R1d,R3e,Arg), (Zd,Rj,R1d,R3e, Arh), (Zd,Rj,R1d,R3e,Ari), (Zd,Rj,R1d,R3e,Arj), (Zd,Rj, R1d,R3e,Ark),(Zd,Rj,R1d,R3e,Arl), (Zd,Rj,R1d,R3e,Arm), (Zd,Rj,R1d,R3e,Arn), (Zd,Rj,R1d,R3e,Aro), (Zd,Rj,R1d, R3e,Arp), (Zd,Rj,R1d,R3f,Ara), (Zd,Rj,R1d,R3f,Arb), (Zd, Rj,R1d,R3f,Arc), (Zd,Rj,R1d,R3f,Ard), (Zd,Rj,R1d,R3f, Are), (Zd,Rj,R1d,R3f,Arf), (Zd,Rj,R1d,R3f,Arg), (Zd,Rj, R1d,R3f,Arh), (Zd,Rj,R1d,R3f,Ari), (Zd,Rj,R1d,R3f,Arj), (Zd,Rj,R1d,R3f,Ark), (Zd,Rj,R1d,R3f,Arl), (Zd,Rj,R1d, R3f,Arm), (Zd,Rj,R1d,R3f,Arn), (Zd,Rj,R1d,R3f,Aro), (Zd, Rj,R1d,R3f,Arp), (Zd,Rj,R1d,R3g,Ara), (Zd,Rj,R1d,R3g, Arb), (Zd,Rj,R1d,R3g,Arc), (Zd,Rj,R1d,R3g,Ard), (Zd,Rj, R1d,R3g,Are), (Zd,Rj,R1d,R3g,Arf), (Zd,Rj,R1d,R3g,Arg), (Zd,Rj,R1d,R3g,Arh), (Zd,Rj,R1d,R3g,Ari), (Zd,Rj,R1d, R3g,Arj), (Zd,Rj,R1d,R3g,Ark), (Zd,Rj,R1d,R3g,Arl), (Zd, Rj,R1d,R3g,Arm), (Zd,Rj,R1d,R3g,Arn), (Zd,Rj,R1d,R3g, Aro), (Zd,Rj,R1d,R3g,Arp), (Zd,Rj,R1d,R3h,Ara), (Zd,Rj, R1d,R3h,Arb), (Zd,Rj,R1d,R3h,Arc), (Zd,Rj,R1d,R3h,Ard), (Zd,Rj,R1d,R3h,Are), (Zd,Rj,R1d,R3h,Arf), (Zd,Rj,R1d, R3h,Arg), (Zd,Rj,R1d,R3h,Arh), (Zd,Rj,R1d,R3h,Ari), (Zd, Rj,R1d,R3h,Arj), (Zd,Rj,R1d,R3h,Ark), (Zd,Rj,R1d,R3h, Arl), (Zd,Rj,R1d,R3h,Arm), (Zd,Rj,R1d,R3h,Arn), (Zd,Rj, R1d,R3h,Aro),(Zd,Rj,R1d,R3h,Arp),(Ze,Ra,R1a,R3a,Ara), (Ze,Ra,R1a,R3a,Arb), (Ze,Ra,R1a,R3a,Arc), (Ze,Ra,R1a, R3a,Ard), (Ze,Ra,R1a,R3a,Are), (Ze,Ra,R1a,R3a,Arf), (Ze, Ra,R1a,R3a,Arg), (Ze,Ra,R1a,R3a,Arh), (Ze,Ra,R1a,R3a, Ari), (Ze,Ra,R1a,R3a,Arj), (Ze,Ra,R1a,R3a,Ark), (Ze,Ra, R1a,R3a,Arl),(Ze,Ra,R1a,R3a,Arm),(Ze,Ra,R1a,R3a,Arn), (Ze,Ra,R1a,R3a,Aro), (Ze,Ra,R1a,R3a,Arp), (Ze,Ra,R1a, R3b,Ara),(Ze,Ra,R1a,R3b,Arb),(Ze,Ra,R1a,R3b,Arc),(Ze, Ra,R1a,R3b,Ard), (Ze,Ra,R1a,R3b,Are), (Ze,Ra,R1a,R3b, Arf), (Ze,Ra,R1a,R3b,Arg), (Ze,Ra,R1a,R3b,Arh), (Ze,Ra, R1a,R3b,Ari), (Ze,Ra,R1a,R3b,Arj), (Ze,Ra,R1a,R3b,Ark), (Ze,Ra,R1a,R3b,Arl), (Ze,Ra,R1a,R3b,Arm), (Ze,Ra,R1a, R3b,Arn),(Ze,Ra,R1a,R3b,Aro),(Ze,Ra,R1a,R3b,Arp),(Ze, Ra,R1a,R3c,Ara), (Ze,Ra,R1a,R3c,Arb), (Ze,Ra,R1a,R3c, Arc), (Ze,Ra,R1a,R3c,Ard), (Ze,Ra,R1a,R3c,Are), (Ze,Ra, R1a,R3c,Arf), (Ze,Ra,R1a,R3c,Arg), (Ze,Ra,R1a,R3c,Arh), (Ze,Ra,R1a,R3c,Ari), (Ze,Ra,R1a,R3c,Arj), (Ze,Ra,R1a, R3c,Ark),(Ze,Ra,R1a,R3c,Arl),(Ze,Ra,R1a,R3c,Arm), (Ze, Ra,R1a,R3c,Arn), (Ze,Ra,R1a,R3c,Aro), (Ze,Ra,R1a,R3c, Arp), (Ze,Ra,R1a,R3d,Ara), (Ze,Ra,R1a,R3d,Arb), (Ze,Ra, R1a,R3d,Arc),(Ze,Ra,R1a,R3d,Ard),(Ze,Ra,R1a,R3d,Are), (Ze,Ra,R1a,R3d,Arf), (Ze,Ra,R1a,R3d,Arg), (Ze,Ra,R1a, R3d,Arh), (Ze,Ra,R1a,R3d,Ari), (Ze,Ra,R1a,R3d,Arj), (Ze, Ra,R1a,R3d,Ark), (Ze,Ra,R1a,R3d,Arl), (Ze,Ra,R1a,R3d, Arm), (Ze,Ra,R1a,R3d,Arn), (Ze,Ra,R1a,R3d,Aro), (Ze,Ra, R1a,R3d,Arp), (Ze,Ra,R1a,R3e,Ara), (Ze,Ra,R1a,R3e,Arb), (Ze,Ra,R1a,R3e,Arc), (Ze,Ra,R1a,R3e,Ard), (Ze,Ra,R1a, R3e,Are), (Ze,Ra,R1a,R3e,Arf), (Ze,Ra,R1a,R3e,Arg), (Ze, Ra,R1a,R3e,Arh), (Ze,Ra,R1a,R3e,Ari), (Ze,Ra,R1a,R3e, Arj), (Ze,Ra,R1a,R3e,Ark), (Ze,Ra,R1a,R3e,Arl), (Ze,Ra, R1a,R3e,Arm), (Ze,Ra,R1a,R3e,Arn), (Ze,Ra,R1a,R3e, Aro), (Ze,Ra,R1a,R3e,Arp), (Ze,Ra,R1a,R3f,Ara), (Ze,Ra, R1a,R3f,Arb), (Ze,Ra,R1a,R3f,Arc), (Ze,Ra,R1a,R3f,Ard), (Ze,Ra,R1a,R3f,Are), (Ze,Ra,R1a,R3f,Arf), (Ze,Ra,R1a, R3f,Arg), (Ze,Ra,R1a,R3f,Arh), (Ze,Ra,R1a,R3f,Ari), (Ze, Ra,R1a,R3f,Arj), (Ze,Ra,R1a,R3f,Ark), (Ze,Ra,R1a,R3f, Arl), (Ze,Ra,R1a,R3f,Arm), (Ze,Ra,R1a,R3f,Arn), (Ze,Ra, R1a,R3f,Aro), (Ze,Ra,R1a,R3f,Arp), (Ze,Ra,R1a,R3g,Ara), (Ze,Ra,R1a,R3g,Arb), (Ze,Ra,R1a,R3g,Arc), (Ze,Ra,R1a, R3g,Ard), (Ze,Ra,R1a,R3g,Are), (Ze,Ra,R1a,R3g,Arf), (Ze, Ra,R1a,R3g,Arg), (Ze,Ra,R1a,R3g,Arh), (Ze,Ra,R1a,R3g, Ari), (Ze,Ra,R1a,R3g,Arj), (Ze,Ra,R1a,R3g,Ark), (Ze,Ra, R1a,R3g,Arl), (Ze,Ra,R1a,R3g,Arm), (Ze,Ra,R1a,R3g, Arn), (Ze,Ra,R1a,R3g,Aro), (Ze,Ra,R1a,R3g,Arp), (Ze,Ra, R1a,R3h,Ara), (Ze,Ra,R1a,R3h,Arb), (Ze,Ra,R1a,R3h,Arc), (Ze,Ra,R1a,R3h,Ard), (Ze,Ra,R1a,R3h,Are), (Ze,Ra,R1a, R3h,Arf), (Ze,Ra,R1a,R3h,Arg), (Ze,Ra,R1a,R3h,Arh), (Ze, Ra,R1a,R3h,Ari), (Ze,Ra,R1a,R3h,Arj), (Ze,Ra,R1a,R3h, Ark), (Ze,Ra,R1a,R3h,Arl), (Ze,Ra,R1a,R3h,Arm), (Ze,Ra, R1a,R3h,Arn), (Ze,Ra,R1a,R3h,Aro), (Ze,Ra,R1a,R3h, Arp), (Ze,Ra,R1b,R3a,Ara), (Ze,Ra,R1b,R3a,Arb), (Ze,Ra, R1b,R3a,Arc),(Ze,Ra,R1b,R3a,Ard),(Ze,Ra,R1b,R3a,Are), (Ze,Ra,R1b,R3a,Arf), (Ze,Ra,R1b,R3a,Arg), (Ze,Ra,R1b, R3a,Arh), (Ze,Ra,R1b,R3a,Ari), (Ze,Ra,R1b,R3a,Arj), (Ze, Ra,R1b,R3a,Ark), (Ze,Ra,R1b,R3a,Arl), (Ze,Ra,R1b,R3a, Arm), (Ze,Ra,R1b,R3a,Arn), (Ze,Ra,R1b,R3a,Aro), (Ze,Ra, R1b,R3a,Arp), (Ze,Ra,R1b,R3b,Ara), (Ze,Ra,R1b,R3b, Arb), (Ze,Ra,R1b,R3b,Arc), (Ze,Ra,R1b,R3b,Ard), (Ze,Ra, R1b,R3b,Are), (Ze,Ra,R1b,R3b,Arf), (Ze,Ra,R1b,R3b,Arg), (Ze,Ra,R1b,R3b,Arh), (Ze,Ra,R1b,R3b,Ari), (Ze,Ra,R1b, R3b,Arj), (Ze,Ra,R1b,R3b,Ark), (Ze,Ra,R1b,R3b,Arl), (Ze, Ra,R1b,R3b,Arm), (Ze,Ra,R1b,R3b,Arn), (Ze,Ra,R1b,R3b, Aro), (Ze,Ra,R1b,R3b,Arp), (Ze,Ra,R1b,R3c,Ara), (Ze,Ra, R1b,R3c,Arb),(Ze,Ra,R1b,R3c,Arc),(Ze,Ra,R1b,R3c,Ard), (Ze,Ra,R1b,R3c,Are), (Ze,Ra,R1b,R3c,Arf), (Ze,Ra,R1b, R3c,Arg), (Ze,Ra,R1b,R3c,Arh), (Ze,Ra,R1b,R3c,Ari), (Ze, Ra,R1b,R3c,Arj), (Ze,Ra,R1b,R3c,Ark), (Ze,Ra,R1b,R3c, Arl), (Ze,Ra,R1b,R3c,Arm), (Ze,Ra,R1b,R3c,Arn), (Ze,Ra, R1b,R3c,Aro), (Ze,Ra,R1b,R3c,Arp), (Ze,Ra,R1b,R3d, Ara), (Ze,Ra,R1b,R3d,Arb), (Ze,Ra,R1b,R3d,Arc), (Ze,Ra, R1b,R3d,Ard),(Ze,Ra,R1b,R3d,Are),(Ze,Ra,R1b,R3d,Arf), (Ze,Ra,R1b,R3d,Arg), (Ze,Ra,R1b,R3d,Arh), (Ze,Ra,R1b, R3d,Ari), (Ze,Ra,R1b,R3d,Arj), (Ze,Ra,R1b,R3d,Ark), (Ze, Ra,R1b,R3d,Arl), (Ze,Ra,R1b,R3d,Arm), (Ze,Ra,R1b,R3d, Arn), (Ze,Ra,R1b,R3d,Aro), (Ze,Ra,R1b,R3d,Arp), (Ze,Ra, R1b,R3e,Ara), (Ze,Ra,R1b,R3e,Arb), (Ze,Ra,R1b,R3e,Arc), (Ze,Ra,R1b,R3e,Ard), (Ze,Ra,R1b,R3e,Are), (Ze,Ra,R1b, R3e,Arf), (Ze,Ra,R1b,R3e,Arg), (Ze,Ra,R1b,R3e,Arh), (Ze, Ra,R1b,R3e,Ari), (Ze,Ra,R1b,R3e,Arj), (Ze,Ra,R1b,R3e, Ark), (Ze,Ra,R1b,R3e,Arl), (Ze,Ra,R1b,R3e,Arm), (Ze,Ra, R1b,R3e,Arn), (Ze,Ra,R1b,R3e,Aro), (Ze,Ra,R1b,R3e, Arp), (Ze,Ra,R1b,R3f,Ara), (Ze,Ra,R1b,R3f,Arb), (Ze,Ra, R1b,R3f,Arc), (Ze,Ra,R1b,R3f,Ard), (Ze,Ra,R1b,R3f,Are), (Ze,Ra,R1b,R3f,Arf), (Ze,Ra,R1b,R3f,Arg), (Ze,Ra,R1b, R3f,Arh), (Ze,Ra,R1b,R3f,Ari), (Ze,Ra,R1b,R3f,Arj), (Ze, Ra,R1b,R3f,Ark), (Ze,Ra,R1b,R3f,Arl), (Ze,Ra,R1b,R3f, Arm), (Ze,Ra,R1b,R3f,Arn), (Ze,Ra,R1b,R3f,Aro), (Ze,Ra, R1b,R3f,Arp),(Ze,Ra,R1b,R3g,Ara),(Ze,Ra,R1b,R3g,Arb), (Ze,Ra,R1b,R3g,Arc), (Ze,Ra,R1b,R3g,Ard), (Ze,Ra,R1b, R3g,Are), (Ze,Ra,R1b,R3g,Arf), (Ze,Ra,R1b,R3g,Arg), (Ze, Ra,R1b,R3g,Arh), (Ze,Ra,R1b,R3g,Ari), (Ze,Ra,R1b,R3g, Arj), (Ze,Ra,R1b,R3g,Ark), (Ze,Ra,R1b,R3g,Arl), (Ze,Ra, R1b,R3g,Arm), (Ze,Ra,R1b,R3g,Arn), (Ze,Ra,R1b,R3g, Aro), (Ze,Ra,R1b,R3g,Arp), (Ze,Ra,R1b,R3h,Ara), (Ze,Ra, R1b,R3h,Arb), (Ze,Ra,R1b,R3h,Arc), (Ze,Ra,R1b,R3h, Ard), (Ze,Ra,R1b,R3h,Are), (Ze,Ra,R1b,R3h,Arf), (Ze,Ra, R1b,R3h,Arg),(Ze,Ra,R1b,R3h,Arh),(Ze,Ra,R1b,R3h,Ari), (Ze,Ra,R1b,R3h,Arj), (Ze,Ra,R1b,R3h,Ark), (Ze,Ra,R1b,R3h,Arl), (Ze,Ra,R1b,R3h,Arm), (Ze,Ra,R1b,R3h,Arn), (Ze,Ra,R1b,R3h,Aro), (Ze,Ra,R1b,R3h,Arp), (Ze,Ra,R1c,R3a,Ara), (Ze,Ra,R1c,R3a,Arb), (Ze,Ra,R1c,R3a,Arc), (Ze,Ra,R1c,R3a,Ard), (Ze,Ra,R1c,R3a,Are), (Ze,Ra,R1c,R3a,Arf), (Ze,Ra,R1c,R3a,Arg), (Ze,Ra,R1c,R3a,Arh), (Ze,Ra,R1c,R3a,Ari), (Ze,Ra,R1c,R3a,Arj), (Ze,Ra,R1c,R3a,Ark), (Ze,Ra,R1c,R3a,Arl), (Ze,Ra,R1c,R3a,Arm), (Ze,Ra,R1c,R3a,Arn), (Ze,Ra,R1c,R3a,Aro), (Ze,Ra,R1c,R3a,Arp), (Ze,Ra,R1c,R3b,Ara), (Ze,Ra,R1c,R3b,Arb), (Ze,Ra,R1c,R3b,Arc), (Ze,Ra,R1c,R3b,Ard), (Ze,Ra,R1c,R3b,Are), (Ze,Ra,R1c,R3b,Arf), (Ze,Ra,R1c,R3b,Arg), (Ze,Ra,R1c,R3b,Arh), (Ze,Ra,R1c,R3b,Ari), (Ze,Ra,R1c,R3b,Arj), (Ze,Ra,R1c,R3b,Ark), (Ze,Ra,R1c,R3b,Arl), (Ze,Ra,R1c,R3b,Arm), (Ze,Ra,R1c,R3b,Arn), (Ze,Ra,R1c,R3b,Aro), (Ze,Ra,R1c,R3b,Arp), (Ze,Ra,R1c,R3c,Ara), (Ze,Ra,R1c,R3c,Arb), (Ze,Ra,R1c,R3c,Arc), (Ze,Ra,R1c,R3c,Ard), (Ze,Ra,R1c,R3c,Are), (Ze,Ra,R1c,R3c,Arf), (Ze,Ra,R1c,R3c,Arg), (Ze,Ra,R1c,R3c,Arh), (Ze,Ra,R1c,R3c,Ari), (Ze,Ra,R1c,R3c,Arj), (Ze,Ra,R1c,R3c,Ark), (Ze,Ra,R1c,R3c,Arl), (Ze,Ra,R1c,R3c,Arm), (Ze,Ra,R1c,R3c,Arn), (Ze,Ra,R1c,R3c,Aro), (Ze,Ra,R1c,R3c,Arp), (Ze,Ra,R1c,R3d,Ara), (Ze,Ra,R1c,R3d,Arb), (Ze,Ra,R1c,R3d,Arc), (Ze,Ra,R1c,R3d,Ard), (Ze,Ra,R1c,R3d,Are), (Ze,Ra,R1c,R3d,Arf), (Ze,Ra,R1c,R3d,Arg), (Ze,Ra,R1c,R3d,Arh), (Ze,Ra,R1c,R3d,Ari), (Ze,Ra,R1c,R3d,Arj), (Ze,Ra,R1c,R3d,Ark), (Ze,Ra,R1c,R3d,Arl), (Ze,Ra,R1c,R3d,Arm), (Ze,Ra,R1c,R3d,Arn), (Ze,Ra,R1c,R3d,Aro), (Ze,Ra,R1c,R3d,Arp), (Ze,Ra,R1c,R3e,Ara), (Ze,Ra,R1c,R3e,Arb), (Ze,Ra,R1c,R3e,Arc), (Ze,Ra,R1c,R3e,Ard), (Ze,Ra,R1c,R3e,Are), (Ze,Ra,R1c,R3e,Arf), (Ze,Ra,R1c,R3e,Arg), (Ze,Ra,R1c,R3e,Arh), (Ze,Ra,R1c,R3e,Ari), (Ze,Ra,R1c,R3e,Arj), (Ze,Ra,R1c,R3e,Ark), (Ze,Ra,R1c,R3e,Arl), (Ze,Ra,R1c,R3e,Arm), (Ze,Ra,R1c,R3e,Arn), (Ze,Ra,R1c,R3e,Aro), (Ze,Ra,R1c,R3e,Arp), (Ze,Ra,R1c,R3f,Ara), (Ze,Ra,R1c,R3f,Arb), (Ze,Ra,R1c,R3f,Arc), (Ze,Ra,R1c,R3f,Ard), (Ze,Ra,R1c,R3f,Are), (Ze,Ra,R1c,R3f,Arf), (Ze,Ra,R1c,R3f,Arg), (Ze,Ra,R1c,R3f,Arh), (Ze,Ra,R1c,R3f,Ari), (Ze,Ra,R1c,R3f,Arj), (Ze,Ra,R1c,R3f,Ark), (Ze,Ra,R1c,R3f,Arl), (Ze,Ra,R1c,R3f,Arm), (Ze,Ra,R1c,R3f,Arn), (Ze,Ra,R1c,R3f,Aro), (Ze,Ra,R1c,R3f,Arp), (Ze,Ra,R1c,R3g,Ara), (Ze,Ra,R1c,R3g,Arb), (Ze,Ra,R1c,R3g,Arc), (Ze,Ra,R1c,R3g,Ard), (Ze,Ra,R1c,R3g,Are), (Ze,Ra,R1c,R3g,Arf), (Ze,Ra,R1c,R3g,Arg), (Ze,Ra,R1c,R3g,Arh), (Ze,Ra,R1c,R3g,Ari), (Ze,Ra,R1c,R3g,Arj), (Ze,Ra,R1c,R3g,Ark), (Ze,Ra,R1c,R3g,Arl), (Ze,Ra,R1c,R3g,Arm), (Ze,Ra,R1c,R3g,Arn), (Ze,Ra,R1c,R3g,Aro), (Ze,Ra,R1c,R3g,Arp), (Ze,Ra,R1c,R3h,Ara), (Ze,Ra,R1c,R3h,Arb), (Ze,Ra,R1c,R3h,Arc), (Ze,Ra,R1c,R3h,Ard), (Ze,Ra,R1c,R3h,Are), (Ze,Ra,R1c,R3h,Arf), (Ze,Ra,R1c,R3h,Arg), (Ze,Ra,R1c,R3h,Arh), (Ze,Ra,R1c,R3h,Ari), (Ze,Ra,R1c,R3h,Arj), (Ze,Ra,R1c,R3h,Ark), (Ze,Ra,R1c,R3h,Arl), (Ze,Ra,R1c,R3h,Arm), (Ze,Ra,R1c,R3h,Arn), (Ze,Ra,R1c,R3h,Aro), (Ze,Ra,R1c,R3h,Arp), (Ze,Ra,R1d,R3a,Ara), (Ze,Ra,R1d,R3a,Arb), (Ze,Ra,R1d,R3a,Arc), (Ze,Ra,R1d,R3a,Ard), (Ze,Ra,R1d,R3a,Are), (Ze,Ra,R1d,R3a,Arf), (Ze,Ra,R1d,R3a,Arg), (Ze,Ra,R1d,R3a,Arh), (Ze,Ra,R1d,R3a,Ari), (Ze,Ra,R1d,R3a,Arj), (Ze,Ra,R1d,R3a,Ark), (Ze,Ra,R1d,R3a,Arl), (Ze,Ra,R1d,R3a,Arm), (Ze,Ra,R1d,R3a,Arn), (Ze,Ra,R1d,R3a,Aro), (Ze,Ra,R1d,R3a,Arp), (Ze,Ra,R1d,R3b,Ara), (Ze,Ra,R1d,R3b,Arb), (Ze,Ra,R1d,R3b,Arc), (Ze,Ra,R1d,R3b,Ard), (Ze,Ra,R1d,R3b,Are), (Ze,Ra,R1d,R3b,Arf), (Ze,Ra,R1d,R3b,Arg), (Ze,Ra,R1d,R3b,Arh), (Ze,Ra,R1d,R3b,Ari), (Ze,Ra,R1d,R3b,Arj), (Ze,Ra,R1d,R3b,Ark), (Ze,Ra,R1d,R3b,Arl), (Ze,Ra,R1d,R3b,Arm), (Ze,Ra,R1d,R3b,Arn), (Ze,Ra,R1d,R3b,Aro), (Ze,Ra,R1d,R3b,Arp), (Ze,Ra,R1d,R3c,Ara), (Ze,Ra,R1d,R3c,Arb), (Ze,Ra,R1d,R3c,Arc), (Ze,Ra,R1d,R3c,Ard), (Ze,Ra,R1d,R3c,Are), (Ze,Ra,R1d,R3c,Arf), (Ze,Ra,R1d,R3c,Arg), (Ze,Ra,R1d,R3c,Arh), (Ze,Ra,R1d,R3c,Ari), (Ze,Ra,R1d,R3c,Arj), (Ze,Ra,R1d,R3c,Ark), (Ze,Ra,R1d,R3c,Arl), (Ze,Ra,R1d,R3c,Arm), (Ze,Ra,R1d,R3c,Arn), (Ze,Ra,R1d,R3c,Aro), (Ze,Ra,R1d,R3c,Arp), (Ze,Ra,R1d,R3d,Ara), (Ze,Ra,R1d,R3d,Arb), (Ze,Ra,R1d,R3d,Arc), (Ze,Ra,R1d,R3d,Ard), (Ze,Ra,R1d,R3d,Are), (Ze,Ra,R1d,R3d,Arf), (Ze,Ra,R1d,R3d,Arg), (Ze,Ra,R1d,R3d,Arh), (Ze,Ra,R1d,R3d,Ari), (Ze,Ra,R1d,R3d,Arj), (Ze,Ra,R1d,R3d,Ark), (Ze,Ra,R1d,R3d,Arl), (Ze,Ra,R1d,R3d,Arm), (Ze,Ra,R1d,R3d,Arn), (Ze,Ra,R1d,R3d,Aro), (Ze,Ra,R1d,R3d,Arp), (Ze,Ra,R1d,R3e,Ara), (Ze,Ra,R1d,R3e,Arb), (Ze,Ra,R1d,R3e,Arc), (Ze,Ra,R1d,R3e,Ard), (Ze,Ra,R1d,R3e,Are), (Ze,Ra,R1d,R3e,Arf), (Ze,Ra,R1d,R3e,Arg), (Ze,Ra,R1d,R3e,Arh), (Ze,Ra,R1d,R3e,Ari), (Ze,Ra,R1d,R3e,Arj), (Ze,Ra,R1d,R3e,Ark), (Ze,Ra,R1d,R3e,Arl), (Ze,Ra,R1d,R3e,Arm), (Ze,Ra,R1d,R3e,Arn), (Ze,Ra,R1d,R3e,Aro), (Ze,Ra,R1d,R3e,Arp), (Ze,Ra,R1d,R3f,Ara), (Ze,Ra,R1d,R3f,Arb), (Ze,Ra,R1d,R3f,Arc), (Ze,Ra,R1d,R3f,Ard), (Ze,Ra,R1d,R3f,Are), (Ze,Ra,R1d,R3f,Arf), (Ze,Ra,R1d,R3f,Arg), (Ze,Ra,R1d,R3f,Arh), (Ze,Ra,R1d,R3f,Ari), (Ze,Ra,R1d,R3f,Arj), (Ze,Ra,R1d,R3f,Ark), (Ze,Ra,R1d,R3f,Arl), (Ze,Ra,R1d,R3f,Arm), (Ze,Ra,R1d,R3f,Arn), (Ze,Ra,R1d,R3f,Aro), (Ze,Ra,R1d,R3f,Arp), (Ze,Ra,R1d,R3g,Ara), (Ze,Ra,R1d,R3g,Arb), (Ze,Ra,R1d,R3g,Arc), (Ze,Ra,R1d,R3g,Ard), (Ze,Ra,R1d,R3g,Are), (Ze,Ra,R1d,R3g,Arf), (Ze,Ra,R1d,R3g,Arg), (Ze,Ra,R1d,R3g,Arh), (Ze,Ra,R1d,R3g,Ari), (Ze,Ra,R1d,R3g,Arj), (Ze,Ra,R1d,R3g,Ark), (Ze,Ra,R1d,R3g,Arl), (Ze,Ra,R1d,R3g,Arm), (Ze,Ra,R1d,R3g,Arn), (Ze,Ra,R1d,R3g,Aro), (Ze,Ra,R1d,R3g,Arp), (Ze,Ra,R1d,R3h,Ara), (Ze,Ra,R1d,R3h,Arb), (Ze,Ra,R1d,R3h,Arc), (Ze,Ra,R1d,R3h,Ard), (Ze,Ra,R1d,R3h,Are), (Ze,Ra,R1d,R3h,Arf), (Ze,Ra,R1d,R3h,Arg), (Ze,Ra,R1d,R3h,Arh), (Ze,Ra,R1d,R3h,Ari), (Ze,Ra,R1d,R3h,Arj), (Ze,Ra,R1d,R3h,Ark), (Ze,Ra,R1d,R3h,Arl), (Ze,Ra,R1d,R3h,Arm), (Ze,Ra,R1d,R3h,Arn), (Ze,Ra,R1d,R3h,Aro), (Ze,Ra,R1d,R3h,Arp), (Ze,Rb,R1a,R3a,Ara), (Ze,Rb,R1a,R3a,Arb), (Ze,Rb,R1a,R3a,Arc), (Ze,Rb,R1a,R3a,Ard), (Ze,Rb,R1a,R3a,Are), (Ze,Rb,R1a,R3a,Arf), (Ze,Rb,R1a,R3a,Arg), (Ze,Rb,R1a,R3a,Arh), (Ze,Rb,R1a,R3a,Ari), (Ze,Rb,R1a,R3a,Arj), (Ze,Rb,R1a,R3a,Ark), (Ze,Rb,R1a,R3a,Arl), (Ze,Rb,R1a,R3a,Arm), (Ze,Rb,R1a,R3a,Arn), (Ze,Rb,R1a,R3a,Aro), (Ze,Rb,R1a,R3a,Arp), (Ze,Rb,R1a,R3b,Ara), (Ze,Rb,R1a,R3b,Arb), (Ze,Rb,R1a,R3b,Arc), (Ze,Rb,R1a,R3b,Ard), (Ze,Rb,R1a,R3b,Are), (Ze,Rb,R1a,R3b,Arf), (Ze,Rb,R1a,R3b,Arg), (Ze,Rb,R1a,R3b,Arh), (Ze,Rb,R1a,R3b,Ari), (Ze,Rb,R1a,R3b,Arj), (Ze,Rb,R1a,R3b,Ark), (Ze,Rb,R1a,R3b,Arl), (Ze,Rb,R1a,R3b,Arm), (Ze,Rb,R1a,R3b,Arn), (Ze,Rb,R1a,R3b,Aro), (Ze,Rb,R1a,R3b,Arp), (Ze,Rb,R1a,R3c,Ara), (Ze,Rb,R1a,R3c,Arb), (Ze,Rb,R1a,R3c,Arc), (Ze,Rb,R1a,R3c,Ard), (Ze,Rb,R1a,R3c,Are), (Ze,Rb,R1a,R3c,Arf), (Ze,Rb,R1a,R3c,Arg), (Ze,Rb,R1a,R3c,Arh), (Ze,Rb,R1a,R3c,Ari), (Ze,Rb,R1a,R3c,Arj), (Ze,Rb,R1a,R3c,Ark), (Ze,Rb,R1a,R3c,Arl), (Ze,Rb,R1a,R3c,Arm), (Ze,Rb,R1a,R3c,Arn), (Ze,Rb,R1a,R3c,Aro), (Ze,Rb,R1a,R3c,Arp), (Ze,Rb,R1a,R3d,Ara), (Ze,Rb,R1a,R3d,Arb), (Ze,Rb,R1a,R3d,Arc), (Ze,Rb,R1a,R3d,Ard), (Ze,Rb,R1a,R3d,Are), (Ze,Rb,R1a,R3d,Arf), (Ze,Rb,R1a,R3d,Arg), (Ze,Rb,R1a,R3d,Arh), (Ze,Rb,R1a,R3d,Ari), (Ze,Rb,R1a,R3d,Arj), (Ze,Rb,R1a,R3d,Ark), (Ze,Rb,R1a,R3d,Arl), (Ze,Rb,R1a,R3d,Arm), (Ze,Rb,R1a,R3d,Arn), (Ze,Rb,R1a,R3d,Aro), (Ze,Rb,R1a,R3d,Arp), (Ze,Rb,R1a,R3e,Ara), (Ze,Rb,R1a,R3e,Arb), (Ze,Rb,R1a,R3e,Arc), (Ze,Rb,R1a,R3e,Ard), (Ze,Rb,R1a,R3e,Are), (Ze,Rb,R1a,R3e,Arf), (Ze,Rb,R1a,R3e,Arg), (Ze,Rb,R1a,R3e,Arh), (Ze,Rb,R1a,R3e,Ari), (Ze,Rb,R1a,R3e,Arj), (Ze,Rb,R1a,R3e,Ark), (Ze,Rb,R1a,R3e,Arl), (Ze,Rb,R1a,R3e,Arm), (Ze,Rb,R1a,R3e,Arn), (Ze,Rb,R1a,R3e,Aro), (Ze,Rb,R1a,R3e,Arp), (Ze,Rb,R1a,R3f,Ara), (Ze,Rb,R1a, R3f,Arb), (Ze,Rb,R1a,R3f,Arc), (Ze,Rb,R1a,R3f,Ard), (Ze,Rb,R1a,R3f,Are), (Ze,Rb,R1a,R3f,Arf), (Ze,Rb,R1a,R3f,Arg), (Ze,Rb,R1a,R3f,Arh), (Ze,Rb,R1a,R3f,Ari), (Ze,Rb,R1a,R3f,Arj), (Ze,Rb,R1a,R3f,Ark), (Ze,Rb,R1a,R3f,Arl), (Ze,Rb,R1a,R3f,Arm), (Ze,Rb,R1a,R3f,Arn), (Ze,Rb,R1a,R3f,Aro), (Ze,Rb,R1a,R3f,Arp), (Ze,Rb,R1a,R3g,Ara), (Ze,Rb,R1a,R3g,Arb), (Ze,Rb,R1a,R3g,Arc), (Ze,Rb,R1a,R3g,Ard), (Ze,Rb,R1a,R3g,Are), (Ze,Rb,R1a,R3g,Arf), (Ze,Rb,R1a,R3g,Arg), (Ze,Rb,R1a,R3g,Arh), (Ze,Rb,R1a,R3g,Ari), (Ze,Rb,R1a,R3g,Arj), (Ze,Rb,R1a,R3g,Ark), (Ze,Rb,R1a,R3g,Arl), (Ze,Rb,R1a,R3g,Arm), (Ze,Rb,R1a,R3g,Arn), (Ze,Rb,R1a,R3g,Aro), (Ze,Rb,R1a,R3g,Arp), (Ze,Rb,R1a,R3h,Ara), (Ze,Rb,R1a,R3h,Arb), (Ze,Rb,R1a,R3h,Arc), (Ze,Rb,R1a,R3h,Ard), (Ze,Rb,R1a,R3h,Are), (Ze,Rb,R1a,R3h,Arf), (Ze,Rb,R1a,R3h,Arg), (Ze,Rb,R1a,R3h,Arh), (Ze,Rb,R1a,R3h,Ari), (Ze,Rb,R1a,R3h,Arj), (Ze,Rb,R1a,R3h,Ark), (Ze,Rb,R1a,R3h,Arl), (Ze,Rb,R1a,R3h,Arm), (Ze,Rb,R1a,R3h,Arn), (Ze,Rb,R1a,R3h,Aro), (Ze,Rb,R1a,R3h,Arp), (Ze,Rb,R1b,R3a,Ara), (Ze,Rb,R1b,R3a,Arb), (Ze,Rb,R1b,R3a,Arc), (Ze,Rb,R1b,R3a,Ard), (Ze,Rb,R1b,R3a,Are), (Ze,Rb,R1b,R3a,Arf), (Ze,Rb,R1b,R3a,Arg), (Ze,Rb,R1b,R3a,Arh), (Ze,Rb,R1b,R3a,Ari), (Ze,Rb,R1b,R3a,Arj), (Ze,Rb,R1b,R3a,Ark), (Ze,Rb,R1b,R3a,Arl), (Ze,Rb,R1b,R3a,Arm), (Ze,Rb,R1b,R3a,Arn), (Ze,Rb,R1b,R3a,Aro), (Ze,Rb,R1b,R3a,Arp), (Ze,Rb,R1b,R3b,Ara), (Ze,Rb,R1b,R3b,Arb), (Ze,Rb,R1b,R3b,Arc), (Ze,Rb,R1b,R3b,Ard), (Ze,Rb,R1b,R3b,Are), (Ze,Rb,R1b,R3b,Arf), (Ze,Rb,R1b,R3b,Arg), (Ze,Rb,R1b,R3b,Arh), (Ze,Rb,R1b,R3b,Ari), (Ze,Rb,R1b,R3b,Arj), (Ze,Rb,R1b,R3b,Ark), (Ze,Rb,R1b,R3b,Arl), (Ze,Rb,R1b,R3b,Arm), (Ze,Rb,R1b,R3b,Arn), (Ze,Rb,R1b,R3b,Aro), (Ze,Rb,R1b,R3b,Arp), (Ze,Rb,R1b,R3c,Ara), (Ze,Rb,R1b,R3c,Arb), (Ze,Rb,R1b,R3c,Arc), (Ze,Rb,R1b,R3c,Ard), (Ze,Rb,R1b,R3c,Are), (Ze,Rb,R1b,R3c,Arf), (Ze,Rb,R1b,R3c,Arg), (Ze,Rb,R1b,R3c,Arh), (Ze,Rb,R1b,R3c,Ari), (Ze,Rb,R1b,R3c,Arj), (Ze,Rb,R1b,R3c,Ark), (Ze,Rb,R1b,R3c,Arl), (Ze,Rb,R1b,R3c,Arm), (Ze,Rb,R1b,R3c,Arn), (Ze,Rb,R1b,R3c,Aro), (Ze,Rb,R1b,R3c,Arp), (Ze,Rb,R1b,R3d,Ara), (Ze,Rb,R1b,R3d,Arb), (Ze,Rb,R1b,R3d,Arc), (Ze,Rb,R1b,R3d,Ard), (Ze,Rb,R1b,R3d,Are), (Ze,Rb,R1b,R3d,Arf), (Ze,Rb,R1b,R3d,Arg), (Ze,Rb,R1b,R3d,Arh), (Ze,Rb,R1b,R3d,Ari), (Ze,Rb,R1b,R3d,Arj), (Ze,Rb,R1b,R3d,Ark), (Ze,Rb,R1b,R3d,Arl), (Ze,Rb,R1b,R3d,Arm), (Ze,Rb,R1b,R3d,Arn), (Ze,Rb,R1b,R3d,Aro), (Ze,Rb,R1b,R3d,Arp), (Ze,Rb,R1b,R3e,Ara), (Ze,Rb,R1b,R3e,Arb), (Ze,Rb,R1b,R3e,Arc), (Ze,Rb,R1b,R3e,Ard), (Ze,Rb,R1b,R3e,Are), (Ze,Rb,R1b,R3e,Arf), (Ze,Rb,R1b,R3e,Arg), (Ze,Rb,R1b,R3e,Arh), (Ze,Rb,R1b,R3e,Ari), (Ze,Rb,R1b,R3e,Arj), (Ze,Rb,R1b,R3e,Ark), (Ze,Rb,R1b,R3e,Arl), (Ze,Rb,R1b,R3e,Arm), (Ze,Rb,R1b,R3e,Arn), (Ze,Rb,R1b,R3e,Aro), (Ze,Rb,R1b,R3e,Arp), (Ze,Rb,R1b,R3f,Ara), (Ze,Rb,R1b,R3f,Arb), (Ze,Rb,R1b,R3f,Arc), (Ze,Rb,R1b,R3f,Ard), (Ze,Rb,R1b,R3f,Are), (Ze,Rb,R1b,R3f,Arf), (Ze,Rb,R1b,R3f,Arg), (Ze,Rb,R1b,R3f,Arh), (Ze,Rb,R1b,R3f,Ari), (Ze,Rb,R1b,R3f,Arj), (Ze,Rb,R1b,R3f,Ark), (Ze,Rb,R1b,R3f,Arl), (Ze,Rb,R1b,R3f,Arm), (Ze,Rb,R1b,R3f,Arn), (Ze,Rb,R1b,R3f,Aro), (Ze,Rb,R1b,R3f,Arp), (Ze,Rb,R1b,R3g,Ara), (Ze,Rb,R1b,R3g,Arb), (Ze,Rb,R1b,R3g,Arc), (Ze,Rb,R1b,R3g,Ard), (Ze,Rb,R1b,R3g,Are), (Ze,Rb,R1b,R3g,Arf), (Ze,Rb,R1b,R3g,Arg), (Ze,Rb,R1b,R3g,Arh), (Ze,Rb,R1b,R3g,Ari), (Ze,Rb,R1b,R3g,Arj), (Ze,Rb,R1b,R3g,Ark), (Ze,Rb,R1b,R3g,Arl), (Ze,Rb,R1b,R3g,Arm), (Ze,Rb,R1b,R3g,Arn), (Ze,Rb,R1b,R3g,Aro), (Ze,Rb,R1b,R3g,Arp), (Ze,Rb,R1b,R3h,Ara), (Ze,Rb,R1b,R3h,Arb), (Ze,Rb,R1b,R3h,Arc), (Ze,Rb,R1b,R3h,Ard), (Ze,Rb,R1b,R3h,Are), (Ze,Rb,R1b,R3h,Arf), (Ze,Rb,R1b,R3h,Arg), (Ze,Rb,R1b,R3h,Arh), (Ze,Rb,R1b,R3h,Ari), (Ze,Rb,R1b,R3h,Arj), (Ze,Rb,R1b,R3h,Ark), (Ze,Rb,R1b,R3h,Arl), (Ze,Rb,R1b,R3h,Arm), (Ze,Rb,R1b,R3h,Arn), (Ze,Rb,R1b,R3h,Aro), (Ze,Rb,R1b,R3h,Arp), (Ze,Rb,R1c,R3a,Ara), (Ze,Rb,R1c,R3a,Arb), (Ze,Rb,R1c,R3a,Arc), (Ze,Rb,R1c,R3a,Ard), (Ze,Rb,R1c,R3a,Are), (Ze,Rb,R1c,R3a,Arf), (Ze,Rb,R1c,R3a,Arg), (Ze,Rb,R1c,R3a,Arh), (Ze,Rb,R1c,R3a,Ari), (Ze,Rb,R1c,R3a,Arj), (Ze,Rb,R1c,R3a,Ark), (Ze,Rb,R1c,R3a,Arl), (Ze,Rb,R1c,R3a,Arm), (Ze,Rb,R1c,R3a,Arn), (Ze,Rb,R1c,R3a,Aro), (Ze,Rb,R1c,R3a,Arp), (Ze,Rb,R1c,R3b,Ara), (Ze,Rb,R1c,R3b,Arb), (Ze,Rb,R1c,R3b,Arc), (Ze,Rb,R1c,R3b,Ard), (Ze,Rb,R1c,R3b,Are), (Ze,Rb,R1c,R3b,Arf), (Ze,Rb,R1c,R3b,Arg), (Ze,Rb,R1c,R3b,Arh), (Ze,Rb,R1c,R3b,Ari), (Ze,Rb,R1c,R3b,Arj), (Ze,Rb,R1c,R3b,Ark), (Ze,Rb,R1c,R3b,Arl), (Ze,Rb,R1c,R3b,Arm), (Ze,Rb,R1c,R3b,Arn), (Ze,Rb,R1c,R3b,Aro), (Ze,Rb,R1c,R3b,Arp), (Ze,Rb,R1c,R3c,Ara), (Ze,Rb,R1c,R3c,Arb), (Ze,Rb,R1c,R3c,Arc), (Ze,Rb,R1c,R3c,Ard), (Ze,Rb,R1c,R3c,Are), (Ze,Rb,R1c,R3c,Arf), (Ze,Rb,R1c,R3c,Arg), (Ze,Rb,R1c,R3c,Arh), (Ze,Rb,R1c,R3c,Ari), (Ze,Rb,R1c,R3c,Arj), (Ze,Rb,R1c,R3c,Ark), (Ze,Rb,R1c,R3c,Arl), (Ze,Rb,R1c,R3c,Arm), (Ze,Rb,R1c,R3c,Arn), (Ze,Rb,R1c,R3c,Aro), (Ze,Rb,R1c,R3c,Arp), (Ze,Rb,R1c,R3d,Ara), (Ze,Rb,R1c,R3d,Arb), (Ze,Rb,R1c,R3d,Arc), (Ze,Rb,R1c,R3d,Ard), (Ze,Rb,R1c,R3d,Are), (Ze,Rb,R1c,R3d,Arf), (Ze,Rb,R1c,R3d,Arg), (Ze,Rb,R1c,R3d,Arh), (Ze,Rb,R1c,R3d,Ari), (Ze,Rb,R1c,R3d,Arj), (Ze,Rb,R1c,R3d,Ark), (Ze,Rb,R1c,R3d,Arl), (Ze,Rb,R1c,R3d,Arm), (Ze,Rb,R1c,R3d,Arn), (Ze,Rb,R1c,R3d,Aro), (Ze,Rb,R1c,R3d,Arp), (Ze,Rb,R1c,R3e,Ara), (Ze,Rb,R1c,R3e,Arb), (Ze,Rb,R1c,R3e,Arc), (Ze,Rb,R1c,R3e,Ard), (Ze,Rb,R1c,R3e,Are), (Ze,Rb,R1c,R3e,Arf), (Ze,Rb,R1c,R3e,Arg), (Ze,Rb,R1c,R3e,Arh), (Ze,Rb,R1c,R3e,Ari), (Ze,Rb,R1c,R3e,Arj), (Ze,Rb,R1c,R3e,Ark), (Ze,Rb,R1c,R3e,Arl), (Ze,Rb,R1c,R3e,Arm), (Ze,Rb,R1c,R3e,Arn), (Ze,Rb,R1c,R3e,Aro), (Ze,Rb,R1c,R3e,Arp), (Ze,Rb,R1c,R3f,Ara), (Ze,Rb,R1c,R3f,Arb), (Ze,Rb,R1c,R3f,Arc), (Ze,Rb,R1c,R3f,Ard), (Ze,Rb,R1c,R3f,Are), (Ze,Rb,R1c,R3f,Arf), (Ze,Rb,R1c,R3f,Arg), (Ze,Rb,R1c,R3f,Arh), (Ze,Rb,R1c,R3f,Ari), (Ze,Rb,R1c,R3f,Arj), (Ze,Rb,R1c,R3f,Ark), (Ze,Rb,R1c,R3f,Arl), (Ze,Rb,R1c,R3f,Arm), (Ze,Rb,R1c,R3f,Arn), (Ze,Rb,R1c,R3f,Aro), (Ze,Rb,R1c,R3f,Arp), (Ze,Rb,R1c,R3g,Ara), (Ze,Rb,R1c,R3g,Arb), (Ze,Rb,R1c,R3g,Arc), (Ze,Rb,R1c,R3g,Ard), (Ze,Rb,R1c,R3g,Are), (Ze,Rb,R1c,R3g,Arf), (Ze,Rb,R1c,R3g,Arg), (Ze,Rb,R1c,R3g,Arh), (Ze,Rb,R1c,R3g,Ari), (Ze,Rb,R1c,R3g,Arj), (Ze,Rb,R1c,R3g,Ark), (Ze,Rb,R1c,R3g,Arl), (Ze,Rb,R1c,R3g,Arm), (Ze,Rb,R1c,R3g,Arn), (Ze,Rb,R1c,R3g,Aro), (Ze,Rb,R1c,R3g,Arp), (Ze,Rb,R1c,R3h,Ara), (Ze,Rb,R1c,R3h,Arb), (Ze,Rb,R1c,R3h,Arc), (Ze,Rb,R1c,R3h,Ard), (Ze,Rb,R1c,R3h,Are), (Ze,Rb,R1c,R3h,Arf), (Ze,Rb,R1c,R3h,Arg), (Ze,Rb,R1c,R3h,Arh), (Ze,Rb,R1c,R3h,Ari), (Ze,Rb,R1c,R3h,Arj), (Ze,Rb,R1c,R3h,Ark), (Ze,Rb,R1c,R3h,Arl), (Ze,Rb,R1c,R3h,Arm), (Ze,Rb,R1c,R3h,Arn), (Ze,Rb,R1c,R3h,Aro), (Ze,Rb,R1c,R3h,Arp), (Ze,Rb,R1d,R3a,Ara), (Ze,Rb,R1d,R3a,Arb), (Ze,Rb,R1d,R3a,Arc), (Ze,Rb,R1d,R3a,Ard), (Ze,Rb,R1d,R3a,Are), (Ze,Rb,R1d,R3a,Arf), (Ze,Rb,R1d,R3a,Arg), (Ze,Rb,R1d,R3a,Arh), (Ze,Rb,R1d,R3a,Ari), (Ze,Rb,R1d,R3a,Arj), (Ze,Rb,R1d,R3a,Ark), (Ze,Rb,R1d,R3a,Arl), (Ze,Rb,R1d,R3a,Arm), (Ze,Rb,R1d,R3a,Arn), (Ze,Rb,R1d,R3a,Aro), (Ze,Rb,R1d,R3a,Arp), (Ze,Rb,R1d,R3b,Ara), (Ze,Rb,R1d,R3b,Arb), (Ze,Rb,R1d,R3b,Arc), (Ze,Rb,R1d,R3b,Ard), (Ze,Rb,R1d,R3b,Are), (Ze,Rb,R1d,R3b,Arf), (Ze,Rb,R1d,R3b,Arg), (Ze,Rb,R1d,R3b,Arh), (Ze,Rb,R1d,R3b,Ari), (Ze,Rb,R1d,R3b,Arj), (Ze,Rb,R1d,R3b,Ark), (Ze,Rb,R1d,R3b,Arl), (Ze,Rb,R1d,R3b,Arm), (Ze,Rb,R1d,R3b,Arn), (Ze,Rb,R1d,R3b,Aro), (Ze,Rb,R1d,R3b,Arp), (Ze,Rb,R1d,R3c,Ara), (Ze,Rb,R1d,R3c,Arb), (Ze,Rb,R1d,R3c,Arc), (Ze,Rb,R1d,R3c,Ard), (Ze,Rb,R1d,R3c,Are), (Ze,Rb,R1d,R3c,Arf), (Ze,Rb,R1d,R3c,Arg), (Ze,Rb,R1d,R3c,Arh), (Ze,Rb,R1d,R3c, Ari), (Ze,Rb,R1d,R3c,Arj), (Ze,Rb,R1d,R3c,Ark), (Ze,Rb, R1d,R3c,Arl), (Ze,Rb,R1d,R3c,Arm), (Ze,Rb,R1d,R3c, Arn), (Ze,Rb,R1d,R3c,Aro), (Ze,Rb,R1d,R3c,Arp), (Ze,Rb, R1d,R3d,Ara), (Ze,Rb,R1d,R3d,Arb), (Ze,Rb,R1d,R3d, Arc), (Ze,Rb,R1d,R3d,Ard), (Ze,Rb,R1d,R3d,Are), (Ze,Rb, R1d,R3d,Arf), (Ze,Rb,R1d,R3d,Arg), (Ze,Rb,R1d,R3d, Arh), (Ze,Rb,R1d,R3d,Ari), (Ze,Rb,R1d,R3d,Arj), (Ze,Rb, R1d,R3d,Ark), (Ze,Rb,R1d,R3d,Arl), (Ze,Rb,R1d,R3d, Arm), (Ze,Rb,R1d,R3d,Arn), (Ze,Rb,R1d,R3d,Aro), (Ze,Rb, R1d,R3d,Arp), (Ze,Rb,R1d,R3e,Ara), (Ze,Rb,R1d,R3e, Arb), (Ze,Rb,R1d,R3e,Arc), (Ze,Rb,R1d,R3e,Ard), (Ze,Rb, R1d,R3e,Are), (Ze,Rb,R1d,R3e,Arf), (Ze,Rb,R1d,R3e,Arg), (Ze,Rb,R1d,R3e,Arh), (Ze,Rb,R1d,R3e,Ari), (Ze,Rb,R1d, R3e,Arj), (Ze,Rb,R1d,R3e,Ark), (Ze,Rb,R1d,R3e,Arl), (Ze, Rb,R1d,R3e,Arm), (Ze,Rb,R1d,R3e,Arn), (Ze,Rb,R1d,R3e, Aro), (Ze,Rb,R1d,R3e,Arp), (Ze,Rb,R1d,R3f,Ara), (Ze,Rb, R1d,R3f,Arb), (Ze,Rb,R1d,R3f,Arc), (Ze,Rb,R1d,R3f,Ard), (Ze,Rb,R1d,R3f,Are), (Ze,Rb,R1d,R3f,Arf), (Ze,Rb,R1d, R3f,Arg), (Ze,Rb,R1d,R3f,Arh), (Ze,Rb,R1d,R3f,Ari), (Ze, Rb,R1d,R3f,Arj), (Ze,Rb,R1d,R3f,Ark), (Ze,Rb,R1d,R3f, Arl), (Ze,Rb,R1d,R3f,Arm), (Ze,Rb,R1d,R3f,Arn), (Ze,Rb, R1d,R3f,Aro), (Ze,Rb,R1d,R3f,Arp), (Ze,Rb,R1d,R3g,Ara), (Ze,Rb,R1d,R3g,Arb), (Ze,Rb,R1d,R3g,Arc), (Ze,Rb,R1d, R3g,Ard), (Ze,Rb,R1d,R3g,Are), (Ze,Rb,R1d,R3g,Arf), (Ze, Rb,R1d,R3g,Arg), (Ze,Rb,R1d,R3g,Arh), (Ze,Rb,R1d,R3g, Ari), (Ze,Rb,R1d,R3g,Arj), (Ze,Rb,R1d,R3g,Ark), (Ze,Rb, R1d,R3g,Arl), (Ze,Rb,R1d,R3g,Arm), (Ze,Rb,R1d,R3g, Arn), (Ze,Rb,R1d,R3g,Aro), (Ze,Rb,R1d,R3g,Arp), (Ze,Rb, R1d,R3h,Ara), (Ze,Rb,R1d,R3h,Arb), (Ze,Rb,R1d,R3h, Arc), (Ze,Rb,R1d,R3h,Ard), (Ze,Rb,R1d,R3h,Are), (Ze,Rb, R1d,R3h,Arf), (Ze,Rb,R1d,R3h,Arg), (Ze,Rb,R1d,R3h, Arh), (Ze,Rb,R1d,R3h,Ari), (Ze,Rb,R1d,R3h,Arj), (Ze,Rb, R1d,R3h,Ark), (Ze,Rb,R1d,R3h,Arl), (Ze,Rb,R1d,R3h, Arm), (Ze,Rb,R1d,R3h,Arn), (Ze,Rb,R1d,R3h,Aro), (Ze,Rb, R1d,R3h,Arp), (Ze,Rc,R1a,R3a,Ara), (Ze,Rc,R1a,R3a,Arb), (Ze,Rc,R1a,R3a,Arc), (Ze,Rc,R1a,R3a,Ard), (Ze,Rc,R1a, R3a,Are), (Ze,Rc,R1a,R3a,Arf), (Ze,Rc,R1a,R3a,Arg), (Ze, Rc,R1a,R3a,Arh), (Ze,Rc,R1a,R3a,Ari), (Ze,Rc,R1a,R3a, Arj), (Ze,Rc,R1a,R3a,Ark), (Ze,Rc,R1a,R3a,Arl), (Ze,Rc, R1a,R3a,Arm), (Ze,Rc,R1a,R3a,Arn), (Ze,Rc,R1a,R3a, Aro), (Ze,Rc,R1a,R3a,Arp), (Ze,Rc,R1a,R3b,Ara), (Ze,Rc, R1a,R3b,Arb), (Ze,Rc,R1a,R3b,Arc), (Ze,Rc,R1a,R3b,Ard), (Ze,Rc,R1a,R3b,Are), (Ze,Rc,R1a,R3b,Arf), (Ze,Rc,R1a, R3b,Arg), (Ze,Rc,R1a,R3b,Arh), (Ze,Rc,R1a,R3b,Ari), (Ze, Rc,R1a,R3b,Arj), (Ze,Rc,R1a,R3b,Ark), (Ze,Rc,R1a,R3b, Arl), (Ze,Rc,R1a,R3b,Arm), (Ze,Rc,R1a,R3b,Arn), (Ze,Rc, R1a,R3b,Aro), (Ze,Rc,R1a,R3b,Arp), (Ze,Rc,R1a,R3c,Ara), (Ze,Rc,R1a,R3c,Arb), (Ze,Rc,R1a,R3c,Arc), (Ze,Rc,R1a, R3c,Ard), (Ze,Rc,R1a,R3c,Are), (Ze,Rc,R1a,R3c,Arf), (Ze, Rc,R1a,R3c,Arg), (Ze,Rc,R1a,R3c,Arh), (Ze,Rc,R1a,R3c, Ari), (Ze,Rc,R1a,R3c,Arj), (Ze,Rc,R1a,R3c,Ark), (Ze,Rc, R1a,R3c,Arl), (Ze,Rc,R1a,R3c,Arm), (Ze,Rc,R1a,R3c,Arn), (Ze,Rc,R1a,R3c,Aro), (Ze,Rc,R1a,R3c,Arp), (Ze,Rc,R1a, R3d,Ara), (Ze,Rc,R1a,R3d,Arb), (Ze,Rc,R1a,R3d,Arc), (Ze, Rc,R1a,R3d,Ard), (Ze,Rc,R1a,R3d,Are), (Ze,Rc,R1a,R3d, Arf), (Ze,Rc,R1a,R3d,Arg), (Ze,Rc,R1a,R3d,Arh), (Ze,Rc, R1a,R3d,Ari), (Ze,Rc,R1a,R3d,Arj), (Ze,Rc,R1a,R3d,Ark), (Ze,Rc,R1a,R3d,Arl), (Ze,Rc,R1a,R3d,Arm), (Ze,Rc,R1a, R3d,Arn), (Ze,Rc,R1a,R3d,Aro), (Ze,Rc,R1a,R3d,Arp), (Ze, Rc,R1a,R3e,Ara), (Ze,Rc,R1a,R3e,Arb), (Ze,Rc,R1a,R3e, Arc), (Ze,Rc,R1a,R3e,Ard), (Ze,Rc,R1a,R3e,Are), (Ze,Rc, R1a,R3e,Arf), (Ze,Rc,R1a,R3e,Arg), (Ze,Rc,R1a,R3e,Arh), (Ze,Rc,R1a,R3e,Ari), (Ze,Rc,R1a,R3e,Arj), (Ze,Rc,R1a, R3e,Ark), (Ze,Rc,R1a,R3e,Arl), (Ze,Rc,R1a,R3e,Arm), (Ze, Rc,R1a,R3e,Arn), (Ze,Rc,R1a,R3e,Aro), (Ze,Rc,R1a,R3e, Arp), (Ze,Rc,R1a,R3f,Ara), (Ze,Rc,R1a,R3f,Arb), (Ze,Rc, R1a,R3f,Arc), (Ze,Rc,R1a,R3f,Ard), (Ze,Rc,R1a,R3f,Are), (Ze,Rc,R1a,R3f,Arf), (Ze,Rc,R1a,R3f,Arg), (Ze,Rc,R1a, R3f,Arh), (Ze,Rc,R1a,R3f,Ari), (Ze,Rc,R1a,R3f,Arj), (Ze, Rc,R1a,R3f,Ark), (Ze,Rc,R1a,R3f,Arl), (Ze,Rc,R1a,R3f, Arm), (Ze,Rc,R1a,R3f,Arn), (Ze,Rc,R1a,R3f,Aro), (Ze,Rc, R1a,R3f,Arp), (Ze,Rc,R1a,R3g,Ara), (Ze,Rc,R1a,R3g,Arb), (Ze,Rc,R1a,R3g,Arc), (Ze,Rc,R1a,R3g,Ard), (Ze,Rc,R1a, R3g,Are), (Ze,Rc,R1a,R3g,Arf), (Ze,Rc,R1a,R3g,Arg), (Ze, Rc,R1a,R3g,Arh), (Ze,Rc,R1a,R3g,Ari), (Ze,Rc,R1a,R3g, Arj), (Ze,Rc,R1a,R3g,Ark), (Ze,Rc,R1a,R3g,Arl), (Ze,Rc, R1a,R3g,Arm), (Ze,Rc,R1a,R3g,Arn), (Ze,Rc,R1a,R3g, Aro), (Ze,Rc,R1a,R3g,Arp), (Ze,Rc,R1a,R3h,Ara), (Ze,Rc, R1a,R3h,Arb), (Ze,Rc,R1a,R3h,Arc), (Ze,Rc,R1a,R3h,Ard), (Ze,Rc,R1a,R3h,Are), (Ze,Rc,R1a,R3h,Arf), (Ze,Rc,R1a, R3h,Arg), (Ze,Rc,R1a,R3h,Arh), (Ze,Rc,R1a,R3h,Ari), (Ze, Rc,R1a,R3h,Arj), (Ze,Rc,R1a,R3h,Ark), (Ze,Rc,R1a,R3h, Arl), (Ze,Rc,R1a,R3h,Arm), (Ze,Rc,R1a,R3h,Arn), (Ze,Rc, R1a,R3h,Aro), (Ze,Rc,R1a,R3h,Arp), (Ze,Rc,R1b,R3a,Ara), (Ze,Rc,R1b,R3a,Arb), (Ze,Rc,R1b,R3a,Arc), (Ze,Rc,R1b, R3a,Ard), (Ze,Rc,R1b,R3a,Are), (Ze,Rc,R1b,R3a,Arf), (Ze, Rc,R1b,R3a,Arg), (Ze,Rc,R1b,R3a,Arh), (Ze,Rc,R1b,R3a, Ari), (Ze,Rc,R1b,R3a,Arj), (Ze,Rc,R1b,R3a,Ark), (Ze,Rc, R1b,R3a,Arl), (Ze,Rc,R1b,R3a,Arm), (Ze,Rc,R1b,R3a, Arn), (Ze,Rc,R1b,R3a,Aro), (Ze,Rc,R1b,R3a,Arp), (Ze,Rc, R1b,R3b,Ara), (Ze,Rc,R1b,R3b,Arb), (Ze,Rc,R1b,R3b, Arc), (Ze,Rc,R1b,R3b,Ard), (Ze,Rc,R1b,R3b,Are), (Ze,Rc, R1b,R3b,Arf), (Ze,Rc,R1b,R3b,Arg), (Ze,Rc,R1b,R3b, Arh), (Ze,Rc,R1b,R3b,Ari), (Ze,Rc,R1b,R3b,Arj), (Ze,Rc, R1b,R3b,Ark), (Ze,Rc,R1b,R3b,Arl), (Ze,Rc,R1b,R3b, Arm), (Ze,Rc,R1b,R3b,Arn), (Ze,Rc,R1b,R3b,Aro), (Ze,Rc, R1b,R3b,Arp), (Ze,Rc,R1b,R3c,Ara), (Ze,Rc,R1b,R3c, Arb), (Ze,Rc,R1b,R3c,Arc), (Ze,Rc,R1b,R3c,Ard), (Ze,Rc, R1b,R3c,Are), (Ze,Rc,R1b,R3c,Arf), (Ze,Rc,R1b,R3c,Arg), (Ze,Rc,R1b,R3c,Arh), (Ze,Rc,R1b,R3c,Ari), (Ze,Rc,R1b, R3c,Arj), (Ze,Rc,R1b,R3c,Ark), (Ze,Rc,R1b,R3c,Arl), (Ze, Rc,R1b,R3c,Arm), (Ze,Rc,R1b,R3c,Arn), (Ze,Rc,R1b,R3c, Aro), (Ze,Rc,R1b,R3c,Arp), (Ze,Rc,R1b,R3d,Ara), (Ze,Rc, R1b,R3d,Arb), (Ze,Rc,R1b,R3d,Arc), (Ze,Rc,R1b,R3d, Ard), (Ze,Rc,R1b,R3d,Are), (Ze,Rc,R1b,R3d,Arf), (Ze,Rc, R1b,R3d,Arg), (Ze,Rc,R1b,R3d,Arh), (Ze,Rc,R1b,R3d,Ari), (Ze,Rc,R1b,R3d,Arj), (Ze,Rc,R1b,R3d,Ark), (Ze,Rc,R1b, R3d,Arl), (Ze,Rc,R1b,R3d,Arm), (Ze,Rc,R1b,R3d,Arn), (Ze,Rc,R1b,R3d,Aro), (Ze,Rc,R1b,R3d,Arp), (Ze,Rc,R1b, R3e,Ara), (Ze,Rc,R1b,R3e,Arb), (Ze,Rc,R1b,R3e,Arc), (Ze, Rc,R1b,R3e,Ard), (Ze,Rc,R1b,R3e,Are), (Ze,Rc,R1b,R3e, Arf), (Ze,Rc,R1b,R3e,Arg), (Ze,Rc,R1b,R3e,Arh), (Ze,Rc, R1b,R3e,Ari), (Ze,Rc,R1b,R3e,Arj), (Ze,Rc,R1b,R3e,Ark), (Ze,Rc,R1b,R3e,Arl), (Ze,Rc,R1b,R3e,Arm), (Ze,Rc,R1b, R3e,Arn), (Ze,Rc,R1b,R3e,Aro), (Ze,Rc,R1b,R3e,Arp), (Ze, Rc,R1b,R3f,Ara), (Ze,Rc,R1b,R3f,Arb), (Ze,Rc,R1b,R3f, Arc), (Ze,Rc,R1b,R3f,Ard), (Ze,Rc,R1b,R3f,Are), (Ze,Rc, R1b,R3f,Arf), (Ze,Rc,R1b,R3f,Arg), (Ze,Rc,R1b,R3f,Arh), (Ze,Rc,R1b,R3f,Ari), (Ze,Rc,R1b,R3f,Arj), (Ze,Rc,R1b, R3f,Ark), (Ze,Rc,R1b,R3f,Arl), (Ze,Rc,R1b,R3f,Arm), (Ze, Rc,R1b,R3f,Arn), (Ze,Rc,R1b,R3f,Aro), (Ze,Rc,R1b,R3f, Arp), (Ze,Rc,R1b,R3g,Ara), (Ze,Rc,R1b,R3g,Arb), (Ze,Rc, R1b,R3g,Arc), (Ze,Rc,R1b,R3g,Ard), (Ze,Rc,R1b,R3g, Are), (Ze,Rc,R1b,R3g,Arf), (Ze,Rc,R1b,R3g,Arg), (Ze,Rc, R1b,R3g,Arh), (Ze,Rc,R1b,R3g,Ari), (Ze,Rc,R1b,R3g,Arj), (Ze,Rc,R1b,R3g,Ark), (Ze,Rc,R1b,R3g,Arl), (Ze,Rc,R1b, R3g,Arm), (Ze,Rc,R1b,R3g,Arn), (Ze,Rc,R1b,R3g,Aro), (Ze,Rc,R1b,R3g,Arp), (Ze,Rc,R1b,R3h,Ara), (Ze,Rc,R1b, R3h,Arb), (Ze,Rc,R1b,R3h,Arc), (Ze,Rc,R1b,R3h,Ard), (Ze,Rc,R1b,R3h,Are), (Ze,Rc,R1b,R3h,Arf), (Ze,Rc,R1b, R3h,Arg), (Ze,Rc,R1b,R3h,Arh), (Ze,Rc,R1b,R3h,Ari), (Ze, Rc,R1b,R3h,Arj), (Ze,Rc,R1b,R3h,Ark), (Ze,Rc,R1b,R3h, Arl), (Ze,Rc,R1b,R3h,Arm), (Ze,Rc,R1b,R3h,Arn), (Ze,Rc, R1b,R3h,Aro), (Ze,Rc,R1b,R3h,Arp), (Ze,Rc,R1c,R3a, Ara), (Ze,Rc,R1c,R3a,Arb), (Ze,Rc,R1c,R3a,Arc), (Ze,Rc,R1c,R3a,Ard), (Ze,Rc,R1c,R3a,Are), (Ze,Rc,R1c,R3a,Arf), (Ze,Rc,R1c,R3a,Arg), (Ze,Rc,R1c,R3a,Arh), (Ze,Rc,R1c,R3a,Ari), (Ze,Rc,R1c,R3a,Arj), (Ze,Rc,R1c,R3a,Ark), (Ze,Rc,R1c,R3a,Arl), (Ze,Rc,R1c,R3a,Arm), (Ze,Rc,R1c,R3a,Arn), (Ze,Rc,R1c,R3a,Aro), (Ze,Rc,R1c,R3a,Arp), (Ze,Rc,R1c,R3b,Ara), (Ze,Rc,R1c,R3b,Arb), (Ze,Rc,R1c,R3b,Arc), (Ze,Rc,R1c,R3b,Ard), (Ze,Rc,R1c,R3b,Are), (Ze,Rc,R1c,R3b,Arf), (Ze,Rc,R1c,R3b,Arg), (Ze,Rc,R1c,R3b,Arh), (Ze,Rc,R1c,R3b,Ari), (Ze,Rc,R1c,R3b,Arj), (Ze,Rc,R1c,R3b,Ark), (Ze,Rc,R1c,R3b,Arl), (Ze,Rc,R1c,R3b,Arm), (Ze,Rc,R1c,R3b,Arn), (Ze,Rc,R1c,R3b,Aro), (Ze,Rc,R1c,R3b,Arp), (Ze,Rc,R1c,R3c,Ara), (Ze,Rc,R1c,R3c,Arb), (Ze,Rc,R1c,R3c,Arc), (Ze,Rc,R1c,R3c,Ard), (Ze,Rc,R1c,R3c,Are), (Ze,Rc,R1c,R3c,Arf), (Ze,Rc,R1c,R3c,Arg), (Ze,Rc,R1c,R3c,Arh), (Ze,Rc,R1c,R3c,Ari), (Ze,Rc,R1c,R3c,Arj), (Ze,Rc,R1c,R3c,Ark), (Ze,Rc,R1c,R3c,Arl), (Ze,Rc,R1c,R3c,Arm), (Ze,Rc,R1c,R3c,Arn), (Ze,Rc,R1c,R3c,Aro), (Ze,Rc,R1c,R3c,Arp), (Ze,Rc,R1c,R3d,Ara), (Ze,Rc,R1c,R3d,Arb), (Ze,Rc,R1c,R3d,Arc), (Ze,Rc,R1c,R3d,Ard), (Ze,Rc,R1c,R3d,Are), (Ze,Rc,R1c,R3d,Arf), (Ze,Rc,R1c,R3d,Arg), (Ze,Rc,R1c,R3d,Arh), (Ze,Rc,R1c,R3d,Ari), (Ze,Rc,R1c,R3d,Arj), (Ze,Rc,R1c,R3d,Ark), (Ze,Rc,R1c,R3d,Arl), (Ze,Rc,R1c,R3d,Arm), (Ze,Rc,R1c,R3d,Arn), (Ze,Rc,R1c,R3d,Aro), (Ze,Rc,R1c,R3d,Arp), (Ze,Rc,R1c,R3e,Ara), (Ze,Rc,R1c,R3e,Arb), (Ze,Rc,R1c,R3e,Arc), (Ze,Rc,R1c,R3e,Ard), (Ze,Rc,R1c,R3e,Are), (Ze,Rc,R1c,R3e,Arf), (Ze,Rc,R1c,R3e,Arg), (Ze,Rc,R1c,R3e,Arh), (Ze,Rc,R1c,R3e,Ari), (Ze,Rc,R1c,R3e,Arj), (Ze,Rc,R1c,R3e,Ark), (Ze,Rc,R1c,R3e,Arl), (Ze,Rc,R1c,R3e,Arm), (Ze,Rc,R1c,R3e,Arn), (Ze,Rc,R1c,R3e,Aro), (Ze,Rc,R1c,R3e,Arp), (Ze,Rc,R1c,R3f,Ara), (Ze,Rc,R1c,R3f,Arb), (Ze,Rc,R1c,R3f,Arc), (Ze,Rc,R1c,R3f,Ard), (Ze,Rc,R1c,R3f,Are), (Ze,Rc,R1c,R3f,Arf), (Ze,Rc,R1c,R3f,Arg), (Ze,Rc,R1c,R3f,Arh), (Ze,Rc,R1c,R3f,Ari), (Ze,Rc,R1c,R3f,Arj), (Ze,Rc,R1c,R3f,Ark), (Ze,Rc,R1c,R3f,Arl), (Ze,Rc,R1c,R3f,Arm), (Ze,Rc,R1c,R3f,Arn), (Ze,Rc,R1c,R3f,Aro), (Ze,Rc,R1c,R3f,Arp), (Ze,Rc,R1c,R3g,Ara), (Ze,Rc,R1c,R3g,Arb), (Ze,Rc,R1c,R3g,Arc), (Ze,Rc,R1c,R3g,Ard), (Ze,Rc,R1c,R3g,Are), (Ze,Rc,R1c,R3g,Arf), (Ze,Rc,R1c,R3g,Arg), (Ze,Rc,R1c,R3g,Arh), (Ze,Rc,R1c,R3g,Ari), (Ze,Rc,R1c,R3g,Arj), (Ze,Rc,R1c,R3g,Ark), (Ze,Rc,R1c,R3g,Arl), (Ze,Rc,R1c,R3g,Arm), (Ze,Rc,R1c,R3g,Arn), (Ze,Rc,R1c,R3g,Aro), (Ze,Rc,R1c,R3g,Arp), (Ze,Rc,R1c,R3h,Ara), (Ze,Rc,R1c,R3h,Arb), (Ze,Rc,R1c,R3h,Arc), (Ze,Rc,R1c,R3h,Ard), (Ze,Rc,R1c,R3h,Are), (Ze,Rc,R1c,R3h,Arf), (Ze,Rc,R1c,R3h,Arg), (Ze,Rc,R1c,R3h,Arh), (Ze,Rc,R1c,R3h,Ari), (Ze,Rc,R1c,R3h,Arj), (Ze,Rc,R1c,R3h,Ark), (Ze,Rc,R1c,R3h,Arl), (Ze,Rc,R1c,R3h,Arm), (Ze,Rc,R1c,R3h,Arn), (Ze,Rc,R1c,R3h,Aro), (Ze,Rc,R1c,R3h,Arp), (Ze,Rc,R1d,R3a,Ara), (Ze,Rc,R1d,R3a,Arb), (Ze,Rc,R1d,R3a,Arc), (Ze,Rc,R1d,R3a,Ard), (Ze,Rc,R1d,R3a,Are), (Ze,Rc,R1d,R3a,Arf), (Ze,Rc,R1d,R3a,Arg), (Ze,Rc,R1d,R3a,Arh), (Ze,Rc,R1d,R3a,Ari), (Ze,Rc,R1d,R3a,Arj), (Ze,Rc,R1d,R3a,Ark), (Ze,Rc,R1d,R3a,Arl), (Ze,Rc,R1d,R3a,Arm), (Ze,Rc,R1d,R3a,Arn), (Ze,Rc,R1d,R3a,Aro), (Ze,Rc,R1d,R3a,Arp), (Ze,Rc,R1d,R3b,Ara), (Ze,Rc,R1d,R3b,Arb), (Ze,Rc,R1d,R3b,Arc), (Ze,Rc,R1d,R3b,Ard), (Ze,Rc,R1d,R3b,Are), (Ze,Rc,R1d,R3b,Arf), (Ze,Rc,R1d,R3b,Arg), (Ze,Rc,R1d,R3b,Arh), (Ze,Rc,R1d,R3b,Ari), (Ze,Rc,R1d,R3b,Arj), (Ze,Rc,R1d,R3b,Ark), (Ze,Rc,R1d,R3b,Arl), (Ze,Rc,R1d,R3b,Arm), (Ze,Rc,R1d,R3b,Arn), (Ze,Rc,R1d,R3b,Aro), (Ze,Rc,R1d,R3b,Arp), (Ze,Rc,R1d,R3c,Ara), (Ze,Rc,R1d,R3c,Arb), (Ze,Rc,R1d,R3c,Arc), (Ze,Rc,R1d,R3c,Ard), (Ze,Rc,R1d,R3c,Are), (Ze,Rc,R1d,R3c,Arf), (Ze,Rc,R1d,R3c,Arg), (Ze,Rc,R1d,R3c,Arh), (Ze,Rc,R1d,R3c,Ari), (Ze,Rc,R1d,R3c,Arj), (Ze,Rc,R1d,R3c,Ark), (Ze,Rc,R1d,R3c,Arl), (Ze,Rc,R1d,R3c,Arm), (Ze,Rc,R1d,R3c,Arn), (Ze,Rc,R1d,R3c,Aro), (Ze,Rc,R1d,R3c,Arp), (Ze,Rc,R1d,R3d,Ara), (Ze,Rc,R1d,R3d,Arb), (Ze,Rc,R1d,R3d,Arc), (Ze,Rc,R1d,R3d,Ard), (Ze,Rc,R1d,R3d,Are), (Ze,Rc,R1d,R3d,Arf), (Ze,Rc,R1d,R3d,Arg), (Ze,Rc,R1d,R3d,Arh), (Ze,Rc,R1d,R3d,Ari), (Ze,Rc,R1d,R3d,Arj), (Ze,Rc,R1d,R3d,Ark), (Ze,Rc,R1d,R3d,Arl), (Ze,Rc,R1d,R3d,Arm), (Ze,Rc,R1d,R3d,Arn), (Ze,Rc,R1d,R3d,Aro), (Ze,Rc,R1d,R3d,Arp), (Ze,Rc,R1d,R3e,Ara), (Ze,Rc,R1d,R3e,Arb), (Ze,Rc,R1d,R3e,Arc), (Ze,Rc,R1d,R3e,Ard), (Ze,Rc,R1d,R3e,Are), (Ze,Rc,R1d,R3e,Arf), (Ze,Rc,R1d,R3e,Arg), (Ze,Rc,R1d,R3e,Arh), (Ze,Rc,R1d,R3e,Ari), (Ze,Rc,R1d,R3e,Arj), (Ze,Rc,R1d,R3e,Ark), (Ze,Rc,R1d,R3e,Arl), (Ze,Rc,R1d,R3e,Arm), (Ze,Rc,R1d,R3e,Arn), (Ze,Rc,R1d,R3e,Aro), (Ze,Rc,R1d,R3e,Arp), (Ze,Rc,R1d,R3f,Ara), (Ze,Rc,R1d,R3f,Arb), (Ze,Rc,R1d,R3f,Arc), (Ze,Rc,R1d,R3f,Ard), (Ze,Rc,R1d,R3f,Are), (Ze,Rc,R1d,R3f,Arf), (Ze,Rc,R1d,R3f,Arg), (Ze,Rc,R1d,R3f,Arh), (Ze,Rc,R1d,R3f,Ari), (Ze,Rc,R1d,R3f,Arj), (Ze,Rc,R1d,R3f,Ark), (Ze,Rc,R1d,R3f,Arl), (Ze,Rc,R1d,R3f,Arm), (Ze,Rc,R1d,R3f,Arn), (Ze,Rc,R1d,R3f,Aro), (Ze,Rc,R1d,R3f,Arp), (Ze,Rc,R1d,R3g,Ara), (Ze,Rc,R1d,R3g,Arb), (Ze,Rc,R1d,R3g,Arc), (Ze,Rc,R1d,R3g,Ard), (Ze,Rc,R1d,R3g,Are), (Ze,Rc,R1d,R3g,Arf), (Ze,Rc,R1d,R3g,Arg), (Ze,Rc,R1d,R3g,Arh), (Ze,Rc,R1d,R3g,Ari), (Ze,Rc,R1d,R3g,Arj), (Ze,Rc,R1d,R3g,Ark), (Ze,Rc,R1d,R3g,Arl), (Ze,Rc,R1d,R3g,Arm), (Ze,Rc,R1d,R3g,Arn), (Ze,Rc,R1d,R3g,Aro), (Ze,Rc,R1d,R3g,Arp), (Ze,Rc,R1d,R3h,Ara), (Ze,Rc,R1d,R3h,Arb), (Ze,Rc,R1d,R3h,Arc), (Ze,Rc,R1d,R3h,Ard), (Ze,Rc,R1d,R3h,Are), (Ze,Rc,R1d,R3h,Arf), (Ze,Rc,R1d,R3h,Arg), (Ze,Rc,R1d,R3h,Arh), (Ze,Rc,R1d,R3h,Ari), (Ze,Rc,R1d,R3h,Arj), (Ze,Rc,R1d,R3h,Ark), (Ze,Rc,R1d,R3h,Arl), (Ze,Rc,R1d,R3h,Arm), (Ze,Rc,R1d,R3h,Arn), (Ze,Rc,R1d,R3h,Aro), (Ze,Rc,R1d,R3h,Arp), (Ze,Rd,R1a,R3a,Ara), (Ze,Rd,R1a,R3a,Arb), (Ze,Rd,R1a,R3a,Arc), (Ze,Rd,R1a,R3a,Ard), (Ze,Rd,R1a,R3a,Are), (Ze,Rd,R1a,R3a,Arf), (Ze,Rd,R1a,R3a,Arg), (Ze,Rd,R1a,R3a,Arh), (Ze,Rd,R1a,R3a,Ari), (Ze,Rd,R1a,R3a,Arj), (Ze,Rd,R1a,R3a,Ark), (Ze,Rd,R1a,R3a,Arl), (Ze,Rd,R1a,R3a,Arm), (Ze,Rd,R1a,R3a,Arn), (Ze,Rd,R1a,R3a,Aro), (Ze,Rd,R1a,R3a,Arp), (Ze,Rd,R1a,R3b,Ara), (Ze,Rd,R1a,R3b,Arb), (Ze,Rd,R1a,R3b,Arc), (Ze,Rd,R1a,R3b,Ard), (Ze,Rd,R1a,R3b,Are), (Ze,Rd,R1a,R3b,Arf), (Ze,Rd,R1a,R3b,Arg), (Ze,Rd,R1a,R3b,Arh), (Ze,Rd,R1a,R3b,Ari), (Ze,Rd,R1a,R3b,Arj), (Ze,Rd,R1a,R3b,Ark), (Ze,Rd,R1a,R3b,Arl), (Ze,Rd,R1a,R3b,Arm), (Ze,Rd,R1a,R3b,Arn), (Ze,Rd,R1a,R3b,Aro), (Ze,Rd,R1a,R3b,Arp), (Ze,Rd,R1a,R3c,Ara), (Ze,Rd,R1a,R3c,Arb), (Ze,Rd,R1a,R3c,Arc), (Ze,Rd,R1a,R3c,Ard), (Ze,Rd,R1a,R3c,Are), (Ze,Rd,R1a,R3c,Arf), (Ze,Rd,R1a,R3c,Arg), (Ze,Rd,R1a,R3c,Arh), (Ze,Rd,R1a,R3c,Ari), (Ze,Rd,R1a,R3c,Arj), (Ze,Rd,R1a,R3c,Ark), (Ze,Rd,R1a,R3c,Arl), (Ze,Rd,R1a,R3c,Arm), (Ze,Rd,R1a,R3c,Arn), (Ze,Rd,R1a,R3c,Aro), (Ze,Rd,R1a,R3c,Arp), (Ze,Rd,R1a,R3d,Ara), (Ze,Rd,R1a,R3d,Arb), (Ze,Rd,R1a,R3d,Arc), (Ze,Rd,R1a,R3d,Ard), (Ze,Rd,R1a,R3d,Are), (Ze,Rd,R1a,R3d,Arf), (Ze,Rd,R1a,R3d,Arg), (Ze,Rd,R1a,R3d,Arh), (Ze,Rd,R1a,R3d,Ari), (Ze,Rd,R1a,R3d,Arj), (Ze,Rd,R1a,R3d,Ark), (Ze,Rd,R1a,R3d,Arl), (Ze,Rd,R1a,R3d,Arm), (Ze,Rd,R1a,R3d,Arn), (Ze,Rd,R1a,R3d,Aro), (Ze,Rd,R1a,R3d,Arp), (Ze,Rd,R1a,R3e,Ara), (Ze,Rd,R1a,R3e,Arb), (Ze,Rd,R1a,R3e,Arc), (Ze,Rd,R1a,R3e,Ard), (Ze,Rd,R1a,R3e,Are), (Ze,Rd,R1a,R3e,Arf), (Ze,Rd,R1a,R3e,Arg), (Ze,Rd,R1a,R3e,Arh), (Ze,Rd,R1a,R3e,Ari), (Ze,Rd,R1a,R3e,Arj), (Ze,Rd,R1a,R3e,Ark), (Ze,Rd,R1a,R3e,Arl), (Ze,Rd,R1a,R3e,Arm), (Ze,Rd,R1a,R3e,Arn), (Ze,Rd,R1a,R3e,Aro), (Ze,Rd,R1a,R3e,Arp), (Ze,Rd,R1a,R3f,Ara), (Ze,Rd,R1a,R3f,Arb), (Ze,Rd,R1a,R3f,Arc), (Ze,Rd,R1a,R3f,Ard), (Ze,Rd,R1a,R3f,Are), (Ze,Rd,R1a,R3f,Arf), (Ze,Rd,R1a,R3f,Arg), (Ze,Rd,R1a,R3f,Arh), (Ze,Rd,R1a,R3f,Ari), (Ze,Rd, R1a,R3f,Arj), (Ze,Rd,R1a,R3f,Ark), (Ze,Rd,R1a,R3f,Arl), (Ze,Rd,R1a,R3f,Arm), (Ze,Rd,R1a,R3f,Arn), (Ze,Rd,R1a,R3f,Aro), (Ze,Rd,R1a,R3f,Arp), (Ze,Rd,R1a,R3g,Ara), (Ze,Rd,R1a,R3g,Arb), (Ze,Rd,R1a,R3g,Arc), (Ze,Rd,R1a,R3g,Ard), (Ze,Rd,R1a,R3g,Are), (Ze,Rd,R1a,R3g,Arf), (Ze,Rd,R1a,R3g,Arg), (Ze,Rd,R1a,R3g,Arh), (Ze,Rd,R1a,R3g,Ari), (Ze,Rd,R1a,R3g,Arj), (Ze,Rd,R1a,R3g,Ark), (Ze,Rd,R1a,R3g,Arl), (Ze,Rd,R1a,R3g,Arm), (Ze,Rd,R1a,R3g,Arn), (Ze,Rd,R1a,R3g,Aro), (Ze,Rd,R1a,R3g,Arp), (Ze,Rd,R1a,R3h,Ara), (Ze,Rd,R1a,R3h,Arb), (Ze,Rd,R1a,R3h,Arc), (Ze,Rd,R1a,R3h,Ard), (Ze,Rd,R1a,R3h,Are), (Ze,Rd,R1a,R3h,Arf), (Ze,Rd,R1a,R3h,Arg), (Ze,Rd,R1a,R3h,Arh), (Ze,Rd,R1a,R3h,Ari), (Ze,Rd,R1a,R3h,Arj), (Ze,Rd,R1a,R3h,Ark), (Ze,Rd,R1a,R3h,Arl), (Ze,Rd,R1a,R3h,Arm), (Ze,Rd,R1a,R3h,Arn), (Ze,Rd,R1a,R3h,Aro), (Ze,Rd,R1a,R3h,Arp), (Ze,Rd,R1b,R3a,Ara), (Ze,Rd,R1b,R3a,Arb), (Ze,Rd,R1b,R3a,Arc), (Ze,Rd,R1b,R3a,Ard), (Ze,Rd,R1b,R3a,Are), (Ze,Rd,R1b,R3a,Arf), (Ze,Rd,R1b,R3a,Arg), (Ze,Rd,R1b,R3a,Arh), (Ze,Rd,R1b,R3a,Ari), (Ze,Rd,R1b,R3a,Arj), (Ze,Rd,R1b,R3a,Ark), (Ze,Rd,R1b,R3a,Arl), (Ze,Rd,R1b,R3a,Arm), (Ze,Rd,R1b,R3a,Arn), (Ze,Rd,R1b,R3a,Aro), (Ze,Rd,R1b,R3a,Arp), (Ze,Rd,R1b,R3b,Ara), (Ze,Rd,R1b,R3b,Arb), (Ze,Rd,R1b,R3b,Arc), (Ze,Rd,R1b,R3b,Ard), (Ze,Rd,R1b,R3b,Are), (Ze,Rd,R1b,R3b,Arf), (Ze,Rd,R1b,R3b,Arg), (Ze,Rd,R1b,R3b,Arh), (Ze,Rd,R1b,R3b,Ari), (Ze,Rd,R1b,R3b,Arj), (Ze,Rd,R1b,R3b,Ark), (Ze,Rd,R1b,R3b,Arl), (Ze,Rd,R1b,R3b,Arm), (Ze,Rd,R1b,R3b,Arn), (Ze,Rd,R1b,R3b,Aro), (Ze,Rd,R1b,R3b,Arp), (Ze,Rd,R1b,R3c,Ara), (Ze,Rd,R1b,R3c,Arb), (Ze,Rd,R1b,R3c,Arc), (Ze,Rd,R1b,R3c,Ard), (Ze,Rd,R1b,R3c,Are), (Ze,Rd,R1b,R3c,Arf), (Ze,Rd,R1b,R3c,Arg), (Ze,Rd,R1b,R3c,Arh), (Ze,Rd,R1b,R3c,Ari), (Ze,Rd,R1b,R3c,Arj), (Ze,Rd,R1b,R3c,Ark), (Ze,Rd,R1b,R3c,Arl), (Ze,Rd,R1b,R3c,Arm), (Ze,Rd,R1b,R3c,Arn), (Ze,Rd,R1b,R3c,Aro), (Ze,Rd,R1b,R3c,Arp), (Ze,Rd,R1b,R3d,Ara), (Ze,Rd,R1b,R3d,Arb), (Ze,Rd,R1b,R3d,Arc), (Ze,Rd,R1b,R3d,Ard), (Ze,Rd,R1b,R3d,Are), (Ze,Rd,R1b,R3d,Arf), (Ze,Rd,R1b,R3d,Arg), (Ze,Rd,R1b,R3d,Arh), (Ze,Rd,R1b,R3d,Ari), (Ze,Rd,R1b,R3d,Arj), (Ze,Rd,R1b,R3d,Ark), (Ze,Rd,R1b,R3d,Arl), (Ze,Rd,R1b,R3d,Arm), (Ze,Rd,R1b,R3d,Arn), (Ze,Rd,R1b,R3d,Aro), (Ze,Rd,R1b,R3d,Arp), (Ze,Rd,R1b,R3e,Ara), (Ze,Rd,R1b,R3e,Arb), (Ze,Rd,R1b,R3e,Arc), (Ze,Rd,R1b,R3e,Ard), (Ze,Rd,R1b,R3e,Are), (Ze,Rd,R1b,R3e,Arf), (Ze,Rd,R1b,R3e,Arg), (Ze,Rd,R1b,R3e,Arh), (Ze,Rd,R1b,R3e,Ari), (Ze,Rd,R1b,R3e,Arj), (Ze,Rd,R1b,R3e,Ark), (Ze,Rd,R1b,R3e,Arl), (Ze,Rd,R1b,R3e,Arm), (Ze,Rd,R1b,R3e,Arn), (Ze,Rd,R1b,R3e,Aro), (Ze,Rd,R1b,R3e,Arp), (Ze,Rd,R1b,R3f,Ara), (Ze,Rd,R1b,R3f,Arb), (Ze,Rd,R1b,R3f,Arc), (Ze,Rd,R1b,R3f,Ard), (Ze,Rd,R1b,R3f,Are), (Ze,Rd,R1b,R3f,Arf), (Ze,Rd,R1b,R3f,Arg), (Ze,Rd,R1b,R3f,Arh), (Ze,Rd,R1b,R3f,Ari), (Ze,Rd,R1b,R3f,Arj), (Ze,Rd,R1b,R3f,Ark), (Ze,Rd,R1b,R3f,Arl), (Ze,Rd,R1b,R3f,Arm), (Ze,Rd,R1b,R3f,Arn), (Ze,Rd,R1b,R3f,Aro), (Ze,Rd,R1b,R3f,Arp), (Ze,Rd,R1b,R3g,Ara), (Ze,Rd,R1b,R3g,Arb), (Ze,Rd,R1b,R3g,Arc), (Ze,Rd,R1b,R3g,Ard), (Ze,Rd,R1b,R3g,Are), (Ze,Rd,R1b,R3g,Arf), (Ze,Rd,R1b,R3g,Arg), (Ze,Rd,R1b,R3g,Arh), (Ze,Rd,R1b,R3g,Ari), (Ze,Rd,R1b,R3g,Arj), (Ze,Rd,R1b,R3g,Ark), (Ze,Rd,R1b,R3g,Arl), (Ze,Rd,R1b,R3g,Arm), (Ze,Rd,R1b,R3g,Arn), (Ze,Rd,R1b,R3g,Aro), (Ze,Rd,R1b,R3g,Arp), (Ze,Rd,R1b,R3h,Ara), (Ze,Rd,R1b,R3h,Arb), (Ze,Rd,R1b,R3h,Arc), (Ze,Rd,R1b,R3h,Ard), (Ze,Rd,R1b,R3h,Are), (Ze,Rd,R1b,R3h,Arf), (Ze,Rd,R1b,R3h,Arg), (Ze,Rd,R1b,R3h,Arh), (Ze,Rd,R1b,R3h,Ari), (Ze,Rd,R1b,R3h,Arj), (Ze,Rd,R1b,R3h,Ark), (Ze,Rd,R1b,R3h,Arl), (Ze,Rd,R1b,R3h,Arm), (Ze,Rd,R1b,R3h,Arn), (Ze,Rd,R1b,R3h,Aro), (Ze,Rd,R1b,R3h,Arp), (Ze,Rd,R1c,R3a,Ara), (Ze,Rd,R1c,R3a,Arb), (Ze,Rd,R1c,R3a,Arc), (Ze,Rd,R1c,R3a,Ard), (Ze,Rd,R1c,R3a,Are), (Ze,Rd,R1c,R3a,Arf), (Ze,Rd,R1c,R3a,Arg), (Ze,Rd,R1c,R3a,Arh), (Ze,Rd,R1c,R3a,Ari), (Ze,Rd,R1c,R3a,Arj), (Ze,Rd,R1c,R3a,Ark), (Ze,Rd,R1c,R3a,Arl), (Ze,Rd,R1c,R3a,Arm), (Ze,Rd,R1c,R3a,Arn), (Ze,Rd,R1c,R3a,Aro), (Ze,Rd,R1c,R3a,Arp), (Ze,Rd,R1c,R3b,Ara), (Ze,Rd,R1c,R3b,Arb), (Ze,Rd,R1c,R3b,Arc), (Ze,Rd,R1c,R3b,Ard), (Ze,Rd,R1c,R3b,Are), (Ze,Rd,R1c,R3b,Arf), (Ze,Rd,R1c,R3b,Arg), (Ze,Rd,R1c,R3b,Arh), (Ze,Rd,R1c,R3b,Ari), (Ze,Rd,R1c,R3b,Arj), (Ze,Rd,R1c,R3b,Ark), (Ze,Rd,R1c,R3b,Arl), (Ze,Rd,R1c,R3b,Arm), (Ze,Rd,R1c,R3b,Arn), (Ze,Rd,R1c,R3b,Aro), (Ze,Rd,R1c,R3b,Arp), (Ze,Rd,R1c,R3c,Ara), (Ze,Rd,R1c,R3c,Arb), (Ze,Rd,R1c,R3c,Arc), (Ze,Rd,R1c,R3c,Ard), (Ze,Rd,R1c,R3c,Are), (Ze,Rd,R1c,R3c,Arf), (Ze,Rd,R1c,R3c,Arg), (Ze,Rd,R1c,R3c,Arh), (Ze,Rd,R1c,R3c,Ari), (Ze,Rd,R1c,R3c,Arj), (Ze,Rd,R1c,R3c,Ark), (Ze,Rd,R1c,R3c,Arl), (Ze,Rd,R1c,R3c,Arm), (Ze,Rd,R1c,R3c,Arn), (Ze,Rd,R1c,R3c,Aro), (Ze,Rd,R1c,R3c,Arp), (Ze,Rd,R1c,R3d,Ara), (Ze,Rd,R1c,R3d,Arb), (Ze,Rd,R1c,R3d,Arc), (Ze,Rd,R1c,R3d,Ard), (Ze,Rd,R1c,R3d,Are), (Ze,Rd,R1c,R3d,Arf), (Ze,Rd,R1c,R3d,Arg), (Ze,Rd,R1c,R3d,Arh), (Ze,Rd,R1c,R3d,Ari), (Ze,Rd,R1c,R3d,Arj), (Ze,Rd,R1c,R3d,Ark), (Ze,Rd,R1c,R3d,Arl), (Ze,Rd,R1c,R3d,Arm), (Ze,Rd,R1c,R3d,Arn), (Ze,Rd,R1c,R3d,Aro), (Ze,Rd,R1c,R3d,Arp), (Ze,Rd,R1c,R3e,Ara), (Ze,Rd,R1c,R3e,Arb), (Ze,Rd,R1c,R3e,Arc), (Ze,Rd,R1c,R3e,Ard), (Ze,Rd,R1c,R3e,Are), (Ze,Rd,R1c,R3e,Arf), (Ze,Rd,R1c,R3e,Arg), (Ze,Rd,R1c,R3e,Arh), (Ze,Rd,R1c,R3e,Ari), (Ze,Rd,R1c,R3e,Arj), (Ze,Rd,R1c,R3e,Ark), (Ze,Rd,R1c,R3e,Arl), (Ze,Rd,R1c,R3e,Arm), (Ze,Rd,R1c,R3e,Arn), (Ze,Rd,R1c,R3e,Aro), (Ze,Rd,R1c,R3e,Arp), (Ze,Rd,R1c,R3f,Ara), (Ze,Rd,R1c,R3f,Arb), (Ze,Rd,R1c,R3f,Arc), (Ze,Rd,R1c,R3f,Ard), (Ze,Rd,R1c,R3f,Are), (Ze,Rd,R1c,R3f,Arf), (Ze,Rd,R1c,R3f,Arg), (Ze,Rd,R1c,R3f,Arh), (Ze,Rd,R1c,R3f,Ari), (Ze,Rd,R1c,R3f,Arj), (Ze,Rd,R1c,R3f,Ark), (Ze,Rd,R1c,R3f,Arl), (Ze,Rd,R1c,R3f,Arm), (Ze,Rd,R1c,R3f,Arn), (Ze,Rd,R1c,R3f,Aro), (Ze,Rd,R1c,R3f,Arp), (Ze,Rd,R1c,R3g,Ara), (Ze,Rd,R1c,R3g,Arb), (Ze,Rd,R1c,R3g,Arc), (Ze,Rd,R1c,R3g,Ard), (Ze,Rd,R1c,R3g,Are), (Ze,Rd,R1c,R3g,Arf), (Ze,Rd,R1c,R3g,Arg), (Ze,Rd,R1c,R3g,Arh), (Ze,Rd,R1c,R3g,Ari), (Ze,Rd,R1c,R3g,Arj), (Ze,Rd,R1c,R3g,Ark), (Ze,Rd,R1c,R3g,Arl), (Ze,Rd,R1c,R3g,Arm), (Ze,Rd,R1c,R3g,Arn), (Ze,Rd,R1c,R3g,Aro), (Ze,Rd,R1c,R3g,Arp), (Ze,Rd,R1c,R3h,Ara), (Ze,Rd,R1c,R3h,Arb), (Ze,Rd,R1c,R3h,Arc), (Ze,Rd,R1c,R3h,Ard), (Ze,Rd,R1c,R3h,Are), (Ze,Rd,R1c,R3h,Arf), (Ze,Rd,R1c,R3h,Arg), (Ze,Rd,R1c,R3h,Arh), (Ze,Rd,R1c,R3h,Ari), (Ze,Rd,R1c,R3h,Arj), (Ze,Rd,R1c,R3h,Ark), (Ze,Rd,R1c,R3h,Arl), (Ze,Rd,R1c,R3h,Arm), (Ze,Rd,R1c,R3h,Arn), (Ze,Rd,R1c,R3h,Aro), (Ze,Rd,R1c,R3h,Arp), (Ze,Rd,R1d,R3a,Ara), (Ze,Rd,R1d,R3a,Arb), (Ze,Rd,R1d,R3a,Arc), (Ze,Rd,R1d,R3a,Ard), (Ze,Rd,R1d,R3a,Are), (Ze,Rd,R1d,R3a,Arf), (Ze,Rd,R1d,R3a,Arg), (Ze,Rd,R1d,R3a,Arh), (Ze,Rd,R1d,R3a,Ari), (Ze,Rd,R1d,R3a,Arj), (Ze,Rd,R1d,R3a,Ark), (Ze,Rd,R1d,R3a,Arl), (Ze,Rd,R1d,R3a,Arm), (Ze,Rd,R1d,R3a,Arn), (Ze,Rd,R1d,R3a,Aro), (Ze,Rd,R1d,R3a,Arp), (Ze,Rd,R1d,R3b,Ara), (Ze,Rd,R1d,R3b,Arb), (Ze,Rd,R1d,R3b,Arc), (Ze,Rd,R1d,R3b,Ard), (Ze,Rd,R1d,R3b,Are), (Ze,Rd,R1d,R3b,Arf), (Ze,Rd,R1d,R3b,Arg), (Ze,Rd,R1d,R3b,Arh), (Ze,Rd,R1d,R3b,Ari), (Ze,Rd,R1d,R3b,Arj), (Ze,Rd,R1d,R3b,Ark), (Ze,Rd,R1d,R3b,Arl), (Ze,Rd,R1d,R3b,Arm), (Ze,Rd,R1d,R3b,Arn), (Ze,Rd,R1d,R3b,Aro), (Ze,Rd,R1d,R3b,Arp), (Ze,Rd,R1d,R3c,Ara), (Ze,Rd,R1d,R3c,Arb), (Ze,Rd,R1d,R3c,Arc), (Ze,Rd,R1d,R3c,Ard), (Ze,Rd,R1d,R3c,Are), (Ze,Rd,R1d,R3c,Arf), (Ze,Rd,R1d,R3c,Arg), (Ze,Rd,R1d,R3c,Arh), (Ze,Rd,R1d,R3c,Ari), (Ze,Rd,R1d,R3c,Arj), (Ze,Rd,R1d,R3c,Ark), (Ze,Rd,R1d,R3c,Arl), (Ze,Rd,R1d,R3c,Arm), (Ze,Rd,R1d,R3c,Arn), (Ze,Rd,R1d,R3c,Aro), (Ze,Rd,R1d,R3c,Arp), (Ze,Rd, R1d,R3d,Ara), (Ze,Rd,R1d,R3d,Arb), (Ze,Rd,R1d,R3d,Arc), (Ze,Rd,R1d,R3d,Ard), (Ze,Rd,R1d,R3d,Are), (Ze,Rd,R1d,R3d,Arf), (Ze,Rd,R1d,R3d,Arg), (Ze,Rd,R1d,R3d,Arh), (Ze,Rd,R1d,R3d,Ari), (Ze,Rd,R1d,R3d,Arj), (Ze,Rd,R1d,R3d,Ark), (Ze,Rd,R1d,R3d,Arl), (Ze,Rd,R1d,R3d,Arm), (Ze,Rd,R1d,R3d,Arn), (Ze,Rd,R1d,R3d,Aro), (Ze,Rd,R1d,R3d,Arp), (Ze,Rd,R1d,R3e,Ara), (Ze,Rd,R1d,R3e,Arb), (Ze,Rd,R1d,R3e,Arc), (Ze,Rd,R1d,R3e,Ard), (Ze,Rd,R1d,R3e,Are), (Ze,Rd,R1d,R3e,Arf), (Ze,Rd,R1d,R3e,Arg), (Ze,Rd,R1d,R3e,Arh), (Ze,Rd,R1d,R3e,Ari), (Ze,Rd,R1d,R3e,Arj), (Ze,Rd,R1d,R3e,Ark), (Ze,Rd,R1d,R3e,Arl), (Ze,Rd,R1d,R3e,Arm), (Ze,Rd,R1d,R3e,Arn), (Ze,Rd,R1d,R3e,Aro), (Ze,Rd,R1d,R3e,Arp), (Ze,Rd,R1d,R3f,Ara), (Ze,Rd,R1d,R3f,Arb), (Ze,Rd,R1d,R3f,Arc), (Ze,Rd,R1d,R3f,Ard), (Ze,Rd,R1d,R3f,Are), (Ze,Rd,R1d,R3f,Arf), (Ze,Rd,R1d,R3f,Arg), (Ze,Rd,R1d,R3f,Arh), (Ze,Rd,R1d,R3f,Ari), (Ze,Rd,R1d,R3f,Arj), (Ze,Rd,R1d,R3f,Ark), (Ze,Rd,R1d,R3f,Arl), (Ze,Rd,R1d,R3f,Arm), (Ze,Rd,R1d,R3f,Arn), (Ze,Rd,R1d,R3f,Aro), (Ze,Rd,R1d,R3f,Arp), (Ze,Rd,R1d,R3g,Ara), (Ze,Rd,R1d,R3g,Arb), (Ze,Rd,R1d,R3g,Arc), (Ze,Rd,R1d,R3g,Ard), (Ze,Rd,R1d,R3g,Are), (Ze,Rd,R1d,R3g,Arf), (Ze,Rd,R1d,R3g,Arg), (Ze,Rd,R1d,R3g,Arh), (Ze,Rd,R1d,R3g,Ari), (Ze,Rd,R1d,R3g,Arj), (Ze,Rd,R1d,R3g,Ark), (Ze,Rd,R1d,R3g,Arl), (Ze,Rd,R1d,R3g,Arm), (Ze,Rd,R1d,R3g,Arn), (Ze,Rd,R1d,R3g,Aro), (Ze,Rd,R1d,R3g,Arp), (Ze,Rd,R1d,R3h,Ara), (Ze,Rd,R1d,R3h,Arb), (Ze,Rd,R1d,R3h,Arc), (Ze,Rd,R1d,R3h,Ard), (Ze,Rd,R1d,R3h,Are), (Ze,Rd,R1d,R3h,Arf), (Ze,Rd,R1d,R3h,Arg), (Ze,Rd,R1d,R3h,Arh), (Ze,Rd,R1d,R3h,Ari), (Ze,Rd,R1d,R3h,Arj), (Ze,Rd,R1d,R3h,Ark), (Ze,Rd,R1d,R3h,Arl), (Ze,Rd,R1d,R3h,Arm), (Ze,Rd,R1d,R3h,Arn), (Ze,Rd,R1d,R3h,Aro), (Ze,Rd,R1d,R3h,Arp), (Ze,Re,R1a,R3a,Ara), (Ze,Re,R1a,R3a,Arb), (Ze,Re,R1a,R3a,Arc), (Ze,Re,R1a,R3a,Ard), (Ze,Re,R1a,R3a,Are), (Ze,Re,R1a,R3a,Arf), (Ze,Re,R1a,R3a,Arg), (Ze,Re,R1a,R3a,Arh), (Ze,Re,R1a,R3a,Ari), (Ze,Re,R1a,R3a,Arj), (Ze,Re,R1a,R3a,Ark), (Ze,Re,R1a,R3a,Arl), (Ze,Re,R1a,R3a,Arm), (Ze,Re,R1a,R3a,Arn), (Ze,Re,R1a,R3a,Aro), (Ze,Re,R1a,R3a,Arp), (Ze,Re,R1a,R3b,Ara), (Ze,Re,R1a,R3b,Arb), (Ze,Re,R1a,R3b,Arc), (Ze,Re,R1a,R3b,Ard), (Ze,Re,R1a,R3b,Are), (Ze,Re,R1a,R3b,Arf), (Ze,Re,R1a,R3b,Arg), (Ze,Re,R1a,R3b,Arh), (Ze,Re,R1a,R3b,Ari), (Ze,Re,R1a,R3b,Arj), (Ze,Re,R1a,R3b,Ark), (Ze,Re,R1a,R3b,Arl), (Ze,Re,R1a,R3b,Arm), (Ze,Re,R1a,R3b,Arn), (Ze,Re,R1a,R3b,Aro), (Ze,Re,R1a,R3b,Arp), (Ze,Re,R1a,R3c,Ara), (Ze,Re,R1a,R3c,Arb), (Ze,Re,R1a,R3c,Arc), (Ze,Re,R1a,R3c,Ard), (Ze,Re,R1a,R3c,Are), (Ze,Re,R1a,R3c,Arf), (Ze,Re,R1a,R3c,Arg), (Ze,Re,R1a,R3c,Arh), (Ze,Re,R1a,R3c,Ari), (Ze,Re,R1a,R3c,Arj), (Ze,Re,R1a,R3c,Ark), (Ze,Re,R1a,R3c,Arl), (Ze,Re,R1a,R3c,Arm), (Ze,Re,R1a,R3c,Arn), (Ze,Re,R1a,R3c,Aro), (Ze,Re,R1a,R3c,Arp), (Ze,Re,R1a,R3d,Ara), (Ze,Re,R1a,R3d,Arb), (Ze,Re,R1a,R3d,Arc), (Ze,Re,R1a,R3d,Ard), (Ze,Re,R1a,R3d,Are), (Ze,Re,R1a,R3d,Arf), (Ze,Re,R1a,R3d,Arg), (Ze,Re,R1a,R3d,Arh), (Ze,Re,R1a,R3d,Ari), (Ze,Re,R1a,R3d,Arj), (Ze,Re,R1a,R3d,Ark), (Ze,Re,R1a,R3d,Arl), (Ze,Re,R1a,R3d,Arm), (Ze,Re,R1a,R3d,Arn), (Ze,Re,R1a,R3d,Aro), (Ze,Re,R1a,R3d,Arp), (Ze,Re,R1a,R3e,Ara), (Ze,Re,R1a,R3e,Arb), (Ze,Re,R1a,R3e,Arc), (Ze,Re,R1a,R3e,Ard), (Ze,Re,R1a,R3e,Are), (Ze,Re,R1a,R3e,Arf), (Ze,Re,R1a,R3e,Arg), (Ze,Re,R1a,R3e,Arh), (Ze,Re,R1a,R3e,Ari), (Ze,Re,R1a,R3e,Arj), (Ze,Re,R1a,R3e,Ark), (Ze,Re,R1a,R3e,Arl), (Ze,Re,R1a,R3e,Arm), (Ze,Re,R1a,R3e,Arn), (Ze,Re,R1a,R3e,Aro), (Ze,Re,R1a,R3e,Arp), (Ze,Re,R1a,R3f,Ara), (Ze,Re,R1a,R3f,Arb), (Ze,Re,R1a,R3f,Arc), (Ze,Re,R1a,R3f,Ard), (Ze,Re,R1a,R3f,Are), (Ze,Re,R1a,R3f,Arf), (Ze,Re,R1a,R3f,Arg), (Ze,Re,R1a,R3f,Arh), (Ze,Re,R1a,R3f,Ari), (Ze,Re,R1a,R3f,Arj), (Ze,Re,R1a,R3f,Ark), (Ze,Re,R1a,R3f,Arl), (Ze,Re,R1a,R3f,Arm), (Ze,Re,R1a,R3f,Arn), (Ze,Re,R1a,R3f,Aro), (Ze,Re,R1a,R3f,Arp), (Ze,Re,R1a,R3g,Ara), (Ze,Re,R1a,R3g,Arb), (Ze,Re,R1a,R3g,Arc), (Ze,Re,R1a,R3g,Ard), (Ze,Re,R1a,R3g,Are), (Ze,Re,R1a,R3g,Arf), (Ze,Re,R1a,R3g,Arg), (Ze,Re,R1a,R3g,Arh), (Ze,Re,R1a,R3g,Ari), (Ze,Re,R1a,R3g,Arj), (Ze,Re,R1a,R3g,Ark), (Ze,Re,R1a,R3g,Arl), (Ze,Re,R1a,R3g,Arm), (Ze,Re,R1a,R3g,Arn), (Ze,Re,R1a,R3g,Aro), (Ze,Re,R1a,R3g,Arp), (Ze,Re,R1a,R3h,Ara), (Ze,Re,R1a,R3h,Arb), (Ze,Re,R1a,R3h,Arc), (Ze,Re,R1a,R3h,Ard), (Ze,Re,R1a,R3h,Are), (Ze,Re,R1a,R3h,Arf), (Ze,Re,R1a,R3h,Arg), (Ze,Re,R1a,R3h,Arh), (Ze,Re,R1a,R3h,Ari), (Ze,Re,R1a,R3h,Arj), (Ze,Re,R1a,R3h,Ark), (Ze,Re,R1a,R3h,Arl), (Ze,Re,R1a,R3h,Arm), (Ze,Re,R1a,R3h,Arn), (Ze,Re,R1a,R3h,Aro), (Ze,Re,R1a,R3h,Arp), (Ze,Re,R1b,R3a,Ara), (Ze,Re,R1b,R3a,Arb), (Ze,Re,R1b,R3a,Arc), (Ze,Re,R1b,R3a,Ard), (Ze,Re,R1b,R3a,Are), (Ze,Re,R1b,R3a,Arf), (Ze,Re,R1b,R3a,Arg), (Ze,Re,R1b,R3a,Arh), (Ze,Re,R1b,R3a,Ari), (Ze,Re,R1b,R3a,Arj), (Ze,Re,R1b,R3a,Ark), (Ze,Re,R1b,R3a,Arl), (Ze,Re,R1b,R3a,Arm), (Ze,Re,R1b,R3a,Arn), (Ze,Re,R1b,R3a,Aro), (Ze,Re,R1b,R3a,Arp), (Ze,Re,R1b,R3b,Ara), (Ze,Re,R1b,R3b,Arb), (Ze,Re,R1b,R3b,Arc), (Ze,Re,R1b,R3b,Ard), (Ze,Re,R1b,R3b,Are), (Ze,Re,R1b,R3b,Arf), (Ze,Re,R1b,R3b,Arg), (Ze,Re,R1b,R3b,Arh), (Ze,Re,R1b,R3b,Ari), (Ze,Re,R1b,R3b,Arj), (Ze,Re,R1b,R3b,Ark), (Ze,Re,R1b,R3b,Arl), (Ze,Re,R1b,R3b,Arm), (Ze,Re,R1b,R3b,Arn), (Ze,Re,R1b,R3b,Aro), (Ze,Re,R1b,R3b,Arp), (Ze,Re,R1b,R3c,Ara), (Ze,Re,R1b,R3c,Arb), (Ze,Re,R1b,R3c,Arc), (Ze,Re,R1b,R3c,Ard), (Ze,Re,R1b,R3c,Are), (Ze,Re,R1b,R3c,Arf), (Ze,Re,R1b,R3c,Arg), (Ze,Re,R1b,R3c,Arh), (Ze,Re,R1b,R3c,Ari), (Ze,Re,R1b,R3c,Arj), (Ze,Re,R1b,R3c,Ark), (Ze,Re,R1b,R3c,Arl), (Ze,Re,R1b,R3c,Arm), (Ze,Re,R1b,R3c,Arn), (Ze,Re,R1b,R3c,Aro), (Ze,Re,R1b,R3c,Arp), (Ze,Re,R1b,R3d,Ara), (Ze,Re,R1b,R3d,Arb), (Ze,Re,R1b,R3d,Arc), (Ze,Re,R1b,R3d,Ard), (Ze,Re,R1b,R3d,Are), (Ze,Re,R1b,R3d,Arf), (Ze,Re,R1b,R3d,Arg), (Ze,Re,R1b,R3d,Arh), (Ze,Re,R1b,R3d,Ari), (Ze,Re,R1b,R3d,Arj), (Ze,Re,R1b,R3d,Ark), (Ze,Re,R1b,R3d,Arl), (Ze,Re,R1b,R3d,Arm), (Ze,Re,R1b,R3d,Arn), (Ze,Re,R1b,R3d,Aro), (Ze,Re,R1b,R3d,Arp), (Ze,Re,R1b,R3e,Ara), (Ze,Re,R1b,R3e,Arb), (Ze,Re,R1b,R3e,Arc), (Ze,Re,R1b,R3e,Ard), (Ze,Re,R1b,R3e,Are), (Ze,Re,R1b,R3e,Arf), (Ze,Re,R1b,R3e,Arg), (Ze,Re,R1b,R3e,Arh), (Ze,Re,R1b,R3e,Ari), (Ze,Re,R1b,R3e,Arj), (Ze,Re,R1b,R3e,Ark), (Ze,Re,R1b,R3e,Arl), (Ze,Re,R1b,R3e,Arm), (Ze,Re,R1b,R3e,Arn), (Ze,Re,R1b,R3e,Aro), (Ze,Re,R1b,R3e,Arp), (Ze,Re,R1b,R3f,Ara), (Ze,Re,R1b,R3f,Arb), (Ze,Re,R1b,R3f,Arc), (Ze,Re,R1b,R3f,Ard), (Ze,Re,R1b,R3f,Are), (Ze,Re,R1b,R3f,Arf), (Ze,Re,R1b,R3f,Arg), (Ze,Re,R1b,R3f,Arh), (Ze,Re,R1b,R3f,Ari), (Ze,Re,R1b,R3f,Arj), (Ze,Re,R1b,R3f,Ark), (Ze,Re,R1b,R3f,Arl), (Ze,Re,R1b,R3f,Arm), (Ze,Re,R1b,R3f,Arn), (Ze,Re,R1b,R3f,Aro), (Ze,Re,R1b,R3f,Arp), (Ze,Re,R1b,R3g,Ara), (Ze,Re,R1b,R3g,Arb), (Ze,Re,R1b,R3g,Arc), (Ze,Re,R1b,R3g,Ard), (Ze,Re,R1b,R3g,Are), (Ze,Re,R1b,R3g,Arf), (Ze,Re,R1b,R3g,Arg), (Ze,Re,R1b,R3g,Arh), (Ze,Re,R1b,R3g,Ari), (Ze,Re,R1b,R3g,Arj), (Ze,Re,R1b,R3g,Ark), (Ze,Re,R1b,R3g,Arl), (Ze,Re,R1b,R3g,Arm), (Ze,Re,R1b,R3g,Arn), (Ze,Re,R1b,R3g,Aro), (Ze,Re,R1b,R3g,Arp), (Ze,Re,R1b,R3h,Ara), (Ze,Re,R1b,R3h,Arb), (Ze,Re,R1b,R3h,Arc), (Ze,Re,R1b,R3h,Ard), (Ze,Re,R1b,R3h,Are), (Ze,Re,R1b,R3h,Arf), (Ze,Re,R1b,R3h,Arg), (Ze,Re,R1b,R3h,Arh), (Ze,Re,R1b,R3h,Ari), (Ze,Re,R1b,R3h,Arj), (Ze,Re,R1b,R3h,Ark), (Ze,Re,R1b,R3h,Arl), (Ze,Re,R1b,R3h,Arm), (Ze,Re,R1b,R3h,Arn), (Ze,Re,R1b,R3h,Aro), (Ze,Re,R1b,R3h,Arp), (Ze,Re,R1c,R3a,Ara), (Ze,Re,R1c,R3a,Arb), (Ze,Re,R1c,R3a,Arc), (Ze,Re,R1c,R3a,Ard), (Ze,Re,R1c,R3a,Are), (Ze,Re,R1c,R3a,Arf), (Ze,Re,R1c,R3a,Arg), (Ze,Re,R1c,R3a,Arh), (Ze,Re,R1c, R3a,Ari), (Ze,Re,R1c,R3a,Arj), (Ze,Re,R1c,R3a,Ark), (Ze,Re,R1c,R3a,Arl), (Ze,Re,R1c,R3a,Arm), (Ze,Re,R1c,R3a,Arn), (Ze,Re,R1c,R3a,Aro), (Ze,Re,R1c,R3a,Arp), (Ze,Re,R1c,R3b,Ara), (Ze,Re,R1c,R3b,Arb), (Ze,Re,R1c,R3b,Arc), (Ze,Re,R1c,R3b,Ard), (Ze,Re,R1c,R3b,Are), (Ze,Re,R1c,R3b,Arf), (Ze,Re,R1c,R3b,Arg), (Ze,Re,R1c,R3b,Arh), (Ze,Re,R1c,R3b,Ari), (Ze,Re,R1c,R3b,Arj), (Ze,Re,R1c,R3b,Ark), (Ze,Re,R1c,R3b,Arl), (Ze,Re,R1c,R3b,Arm), (Ze,Re,R1c,R3b,Arn), (Ze,Re,R1c,R3b,Aro), (Ze,Re,R1c,R3b,Arp), (Ze,Re,R1c,R3c,Ara), (Ze,Re,R1c,R3c,Arb), (Ze,Re,R1c,R3c,Arc), (Ze,Re,R1c,R3c,Ard), (Ze,Re,R1c,R3c,Are), (Ze,Re,R1c,R3c,Arf), (Ze,Re,R1c,R3c,Arg), (Ze,Re,R1c,R3c,Arh), (Ze,Re,R1c,R3c,Ari), (Ze,Re,R1c,R3c,Arj), (Ze,Re,R1c,R3c,Ark), (Ze,Re,R1c,R3c,Arl), (Ze,Re,R1c,R3c,Arm), (Ze,Re,R1c,R3c,Arn), (Ze,Re,R1c,R3c,Aro), (Ze,Re,R1c,R3c,Arp), (Ze,Re,R1c,R3d,Ara), (Ze,Re,R1c,R3d,Arb), (Ze,Re,R1c,R3d,Arc), (Ze,Re,R1c,R3d,Ard), (Ze,Re,R1c,R3d,Are), (Ze,Re,R1c,R3d,Arf), (Ze,Re,R1c,R3d,Arg), (Ze,Re,R1c,R3d,Arh), (Ze,Re,R1c,R3d,Ari), (Ze,Re,R1c,R3d,Arj), (Ze,Re,R1c,R3d,Ark), (Ze,Re,R1c,R3d,Arl), (Ze,Re,R1c,R3d,Arm), (Ze,Re,R1c,R3d,Arn), (Ze,Re,R1c,R3d,Aro), (Ze,Re,R1c,R3d,Arp), (Ze,Re,R1c,R3e,Ara), (Ze,Re,R1c,R3e,Arb), (Ze,Re,R1c,R3e,Arc), (Ze,Re,R1c,R3e,Ard), (Ze,Re,R1c,R3e,Are), (Ze,Re,R1c,R3e,Arf), (Ze,Re,R1c,R3e,Arg), (Ze,Re,R1c,R3e,Arh), (Ze,Re,R1c,R3e,Ari), (Ze,Re,R1c,R3e,Arj), (Ze,Re,R1c,R3e,Ark), (Ze,Re,R1c,R3e,Arl), (Ze,Re,R1c,R3e,Arm), (Ze,Re,R1c,R3e,Arn), (Ze,Re,R1c,R3e,Aro), (Ze,Re,R1c,R3e,Arp), (Ze,Re,R1c,R3f,Ara), (Ze,Re,R1c,R3f,Arb), (Ze,Re,R1c,R3f,Arc), (Ze,Re,R1c,R3f,Ard), (Ze,Re,R1c,R3f,Are), (Ze,Re,R1c,R3f,Arf), (Ze,Re,R1c,R3f,Arg), (Ze,Re,R1c,R3f,Arh), (Ze,Re,R1c,R3f,Ari), (Ze,Re,R1c,R3f,Arj), (Ze,Re,R1c,R3f,Ark), (Ze,Re,R1c,R3f,Arl), (Ze,Re,R1c,R3f,Arm), (Ze,Re,R1c,R3f,Arn), (Ze,Re,R1c,R3f,Aro), (Ze,Re,R1c,R3f,Arp), (Ze,Re,R1c,R3g,Ara), (Ze,Re,R1c,R3g,Arb), (Ze,Re,R1c,R3g,Arc), (Ze,Re,R1c,R3g,Ard), (Ze,Re,R1c,R3g,Are), (Ze,Re,R1c,R3g,Arf), (Ze,Re,R1c,R3g,Arg), (Ze,Re,R1c,R3g,Arh), (Ze,Re,R1c,R3g,Ari), (Ze,Re,R1c,R3g,Arj), (Ze,Re,R1c,R3g,Ark), (Ze,Re,R1c,R3g,Arl), (Ze,Re,R1c,R3g,Arm), (Ze,Re,R1c,R3g,Arn), (Ze,Re,R1c,R3g,Aro), (Ze,Re,R1c,R3g,Arp), (Ze,Re,R1c,R3h,Ara), (Ze,Re,R1c,R3h,Arb), (Ze,Re,R1c,R3h,Arc), (Ze,Re,R1c,R3h,Ard), (Ze,Re,R1c,R3h,Are), (Ze,Re,R1c,R3h,Arf), (Ze,Re,R1c,R3h,Arg), (Ze,Re,R1c,R3h,Arh), (Ze,Re,R1c,R3h,Ari), (Ze,Re,R1c,R3h,Arj), (Ze,Re,R1c,R3h,Ark), (Ze,Re,R1c,R3h,Arl), (Ze,Re,R1c,R3h,Arm), (Ze,Re,R1c,R3h,Arn), (Ze,Re,R1c,R3h,Aro), (Ze,Re,R1c,R3h,Arp), (Ze,Re,R1d,R3a,Ara), (Ze,Re,R1d,R3a,Arb), (Ze,Re,R1d,R3a,Arc), (Ze,Re,R1d,R3a,Ard), (Ze,Re,R1d,R3a,Are), (Ze,Re,R1d,R3a,Arf), (Ze,Re,R1d,R3a,Arg), (Ze,Re,R1d,R3a,Arh), (Ze,Re,R1d,R3a,Ari), (Ze,Re,R1d,R3a,Arj), (Ze,Re,R1d,R3a,Ark), (Ze,Re,R1d,R3a,Arl), (Ze,Re,R1d,R3a,Arm), (Ze,Re,R1d,R3a,Arn), (Ze,Re,R1d,R3a,Aro), (Ze,Re,R1d,R3a,Arp), (Ze,Re,R1d,R3b,Ara), (Ze,Re,R1d,R3b,Arb), (Ze,Re,R1d,R3b,Arc), (Ze,Re,R1d,R3b,Ard), (Ze,Re,R1d,R3b,Are), (Ze,Re,R1d,R3b,Arf), (Ze,Re,R1d,R3b,Arg), (Ze,Re,R1d,R3b,Arh), (Ze,Re,R1d,R3b,Ari), (Ze,Re,R1d,R3b,Arj), (Ze,Re,R1d,R3b,Ark), (Ze,Re,R1d,R3b,Arl), (Ze,Re,R1d,R3b,Arm), (Ze,Re,R1d,R3b,Arn), (Ze,Re,R1d,R3b,Aro), (Ze,Re,R1d,R3b,Arp), (Ze,Re,R1d,R3c,Ara), (Ze,Re,R1d,R3c,Arb), (Ze,Re,R1d,R3c,Arc), (Ze,Re,R1d,R3c,Ard), (Ze,Re,R1d,R3c,Are), (Ze,Re,R1d,R3c,Arf), (Ze,Re,R1d,R3c,Arg), (Ze,Re,R1d,R3c,Arh), (Ze,Re,R1d,R3c,Ari), (Ze,Re,R1d,R3c,Arj), (Ze,Re,R1d,R3c,Ark), (Ze,Re,R1d,R3c,Arl), (Ze,Re,R1d,R3c,Arm), (Ze,Re,R1d,R3c,Arn), (Ze,Re,R1d,R3c,Aro), (Ze,Re,R1d,R3c,Arp), (Ze,Re,R1d,R3d,Ara), (Ze,Re,R1d,R3d,Arb), (Ze,Re,R1d,R3d,Arc), (Ze,Re,R1d,R3d,Ard), (Ze,Re,R1d,R3d,Are), (Ze,Re,R1d,R3d,Arf), (Ze,Re,R1d,R3d,Arg), (Ze,Re,R1d,R3d,Arh), (Ze,Re,R1d,R3d,Ari), (Ze,Re,R1d,R3d,Arj), (Ze,Re,R1d,R3d,Ark), (Ze,Re,R1d,R3d,Arl), (Ze,Re,R1d,R3d,Arm), (Ze,Re,R1d,R3d,Arn), (Ze,Re,R1d,R3d,Aro), (Ze,Re,R1d,R3d,Arp), (Ze,Re,R1d,R3e,Ara), (Ze,Re,R1d,R3e,Arb), (Ze,Re,R1d,R3e,Arc), (Ze,Re,R1d,R3e,Ard), (Ze,Re,R1d,R3e,Are), (Ze,Re,R1d,R3e,Arf), (Ze,Re,R1d,R3e,Arg), (Ze,Re,R1d,R3e,Arh), (Ze,Re,R1d,R3e,Ari), (Ze,Re,R1d,R3e,Arj), (Ze,Re,R1d,R3e,Ark), (Ze,Re,R1d,R3e,Arl), (Ze,Re,R1d,R3e,Arm), (Ze,Re,R1d,R3e,Arn), (Ze,Re,R1d,R3e,Aro), (Ze,Re,R1d,R3e,Arp), (Ze,Re,R1d,R3f,Ara), (Ze,Re,R1d,R3f,Arb), (Ze,Re,R1d,R3f,Arc), (Ze,Re,R1d,R3f,Ard), (Ze,Re,R1d,R3f,Are), (Ze,Re,R1d,R3f,Arf), (Ze,Re,R1d,R3f,Arg), (Ze,Re,R1d,R3f,Arh), (Ze,Re,R1d,R3f,Ari), (Ze,Re,R1d,R3f,Atj), (Ze,Re,R1d,R3f,Ark), (Ze,Re,R1d,R3f,Arl), (Ze,Re,R1d,R3f,Arm), (Ze,Re,R1d,R3f,Arn), (Ze,Re,R1d,R3f,Aro), (Ze,Re,R1d,R3f,Arp), (Ze,Re,R1d,R3g,Ara), (Ze,Re,R1d,R3g,Arb), (Ze,Re,R1d,R3g,Arc), (Ze,Re,R1d,R3g,Ard), (Ze,Re,R1d,R3g,Are), (Ze,Re,R1d,R3g,Arf), (Ze,Re,R1d,R3g,Arg), (Ze,Re,R1d,R3g,Arh), (Ze,Re,R1d,R3g,Ari), (Ze,Re,R1d,R3g,Arj), (Ze,Re,R1d,R3g,Ark), (Ze,Re,R1d,R3g,Arl), (Ze,Re,R1d,R3g,Arm), (Ze,Re,R1d,R3g,Arn), (Ze,Re,R1d,R3g,Aro), (Ze,Re,R1d,R3g,Arp), (Ze,Re,R1d,R3h,Ara), (Ze,Re,R1d,R3h,Arb), (Ze,Re,R1d,R3h,Arc), (Ze,Re,R1d,R3h,Ard), (Ze,Re,R1d,R3h,Are), (Ze,Re,R1d,R3h,Arf), (Ze,Re,R1d,R3h,Arg), (Ze,Re,R1d,R3h,Arh), (Ze,Re,R1d,R3h,Ari), (Ze,Re,R1d,R3h,Arj), (Ze,Re,R1d,R3h,Ark), (Ze,Re,R1d,R3h,Arl), (Ze,Re,R1d,R3h,Arm), (Ze,Re,R1d,R3h,Arn), (Ze,Re,R1d,R3h,Aro), (Ze,Re,R1d,R3h,Arp), (Ze,Rf,R1a,R3a,Ara), (Ze,Rf,R1a,R3a,Arb), (Ze,Rf,R1a,R3a,Arc), (Ze,Rf,R1a,R3a,Ard), (Ze,Rf,R1a,R3a,Are), (Ze,Rf,R1a,R3a,Arf), (Ze,Rf,R1a,R3a,Arg), (Ze,Rf,R1a,R3a,Arh), (Ze,Rf,R1a,R3a,Ari), (Ze,Rf,R1a,R3a,Arj), (Ze,Rf,R1a,R3a,Ark), (Ze,Rf,R1a,R3a,Arl), (Ze,Rf,R1a,R3a,Arm), (Ze,Rf,R1a,R3a,Arn), (Ze,Rf,R1a,R3a,Aro), (Ze,Rf,R1a,R3a,Arp), (Ze,Rf,R1a,R3b,Ara), (Ze,Rf,R1a,R3b,Arb), (Ze,Rf,R1a,R3b,Arc), (Ze,Rf,R1a,R3b,Ard), (Ze,Rf,R1a,R3b,Are), (Ze,Rf,R1a,R3b,Arf), (Ze,Rf,R1a,R3b,Arg), (Ze,Rf,R1a,R3b,Arh), (Ze,Rf,R1a,R3b,Ari), (Ze,Rf,R1a,R3b,Arj), (Ze,Rf,R1a,R3b,Ark), (Ze,Rf,R1a,R3b,Arl), (Ze,Rf,R1a,R3b,Arm), (Ze,Rf,R1a,R3b,Arn), (Ze,Rf,R1a,R3b,Aro), (Ze,Rf,R1a,R3b,Arp), (Ze,Rf,R1a,R3c,Ara), (Ze,Rf,R1a,R3c,Arb), (Ze,Rf,R1a,R3c,Arc), (Ze,Rf,R1a,R3c,Ard), (Ze,Rf,R1a,R3c,Are), (Ze,Rf,R1a,R3c,Arf), (Ze,Rf,R1a,R3c,Arg), (Ze,Rf,R1a,R3c,Arh), (Ze,Rf,R1a,R3c,Ari), (Ze,Rf,R1a,R3c,Arj), (Ze,Rf,R1a,R3c,Ark), (Ze,Rf,R1a,R3c,Arl), (Ze,Rf,R1a,R3c,Arm), (Ze,Rf,R1a,R3c,Arn), (Ze,Rf,R1a,R3c,Aro), (Ze,Rf,R1a,R3c,Arp), (Ze,Rf,R1a,R3d,Ara), (Ze,Rf,R1a,R3d,Arb), (Ze,Rf,R1a,R3d,Arc), (Ze,Rf,R1a,R3d,Ard), (Ze,Rf,R1a,R3d,Are), (Ze,Rf,R1a,R3d,Arf), (Ze,Rf,R1a,R3d,Arg), (Ze,Rf,R1a,R3d,Arh), (Ze,Rf,R1a,R3d,Ari), (Ze,Rf,R1a,R3d,Arj), (Ze,Rf,R1a,R3d,Ark), (Ze,Rf,R1a,R3d,Arl), (Ze,Rf,R1a,R3d,Arm), (Ze,Rf,R1a,R3d,Arn), (Ze,Rf,R1a,R3d,Aro), (Ze,Rf,R1a,R3d,Arp), (Ze,Rf,R1a,R3e,Ara), (Ze,Rf,R1a,R3e,Arb), (Ze,Rf,R1a,R3e,Arc), (Ze,Rf,R1a,R3e,Ard), (Ze,Rf,R1a,R3e,Are), (Ze,Rf,R1a,R3e,Arf), (Ze,Rf,R1a,R3e,Arg), (Ze,Rf,R1a,R3e,Arh), (Ze,Rf,R1a,R3e,Ari), (Ze,Rf,R1a,R3e,Arj), (Ze,Rf,R1a,R3e,Ark), (Ze,Rf,R1a,R3e,Arl), (Ze,Rf,R1a,R3e,Arm), (Ze,Rf,R1a,R3e,Arn), (Ze,Rf,R1a,R3e,Aro), (Ze,Rf,R1a,R3e,Arp), (Ze,Rf,R1a,R3f,Ara), (Ze,Rf,R1a,R3f,Arb), (Ze,Rf,R1a,R3f,Arc), (Ze,Rf,R1a,R3f,Ard), (Ze,Rf,R1a,R3f,Are), (Ze,Rf,R1a,R3f,Arf), (Ze,Rf,R1a,R3f,Arg), (Ze,Rf,R1a,R3f,Arh), (Ze,Rf,R1a,R3f,Ari), (Ze,Rf,R1a,R3f,Arj), (Ze,Rf,R1a,R3f,Ark), (Ze,Rf,R1a,R3f,Arl), (Ze,Rf,R1a,R3f,Arm), (Ze,Rf,R1a,R3f,Arn), (Ze,Rf,R1a,R3f,Aro), (Ze,Rf,R1a,R3f,Arp), (Ze,Rf,R1a,R3g,Ara), (Ze,Rf,R1a,R3g,Arb), (Ze, Rf,R1a,R3g,Arc), (Ze,Rf,R1a,R3g,Ard), (Ze,Rf,R1a,R3g,Are), (Ze,Rf,R1a,R3g,Arf), (Ze,Rf,R1a,R3g,Arg), (Ze,Rf,R1a,R3g,Arh), (Ze,Rf,R1a,R3g,Ari), (Ze,Rf,R1a,R3g,Arj), (Ze,Rf,R1a,R3g,Ark), (Ze,Rf,R1a,R3g,Arl), (Ze,Rf,R1a,R3g,Arm), (Ze,Rf,R1a,R3g,Arn), (Ze,Rf,R1a,R3g,Aro), (Ze,Rf,R1a,R3g,Arp), (Ze,Rf,R1a,R3h,Ara), (Ze,Rf,R1a,R3h,Arb), (Ze,Rf,R1a,R3h,Arc), (Ze,Rf,R1a,R3h,Ard), (Ze,Rf,R1a,R3h,Are), (Ze,Rf,R1a,R3h,Arf), (Ze,Rf,R1a,R3h,Arg), (Ze,Rf,R1a,R3h,Arh), (Ze,Rf,R1a,R3h,Ari), (Ze,Rf,R1a,R3h,Arj), (Ze,Rf,R1a,R3h,Ark), (Ze,Rf,R1a,R3h,Arl), (Ze,Rf,R1a,R3h,Arm), (Ze,Rf,R1a,R3h,Arn), (Ze,Rf,R1a,R3h,Aro), (Ze,Rf,R1a,R3h,Arp), (Ze,Rf,R1b,R3a,Ara), (Ze,Rf,R1b,R3a,Arb), (Ze,Rf,R1b,R3a,Arc), (Ze,Rf,R1b,R3a,Ard), (Ze,Rf,R1b,R3a,Are), (Ze,Rf,R1b,R3a,Arf), (Ze,Rf,R1b,R3a,Arg), (Ze,Rf,R1b,R3a,Arh), (Ze,Rf,R1b,R3a,Ari), (Ze,Rf,R1b,R3a,Arj), (Ze,Rf,R1b,R3a,Ark), (Ze,Rf,R1b,R3a,Arl), (Ze,Rf,R1b,R3a,Arm), (Ze,Rf,R1b,R3a,Arn), (Ze,Rf,R1b,R3a,Aro), (Ze,Rf,R1b,R3a,Arp), (Ze,Rf,R1b,R3b,Ara), (Ze,Rf,R1b,R3b,Arb), (Ze,Rf,R1b,R3b,Arc), (Ze,Rf,R1b,R3b,Ard), (Ze,Rf,R1b,R3b,Are), (Ze,Rf,R1b,R3b,Arf), (Ze,Rf,R1b,R3b,Arg), (Ze,Rf,R1b,R3b,Arh), (Ze,Rf,R1b,R3b,Ari), (Ze,Rf,R1b,R3b,Arj), (Ze,Rf,R1b,R3b,Ark), (Ze,Rf,R1b,R3b,Arl), (Ze,Rf,R1b,R3b,Arm), (Ze,Rf,R1b,R3b,Arn), (Ze,Rf,R1b,R3b,Aro), (Ze,Rf,R1b,R3b,Arp), (Ze,Rf,R1b,R3c,Ara), (Ze,Rf,R1b,R3c,Arb), (Ze,Rf,R1b,R3c,Arc), (Ze,Rf,R1b,R3c,Ard), (Ze,Rf,R1b,R3c,Are), (Ze,Rf,R1b,R3c,Arf), (Ze,Rf,R1b,R3c,Arg), (Ze,Rf,R1b,R3c,Arh), (Ze,Rf,R1b,R3c,Ari), (Ze,Rf,R1b,R3c,Arj), (Ze,Rf,R1b,R3c,Ark), (Ze,Rf,R1b,R3c,Arl), (Ze,Rf,R1b,R3c,Arm), (Ze,Rf,R1b,R3c,Arn), (Ze,Rf,R1b,R3c,Aro), (Ze,Rf,R1b,R3c,Arp), (Ze,Rf,R1b,R3d,Ara), (Ze,Rf,R1b,R3d,Arb), (Ze,Rf,R1b,R3d,Arc), (Ze,Rf,R1b,R3d,Ard), (Ze,Rf,R1b,R3d,Are), (Ze,Rf,R1b,R3d,Arf), (Ze,Rf,R1b,R3d,Arg), (Ze,Rf,R1b,R3d,Arh), (Ze,Rf,R1b,R3d,Ari), (Ze,Rf,R1b,R3d,Arj), (Ze,Rf,R1b,R3d,Ark), (Ze,Rf,R1b,R3d,Arl), (Ze,Rf,R1b,R3d,Arm), (Ze,Rf,R1b,R3d,Arn), (Ze,Rf,R1b,R3d,Aro), (Ze,Rf,R1b,R3d,Arp), (Ze,Rf,R1b,R3e,Ara), (Ze,Rf,R1b,R3e,Arb), (Ze,Rf,R1b,R3e,Arc), (Ze,Rf,R1b,R3e,Ard), (Ze,Rf,R1b,R3e,Are), (Ze,Rf,R1b,R3e,Arf), (Ze,Rf,R1b,R3e,Arg), (Ze,Rf,R1b,R3e,Arh), (Ze,Rf,R1b,R3e,Ari), (Ze,Rf,R1b,R3e,Arj), (Ze,Rf,R1b,R3e,Ark), (Ze,Rf,R1b,R3e,Arl), (Ze,Rf,R1b,R3e,Arm), (Ze,Rf,R1b,R3e,Arn), (Ze,Rf,R1b,R3e,Aro), (Ze,Rf,R1b,R3e,Arp), (Ze,Rf,R1b,R3f,Ara), (Ze,Rf,R1b,R3f,Arb), (Ze,Rf,R1b,R3f,Arc), (Ze,Rf,R1b,R3f,Ard), (Ze,Rf,R1b,R3f,Are), (Ze,Rf,R1b,R3f,Arf), (Ze,Rf,R1b,R3f,Arg), (Ze,Rf,R1b,R3f,Arh), (Ze,Rf,R1b,R3f,Ari), (Ze,Rf,R1b,R3f,Arj), (Ze,Rf,R1b,R3f,Ark), (Ze,Rf,R1b,R3f,Arl), (Ze,Rf,R1b,R3f,Arm), (Ze,Rf,R1b,R3f,Arn), (Ze,Rf,R1b,R3f,Aro), (Ze,Rf,R1b,R3f,Arp), (Ze,Rf,R1b,R3g,Ara), (Ze,Rf,R1b,R3g,Arb), (Ze,Rf,R1b,R3g,Arc), (Ze,Rf,R1b,R3g,Ard), (Ze,Rf,R1b,R3g,Are), (Ze,Rf,R1b,R3g,Arf), (Ze,Rf,R1b,R3g,Arg), (Ze,Rf,R1b,R3g,Arh), (Ze,Rf,R1b,R3g,Ari), (Ze,Rf,R1b,R3g,Arj), (Ze,Rf,R1b,R3g,Ark), (Ze,Rf,R1b,R3g,Arl), (Ze,Rf,R1b,R3g,Arm), (Ze,Rf,R1b,R3g,Arn), (Ze,Rf,R1b,R3g,Aro), (Ze,Rf,R1b,R3g,Arp), (Ze,Rf,R1b,R3h,Ara), (Ze,Rf,R1b,R3h,Arb), (Ze,Rf,R1b,R3h,Arc), (Ze,Rf,R1b,R3h,Ard), (Ze,Rf,R1b,R3h,Are), (Ze,Rf,R1b,R3h,Arf), (Ze,Rf,R1b,R3h,Arg), (Ze,Rf,R1b,R3h,Arh), (Ze,Rf,R1b,R3h,Ari), (Ze,Rf,R1b,R3h,Arj), (Ze,Rf,R1b,R3h,Ark), (Ze,Rf,R1b,R3h,Arl), (Ze,Rf,R1b,R3h,Arm), (Ze,Rf,R1b,R3h,Arn), (Ze,Rf,R1b,R3h,Aro), (Ze,Rf,R1b,R3h,Arp), (Ze,Rf,R1c,R3a,Ara), (Ze,Rf,R1c,R3a,Arb), (Ze,Rf,R1c,R3a,Arc), (Ze,Rf,R1c,R3a,Ard), (Ze,Rf,R1c,R3a,Are), (Ze,Rf,R1c,R3a,Arf), (Ze,Rf,R1c,R3a,Arg), (Ze,Rf,R1c,R3a,Arh), (Ze,Rf,R1c,R3a,Ari), (Ze,Rf,R1c,R3a,Arj), (Ze,Rf,R1c,R3a,Ark), (Ze,Rf,R1c,R3a,Arl), (Ze,Rf,R1c,R3a,Arm), (Ze,Rf,R1c,R3a,Arn), (Ze,Rf,R1c,R3a,Aro), (Ze,Rf,R1c,R3a,Arp), (Ze,Rf,R1c,R3b,Ara), (Ze,Rf,R1c,R3b,Arb), (Ze,Rf,R1c,R3b,Arc), (Ze,Rf,R1c,R3b,Ard), (Ze,Rf,R1c,R3b,Are), (Ze,Rf,R1c,R3b,Arf), (Ze,Rf,R1c,R3b,Arg), (Ze,Rf,R1c,R3b,Arh), (Ze,Rf,R1c,R3b,Ari), (Ze,Rf,R1c,R3b,M), (Ze,Rf,R1c,R3b,Ark), (Ze,Rf,R1c,R3b,Arl), (Ze,Rf,R1c,R3b,Arm), (Ze,Rf,R1c,R3b,Arn), (Ze,Rf,R1c,R3b,Aro), (Ze,Rf,R1c,R3b,Arp), (Ze,Rf,R1c,R3c,Ara), (Ze,Rf,R1c,R3c,Arb), (Ze,Rf,R1c,R3c,Arc), (Ze,Rf,R1c,R3c,Ard), (Ze,Rf,R1c,R3c,Are), (Ze,Rf,R1c,R3c,Arf), (Ze,Rf,R1c,R3c,Arg), (Ze,Rf,R1c,R3c,Arh), (Ze,Rf,R1c,R3c,Ari), (Ze,Rf,R1c,R3c,Arj), (Ze,Rf,R1c,R3c,Ark), (Ze,Rf,R1c,R3c,Arl), (Ze,Rf,R1c,R3c,Arm), (Ze,Rf,R1c,R3c,Arn), (Ze,Rf,R1c,R3c,Aro), (Ze,Rf,R1c,R3c,Arp), (Ze,Rf,R1c,R3d,Ara), (Ze,Rf,R1c,R3d,Arb), (Ze,Rf,R1c,R3d,Arc), (Ze,Rf,R1c,R3d,Ard), (Ze,Rf,R1c,R3d,Are), (Ze,Rf,R1c,R3d,Arf), (Ze,Rf,R1c,R3d,Arg), (Ze,Rf,R1c,R3d,Arh), (Ze,Rf,R1c,R3d,Ari), (Ze,Rf,R1c,R3d,Arj), (Ze,Rf,R1c,R3d,Ark), (Ze,Rf,R1c,R3d,Arl), (Ze,Rf,R1c,R3d,Arm), (Ze,Rf,R1c,R3d,Arn), (Ze,Rf,R1c,R3d,Aro), (Ze,Rf,R1c,R3d,Arp), (Ze,Rf,R1c,R3e,Ara), (Ze,Rf,R1c,R3e,Arb), (Ze,Rf,R1c,R3e,Arc), (Ze,Rf,R1c,R3e,Ard), (Ze,Rf,R1c,R3e,Are), (Ze,Rf,R1c,R3e,Arf), (Ze,Rf,R1c,R3e,Arg), (Ze,Rf,R1c,R3e,Arh), (Ze,Rf,R1c,R3e,Ari), (Ze,Rf,R1c,R3e,Arj), (Ze,Rf,R1c,R3e,Ark), (Ze,Rf,R1c,R3e,Arl), (Ze,Rf,R1c,R3e,Arm), (Ze,Rf,R1c,R3e,Arn), (Ze,Rf,R1c,R3e,Aro), (Ze,Rf,R1c,R3e,Arp), (Ze,Rf,R1c,R3f,Ara), (Ze,Rf,R1c,R3f,Arb), (Ze,Rf,R1c,R3f,Arc), (Ze,Rf,R1c,R3f,Ard), (Ze,Rf,R1c,R3f,Are), (Ze,Rf,R1c,R3f,Arf), (Ze,Rf,R1c,R3f,Arg), (Ze,Rf,R1c,R3f,Arh), (Ze,Rf,R1c,R3f,Ari), (Ze,Rf,R1c,R3f,Arj), (Ze,Rf,R1c,R3f,Ark), (Ze,Rf,R1c,R3f,Arl), (Ze,Rf,R1c,R3f,Arm), (Ze,Rf,R1c,R3f,Arn), (Ze,Rf,R1c,R3f,Aro), (Ze,Rf,R1c,R3f,Arp), (Ze,Rf,R1c,R3g,Ara), (Ze,Rf,R1c,R3g,Arb), (Ze,Rf,R1c,R3g,Arc), (Ze,Rf,R1c,R3g,Ard), (Ze,Rf,R1c,R3g,Are), (Ze,Rf,R1c,R3g,Arf), (Ze,Rf,R1c,R3g,Arg), (Ze,Rf,R1c,R3g,Arh), (Ze,Rf,R1c,R3g,Ari), (Ze,Rf,R1c,R3g,Arj), (Ze,Rf,R1c,R3g,Ark), (Ze,Rf,R1c,R3g,Arl), (Ze,Rf,R1c,R3g,Arm), (Ze,Rf,R1c,R3g,Arn), (Ze,Rf,R1c,R3g,Aro), (Ze,Rf,R1c,R3g,Arp), (Ze,Rf,R1c,R3h,Ara), (Ze,Rf,R1c,R3h,Arb), (Ze,Rf,R1c,R3h,Arc), (Ze,Rf,R1c,R3h,Ard), (Ze,Rf,R1c,R3h,Are), (Ze,Rf,R1c,R3h,Arf), (Ze,Rf,R1c,R3h,Arg), (Ze,Rf,R1c,R3h,Arh), (Ze,Rf,R1c,R3h,Ari), (Ze,Rf,R1c,R3h,Arj), (Ze,Rf,R1c,R3h,Ark), (Ze,Rf,R1c,R3h,Arl), (Ze,Rf,R1c,R3h,Arm), (Ze,Rf,R1c,R3h,Arn), (Ze,Rf,R1c,R3h,Aro), (Ze,Rf,R1c,R3h,Arp), (Ze,Rf,R1d,R3a,Ara), (Ze,Rf,R1d,R3a,Arb), (Ze,Rf,R1d,R3a,Arc), (Ze,Rf,R1d,R3a,Ard), (Ze,Rf,R1d,R3a,Are), (Ze,Rf,R1d,R3a,Arf), (Ze,Rf,R1d,R3a,Arg), (Ze,Rf,R1d,R3a,Arh), (Ze,Rf,R1d,R3a,Ari), (Ze,Rf,R1d,R3a,Arj), (Ze,Rf,R1d,R3a,Ark), (Ze,Rf,R1d,R3a,Arl), (Ze,Rf,R1d,R3a,Arm), (Ze,Rf,R1d,R3a,Arn), (Ze,Rf,R1d,R3a,Aro), (Ze,Rf,R1d,R3a,Arp), (Ze,Rf,R1d,R3b,Ara), (Ze,Rf,R1d,R3b,Arb), (Ze,Rf,R1d,R3b,Arc), (Ze,Rf,R1d,R3b,Ard), (Ze,Rf,R1d,R3b,Are), (Ze,Rf,R1d,R3b,Arf), (Ze,Rf,R1d,R3b,Arg), (Ze,Rf,R1d,R3b,Arh), (Ze,Rf,R1d,R3b,Ari), (Ze,Rf,R1d,R3b,Arj), (Ze,Rf,R1d,R3b,Ark), (Ze,Rf,R1d,R3b,Arl), (Ze,Rf,R1d,R3b,Arm), (Ze,Rf,R1d,R3b,Arn), (Ze,Rf,R1d,R3b,Aro), (Ze,Rf,R1d,R3b,Arp), (Ze,Rf,R1d,R3c,Ara), (Ze,Rf,R1d,R3c,Arb), (Ze,Rf,R1d,R3c,Arc), (Ze,Rf,R1d,R3c,Ard), (Ze,Rf,R1d,R3c,Are), (Ze,Rf,R1d,R3c,Arf), (Ze,Rf,R1d,R3c,Arg), (Ze,Rf,R1d,R3c,Arh), (Ze,Rf,R1d,R3c,Ari), (Ze,Rf,R1d,R3c,Arj), (Ze,Rf,R1d,R3c,Ark), (Ze,Rf,R1d,R3c,Arl), (Ze,Rf,R1d,R3c,Arm), (Ze,Rf,R1d,R3c,Arn), (Ze,Rf,R1d,R3c,Aro), (Ze,Rf,R1d,R3c,Arp), (Ze,Rf,R1d,R3d,Ara), (Ze,Rf,R1d,R3d,Arb), (Ze,Rf,R1d,R3d,Arc), (Ze,Rf,R1d,R3d,Ard), (Ze,Rf,R1d,R3d,Are), (Ze,Rf,R1d,R3d,Arf), (Ze,Rf,R1d,R3d,Arg), (Ze,Rf,R1d,R3d,Arh), (Ze,Rf,R1d,R3d,Ari), (Ze,Rf,R1d,R3d,Arj), (Ze,Rf,R1d,R3d,Ark), (Ze,Rf,R1d,R3d,Arl), (Ze,Rf,R1d,R3d,Arm), (Ze,Rf, R1d,R3d,Arn), (Ze,Rf,R1d,R3d,Aro), (Ze,Rf,R1d,R3d,Arp), (Ze,Rf,R1d,R3e,Ara), (Ze,Rf,R1d,R3e,Arb), (Ze,Rf,R1d,R3e,Arc), (Ze,Rf,R1d,R3e,Ard), (Ze,Rf,R1d,R3e,Are), (Ze,Rf,R1d,R3e,Arf), (Ze,Rf,R1d,R3e,Arg), (Ze,Rf,R1d,R3e,Arh), (Ze,Rf,R1d,R3e,Ari), (Ze,Rf,R1d,R3e,Arj), (Ze,Rf,R1d,R3e,Ark), (Ze,Rf,R1d,R3e,Arl), (Ze,Rf,R1d,R3e,Arm), (Ze,Rf,R1d,R3e,Arn), (Ze,Rf,R1d,R3e,Aro), (Ze,Rf,R1d,R3e,Arp), (Ze,Rf,R1d,R3f,Ara), (Ze,Rf,R1d,R3f,Arb), (Ze,Rf,R1d,R3f,Arc), (Ze,Rf,R1d,R3f,Ard), (Ze,Rf,R1d,R3f,Are), (Ze,Rf,R1d,R3f,Arf), (Ze,Rf,R1d,R3f,Arg), (Ze,Rf,R1d,R3f,Arh), (Ze,Rf,R1d,R3f,Ari), (Ze,Rf,R1d,R3f,Arj), (Ze,Rf,R1d,R3f,Ark), (Ze,Rf,R1d,R3f,Arl), (Ze,Rf,R1d,R3f,Arm), (Ze,Rf,R1d,R3f,Arn), (Ze,Rf,R1d,R3f,Aro), (Ze,Rf,R1d,R3f,Arp), (Ze,Rf,R1d,R3g,Ara), (Ze,Rf,R1d,R3g,Arb), (Ze,Rf,R1d,R3g,Arc), (Ze,Rf,R1d,R3g,Ard), (Ze,Rf,R1d,R3g,Are), (Ze,Rf,R1d,R3g,Arf), (Ze,Rf,R1d,R3g,Arg), (Ze,Rf,R1d,R3g,Arh), (Ze,Rf,R1d,R3g,Ari), (Ze,Rf,R1d,R3g,Arj), (Ze,Rf,R1d,R3g,Ark), (Ze,Rf,R1d,R3g,Arl), (Ze,Rf,R1d,R3g,Arm), (Ze,Rf,R1d,R3g,Arn), (Ze,Rf,R1d,R3g,Aro), (Ze,Rf,R1d,R3g,Arp), (Ze,Rf,R1d,R3h,Ara), (Ze,Rf,R1d,R3h,Arb), (Ze,Rf,R1d,R3h,Arc), (Ze,Rf,R1d,R3h,Ard), (Ze,Rf,R1d,R3h,Are), (Ze,Rf,R1d,R3h,Arf), (Ze,Rf,R1d,R3h,Arg), (Ze,Rf,R1d,R3h,Arh), (Ze,Rf,R1d,R3h,Ari), (Ze,Rf,R1d,R3h,Arj), (Ze,Rf,R1d,R3h,Ark), (Ze,Rf,R1d,R3h,Arl), (Ze,Rf,R1d,R3h,Arm), (Ze,Rf,R1d,R3h,Arn), (Ze,Rf,R1d,R3h,Aro), (Ze,Rf,R1d,R3h,Arp), (Ze,Rg,R1a,R3a,Ara), (Ze,Rg,R1a,R3a,Arb), (Ze,Rg,R1a,R3a,Arc), (Ze,Rg,R1a,R3a,Ard), (Ze,Rg,R1a,R3a,Are), (Ze,Rg,R1a,R3a,Arf), (Ze,Rg,R1a,R3a,Arg), (Ze,Rg,R1a,R3a,Arh), (Ze,Rg,R1a,R3a,Ari), (Ze,Rg,R1a,R3a,Arj), (Ze,Rg,R1a,R3a,Ark), (Ze,Rg,R1a,R3a,Arl), (Ze,Rg,R1a,R3a,Arm), (Ze,Rg,R1a,R3a,Arn), (Ze,Rg,R1a,R3a,Aro), (Ze,Rg,R1a,R3a,Arp), (Ze,Rg,R1a,R3b,Ara), (Ze,Rg,R1a,R3b,Arb), (Ze,Rg,R1a,R3b,Arc), (Ze,Rg,R1a,R3b,Ard), (Ze,Rg,R1a,R3b,Are), (Ze,Rg,R1a,R3b,Arf), (Ze,Rg,R1a,R3b,Arg), (Ze,Rg,R1a,R3b,Arh), (Ze,Rg,R1a,R3b,Ari), (Ze,Rg,R1a,R3b,Arj), (Ze,Rg,R1a,R3b,Ark), (Ze,Rg,R1a,R3b,Arl), (Ze,Rg,R1a,R3b,Arm), (Ze,Rg,R1a,R3b,Arn), (Ze,Rg,R1a,R3b,Aro), (Ze,Rg,R1a,R3b,Arp), (Ze,Rg,R1a,R3c,Ara), (Ze,Rg,R1a,R3c,Arb), (Ze,Rg,R1a,R3c,Arc), (Ze,Rg,R1a,R3c,Ard), (Ze,Rg,R1a,R3c,Are), (Ze,Rg,R1a,R3c,Arf), (Ze,Rg,R1a,R3c,Arg), (Ze,Rg,R1a,R3c,Arh), (Ze,Rg,R1a,R3c,Ari), (Ze,Rg,R1a,R3c,Arj), (Ze,Rg,R1a,R3c,Ark), (Ze,Rg,R1a,R3c,Arl), (Ze,Rg,R1a,R3c,Arm), (Ze,Rg,R1a,R3c,Arn), (Ze,Rg,R1a,R3c,Aro), (Ze,Rg,R1a,R3c,Arp), (Ze,Rg,R1a,R3d,Ara), (Ze,Rg,R1a,R3d,Arb), (Ze,Rg,R1a,R3d,Arc), (Ze,Rg,R1a,R3d,Ard), (Ze,Rg,R1a,R3d,Are), (Ze,Rg,R1a,R3d,Arf), (Ze,Rg,R1a,R3d,Arg), (Ze,Rg,R1a,R3d,Arh), (Ze,Rg,R1a,R3d,Ari), (Ze,Rg,R1a,R3d,Arj), (Ze,Rg,R1a,R3d,Ark), (Ze,Rg,R1a,R3d,Arl), (Ze,Rg,R1a,R3d,Arm), (Ze,Rg,R1a,R3d,Arn), (Ze,Rg,R1a,R3d,Aro), (Ze,Rg,R1a,R3d,Arp), (Ze,Rg,R1a,R3e,Ara), (Ze,Rg,R1a,R3e,Arb), (Ze,Rg,R1a,R3e,Arc), (Ze,Rg,R1a,R3e,Ard), (Ze,Rg,R1a,R3e,Are), (Ze,Rg,R1a,R3e,Arf), (Ze,Rg,R1a,R3e,Arg), (Ze,Rg,R1a,R3e,Arh), (Ze,Rg,R1a,R3e,Ari), (Ze,Rg,R1a,R3e,Arj), (Ze,Rg,R1a,R3e,Ark), (Ze,Rg,R1a,R3e,Arl), (Ze,Rg,R1a,R3e,Arm), (Ze,Rg,R1a,R3e,Arn), (Ze,Rg,R1a,R3e,Aro), (Ze,Rg,R1a,R3e,Arp), (Ze,Rg,R1a,R3f,Ara), (Ze,Rg,R1a,R3f,Arb), (Ze,Rg,R1a,R3f,Arc), (Ze,Rg,R1a,R3f,Ard), (Ze,Rg,R1a,R3f,Are), (Ze,Rg,R1a,R3f,Arf), (Ze,Rg,R1a,R3f,Arg), (Ze,Rg,R1a,R3f,Arh), (Ze,Rg,R1a,R3f,Ari), (Ze,Rg,R1a,R3f,Arj), (Ze,Rg,R1a,R3f,Ark), (Ze,Rg,R1a,R3f,Arl), (Ze,Rg,R1a,R3f,Arm), (Ze,Rg,R1a,R3f,Arn), (Ze,Rg,R1a,R3f,Aro), (Ze,Rg,R1a,R3f,Arp), (Ze,Rg,R1a,R3g,Ara), (Ze,Rg,R1a,R3g,Arb), (Ze,Rg,R1a,R3g,Arc), (Ze,Rg,R1a,R3g,Ard), (Ze,Rg,R1a,R3g,Are), (Ze,Rg,R1a,R3g,Arf), (Ze,Rg,R1a,R3g,Arg), (Ze,Rg,R1a,R3g,Arh), (Ze,Rg,R1a,R3g,Ari), (Ze,Rg,R1a,R3g,Arj), (Ze,Rg,R1a,R3g,Ark), (Ze,Rg,R1a,R3g,Arl), (Ze,Rg,R1a,R3g,Arm), (Ze,Rg,R1a,R3g,Arn), (Ze,Rg,R1a,R3g,Aro), (Ze,Rg,R1a,R3g,Arp), (Ze,Rg,R1a,R3h,Ara), (Ze,Rg,R1a,R3h,Arb), (Ze,Rg,R1a,R3h,Arc), (Ze,Rg,R1a,R3h,Ard), (Ze,Rg,R1a,R3h,Are), (Ze,Rg,R1a,R3h,Arf), (Ze,Rg,R1a,R3h,Arg), (Ze,Rg,R1a,R3h,Arh), (Ze,Rg,R1a,R3h,Ari), (Ze,Rg,R1a,R3h,Arj), (Ze,Rg,R1a,R3h,Ark), (Ze,Rg,R1a,R3h,Arl), (Ze,Rg,R1a,R3h,Arm), (Ze,Rg,R1a,R3h,Arn), (Ze,Rg,R1a,R3h,Aro), (Ze,Rg,R1a,R3h,Arp), (Ze,Rg,R1b,R3a,Ara), (Ze,Rg,R1b,R3a,Arb), (Ze,Rg,R1b,R3a,Arc), (Ze,Rg,R1b,R3a,Ard), (Ze,Rg,R1b,R3a,Are), (Ze,Rg,R1b,R3a,Arf), (Ze,Rg,R1b,R3a,Arg), (Ze,Rg,R1b,R3a,Arh), (Ze,Rg,R1b,R3a,Ari), (Ze,Rg,R1b,R3a,Arj), (Ze,Rg,R1b,R3a,Ark), (Ze,Rg,R1b,R3a,Arl), (Ze,Rg,R1b,R3a,Arm), (Ze,Rg,R1b,R3a,Arn), (Ze,Rg,R1b,R3a,Aro), (Ze,Rg,R1b,R3a,Arp), (Ze,Rg,R1b,R3b,Ara), (Ze,Rg,R1b,R3b,Arb), (Ze,Rg,R1b,R3b,Arc), (Ze,Rg,R1b,R3b,Ard), (Ze,Rg,R1b,R3b,Are), (Ze,Rg,R1b,R3b,Arf), (Ze,Rg,R1b,R3b,Arg), (Ze,Rg,R1b,R3b,Arh), (Ze,Rg,R1b,R3b,Ari), (Ze,Rg,R1b,R3b,Arj), (Ze,Rg,R1b,R3b,Ark), (Ze,Rg,R1b,R3b,Arl), (Ze,Rg,R1b,R3b,Arm), (Ze,Rg,R1b,R3b,Arn), (Ze,Rg,R1b,R3b,Aro), (Ze,Rg,R1b,R3b,Arp), (Ze,Rg,R1b,R3c,Ara), (Ze,Rg,R1b,R3c,Arb), (Ze,Rg,R1b,R3c,Arc), (Ze,Rg,R1b,R3c,Ard), (Ze,Rg,R1b,R3c,Are), (Ze,Rg,R1b,R3c,Arf), (Ze,Rg,R1b,R3c,Arg), (Ze,Rg,R1b,R3c,Arh), (Ze,Rg,R1b,R3c,Ari), (Ze,Rg,R1b,R3c,Arj), (Ze,Rg,R1b,R3c,Ark), (Ze,Rg,R1b,R3c,Arl), (Ze,Rg,R1b,R3c,Arm), (Ze,Rg,R1b,R3c,Arn), (Ze,Rg,R1b,R3c,Aro), (Ze,Rg,R1b,R3c,Arp), (Ze,Rg,R1b,R3d,Ara), (Ze,Rg,R1b,R3d,Arb), (Ze,Rg,R1b,R3d,Arc), (Ze,Rg,R1b,R3d,Ard), (Ze,Rg,R1b,R3d,Are), (Ze,Rg,R1b,R3d,Arf), (Ze,Rg,R1b,R3d,Arg), (Ze,Rg,R1b,R3d,Arh), (Ze,Rg,R1b,R3d,Ari), (Ze,Rg,R1b,R3d,Arj), (Ze,Rg,R1b,R3d,Ark), (Ze,Rg,R1b,R3d,Arl), (Ze,Rg,R1b,R3d,Arm), (Ze,Rg,R1b,R3d,Arn), (Ze,Rg,R1b,R3d,Aro), (Ze,Rg,R1b,R3d,Arp), (Ze,Rg,R1b,R3e,Ara), (Ze,Rg,R1b,R3e,Arb), (Ze,Rg,R1b,R3e,Arc), (Ze,Rg,R1b,R3e,Ard), (Ze,Rg,R1b,R3e,Are), (Ze,Rg,R1b,R3e,Arf), (Ze,Rg,R1b,R3e,Arg), (Ze,Rg,R1b,R3e,Arh), (Ze,Rg,R1b,R3e,Ari), (Ze,Rg,R1b,R3e,Arj), (Ze,Rg,R1b,R3e,Ark), (Ze,Rg,R1b,R3e,Arl), (Ze,Rg,R1b,R3e,Arm), (Ze,Rg,R1b,R3e,Arn), (Ze,Rg,R1b,R3e,Aro), (Ze,Rg,R1b,R3e,Arp), (Ze,Rg,R1b,R3f,Ara), (Ze,Rg,R1b,R3f,Arb), (Ze,Rg,R1b,R3f,Arc), (Ze,Rg,R1b,R3f,Ard), (Ze,Rg,R1b,R3f,Are), (Ze,Rg,R1b,R3f,Arf), (Ze,Rg,R1b,R3f,Arg), (Ze,Rg,R1b,R3f,Arh), (Ze,Rg,R1b,R3f,Ari), (Ze,Rg,R1b,R3f,Arj), (Ze,Rg,R1b,R3f,Ark), (Ze,Rg,R1b,R3f,Arl), (Ze,Rg,R1b,R3f,Arm), (Ze,Rg,R1b,R3f,Arn), (Ze,Rg,R1b,R3f,Aro), (Ze,Rg,R1b,R3f,Arp), (Ze,Rg,R1b,R3g,Ara), (Ze,Rg,R1b,R3g,Arb), (Ze,Rg,R1b,R3g,Arc), (Ze,Rg,R1b,R3g,Ard), (Ze,Rg,R1b,R3g,Are), (Ze,Rg,R1b,R3g,Arf), (Ze,Rg,R1b,R3g,Arg), (Ze,Rg,R1b,R3g,Arh), (Ze,Rg,R1b,R3g,Ari), (Ze,Rg,R1b,R3g,Arj), (Ze,Rg,R1b,R3g,Ark), (Ze,Rg,R1b,R3g,Arl), (Ze,Rg,R1b,R3g,Arm), (Ze,Rg,R1b,R3g,Arn), (Ze,Rg,R1b,R3g,Aro), (Ze,Rg,R1b,R3g,Arp), (Ze,Rg,R1b,R3h,Ara), (Ze,Rg,R1b,R3h,Arb), (Ze,Rg,R1b,R3h,Arc), (Ze,Rg,R1b,R3h,Ard), (Ze,Rg,R1b,R3h,Are), (Ze,Rg,R1b,R3h,Arf), (Ze,Rg,R1b,R3h,Arg), (Ze,Rg,R1b,R3h,Arh), (Ze,Rg,R1b,R3h,Ari), (Ze,Rg,R1b,R3h,Arj), (Ze,Rg,R1b,R3h,Ark), (Ze,Rg,R1b,R3h,Arl), (Ze,Rg,R1b,R3h,Arm), (Ze,Rg,R1b,R3h,Arn), (Ze,Rg,R1b,R3h,Aro), (Ze,Rg,R1b,R3h,Arp), (Ze,Rg,R1c,R3a,Ara), (Ze,Rg,R1c,R3a,Arb), (Ze,Rg,R1c,R3a,Arc), (Ze,Rg,R1c,R3a,Ard), (Ze,Rg,R1c,R3a,Are), (Ze,Rg,R1c,R3a,Arf), (Ze,Rg,R1c,R3a,Arg), (Ze,Rg,R1c,R3a,Arh), (Ze,Rg,R1c,R3a,Ari), (Ze,Rg,R1c,R3a,Arj), (Ze,Rg,R1c,R3a,Ark), (Ze,Rg,R1c,R3a,Arl), (Ze,Rg,R1c,R3a,Arm), (Ze,Rg,R1c,R3a,Arn), (Ze,Rg,R1c,R3a,Aro), (Ze,Rg,R1c,R3a,Arp), (Ze,Rg,R1c,R3b,Ara), (Ze,Rg,R1c,R3b,Arb), (Ze,Rg,R1c,R3b,Arc), (Ze,Rg,R1c,R3b,Ard), (Ze,Rg,R1c,R3b,Are), (Ze, Rg,R1c,R3b,Arf), (Ze,Rg,R1c,R3b,Arg), (Ze,Rg,R1c,R3b, Arh), (Ze,Rg,R1c,R3b,Ari), (Ze,Rg,R1c,R3b,Arj), (Ze,Rg, R1c,R3b,Ark), (Ze,Rg,R1c,R3b,Arl), (Ze,Rg,R1c,R3b, Arm), (Ze,Rg,R1c,R3b,Arn), (Ze,Rg,R1c,R3b,Aro), (Ze,Rg, R1c,R3b,Arp), (Ze,Rg,R1c,R3c,Ara), (Ze,Rg,R1c,R3c,Arb), (Ze,Rg,R1c,R3c,Arc), (Ze,Rg,R1c,R3c,Ard), (Ze,Rg,R1c, R3c,Are), (Ze,Rg,R1c,R3c,Arf), (Ze,Rg,R1c,R3c,Arg), (Ze, Rg,R1c,R3c,Arh), (Ze,Rg,R1c,R3c,Ari), (Ze,Rg,R1c,R3c, Arj), (Ze,Rg,R1c,R3c,Ark), (Ze,Rg,R1c,R3c,Arl), (Ze,Rg, R1c,R3c,Arm), (Ze,Rg,R1c,R3c,Arn), (Ze,Rg,R1c,R3c, Aro), (Ze,Rg,R1c,R3c,Arp), (Ze,Rg,R1c,R3d,Ara), (Ze,Rg, R1c,R3d,Arb), (Ze,Rg,R1c,R3d,Arc), (Ze,Rg,R1c,R3d, Ard), (Ze,Rg,R1c,R3d,Are), (Ze,Rg,R1c,R3d,Arf), (Ze,Rg, R1c,R3d,Arg), (Ze,Rg,R1c,R3d,Arh), (Ze,Rg,R1c,R3d,Ari), (Ze,Rg,R1c,R3d,Arj), (Ze,Rg,R1c,R3d,Ark), (Ze,Rg,R1c, R3d,Arl), (Ze,Rg,R1c,R3d,Arm), (Ze,Rg,R1c,R3d,Arn), (Ze,Rg,R1c,R3d,Aro), (Ze,Rg,R1c,R3d,Arp), (Ze,Rg,R1c, R3e,Ara), (Ze,Rg,R1c,R3e,Arb), (Ze,Rg,R1c,R3e,Arc), (Ze, Rg,R1c,R3e,Ard), (Ze,Rg,R1c,R3e,Are), (Ze,Rg,R1c,R3e, Arf), (Ze,Rg,R1c,R3e,Arg), (Ze,Rg,R1c,R3e,Arh), (Ze,Rg, R1c,R3e,Ari), (Ze,Rg,R1c,R3e,Arj), (Ze,Rg,R1c,R3e,Ark), (Ze,Rg,R1c,R3e,Arl), (Ze,Rg,R1c,R3e,Arm), (Ze,Rg,R1c, R3e,Arn), (Ze,Rg,R1c,R3e,Aro), (Ze,Rg,R1c,R3e,Arp), (Ze, Rg,R1c,R3f,Ara), (Ze,Rg,R1c,R3f,Arb), (Ze,Rg,R1c,R3f, Arc), (Ze,Rg,R1c,R3f,Ard), (Ze,Rg,R1c,R3f,Are), (Ze,Rg, R1c,R3f,Arf), (Ze,Rg,R1c,R3f,Arg), (Ze,Rg,R1c,R3f,Arh), (Ze,Rg,R1c,R3f,Ari), (Ze,Rg,R1c,R3f,Arj), (Ze,Rg,R1c, R3f,Ark), (Ze,Rg,R1c,R3f,Arl), (Ze,Rg,R1c,R3f,Arm), (Ze, Rg,R1c,R3f,Arn), (Ze,Rg,R1c,R3f,Aro), (Ze,Rg,R1c,R3f, Arp), (Ze,Rg,R1c,R3g,Ara), (Ze,Rg,R1c,R3g,Arb), (Ze,Rg, R1c,R3g,Arc), (Ze,Rg,R1c,R3g,Ard), (Ze,Rg,R1c,R3g, Are), (Ze,Rg,R1c,R3g,Arf), (Ze,Rg,R1c,R3g,Arg), (Ze,Rg, R1c,R3g,Arh), (Ze,Rg,R1c,R3g,Ari), (Ze,Rg,R1c,R3g,Arj), (Ze,Rg,R1c,R3g,Ark), (Ze,Rg,R1c,R3g,Arl), (Ze,Rg,R1c, R3g,Arm), (Ze,Rg,R1c,R3g,Arn), (Ze,Rg,R1c,R3g,Aro), (Ze,Rg,R1c,R3g,Arp), (Ze,Rg,R1c,R3h,Ara), (Ze,Rg,R1c, R3h,Arb), (Ze,Rg,R1c,R3h,Arc), (Ze,Rg,R1c,R3h,Ard), (Ze,Rg,R1c,R3h,Are), (Ze,Rg,R1c,R3h,Arf), (Ze,Rg,R1c, R3h,Arg), (Ze,Rg,R1c,R3h,Arh), (Ze,Rg,R1c,R3h,Ari), (Ze, Rg,R1c,R3h,Arj), (Ze,Rg,R1c,R3h,Ark), (Ze,Rg,R1c,R3h, Arl), (Ze,Rg,R1c,R3h,Arm), (Ze,Rg,R1c,R3h,Arn), (Ze,Rg, R1c,R3h,Aro), (Ze,Rg,R1c,R3h,Arp), (Ze,Rg,R1d,R3a, Ara), (Ze,Rg,R1d,R3a,Arb), (Ze,Rg,R1d,R3a,Arc), (Ze,Rg, R1d,R3a,Ard), (Ze,Rg,R1d,R3a,Are), (Ze,Rg,R1d,R3a,Arf), (Ze,Rg,R1d,R3a,Arg), (Ze,Rg,R1d,R3a,Arh), (Ze,Rg,R1d, R3a,Ari), (Ze,Rg,R1d,R3a,Arj), (Ze,Rg,R1d,R3a,Ark), (Ze, Rg,R1d,R3a,Arl), (Ze,Rg,R1d,R3a,Arm), (Ze,Rg,R1d,R3a, Arn), (Ze,Rg,R1d,R3a,Aro), (Ze,Rg,R1d,R3a,Arp), (Ze,Rg, R1d,R3b,Ara), (Ze,Rg,R1d,R3b,Arb), (Ze,Rg,R1d,R3b, Arc), (Ze,Rg,R1d,R3b,Ard), (Ze,Rg,R1d,R3b,Are), (Ze,Rg, R1d,R3b,Arf), (Ze,Rg,R1d,R3b,Arg), (Ze,Rg,R1d,R3b, Arh), (Ze,Rg,R1d,R3b,Ari), (Ze,Rg,R1d,R3b,Arj), (Ze,Rg, R1d,R3b,Ark), (Ze,Rg,R1d,R3b,Arl), (Ze,Rg,R1d,R3b, Arm), (Ze,Rg,R1d,R3b,Arn), (Ze,Rg,R1d,R3b,Aro), (Ze,Rg, R1d,R3b,Arp), (Ze,Rg,R1d,R3c,Ara), (Ze,Rg,R1d,R3c, Arb), (Ze,Rg,R1d,R3c,Arc), (Ze,Rg,R1d,R3c,Ard), (Ze,Rg, R1d,R3c,Are), (Ze,Rg,R1d,R3c,Arf), (Ze,Rg,R1d,R3c,Arg), (Ze,Rg,R1d,R3c,Arh), (Ze,Rg,R1d,R3c,Ari), (Ze,Rg,R1d, R3c,Arj), (Ze,Rg,R1d,R3c,Ark), (Ze,Rg,R1d,R3c,Arl), (Ze, Rg,R1d,R3c,Arm), (Ze,Rg,R1d,R3c,Arn), (Ze,Rg,R1d,R3c, Aro), (Ze,Rg,R1d,R3c,Arp), (Ze,Rg,R1d,R3d,Ara), (Ze,Rg, R1d,R3d,Arb), (Ze,Rg,R1d,R3d,Arc), (Ze,Rg,R1d,R3d, Ard), (Ze,Rg,R1d,R3d,Are), (Ze,Rg,R1d,R3d,Arf), (Ze,Rg, R1d,R3d,Arg), (Ze,Rg,R1d,R3d,Arh), (Ze,Rg,R1d,R3d, Ari), (Ze,Rg,R1d,R3d,Arj), (Ze,Rg,R1d,R3d,Ark), (Ze,Rg, R1d,R3d,Arl), (Ze,Rg,R1d,R3d,Arm), (Ze,Rg,R1d,R3d, Arn), (Ze,Rg,R1d,R3d,Aro), (Ze,Rg,R1d,R3d,Arp), (Ze,Rg, R1d,R3e,Ara), (Ze,Rg,R1d,R3e,Arb), (Ze,Rg,R1d,R3e, Arc), (Ze,Rg,R1d,R3e,Ard), (Ze,Rg,R1d,R3e,Are), (Ze,Rg, R1d,R3e,Arf), (Ze,Rg,R1d,R3e,Arg), (Ze,Rg,R1d,R3e,Arh), (Ze,Rg,R1d,R3e,Ari), (Ze,Rg,R1d,R3e,Arj), (Ze,Rg,R1d, R3e,Ark), (Ze,Rg,R1d,R3e,Arl), (Ze,Rg,R1d,R3e,Arm), (Ze,Rg,R1d,R3e,Arn), (Ze,Rg,R1d,R3e,Aro), (Ze,Rg,R1d, R3e,Arp), (Ze,Rg,R1d,R3f,Ara), (Ze,Rg,R1d,R3f,Arb), (Ze, Rg,R1d,R3f,Arc), (Ze,Rg,R1d,R3f,Ard), (Ze,Rg,R1d,R3f, Are), (Ze,Rg,R1d,R3f,Arf), (Ze,Rg,R1d,R3f,Arg), (Ze,Rg, R1d,R3f,Arh), (Ze,Rg,R1d,R3f,Ari), (Ze,Rg,R1d,R3f,Arj), (Ze,Rg,R1d,R3f,Ark), (Ze,Rg,R1d,R3f,Arl), (Ze,Rg,R1d, R3f,Arm), (Ze,Rg,R1d,R3f,Arn), (Ze,Rg,R1d,R3f,Aro), (Ze, Rg,R1d,R3f,Arp), (Ze,Rg,R1d,R3g,Ara), (Ze,Rg,R1d,R3g, Arb), (Ze,Rg,R1d,R3g,Arc), (Ze,Rg,R1d,R3g,Ard), (Ze,Rg, R1d,R3g,Are), (Ze,Rg,R1d,R3g,Arf), (Ze,Rg,R1d,R3g, Arg), (Ze,Rg,R1d,R3g,Arh), (Ze,Rg,R1d,R3g,Ari), (Ze,Rg, R1d,R3g,Arj), (Ze,Rg,R1d,R3g,Ark), (Ze,Rg,R1d,R3g,Arl), (Ze,Rg,R1d,R3g,Arm), (Ze,Rg,R1d,R3g,Arn), (Ze,Rg,R1d, R3g,Aro), (Ze,Rg,R1d,R3g,Arp), (Ze,Rg,R1d,R3h,Ara), (Ze,Rg,R1d,R3h,Arb), (Ze,Rg,R1d,R3h,Arc), (Ze,Rg,R1d, R3h,Ard), (Ze,Rg,R1d,R3h,Are), (Ze,Rg,R1d,R3h,Arf), (Ze, Rg,R1d,R3h,Arg), (Ze,Rg,R1d,R3h,Arh), (Ze,Rg,R1d,R3h, Ari), (Ze,Rg,R1d,R3h,Arj), (Ze,Rg,R1d,R3h,Ark), (Ze,Rg, R1d,R3h,Arl), (Ze,Rg,R1d,R3h,Arm), (Ze,Rg,R1d,R3h, Arn), (Ze,Rg,R1d,R3h,Aro), (Ze,Rg,R1d,R3h,Arp), (Ze,Rh, R1a,R3a,Ara), (Ze,Rh,R1a,R3a,Arb), (Ze,Rh,R1a,R3a,Arc), (Ze,Rh,R1a,R3a,Ard), (Ze,Rh,R1a,R3a,Are), (Ze,Rh,R1a, R3a,Arf), (Ze,Rh,R1a,R3a,Arg), (Ze,Rh,R1a,R3a,Arh), (Ze, Rh,R1a,R3a,Ari), (Ze,Rh,R1a,R3a,Arj), (Ze,Rh,R1a,R3a, Ark), (Ze,Rh,R1a,R3a,Arl), (Ze,Rh,R1a,R3a,Arm), (Ze,Rh, R1a,R3a,Arn), (Ze,Rh,R1a,R3a,Aro), (Ze,Rh,R1a,R3a,Arp), (Ze,Rh,R1a,R3b,Ara), (Ze,Rh,R1a,R3b,Arb), (Ze,Rh,R1a, R3b,Arc), (Ze,Rh,R1a,R3b,Ard), (Ze,Rh,R1a,R3b,Are), (Ze, Rh,R1a,R3b,Arf), (Ze,Rh,R1a,R3b,Arg), (Ze,Rh,R1a,R3b, Arh), (Ze,Rh,R1a,R3b,Ari), (Ze,Rh,R1a,R3b,Arj), (Ze,Rh, R1a,R3b,Ark), (Ze,Rh,R1a,R3b,Arl), (Ze,Rh,R1a,R3b, Arm), (Ze,Rh,R1a,R3b,Arn), (Ze,Rh,R1a,R3b,Aro), (Ze,Rh, R1a,R3b,Arp), (Ze,Rh,R1a,R3c,Ara), (Ze,Rh,R1a,R3c,Arb), (Ze,Rh,R1a,R3c,Arc), (Ze,Rh,R1a,R3c,Ard), (Ze,Rh,R1a, R3c,Are), (Ze,Rh,R1a,R3c,Arf), (Ze,Rh,R1a,R3c,Arg), (Ze, Rh,R1a,R3c,Arh), (Ze,Rh,R1a,R3c,Ari), (Ze,Rh,R1a,R3c, Arj), (Ze,Rh,R1a,R3c,Ark), (Ze,Rh,R1a,R3c,Arl), (Ze,Rh, R1a,R3c,Arm), (Ze,Rh,R1a,R3c,Arn), (Ze,Rh,R1a,R3c, Aro), (Ze,Rh,R1a,R3c,Arp), (Ze,Rh,R1a,R3d,Ara), (Ze,Rh, R1a,R3d,Arb), (Ze,Rh,R1a,R3d,Arc), (Ze,Rh,R1a,R3d, Ard), (Ze,Rh,R1a,R3d,Are), (Ze,Rh,R1a,R3d,Arf), (Ze,Rh, R1a,R3d,Arg), (Ze,Rh,R1a,R3d,Arh), (Ze,Rh,R1a,R3d,Ari), (Ze,Rh,R1a,R3d,Arj), (Ze,Rh,R1a,R3d,Ark), (Ze,Rh,R1a, R3d,Arl), (Ze,Rh,R1a,R3d,Arm), (Ze,Rh,R1a,R3d,Arn), (Ze,Rh,R1a,R3d,Aro), (Ze,Rh,R1a,R3d,Arp), (Ze,Rh,R1a, R3e,Ara), (Ze,Rh,R1a,R3e,Arb), (Ze,Rh,R1a,R3e,Arc), (Ze, Rh,R1a,R3e,Ard), (Ze,Rh,R1a,R3e,Are), (Ze,Rh,R1a,R3e, Arf), (Ze,Rh,R1a,R3e,Arg), (Ze,Rh,R1a,R3e,Arh), (Ze,Rh, R1a,R3e,Ari), (Ze,Rh,R1a,R3e,Arj), (Ze,Rh,R1a,R3e,Ark), (Ze,Rh,R1a,R3e,Arl), (Ze,Rh,R1a,R3e,Arm), (Ze,Rh,R1a, R3e,Arn), (Ze,Rh,R1a,R3e,Aro), (Ze,Rh,R1a,R3e,Arp), (Ze, Rh,R1a,R3f,Ara), (Ze,Rh,R1a,R3f,Arb), (Ze,Rh,R1a,R3f, Arc), (Ze,Rh,R1a,R3f,Ard), (Ze,Rh,R1a,R3f,Are), (Ze,Rh, R1a,R3f,Arf), (Ze,Rh,R1a,R3f,Arg), (Ze,Rh,R1a,R3f,Arh), (Ze,Rh,R1a,R3f,Ari), (Ze,Rh,R1a,R3f,Arj), (Ze,Rh,R1a, R3f,Ark), (Ze,Rh,R1a,R3f,Arl), (Ze,Rh,R1a,R3f,Arm), (Ze, Rh,R1a,R3f,Arn), (Ze,Rh,R1a,R3f,Aro), (Ze,Rh,R1a,R3f, Arp), (Ze,Rh,R1a,R3g,Ara), (Ze,Rh,R1a,R3g,Arb), (Ze,Rh, R1a,R3g,Arc), (Ze,Rh,R1a,R3g,Ard), (Ze,Rh,R1a,R3g, Are), (Ze,Rh,R1a,R3g,Arf), (Ze,Rh,R1a,R3g,Arg), (Ze,Rh, R1a,R3g,Arh), (Ze,Rh,R1a,R3g,Ari), (Ze,Rh,R1a,R3g,Arj), (Ze,Rh,R1a,R3g,Ark), (Ze,Rh,R1a,R3g,Arl), (Ze,Rh,R1a, R3g,Arm), (Ze,Rh,R1a,R3g,Arn), (Ze,Rh,R1a,R3g,Aro), (Ze,Rh,R1a,R3g,Arp), (Ze,Rh,R1a,R3h,Ara), (Ze,Rh,R1a, R3h,Arb), (Ze,Rh,R1a,R3h,Arc), (Ze,Rh,R1a,R3h,Ard), (Ze,Rh,R1a,R3h,Are), (Ze,Rh,R1a,R3h,Arf), (Ze,Rh,R1a, R3h,Arg), (Ze,Rh,R1a,R3h,Arh), (Ze,Rh,R1a,R3h,Ari), (Ze, Rh,R1a,R3h,Arj), (Ze,Rh,R1a,R3h,Ark), (Ze,Rh,R1a,R3h, Arl), (Ze,Rh,R1a,R3h,Arm), (Ze,Rh,R1a,R3h,Arn), (Ze,Rh, R1a,R3h,Aro), (Ze,Rh,R1a,R3h,Arp), (Ze,Rh,R1b,R3a, Ara), (Ze,Rh,R1b,R3a,Arb), (Ze,Rh,R1b,R3a,Arc), (Ze,Rh, R1b,R3a,Ard), (Ze,Rh,R1b,R3a,Are), (Ze,Rh,R1b,R3a,Arf), (Ze,Rh,R1b,R3a,Arg), (Ze,Rh,R1b,R3a,Arh), (Ze,Rh,R1b, R3a,Ari), (Ze,Rh,R1b,R3a,Arj), (Ze,Rh,R1b,R3a,Ark), (Ze, Rh,R1b,R3a,Arl), (Ze,Rh,R1b,R3a,Arm), (Ze,Rh,R1b,R3a, Arn), (Ze,Rh,R1b,R3a,Aro), (Ze,Rh,R1b,R3a,Arp), (Ze,Rh, R1b,R3b,Ara), (Ze,Rh,R1b,R3b,Arb), (Ze,Rh,R1b,R3b, Arc), (Ze,Rh,R1b,R3b,Ard), (Ze,Rh,R1b,R3b,Are), (Ze,Rh, R1b,R3b,Arf), (Ze,Rh,R1b,R3b,Arg), (Ze,Rh,R1b,R3b, Arh), (Ze,Rh,R1b,R3b,Ari), (Ze,Rh,R1b,R3b,Arj), (Ze,Rh, R1b,R3b,Ark), (Ze,Rh,R1b,R3b,Arl), (Ze,Rh,R1b,R3b, Arm), (Ze,Rh,R1b,R3b,Arn), (Ze,Rh,R1b,R3b,Aro), (Ze,Rh, R1b,R3b,Arp), (Ze,Rh,R1b,R3c,Ara), (Ze,Rh,R1b,R3c, Arb), (Ze,Rh,R1b,R3c,Arc), (Ze,Rh,R1b,R3c,Ard), (Ze,Rh, R1b,R3c,Are), (Ze,Rh,R1b,R3c,Arf), (Ze,Rh,R1b,R3c,Arg), (Ze,Rh,R1b,R3c,Arh), (Ze,Rh,R1b,R3c,Ari), (Ze,Rh,R1b, R3c,Arj), (Ze,Rh,R1b,R3c,Ark), (Ze,Rh,R1b,R3c,Arl), (Ze, Rh,R1b,R3c,Arm), (Ze,Rh,R1b,R3c,Arn), (Ze,Rh,R1b,R3c, Aro), (Ze,Rh,R1b,R3c,Arp), (Ze,Rh,R1b,R3d,Ara), (Ze,Rh, R1b,R3d,Arb), (Ze,Rh,R1b,R3d,Arc), (Ze,Rh,R1b,R3d, Ard), (Ze,Rh,R1b,R3d,Are), (Ze,Rh,R1b,R3d,Arf), (Ze,Rh, R1b,R3d,Arg), (Ze,Rh,R1b,R3d,Arh), (Ze,Rh,R1b,R3d, Ari), (Ze,Rh,R1b,R3d,Arj), (Ze,Rh,R1b,R3d,Ark), (Ze,Rh, R1b,R3d,Arl), (Ze,Rh,R1b,R3d,Arm), (Ze,Rh,R1b,R3d, Arn), (Ze,Rh,R1b,R3d,Aro), (Ze,Rh,R1b,R3d,Arp), (Ze,Rh, R1b,R3e,Ara), (Ze,Rh,R1b,R3e,Arb), (Ze,Rh,R1b,R3e, Arc), (Ze,Rh,R1b,R3e,Ard), (Ze,Rh,R1b,R3e,Are), (Ze,Rh, R1b,R3e,Arf), (Ze,Rh,R1b,R3e,Arg), (Ze,Rh,R1b,R3e,Arh), (Ze,Rh,R1b,R3e,Ari), (Ze,Rh,R1b,R3e,Arj), (Ze,Rh,R1b, R3e,Ark), (Ze,Rh,R1b,R3e,Arl), (Ze,Rh,R1b,R3e,Arm), (Ze,Rh,R1b,R3e,Arn), (Ze,Rh,R1b,R3e,Aro), (Ze,Rh,R1b, R3e,Arp), (Ze,Rh,R1b,R3f,Ara), (Ze,Rh,R1b,R3f,Arb), (Ze, Rh,R1b,R3f,Arc), (Ze,Rh,R1b,R3f,Ard), (Ze,Rh,R1b,R3f, Are), (Ze,Rh,R1b,R3f,Arf), (Ze,Rh,R1b,R3f,Arg), (Ze,Rh, R1b,R3f,Arh), (Ze,Rh,R1b,R3f,Ari), (Ze,Rh,R1b,R3f,Arj), (Ze,Rh,R1b,R3f,Ark), (Ze,Rh,R1b,R3f,Arl), (Ze,Rh,R1b, R3f,Arm), (Ze,Rh,R1b,R3f,Arn), (Ze,Rh,R1b,R3f,Aro), (Ze, Rh,R1b,R3f,Arp), (Ze,Rh,R1b,R3g,Ara), (Ze,Rh,R1b,R3g, Arb), (Ze,Rh,R1b,R3g,Arc), (Ze,Rh,R1b,R3g,Ard), (Ze,Rh, R1b,R3g,Are), (Ze,Rh,R1b,R3g,Arf), (Ze,Rh,R1b,R3g, Arg), (Ze,Rh,R1b,R3g,Arh), (Ze,Rh,R1b,R3g,Ari), (Ze,Rh, R1b,R3g,Arj), (Ze,Rh,R1b,R3g,Ark), (Ze,Rh,R1b,R3g,Arl), (Ze,Rh,R1b,R3g,Arm), (Ze,Rh,R1b,R3g,Arn), (Ze,Rh,R1b, R3g,Aro), (Ze,Rh,R1b,R3g,Arp), (Ze,Rh,R1b,R3h,Ara), (Ze,Rh,R1b,R3h,Arb), (Ze,Rh,R1b,R3h,Arc), (Ze,Rh,R1b, R3h,Ard), (Ze,Rh,R1b,R3h,Are), (Ze,Rh,R1b,R3h,Arf), (Ze, Rh,R1b,R3h,Arg), (Ze,Rh,R1b,R3h,Arh), (Ze,Rh,R1b,R3h, Ari), (Ze,Rh,R1b,R3h,Arj), (Ze,Rh,R1b,R3h,Ark), (Ze,Rh, R1b,R3h,Arl), (Ze,Rh,R1b,R3h,Arm), (Ze,Rh,R1b,R3h, Arn), (Ze,Rh,R1b,R3h,Aro), (Ze,Rh,R1b,R3h,Arp), (Ze,Rh, R1c,R3a,Ara), (Ze,Rh,R1c,R3a,Arb), (Ze,Rh,R1c,R3a,Arc), (Ze,Rh,R1c,R3a,Ard), (Ze,Rh,R1c,R3a,Are), (Ze,Rh,R1c, R3a,Arf), (Ze,Rh,R1c,R3a,Arg), (Ze,Rh,R1c,R3a,Arh), (Ze, Rh,R1c,R3a,Ari), (Ze,Rh,R1c,R3a,Arj), (Ze,Rh,R1c,R3a, Ark), (Ze,Rh,R1c,R3a,Arl), (Ze,Rh,R1c,R3a,Arm), (Ze,Rh, R1c,R3a,Arn), (Ze,Rh,R1c,R3a,Aro), (Ze,Rh,R1c,R3a,Arp), (Ze,Rh,R1c,R3b,Ara), (Ze,Rh,R1c,R3b,Arb), (Ze,Rh,R1c, R3b,Arc), (Ze,Rh,R1c,R3b,Ard), (Ze,Rh,R1c,R3b,Are), (Ze, Rh,R1c,R3b,Arf), (Ze,Rh,R1c,R3b,Arg), (Ze,Rh,R1c,R3b, Arh), (Ze,Rh,R1c,R3b,Ari), (Ze,Rh,R1c,R3b,Arj), (Ze,Rh, R1c,R3b,Ark), (Ze,Rh,R1c,R3b,Arl), (Ze,Rh,R1c,R3b, Arm), (Ze,Rh,R1c,R3b,Arn), (Ze,Rh,R1c,R3b,Aro), (Ze,Rh, R1c,R3b,Arp), (Ze,Rh,R1c,R3c,Ara), (Ze,Rh,R1c,R3c,Arb), (Ze,Rh,R1c,R3c,Arc), (Ze,Rh,R1c,R3c,Ard), (Ze,Rh,R1c, R3c,Are), (Ze,Rh,R1c,R3c,Arf), (Ze,Rh,R1c,R3c,Arg), (Ze, Rh,R1c,R3c,Arh), (Ze,Rh,R1c,R3c,Ari), (Ze,Rh,R1c,R3c, Arj), (Ze,Rh,R1c,R3c,Ark), (Ze,Rh,R1c,R3c,Arl), (Ze,Rh, R1c,R3c,Arm), (Ze,Rh,R1c,R3c,Arn), (Ze,Rh,R1c,R3c, Aro), (Ze,Rh,R1c,R3c,Arp), (Ze,Rh,R1c,R3d,Ara), (Ze,Rh, R1c,R3d,Arb), (Ze,Rh,R1c,R3d,Arc), (Ze,Rh,R1c,R3d, Ard), (Ze,Rh,R1c,R3d,Are), (Ze,Rh,R1c,R3d,Arf), (Ze,Rh, R1c,R3d,Arg), (Ze,Rh,R1c,R3d,Arh), (Ze,Rh,R1c,R3d,Ari), (Ze,Rh,R1c,R3d,Arj), (Ze,Rh,R1c,R3d,Ark), (Ze,Rh,R1c, R3d,Arl), (Ze,Rh,R1c,R3d,Arm), (Ze,Rh,R1c,R3d,Arn), (Ze,Rh,R1c,R3d,Aro), (Ze,Rh,R1c,R3d,Arp), (Ze,Rh,R1c, R3e,Ara), (Ze,Rh,R1c,R3e,Arb), (Ze,Rh,R1c,R3e,Arc), (Ze, Rh,R1c,R3e,Ard), (Ze,Rh,R1c,R3e,Are), (Ze,Rh,R1c,R3e, Arf), (Ze,Rh,R1c,R3e,Arg), (Ze,Rh,R1c,R3e,Arh), (Ze,Rh, R1c,R3e,Ari), (Ze,Rh,R1c,R3e,Arj), (Ze,Rh,R1c,R3e,Ark), (Ze,Rh,R1c,R3e,Arl), (Ze,Rh,R1c,R3e,Arm), (Ze,Rh,R1c, R3e,Arn), (Ze,Rh,R1c,R3e,Aro), (Ze,Rh,R1c,R3e,Arp), (Ze, Rh,R1c,R3f,Ara), (Ze,Rh,R1c,R3f,Arb), (Ze,Rh,R1c,R3f, Arc), (Ze,Rh,R1c,R3f,Ard), (Ze,Rh,R1c,R3f,Are), (Ze,Rh, R1c,R3f,Arf), (Ze,Rh,R1c,R3f,Arg), (Ze,Rh,R1c,R3f,Arh), (Ze,Rh,R1c,R3f,Ari), (Ze,Rh,R1c,R3f,Arj), (Ze,Rh,R1c, R3f,Ark), (Ze,Rh,R1c,R3f,Arl), (Ze,Rh,R1c,R3f,Arm), (Ze, Rh,R1c,R3f,Arn), (Ze,Rh,R1c,R3f,Aro), (Ze,Rh,R1c,R3f, Arp), (Ze,Rh,R1c,R3g,Ara), (Ze,Rh,R1c,R3g,Arb), (Ze,Rh, R1c,R3g,Arc), (Ze,Rh,R1c,R3g,Ard), (Ze,Rh,R1c,R3g, Are), (Ze,Rh,R1c,R3g,Arf), (Ze,Rh,R1c,R3g,Arg), (Ze,Rh, R1c,R3g,Arh), (Ze,Rh,R1c,R3g,Ari), (Ze,Rh,R1c,R3g,Arj), (Ze,Rh,R1c,R3g,Ark), (Ze,Rh,R1c,R3g,Arl), (Ze,Rh,R1c, R3g,Arm), (Ze,Rh,R1c,R3g,Arn), (Ze,Rh,R1c,R3g,Aro), (Ze,Rh,R1c,R3g,Arp), (Ze,Rh,R1c,R3h,Ara), (Ze,Rh,R1c, R3h,Arb), (Ze,Rh,R1c,R3h,Arc), (Ze,Rh,R1c,R3h,Ard), (Ze,Rh,R1c,R3h,Are), (Ze,Rh,R1c,R3h,Arf), (Ze,Rh,R1c, R3h,Arg), (Ze,Rh,R1c,R3h,Arh), (Ze,Rh,R1c,R3h,Ari), (Ze, Rh,R1c,R3h,Arj), (Ze,Rh,R1c,R3h,Ark), (Ze,Rh,R1c,R3h, Arl), (Ze,Rh,R1c,R3h,Arm), (Ze,Rh,R1c,R3h,Arn), (Ze,Rh, R1c,R3h,Aro), (Ze,Rh,R1c,R3h,Arp), (Ze,Rh,R1d,R3a, Ara), (Ze,Rh,R1d,R3a,Arb), (Ze,Rh,R1d,R3a,Arc), (Ze,Rh, R1d,R3a,Ard), (Ze,Rh,R1d,R3a,Are), (Ze,Rh,R1d,R3a,Arf), (Ze,Rh,R1d,R3a,Arg), (Ze,Rh,R1d,R3a,Arh), (Ze,Rh,R1d, R3a,Ari), (Ze,Rh,R1d,R3a,Arj), (Ze,Rh,R1d,R3a,Ark), (Ze, Rh,R1d,R3a,Arl), (Ze,Rh,R1d,R3a,Arm), (Ze,Rh,R1d,R3a, Arn), (Ze,Rh,R1d,R3a,Aro), (Ze,Rh,R1d,R3a,Arp), (Ze,Rh, R1d,R3b,Ara), (Ze,Rh,R1d,R3b,Arb), (Ze,Rh,R1d,R3b, Arc), (Ze,Rh,R1d,R3b,Ard), (Ze,Rh,R1d,R3b,Are), (Ze,Rh, R1d,R3b,Arf), (Ze,Rh,R1d,R3b,Arg), (Ze,Rh,R1d,R3b, Arh), (Ze,Rh,R1d,R3b,Ari), (Ze,Rh,R1d,R3b,Arj), (Ze,Rh, R1d,R3b,Ark), (Ze,Rh,R1d,R3b,Arl), (Ze,Rh,R1d,R3b, Arm), (Ze,Rh,R1d,R3b,Arn), (Ze,Rh,R1d,R3b,Aro), (Ze,Rh, R1d,R3b,Arp), (Ze,Rh,R1d,R3c,Ara), (Ze,Rh,R1d,R3c, Arb), (Ze,Rh,R1d,R3c,Arc), (Ze,Rh,R1d,R3c,Ard), (Ze,Rh, R1d,R3c,Are), (Ze,Rh,R1d,R3c,Arf), (Ze,Rh,R1d,R3c,Arg), (Ze,Rh,R1d,R3c,Arh), (Ze,Rh,R1d,R3c,Ari), (Ze,Rh,R1d, R3c,Arj), (Ze,Rh,R1d,R3c,Ark), (Ze,Rh,R1d,R3c,Arl), (Ze, Rh,R1d,R3c,Arm), (Ze,Rh,R1d,R3c,Arn), (Ze,Rh,R1d,R3c, Aro), (Ze,Rh,R1d,R3c,Arp), (Ze,Rh,R1d,R3d,Ara), (Ze,Rh, R1d,R3d,Arb), (Ze,Rh,R1d,R3d,Arc), (Ze,Rh,R1d,R3d, Ard), (Ze,Rh,R1d,R3d,Are), (Ze,Rh,R1d,R3d,Arf), (Ze,Rh, R1d,R3d,Arg), (Ze,Rh,R1d,R3d,Arh), (Ze,Rh,R1d,R3d, Ari), (Ze,Rh,R1d,R3d,Arj), (Ze,Rh,R1d,R3d,Ark), (Ze,Rh, R1d,R3d,Arl), (Ze,Rh,R1d,R3d,Arm), (Ze,Rh,R1d,R3d, Arn), (Ze,Rh,R1d,R3d,Aro), (Ze,Rh,R1d,R3d,Arp), (Ze,Rh, R1d,R3e,Ara), (Ze,Rh,R1d,R3e,Arb), (Ze,Rh,R1d,R3e, Arc), (Ze,Rh,R1d,R3e,Ard), (Ze,Rh,R1d,R3e,Are), (Ze,Rh, R1d,R3e,Arf), (Ze,Rh,R1d,R3e,Arg), (Ze,Rh,R1d,R3e,Arh), (Ze,Rh,R1d,R3e,Ari), (Ze,Rh,R1d,R3e,Arj), (Ze,Rh,R1d, R3e,Ark), (Ze,Rh,R1d,R3e,Arl), (Ze,Rh,R1d,R3e,Arm), (Ze,Rh,R1d,R3e,Arn), (Ze,Rh,R1d,R3e,Aro), (Ze,Rh,R1d, R3e,Arp), (Ze,Rh,R1d,R3f,Ara), (Ze,Rh,R1d,R3f,Arb), (Ze, Rh,R1d,R3f,Arc), (Ze,Rh,R1d,R3f,Ard), (Ze,Rh,R1d,R3f, Are), (Ze,Rh,R1d,R3f,Arf), (Ze,Rh,R1d,R3f,Arg), (Ze,Rh, R1d,R3f,Arh), (Ze,Rh,R1d,R3f,Ari), (Ze,Rh,R1d,R3f,Arj), (Ze,Rh,R1d,R3f,Ark), (Ze,Rh,R1d,R3f,Arl), (Ze,Rh,R1d, R3f,Arm), (Ze,Rh,R1d,R3f,Arn), (Ze,Rh,R1d,R3f,Aro), (Ze, Rh,R1d,R3f,Arp), (Ze,Rh,R1d,R3g,Ara), (Ze,Rh,R1d,R3g, Arb), (Ze,Rh,R1d,R3g,Arc), (Ze,Rh,R1d,R3g,Ard), (Ze,Rh, R1d,R3g,Are), (Ze,Rh,R1d,R3g,Arf), (Ze,Rh,R1d,R3g, Arg), (Ze,Rh,R1d,R3g,Arh), (Ze,Rh,R1d,R3g,Ari), (Ze,Rh, R1d,R3g,Arj), (Ze,Rh,R1d,R3g,Ark), (Ze,Rh,R1d,R3g,Arl), (Ze,Rh,R1d,R3g,Arm), (Ze,Rh,R1d,R3g,Arn), (Ze,Rh,R1d, R3g,Aro), (Ze,Rh,R1d,R3g,Arp), (Ze,Rh,R1d,R3h,Ara), (Ze,Rh,R1d,R3h,Arb), (Ze,Rh,R1d,R3h,Arc), (Ze,Rh,R1d, R3h,Ard), (Ze,Rh,R1d,R3h,Are), (Ze,Rh,R1d,R3h,Arf), (Ze, Rh,R1d,R3h,Arg), (Ze,Rh,R1d,R3h,Arh), (Ze,Rh,R1d,R3h, Ari), (Ze,Rh,R1d,R3h,Arj), (Ze,Rh,R1d,R3h,Ark), (Ze,Rh, R1d,R3h,Arl), (Ze,Rh,R1d,R3h,Arm), (Ze,Rh,R1d,R3h, Arn), (Ze,Rh,R1d,R3h,Aro), (Ze,Rh,R1d,R3h,Arp), (Ze,Ri, R1a,R3a,Ara), (Ze,Ri,R1a,R3a,Arb), (Ze,Ri,R1a,R3a,Arc), (Ze,Ri,R1a,R3a,Ard), (Ze,Ri,R1a,R3a,Are), (Ze,Ri,R1a, R3a,Arf), (Ze,Ri,R1a,R3a,Arg), (Ze,Ri,R1a,R3a,Arh), (Ze, Ri,R1a,R3a,Ari), (Ze,Ri,R1a,R3a,Arj), (Ze,Ri,R1a,R3a, Ark), (Ze,Ri,R1a,R3a,Arl), (Ze,Ri,R1a,R3a,Arm), (Ze,Ri, R1a,R3a,Arn), (Ze,Ri,R1a,R3a,Aro), (Ze,Ri,R1a,R3a,Arp), (Ze,Ri,R1a,R3b,Ara), (Ze,Ri,R1a,R3b,Arb), (Ze,Ri,R1a, R3b,Arc), (Ze,Ri,R1a,R3b,Ard), (Ze,Ri,R1a,R3b,Are), (Ze, Ri,R1a,R3b,Arf), (Ze,Ri,R1a,R3b,Arg), (Ze,Ri,R1a,R3b, Arh), (Ze,Ri,R1a,R3b,Ari), (Ze,Ri,R1a,R3b,Arj), (Ze,Ri, R1a,R3b,Ark), (Ze,Ri,R1a,R3b,Arl), (Ze,Ri,R1a,R3b,Arm), (Ze,Ri,R1a,R3b,Arn), (Ze,Ri,R1a,R3b,Aro), (Ze,Ri,R1a, R3b,Arp), (Ze,Ri,R1a,R3c,Ara), (Ze,Ri,R1a,R3c,Arb), (Ze, Ri,R1a,R3c,Arc), (Ze,Ri,R1a,R3c,Ard), (Ze,Ri,R1a,R3c, Are), (Ze,Ri,R1a,R3c,Arf), (Ze,Ri,R1a,R3c,Arg), (Ze,Ri, R1a,R3c,Arh), (Ze,Ri,R1a,R3c,Ari), (Ze,Ri,R1a,R3c,Arj), (Ze,Ri,R1a,R3c,Ark), (Ze,Ri,R1a,R3c,Arl), (Ze,Ri,R1a, R3c,Arm), (Ze,Ri,R1a,R3c,Arn), (Ze,Ri,R1a,R3c,Aro), (Ze, Ri,R1a,R3c,Arp), (Ze,Ri,R1a,R3d,Ara), (Ze,Ri,R1a,R3d, Arb), (Ze,Ri,R1a,R3d,Arc), (Ze,Ri,R1a,R3d,Ard), (Ze,Ri, R1a,R3d,Are), (Ze,Ri,R1a,R3d,Arf), (Ze,Ri,R1a,R3d,Arg), (Ze,Ri,R1a,R3d,Arh), (Ze,Ri,R1a,R3d,Ari), (Ze,Ri,R1a, R3d,Arj), (Ze,Ri,R1a,R3d,Ark), (Ze,Ri,R1a,R3d,Arl), (Ze, Ri,R1a,R3d,Arm), (Ze,Ri,R1a,R3d,Arn), (Ze,Ri,R1a,R3d, Aro), (Ze,Ri,R1a,R3d,Arp), (Ze,Ri,R1a,R3e,Ara), (Ze,Ri, R1a,R3e,Arb), (Ze,Ri,R1a,R3e,Arc), (Ze,Ri,R1a,R3e,Ard), (Ze,Ri,R1a,R3e,Are), (Ze,Ri,R1a,R3e,Arf), (Ze,Ri,R1a, R3e,Arg), (Ze,Ri,R1a,R3e,Arh), (Ze,Ri,R1a,R3e,Ari), (Ze, Ri,R1a,R3e,Arj), (Ze,Ri,R1a,R3e,Ark), (Ze,Ri,R1a,R3e, Arl), (Ze,Ri,R1a,R3e,Arm), (Ze,Ri,R1a,R3e,Arn), (Ze,Ri, R1a,R3e,Aro), (Ze,Ri,R1a,R3e,Arp), (Ze,Ri,R1a,R3f,Ara), (Ze,Ri,R1a,R3f,Arb), (Ze,Ri,R1a,R3f,Arc), (Ze,Ri,R1a,R3f, Ard), (Ze,Ri,R1a,R3f,Are), (Ze,Ri,R1a,R3f,Arf), (Ze,Ri, R1a,R3f,Arg), (Ze,Ri,R1a,R3f,Arh), (Ze,Ri,R1a,R3f,Ari), (Ze,Ri,R1a,R3f,Arj), (Ze,Ri,R1a,R3f,Ark), (Ze,Ri,R1a,R3f, Arl), (Ze,Ri,R1a,R3f,Arm), (Ze,Ri,R1a,R3f,Arn), (Ze,Ri, R1a,R3f,Aro), (Ze,Ri,R1a,R3f,Arp), (Ze,Ri,R1a,R3g,Ara), (Ze,Ri,R1a,R3g,Arb), (Ze,Ri,R1a,R3g,Arc), (Ze,Ri,R1a, R3g,Ard), (Ze,Ri,R1a,R3g,Are), (Ze,Ri,R1a,R3g,Arf), (Ze, Ri,R1a,R3g,Arg), (Ze,Ri,R1a,R3g,Arh), (Ze,Ri,R1a,R3g, Ari), (Ze,Ri,R1a,R3g,Arj), (Ze,Ri,R1a,R3g,Ark), (Ze,Ri, R1a,R3g,Arl), (Ze,Ri,R1a,R3g,Arm), (Ze,Ri,R1a,R3g,Arn), (Ze,Ri,R1a,R3g,Aro), (Ze,Ri,R1a,R3g,Arp), (Ze,Ri,R1a, R3h,Ara), (Ze,Ri,R1a,R3h,Arb), (Ze,Ri,R1a,R3h,Arc), (Ze, Ri,R1a,R3h,Ard), (Ze,Ri,R1a,R3h,Are), (Ze,Ri,R1a,R3h, Arf), (Ze,Ri,R1a,R3h,Arg), (Ze,Ri,R1a,R3h,Arh), (Ze,Ri, R1a,R3h,Ari), (Ze,Ri,R1a,R3h,Arj), (Ze,Ri,R1a,R3h,Ark), (Ze,Ri,R1a,R3h,Arl), (Ze,Ri,R1a,R3h,Arm), (Ze,Ri,R1a, R3h,Arn), (Ze,Ri,R1a,R3h,Aro), (Ze,Ri,R1a,R3h,Arp), (Ze, Ri,R1b,R3a,Ara), (Ze,Ri,R1b,R3a,Arb), (Ze,Ri,R1b,R3a, Arc), (Ze,Ri,R1b,R3a,Ard), (Ze,Ri,R1b,R3a,Are), (Ze,Ri, R1b,R3a,Arf), (Ze,Ri,R1b,R3a,Arg), (Ze,Ri,R1b,R3a,Arh), (Ze,Ri,R1b,R3a,Ari), (Ze,Ri,R1b,R3a,Arj), (Ze,Ri,R1b,R3a, Ark), (Ze,Ri,R1b,R3a,Arl), (Ze,Ri,R1b,R3a,Arm), (Ze,Ri, R1b,R3a,Arn), (Ze,Ri,R1b,R3a,Aro), (Ze,Ri,R1b,R3a,Arp), (Ze,Ri,R1b,R3b,Ara), (Ze,Ri,R1b,R3b,Arb), (Ze,Ri,R1b, R3b,Arc), (Ze,Ri,R1b,R3b,Ard), (Ze,Ri,R1b,R3b,Are), (Ze, Ri,R1b,R3b,Arf), (Ze,Ri,R1b,R3b,Arg), (Ze,Ri,R1b,R3b, Arh), (Ze,Ri,R1b,R3b,Ari), (Ze,Ri,R1b,R3b,Arj), (Ze,Ri, R1b,R3b,Ark), (Ze,Ri,R1b,R3b,Arl), (Ze,Ri,R1b,R3b,Arm), (Ze,Ri,R1b,R3b,Arn), (Ze,Ri,R1b,R3b,Aro), (Ze,Ri,R1b, R3b,Arp), (Ze,Ri,R1b,R3c,Ara), (Ze,Ri,R1b,R3c,Arb), (Ze, Ri,R1b,R3c,Arc), (Ze,Ri,R1b,R3c,Ard), (Ze,Ri,R1b,R3c, Are), (Ze,Ri,R1b,R3c,Arf), (Ze,Ri,R1b,R3c,Arg), (Ze,Ri, R1b,R3c,Arh), (Ze,Ri,R1b,R3c,Ari), (Ze,Ri,R1b,R3c,Arj), (Ze,Ri,R1b,R3c,Ark), (Ze,Ri,R1b,R3c,Arl), (Ze,Ri,R1b, R3c,Arm), (Ze,Ri,R1b,R3c,Arn), (Ze,Ri,R1b,R3c,Aro), (Ze, Ri,R1b,R3c,Arp), (Ze,Ri,R1b,R3d,Ara), (Ze,Ri,R1b,R3d, Arb), (Ze,Ri,R1b,R3d,Arc), (Ze,Ri,R1b,R3d,Ard), (Ze,Ri, R1b,R3d,Are), (Ze,Ri,R1b,R3d,Arf), (Ze,Ri,R1b,R3d,Arg), (Ze,Ri,R1b,R3d,Arh), (Ze,Ri,R1b,R3d,Ari), (Ze,Ri,R1b, R3d,Arj), (Ze,Ri,R1b,R3d,Ark), (Ze,Ri,R1b,R3d,Arl), (Ze, Ri,R1b,R3d,Arm), (Ze,Ri,R1b,R3d,Arn), (Ze,Ri,R1b,R3d, Aro), (Ze,Ri,R1b,R3d,Arp), (Ze,Ri,R1b,R3e,Ara), (Ze,Ri, R1b,R3e,Arb), (Ze,Ri,R1b,R3e,Arc), (Ze,Ri,R1b,R3e,Ard), (Ze,Ri,R1b,R3e,Are), (Ze,Ri,R1b,R3e,Arf), (Ze,Ri,R1b, R3e,Arg), (Ze,Ri,R1b,R3e,Arh), (Ze,Ri,R1b,R3e,Ari), (Ze, Ri,R1b,R3e,Arj), (Ze,Ri,R1b,R3e,Ark), (Ze,Ri,R1b,R3e, Arl), (Ze,Ri,R1b,R3e,Arm), (Ze,Ri,R1b,R3e,Arn), (Ze,Ri, R1b,R3e,Aro), (Ze,Ri,R1b,R3e,Arp), (Ze,Ri,R1b,R3f,Ara), (Ze,Ri,R1b,R3f,Arb), (Ze,Ri,R1b,R3f,Arc), (Ze,Ri,R1b, R3f,Ard), (Ze,Ri,R1b,R3f,Are), (Ze,Ri,R1b,R3f,Arf), (Ze, Ri,R1b,R3f,Arg), (Ze,Ri,R1b,R3f,Arh), (Ze,Ri,R1b,R3f, Ari), (Ze,Ri,R1b,R3f,Arj), (Ze,Ri,R1b,R3f,Ark), (Ze,Ri, R1b,R3f,Arl), (Ze,Ri,R1b,R3f,Arm), (Ze,Ri,R1b,R3f,Arn), (Ze,Ri,R1b,R3f,Aro), (Ze,Ri,R1b,R3f,Arp), (Ze,Ri,R1b, R3g,Ara), (Ze,Ri,R1b,R3g,Arb), (Ze,Ri,R1b,R3g,Arc), (Ze, Ri,R1b,R3g,Ard), (Ze,Ri,R1b,R3g,Are), (Ze,Ri,R1b,R3g, Arf), (Ze,Ri,R1b,R3g,Arg), (Ze,Ri,R1b,R3g,Arh), (Ze,Ri, R1b,R3g,Ari), (Ze,Ri,R1b,R3g,Arj), (Ze,Ri,R1b,R3g,Ark), (Ze,Ri,R1b,R3g,Arl), (Ze,Ri,R1b,R3g,Arm), (Ze,Ri,R1b, R3g,Arn), (Ze,Ri,R1b,R3g,Aro), (Ze,Ri,R1b,R3g,Arp), (Ze, R1,R1b,R3h,Ara), (Ze,Ri,R1b,R3h,Arb), (Ze,Ri,R1b,R3h, Arc), (Ze,Ri,R1b,R3h,Ard), (Ze,Ri,R1b,R3h,Are), (Ze,Ri, R1b,R3h,Arf), (Ze,Ri,R1b,R3h,Arg), (Ze,Ri,R1b,R3h,Arh), (Ze,Ri,R1b,R3h,Ari), (Ze,Ri,R1b,R3h,Arj), (Ze,Ri,R1b, R3h,Ark), (Ze,Ri,R1b,R3h,Arl), (Ze,Ri,R1b,R3h,Arm), (Ze, Ri,R1b,R3h,Arn), (Ze,Ri,R1b,R3h,Aro), (Ze,Ri,R1b,R3h, Arp), (Ze,Ri,R1c,R3a,Ara), (Ze,Ri,R1c,R3a,Arb), (Ze,Ri, R1c,R3a,Arc), (Ze,Ri,R1c,R3a,Ard), (Ze,Ri,R1c,R3a,Are), (Ze,Ri,R1c,R3a,Arf), (Ze,Ri,R1c,R3a,Arg), (Ze,Ri,R1c, R3a,Arh), (Ze,Ri,R1c,R3a,Ari), (Ze,Ri,R1c,R3a,Arj), (Ze, Ri,R1c,R3a,Ark), (Ze,Ri,R1c,R3a,Arl), (Ze,Ri,R1c,R3a, Arm), (Ze,Ri,R1c,R3a,Arn), (Ze,Ri,R1c,R3a,Aro), (Ze,Ri, R1c,R3a,Arp), (Ze,Ri,R1c,R3b,Ara), (Ze,Ri,R1c,R3b,Arb), (Ze,Ri,R1c,R3b,Arc), (Ze,Ri,R1c,R3b,Ard), (Ze,Ri,R1c, R3b,Are), (Ze,Ri,R1c,R3b,Arf), (Ze,Ri,R1c,R3b,Arg), (Ze, Ri,R1c,R3b,Arh), (Ze,Ri,R1c,R3b,Ari), (Ze,Ri,R1c,R3b, Arj), (Ze,Ri,R1c,R3b,Ark), (Ze,Ri,R1c,R3b,Arl), (Ze,Ri, R1c,R3b,Arm), (Ze,Ri,R1c,R3b,Arn), (Ze,Ri,R1c,R3b,Aro), (Ze,Ri,R1c,R3b,Arp), (Ze,Ri,R1c,R3c,Ara), (Ze,Ri,R1c,R3c,Arb), (Ze,Ri,R1c,R3c,Arc), (Ze,Ri,R1c,R3c,Ard), (Ze,Ri,R1c,R3c,Are), (Ze,Ri,R1c,R3c,Arf), (Ze,Ri,R1c,R3c,Arg), (Ze,Ri,R1c,R3c,Arh), (Ze,Ri,R1c,R3c,Ari), (Ze,Ri,R1c,R3c,Arj), (Ze,Ri,R1c,R3c,Ark), (Ze,Ri,R1c,R3c,Arl), (Ze,Ri,R1c,R3c,Arm), (Ze,Ri,R1c,R3c,Arn), (Ze,Ri,R1c,R3c,Aro), (Ze,Ri,R1c,R3c,Arp), (Ze,Ri,R1c,R3d,Ara), (Ze,Ri,R1c,R3d,Arb), (Ze,Ri,R1c,R3d,Arc), (Ze,Ri,R1c,R3d,Ard), (Ze,Ri,R1c,R3d,Are), (Ze,Ri,R1c,R3d,Arf), (Ze,Ri,R1c,R3d,Arg), (Ze,Ri,R1c,R3d,Arh), (Ze,Ri,R1c,R3d,Ari), (Ze,Ri,R1c,R3d,Arj), (Ze,Ri,R1c,R3d,Ark), (Ze,Ri,R1c,R3d,Arl), (Ze,Ri,R1c,R3d,Arm), (Ze,Ri,R1c,R3d,Arn), (Ze,Ri,R1c,R3d,Aro), (Ze,Ri,R1c,R3d,Arp), (Ze,Ri,R1c,R3e,Ara), (Ze,Ri,R1c,R3e,Arb), (Ze,Ri,R1c,R3e,Arc), (Ze,Ri,R1c,R3e,Ard), (Ze,Ri,R1c,R3e,Are), (Ze,Ri,R1c,R3e,Arf), (Ze,Ri,R1c,R3e,Arg), (Ze,Ri,R1c,R3e,Arh), (Ze,Ri,R1c,R3e,Ari), (Ze,Ri,R1c,R3e,Arj), (Ze,Ri,R1c,R3e,Ark), (Ze,Ri,R1c,R3e,Arl), (Ze,Ri,R1c,R3e,Arm), (Ze,Ri,R1c,R3e,Arn), (Ze,Ri,R1c,R3e,Aro), (Ze,Ri,R1c,R3e,Arp), (Ze,Ri,R1c,R3f,Ara), (Ze,Ri,R1c,R3f,Arb), (Ze,Ri,R1c,R3f,Arc), (Ze,Ri,R1c,R3f,Ard), (Ze,Ri,R1c,R3f,Are), (Ze,Ri,R1c,R3f,Arf), (Ze,Ri,R1c,R3f,Arg), (Ze,Ri,R1c,R3f,Arh), (Ze,Ri,R1c,R3f,Ari), (Ze,Ri,R1c,R3f,Arj), (Ze,Ri,R1c,R3f,Ark), (Ze,Ri,R1c,R3f,Arl), (Ze,Ri,R1c,R3f,Arm), (Ze,Ri,R1c,R3f,Arn), (Ze,Ri,R1c,R3f,Aro), (Ze,Ri,R1c,R3f,Arp), (Ze,Ri,R1c,R3g,Ara), (Ze,Ri,R1c,R3g,Arb), (Ze,Ri,R1c,R3g,Arc), (Ze,Ri,R1c,R3g,Ard), (Ze,Ri,R1c,R3g,Are), (Ze,Ri,R1c,R3g,Arf), (Ze,Ri,R1c,R3g,Arg), (Ze,Ri,R1c,R3g,Arh), (Ze,Ri,R1c,R3g,Ari), (Ze,Ri,R1c,R3g,Arj), (Ze,Ri,R1c,R3g,Ark), (Ze,Ri,R1c,R3g,Arl), (Ze,Ri,R1c,R3g,Arm), (Ze,Ri,R1c,R3g,Arn), (Ze,Ri,R1c,R3g,Aro), (Ze,Ri,R1c,R3g,Arp), (Ze,Ri,R1c,R3h,Ara), (Ze,Ri,R1c,R3h,Arb), (Ze,Ri,R1c,R3h,Arc), (Ze,Ri,R1c,R3h,Ard), (Ze,Ri,R1c,R3h,Are), (Ze,Ri,R1c,R3h,Arf), (Ze,Ri,R1c,R3h,Arg), (Ze,Ri,R1c,R3h,Arh), (Ze,Ri,R1c,R3h,Ari), (Ze,Ri,R1c,R3h,Arj), (Ze,Ri,R1c,R3h,Ark), (Ze,Ri,R1c,R3h,Arl), (Ze,Ri,R1c,R3h,Arm), (Ze,Ri,R1c,R3h,Arn), (Ze,Ri,R1c,R3h,Aro), (Ze,Ri,R1c,R3h,Arp), (Ze,Ri,R1d,R3a,Ara), (Ze,Ri,R1d,R3a,Arb), (Ze,Ri,R1d,R3a,Arc), (Ze,Ri,R1d,R3a,Ard), (Ze,Ri,R1d,R3a,Are), (Ze,Ri,R1d,R3a,Arf), (Ze,Ri,R1d,R3a,Arg), (Ze,Ri,R1d,R3a,Arh), (Ze,Ri,R1d,R3a,Ari), (Ze,Ri,R1d,R3a,Arj), (Ze,Ri,R1d,R3a,Ark), (Ze,Ri,R1d,R3a,Arl), (Ze,Ri,R1d,R3a,Arm), (Ze,Ri,R1d,R3a,Arn), (Ze,Ri,R1d,R3a,Aro), (Ze,Ri,R1d,R3a,Arp), (Ze,Ri,R1d,R3b,Ara), (Ze,Ri,R1d,R3b,Arb), (Ze,Ri,R1d,R3b,Arc), (Ze,Ri,R1d,R3b,Ard), (Ze,Ri,R1d,R3b,Are), (Ze,Ri,R1d,R3b,Arf), (Ze,Ri,R1d,R3b,Arg), (Ze,Ri,R1d,R3b,Arh), (Ze,Ri,R1d,R3b,Ari), (Ze,Ri,R1d,R3b,Arj), (Ze,Ri,R1d,R3b,Ark), (Ze,Ri,R1d,R3b,Arl), (Ze,Ri,R1d,R3b,Arm), (Ze,Ri,R1d,R3b,Arn), (Ze,Ri,R1d,R3b,Aro), (Ze,Ri,R1d,R3b,Arp), (Ze,Ri,R1d,R3c,Ara), (Ze,Ri,R1d,R3c,Arb), (Ze,Ri,R1d,R3c,Arc), (Ze,Ri,R1d,R3c,Ard), (Ze,Ri,R1d,R3c,Are), (Ze,Ri,R1d,R3c,Arf), (Ze,Ri,R1d,R3c,Arg), (Ze,Ri,R1d,R3c,Arh), (Ze,Ri,R1d,R3c,Ari), (Ze,Ri,R1d,R3c,Arj), (Ze,Ri,R1d,R3c,Ark), (Ze,Ri,R1d,R3c,Arl), (Ze,Ri,R1d,R3c,Arm), (Ze,Ri,R1d,R3c,Arn), (Ze,Ri,R1d,R3c,Aro), (Ze,Ri,R1d,R3c,Arp), (Ze,Ri,R1d,R3d,Ara), (Ze,Ri,R1d,R3d,Arb), (Ze,Ri,R1d,R3d,Arc), (Ze,Ri,R1d,R3d,Ard), (Ze,Ri,R1d,R3d,Are), (Ze,Ri,R1d,R3d,Arf), (Ze,Ri,R1d,R3d,Arg), (Ze,Ri,R1d,R3d,Arh), (Ze,Ri,R1d,R3d,Ari), (Ze,Ri,R1d,R3d,Arj), (Ze,Ri,R1d,R3d,Ark), (Ze,Ri,R1d,R3d,Arl), (Ze,Ri,R1d,R3d,Arm), (Ze,Ri,R1d,R3d,Arn), (Ze,Ri,R1d,R3d,Aro), (Ze,Ri,R1d,R3d,Arp), (Ze,Ri,R1d,R3e,Ara), (Ze,Ri,R1d,R3e,Arb), (Ze,Ri,R1d,R3e,Arc), (Ze,Ri,R1d,R3e,Ard), (Ze,Ri,R1d,R3e,Are), (Ze,Ri,R1d,R3e,Arf), (Ze,Ri,R1d,R3e,Arg), (Ze,Ri,R1d,R3e,Arh), (Ze,Ri,R1d,R3e,Ari), (Ze,Ri,R1d,R3e,Arj), (Ze,Ri,R1d,R3e,Ark), (Ze,Ri,R1d,R3e,Arl), (Ze,Ri,R1d,R3e,Arm), (Ze,Ri,R1d,R3e,Arn), (Ze,Ri,R1d,R3e,Aro), (Ze,Ri,R1d,R3e,Arp), (Ze,Ri,R1d,R3f,Ara), (Ze,Ri,R1d,R3f,Arb), (Ze,Ri,R1d,R3f,Arc), (Ze,Ri,R1d,R3f,Ard), (Ze,Ri,R1d,R3f,Are), (Ze,Ri,R1d,R3f,Arf), (Ze,Ri,R1d,R3f,Arg), (Ze,Ri,R1d,R3f,Arh), (Ze,Ri,R1d,R3f,Ari), (Ze,Ri,R1d,R3f,Arj), (Ze,Ri,R1d,R3f,Ark), (Ze,Ri,R1d,R3f,Arl), (Ze,Ri,R1d,R3f,Arm), (Ze,Ri,R1d,R3f,Arn), (Ze,Ri,R1d,R3f,Aro), (Ze,Ri,R1d,R3f,Arp), (Ze,Ri,R1d,R3g,Ara), (Ze,Ri,R1d,R3g,Arb), (Ze,Ri,R1d,R3g,Arc), (Ze,Ri,R1d,R3g,Ard), (Ze,Ri,R1d,R3g,Are), (Ze,Ri,R1d,R3g,Arf), (Ze,Ri,R1d,R3g,Arg), (Ze,Ri,R1d,R3g,Arh), (Ze,Ri,R1d,R3g,Ari), (Ze,Ri,R1d,R3g,Arj), (Ze,Ri,R1d,R3g,Ark), (Ze,Ri,R1d,R3g,Arl), (Ze,Ri,R1d,R3g,Arm), (Ze,Ri,R1d,R3g,Arn), (Ze,Ri,R1d,R3g,Aro), (Ze,Ri,R1d,R3g,Arp), (Ze,Ri,R1d,R3h,Ara), (Ze,Ri,R1d,R3h,Arb), (Ze,Ri,R1d,R3h,Arc), (Ze,Ri,R1d,R3h,Ard), (Ze,Ri,R1d,R3h,Are), (Ze,Ri,R1d,R3h,Arf), (Ze,Ri,R1d,R3h,Arg), (Ze,Ri,R1d,R3h,Arh), (Ze,Ri,R1d,R3h,Ari), (Ze,Ri,R1d,R3h,Arj), (Ze,Ri,R1d,R3h,Ark), (Ze,Ri,R1d,R3h,Arl), (Ze,Ri,R1d,R3h,Arm), (Ze,Ri,R1d,R3h,Arn), (Ze,Ri,R1d,R3h,Aro), (Ze,Ri,R1d,R3h,Arp), (Ze,Rj,R1a,R3a,Ara), (Ze,Rj,R1a,R3a,Arb), (Ze,Rj,R1a,R3a,Arc), (Ze,Rj,R1a,R3a,Ard), (Ze,Rj,R1a,R3a,Are), (Ze,Rj,R1a,R3a,Arf), (Ze,Rj,R1a,R3a,Arg), (Ze,Rj,R1a,R3a,Arh), (Ze,Rj,R1a,R3a,Ari), (Ze,Rj,R1a,R3a,Arj), (Ze,Rj,R1a,R3a,Ark), (Ze,Rj,R1a,R3a,Arl), (Ze,Rj,R1a,R3a,Arm), (Ze,Rj,R1a,R3a,Arn), (Ze,Rj,R1a,R3a,Aro), (Ze,Rj,R1a,R3a,Arp), (Ze,Rj,R1a,R3b,Ara), (Ze,Rj,R1a,R3b,Arb), (Ze,Rj,R1a,R3b,Arc), (Ze,Rj,R1a,R3b,Ard), (Ze,Rj,R1a,R3b,Are), (Ze,Rj,R1a,R3b,Arf), (Ze,Rj,R1a,R3b,Arg), (Ze,Rj,R1a,R3b,Arh), (Ze,Rj,R1a,R3b,Ari), (Ze,Rj,R1a,R3b,Arj), (Ze,Rj,R1a,R3b,Ark), (Ze,Rj,R1a,R3b,Arl), (Ze,Rj,R1a,R3b,Arm), (Ze,Rj,R1a,R3b,Arn), (Ze,Rj,R1a,R3b,Aro), (Ze,Rj,R1a,R3b,Arp), (Ze,Rj,R1a,R3c,Ara), (Ze,Rj,R1a,R3c,Arb), (Ze,Rj,R1a,R3c,Arc), (Ze,Rj,R1a,R3c,Ard), (Ze,Rj,R1a,R3c,Are), (Ze,Rj,R1a,R3c,Arf), (Ze,Rj,R1a,R3c,Arg), (Ze,Rj,R1a,R3c,Arh), (Ze,Rj,R1a,R3c,Ari), (Ze,Rj,R1a,R3c,Arj), (Ze,Rj,R1a,R3c,Ark), (Ze,Rj,R1a,R3c,Arl), (Ze,Rj,R1a,R3c,Arm), (Ze,Rj,R1a,R3c,Arn), (Ze,Rj,R1a,R3c,Aro), (Ze,Rj,R1a,R3c,Arp), (Ze,Rj,R1a,R3d,Ara), (Ze,Rj,R1a,R3d,Arb), (Ze,Rj,R1a,R3d,Arc), (Ze,Rj,R1a,R3d,Ard), (Ze,Rj,R1a,R3d,Are), (Ze,Rj,R1a,R3d,Arf), (Ze,Rj,R1a,R3d,Arg), (Ze,Rj,R1a,R3d,Arh), (Ze,Rj,R1a,R3d,Ari), (Ze,Rj,R1a,R3d,Arj), (Ze,Rj,R1a,R3d,Ark), (Ze,Rj,R1a,R3d,Arl), (Ze,Rj,R1a,R3d,Arm), (Ze,Rj,R1a,R3d,Arn), (Ze,Rj,R1a,R3d,Aro), (Ze,Rj,R1a,R3d,Arp), (Ze,Rj,R1a,R3e,Ara), (Ze,Rj,R1a,R3e,Arb), (Ze,Rj,R1a,R3e,Arc), (Ze,Rj,R1a,R3e,Ard), (Ze,Rj,R1a,R3e,Are), (Ze,Rj,R1a,R3e,Arf), (Ze,Rj,R1a,R3e,Arg), (Ze,Rj,R1a,R3e,Arh), (Ze,Rj,R1a,R3e,Ari), (Ze,Rj,R1a,R3e,Arj), (Ze,Rj,R1a,R3e,Ark), (Ze,Rj,R1a,R3e,Arl), (Ze,Rj,R1a,R3e,Arm), (Ze,Rj,R1a,R3e,Arn), (Ze,Rj,R1a,R3e,Aro), (Ze,Rj,R1a,R3e,Arp), (Ze,Rj,R1a,R3f,Ara), (Ze,Rj,R1a,R3f,Arb), (Ze,Rj,R1a,R3f,Arc), (Ze,Rj,R1a,R3f,Ard), (Ze,Rj,R1a,R3f,Are), (Ze,Rj,R1a,R3f,Arf), (Ze,Rj,R1a,R3f,Arg), (Ze,Rj,R1a,R3f,Arh), (Ze,Rj,R1a,R3f,Ari), (Ze,Rj,R1a,R3f,Arj), (Ze,Rj,R1a,R3f,Ark), (Ze,Rj,R1a,R3f,Arl), (Ze,Rj,R1a,R3f,Arm), (Ze,Rj,R1a,R3f,Arn), (Ze,Rj,R1a,R3f,Aro), (Ze,Rj,R1a,R3f,Arp), (Ze,Rj,R1a,R3g,Ara), (Ze,Rj,R1a,R3g,Arb), (Ze,Rj,R1a,R3g,Arc), (Ze,Rj,R1a,R3g,Ard), (Ze,Rj,R1a,R3g,Are), (Ze,Rj,R1a,R3g,Arf), (Ze,Rj,R1a,R3g,Arg), (Ze,Rj,R1a,R3g,Arh), (Ze,Rj,R1a,R3g,Ari), (Ze,Rj,R1a,R3g,Arj), (Ze,Rj,R1a,R3g,Ark), (Ze,Rj,R1a,R3g,Arl), (Ze,Rj,R1a,R3g,Arm), (Ze,Rj,R1a,R3g,Arn), (Ze,Rj,R1a,R3g,Aro), (Ze,Rj,R1a,R3g,Arp), (Ze,Rj,R1a,R3h,Ara), (Ze,Rj,R1a,R3h,Arb), (Ze,Rj,R1a,R3h,Arc), (Ze,Rj,R1a,R3h,Ard), (Ze,Rj,R1a,R3h,Are), (Ze,Rj,R1a,R3h,Arf), (Ze,Rj,R1a,R3h,Arg), (Ze,Rj,R1a,R3h,Arh), (Ze,Rj,R1a,R3h,Ari), (Ze,Rj,R1a,R3h,Arj), (Ze,Rj,R1a,R3h,Ark), (Ze,Rj,R1a,R3h,Arl), (Ze,Rj,R1a,R3h,Arm), (Ze,Rj,R1a,R3h,Arn), (Ze,Rj,R1a,R3h,Aro), (Ze,Rj,R1a,R3h,Arp), (Ze,Rj,R1b,R3a,Ara), (Ze,Rj,R1b,R3a,Arb), (Ze,Rj,R1b,R3a,Arc), (Ze,Rj,R1b,R3a,Ard), (Ze,Rj,R1b,R3a,Are), (Ze,Rj,R1b,R3a,Arf), (Ze,Rj,R1b,R3a,Arg), (Ze,Rj,R1b,R3a,Arh), (Ze,Rj,R1b,R3a,Ari), (Ze,Rj,R1b,R3a,Arj), (Ze,Rj,R1b,R3a,Ark), (Ze,Rj,R1b,R3a,Arl), (Ze,Rj,R1b,R3a,Arm), (Ze,Rj,R1b,R3a,Arn), (Ze,Rj,R1b,R3a,Aro), (Ze,Rj,R1b,R3a,Arp), (Ze,Rj,R1b,R3b,Ara), (Ze,Rj,R1b,R3b,Arb), (Ze,Rj,R1b,R3b,Arc), (Ze,Rj,R1b,R3b,Ard), (Ze,Rj,R1b,R3b,Are), (Ze,Rj,R1b,R3b,Arf), (Ze,Rj,R1b,R3b,Arg), (Ze,Rj,R1b,R3b,Arh), (Ze,Rj,R1b,R3b,Ari), (Ze,Rj,R1b,R3b,Arj), (Ze,Rj,R1b,R3b,Ark), (Ze,Rj,R1b,R3b,Arl), (Ze,Rj,R1b,R3b,Arm), (Ze,Rj,R1b,R3b,Arn), (Ze,Rj,R1b,R3b,Aro), (Ze,Rj,R1b,R3b,Arp), (Ze,Rj,R1b,R3c,Ara), (Ze,Rj,R1b,R3c,Arb), (Ze,Rj,R1b,R3c,Arc), (Ze,Rj,R1b,R3c,Ard), (Ze,Rj,R1b,R3c,Are), (Ze,Rj,R1b,R3c,Arf), (Ze,Rj,R1b,R3c,Arg), (Ze,Rj,R1b,R3c,Arh), (Ze,Rj,R1b,R3c,Ari), (Ze,Rj,R1b,R3c,Arj), (Ze,Rj,R1b,R3c,Ark), (Ze,Rj,R1b,R3c,Arl), (Ze,Rj,R1b,R3c,Arm), (Ze,Rj,R1b,R3c,Arn), (Ze,Rj,R1b,R3c,Aro), (Ze,Rj,R1b,R3c,Arp), (Ze,Rj,R1b,R3d,Ara), (Ze,Rj,R1b,R3d,Arb), (Ze,Rj,R1b,R3d,Arc), (Ze,Rj,R1b,R3d,Ard), (Ze,Rj,R1b,R3d,Are), (Ze,Rj,R1b,R3d,Arf), (Ze,Rj,R1b,R3d,Arg), (Ze,Rj,R1b,R3d,Arh), (Ze,Rj,R1b,R3d,Ari), (Ze,Rj,R1b,R3d,Arj), (Ze,Rj,R1b,R3d,Ark), (Ze,Rj,R1b,R3d,Arl), (Ze,Rj,R1b,R3d,Arm), (Ze,Rj,R1b,R3d,Arn), (Ze,Rj,R1b,R3d,Aro), (Ze,Rj,R1b,R3d,Arp), (Ze,Rj,R1b,R3e,Ara), (Ze,Rj,R1b,R3e,Arb), (Ze,Rj,R1b,R3e,Arc), (Ze,Rj,R1b,R3e,Ard), (Ze,Rj,R1b,R3e,Are), (Ze,Rj,R1b,R3e,Arf), (Ze,Rj,R1b,R3e,Arg), (Ze,Rj,R1b,R3e,Arh), (Ze,Rj,R1b,R3e,Ari), (Ze,Rj,R1b,R3e,Arj), (Ze,Rj,R1b,R3e,Ark), (Ze,Rj,R1b,R3e,Arl), (Ze,Rj,R1b,R3e,Arm), (Ze,Rj,R1b,R3e,Arn), (Ze,Rj,R1b,R3e,Aro), (Ze,Rj,R1b,R3e,Arp), (Ze,Rj,R1b,R3f,Ara), (Ze,Rj,R1b,R3f,Arb), (Ze,Rj,R1b,R3f,Arc), (Ze,Rj,R1b,R3f,Ard), (Ze,Rj,R1b,R3f,Are), (Ze,Rj,R1b,R3f,Arf), (Ze,Rj,R1b,R3f,Arg), (Ze,Rj,R1b,R3f,Arh), (Ze,Rj,R1b,R3f,Ari), (Ze,Rj,R1b,R3f,Arj), (Ze,Rj,R1b,R3f,Ark), (Ze,Rj,R1b,R3f,Arl), (Ze,Rj,R1b,R3f,Arm), (Ze,Rj,R1b,R3f,Arn), (Ze,Rj,R1b,R3f,Aro), (Ze,Rj,R1b,R3f,Arp), (Ze,Rj,R1b,R3g,Ara), (Ze,Rj,R1b,R3g,Arb), (Ze,Rj,R1b,R3g,Arc), (Ze,Rj,R1b,R3g,Ard), (Ze,Rj,R1b,R3g,Are), (Ze,Rj,R1b,R3g,Arf), (Ze,Rj,R1b,R3g,Arg), (Ze,Rj,R1b,R3g,Arh), (Ze,Rj,R1b,R3g,Ari), (Ze,Rj,R1b,R3g,Arj), (Ze,Rj,R1b,R3g,Ark), (Ze,Rj,R1b,R3g,Arl), (Ze,Rj,R1b,R3g,Arm), (Ze,Rj,R1b,R3g,Arn), (Ze,Rj,R1b,R3g,Aro), (Ze,Rj,R1b,R3g,Arp), (Ze,Rj,R1b,R3h,Ara), (Ze,Rj,R1b,R3h,Arb), (Ze,Rj,R1b,R3h,Arc), (Ze,Rj,R1b,R3h,Ard), (Ze,Rj,R1b,R3h,Are), (Ze,Rj,R1b,R3h,Arf), (Ze,Rj,R1b,R3h,Arg), (Ze,Rj,R1b,R3h,Arh), (Ze,Rj,R1b,R3h,Ari), (Ze,Rj,R1b,R3h,Arj), (Ze,Rj,R1b,R3h,Ark), (Ze,Rj,R1b,R3h,Arl), (Ze,Rj,R1b,R3h,Arm), (Ze,Rj,R1b,R3h,Arn), (Ze,Rj,R1b,R3h,Aro), (Ze,Rj,R1b,R3h,Arp), (Ze,Rj,R1c,R3a,Ara), (Ze,Rj,R1c,R3a,Arb), (Ze,Rj,R1c,R3a,Arc), (Ze,Rj,R1c,R3a,Ard), (Ze,Rj,R1c,R3a,Are), (Ze,Rj,R1c,R3a,Arf), (Ze,Rj,R1c,R3a,Arg), (Ze,Rj,R1c,R3a,Arh), (Ze,Rj,R1c,R3a,Ari), (Ze,Rj,R1c,R3a,Arj), (Ze,Rj,R1c,R3a,Ark), (Ze,Rj,R1c,R3a,Arl), (Ze,Rj,R1c,R3a,Arm), (Ze,Rj,R1c,R3a,Arn), (Ze,Rj,R1c,R3a,Aro), (Ze,Rj,R1c,R3a,Arp), (Ze,Rj,R1c,R3b,Ara), (Ze,Rj,R1c,R3b,Arb), (Ze,Rj,R1c,R3b,Arc), (Ze,Rj,R1c,R3b,Ard), (Ze,Rj,R1c,R3b,Are), (Ze,Rj,R1c,R3b,Arf), (Ze,Rj,R1c,R3b,Arg), (Ze,Rj,R1c,R3b,Arh), (Ze,Rj,R1c,R3b,Ari), (Ze,Rj,R1c,R3b,Arj), (Ze,Rj,R1c,R3b,Ark), (Ze,Rj,R1c,R3b,Arl), (Ze,Rj,R1c,R3b,Arm), (Ze,Rj,R1c,R3b,Arn), (Ze,Rj,R1c,R3b,Aro), (Ze,Rj,R1c,R3b,Arp), (Ze,Rj,R1c,R3c,Ara), (Ze,Rj,R1c,R3c,Arb), (Ze,Rj,R1c,R3c,Arc), (Ze,Rj,R1c,R3c,Ard), (Ze,Rj,R1c,R3c,Are), (Ze,Rj,R1c,R3c,Arf), (Ze,Rj,R1c,R3c,Arg), (Ze,Rj,R1c,R3c,Arh), (Ze,Rj,R1c,R3c,Ari), (Ze,Rj,R1c,R3c,Arj), (Ze,Rj,R1c,R3c,Ark), (Ze,Rj,R1c,R3c,Arl), (Ze,Rj,R1c,R3c,Arm), (Ze,Rj,R1c,R3c,Arn), (Ze,Rj,R1c,R3c,Aro), (Ze,Rj,R1c,R3c,Arp), (Ze,Rj,R1c,R3d,Ara), (Ze,Rj,R1c,R3d,Arb), (Ze,Rj,R1c,R3d,Arc), (Ze,Rj,R1c,R3d,Ard), (Ze,Rj,R1c,R3d,Are), (Ze,Rj,R1c,R3d,Arf), (Ze,Rj,R1c,R3d,Arg), (Ze,Rj,R1c,R3d,Arh), (Ze,Rj,R1c,R3d,Ari), (Ze,Rj,R1c,R3d,Arj), (Ze,Rj,R1c,R3d,Ark), (Ze,Rj,R1c,R3d,Arl), (Ze,Rj,R1c,R3d,Arm), (Ze,Rj,R1c,R3d,Arn), (Ze,Rj,R1c,R3d,Aro), (Ze,Rj,R1c,R3d,Arp), (Ze,Rj,R1c,R3e,Ara), (Ze,Rj,R1c,R3e,Arb), (Ze,Rj,R1c,R3e,Arc), (Ze,Rj,R1c,R3e,Ard), (Ze,Rj,R1c,R3e,Are), (Ze,Rj,R1c,R3e,Arf), (Ze,Rj,R1c,R3e,Arg), (Ze,Rj,R1c,R3e,Arh), (Ze,Rj,R1c,R3e,Ari), (Ze,Rj,R1c,R3e,Arj), (Ze,Rj,R1c,R3e,Ark), (Ze,Rj,R1c,R3e,Arl), (Ze,Rj,R1c,R3e,Arm), (Ze,Rj,R1c,R3e,Arn), (Ze,Rj,R1c,R3e,Aro), (Ze,Rj,R1c,R3e,Arp), (Ze,Rj,R1c,R3f,Ara), (Ze,Rj,R1c,R3f,Arb), (Ze,Rj,R1c,R3f,Arc), (Ze,Rj,R1c,R3f,Ard), (Ze,Rj,R1c,R3f,Are), (Ze,Rj,R1c,R3f,Arf), (Ze,Rj,R1c,R3f,Arg), (Ze,Rj,R1c,R3f,Arh), (Ze,Rj,R1c,R3f,Ari), (Ze,Rj,R1c,R3f,Arj), (Ze,Rj,R1c,R3f,Ark), (Ze,Rj,R1c,R3f,Arl), (Ze,Rj,R1c,R3f,Arm), (Ze,Rj,R1c,R3f,Arn), (Ze,Rj,R1c,R3f,Aro), (Ze,Rj,R1c,R3f,Arp), (Ze,Rj,R1c,R3g,Ara), (Ze,Rj,R1c,R3g,Arb), (Ze,Rj,R1c,R3g,Arc), (Ze,Rj,R1c,R3g,Ard), (Ze,Rj,R1c,R3g,Are), (Ze,Rj,R1c,R3g,Arf), (Ze,Rj,R1c,R3g,Arg), (Ze,Rj,R1c,R3g,Arh), (Ze,Rj,R1c,R3g,Ari), (Ze,Rj,R1c,R3g,Arj), (Ze,Rj,R1c,R3g,Ark), (Ze,Rj,R1c,R3g,Arl), (Ze,Rj,R1c,R3g,Arm), (Ze,Rj,R1c,R3g,Arn), (Ze,Rj,R1c,R3g,Aro), (Ze,Rj,R1c,R3g,Arp), (Ze,Rj,R1c,R3h,Ara), (Ze,Rj,R1c,R3h,Arb), (Ze,Rj,R1c,R3h,Arc), (Ze,Rj,R1c,R3h,Ard), (Ze,Rj,R1c,R3h,Are), (Ze,Rj,R1c,R3h,Arf), (Ze,Rj,R1c,R3h,Arg), (Ze,Rj,R1c,R3h,Arh), (Ze,Rj,R1c,R3h,Ari), (Ze,Rj,R1c,R3h,Arj), (Ze,Rj,R1c,R3h,Ark), (Ze,Rj,R1c,R3h,Arl), (Ze,Rj,R1c,R3h,Arm), (Ze,Rj,R1c,R3h,Arn), (Ze,Rj,R1c,R3h,Aro), (Ze,Rj,R1c,R3h,Arp), (Ze,Rj,R1d,R3a,Ara), (Ze,Rj,R1d,R3a,Arb), (Ze,Rj,R1d,R3a,Arc), (Ze,Rj,R1d,R3a,Ard), (Ze,Rj,R1d,R3a,Are), (Ze,Rj,R1d,R3a,Arf), (Ze,Rj,R1d,R3a,Arg), (Ze,Rj,R1d,R3a,Arh), (Ze,Rj,R1d,R3a,Ari), (Ze,Rj,R1d,R3a,Arj), (Ze,Rj,R1d,R3a,Ark), (Ze,Rj,R1d,R3a,Arl), (Ze,Rj,R1d,R3a,Arm), (Ze,Rj,R1d,R3a,Arn), (Ze,Rj,R1d,R3a,Aro), (Ze,Rj,R1d,R3a,Arp), (Ze,Rj,R1d,R3b,Ara), (Ze,Rj,R1d,R3b,Arb), (Ze,Rj,R1d,R3b,Arc), (Ze,Rj,R1d,R3b,Ard), (Ze,Rj,R1d,R3b,Are), (Ze,Rj,R1d,R3b,Arf), (Ze,Rj,R1d,R3b,Arg), (Ze,Rj,R1d,R3b,Arh), (Ze,Rj,R1d,R3b,Ari), (Ze,Rj,R1d,R3b,Arj), (Ze,Rj,R1d,R3b,Ark), (Ze,Rj,R1d,R3b,Arl), (Ze,Rj,R1d,R3b,Arm), (Ze,Rj,R1d,R3b,Arn), (Ze,Rj,R1d,R3b,Aro), (Ze,Rj,R1d,R3b,Arp), (Ze,Rj,R1d,R3c,Ara), (Ze,Rj,R1d,R3c,Arb), (Ze,Rj,R1d,R3c,Arc), (Ze,Rj,R1d,R3c,Ard), (Ze,Rj,R1d,R3c,Are), (Ze,Rj,R1d,R3c,Arf), (Ze,Rj,R1d,R3c,Arg), (Ze,Rj,R1d,R3c,Arh), (Ze,Rj,R1d,R3c,Ari), (Ze,Rj,R1d,R3c,Arj), (Ze,Rj,R1d,R3c,Ark), (Ze,Rj,R1d,R3c,Arl), (Ze,Rj,R1d,R3c,Arm), (Ze,Rj,R1d,R3c,Arn), (Ze,Rj,R1d,R3c,Aro), (Ze,Rj,R1d,R3c,Arp), (Ze,Rj,R1d,R3d,Ara), (Ze,Rj,R1d,R3d,Arb), (Ze,Rj,R1d,R3d,Arc), (Ze,Rj,R1d,R3d,Ard), (Ze,Rj,R1d,R3d,Are), (Ze,Rj,R1d,R3d,Arf), (Ze,Rj,R1d,R3d,Arg), (Ze,Rj,R1d,R3d,Arh), (Ze,Rj,R1d,R3d,Ari), (Ze,Rj,R1d,R3d,Arj), (Ze,Rj,R1d,R3d,Ark), (Ze,Rj,R1d,R3d,Arl), (Ze,Rj,R1d,R3d,Arm), (Ze,Rj,R1d,R3d,Arn), (Ze,Rj,R1d,R3d,Aro), (Ze,Rj,R1d,R3d,Arp), (Ze,Rj,R1d,R3e,Ara), (Ze,Rj,R1d,R3e,Arb), (Ze,Rj,R1d,R3e,Arc), (Ze,Rj,R1d,R3e,Ard), (Ze,Rj,R1d,R3e,Are), (Ze,Rj,R1d,R3e,Arf), (Ze,Rj,R1d,R3e,Arg), (Ze,Rj,R1d,R3e,Arh), (Ze,Rj,R1d,R3e,Ari), (Ze,Rj,R1d,R3e,Arj), (Ze,Rj,R1d,R3e,Ark), (Ze,Rj,R1d,R3e,Arl), (Ze,Rj,R1d,R3e,Arm), (Ze,Rj,R1d,R3e,Arn), (Ze,Rj,R1d,R3e,Aro), (Ze,Rj,R1d,R3e,Arp), (Ze,Rj,R1d,R3f,Ara), (Ze,Rj,R1d,R3f,Arb), (Ze,Rj,R1d,R3f,Arc), (Ze,Rj,R1d,R3f,Ard), (Ze,Rj,R1d,R3f,Are), (Ze,Rj,R1d,R3f,Arf), (Ze,Rj,R1d,R3f,Arg), (Ze,Rj,R1d,R3f,Arh), (Ze,Rj,R1d,R3f, Ari), (Ze,Rj,R1d,R3f,Arj), (Ze,Rj,R1d,R3f,Ark), (Ze,Rj, R1d,R3f,Arl), (Ze,Rj,R1d,R3f,Arm), (Ze,Rj,R1d,R3f,Arn), (Ze,Rj,R1d,R3f,Aro), (Ze,Rj,R1d,R3f,Arp), (Ze,Rj,R1d, R3g,Ara), (Ze,Rj,R1d,R3g,Arb), (Ze,Rj,R1d,R3g,Arc), (Ze, Rj,R1d,R3g,Ard), (Ze,Rj,R1d,R3g,Are), (Ze,Rj,R1d,R3g, Arf), (Ze,Rj,R1d,R3g,Arg), (Ze,Rj,R1d,R3g,Arh), (Ze,Rj, R1d,R3g,Ari), (Ze,Rj,R1d,R3g,Arj), (Ze,Rj,R1d,R3g,Ark), (Ze,Rj,R1d,R3g,Arl), (Ze,Rj,R1d,R3g,Arm), (Ze,Rj,R1d, R3g,Arn), (Ze,Rj,R1d,R3g,Aro), (Ze,Rj,R1d,R3g,Arp), (Ze, Rj,R1d,R3h,Ara), (Ze,Rj,R1d,R3h,Arb), (Ze,Rj,R1d,R3h, Arc), (Ze,Rj,R1d,R3h,Ard), (Ze,Rj,R1d,R3h,Are), (Ze,Rj, R1d,R3h,Arf), (Ze,Rj,R1d,R3h,Arg), (Ze,Rj,R1d,R3h,Arh), (Ze,Rj,R1d,R3h,Ari), (Ze,Rj,R1d,R3h,Arj), (Ze,Rj,R1d, R3h,Ark), (Ze,Rj,R1d,R3h,Arl), (Ze,Rj,R1d,R3h,Arm), (Ze, Rj,R1d,R3h,Arn), (Ze,Rj,R1d,R3h,Aro), (Ze,Rj,R1d,R3h, Arp), (Zf,Ra,R1a,R3a,Ara), (Zf,Ra,R1a,R3a,Arb), (Zf,Ra, R1a,R3a,Arc), (Zf,Ra,R1a,R3a,Ard), (Zf,Ra,R1a,R3a,Are), (Zf,Ra,R1a,R3a,Arf), (Zf,Ra,R1a,R3a,Arg), (Zf,Ra,R1a, R3a,Arh), (Zf,Ra,R1a,R3a,Ari), (Zf,Ra,R1a,R3a,Arj), (Zf, Ra,R1a,R3a,Ark), (Zf,Ra,R1a,R3a,Arl), (Zf,Ra,R1a,R3a, Arm), (Zf,Ra,R1a,R3a,Arn), (Zf,Ra,R1a,R3a,Aro), (Zf,Ra, R1a,R3a,Arp), (Zf,Ra,R1a,R3b,Ara), (Zf,Ra,R1a,R3b,Arb), (Zf,Ra,R1a,R3b,Arc), (Zf,Ra,R1a,R3b,Ard), (Zf,Ra,R1a, R3b,Are), (Zf,Ra,R1a,R3b,Arf), (Zf,Ra,R1a,R3b,Arg), (Zf, Ra,R1a,R3b,Arh), (Zf,Ra,R1a,R3b,Ari), (Zf,Ra,R1a,R3b, Arj), (Zf,Ra,R1a,R3b,Ark), (Zf,Ra,R1a,R3b,Arl), (Zf,Ra, R1a,R3b,Arm), (Zf,Ra,R1a,R3b,Arn), (Zf,Ra,R1a,R3b, Aro), (Zf,Ra,R1a,R3b,Arp), (Zf,Ra,R1a,R3c,Ara), (Zf,Ra, R1a,R3c,Arb), (Zf,Ra,R1a,R3c,Arc), (Zf,Ra,R1a,R3c,Ard), (Zf,Ra,R1a,R3c,Are), (Zf,Ra,R1a,R3c,Arf), (Zf,Ra,R1a, R3c,Arg), (Zf,Ra,R1a,R3c,Arh), (Zf,Ra,R1a,R3c,Ari), (Zf, Ra,R1a,R3c,Arj), (Zf,Ra,R1a,R3c,Ark), (Zf,Ra,R1a,R3c, Arl), (Zf,Ra,R1a,R3c,Arm), (Zf,Ra,R1a,R3c,Arn), (Zf,Ra, R1a,R3c,Aro), (Zf,Ra,R1a,R3c,Arp), (Zf,Ra,R1a,R3d,Ara), (Zf,Ra,R1a,R3d,Arb), (Zf,Ra,R1a,R3d,Arc), (Zf,Ra,R1a, R3d,Ard), (Zf,Ra,R1a,R3d,Are), (Zf,Ra,R1a,R3d,Arf), (Zf, Ra,R1a,R3d,Arg), (Zf,Ra,R1a,R3d,Arh), (Zf,Ra,R1a,R3d, Ari), (Zf,Ra,R1a,R3d,Arj), (Zf,Ra,R1a,R3d,Ark), (Zf,Ra, R1a,R3d,Arl), (Zf,Ra,R1a,R3d,Arm), (Zf,Ra,R1a,R3d,Arn), (Zf,Ra,R1a,R3d,Aro), (Zf,Ra,R1a,R3d,Arp), (Zf,Ra,R1a, R3e,Ara), (Zf,Ra,R1a,R3e,Arb), (Zf,Ra,R1a,R3e,Arc), (Zf, Ra,R1a,R3e,Ard), (Zf,Ra,R1a,R3e,Are), (Zf,Ra,R1a,R3e, Arf), (Zf,Ra,R1a,R3e,Arg), (Zf,Ra,R1a,R3e,Arh), (Zf,Ra, R1a,R3e,Ari), (Zf,Ra,R1a,R3e,Arj), (Zf,Ra,R1a,R3e,Ark), (Zf,Ra,R1a,R3e,Arl), (Zf,Ra,R1a,R3e,Arm), (Zf,Ra,R1a, R3e,Arn), (Zf,Ra,R1a,R3e,Aro), (Zf,Ra,R1a,R3e,Arp), (Zf, Ra,R1a,R3f,Ara), (Zf,Ra,R1a,R3f,Arb), (Zf,Ra,R1a,R3f, Arc), (Zf,Ra,R1a,R3f,Ard), (Zf,Ra,R1a,R3f,Are), (Zf,Ra, R1a,R3f,Arf), (Zf,Ra,R1a,R3f,Arg), (Zf,Ra,R1a,R3f,Arh), (Zf,Ra,R1a,R3f,Ari), (Zf,Ra,R1a,R3f,Arj), (Zf,Ra,R1a,R3f, Ark), (Zf,Ra,R1a,R3f,Arl), (Zf,Ra,R1a,R3f,Arm), (Zf,Ra, R1a,R3f,Arn), (Zf,Ra,R1a,R3f,Aro), (Zf,Ra,R1a,R3f,Arp), (Zf,Ra,R1a,R3g,Ara), (Zf,Ra,R1a,R3g,Arb), (Zf,Ra,R1a, R3g,Arc), (Zf,Ra,R1a,R3g,Ard), (Zf,Ra,R1a,R3g,Are), (Zf, Ra,R1a,R3g,Arf), (Zf,Ra,R1a,R3g,Arg), (Zf,Ra,R1a,R3g, Arh), (Zf,Ra,R1a,R3g,Ari), (Zf,Ra,R1a,R3g,Arj), (Zf,Ra, R1a,R3g,Ark), (Zf,Ra,R1a,R3g,Arl), (Zf,Ra,R1a,R3g,Arm), (Zf,Ra,R1a,R3g,Arn), (Zf,Ra,R1a,R3g,Aro), (Zf,Ra,R1a, R3g,Arp), (Zf,Ra,R1a,R3h,Ara), (Zf,Ra,R1a,R3h,Arb), (Zf, Ra,R1a,R3h,Arc), (Zf,Ra,R1a,R3h,Ard), (Zf,Ra,R1a,R3h, Are), (Zf,Ra,R1a,R3h,Arf), (Zf,Ra,R1a,R3h,Arg), (Zf,Ra, R1a,R3h,Arh), (Zf,Ra,R1a,R3h,Ari), (Zf,Ra,R1a,R3h,Arj), (Zf,Ra,R1a,R3h,Ark), (Zf,Ra,R1a,R3h,Arl), (Zf,Ra,R1a, R3h,Arm), (Zf,Ra,R1a,R3h,Arn), (Zf,Ra,R1a,R3h,Aro), (Zf, Ra,R1a,R3h,Arp), (Zf,Ra,R1b,R3a,Ara), (Zf,Ra,R1b,R3a, Arb), (Zf,Ra,R1b,R3a,Arc), (Zf,Ra,R1b,R3a,Ard), (Zf,Ra, R1b,R3a,Are), (Zf,Ra,R1b,R3a,Arf), (Zf,Ra,R1b,R3a,Arg), (Zf,Ra,R1b,R3a,Arh), (Zf,Ra,R1b,R3a,Ari), (Zf,Ra,R1b, R3a,Arj), (Zf,Ra,R1b,R3a,Ark), (Zf,Ra,R1b,R3a,Arl), (Zf, Ra,R1b,R3a,Arm), (Zf,Ra,R1b,R3a,Arn), (Zf,Ra,R1b,R3a, Aro), (Zf,Ra,R1b,R3a,Arp), (Zf,Ra,R1b,R3b,Ara), (Zf,Ra, R1b,R3b,Arb), (Zf,Ra,R1b,R3b,Arc), (Zf,Ra,R1b,R3b,Ard), (Zf,Ra,R1b,R3b,Are), (Zf,Ra,R1b,R3b,Arf), (Zf,Ra,R1b, R3b,Arg), (Zf,Ra,R1b,R3b,Arh), (Zf,Ra,R1b,R3b,Ari), (Zf, Ra,R1b,R3b,Arj), (Zf,Ra,R1b,R3b,Ark), (Zf,Ra,R1b,R3b, Arl), (Zf,Ra,R1b,R3b,Arm), (Zf,Ra,R1b,R3b,Arn), (Zf,Ra, R1b,R3b,Aro), (Zf,Ra,R1b,R3b,Arp), (Zf,Ra,R1b,R3c,Ara), (Zf,Ra,R1b,R3c,Arb), (Zf,Ra,R1b,R3c,Arc), (Zf,Ra,R1b, R3c,Ard), (Zf,Ra,R1b,R3c,Are), (Zf,Ra,R1b,R3c,Arf), (Zf, Ra,R1b,R3c,Arg), (Zf,Ra,R1b,R3c,Arh), (Zf,Ra,R1b,R3c, Ari), (Zf,Ra,R1b,R3c,Arj), (Zf,Ra,R1b,R3c,Ark), (Zf,Ra, R1b,R3c,Arl), (Zf,Ra,R1b,R3c,Arm), (Zf,Ra,R1b,R3c,Arn), (Zf,Ra,R1b,R3c,Aro), (Zf,Ra,R1b,R3c,Arp), (Zf,Ra,R1b, R3d,Ara), (Zf,Ra,R1b,R3d,Arb), (Zf,Ra,R1b,R3d,Arc), (Zf, Ra,R1b,R3d,Ard), (Zf,Ra,R1b,R3d,Are), (Zf,Ra,R1b,R3d, Arf), (Zf,Ra,R1b,R3d,Arg), (Zf,Ra,R1b,R3d,Arh), (Zf,Ra, R1b,R3d,Ari), (Zf,Ra,R1b,R3d,Arj), (Zf,Ra,R1b,R3d,Ark), (Zf,Ra,R1b,R3d,Arl), (Zf,Ra,R1b,R3d,Arm), (Zf,Ra,R1b, R3d,Arn), (Zf,Ra,R1b,R3d,Aro), (Zf,Ra,R1b,R3d,Arp), (Zf, Ra,R1b,R3e,Ara), (Zf,Ra,R1b,R3e,Arb), (Zf,Ra,R1b,R3e, Arc), (Zf,Ra,R1b,R3e,Ard), (Zf,Ra,R1b,R3e,Are), (Zf,Ra, R1b,R3e,Arf), (Zf,Ra,R1b,R3e,Arg), (Zf,Ra,R1b,R3e,Arh), (Zf,Ra,R1b,R3e,Ari), (Zf,Ra,R1b,R3e,Arj), (Zf,Ra,R1b, R3e,Ark), (Zf,Ra,R1b,R3e,Arl), (Zf,Ra,R1b,R3e,Arm), (Zf, Ra,R1b,R3e,Arn), (Zf,Ra,R1b,R3e,Aro), (Zf,Ra,R1b,R3e, Arp), (Zf,Ra,R1b,R3f,Ara), (Zf,Ra,R1b,R3f,Arb), (Zf,Ra, R1b,R3f,Arc), (Zf,Ra,R1b,R3f,Ard), (Zf,Ra,R1b,R3f,Are), (Zf,Ra,R1b,R3f,Arf), (Zf,Ra,R1b,R3f,Arg), (Zf,Ra,R1b, R3f,Arh), (Zf,Ra,R1b,R3f,Ari), (Zf,Ra,R1b,R3f,Arj), (Zf, Ra,R1b,R3f,Ark), (Zf,Ra,R1b,R3f,Arl), (Zf,Ra,R1b,R3f, Arm), (Zf,Ra,R1b,R3f,Arn), (Zf,Ra,R1b,R3f,Aro), (Zf,Ra, R1b,R3f,Arp), (Zf,Ra,R1b,R3g,Ara), (Zf,Ra,R1b,R3g,Arb), (Zf,Ra,R1b,R3g,Arc), (Zf,Ra,R1b,R3g,Ard), (Zf,Ra,R1b, R3g,Are), (Zf,Ra,R1b,R3g,Arf), (Zf,Ra,R1b,R3g,Arg), (Zf, Ra,R1b,R3g,Arh), (Zf,Ra,R1b,R3g,Ari), (Zf,Ra,R1b,R3g, Arj), (Zf,Ra,R1b,R3g,Ark), (Zf,Ra,R1b,R3g,Arl), (Zf,Ra, R1b,R3g,Arm), (Zf,Ra,R1b,R3g,Arn), (Zf,Ra,R1b,R3g, Aro), (Zf,Ra,R1b,R3g,Arp), (Zf,Ra,R1b,R3h,Ara), (Zf,Ra, R1b,R3h,Arb), (Zf,Ra,R1b,R3h,Arc), (Zf,Ra,R1b,R3h,Ard), (Zf,Ra,R1b,R3h,Are), (Zf,Ra,R1b,R3h,Arf), (Zf,Ra,R1b, R3h,Arg), (Zf,Ra,R1b,R3h,Arh), (Zf,Ra,R1b,R3h,Ari), (Zf, Ra,R1b,R3h,Arj), (Zf,Ra,R1b,R3h,Ark), (Zf,Ra,R1b,R3h, Arl), (Zf,Ra,R1b,R3h,Arm), (Zf,Ra,R1b,R3h,Arn), (Zf,Ra, R1b,R3h,Aro), (Zf,Ra,R1b,R3h,Arp), (Zf,Ra,R1c,R3a,Ara), (Zf,Ra,R1c,R3a,Arb), (Zf,Ra,R1c,R3a,Arc), (Zf,Ra,R1c, R3a,Ard), (Zf,Ra,R1c,R3a,Are), (Zf,Ra,R1c,R3a,Arf), (Zf, Ra,R1c,R3a,Arg), (Zf,Ra,R1c,R3a,Arh), (Zf,Ra,R1c,R3a, Ari), (Zf,Ra,R1c,R3a,Arj), (Zf,Ra,R1c,R3a,Ark), (Zf,Ra, R1c,R3a,Arl), (Zf,Ra,R1c,R3a,Arm), (Zf,Ra,R1c,R3a,Arn), (Zf,Ra,R1c,R3a,Aro), (Zf,Ra,R1c,R3a,Arp), (Zf,Ra,R1c, R3b,Ara), (Zf,Ra,R1c,R3b,Arb), (Zf,Ra,R1c,R3b,Arc), (Zf, Ra,R1c,R3b,Ard), (Zf,Ra,R1c,R3b,Are), (Zf,Ra,R1c,R3b, Arf), (Zf,Ra,R1c,R3b,Arg), (Zf,Ra,R1c,R3b,Arh), (Zf,Ra, R1c,R3b,Ari), (Zf,Ra,R1c,R3b,Arj), (Zf,Ra,R1c,R3b,Ark), (Zf,Ra,R1c,R3b,Arl), (Zf,Ra,R1c,R3b,Arm), (Zf,Ra,R1c, R3b,Arn), (Zf,Ra,R1c,R3b,Aro), (Zf,Ra,R1c,R3b,Arp), (Zf, Ra,R1c,R3c,Ara), (Zf,Ra,R1c,R3c,Arb), (Zf,Ra,R1c,R3c, Arc), (Zf,Ra,R1c,R3c,Ard), (Zf,Ra,R1c,R3c,Are), (Zf,Ra, R1c,R3c,Arf), (Zf,Ra,R1c,R3c,Arg), (Zf,Ra,R1c,R3c,Arh), (Zf,Ra,R1c,R3c,Ari), (Zf,Ra,R1c,R3c,Arj), (Zf,Ra,R1c,R3c, Ark), (Zf,Ra,R1c,R3c,Arl), (Zf,Ra,R1c,R3c,Arm), (Zf,Ra, R1c,R3c,Arn), (Zf,Ra,R1c,R3c,Aro), (Zf,Ra,R1c,R3c,Arp), (Zf,Ra,R1c,R3d,Ara), (Zf,Ra,R1c,R3d,Arb), (Zf,Ra,R1c, R3d,Arc), (Zf,Ra,R1c,R3d,Ard), (Zf,Ra,R1c,R3d,Are), (Zf, Ra,R1c,R3d,Arf), (Zf,Ra,R1c,R3d,Arg), (Zf,Ra,R1c,R3d, Arh), (Zf,Ra,R1c,R3d,Ari), (Zf,Ra,R1c,R3d,Arj), (Zf,Ra, R1c,R3d,Ark), (Zf,Ra,R1c,R3d,Arl), (Zf,Ra,R1c,R3d,Arm), (Zf,Ra,R1c,R3d,Arn), (Zf,Ra,R1c,R3d,Aro), (Zf,Ra,R1c, R3d,Arp), (Zf,Ra,R1c,R3e,Ara), (Zf,Ra,R1c,R3e,Arb), (Zf, Ra,R1c,R3e,Arc), (Zf,Ra,R1c,R3e,Ard), (Zf,Ra,R1c,R3e, Are), (Zf,Ra,R1c,R3e,Arf), (Zf,Ra,R1c,R3e,Arg), (Zf,Ra, R1c,R3e,Arh), (Zf,Ra,R1c,R3e,Ari), (Zf,Ra,R1c,R3e,Arj), (Zf,Ra,R1c,R3e,Ark), (Zf,Ra,R1c,R3e,Arl), (Zf,Ra,R1c, R3e,Arm), (Zf,Ra,R1c,R3e,Arn), (Zf,Ra,R1c,R3e,Aro), (Zf, Ra,R1c,R3e,Arp), (Zf,Ra,R1c,R3f,Ara), (Zf,Ra,R1c,R3f, Arb), (Zf,Ra,R1c,R3f,Arc), (Zf,Ra,R1c,R3f,Ard), (Zf,Ra, R1c,R3f,Are), (Zf,Ra,R1c,R3f,Arf), (Zf,Ra,R1c,R3f,Arg), (Zf,Ra,R1c,R3f,Arh), (Zf,Ra,R1c,R3f,Ari), (Zf,Ra,R1c,R3f, Arj), (Zf,Ra,R1c,R3f,Ark), (Zf,Ra,R1c,R3f,Arl), (Zf,Ra, R1c,R3f,Arm), (Zf,Ra,R1c,R3f,Arn), (Zf,Ra,R1c,R3f,Aro), (Zf,Ra,R1c,R3f,Arp), (Zf,Ra,R1c,R3g,Ara), (Zf,Ra,R1c, R3g,Arb), (Zf,Ra,R1c,R3g,Arc), (Zf,Ra,R1c,R3g,Ard), (Zf, Ra,R1c,R3g,Are), (Zf,Ra,R1c,R3g,Arf), (Zf,Ra,R1c,R3g, Arg), (Zf,Ra,R1c,R3g,Arh), (Zf,Ra,R1c,R3g,Ari), (Zf,Ra, R1c,R3g,Arj), (Zf,Ra,R1c,R3g,Ark), (Zf,Ra,R1c,R3g,Arl), (Zf,Ra,R1c,R3g,Arm), (Zf,Ra,R1c,R3g,Arn), (Zf,Ra,R1c, R3g,Aro), (Zf,Ra,R1c,R3g,Arp), (Zf,Ra,R1c,R3h,Ara), (Zf, Ra,R1c,R3h,Arb), (Zf,Ra,R1c,R3h,Arc), (Zf,Ra,R1c,R3h, Ard), (Zf,Ra,R1c,R3h,Are), (Zf,Ra,R1c,R3h,Arf), (Zf,Ra, R1c,R3h,Arg), (Zf,Ra,R1c,R3h,Arh), (Zf,Ra,R1c,R3h,Ari), (Zf,Ra,R1c,R3h,Arj), (Zf,Ra,R1c,R3h,Ark), (Zf,Ra,R1c, R3h,Arl), (Zf,Ra,R1c,R3h,Arm), (Zf,Ra,R1c,R3h,Arn), (Zf, Ra,R1c,R3h,Aro), (Zf,Ra,R1c,R3h,Arp), (Zf,Ra,R1d,R3a, Ara), (Zf,Ra,R1d,R3a,Arb), (Zf,Ra,R1d,R3a,Arc), (Zf,Ra, R1d,R3a,Ard), (Zf,Ra,R1d,R3a,Are), (Zf,Ra,R1d,R3a,Arf), (Zf,Ra,R1d,R3a,Arg), (Zf,Ra,R1d,R3a,Arh), (Zf,Ra,R1d, R3a,Ari), (Zf,Ra,R1d,R3a,Arj), (Zf,Ra,R1d,R3a,Ark), (Zf, Ra,R1d,R3a,Arl), (Zf,Ra,R1d,R3a,Arm), (Zf,Ra,R1d,R3a, Arn), (Zf,Ra,R1d,R3a,Aro), (Zf,Ra,R1d,R3a,Arp), (Zf,Ra, R1d,R3b,Ara), (Zf,Ra,R1d,R3b,Arb), (Zf,Ra,R1d,R3b,Arc), (Zf,Ra,R1d,R3b,Ard), (Zf,Ra,R1d,R3b,Are), (Zf,Ra,R1d, R3b,Arf), (Zf,Ra,R1d,R3b,Arg), (Zf,Ra,R1d,R3b,Arh), (Zf, Ra,R1d,R3b,Ari), (Zf,Ra,R1d,R3b,Arj), (Zf,Ra,R1d,R3b, Ark), (Zf,Ra,R1d,R3b,Arl), (Zf,Ra,R1d,R3b,Arm), (Zf,Ra, R1d,R3b,Arn), (Zf,Ra,R1d,R3b,Aro), (Zf,Ra,R1d,R3b,Arp), (Zf,Ra,R1d,R3c,Ara), (Zf,Ra,R1d,R3c,Arb), (Zf,Ra,R1d, R3c,Arc), (Zf,Ra,R1d,R3c,Ard), (Zf,Ra,R1d,R3c,Are), (Zf, Ra,R1d,R3c,Arf), (Zf,Ra,R1d,R3c,Arg), (Zf,Ra,R1d,R3c, Arh), (Zf,Ra,R1d,R3c,Ari), (Zf,Ra,R1d,R3c,Arj), (Zf,Ra, R1d,R3c,Ark), (Zf,Ra,R1d,R3c,Arl), (Zf,Ra,R1d,R3c,Arm), (Zf,Ra,R1d,R3c,Arn), (Zf,Ra,R1d,R3c,Aro), (Zf,Ra,R1d, R3c,Arp), (Zf,Ra,R1d,R3d,Ara), (Zf,Ra,R1d,R3d,Arb), (Zf, Ra,R1d,R3d,Arc), (Zf,Ra,R1d,R3d,Ard), (Zf,Ra,R1d,R3d, Are), (Zf,Ra,R1d,R3d,Arf), (Zf,Ra,R1d,R3d,Arg), (Zf,Ra, R1d,R3d,Arh), (Zf,Ra,R1d,R3d,Ari), (Zf,Ra,R1d,R3d,Arj), (Zf,Ra,R1d,R3d,Ark), (Zf,Ra,R1d,R3d,Arl), (Zf,Ra,R1d, R3d,Arm), (Zf,Ra,R1d,R3d,Arn), (Zf,Ra,R1d,R3d,Aro), (Zf,Ra,R1d,R3d,Arp), (Zf,Ra,R1d,R3e,Ara), (Zf,Ra,R1d, R3e,Arb), (Zf,Ra,R1d,R3e,Arc), (Zf,Ra,R1d,R3e,Ard), (Zf, Ra,R1d,R3e,Are), (Zf,Ra,R1d,R3e,Arf), (Zf,Ra,R1d,R3e, Arg), (Zf,Ra,R1d,R3e,Arh), (Zf,Ra,R1d,R3e,Ari), (Zf,Ra, R1d,R3e,Arj), (Zf,Ra,R1d,R3e,Ark), (Zf,Ra,R1d,R3e,Arl), (Zf,Ra,R1d,R3e,Arm), (Zf,Ra,R1d,R3e,Arn), (Zf,Ra,R1d, R3e,Aro), (Zf,Ra,R1d,R3e,Arp), (Zf,Ra,R1d,R3f,Ara), (Zf, Ra,R1d,R3f,Arb), (Zf,Ra,R1d,R3f,Arc), (Zf,Ra,R1d,R3f, Ard), (Zf,Ra,R1d,R3f,Are), (Zf,Ra,R1d,R3f,Arf), (Zf,Ra, R1d,R3f,Arg), (Zf,Ra,R1d,R3f,Arh), (Zf,Ra,R1d,R3f,Ari), (Zf,Ra,R1d,R3f,Arj), (Zf,Ra,R1d,R3f,Ark), (Zf,Ra,R1d, R3f,Arl), (Zf,Ra,R1d,R3f,Arm), (Zf,Ra,R1d,R3f,Arn), (Zf, Ra,R1d,R3f,Aro), (Zf,Ra,R1d,R3f,Arp), (Zf,Ra,R1d,R3g, Ara), (Zf,Ra,R1d,R3g,Arb), (Zf,Ra,R1d,R3g,Arc), (Zf,Ra, R1d,R3g,Ard), (Zf,Ra,R1d,R3g,Are), (Zf,Ra,R1d,R3g,Arf), (Zf,Ra,R1d,R3g,Arg), (Zf,Ra,R1d,R3g,Arh), (Zf,Ra,R1d, R3g,Ari), (Zf,Ra,R1d,R3g,Arj), (Zf,Ra,R1d,R3g,Ark), (Zf, Ra,R1d,R3g,Arl), (Zf,Ra,R1d,R3g,Arm), (Zf,Ra,R1d,R3g, Arn), (Zf,Ra,R1d,R3g,Aro), (Zf,Ra,R1d,R3g,Arp), (Zf,Ra, R1d,R3h,Ara), (Zf,Ra,R1d,R3h,Arb), (Zf,Ra,R1d,R3h,Arc), (Zf,Ra,R1d,R3h,Ard), (Zf,Ra,R1d,R3h,Are), (Zf,Ra,R1d, R3h,Arf), (Zf,Ra,R1d,R3h,Arg), (Zf,Ra,R1d,R3h,Arh), (Zf, Ra,R1d,R3h,Ari), (Zf,Ra,R1d,R3h,Arj), (Zf,Ra,R1d,R3h, Ark), (Zf,Ra,R1d,R3h,Arl), (Zf,Ra,R1d,R3h,Arm), (Zf,Ra, R1d,R3h,Arn), (Zf,Ra,R1d,R3h,Aro), (Zf,Ra,R1d,R3h,Arp), (Zf,Rb,R1a,R3a,Ara), (Zf,Rb,R1a,R3a,Arb), (Zf,Rb,R1a, R3a,Arc), (Zf,Rb,R1a,R3a,Ard), (Zf,Rb,R1a,R3a,Are), (Zf, Rb,R1a,R3a,Arf), (Zf,Rb,R1a,R3a,Arg), (Zf,Rb,R1a,R3a, Arh), (Zf,Rb,R1a,R3a,Ari), (Zf,Rb,R1a,R3a,Arj), (Zf,Rb, R1a,R3a,Ark), (Zf,Rb,R1a,R3a,Arl), (Zf,Rb,R1a,R3a,Arm), (Zf,Rb,R1a,R3a,Arn), (Zf,Rb,R1a,R3a,Aro), (Zf,Rb,R1a, R3a,Arp), (Zf,Rb,R1a,R3b,Ara), (Zf,Rb,R1a,R3b,Arb), (Zf, Rb,R1a,R3b,Arc), (Zf,Rb,R1a,R3b,Ard), (Zf,Rb,R1a,R3b, Are), (Zf,Rb,R1a,R3b,Arf), (Zf,Rb,R1a,R3b,Arg), (Zf,Rb, R1a,R3b,Arh), (Zf,Rb,R1a,R3b,Ari), (Zf,Rb,R1a,R3b,Arj), (Zf,Rb,R1a,R3b,Ark), (Zf,Rb,R1a,R3b,Arl), (Zf,Rb,R1a, R3b,Arm), (Zf,Rb,R1a,R3b,Arn), (Zf,Rb,R1a,R3b,Aro), (Zf,Rb,R1a,R3b,Arp), (Zf,Rb,R1a,R3c,Ara), (Zf,Rb,R1a, R3c,Arb), (Zf,Rb,R1a,R3c,Arc), (Zf,Rb,R1a,R3c,Ard), (Zf, Rb,R1a,R3c,Are), (Zf,Rb,R1a,R3c,Arf), (Zf,Rb,R1a,R3c, Arg), (Zf,Rb,R1a,R3c,Arh), (Zf,Rb,R1a,R3c,Ari), (Zf,Rb, R1a,R3c,Arj), (Zf,Rb,R1a,R3c,Ark), (Zf,Rb,R1a,R3c,Arl), (Zf,Rb,R1a,R3c,Arm), (Zf,Rb,R1a,R3c,Arn), (Zf,Rb,R1a, R3c,Aro), (Zf,Rb,R1a,R3c,Arp), (Zf,Rb,R1a,R3d,Ara), (Zf, Rb,R1a,R3d,Arb), (Zf,Rb,R1a,R3d,Arc), (Zf,Rb,R1a,R3d, Ard), (Zf,Rb,R1a,R3d,Are), (Zf,Rb,R1a,R3d,Arf), (Zf,Rb, R1a,R3d,Arg), (Zf,Rb,R1a,R3d,Arh), (Zf,Rb,R1a,R3d,Ari), (Zf,Rb,R1a,R3d,Arj), (Zf,Rb,R1a,R3d,Ark), (Zf,Rb,R1a, R3d,Arl), (Zf,Rb,R1a,R3d,Arm), (Zf,Rb,R1a,R3d,Arn), (Zf, Rb,R1a,R3d,Aro), (Zf,Rb,R1a,R3d,Arp), (Zf,Rb,R1a,R3e, Ara), (Zf,Rb,R1a,R3e,Arb), (Zf,Rb,R1a,R3e,Arc), (Zf,Rb, R1a,R3e,Ard), (Zf,Rb,R1a,R3e,Are), (Zf,Rb,R1a,R3e,Arf), (Zf,Rb,R1a,R3e,Arg), (Zf,Rb,R1a,R3e,Arh), (Zf,Rb,R1a, R3e,Ari), (Zf,Rb,R1a,R3e,Arj), (Zf,Rb,R1a,R3e,Ark), (Zf, Rb,R1a,R3e,Arl), (Zf,Rb,R1a,R3e,Arm), (Zf,Rb,R1a,R3e, Arn), (Zf,Rb,R1a,R3e,Aro), (Zf,Rb,R1a,R3e,Arp), (Zf,Rb, R1a,R3f,Ara), (Zf,Rb,R1a,R3f,Arb), (Zf,Rb,R1a,R3f,Arc), (Zf,Rb,R1a,R3f,Ard), (Zf,Rb,R1a,R3f,Are), (Zf,Rb,R1a, R3f,Arf), (Zf,Rb,R1a,R3f,Arg), (Zf,Rb,R1a,R3f,Arh), (Zf, Rb,R1a,R3f,Ari), (Zf,Rb,R1a,R3f,Arj), (Zf,Rb,R1a,R3f, Ark), (Zf,Rb,R1a,R3f,Arl), (Zf,Rb,R1a,R3f,Arm), (Zf,Rb, R1a,R3f,Arn), (Zf,Rb,R1a,R3f,Aro), (Zf,Rb,R1a,R3f,Arp), (Zf,Rb,R1a,R3g,Ara), (Zf,Rb,R1a,R3g,Arb), (Zf,Rb,R1a, R3g,Arc), (Zf,Rb,R1a,R3g,Ard), (Zf,Rb,R1a,R3g,Are), (Zf, Rb,R1a,R3g,Arf), (Zf,Rb,R1a,R3g,Arg), (Zf,Rb,R1a,R3g, Arh), (Zf,Rb,R1a,R3g,Ari), (Zf,Rb,R1a,R3g,Arj), (Zf,Rb, R1a,R3g,Ark), (Zf,Rb,R1a,R3g,Arl), (Zf,Rb,R1a,R3g,Arm), (Zf,Rb,R1a,R3g,Arn), (Zf,Rb,R1a,R3g,Aro), (Zf,Rb,R1a, R3g,Arp), (Zf,Rb,R1a,R3h,Ara), (Zf,Rb,R1a,R3h,Arb), (Zf, Rb,R1a,R3h,Arc), (Zf,Rb,R1a,R3h,Ard), (Zf,Rb,R1a,R3h, Are), (Zf,Rb,R1a,R3h,Arf), (Zf,Rb,R1a,R3h,Arg), (Zf,Rb, R1a,R3h,Arh), (Zf,Rb,R1a,R3h,Ari), (Zf,Rb,R1a,R3h,Arj), (Zf,Rb,R1a,R3h,Ark), (Zf,Rb,R1a,R3h,Arl), (Zf,Rb,R1a, R3h,Arm), (Zf,Rb,R1a,R3h,Arn), (Zf,Rb,R1a,R3h,Aro), (Zf,Rb,R1a,R3h,Arp), (Zf,Rb,R1b,R3a,Ara), (Zf,Rb,R1b, R3a,Arb), (Zf,Rb,R1b,R3a,Arc), (Zf,Rb,R1b,R3a,Ard), (Zf, Rb,R1b,R3a,Are), (Zf,Rb,R1b,R3a,Arf), (Zf,Rb,R1b,R3a, Arg), (Zf,Rb,R1b,R3a,Arh), (Zf,Rb,R1b,R3a,Ari), (Zf,Rb, R1b,R3a,Arj), (Zf,Rb,R1b,R3a,Ark), (Zf,Rb,R1b,R3a,Arl), (Zf,Rb,R1b,R3a,Arm), (Zf,Rb,R1b,R3a,Arn), (Zf,Rb,R1b, R3a,Aro), (Zf,Rb,R1b,R3a,Arp), (Zf,Rb,R1b,R3b,Ara), (Zf, Rb,R1b,R3b,Arb), (Zf,Rb,R1b,R3b,Arc), (Zf,Rb,R1b,R3b,Ard), (Zf,Rb,R1b,R3b,Are), (Zf,Rb,R1b,R3b,Arf), (Zf,Rb,R1b,R3b,Arg), (Zf,Rb,R1b,R3b,Arh), (Zf,Rb,R1b,R3b,Ari), (Zf,Rb,R1b,R3b,Arj), (Zf,Rb,R1b,R3b,Ark), (Zf,Rb,R1b,R3b,Arl), (Zf,Rb,R1b,R3b,Arm), (Zf,Rb,R1b,R3b,Arn), (Zf,Rb,R1b,R3b,Aro), (Zf,Rb,R1b,R3b,Arp), (Zf,Rb,R1b,R3c,Ara), (Zf,Rb,R1b,R3c,Arb), (Zf,Rb,R1b,R3c,Arc), (Zf,Rb,R1b,R3c,Ard), (Zf,Rb,R1b,R3c,Are), (Zf,Rb,R1b,R3c,Arf), (Zf,Rb,R1b,R3c,Arg), (Zf,Rb,R1b,R3c,Arh), (Zf,Rb,R1b,R3c,Ari), (Zf,Rb,R1b,R3c,Arj), (Zf,Rb,R1b,R3c,Ark), (Zf,Rb,R1b,R3c,Arl), (Zf,Rb,R1b,R3c,Arm), (Zf,Rb,R1b,R3c,Arn), (Zf,Rb,R1b,R3c,Aro), (Zf,Rb,R1b,R3c,Arp), (Zf,Rb,R1b,R3d,Ara), (Zf,Rb,R1b,R3d,Arb), (Zf,Rb,R1b,R3d,Arc), (Zf,Rb,R1b,R3d,Ard), (Zf,Rb,R1b,R3d,Are), (Zf,Rb,R1b,R3d,Arf), (Zf,Rb,R1b,R3d,Arg), (Zf,Rb,R1b,R3d,Arh), (Zf,Rb,R1b,R3d,Ari), (Zf,Rb,R1b,R3d,Arj), (Zf,Rb,R1b,R3d,Ark), (Zf,Rb,R1b,R3d,Arl), (Zf,Rb,R1b,R3d,Arm), (Zf,Rb,R1b,R3d,Arn), (Zf,Rb,R1b,R3d,Aro), (Zf,Rb,R1b,R3d,Arp), (Zf,Rb,R1b,R3e,Ara), (Zf,Rb,R1b,R3e,Arb), (Zf,Rb,R1b,R3e,Arc), (Zf,Rb,R1b,R3e,Ard), (Zf,Rb,R1b,R3e,Are), (Zf,Rb,R1b,R3e,Arf), (Zf,Rb,R1b,R3e,Arg), (Zf,Rb,R1b,R3e,Arh), (Zf,Rb,R1b,R3e,Ari), (Zf,Rb,R1b,R3e,Arj), (Zf,Rb,R1b,R3e,Ark), (Zf,Rb,R1b,R3e,Arl), (Zf,Rb,R1b,R3e,Arm), (Zf,Rb,R1b,R3e,Arn), (Zf,Rb,R1b,R3e,Aro), (Zf,Rb,R1b,R3e,Arp), (Zf,Rb,R1b,R3f,Ara), (Zf,Rb,R1b,R3f,Arb), (Zf,Rb,R1b,R3f,Arc), (Zf,Rb,R1b,R3f,Ard), (Zf,Rb,R1b,R3f,Are), (Zf,Rb,R1b,R3f,Arf), (Zf,Rb,R1b,R3f,Arg), (Zf,Rb,R1b,R3f,Arh), (Zf,Rb,R1b,R3f,Ari), (Zf,Rb,R1b,R3f,Arj), (Zf,Rb,R1b,R3f,Ark), (Zf,Rb,R1b,R3f,Arl), (Zf,Rb,R1b,R3f,Arm), (Zf,Rb,R1b,R3f,Arn), (Zf,Rb,R1b,R3f,Aro), (Zf,Rb,R1b,R3f,Arp), (Zf,Rb,R1b,R3g,Ara), (Zf,Rb,R1b,R3g,Arb), (Zf,Rb,R1b,R3g,Arc), (Zf,Rb,R1b,R3g,Ard), (Zf,Rb,R1b,R3g,Are), (Zf,Rb,R1b,R3g,Arf), (Zf,Rb,R1b,R3g,Arg), (Zf,Rb,R1b,R3g,Arh), (Zf,Rb,R1b,R3g,Ari), (Zf,Rb,R1b,R3g,Arj), (Zf,Rb,R1b,R3g,Ark), (Zf,Rb,R1b,R3g,Arl), (Zf,Rb,R1b,R3g,Arm), (Zf,Rb,R1b,R3g,Arn), (Zf,Rb,R1b,R3g,Aro), (Zf,Rb,R1b,R3g,Arp), (Zf,Rb,R1b,R3h,Ara), (Zf,Rb,R1b,R3h,Arb), (Zf,Rb,R1b,R3h,Arc), (Zf,Rb,R1b,R3h,Ard), (Zf,Rb,R1b,R3h,Are), (Zf,Rb,R1b,R3h,Arf), (Zf,Rb,R1b,R3h,Arg), (Zf,Rb,R1b,R3h,Arh), (Zf,Rb,R1b,R3h,Ari), (Zf,Rb,R1b,R3h,Arj), (Zf,Rb,R1b,R3h,Ark), (Zf,Rb,R1b,R3h,Arl), (Zf,Rb,R1b,R3h,Arm), (Zf,Rb,R1b,R3h,Arn), (Zf,Rb,R1b,R3h,Aro), (Zf,Rb,R1b,R3h,Arp), (Zf,Rb,R1c,R3a,Ara), (Zf,Rb,R1c,R3a,Arb), (Zf,Rb,R1c,R3a,Arc), (Zf,Rb,R1c,R3a,Ard), (Zf,Rb,R1c,R3a,Are), (Zf,Rb,R1c,R3a,Arf), (Zf,Rb,R1c,R3a,Arg), (Zf,Rb,R1c,R3a,Arh), (Zf,Rb,R1c,R3a,Ari), (Zf,Rb,R1c,R3a,Arj), (Zf,Rb,R1c,R3a,Ark), (Zf,Rb,R1c,R3a,Arl), (Zf,Rb,R1c,R3a,Arm), (Zf,Rb,R1c,R3a,Arn), (Zf,Rb,R1c,R3a,Aro), (Zf,Rb,R1c,R3a,Arp), (Zf,Rb,R1c,R3b,Ara), (Zf,Rb,R1c,R3b,Arb), (Zf,Rb,R1c,R3b,Arc), (Zf,Rb,R1c,R3b,Ard), (Zf,Rb,R1c,R3b,Are), (Zf,Rb,R1c,R3b,Arf), (Zf,Rb,R1c,R3b,Arg), (Zf,Rb,R1c,R3b,Arh), (Zf,Rb,R1c,R3b,Ari), (Zf,Rb,R1c,R3b,Arj), (Zf,Rb,R1c,R3b,Ark), (Zf,Rb,R1c,R3b,Arl), (Zf,Rb,R1c,R3b,Arm), (Zf,Rb,R1c,R3b,Arn), (Zf,Rb,R1c,R3b,Aro), (Zf,Rb,R1c,R3b,Arp), (Zf,Rb,R1c,R3c,Ara), (Zf,Rb,R1c,R3c,Arb), (Zf,Rb,R1c,R3c,Arc), (Zf,Rb,R1c,R3c,Ard), (Zf,Rb,R1c,R3c,Are), (Zf,Rb,R1c,R3c,Arf), (Zf,Rb,R1c,R3c,Arg), (Zf,Rb,R1c,R3c,Arh), (Zf,Rb,R1c,R3c,Ari), (Zf,Rb,R1c,R3c,Arj), (Zf,Rb,R1c,R3c,Ark), (Zf,Rb,R1c,R3c,Arl), (Zf,Rb,R1c,R3c,Arm), (Zf,Rb,R1c,R3c,Arn), (Zf,Rb,R1c,R3c,Aro), (Zf,Rb,R1c,R3c,Arp), (Zf,Rb,R1c,R3d,Ara), (Zf,Rb,R1c,R3d,Arb), (Zf,Rb,R1c,R3d,Arc), (Zf,Rb,R1c,R3d,Ard), (Zf,Rb,R1c,R3d,Are), (Zf,Rb,R1c,R3d,Arf), (Zf,Rb,R1c,R3d,Arg), (Zf,Rb,R1c,R3d,Arh), (Zf,Rb,R1c,R3d,Ari), (Zf,Rb,R1c,R3d,Arj), (Zf,Rb,R1c,R3d,Ark), (Zf,Rb,R1c,R3d,Arl), (Zf,Rb,R1c,R3d,Arm), (Zf,Rb,R1c,R3d,Arn), (Zf,Rb,R1c,R3d,Aro), (Zf,Rb,R1c,R3d,Arp), (Zf,Rb,R1c,R3e,Ara), (Zf,Rb,R1c,R3e,Arb), (Zf,Rb,R1c,R3e,Arc), (Zf,Rb,R1c,R3e,Ard), (Zf,Rb,R1c,R3e,Are), (Zf,Rb,R1c,R3e,Arf), (Zf,Rb,R1c,R3e,Arg), (Zf,Rb,R1c,R3e,Arh), (Zf,Rb,R1c,R3e,Ari), (Zf,Rb,R1c,R3e,Arj), (Zf,Rb,R1c,R3e,Ark), (Zf,Rb,R1c,R3e,Arl), (Zf,Rb,R1c,R3e,Arm), (Zf,Rb,R1c,R3e,Arn), (Zf,Rb,R1c,R3e,Aro), (Zf,Rb,R1c,R3e,Arp), (Zf,Rb,R1c,R3f,Ara), (Zf,Rb,R1c,R3f,Arb), (Zf,Rb,R1c,R3f,Arc), (Zf,Rb,R1c,R3f,Ard), (Zf,Rb,R1c,R3f,Are), (Zf,Rb,R1c,R3f,Arf), (Zf,Rb,R1c,R3f,Arg), (Zf,Rb,R1c,R3f,Arh), (Zf,Rb,R1c,R3f,Ari), (Zf,Rb,R1c,R3f,Arj), (Zf,Rb,R1c,R3f,Ark), (Zf,Rb,R1c,R3f,Arl), (Zf,Rb,R1c,R3f,Arm), (Zf,Rb,R1c,R3f,Arn), (Zf,Rb,R1c,R3f,Aro), (Zf,Rb,R1c,R3f,Arp), (Zf,Rb,R1c,R3g,Ara), (Zf,Rb,R1c,R3g,Arb), (Zf,Rb,R1c,R3g,Arc), (Zf,Rb,R1c,R3g,Ard), (Zf,Rb,R1c,R3g,Are), (Zf,Rb,R1c,R3g,Arf), (Zf,Rb,R1c,R3g,Arg), (Zf,Rb,R1c,R3g,Arh), (Zf,Rb,R1c,R3g,Ari), (Zf,Rb,R1c,R3g,Arj), (Zf,Rb,R1c,R3g,Ark), (Zf,Rb,R1c,R3g,Arl), (Zf,Rb,R1c,R3g,Arm), (Zf,Rb,R1c,R3g,Arn), (Zf,Rb,R1c,R3g,Aro), (Zf,Rb,R1c,R3g,Arp), (Zf,Rb,R1c,R3h,Ara), (Zf,Rb,R1c,R3h,Arb), (Zf,Rb,R1c,R3h,Arc), (Zf,Rb,R1c,R3h,Ard), (Zf,Rb,R1c,R3h,Are), (Zf,Rb,R1c,R3h,Arf), (Zf,Rb,R1c,R3h,Arg), (Zf,Rb,R1c,R3h,Arh), (Zf,Rb,R1c,R3h,Ari), (Zf,Rb,R1c,R3h,Arj), (Zf,Rb,R1c,R3h,Ark), (Zf,Rb,R1c,R3h,Arl), (Zf,Rb,R1c,R3h,Arm), (Zf,Rb,R1c,R3h,Arn), (Zf,Rb,R1c,R3h,Aro), (Zf,Rb,R1c,R3h,Arp), (Zf,Rb,R1d,R3a,Ara), (Zf,Rb,R1d,R3a,Arb), (Zf,Rb,R1d,R3a,Arc), (Zf,Rb,R1d,R3a,Ard), (Zf,Rb,R1d,R3a,Are), (Zf,Rb,R1d,R3a,Arf), (Zf,Rb,R1d,R3a,Arg), (Zf,Rb,R1d,R3a,Arh), (Zf,Rb,R1d,R3a,Ari), (Zf,Rb,R1d,R3a,Arj), (Zf,Rb,R1d,R3a,Ark), (Zf,Rb,R1d,R3a,Arl), (Zf,Rb,R1d,R3a,Arm), (Zf,Rb,R1d,R3a,Arn), (Zf,Rb,R1d,R3a,Aro), (Zf,Rb,R1d,R3a,Arp), (Zf,Rb,R1d,R3b,Ara), (Zf,Rb,R1d,R3b,Arb), (Zf,Rb,R1d,R3b,Arc), (Zf,Rb,R1d,R3b,Ard), (Zf,Rb,R1d,R3b,Are), (Zf,Rb,R1d,R3b,Arf), (Zf,Rb,R1d,R3b,Arg), (Zf,Rb,R1d,R3b,Arh), (Zf,Rb,R1d,R3b,Ari), (Zf,Rb,R1d,R3b,Arj), (Zf,Rb,R1d,R3b,Ark), (Zf,Rb,R1d,R3b,Arl), (Zf,Rb,R1d,R3b,Arm), (Zf,Rb,R1d,R3b,Arn), (Zf,Rb,R1d,R3b,Aro), (Zf,Rb,R1d,R3b,Arp), (Zf,Rb,R1d,R3c,Ara), (Zf,Rb,R1d,R3c,Arb), (Zf,Rb,R1d,R3c,Arc), (Zf,Rb,R1d,R3c,Ard), (Zf,Rb,R1d,R3c,Are), (Zf,Rb,R1d,R3c,Arf), (Zf,Rb,R1d,R3c,Arg), (Zf,Rb,R1d,R3c,Arh), (Zf,Rb,R1d,R3c,Ari), (Zf,Rb,R1d,R3c,Arj), (Zf,Rb,R1d,R3c,Ark), (Zf,Rb,R1d,R3c,Arl), (Zf,Rb,R1d,R3c,Arm), (Zf,Rb,R1d,R3c,Arn), (Zf,Rb,R1d,R3c,Aro), (Zf,Rb,R1d,R3c,Arp), (Zf,Rb,R1d,R3d,Ara), (Zf,Rb,R1d,R3d,Arb), (Zf,Rb,R1d,R3d,Arc), (Zf,Rb,R1d,R3d,Ard), (Zf,Rb,R1d,R3d,Are), (Zf,Rb,R1d,R3d,Arf), (Zf,Rb,R1d,R3d,Arg), (Zf,Rb,R1d,R3d,Arh), (Zf,Rb,R1d,R3d,Ari), (Zf,Rb,R1d,R3d,Arj), (Zf,Rb,R1d,R3d,Ark), (Zf,Rb,R1d,R3d,Arl), (Zf,Rb,R1d,R3d,Arm), (Zf,Rb,R1d,R3d,Arn), (Zf,Rb,R1d,R3d,Aro), (Zf,Rb,R1d,R3d,Arp), (Zf,Rb,R1d,R3e,Ara), (Zf,Rb,R1d,R3e,Arb), (Zf,Rb,R1d,R3e,Arc), (Zf,Rb,R1d,R3e,Ard), (Zf,Rb,R1d,R3e,Are), (Zf,Rb,R1d,R3e,Arf), (Zf,Rb,R1d,R3e,Arg), (Zf,Rb,R1d,R3e,Arh), (Zf,Rb,R1d,R3e,Ari), (Zf,Rb,R1d,R3e,Arj), (Zf,Rb,R1d,R3e,Ark), (Zf,Rb,R1d,R3e,Arl), (Zf,Rb,R1d,R3e,Arm), (Zf,Rb,R1d,R3e,Arn), (Zf,Rb,R1d,R3e,Aro), (Zf,Rb,R1d,R3e,Arp), (Zf,Rb,R1d,R3f,Ara), (Zf,Rb,R1d,R3f,Arb), (Zf,Rb,R1d,R3f,Arc), (Zf,Rb,R1d,R3f,Ard), (Zf,Rb,R1d,R3f,Are), (Zf,Rb,R1d,R3f,Arf), (Zf,Rb,R1d,R3f,Arg), (Zf,Rb,R1d,R3f,Arh), (Zf,Rb,R1d,R3f,Ari), (Zf,Rb,R1d,R3f,Arj), (Zf,Rb,R1d,R3f,Ark), (Zf,Rb,R1d,R3f,Arl), (Zf,Rb,R1d,R3f,Arm), (Zf,Rb,R1d,R3f,Arn), (Zf,Rb,R1d,R3f,Aro), (Zf,Rb,R1d,R3f,Arp), (Zf,Rb,R1d,R3g,Ara), (Zf,Rb,R1d,R3g,Arb), (Zf,Rb,R1d,R3g,Arc), (Zf,Rb,R1d,R3g,Ard), (Zf,Rb,R1d,R3g,Are), (Zf,Rb,R1d,R3g,Arf), (Zf,Rb,R1d,R3g,Arg), (Zf,Rb,R1d,R3g,Arh), (Zf,Rb,R1d,R3g,Ari), (Zf,Rb,R1d,R3g,Arj), (Zf,Rb,R1d,R3g,Ark), (Zf,Rb,R1d,R3g,Arl), (Zf,Rb,R1d,R3g, Arm), (Zf,Rb,R1d,R3g,Arn), (Zf,Rb,R1d,R3g,Aro), (Zf,Rb,R1d,R3g,Arp), (Zf,Rb,R1d,R3h,Ara), (Zf,Rb,R1d,R3h,Arb), (Zf,Rb,R1d,R3h,Arc), (Zf,Rb,R1d,R3h,Ard), (Zf,Rb,R1d,R3h,Are), (Zf,Rb,R1d,R3h,Arf), (Zf,Rb,R1d,R3h,Arg), (Zf,Rb,R1d,R3h,Arh), (Zf,Rb,R1d,R3h,Ari), (Zf,Rb,R1d,R3h,Arj), (Zf,Rb,R1d,R3h,Ark), (Zf,Rb,R1d,R3h,Arl), (Zf,Rb,R1d,R3h,Arm), (Zf,Rb,R1d,R3h,Arn), (Zf,Rb,R1d,R3h,Aro), (Zf,Rb,R1d,R3h,Arp), (Zf,Rc,R1a,R3a,Ara), (Zf,Rc,R1a,R3a,Arb), (Zf,Rc,R1a,R3a,Arc), (Zf,Rc,R1a,R3a,Ard), (Zf,Rc,R1a,R3a,Are), (Zf,Rc,R1a,R3a,Arf), (Zf,Rc,R1a,R3a,Arg), (Zf,Rc,R1a,R3a,Arh), (Zf,Rc,R1a,R3a,Ari), (Zf,Rc,R1a,R3a,Arj), (Zf,Rc,R1a,R3a,Ark), (Zf,Rc,R1a,R3a,Arl), (Zf,Rc,R1a,R3a,Arm), (Zf,Rc,R1a,R3a,Arn), (Zf,Rc,R1a,R3a,Aro), (Zf,Rc,R1a,R3a,Arp), (Zf,Rc,R1a,R3b,Ara), (Zf,Rc,R1a,R3b,Arb), (Zf,Rc,R1a,R3b,Arc), (Zf,Rc,R1a,R3b,Ard), (Zf,Rc,R1a,R3b,Are), (Zf,Rc,R1a,R3b,Arf), (Zf,Rc,R1a,R3b,Arg), (Zf,Rc,R1a,R3b,Arh), (Zf,Rc,R1a,R3b,Ari), (Zf,Rc,R1a,R3b,Arj), (Zf,Rc,R1a,R3b,Ark), (Zf,Rc,R1a,R3b,Arl), (Zf,Rc,R1a,R3b,Arm), (Zf,Rc,R1a,R3b,Arn), (Zf,Rc,R1a,R3b,Aro), (Zf,Rc,R1a,R3b,Arp), (Zf,Rc,R1a,R3c,Ara), (Zf,Rc,R1a,R3c,Arb), (Zf,Rc,R1a,R3c,Arc), (Zf,Rc,R1a,R3c,Ard), (Zf,Rc,R1a,R3c,Are), (Zf,Rc,R1a,R3c,Arf), (Zf,Rc,R1a,R3c,Arg), (Zf,Rc,R1a,R3c,Arh), (Zf,Rc,R1a,R3c,Ari), (Zf,Rc,R1a,R3c,Arj), (Zf,Rc,R1a,R3c,Ark), (Zf,Rc,R1a,R3c,Arl), (Zf,Rc,R1a,R3c,Arm), (Zf,Rc,R1a,R3c,Arn), (Zf,Rc,R1a,R3c,Aro), (Zf,Rc,R1a,R3c,Arp), (Zf,Rc,R1a,R3d,Ara), (Zf,Rc,R1a,R3d,Arb), (Zf,Rc,R1a,R3d,Arc), (Zf,Rc,R1a,R3d,Ard), (Zf,Rc,R1a,R3d,Are), (Zf,Rc,R1a,R3d,Arf), (Zf,Rc,R1a,R3d,Arg), (Zf,Rc,R1a,R3d,Arh), (Zf,Rc,R1a,R3d,Ari), (Zf,Rc,R1a,R3d,Arj), (Zf,Rc,R1a,R3d,Ark), (Zf,Rc,R1a,R3d,Arl), (Zf,Rc,R1a,R3d,Arm), (Zf,Rc,R1a,R3d,Arn), (Zf,Rc,R1a,R3d,Aro), (Zf,Rc,R1a,R3d,Arp), (Zf,Rc,R1a,R3e,Ara), (Zf,Rc,R1a,R3e,Arb), (Zf,Rc,R1a,R3e,Arc), (Zf,Rc,R1a,R3e,Ard), (Zf,Rc,R1a,R3e,Are), (Zf,Rc,R1a,R3e,Arf), (Zf,Rc,R1a,R3e,Arg), (Zf,Rc,R1a,R3e,Arh), (Zf,Rc,R1a,R3e,Ari), (Zf,Rc,R1a,R3e,Arj), (Zf,Rc,R1a,R3e,Ark), (Zf,Rc,R1a,R3e,Arl), (Zf,Rc,R1a,R3e,Arm), (Zf,Rc,R1a,R3e,Arn), (Zf,Rc,R1a,R3e,Aro), (Zf,Rc,R1a,R3e,Arp), (Zf,Rc,R1a,R3f,Ara), (Zf,Rc,R1a,R3f,Arb), (Zf,Rc,R1a,R3f,Arc), (Zf,Rc,R1a,R3f,Ard), (Zf,Rc,R1a,R3f,Are), (Zf,Rc,R1a,R3f,Arf), (Zf,Rc,R1a,R3f,Arg), (Zf,Rc,R1a,R3f,Arh), (Zf,Rc,R1a,R3f,Ari), (Zf,Rc,R1a,R3f,Arj), (Zf,Rc,R1a,R3f,Ark), (Zf,Rc,R1a,R3f,Arl), (Zf,Rc,R1a,R3f,Arm), (Zf,Rc,R1a,R3f,Arn), (Zf,Rc,R1a,R3f,Aro), (Zf,Rc,R1a,R3f,Arp), (Zf,Rc,R1a,R3g,Ara), (Zf,Rc,R1a,R3g,Arb), (Zf,Rc,R1a,R3g,Arc), (Zf,Rc,R1a,R3g,Ard), (Zf,Rc,R1a,R3g,Are), (Zf,Rc,R1a,R3g,Arf), (Zf,Rc,R1a,R3g,Arg), (Zf,Rc,R1a,R3g,Arh), (Zf,Rc,R1a,R3g,Ari), (Zf,Rc,R1a,R3g,Arj), (Zf,Rc,R1a,R3g,Ark), (Zf,Rc,R1a,R3g,Arl), (Zf,Rc,R1a,R3g,Arm), (Zf,Rc,R1a,R3g,Arn), (Zf,Rc,R1a,R3g,Aro), (Zf,Rc,R1a,R3g,Arp), (Zf,Rc,R1a,R3h,Ara), (Zf,Rc,R1a,R3h,Arb), (Zf,Rc,R1a,R3h,Arc), (Zf,Rc,R1a,R3h,Ard), (Zf,Rc,R1a,R3h,Are), (Zf,Rc,R1a,R3h,Arf), (Zf,Rc,R1a,R3h,Arg), (Zf,Rc,R1a,R3h,Arh), (Zf,Rc,R1a,R3h,Ari), (Zf,Rc,R1a,R3h,Arj), (Zf,Rc,R1a,R3h,Ark), (Zf,Rc,R1a,R3h,Arl), (Zf,Rc,R1a,R3h,Arm), (Zf,Rc,R1a,R3h,Arn), (Zf,Rc,R1a,R3h,Aro), (Zf,Rc,R1a,R3h,Arp), (Zf,Rc,R1b,R3a,Ara), (Zf,Rc,R1b,R3a,Arb), (Zf,Rc,R1b,R3a,Arc), (Zf,Rc,R1b,R3a,Ard), (Zf,Rc,R1b,R3a,Are), (Zf,Rc,R1b,R3a,Arf), (Zf,Rc,R1b,R3a,Arg), (Zf,Rc,R1b,R3a,Arh), (Zf,Rc,R1b,R3a,Ari), (Zf,Rc,R1b,R3a,Arj), (Zf,Rc,R1b,R3a,Ark), (Zf,Rc,R1b,R3a,Arl), (Zf,Rc,R1b,R3a,Arm), (Zf,Rc,R1b,R3a,Arn), (Zf,Rc,R1b,R3a,Aro), (Zf,Rc,R1b,R3a,Arp), (Zf,Rc,R1b,R3b,Ara), (Zf,Rc,R1b,R3b,Arb), (Zf,Rc,R1b,R3b,Arc), (Zf,Rc,R1b,R3b,Ard), (Zf,Rc,R1b,R3b,Are), (Zf,Rc,R1b,R3b,Arf), (Zf,Rc,R1b,R3b,Arg), (Zf,Rc,R1b,R3b,Arh), (Zf,Rc,R1b,R3b,Ari), (Zf,Rc,R1b,R3b,Arj), (Zf,Rc,R1b,R3b,Ark), (Zf,Rc,R1b,R3b,Arl), (Zf,Rc,R1b,R3b,Arm), (Zf,Rc,R1b,R3b,Arn), (Zf,Rc,R1b,R3b,Aro), (Zf,Rc,R1b,R3b,Arp), (Zf,Rc,R1b,R3c,Ara), (Zf,Rc,R1b,R3c,Arb), (Zf,Rc,R1b,R3c,Arc), (Zf,Rc,R1b,R3c,Ard), (Zf,Rc,R1b,R3c,Are), (Zf,Rc,R1b,R3c,Arf), (Zf,Rc,R1b,R3c,Arg), (Zf,Rc,R1b,R3c,Arh), (Zf,Rc,R1b,R3c,Ari), (Zf,Rc,R1b,R3c,Arj), (Zf,Rc,R1b,R3c,Ark), (Zf,Rc,R1b,R3c,Arl), (Zf,Rc,R1b,R3c,Arm), (Zf,Rc,R1b,R3c,Arn), (Zf,Rc,R1b,R3c,Aro), (Zf,Rc,R1b,R3c,Arp), (Zf,Rc,R1b,R3d,Ara), (Zf,Rc,R1b,R3d,Arb), (Zf,Rc,R1b,R3d,Arc), (Zf,Rc,R1b,R3d,Ard), (Zf,Rc,R1b,R3d,Are), (Zf,Rc,R1b,R3d,Arf), (Zf,Rc,R1b,R3d,Arg), (Zf,Rc,R1b,R3d,Arh), (Zf,Rc,R1b,R3d,Ari), (Zf,Rc,R1b,R3d,Arj), (Zf,Rc,R1b,R3d,Ark), (Zf,Rc,R1b,R3d,Arl), (Zf,Rc,R1b,R3d,Arm), (Zf,Rc,R1b,R3d,Arn), (Zf,Rc,R1b,R3d,Aro), (Zf,Rc,R1b,R3d,Arp), (Zf,Rc,R1b,R3e,Ara), (Zf,Rc,R1b,R3e,Arb), (Zf,Rc,R1b,R3e,Arc), (Zf,Rc,R1b,R3e,Ard), (Zf,Rc,R1b,R3e,Are), (Zf,Rc,R1b,R3e,Arf), (Zf,Rc,R1b,R3e,Arg), (Zf,Rc,R1b,R3e,Arh), (Zf,Rc,R1b,R3e,Ari), (Zf,Rc,R1b,R3e,Arj), (Zf,Rc,R1b,R3e,Ark), (Zf,Rc,R1b,R3e,Arl), (Zf,Rc,R1b,R3e,Arm), (Zf,Rc,R1b,R3e,Arn), (Zf,Rc,R1b,R3e,Aro), (Zf,Rc,R1b,R3e,Arp), (Zf,Rc,R1b,R3f,Ara), (Zf,Rc,R1b,R3f,Arb), (Zf,Rc,R1b,R3f,Arc), (Zf,Rc,R1b,R3f,Ard), (Zf,Rc,R1b,R3f,Are), (Zf,Rc,R1b,R3f,Arf), (Zf,Rc,R1b,R3f,Arg), (Zf,Rc,R1b,R3f,Arh), (Zf,Rc,R1b,R3f,Ari), (Zf,Rc,R1b,R3f,Arj), (Zf,Rc,R1b,R3f,Ark), (Zf,Rc,R1b,R3f,Arl), (Zf,Rc,R1b,R3f,Arm), (Zf,Rc,R1b,R3f,Arn), (Zf,Rc,R1b,R3f,Aro), (Zf,Rc,R1b,R3f,Arp), (Zf,Rc,R1b,R3g,Ara), (Zf,Rc,R1b,R3g,Arb), (Zf,Rc,R1b,R3g,Arc), (Zf,Rc,R1b,R3g,Ard), (Zf,Rc,R1b,R3g,Are), (Zf,Rc,R1b,R3g,Arf), (Zf,Rc,R1b,R3g,Arg), (Zf,Rc,R1b,R3g,Arh), (Zf,Rc,R1b,R3g,Ari), (Zf,Rc,R1b,R3g,Arj), (Zf,Rc,R1b,R3g,Ark), (Zf,Rc,R1b,R3g,Arl), (Zf,Rc,R1b,R3g,Arm), (Zf,Rc,R1b,R3g,Arn), (Zf,Rc,R1b,R3g,Aro), (Zf,Rc,R1b,R3g,Arp), (Zf,Rc,R1b,R3h,Ara), (Zf,Rc,R1b,R3h,Arb), (Zf,Rc,R1b,R3h,Arc), (Zf,Rc,R1b,R3h,Ard), (Zf,Rc,R1b,R3h,Are), (Zf,Rc,R1b,R3h,Arf), (Zf,Rc,R1b,R3h,Arg), (Zf,Rc,R1b,R3h,Arh), (Zf,Rc,R1b,R3h,Ari), (Zf,Rc,R1b,R3h,Arj), (Zf,Rc,R1b,R3h,Ark), (Zf,Rc,R1b,R3h,Arl), (Zf,Rc,R1b,R3h,Arm), (Zf,Rc,R1b,R3h,Arn), (Zf,Rc,R1b,R3h,Aro), (Zf,Rc,R1b,R3h,Arp), (Zf,Rc,R1c,R3a,Ara), (Zf,Rc,R1c,R3a,Arb), (Zf,Rc,R1c,R3a,Arc), (Zf,Rc,R1c,R3a,Ard), (Zf,Rc,R1c,R3a,Are), (Zf,Rc,R1c,R3a,Arf), (Zf,Rc,R1c,R3a,Arg), (Zf,Rc,R1c,R3a,Arh), (Zf,Rc,R1c,R3a,Ari), (Zf,Rc,R1c,R3a,Arj), (Zf,Rc,R1c,R3a,Ark), (Zf,Rc,R1c,R3a,Arl), (Zf,Rc,R1c,R3a,Arm), (Zf,Rc,R1c,R3a,Arn), (Zf,Rc,R1c,R3a,Aro), (Zf,Rc,R1c,R3a,Arp), (Zf,Rc,R1c,R3b,Ara), (Zf,Rc,R1c,R3b,Arb), (Zf,Rc,R1c,R3b,Arc), (Zf,Rc,R1c,R3b,Ard), (Zf,Rc,R1c,R3b,Are), (Zf,Rc,R1c,R3b,Arf), (Zf,Rc,R1c,R3b,Arg), (Zf,Rc,R1c,R3b,Arh), (Zf,Rc,R1c,R3b,Ari), (Zf,Rc,R1c,R3b,Arj), (Zf,Rc,R1c,R3b,Ark), (Zf,Rc,R1c,R3b,Arl), (Zf,Rc,R1c,R3b,Arm), (Zf,Rc,R1c,R3b,Arn), (Zf,Rc,R1c,R3b,Aro), (Zf,Rc,R1c,R3b,Arp), (Zf,Rc,R1c,R3c,Ara), (Zf,Rc,R1c,R3c,Arb), (Zf,Rc,R1c,R3c,Arc), (Zf,Rc,R1c,R3c,Ard), (Zf,Rc,R1c,R3c,Are), (Zf,Rc,R1c,R3c,Arf), (Zf,Rc,R1c,R3c,Arg), (Zf,Rc,R1c,R3c,Arh), (Zf,Rc,R1c,R3c,Ari), (Zf,Rc,R1c,R3c,Arj), (Zf,Rc,R1c,R3c,Ark), (Zf,Rc,R1c,R3c,Arl), (Zf,Rc,R1c,R3c,Arm), (Zf,Rc,R1c,R3c,Arn), (Zf,Rc,R1c,R3c,Aro), (Zf,Rc,R1c,R3c,Arp), (Zf,Rc,R1c,R3d,Ara), (Zf,Rc,R1c,R3d,Arb), (Zf,Rc,R1c,R3d,Arc), (Zf,Rc,R1c,R3d,Ard), (Zf,Rc,R1c,R3d,Are), (Zf,Rc,R1c,R3d,Arf), (Zf,Rc,R1c,R3d,Arg), (Zf,Rc,R1c,R3d,Arh), (Zf,Rc,R1c,R3d,Ari), (Zf,Rc,R1c,R3d,Arj), (Zf,Rc,R1c,R3d,Ark), (Zf,Rc,R1c,R3d,Arl), (Zf,Rc,R1c,R3d,Arm), (Zf,Rc,R1c,R3d,Arn), (Zf,Rc,R1c,R3d,Aro), (Zf,Rc,R1c,R3d,Arp), (Zf,Rc,R1c,R3e,Ara), (Zf,Rc,R1c,R3e,Arb), (Zf,Rc,R1c,R3e,Arc), (Zf,Rc,R1c,R3e,Ard), (Zf,Rc,R1c,R3e,Are), (Zf,Rc,R1c,R3e,Arf), (Zf,Rc,R1c,R3e,Arg), (Zf,Rc,R1c,R3e,Arh), (Zf,Rc,R1c,R3e, Ari), (Zf,Rc,R1c,R3e,Arj), (Zf,Rc,R1c,R3e,Ark), (Zf,Rc, R1c,R3e,Arl), (Zf,Rc,R1c,R3e,Arm), (Zf,Rc,R1c,R3e,Arn), (Zf,Rc,R1c,R3e,Aro), (Zf,Rc,R1c,R3e,Arp), (Zf,Rc,R1c, R3f,Ara), (Zf,Rc,R1c,R3f,Arb), (Zf,Rc,R1c,R3f,Arc), (Zf, Rc,R1c,R3f,Ard), (Zf,Rc,R1c,R3f,Are), (Zf,Rc,R1c,R3f, Arf), (Zf,Rc,R1c,R3f,Arg), (Zf,Rc,R1c,R3f,Arh), (Zf,Rc, R1c,R3f,Ari), (Zf,Rc,R1c,R3f,Arj), (Zf,Rc,R1c,R3f,Ark), (Zf,Rc,R1c,R3f,Arl), (Zf,Rc,R1c,R3f,Arm), (Zf,Rc,R1c, R3f,Arn), (Zf,Rc,R1c,R3f,Aro), (Zf,Rc,R1c,R3f,Arp), (Zf, Rc,R1c,R3g,Ara), (Zf,Rc,R1c,R3g,Arb), (Zf,Rc,R1c,R3g, Arc), (Zf,Rc,R1c,R3g,Ard), (Zf,Rc,R1c,R3g,Are), (Zf,Rc, R1c,R3g,Arf), (Zf,Rc,R1c,R3g,Arg), (Zf,Rc,R1c,R3g,Arh), (Zf,Rc,R1c,R3g,Ari), (Zf,Rc,R1c,R3g,Arj), (Zf,Rc,R1c, R3g,Ark), (Zf,Rc,R1c,R3g,Arl), (Zf,Rc,R1c,R3g,Arm), (Zf, Rc,R1c,R3g,Arn), (Zf,Rc,R1c,R3g,Aro), (Zf,Rc,R1c,R3g, Arp), (Zf,Rc,R1c,R3h,Ara), (Zf,Rc,R1c,R3h,Arb), (Zf,Rc, R1c,R3h,Arc), (Zf,Rc,R1c,R3h,Ard), (Zf,Rc,R1c,R3h,Are), (Zf,Rc,R1c,R3h,Arf), (Zf,Rc,R1c,R3h,Arg), (Zf,Rc,R1c, R3h,Arh), (Zf,Rc,R1c,R3h,Ari), (Zf,Rc,R1c,R3h,Arj), (Zf, Rc,R1c,R3h,Ark), (Zf,Rc,R1c,R3h,Arl), (Zf,Rc,R1c,R3h, Arm), (Zf,Rc,R1c,R3h,Arn), (Zf,Rc,R1c,R3h,Aro), (Zf,Rc, R1c,R3h,Arp), (Zf,Rc,R1d,R3a,Ara), (Zf,Rc,R1d,R3a,Arb), (Zf,Rc,R1d,R3a,Arc), (Zf,Rc,R1d,R3a,Ard), (Zf,Rc,R1d, R3a,Are), (Zf,Rc,R1d,R3a,Arf), (Zf,Rc,R1d,R3a,Arg), (Zf, Rc,R1d,R3a,Arh), (Zf,Rc,R1d,R3a,Ari), (Zf,Rc,R1d,R3a, Arj), (Zf,Rc,R1d,R3a,Ark), (Zf,Rc,R1d,R3a,Arl), (Zf,Rc, R1d,R3a,Arm), (Zf,Rc,R1d,R3a,Arn), (Zf,Rc,R1d,R3a, Aro), (Zf,Rc,R1d,R3a,Arp), (Zf,Rc,R1d,R3b,Ara), (Zf,Rc, R1d,R3b,Arb), (Zf,Rc,R1d,R3b,Arc), (Zf,Rc,R1d,R3b,Ard), (Zf,Rc,R1d,R3b,Are), (Zf,Rc,R1d,R3b,Arf), (Zf,Rc,R1d, R3b,Arg), (Zf,Rc,R1d,R3b,Arh), (Zf,Rc,R1d,R3b,Ari), (Zf, Rc,R1d,R3b,Arj), (Zf,Rc,R1d,R3b,Ark), (Zf,Rc,R1d,R3b, Arl), (Zf,Rc,R1d,R3b,Arm), (Zf,Rc,R1d,R3b,Arn), (Zf,Rc, R1d,R3b,Aro), (Zf,Rc,R1d,R3b,Arp), (Zf,Rc,R1d,R3c,Ara), (Zf,Rc,R1d,R3c,Arb), (Zf,Rc,R1d,R3c,Arc), (Zf,Rc,R1d, R3c,Ard), (Zf,Rc,R1d,R3c,Are), (Zf,Rc,R1d,R3c,Arf), (Zf, Rc,R1d,R3c,Arg), (Zf,Rc,R1d,R3c,Arh), (Zf,Rc,R1d,R3c, Ari), (Zf,Rc,R1d,R3c,Arj), (Zf,Rc,R1d,R3c,Ark), (Zf,Rc, R1d,R3c,Arl), (Zf,Rc,R1d,R3c,Arm), (Zf,Rc,R1d,R3c,Arn), (Zf,Rc,R1d,R3c,Aro), (Zf,Rc,R1d,R3c,Arp), (Zf,Rc,R1d, R3d,Ara), (Zf,Rc,R1d,R3d,Arb), (Zf,Rc,R1d,R3d,Arc), (Zf, Rc,R1d,R3d,Ard), (Zf,Rc,R1d,R3d,Are), (Zf,Rc,R1d,R3d, Arf), (Zf,Rc,R1d,R3d,Arg), (Zf,Rc,R1d,R3d,Arh), (Zf,Rc, R1d,R3d,Ari), (Zf,Rc,R1d,R3d,Arj), (Zf,Rc,R1d,R3d,Ark), (Zf,Rc,R1d,R3d,Arl), (Zf,Rc,R1d,R3d,Arm), (Zf,Rc,R1d, R3d,Arn), (Zf,Rc,R1d,R3d,Aro), (Zf,Rc,R1d,R3d,Arp), (Zf, Rc,R1d,R3e,Ara), (Zf,Rc,R1d,R3e,Arb), (Zf,Rc,R1d,R3e, Arc), (Zf,Rc,R1d,R3e,Ard), (Zf,Rc,R1d,R3e,Are), (Zf,Rc, R1d,R3e,Arf), (Zf,Rc,R1d,R3e,Arg), (Zf,Rc,R1d,R3e,Arh), (Zf,Rc,R1d,R3e,Ari), (Zf,Rc,R1d,R3e,Arj), (Zf,Rc,R1d, R3e,Ark), (Zf,Rc,R1d,R3e,Arl), (Zf,Rc,R1d,R3e,Arm), (Zf, Rc,R1d,R3e,Arn), (Zf,Rc,R1d,R3e,Aro), (Zf,Rc,R1d,R3e, Arp), (Zf,Rc,R1d,R3f,Ara), (Zf,Rc,R1d,R3f,Arb), (Zf,Rc, R1d,R3f,Arc), (Zf,Rc,R1d,R3f,Ard), (Zf,Rc,R1d,R3f,Are), (Zf,Rc,R1d,R3f,Arf), (Zf,Rc,R1d,R3f,Arg), (Zf,Rc,R1d, R3f,Arh), (Zf,Rc,R1d,R3f,Ari), (Zf,Rc,R1d,R3f,Arj), (Zf, Rc,R1d,R3f,Ark), (Zf,Rc,R1d,R3f,Arl), (Zf,Rc,R1d,R3f, Arm), (Zf,Rc,R1d,R3f,Arn), (Zf,Rc,R1d,R3f,Aro), (Zf,Rc, R1d,R3f,Arp), (Zf,Rc,R1d,R3g,Ara), (Zf,Rc,R1d,R3g,Arb), (Zf,Rc,R1d,R3g,Arc), (Zf,Rc,R1d,R3g,Ard), (Zf,Rc,R1d, R3g,Are), (Zf,Rc,R1d,R3g,Arf), (Zf,Rc,R1d,R3g,Arg), (Zf, Rc,R1d,R3g,Arh), (Zf,Rc,R1d,R3g,Ari), (Zf,Rc,R1d,R3g, Arj), (Zf,Rc,R1d,R3g,Ark), (Zf,Rc,R1d,R3g,Arl), (Zf,Rc, R1d,R3g,Arm), (Zf,Rc,R1d,R3g,Arn), (Zf,Rc,R1d,R3g, Aro), (Zf,Rc,R1d,R3g,Arp), (Zf,Rc,R1d,R3h,Ara), (Zf,Rc, R1d,R3h,Arb), (Zf,Rc,R1d,R3h,Arc), (Zf,Rc,R1d,R3h,Ard), (Zf,Rc,R1d,R3h,Are), (Zf,Rc,R1d,R3h,Arf), (Zf,Rc,R1d, R3h,Arg), (Zf,Rc,R1d,R3h,Arh), (Zf,Rc,R1d,R3h,Ari), (Zf, Rc,R1d,R3h,Arj), (Zf,Rc,R1d,R3h,Ark), (Zf,Rc,R1d,R3h, Arl), (Zf,Rc,R1d,R3h,Arm), (Zf,Rc,R1d,R3h,Arn), (Zf,Rc, R1d,R3h,Aro), (Zf,Rc,R1d,R3h,Arp), (Zf,Rd,R1a,R3a,Ara), (Zf,Rd,R1a,R3a,Arb), (Zf,Rd,R1a,R3a,Arc), (Zf,Rd,R1a, R3a,Ard), (Zf,Rd,R1a,R3a,Are), (Zf,Rd,R1a,R3a,Arf), (Zf, Rd,R1a,R3a,Arg), (Zf,Rd,R1a,R3a,Arh), (Zf,Rd,R1a,R3a, Ari), (Zf,Rd,R1a,R3a,Arj), (Zf,Rd,R1a,R3a,Ark), (Zf,Rd, R1a,R3a,Arl), (Zf,Rd,R1a,R3a,Arm), (Zf,Rd,R1a,R3a,Arn), (Zf,Rd,R1a,R3a,Aro), (Zf,Rd,R1a,R3a,Arp), (Zf,Rd,R1a, R3b,Ara), (Zf,Rd,R1a,R3b,Arb), (Zf,Rd,R1a,R3b,Arc), (Zf, Rd,R1a,R3b,Ard), (Zf,Rd,R1a,R3b,Are), (Zf,Rd,R1a,R3b, Arf), (Zf,Rd,R1a,R3b,Arg), (Zf,Rd,R1a,R3b,Arh), (Zf,Rd, R1a,R3b,Ari), (Zf,Rd,R1a,R3b,Arj), (Zf,Rd,R1a,R3b,Ark), (Zf,Rd,R1a,R3b,Arl), (Zf,Rd,R1a,R3b,Arm), (Zf,Rd,R1a, R3b,Arn), (Zf,Rd,R1a,R3b,Aro), (Zf,Rd,R1a,R3b,Arp), (Zf, Rd,R1a,R3c,Ara), (Zf,Rd,R1a,R3c,Arb), (Zf,Rd,R1a,R3c, Arc), (Zf,Rd,R1a,R3c,Ard), (Zf,Rd,R1a,R3c,Are), (Zf,Rd, R1a,R3c,Arf), (Zf,Rd,R1a,R3c,Arg), (Zf,Rd,R1a,R3c,Arh), (Zf,Rd,R1a,R3c,Ari), (Zf,Rd,R1a,R3c,Arj), (Zf,Rd,R1a, R3c,Ark), (Zf,Rd,R1a,R3c,Arl), (Zf,Rd,R1a,R3c,Arm), (Zf, Rd,R1a,R3c,Arn), (Zf,Rd,R1a,R3c,Aro), (Zf,Rd,R1a,R3c, Arp), (Zf,Rd,R1a,R3d,Ara), (Zf,Rd,R1a,R3d,Arb), (Zf,Rd, R1a,R3d,Arc), (Zf,Rd,R1a,R3d,Ard), (Zf,Rd,R1a,R3d,Are), (Zf,Rd,R1a,R3d,Arf), (Zf,Rd,R1a,R3d,Arg), (Zf,Rd,R1a, R3d,Arh), (Zf,Rd,R1a,R3d,Ari), (Zf,Rd,R1a,R3d,Arj), (Zf, Rd,R1a,R3d,Ark), (Zf,Rd,R1a,R3d,Arl), (Zf,Rd,R1a,R3d, Arm), (Zf,Rd,R1a,R3d,Arn), (Zf,Rd,R1a,R3d,Aro), (Zf,Rd, R1a,R3d,Arp), (Zf,Rd,R1a,R3e,Ara), (Zf,Rd,R1a,R3e,Arb), (Zf,Rd,R1a,R3e,Arc), (Zf,Rd,R1a,R3e,Ard), (Zf,Rd,R1a, R3e,Are), (Zf,Rd,R1a,R3e,Arf), (Zf,Rd,R1a,R3e,Arg), (Zf, Rd,R1a,R3e,Arh), (Zf,Rd,R1a,R3e,Ari), (Zf,Rd,R1a,R3e, Arj), (Zf,Rd,R1a,R3e,Ark), (Zf,Rd,R1a,R3e,Arl), (Zf,Rd, R1a,R3e,Arm), (Zf,Rd,R1a,R3e,Arn), (Zf,Rd,R1a,R3e, Aro), (Zf,Rd,R1a,R3e,Arp), (Zf,Rd,R1a,R3f,Ara), (Zf,Rd, R1a,R3f,Arb), (Zf,Rd,R1a,R3f,Arc), (Zf,Rd,R1a,R3f,Ard), (Zf,Rd,R1a,R3f,Are), (Zf,Rd,R1a,R3f,Arf), (Zf,Rd,R1a, R3f,Arg), (Zf,Rd,R1a,R3f,Arh), (Zf,Rd,R1a,R3f,Ari), (Zf, Rd,R1a,R3f,Arj), (Zf,Rd,R1a,R3f,Ark), (Zf,Rd,R1a,R3f, Arl), (Zf,Rd,R1a,R3f,Arm), (Zf,Rd,R1a,R3f,Arn), (Zf,Rd, R1a,R3f,Aro), (Zf,Rd,R1a,R3f,Arp), (Zf,Rd,R1a,R3g,Ara), (Zf,Rd,R1a,R3g,Arb), (Zf,Rd,R1a,R3g,Arc), (Zf,Rd,R1a, R3g,Ard), (Zf,Rd,R1a,R3g,Are), (Zf,Rd,R1a,R3g,Arf), (Zf, Rd,R1a,R3g,Arg), (Zf,Rd,R1a,R3g,Arh), (Zf,Rd,R1a,R3g, Ari), (Zf,Rd,R1a,R3g,Arj), (Zf,Rd,R1a,R3g,Ark), (Zf,Rd, R1a,R3g,Arl), (Zf,Rd,R1a,R3g,Arm), (Zf,Rd,R1a,R3g,Arn), (Zf,Rd,R1a,R3g,Aro), (Zf,Rd,R1a,R3g,Arp), (Zf,Rd,R1a, R3h,Ara), (Zf,Rd,R1a,R3h,Arb), (Zf,Rd,R1a,R3h,Arc), (Zf, Rd,R1a,R3h,Ard), (Zf,Rd,R1a,R3h,Are), (Zf,Rd,R1a,R3h, Arf), (Zf,Rd,R1a,R3h,Arg), (Zf,Rd,R1a,R3h,Arh), (Zf,Rd, R1a,R3h,Ari), (Zf,Rd,R1a,R3h,Arj), (Zf,Rd,R1a,R3h,Ark), (Zf,Rd,R1a,R3h,Arl), (Zf,Rd,R1a,R3h,Arm), (Zf,Rd,R1a, R3h,Arn), (Zf,Rd,R1a,R3h,Aro), (Zf,Rd,R1a,R3h,Arp), (Zf, Rd,R1b,R3a,Ara), (Zf,Rd,R1b,R3a,Arb), (Zf,Rd,R1b,R3a, Arc), (Zf,Rd,R1b,R3a,Ard), (Zf,Rd,R1b,R3a,Are), (Zf,Rd, R1b,R3a,Arf), (Zf,Rd,R1b,R3a,Arg), (Zf,Rd,R1b,R3a,Arh), (Zf,Rd,R1b,R3a,Ari), (Zf,Rd,R1b,R3a,Arj), (Zf,Rd,R1b, R3a,Ark), (Zf,Rd,R1b,R3a,Arl), (Zf,Rd,R1b,R3a,Arm), (Zf, Rd,R1b,R3a,Arn), (Zf,Rd,R1b,R3a,Aro), (Zf,Rd,R1b,R3a, Arp), (Zf,Rd,R1b,R3b,Ara), (Zf,Rd,R1b,R3b,Arb), (Zf,Rd, R1b,R3b,Arc), (Zf,Rd,R1b,R3b,Ard), (Zf,Rd,R1b,R3b,Are), (Zf,Rd,R1b,R3b,Arf), (Zf,Rd,R1b,R3b,Arg), (Zf,Rd,R1b, R3b,Arh), (Zf,Rd,R1b,R3b,Ari), (Zf,Rd,R1b,R3b,Arj), (Zf, Rd,R1b,R3b,Ark), (Zf,Rd,R1b,R3b,Arl), (Zf,Rd,R1b,R3b, Arm), (Zf,Rd,R1b,R3b,Arn), (Zf,Rd,R1b,R3b,Aro), (Zf,Rd, R1b,R3b,Arp), (Zf,Rd,R1b,R3c,Ara), (Zf,Rd,R1b,R3c,Arb), (Zf,Rd,R1b,R3c,Arc), (Zf,Rd,R1b,R3c,Ard), (Zf,Rd,R1b, R3c,Are), (Zf,Rd,R1b,R3c,Arf), (Zf,Rd,R1b,R3c,Arg), (Zf,Rd,R1b,R3c,Arh), (Zf,Rd,R1b,R3c,Ari), (Zf,Rd,R1b,R3c,Arj), (Zf,Rd,R1b,R3c,Ark), (Zf,Rd,R1b,R3c,Arl), (Zf,Rd,R1b,R3c,Arm), (Zf,Rd,R1b,R3c,Arn), (Zf,Rd,R1b,R3c,Aro), (Zf,Rd,R1b,R3c,Arp), (Zf,Rd,R1b,R3d,Ara), (Zf,Rd,R1b,R3d,Arb), (Zf,Rd,R1b,R3d,Arc), (Zf,Rd,R1b,R3d,Ard), (Zf,Rd,R1b,R3d,Are), (Zf,Rd,R1b,R3d,Arf), (Zf,Rd,R1b,R3d,Arg), (Zf,Rd,R1b,R3d,Arh), (Zf,Rd,R1b,R3d,Ari), (Zf,Rd,R1b,R3d,Arj), (Zf,Rd,R1b,R3d,Ark), (Zf,Rd,R1b,R3d,Arl), (Zf,Rd,R1b,R3d,Arm), (Zf,Rd,R1b,R3d,Arn), (Zf,Rd,R1b,R3d,Aro), (Zf,Rd,R1b,R3d,Arp), (Zf,Rd,R1b,R3e,Ara), (Zf,Rd,R1b,R3e,Arb), (Zf,Rd,R1b,R3e,Arc), (Zf,Rd,R1b,R3e,Ard), (Zf,Rd,R1b,R3e,Are), (Zf,Rd,R1b,R3e,Arf), (Zf,Rd,R1b,R3e,Arg), (Zf,Rd,R1b,R3e,Arh), (Zf,Rd,R1b,R3e,Ari), (Zf,Rd,R1b,R3e,Arj), (Zf,Rd,R1b,R3e,Ark), (Zf,Rd,R1b,R3e,Arl), (Zf,Rd,R1b,R3e,Arm), (Zf,Rd,R1b,R3e,Arn), (Zf,Rd,R1b,R3e,Aro), (Zf,Rd,R1b,R3e,Arp), (Zf,Rd,R1b,R3f,Ara), (Zf,Rd,R1b,R3f,Arb), (Zf,Rd,R1b,R3f,Arc), (Zf,Rd,R1b,R3f,Ard), (Zf,Rd,R1b,R3f,Are), (Zf,Rd,R1b,R3f,Arf), (Zf,Rd,R1b,R3f,Arg), (Zf,Rd,R1b,R3f,Arh), (Zf,Rd,R1b,R3f,Ari), (Zf,Rd,R1b,R3f,Arj), (Zf,Rd,R1b,R3f,Ark), (Zf,Rd,R1b,R3f,Arl), (Zf,Rd,R1b,R3f,Arm), (Zf,Rd,R1b,R3f,Arn), (Zf,Rd,R1b,R3f,Aro), (Zf,Rd,R1b,R3f,Arp), (Zf,Rd,R1b,R3g,Ara), (Zf,Rd,R1b,R3g,Arb), (Zf,Rd,R1b,R3g,Arc), (Zf,Rd,R1b,R3g,Ard), (Zf,Rd,R1b,R3g,Are), (Zf,Rd,R1b,R3g,Arf), (Zf,Rd,R1b,R3g,Arg), (Zf,Rd,R1b,R3g,Arh), (Zf,Rd,R1b,R3g,Ari), (Zf,Rd,R1b,R3g,Arj), (Zf,Rd,R1b,R3g,Ark), (Zf,Rd,R1b,R3g,Arl), (Zf,Rd,R1b,R3g,Arm), (Zf,Rd,R1b,R3g,Arn), (Zf,Rd,R1b,R3g,Aro), (Zf,Rd,R1b,R3g,Arp), (Zf,Rd,R1b,R3h,Ara), (Zf,Rd,R1b,R3h,Arb), (Zf,Rd,R1b,R3h,Arc), (Zf,Rd,R1b,R3h,Ard), (Zf,Rd,R1b,R3h,Are), (Zf,Rd,R1b,R3h,Arf), (Zf,Rd,R1b,R3h,Arg), (Zf,Rd,R1b,R3h,Arh), (Zf,Rd,R1b,R3h,Ari), (Zf,Rd,R1b,R3h,Arj), (Zf,Rd,R1b,R3h,Ark), (Zf,Rd,R1b,R3h,Arl), (Zf,Rd,R1b,R3h,Arm), (Zf,Rd,R1b,R3h,Arn), (Zf,Rd,R1b,R3h,Aro), (Zf,Rd,R1b,R3h,Arp), (Zf,Rd,R1c,R3a,Ara), (Zf,Rd,R1c,R3a,Arb), (Zf,Rd,R1c,R3a,Arc), (Zf,Rd,R1c,R3a,Ard), (Zf,Rd,R1c,R3a,Are), (Zf,Rd,R1c,R3a,Arf), (Zf,Rd,R1c,R3a,Arg), (Zf,Rd,R1c,R3a,Arh), (Zf,Rd,R1c,R3a,Ari), (Zf,Rd,R1c,R3a,Arj), (Zf,Rd,R1c,R3a,Ark), (Zf,Rd,R1c,R3a,Arl), (Zf,Rd,R1c,R3a,Arm), (Zf,Rd,R1c,R3a,Arn), (Zf,Rd,R1c,R3a,Aro), (Zf,Rd,R1c,R3a,Arp), (Zf,Rd,R1c,R3b,Ara), (Zf,Rd,R1c,R3b,Arb), (Zf,Rd,R1c,R3b,Arc), (Zf,Rd,R1c,R3b,Ard), (Zf,Rd,R1c,R3b,Are), (Zf,Rd,R1c,R3b,Arf), (Zf,Rd,R1c,R3b,Arg), (Zf,Rd,R1c,R3b,Arh), (Zf,Rd,R1c,R3b,Ari), (Zf,Rd,R1c,R3b,Arj), (Zf,Rd,R1c,R3b,Ark), (Zf,Rd,R1c,R3b,Arl), (Zf,Rd,R1c,R3b,Arm), (Zf,Rd,R1c,R3b,Arn), (Zf,Rd,R1c,R3b,Aro), (Zf,Rd,R1c,R3b,Arp), (Zf,Rd,R1c,R3c,Ara), (Zf,Rd,R1c,R3c,Arb), (Zf,Rd,R1c,R3c,Arc), (Zf,Rd,R1c,R3c,Ard), (Zf,Rd,R1c,R3c,Are), (Zf,Rd,R1c,R3c,Arf), (Zf,Rd,R1c,R3c,Arg), (Zf,Rd,R1c,R3c,Arh), (Zf,Rd,R1c,R3c,Ari), (Zf,Rd,R1c,R3c,Arj), (Zf,Rd,R1c,R3c,Ark), (Zf,Rd,R1c,R3c,Arl), (Zf,Rd,R1c,R3c,Arm), (Zf,Rd,R1c,R3c,Arn), (Zf,Rd,R1c,R3c,Aro), (Zf,Rd,R1c,R3c,Arp), (Zf,Rd,R1c,R3d,Ara), (Zf,Rd,R1c,R3d,Arb), (Zf,Rd,R1c,R3d,Arc), (Zf,Rd,R1c,R3d,Ard), (Zf,Rd,R1c,R3d,Are), (Zf,Rd,R1c,R3d,Arf), (Zf,Rd,R1c,R3d,Arg), (Zf,Rd,R1c,R3d,Arh), (Zf,Rd,R1c,R3d,Ari), (Zf,Rd,R1c,R3d,Arj), (Zf,Rd,R1c,R3d,Ark), (Zf,Rd,R1c,R3d,Arl), (Zf,Rd,R1c,R3d,Arm), (Zf,Rd,R1c,R3d,Arn), (Zf,Rd,R1c,R3d,Aro), (Zf,Rd,R1c,R3d,Arp), (Zf,Rd,R1c,R3e,Ara), (Zf,Rd,R1c,R3e,Arb), (Zf,Rd,R1c,R3e,Arc), (Zf,Rd,R1c,R3e,Ard), (Zf,Rd,R1c,R3e,Are), (Zf,Rd,R1c,R3e,Arf), (Zf,Rd,R1c,R3e,Arg), (Zf,Rd,R1c,R3e,Arh), (Zf,Rd,R1c,R3e,Ari), (Zf,Rd,R1c,R3e,Arj), (Zf,Rd,R1c,R3e,Ark), (Zf,Rd,R1c,R3e,Arl), (Zf,Rd,R1c,R3e,Arm), (Zf,Rd,R1c,R3e,Arn), (Zf,Rd,R1c,R3e,Aro), (Zf,Rd,R1c,R3e,Arp), (Zf,Rd,R1c,R3f,Ara), (Zf,Rd,R1c,R3f,Arb), (Zf,Rd,R1c,R3f,Arc), (Zf,Rd,R1c,R3f,Ard), (Zf,Rd,R1c,R3f,Are), (Zf,Rd,R1c,R3f,Arf), (Zf,Rd,R1c,R3f,Arg), (Zf,Rd,R1c,R3f,Arh), (Zf,Rd,R1c,R3f,Ari), (Zf,Rd,R1c,R3f,Arj), (Zf,Rd,R1c,R3f,Ark), (Zf,Rd,R1c,R3f,Arl), (Zf,Rd,R1c,R3f,Arm), (Zf,Rd,R1c,R3f,Arn), (Zf,Rd,R1c,R3f,Aro), (Zf,Rd,R1c,R3f,Arp), (Zf,Rd,R1c,R3g,Ara), (Zf,Rd,R1c,R3g,Arb), (Zf,Rd,R1c,R3g,Arc), (Zf,Rd,R1c,R3g,Ard), (Zf,Rd,R1c,R3g,Are), (Zf,Rd,R1c,R3g,Arf), (Zf,Rd,R1c,R3g,Arg), (Zf,Rd,R1c,R3g,Arh), (Zf,Rd,R1c,R3g,Ari), (Zf,Rd,R1c,R3g,Arj), (Zf,Rd,R1c,R3g,Ark), (Zf,Rd,R1c,R3g,Arl), (Zf,Rd,R1c,R3g,Arm), (Zf,Rd,R1c,R3g,Arn), (Zf,Rd,R1c,R3g,Aro), (Zf,Rd,R1c,R3g,Arp), (Zf,Rd,R1c,R3h,Ara), (Zf,Rd,R1c,R3h,Arb), (Zf,Rd,R1c,R3h,Arc), (Zf,Rd,R1c,R3h,Ard), (Zf,Rd,R1c,R3h,Are), (Zf,Rd,R1c,R3h,Arf), (Zf,Rd,R1c,R3h,Arg), (Zf,Rd,R1c,R3h,Arh), (Zf,Rd,R1c,R3h,Ari), (Zf,Rd,R1c,R3h,Arj), (Zf,Rd,R1c,R3h,Ark), (Zf,Rd,R1c,R3h,Arl), (Zf,Rd,R1c,R3h,Arm), (Zf,Rd,R1c,R3h,Arn), (Zf,Rd,R1c,R3h,Aro), (Zf,Rd,R1c,R3h,Arp), (Zf,Rd,R1d,R3a,Ara), (Zf,Rd,R1d,R3a,Arb), (Zf,Rd,R1d,R3a,Arc), (Zf,Rd,R1d,R3a,Ard), (Zf,Rd,R1d,R3a,Are), (Zf,Rd,R1d,R3a,Arf), (Zf,Rd,R1d,R3a,Arg), (Zf,Rd,R1d,R3a,Arh), (Zf,Rd,R1d,R3a,Ari), (Zf,Rd,R1d,R3a,Arj), (Zf,Rd,R1d,R3a,Ark), (Zf,Rd,R1d,R3a,Arl), (Zf,Rd,R1d,R3a,Arm), (Zf,Rd,R1d,R3a,Arn), (Zf,Rd,R1d,R3a,Aro), (Zf,Rd,R1d,R3a,Arp), (Zf,Rd,R1d,R3b,Ara), (Zf,Rd,R1d,R3b,Arb), (Zf,Rd,R1d,R3b,Arc), (Zf,Rd,R1d,R3b,Ard), (Zf,Rd,R1d,R3b,Are), (Zf,Rd,R1d,R3b,Arf), (Zf,Rd,R1d,R3b,Arg), (Zf,Rd,R1d,R3b,Arh), (Zf,Rd,R1d,R3b,Ari), (Zf,Rd,R1d,R3b,Arj), (Zf,Rd,R1d,R3b,Ark), (Zf,Rd,R1d,R3b,Arl), (Zf,Rd,R1d,R3b,Arm), (Zf,Rd,R1d,R3b,Arn), (Zf,Rd,R1d,R3b,Aro), (Zf,Rd,R1d,R3b,Arp), (Zf,Rd,R1d,R3c,Ara), (Zf,Rd,R1d,R3c,Arb), (Zf,Rd,R1d,R3c,Arc), (Zf,Rd,R1d,R3c,Ard), (Zf,Rd,R1d,R3c,Are), (Zf,Rd,R1d,R3c,Arf), (Zf,Rd,R1d,R3c,Arg), (Zf,Rd,R1d,R3c,Arh), (Zf,Rd,R1d,R3c,Ari), (Zf,Rd,R1d,R3c,Arj), (Zf,Rd,R1d,R3c,Ark), (Zf,Rd,R1d,R3c,Arl), (Zf,Rd,R1d,R3c,Arm), (Zf,Rd,R1d,R3c,Arn), (Zf,Rd,R1d,R3c,Aro), (Zf,Rd,R1d,R3c,Arp), (Zf,Rd,R1d,R3d,Ara), (Zf,Rd,R1d,R3d,Arb), (Zf,Rd,R1d,R3d,Arc), (Zf,Rd,R1d,R3d,Ard), (Zf,Rd,R1d,R3d,Are), (Zf,Rd,R1d,R3d,Arf), (Zf,Rd,R1d,R3d,Arg), (Zf,Rd,R1d,R3d,Arh), (Zf,Rd,R1d,R3d,Ari), (Zf,Rd,R1d,R3d,Arj), (Zf,Rd,R1d,R3d,Ark), (Zf,Rd,R1d,R3d,Arl), (Zf,Rd,R1d,R3d,Arm), (Zf,Rd,R1d,R3d,Arn), (Zf,Rd,R1d,R3d,Aro), (Zf,Rd,R1d,R3d,Arp), (Zf,Rd,R1d,R3e,Ara), (Zf,Rd,R1d,R3e,Arb), (Zf,Rd,R1d,R3e,Arc), (Zf,Rd,R1d,R3e,Ard), (Zf,Rd,R1d,R3e,Are), (Zf,Rd,R1d,R3e,Arf), (Zf,Rd,R1d,R3e,Arg), (Zf,Rd,R1d,R3e,Arh), (Zf,Rd,R1d,R3e,Ari), (Zf,Rd,R1d,R3e,Arj), (Zf,Rd,R1d,R3e,Ark), (Zf,Rd,R1d,R3e,Arl), (Zf,Rd,R1d,R3e,Arm), (Zf,Rd,R1d,R3e,Arn), (Zf,Rd,R1d,R3e,Aro), (Zf,Rd,R1d,R3e,Arp), (Zf,Rd,R1d,R3f,Ara), (Zf,Rd,R1d,R3f,Arb), (Zf,Rd,R1d,R3f,Arc), (Zf,Rd,R1d,R3f,Ard), (Zf,Rd,R1d,R3f,Are), (Zf,Rd,R1d,R3f,Arf), (Zf,Rd,R1d,R3f,Arg), (Zf,Rd,R1d,R3f,Arh), (Zf,Rd,R1d,R3f,Ari), (Zf,Rd,R1d,R3f,Arj), (Zf,Rd,R1d,R3f,Ark), (Zf,Rd,R1d,R3f,Arl), (Zf,Rd,R1d,R3f,Arm), (Zf,Rd,R1d,R3f,Arn), (Zf,Rd,R1d,R3f,Aro), (Zf,Rd,R1d,R3f,Arp), (Zf,Rd,R1d,R3g,Ara), (Zf,Rd,R1d,R3g,Arb), (Zf,Rd,R1d,R3g,Arc), (Zf,Rd,R1d,R3g,Ard), (Zf,Rd,R1d,R3g,Are), (Zf,Rd,R1d,R3g,Arf), (Zf,Rd,R1d,R3g,Arg), (Zf,Rd,R1d,R3g,Arh), (Zf,Rd,R1d,R3g,Ari), (Zf,Rd,R1d,R3g,Arj), (Zf,Rd,R1d,R3g,Ark), (Zf,Rd,R1d,R3g,Arl), (Zf,Rd,R1d,R3g,Arm), (Zf,Rd,R1d,R3g,Arn), (Zf,Rd,R1d,R3g,Aro), (Zf,Rd,R1d,R3g,Arp), (Zf,Rd,R1d,R3h,Ara), (Zf,Rd,R1d,R3h,Arb), (Zf,Rd,R1d,R3h,Arc), (Zf,Rd,R1d,R3h,Ard), (Zf,Rd,R1d,R3h,Are), (Zf,Rd,R1d,R3h,Arf), (Zf,Rd,R1d,R3h,Arg), (Zf,Rd,R1d,R3h,Arh), (Zf,Rd,R1d,R3h,Ari), (Zf,Rd,R1d,R3h,Arj), (Zf,Rd,R1d,R3h,Ark), (Zf,Rd,R1d,R3h,Arl), (Zf,Rd,R1d,R3h,Arm), (Zf,Rd,R1d,R3h,Arn), (Zf,Rd,R1d,R3h,Aro), (Zf,Rd,R1d,R3h, Arp), (Zf,Re,R1a,R3a,Ara), (Zf,Re,R1a,R3a,Arb), (Zf,Re,R1a,R3a,Arc), (Zf,Re,R1a,R3a,Ard), (Zf,Re,R1a,R3a,Are), (Zf,Re,R1a,R3a,Arf), (Zf,Re,R1a,R3a,Arg), (Zf,Re,R1a,R3a,Arh), (Zf,Re,R1a,R3a,Ari), (Zf,Re,R1a,R3a,Arj), (Zf,Re,R1a,R3a,Ark), (Zf,Re,R1a,R3a,Arl), (Zf,Re,R1a,R3a,Arm), (Zf,Re,R1a,R3a,Arn), (Zf,Re,R1a,R3a,Aro), (Zf,Re,R1a,R3a,Arp), (Zf,Re,R1a,R3b,Ara), (Zf,Re,R1a,R3b,Arb), (Zf,Re,R1a,R3b,Arc), (Zf,Re,R1a,R3b,Ard), (Zf,Re,R1a,R3b,Are), (Zf,Re,R1a,R3b,Arf), (Zf,Re,R1a,R3b,Arg), (Zf,Re,R1a,R3b,Arh), (Zf,Re,R1a,R3b,Ari), (Zf,Re,R1a,R3b,Arj), (Zf,Re,R1a,R3b,Ark), (Zf,Re,R1a,R3b,Arl), (Zf,Re,R1a,R3b,Arm), (Zf,Re,R1a,R3b,Arn), (Zf,Re,R1a,R3b,Aro), (Zf,Re,R1a,R3b,Arp), (Zf,Re,R1a,R3c,Ara), (Zf,Re,R1a,R3c,Arb), (Zf,Re,R1a,R3c,Arc), (Zf,Re,R1a,R3c,Ard), (Zf,Re,R1a,R3c,Are), (Zf,Re,R1a,R3c,Arf), (Zf,Re,R1a,R3c,Arg), (Zf,Re,R1a,R3c,Arh), (Zf,Re,R1a,R3c,Ari), (Zf,Re,R1a,R3c,Arj), (Zf,Re,R1a,R3c,Ark), (Zf,Re,R1a,R3c,Arl), (Zf,Re,R1a,R3c,Arm), (Zf,Re,R1a,R3c,Arn), (Zf,Re,R1a,R3c,Aro), (Zf,Re,R1a,R3c,Arp), (Zf,Re,R1a,R3d,Ara), (Zf,Re,R1a,R3d,Arb), (Zf,Re,R1a,R3d,Arc), (Zf,Re,R1a,R3d,Ard), (Zf,Re,R1a,R3d,Are), (Zf,Re,R1a,R3d,Arf), (Zf,Re,R1a,R3d,Arg), (Zf,Re,R1a,R3d,Arh), (Zf,Re,R1a,R3d,Ari), (Zf,Re,R1a,R3d,Arj), (Zf,Re,R1a,R3d,Ark), (Zf,Re,R1a,R3d,Arl), (Zf,Re,R1a,R3d,Arm), (Zf,Re,R1a,R3d,Arn), (Zf,Re,R1a,R3d,Aro), (Zf,Re,R1a,R3d,Arp), (Zf,Re,R1a,R3e,Ara), (Zf,Re,R1a,R3e,Arb), (Zf,Re,R1a,R3e,Arc), (Zf,Re,R1a,R3e,Ard), (Zf,Re,R1a,R3e,Are), (Zf,Re,R1a,R3e,Arf), (Zf,Re,R1a,R3e,Arg), (Zf,Re,R1a,R3e,Arh), (Zf,Re,R1a,R3e,Ari), (Zf,Re,R1a,R3e,Arj), (Zf,Re,R1a,R3e,Ark), (Zf,Re,R1a,R3e,Arl), (Zf,Re,R1a,R3e,Arm), (Zf,Re,R1a,R3e,Arn), (Zf,Re,R1a,R3e,Aro), (Zf,Re,R1a,R3e,Arp), (Zf,Re,R1a,R3f,Ara), (Zf,Re,R1a,R3f,Arb), (Zf,Re,R1a,R3f,Arc), (Zf,Re,R1a,R3f,Ard), (Zf,Re,R1a,R3f,Are), (Zf,Re,R1a,R3f,Arf), (Zf,Re,R1a,R3f,Arg), (Zf,Re,R1a,R3f,Arh), (Zf,Re,R1a,R3f,Ari), (Zf,Re,R1a,R3f,Arj), (Zf,Re,R1a,R3f,Ark), (Zf,Re,R1a,R3f,Arl), (Zf,Re,R1a,R3f,Arm), (Zf,Re,R1a,R3f,Arn), (Zf,Re,R1a,R3f,Aro), (Zf,Re,R1a,R3f,Arp), (Zf,Re,R1a,R3g,Ara), (Zf,Re,R1a,R3g,Arb), (Zf,Re,R1a,R3g,Arc), (Zf,Re,R1a,R3g,Ard), (Zf,Re,R1a,R3g,Are), (Zf,Re,R1a,R3g,Arf), (Zf,Re,R1a,R3g,Arg), (Zf,Re,R1a,R3g,Arh), (Zf,Re,R1a,R3g,Ari), (Zf,Re,R1a,R3g,Arj), (Zf,Re,R1a,R3g,Ark), (Zf,Re,R1a,R3g,Arl), (Zf,Re,R1a,R3g,Arm), (Zf,Re,R1a,R3g,Arn), (Zf,Re,R1a,R3g,Aro), (Zf,Re,R1a,R3g,Arp), (Zf,Re,R1a,R3h,Ara), (Zf,Re,R1a,R3h,Arb), (Zf,Re,R1a,R3h,Arc), (Zf,Re,R1a,R3h,Ard), (Zf,Re,R1a,R3h,Are), (Zf,Re,R1a,R3h,Arf), (Zf,Re,R1a,R3h,Arg), (Zf,Re,R1a,R3h,Arh), (Zf,Re,R1a,R3h,Ari), (Zf,Re,R1a,R3h,Arj), (Zf,Re,R1a,R3h,Ark), (Zf,Re,R1a,R3h,Arl), (Zf,Re,R1a,R3h,Arm), (Zf,Re,R1a,R3h,Arn), (Zf,Re,R1a,R3h,Aro), (Zf,Re,R1a,R3h,Arp), (Zf,Re,R1b,R3a,Ara), (Zf,Re,R1b,R3a,Arb), (Zf,Re,R1b,R3a,Arc), (Zf,Re,R1b,R3a,Ard), (Zf,Re,R1b,R3a,Are), (Zf,Re,R1b,R3a,Arf), (Zf,Re,R1b,R3a,Arg), (Zf,Re,R1b,R3a,Arh), (Zf,Re,R1b,R3a,Ari), (Zf,Re,R1b,R3a,Arj), (Zf,Re,R1b,R3a,Ark), (Zf,Re,R1b,R3a,Arl), (Zf,Re,R1b,R3a,Arm), (Zf,Re,R1b,R3a,Arn), (Zf,Re,R1b,R3a,Aro), (Zf,Re,R1b,R3a,Arp), (Zf,Re,R1b,R3b,Ara), (Zf,Re,R1b,R3b,Arb), (Zf,Re,R1b,R3b,Arc), (Zf,Re,R1b,R3b,Ard), (Zf,Re,R1b,R3b,Are), (Zf,Re,R1b,R3b,Arf), (Zf,Re,R1b,R3b,Arg), (Zf,Re,R1b,R3b,Arh), (Zf,Re,R1b,R3b,Ari), (Zf,Re,R1b,R3b,Arj), (Zf,Re,R1b,R3b,Ark), (Zf,Re,R1b,R3b,Arl), (Zf,Re,R1b,R3b,Arm), (Zf,Re,R1b,R3b,Arn), (Zf,Re,R1b,R3b,Aro), (Zf,Re,R1b,R3b,Arp), (Zf,Re,R1b,R3c,Ara), (Zf,Re,R1b,R3c,Arb), (Zf,Re,R1b,R3c,Arc), (Zf,Re,R1b,R3c,Ard), (Zf,Re,R1b,R3c,Are), (Zf,Re,R1b,R3c,Arf), (Zf,Re,R1b,R3c,Arg), (Zf,Re,R1b,R3c,Arh), (Zf,Re,R1b,R3c,Ari), (Zf,Re,R1b,R3c,Arj), (Zf,Re,R1b,R3c,Ark), (Zf,Re,R1b,R3c,Arl), (Zf,Re,R1b,R3c,Arm), (Zf,Re,R1b,R3c,Arn), (Zf,Re,R1b,R3c,Aro), (Zf,Re,R1b,R3c,Arp), (Zf,Re,R1b,R3d,Ara), (Zf,Re,R1b,R3d,Arb), (Zf,Re,R1b,R3d,Arc), (Zf,Re,R1b,R3d,Ard), (Zf,Re,R1b,R3d,Are), (Zf,Re,R1b,R3d,Arf), (Zf,Re,R1b,R3d,Arg), (Zf,Re,R1b,R3d,Arh), (Zf,Re,R1b,R3d,Ari), (Zf,Re,R1b,R3d,Arj), (Zf,Re,R1b,R3d,Ark), (Zf,Re,R1b,R3d,Arl), (Zf,Re,R1b,R3d,Arm), (Zf,Re,R1b,R3d,Arn), (Zf,Re,R1b,R3d,Aro), (Zf,Re,R1b,R3d,Arp), (Zf,Re,R1b,R3e,Ara), (Zf,Re,R1b,R3e,Arb), (Zf,Re,R1b,R3e,Arc), (Zf,Re,R1b,R3e,Ard), (Zf,Re,R1b,R3e,Are), (Zf,Re,R1b,R3e,Arf), (Zf,Re,R1b,R3e,Arg), (Zf,Re,R1b,R3e,Arh), (Zf,Re,R1b,R3e,Ari), (Zf,Re,R1b,R3e,Arj), (Zf,Re,R1b,R3e,Ark), (Zf,Re,R1b,R3e,Arl), (Zf,Re,R1b,R3e,Arm), (Zf,Re,R1b,R3e,Arn), (Zf,Re,R1b,R3e,Aro), (Zf,Re,R1b,R3e,Arp), (Zf,Re,R1b,R3f,Ara), (Zf,Re,R1b,R3f,Arb), (Zf,Re,R1b,R3f,Arc), (Zf,Re,R1b,R3f,Ard), (Zf,Re,R1b,R3f,Are), (Zf,Re,R1b,R3f,Arf), (Zf,Re,R1b,R3f,Arg), (Zf,Re,R1b,R3f,Arh), (Zf,Re,R1b,R3f,Ari), (Zf,Re,R1b,R3f,Arj), (Zf,Re,R1b,R3f,Ark), (Zf,Re,R1b,R3f,Arl), (Zf,Re,R1b,R3f,Arm), (Zf,Re,R1b,R3f,Arn), (Zf,Re,R1b,R3f,Aro), (Zf,Re,R1b,R3f,Arp), (Zf,Re,R1b,R3g,Ara), (Zf,Re,R1b,R3g,Arb), (Zf,Re,R1b,R3g,Arc), (Zf,Re,R1b,R3g,Ard), (Zf,Re,R1b,R3g,Are), (Zf,Re,R1b,R3g,Arf), (Zf,Re,R1b,R3g,Arg), (Zf,Re,R1b,R3g,Arh), (Zf,Re,R1b,R3g,Ari), (Zf,Re,R1b,R3g,Arj), (Zf,Re,R1b,R3g,Ark), (Zf,Re,R1b,R3g,Arl), (Zf,Re,R1b,R3g,Arm), (Zf,Re,R1b,R3g,Arn), (Zf,Re,R1b,R3g,Aro), (Zf,Re,R1b,R3g,Arp), (Zf,Re,R1b,R3h,Ara), (Zf,Re,R1b,R3h,Arb), (Zf,Re,R1b,R3h,Arc), (Zf,Re,R1b,R3h,Ard), (Zf,Re,R1b,R3h,Are), (Zf,Re,R1b,R3h,Arf), (Zf,Re,R1b,R3h,Arg), (Zf,Re,R1b,R3h,Arh), (Zf,Re,R1b,R3h,Ari), (Zf,Re,R1b,R3h,Arj), (Zf,Re,R1b,R3h,Ark), (Zf,Re,R1b,R3h,Arl), (Zf,Re,R1b,R3h,Arm), (Zf,Re,R1b,R3h,Arn), (Zf,Re,R1b,R3h,Aro), (Zf,Re,R1b,R3h,Arp), (Zf,Re,R1c,R3a,Ara), (Zf,Re,R1c,R3a,Arb), (Zf,Re,R1c,R3a,Arc), (Zf,Re,R1c,R3a,Ard), (Zf,Re,R1c,R3a,Are), (Zf,Re,R1c,R3a,Arf), (Zf,Re,R1c,R3a,Arg), (Zf,Re,R1c,R3a,Arh), (Zf,Re,R1c,R3a,Ari), (Zf,Re,R1c,R3a,Arj), (Zf,Re,R1c,R3a,Ark), (Zf,Re,R1c,R3a,Arl), (Zf,Re,R1c,R3a,Arm), (Zf,Re,R1c,R3a,Arn), (Zf,Re,R1c,R3a,Aro), (Zf,Re,R1c,R3a,Arp), (Zf,Re,R1c,R3b,Ara), (Zf,Re,R1c,R3b,Arb), (Zf,Re,R1c,R3b,Arc), (Zf,Re,R1c,R3b,Ard), (Zf,Re,R1c,R3b,Are), (Zf,Re,R1c,R3b,Arf), (Zf,Re,R1c,R3b,Arg), (Zf,Re,R1c,R3b,Arh), (Zf,Re,R1c,R3b,Ari), (Zf,Re,R1c,R3b,Arj), (Zf,Re,R1c,R3b,Ark), (Zf,Re,R1c,R3b,Arl), (Zf,Re,R1c,R3b,Arm), (Zf,Re,R1c,R3b,Arn), (Zf,Re,R1c,R3b,Aro), (Zf,Re,R1c,R3b,Arp), (Zf,Re,R1c,R3c,Ara), (Zf,Re,R1c,R3c,Arb), (Zf,Re,R1c,R3c,Arc), (Zf,Re,R1c,R3c,Ard), (Zf,Re,R1c,R3c,Are), (Zf,Re,R1c,R3c,Arf), (Zf,Re,R1c,R3c,Arg), (Zf,Re,R1c,R3c,Arh), (Zf,Re,R1c,R3c,Ari), (Zf,Re,R1c,R3c,Arj), (Zf,Re,R1c,R3c,Ark), (Zf,Re,R1c,R3c,Arl), (Zf,Re,R1c,R3c,Arm), (Zf,Re,R1c,R3c,Arn), (Zf,Re,R1c,R3c,Aro), (Zf,Re,R1c,R3c,Arp), (Zf,Re,R1c,R3d,Ara), (Zf,Re,R1c,R3d,Arb), (Zf,Re,R1c,R3d,Arc), (Zf,Re,R1c,R3d,Ard), (Zf,Re,R1c,R3d,Are), (Zf,Re,R1c,R3d,Arf), (Zf,Re,R1c,R3d,Arg), (Zf,Re,R1c,R3d,Arh), (Zf,Re,R1c,R3d,Ari), (Zf,Re,R1c,R3d,Arj), (Zf,Re,R1c,R3d,Ark), (Zf,Re,R1c,R3d,Arl), (Zf,Re,R1c,R3d,Arm), (Zf,Re,R1c,R3d,Arn), (Zf,Re,R1c,R3d,Aro), (Zf,Re,R1c,R3d,Arp), (Zf,Re,R1c,R3e,Ara), (Zf,Re,R1c,R3e,Arb), (Zf,Re,R1c,R3e,Arc), (Zf,Re,R1c,R3e,Ard), (Zf,Re,R1c,R3e,Are), (Zf,Re,R1c,R3e,Arf), (Zf,Re,R1c,R3e,Arg), (Zf,Re,R1c,R3e,Arh), (Zf,Re,R1c,R3e,Ari), (Zf,Re,R1c,R3e,Arj), (Zf,Re,R1c,R3e,Ark), (Zf,Re,R1c,R3e,Arl), (Zf,Re,R1c,R3e,Arm), (Zf,Re,R1c,R3e,Arn), (Zf,Re,R1c,R3e,Aro), (Zf,Re,R1c,R3e,Arp), (Zf,Re,R1c,R3f,Ara), (Zf,Re,R1c,R3f,Arb), (Zf,Re,R1c,R3f,Arc), (Zf,Re,R1c,R3f,Ard), (Zf,Re,R1c,R3f,Are), (Zf,Re,R1c,R3f,Arf), (Zf,Re,R1c,R3f,Arg), (Zf,Re,R1c,R3f,Arh), (Zf,Re,R1c,R3f,Ari), (Zf,Re,R1c,R3f,Arj), (Zf,Re,R1c,R3f,Ark), (Zf,Re,R1c,R3f,Arl), (Zf,Re, R1c,R3f,Arm), (Zf,Re,R1c,R3f,Arn), (Zf,Re,R1c,R3f,Aro), (Zf,Re,R1c,R3f,Arp), (Zf,Re,R1c,R3g,Ara), (Zf,Re,R1c,R3g,Arb), (Zf,Re,R1c,R3g,Arc), (Zf,Re,R1c,R3g,Ard), (Zf,Re,R1c,R3g,Are), (Zf,Re,R1c,R3g,Arf), (Zf,Re,R1c,R3g,Arg), (Zf,Re,R1c,R3g,Arh), (Zf,Re,R1c,R3g,Ari), (Zf,Re,R1c,R3g,Arj), (Zf,Re,R1c,R3g,Ark), (Zf,Re,R1c,R3g,Arl), (Zf,Re,R1c,R3g,Arm), (Zf,Re,R1c,R3g,Arn), (Zf,Re,R1c,R3g,Aro), (Zf,Re,R1c,R3g,Arp), (Zf,Re,R1c,R3h,Ara), (Zf,Re,R1c,R3h,Arb), (Zf,Re,R1c,R3h,Arc), (Zf,Re,R1c,R3h,Ard), (Zf,Re,R1c,R3h,Are), (Zf,Re,R1c,R3h,Arf), (Zf,Re,R1c,R3h,Arg), (Zf,Re,R1c,R3h,Arh), (Zf,Re,R1c,R3h,Ari), (Zf,Re,R1c,R3h,Arj), (Zf,Re,R1c,R3h,Ark), (Zf,Re,R1c,R3h,Arl), (Zf,Re,R1c,R3h,Arm), (Zf,Re,R1c,R3h,Arn), (Zf,Re,R1c,R3h,Aro), (Zf,Re,R1c,R3h,Arp), (Zf,Re,R1d,R3a,Ara), (Zf,Re,R1d,R3a,Arb), (Zf,Re,R1d,R3a,Arc), (Zf,Re,R1d,R3a,Ard), (Zf,Re,R1d,R3a,Are), (Zf,Re,R1d,R3a,Arf), (Zf,Re,R1d,R3a,Arg), (Zf,Re,R1d,R3a,Arh), (Zf,Re,R1d,R3a,Ari), (Zf,Re,R1d,R3a,Arj), (Zf,Re,R1d,R3a,Ark), (Zf,Re,R1d,R3a,Arl), (Zf,Re,R1d,R3a,Arm), (Zf,Re,R1d,R3a,Arn), (Zf,Re,R1d,R3a,Aro), (Zf,Re,R1d,R3a,Arp), (Zf,Re,R1d,R3b,Ara), (Zf,Re,R1d,R3b,Arb), (Zf,Re,R1d,R3b,Arc), (Zf,Re,R1d,R3b,Ard), (Zf,Re,R1d,R3b,Are), (Zf,Re,R1d,R3b,Arf), (Zf,Re,R1d,R3b,Arg), (Zf,Re,R1d,R3b,Arh), (Zf,Re,R1d,R3b,Ari), (Zf,Re,R1d,R3b,Arj), (Zf,Re,R1d,R3b,Ark), (Zf,Re,R1d,R3b,Arl), (Zf,Re,R1d,R3b,Arm), (Zf,Re,R1d,R3b,Arn), (Zf,Re,R1d,R3b,Aro), (Zf,Re,R1d,R3b,Arp), (Zf,Re,R1d,R3c,Ara), (Zf,Re,R1d,R3c,Arb), (Zf,Re,R1d,R3c,Arc), (Zf,Re,R1d,R3c,Ard), (Zf,Re,R1d,R3c,Are), (Zf,Re,R1d,R3c,Arf), (Zf,Re,R1d,R3c,Arg), (Zf,Re,R1d,R3c,Arh), (Zf,Re,R1d,R3c,Ari), (Zf,Re,R1d,R3c,Arj), (Zf,Re,R1d,R3c,Ark), (Zf,Re,R1d,R3c,Arl), (Zf,Re,R1d,R3c,Arm), (Zf,Re,R1d,R3c,Arn), (Zf,Re,R1d,R3c,Aro), (Zf,Re,R1d,R3c,Arp), (Zf,Re,R1d,R3d,Ara), (Zf,Re,R1d,R3d,Arb), (Zf,Re,R1d,R3d,Arc), (Zf,Re,R1d,R3d,Ard), (Zf,Re,R1d,R3d,Are), (Zf,Re,R1d,R3d,Arf), (Zf,Re,R1d,R3d,Arg), (Zf,Re,R1d,R3d,Arh), (Zf,Re,R1d,R3d,Ari), (Zf,Re,R1d,R3d,Arj), (Zf,Re,R1d,R3d,Ark), (Zf,Re,R1d,R3d,Arl), (Zf,Re,R1d,R3d,Arm), (Zf,Re,R1d,R3d,Arn), (Zf,Re,R1d,R3d,Aro), (Zf,Re,R1d,R3d,Arp), (Zf,Re,R1d,R3e,Ara), (Zf,Re,R1d,R3e,Arb), (Zf,Re,R1d,R3e,Arc), (Zf,Re,R1d,R3e,Ard), (Zf,Re,R1d,R3e,Are), (Zf,Re,R1d,R3e,Arf), (Zf,Re,R1d,R3e,Arg), (Zf,Re,R1d,R3e,Arh), (Zf,Re,R1d,R3e,Ari), (Zf,Re,R1d,R3e,Arj), (Zf,Re,R1d,R3e,Ark), (Zf,Re,R1d,R3e,Arl), (Zf,Re,R1d,R3e,Arm), (Zf,Re,R1d,R3e,Arn), (Zf,Re,R1d,R3e,Aro), (Zf,Re,R1d,R3e,Arp), (Zf,Re,R1d,R3f,Ara), (Zf,Re,R1d,R3f,Arb), (Zf,Re,R1d,R3f,Arc), (Zf,Re,R1d,R3f,Ard), (Zf,Re,R1d,R3f,Are), (Zf,Re,R1d,R3f,Arf), (Zf,Re,R1d,R3f,Arg), (Zf,Re,R1d,R3f,Arh), (Zf,Re,R1d,R3f,Ari), (Zf,Re,R1d,R3f,Arj), (Zf,Re,R1d,R3f,Ark), (Zf,Re,R1d,R3f,Arl), (Zf,Re,R1d,R3f,Arm), (Zf,Re,R1d,R3f,Arn), (Zf,Re,R1d,R3f,Aro), (Zf,Re,R1d,R3f,Arp), (Zf,Re,R1d,R3g,Ara), (Zf,Re,R1d,R3g,Arb), (Zf,Re,R1d,R3g,Arc), (Zf,Re,R1d,R3g,Ard), (Zf,Re,R1d,R3g,Are), (Zf,Re,R1d,R3g,Arf), (Zf,Re,R1d,R3g,Arg), (Zf,Re,R1d,R3g,Arh), (Zf,Re,R1d,R3g,Ari), (Zf,Re,R1d,R3g,Arj), (Zf,Re,R1d,R3g,Ark), (Zf,Re,R1d,R3g,Arl), (Zf,Re,R1d,R3g,Arm), (Zf,Re,R1d,R3g,Arn), (Zf,Re,R1d,R3g,Aro), (Zf,Re,R1d,R3g,Arp), (Zf,Re,R1d,R3h,Ara), (Zf,Re,R1d,R3h,Arb), (Zf,Re,R1d,R3h,Arc), (Zf,Re,R1d,R3h,Ard), (Zf,Re,R1d,R3h,Are), (Zf,Re,R1d,R3h,Arf), (Zf,Re,R1d,R3h,Arg), (Zf,Re,R1d,R3h,Arh), (Zf,Re,R1d,R3h,Ari), (Zf,Re,R1d,R3h,Arj), (Zf,Re,R1d,R3h,Ark), (Zf,Re,R1d,R3h,Arl), (Zf,Re,R1d,R3h,Arm), (Zf,Re,R1d,R3h,Arn), (Zf,Re,R1d,R3h,Aro), (Zf,Re,R1d,R3h,Arp), (Zf,Rf,R1a,R3a,Ara), (Zf,Rf,R1a,R3a,Arb), (Zf,Rf,R1a,R3a,Arc), (Zf,Rf,R1a,R3a,Ard), (Zf,Rf,R1a,R3a,Are), (Zf,Rf,R1a,R3a,Arf), (Zf,Rf,R1a,R3a,Arg), (Zf,Rf,R1a,R3a,Arh), (Zf,Rf,R1a,R3a,Ari), (Zf,Rf,R1a,R3a,Arj), (Zf,Rf,R1a,R3a,Ark), (Zf,Rf,R1a,R3a,Arl), (Zf,Rf,R1a,R3a,Arm), (Zf,Rf,R1a,R3a,Arn), (Zf,Rf,R1a,R3a,Aro), (Zf,Rf,R1a,R3a,Arp), (Zf,Rf,R1a,R3b,Ara), (Zf,Rf,R1a,R3b,Arb), (Zf,Rf,R1a,R3b,Arc), (Zf,Rf,R1a,R3b,Ard), (Zf,Rf,R1a,R3b,Are), (Zf,Rf,R1a,R3b,Arf), (Zf,Rf,R1a,R3b,Arg), (Zf,Rf,R1a,R3b,Arh), (Zf,Rf,R1a,R3b,Ari), (Zf,Rf,R1a,R3b,Arj), (Zf,Rf,R1a,R3b,Ark), (Zf,Rf,R1a,R3b,Arl), (Zf,Rf,R1a,R3b,Arm), (Zf,Rf,R1a,R3b,Arn), (Zf,Rf,R1a,R3b,Aro), (Zf,Rf,R1a,R3b,Arp), (Zf,Rf,R1a,R3c,Ara), (Zf,Rf,R1a,R3c,Arb), (Zf,Rf,R1a,R3c,Arc), (Zf,Rf,R1a,R3c,Ard), (Zf,Rf,R1a,R3c,Are), (Zf,Rf,R1a,R3c,Arf), (Zf,Rf,R1a,R3c,Arg), (Zf,Rf,R1a,R3c,Arh), (Zf,Rf,R1a,R3c,Ari), (Zf,Rf,R1a,R3c,Arj), (Zf,Rf,R1a,R3c,Ark), (Zf,Rf,R1a,R3c,Arl), (Zf,Rf,R1a,R3c,Arm), (Zf,Rf,R1a,R3c,Arn), (Zf,Rf,R1a,R3c,Aro), (Zf,Rf,R1a,R3c,Arp), (Zf,Rf,R1a,R3d,Ara), (Zf,Rf,R1a,R3d,Arb), (Zf,Rf,R1a,R3d,Arc), (Zf,Rf,R1a,R3d,Ard), (Zf,Rf,R1a,R3d,Are), (Zf,Rf,R1a,R3d,Arf), (Zf,Rf,R1a,R3d,Arg), (Zf,Rf,R1a,R3d,Arh), (Zf,Rf,R1a,R3d,Ari), (Zf,Rf,R1a,R3d,Arj), (Zf,Rf,R1a,R3d,Ark), (Zf,Rf,R1a,R3d,Arl), (Zf,Rf,R1a,R3d,Arm), (Zf,Rf,R1a,R3d,Arn), (Zf,Rf,R1a,R3d,Aro), (Zf,Rf,R1a,R3d,Arp), (Zf,Rf,R1a,R3e,Ara), (Zf,Rf,R1a,R3e,Arb), (Zf,Rf,R1a,R3e,Arc), (Zf,Rf,R1a,R3e,Ard), (Zf,Rf,R1a,R3e,Are), (Zf,Rf,R1a,R3e,Arf), (Zf,Rf,R1a,R3e,Arg), (Zf,Rf,R1a,R3e,Arh), (Zf,Rf,R1a,R3e,Ari), (Zf,Rf,R1a,R3e,Arj), (Zf,Rf,R1a,R3e,Ark), (Zf,Rf,R1a,R3e,Arl), (Zf,Rf,R1a,R3e,Arm), (Zf,Rf,R1a,R3e,Arn), (Zf,Rf,R1a,R3e,Aro), (Zf,Rf,R1a,R3e,Arp), (Zf,Rf,R1a,R3f,Ara), (Zf,Rf,R1a,R3f,Arb), (Zf,Rf,R1a,R3f,Arc), (Zf,Rf,R1a,R3f,Ard), (Zf,Rf,R1a,R3f,Are), (Zf,Rf,R1a,R3f,Arf), (Zf,Rf,R1a,R3f,Arg), (Zf,Rf,R1a,R3f,Arh), (Zf,Rf,R1a,R3f,Ari), (Zf,Rf,R1a,R3f,Arj), (Zf,Rf,R1a,R3f,Ark), (Zf,Rf,R1a,R3f,Arl), (Zf,Rf,R1a,R3f,Arm), (Zf,Rf,R1a,R3f,Arn), (Zf,Rf,R1a,R3f,Aro), (Zf,Rf,R1a,R3f,Arp), (Zf,Rf,R1a,R3g,Ara), (Zf,Rf,R1a,R3g,Arb), (Zf,Rf,R1a,R3g,Arc), (Zf,Rf,R1a,R3g,Ard), (Zf,Rf,R1a,R3g,Are), (Zf,Rf,R1a,R3g,Arf), (Zf,Rf,R1a,R3g,Arg), (Zf,Rf,R1a,R3g,Arh), (Zf,Rf,R1a,R3g,Ari), (Zf,Rf,R1a,R3g,Arj), (Zf,Rf,R1a,R3g,Ark), (Zf,Rf,R1a,R3g,Arl), (Zf,Rf,R1a,R3g,Arm), (Zf,Rf,R1a,R3g,Arn), (Zf,Rf,R1a,R3g,Aro), (Zf,Rf,R1a,R3g,Arp), (Zf,Rf,R1a,R3h,Ara), (Zf,Rf,R1a,R3h,Arb), (Zf,Rf,R1a,R3h,Arc), (Zf,Rf,R1a,R3h,Ard), (Zf,Rf,R1a,R3h,Are), (Zf,Rf,R1a,R3h,Arf), (Zf,Rf,R1a,R3h,Arg), (Zf,Rf,R1a,R3h,Arh), (Zf,Rf,R1a,R3h,Ari), (Zf,Rf,R1a,R3h,Arj), (Zf,Rf,R1a,R3h,Ark), (Zf,Rf,R1a,R3h,Arl), (Zf,Rf,R1a,R3h,Arm), (Zf,Rf,R1a,R3h,Arn), (Zf,Rf,R1a,R3h,Aro), (Zf,Rf,R1a,R3h,Arp), (Zf,Rf,R1b,R3a,Ara), (Zf,Rf,R1b,R3a,Arb), (Zf,Rf,R1b,R3a,Arc), (Zf,Rf,R1b,R3a,Ard), (Zf,Rf,R1b,R3a,Are), (Zf,Rf,R1b,R3a,Arf), (Zf,Rf,R1b,R3a,Arg), (Zf,Rf,R1b,R3a,Arh), (Zf,Rf,R1b,R3a,Ari), (Zf,Rf,R1b,R3a,Arj), (Zf,Rf,R1b,R3a,Ark), (Zf,Rf,R1b,R3a,Arl), (Zf,Rf,R1b,R3a,Arm), (Zf,Rf,R1b,R3a,Arn), (Zf,Rf,R1b,R3a,Aro), (Zf,Rf,R1b,R3a,Arp), (Zf,Rf,R1b,R3b,Ara), (Zf,Rf,R1b,R3b,Arb), (Zf,Rf,R1b,R3b,Arc), (Zf,Rf,R1b,R3b,Ard), (Zf,Rf,R1b,R3b,Are), (Zf,Rf,R1b,R3b,Arf), (Zf,Rf,R1b,R3b,Arg), (Zf,Rf,R1b,R3b,Arh), (Zf,Rf,R1b,R3b,Ari), (Zf,Rf,R1b,R3b,Arj), (Zf,Rf,R1b,R3b,Ark), (Zf,Rf,R1b,R3b,Arl), (Zf,Rf,R1b,R3b,Arm), (Zf,Rf,R1b,R3b,Arn), (Zf,Rf,R1b,R3b,Aro), (Zf,Rf,R1b,R3b,Arp), (Zf,Rf,R1b,R3c,Ara), (Zf,Rf,R1b,R3c,Arb), (Zf,Rf,R1b,R3c,Arc), (Zf,Rf,R1b,R3c,Ard), (Zf,Rf,R1b,R3c,Are), (Zf,Rf,R1b,R3c,Arf), (Zf,Rf,R1b,R3c,Arg), (Zf,Rf,R1b,R3c,Arh), (Zf,Rf,R1b,R3c,Ari), (Zf,Rf,R1b,R3c,Arj), (Zf,Rf,R1b,R3c,Ark), (Zf,Rf,R1b,R3c,Arl), (Zf,Rf,R1b,R3c,Arm), (Zf,Rf,R1b,R3c,Arn), (Zf,Rf,R1b,R3c,Aro), (Zf,Rf,R1b,R3c,Arp), (Zf,Rf,R1b,R3d,Ara), (Zf,Rf,R1b,R3d,Arb), (Zf,Rf,R1b,R3d,Arc), (Zf,Rf,R1b,R3d,Ard), (Zf,Rf,R1b,R3d,Are), (Zf,Rf,R1b,R3d,Arf), (Zf,Rf,R1b,R3d,Arg), (Zf,Rf,R1b,R3d,Arh), (Zf,Rf,R1b,R3d,Ari), (Zf,Rf,R1b, R3d,Arj), (Zf,Rf,R1b,R3d,Ark), (Zf,Rf,R1b,R3d,Arl), (Zf,Rf,R1b,R3d,Arm), (Zf,Rf,R1b,R3d,Arn), (Zf,Rf,R1b,R3d,Aro), (Zf,Rf,R1b,R3d,Arp), (Zf,Rf,R1b,R3e,Ara), (Zf,Rf,R1b,R3e,Arb), (Zf,Rf,R1b,R3e,Arc), (Zf,Rf,R1b,R3e,Ard), (Zf,Rf,R1b,R3e,Are), (Zf,Rf,R1b,R3e,Arf), (Zf,Rf,R1b,R3e,Arg), (Zf,Rf,R1b,R3e,Arh), (Zf,Rf,R1b,R3e,Ari), (Zf,Rf,R1b,R3e,Arj), (Zf,Rf,R1b,R3e,Ark), (Zf,Rf,R1b,R3e,Arl), (Zf,Rf,R1b,R3e,Arm), (Zf,Rf,R1b,R3e,Arn), (Zf,Rf,R1b,R3e,Aro), (Zf,Rf,R1b,R3e,Arp), (Zf,Rf,R1b,R3f,Ara), (Zf,Rf,R1b,R3f,Arb), (Zf,Rf,R1b,R3f,Arc), (Zf,Rf,R1b,R3f,Ard), (Zf,Rf,R1b,R3f,Are), (Zf,Rf,R1b,R3f,Arf), (Zf,Rf,R1b,R3f,Arg), (Zf,Rf,R1b,R3f,Arh), (Zf,Rf,R1b,R3f,Ari), (Zf,Rf,R1b,R3f,Arj), (Zf,Rf,R1b,R3f,Ark), (Zf,Rf,R1b,R3f,Arl), (Zf,Rf,R1b,R3f,Arm), (Zf,Rf,R1b,R3f,Arn), (Zf,Rf,R1b,R3f,Aro), (Zf,Rf,R1b,R3f,Arp), (Zf,Rf,R1b,R3g,Ara), (Zf,Rf,R1b,R3g,Arb), (Zf,Rf,R1b,R3g,Arc), (Zf,Rf,R1b,R3g,Ard), (Zf,Rf,R1b,R3g,Are), (Zf,Rf,R1b,R3g,Arf), (Zf,Rf,R1b,R3g,Arg), (Zf,Rf,R1b,R3g,Arh), (Zf,Rf,R1b,R3g,Ari), (Zf,Rf,R1b,R3g,Arj), (Zf,Rf,R1b,R3g,Ark), (Zf,Rf,R1b,R3g,Arl), (Zf,Rf,R1b,R3g,Arm), (Zf,Rf,R1b,R3g,Arn), (Zf,Rf,R1b,R3g,Aro), (Zf,Rf,R1b,R3g,Arp), (Zf,Rf,R1b,R3h,Ara), (Zf,Rf,R1b,R3h,Arb), (Zf,Rf,R1b,R3h,Arc), (Zf,Rf,R1b,R3h,Ard), (Zf,Rf,R1b,R3h,Are), (Zf,Rf,R1b,R3h,Arf), (Zf,Rf,R1b,R3h,Arg), (Zf,Rf,R1b,R3h,Arh), (Zf,Rf,R1b,R3h,Ari), (Zf,Rf,R1b,R3h,Arj), (Zf,Rf,R1b,R3h,Ark), (Zf,Rf,R1b,R3h,Arl), (Zf,Rf,R1b,R3h,Arm), (Zf,Rf,R1b,R3h,Arn), (Zf,Rf,R1b,R3h,Aro), (Zf,Rf,R1b,R3h,Arp), (Zf,Rf,R1c,R3a,Ara), (Zf,Rf,R1c,R3a,Arb), (Zf,Rf,R1c,R3a,Arc), (Zf,Rf,R1c,R3a,Ard), (Zf,Rf,R1c,R3a,Are), (Zf,Rf,R1c,R3a,Arf), (Zf,Rf,R1c,R3a,Arg), (Zf,Rf,R1c,R3a,Arh), (Zf,Rf,R1c,R3a,Ari), (Zf,Rf,R1c,R3a,Arj), (Zf,Rf,R1c,R3a,Ark), (Zf,Rf,R1c,R3a,Arl), (Zf,Rf,R1c,R3a,Arm), (Zf,Rf,R1c,R3a,Arn), (Zf,Rf,R1c,R3a,Aro), (Zf,Rf,R1c,R3a,Arp), (Zf,Rf,R1c,R3b,Ara), (Zf,Rf,R1c,R3b,Arb), (Zf,Rf,R1c,R3b,Arc), (Zf,Rf,R1c,R3b,Ard), (Zf,Rf,R1c,R3b,Are), (Zf,Rf,R1c,R3b,Arf), (Zf,Rf,R1c,R3b,Arg), (Zf,Rf,R1c,R3b,Arh), (Zf,Rf,R1c,R3b,Ari), (Zf,Rf,R1c,R3b,Arj), (Zf,Rf,R1c,R3b,Ark), (Zf,Rf,R1c,R3b,Arl), (Zf,Rf,R1c,R3b,Arm), (Zf,Rf,R1c,R3b,Arn), (Zf,Rf,R1c,R3b,Aro), (Zf,Rf,R1c,R3b,Arp), (Zf,Rf,R1c,R3c,Ara), (Zf,Rf,R1c,R3c,Arb), (Zf,Rf,R1c,R3c,Arc), (Zf,Rf,R1c,R3c,Ard), (Zf,Rf,R1c,R3c,Are), (Zf,Rf,R1c,R3c,Arf), (Zf,Rf,R1c,R3c,Arg), (Zf,Rf,R1c,R3c,Arh), (Zf,Rf,R1c,R3c,Ari), (Zf,Rf,R1c,R3c,Arj), (Zf,Rf,R1c,R3c,Ark), (Zf,Rf,R1c,R3c,Arl), (Zf,Rf,R1c,R3c,Arm), (Zf,Rf,R1c,R3c,Arn), (Zf,Rf,R1c,R3c,Aro), (Zf,Rf,R1c,R3c,Arp), (Zf,Rf,R1c,R3d,Ara), (Zf,Rf,R1c,R3d,Arb), (Zf,Rf,R1c,R3d,Arc), (Zf,Rf,R1c,R3d,Ard), (Zf,Rf,R1c,R3d,Are), (Zf,Rf,R1c,R3d,Arf), (Zf,Rf,R1c,R3d,Arg), (Zf,Rf,R1c,R3d,Arh), (Zf,Rf,R1c,R3d,Ari), (Zf,Rf,R1c,R3d,Arj), (Zf,Rf,R1c,R3d,Ark), (Zf,Rf,R1c,R3d,Arl), (Zf,Rf,R1c,R3d,Arm), (Zf,Rf,R1c,R3d,Arn), (Zf,Rf,R1c,R3d,Aro), (Zf,Rf,R1c,R3d,Arp), (Zf,Rf,R1c,R3e,Ara), (Zf,Rf,R1c,R3e,Arb), (Zf,Rf,R1c,R3e,Arc), (Zf,Rf,R1c,R3e,Ard), (Zf,Rf,R1c,R3e,Are), (Zf,Rf,R1c,R3e,Arf), (Zf,Rf,R1c,R3e,Arg), (Zf,Rf,R1c,R3e,Arh), (Zf,Rf,R1c,R3e,Ari), (Zf,Rf,R1c,R3e,Arj), (Zf,Rf,R1c,R3e,Ark), (Zf,Rf,R1c,R3e,Arl), (Zf,Rf,R1c,R3e,Arm), (Zf,Rf,R1c,R3e,Arn), (Zf,Rf,R1c,R3e,Aro), (Zf,Rf,R1c,R3e,Arp), (Zf,Rf,R1c,R3f,Ara), (Zf,Rf,R1c,R3f,Arb), (Zf,Rf,R1c,R3f,Arc), (Zf,Rf,R1c,R3f,Ard), (Zf,Rf,R1c,R3f,Are), (Zf,Rf,R1c,R3f,Arf), (Zf,Rf,R1c,R3f,Arg), (Zf,Rf,R1c,R3f,Arh), (Zf,Rf,R1c,R3f,Ari), (Zf,Rf,R1c,R3f,Arj), (Zf,Rf,R1c,R3f,Ark), (Zf,Rf,R1c,R3f,Arl), (Zf,Rf,R1c,R3f,Arm), (Zf,Rf,R1c,R3f,Arn), (Zf,Rf,R1c,R3f,Aro), (Zf,Rf,R1c,R3f,Arp), (Zf,Rf,R1c,R3g,Ara), (Zf,Rf,R1c,R3g,Arb), (Zf,Rf,R1c,R3g,Arc), (Zf,Rf,R1c,R3g,Ard), (Zf,Rf,R1c,R3g,Are), (Zf,Rf,R1c,R3g,Arf), (Zf,Rf,R1c,R3g,Arg), (Zf,Rf,R1c,R3g,Arh), (Zf,Rf,R1c,R3g,Ari), (Zf,Rf,R1c,R3g,Arj), (Zf,Rf,R1c,R3g,Ark), (Zf,Rf,R1c,R3g,Arl), (Zf,Rf,R1c,R3g,Arm), (Zf,Rf,R1c,R3g,Arn), (Zf,Rf,R1c,R3g,Aro), (Zf,Rf,R1c,R3g,Arp), (Zf,Rf,R1c,R3h,Ara), (Zf,Rf,R1c,R3h,Arb), (Zf,Rf,R1c,R3h,Arc), (Zf,Rf,R1c,R3h,Ard), (Zf,Rf,R1c,R3h,Are), (Zf,Rf,R1c,R3h,Arf), (Zf,Rf,R1c,R3h,Arg), (Zf,Rf,R1c,R3h,Arh), (Zf,Rf,R1c,R3h,Ari), (Zf,Rf,R1c,R3h,Arj), (Zf,Rf,R1c,R3h,Ark), (Zf,Rf,R1c,R3h,Arl), (Zf,Rf,R1c,R3h,Arm), (Zf,Rf,R1c,R3h,Arn), (Zf,Rf,R1c,R3h,Aro), (Zf,Rf,R1c,R3h,Arp), (Zf,Rf,R1d,R3a,Ara), (Zf,Rf,R1d,R3a,Arb), (Zf,Rf,R1d,R3a,Arc), (Zf,Rf,R1d,R3a,Ard), (Zf,Rf,R1d,R3a,Are), (Zf,Rf,R1d,R3a,Arf), (Zf,Rf,R1d,R3a,Arg), (Zf,Rf,R1d,R3a,Arh), (Zf,Rf,R1d,R3a,Ari), (Zf,Rf,R1d,R3a,Arj), (Zf,Rf,R1d,R3a,Ark), (Zf,Rf,R1d,R3a,Arl), (Zf,Rf,R1d,R3a,Arm), (Zf,Rf,R1d,R3a,Arn), (Zf,Rf,R1d,R3a,Aro), (Zf,Rf,R1d,R3a,Arp), (Zf,Rf,R1d,R3b,Ara), (Zf,Rf,R1d,R3b,Arb), (Zf,Rf,R1d,R3b,Arc), (Zf,Rf,R1d,R3b,Ard), (Zf,Rf,R1d,R3b,Are), (Zf,Rf,R1d,R3b,Arf), (Zf,Rf,R1d,R3b,Arg), (Zf,Rf,R1d,R3b,Arh), (Zf,Rf,R1d,R3b,Ari), (Zf,Rf,R1d,R3b,Arj), (Zf,Rf,R1d,R3b,Ark), (Zf,Rf,R1d,R3b,Arl), (Zf,Rf,R1d,R3b,Arm), (Zf,Rf,R1d,R3b,Arn), (Zf,Rf,R1d,R3b,Aro), (Zf,Rf,R1d,R3b,Arp), (Zf,Rf,R1d,R3c,Ara), (Zf,Rf,R1d,R3c,Arb), (Zf,Rf,R1d,R3c,Arc), (Zf,Rf,R1d,R3c,Ard), (Zf,Rf,R1d,R3c,Are), (Zf,Rf,R1d,R3c,Arf), (Zf,Rf,R1d,R3c,Arg), (Zf,Rf,R1d,R3c,Arh), (Zf,Rf,R1d,R3c,Ari), (Zf,Rf,R1d,R3c,Arj), (Zf,Rf,R1d,R3c,Ark), (Zf,Rf,R1d,R3c,Arl), (Zf,Rf,R1d,R3c,Arm), (Zf,Rf,R1d,R3c,Arn), (Zf,Rf,R1d,R3c,Aro), (Zf,Rf,R1d,R3c,Arp), (Zf,Rf,R1d,R3d,Ara), (Zf,Rf,R1d,R3d,Arb), (Zf,Rf,R1d,R3d,Arc), (Zf,Rf,R1d,R3d,Ard), (Zf,Rf,R1d,R3d,Are), (Zf,Rf,R1d,R3d,Arf), (Zf,Rf,R1d,R3d,Arg), (Zf,Rf,R1d,R3d,Arh), (Zf,Rf,R1d,R3d,Ari), (Zf,Rf,R1d,R3d,Arj), (Zf,Rf,R1d,R3d,Ark), (Zf,Rf,R1d,R3d,Arl), (Zf,Rf,R1d,R3d,Arm), (Zf,Rf,R1d,R3d,Arn), (Zf,Rf,R1d,R3d,Aro), (Zf,Rf,R1d,R3d,Arp), (Zf,Rf,R1d,R3e,Ara), (Zf,Rf,R1d,R3e,Arb), (Zf,Rf,R1d,R3e,Arc), (Zf,Rf,R1d,R3e,Ard), (Zf,Rf,R1d,R3e,Are), (Zf,Rf,R1d,R3e,Arf), (Zf,Rf,R1d,R3e,Arg), (Zf,Rf,R1d,R3e,Arh), (Zf,Rf,R1d,R3e,Ari), (Zf,Rf,R1d,R3e,Arj), (Zf,Rf,R1d,R3e,Ark), (Zf,Rf,R1d,R3e,Arl), (Zf,Rf,R1d,R3e,Arm), (Zf,Rf,R1d,R3e,Arn), (Zf,Rf,R1d,R3e,Aro), (Zf,Rf,R1d,R3e,Arp), (Zf,Rf,R1d,R3f,Ara), (Zf,Rf,R1d,R3f,Arb), (Zf,Rf,R1d,R3f,Arc), (Zf,Rf,R1d,R3f,Ard), (Zf,Rf,R1d,R3f,Are), (Zf,Rf,R1d,R3f,Arf), (Zf,Rf,R1d,R3f,Arg), (Zf,Rf,R1d,R3f,Arh), (Zf,Rf,R1d,R3f,Ari), (Zf,Rf,R1d,R3f,Arj), (Zf,Rf,R1d,R3f,Ark), (Zf,Rf,R1d,R3f,Arl), (Zf,Rf,R1d,R3f,Arm), (Zf,Rf,R1d,R3f,Arn), (Zf,Rf,R1d,R3f,Aro), (Zf,Rf,R1d,R3f,Arp), (Zf,Rf,R1d,R3g,Ara), (Zf,Rf,R1d,R3g,Arb), (Zf,Rf,R1d,R3g,Arc), (Zf,Rf,R1d,R3g,Ard), (Zf,Rf,R1d,R3g,Are), (Zf,Rf,R1d,R3g,Arf), (Zf,Rf,R1d,R3g,Arg), (Zf,Rf,R1d,R3g,Arh), (Zf,Rf,R1d,R3g,Ari), (Zf,Rf,R1d,R3g,Arj), (Zf,Rf,R1d,R3g,Ark), (Zf,Rf,R1d,R3g,Arl), (Zf,Rf,R1d,R3g,Arm), (Zf,Rf,R1d,R3g,Arn), (Zf,Rf,R1d,R3g,Aro), (Zf,Rf,R1d,R3g,Arp), (Zf,Rf,R1d,R3h,Ara), (Zf,Rf,R1d,R3h,Arb), (Zf,Rf,R1d,R3h,Arc), (Zf,Rf,R1d,R3h,Ard), (Zf,Rf,R1d,R3h,Are), (Zf,Rf,R1d,R3h,Arf), (Zf,Rf,R1d,R3h,Arg), (Zf,Rf,R1d,R3h,Arh), (Zf,Rf,R1d,R3h,Ari), (Zf,Rf,R1d,R3h,Arj), (Zf,Rf,R1d,R3h,Ark), (Zf,Rf,R1d,R3h,Arl), (Zf,Rf,R1d,R3h,Arm), (Zf,Rf,R1d,R3h,Arn), (Zf,Rf,R1d,R3h,Aro), (Zf,Rf,R1d,R3h,Arp), (Zf,Rg,R1a,R3a,Ara), (Zf,Rg,R1a,R3a,Arb), (Zf,Rg,R1a,R3a,Arc), (Zf,Rg,R1a,R3a,Ard), (Zf,Rg,R1a,R3a,Are), (Zf,Rg,R1a,R3a,Arf), (Zf,Rg,R1a,R3a,Arg), (Zf,Rg,R1a,R3a,Arh), (Zf,Rg,R1a,R3a,Ari), (Zf,Rg,R1a,R3a,Arj), (Zf,Rg,R1a,R3a,Ark), (Zf,Rg,R1a,R3a,Arl), (Zf,Rg,R1a,R3a,Arm), (Zf,Rg,R1a,R3a,Arn), (Zf,Rg,R1a,R3a,Aro), (Zf,Rg,R1a,R3a,Arp), (Zf,Rg,R1a,R3b,Ara), (Zf,Rg,R1a,R3b,Arb), (Zf,Rg,R1a,R3b,Arc), (Zf,Rg,R1a,R3b,Ard), (Zf,Rg,R1a,R3b,Are), (Zf,Rg,R1a,R3b,Arf), (Zf,Rg,R1a,R3b,Arg), (Zf,Rg,R1a, R3b,Arh), (Zf,Rg,R1a,R3b,Ari), (Zf,Rg,R1a,R3b,Arj), (Zf,Rg,R1a,R3b,Ark), (Zf,Rg,R1a,R3b,Arl), (Zf,Rg,R1a,R3b,Arm), (Zf,Rg,R1a,R3b,Arn), (Zf,Rg,R1a,R3b,Aro), (Zf,Rg,R1a,R3b,Arp), (Zf,Rg,R1a,R3c,Ara), (Zf,Rg,R1a,R3c,Arb), (Zf,Rg,R1a,R3c,Arc), (Zf,Rg,R1a,R3c,Ard), (Zf,Rg,R1a,R3c,Are), (Zf,Rg,R1a,R3c,Arf), (Zf,Rg,R1a,R3c,Arg), (Zf,Rg,R1a,R3c,Arh), (Zf,Rg,R1a,R3c,Ari), (Zf,Rg,R1a,R3c,Arj), (Zf,Rg,R1a,R3c,Ark), (Zf,Rg,R1a,R3c,Arl), (Zf,Rg,R1a,R3c,Arm), (Zf,Rg,R1a,R3c,Arn), (Zf,Rg,R1a,R3c,Aro), (Zf,Rg,R1a,R3c,Arp), (Zf,Rg,R1a,R3d,Ara), (Zf,Rg,R1a,R3d,Arb), (Zf,Rg,R1a,R3d,Arc), (Zf,Rg,R1a,R3d,Ard), (Zf,Rg,R1a,R3d,Are), (Zf,Rg,R1a,R3d,Arf), (Zf,Rg,R1a,R3d,Arg), (Zf,Rg,R1a,R3d,Arh), (Zf,Rg,R1a,R3d,Ari), (Zf,Rg,R1a,R3d,Arj), (Zf,Rg,R1a,R3d,Ark), (Zf,Rg,R1a,R3d,Arl), (Zf,Rg,R1a,R3d,Arm), (Zf,Rg,R1a,R3d,Arn), (Zf,Rg,R1a,R3d,Aro), (Zf,Rg,R1a,R3d,Arp), (Zf,Rg,R1a,R3e,Ara), (Zf,Rg,R1a,R3e,Arb), (Zf,Rg,R1a,R3e,Arc), (Zf,Rg,R1a,R3e,Ard), (Zf,Rg,R1a,R3e,Are), (Zf,Rg,R1a,R3e,Arf), (Zf,Rg,R1a,R3e,Arg), (Zf,Rg,R1a,R3e,Arh), (Zf,Rg,R1a,R3e,Ari), (Zf,Rg,R1a,R3e,Arj), (Zf,Rg,R1a,R3e,Ark), (Zf,Rg,R1a,R3e,Arl), (Zf,Rg,R1a,R3e,Arm), (Zf,Rg,R1a,R3e,Arn), (Zf,Rg,R1a,R3e,Aro), (Zf,Rg,R1a,R3e,Arp), (Zf,Rg,R1a,R3f,Ara), (Zf,Rg,R1a,R3f,Arb), (Zf,Rg,R1a,R3f,Arc), (Zf,Rg,R1a,R3f,Ard), (Zf,Rg,R1a,R3f,Are), (Zf,Rg,R1a,R3f,Arf), (Zf,Rg,R1a,R3f,Arg), (Zf,Rg,R1a,R3f,Arh), (Zf,Rg,R1a,R3f,Ari), (Zf,Rg,R1a,R3f,Arj), (Zf,Rg,R1a,R3f,Ark), (Zf,Rg,R1a,R3f,Arl), (Zf,Rg,R1a,R3f,Arm), (Zf,Rg,R1a,R3f,Arn), (Zf,Rg,R1a,R3f,Aro), (Zf,Rg,R1a,R3f,Arp), (Zf,Rg,R1a,R3g,Ara), (Zf,Rg,R1a,R3g,Arb), (Zf,Rg,R1a,R3g,Arc), (Zf,Rg,R1a,R3g,Ard), (Zf,Rg,R1a,R3g,Are), (Zf,Rg,R1a,R3g,Arf), (Zf,Rg,R1a,R3g,Arg), (Zf,Rg,R1a,R3g,Arh), (Zf,Rg,R1a,R3g,Ari), (Zf,Rg,R1a,R3g,Arj), (Zf,Rg,R1a,R3g,Ark), (Zf,Rg,R1a,R3g,Arl), (Zf,Rg,R1a,R3g,Arm), (Zf,Rg,R1a,R3g,Arn), (Zf,Rg,R1a,R3g,Aro), (Zf,Rg,R1a,R3g,Arp), (Zf,Rg,R1a,R3h,Ara), (Zf,Rg,R1a,R3h,Arb), (Zf,Rg,R1a,R3h,Arc), (Zf,Rg,R1a,R3h,Ard), (Zf,Rg,R1a,R3h,Are), (Zf,Rg,R1a,R3h,Arf), (Zf,Rg,R1a,R3h,Arg), (Zf,Rg,R1a,R3h,Arh), (Zf,Rg,R1a,R3h,Ari), (Zf,Rg,R1a,R3h,Arj), (Zf,Rg,R1a,R3h,Ark), (Zf,Rg,R1a,R3h,Arl), (Zf,Rg,R1a,R3h,Arm), (Zf,Rg,R1a,R3h,Arn), (Zf,Rg,R1a,R3h,Aro), (Zf,Rg,R1a,R3h,Arp), (Zf,Rg,R1b,R3a,Ara), (Zf,Rg,R1b,R3a,Arb), (Zf,Rg,R1b,R3a,Arc), (Zf,Rg,R1b,R3a,Ard), (Zf,Rg,R1b,R3a,Are), (Zf,Rg,R1b,R3a,Arf), (Zf,Rg,R1b,R3a,Arg), (Zf,Rg,R1b,R3a,Arh), (Zf,Rg,R1b,R3a,Ari), (Zf,Rg,R1b,R3a,Arj), (Zf,Rg,R1b,R3a,Ark), (Zf,Rg,R1b,R3a,Arl), (Zf,Rg,R1b,R3a,Arm), (Zf,Rg,R1b,R3a,Arn), (Zf,Rg,R1b,R3a,Aro), (Zf,Rg,R1b,R3a,Arp), (Zf,Rg,R1b,R3b,Ara), (Zf,Rg,R1b,R3b,Arb), (Zf,Rg,R1b,R3b,Arc), (Zf,Rg,R1b,R3b,Ard), (Zf,Rg,R1b,R3b,Are), (Zf,Rg,R1b,R3b,Arf), (Zf,Rg,R1b,R3b,Arg), (Zf,Rg,R1b,R3b,Arh), (Zf,Rg,R1b,R3b,Ari), (Zf,Rg,R1b,R3b,Arj), (Zf,Rg,R1b,R3b,Ark), (Zf,Rg,R1b,R3b,Arl), (Zf,Rg,R1b,R3b,Arm), (Zf,Rg,R1b,R3b,Arn), (Zf,Rg,R1b,R3b,Aro), (Zf,Rg,R1b,R3b,Arp), (Zf,Rg,R1b,R3c,Ara), (Zf,Rg,R1b,R3c,Arb), (Zf,Rg,R1b,R3c,Arc), (Zf,Rg,R1b,R3c,Ard), (Zf,Rg,R1b,R3c,Are), (Zf,Rg,R1b,R3c,Arf), (Zf,Rg,R1b,R3c,Arg), (Zf,Rg,R1b,R3c,Arh), (Zf,Rg,R1b,R3c,Ari), (Zf,Rg,R1b,R3c,Arj), (Zf,Rg,R1b,R3c,Ark), (Zf,Rg,R1b,R3c,Arl), (Zf,Rg,R1b,R3c,Arm), (Zf,Rg,R1b,R3c,Arn), (Zf,Rg,R1b,R3c,Aro), (Zf,Rg,R1b,R3c,Arp), (Zf,Rg,R1b,R3d,Ara), (Zf,Rg,R1b,R3d,Arb), (Zf,Rg,R1b,R3d,Arc), (Zf,Rg,R1b,R3d,Ard), (Zf,Rg,R1b,R3d,Are), (Zf,Rg,R1b,R3d,Arf), (Zf,Rg,R1b,R3d,Arg), (Zf,Rg,R1b,R3d,Arh), (Zf,Rg,R1b,R3d,Ari), (Zf,Rg,R1b,R3d,Arj), (Zf,Rg,R1b,R3d,Ark), (Zf,Rg,R1b,R3d,Arl), (Zf,Rg,R1b,R3d,Arm), (Zf,Rg,R1b,R3d,Arn), (Zf,Rg,R1b,R3d,Aro), (Zf,Rg,R1b,R3d,Arp), (Zf,Rg,R1b,R3e,Ara), (Zf,Rg,R1b,R3e,Arb), (Zf,Rg,R1b,R3e,Arc), (Zf,Rg,R1b,R3e,Ard), (Zf,Rg,R1b,R3e,Are), (Zf,Rg,R1b,R3e,Arf), (Zf,Rg,R1b,R3e,Arg), (Zf,Rg,R1b,R3e,Arh), (Zf,Rg,R1b,R3e,Ari), (Zf,Rg,R1b,R3e,Arj), (Zf,Rg,R1b,R3e,Ark), (Zf,Rg,R1b,R3e,Arl), (Zf,Rg,R1b,R3e,Arm), (Zf,Rg,R1b,R3e,Arn), (Zf,Rg,R1b,R3e,Aro), (Zf,Rg,R1b,R3e,Arp), (Zf,Rg,R1b,R3f,Ara), (Zf,Rg,R1b,R3f,Arb), (Zf,Rg,R1b,R3f,Arc), (Zf,Rg,R1b,R3f,Ard), (Zf,Rg,R1b,R3f,Are), (Zf,Rg,R1b,R3f,Arf), (Zf,Rg,R1b,R3f,Arg), (Zf,Rg,R1b,R3f,Arh), (Zf,Rg,R1b,R3f,Ari), (Zf,Rg,R1b,R3f,Arj), (Zf,Rg,R1b,R3f,Ark), (Zf,Rg,R1b,R3f,Arl), (Zf,Rg,R1b,R3f,Arm), (Zf,Rg,R1b,R3f,Arn), (Zf,Rg,R1b,R3f,Aro), (Zf,Rg,R1b,R3f,Arp), (Zf,Rg,R1b,R3g,Ara), (Zf,Rg,R1b,R3g,Arb), (Zf,Rg,R1b,R3g,Arc), (Zf,Rg,R1b,R3g,Ard), (Zf,Rg,R1b,R3g,Are), (Zf,Rg,R1b,R3g,Arf), (Zf,Rg,R1b,R3g,Arg), (Zf,Rg,R1b,R3g,Arh), (Zf,Rg,R1b,R3g,Ari), (Zf,Rg,R1b,R3g,Arj), (Zf,Rg,R1b,R3g,Ark), (Zf,Rg,R1b,R3g,Arl), (Zf,Rg,R1b,R3g,Arm), (Zf,Rg,R1b,R3g,Arn), (Zf,Rg,R1b,R3g,Aro), (Zf,Rg,R1b,R3g,Arp), (Zf,Rg,R1b,R3h,Ara), (Zf,Rg,R1b,R3h,Arb), (Zf,Rg,R1b,R3h,Arc), (Zf,Rg,R1b,R3h,Ard), (Zf,Rg,R1b,R3h,Are), (Zf,Rg,R1b,R3h,Arf), (Zf,Rg,R1b,R3h,Arg), (Zf,Rg,R1b,R3h,Arh), (Zf,Rg,R1b,R3h,Ari), (Zf,Rg,R1b,R3h,Arj), (Zf,Rg,R1b,R3h,Ark), (Zf,Rg,R1b,R3h,Arl), (Zf,Rg,R1b,R3h,Arm), (Zf,Rg,R1b,R3h,Arn), (Zf,Rg,R1b,R3h,Aro), (Zf,Rg,R1b,R3h,Arp), (Zf,Rg,R1c,R3a,Ara), (Zf,Rg,R1c,R3a,Arb), (Zf,Rg,R1c,R3a,Arc), (Zf,Rg,R1c,R3a,Ard), (Zf,Rg,R1c,R3a,Are), (Zf,Rg,R1c,R3a,Arf), (Zf,Rg,R1c,R3a,Arg), (Zf,Rg,R1c,R3a,Arh), (Zf,Rg,R1c,R3a,Ari), (Zf,Rg,R1c,R3a,Arj), (Zf,Rg,R1c,R3a,Ark), (Zf,Rg,R1c,R3a,Arl), (Zf,Rg,R1c,R3a,Arm), (Zf,Rg,R1c,R3a,Arn), (Zf,Rg,R1c,R3a,Aro), (Zf,Rg,R1c,R3a,Arp), (Zf,Rg,R1c,R3b,Ara), (Zf,Rg,R1c,R3b,Arb), (Zf,Rg,R1c,R3b,Arc), (Zf,Rg,R1c,R3b,Ard), (Zf,Rg,R1c,R3b,Are), (Zf,Rg,R1c,R3b,Arf), (Zf,Rg,R1c,R3b,Arg), (Zf,Rg,R1c,R3b,Arh), (Zf,Rg,R1c,R3b,Ari), (Zf,Rg,R1c,R3b,Arj), (Zf,Rg,R1c,R3b,Ark), (Zf,Rg,R1c,R3b,Arl), (Zf,Rg,R1c,R3b,Arm), (Zf,Rg,R1c,R3b,Arn), (Zf,Rg,R1c,R3b,Aro), (Zf,Rg,R1c,R3b,Arp), (Zf,Rg,Rc,R3c,Ara), (Zf,Rg,R1c,R3c,Arb), (Zf,Rg,R1c,R3c,Arc), (Zf,Rg,R1c,R3c,Ard), (Zf,Rg,R1c,R3c,Are), (Zf,Rg,R1c,R3c,Arf), (Zf,Rg,R1c,R3c,Arg), (Zf,Rg,R1c,R3c,Arh), (Zf,Rg,R1c,R3c,Ari), (Zf,Rg,R1c,R3c,Arj), (Zf,Rg,R1c,R3c,Ark), (Zf,Rg,R1c,R3c,Arl), (Zf,Rg,R1c,R3c,Arm), (Zf,Rg,R1c,R3c,Arn), (Zf,Rg,R1c,R3c,Aro), (Zf,Rg,R1c,R3c,Arp), (Zf,Rg,R1c,R3d,Ara), (Zf,Rg,R1c,R3d,Arb), (Zf,Rg,R1c,R3d,Arc), (Zf,Rg,R1c,R3d,Ard), (Zf,Rg,R1c,R3d,Are), (Zf,Rg,R1c,R3d,Arf), (Zf,Rg,R1c,R3d,Arg), (Zf,Rg,R1c,R3d,Arh), (Zf,Rg,R1c,R3d,Ari), (Zf,Rg,R1c,R3d,Arj), (Zf,Rg,R1c,R3d,Ark), (Zf,Rg,R1c,R3d,Arl), (Zf,Rg,R1c,R3d,Arm), (Zf,Rg,R1c,R3d,Arn), (Zf,Rg,R1c,R3d,Aro), (Zf,Rg,R1c,R3d,Arp), (Zf,Rg,R1c,R3e,Ara), (Zf,Rg,R1c,R3e,Arb), (Zf,Rg,R1c,R3e,Arc), (Zf,Rg,R1c,R3e,Ard), (Zf,Rg,R1c,R3e,Are), (Zf,Rg,R1c,R3e,Arf), (Zf,Rg,R1c,R3e,Arg), (Zf,Rg,R1c,R3e,Arh), (Zf,Rg,R1c,R3e,Ari), (Zf,Rg,R1c,R3e,Arj), (Zf,Rg,R1c,R3e,Ark), (Zf,Rg,R1c,R3e,Arl), (Zf,Rg,R1c,R3e,Arm), (Zf,Rg,R1c,R3e,Arn), (Zf,Rg,R1c,R3e,Aro), (Zf,Rg,R1c,R3e,Arp), (Zf,Rg,R1c,R3f,Ara), (Zf,Rg,R1c,R3f,Arb), (Zf,Rg,R1c,R3f,Arc), (Zf,Rg,R1c,R3f,Ard), (Zf,Rg,R1c,R3f,Are), (Zf,Rg,R1c,R3f,Arf), (Zf,Rg,R1c,R3f,Arg), (Zf,Rg,R1c,R3f,Arh), (Zf,Rg,R1c,R3f,Ari), (Zf,Rg,R1c,R3f,Arj), (Zf,Rg,R1c,R3f,Ark), (Zf,Rg,R1c,R3f,Arl), (Zf,Rg,R1c,R3f,Arm), (Zf,Rg,R1c,R3f,Arn), (Zf,Rg,R1c,R3f,Aro), (Zf,Rg,R1c,R3f,Arp), (Zf,Rg,R1c,R3g,Ara), (Zf,Rg,R1c,R3g,Arb), (Zf,Rg,R1c,R3g,Arc), (Zf,Rg,R1c,R3g,Ard), (Zf,Rg,R1c,R3g,Are), (Zf,Rg,R1c,R3g,Arf), (Zf,Rg,R1c,R3g,Arg), (Zf,Rg,R1c,R3g,Arh), (Zf,Rg,R1c,R3g,Ari), (Zf,Rg,R1c,R3g,Arj), (Zf,Rg,R1c,R3g,Ark), (Zf,Rg,R1c,R3g,Arl), (Zf,Rg,R1c,R3g,Arm), (Zf,Rg,R1c,R3g,Arn), (Zf,Rg,R1c,R3g,Aro), (Zf,Rg,R1c,R3g,Arp), (Zf,Rg,R1c,R3h,Ara), (Zf,Rg,R1c,R3h,Arb), (Zf,Rg,R1c,R3h,Arc), (Zf,Rg,R1c,R3h,Ard), (Zf,Rg,R1c,R3h,Are), (Zf,Rg,R1c,R3h,Arf), (Zf,Rg,R1c,R3h,Arg), (Zf,Rg,R1c,R3h,Arh), (Zf,Rg,R1c,R3h,Ari), (Zf,Rg,R1c,R3h,Arj), (Zf,Rg,R1c,R3h,Ark), (Zf,Rg,R1c,R3h,Arl), (Zf,Rg,R1c,R3h,Arm), (Zf,Rg,R1c,R3h,Arn), (Zf,Rg,R1c,R3h,Aro), (Zf,Rg,R1c,R3h,Arp), (Zf,Rg,R1d,R3a,Ara), (Zf,Rg,R1d,R3a,Arb), (Zf,Rg,R1d,R3a,Arc), (Zf,Rg,R1d,R3a,Ard), (Zf,Rg,R1d,R3a,Are), (Zf,Rg,R1d,R3a,Arf), (Zf,Rg,R1d,R3a,Arg), (Zf,Rg,R1d,R3a,Arh), (Zf,Rg,R1d,R3a,Ari), (Zf,Rg,R1d,R3a,Arj), (Zf,Rg,R1d,R3a,Ark), (Zf,Rg,R1d,R3a,Arl), (Zf,Rg,R1d,R3a,Arm), (Zf,Rg,R1d,R3a,Arn), (Zf,Rg,R1d,R3a,Aro), (Zf,Rg,R1d,R3a,Arp), (Zf,Rg,R1d,R3b,Ara), (Zf,Rg,R1d,R3b,Arb), (Zf,Rg,R1d,R3b,Arc), (Zf,Rg,R1d,R3b,Ard), (Zf,Rg,R1d,R3b,Are), (Zf,Rg,R1d,R3b,Arf), (Zf,Rg,R1d,R3b,Arg), (Zf,Rg,R1d,R3b,Arh), (Zf,Rg,R1d,R3b,Ari), (Zf,Rg,R1d,R3b,Arj), (Zf,Rg,R1d,R3b,Ark), (Zf,Rg,R1d,R3b,Arl), (Zf,Rg,R1d,R3b,Arm), (Zf,Rg,R1d,R3b,Arn), (Zf,Rg,R1d,R3b,Aro), (Zf,Rg,R1d,R3b,Arp), (Zf,Rg,R1d,R3c,Ara), (Zf,Rg,R1d,R3c,Arb), (Zf,Rg,R1d,R3c,Arc), (Zf,Rg,R1d,R3c,Ard), (Zf,Rg,R1d,R3c,Are), (Zf,Rg,R1d,R3c,Arf), (Zf,Rg,R1d,R3c,Arg), (Zf,Rg,R1d,R3c,Arh), (Zf,Rg,R1d,R3c,Ari), (Zf,Rg,R1d,R3c,Arj), (Zf,Rg,R1d,R3c,Ark), (Zf,Rg,R1d,R3c,Arl), (Zf,Rg,R1d,R3c,Arm), (Zf,Rg,R1d,R3c,Arn), (Zf,Rg,R1d,R3c,Aro), (Zf,Rg,R1d,R3c,Arp), (Zf,Rg,R1d,R3d,Ara), (Zf,Rg,R1d,R3d,Arb), (Zf,Rg,R1d,R3d,Arc), (Zf,Rg,R1d,R3d,Ard), (Zf,Rg,R1d,R3d,Are), (Zf,Rg,R1d,R3d,Arf), (Zf,Rg,R1d,R3d,Arg), (Zf,Rg,R1d,R3d,Arh), (Zf,Rg,R1d,R3d,Ari), (Zf,Rg,R1d,R3d,Arj), (Zf,Rg,R1d,R3d,Ark), (Zf,Rg,R1d,R3d,Arl), (Zf,Rg,R1d,R3d,Arm), (Zf,Rg,R1d,R3d,Arn), (Zf,Rg,R1d,R3d,Aro), (Zf,Rg,R1d,R3d,Arp), (Zf,Rg,R1d,R3e,Ara), (Zf,Rg,R1d,R3e,Arb), (Zf,Rg,R1d,R3e,Arc), (Zf,Rg,R1d,R3e,Ard), (Zf,Rg,R1d,R3e,Are), (Zf,Rg,R1d,R3e,Arf), (Zf,Rg,R1d,R3e,Arg), (Zf,Rg,R1d,R3e,Arh), (Zf,Rg,R1d,R3e,Ari), (Zf,Rg,R1d,R3e,Arj), (Zf,Rg,R1d,R3e,Ark), (Zf,Rg,R1d,R3e,Arl), (Zf,Rg,R1d,R3e,Arm), (Zf,Rg,R1d,R3e,Arn), (Zf,Rg,R1d,R3e,Aro), (Zf,Rg,R1d,R3e,Arp), (Zf,Rg,R1d,R3f,Ara), (Zf,Rg,R1d,R3f,Arb), (Zf,Rg,R1d,R3f,Arc), (Zf,Rg,R1d,R3f,Ard), (Zf,Rg,R1d,R3f,Are), (Zf,Rg,R1d,R3f,Arf), (Zf,Rg,R1d,R3f,Arg), (Zf,Rg,R1d,R3f,Arh), (Zf,Rg,R1d,R3f,Ari), (Zf,Rg,R1d,R3f,Arj), (Zf,Rg,R1d,R3f,Ark), (Zf,Rg,R1d,R3f,Arl), (Zf,Rg,R1d,R3f,Arm), (Zf,Rg,R1d,R3f,Arn), (Zf,Rg,R1d,R3f,Aro), (Zf,Rg,R1d,R3f,Arp), (Zf,Rg,R1d,R3g,Ara), (Zf,Rg,R1d,R3g,Arb), (Zf,Rg,R1d,R3g,Arc), (Zf,Rg,R1d,R3g,Ard), (Zf,Rg,R1d,R3g,Are), (Zf,Rg,R1d,R3g,Arf), (Zf,Rg,R1d,R3g,Arg), (Zf,Rg,R1d,R3g,Arh), (Zf,Rg,R1d,R3g,Ari), (Zf,Rg,R1d,R3g,Arj), (Zf,Rg,R1d,R3g,Ark), (Zf,Rg,R1d,R3g,Arl), (Zf,Rg,R1d,R3g,Arm), (Zf,Rg,R1d,R3g,Arn), (Zf,Rg,R1d,R3g,Aro), (Zf,Rg,R1d,R3g,Arp), (Zf,Rg,R1d,R3h,Ara), (Zf,Rg,R1d,R3h,Arb), (Zf,Rg,R1d,R3h,Arc), (Zf,Rg,R1d,R3h,Ard), (Zf,Rg,R1d,R3h,Are), (Zf,Rg,R1d,R3h,Arf), (Zf,Rg,R1d,R3h,Arg), (Zf,Rg,R1d,R3h,Arh), (Zf,Rg,R1d,R3h,Ari), (Zf,Rg,R1d,R3h,Arj), (Zf,Rg,R1d,R3h,Ark), (Zf,Rg,R1d,R3h,Arl), (Zf,Rg,R1d,R3h,Arm), (Zf,Rg,R1d,R3h,Arn), (Zf,Rg,R1d,R3h,Aro), (Zf,Rg,R1d,R3h,Arp), (Zf,Rh,R1a,R3a,Ara), (Zf,Rh,R1a,R3a,Arb), (Zf,Rh,R1a,R3a,Arc), (Zf,Rh,R1a,R3a,Ard), (Zf,Rh,R1a,R3a,Are), (Zf,Rh,R1a,R3a,Arf), (Zf,Rh,R1a,R3a,Arg), (Zf,Rh,R1a,R3a,Arh), (Zf,Rh,R1a,R3a,Ari), (Zf,Rh,R1a,R3a,Arj), (Zf,Rh,R1a,R3a,Ark), (Zf,Rh,R1a,R3a,Arl), (Zf,Rh,R1a,R3a,Arm), (Zf,Rh,R1a,R3a,Arn), (Zf,Rh,R1a,R3a,Aro), (Zf,Rh,R1a,R3a,Arp), (Zf,Rh,R1a,R3b,Ara), (Zf,Rh,R1a,R3b,Arb), (Zf,Rh,R1a,R3b,Arc), (Zf,Rh,R1a,R3b,Ard), (Zf,Rh,R1a,R3b,Are), (Zf,Rh,R1a,R3b,Arf), (Zf,Rh,R1a,R3b,Arg), (Zf,Rh,R1a,R3b,Arh), (Zf,Rh,R1a,R3b,Ari), (Zf,Rh,R1a,R3b,Arj), (Zf,Rh,R1a,R3b,Ark), (Zf,Rh,R1a,R3b,Arl), (Zf,Rh,R1a,R3b,Arm), (Zf,Rh,R1a,R3b,Arn), (Zf,Rh,R1a,R3b,Aro), (Zf,Rh,R1a,R3b,Arp), (Zf,Rh,R1a,R3c,Ara), (Zf,Rh,R1a,R3c,Arb), (Zf,Rh,R1a,R3c,Arc), (Zf,Rh,R1a,R3c,Ard), (Zf,Rh,R1a,R3c,Are), (Zf,Rh,R1a,R3c,Arf), (Zf,Rh,R1a,R3c,Arg), (Zf,Rh,R1a,R3c,Arh), (Zf,Rh,R1a,R3c,Ari), (Zf,Rh,R1a,R3c,Arj), (Zf,Rh,R1a,R3c,Ark), (Zf,Rh,R1a,R3c,Arl), (Zf,Rh,R1a,R3c,Arm), (Zf,Rh,R1a,R3c,Arn), (Zf,Rh,R1a,R3c,Aro), (Zf,Rh,R1a,R3c,Arp), (Zf,Rh,R1a,R3d,Ara), (Zf,Rh,R1a,R3d,Arb), (Zf,Rh,R1a,R3d,Arc), (Zf,Rh,R1a,R3d,Ard), (Zf,Rh,R1a,R3d,Are), (Zf,Rh,R1a,R3d,Arf), (Zf,Rh,R1a,R3d,Arg), (Zf,Rh,R1a,R3d,Arh), (Zf,Rh,R1a,R3d,Ari), (Zf,Rh,R1a,R3d,Arj), (Zf,Rh,R1a,R3d,Ark), (Zf,Rh,R1a,R3d,Arl), (Zf,Rh,R1a,R3d,Arm), (Zf,Rh,R1a,R3d,Arn), (Zf,Rh,R1a,R3d,Aro), (Zf,Rh,R1a,R3d,Arp), (Zf,Rh,R1a,R3e,Ara), (Zf,Rh,R1a,R3e,Arb), (Zf,Rh,R1a,R3e,Arc), (Zf,Rh,R1a,R3e,Ard), (Zf,Rh,R1a,R3e,Are), (Zf,Rh,R1a,R3e,Arf), (Zf,Rh,R1a,R3e,Arg), (Zf,Rh,R1a,R3e,Arh), (Zf,Rh,R1a,R3e,Ari), (Zf,Rh,R1a,R3e,Arj), (Zf,Rh,R1a,R3e,Ark), (Zf,Rh,R1a,R3e,Arl), (Zf,Rh,R1a,R3e,Arm), (Zf,Rh,R1a,R3e,Arn), (Zf,Rh,R1a,R3e,Aro), (Zf,Rh,R1a,R3e,Arp), (Zf,Rh,R1a,R3f,Ara), (Zf,Rh,R1a,R3f,Arb), (Zf,Rh,R1a,R3f,Arc), (Zf,Rh,R1a,R3f,Ard), (Zf,Rh,R1a,R3f,Are), (Zf,Rh,R1a,R3f,Arf), (Zf,Rh,R1a,R3f,Arg), (Zf,Rh,R1a,R3f,Arh), (Zf,Rh,R1a,R3f,Ari), (Zf,Rh,R1a,R3f,Arj), (Zf,Rh,R1a,R3f,Ark), (Zf,Rh,R1a,R3f,Arl), (Zf,Rh,R1a,R3f,Arm), (Zf,Rh,R1a,R3f,Arn), (Zf,Rh,R1a,R3f,Aro), (Zf,Rh,R1a,R3f,Arp), (Zf,Rh,R1a,R3g,Ara), (Zf,Rh,R1a,R3g,Arb), (Zf,Rh,R1a,R3g,Arc), (Zf,Rh,R1a,R3g,Ard), (Zf,Rh,R1a,R3g,Are), (Zf,Rh,R1a,R3g,Arf), (Zf,Rh,R1a,R3g,Arg), (Zf,Rh,R1a,R3g,Arh), (Zf,Rh,R1a,R3g,Ari), (Zf,Rh,R1a,R3g,Arj), (Zf,Rh,R1a,R3g,Ark), (Zf,Rh,R1a,R3g,Arl), (Zf,Rh,R1a,R3g,Arm), (Zf,Rh,R1a,R3g,Arn), (Zf,Rh,R1a,R3g,Aro), (Zf,Rh,R1a,R3g,Arp), (Zf,Rh,R1a,R3h,Ara), (Zf,Rh,R1a,R3h,Arb), (Zf,Rh,R1a,R3h,Arc), (Zf,Rh,R1a,R3h,Ard), (Zf,Rh,R1a,R3h,Are), (Zf,Rh,R1a,R3h,Arf), (Zf,Rh,R1a,R3h,Arg), (Zf,Rh,R1a,R3h,Arh), (Zf,Rh,R1a,R3h,Ari), (Zf,Rh,R1a,R3h,Arj), (Zf,Rh,R1a,R3h,Ark), (Zf,Rh,R1a,R3h,Arl), (Zf,Rh,R1a,R3h,Arm), (Zf,Rh,R1a,R3h,Arn), (Zf,Rh,R1a,R3h,Aro), (Zf,Rh,R1a,R3h,Arp), (Zf,Rh,R1b,R3a,Ara), (Zf,Rh,R1b,R3a,Arb), (Zf,Rh,R1b,R3a,Arc), (Zf,Rh,R1b,R3a,Ard), (Zf,Rh,R1b,R3a,Are), (Zf,Rh,R1b,R3a,Arf), (Zf,Rh,R1b,R3a,Arg), (Zf,Rh,R1b,R3a,Arh), (Zf,Rh,R1b,R3a,Ari), (Zf,Rh,R1b,R3a,Arj), (Zf,Rh,R1b,R3a,Ark), (Zf,Rh,R1b,R3a,Arl), (Zf,Rh,R1b,R3a,Arm), (Zf,Rh,R1b,R3a,Arn), (Zf,Rh,R1b,R3a,Aro), (Zf,Rh,R1b,R3a,Arp), (Zf,Rh,R1b,R3b,Ara), (Zf,Rh,R1b,R3b,Arb), (Zf,Rh,R1b,R3b,Arc), (Zf,Rh,R1b,R3b,Ard), (Zf,Rh,R1b,R3b,Are), (Zf,Rh,R1b,R3b,Arf), (Zf,Rh,R1b,R3b,Arg), (Zf,Rh,R1b,R3b,Arh), (Zf,Rh,R1b,R3b,Ari), (Zf,Rh,R1b,R3b,Arj), (Zf,Rh,R1b,R3b,Ark), (Zf,Rh,R1b,R3b,Arl), (Zf,Rh,R1b,R3b,Arm), (Zf,Rh,R1b,R3b,Arn), (Zf,Rh,R1b,R3b,Aro), (Zf,Rh,R1b,R3b,Arp), (Zf,Rh,R1b,R3c,Ara), (Zf,Rh,R1b,R3c,Arb), (Zf,Rh,R1b,R3c,Arc), (Zf,Rh,R1b,R3c,Ard), (Zf,Rh,R1b,R3c,Are), (Zf,Rh,R1b,R3c,Arf), (Zf,Rh,R1b,R3c,Arg), (Zf,Rh,R1b,R3c,Arh), (Zf,Rh,R1b,R3c,Ari), (Zf,Rh,R1b,R3c,Arj), (Zf,Rh,R1b,R3c,Ark), (Zf,Rh,R1b,R3c,Arl), (Zf,Rh,R1b,R3c,Arm), (Zf,Rh,R1b,R3c,Arn), (Zf,Rh,R1b,R3c,Aro), (Zf,Rh,R1b,R3c,Arp), (Zf,Rh,R1b,R3d,Ara), (Zf,Rh,R1b,R3d,Arb), (Zf,Rh,R1b,R3d,Arc), (Zf,Rh,R1b,R3d,Ard), (Zf,Rh,R1b,R3d,Are), (Zf,Rh,R1b,R3d,Arf), (Zf,Rh,R1b,R3d,Arg), (Zf,Rh,R1b,R3d,Arh), (Zf,Rh,R1b,R3d,Ari), (Zf,Rh,R1b,R3d,Arj), (Zf,Rh,R1b,R3d,Ark), (Zf,Rh,R1b,R3d,Arl), (Zf,Rh,R1b,R3d,Arm), (Zf,Rh,R1b,R3d,Arn), (Zf,Rh,R1b,R3d,Aro), (Zf,Rh,R1b,R3d,Arp), (Zf,Rh,R1b,R3e,Ara), (Zf,Rh,R1b,R3e,Arb), (Zf,Rh,R1b,R3e,Arc), (Zf,Rh,R1b,R3e,Ard), (Zf,Rh,R1b,R3e,Are), (Zf,Rh,R1b,R3e,Arf), (Zf,Rh,R1b,R3e,Arg), (Zf,Rh,R1b,R3e,Arh), (Zf,Rh,R1b,R3e,Ari), (Zf,Rh,R1b,R3e,Arj), (Zf,Rh,R1b,R3e,Ark), (Zf,Rh,R1b,R3e,Arl), (Zf,Rh,R1b,R3e,Arm), (Zf,Rh,R1b,R3e,Arn), (Zf,Rh, R1b,R3e,Aro), (Zf,Rh,R1b,R3e,Arp), (Zf,Rh,R1b,R3f,Ara), (Zf,Rh,R1b,R3f,Arb), (Zf,Rh,R1b,R3f,Arc), (Zf,Rh,R1b,R3f,Ard), (Zf,Rh,R1b,R3f,Are), (Zf,Rh,R1b,R3f,Arf), (Zf,Rh,R1b,R3f,Arg), (Zf,Rh,R1b,R3f,Arh), (Zf,Rh,R1b,R3f,Ari), (Zf,Rh,R1b,R3f,Arj), (Zf,Rh,R1b,R3f,Ark), (Zf,Rh,R1b,R3f,Arl), (Zf,Rh,R1b,R3f,Arm), (Zf,Rh,R1b,R3f,Arn), (Zf,Rh,R1b,R3f,Aro), (Zf,Rh,R1b,R3f,Arp), (Zf,Rh,R1b,R3g,Ara), (Zf,Rh,R1b,R3g,Arb), (Zf,Rh,R1b,R3g,Arc), (Zf,Rh,R1b,R3g,Ard), (Zf,Rh,R1b,R3g,Are), (Zf,Rh,R1b,R3g,Arf), (Zf,Rh,R1b,R3g,Arg), (Zf,Rh,R1b,R3g,Arh), (Zf,Rh,R1b,R3g,Ari), (Zf,Rh,R1b,R3g,Arj), (Zf,Rh,R1b,R3g,Ark), (Zf,Rh,R1b,R3g,Arl), (Zf,Rh,R1b,R3g,Arm), (Zf,Rh,R1b,R3g,Arn), (Zf,Rh,R1b,R3g,Aro), (Zf,Rh,R1b,R3g,Arp), (Zf,Rh,R1b,R3h,Ara), (Zf,Rh,R1b,R3h,Arb), (Zf,Rh,R1b,R3h,Arc), (Zf,Rh,R1b,R3h,Ard), (Zf,Rh,R1b,R3h,Are), (Zf,Rh,R1b,R3h,Arf), (Zf,Rh,R1b,R3h,Arg), (Zf,Rh,R1b,R3h,Arh), (Zf,Rh,R1b,R3h,Ari), (Zf,Rh,R1b,R3h,Arj), (Zf,Rh,R1b,R3h,Ark), (Zf,Rh,R1b,R3h,Arl), (Zf,Rh,R1b,R3h,Arm), (Zf,Rh,R1b,R3h,Arn), (Zf,Rh,R1b,R3h,Aro), (Zf,Rh,R1b,R3h,Arp), (Zf,Rh,R1c,R3a,Ara), (Zf,Rh,R1c,R3a,Arb), (Zf,Rh,R1c,R3a,Arc), (Zf,Rh,R1c,R3a,Ard), (Zf,Rh,R1c,R3a,Are), (Zf,Rh,R1c,R3a,Arf), (Zf,Rh,R1c,R3a,Arg), (Zf,Rh,R1c,R3a,Arh), (Zf,Rh,R1c,R3a,Ari), (Zf,Rh,R1c,R3a,Arj), (Zf,Rh,R1c,R3a,Ark), (Zf,Rh,R1c,R3a,Arl), (Zf,Rh,R1c,R3a,Arm), (Zf,Rh,R1c,R3a,Arn), (Zf,Rh,R1c,R3a,Aro), (Zf,Rh,R1c,R3a,Arp), (Zf,Rh,R1c,R3b,Ara), (Zf,Rh,R1c,R3b,Arb), (Zf,Rh,R1c,R3b,Arc), (Zf,Rh,R1c,R3b,Ard), (Zf,Rh,R1c,R3b,Are), (Zf,Rh,R1c,R3b,Arf), (Zf,Rh,R1c,R3b,Arg), (Zf,Rh,R1c,R3b,Arh), (Zf,Rh,R1c,R3b,Ari), (Zf,Rh,R1c,R3b,Arj), (Zf,Rh,R1c,R3b,Ark), (Zf,Rh,R1c,R3b,Arl), (Zf,Rh,R1c,R3b,Arm), (Zf,Rh,R1c,R3b,Arn), (Zf,Rh,R1c,R3b,Aro), (Zf,Rh,R1c,R3b,Arp), (Zf,Rh,R1c,R3c,Ara), (Zf,Rh,R1c,R3c,Arb), (Zf,Rh,R1c,R3c,Arc), (Zf,Rh,R1c,R3c,Ard), (Zf,Rh,R1c,R3c,Are), (Zf,Rh,R1c,R3c,Arf), (Zf,Rh,R1c,R3c,Arg), (Zf,Rh,R1c,R3c,Arh), (Zf,Rh,R1c,R3c,Ari), (Zf,Rh,R1c,R3c,Arj), (Zf,Rh,R1c,R3c,Ark), (Zf,Rh,R1c,R3c,Arl), (Zf,Rh,R1c,R3c,Arm), (Zf,Rh,R1c,R3c,Arn), (Zf,Rh,R1c,R3c,Aro), (Zf,Rh,R1c,R3c,Arp), (Zf,Rh,R1c,R3d,Ara), (Zf,Rh,R1c,R3d,Arb), (Zf,Rh,R1c,R3d,Arc), (Zf,Rh,R1c,R3d,Ard), (Zf,Rh,R1c,R3d,Are), (Zf,Rh,R1c,R3d,Arf), (Zf,Rh,R1c,R3d,Arg), (Zf,Rh,R1c,R3d,Arh), (Zf,Rh,R1c,R3d,Ari), (Zf,Rh,R1c,R3d,Arj), (Zf,Rh,R1c,R3d,Ark), (Zf,Rh,R1c,R3d,Arl), (Zf,Rh,R1c,R3d,Arm), (Zf,Rh,R1c,R3d,Arn), (Zf,Rh,R1c,R3d,Aro), (Zf,Rh,R1c,R3d,Arp), (Zf,Rh,R1c,R3e,Ara), (Zf,Rh,R1c,R3e,Arb), (Zf,Rh,R1c,R3e,Arc), (Zf,Rh,R1c,R3e,Ard), (Zf,Rh,R1c,R3e,Are), (Zf,Rh,R1c,R3e,Arf), (Zf,Rh,R1c,R3e,Arg), (Zf,Rh,R1c,R3e,Arh), (Zf,Rh,R1c,R3e,Ari), (Zf,Rh,R1c,R3e,Arj), (Zf,Rh,R1c,R3e,Ark), (Zf,Rh,R1c,R3e,Arl), (Zf,Rh,R1c,R3e,Arm), (Zf,Rh,R1c,R3e,Arn), (Zf,Rh,R1c,R3e,Aro), (Zf,Rh,R1c,R3e,Arp), (Zf,Rh,R1c,R3f,Ara), (Zf,Rh,R1c,R3f,Arb), (Zf,Rh,R1c,R3f,Arc), (Zf,Rh,R1c,R3f,Ard), (Zf,Rh,R1c,R3f,Are), (Zf,Rh,R1c,R3f,Arf), (Zf,Rh,R1c,R3f,Arg), (Zf,Rh,R1c,R3f,Arh), (Zf,Rh,R1c,R3f,Ari), (Zf,Rh,R1c,R3f,Arj), (Zf,Rh,R1c,R3f,Ark), (Zf,Rh,R1c,R3f,Arl), (Zf,Rh,R1c,R3f,Arm), (Zf,Rh,R1c,R3f,Arn), (Zf,Rh,R1c,R3f,Aro), (Zf,Rh,R1c,R3f,Arp), (Zf,Rh,R1c,R3g,Ara), (Zf,Rh,R1c,R3g,Arb), (Zf,Rh,R1c,R3g,Arc), (Zf,Rh,R1c,R3g,Ard), (Zf,Rh,R1c,R3g,Are), (Zf,Rh,R1c,R3g,Arf), (Zf,Rh,R1c,R3g,Arg), (Zf,Rh,R1c,R3g,Arh), (Zf,Rh,R1c,R3g,Ari), (Zf,Rh,R1c,R3g,Arj), (Zf,Rh,R1c,R3g,Ark), (Zf,Rh,R1c,R3g,Arl), (Zf,Rh,R1c,R3g,Arm), (Zf,Rh,R1c,R3g,Arn), (Zf,Rh,R1c,R3g,Aro), (Zf,Rh,R1c,R3g,Arp), (Zf,Rh,R1c,R3h,Ara), (Zf,Rh,R1c,R3h,Arb), (Zf,Rh,R1c,R3h,Arc), (Zf,Rh,R1c,R3h,Ard), (Zf,Rh,R1c,R3h,Are), (Zf,Rh,R1c,R3h,Arf), (Zf,Rh,R1c,R3h,Arg), (Zf,Rh,R1c,R3h,Arh), (Zf,Rh,R1c,R3h,Ari), (Zf,Rh,R1c,R3h,Arj), (Zf,Rh,R1c,R3h,Ark), (Zf,Rh,R1c,R3h,Arl), (Zf,Rh,R1c,R3h,Arm), (Zf,Rh,R1c,R3h,Arn), (Zf,Rh,R1c,R3h,Aro), (Zf,Rh,R1c,R3h,Arp), (Zf,Rh,R1d,R3a,Ara), (Zf,Rh,R1d,R3a,Arb), (Zf,Rh,R1d,R3a,Arc), (Zf,Rh,R1d,R3a,Ard), (Zf,Rh,R1d,R3a,Are), (Zf,Rh,R1d,R3a,Arf), (Zf,Rh,R1d,R3a,Arg), (Zf,Rh,R1d,R3a,Arh), (Zf,Rh,R1d,R3a,Ari), (Zf,Rh,R1d,R3a,Arj), (Zf,Rh,R1d,R3a,Ark), (Zf,Rh,R1d,R3a,Arl), (Zf,Rh,R1d,R3a,Arm), (Zf,Rh,R1d,R3a,Arn), (Zf,Rh,R1d,R3a,Aro), (Zf,Rh,R1d,R3a,Arp), (Zf,Rh,R1d,R3b,Ara), (Zf,Rh,R1d,R3b,Arb), (Zf,Rh,R1d,R3b,Arc), (Zf,Rh,R1d,R3b,Ard), (Zf,Rh,R1d,R3b,Are), (Zf,Rh,R1d,R3b,Arf), (Zf,Rh,R1d,R3b,Arg), (Zf,Rh,R1d,R3b,Arh), (Zf,Rh,R1d,R3b,Ari), (Zf,Rh,R1d,R3b,Arj), (Zf,Rh,R1d,R3b,Ark), (Zf,Rh,R1d,R3b,Arl), (Zf,Rh,R1d,R3b,Arm), (Zf,Rh,R1d,R3b,Arn), (Zf,Rh,R1d,R3b,Aro), (Zf,Rh,R1d,R3b,Arp), (Zf,Rh,R1d,R3c,Ara), (Zf,Rh,R1d,R3c,Arb), (Zf,Rh,R1d,R3c,Arc), (Zf,Rh,R1d,R3c,Ard), (Zf,Rh,R1d,R3c,Are), (Zf,Rh,R1d,R3c,Arf), (Zf,Rh,R1d,R3c,Arg), (Zf,Rh,R1d,R3c,Arh), (Zf,Rh,R1d,R3c,Ari), (Zf,Rh,R1d,R3c,Arj), (Zf,Rh,R1d,R3c,Ark), (Zf,Rh,R1d,R3c,Arl), (Zf,Rh,R1d,R3c,Arm), (Zf,Rh,R1d,R3c,Arn), (Zf,Rh,R1d,R3c,Aro), (Zf,Rh,R1d,R3c,Arp), (Zf,Rh,R1d,R3d,Ara), (Zf,Rh,R1d,R3d,Arb), (Zf,Rh,R1d,R3d,Arc), (Zf,Rh,R1d,R3d,Ard), (Zf,Rh,R1d,R3d,Are), (Zf,Rh,R1d,R3d,Arf), (Zf,Rh,R1d,R3d,Arg), (Zf,Rh,R1d,R3d,Arh), (Zf,Rh,R1d,R3d,Ari), (Zf,Rh,R1d,R3d,Arj), (Zf,Rh,R1d,R3d,Ark), (Zf,Rh,R1d,R3d,Arl), (Zf,Rh,R1d,R3d,Arm), (Zf,Rh,R1d,R3d,Arn), (Zf,Rh,R1d,R3d,Aro), (Zf,Rh,R1d,R3d,Arp), (Zf,Rh,R1d,R3e,Ara), (Zf,Rh,R1d,R3e,Arb), (Zf,Rh,R1d,R3e,Arc), (Zf,Rh,R1d,R3e,Ard), (Zf,Rh,R1d,R3e,Are), (Zf,Rh,R1d,R3e,Arf), (Zf,Rh,R1d,R3e,Arg), (Zf,Rh,R1d,R3e,Arh), (Zf,Rh,R1d,R3e,Ari), (Zf,Rh,R1d,R3e,Arj), (Zf,Rh,R1d,R3e,Ark), (Zf,Rh,R1d,R3e,Arl), (Zf,Rh,R1d,R3e,Arm), (Zf,Rh,R1d,R3e,Arn), (Zf,Rh,R1d,R3e,Aro), (Zf,Rh,R1d,R3e,Arp), (Zf,Rh,R1d,R3f,Ara), (Zf,Rh,R1d,R3f,Arb), (Zf,Rh,R1d,R3f,Arc), (Zf,Rh,R1d,R3f,Ard), (Zf,Rh,R1d,R3f,Are), (Zf,Rh,R1d,R3f,Arf), (Zf,Rh,R1d,R3f,Arg), (Zf,Rh,R1d,R3f,Arh), (Zf,Rh,R1d,R3f,Ari), (Zf,Rh,R1d,R3f,Arj), (Zf,Rh,R1d,R3f,Ark), (Zf,Rh,R1d,R3f,Arl), (Zf,Rh,R1d,R3f,Arm), (Zf,Rh,R1d,R3f,Arn), (Zf,Rh,R1d,R3f,Aro), (Zf,Rh,R1d,R3f,Arp), (Zf,Rh,R1d,R3g,Ara), (Zf,Rh,R1d,R3g,Arb), (Zf,Rh,R1d,R3g,Arc), (Zf,Rh,R1d,R3g,Ard), (Zf,Rh,R1d,R3g,Are), (Zf,Rh,R1d,R3g,Arf), (Zf,Rh,R1d,R3g,Arg), (Zf,Rh,R1d,R3g,Arh), (Zf,Rh,R1d,R3g,Ari), (Zf,Rh,R1d,R3g,Arj), (Zf,Rh,R1d,R3g,Ark), (Zf,Rh,R1d,R3g,Arl), (Zf,Rh,R1d,R3g,Arm), (Zf,Rh,R1d,R3g,Arn), (Zf,Rh,R1d,R3g,Aro), (Zf,Rh,R1d,R3g,Arp), (Zf,Rh,R1d,R3h,Ara), (Zf,Rh,R1d,R3h,Arb), (Zf,Rh,R1d,R3h,Arc), (Zf,Rh,R1d,R3h,Ard), (Zf,Rh,R1d,R3h,Are), (Zf,Rh,R1d,R3h,Arf), (Zf,Rh,R1d,R3h,Arg), (Zf,Rh,R1d,R3h,Arh), (Zf,Rh,R1d,R3h,Ari), (Zf,Rh,R1d,R3h,Arj), (Zf,Rh,R1d,R3h,Ark), (Zf,Rh,R1d,R3h,Arl), (Zf,Rh,R1d,R3h,Arm), (Zf,Rh,R1d,R3h,Arn), (Zf,Rh,R1d,R3h,Aro), (Zf,Rh,R1d,R3h,Arp), (Zf,Ri,R1a,R3a,Ara), (Zf,Ri,R1a,R3a,Arb), (Zf,Ri,R1a,R3a,Arc), (Zf,Ri,R1a,R3a,Ard), (Zf,Ri,R1a,R3a,Are), (Zf,Ri,R1a,R3a,Arf), (Zf,Ri,R1a,R3a,Arg), (Zf,Ri,R1a,R3a,Arh), (Zf,Ri,R1a,R3a,Ari), (Zf,Ri,R1a,R3a,Arj), (Zf,Ri,R1a,R3a,Ark), (Zf,Ri,R1a,R3a,Arl), (Zf,Ri,R1a,R3a,Arm), (Zf,Ri,R1a,R3a,Arn), (Zf,Ri,R1a,R3a,Aro), (Zf,Ri,R1a,R3a,Arp), (Zf,Ri,R1a,R3b,Ara), (Zf,Ri,R1a,R3b,Arb), (Zf,Ri,R1a,R3b,Arc), (Zf,Ri,R1a,R3b,Ard), (Zf,Ri,R1a,R3b,Are), (Zf,Ri,R1a,R3b,Arf), (Zf,Ri,R1a,R3b,Arg), (Zf,Ri,R1a,R3b,Arh), (Zf,Ri,R1a,R3b,Ari), (Zf,Ri,R1a,R3b,Arj), (Zf,Ri,R1a,R3b,Ark), (Zf,Ri,R1a,R3b,Arl), (Zf,Ri,R1a,R3b,Arm), (Zf,Ri,R1a,R3b,Arn), (Zf,Ri,R1a,R3b,Aro), (Zf,Ri,R1a,R3b,Arp), (Zf,Ri,R1a,R3c,Ara), (Zf,Ri,R1a,R3c,Arb), (Zf,Ri,R1a,R3c,Arc), (Zf,Ri,R1a,R3c,Ard), (Zf,Ri,R1a,R3c,Are), (Zf,Ri,R1a,R3c,Arf), (Zf,Ri,R1a,R3c,Arg), (Zf,Ri,R1a,R3c,Arh), (Zf,Ri,R1a,R3c,Ari), (Zf,Ri,R1a,R3c,Arj), (Zf,Ri,R1a,R3c,Ark), (Zf,Ri,R1a,R3c,Arl), (Zf,Ri,R1a,R3c,Arm), (Zf,Ri,R1a,R3c,Arn), (Zf,Ri,R1a,R3c,Aro), (Zf,Ri,R1a,R3c,Arp), (Zf,Ri,R1a,R3d,Ara), (Zf,Ri,R1a,R3d,Arb), (Zf,Ri,R1a,R3d,Arc), (Zf,Ri,R1a,R3d,Ard), (Zf,Ri,R1a,R3d,Are), (Zf,Ri,R1a,R3d,Arf), (Zf,Ri,R1a,R3d,Arg), (Zf,Ri,R1a,R3d,Arh), (Zf,Ri,R1a,R3d,Ari), (Zf,Ri,R1a,R3d,Arj), (Zf,Ri,R1a,R3d,Ark), (Zf,Ri,R1a,R3d,Arl), (Zf,Ri,R1a,R3d,Arm), (Zf,Ri,R1a,R3d,Arn), (Zf,Ri,R1a,R3d,Aro), (Zf,Ri,R1a,R3d,Arp), (Zf,Ri,R1a,R3e,Ara), (Zf,Ri,R1a,R3e,Arb), (Zf,Ri,R1a,R3e,Arc), (Zf,Ri,R1a,R3e,Ard), (Zf,Ri,R1a,R3e,Are), (Zf,Ri,R1a,R3e,Arf), (Zf,Ri,R1a,R3e,Arg), (Zf,Ri,R1a,R3e,Arh), (Zf,Ri,R1a,R3e,Ari), (Zf,Ri,R1a,R3e,Arj), (Zf,Ri,R1a,R3e,Ark), (Zf,Ri,R1a,R3e,Arl), (Zf,Ri,R1a,R3e,Arm), (Zf,Ri,R1a,R3e,Arn), (Zf,Ri,R1a,R3e,Aro), (Zf,Ri,R1a,R3e,Arp), (Zf,Ri,R1a,R3f,Ara), (Zf,Ri,R1a,R3f,Arb), (Zf,Ri,R1a,R3f,Arc), (Zf,Ri,R1a,R3f,Ard), (Zf,Ri,R1a,R3f,Are), (Zf,Ri,R1a,R3f,Arf), (Zf,Ri,R1a,R3f,Arg), (Zf,Ri,R1a,R3f,Arh), (Zf,Ri,R1a,R3f,Ari), (Zf,Ri,R1a,R3f,Arj), (Zf,Ri,R1a,R3f,Ark), (Zf,Ri,R1a,R3f,Arl), (Zf,Ri,R1a,R3f,Arm), (Zf,Ri,R1a,R3f,Arn), (Zf,Ri,R1a,R3f,Aro), (Zf,Ri,R1a,R3f,Arp), (Zf,Ri,R1a,R3g,Ara), (Zf,Ri,R1a,R3g,Arb), (Zf,Ri,R1a,R3g,Arc), (Zf,Ri,R1a,R3g,Ard), (Zf,Ri,R1a,R3g,Are), (Zf,Ri,R1a,R3g,Arf), (Zf,Ri,R1a,R3g,Arg), (Zf,Ri,R1a,R3g,Arh), (Zf,Ri,R1a,R3g,Ari), (Zf,Ri,R1a,R3g,Arj), (Zf,Ri,R1a,R3g,Ark), (Zf,Ri,R1a,R3g,Arl), (Zf,Ri,R1a,R3g,Arm), (Zf,Ri,R1a,R3g,Arn), (Zf,Ri,R1a,R3g,Aro), (Zf,Ri,R1a,R3g,Arp), (Zf,Ri,R1a,R3h,Ara), (Zf,Ri,R1a,R3h,Arb), (Zf,Ri,R1a,R3h,Arc), (Zf,Ri,R1a,R3h,Ard), (Zf,Ri,R1a,R3h,Are), (Zf,Ri,R1a,R3h,Arp), (Zf,Ri,R1a,R3h,Arg), (Zf,Ri,R1a,R3h,Arh), (Zf,Ri,R1a,R3h,Ari), (Zf,Ri,R1a,R3h,Arj), (Zf,Ri,R1a,R3h,Ark), (Zf,Ri,R1a,R3h,Arl), (Zf,Ri,R1a,R3h,Arm), (Zf,Ri,R1a,R3h,Arn), (Zf,Ri,R1a,R3h,Aro), (Zf,Ri,R1a,R3h,Arp), (Zf,Ri,R1b,R3a,Ara), (Zf,Ri,R1b,R3a,Arb), (Zf,Ri,R1b,R3a,Arc), (Zf,Ri,R1b,R3a,Ard), (Zf,Ri,R1b,R3a,Are), (Zf,Ri,R1b,R3a,Arf), (Zf,Ri,R1b,R3a,Arg), (Zf,Ri,R1b,R3a,Arh), (Zf,Ri,R1b,R3a,Ari), (Zf,Ri,R1b,R3a,Arj), (Zf,Ri,R1b,R3a,Ark), (Zf,Ri,R1b,R3a,Arl), (Zf,Ri,R1b,R3a,Arm), (Zf,Ri,R1b,R3a,Arn), (Zf,Ri,R1b,R3a,Aro), (Zf,Ri,R1b,R3a,Arp), (Zf,Ri,R1b,R3b,Ara), (Zf,Ri,R1b,R3b,Arb), (Zf,Ri,R1b,R3b,Arc), (Zf,Ri,R1b,R3b,Ard), (Zf,Ri,R1b,R3b,Are), (Zf,Ri,R1b,R3b,Arf), (Zf,Ri,R1b,R3b,Arg), (Zf,Ri,R1b,R3b,Arh), (Zf,Ri,R1b,R3b,Ari), (Zf,Ri,R1b,R3b,Arj), (Zf,Ri,R1b,R3b,Ark), (Zf,Ri,R1b,R3b,Arl), (Zf,Ri,R1b,R3b,Arm), (Zf,Ri,R1b,R3b,Arn), (Zf,Ri,R1b,R3b,Aro), (Zf,Ri,R1b,R3b,Arp), (Zf,Ri,R1b,R3c,Ara), (Zf,Ri,R1b,R3c,Arb), (Zf,Ri,R1b,R3c,Arc), (Zf,Ri,R1b,R3c,Ard), (Zf,Ri,R1b,R3c,Are), (Zf,Ri,R1b,R3c,Arf), (Zf,Ri,R1b,R3c,Arg), (Zf,Ri,R1b,R3c,Arh), (Zf,Ri,R1b,R3c,Ari), (Zf,Ri,R1b,R3c,Arj), (Zf,Ri,R1b,R3c,Ark), (Zf,Ri,R1b,R3c,Arl), (Zf,Ri,R1b,R3c,Arm), (Zf,Ri,R1b,R3c,Arn), (Zf,Ri,R1b,R3c,Aro), (Zf,Ri,R1b,R3c,Arp), (Zf,Ri,R1b,R3d,Ara), (Zf,Ri,R1b,R3d,Arb), (Zf,Ri,R1b,R3d,Arc), (Zf,Ri,R1b,R3d,Ard), (Zf,Ri,R1b,R3d,Are), (Zf,Ri,R1b,R3d,Arf), (Zf,Ri,R1b,R3d,Arg), (Zf,Ri,R1b,R3d,Arh), (Zf,Ri,R1b,R3d,Ari), (Zf,Ri,R1b,R3d,Arj), (Zf,Ri,R1b,R3d,Ark), (Zf,Ri,R1b,R3d,Arl), (Zf,Ri,R1b,R3d,Arm), (Zf,Ri,R1b,R3d,Arn), (Zf,Ri,R1b,R3d,Aro), (Zf,Ri,R1b,R3d,Arp), (Zf,Ri,R1b,R3e,Ara), (Zf,Ri,R1b,R3e,Arb), (Zf,Ri,R1b,R3e,Arc), (Zf,Ri,R1b,R3e,Ard), (Zf,Ri,R1b,R3e,Are), (Zf,Ri,R1b,R3e,Arf), (Zf,Ri,R1b,R3e,Arg), (Zf,Ri,R1b,R3e,Arh), (Zf,Ri,R1b,R3e,Ari), (Zf,Ri,R1b,R3e,Arj), (Zf,Ri,R1b,R3e,Ark), (Zf,Ri,R1b,R3e,Arl), (Zf,Ri,R1b,R3e,Arm), (Zf,Ri,R1b,R3e,Arn), (Zf,Ri,R1b,R3e,Aro), (Zf,Ri,R1b,R3e,Arp), (Zf,Ri,R1b,R3f,Ara), (Zf,Ri,R1b,R3f,Arb), (Zf,Ri,R1b,R3f,Arc), (Zf,Ri,R1b,R3f,Ard), (Zf,Ri,R1b,R3f,Are), (Zf,Ri,R1b,R3f,Arf), (Zf,Ri,R1b,R3f,Arg), (Zf,Ri,R1b,R3f,Arh), (Zf,Ri,R1b,R3f,Ari), (Zf,Ri,R1b,R3f,Arj), (Zf,Ri,R1b,R3f,Ark), (Zf,Ri,R1b,R3f,Arl), (Zf,Ri,R1b,R3f,Arm), (Zf,Ri,R1b,R3f,Arn), (Zf,Ri,R1b,R3f,Aro), (Zf,Ri,R1b,R3f,Arp), (Zf,Ri,R1b,R3g,Ara), (Zf,Ri,R1b,R3g,Arb), (Zf,Ri,R1b,R3g,Arc), (Zf,Ri,R1b,R3g,Ard), (Zf,Ri,R1b,R3g,Are), (Zf,Ri,R1b,R3g,Arf), (Zf,Ri,R1b,R3g,Arg), (Zf,Ri,R1b,R3g,Arh), (Zf,Ri,R1b,R3g,Ari), (Zf,Ri,R1b,R3g,Arj), (Zf,Ri,R1b,R3g,Ark), (Zf,Ri,R1b,R3g,Arl), (Zf,Ri,R1b,R3g,Arm), (Zf,Ri,R1b,R3g,Arn), (Zf,Ri,R1b,R3g,Aro), (Zf,Ri,R1b,R3g,Arp), (Zf,Ri,R1b,R3h,Ara), (Zf,Ri,R1b,R3h,Arb), (Zf,Ri,R1b,R3h,Arc), (Zf,Ri,R1b,R3h,Ard), (Zf,Ri,R1b,R3h,Are), (Zf,Ri,R1b,R3h,Arf), (Zf,Ri,R1b,R3h,Arg), (Zf,Ri,R1b,R3h,Arh), (Zf,Ri,R1b,R3h,Ari), (Zf,Ri,R1b,R3h,Arj), (Zf,Ri,R1b,R3h,Ark), (Zf,Ri,R1b,R3h,Arl), (Zf,Ri,R1b,R3h,Arm), (Zf,Ri,R1b,R3h,Arn), (Zf,Ri,R1b,R3h,Aro), (Zf,Ri,R1b,R3h,Arp), (Zf,Ri,R1c,R3a,Ara), (Zf,Ri,R1c,R3a,Arb), (Zf,Ri,R1c,R3a,Arc), (Zf,Ri,R1c,R3a,Ard), (Zf,Ri,R1c,R3a,Are), (Zf,Ri,R1c,R3a,Arf), (Zf,Ri,R1c,R3a,Arg), (Zf,Ri,R1c,R3a,Arh), (Zf,Ri,R1c,R3a,Ari), (Zf,Ri,R1c,R3a,Arj), (Zf,Ri,R1c,R3a,Ark), (Zf,Ri,R1c,R3a,Arl), (Zf,Ri,R1c,R3a,Arm), (Zf,Ri,R1c,R3a,Arn), (Zf,Ri,R1c,R3a,Aro), (Zf,Ri,R1c,R3a,Arp), (Zf,Ri,R1c,R3b,Ara), (Zf,Ri,R1c,R3b,Arb), (Zf,Ri,R1c,R3b,Arc), (Zf,Ri,R1c,R3b,Ard), (Zf,Ri,R1c,R3b,Are), (Zf,Ri,R1c,R3b,Arf), (Zf,Ri,R1c,R3b,Arg), (Zf,Ri,R1c,R3b,Arh), (Zf,Ri,R1c,R3b,Ari), (Zf,Ri,R1c,R3b,Arj), (Zf,Ri,R1c,R3b,Ark), (Zf,Ri,R1c,R3b,Arl), (Zf,Ri,R1c,R3b,Arm), (Zf,Ri,R1c,R3b,Arn), (Zf,Ri,R1c,R3b,Aro), (Zf,Ri,R1c,R3b,Arp), (Zf,Ri,R1c,R3c,Ara), (Zf,Ri,R1c,R3c,Arb), (Zf,Ri,R1c,R3c,Arc), (Zf,Ri,R1c,R3c,Ard), (Zf,Ri,R1c,R3c,Are), (Zf,Ri,R1c,R3c,Arf), (Zf,Ri,R1c,R3c,Arg), (Zf,Ri,R1c,R3c,Arh), (Zf,Ri,R1c,R3c,Ari), (Zf,Ri,R1c,R3c,Arj), (Zf,Ri,R1c,R3c,Ark), (Zf,Ri,R1c,R3c,Arl), (Zf,Ri,R1c,R3c,Arm), (Zf,Ri,R1c,R3c,Arn), (Zf,Ri,R1c,R3c,Aro), (Zf,Ri,R1c,R3c,Arp), (Zf,Ri,R1c,R3d,Ara), (Zf,Ri,R1c,R3d,Arb), (Zf,Ri,R1c,R3d,Arc), (Zf,Ri,R1c,R3d,Ard), (Zf,Ri,R1c,R3d,Are), (Zf,Ri,R1c,R3d,Arf), (Zf,Ri,R1c,R3d,Arg), (Zf,Ri,R1c,R3d,Arh), (Zf,Ri,R1c,R3d,Ari), (Zf,Ri,R1c,R3d,Arj), (Zf,Ri,R1c,R3d,Ark), (Zf,Ri,R1c,R3d,Arl), (Zf,Ri,R1c,R3d,Arm), (Zf,Ri,R1c,R3d,Arn), (Zf,Ri,R1c,R3d,Aro), (Zf,Ri,R1c,R3d,Arp), (Zf,Ri,R1c,R3e,Ara), (Zf,Ri,R1c,R3e,Arb), (Zf,Ri,R1c,R3e,Arc), (Zf,Ri,R1c,R3e,Ard), (Zf,Ri,R1c,R3e,Are), (Zf,Ri,R1c,R3e,Arf), (Zf,Ri,R1c,R3e,Arg), (Zf,Ri,R1c,R3e,Arh), (Zf,Ri,R1c,R3e,Ari), (Zf,Ri,R1c,R3e,Arj), (Zf,Ri,R1c,R3e,Ark), (Zf,Ri,R1c,R3e,Arl), (Zf,Ri,R1c,R3e,Arm), (Zf,Ri,R1c,R3e,Arn), (Zf,Ri,R1c,R3e,Aro), (Zf,Ri,R1c,R3e,Arp), (Zf,Ri,R1c,R3f,Ara), (Zf,Ri,R1c,R3f,Arb), (Zf,Ri,R1c,R3f,Arc), (Zf,Ri,R1c,R3f,Ard), (Zf,Ri,R1c,R3f,Are), (Zf,Ri,R1c,R3f,Arf), (Zf,Ri,R1c,R3f,Arg), (Zf,Ri,R1c,R3f,Arh), (Zf,Ri,R1c,R3f,Ari), (Zf,Ri,R1c,R3f,Arj), (Zf,Ri,R1c,R3f,Ark), (Zf,Ri,R1c,R3f,Arl), (Zf,Ri,R1c,R3f,Arm), (Zf,Ri,R1c,R3f,Arn), (Zf,Ri,R1c,R3f,Aro), (Zf,Ri,R1c,R3f,Arp), (Zf,Ri,R1c,R3g,Ara), (Zf,Ri,R1c,R3g,Arb), (Zf,Ri,R1c,R3g,Arc), (Zf,Ri,R1c,R3g,Ard), (Zf,Ri,R1c,R3g,Are), (Zf,Ri,R1c,R3g,Arf), (Zf,Ri,R1c,R3g,Arg), (Zf,Ri,R1c,R3g,Arh), (Zf,Ri,R1c,R3g,Ari), (Zf,Ri,R1c,R3g,Arj), (Zf,Ri,R1c,R3g,Ark), (Zf,Ri,R1c,R3g,Arl), (Zf,Ri,R1c,R3g,Arm), (Zf,Ri,R1c,R3g,Arn), (Zf,Ri,R1c,R3g,Aro), (Zf,Ri,R1c,R3g,Arp), (Zf,Ri,R1c,R3h,Ara), (Zf,Ri,R1c,R3h,Arb), (Zf,Ri,R1c,R3h,Arc), (Zf,Ri,R1c,R3h,Ard), (Zf,Ri,R1c,R3h,Are), (Zf,Ri,R1c,R3h,Arf), (Zf,Ri,R1c,R3h,Arg), (Zf,Ri,R1c,R3h,Arh), (Zf,Ri,R1c,R3h,Ari), (Zf,Ri,R1c,R3h,Arj), (Zf,Ri,R1c,R3h,Ark), (Zf,Ri,R1c,R3h,Arl), (Zf,Ri,R1c,R3h,Arm), (Zf,Ri,R1c,R3h,Arn), (Zf,Ri,R1c,R3h,Aro), (Zf,Ri,R1c,R3h,Arp), (Zf,Ri,R1d,R3a,Ara), (Zf,Ri,R1d,R3a,Arb), (Zf,Ri,R1d,R3a,Arc), (Zf,Ri,R1d,R3a,Ard), (Zf,Ri,R1d,R3a,Are), (Zf,Ri,R1d,R3a,Arf), (Zf,Ri,R1d,R3a,Arg), (Zf,Ri,R1d,R3a,Arh), (Zf,Ri,R1d,R3a,Ari), (Zf,Ri,R1d,R3a,Arj), (Zf,Ri,R1d,R3a,Ark), (Zf,Ri,R1d,R3a,Arl), (Zf,Ri,R1d,R3a,Arm), (Zf,Ri,R1d,R3a,Arn), (Zf,Ri,R1d,R3a,Aro), (Zf,Ri,R1d,R3a,Arp), (Zf,Ri,R1d,R3b,Ara), (Zf,Ri,R1d,R3b,Arb), (Zf,Ri,R1d,R3b,Arc), (Zf,Ri,R1d,R3b,Ard), (Zf,Ri,R1d,R3b,Are), (Zf,Ri,R1d,R3b,Arf), (Zf,Ri,R1d,R3b,Arg), (Zf,Ri,R1d,R3b,Arh), (Zf,Ri,R1d,R3b,Ari), (Zf,Ri,R1d,R3b,Arj), (Zf,Ri,R1d,R3b,Ark), (Zf,Ri,R1d,R3b,Arl), (Zf,Ri,R1d,R3b,Arm), (Zf,Ri,R1d,R3b,Arn), (Zf,Ri,R1d,R3b,Aro), (Zf,Ri,R1d,R3b,Arp), (Zf,Ri,R1d,R3c,Ara), (Zf,Ri,R1d,R3c,Arb), (Zf,Ri,R1d,R3c,Arc), (Zf,Ri,R1d,R3c,Ard), (Zf,Ri,R1d,R3c,Are), (Zf,Ri,R1d,R3c,Arf), (Zf,Ri,R1d,R3c,Arg), (Zf,Ri,R1d,R3c,Arh), (Zf,Ri,R1d,R3c,Ari), (Zf,Ri,R1d,R3c,Arj), (Zf,Ri,R1d,R3c,Ark), (Zf,Ri,R1d,R3c,Arl), (Zf,Ri,R1d,R3c,Arm), (Zf,Ri,R1d,R3c,Arn), (Zf,Ri,R1d,R3c,Aro), (Zf,Ri,R1d,R3c,Arp), (Zf,Ri,R1d,R3d,Ara), (Zf,Ri,R1d,R3d,Arb), (Zf,Ri,R1d,R3d,Arc), (Zf,Ri,R1d,R3d,Ard), (Zf,Ri,R1d,R3d,Are), (Zf,Ri,R1d,R3d,Arf), (Zf,Ri,R1d,R3d,Arg), (Zf,Ri,R1d,R3d,Arh), (Zf,Ri,R1d,R3d,Ari), (Zf,Ri,R1d,R3d,Arj), (Zf,Ri,R1d,R3d,Ark), (Zf,Ri,R1d,R3d,Arl), (Zf,Ri,R1d,R3d,Arm), (Zf,Ri,R1d,R3d,Arn), (Zf,Ri,R1d,R3d,Aro), (Zf,Ri,R1d,R3d,Arp), (Zf,Ri,R1d,R3e,Ara), (Zf,Ri,R1d,R3e,Arb), (Zf,Ri,R1d,R3e,Arc), (Zf,Ri,R1d,R3e,Ard), (Zf,Ri,R1d,R3e,Are), (Zf,Ri,R1d,R3e,Arf), (Zf,Ri,R1d,R3e,Arg), (Zf,Ri,R1d,R3e,Arh), (Zf,Ri,R1d,R3e,Ari), (Zf,Ri,R1d,R3e,Arj), (Zf,Ri,R1d,R3e,Ark), (Zf,Ri,R1d,R3e,Arl), (Zf,Ri,R1d,R3e,Arm), (Zf,Ri,R1d,R3e,Arn), (Zf,Ri,R1d,R3e,Aro), (Zf,Ri,R1d,R3e,Arp), (Zf,Ri,R1d,R3f,Ara), (Zf,Ri,R1d,R3f,Arb), (Zf,Ri,R1d,R3f,Arc), (Zf,Ri,R1d,R3f,Ard), (Zf,Ri,R1d,R3f,Are), (Zf,Ri,R1d,R3f,Arf), (Zf,Ri,R1d,R3f,Arg), (Zf,Ri,R1d,R3f,Arh), (Zf,Ri,R1d,R3f,Ari), (Zf,Ri,R1d,R3f,Arj), (Zf,Ri,R1d,R3f,Ark), (Zf,Ri,R1d,R3f,Arl), (Zf,Ri,R1d,R3f,Arm), (Zf,Ri,R1d,R3f,Arn), (Zf,Ri,R1d,R3f,Aro), (Zf,Ri,R1d,R3f,Arp), (Zf,Ri,R1d,R3g,Ara), (Zf,Ri,R1d,R3g,Arb), (Zf,Ri,R1d,R3g,Arc), (Zf,Ri,R1d,R3g,Ard), (Zf,Ri,R1d,R3g,Are), (Zf,Ri,R1d,R3g,Arf), (Zf,Ri,R1d,R3g,Arg), (Zf,Ri,R1d,R3g,Arh), (Zf,Ri,R1d,R3g,Ari), (Zf,Ri,R1d,R3g,Arj), (Zf,Ri,R1d,R3g,Ark), (Zf,Ri,R1d,R3g,Arl), (Zf,Ri,R1d,R3g,Arm), (Zf,Ri,R1d,R3g,Arn), (Zf,Ri,R1d,R3g,Aro), (Zf,Ri,R1d,R3g,Arp), (Zf,Ri,R1d,R3h,Ara), (Zf,Ri,R1d,R3h,Arb), (Zf,Ri,R1d,R3h,Arc), (Zf,Ri,R1d,R3h,Ard), (Zf,Ri,R1d,R3h,Are), (Zf,Ri,R1d,R3h,Arf), (Zf,Ri,R1d,R3h,Arg), (Zf,Ri,R1d,R3h,Arh), (Zf,Ri,R1d,R3h,Ari), (Zf,Ri,R1d,R3h,Arj), (Zf,Ri,R1d,R3h,Ark), (Zf,Ri,R1d,R3h,Arl), (Zf,Ri,R1d,R3h,Arm), (Zf,Ri,R1d,R3h,Arn), (Zf,Ri,R1d,R3h,Aro), (Zf,Ri,R1d,R3h,Arp), (Zf,Rj,R1a,R3a,Ara), (Zf,Rj,R1a,R3a,Arb), (Zf,Rj,R1a,R3a,Arc), (Zf,Rj,R1a,R3a,Ard), (Zf,Rj,R1a,R3a,Are), (Zf,Rj,R1a,R3a,Arf), (Zf,Rj,R1a,R3a,Arg), (Zf,Rj,R1a,R3a,Arh), (Zf,Rj,R1a,R3a,Ari), (Zf,Rj,R1a,R3a,Arj), (Zf,Rj,R1a,R3a,Ark), (Zf,Rj,R1a,R3a,Arl), (Zf,Rj,R1a,R3a,Arm), (Zf,Rj,R1a,R3a,Arn), (Zf,Rj,R1a,R3a,Aro), (Zf,Rj,R1a,R3a,Arp), (Zf,Rj,R1a,R3b,Ara), (Zf,Rj,R1a,R3b,Arb), (Zf,Rj,R1a,R3b,Arc), (Zf,Rj,R1a,R3b,Ard), (Zf,Rj,R1a,R3b,Are), (Zf,Rj,R1a,R3b,Arf), (Zf,Rj,R1a,R3b,Arg), (Zf,Rj,R1a,R3b,Arh), (Zf,Rj,R1a,R3b,Ari), (Zf,Rj,R1a,R3b,Arj), (Zf,Rj,R1a,R3b,Ark), (Zf,Rj,R1a,R3b,Arl), (Zf,Rj,R1a,R3b,Arm), (Zf,Rj,R1a,R3b,Arn), (Zf,Rj,R1a,R3b,Aro), (Zf,Rj,R1a,R3b,Arp), (Zf,Rj,R1a,R3c,Ara), (Zf,Rj,R1a,R3c,Arb), (Zf,Rj,R1a,R3c,Arc), (Zf,Rj,R1a,R3c,Ard), (Zf,Rj,R1a,R3c,Are), (Zf,Rj,R1a,R3c,Arf), (Zf,Rj,R1a,R3c,Arg), (Zf,Rj,R1a,R3c,Arh), (Zf,Rj,R1a,R3c,Ari), (Zf,Rj,R1a,R3c,Arj), (Zf,Rj,R1a,R3c,Ark), (Zf,Rj,R1a,R3c,Arl), (Zf,Rj,R1a,R3c,Arm), (Zf,Rj,R1a,R3c,Arn), (Zf,Rj,R1a,R3c,Aro), (Zf,Rj,R1a,R3c,Alp), (Zf,Rj,R1a,R3d,Ara), (Zf,Rj,R1a,R3d,Arb), (Zf,Rj,R1a,R3d,Arc), (Zf,Rj,R1a,R3d,Ard), (Zf,Rj,R1a,R3d,Are), (Zf,Rj,R1a,R3d,Arf), (Zf,Rj,R1a,R3d,Arg), (Zf,Rj,R1a,R3d,Arh), (Zf,Rj,R1a,R3d,Ari), (Zf,Rj,R1a,R3d,Arj), (Zf,Rj,R1a,R3d,Ark), (Zf,Rj,R1a,R3d,Arl), (Zf,Rj,R1a,R3d,Arm), (Zf,Rj,R1a,R3d,Arn), (Zf,Rj,R1a,R3d,Aro), (Zf,Rj,R1a,R3d,Arp), (Zf,Rj,R1a,R3e,Ara), (Zf,Rj,R1a,R3e,Arb), (Zf,Rj,R1a,R3e,Arc), (Zf,Rj,R1a,R3e,Ard), (Zf,Rj,R1a,R3e,Are), (Zf,Rj,R1a,R3e,Arf), (Zf,Rj,R1a,R3e,Arg), (Zf,Rj,R1a,R3e,Arh), (Zf,Rj,R1a,R3e,Ari), (Zf,Rj,R1a,R3e,Arj), (Zf,Rj,R1a,R3e,Ark), (Zf,Rj,R1a,R3e,Arl), (Zf,Rj,R1a,R3e,Arm), (Zf,Rj,R1a,R3e,Arn), (Zf,Rj,R1a,R3e,Aro), (Zf,Rj,R1a,R3e,Arp), (Zf,Rj,R1a,R3f,Ara), (Zf,Rj,R1a,R3f,Arb), (Zf,Rj,R1a,R3f,Arc), (Zf,Rj,R1a,R3f,Ard), (Zf,Rj,R1a,R3f,Are), (Zf,Rj,R1a,R3f,Arf), (Zf,Rj,R1a,R3f,Arg), (Zf,Rj,R1a,R3f,Arh), (Zf,Rj,R1a,R3f,Ari), (Zf,Rj,R1a,R3f,Arj), (Zf,Rj,R1a,R3f,Ark), (Zf,Rj,R1a,R3f,Arl), (Zf,Rj,R1a,R3f,Arm), (Zf,Rj,R1a,R3f,Arn), (Zf,Rj,R1a,R3f,Aro), (Zf,Rj,R1a,R3f,Arp), (Zf,Rj,R1a,R3g,Ara), (Zf,Rj,R1a,R3g,Arb), (Zf,Rj,R1a,R3g,Arc), (Zf,Rj,R1a,R3g,Ard), (Zf,Rj,R1a,R3g,Are), (Zf,Rj,R1a,R3g,Arf), (Zf,Rj,R1a,R3g,Arg), (Zf,Rj,R1a,R3g,Arh), (Zf,Rj,R1a,R3g,Ari), (Zf,Rj,R1a,R3g,Arj), (Zf,Rj,R1a,R3g,Ark), (Zf,Rj,R1a,R3g,Arl), (Zf,Rj,R1a,R3g,Arm), (Zf,Rj,R1a,R3g,Arn), (Zf,Rj,R1a,R3g,Aro), (Zf,Rj,R1a,R3g,Arp), (Zf,Rj,R1a,R3h,Ara), (Zf,Rj,R1a,R3h,Arb), (Zf,Rj,R1a,R3h,Arc), (Zf,Rj,R1a,R3h,Ard), (Zf,Rj,R1a,R3h,Are), (Zf,Rj,R1a,R3h,Arf), (Zf,Rj,R1a,R3h,Arg), (Zf,Rj,R1a,R3h,Arh), (Zf,Rj,R1a,R3h,Ari), (Zf,Rj,R1a,R3h,Arj), (Zf,Rj,R1a,R3h,Ark), (Zf,Rj,R1a,R3h,Arl), (Zf,Rj,R1a,R3h,Arm), (Zf,Rj,R1a,R3h,Arn), (Zf,Rj,R1a,R3h,Aro), (Zf,Rj,R1a,R3h,Arp), (Zf,Rj,R1b,R3a,Ara), (Zf,Rj,R1b,R3a,Arb), (Zf,Rj,R1b,R3a,Arc), (Zf,Rj,R1b,R3a,Ard), (Zf,Rj,R1b,R3a,Are), (Zf,Rj,R1b,R3a,Arf), (Zf,Rj,R1b,R3a,Arg), (Zf,Rj,R1b,R3a,Arh), (Zf,Rj,R1b,R3a,Ari), (Zf,Rj,R1b,R3a,Arj), (Zf,Rj,R1b,R3a,Ark), (Zf,Rj,R1b,R3a,Arl), (Zf,Rj,R1b,R3a,Arm), (Zf,Rj,R1b,R3a,Arn), (Zf,Rj,R1b,R3a,Aro), (Zf,Rj,R1b,R3a,Arp), (Zf,Rj,R1b,R3b,Ara), (Zf,Rj,R1b,R3b,Arb), (Zf,Rj,R1b,R3b,Arc), (Zf,Rj,R1b,R3b,Ard), (Zf,Rj,R1b,R3b,Are), (Zf,Rj,R1b,R3b,Arf), (Zf,Rj,R1b,R3b,Arg), (Zf,Rj,R1b,R3b,Arh), (Zf,Rj,R1b,R3b,Ari), (Zf,Rj,R1b,R3b,Arj), (Zf,Rj,R1b,R3b,Ark), (Zf,Rj,R1b,R3b,Arl), (Zf,Rj,R1b,R3b,Arm), (Zf,Rj,R1b,R3b,Arn), (Zf,Rj,R1b,R3b,Aro), (Zf,Rj,R1b,R3b,Arp), (Zf,Rj,R1b,R3c,Ara), (Zf,Rj,R1b,R3c,Arb), (Zf,Rj,R1b,R3c,Arc), (Zf,Rj,R1b,R3c,Ard), (Zf,Rj,R1b,R3c,Are), (Zf,Rj,R1b,R3c,Arf), (Zf,Rj,R1b,R3c,Arg), (Zf,Rj,R1b,R3c,Arh), (Zf,Rj,R1b,R3c,Ari), (Zf,Rj,R1b,R3c,Arj), (Zf,Rj,R1b,R3c,Ark), (Zf,Rj,R1b,R3c,Arl), (Zf,Rj,R1b,R3c,Arm), (Zf,Rj,R1b,R3c,Arn), (Zf,Rj,R1b,R3c,Aro), (Zf,Rj,R1b,R3c,Arp), (Zf,Rj,R1b,R3d,Ara), (Zf,Rj,R1b,R3d,Arb), (Zf,Rj,R1b,R3d,Arc), (Zf,Rj,R1b,R3d,Ard), (Zf,Rj,R1b,R3d,Are), (Zf,Rj,R1b,R3d,Arf), (Zf,Rj,R1b,R3d,Arg), (Zf,Rj,R1b,R3d,Arh), (Zf,Rj,R1b,R3d,Ari), (Zf,Rj,R1b,R3d,Arj), (Zf,Rj,R1b,R3d,Ark), (Zf,Rj,R1b,R3d,Arl), (Zf,Rj,R1b,R3d,Arm), (Zf,Rj,R1b,R3d,Arm), (Zf,Rj,R1b,R3d,Aro), (Zf,Rj,R1b,R3d,Arp), (Zf,Rj,R1b,R3e,Ara), (Zf,Rj,R1b,R3e,Arb), (Zf,Rj,R1b,R3e,Arc), (Zf,Rj,R1b,R3e,Ard), (Zf,Rj,R1b,R3e,Are), (Zf,Rj,R1b,R3e,Arf), (Zf,Rj,R1b,R3e,Arg), (Zf,Rj,R1b,R3e,Arh), (Zf,Rj,R1b,R3e,Ari), (Zf,Rj,R1b,R3e,Arj), (Zf,Rj,R1b,R3e,Ark), (Zf,Rj,R1b,R3e,Arl), (Zf,Rj,R1b,R3e,Arm), (Zf,Rj,R1b,R3e,Arn), (Zf,Rj,R1b,R3e,Aro), (Zf,Rj,R1b,R3e,Arp), (Zf,Rj,R1b,R3f,Ara), (Zf,Rj,R1b,R3f,Arb), (Zf,Rj,R1b,R3f,Arc), (Zf,Rj,R1b,R3f,Ard), (Zf,Rj,R1b,R3f,Are), (Zf,Rj,R1b,R3f,Arf), (Zf,Rj,R1b,R3f,Arg), (Zf,Rj,R1b,R3f,Arh), (Zf,Rj,R1b,R3f,Ari), (Zf,Rj,R1b,R3f,Arj), (Zf,Rj,R1b,R3f,Ark), (Zf,Rj,R1b,R3f,Arl), (Zf,Rj,R1b,R3f,Arm), (Zf,Rj,R1b,R3f,Arn), (Zf,Rj,R1b,R3f,Aro), (Zf,Rj,R1b,R3f,Arp), (Zf,Rj,R1b,R3g,Ara), (Zf,Rj,R1b,R3g,Arb), (Zf,Rj,R1b,R3g,Arc), (Zf,Rj,R1b,R3g,Ard), (Zf,Rj,R1b,R3g,Are), (Zf,Rj,R1b,R3g,Arf), (Zf,Rj,R1b,R3g,Arg), (Zf,Rj,R1b,R3g,Arh), (Zf,Rj,R1b,R3g,Ari), (Zf,Rj,R1b,R3g,Arj), (Zf,Rj,R1b,R3g,Ark), (Zf,Rj,R1b,R3g,Arl), (Zf,Rj,R1b,R3g,Arm), (Zf,Rj,R1b,R3g,Arn), (Zf,Rj,R1b,R3g,Aro), (Zf,Rj,R1b,R3g,Arp), (Zf,Rj,R1b,R3h,Ara), (Zf,Rj,R1b,R3h,Arb), (Zf,Rj,R1b,R3h,Arc), (Zf,Rj,R1b,R3h,Ard), (Zf,Rj,R1b,R3h,Are), (Zf,Rj,R1b,R3h,Arf), (Zf,Rj,R1b,R3h,Arg), (Zf,Rj,R1b,R3h,Arh), (Zf,Rj,R1b,R3h,Ari), (Zf,Rj,R1b,R3h,Arj), (Zf,Rj,R1b,R3h,Ark), (Zf,Rj,R1b,R3h,Arl), (Zf,Rj,R1b,R3h,Arm), (Zf,Rj,R1b,R3h,Arn), (Zf,Rj,R1b,R3h,Aro), (Zf,Rj,R1b,R3h,Arp), (Zf,Rj,R1c,R3a,Ara), (Zf,Rj,R1c,R3a,Arb), (Zf,Rj,R1c,R3a,Arc), (Zf,Rj,R1c,R3a,Ard), (Zf,Rj,R1c,R3a,Are), (Zf,Rj,R1c,R3a,Arf), (Zf,Rj,R1c,R3a,Arg), (Zf,Rj,R1c,R3a,Arh), (Zf,Rj,R1c,R3a,Ari), (Zf,Rj,R1c,R3a,Arj), (Zf,Rj,R1c,R3a,Ark), (Zf,Rj,R1c,R3a,Arl), (Zf,Rj,R1c,R3a,Arm), (Zf,Rj,R1c,R3a,Arn), (Zf,Rj,R1c,R3a,Aro), (Zf,Rj,R1c,R3a,Arp), (Zf,Rj,R1c,R3b,Ara), (Zf,Rj,R1c,R3b,Arb), (Zf,Rj,R1c,R3b,Arc), (Zf,Rj,R1c,R3b,Ard), (Zf,Rj,R1c,R3b,Are), (Zf,Rj,R1c,R3b,Arf), (Zf,Rj,R1c,R3b,Arg), (Zf,Rj,R1c,R3b,Arh), (Zf,Rj,R1c,R3b,Ari), (Zf,Rj,R1c,R3b,Arj), (Zf,Rj,R1c,R3b,Ark), (Zf,Rj,R1c,R3b,Arl), (Zf,Rj,R1c,R3b,Arm), (Zf,Rj,R1c,R3b,Arn), (Zf,Rj,R1c,R3b,Aro), (Zf,Rj,R1c,R3b,Arp), (Zf,Rj,R1c,R3c,Ara), (Zf,Rj,R1c,R3c,Arb), (Zf,Rj,R1c,R3c,Arc), (Zf,Rj,R1c,R3c,Ard), (Zf,Rj,R1c,R3c,Are), (Zf,Rj,R1c,R3c,Arf), (Zf,Rj,R1c,R3c,Arg), (Zf,Rj,R1c,R3c,Arh), (Zf,Rj,R1c,R3c,Ari), (Zf,Rj,R1c,R3c,Arj), (Zf,Rj,R1c,R3c,Ark), (Zf,Rj,R1c,R3c,Arl), (Zf,Rj,R1c,R3c,Arm), (Zf,Rj,R1c,R3c,Arn), (Zf,Rj,R1c,R3c,Aro), (Zf,Rj,R1c,R3c,Arp), (Zf,Rj,R1c,R3d,Ara), (Zf,Rj,R1c,R3d,Arb), (Zf,Rj,R1c,R3d,Arc), (Zf,Rj,R1c,R3d,Ard), (Zf,Rj,R1c,R3d,Are), (Zf,Rj,R1c,R3d,Arf), (Zf,Rj,R1c,R3d,Arg), (Zf,Rj,R1c,R3d,Arh), (Zf,Rj,R1c,R3d,Ari), (Zf,Rj,R1c,R3d,Arj), (Zf,Rj,R1c,R3d,Ark), (Zf,Rj,R1c,R3d,Arl), (Zf,Rj,R1c,R3d,Arm), (Zf,Rj,R1c,R3d,Arn), (Zf,Rj,R1c,R3d,Aro), (Zf,Rj,R1c,R3d,Arp), (Zf,Rj,R1c,R3e,Ara), (Zf,Rj,R1c,R3e,Arb), (Zf,Rj,R1c,R3e,Arc), (Zf,Rj,R1c,R3e,Ard), (Zf,Rj,R1c,R3e,Are), (Zf,Rj,R1c,R3e,Arf), (Zf,Rj,R1c,R3e,Arg), (Zf,Rj,R1c,R3e,Arh), (Zf,Rj,R1c,R3e,Ari), (Zf,Rj,R1c,R3e,Arj), (Zf,Rj,R1c,R3e,Ark), (Zf,Rj,R1c,R3e,Arl), (Zf,Rj,R1c,R3e,Arm), (Zf,Rj,R1c,R3e,Arn), (Zf,Rj,R1c,R3e,Aro), (Zf,Rj,R1c,R3e,Arp), (Zf,Rj,R1c,R3f,Ara), (Zf,Rj,R1c,R3f,Arb), (Zf,Rj,R1c,R3f,Arc), (Zf,Rj,R1c,R3f,Ard), (Zf,Rj,R1c,R3f,Are), (Zf,Rj,R1c,R3f,Arf), (Zf,Rj,R1c,R3f,Arg), (Zf,Rj,R1c,R3f,Arh), (Zf,Rj,R1c,R3f,Ari), (Zf,Rj,R1c,R3f,Arj), (Zf,Rj,R1c,R3f,Ark), (Zf,Rj,R1c,R3f,Arl), (Zf,Rj,R1c,R3f,Arm), (Zf,Rj,R1c,R3f,Arn), (Zf,Rj,R1c,R3f,Aro), (Zf,Rj,R1c,R3f,Arp), (Zf,Rj,R1c,R3g,Ara), (Zf,Rj,R1c,R3g,Arb), (Zf,Rj,R1c,R3g,Arc), (Zf,Rj,R1c,R3g,Ard), (Zf,Rj,R1c,R3g,Are), (Zf,Rj,R1c,R3g,Arf), (Zf,Rj,R1c,R3g,Arg), (Zf,Rj,R1c,R3g,Arh), (Zf,Rj,R1c,R3g,Ari), (Zf,Rj,R1c,R3g,Arj), (Zf,Rj,R1c,R3g,Ark), (Zf,Rj,R1c,R3g,Arl), (Zf,Rj,R1c,R3g,Arm), (Zf,Rj,R1c,R3g,Arn), (Zf,Rj,R1c,R3g,Aro), (Zf,Rj,R1c,R3g,Arp), (Zf,Rj,R1c,R3h,Ara), (Zf,Rj,R1c,R3h,Arb), (Zf,Rj,R1c,R3h,Arc), (Zf,Rj,R1c,R3h,Ard), (Zf,Rj,R1c,R3h,Are), (Zf,Rj,R1c,R3h,Arf), (Zf,Rj,R1c,R3h,Arg), (Zf,Rj,R1c,R3h,Arh), (Zf,Rj,R1c,R3h,Ari), (Zf,Rj,R1c,R3h,Arj), (Zf,Rj,R1c,R3h,Ark), (Zf,Rj,R1c,R3h,Arl), (Zf,Rj,R1c,R3h,Arm), (Zf,Rj,R1c,R3h,Arn), (Zf,Rj,R1c,R3h,Aro), (Zf,Rj,R1c,R3h,Arp), (Zf,Rj,R1d,R3a,Ara), (Zf,Rj,R1d,R3a,Arb), (Zf,Rj,R1d,R3a,Arc), (Zf,Rj,R1d,R3a,Ard), (Zf,Rj,R1d,R3a,Are), (Zf,Rj,R1d,R3a,Arf), (Zf,Rj,R1d,R3a,Arg), (Zf,Rj,R1d,R3a,Arh), (Zf,Rj,R1d,R3a,Ari), (Zf,Rj,R1d,R3a,Arj), (Zf,Rj,R1d,R3a,Ark), (Zf,Rj,R1d,R3a,Arl), (Zf,Rj,R1d,R3a,Arm), (Zf,Rj,R1d,R3a,Arn), (Zf,Rj,R1d,R3a,Aro), (Zf,Rj,R1d,R3a,Arp), (Zf,Rj,R1d,R3b,Ara), (Zf,Rj,R1d,R3b,Arb), (Zf,Rj,R1d,R3b,Arc), (Zf,Rj,R1d,R3b,Ard), (Zf,Rj,R1d,R3b,Are), (Zf,Rj,R1d,R3b,Arf), (Zf,Rj,R1d,R3b,Arg), (Zf,Rj,R1d,R3b,Arh), (Zf,Rj,R1d,R3b,Ari), (Zf,Rj,R1d,R3b,Arj), (Zf,Rj,R1d,R3b,Ark), (Zf,Rj,R1d,R3b,Arl), (Zf,Rj,R1d,R3b,Arm), (Zf,Rj,R1d,R3b,Arn), (Zf,Rj,R1d,R3b,Aro), (Zf,Rj,R1d,R3b,Arp), (Zf,Rj,R1d,R3c,Ara), (Zf,Rj,R1d,R3c,Arb), (Zf,Rj,R1d,R3c,Arc), (Zf,Rj,R1d,R3c,Ard), (Zf,Rj,R1d,R3c,Are), (Zf,Rj,R1d,R3c,Arf), (Zf,Rj,R1d,R3c,Arg), (Zf,Rj,R1d,R3c,Arh), (Zf,Rj,R1d,R3c,Ari), (Zf,Rj,R1d,R3c,Arj), (Zf,Rj,R1d,R3c,Ark), (Zf,Rj,R1d,R3c,Arl), (Zf,Rj,R1d,R3c,Arm), (Zf,Rj,R1d,R3c,Arn), (Zf,Rj,R1d,R3c,Aro), (Zf,Rj,R1d,R3c,Arp), (Zf,Rj,R1d,R3d,Ara), (Zf,Rj,R1d,R3d,Arb), (Zf,Rj,R1d,R3d,Arc), (Zf,Rj,R1d,R3d,Ard), (Zf,Rj,R1d,R3d,Are), (Zf,Rj,R1d,R3d,Arf), (Zf,Rj,R1d,R3d,Arg), (Zf,Rj,R1d,R3d,Arh), (Zf,Rj,R1d,R3d,Ari), (Zf,Rj,R1d,R3d,Arj), (Zf,Rj,R1d,R3d,Ark), (Zf,Rj,R1d,R3d,Arl), (Zf,Rj,R1d,R3d,Arm), (Zf,Rj,R1d,R3d,Arn), (Zf,Rj,R1d,R3d,Aro), (Zf,Rj,R1d,R3d,Arp), (Zf,Rj,R1d,R3e,Ara), (Zf,Rj,R1d,R3e,Arb), (Zf,Rj,R1d,R3e,Arc), (Zf,Rj,R1d,R3e,Ard), (Zf,Rj,R1d,R3e,Are), (Zf,Rj,R1d,R3e,Arf), (Zf,Rj,R1d,R3e,Arg), (Zf,Rj,R1d,R3e,Arh), (Zf,Rj,R1d,R3e,Ari), (Zf,Rj,R1d,R3e,Arj), (Zf,Rj,R1d,R3e,Ark), (Zf,Rj,R1d,R3e,Arl), (Zf,Rj,R1d,R3e,Arm), (Zf,Rj,R1d,R3e,Arm), (Zf,Rj,R1d,R3e,Aro), (Zf,Rj,R1d,R3e,Arp), (Zf,Rj,R1d,R3f,Ara), (Zf,Rj,R1d,R3f,Arb), (Zf,Rj,R1d,R3f,Arc), (Zf,Rj,R1d,R3f,Ard), (Zf,Rj,R1d,R3f,Are), (Zf,Rj,R1d,R3f,Arf), (Zf,Rj,R1d,R3f,Arg), (Zf,Rj,R1d,R3f,Arh), (Zf,Rj,R1d,R3f,Ari), (Zf,Rj,R1d,R3f,Arj), (Zf,Rj,R1d,R3f,Ark), (Zf,Rj,R1d,R3f,Arl), (Zf,Rj,R1d,R3f,Arm), (Zf,Rj,R1d,R3f,Arn), (Zf,Rj,R1d,R3f,Aro), (Zf,Rj,R1d,R3f,Arp), (Zf,Rj,R1d,R3g,Ara), (Zf,Rj,R1d,R3g,Arb), (Zf,Rj,R1d,R3g,Arc), (Zf,Rj,R1d,R3g,Ard), (Zf,Rj,R1d,R3g,Are), (Zf,Rj,R1d,R3g,Arf), (Zf,Rj,R1d,R3g,Arg), (Zf,Rj,R1d,R3g,Arh), (Zf,Rj,R1d,R3g,Ari), (Zf,Rj,R1d,R3g,Arj), (Zf,Rj,R1d,R3g,Ark), (Zf,Rj,R1d,R3g,Arl), (Zf,Rj,R1d,R3g,Arm), (Zf,Rj,R1d,R3g,Arn), (Zf,Rj,R1d,R3g,Aro), (Zf,Rj,R1d,R3g,Arp), (Zf,Rj,R1d,R3h,Ara), (Zf,Rj,R1d,R3h,Arb), (Zf,Rj,R1d,R3h,Arc), (Zf,Rj,R1d,R3h,Ard), (Zf,Rj,R1d,R3h,Are), (Zf,Rj,R1d,R3h,Arf), (Zf,Rj,R1d,R3h,Arg), (Zf,Rj,R1d,R3h,Arh), (Zf,Rj,R1d,R3h,Ari), (Zf,Rj,R1d,R3h,Arj), (Zf,Rj,R1d,R3h,Ark), (Zf,Rj,R1d,R3h,Arl), (Zf,Rj,R1d,R3h,Arm), (Zf,Rj,R1d,R3h,Arn), (Zf,Rj,R1d,R3h,Aro), (Zf,Rj,R1d,R3h,Arp).

Definitions

As used herein, the terms used above having following meaning:

"—($C_1$-$C_{10}$)alkyl" means a straight chain or branched non-cyclic hydrocarbon having from 1 to 10 carbon atoms. Representative straight chain —($C_1$-$C_{10}$)alkyls include -methyl, -ethyl, -n-propyl, -n-butyl, -n-pentyl, -n-hexyl, -n-heptyl, -n-octyl, -n-nonyl, and -n-decyl. Representative branched —($C_1$-$C_{10}$)alkyls include -iso-propyl, -sec-butyl, -iso-butyl, -tert-butyl, -iso-pentyl, -neo-pentyl, 1-methylbutyl, 2-methylbutyl, 3-methylbutyl, 1,1-dimethylpropyl, 1,2-dimethylpropyl, 1-methylpentyl, 2-methylpentyl, 3-methylpentyl, 4-methylpentyl, 1-ethylbutyl, 2-ethylbutyl, 3-ethylbutyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-methylhexyl, 2-methylhexyl, 3-methylhexyl, 4-methylhexyl, 5-methylhexyl, 1,2-dimethylpentyl, 1,3-dimethylpentyl, 1,2-dimethylhexyl, 1,3-dimethylhexyl, 3,3-dimethylhexyl, 1,2-dimethylheptyl, 1,3-dimethylheptyl, and 3,3-dimethylheptyl.

"—($C_1$-$C_6$)alkyl" means a straight chain or branched non-cyclic hydrocarbon having from 1 to 6 carbon atoms. Representative straight chain —($C_1$-$C_6$)alkyls include -methyl, -ethyl, -n-propyl, -n-butyl, -n-pentyl, and -n-hexyl. Representative branched —($C_1$-$C_6$)alkyls include -iso-propyl, -sec-butyl, -iso-butyl, -tert-butyl, -iso-pentyl, -neo-pentyl, 1-methylbutyl, 2-methylbutyl, 3-methylbutyl, 1,1-dimethylpropyl, 1,2-dimethylpropyl, 1-methylpentyl, 2-methylpentyl, 3-methylpentyl, 4-methylpentyl, 1-ethylbutyl, 2-ethylbutyl, 3-ethylbutyl, 1,1-dimethylbutyl, 1,2-dimethylbutyl, 1,3-dimethylbutyl, 2,2-dimethylbutyl, 2,3-dimethylbutyl, and 3,3-dimethylbutyl.

Each of $(C_1-C_6)$alkyl part for "—$(C_1-C_6)$alkyl-$OR_{13}$", "—$(C_1-C_6)$alkyl-OC(O)$R_7$", "—$(C_1-C_6)$alkyl-C=N—$OR_{13}$", "—$(C_1-C_6)$alkyl-C(O)N$(R_{13})_2$", "—$(C_1-C_6)$alkyl-NHS(O)$_2$N$(R_{13})_2$" "—$(C_1-C_6)$alkyl-C(=NH)—N$(R_{13})_2$" and "—$(C_1-C_6)$alkyl-N$(R_8)_2$" is the same as the above "—$(C_1-C_6)$alkyl".

"—$(C_1-C_6)$haloalkyl" means a straight chain or branched non-cyclic hydrocarbon having from 1 to 6 carbon atoms as defined above for —$(C_1-C_6)$alkyl that is substituted with 1, 2 or 3 independently selected halo groups.

"—$(C_1-C_6)$hydroxyalkyl" means a straight chain or branched non-cyclic hydrocarbon having from 1 to 6 carbon atoms as defined above for —$(C_1-C_6)$alkyl that is substituted with 1, 2 or 3 hydroxyl groups.

"—$(C_1-C_4)$alkyl" means a straight chain or branched non-cyclic hydrocarbon having from 1 to 4 carbon atoms. Representative straight chain —$(C_1-C_4)$alkyls include -methyl, -ethyl, -n-propyl, and -n-butyl. Representative branched —$(C_1-C_4)$alkyls include -iso-propyl, -sec-butyl, -iso-butyl, and -tert-butyl.

"—$(C_2-C_{10})$alkenyl" means a straight chain or branched non cyclic hydrocarbon having from 2 to 10 carbon atoms and including at least one carbon-carbon double bond. Representative straight chain and branched $(C_2-C_{10})$alkenyls include -vinyl, -allyl, -1-butenyl, -2-butenyl, -iso-butylenyl, -1-pentenyl, -2-pentenyl, -3-methyl-1-butenyl, -2-methyl-2-butenyl, -2,3-dimethyl-2-butenyl, -1-hexenyl, -2-hexenyl, -3-hexenyl, -1-heptenyl, -2-heptenyl, -3-heptenyl, -1-octenyl, -2-octenyl, -3-octenyl, -1-nonenyl, -2-nonenyl, -3-nonenyl, -1-decenyl, -2-decenyl, -3-decenyl and the like.

"—$(C_2-C_6)$alkenyl" means a straight chain or branched non-cyclic hydrocarbon having from 2 to 6 carbon atoms and including at least one carbon-carbon double bond. Representative straight chain and branched $(C_2-C_6)$alkenyls include -vinyl, -allyl, -1-butenyl, -2-butenyl, -iso-butylenyl, -1-pentenyl, -2-pentenyl, -3-methyl-1-butenyl, -2-methyl-2-butenyl, -2,3-dimethyl-2-butenyl, -1-hexenyl, 2-hexenyl, 3-hexenyl and the like.

The $(C_2-C_6)$alkenyl part of "=CH$(C_2-C_6)$alkenyl" is defined in the same way as the above "—$(C_2-C_6)$alkenyl".

"—$(C_2-C_6)$haloalkenyl" means a straight chain or branched non-cyclic hydrocarbon having from 2 to 6 carbon atoms and including at least one carbon-carbon double bond as defined above for —$(C_2-C_6)$alkenyl that is substituted with 1, 2 or 3 independently selected halo groups.

"—$(C_2-C_6)$hydroxyalkenyl" means a straight chain or branched non-cyclic hydrocarbon having from 2 to 6 carbon atoms and including at least one carbon-carbon double bond as defined above for —$(C_2-C_6)$alkenyl that is substituted with 1, 2 or 3 hydroxyl groups.

"—$(C_2-C_{10})$alkynyl" means a straight chain or branched non-cyclic hydrocarbon having from 2 to 10 carbon atoms and including at least one carbon-carbon triple bond. Representative straight chain and branched —$(C_2-C_{10})$alkynyls include -acetylenyl, -propynyl, -1-butynyl, -2-butynyl, -1-pentynyl, -2-pentynyl, -3-methyl-1-butynyl, -4-pentynyl, -1-hexynyl, -2-hexynyl, -5-hexynyl, -1-heptynyl, -2-heptynyl, -6-heptynyl, -1-octynyl, -2-octynyl, -7-octynyl, -1-nonynyl, -2-nonynyl, -8-nonynyl, -1-decynyl, -2-decynyl, -9-decynyl and the like.

"—$(C_2-C_6)$alkynyl" means a straight chain or branched non-cyclic hydrocarbon having from 2 to 6 carbon atoms and including at least one carbon-carbon triple bond. Representative straight chain and branched $(C_2-C_6)$alkynyls include -ethynyl, -propynyl, -1-butynyl, -2-butynyl, -1-pentynyl, -2-pentynyl, -3-methyl-1-butynyl, -4-pentynyl, -1-hexynyl, -2-hexynyl, -5-hexynyl and the like.

"—$(C_2-C_6)$haloalkynyl" means a straight chain or branched non-cyclic hydrocarbon having from 2 to 6 carbon atoms and including at least one carbon-carbon triple bond that is substituted with 1, 2 or 3 independently selected halo groups.

"—$(C_2-C_6)$hydroxyalkynyl" means a straight chain or branched non-cyclic hydrocarbon having from 2 to 6 carbon atoms and including at least one carbon-carbon triple bond that is substituted with 1, 2 or 3 hydroxyl groups.

"—$(C_1-C_6)$alkoxy" means a straight chain or branched non-cyclic hydrocarbon having one or more ether groups and from 1 to 6 carbon atoms. Representative straight chain and branched —$(C_1-C_6)$alkoxys include methoxy, ethoxy, propoxy, butoxy, pentoxy, hexoxy and the like.

"—$(C_1-C_6)$haloalkoxy" means a straight chain or branched non-cyclic hydrocarbon having from 1 to 6 carbon atoms as defined above for —$(C_1-C_6)$alkoxy that is substituted with 1, 2 or 3 independently selected halo groups.

"—$(C_1-C_6)$alkoxy$(C_1-C_6)$alkyl" means a straight chain or branched non cyclic hydrocarbon having one or more ether groups and from 1 to 6 carbon atoms as defined above for —$(C_1-C_6)$alkyl group that is substituted with a —$(C_2-C_6)$alkoxy group.

"—$(C_1-C_6)$alkoxy-$(C_2-C_6)$alkenyl" means a straight chain or branched non cyclic hydrocarbon from 2 to 6 carbon atoms and including at least one carbon-carbon double bond as defined above for —$(C_2-C_6)$alkenyl group that is substituted with a —$(C_1-C_6)$alkoxy group.

"—$(C_1-C_6)$alkoxy-$(C_2-C_6)$alkynyl" means a straight chain or branched non cyclic hydrocarbon having from 2 to 10 carbon atoms and including at least one carbon-carbon triple bond as defined above for $(C_2-C_6)$alkynyl that is substituted with a —$(C_1-C_6)$alkoxy group.

"—$(C_3-C_8)$cycloalkyl" means a saturated cyclic hydrocarbon having from 3 to 8 carbon atoms. Representative $(C_3-C_8)$ cycloalkyls include -cyclopropyl, -cyclobutyl, -cyclopentyl, -cyclohexyl, -cycloheptyl, and -cyclooctyl.

The cycloalkyl part of "—N$(R_c)$—$(C_3-C_8)$cycloalkyl" is defined in the same way as the above "—$(C_3-C_8)$cycloalkyl".

"—$(C_5-C_8)$cycloalkenyl" means a cyclic non-aromatic hydrocarbon having at least one carbon-carbon double bond in the cyclic system and from 5 to 8 carbon atoms. Representative —$(C_5-C_8)$cycloalkenyls include -cyclopentenyl, -cyclopentadienyl, -cyclohexenyl, -cyclohexadienyl, -cycloheptenyl, -cycloheptadienyl, -cycloheptatrienyl, -cyclooctenyl, -cyclooctadienyl, -cyclooctatrienyl, -cyclooctatetraenyl and the like.

"-(3- to 7-membered)heterocycle" means a 3- to 7-membered monocyclic heterocyclic ring which is either saturated, unsaturated non-aromatic, or aromatic. A 3-membered heterocycle can contain up to 1 heteroatom, a 4-membered heterocycle can contain up to 2 heteroatoms, a 5-membered heterocycle can contain up to 4 heteroatoms, a 6-membered heterocycle can contain up to 4 heteroatoms, and a 7-membered heterocycle can contain up to 5 heteroatoms. Each heteroatom is independently selected from nitrogen, which can be quaternized; oxygen; and sulfur, including sulfoxide and sulfone. The -(3- to 7-membered)heterocycle can be attached via a nitrogen or carbon atom. Representative -(3- to 7-membered)heterocycles include pyridyl, furyl, thienyl, pyrrolyl, oxazolyl, imidazolyl, triazolyl, thiazolidinyl, thiadiazolyl, thiazolyl, isoxazolyl, oxadiazolyl, pyrazolyl, tetrazolyl, isothiazolyl, pyridazinyl, pyrimidinyl, pyrazinyl, triazinyl, morpholinyl, morpholino, thiomorpholinyl, thiomorpholino, pyrrolidinyl, pyrrolinyl, piperidinyl, piperazinyl, thiazolidinyl, 2,3-dihydrofuryl, dihydrooxazolyl, dihydropyranyl, oxiranyl, oxetanyl, tetrahydrofuryl, tetrahydropyranyl, dihydropyridinyl, tetrahydropyridinyl, tetrahydropyrimidinyl, tetrahydrothiophenyl, tetrahydrothiopyranyl, dioxanyl, thiiranyl, oxiranyl, oxathioranyl, azetidinyl, thianyl, imidazolidinyl, imidazolinyl, pyrazolidinyl, pyrazolinyl, dihydropyridinyl, dihydrothiazolyl, tetrahydrothiazolyl, tetrahydroisothiazolyl, dihydrooxazinyl, hexahydroazepinyl, tetrahydrodiazepinyl, tetrahydropyridazinyl and the like.

Each of heterocycle part for "—N($R_c$)-(3- to 7-membered)heterocycle" and "—S(O)$_2$-(3- to 7-membered)heterocycle" is the same as the above "-(3- to 7-membered)heterocycle".

"-(5- to 10-membered)heteroaryl" means an aromatic heterocycle ring of 5 to 10 members, including both mono- and bicyclic ring systems, where at least one carbon atom of one or both of the rings is replaced with a heteroatom independently selected from nitrogen, oxygen, and sulfur, or at least two carbon atoms of one or both of the rings are replaced with a heteroatom independently selected from nitrogen, oxygen, and sulfur. In one embodiment, one of the -(5- to 10-membered)heteroaryl's rings contain at least one carbon atom. In another embodiment, both of the -(5- to 10-membered)heteroaryl's rings contain at least one carbon atom. Representative -(5- to 10-membered)heteroaryls include pyridyl, furyl, benzofuranyl, thienyl, benzothienyl, quinolinyl, isoquinolinyl, pyrrolyl, indolyl, oxazolyl, benzoxazolyl, benzisoxazolyl, imidazolyl, benzimidazolyl, indazolyl, triazolyl, thiadiazolyl, thiazolyl, benzothiazolyl, benzisothiazolyl, isoxazolyl, oxadiazolyl, pyrazolyl, tetrazolyl, isothiazolyl, pyridazinyl, pyrimidyl, pyrimidinyl, pyrazinyl, triazinyl, cinnolinyl, phthalazinyl, and quinazolinyl.

Heteroaryl part for "—N($R_c$)-(5- to 10-membered)heteroaryl" is the same as the above "-(5- to 10-membered)heteroaryl", "-(5- or 6-membered)heteroaryl" means a monocyclic aromatic heterocycle ring of 5 or 6 members where at least one carbon atom is replaced with a heteroatom independently selected from nitrogen, oxygen, and sulfur. In one embodiment, one of the -(5- or 6-membered)heteroaryl's ring contains at least one carbon atom. Representative -(5- or 6-membered)heteroaryls include pyridyl, furyl, thienyl, pyrrolyl, oxazolyl, imidazolyl, thiazolyl, isoxazolyl, thiadiazolyl, thiazolyl, isoxazolyl, oxadiazolyl, triazolyl, pyrazolyl, tetrazolyl, isothiazolyl, pyridazinyl, pyrimidyl, pyrazinyl, and triazinyl.

"—CH$_2$(halo)" means a methyl group where one of the hydrogens of the methyl group has been replaced with a halogen. Representative —CH$_2$(halo) groups include —CH$_2$F, —CH$_2$Cl, —CH$_2$Br, and —CH$_2$I.

"—CH(halo)$_2$" means a methyl group where two of the hydrogens of the methyl group have been replaced with a halogen. Representative —CH(halo)$_2$ groups include —CHF$_2$, —CHCl$_2$, —CHBr$_2$, CHBrCl, CHClI, and —CHI$_2$.

"—C(halo)$_3$" means a methyl group where each of the hydrogens of the methyl group has been replaced with a halogen. Representative —C(halo)$_3$ groups include —CF$_3$, —CCl$_3$, —CBr$_3$, and —Cl$_3$.

C(halo)$_3$ part for "—S(O)$_2$C(halo)$_3$" is the same as the above "—C(halo)$_3$".

"—OCH$_2$(halo)" means a methoxy group where one of the hydrogens of the methoxy group has been replaced with a halogen. Representative —OCH$_2$(halo) groups include —OCH$_2$F, —OCH$_2$Cl, —OCH$_2$Br, and —OCH$_2$I.

"—OCH(halo)$_2$" means a methoxy group where two of the hydrogens of the methoxy group have been replaced with a halogen. Representative —OCH(halo)$_2$ groups include —OCHF$_2$, —OCHCl$_2$, —OCHBr$_2$, —OCHBrCl, —OCHClI, and —OCHI$_2$.

"—OC(halo)$_3$" means a methoxy group where each of the hydrogens of the methoxy group has been replaced with a halogen. Representative —OC(halo)$_3$ groups include —OCF$_3$, —OCCl$_3$, —OCBr$_3$, and —OCl$_3$.

"halogen" or "-halo" means —F, —Cl, —Br, or —I.

"(C$_2$-C$_6$)bridge" as used herein means a hydrocarbon chain containing 2 to 6 carbon atoms joining two atoms of the piperidine, 1,2,3,6-tetrahydropyridine or piperazine ring of the compounds of formulas (a), (b) and/or (c) to form a fused bicyclic ring system. The positions of the piperidine, 1,2,3,6-tetrahydropyridine or piperazine ring are denoted as follows:

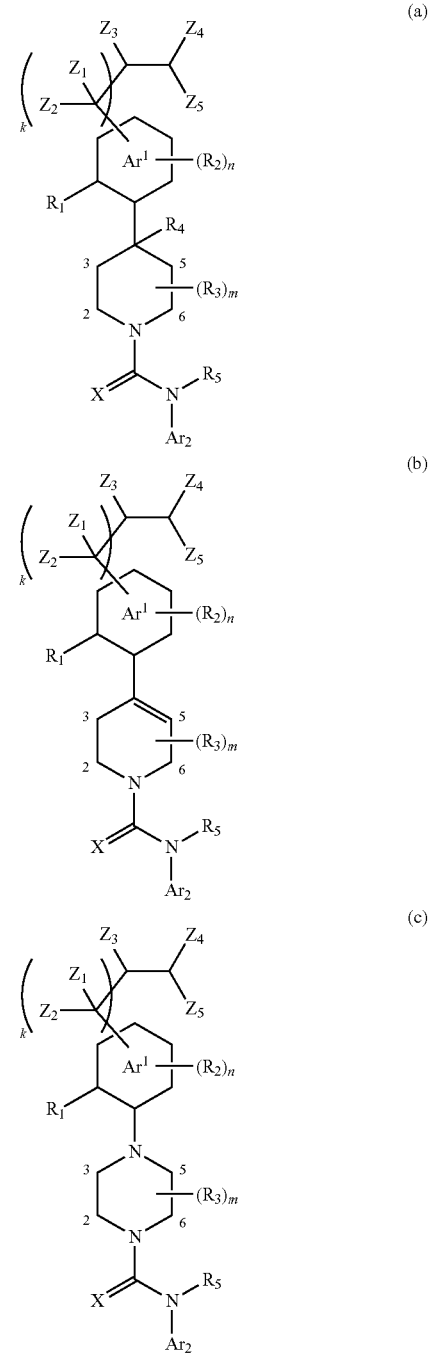

For example, compounds of the invention can comprise a (C$_2$-C$_6$)bridge joining positions 2 and 6 of the piperidine, 1,2,3,6-tetrahydropyridine or piperazine ring (two R$_3$ groups can together form a (C$_2$-C$_6$)bridge). Examples of compounds where two $R_3$ groups can together form a $(C_2$-$C_6)$bridge include compounds comprising the following ring systems: 8-aza-bicyclo[3.2.1]octane; 8-azabicyclo[3.2.1]oct-3-ene; 3,8-diazabicyclo[3.2.1]octane; 8-azabicyclo[3.2.1]oct-6-ene; 8-azabicyclo[3.2.1]octa-3,6-diene; 3,8-diazabicyclo[3.2.1]oct-6-ene; 9-aza-bicyclo[3.3.1]nonane; 9-azabicyclo[3.3.1]non-3-ene; 9-azabicyclo[3.3.1]non-6-ene; 9-azabicyclo[3.3.1]nona-3,6-diene; 9-azabicyclo[3.3.1]nona-3,7-diene; 3,9-diazabicyclo[3.3.1]nonane; 3,9-diazabicyclo[3.3.1]non-6-ene; 3,9-diazabicyclo[3.3.1]non-7-ene; 10-aza-bicyclo[4.3.1]decane; 10-azabicyclo[4.3.1]dec-8-ene; 8,10-diazabicyclo[4.3.1]decane; 8,10-diazabicyclo[4.3.1]dec-3-ene; 8,10-diazabicyclo[4.3.1]dec-4-ene; 8-azabicyclo[4.3.1]dec-4-ene; 8-azabicyclo[4.3.1]dec-3-ene; 8-azabicyclo[4.3.1]deca-2,6(10)-diene; 8-azabicyclo[4.3.1]deca-3,6(10)-diene; 8-azabicyclo[4.3.1]deca-4,6(10)-diene; 11-aza-bicyclo[5.3.1]undecane; 11-azabicyclo[5.3.1]undec-8-ene; 9,11-diazabicyclo[5.3.1]undecane; 12-aza-bicyclo[6.3.1]dodecane; 12-azabicyclo[6.3.1]dodec-9-ene; and 10,12-diazabicyclo[6.3.1]dodecane.

"A 3-8 member carbocyclic ring" as used herein means a $(C_3$-$C_8)$cycloalkane ring and a $(C_5$-$C_8)$cycloalkene ring, and includes cyclopropane, cyclobutane, cyclopentane, cyclohexane, cyclopentene, cyclopentadiene, cyclohexene, cyclohexadiene and the like. Examples of compounds where $Y_a$ and $Y_b$, together with the carbon to which they are attached, form a 3-8 member carbocyclic ring include compounds comprising the following:

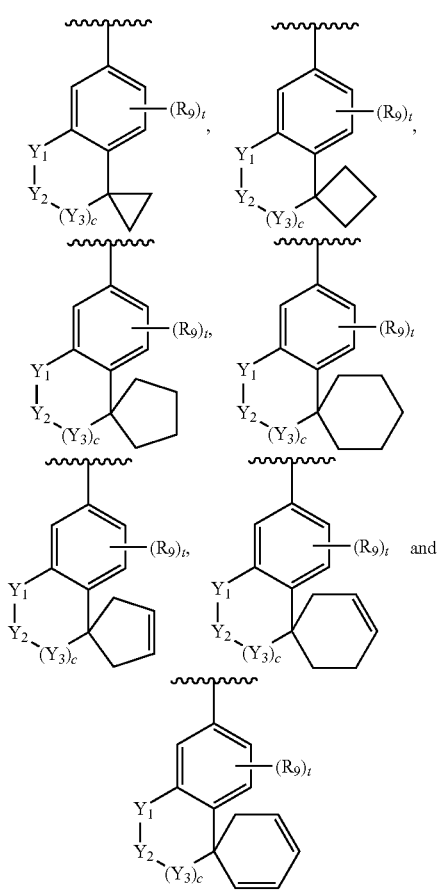

In connection with the $Ar_2$ group

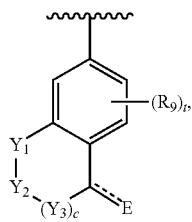

when E is —$N(R_7)_2$ it is to be understood that the dashed line in the above $Ar_2$ group is absent, i.e., the $Ar_2$ group is

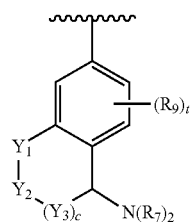

where $Y_1$, $Y_2$, $Y_3$, $R_9$, c and t are as defined above for compounds of Formula I. When E is =O, =S, =$C(R_7)_2$, =CH$(C_2$-$C_6)$alkenyl, or =N—$OR_5$, it is to be understood that the dashed line in the above $Ar_2$ group is present, i.e., the $Ar_2$ group is

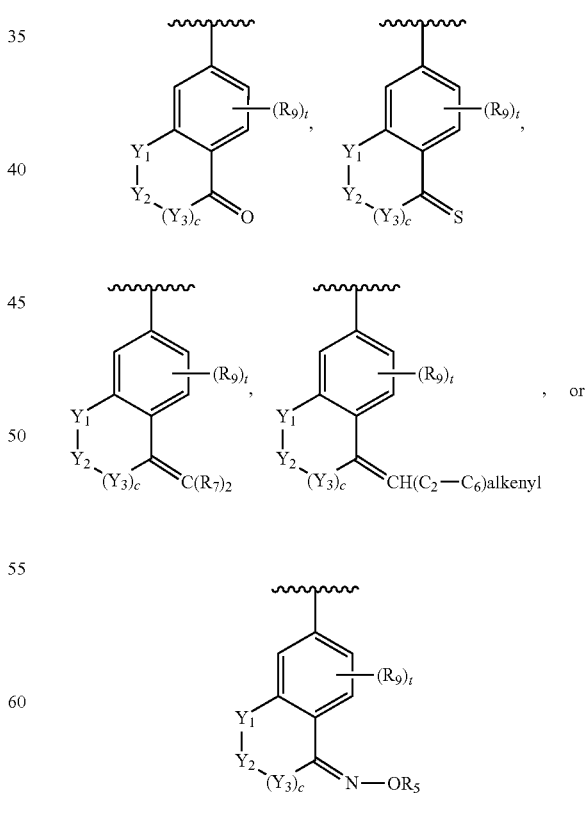

respectively, where $Y_1$, $Y_2$, $Y_3$, $R_9$, $R_{20}$, c and t are as defined above for compounds of Formula I.

The phrase "$Ar_1$ is a phenyl group" means

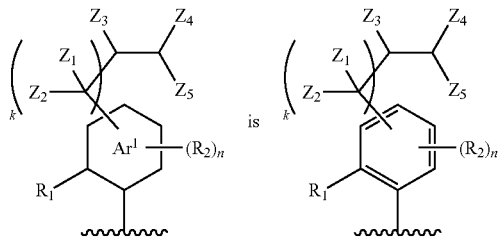

where $Z_1$, $Z_2$, $Z_3$, $Z_4$, $Z_5$, $R_1$, $R_2$, n and k are as defined above for compounds of Formula I.

The phrase "$Ar_1$ is a pyridyl group" means

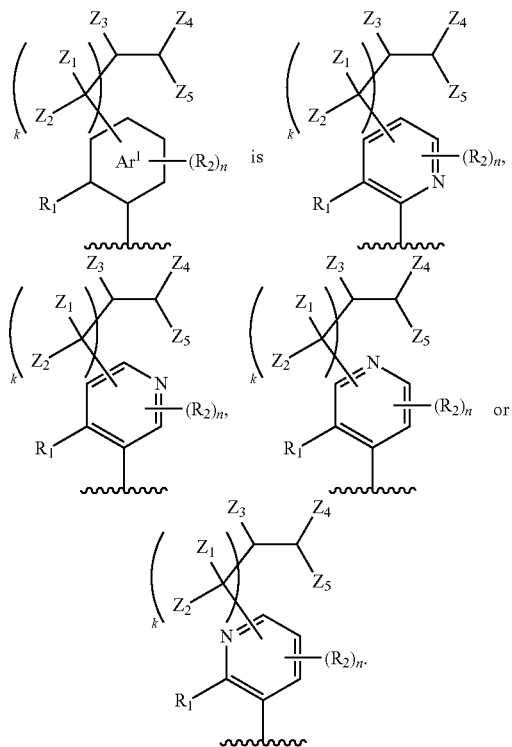

where $Z_1$, $Z_2$, $Z_3$, $Z_4$, $Z_5$, $R_1$, $R_2$, n and k are as defined above for compounds of Formula I.

The phrase "$Ar_1$ is a pyrazinyl group" means

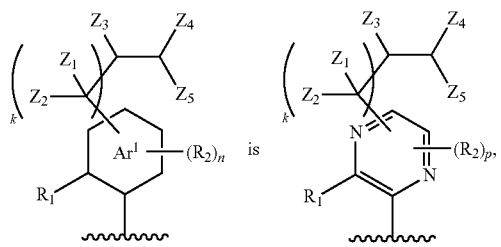

where $Z_1$, $Z_2$, $Z_3$, $Z_4$, $Z_5$, $R_1$, $R_2$, n and k are as defined above for compounds of Formula I.

The phrase "$Ar_1$ is a pyrimidinyl group" means

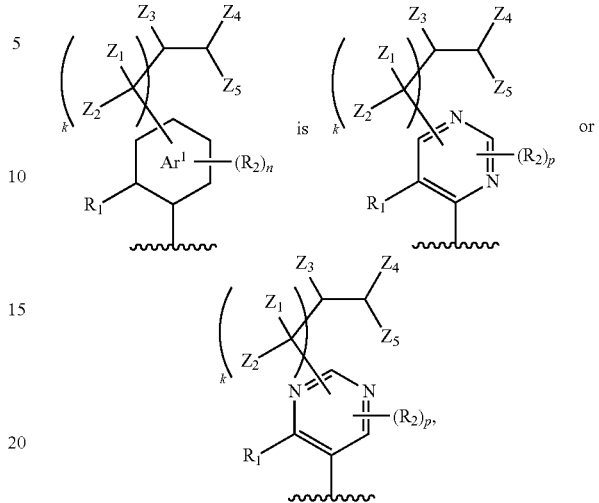

where $Z_1$, $Z_2$, $Z_3$, $Z_4$, $Z_5$, $R_1$, $R_2$, n and k are as defined above for compounds of Formula I.

The phrase "$Ar_1$ is a pyridazinyl group" means

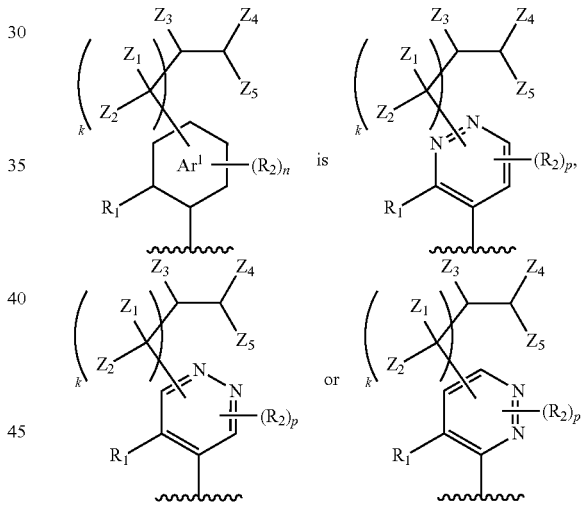

where $Z_1$, $Z_2$, $Z_3$, $Z_4$, $Z_5$, $R_1$, $R_2$, n and k are as defined above for compounds of Formula I.

The phrase "no more than one of $Y_1$, $Y_2$, or $Y_3$ can be O" means only one of $Y_1$, $Y_2$, and $Y_3$ can be O.

The phrase "no more than two of $Y_1$, $Y_2$, or $Y_3$ can be N" means that zero, one or two of $Y_1$, $Y_2$ and $Y_3$ can be N.

The term "animal," includes, but is not limited to, a cow, monkey, baboon, chimpanzee, horse, sheep, pig, chicken, turkey, quail, cat, dog, mouse, rat, rabbit, guinea pig, and human.

The phrase "pharmaceutically acceptable derivative," as used herein, includes any pharmaceutically acceptable salt, solvate, prodrug, radiolabeled form, stereoisomer, enantiomer, diastereomer, other stereoisomeric form, racemic mixture, geometric isomer, tautomer and/or co-crystal, e.g., of a compound of Formula I of the invention. In one embodiment, the pharmaceutically acceptable derivative is a pharmaceutically acceptable salt, solvate, radiolabeled form, stereoisomer, enantiomer, diastereomer, other stereoisomeric form, racemic mixture, geometric isomer, tautomer and/or co-crystal, e.g., of a compound of Formula I of the invention. In another embodiment, the pharmaceutically acceptable derivative is a pharmaceutically acceptable salt, radiolabeled form, stereoisomer, enantiomer, diastereomer, other stereoisomeric form, racemic mixture, geometric isomer, tautomer and/or co-crystal, e.g., of a compound of Formula I of the invention. In another embodiment, the pharmaceutically acceptable derivative is a pharmaceutically acceptable salt, radiolabeled form, stereoisomer, enantiomer, diastereomer, racemic mixture, geometric isomer, tautomer and/or co-crystal, e.g., of a compound of Formula I of the invention. In another embodiment, the pharmaceutically acceptable derivative is a pharmaceutically acceptable salt, e.g., of a compound of Formula I of the invention.

The phrase "pharmaceutically acceptable salt," as used herein, is any pharmaceutically acceptable salt that can be prepared from a compound of Formula I including a salt formed from an acid and a basic functional group, such as a nitrogen group, of a compound of Formula I. Illustrative salts include, but are not limited, to sulfate, citrate, acetate, trifluoroacetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, malate, maleate, gentisinate, fumarate, gluconate, glucoronate, saccharate, formate, benzoate, phthalate, glutamate, methanesulfonate, ethanesulfonate, benzenesulfonate, p-toluenesulfonate, and pamoate (i.e., 1,1'-methylene-bis-(2-hydroxy-3-naphthoate)) salts. The term "pharmaceutically acceptable salt" also includes a salt prepared from a compound of Formula I having an acidic functional group, such as a carboxylic acid functional group, and a pharmaceutically acceptable inorganic or organic base. Suitable bases include, but are not limited to, hydroxides of alkali metals such as sodium, potassium, cesium, and lithium; hydroxides of alkaline earth metal such as calcium and magnesium; hydroxides of other metals, such as aluminum and zinc; ammonia and organic amines, such as unsubstituted or hydroxy-substituted mono-, di-, or trialkylamines; dicyclohexylamine; tributyl amine; pyridine; picoline; N-methyl,N-ethylamine; diethylamine; triethylamine; mono-, bis-, or tris-(2-hydroxy-($C_1$-$C_3$)alkyl amines), such as mono-, bis-, or tris-(2-hydroxyethyl)amine, 2-hydroxy-tert-butylamine, or tris-(hydroxymethyl)methylamine, N,N-di-[($C_1$-$C_3$)alkyl]-N-(hydroxy-($C_1$-$C_3$)alkyl)-amines, such as N,N-dimethyl-N-(2-hydroxyethyl)amine, or tri-(2-hydroxyethyl)amine; N-methyl-D-glucamine; and amino acids such as arginine, lysine, and the like. One skilled in the art will recognize that, e.g., acid addition salts of a compound of Formula I can be prepared by reaction of the compounds with the appropriate acid via a variety of known methods.

Compounds of Formula I encompass all solvates of compounds of Formula I. "Solvates" are known in the art and are considered to be a combination, physical association and/or solvation of a compound of Formula I with a solvent molecule, e.g., a disolvate, monosolvate or hemisolvate when the ratio of the solvent molecule to the molecule of the compound of Formula I is 2:1, 1:1 or 1:2, respectively. This physical association involves varying degrees of ionic and covalent bonding, including hydrogen bonding. In certain instances, the solvate can be isolated, for example when one or more solvent molecules are incorporated into the crystal lattice of a crystalline solid. Thus, "solvate," as used herein, encompasses both solution-phase and isolatable solvates. A compound of Formula I of the invention may be present as a solvated form with a pharmaceutically acceptable solvent, such as water, methanol, ethanol, and the like, and it is intended that the invention include both solvated and unsolvated compound of Formula I forms. As "hydrate" relates to a particular subgroup of solvates, i.e., where the solvent molecule is water, hydrates are included within the solvates of the invention. Preparation of solvates is known in the art. For example, M. Caira et al., *J. Pharmaceut. Sci.*, 93(3):601-611 (2004), describes the preparation of solvates of fluconazole with ethyl acetate and with water. Similar preparations of solvates, hemisolvate, hydrates, and the like are described by E. C. van Tonder et al., *AAPS Pharm. Sci. Tech.*, 5(1), article 12 (2004), and A. L. Bingham et al., *Chem. Commun., pp.* 603-604 (2001). A typical, non-limiting, process involves dissolving the compound of Formula I in a desired amount of the desired solvent (organic, water or mixtures thereof) at temperatures above from about 20° C. to about 25° C., cooling the solution at a rate sufficient to form crystals, and isolating the crystals by known methods, e.g., filtration. Analytical techniques, for example, infrared spectroscopy, can be used to show the presence of the solvent in a crystal of the solvate.

The invention disclosed herein is also meant to encompass all prodrugs of the compounds of the invention. "Prodrugs" are known in the art and, while not necessarily possessing any pharmaceutical activity as such, are considered to be any covalently bonded carrier(s) that releases the active parent drug in vivo. In general, such prodrugs will be a functional derivative of a compound of Formula I which is readily convertible in vivo, e.g., by being metabolized, into the required compound of Formula I. Conventional procedures for the selection and preparation of suitable prodrug derivatives are described in, for example, *Design of Prodrugs*, H. Bundgaard ed., Elsevier (1985); "Drug and Enzyme Targeting, Part A," K. Widder et al. eds., Vol. 112 in *Methods in Enzymology*, Academic Press (1985); Bundgaard, "Design and Application of Prodrugs," Chapter 5 (pp. 113-191) in *A Textbook of Drug Design and Development*, P. Krogsgaard-Larsen and H. Bundgaard eds., Harwood Academic Publishers (1991); Bundgaard et al., *Adv. Drug Delivery Revs.* 8:1-38 (1992); Bundgaard et al., *J. Pharmaceut. Sci.* 77:285 (1988); and Kakeya et al., *Chem. Pharm. Bull.* 32:692-698 (1984).

In addition, one or more hydrogen, carbon or other atoms of a compound of Formula I can be replaced by an isotope of the hydrogen, carbon or other atoms. Compounds of Formula I include all radiolabeled forms of compounds of Formula I "radiolabeled," "radiolabeled form", and the like of a compound of Formula I, each of which is encompassed by the invention, is useful as a research and/or diagnostic tool in metabolism pharmacokinetic studies and in binding assays. Examples of isotopes that can be incorporated into a compound of Formula I of the invention include isotopes of hydrogen, carbon, nitrogen, oxygen, phosphorous, sulfur, fluorine and chlorine, such as $^2H$, $^3H$, $^{13}C$, $^{14}C$, $^{15}N$, $^{18}O$, $^{17}O$, $^{31}P$, $^{32}P$, $^{35}S$, $^{18}F$, and $^{36}Cl$, respectively. Radiolabeled compounds of the invention can be prepared by methods known in the art. For example, tritiated compounds of Formula I can be prepared by introducing tritium into the particular compound of Formula I, for example, by catalytic dehalogenation with tritium. This method may include reacting a suitably halogen-substituted precursor of a compound of Formula I with tritium gas in the presence of a suitable catalyst, for example, Pd/C, in the presence or absence of a base. Other suitable methods for preparing tritiated compounds can be found in Filer, "The Preparation and Characterization of Tritiated Neurochemicals," Chapter 6, pp. 155-192 in *Isotopes in the Physical and Biomedical Sciences, Vol. 1, Labeled Compounds (Part A)*

(1987). $^{14}$C-labeled compounds can be prepared by employing starting materials having a $^{14}$C carbon.

A compound of Formula I can contain one or more asymmetric centers and may thus give rise to enantiomers, diastereomers, and other stereoisomeric forms. Compounds of Formula I encompass all such possible forms as well as their racemic and resolved forms or any mixture thereof. When a compound of Formula I contains an olefinic double bond or other center of geometric asymmetry, and unless specified otherwise, it is intended to include all "geometric isomers," e.g., both E and Z geometric isomers. All "tautomers," e.g., ketone-enol, amide-imidic acid, lactam-lactim, enamine-imine, amine-imine, and enamine-enimine tautomers, are intended to be encompassed by the invention as well.

As used herein, the terms "stereoisomer," "stereoisomeric form", and the like are general terms for all isomers of individual molecules that differ only in the orientation of their atoms in space. It includes enantiomers and isomers of compounds with more than one chiral center that are not mirror images of one another ("diastereomers").

The term "chiral center" refers to a carbon atom to which four different groups are attached.

The term "enantiomer" or "enantiomeric" refers to a molecule that is nonsuperimposeable on its mirror image and hence optically active where the enantiomer rotates the plane of polarized light in one direction and its mirror image rotates the plane of polarized light in the opposite direction.

The term "racemic" refers to a mixture of equal parts of enantiomers which is optically inactive.

The compounds of the disclosure provided herein also encompass all co-crystals of the Compounds of Formula (I). "Co-crystals" are known in the art; a co-crystal is considered to be a structurally homogeneous crystalline material that contains two or more neutral building blocks, e.g., a Compound of Formula (I) with a co-former material, that are present in definite stoichiometric amounts. Aakeroy et al., "Co-crystal or Salt: Does it Really Matter?" Mol. Pharmaceutics 4(3):317-322 (2007). The main difference between solvates and co-crystals is the physical state of the isolated pure components. For, e.g., a two component system, if one component is a liquid at a temperature of about 25° C. then the crystal containing both components is designated as a solvate; if both components are solids at that temperature then the crystal containing both components is designated as a co-crystal. Sekhon, "Pharmaceutical Co-crystals—A Review," Ars. Pharm. 50(3):99-117 (2009). Furthermore, co-crystals and salts can be considered as opposite "extremes" on the scale of the multi-component structures possible. Salts are formed through ionization, e.g., an acid-base reaction or proton donation occurring between the active pharmaceutical ingredient and an acidic or basic substance. In contrast, when the active pharmaceutical ingredient(s) lacks an ionizable site amenable to salt formation, a co-crystal can be formed through unionization, e.g., hydrogen bonding, p-p, or van der Waals interactions between the components. The differences in structure among a co-crystal, salt, and hydrate are illustrated in, e.g., FIGS. 1 and 2 of Schultheiss et al., "Pharmaceutical Co-crystals and their Physicochemical Properties," Crystal Growth & Design 9(6):2950-2967 (2009), which is hereby incorporated by reference. Preparation of co-crystals is known in the art; for example, as described in the above-cited references and in U.S. Pat. Nos. 7,452,555B2 and 7,935,817B2. In one embodiment, a co-crystal with a Compound of Formula (I) comprises tartaric acid, succinic acid, fumaric acid, citric acid, oxalic acid, benzoic acid, or any mixture thereof. In another embodiment, a co-crystal with a Compound of Formula (I) comprises L-tartaric acid, fumaric acid, or any mixture thereof. In another embodiment, the co-crystal is of a Compound of Formula (I) and L-tartaric acid. In another embodiment, the co-crystal is of a Compound of Formula (I) and fumaric acid. In another embodiment, the co-crystal contains about one equivalent of a Compound of Formula (I) and about 0.5 equivalents of fumaric acid. In another embodiment, the co-crystal contains one equivalent of a Compound of Formula (I) and 0.5 equivalents of fumaric acid. Analytical techniques, for example, infrared spectroscopy, single crystal x-ray diffraction (XRD), powder x-ray diffraction (PXRD), melting point determination, differential scanning calorimetry (DSC), differential thermal analysis (DTA), thermogravimetric analysis (TGA), solid-state NMR (SSNMR), and x-ray photoelectron spectroscopy (XPS), can be used to elucidate the structure of a co-crystal. In certain embodiments, XRD, SSNMR, and/or XPS is used to determine whether a co-crystal or a salt is present. In certain embodiments when a sufficiently large single crystal cannot be grown, SSNMR or XPS is used to determine whether a co-crystal or a salt is present.

However, the art recognizes that "the exact classification of a compound as a salt or a co-crystal can at times be somewhat ambiguous." Aakeroy et al., at 321. For example, Aakeroy et al. describe a study where x-ray and neutron diffraction were used to study hydrogen bonding between urotropine N-oxide and formic acid as a function of temperature in which the exact location of the proton was found to change with temperature and, under certain conditions, the system displayed partial proton transfer from the acid to the N-oxide moiety, i.e., the system possessed characteristics intermediate between a salt and a co-crystal. Id. Moreover, Pop et al. describe tiotropium fumarate as, simultaneously, a salt and a co-crystal with a stoichiometry of cation:anion:co-former of 2:1:1. Pop et al., "Tiotropium Fumarate: An Interesting Pharmaceutical Co-crystal," J. Pharma. Sci. 98(5):1820-1834 (2009). The structure, determined by XRD, is described as "made up of two monovalent tiotropium cations combined with a divalent fumarate anion to make the salt, plus a non-ionized free fumaric acid moiety to make the co-crystal." Id. Thus in connection with the absence of an indisputably clear distinction between a salt and a co-crystal, it should be understood that the phrase "and combinations thereof", when used in the context of a salt and/or a co-crystal, means that a characteristic attributable to a salt and another characteristic attributable to a co-crystal are simultaneously present in one embodiment; in another embodiment, a characteristic intermediate between the characteristic attributable to a salt and the characteristic attributable to a co-crystal is present.

The term "resolution" refers to the separation or concentration or depletion of one of the two enantiomeric forms of a molecule.

Optical isomers of a compound of Formula I can be obtained by known techniques such as chiral chromatography or formation of diastereomeric salts from an optically active acid or base.

Optical purity can be stated in terms of enantiomeric excess (% ee), which is determined by the formula:

$$\% \ ee = \left[ \frac{\text{major enantiomer(mol)} - \text{minor enantiomer(mol)}}{\text{major enantiomer(mol)} + \text{minor enantiomer(mol)}} \right] \times 100\%.$$

The phrase "effective amount," when used in connection with a compound of Formula I means an amount effective for: (a) treating or preventing a Condition; or (b) inhibiting TRPV1 function in a cell.

The phrase "effective amount," when used in connection with the another therapeutic agent means an amount for providing the therapeutic effect of the therapeutic agent.

The phrase "therapeutic index," describes the gap between the dose that is effective, and the dose that induces adverse effects.

When a first group is "substituted with 1 or 2" second groups or "substituted with 1, 2 or 3" second groups, one or more hydrogen atoms of the first group is replaced with a corresponding number of second groups. When the number of second groups is two or three, each second group can be the same or different. In one embodiment, the number of second groups is one or two. In another embodiment, the number of second groups is two. In another embodiment, the number of second groups is one.

The term "MeOH" means methanol, i.e., methyl alcohol.

The term "EtOH" means ethanol, i.e., ethyl alcohol.

The term "i-Pr" means iso-propyl.

The term "t-BuOH" means tert-butyl alcohol, i.e., 2-methylpropan-2-ol.

The term "THF" means tetrahydrofuran.

The term "DEE" means diethyl ether, i.e., ethoxyethane.

The term "t-BME" means tert-butyl methyl ether, i.e., 2-methoxy-2-methylpropane.

The term "CME" means cyclopentyl methyl ether, i.e., methoxycyclopentane.

The term "DMF" means N,N-dimethylformamide.

The term "DCM" means methylene chloride, i.e., dichloromethane.

The term "DCE" means dichloroethane.

The term "DME" means 1,2-dimethoxyethane, i.e., ethylene glycol dimethyl ether.

The term "EtOAc" means ethyl acetate.

The term "NH$_4$OH" means ammonium hydroxide.

The term "TEA" means triethylamine.

The term "MeCN" means acetonitrile.

The term "NaH" means sodium hydride.

The term "PTSA" means paratoluene sulfonic acid monohydrate.

The term "Py" means pyridine.

The term "Ph" means phenyl.

The term "Me" means methyl.

The term "Et" means ethyl.

The term "AcOH" means acetic acid.

The term "AIBN" means azobisisobutyronitrile.

The term "DIEA" means N,N-diisopropylethylamine or N-ethyldiisopropylamine, i.e., N-ethyl-N-isopropylpropan-2-amine.

The term "DMSO" means dimethylsulfoxide, i.e., methylsulfinylmethane.

The term "DAST" means (diethylamino) sulfur trifluoride.

The term "LiHMDS" means lithium hexamethyldisilazide.

The term "BuLi" means butyl lithium.

The term "DPPP" means 1,3-bis(diphenylphosphino)propane.

The term "X-Phos" means 2-dicyclohexylphosphino-2',4',6'-triisopropylbiphenyl.

The term "Pd$_2$(DBA)$_3$" means tris(dibenzylideneacetone) dipalladium.

The term "BOC" means tert-butyloxycarbonyl:

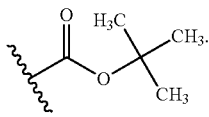

The term "TBS" means tert-butyldimethylsilyl:

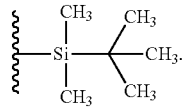

The term "TsOH" means p-toluenesulfonic acid or toluene-4-sulfonic acid.

The term "TMSBr" means trimethylsilyl bromide or (CH$_3$)$_3$SiBr.

The term "TMSCl" means trimethylsilyl chloride or (CH$_3$)$_3$SiCl.

The term "UI" means urinary incontinence.

The term "IBD" means inflammatory-bowel disease.

The term "IBS" means irritable-bowel syndrome.

The term "ALS" means amyotrophic lateral sclerosis.

The phrases "treatment of," "treating" and the like include the amelioration or cessation of a Condition or a symptom thereof.

In one embodiment, treating includes inhibiting, for example, decreasing the overall frequency of episodes of a Condition or a symptom thereof.

The phrases "prevention of," "preventing" and the like include the avoidance of the onset of a Condition or a symptom thereof.

Methods for Making Compounds of Formula I

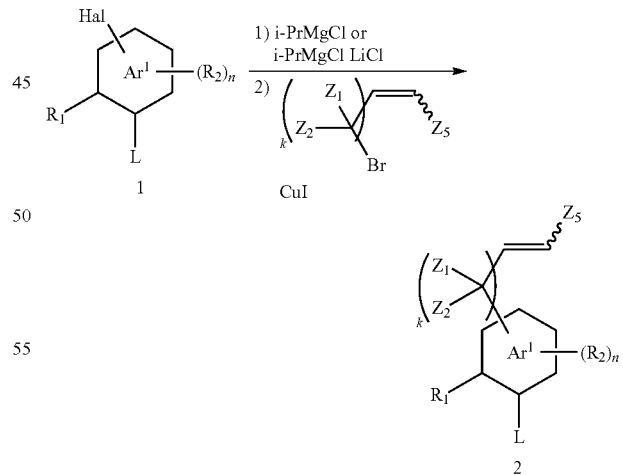

wherein Hal is a halogen such as Br or I, L is a leaving group such as halogen, and Ar$^1$, Z$_1$, Z$_2$, Z$_5$, R$_1$, R$_2$, k and n are as defined above for compounds of Formula I.

To a solution of a compound of formula 1 in THF, DEE, t-BME or CME is added 1 to 3 equivalents of isopropylmagnesium chloride or 1 to 3 equivalent of isopropylmagnesium chloride lithium chloride complex at a temperature of from −20° C. to 25° C. and stirred at a temperature of from −20° C. to 25° C. for from 10 min to 24 hours, preferably from about 30 min to 2 hours. 0.1 to 1 equivalent of copper iodide and 1 to 3 equivalent of allyl bromide or allyl chloride are added to the reaction mixture at a temperature of from −20° C. to 25° C. and stirred at a temperature of from −20° C. to 25° C. for from 10 min to 24 hours, preferably from about 30 min to 2 hours. Then the reaction mixture is quenched with an aqueous acidic solution and extracted with EtOAc or DEE. The resulting organic layer is washed with brine, dried over anhydrous sodium sulfate or magnesium sulfate and concentrated under reduced pressure. The resulting product can be chromatographed with a silica gel column to provide a compound of formula 2.

Once functionalized, 2 can undergo further transformations. Exemplified in scheme 1.2 is the allyl group of 2 undergoing an asymmetric dihydroxylation.

Scheme 1.2

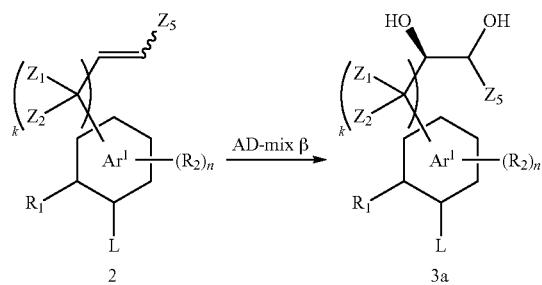

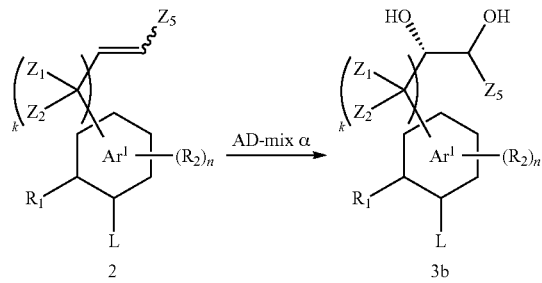

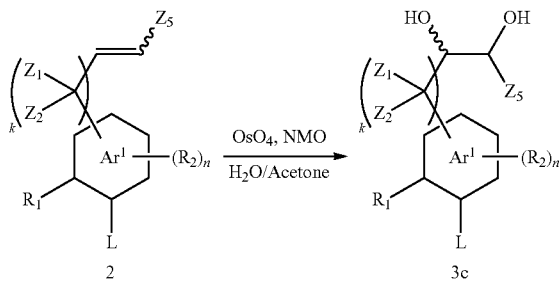

wherein L is a leaving group such as halogen and $Ar^1$, $Z_1$, $Z_2$, $Z_5$, $R_1$, $R_2$, k and n are as defined above for compounds of Formula I.

To a solution of a compound of formula 2 in a mixed solvent of t-butanol or isopropanol and water is added AD-mix 13 (about 0.6 to 2 g/1 mmol of 2) at a temperature of from 0° C. to 25° C. The mixture is stirred at a temperature from 0° C. to 25° C. for 1 hour to 48 hours. The mixture is diluted with EtOAc and saturated $Na_2S_2O_5$. The resulting organic layer is washed with water and brine, dried over anhydrous sodium sulfate or magnesium sulfate and concentrated under reduced pressure. The resulting product can be chromatographed with a silica gel column or recrystallized to provide a compound of formula 3a. The other enantiomer, can be synthesized by the reaction of a compound of formula 2 with AD-mix a to yield a compound of formula 3b. As demonstrated in scheme 1.3, the stereochemistry (R or S) of the resulting diol, is dependent upon the chirality of the ligand used in the AD mix as described in K. B. Sharpless et al., *J. Org. Chem.* 57:2768-2771 (1992). AD-mix is composed of the following components: potassium osmate ($K_2OsO_2(OH)_4$), potassium ferricyanide ($K_3Fe(CN)_6$), potassium carbonate ($K_2CO_3$), and the chiral ligands, $(DHQ)_2PHAL$ and $(DHQD)_2PHAL$ are shown in scheme 1.3.

Scheme 1.3

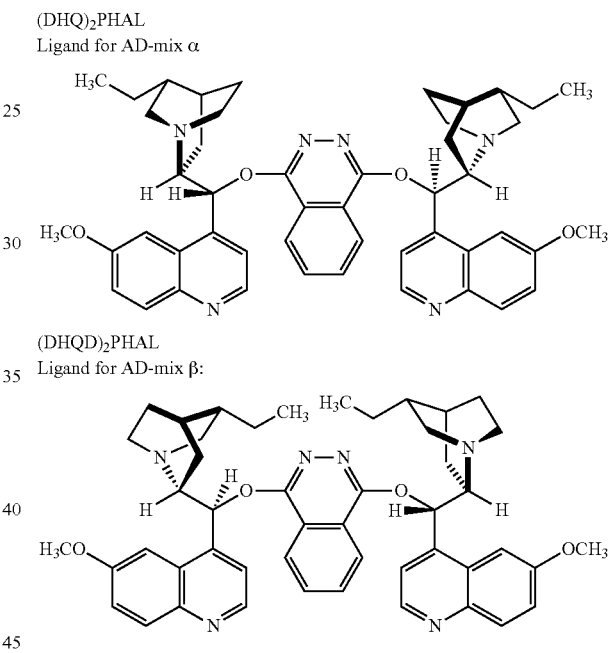

The racemic diol, 3c, can be synthesized by methods known in the art, using osmium tetroxide ($OsO_4$) and N-methyl morpholine N-oxide (NMO) in an aqueous acetone solution.

Scheme 1.4

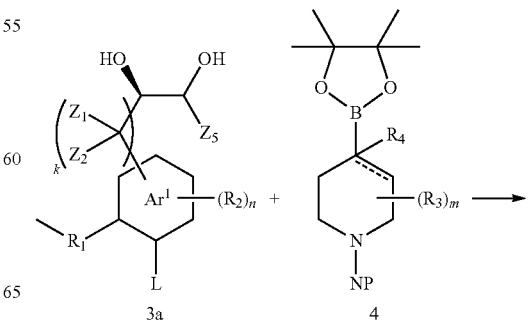

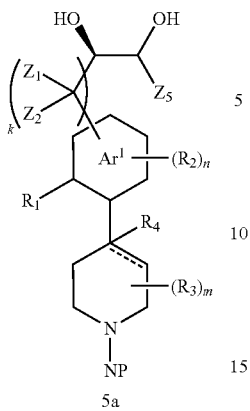

5a

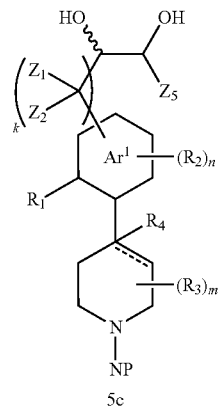

5c wherein NP is an amino protecting group and the dashed line, $Ar^1, Z_1, Z_2, Z_5, R_1, R_2, R_3, R_4$, k, m, and n are as defined above for compounds of Formula I.

To a solution of a compound of formula 3a in toluene, ethanol, DME 1,4-dioxane, THF or the like or a mixed solvent of these are added 1 to 3 equivalents of a compound of formula 4, 0.01 to 0.1 equivalents of a palladium catalyst such palladium acetate, bis(diphenylphosphino)ferrocene palladium chloride, tris(dibenzylideneacetone)dipalladium(0) or bis(triphenylphosphine)palladium dichloride and 2 to 5 equivalents of a base such potassium carbonate or sodium carbonate at from 25° C. to reflux temperature, preferably from 60° C. to reflux temperature for from 0.5 hour to 24 hours preferably from 1 hour to 8 hours. Then the reaction mixture is quenched with an aqueous acidic solution and extracted with EtOAc or DEE. The resulting organic layer is washed with brine, dried over anhydrous sodium sulfate or magnesium sulfate and concentrated under reduced pressure. The resulting product can be chromatographed with a silica gel column or recrystallized to provide a compound of formula 5a. Similarly, a compound of formula 3b or 3c can be reacted to provide a compound of formula 5b or 5c, respectively.

A compound of formula 5a, 5b or 5c wherein the dashed line demotes the absence of a bond can be obtained by a coupling reaction known to one skilled in the art using an alkylboronate in place of the compound of formula 4.

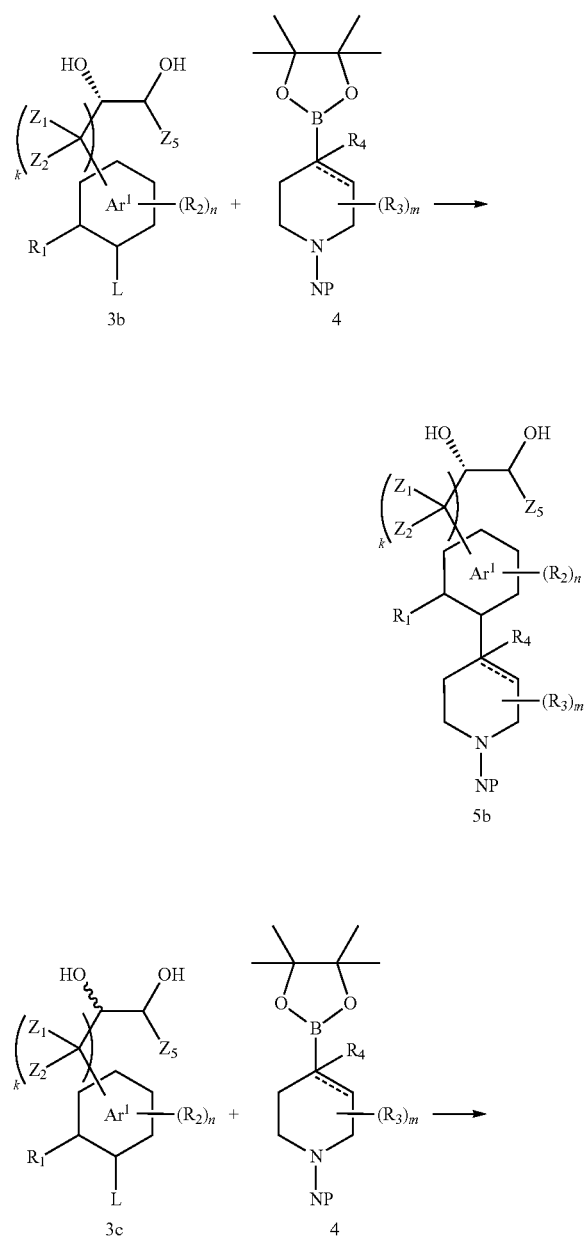

Scheme 1.5

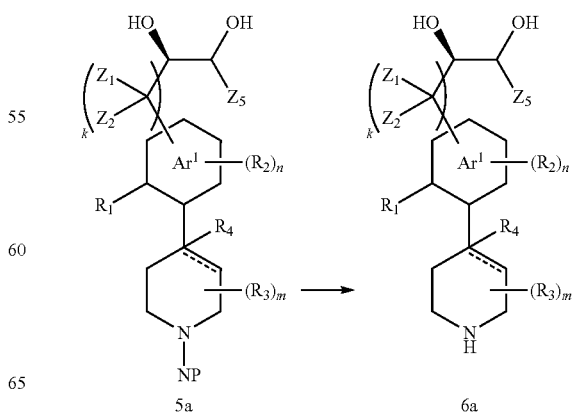

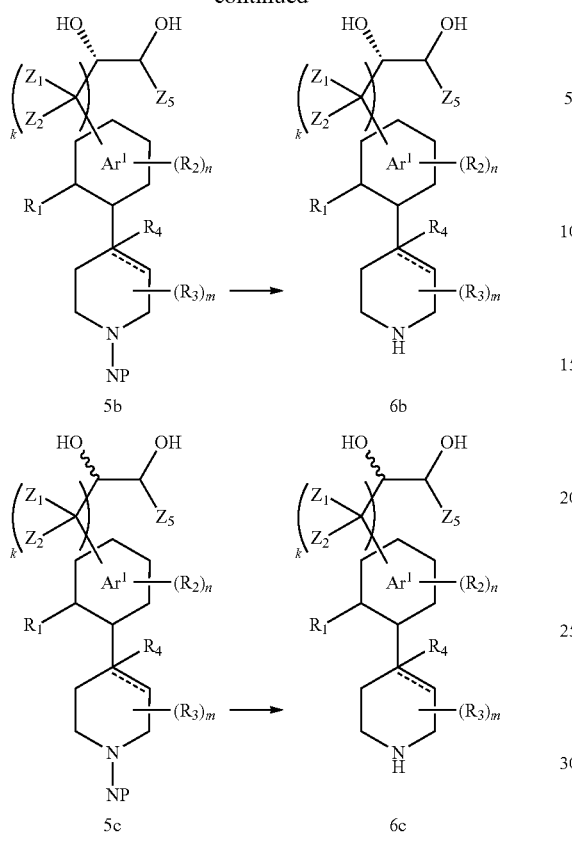

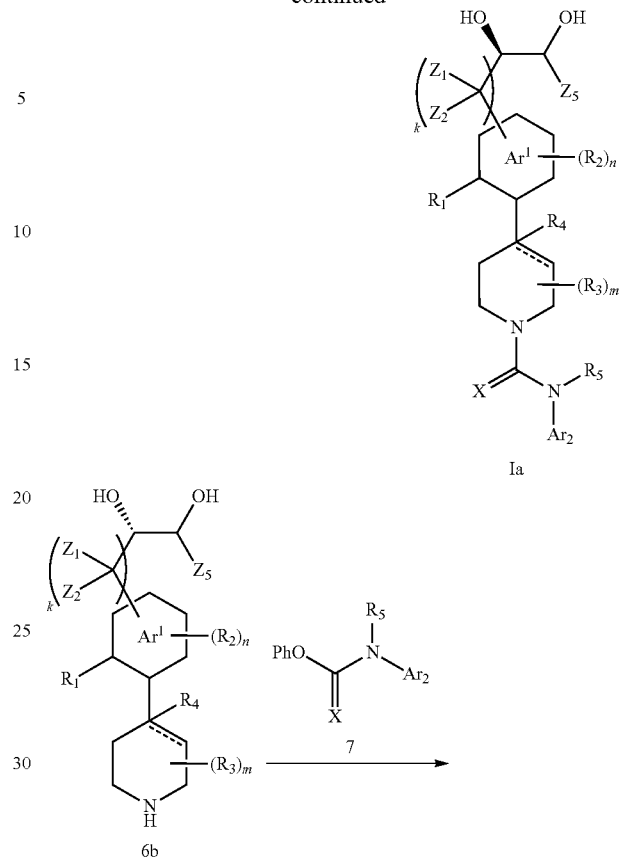

wherein NP is an amino protecting group and the dashed line, $Ar^1$, $Z_1$, $Z_2$, $Z_5$, $R_1$, $R_2$, $R_3$, $R_4$, k, m, and n are as defined above for compounds of Formula I.

To a solution of a compound of formula 5a in 1,4-dioxane, THF, dichloromethane or methanol or a mixed solvent of these are added 1 to 30 equivalents of HCl at a temperature of from −20° C. to 25° C. and stirred at a temperature of from −20° C. to 25° C. for from 1 hour to 48 hours, preferably from about 2 hours to 24 hours. Then the resulting solid is filtered to provide a compound of formula 6a as a salt of HCl. Similarly, a compound of formula 5b or 5c can be reacted to provide a compound of formula 6b or 6c, respectively.

Scheme 1.6

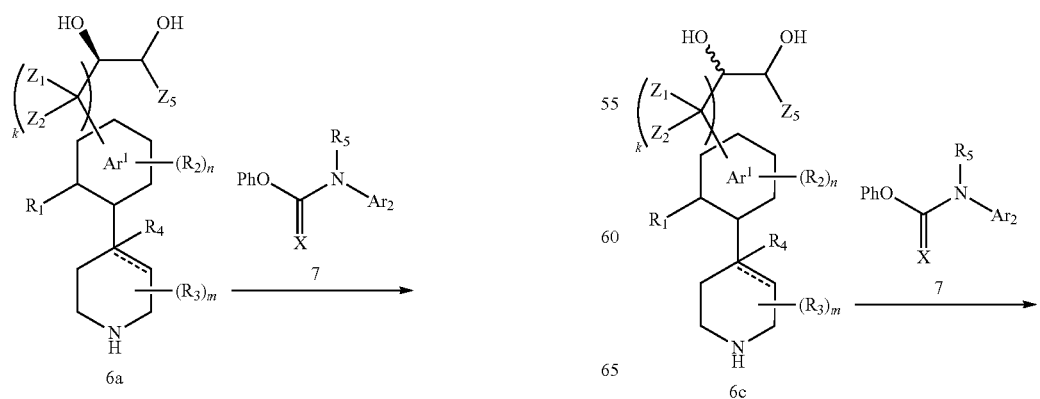

-continued

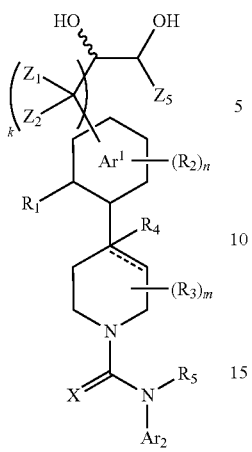

Ic wherein $Ar^1$, $Ar^2$, X, $Z_1$, $Z_2$, $Z_5$, $R_1$, $R_2$, $R_3$, $R_4$, $R_5$, k, m, and n are as defined above for compounds of Formula I.

To a suspension of a compound of formula 6a in dichloromethane, chloroform or THF are added 1 to 5 equivalents of triethylamine, diisopropylethylamine or pyridine and 1 to 3 equivalents of a compound of formula 7 at a temperature of from −20° C. to 25° C. The reaction is stirred at a temperature from 0° C. to 25° C. for from 10 min to 48 hours, preferably from 1 hour to 8 hours. Then the reaction mixture is quenched with an aqueous acidic solution and extracted with EtOAc or DEE. The resulting organic layer is washed with brine, dried over anhydrous sodium sulfate or magnesium sulfate and concentrated under reduced pressure. The resulting product can be chromatographed with a silica gel column or recrystallized to provide a compound of Formula Ia. Similarly, a compound of formula 6b or 6c can be reacted to provide a compound of Formula Ib or Ic, respectively.

Thus-obtained compound wherein $Z_3$ and $Z_4$ is —OH can be converted to the compounds wherein $Z_3$ and/or $Z_4$ is —N$(R_{12})_2$ or compounds wherein $Z_3$ and/or $Z_4$ is —OR$_{12}$ using ordinary methods known to one skilled in the art.

Scheme 2.1

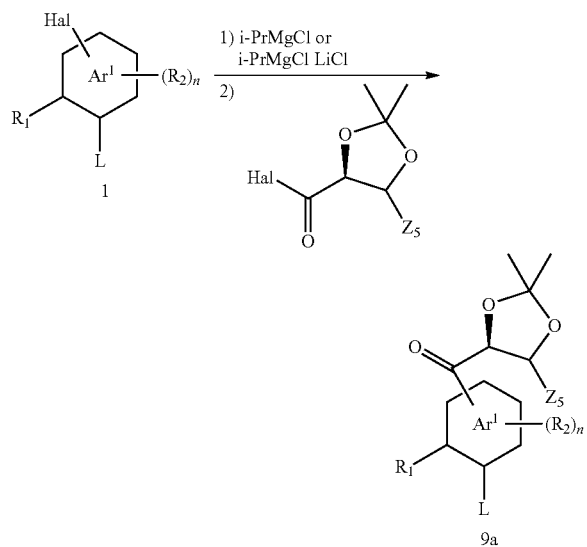

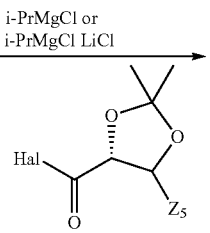

wherein Hal is a halogen such as Br or I, L is a leaving group such as halogen, and $Ar^1$, $Z_5$, $R_1$, $R_2$, and n are as defined above for compounds of Formula I.

To the solution of a compound of formula 1 in THF, DEE, t-BME or CME is added 1 to 3 equivalents of isopropylmagnesium chloride or 1 to 3 equivalents of isopropylmagnesium chloride lithium chloride complex at a temperature of from −20° C. to 25° C. and stirred at a temperature of from −20° C. to 25° C. for from 10 min to 24 hours, preferably from about 30 min to 2 hours. One to 3 equivalents of (S)-N-methoxy-N,2,2-trimethyl-1,3-dioxolane-4-carboxamide, (S)-(2,2-dimethyl-1,3-dioxolan-4-yl)(morpholino)methanone, or (S)-(2,2-dimethyl-1,3-dioxolan-4-yl)(pyrrolidin-1-yl) methanone is added to the reaction mixture at a temperature of from −20° C. to 25° C. and stirred at a temperature of from −20° C. to 25° C. for from 10 min to 24 hours, preferably from about 30 min to 2 hours. Then the reaction mixture is quenched with an aqueous acidic solution and extracted with EtOAc or DEE. The resulting organic layer is washed with brine, dried over anhydrous sodium sulfate or magnesium sulfate and concentrated under reduced pressure. The resulting product can be chromatographed with a silica gel column or recrystallized to provide a compound of formula 9a. The other enantiomer, can be synthesized by the reaction of a compound of formula 1 with (R)-N-methoxy-N,2,2-trimethyl-1,3-dioxolane-4-carboxamide, (R)-(2,2-dimethyl-1,3-dioxolan-4-yl)(morpholino)methanone or (R)-(2,2-dimethyl-1,3-dioxolan-4-yl)(pyrrolidin-1-yl)methanone to yield a compound of formula 9b.

Scheme 2.2

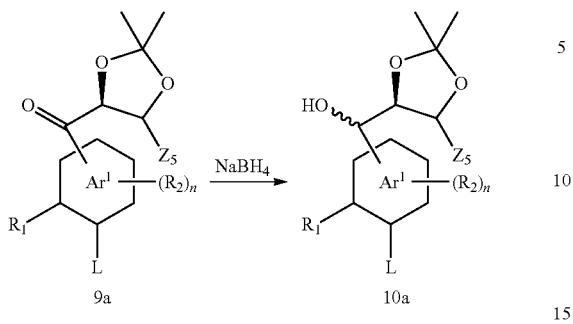

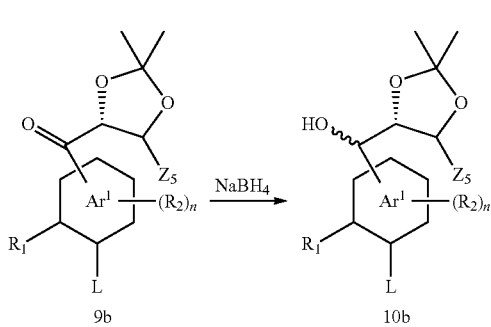

wherein L is a leaving group such as halogen and Ar¹, Z₅, R₁, R₂, and n are as defined above for compounds of Formula I.

To the solution of a compound of formula 9a in methanol, ethanol, THF or a mixed solvent of these is added 0.25 to 2 equivalents of sodium borohydride at a temperature of from −20° C. to 25° C. and stirred at a temperature of from −20° C. to 25° C. for from 10 min to 24 hours, preferably from about 30 min to 2 hours. Then the reaction mixture is quenched with an aqueous acidic solution or acetic acid and extracted with EtOAc or DEE. The resulting organic layer is washed with brine, dried over anhydrous sodium sulfate or magnesium sulfate and concentrated under reduced pressure. The resulting product can be chromatographed with a silica gel column or recrystallized to provide a compound of formula 10a. The other enantiomer, can be synthesized by the reaction of a compound of formula 9b to yield a compound of formula 10b.

Scheme 2.3

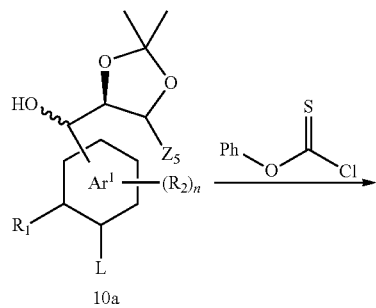

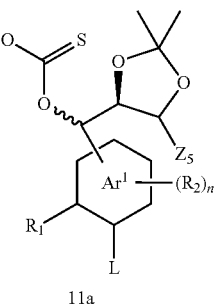

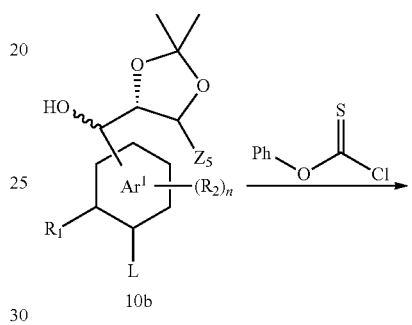

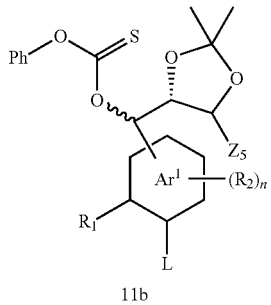

wherein L is a leaving group such as halogen and Ar¹, R₁, R₂, and n are as defined above for compounds of Formula I.

To a solution of a compound of formula 10a in dichloromethane, chloroform or THF is added 1 to 3 equivalents of phenyl chlorothioformate with 1 to 30 equivalents of pyridine, triethylamine or diisopropylethylamine at a temperature of from −20° C. to 25° C. and stirred at a temperature of from −20° C. to 25° C. for from 10 min to 24 hours, preferably from about 1 hour to 4 hours. Then the reaction mixture is quenched with an aqueous acidic solution and extracted with or dichloromethane, chloroform or EtOAc. The resulting organic layer is washed with brine, dried over anhydrous sodium sulfate or magnesium sulfate and concentrated under reduced pressure. The resulting product can be chromatographed with a silica gel column or recrystallized to provide a compound of formula 11a. The other enantiomer, can be synthesized by the reaction of a compound of formula 10b to yield a compound of formula 11b.

Scheme 2.4

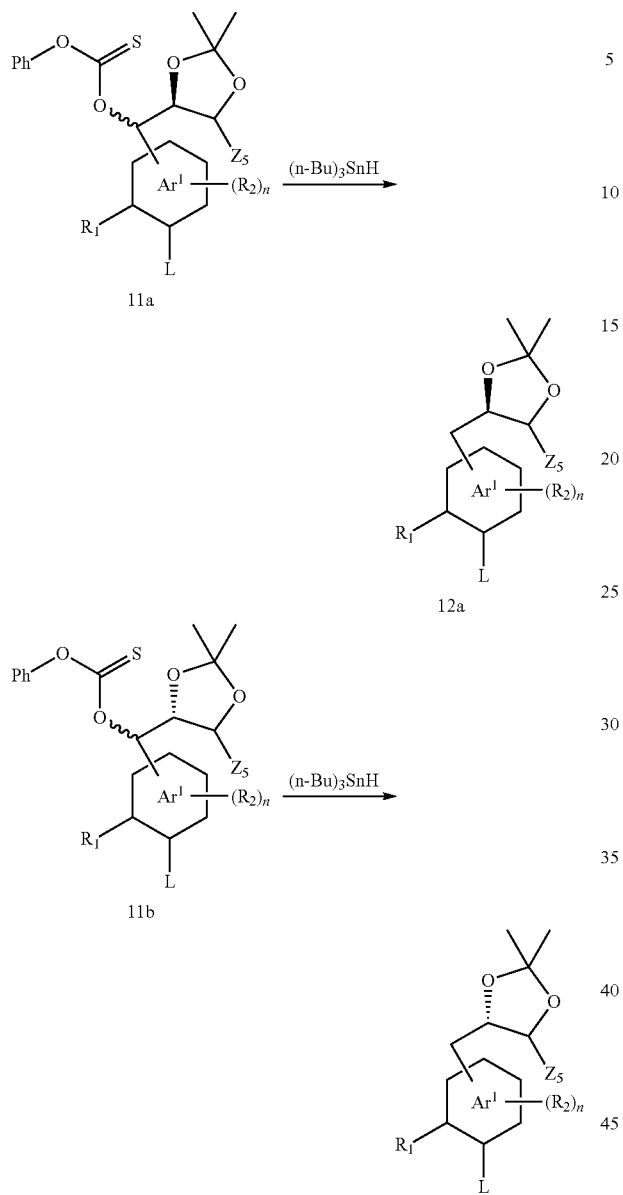

Scheme 2.5

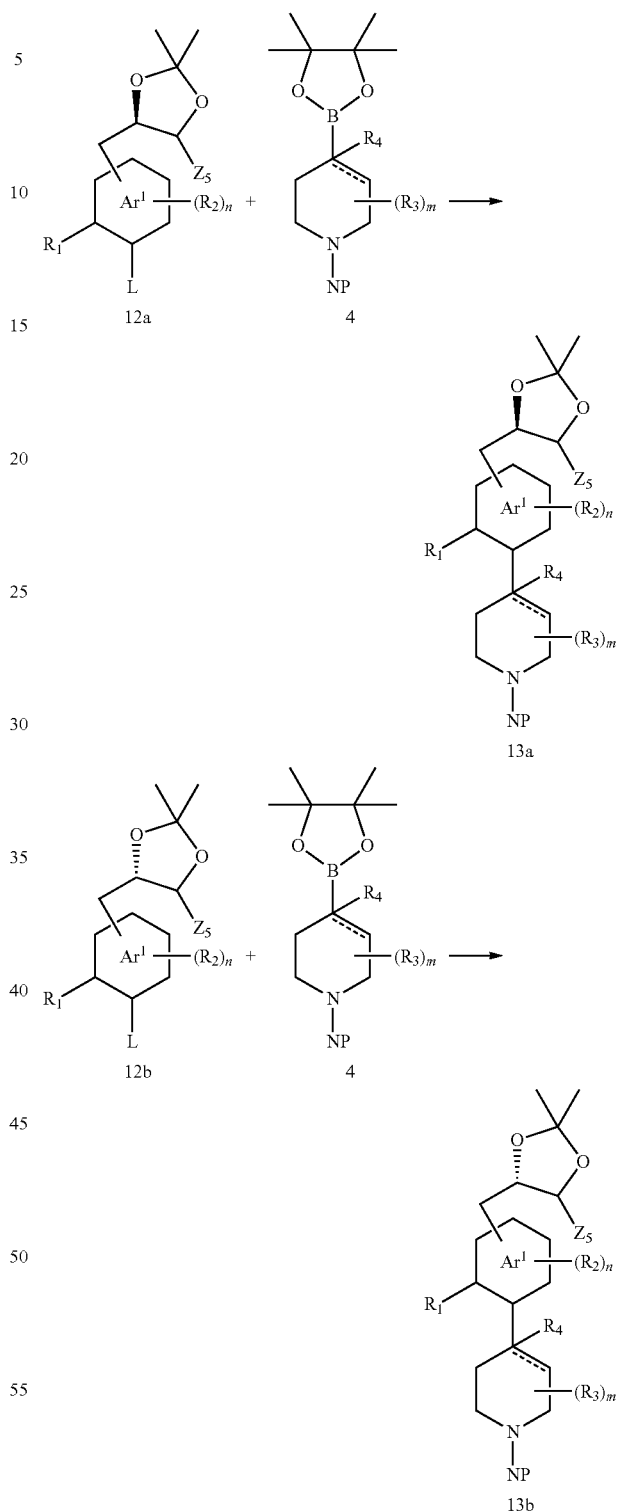

wherein L is a leaving group such as halogen and $Ar^1$, $Z_5$, $R_1$, $R_2$, and n are as defined above for compounds of Formula I.

To a solution of a compound of formula 11a in benzene or toluene is added 1 to 3 equivalents of tributylstannane with 0.1 to 1 equivalent of azoisobutylonitrile at a temperature of from 25° C. to 50° C. and stirred at from 50° C. to reflux temperature for from 10 min to 24 hours, preferably from about 2 hours to 8 hours. Then the reaction mixture is quenched with aqueous potassium fluoride solution and extracted with EtOAc or DEE. The resulting organic layer is washed with brine, dried over anhydrous sodium sulfate or magnesium sulfate and concentrated under reduced pressure. The resulting product can be chromatographed with a silica gel column or recrystallized to provide a compound of formula 12a. The other enantiomer, can be synthesized by the reaction of a compound of formula 11b to yield a compound of formula 12b.

wherein L is a leaving group such as halogen, NP is an amino protecting group, and the dashed line, $Ar^1$, $Z_5$, $R_1$, $R_2$, $R_3$, $R_4$, m, and n are as defined above for compounds of Formula I.

A compound of formula 13a or 13b is synthesized according to a procedure analogous to that described above in Scheme 1.4.

Scheme 2.6

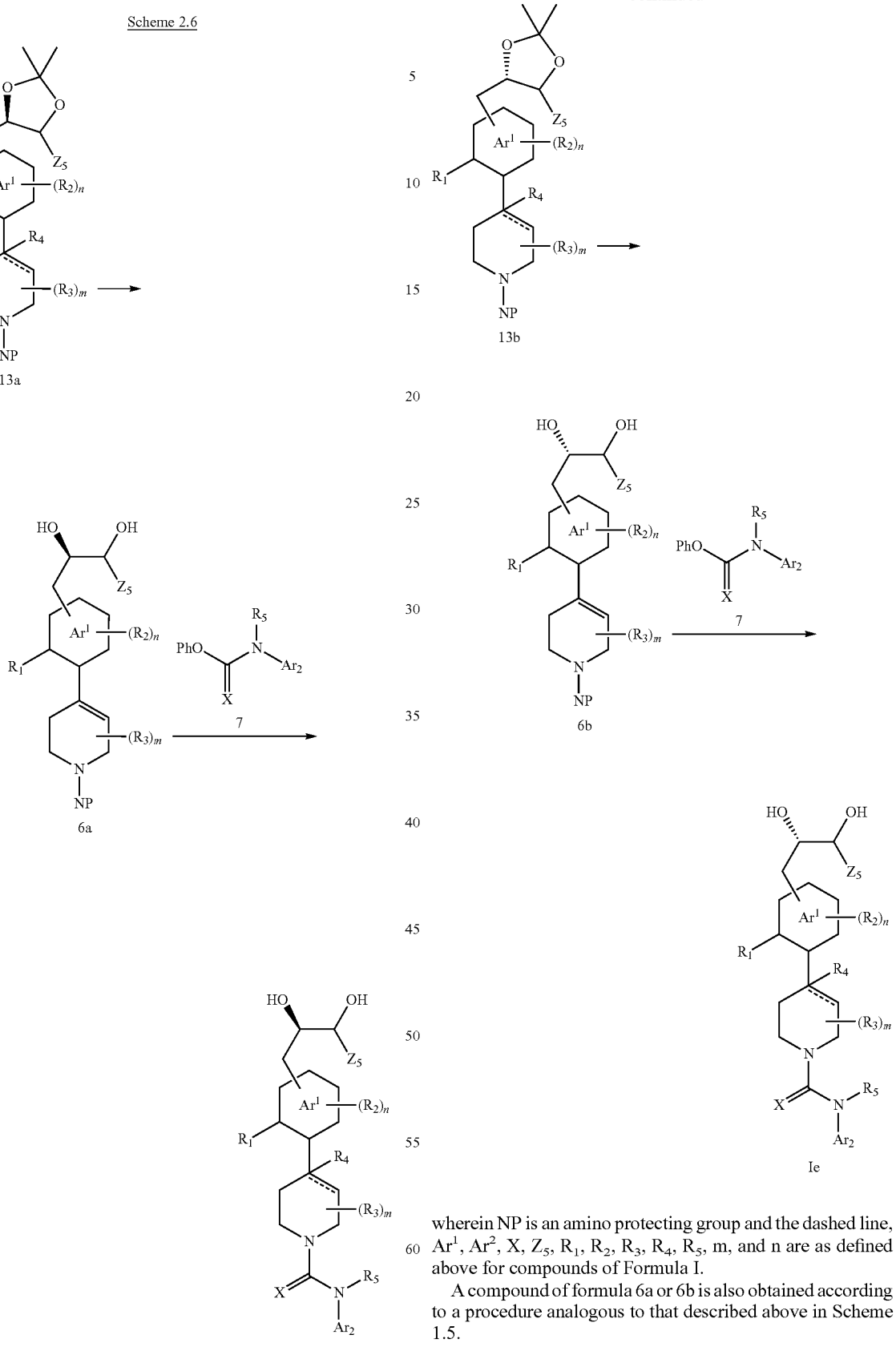

wherein NP is an amino protecting group and the dashed line, Ar¹, Ar², X, $Z_5$, $R_1$, $R_2$, $R_3$, $R_4$, $R_5$, m, and n are as defined above for compounds of Formula I.

A compound of formula 6a or 6b is also obtained according to a procedure analogous to that described above in Scheme 1.5.

Compound of formula Id or Ie can be obtained from compound of formula 6a or 6b by the procedures described above in Scheme 1.6.

Scheme 3.1

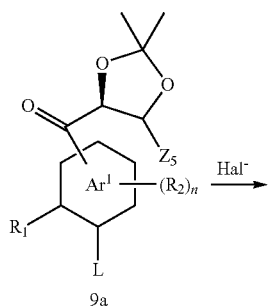
9a

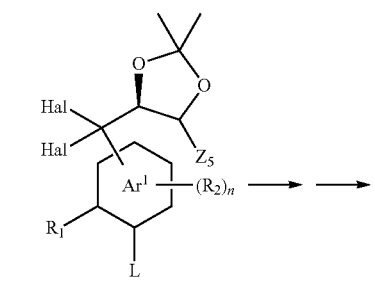
14a

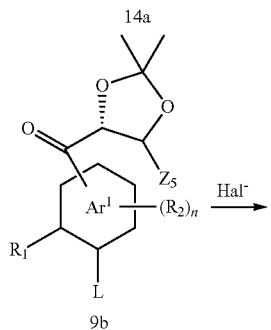
9b

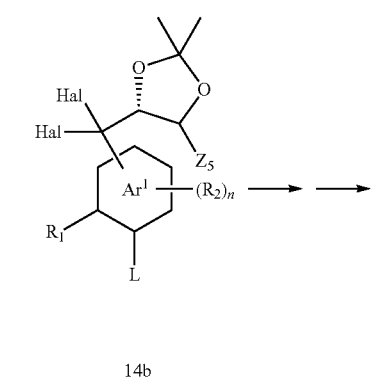
14b

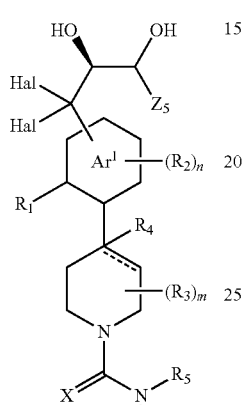

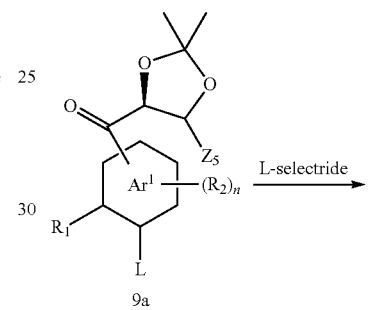
If

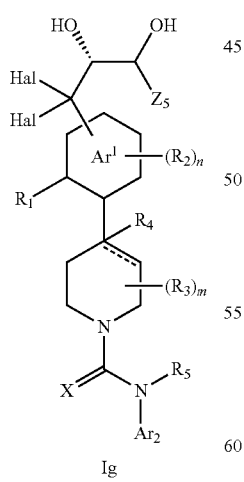
Ig wherein Hal is a halogen such as Br or I, L is a leaving group such as halogen, and the dashed line, $Ar^1$, $Ar^2$, X, $Z_5$, $R_1$, $R_2$, $R_3$, $R_4$, $R_5$, m, and n are as defined above for compounds of Formula I.

To a solution of a compound of formula 9a in benzene, toluene is added 1 to 3 equivalents of (diethylamino) sulfur trihalide or bis(methoxyethyl)aminosulfur trihalide at a temperature of from 0° C. to 25° C. and stirred at from 25° C. to reflux temperature for from 10 min to 24 hours, preferably from about 2 hours to 8 hours. Then the reaction mixture is quenched with an aqueous acidic solution and extracted with EtOAc or DEE. The resulting organic layer is washed with brine, dried over anhydrous sodium sulfate or magnesium sulfate and concentrated under reduced pressure. The resulting product can be chromatographed with a silica gel column or recrystallized to provide a compound of formula 14a. The other enantiomer, can be synthesized by the reaction of a compound of formula 9b to yield a compound of formula 14b.

Compound of formula If or Ig can be obtained from compound of formula 14a or 14b by the procedures described above in Schemes 2.5 and 2.6.

Scheme 4.1

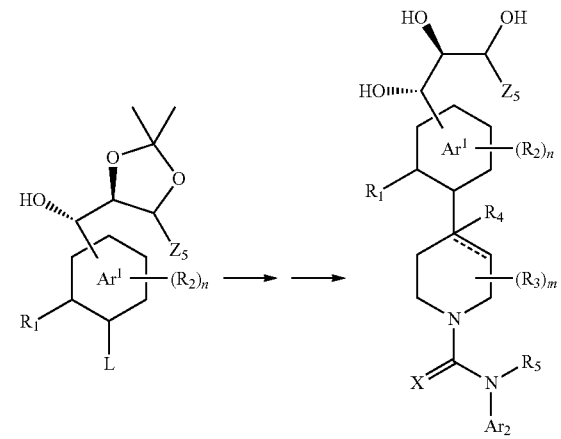

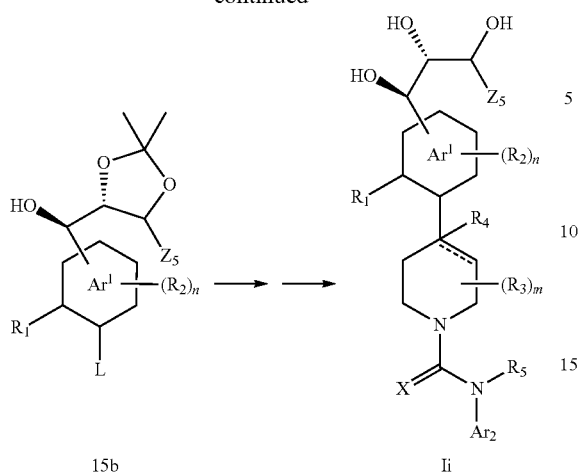

wherein L is a leaving group such as halogen and the dashed line, $Ar^1, Ar^2, X, Z_5, R_1, R_2, R_3, R_4, R_5$, m, and n are as defined above for compounds of Formula I.

To a solution of a compound of formula 9a in hexane, THF, DEE or the like solvent is added 1 to 3 equivalents of L-selectride at a temperature of from −78° C. to 25° C. and stirred at a temperature of from −20° C. to 25° C. for from 10 min to 24 hours, preferably from about 30 min to 2 hours. Then the reaction mixture is quenched with an aqueous acidic solution or acetic acid and extracted with EtOAc or DEE. The resulting organic layer is washed with brine, dried over anhydrous sodium sulfate or magnesium sulfate and concentrated under reduced pressure. The resulting product can be chromatographed with a silica gel column or recrystallized to provide a compound of formula 15a. The other enantiomer, can be synthesized by the reaction of a compound of formula 9b to yield a compound of formula 15b. As demonstrated in scheme 4.1, the stereochemistry (R or S) of the resulting alcohol at 1-position, is dependent upon the chirality of the 2,2-trimethyl-1,3-dioxolane moiety as described in H. Chikashita et al., *Bull. Chem. Soc. Jpn.* 62:2121-2123 (1989).

Compound of formula Ih or Ii can be obtained from compound of formula 15a or 15b by the procedures described above in Schemes 2.5 and 2.6.

Scheme 5.1

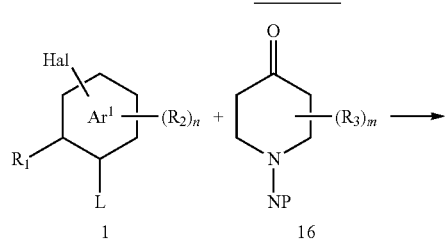

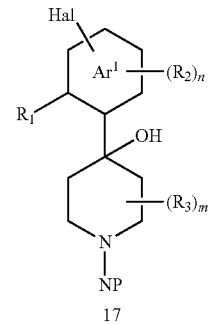

wherein Hal is a halogen such as Br or I, L is a leaving group such as halogen, NP is an amino protecting group, and $Ar^1$, $R_1, R_2, R_3$, m, and n are as defined above for compounds of Formula I.

To a solution of a compound of formula 1 in THF, DEE or toluene is added 1 to 2 equivalents of n-butyl lithium, sec-butyl lithium or tert-butyl lithium at a temperature of from −78° C. to 25° C., preferably from −78° C. to −20° C., and stirred at a temperature of from −78° C. to 25° C. for from 10 min to 24 hours, preferably from about 15 min to 2 hours. The compound of formula 16 is added to the reaction mixture at a temperature of from −78° C. to 25° C., preferably from −78° C. to 0° C., for from 10 min to 24 hours, preferably from 1 hour to 4 hours. Then the reaction mixture is quenched with an aqueous acidic solution and extracted with EtOAc or DEE. The resulting organic layer is washed with brine, dried over anhydrous sodium sulfate or magnesium sulfate and concentrated under reduced pressure. The resulting product can be chromatographed with a silica gel column or recrystallized to provide a compound of formula 17.

Scheme 5.2

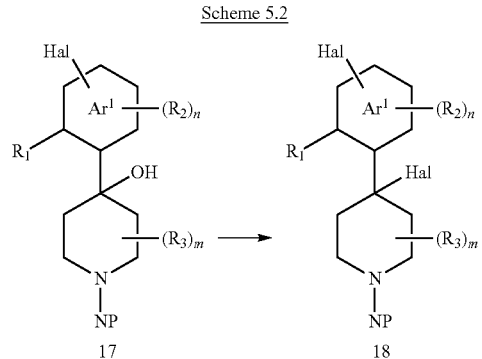

wherein Hal is a halogen such as Br or I, NP is an amino protecting group, and $Ar^1, R_1, R_2, R_3$, m, and n are as defined above for compounds of Formula I.

To a solution of a compound of formula 17 in dichloromethane or toluene is added 1 to 3 equivalents of (diethylamino) sulfur trihalide or bis(methoxyethyl)aminosulfur trihalide at a temperature of from −78° C. to 0° C. and stirred at a temperature of from −78° C. to 0° C. for from 10 min to 24 hours, preferably from about 1 hours to 4 hours. Then the reaction mixture is quenched with an aqueous acidic solution and extracted with dichloromethane or EtOAc. The resulting organic layer is washed with brine, dried over anhydrous sodium sulfate or magnesium sulfate and concentrated under reduced pressure. The resulting product can be chromatographed with a silica gel column or recrystallized to provide a compound of formula 18.

Scheme 5.3

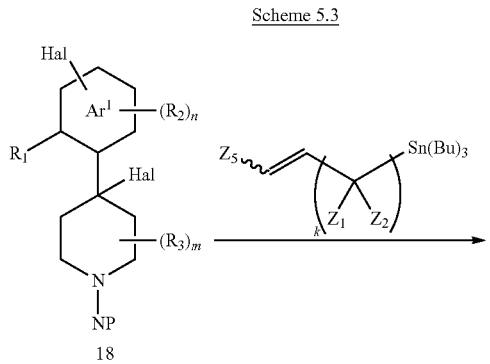

Scheme 5.4

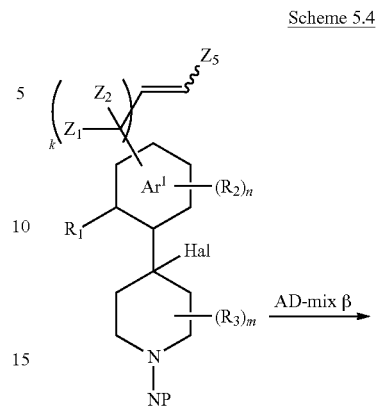

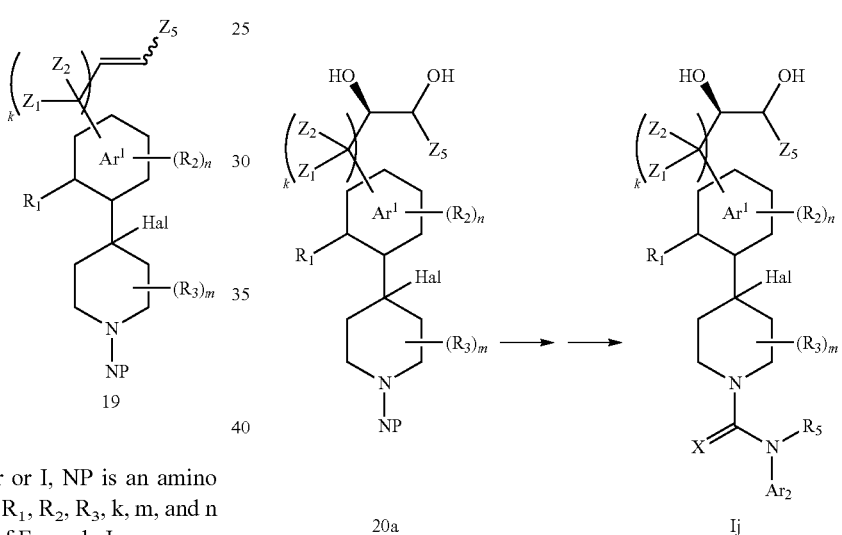

wherein Hal is a halogen such as Br or I, NP is an amino protecting group, and $Ar^1$, $Z_1$, $Z_2$, $Z_5$, $R_1$, $R_2$, $R_3$, k, m, and n are as defined above for compounds of Formula I.

To a solution of a compound of formula 18 in toluene, 1,4-dioxane, THF or the like or a mixed solvent of these are added 1 to 3 equivalents of allyltributylstannane, together with 0.01 to 0.1 equivalents of a palladium catalyst such palladium acetate, bis(diphenylphosphino)ferrocene palladium chloride, tris(dibenzylideneacetone)dipalladium(0) or bis(triphenylphosphine)palladium dichloride and 2 to 5 equivalents of a base such potassium fluoride, cesium fluoride or tetrabuthylammonium fluoride, at from 25° C. to reflux temperature, preferably from 50° C. to reflux temperature for from 0.5 hour to 24 hours preferably from 1 hour to 8 hours. Then the reaction mixture is quenched with an aqueous acidic solution and extracted with EtOAc or DEE. The resulting organic layer is washed with brine, dried over anhydrous sodium sulfate or magnesium sulfate and concentrated under reduced pressure. The resulting product can be chromatographed with a silica gel column or recrystallized to provide a compound of formula 19.

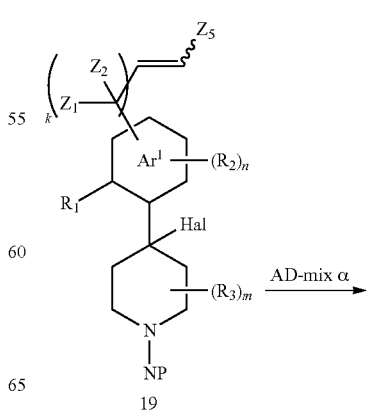

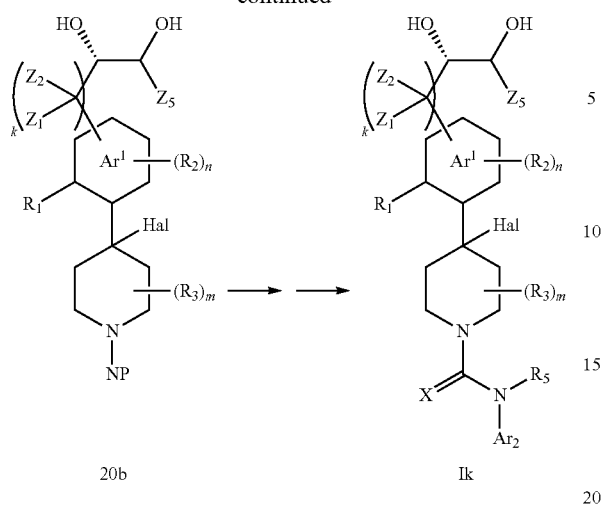

20b    Ik wherein NP is an amino protecting group and $Ar^1$, $Ar^2$, X, $Z_1$, $Z_2$, $Z_5$, $R_1$, $R_2$, $R_3$, $R_5$, k, m, and n are as defined above for compounds of Formula I.

A compound of formula 20a or 20b is obtained according to a procedure analogous to that described above in Scheme 1.2.

Compound of formula Ij or Ik can be obtained from compound of formula 20a or 20b by the procedures described above in Schemes 1.5 and 1.6.

Scheme 6.1

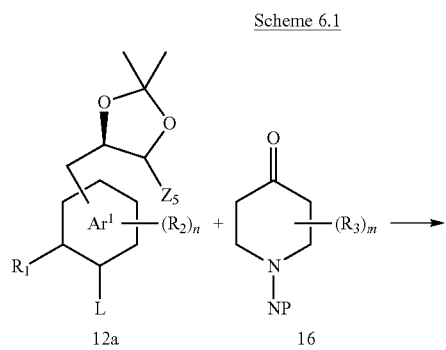

12a    16

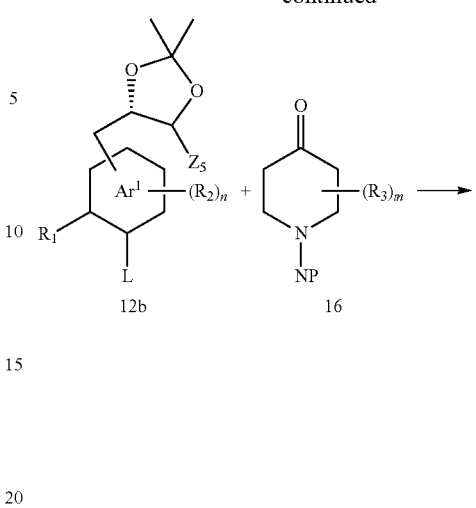

12b    16

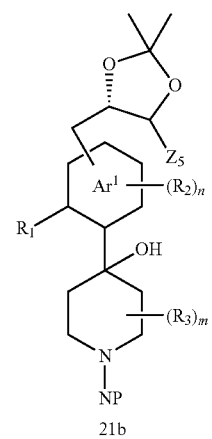

21b wherein L is a leaving group such as halogen, NP is an amino protecting group, and $Ar^1$, $Z_5$, $R_1$, $R_2$, $R_3$, m, and n are as defined above for compounds of Formula I.

A compound of formula 21a or 21b is obtained according to a procedure analogous to that described above in Scheme 5.1.

Scheme 6.2

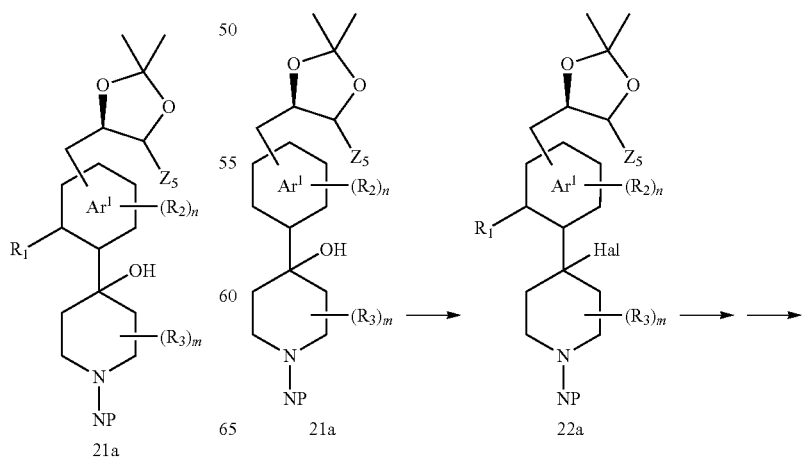

21a    21a    22a

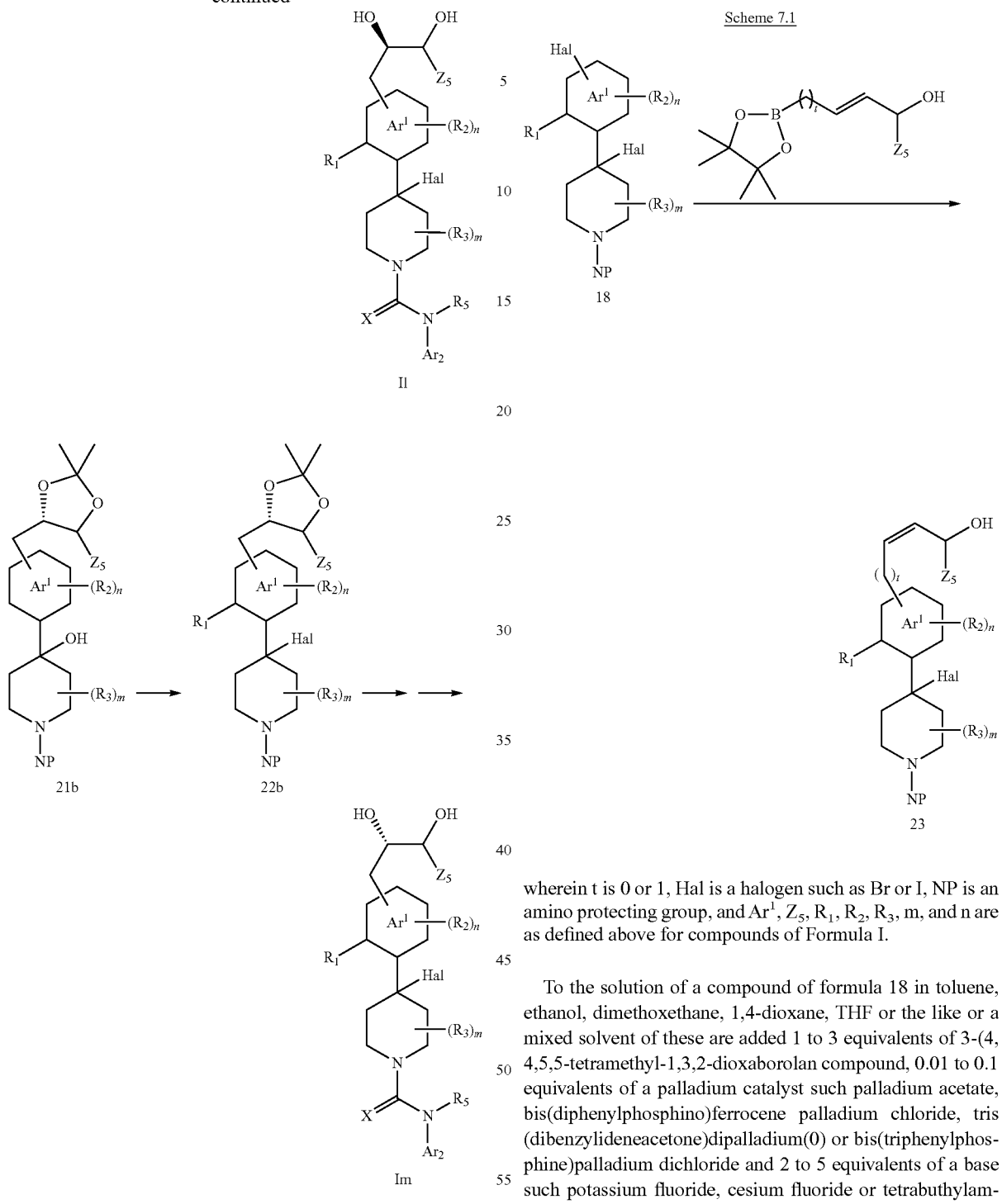

wherein t is 0 or 1, Hal is a halogen such as Br or I, NP is an amino protecting group, and $Ar^1$, $Z_5$, $R_1$, $R_2$, $R_3$, m, and n are as defined above for compounds of Formula I.

To the solution of a compound of formula 18 in toluene, ethanol, dimethoxethane, 1,4-dioxane, THF or the like or a mixed solvent of these are added 1 to 3 equivalents of 3-(4, 4,5,5-tetramethyl-1,3,2-dioxaborolan compound, 0.01 to 0.1 equivalents of a palladium catalyst such palladium acetate, bis(diphenylphosphino)ferrocene palladium chloride, tris (dibenzylideneacetone)dipalladium(0) or bis(triphenylphosphine)palladium dichloride and 2 to 5 equivalents of a base such potassium fluoride, cesium fluoride or tetrabuthylammonium fluoride, at from 25° C. to reflux temperature, preferably from 60° C. to reflux temperature for from 0.5 hour to 24 hours preferably from 1 hour to 4 hours. Then the reaction mixture is quenched with an aqueous acidic solution and extracted with EtOAc or DEE. The resulting organic layer is washed with brine, dried over anhydrous sodium sulfate or magnesium sulfate and concentrated under reduced pressure. The resulting product can be chromatographed with a silica gel column or recrystallized to provide a compound of formula 23.

wherein Hal is a halogen such as Br or I, NP is an amino protecting group, and $Ar^1$, $Ar^2$, X, $Z_5$, $R_1$, $R_2$, $R_3$, $R_5$, m, and n are as defined above for compounds of Formula I.

A compound of formula 22a or 22b is obtained according to a procedure analogous to that described above in Scheme 5.2.

Compound Il or Im can be obtained from compound of formula 6a or 6b by the procedures described above in Schemes 2.5 and 2.6.

Scheme 7.2

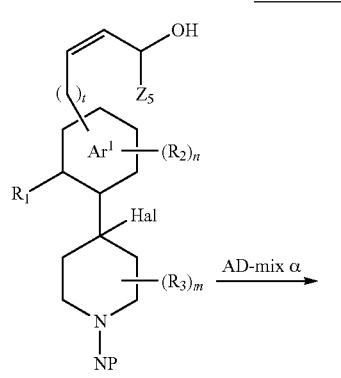

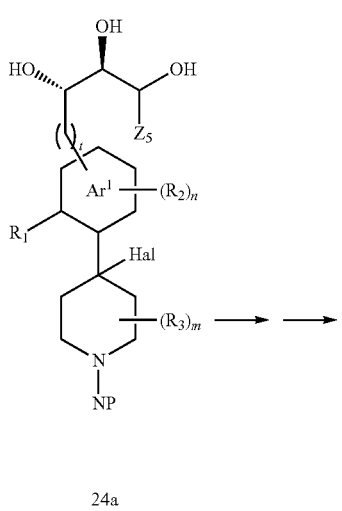

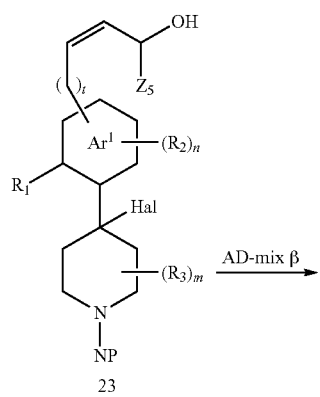

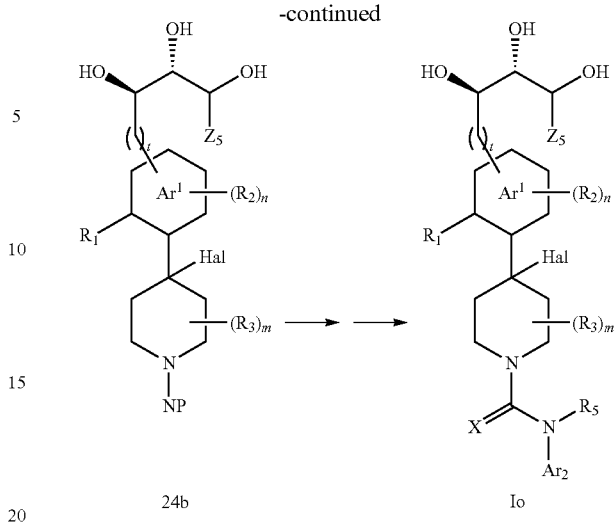

wherein t is 0 or 1, Hal is a halogen such as Br or I, NP is an amino protecting group, and $Ar^1$, $Ar^2$, X, $Z_5$, $R_1$, $R_2$, $R_3$, $R_5$, m, and n are as defined above for compounds of Formula I.

A compound of formula 24a or 24b is obtained according to a procedure analogous to that described above in Scheme 1.2.

Compound of formula In or Io can be obtained from compound of formula 24a or 24b by the procedures described above in Schemes 1.5 and 1.6.

Scheme 8.1

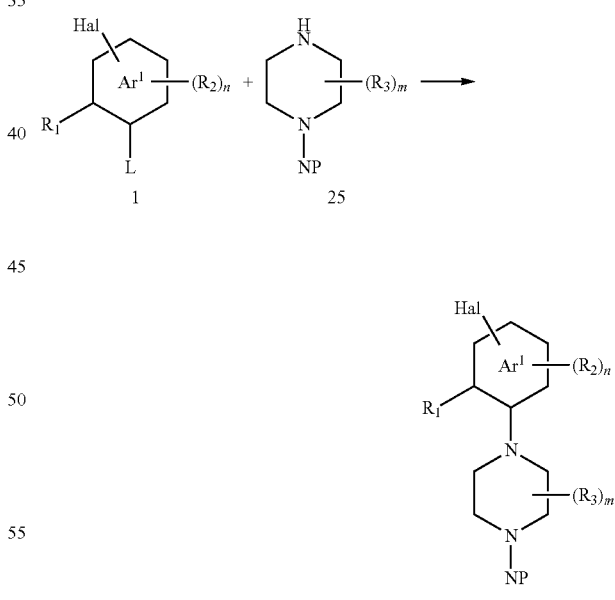

wherein Hal is a halogen such as Br or I, L is a leaving group such as halogen, NP is an amino protecting group, and $Ar^1$, $R_1$, $R_2$, $R_3$, m, and n are as defined above for compounds of Formula I.

A compound of formula 26 is obtained according to a procedure analogous to that described in Scheme 3.4 in WO2008/132600.

Scheme 8.2
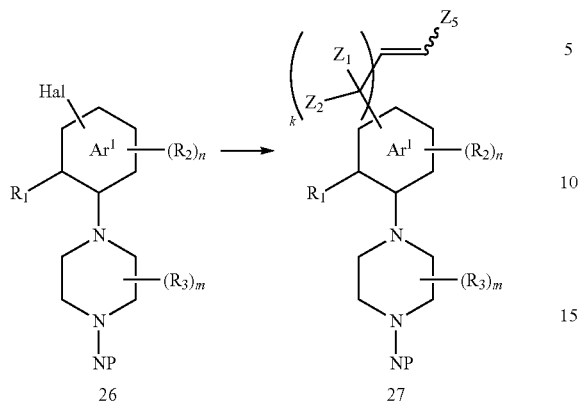
wherein Hal is a halogen such as Br or I, NP is an amino protecting group, and $Ar^1$, $Z_1$, $Z_2$, $Z_5$, $R_1$, $R_2$, $R_3$, k, m, and n are as defined above for compounds of Formula I.
A compound of formula 27 is obtained according to a procedure analogous to that described above in Scheme 1.1.
Scheme 8.3
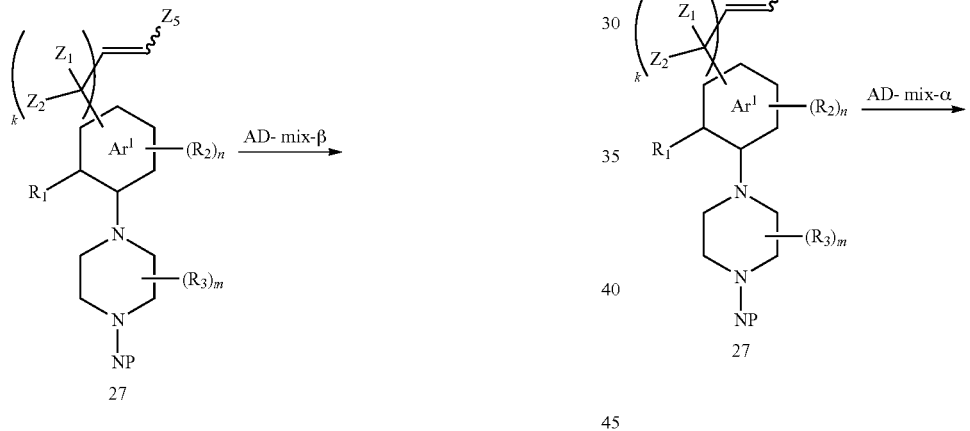
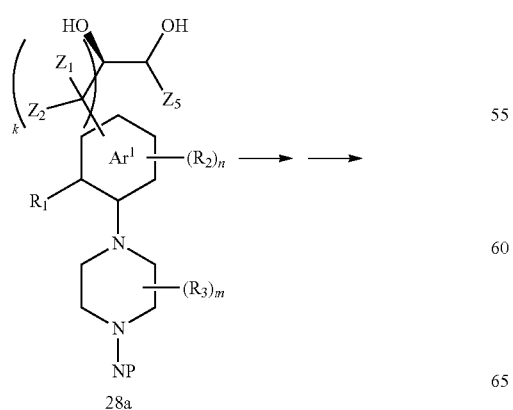
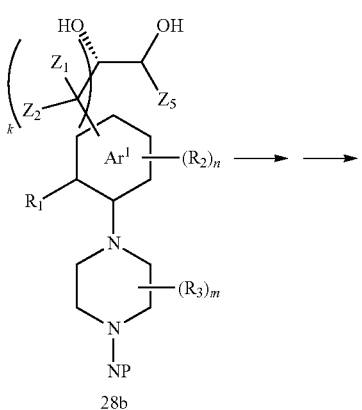

283
-continued

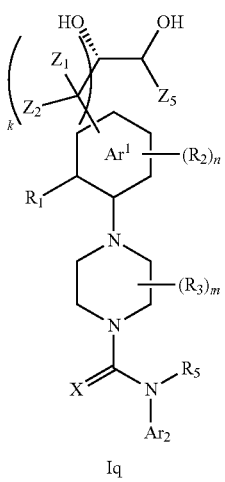

Iq wherein NP is an amino protecting group and $Ar^1$, $Ar^2$, X, $Z_1$, $Z_2$, $Z_5$, $R_1$, $R_2$, $R_3$, $R_5$, k, m, and n are as defined above for compounds of Formula I.

A compound of formula 28a or 28b is obtained according to a procedure analogous to that described above in Scheme 1.2.

Compound of formula Ip or Iq can be obtained from compound of formula 28a or 28b by the procedures described above in Schemes 1.5 and 1.6.

Scheme 9.1

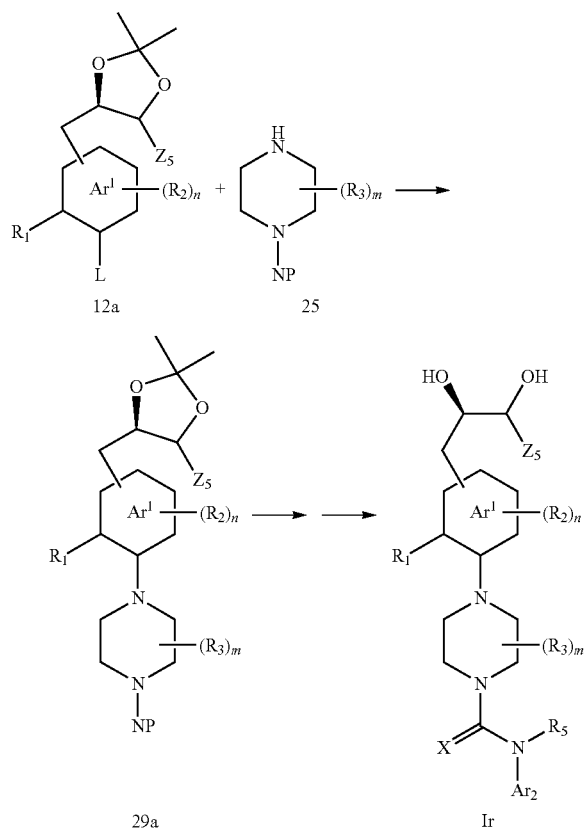

29a

Ir

284
-continued

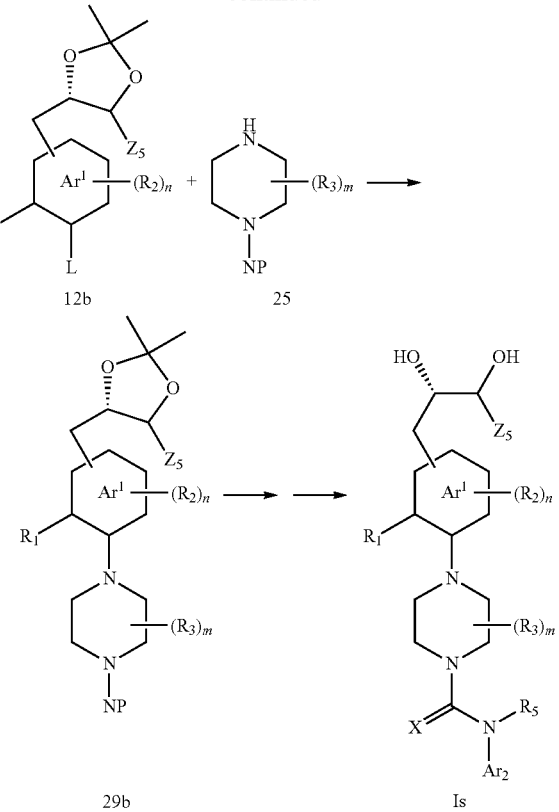

29b

Is wherein L is a leaving group such as halogen, NP is an amino protecting group, and $Ar^1$, $Ar^2$, X, $Z_5$, $R_1$, $R_2$, $R_3$, $R_5$, m, and n are as defined above for compounds of Formula I.

To a solution of a compound of formula 12a in 1,4-dioxane, toluene or the like or a mixed solvent of these are added 1 to 3 equivalents of a compound of formula 25, 0.01 to 0.1 equivalents of a palladium catalyst such palladium acetate, bis(diphenylphosphino)ferrocene palladium chloride, tris(dibenzylideneacetone)dipalladium(0) or bis(triphenylphosphine)palladium dichloride together with 0.01 to 0.3 equivalents of a phosphine ligand such dicyclohexyl- and di-tert-butylphosphinobiphenyl or the like and 2 to 5 equivalents of a base such potassium tert-butoxide, sodium tert-butoxide, potassium phosphate or potassium carbonate, at from 25° C. to reflux temperature, preferably from 50° C. to reflux temperature for from 0.5 hour to 48 hours preferably from 1 hour to 24 hours. Then the reaction mixture is quenched with an aqueous acidic solution and extracted with EtOAc or DEE. The resulting organic layer is washed with brine, dried over anhydrous sodium sulfate or magnesium sulfate and concentrated under reduced pressure. The resulting product can be chromatographed with a silica gel column to provide a compound of formula 29a. The other enantiomer, can be synthesized by the reaction of a compound of formula 12b to yield a compound of formula 29b. As demonstrated in scheme 9.1, the review of amination is described in S. L. Buchwald et al., Angew. Chem. Int. Ed. 47:6338-6361 (2008).

Compound of formula Ir or Is can be obtained from compound of formula 29a or 29b by the procedures described above in Schemes 2.6 and 1.6.

Scheme 10.1

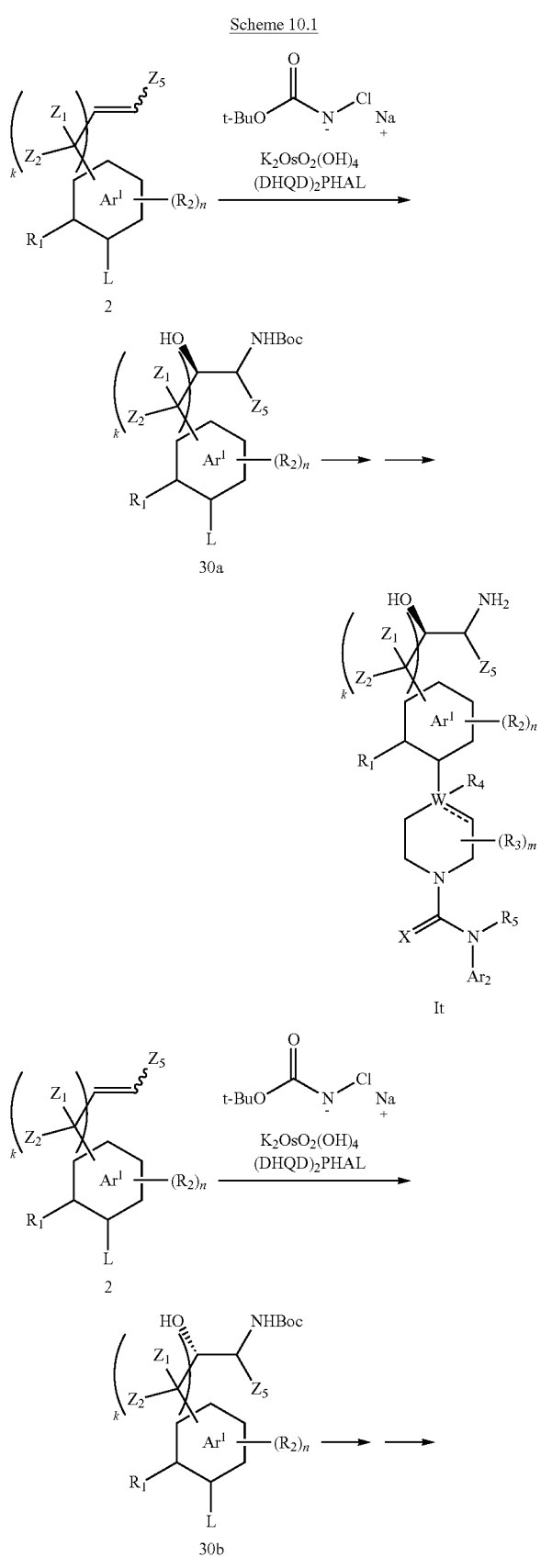

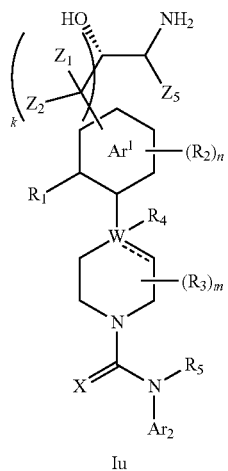

wherein L is a leaving group such as halogen, and the dashed line, Ar$^1$, Ar$^2$, W, X, Z$_1$, Z$_2$, Z$_5$, R$_1$, R$_2$, R$_3$, R$_4$, R$_5$, k, m, and n are as defined above for compounds of Formula I.

To a solution of a compound of formula 2 in n-propanol, isopropanol or the like solvent is added 0.01 to 0.1 equivalents of potassium osmate dihydrate and a prepared solution of 1 to 5 equivalents of sodium N-chloro tert-butyl carbamate in a mixed solvent of n-propanol, isopropanol or the like and water, prepared tert-butyl carbamate, sodium hydroxide and tert-butyl hypochlorite at a temperature of from −20° C. to 25° C. and stirred at a temperature of from −20° C. to 25° C. for from 5 min to 1 hour. Then 0.01 to 0.1 equivalents of (DHQD)$_2$PHAL is added to the reaction mixture at a temperature of from −20° C. to 25° C. and stirred at a temperature of from −20° C. to 25° C. for 1 hour to 24 hours, preferably from about 1 hour to 6 hours. Then the reaction mixture is quenched with an aqueous NaHSO$_3$ solution and extracted with EtOAc or DEE. The resulting organic layer is washed with brine, dried over anhydrous sodium sulfate or magnesium sulfate and concentrated under reduced pressure. The resulting product can be chromatographed with a silica gel column to provide a compound of formula 30a. The other enantiomer, can be synthesized by the reaction of a compound of formula 2 with (DHQ)$_2$PHAL to yield a compound of formula 30b. As demonstrated in scheme 10.1, the stereochemistry (R or S) of the resulting aminoalcohol, is dependent upon the chirality of the ligand used in the (DHQ)$_2$PHAL and (DHQD)$_2$PHAL as described in K. B. Sharpless et al., J. Am. Chem. Soc. 120:1207-1217 (1998).

Compound of formula It or Iu (Z$_3$=OH and Z$_4$=NH$_2$) can be obtained from compound of formula 30a or 30b by the procedures described above in Schemes 1.4, 1.5, 1.6 and/or 8.1.

Compounds of formula I wherein Z$_3$ is NH$_2$ and Z$_4$ is OH can be obtained in a similar manner.

Compounds obtained by the above procedures wherein Z$_3$ and/or Z$_4$ is OH and/or NH$_2$ can be converted to compounds wherein Z$_3$ and/or Z$_4$ is OR$_{12}$ and/or N(R$_{12}$)$_2$ (R$_{12}$ is not hydrogen) using ordinary methods known to one skilled in the art.

In every step described above, if a starting compound has a functional group which disturb the reaction (e.g., hydroxyl, mercapto, amino, formyl, carbonyl, carboxyl etc.), it is recommended to protect the functional group and deprotect it at a subsequent appropriate step with a method described in Protective Groups in Organic Synthesis, 2$^{nd}$ Ed., Theodora W Green et al., (John Wiley & Sons, 1991), etc.

Further the order of steps may be changed and each reaction intermediate may be isolated and used in the subsequent step.

Therapeutic Uses of Compounds of Formula I

In accordance with the invention, the compounds of Formula I are administered to an animal in need of treatment or prevention of a Condition.

In one embodiment, an effective amount of a compound of Formula I can be used to treat or prevent any condition treatable or preventable by inhibiting TRPV1. Examples of Conditions that are treatable or preventable by inhibiting TRPV1 include, but are not limited to, pain, UI, an ulcer, IBD, and IBS.

The compounds of Formula I, or a pharmaceutically acceptable derivative thereof, can be used to treat or prevent acute or chronic pain. Examples of pain treatable or preventable using the compounds of Formula I include, but are not limited to, cancer pain, labor pain, myocardial infarction pain, pancreatic pain, colic pain, post-operative pain, headache pain, muscle pain, arthritic pain, and pain associated with a periodontal disease, including gingivitis and periodontitis.

The compounds of Formula I, or a pharmaceutically acceptable derivative thereof, can also be used for treating or preventing pain associated with inflammation or with an inflammatory disease in an animal. Such pain can arise where there is an inflammation of the body tissue which can be a local inflammatory response and/or a systemic inflammation. For example, the compounds of Formula I can be used to treat or prevent pain associated with inflammatory diseases including, but not limited to: organ transplant rejection; reoxygenation injury resulting from organ transplantation (see Grupp et al., *J. Mol. Cell. Cardiol.* 31:297-303 (1999)) including, but not limited to, transplantation of the heart, lung, liver, or kidney; chronic inflammatory diseases of the joints, including arthritis, rheumatoid arthritis, osteoarthritis and bone diseases associated with increased bone resorption; inflammatory bowel diseases, such as ileitis, ulcerative colitis, Barrett's syndrome, and Crohn's disease; inflammatory lung diseases, such as asthma, adult respiratory distress syndrome, and chronic obstructive airway disease; inflammatory diseases of the eye, including corneal dystrophy, trachoma, onchocerciasis, uveitis, sympathetic ophthalmitis and endophthalmitis; chronic inflammatory diseases of the gum, including gingivitis and periodontitis; tuberculosis; leprosy; inflammatory diseases of the kidney, including uremic complications, glomerulonephritis and nephrosis; inflammatory diseases of the skin, including sclerodermatitis, psoriasis and eczema; inflammatory diseases of the central nervous system, including chronic demyelinating diseases of the nervous system, multiple sclerosis, AIDS-related neurodegeneration and Alzheimer s disease, infectious meningitis, encephalomyelitis, Parkinson's disease, Huntington's disease, amyotrophic lateral sclerosis and viral or autoimmune encephalitis; autoimmune diseases, including Type I and Type II diabetes mellitus; diabetic complications, including, but not limited to, diabetic cataract, glaucoma, retinopathy, nephropathy (such as microaluminuria and progressive diabetic nephropathy), polyneuropathy, mononeuropathies, autonomic neuropathy, gangrene of the feet, atherosclerotic coronary arterial disease, peripheral arterial disease, nonketotic hyperglycemic-hyperosmolar coma, foot ulcers, joint problems, and a skin or mucous membrane complication (such as an infection, a shin spot, a candidal infection or necrobiosis lipoidica diabeticorum); immune-complex vasculitis, and systemic lupus erythematosus (SLE); inflammatory diseases of the heart, such as cardiomyopathy, ischemic heart disease hypercholesterolemia, and atherosclerosis; as well as various other diseases that can have significant inflammatory components, including preeclampsia, chronic liver failure, brain and spinal cord trauma, and cancer. The compounds of Formula I can also be used for inhibiting, treating, or preventing pain associated with inflammatory disease that can, for example, be a systemic inflammation of the body, exemplified by gram-positive or gram negative shock, hemorrhagic or anaphylactic shock, or shock induced by cancer chemotherapy in response to pro-inflammatory cytokines, e.g., shock associated with pro-inflammatory cytokines. Such shock can be induced, e.g., by a chemotherapeutic agent that is adminstered as a treatment for cancer.

The compounds of Formula I, or a pharmaceutically acceptable derivative thereof, can be used to treat or prevent UI. Examples of UI treatable or preventable using the compounds of Formula I include, but are not limited to, urge incontinence, stress incontinence, overflow incontinence, neurogenic incontinence, and total incontinence.

The compounds of Formula I, or a pharmaceutically acceptable derivative thereof, can be used to treat or prevent an ulcer. Examples of ulcers treatable or preventable using the compounds of Formula I include, but are not limited to, a duodenal ulcer, a gastric ulcer, a marginal ulcer, an esophageal ulcer, or a stress ulcer.

The compounds of Formula I, or a pharmaceutically acceptable derivative thereof, can be used to treat or prevent IBD, including Crohn's disease and ulcerative colitis.

The compounds of Formula I, or a pharmaceutically acceptable derivative thereof, can be used to treat or prevent IBS. Examples of IBS treatable or preventable using the compounds of Formula I include, but are not limited to, spastic-colon-type IBS and constipation-predominant IBS.

Applicants believe that the compounds of Formula I, or a pharmaceutically acceptable derivative thereof, are antagonists for TRPV1. The invention also relates to methods for inhibiting TRPV1 function in a cell comprising contacting a cell capable of expressing TRPV1 with an effective amount of a compound of Formula I, or a pharmaceutically acceptable derivative thereof. This method can be used in vitro, for example, as an assay to select cells that express TRPV1 and, accordingly, are useful as part of an assay to select compounds useful for treating or preventing pain, UI, an ulcer, IBD, or IBS. The method is also useful for inhibiting TRPV1 function in a cell in vivo, in an animal, a human in one embodiment, by contacting a cell, in an animal, with an effective amount of a compound of Formula I, or a pharmaceutically acceptable derivative thereof. In one embodiment, the method is useful for treating or preventing pain in an animal. In another embodiment, the method is useful for treating or preventing UI in an animal. In another embodiment, the method is useful for treating or preventing an ulcer in an animal. In another embodiment, the method is useful for treating or preventing IBD in an animal. In another embodiment, the method is useful for treating or preventing IBS in an animal.

Examples of tissue comprising cells capable of expressing TRPV1 include, but are not limited to, neuronal, brain, kidney, urothelium, and bladder tissue. Methods for assaying cells that express TRPV1 are known in the art.

Therapeutic/Prophylactic Administration and Compositions of the Invention

Due to their activity, compounds of Formula I, or a pharmaceutically acceptable derivative thereof, are advantageously useful in veterinary and human medicine. As described above, compounds of Formula I, or a pharmaceutically acceptable derivative thereof, are useful for treating or preventing a Condition.

When administered to an animal, compounds of Formula I, or a pharmaceutically acceptable derivative thereof, are typically administered as a component of a composition that comprises a pharmaceutically acceptable carrier or excipient. The invention compositions, which comprise a compound of Formula I, or a pharmaceutically acceptable derivative thereof, can be administered orally. Compounds of Formula I, or a pharmaceutically acceptable derivative thereof, can also be administered by any other convenient route, for example, by infusion or bolus injection, by absorption through epithelial or mucocutaneous linings (e.g., oral, rectal, and intestinal mucosa, etc.) and can be administered together with another therapeutically active agent. Administration can be systemic or local. Various delivery systems are known, e.g., encapsulation in liposomes, microparticles, microcapsules, capsules, etc., and can be used to administer the compound of Formula I, or a pharmaceutically acceptable derivative thereof.

Methods of administration include, but are not limited to, intradermal, intramuscular, intraperitoneal, intravenous, subcutaneous, intranasal, epidural, oral, sublingual, intracerebral, intravaginal, transdermal, rectal, by inhalation, or topical, particularly to the ears, nose, eyes, or skin. The mode of administration is left to the discretion of the practitioner. In most instances, administration will result in the release of compounds of Formula I, or a pharmaceutically acceptable derivative thereof, into the bloodstream.

In specific embodiments, it can be desirable to administer the compounds of Formula I, or a pharmaceutically acceptable derivative thereof, locally. This can be achieved, for example, and not by way of limitation, by local infusion during surgery, topical application, e.g., in conjunction with a wound dressing after surgery, by injection, by means of a catheter, by means of a suppository or enema, or by means of an implant, said implant being of a porous, non porous, or gelatinous material, including membranes, such as sialastic membranes, or fibers.

In certain embodiments, it can be desirable to introduce the compounds of Formula I, or a pharmaceutically acceptable derivative thereof, into the central nervous system or gastrointestinal tract by any suitable route, including intraventricular, intrathecal, and epidural injection, and enema. Intraventricular injection can be facilitated by an intraventricular catheter, for example, attached to a reservoir, such as an Ommaya reservoir.

Pulmonary administration can also be employed, e.g., by use of an inhaler or nebulizer, and formulation with an aerosolizing agent, or via perfusion in a fluorocarbon or synthetic pulmonary surfactant. In certain embodiments, the compounds of Formula I can be formulated as a suppository, with traditional binders and excipients such as triglycerides.

In another embodiment, the compounds of Formula I, or a pharmaceutically acceptable derivative thereof, can be delivered in a vesicle, in particular a liposome (see Langer, *Science* 249:1527-1533 (1990) and Treat et al., "Liposome Encapsulated Doxorubicin Preliminary Results of Phase I and Phase II Trials," pp. 317-327 and 353-365 in *Liposomes in the Therapy of Infectious Disease and Cancer* (1989)).

In yet another embodiment, the compounds of Formula I, or a pharmaceutically acceptable derivative thereof, can be delivered in a controlled-release system or sustained-release system (see, e.g., Goodson, "Dental Applications," pp. 115-138 in *Medical Applications of Controlled Release, Vol. 2, Applications and Evaluation*, Langer and Wise, Eds., CRC Press (1984)). Other controlled- or sustained-release systems discussed in the review by Langer, *Science* 249:1527-1533 (1990) can be used. In one embodiment, a pump can be used (Langer, *Science* 249:1527-1533 (1990); Sefton, "Implantable Pumps," in *CRC Crit. Rev. Biomed Eng.* 14:201-240 (1987); Buchwald et al., *Surgery*, 88:507-516 (1980); and Saudek et al., *N. Engl. J. Med.* 321:574-579 (1989)). In another embodiment, polymeric materials can be used (see Langer et al., "Classes of Systems," *Medical Applications of Controlled Release* Vol. I, CRC Press, Boca Raton, Fla. (1984); Smolen et al., "Drug Product Design and Performance," *Controlled Drug Bioavailability* Vol. 1, John Wiley & Sons, New York (1984); Langer and Peppas, *J. Macromol. Sci. Rev. Macromol. Chem.* C23(1):61-126 (1983); Levy et al., *Science* 228:190-192 (1985); During et al., *Ann. Neurol.* 25:351-356 (1989); and Howard et al., *J. Neurosurg.* 71:105 (1989)). In yet another embodiment, a controlled- or sustained-release system can be placed in proximity of a target of the compounds of Formula I, e.g., the spinal column, brain, or gastrointestinal tract, thus requiring only a fraction of the systemic dose.

The invention compositions can optionally comprise a suitable amount of a pharmaceutically acceptable excipient so as to provide the form for proper administration to the animal.

Such pharmaceutical excipients can be liquids, such as water and oils, including those of petroleum, animal, vegetable, or synthetic origin, such as peanut oil, soybean oil, mineral oil, sesame oil and the like. The pharmaceutical excipients can be saline, gum acacia, gelatin, starch paste, talc, keratin, colloidal silica, urea and the like. In addition, auxiliary, stabilizing, thickening, lubricating, and coloring agents can be used. In one embodiment, the pharmaceutically acceptable excipients are sterile when administered to an animal. Water is a particularly useful excipient when the compound of Formula I is administered intravenously. Saline solutions and aqueous dextrose and glycerol solutions can also be employed as liquid excipients, particularly for injectable solutions. Suitable pharmaceutical excipients also include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The invention compositions, if desired, can also contain minor amounts of wetting or emulsifying agents, or can contain pH buffering agents.

The invention compositions can take the form of solutions, suspensions, emulsion, tablets, pills, pellets, multiparticulates, capsules, capsules containing liquids, powders, multiparticulates, sustained-release formulations, suppositories, emulsions, aerosols, sprays, suspensions, or any other form suitable for use. In one embodiment, the composition is in the form of a capsule (see e.g., U.S. Pat. No. 5,698,155). Other examples of suitable pharmaceutical excipients are described in Radebough et al., "Preformulation," pp. 1447-1676 in *Remington's Pharmaceutical Sciences* (Alfonso R. Gennaro ed., 19th ed. 1995), incorporated herein by reference.

In one embodiment, the compounds of Formula I, or a pharmaceutically acceptable derivative thereof, are formulated in accordance with routine procedures as a composition adapted for oral administration to human beings. Compositions for oral delivery can be in the form of tablets, lozenges, aqueous or oily suspensions, granules, powders, emulsions, capsules, syrups, or elixirs, for example. Orally administered compositions can contain one or more agents, for example, sweetening agents such as fructose, aspartame or saccharin; flavoring agents such as peppermint, oil of wintergreen, or cherry; coloring agents; and preserving agents, to provide a pharmaceutically palatable preparation. Moreover, where in tablet or pill form, the compositions can be coated to delay disintegration and absorption in the gastrointestinal tract thereby providing a sustained action over an extended period of time. Selectively permeable membranes surrounding an osmotically active driving compound are also suitable for orally administered compositions. In these latter platforms, fluid from the environment surrounding the capsule is imbibed by the driving compound, which swells to displace the agent or agent composition through an aperture. These delivery platforms can provide an essentially zero order delivery profile as opposed to the spiked profiles of immediate release formulations. A time-delay material such as glycerol monostearate or glycerol stearate can also be used. Oral compositions can include standard excipients such as mannitol, lactose, starch, magnesium stearate, sodium saccharin, cellulose, and magnesium carbonate. In one embodiment, the excipients are of pharmaceutical grade.

The compounds of Formula I, or a pharmaceutically acceptable derivative thereof, can be administered by controlled-release or sustained-release means or by delivery devices that are known to those of ordinary skill in the art. Examples include, but are not limited to, those described in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; and 5,733,566, each of which is incorporated herein by reference. Such dosage forms can be used to provide controlled- or sustained-release of one or more active ingredients using, for example, hydropropylmethyl cellulose, ethylcellulose, other polymer matrices, gels, permeable membranes, osmotic systems, multilayer coatings, microparticles, liposomes, microspheres, or a combination thereof to provide the desired release profile in varying proportions. Suitable controlled- or sustained-release formulations known to those of ordinary skill in the art, including those described herein, can be readily selected for use with the active ingredients of the invention. The invention thus encompasses single unit dosage forms suitable for oral administration such as, but not limited to, tablets, capsules, gelcaps, and caplets that are adapted for controlled- or sustained-release.

Controlled- or sustained-release pharmaceutical compositions can have a common goal of improving drug therapy over that achieved by their non-controlled or non-sustained release counterparts. In one embodiment, a controlled- or sustained-release composition comprises a minimal amount of a compound of Formula I to cure or control the condition in a minimum amount of time. Advantages of controlled- or sustained-release compositions include extended activity of the drug, reduced dosage frequency, and increased patient compliance. In addition, controlled- or sustained-release compositions can favorably affect the time of onset of action or other characteristics, such as blood levels of the compound of Formula I, and can thus reduce the occurrence of adverse side effects.

Controlled- or sustained-release compositions can be designed to immediately release an amount of a compound of Formula I, or a pharmaceutically acceptable derivative thereof, that promptly produces the desired therapeutic or prophylactic effect, and gradually and continually release other amounts of the compound of Formula I to maintain this level of therapeutic or prophylactic effect over an extended period of time. To maintain a constant level of the compound of Formula I in the body, the compound of Formula I can be released from the dosage form at a rate that will replace the amount of compound of Formula I being metabolized and excreted from the body. Controlled- or sustained-release of an active ingredient can be stimulated by various conditions, including but not limited to, changes in pH, changes in temperature, concentration or availability of enzymes, concentration or availability of water, or other physiological conditions or compounds.

In another embodiment, the compounds of Formula I, or a pharmaceutically acceptable derivative thereof, can be formulated for intravenous administration. Typically, compositions for intravenous administration comprise sterile isotonic aqueous buffer. Where necessary, the compositions can also include a solubilizing agent. Compositions for intravenous administration can optionally include a local anaesthetic such as lignocaine to lessen pain at the site of the injection. Generally, the ingredients are supplied either separately or a mixed together in unit dosage form, for example, as a dry lyophilized powder or water free concentrate in a hermetically sealed container such as an ampoule or sachette indicating the quantity of active agent. Where the compounds of Formula I are to be administered by infusion, they can be dispensed, for example, with an infusion bottle containing sterile pharmaceutical grade water or saline. Where the compounds of Formula I, or a pharmaceutically acceptable derivative thereof, are administered by injection, an ampoule of sterile water for injection or saline can be provided so that the ingredients can be mixed prior to administration.

The amount of the compound of Formula I, or a pharmaceutically acceptable derivative thereof, that is effective in the treatment or prevention of a Condition can be determined by standard clinical techniques. In addition, in vitro or in vivo assays can optionally be employed to help identify optimal dosage ranges. The precise dose to be employed will also depend on the route of administration, and the seriousness of the Condition and can be decided according to the judgment of a practitioner and/or each animal's circumstances. Suitable effective dosage amounts, however, will typically range from about 0.01 mg/kg of body weight to about 2500 mg/kg of body weight, although they are typically about 100 mg/kg of body weight or less. In one embodiment, the effective dosage amount ranges from about 0.01 mg/kg of body weight to about 100 mg/kg of body weight of a compound of Formula I; in another embodiment, about 0.02 mg/kg of body weight to about 50 mg/kg of body weight; and in another embodiment, about 0.025 mg/kg of body weight to about 20 mg/kg of body weight.

In one embodiment, an effective dosage amount is administered about every 24 h until the Condition is abated. In another embodiment, an effective dosage amount is administered about every 12 h until the Condition is abated. In another embodiment, an effective dosage amount is administered about every 8 h until the Condition is abated. In another embodiment, an effective dosage amount is administered about every 6 h until the Condition is abated. In another embodiment, an effective dosage amount is administered about every 4 h until the Condition is abated.

The effective dosage amounts described herein refer to total amounts administered; that is, if more than one compound of Formula I, or a pharmaceutically acceptable derivative thereof, is administered, the effective dosage amounts correspond to the total amount administered.

Where a cell capable of expressing TRPV1 is contacted with a compound of Formula I in vitro, the amount effective for inhibiting the TRPV1 receptor function in a cell will typically range from about 0.01 µg/L to about 5 mg/L; in one embodiment, from about 0.01 µg/L to about 2.5 mg/L; in another embodiment, from about 0.01 µg/L to about 0.5 mg/L; and in another embodiment, from about 0.01 µg/L to about 0.25 mg/L, of a solution or suspension of a pharmaceutically acceptable carrier or excipient. In one embodiment, the volume of solution or suspension comprising the compound of Formula I, or a pharmaceutically acceptable derivative thereof, is from about 0.01 µL to about 1 mL. In another embodiment, the volume of solution or suspension is about 200 µL.

The compounds of Formula I, or a pharmaceutically acceptable derivative thereof, can be assayed in vitro or in vivo for the desired therapeutic or prophylactic activity prior to use in humans. Animal model systems can be used to demonstrate safety and efficacy.

The invention methods for treating or preventing a Condition in an animal in need thereof can further comprise administering to the animal being administered a compound of Formula I, or a pharmaceutically acceptable derivative thereof, another therapeutic agent. In one embodiment, the other therapeutic agent is administered in an effective amount.

The invention methods for inhibiting TRPV1 function in a cell capable of expressing TRPV1 can further comprise contacting the cell with an effective amount of another therapeutic agent.

Effective amounts of the other therapeutic agents are known in the art. However, it is within the skilled artisan's purview to determine the other therapeutic agent's optimal effective-amount range. In one embodiment of the invention, where another therapeutic agent is administered to an animal, the effective amount of the compound of Formula I is less than its effective amount would be where the other therapeutic agent is not administered. In this case, without being bound by theory, it is believed that the compounds of Formula I and the other therapeutic agent act synergistically to treat or prevent a Condition.

The other therapeutic agent can be, but is not limited to, an opioid agonist, a non-opioid analgesic, a non-steroid anti-inflammatory agent, an antimigraine agent, a Cox-II inhibitor, an antiemetic, a β-adrenergic blocker, an anticonvulsant, an antidepressant, a $Ca^{2+}$-channel blocker, an anticancer agent, an agent for treating or preventing UI, an agent for treating or preventing an ulcer, an agent for treating or preventing IBD, an agent for treating or preventing IBS, an agent for treating addictive disorder, an agent for treating Parkinson's disease and parkinsonism, an agent for treating anxiety, an agent for treating epilepsy, an agent for treating a stroke, an agent for treating a seizure, an agent for treating a pruritic condition, an agent for treating psychosis, an agent for treating Huntington's chorea, an agent for treating ALS, an agent for treating a cognitive disorder, an agent for treating a migraine, an agent for treating vomiting, an agent for treating dyskinesia, or an agent for treating depression, and mixtures thereof. In one embodiment, the other therapeutic agent is an opioid agonist, e.g., an opioid analgesic. In another embodiment, the other therapeutic agent is a non-opioid analgesic. In another embodiment, the other therapeutic agent is an antiemetic agent. In another embodiment, the other therapeutic agent is an anticonvulsant. In another embodiment, the other therapeutic agent is an antidepressant. In another embodiment, the other therapeutic agent is duloxetine, hydrocodone, hydromorphone, morphine, oxycodone, pregabaline, pharmaceutically acceptable derivatives thereof, and mixtures thereof. In another embodiment, the other therapeutic agent is a 4-Tetrazolyl-4-phenylpiperidine Compound or pharmaceutically acceptable derivatives thereof, such as is disclosed in U.S. Pat. No. 7,202,259 at column 2, line 5 to column 6, line 2 and exemplified therein, which patent is hereby incorporated by reference in its entirety. In another embodiment, the 4-Tetrazolyl-4-phenylpiperidine Compound other therapeutic agent is administered intrathecally, e.g., as described at column 74, lines 14-17 of U.S. Pat. No. 7,202,259.

Examples of useful opioid agonists include, but are not limited to, alfentanil, allylprodine, alphaprodine, anileridine, benzylmorphine, bezitramide, buprenorphine, butorphanol, clonitazene, codeine, desomorphine, dextromoramide, dezocine, diampromide, diamorphone, dihydrocodeine, dihydromorphine, dimenoxadol, dimepheptanol, dimethylthiambutene, dioxaphetyl butyrate, dipipanone, eptazocine, ethoheptazine, ethylmethylthiambutene, ethylmorphine, etonitazene fentanyl, heroin, hydrocodone, hydromorphone, hydroxypethidine, isomethadone, ketobemidone, levorphanol, levophenacylmorphan, lofentanil, meperidine, meptazinol, metazocine, methadone, metopon, morphine, myrophine, nalbuphine, narceine, nicomorphine, norlevorphanol, normethadone, nalorphine, normorphine, norpipanone, opium, oxycodone, oxymorphone, papavereturn, pentazocine, phenadoxone, phenomorphan, phenazocine, phenoperidine, piminodine, piritramide, proheptazine, promedol, properidine, propiram, propoxyphene, sufentanil, tilidine, tramadol, pharmaceutically acceptable derivatives thereof, and mixtures thereof.

In certain embodiments, the opioid agonist is selected from codeine, hydromorphone, hydrocodone, oxycodone, dihydrocodeine, dihydromorphine, morphine, tramadol, oxymorphone, pharmaceutically acceptable derivatives thereof, and mixtures thereof. In other embodiments, the opioid agonist is selected from hydrocodone, hydromorphone, morphine, oxycodone, pharmaceutically acceptable derivatives thereof, and mixtures thereof.

Examples of useful non-opioid analgesics include non-steroidal anti-inflammatory agents, such as aspirin, ibuprofen, diclofenac, naproxen, benoxaprofen, flurbiprofen, fenoprofen, flubufen, ketoprofen, indoprofen, piroprofen, carprofen, oxaprozin, pramoprofen, muroprofen, trioxaprofen, suprofen, aminoprofen, tiaprofenic acid, fluprofen, bucloxic acid, indomethacin, sulindac, tolmetin, zomepirac, tiopinac, zidometacin, acemetacin, fentiazac, clidanac, oxpinac, mefenamic acid, meclofenamic acid, flufenamic acid, niflumic acid, tolfenamic acid, diflurisal, flufenisal, piroxicam, sudoxicam, isoxicam, and pharmaceutically acceptable derivatives thereof, and mixtures thereof. Other suitable non-opioid analgesics include the following, non-limiting, chemical classes of analgesic, antipyretic, nonsteroidal anti-inflammatory drugs: salicylic acid derivatives, including aspirin, sodium salicylate, choline magnesium trisalicylate, salsalate, diflunisal, salkylsalicylic acid, sulfasalazine, and olsalazin; para-aminophennol derivatives including acetaminophen and phenacetin; indole and indene acetic acids, including indomethacin, sulindac, and etodolac; heteroaryl acetic acids, including tolmetin, diclofenac, and ketorolac; anthranilic acids (fenamates), including mefenamic acid and meclofenamic acid; enolic acids, including oxicams (piroxicam, tenoxicam), and pyrazolidinediones (phenylbutazone, oxyphenthartazone); and alkanones, including nabumetone. For a more detailed description of the NSAIDs, see Paul A. Insel, *Analgesic-Antipyretic and Anti-inflammatory Agents and Drugs Employed in the Treatment of Gout, in Goodman & Gilman's The Pharmacological Basis of Therapeutics* pp. 617-657 (Goodman et al. eds., $9^{th}$ ed., McGraw-Hill, New York, 1996) and Glen R. Hanson, *Analgesic, Antipyretic and Anti-Inflammatory Drugs in Remington: The Science and Practice of Pharmacy Vol II* pp. 1196-1221 (A. R. Gennaro ed., 19th ed. 1995) which are hereby incorporated by reference in their entireties.

Examples of useful Cox-II inhibitors and 5-lipoxygenase inhibitors, as well as combinations thereof, are described in U.S. Pat. No. 6,136,839, which is hereby incorporated by reference in its entirety. Examples of useful Cox-II inhibitors include, but are not limited to, rofecoxib and celecoxib.

Examples of useful antimigraine agents include, but are not limited to, alpiropride, bromocriptine, dihydroergotamine, dolasetron, ergocornine, ergocorninine, ergocryptine, ergonovine, ergot, ergotamine, flumedroxone acetate, fonazine, ketanserin, lisuride, lomerizine, methylergonovine, methysergide, metoprolol, naratriptan, oxetorone, pizotyline, propranolol, risperidone, rizatriptan, sumatriptan, timolol, trazodone, zolmitriptan, and mixtures thereof.

The other therapeutic agent can also be an agent useful for reducing any potential side effects of a compound of Formula I. For example, the other therapeutic agent can be an antiemetic agent. Examples of useful antiemetic agents include, but are not limited to, metoclopromide, domperidone, prochlorperazine, promethazine, chlorpromazine, trimethobenzamide, ondansetron, granisetron, hydroxyzine, acetylleucine monoethanolamine, alizapride, azasetron, benzquinamide, bietanautine, bromopride, buclizine, clebopride, cyclizine, dimenhydrinate, diphenidol, dolasetron, meclizine, methallatal, metopimazine, nabilone, oxypemdyl, pipamazine, scopolamine, sulpiride, tetrahydrocannabinol, thiethylperazine, thioproperazine, tropisetron, and mixtures thereof.

Examples of useful β-adrenergic blockers include, but are not limited to, acebutolol, alprenolol, amosulabol, arotinolol, atenolol, befunolol, betaxolol, bevantolol, bisoprolol, bopindolol, bucumolol, bufetolol, bufuralol, bunitrolol, bupranolol, butidrine hydrochloride, butofilolol, carazolol, carteolol, carvedilol, celiprolol, cetamolol, cloranolol, dilevalol, epanolol, esmolol, indenolol, labetalol, levobunolol, mepindolol, metipranolol, metoprolol, moprolol, nadolol, nadoxolol, nebivalol, nifenalol, nipradilol, oxprenolol, penbutolol, pindolol, practolol, pronethalol, propranolol, sotalol, sulfinalol, talinolol, tertatolol, tilisolol, timolol, toliprolol, and xibenolol.

Examples of useful anticonvulsants include, but are not limited to, acetylpheneturide, albutoin, aloxidone, aminoglutethimide, 4-amino-3-hydroxybutyric acid, atrolactamide, beclamide, buramate, calcium bromide, carbamazepine, cinromide, clomethiazole, clonazepam, decimemide, diethadione, dimethadione, doxenitroin, eterobarb, ethadione, ethosuximide, ethotoin, felbamate, fluoresone, gabapentin, 5-hydroxytryptophan, lamotrigine, magnesium bromide, magnesium sulfate, mephenyloin, mephobarbital, metharbital, methetoin, methsuximide, 5-methyl-5-(3-phenanthryl)-hydantoin, 3-methyl-5-phenylhydantoin, narcobarbital, nimetazepam, nitrazepam, oxcarbazepine, paramethadione, phenacemide, phenetharbital, pheneturide, phenobarbital, phensuximide, phenylmethylbarbituric acid, phenyloin, phethenylate sodium, potassium bromide, pregabaline, e.g., Lyrica, primidone, progabide, sodium bromide, solanum, strontium bromide, suclofenide, sulthiame, tetrantoin, tiagabine, topiramate, trimethadione, valproic acid, valpromide, vigabatrin, and zonisamide.

Examples of useful antidepressants include, but are not limited to, binedaline, caroxazone, citalopram, (S)-citalopram, dimethazan, fencamine, indalpine, indeloxazine hydrocholoride, nefopam, nomifensine, oxitriptan, oxypertine, paroxetine, sertraline, thiazesim, trazodone, benmoxine, iproclozide, iproniazid, isocarboxazid, nialamide, octamoxin, phenelzine, cotinine, rolicyprine, rolipram, maprotiline, metralindole, mianserin, mirtazepine, adinazolam, amitriptyline, amitriptylinoxide, amoxapine, butriptyline, clomipramine, demexiptiline, desipramine, dibenzepin, dimetacrine, dothiepin, doxepin, fluacizine, imipramine, imipramine N-oxide, iprindole, lofepramine, melitracen, metapramine, nortriptyline, noxiptilin, opipramol, pizotyline, propizepine, protriptyline, quinupramine, tianeptine, trimipramine, adrafinil, benactyzine, bupropion, butacetin, dioxadrol, duloxetine, e.g., Cymbalta, etoperidone, febarbamate, femoxetine, fenpentadiol, fluoxetine, fluvoxamine, hematoporphyrin, hypericin, levophacetoperane, medifoxamine, milnacipran, minaprine, moclobemide, nefazodone, oxaflozane, piberaline, prolintane, pyrisuccideanol, ritanserin, roxindole, rubidium chloride, sulpiride, tandospirone, thozalinone, tofenacin, toloxatone, tranylcypromine, L-tryptophan, venlafaxine, viloxazine, and zimeldine.

Examples of useful $Ca^{2+}$-channel blockers include, but are not limited to, bepridil, clentiazem, diltiazem, fendiline, gallopamil, mibefradil, prenylamine, semotiadil, terodiline, verapamil, amlodipine, aranidipine, barnidipine, benidipine, cilnidipine, efonidipine, elgodipine, felodipine, isradipine, lacidipine, lercanidipine, manidipine, nicardipine, nifedipine, nilvadipine, nimodipine, nisoldipine, nitrendipine, cinnarizine, flunarizine, lidoflazine, lomerizine, bencyclane, etafenone, fantofarone, and perhexyline.

Examples of useful anticancer agents include, but are not limited to, acivicin, aclarubicin, acodazole hydrochloride, acronine, adozelesin, aldesleukin, altretamine, ambomycin, ametantrone acetate, aminoglutethimide, amsacrine, anastrozole, anthramycin, asparaginase, asperlin, azacitidine, azetepa, azotomycin, batimastat, benzodepa, bicalutamide, bisantrene hydrochloride, bisnafide dimesylate, bizelesin, bleomycin sulfate, brequinar sodium, bropirimine, busulfan, cactinomycin, calusterone, caracemide, carbetimer, carboplatin, carmustine, carubicin hydrochloride, carzelesin, cedefingol, chlorambucil, cirolemycin, cisplatin, cladribine, crisnatol mesylate, cyclophosphamide, cytarabine, dacarbazine, dactinomycin, daunorubicin hydrochloride, decitabine, dexormaplatin, dezaguanine, dezaguanine mesylate, diaziquone, docetaxel, doxorubicin, doxorubicin hydrochloride, droloxifene, droloxifene citrate, dromostanolone propionate, duazomycin, edatrexate, eflornithine hydrochloride, elsamitrucin, enloplatin, enpromate, epipropidine, epirubicin hydrochloride, erbulozole, esorubicin hydrochloride, estramustine, estramustine phosphate sodium, etanidazole, etoposide, etoposide phosphate, etoprine, fadrozole hydrochloride, fazarabine, fenretinide, floxuridine, fludarabine phosphate, fluorouracil, fluorocitabine, fosquidone, fostriecin sodium, gemcitabine, gemcitabine hydrochloride, hydroxyurea, idarubicin hydrochloride, ifosfamide, ilmofosine, interleukin II (including recombinant interleukin II or rIL2), interferon alpha-2a, interferon alpha-2b, interferon alpha-n1, interferon alpha-n3, interferon beta-Ia, interferon gamma-Ib, iproplatin, irinotecan hydrochloride, lanreotide acetate, letrozole, leuprolide acetate, liarozole hydrochloride, lometrexol sodium, lomustine, losoxantrone hydrochloride, masoprocol, maytansine, mechlorethamine hydrochloride, megestrol acetate, melengestrol acetate, melphalan, menogaril, mercaptopurine, methotrexate, methotrexate sodium, metoprine, meturedepa, mitindomide, mitocarcin, mitocromin, mitogillin, mitomalcin, mitomycin, mitosper, mitotane, mitoxantrone hydrochloride, mycophenolic acid, nocodazole, nogalamycin, ormaplatin, oxisuran, paclitaxel, pegaspargase, peliomycin, pentamustine, peplomycin sulfate, perfosfamide, pipobroman, piposulfan, piroxantrone hydrochloride, plicamycin, plomestane, porfimer sodium, porfiromycin, prednimustine, procarbazine hydrochloride, puromycin, puromycin hydrochloride, pyrazofurin, riboprine, rogletimide, safingol, safingol hydrochloride, semustine, simtrazene, sparfosate sodium, sparsomycin, spirogermanium hydrochloride, spiromustine, spiroplatin, streptonigrin, streptozocin, sulofenur, talisomycin, tecogalan sodium, tegafur, teloxantrone hydrochloride, temoporfin, teniposide, teroxirone, testolactone, thiamiprine, thioguanine, thiotepa, tiazofurin, tirapazamine, toremifene citrate, trestolone acetate, triciribine phosphate, trimetrexate, trimetrexate glucuronate, triptorelin, tubulozole hydrochloride, uracil mustard, uredepa, vapreotide, verteporfin, vinblastine sulfate, vincristine sulfate, vindesine, vindesine sulfate, vinepidine sulfate, vinglycinate sulfate, vinleurosine sulfate, vinorelbine tartrate, vinrosidine sulfate, vinzolidine sulfate, vorozole, zeniplatin, zinostatin, zorubicin hydrochloride.

Examples of other anti-cancer drugs include, but are not limited to, 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-aminotriazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; 9-dihydrotaxol; dioxamycin; diphenyl spiromustine; docetaxel; docosanol; dolasetron; doxifluridine; droloxifene; dronabinol; duocarmycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; 4-ipomeanol; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; ondansetron; oracin; oral cytokine inducer; ormaplatin; osaterone; oxaliplatin; oxaunomycin; paclitaxel; paclitaxel analogues; paclitaxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen binding protein; sizofuran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; and zinostatin stimalamer.

Examples of useful therapeutic agents for treating or preventing UI include, but are not limited to, propantheline, imipramine, hyoscyamine, oxybutynin, and dicyclomine.

Examples of useful therapeutic agents for treating or preventing an ulcer include, antacids such as aluminum hydroxide, magnesium hydroxide, sodium bicarbonate, and calcium bicarbonate; sucraflate; bismuth compounds such as bismuth subsalicylate and bismuth subcitrate; $H_2$ antagonists such as cimetidine, ranitidine, famotidine, and nizatidine; $H^+$, $K^+$-ATPase inhibitors such as omeprazole, iansoprazole, and lansoprazole; carbenoxolone; misprostol; and antibiotics such as tetracycline, metronidazole, timidazole, clarithromycin, and amoxicillin.

Examples of useful therapeutic agents for treating or preventing IBD include, but are not limited to, anticholinergic drugs; diphenoxylate; loperamide; deodorized opium tincture; codeine; broad-spectrum antibiotics such as metronidazole; sulfasalazine; olsalazie; mesalamine; prednisone; azathioprine; mercaptopurine; and methotrexate.

Examples of useful therapeutic agents for treating or preventing IBS include, but are not limited to, propantheline; muscarine receptor antagonists such as pirenzapine, methoctramine, ipratropium, tiotropium, scopolamine, methscopolamine, homatropine, homatropine methylbromide, and methantheline; and antidiarrheal drugs such as diphenoxylate and loperamide.

Examples of useful therapeutic agents for treating or preventing an addictive disorder include, but are not limited to, methadone, desipramine, amantadine, fluoxetine, buprenorphine, an opiate agonist, 3-phenoxypyridine, levomethadyl acetate hydrochloride, and serotonin antagonists.

Examples of useful therapeutic agents for treating or preventing Parkinson's disease and parkinsonism include, but are not limited to, carbidopa/levodopa, pergolide, bromocriptine, ropinirole, pramipexole, entacapone, tolcapone, selegiline, amantadine, and trihexyphenidyl hydrochloride.

Examples of useful therapeutic agents for treating or preventing anxiety include, but are not limited to, benzodiazepines, such as alprazolam, brotizolam, chlordiazepoxide, clobazam, clonazepam, clorazepate, demoxepam, diazepam, estazolam, flumazenil, flurazepam, halazepam, lorazepam, midazolam, nitrazepam, nordazepam, oxazepam, prazepam, quazepam, temazepam, and triazolam; non-benzodiazepine agents, such as buspirone, gepirone, ipsaprione, tiospirone, zolpicone, zolpidem, and zaleplon; tranquilizers, such as barbituates, e.g., amobarbital, aprobarbital, butabarbital, butalbital, mephobarbital, methohexital, pentobarbital, phenobarbital, secobarbital, and thiopental; and propanediol carbamates, such as meprobamate and tybamate.

Examples of useful therapeutic agents for treating or preventing epilepsy include, but are not limited to, carbamazepine, ethosuximide, gabapentin, lamotrignine, phenobarbital, phenyloin, primidone, valproic acid, trimethadione, bemzodiaepines, gabapentin, lamotrigine, γ-vinyl GABA, acetazolamide, and felbamate.

Examples of useful therapeutic agents for treating or preventing stroke include, but are not limited to, anticoagulants such as heparin, agents that break up clots such as streptokinase or tissue plasminogen activator, agents that reduce swelling such as mannitol or corticosteroids, and acetylsalicylic acid.

Examples of useful therapeutic agents for treating or preventing a seizure include, but are not limited to, carbamazepine, ethosuximide, gabapentin, lamotrignine, phenobarbital, phenyloin, primidone, valproic acid, trimethadione, bemzodiaepines, gabapentin, lamotrigine, γ-vinyl GABA, acetazolamide, and felbamate.

Examples of useful therapeutic agents for treating or preventing a pruritic condition include, but are not limited to, naltrexone; nalmefene; danazol; tricyclics such as amitriptyline, imipramine, and doxepin; antidepressants such as those given below, menthol; camphor; phenol; pramoxine; capsaicin; tar; steroids; and antihistamines.

Examples of useful therapeutic agents for treating or preventing psychosis include, but are not limited to, phenothiazines such as chlorpromazine hydrochloride, mesoridazine besylate, and thoridazine hydrochloride; thioxanthenes such as chloroprothixene and thiothixene hydrochloride; clozapine; risperidone; olanzapine; quetiapine; quetiapine fumarate; haloperidol; haloperidol decanoate; loxapine succinate; molindone hydrochloride; pimozide; and ziprasidone.

Examples of useful therapeutic agents for treating or preventing Huntington's chorea include, but are not limited to, haloperidol and pimozide.

Examples of useful therapeutic agents for treating or preventing ALS include, but are not limited to, baclofen, neurotrophic factors, riluzole, tizanidine, benzodiazepines such as clonazepan and dantrolene.

Examples of useful therapeutic agents for treating or preventing cognitive disorders include, but are not limited to, agents for treating or preventing dementia such as tacrine; donepezil; ibuprofen; antipsychotic drugs such as thioridazine and haloperidol; and antidepressant drugs such as those given below.

Examples of useful therapeutic agents for treating or preventing a migraine include, but are not limited to, sumatriptan; methysergide; ergotamine; caffeine; and beta-blockers such as propranolol, verapamil, and divalproex.

Examples of useful therapeutic agents for treating or preventing vomiting include, but are not limited to, 5-$HT_3$ receptor antagonists such as ondansetron, dolasetron, granisetron, and tropisetron; dopamine receptor antagonists such as prochlorperazine, thiethylperazine, chlorpromazin, metoclopramide, and domperidone; glucocorticoids such as dexamethasone; and benzodiazepines such as lorazepam and alprazolam.

Examples of useful therapeutic agents for treating or preventing dyskinesia include, but are not limited to, reserpine and tetrabenazine.

Examples of useful therapeutic agents for treating or preventing depression include, but are not limited to, tricyclic antidepressants such as amitryptyline, amoxapine, bupropion, clomipramine, desipramine, doxepin, imipramine, maprotilinr, nefazadone, nortriptyline, protriptyline, trazodone, trimipramine, and venlaflaxine; selective serotonin reuptake inhibitors such as citalopram, (S)-citalopram, fluoxetine, fluvoxamine, paroxetine, and setraline; monoamine oxidase inhibitors such as isocarboxazid, pargyline, phenelzine, and tranylcypromine; and psychostimulants such as dextroamphetamine and methylphenidate.

A compound of Formula I, or a pharmaceutically acceptable derivative thereof, and the other therapeutic agent can act additively or, in one embodiment, synergistically. In one embodiment, a compound of Formula I is administered concurrently with another therapeutic agent; for example, a composition comprising an effective amount of a compound of Formula I and an effective amount of another therapeutic agent can be administered. Alternatively, a composition comprising an effective amount of a compound of Formula I and a different composition comprising an effective amount of another therapeutic agent can be concurrently administered. In another embodiment, an effective amount of a compound of Formula I is administered prior or subsequent to administration of an effective amount of another therapeutic agent. In this embodiment, the compound of Formula I is administered while the other therapeutic agent exerts its therapeutic effect, or the other therapeutic agent is administered while the compound of Formula I exerts its therapeutic effect for treating or preventing a Condition.

A composition of the invention is prepared by a method comprising admixing a compound of Formula I or a pharmaceutically acceptable derivative and a pharmaceutically acceptable carrier or excipient. Admixing can be accomplished using methods known for admixing a compound (or salt) and a pharmaceutically acceptable carrier or excipient. In one embodiment, the compound of Formula I is present in the composition in an effective amount.

Kits

The invention further encompasses kits that can simplify the administration of a compound of Formula I, or a pharmaceutically acceptable derivative thereof, to an animal.

A typical kit of the invention comprises a unit dosage form of a compound of Formula I. In one embodiment, the unit dosage form is a container, which can be sterile, containing an effective amount of a compound of Formula I and a pharmaceutically acceptable carrier or excipient. The kit can further comprise a label or printed instructions instructing the use of the compound of Formula I to treat a Condition. The kit can also further comprise a unit dosage form of another therapeutic agent, for example, a second container containing an effective amount of the other therapeutic agent and a pharmaceutically acceptable carrier or excipient. In another embodiment, the kit comprises a container containing an effective amount of a compound of Formula I, an effective amount of another therapeutic agent and a pharmaceutically acceptable carrier or excipient. Examples of other therapeutic agents include, but are not limited to, those listed above.

Kits of the invention can further comprise a device that is useful for administering the unit dosage forms. Examples of such a device include, but are not limited to, a syringe, a drip bag, a patch, an inhaler, and an enema bag.

The following examples are set forth to assist in understanding the invention and should not be construed as specifically limiting the invention described and claimed herein. Such variations of the invention, including the substitution of all equivalents now known or later developed, which would be within the purview of those skilled in the art, and changes in formulation or minor changes in experimental design, are to be considered to fall within the scope of the invention incorporated herein.

EXAMPLES

Reference Example 1

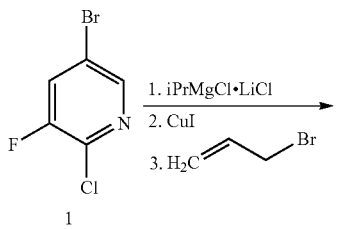

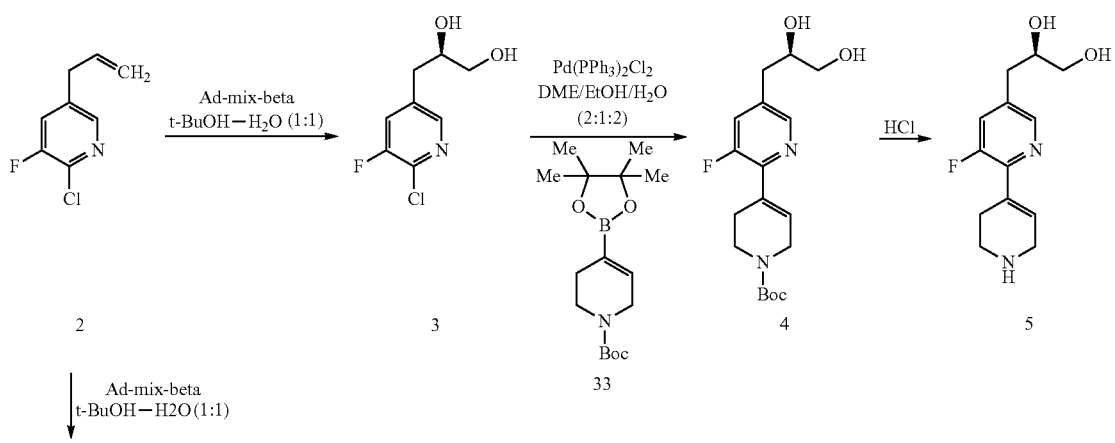

33

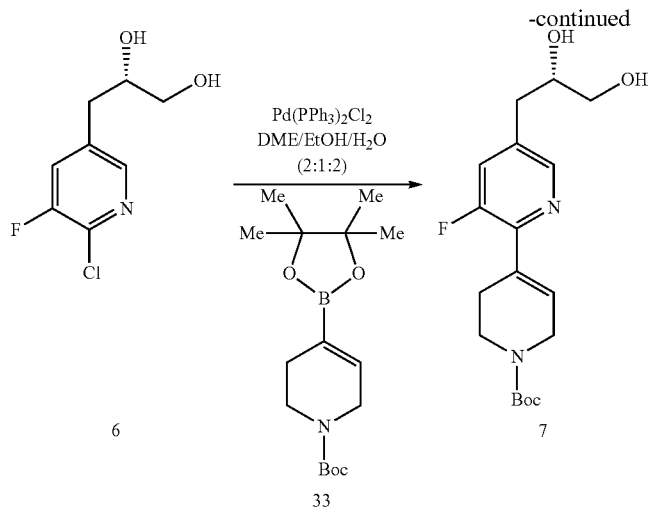
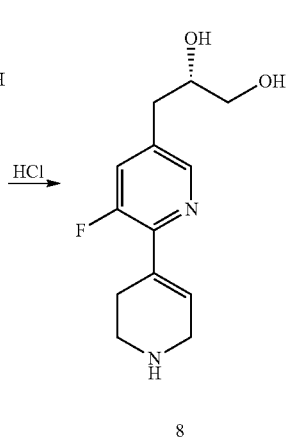

Step 1. Preparation of 5-allyl-2-chloro-3-fluoropyridine (2)

In a dry 3-necked flask flushed with argon containing a solution of 5-bromo-2-chloro-3-fluoro pyridine (4.0 g, 19.05 mmol) at 0° C. was added isopropyl magnesium chloride lithium chloride complex (1.3 M THF solution, 24.8 mmol, 19.1 mL) over 10 min. After additional 10 min of stirring at 0° C., CuI (0.73 g, 3.81 mmol) was added, and the mixture was stirred for 10 minutes at 0° C. and then a solution of allyl bromide (38.1 mmol, 3.3 mL) in THF (4.0 mL) was added at 0° C. over 10 min. After further stirring for 1 h at 0° C., the reaction was quenched with 10% citric acid and extracted with ethyl acetate (100 mL×2). The organic layers were washed with brine, dried over $Na_2SO_4$, and concentrated. The obtained residue was chromatographed on silica gel eluted with hexane and 10% ethyl acetate in hexanes to afford 2.5 g of 2 (77%) as a colorless oil. $^1$H NMR ($CDCl_3$) δ 3.40 (2 H, d, J=6.60 Hz), 5.16 (2 H, m), 5.91 (1 H, m), 7.32 (1 H, dd, J=2.20, 9.00 Hz), 8.06 (1 H, d, J=1.76 Hz); LC/MS (M+1) 172.

Step 2. Preparation of (R)-3-(6-chloro-5-fluoropyridin-3-yl)propane-1,2-diol (3)

To a solution of 2 (2.7 g, 16.2 mmol) in t-butanol (80 mL) and $H_2O$ (80 mL), AD-mix-beta (27.8 g) was added portion wise at 5° C. The reaction was slowly warmed to room temperature and further stirred at this temperature for 16 hrs. The reaction mixture was cooled down to 5° C. and then quenched by adding excess sodium sulfite and stirred for 20 min. The resulting mixture was diluted with water (100 mL) and extracted with ethyl acetate (100 mL×2). The organic layers were combined which was washed with brine, dried over $Na_2SO_4$, and concentrated. The obtained residue was chromatographed on silica gel eluted with hexane/ethyl acetate (20%-100%) to afford 3.2 g (98%) of 3 as a colorless oil which was slowly solidified.

$^1$H NMR ($CDCl_3$) δ 2.36 (1 H, t, J=4.96 Hz), 2.79 (3 H, m), 3.51 (1 H, m), 3.72 (1 H, m), 3.92 (1 H, m), 7.46 (1 H, dd, J=1.96, 8.76 Hz), 8.07 (1 H, d, J=1.76 Hz); LC/MS (M+1) 206.

Step 3. Preparation of (R)-tert-butyl 5-(2,3-dihydroxypropyl)-3-fluoro-5',6'-dihydro-[2,4'-bipyridine]-1'(2'H)-carboxylate (4)

A solution of 3 (2.00 g, 9.76 mmol) and boronic ester 33 (3.62 g, 11.71 mmol) in a mixture of ethanol (15 mL) and THF (15 mL) was treated under argon with $K_2CO_3$ (3.37 g, 24.4 mmol) and bis(triphenylphosphine)dichloropalladium (II) catalyst (0.55 g, 0.781 mmol) at 85° C. for 2 hrs. The mixture was cooled down to room temperature, diluted with water (100 mL) and extracted with ethyl acetate (100 mL×2). The combined organic layers were washed with brine, dried, and concentrated. The obtained residue was chromatographed on silica gel eluted with 50% ethyl acetate in hexanes and ethyl acetate to afford 2.30 g (67%) of 4 as an oil.

$^1$H NMR ($CD_3OD$) δ 1.51 (9 H, s), 2.64 (2 H, m), 2.70 (1 H, dd, J=8.76, 14.00 Hz), 2.93 (1 H, dd, J=4.16, 14.24 Hz), 3.52 (2 H, m), 3.65 (2 H, m), 3.82 (1 H, m), 4.13 (2 H, m), 6.45 (1 H, s), 7.53 (1 H, dd, J=1.52, 12.28 Hz), 8.27 (1 H, s); LC/MS (M+1) 353.

Step 4. Preparation of (R)-3-(3-fluoro-1',2',3',6'-tetrahydro-[2,4'-bipyridin]-5-yl)-propane-1,2-diol (5)

A solution of 4 (2.30 g, 6.53 mmol) in dichloromethane (10 mL) was stirred with 4 mol/L HCl in dioxane (25 mL) in a closed vessel at room temperature overnight. The resulting suspension was stirred for 1 h with ethyl ether. The solid precipitated was collected by filtration and washed several times with ethyl ether to afford 1.95 g (92%) of 5 as a pale yellow solid (HCl salt). The identity of compound 5 was confirmed by LC/MS and 5 was used directly for the next step.

Step 5. Preparation of (S)-3-(6-chloro-5-fluoropyridin-3-yl)propane-1,2-diol (6)

3.2 g (98%) of 6 was obtained in the same manner as Step 2 in this example, except this compound prepared by using AD-mix-alpha in Step 5 instead of AD-mix-beta in Step 2. $^1$H NMR ($CDCl_3$) δ 2.36 (1 H, t, J=4.96 Hz), 2.79 (3 H, m), 3.51 (1 H, m), 3.72 (1 H, m), 3.92 (1 H, m), 7.46 (1 H, dd, J=1.96, 8.76 Hz), 8.07 (1 H, d, J=1.76 Hz); LC/MS (M+1) 206.

Step 6. Preparation of (S)-tert-butyl 5-(2,3-dihydroxypropyl)-3-fluoro-5',6'-dihydro-[2,4'-bipyridine]-1'(2'H)-carboxylate (7)

2.40 g (70%) of 7 was obtained from 6 in the same manner as Step 3 in this example. $^1$H NMR (CD$_3$OD) δ 1.51 (9 H, s), 2.64 (2 H, m), 2.70 (1 H, dd, J=8.76, 14.00 Hz), 2.93 (1 H, dd, J=4.16, 14.24 Hz), 3.52 (2 H, m), 3.65 (2 H, m), 3.82 (1 H, m), 4.13 (2 H, m), 6.45 (1 H, s), 7.53 (1 H, dd, J=1.52, 12.28 Hz), 8.27 (1 H, s); LC/MS (M+1) 353.

Step 7. Preparation of (S)-3-(3-fluoro-1',2',3',6'-tetrahydro-[2,4'-bipyridin]-5-yl)-propane-1,2-diol (8)

1.90 g (95%) of 8 was obtained from 7 in the same manner as Step 4 in this example. The identity of compound was confirmed by LC/MS and 8 was used directly for the Example 11.

Example 1

Preparation of (R)-5-(2,3-dihydroxypropyl)-3-fluoro-N-(5-(trifluoromethyl)-pyridin-2-yl)-5',6'-dihydro-[2,4'-bipyridine]-1'(2'H)-carboxamide (AAO)

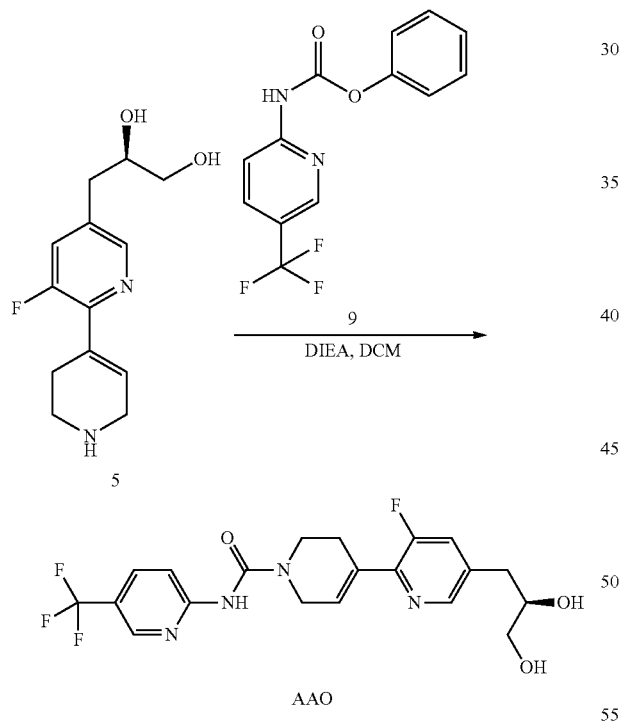

A suspension of 5 (0.15 g, 0.52 mmol) and 9 (0.15 g, 0.52 mmol) in dichloromethane (10 mL) was cooled with an ice bath and treated with diisopropylethylamine (2.0 mL). The resulting mixture was stirred at room temperature overnight. The solution was diluted with EtOAc (100 mL) which was washed with sat. NaHCO$_3$, brine (×2), dried and concentrated. The obtained residue was chromatographed on silica gel eluted with 0-10% MeOH in DCM to obtain 0.10 g (44%) Compound AAO as a white foam. $^1$H NMR (CD$_3$OD) δ 2.57 (1 H, dd, J=7.92, 13.60 Hz), 2.66 (1 H, m), 2.85 (1 H, dd, J=3.92, 13.80 Hz), 3.30 (2 H, m), 3.68 (3H, m), 4.25 (2 H, m), 4.70 (1 H, t, J=5.72 Hz), 4.76 (1 H, d, J=4.84 Hz), 6.52 (1, m), 7.56 (1 H, dd, J=1.32, 13.16 Hz), 7.99 (1 H, d, J=9.20 Hz), 8.06 (1 H, dd, J=1.96, 9.00 Hz), 8.28 (1 H, s), 8.62 (1 H, s), 9.82 (1 H, s); LC/MS (M+1) 441.

Example 2

Preparation of (R)-N-(3-chloro-4-(trifluoromethyl)phenyl)-5-(2,3-dihydroxypropyl)-3-fluoro-5',6'-dihydro-[2,4'-bipyridine]-1'(2'H)-carboxamide (AAY)

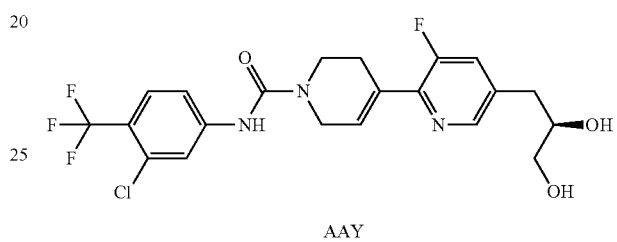

AAY 0.12 g (48%) of Compound AAY was obtained in the same manner as Example 1. $^1$H NMR (CD$_3$OD) δ 1.61 (3 H, m), 2.82 (1 H, dd, J=4.16, 14.24 Hz), 3.41 (2 H, d, J=5.24 Hz), 3.68 (3 H, m), 4.17 (2 H, d, J=2.84 Hz), 6.42 (1 H, m), 7.42 (2 H, m), 7.53 (1 H, d, J=8.84 Hz), 7.71 (1 H, d, J=2.20 Hz), 8.18 (1 H, s); LC/MS (M+1) 474.

Example 3

Preparation of (R)-5-(2,3-dihydroxypropyl)-3-fluoro-N-(3-methoxy-4-(trifluoromethyl)-phenyl)-5',6'-dihydro-[2,4'-bipyridine]-1'(2'H)-carboxamide (ABC)

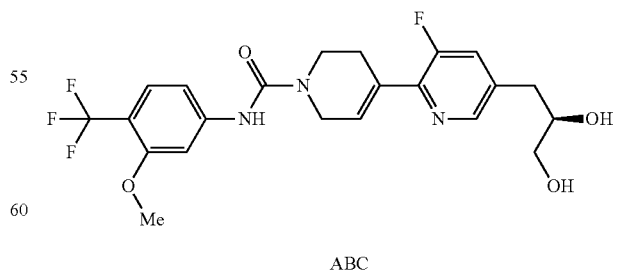

ABC 0.16 g (66%) of Compound ABC was obtained in the same manner as Example 1. $^1$H NMR (CD$_3$OD) δ 2.61 (3 H, m), 2.82 (1 H, dd, J=3.96 Hz), 3.41 (2 H, d, J=5.28 Hz), 3.69 (6 H, m), 4.17 (2 H, m), 6.41 (1 H, m), 6.96 (1 H, dd, J=1.82, 8.56 Hz), 7.32 (2 H, m), 7.42 (1 H, dd, J=1.52, 12.30 Hz), 8.17 (1 H, s); LC/MS (M+1) 470.

Example 4

Preparation of (R)-5-(2,3-dihydroxypropyl)-3-fluoro-N-(3-methyl-4-(trifluoro-methyl) phenyl)-5',6'-dihydro-[2,4'-bipyridine]-1'(2'H)-carboxamide (ACA)

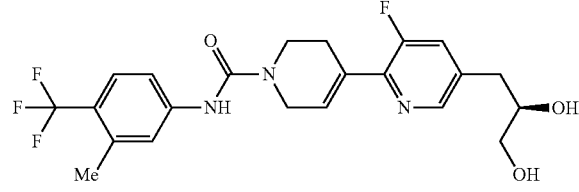

ACA 0.13 g (55%) of Compound ACA was obtained in the same manner as Example 1. $^1$H NMR (CD$_3$OD) δ 2.33 (3 H, s, 2.61 (3 H, m), 2.83 (1 H, dd, J=3.96, 14.24 Hz), 3.41 (2 H, d, J=5.48 Hz), 3.64-3.74 (3 H, m), 4.17 (2 H, m), 6.42 (1 H, m), 7.28-7.45 (4 H, m), 8.18 (1 H, s); LC/MS (M+1) 454.

Example 5

Preparation of (S)-5-(2,3-dihydroxypropyl)-3-fluoro-N-(5-(trifluoro-methyl)-pyridin-2-yl)-5',6'-dihydro-[2,4'-bipyridine]-1'(2'H)-carboxamide (AAP)

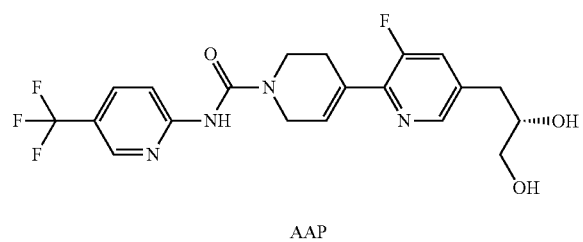 [SMILES: O=C(Nc1ccc(C(F)(F)F)cn1)N1CC=C(c2ncc(C[C@H](O)CO)cc2F)CC1]

AAP 0.10 g (44%) of Compound AAP was obtained in the same manner as Example 1 except 8 replaced 5. $^1$H NMR (CD$_3$OD) δ 2.57 (1 H, dd, J=7.92, 13.60 Hz), 2.66 (1 H, m), 2.85 (1 H, dd, J=3.92, 13.80 Hz), 3.30 (2 H, m), 3.68 (3 H, m), 4.25 (2 H, m), 4.70 (1 H, t, J=5.72 Hz), 4.76 (1 H, d, J=4.84 Hz), 6.52 (1, m), 7.56 (1 H, dd, J=1.32, 13.16 Hz), 7.99 (1 H, d, J=9.20 Hz), 8.06 (1 H, dd, J=1.96, 9.00 Hz), 8.28 (1H, s), 8.62 (1 H, s), 9.82 (1 H, s); LC/MS (M+1) 441.

Example 6

Preparation of (S)-N-(3-chloro-4-(trifluoromethyl) phenyl)-5-(2,3-dihydroxy-propyl)-3-fluoro-5',6'-dihydro-[2,4'-bipyridine]-1'(2'H)-carboxamide (AAZ)

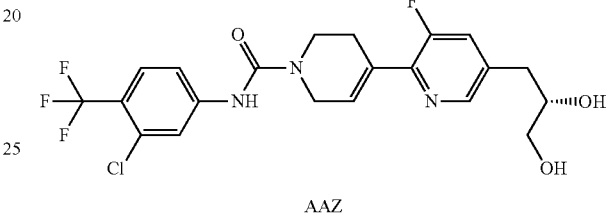

AAZ 0.12 g (49%) of Compound AAZ was obtained in the same manner as Example 1 except 8 replaced 5. $^1$H NMR (CD$_3$OD) δ 1.61 (3 H, m), 2.82 (1 H, dd, J=4.16, 14.24 Hz), 3.41 (2 H, d, J=5.24 Hz), 3.68 (3 H, m), 4.17 (2 H, d, J=2.84 Hz), 6.42 (1 H, m), 7.42 (2 H, m), 7.53 (1 H, d, J=8.84 Hz), 7.71 (1 H, d, J=2.20 Hz), 8.18 (1 H, s); LC/MS (M+1) 474.

Example 7

Preparation of (S)-5-(2,3-dihydroxypropyl)-3-fluoro-N-(3-methoxy-4-(trifluoromethyl)-phenyl)-5',6'-dihydro-[2,4'-bipyridine]-1'(2'H)-carboxamide (ABA)

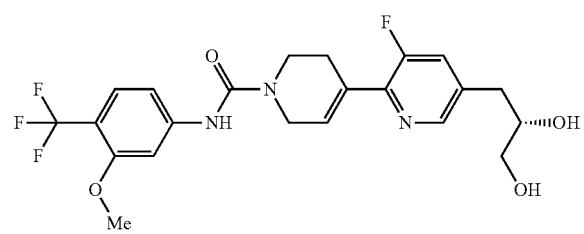

ABA 0.15 g (51%) of Compound ABA was obtained in the same manner as Example 1. $^1$H NMR (CD$_3$OD) δ 2.61 (3 H, m), 2.82 (1 H, dd, J=3.96 Hz), 3.41 (2 H, d, J=5.28 Hz), 3.69 (6 H, m), 4.17 (2 H, m), 6.41 (1 H, m), 6.96 (1 H, dd, J=1.82, 8.56 Hz), 7.32 (2 H, m), 7.42 (1 H, dd, J=1.52, 12.30 Hz), 8.17 (1 H, s); LC/MS (M+1) 470.

Example 8

Preparation of (S)-5-(2,3-dihydroxypropyl)-3-fluoro-N-(3-methyl-4-(trifluoromethyl)phenyl)-5',6'-dihydro-[2,4'-bipyridine]-1'(2'H)-carboxamide (ABY)

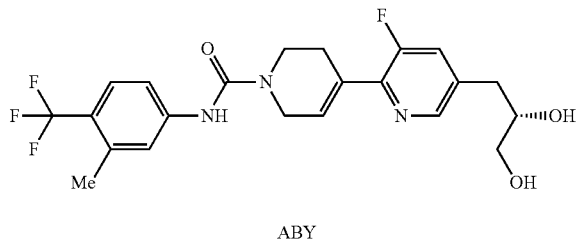 [SMILES: Cc1cc(NC(=O)N2CC=C(c3ncc(C[C@H](O)CO)cc3F)CC2)ccc1C(F)(F)F]

ABY 0.13 g (55%) of Compound ABY was obtained in the same manner as Example 1. $^1$H NMR (CD$_3$OD) δ 2.33 (3 H, s0, 2.61 (3 H, m), 2.83 (1 H, dd, J=3.96, 14.24 Hz), 3.41 (2 H, d, J=5.48 Hz), 3.64-3.74 (3 H, m), 4.17 (2 H, m), 6.42 (1 H, m), 7.28-7.45 (4 H, m), 8.18 (1 H, s); LC/MS (M+1) 454.

Example 9

Preparation of (S)-5-(2,3-dihydroxypropyl)-3-fluoro-N-(3-methyl-4-(trifluoromethoxy)-phenyl)-5',6'-dihydro-[2,4'-bipyridine]-1'(2'H)-carboxamide (ABZ)

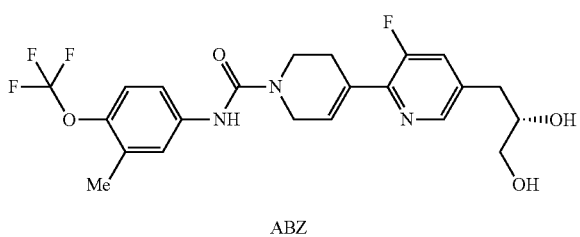 [SMILES: Cc1cc(NC(=O)N2CC=C(c3ncc(C[C@H](O)CO)cc3F)CC2)ccc1OC(F)(F)F]

ABZ 0.065 g (27%) of Compound ABZ was obtained in the same manner as Example 1. $^1$H NMR (CD$_3$OD) δ 2.23 (3 H, s), 2.57 (1 H, m), 2.65 (2 H, m), 2.85 (1 H, m), 3.28 (2 H, m), 3.67 (3 H, m), 4.20 (2 H, d, J=2.64 Hz), 4.67 (1 H, t, J=5.04 Hz), 4.72 (2 H, d, J=5.24 Hz), 6.53 (1 H, m), 7.18 (1 H, d, J=7.88 Hz), 7.49 (3 H, m), 8.30 (1 H, s), 8.67 (1 H, s); LC/MS (M+1) 470.

Example 10

Preparation of (R)-5-(2,3-dihydroxypropyl)-3-fluoro-N-(6-fluorobenzo[d]-thiazol-2-yl)-5',6'-dihydro-[2,4'-bipyridine]-1'(2'H)-carboxamide (AAQ)

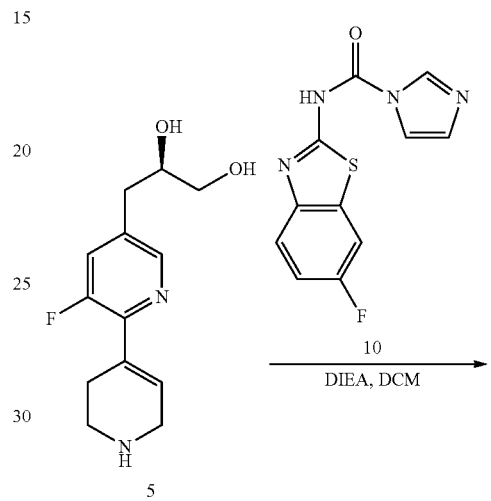

AAQ

A suspension of 5 (0.15 g, 0.52 mmol) and 10 (0.14 g, 0.52 mmol) in dichloromethane (10 mL) was cooled with an ice bath and treated with diisopropylethylamine (2.0 mL). The resulting mixture was stirred at room temperature overnight. The precipitate was collected by filtration and washed several times with ethyl ether. The obtained solid was suspend in 2 mol/L HCl aq. solution which was stirred at room temperature 12 hrs, then 1 mol/L NaOH was added to neutralize to a pH of about 6. The collected solid by filtration was dried by oven to afford 0.16 g (yield 69%) Compound AAQ as a white solid. $^1$H NMR (CD$_3$OD) δ 2.58 (1 H, dd, J=8.32, 13.80 Hz), 2.66 (2 H, m), 2.85 (1 H, dd, J=4.16, 14.00 Hz), 3.31 (2 H, m), 3.66 (1 H, m), 3.78 (2 H, m), 4.29 (2 H, m), 5.13 (2 H, s), 6.55

(1H, m), 7.22 (1 H, m), 7.56 (1 H, m), 7.60 (1 H, dd, J=1.52, 13.00 Hz), 7.79 (1 H, dd, J=2.40, 8.76 Hz), 8.29 (1 H, s); LC/MS (M+1) 447.
Example 11
Preparation of (S)-5-(2,3-dihydroxypropyl)-3-fluoro-N-(6-fluorobenzo[d]-thiazol-2-yl)-5',6'-dihydro-[2,4'-bipyridine]-1'(2'H)-carboxamide (AAR)
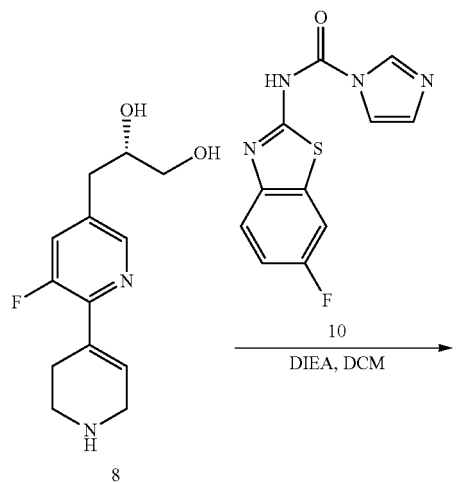
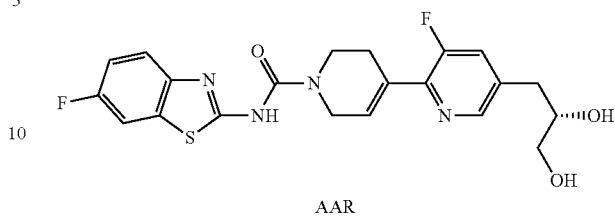
AAR
0.18 g (yield 78%) of Compound AAR was obtained in the same manner as Example 10 except 8 replaced 5. $^1$H NMR (CD$_3$OD) δ 2.58 (1 H, dd, J=8.32, 13.80 Hz), 2.66 (2 H, m), 2.85 (1 H, dd, J=4.16, 14.00 Hz), 3.31 (2 H, m), 3.66 (1 H, m), 3.78 (2 H, m), 4.29 (2 H, m), 5.13 (2 H, s), 6.55 (1 H, m), 7.22 (1 H, m), 7.56 (1 H, m), 7.60 (1 H, dd, J=1.52, 13.00 Hz), 7.79 (1 H, dd, J=2.40, 8.76 Hz), 8.29 (1H, s); LC/MS (M+1) 447.
Reference Example 2
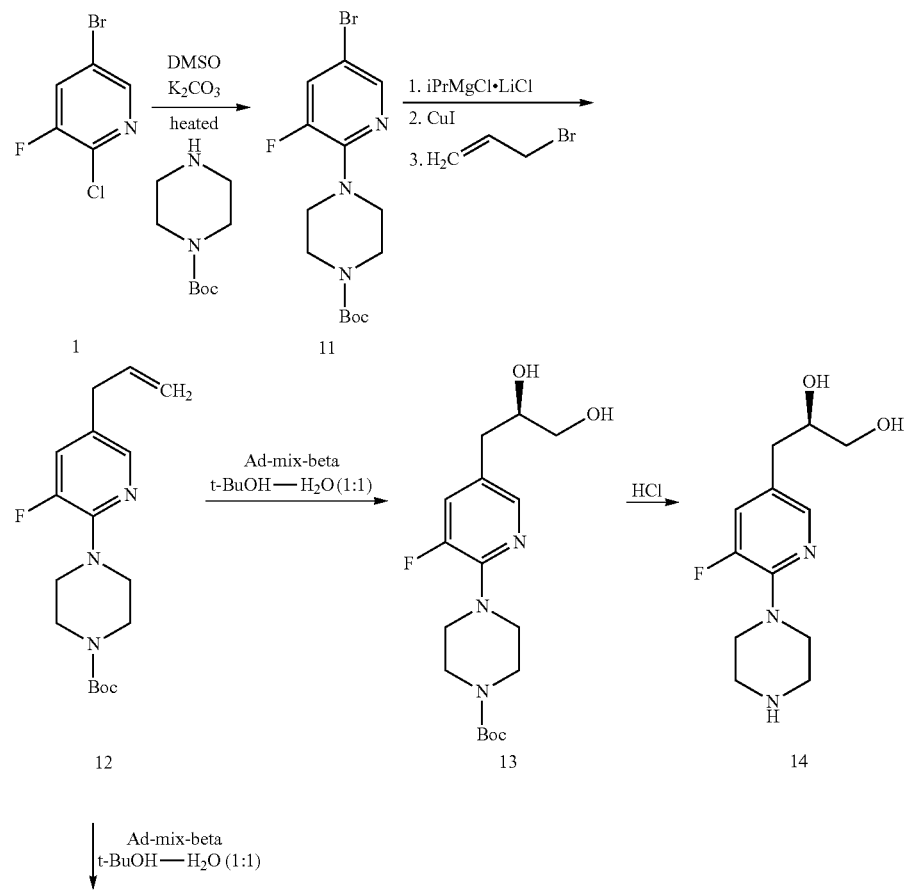

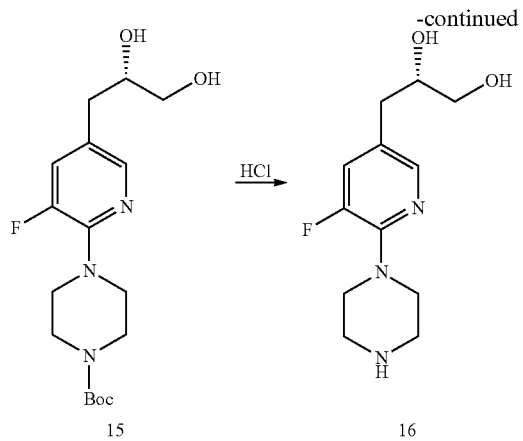
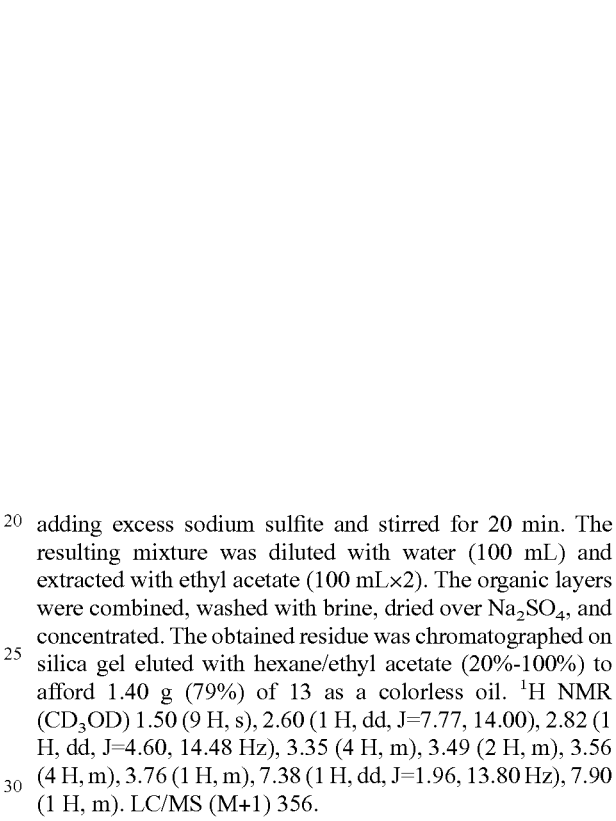

Step 1. Preparation of tert-butyl 4-(5-bromo-3-fluoropyridin-2-yl)piperazine-1-carboxylate (11)

To a sealed vessel were added 2-chloro-3-fluoro-5-bromopyridine (1) (10.50 g, 50 mmol), N-Boc-piperazine (9.30 g, 50 mmol), $K_2CO_3$ (8.28 g, 60 mmol), and DMSO (40 mL). The resulting mixture was heated at 120° C. for 12 hrs, then cooled down and diluted with ethyl ether (200 mL). The solution was washed with water (80 mL×2), brine (100 mL), dried, and concentrated. The residue was suspended in hexanes (150 mL) and the precipitation was formed. After removed the solid, the remaining solvents which contained the desired product were evaporated and subjected to chromatography column eluted with ethyl acetate/hexanes (0-10%) to afford 4.60 g (26%) of 11 as a colorless oil which was slowly solidified to be white solid. $^1$H NMR (CDCl$_3$) δ 1.48 (9 H, s), 3.43 (4 H, m), 3.54 (4 H, m), 7.39 (4 H, dd, J=1.96, 12.04 Hz), 8.05 (1 H, m). LC/MS (M+1) 361.

Step 2. Preparation of tert-butyl 4-(5-allyl-3-fluoropyridin-2-yl)piperazine-1-carboxylate (12)

In a dry 3-necked flask flushed with argon containing a solution of 11 (6.86 g, 19.05 mmol) in THF (40 mL) at 0° C. was added a 1.3 M THF solution of isopropyl magnesium chloride lithium chloride complex (19.1 mL, 24.8 mmol) over 10 min. After 10 additional minutes of stirring at 0° C., CuI (0.73 g, 3.81 mmol) was added, the mixture was stirred for 10 minutes at 0° C. and then a solution of allyl bromide (3.3 mL, 38.1 mmol) in THF (4.0 mL) was added at 0° C. over 10 min. After further stirring for 1 h at 0° C., the reaction was quenched with 10% citric acid and extracted with ethyl acetate (100 mL×2). The organic layers were combined which was washed with brine, dried over Na$_2$SO$_4$, and concentrated. The obtained residue was chromatographed on silica gel eluted with hexane and 10% ethyl acetate in hexanes to afford 4.22 g of 12 (69%) as a colorless oil which was used directly for the next step. LC/MS (M+1) 322.

Step 3. Preparation of (R)-tert-butyl 4-(5-(2,3-dihydroxypropyl)-3-fluoropyridin-2-yl)piperazine-1-carboxylate (13)

To a solution of 12 (1.60 g, 5.0 mmol) in t-butanol (40 mL) and H$_2$O (40 mL) AD-mix beta (8.6 g) was added portion wise at 5° C. The reaction was slowly warmed to room temperature and further stirred at this temperature for 16 hrs. The reaction mixture was cooled down to 5° C. and then quenched by adding excess sodium sulfite and stirred for 20 min. The resulting mixture was diluted with water (100 mL) and extracted with ethyl acetate (100 mL×2). The organic layers were combined, washed with brine, dried over Na$_2$SO$_4$, and concentrated. The obtained residue was chromatographed on silica gel eluted with hexane/ethyl acetate (20%-100%) to afford 1.40 g (79%) of 13 as a colorless oil. $^1$H NMR (CD$_3$OD) 1.50 (9 H, s), 2.60 (1 H, dd, J=7.77, 14.00), 2.82 (1 H, dd, J=4.60, 14.48 Hz), 3.35 (4 H, m), 3.49 (2 H, m), 3.56 (4 H, m), 3.76 (1 H, m), 7.38 (1 H, dd, J=1.96, 13.80 Hz), 7.90 (1 H, m). LC/MS (M+1) 356.

Step 4. Preparation of (R)-3-(5-fluoro-6-(piperazin-1-yl)pyridin-3-yl)propane-1,2-diol (14)

A solution of 13 (1.40 g, 3.94 mmol) in dichloromethane (10 mL) was stirred with 4 mol/L HCl in dioxane (25 mL) in a closed vessel overnight at room temperature. The resulting suspension was stirred for 1 h with ethyl ether. The solid precipitated was collected by filtration and washed several times with ethyl ether to afford 1.15 g (yield 100%) of 14 as a pale yellow foam (HCl salt). The identity of compound 14 was confirmed by LC/MS and was used directly for the next step. LC/MS (M+1) 256.

Step 5. Preparation of (S)-tert-butyl 4-(5-(2,3-dihydroxypropyl)-3-fluoropyridin-2-yl)piperazine-1-carboxylate (15)

4.80 g (79%) of 15 was obtained in the same manner as Step 3 in this example except this compound prepared by using AD-mix-alpha in Step 5 instead of AD-mix-beta in Step 3.

$^1$H NMR (CD$_3$OD) δ 1.50 (9 H, s), 2.60 (1 H, dd, J=7.77, 14.00), 2.82 (1 H, dd, J=4.60, 14.48 Hz), 3.35 (4 H, m), 3.49 (2 H, m), 3.56 (4 H, m), 3.76 (1 H, m), 7.38 (1 H, dd, J=1.96, 13.80 Hz), 7.90 (1 H, m). LC/MS (M+1) 356.

Step 6. Preparation of (S)-3-(5-fluoro-6-(piperazin-1-yl)pyridin-3-yl)propane-1,2-diol (16)

2.30 g (100%) of 16 was obtained in the same manner as Step 4 in this example.

Example 12

Preparation of (R)-4-(5-(2,3-dihydroxypropyl)-3-fluoropyridin-2-yl)-N-(6-fluorobenzo[d]-thiazol-2-yl)piperazine-1-carboxamide (ACW)

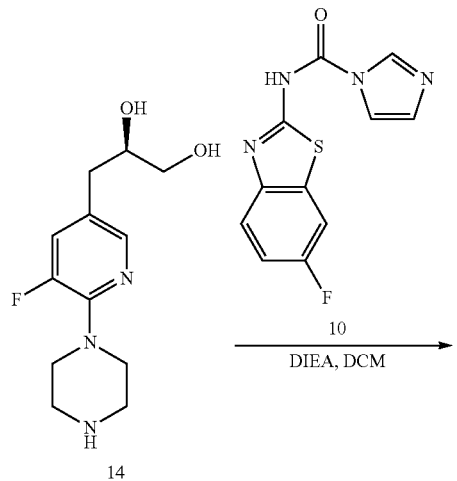

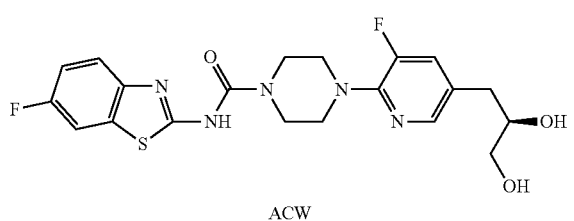

A suspension of 14 (0.20 g, 0.69 mmol) and 10 (0.18 g, 0.69 mmol) in dichloromethane (10 mL) was cooled with an ice bath and treated with diisopropylethylamine (2.0 mL). The resulting mixture was stirred at room temperature overnight. The precipitate was collected by filtration and washed several times with ethyl ether. The obtained solid was suspend in 2 mol/L HCl aq. solution which was stirred at room temperature 12 hrs, then 1 mol/L NaOH was added to neutralize to a pH of about 6. The solid collected by filtration was dried by oven to afford 0.20 g (yield 65%) Compound ACW as a white solid. $^1$H NMR (CD$_3$OD) δ 2.48 (1 H, m), 2.73 (1 H, dd, J=3.92, 13.80 Hz), 3.21-3.43 (6 H, m), 3.59 (1 H, m), 3.70 (4 H, m), 5.05 (2 H, brs), 7.22 (1 H, m), 7.45 (2 H, m), 7.55 (2 H, m), 7.78 (1 H, dd, J=2.40, 9.00 Hz), 7.89 (1 H, s); LC/MS (M+1) 450.

Example 13

Preparation of (R)-N-(6-chlorobenzo[d]thiazol-2-yl)-4-(5-(2,3-dihydroxypropyl)-3-fluoropyridin-2-yl)piperazine-1-carboxamide (ACX)

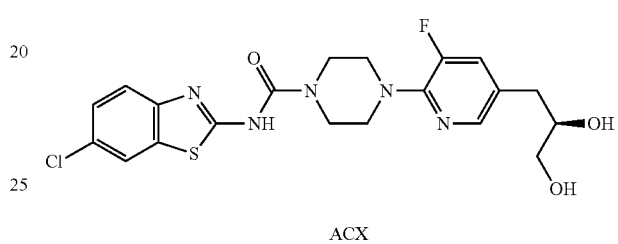

0.185 g (58%) of Compound ACX was obtained in the same manner as Example 12. $^1$H NMR (CD$_3$OD) δ 2.47 (1 H, m), 2.73 (1 H, dd, J=3.96, 13.60 Hz), 3.21-3.42 (6 H, m), 3.59 (1 H, m), 3.71 (4 H, m), 4.27 (2 H, brs), 7.39 (1 H, dd, J=2.20, 8.52 Hz), 7.45 (1 H, dd, J=1.52, 14.24 Hz), 7.54 (1 H, m), 7.89 (1 H, s), 7.99 (1 H, d, J=1.32 Hz); LC/MS (M+1) 466.

Example 14

Preparation of (R)-4-(5-(2,3-dihydroxypropyl)-3-fluoropyridin-2-yl)-N-(6-methylbenzo[d]-thiazol-2-yl)piperazine-1-carboxamide (ACY)

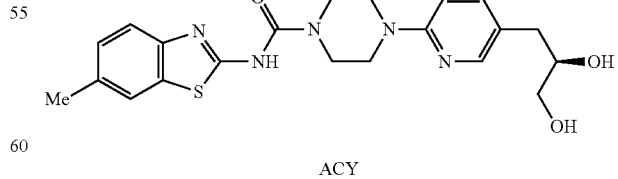

0.178 g (60%) of Compound ACY was obtained in the same manner as Example 12. $^1$H NMR (CD$_3$OD) δ 2.37 (3 H, s), 2.47 (1 H, m), 2.73 (1 H, dd, J=4.36, 14.04 Hz), 3.19-3.40

(6 H, m), 3.53-3.80 (5 H, m), 4.26 (2 H, m), 7.17 (1 H, d, J=6.36 Hz), 7.37-7.76 (3 H, m), 7.89 (1 H, s), 11.20 (1 H, brs); LC/MS (M+1) 446.

Example 15

Preparation of (R)-4-(5-(2,3-dihydroxypropyl)-3-fluoropyridin-2-yl)-N-(5,6-dimethylbenzo[d]thiazol-2-yl)piperazine-1-carboxamide (ACZ)

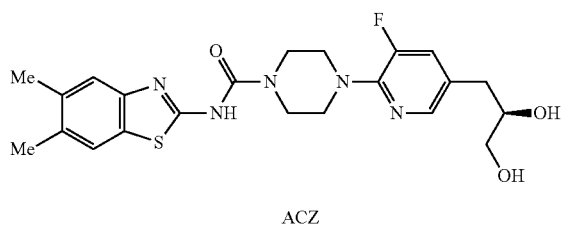 [SMILES: Cc1cc2nc(NC(=O)N3CCN(c4ncc(C[C@@H](O)CO)cc4F)CC3)sc2cc1C]

ACZ 0.188 g (59%) of Compound ACZ was obtained in the same manner as Example 12. $^1$H NMR (CD$_3$OD) δ 2.29 (6 H, m), 2.47 (1 H, m), 2.73 (1 H, dd, J=4.16, 14.04 Hz), 3.19-3.42 (6 H, m), 3.53-3.82 (5 H, m), 4.62 (2 H, m), 6.92-7.68 (3 H, m), 7.88 (1 H, s), 11.16 (1 H, s); LC/MS (M+1) 460.

Example 16

Preparation of (S)-4-(5-(2,3-dihydroxypropyl)-3-fluoropyridin-2-yl)-N-(6-fluorobenzo[d]-thiazol-2-yl)piperazine-1-carboxamide (ADD)

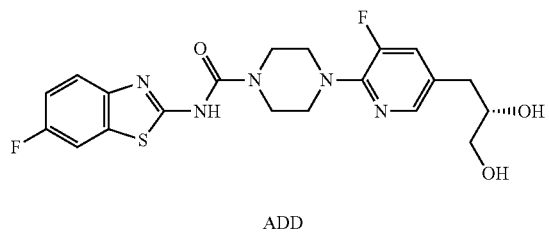 [SMILES: O=C(Nc1nc2ccc(F)cc2s1)N1CCN(c2ncc(C[C@H](O)CO)cc2F)CC1 ; "ADD"]

ADD 0.16 g (52%) of Compound ADD was obtained in the same manner as Example 12 except 16 replaced 14. $^1$H NMR (CD$_3$OD) δ 2.45 (1 H, m), 2.73 (1 H, dd, J=4.16, 14.00 Hz), 3.19-3.42 (6 H, m), 3.59 (1 H, m), 3.70 (4 H, m), 5.11 (2 H, brs), 7.22 (1 H, m), 7.41-7.61 (2 H, m), 7.78 (1 H, dd, J=2.40, 8.56 Hz), 7.89 (1 H, s); LC/MS (M+1) 450.

Example 17

Preparation of (S)-N-(6-chlorobenzo[d]thiazol-2-yl)-4-(5-(2,3-dihydroxypropyl)-3-fluoropyridin-2-yl)piperazine-1-carboxamide (ADE)

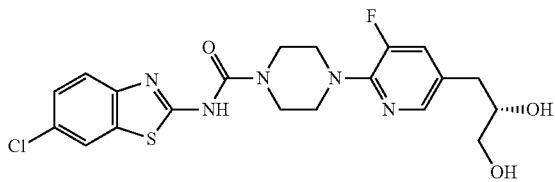

ADE 0.20 g (62%) of Compound ADE was obtained in the same manner as Example 12 except 16 replaced 14. $^1$H NMR (CD$_3$OD) δ 2.48 (1 H, m), 2.73 (1 H, dd, J=3.92, 14.04 Hz), 3.22-3.42 (6 H, m), 3.59 (1 H, m), 3.71 (4 H, m), 5.20 (2 H, brs), 7.39 (1 H, dd, J=2.20, 8.56 Hz), 7.46 (1 H, dd, J=1.76, 14.24 Hz), 7.55 (1 H, m), 7.89 (1 H, s), 8.00 (1 H, d, J=1.52 Hz); LC/MS (M+1) 466.

Example 18

Preparation of (R)-4-(5-(2,3-dihydroxypropyl)-3-methylpyridin-2-yl)-N-(6-fluorobenzo[d]-thiazol-2-yl)piperazine-1-carboxamide (ADA)

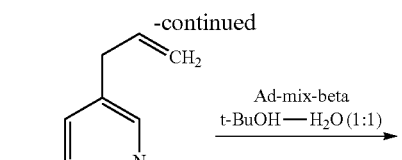

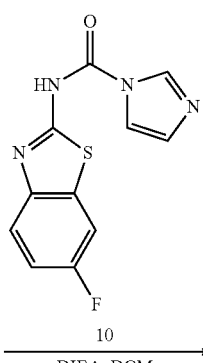

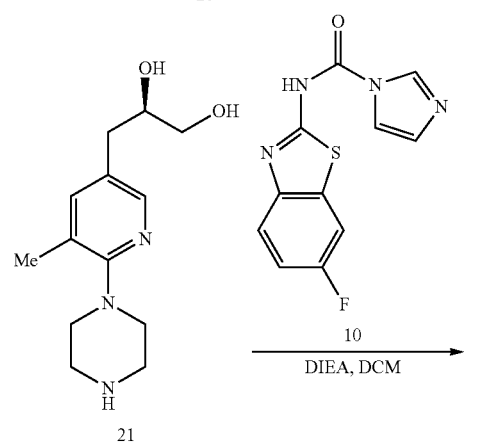

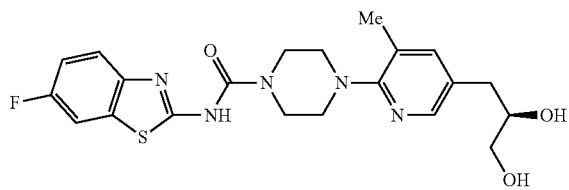

Step 1. Preparation of tert-butyl 4-(5-bromo-3-methylpyridin-2-yl)piperazine-1-carboxylate (18)

2.60 g (37%) of 18 was obtained in the same manner as Reference Example 2, Step 1.

Step 2. Preparation of tert-butyl 4-(5-allyl-3-methylpyridin-2-yl)piperazine-1-carboxylate (19)

0.75 g of 19 (77%, based on the consumed start material) as a colorless oil in the same manner as Reference Example 2, Step 2. $^1$H NMR (CDCl$_3$) δ 1.48 (9 H, s), 2.26 (3 H, s), 3.05 (4 H, m), 3.28 (2 H, m), 3.56 (4 H, m), 5.07 (2 H, m), 5.90 (1 H, m), 7.25 (1 H, d, J=1.76 Hz), 7.98 (1 H, d, J=2.20 Hz); LC/MS (M+1) 318.

Step 3. Preparation of (R)-tert-butyl 4-(5-(2,3-dihydroxypropyl)-3-methylpyridin-2-yl)piperazine-1-carboxylate (20)

0.65 g (77%) of 20 was obtained in the same manner as Reference Example 2, Step 3.

$^1$H NMR (CD$_3$OD) δ 150 (9 H, s), 2.32 (3 H, s), 2.59 (1 H, dd, J=7.90, 14.04 Hz), 2.80 (1 H, dd, J=4.60, 14.00 Hz), 3.03 (4 H, m), 3.49 (2 H, m), 3.58 (4 H, m), 3.76 (1 H, m), 7.50 (1 H, d, J=2.00 Hz), 7.98 (1 H, d, J=2.20 Hz); LC/MS (M+1) 352.

Step 4. Preparation of (R)-3-(5-methyl-6-(piperazin-1-yl)pyridin-3-yl)propane-1,2-diol (21)

0.53 g (100%) of 21 was obtained in the same manner as Reference Example 2, Step 4.

Step 5. Preparation of (R)-4-(5-(2,3-dihydroxypropyl)-3-methylpyridin-2-yl)-N-(6-fluorobenzo[d]-thiazol-2-yl)piperazine-1-carboxamide (ADA)

0.20 g (90%) of Compound ADA was obtained in the same manner as Example 12. $^1$H NMR (CD$_3$OD) δ 2.26 (3 H, s), 2.45 (1 H, m), 2.70 (1 H, m), 3.05 (4 H, m), 3.28 (2 H, m), 3.50-3.84 (5 H, m), 4.58 (2 H, brs), 7.22-7.95 (5 H, m), 11.31 (1 H, s); LC/MS (M+1) 445.

Example 19

Preparation of (R)-N-(6-chlorobenzo[d]thiazol-2-yl)-4-(5-(2,3-dihydroxypropyl)-3-fluoropyridin-2-yl)piperazine-1-carboxamide (ADB)

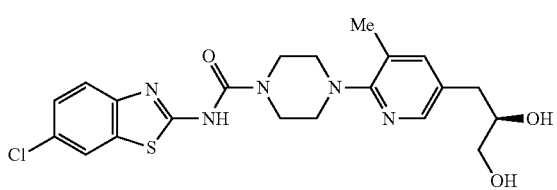

0.23 g (96%) of Compound ADB was obtained in the same manner as Example 12. $^1$H NMR (CD$_3$OD) δ 2.26 (3 H, s), 2.43 (1 H, m), 2.70 (1 H, m), 3.06 (4 H, m), 3.28 (2 H, m), 3.49-3.94 (5 H, m), 4.58 (2 H, brs), 7.43-7.95 (5 H, m), 11.40 (1 H, s); LC/MS (M+1) 461.

Example 20

Preparation of (R)-4-(5-(2,3-dihydroxypropyl)-3-fluoropyridin-2-yl)-4-fluoro-N-(3-methyl-4-(trifluoromethyl)phenyl)piperidine-1-carboxamide (ACO)

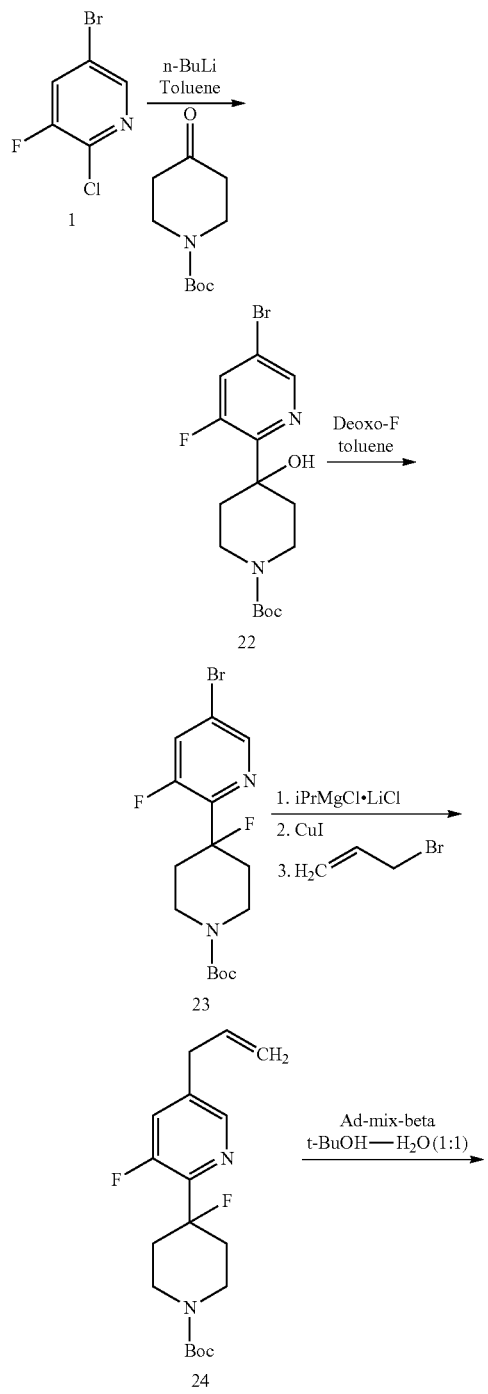

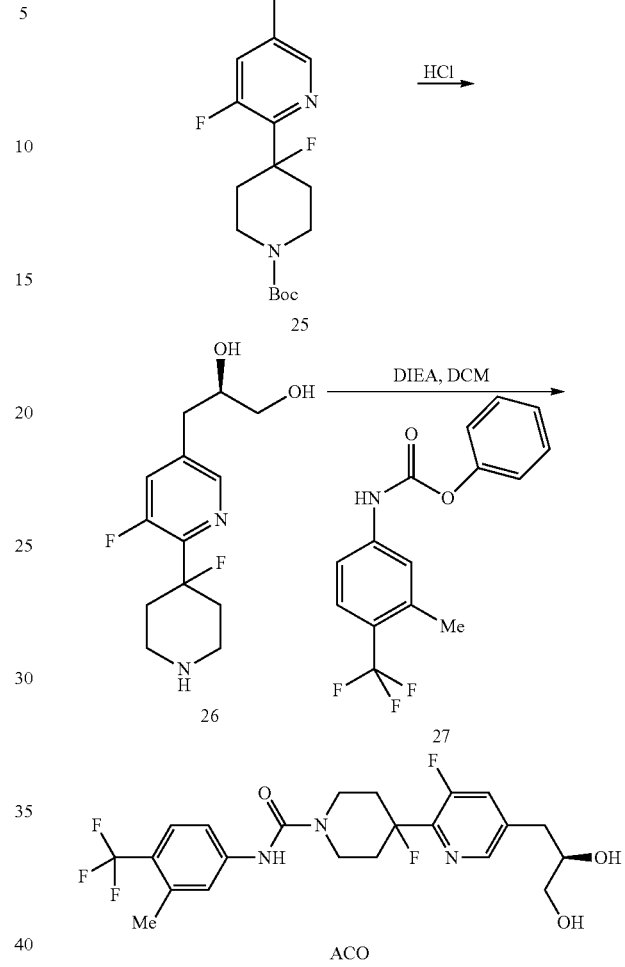

Step 1. Preparation of tert-butyl 4-(5-bromo-3-fluoropyridin-2-yl)-4-hydroxypiperidine-1-carboxylate (22)

To a round-bottomed flask was charged 1 (2.55 g, 10 mmol) in toluene (40 mL) which was cooled down to −60° C., n-BuLi (2M in hexanes, 4.2 mL, 10.5 mmol) was added dropwise and the resulting mixture was stirred at this temperature for 30 min. Then N-Boc-piperidone (2.13 g, 10.5 mmol) dissolved in toluene (10 mL) was added slowly and the mixture was further stirred for 1 h. The reaction was quenched with 10% citric acid solution and diluted with EtOAc (100 mL). The organic layer was washed with brine, dried, and evaporated. The obtained residue was chromatographed on silica gel eluted with EtOAc/hexanes (0-10%) to obtain 2.0 g (53%) of 22 as a white solid which was used directly for the next step. LC/MS (M+1) 376.

Step 2. Preparation of tert-butyl 4-(5-bromo-3-fluoropyridin-2-yl)-4-fluoropiperidine-1-carboxylate (23)

To a round-bottomed flask was charged 22 (10.8 g, 31.5 mmol) in toluene (100 mL) which was cooled down to −40°

C., Deoxo-F (7.5 mL, 40.9 mmol) dissolved in toluene (20 mL) was added slowly and the resulting mixture was further stirred for 2 hrs at this temperature. The reaction was slowly warmed to room temperature in a 2 hr period, quenched with brine (100 mL), and then diluted with EtOAc (200 mL). The organic layer was washed with brine, dried, and evaporated. The obtained residue was chromatographed on silica gel eluted with EtOAc/hexanes (0-5%) to obtain 10.0 g (84%) of 23 as a colorless oil. NMR (CDCl$_3$) δ 1.10 (1 H, m), 1.49 (9 H, s), 2.22 (2 H, m), 3.29 (2 H, m), 3.49 (2 H, d, J=5.48 Hz), 4.08 (2 H, m), 7.63 (1 H, dd, J=1.76, 10.08 Hz), 8.45 (1 H, t, J=1.56 Hz); LC/MS (M+1) 378.

Step 3. Preparation of tert-butyl 4-(5-allyl-3-fluoropyridin-2-yl)-4-fluoropiperidine-1-carboxylate (24)

In a dry 3-necked flask flushed with argon containing a solution of 23 (3.77 g, 10.0 mmol) in THF (50 mL) at 0° C. was added isopropyl magnesium chloride lithium chloride complex (1.3 M in THF, 10 mL, 13 mmol) over 10 min. After additional 10 min of stirring at 0° C., CuI (0.2 eq, 0.38 g) was added, the mixture was stirred for 10 minutes at 0° C. and then a solution of allyl bromide (1.73 mL, 20 mmol) in THF (4.0 mL) was added at 0° C. over 10 min. After further stirring for 1 h at 0° C., the reaction was quenched with 10% citric acid and extracted with ethyl acetate (100 mL×2). The organic layers were combined which was washed with brine, dried over Na$_2$SO$_4$, and concentrated. The obtained residue was chromatographed on silica gel eluted with EtOAc/hexane (0-10%) to afford 2.84 g (84%) of 24 as a colorless oil. NMR (CDCl$_3$) δ 1.48 (9 H, s), 2.21 (4 H, m), 3.28 (2 H, m), 3.41 (2 H, d, J=6.16 Hz), 4.05 (2 H, m), 5.92 (1 H, m), 7.26 (1 H, dd, J=1.56, 12.08 Hz); LC/MS (M+1) 339.

Step 4. Preparation of (R)-tert-butyl 4-(5-(2,3-dihydroxypropyl)-3-fluoropyridin-2-yl)-4-fluoropiperidine-1-carboxylate (25)

To a solution of 24 (1.60 g, 4.7 mmol) in t-butanol (20 mL) and H$_2$O (20 mL) AD-mix-beta (5.0 g) was added portion wise at 5° C. The reaction was slowly warmed to room temperature and further stirred at this temperature for 16 hrs. The reaction mixture was cooled down to 5° C. and then quenched by adding excess sodium sulfite and stirred for 20 min. The resulting mixture was diluted with water (100 mL) and extracted with ethyl acetate (100 mL×2). The organic layers were combined which was washed with brine, dried over Na$_2$SO$_4$, and concentrated. The obtained residue was and chromatographed on silica gel eluted with hexane/ethyl acetate (20%-100%) to afford 1.70 g (97%) of 25 as a colorless oil which was use directly for the next step. LC/Ms (M+1) 373.

Step 5. Preparation of (R)-3-(5-fluoro-6-(4-fluoropiperidin-4-yl)pyridin-3-yl)propane-1,2-diol (26)

A solution of 25 (1.70 g, 4.6 mmol) in dichloromethane (10 mL) was stirred with 4 mol/L HCl in dioxane (15 mL) in a closed vessel overnight at room temperature. The resulting suspension was stirred for 1 h with ethyl ether. The solid precipitated was collected by filtration and washed several times with ethyl ether to afford 1.42 g (100%) of 26 as a pale yellow foam (HCl salt). The identity of compound 26 was confirmed by LC/MS and was used directly for the next step. LC/MS (M+1) 310.

Step 6. Preparation of (R)-4-(5-(2,3-dihydroxypropyl)-3-fluoropyridin-2-yl)-4-fluoro-N-(3-methyl-4-(trifluoromethyl)phenyl)piperidine-1-carboxamide (ACO)

0.14 g (45%) of Compound ACO was obtained in the same manner as Example 1. $^1$H NMR (CD$_3$OD) 2.21-2.40 (7 H, m), 2.72 (1 H, dd, J=8.76, 14.00 Hz), 2.95 (1 H, dd, J=3.48, 13.80 Hz), 3.38-3.56 (4 H, m), 3.82 (1 H, m), 4.14 (2 H, m), 7.35-7.60 (4 H, m), 8.30 (1 H, s); LC/MS (M+1) 474.

Example 21

Preparation of (R)-4-(5-(2,3-dihydroxypropyl)-3-fluoropyridin-2-yl)-4-fluoro-N-(3-methyl-4-(trifluoromethoxy)phenyl)piperidine-1-carboxamide (ACP)

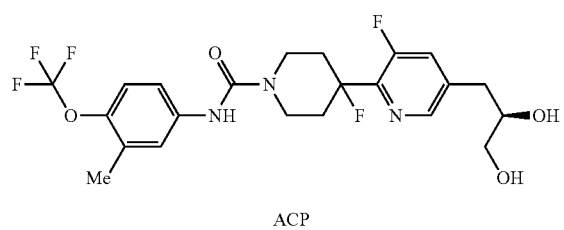 [SMILES: Cc1cc(NC(=O)N2CCC(F)(c3ncc(C[C@@H](O)CO)cc3F)CC2)ccc1OC(F)(F)F]

ACP 0.13 g (40%) of Compound ACP was obtained in the same manner as Example 1. $^1$H NMR (CD$_3$OD) δ 2.24-2.43 (7 H, m), 2.72 (1 H, dd, J=8.52, 13.80 Hz), 2.95 (1 H, dd, J=3.72, 14.00 Hz), 3.39-3.54 (4 H, m), 3.82 (1 H, m), 4.12 (2H, m), 7.14 (1 H, dd, J=1.32, 8.76 Hz), 7.29 (1 H, dd, J=2.44, 8.80 Hz), 7.36 (1 H, d, J=2.64 Hz), 7.57 (1 H, dd, J=1.56, 12.52 Hz), 8.30 (1 H, s); LC/MS (M+1) 490.

Example 22

Preparation of (S)-4-(5-(2,3-dihydroxypropyl)-3-fluoropyridin-2-yl)-4-fluoro-N-(3-methyl-4-(trifluoromethyl)phenyl)piperidine-1-carboxamide (ACQ)

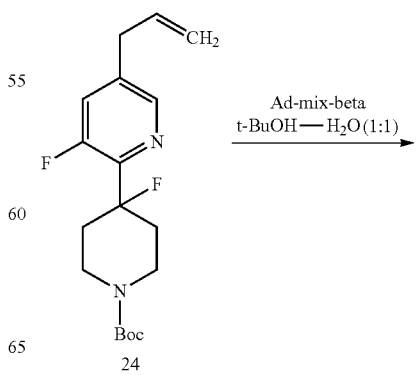

J=3.48, 13.80 Hz), 3.38-3.56 (4 H, m), 3.82 (1 H, m), 4.14 (2 H, m), 7.35-7.60 (4 H, m), 8.30 (1 H, s); LC/MS (M+1) 474.

Example 23

Preparation of (S)-4-(5-(2,3-dihydroxypropyl)-3-fluoropyridin-2-yl)-4-fluoro-N-(3-methyl-4-(trifluoromethoxy)phenyl)piperidine-1-carboxamide (ACR)

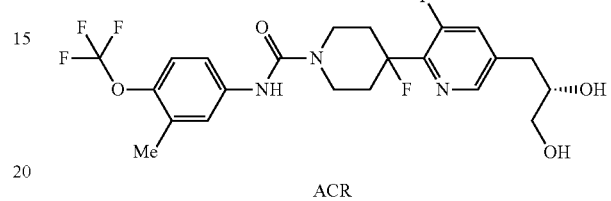

ACR 0.13 g (40%) of Compound ACR was obtained in the same manner as Example 1. $^1$H NMR (CD$_3$OD) δ 2.24-2.43 (7 H, m), 2.72 (1 H, dd, J=8.52, 13.80 Hz), 2.95 (1 H, dd, J=3.72, 14.00 Hz), 3.39-3.54 (4 H, m), 3.82 (1 H, m), 4.12 (2 H, m), 7.14 (1 H, dd, J=1.32, 8.76 Hz), 7.29 (1 H, dd, J=2.44, 8.80 Hz), 7.36 (1 H, d, J=2.64 Hz), 7.57 (1 H, dd, J=1.56, 12.52 Hz), 8.30 (1 H, s); LC/MS (M+1) 490.

Reference Example 3

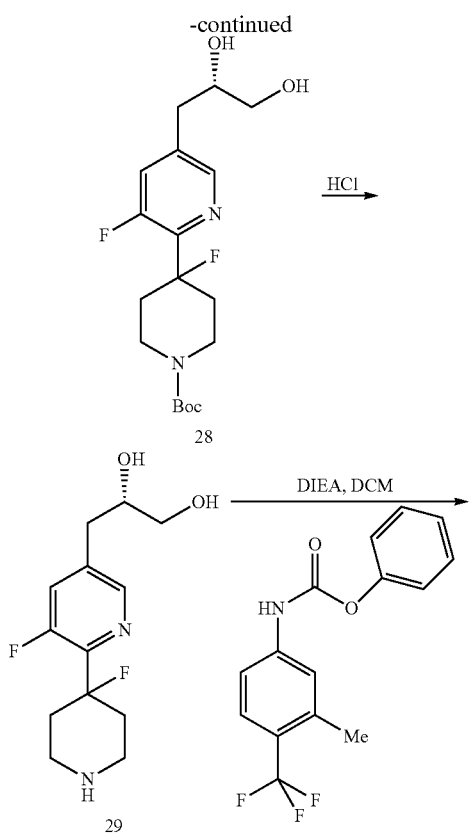

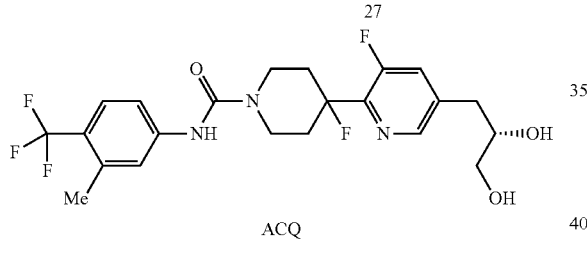

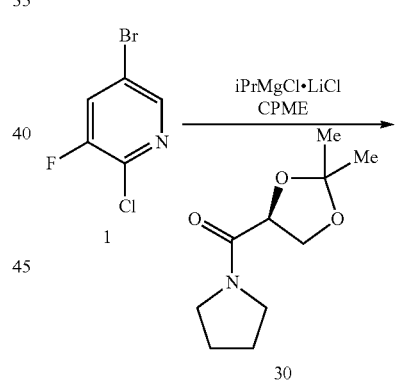

Step 1. Preparation of (S)-tert-butyl 4-(5-(2,3-dihydroxypropyl)-3-fluoropyridin-2-yl)-4-fluoropiperidine-1-carboxylate (28)

1.70 g (97%) of 28 was obtained in the same manner as Example 20, Step 4.

Step 2. Preparation of (R)-3-(5-fluoro-6-(4-fluoropiperidin-4-yl)pyridin-3-yl)propane-1,2-diol (29)

1.42 g (100%) of 29 was obtained in the same manner as Example 20, Step 5.

Step 3. Preparation of (S)-4-(5-(2,3-dihydroxypropyl)-3-fluoropyridin-2-yl)-4-fluoro-N-(3-methyl-4-(trifluoromethyl)phenyl)piperidine-1-carboxamide (ACQ)

0.137 g (44%) of Compound ACQ was obtained in the same manner as Example 1. $^1$H NMR (CD$_3$OD) δ 2.21-2.40 (7 H, m), 2.72 (1 H, dd, J=8.76, 14.00 Hz), 2.95 (1 H, dd,

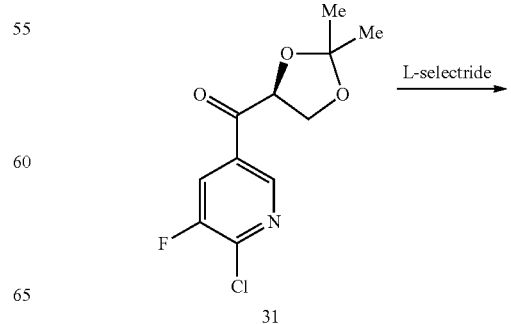

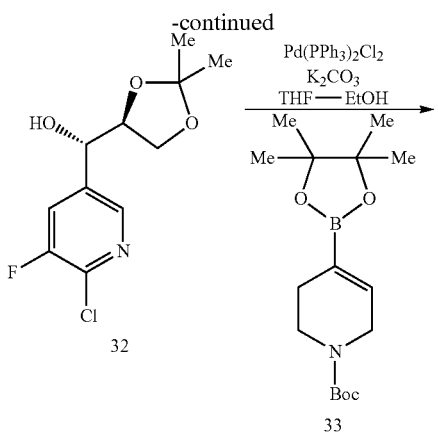

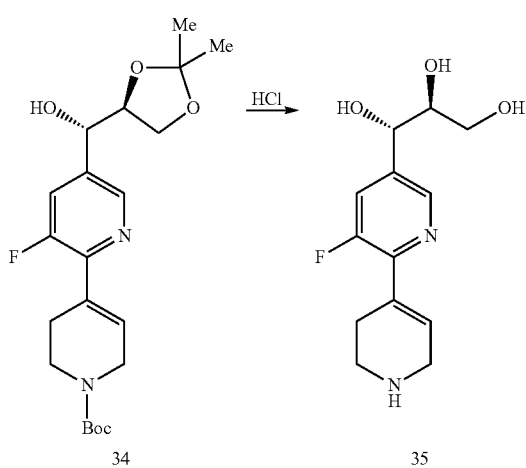

Step 1. Preparation of (S)-(6-chloro-5-fluoropyridin-3-yl)-(2,2-dimethyl-1,3-dioxolan-4-yl)methanone (31)

To a round-bottomed flask was charged 1 (4.20 g, 20 mmol) in CPME (70 mL) which was cooled down to −10° C. under N$_2$, isopropyl magnesium chloride lithium chloride complex (1.3 M in THF, 16.9 mL, 22 mmol) was added over 10 min. After additional 15 min of stirring at −10° C., 30 (4.40 g, 22 mmol) in CPME (20 mL) was added dropwise. After further stirring for 1 h at room temperature, the reaction was quenched with 10% citric acid solution and diluted with EtOAc (100 mL). The organic layer was washed with brine, dried, and evaporated. The obtained residue was chromatographed on silica gel eluted with EtOAc/hexanes (0-10%) to obtain 2.5 g (48%) of 31 as a white solid. NMR (CDCl$_3$) δ 1.36 (3 H, s), 1.46 (3 H, s), 4.29 (1 H, dd, J=7.20, 8.76 Hz), 4.44 (1 H, dd, J=4.96, 8.76 Hz), 5.06 (1 H, dd, J=4.84, 7.04 Hz), 8.13 (1 H, dd, J=1.96, 8.32 Hz), 8.93 (1 H, d, J=1.72); LC/MS (M+1) 260.

Step 2. Preparation of (S)-(6-chloro-5-fluoropyridin-3-yl)-[(S)-2,2-dimethyl-1,3-dioxolan-4-yl]methanol (32)

To a solution of 31 (1.30 g, 5 mmol) in hexanes (30 mL) which was cooled down to −78° C. under N$_2$, L-selectride (20 mL, 10 mmol) was added dropwise. The resulting mixture was further stirred at this temperature for 1 h, and then quenched with brine and diluted with EtOAc (100 mL). The organic layers were washed with brine, dried, and evaporated. The obtained residue was chromatographed on silica gel eluted with EtOAc/hexanes (0-20%) to obtain 0.80 g (31%) of 32 as a yellowish oil. NMR (CD$_3$OD) δ 1.21 (3 H, s), 1.22 (3 H, s), 3.68 (1 H, dd, J=6.36, 8.36 Hz), 3.84 (1 H, dd, J=6.78, 8.52 Hz), 4.00 (1 H, m), 4.23 (1 H, m), 4.70 (1 H, d, J=5.04 Hz), 7.68 (1 H, dd, J=1.52, 9.20 Hz), 8.15 (1 H, d, J=1.96 Hz); LC/MS (M+1) 262.

Step 3. Preparation of tert-butyl 5-{(S)-[(S)-2,2-dimethyl-1,3-dioxolan-4-yl](hydroxy)methyl}-3-fluoro-5',6'-dihydro-[2,4'-bipyridine]-1'(2'H)-carboxylate (34)

A solution of 32 (1.12 g, 4.6 mmol) and boronic ester 33 (1.70 g, 5.5 mmol) in a mixture of ethanol (7.5 mL) and THF (15 mL) was treated under argon with K$_2$CO$_3$ (3M, 3.4 mL, 10.12 mmol) and bis(triphenylphosphine)dichloropalladium (II) catalyst (0.16 g, 0.23 mmol) at 85° C. for 2 hrs. The mixture was cooled down to room temperature, diluted with water (100 mL) and extracted with ethyl acetate (100 mL×2). The combined organic layers were washed with brine, dried, and concentrated. The obtained residue was chromatographed on silica gel eluted with EtOAc/hexanes (0-40%) to afford 1.2 g (64%) of 34 as a pale yellow oil. NMR (CD$_3$OD) δ 1.33 (3 H, s), 1.35 (3 H, s), 1.51 (9 H, s), 2.66 (2 H, m), 3.65 (2 H, m), 3.78 (1 H, dd, J=0.66, 8.32 Hz), 3.93 (1 H, dd, J=6.80, 8.56 Hz), 4.14 (2 H, m), 4.35 (1 H, m), 4.79 (1 H, d, J=5.28 Hz), 6.50 (1 H, m), 7.65 (1 H, dd, J=0.64, 12.48 Hz), 8.40 (1 H, m); LC/MS (M+1) 409.

Step 4. Preparation of (1S,2S)-1-(3-fluoro-1',2',3',6'-tetrahydro-[2,4'-bipyridin]-5-yl)propane-1,2,3-triol (35)

0.89 g (99%) of 35 was obtained in the same manner as Reference Example 1, Step 4.

Reference Example 4

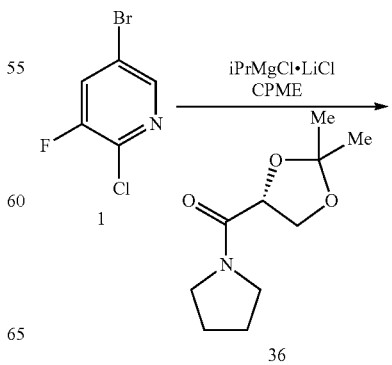

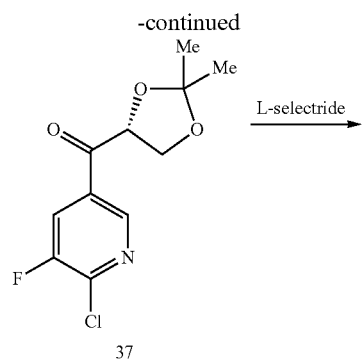
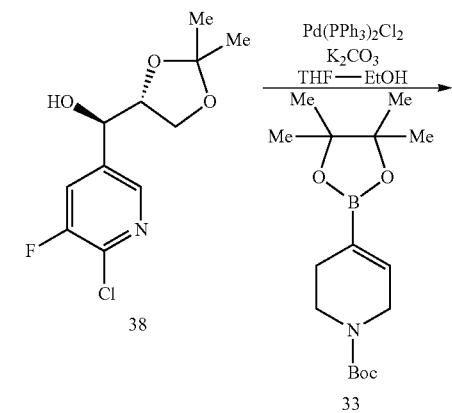
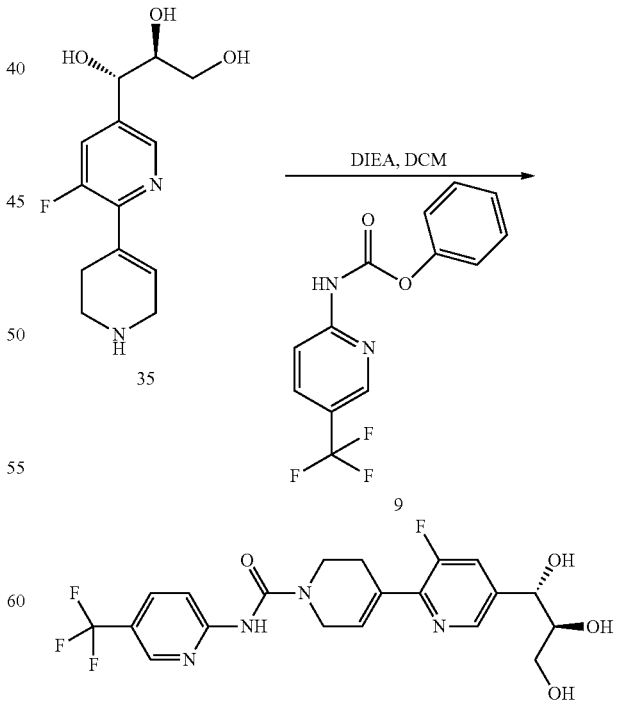

Step 1. Preparation of (R)-(6-chloro-5-fluoropyridin-3-yl)-(2,2-dimethyl-1,3-dioxolan-4-yl)methanone (37)

5.0 g (48%) of 37 was obtained in the same manner as Reference Example 3, Step 1.

Step 2. Preparation of (R)-(6-chloro-5-fluoropyridin-3-yl)-[(R)-2,2-dimethyl-1,3-dioxolan-4-yl]methanol (38)

1.81 g (35%) of 38 was obtained in the same manner as Reference Example 3, Step 2.

Step 3. Preparation of tert-butyl 5-{(R)-[(R)-2,2-dimethyl-1,3-dioxolan-4-yl](hydroxy)methyl}-3-fluoro-5',6'-dihydro-[2,4'-bipyridine]-1'(2'H)-carboxylate (39)

2.5 g (67%) of 39 was obtained in the same manner as Reference Example 3, Step 3.

Step 4. Preparation of (1R,2R)-1-(3-fluoro-1',2',3',6'-tetrahydro-[2,4'-bipyridin]-5-yl)propane-1,2,3-triol (40)

1.85 g (99%) of 40 was obtained in the same manner as Reference Example 1, Step 4.

Example 24

Preparation of 3-fluoro-N-(5-(trifluoromethyl)pyridin-2-yl)-5-[(1S,2S)-1,2,3-trihydroxypropyl]-5',6'-dihydro-[2,4'-bipyridine]-1'(2'H)-carboxamide (ABI)

Example 25

Preparation of 3-fluoro-N-(5-(trifluoromethyl)pyridin-2-yl)-5-[(1R,2R)-1,2,3-trihydroxypropyl]-5',6'-dihydro-[2,4'-bipyridine]-1'(2'H)-carboxamide (ABJ)

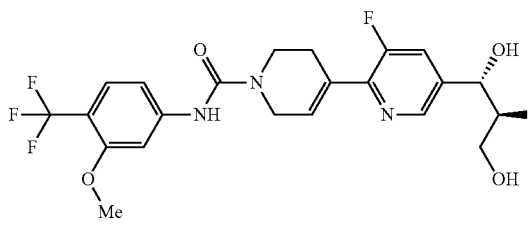

ABJ 0.090 g (34%) of Compound ABJ was obtained in the same manner as Example 1 ¹H NMR (CD₃OD) δ 2.66 (2 H, m), 3.39 (1 H, m), 3.57 (2 H, m), 3.67 (2 H, m), 3.78 (3 H, s), 4.18 (1 H, m), 6.45 (1 H, m), 6.97 (1 H, dd, J=1.32, 8.12 Hz), 7.32 (2 H, m), 7.54 (1 H, dd, J=1.72, 12.48 Hz), 8.30 (1 H, m); LC/MS (M+1) 486.

Example 26

Preparation of 3-fluoro-N-(3-methoxy-4-(trifluoromethyl)phenyl)-5-[(1S,2S)-1,2,3-trihydroxypropyl]-5',6'-dihydro-[2,4'-bipyridine]-1'(2'H)-carboxamide (ABQ)

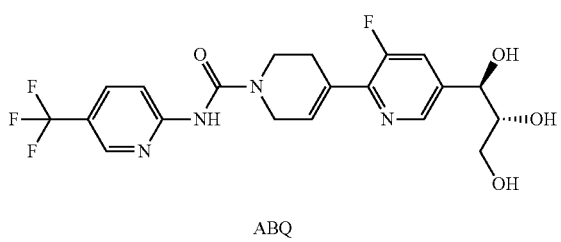 [SMILES: O=C(Nc1ccc(C(F)(F)F)cn1)N1CC=C(c2ncc([C@@H](O)[C@H](O)CO)cc2F)CC1]

ABQ 0.092 g (37%) of Compound ABQ was obtained in the same manner as Example 1. ¹H NMR (CD₃OD) δ 2.78 (2 H, m), 3.51 (1 H, m), 3.69 (2 H, m), 3.82 (2 H, t, J=5.92 Hz), 4.33 (2 H, m), 4.86 (1 H, d, J=3.08 Hz), 6.57 (1 H, m), 7.66 (1 H, d, J=12.48 Hz), 8.01 (2 H, m), 8.42 (1 H, s), 8.55 (1 H, s); LC/MS (M+1) 457.

Example 27

Preparation of 3-fluoro-N-(3-methoxy-4-(trifluoromethyl)phenyl)-5-[(1R,2R)-1,2,3-trihydroxypropyl]-5',6'-dihydro-[2,4'-bipyridine]-1'(2'H)-carboxamide (ABO)

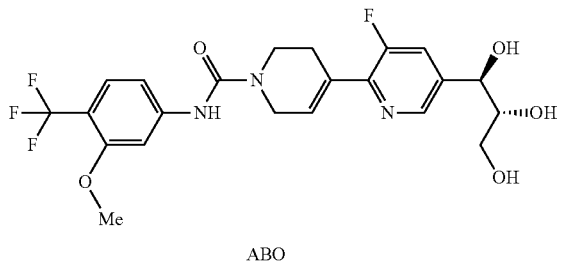 [SMILES: COc1cc(NC(=O)N2CC=C(c3ncc([C@@H](O)[C@H](O)CO)cc3F)CC2)ccc1C(F)(F)F ; "ABO"]

ABO 0.092 g (34%) of Compound ABO was obtained in the same manner as Example 1. ¹H NMR (CD₃OD) δ 2.66 (2 H, m), 3.39 (1 H, m), 3.57 (2 H, m), 3.67 (2 H, m), 3.78 (3 H, s), 4.18 (1 H, m), 6.45 (1 H, m), 6.97 (1 H, dd, J=1.32, 8.12 Hz), 7.32 (2 H, m), 7.54 (1 H, dd, J=1.72, 12.48 Hz), 8.30 (1 H, m); LC/MS (M+1) 486.

Example 28

Preparation of 3-fluoro-N-(6-fluorobenzo[d]thiazol-2-yl)-5-[(1S,2S)-1,2,3-trihydroxypropyl]-5',6'-dihydro-[2,4'-bipyridine]-1'(2'H)-carboxamide (ABT)

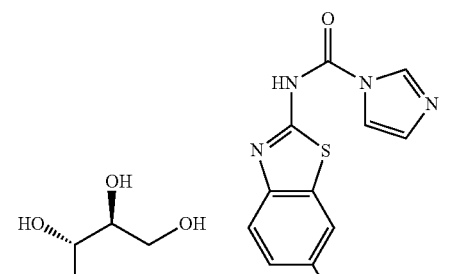

35

-continued

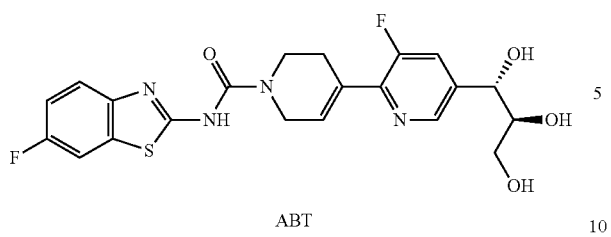

ABT 0.070 g (23%) of Compound ABT was obtained in the same manner as Example 10. $^1$H NMR (CD$_3$OD) δ 2.61 (2 H, m), 3.17 (1 H, m), 3.41-3.48 (2 H, m), 3.72 (2 H, m), 4.23 (2 H, m), 4.50 (1 H, t, J=5.24 Hz), 4.66 (2 H, m), 5.33 (1 H, d, J=5.68 Hz), 6.50 (1 H, m), 7.16 (1 H, m), 7.54 (2 H, m), 7.73 (1 H, m), 8.31 (1 H, s), 11.30 (1 H, brs); LC/MS (M+1) 463.

Example 29

Preparation of 3-fluoro-N-(6-fluorobenzo[d]thiazol-2-yl)-5-[(1R,2R)-1,2,3-trihydroxypropyl]-5',6'-dihydro-[2,4'-bipyridine]-1'(2'H)-carboxamide (ABU)

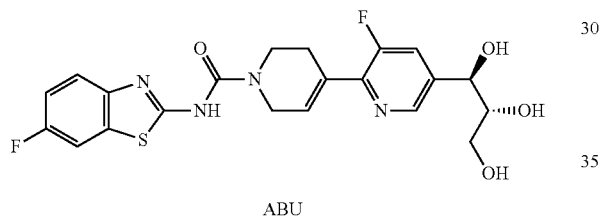

ABU 0.090 g (30%) of Compound ABU was obtained in the same manner as Example 10. $^1$H NMR (CD$_3$OD) δ 2.66 (2 H, m), 3.39 (1 H, m), 3.58 (2 H, m), 3.75 (2 H, m), 4.24 (2 H, m), 4.74 (1 H, d, J=3.52 Hz), 6.46 (1 H, s), 7.03 (1 H, m), 7.43 (2 H, m), 7.55 (1 H, dd, J=1.52, 12.48 Hz), 8.30 (1 H, s); LC/MS (M+1) 463.

Example 30

Preparation of 5-(2,3-dihydroxypropyl)-3-fluoro-N-(5-(trifluoromethyl)pyridin-2-yl)-5',6'-dihydro-[2,4'-bipyridine]-1'(2'H)-carboxamide (ABB)

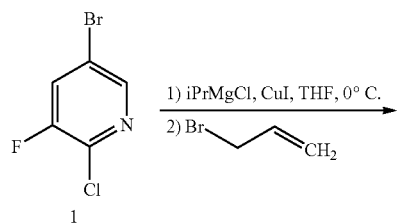

1

-continued

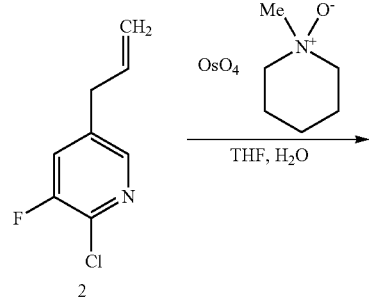

2

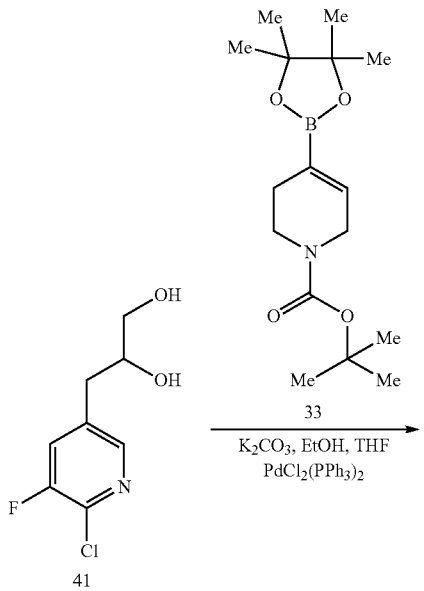

41

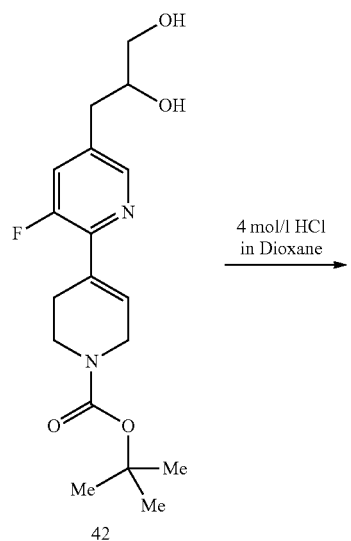

42

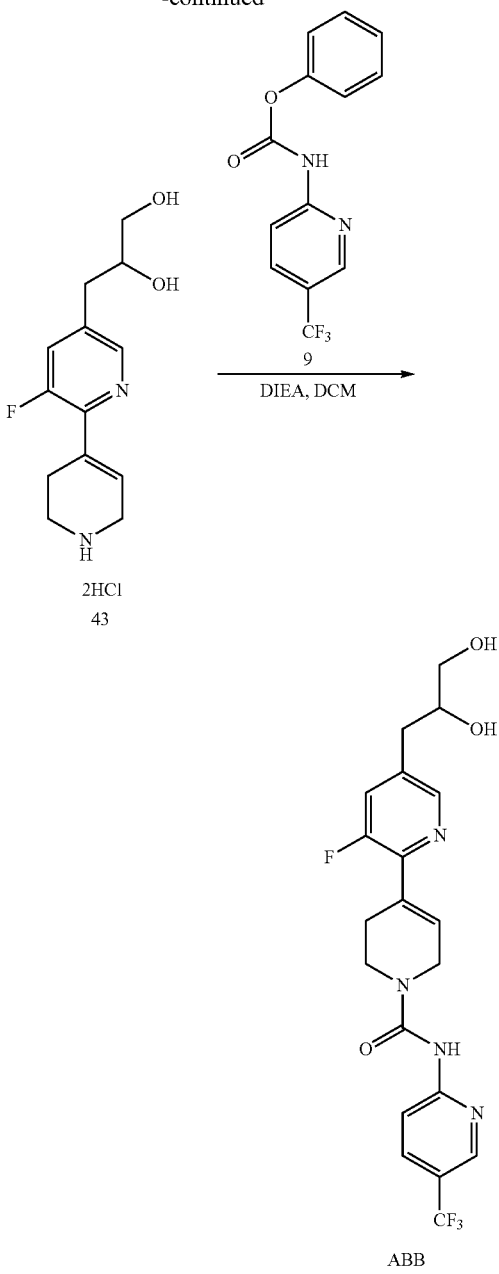

Step 1. Preparation of 5-allyl-2-chloro-3-fluoropyridine (2)

In a dry 3-necked flask flushed with argon containing a solution of 5-bromo-2-chloro-3-fluoro-pyridine (4.0 g, 19.05 mmol) at 0° C. was added isopropyl magnesium chloride lithium chloride complex (1.3 M THF solution, 24.76 mmol, 19.1 mL) over 10 minutes. After additional 10 min of stirring at 0° C., CuI (0.73 g, 3.81 mmol) was added and stirred for 10 min at 0° C. Then a solution of allyl bromide (38.1 mmol, 3.3 mL) in THF (4.0 mL) was added to the above mixture at 0° C. over a 10 min period. The resulting mixture was stirred for 1 h at 0° C., then quenched with 10% citric acid and extracted with ethyl acetate. The organic layers were separated, washed with brine, and concentrated. The obtained residue was chromatographed on silica gel eluted with hexane and 10% ethyl acetate in hexanes to afford 2.5 g (77%) of 2 as a colorless oil. $^1$HNMR (CDCl$_3$) δ 3.41 (2 H, d, J=7.0 Hz) 5.18 (2 H, m), 5.92 (1 H, m), 7.33 (1 H, d, J=8.0 Hz), 8.06 (1 H, m); LC/MS (M+1) 173.

Step 2. Preparation of 3-(6-chloro-5-fluoropyridin-3-yl)propane-1,2-diol (41)

In a flask containing a solution of 2 (1.0 g, 5.81 mmol) in THF (7.2 mL) was added H$_2$O (3.5 mL). The mixture was cooled with an ice bath and then N-methylmorpholine N-oxide (1.0 g, 8.71 mmol) was added followed by osmium tetroxide (0.074 g, 0.291 mmol) and the mixture stirred at 0° C. for 1 h. The reaction mixture was diluted with water (50 mL) and extracted with ethyl acetate (50 mL×2). The organic layer was separated, washed with brine, concentrated, and chromatographed on silica gel eluted with ethyl acetate/hexanes (0-20%) to afford 0.66 g (55%) of 41 as an oil. $^1$HNMR (CDCl$_3$) δ 1.92 (1 H, t, J=5.0 Hz), 2.36 (1 H, d, J=5.0 Hz), 2.80 (2 H, m), 3.52 (1 H, m), 3.73 (1 H, m), 3.93 (1 H, m), 7.46 (1 H, d, J=11.0 Hz), 8.10 (1 H, s); LC/MS (M+1) 207.

Step 3. Preparation of tert-butyl 5-(2,3-dihydroxypropyl)-3-fluoro-5',6'-dihydro-[2,4'-bipyridine]-1' (2'H)-carboxylate (42)

A solution of 41 (0.30 g, 1.46 mmol) and 33 (0.54 g, 1.75 mmol) in a mixture of ethanol (2.3 mL) and THF (2.3 mL) was treated under argon with K$_2$CO$_3$ (0.50 g, 3.64 mmol) and bis-(triphenylphosphine)dichloropalladium (II) catalyst (0.082 g, 0.116 mmol) at 85° C. for 2 hrs. The mixture was cooled down to room temperature, diluted with water and extracted with ethyl acetate. The organic layer was separated, washed with brine, concentrated, and chromatographed on silica gel eluted with ethyl acetate/hexanes (50-100%) to afford 0.31 g (60%) of 42 as an oil. $^1$HNMR (CDCl$_3$) δ 1.49 (9 H, s), 1.98 (1 H, t, J=6.0 Hz), 2.33 (1 H, d, J=4.0 Hz), 2.67 (2 H, m), 2.80 (2 H, m), 3.52 (1 H, m), 3.63 (2 H, d, J=5.0 Hz), 3.73 (1 H, m), 3.95 (1 H, m), 4.13 (2 H, m), 6.50 (1 H, brs), 7.31 (1 H, d, J=12.0 Hz), 8.26 (1 H, s); LC/MS (M+1) 353.

Step 4. Preparation of 3-(3-fluoro-1',2',3',6'-tetrahydro-[2,4'-bipyridin]-5-yl)propane-1,2-diol (43)

A solution of 42 (0.31 g, 0.868 mmol) in dichloromethane (2.0 mL) was treated at 38° C. with 4 mol/L HCl in 1,4-dioxane (4.34 mmol, 1.1 mL) in a sealed vessel for 16 hrs. The resulting suspension was stirred for 1 h with ethyl ether. The solid precipitate was collected on filter paper and washed several times with ethyl ether to afford 200 mg (70%) of 43 as a tan solid which was used directly for the next step. LC/MS (M+1) 253.

Step 5. Preparation of 5-(2,3-dihydroxypropyl)-3-fluoro-N-(5-(trifluoromethyl)pyridin-2-yl)-5',6'-dihydro-[2,4-bipyridine]-1'(2'H)-carboxamide (ABB)

A suspension of 43 (200 mg, 0.615 mmol) and 9 (191 mg, 0.676 mmol) in dichloromethane (6.0 mL) was treated with DIEA (12.3 mmol, 2.0 mL) at 0° C. The mixture was then allowed to stir for 16 hrs at room temperature. The reaction was concentrated and chromatographed on silica gel eluted with 50% ethyl acetate in hexanes and ethyl acetate to afford 110 mg, 41% of ABB as a solid. $^1$HNMR (CD$_3$OD) 2.79-2.64 (3 H, m), 2.92 (1 H, d, J=15.0 Hz), 3.50 (2 H, d, J=5.6 Hz), 3.80 (3 H, t, J=6.0 Hz), 4.30 (2 H, s), 6.52 (1 H, s), 7.52 (1 H, d, J=7.5 Hz), 8.00 (2 H, m, J=10.0 Hz), 8.27 (1 H, s), 8.50 (1 H, s); LC/MS (M+1) 441.

Example 31

Preparation of (R)-5-(2,3-dihydroxypropyl)-3-fluoro-N-(3-methyl-4-(trifluoromethoxy)phenyl)-5',6-dihydro-[2,4'-bipyridine]-1'(2'H)-carboxamide (ACB)

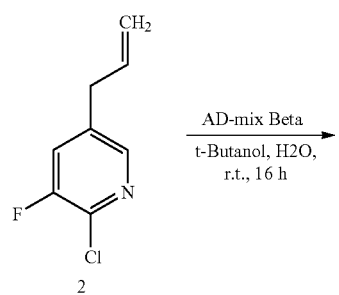

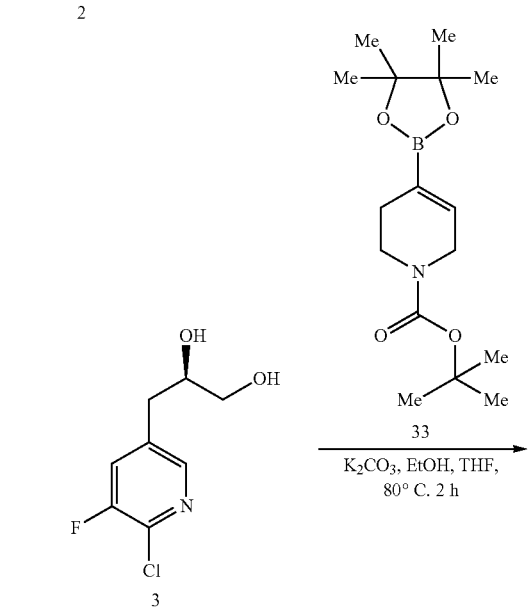

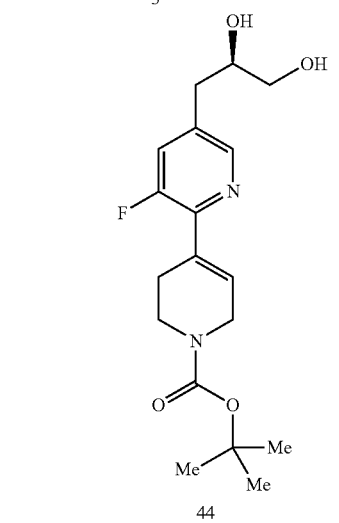

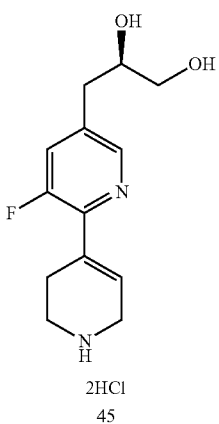

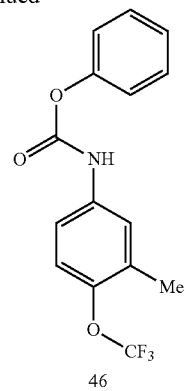

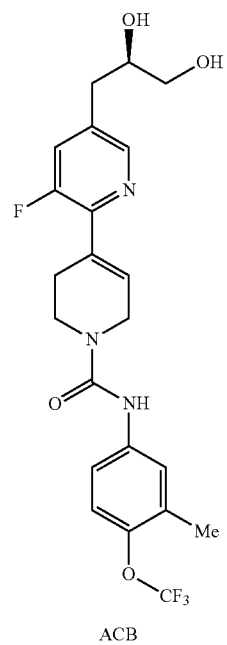

Step 1. Preparation of (R)-3-(6-chloro-5-fluoropyridin-3-yl)propane-1,2-diol (3)

AD-mix-beta (45 g) was added portionwise to a solution of 2 (4.5 g, 26.2 mmol) in t-butanol (135 mL) and H$_2$O (135 mL) at 5° C. The mixture was stirred at room temperature for 16 hrs, and then cooled to 5° C. and treated with excess sodium sulfite for 20 min. The mixture was diluted with water (100 mL) and extracted with ethyl acetate (100 mL×2). The combined organic layers were washed with brine, dried over sodium sulfate, concentrated, and chromatographed on silica gel eluted with 67% ethyl acetate in hexanes and ethyl acetate to afford 5.0 g (92%) of 3 as a colorless oil. $^1$HNMR (CDCl$_3$) δ 2.04 (2 H, brs), 2.81 (2 H, m), 3.54 (1 H, t, J=5.0 Hz), 3.75 (1 H d, J=11.0 Hz), 3.94 (1 H, m), 7.46 (1 H, d, J=9.0 Hz), 8.10 (1 H, s); LC/MS (M+1) 207.

Step 2. Preparation of (R)-tert-butyl 5-(2,3-dihydroxypropyl)-3-fluoro-5',6'-dihydro-[2,4-bipyridine]-1' (2'H)-carboxylate (44)

A solution of 3 (2.00 g, 9.76 mmol) and 33 (3.62 g, 11.71 mmol) in a mixture of ethanol (15.1 mL) and THF (15.1 mL) was treated under argon with K$_2$CO$_3$ (3.37 g, 24.4 mmol) and bis-(triphenylphosphine)dichloropalladium (II) catalyst (0.55 g, 0.781 mmol) at 85° C. for 2 hrs. The mixture was cooled down to room temperature, diluted with water (100 mL) and extracted with ethyl acetate (100 mL×2). The combined organic layers were washed with brine, concentrated and chromatographed on silica gel eluted with 50% ethyl acetate in hexanes and ethyl acetate to afford 2.3 g (67%) of 44 as an oil which was confirmed by LC/MS and used directly in the next step.

Step 3. Preparation of (R)-3-(3-fluoro-1',2',3',6-tetrahydro-[2,4'-bipyridin]-5-yl)propane-1,2-diol (45)

A solution of 44 (2.30 g, 6.53 mmol) in dichloromethane (14.6 mL) was treated with 4 mol/L HCl in 1,4-dioxane (32.6 mmol, 8.4 mL) in a sealed vessel for 2 hrs at room temperature. The resulting suspension was stirred for 1 hour with ethyl ether. The solid precipitate was collected by filtration and washed several times with ethyl ether to afford 1.95 g (92%) of 45 which was confirmed by LC/MS and was used directly for the next step.

Step 4. Preparation of (R)-5-(2,3-dihydroxypropyl)-3-fluoro-N-(3-methyl-4-(trifluoromethoxy)phenyl)-5',6'-dihydro-[2,4'-bipyridine]-1'(2'H)-carboxamide (ACB)

A suspension of 45 (250 mg, 0.77 mmol) and 46 (240 mg, 0.77 mmol) in dichloromethane (7.5 mL) was treated with DIEA (2.5 mL) at 0° C. The mixture was then allowed to stir for 16 hrs at room temperature. The reaction was concentrated and chromatographed on silica gel eluted with ethyl acetate and 2% methanol in ethyl acetate to afford 87 mg (24%) of ACB as a syrup which was confirmed by LC/MS and was used directly for the next step. $^1$HNMR (CD$_3$OD) δ 2.20 (3 H, s), 2.79-2.64 (3 H, m), 2.92 (1 H, d, J=15.0 Hz), 3.50 (2 H, d, J=5.6 Hz), 3.70 (3H, m), 4.20 (2H, s), 4.57 (1 H, s), 6.51 (1 H, s), 7.13 (1 H, d, J=9.0 Hz), 7.29 (1 H, d, J=9.0 Hz), 7.36 (1 H, s), 7.52 (1 H, d, J=15.0 Hz), 8.27 (1 H, s); LC/MS (M+1) 471.

Example 32

Preparation of (R)-4-(5-[(R)-2,3-dihydroxypropyl)-3-fluoropyridin-2-yl)-N-(6-fluorobenzo[d]thiazol-2-yl]-2-methylpiperazine-1-carboxamide (ADH)

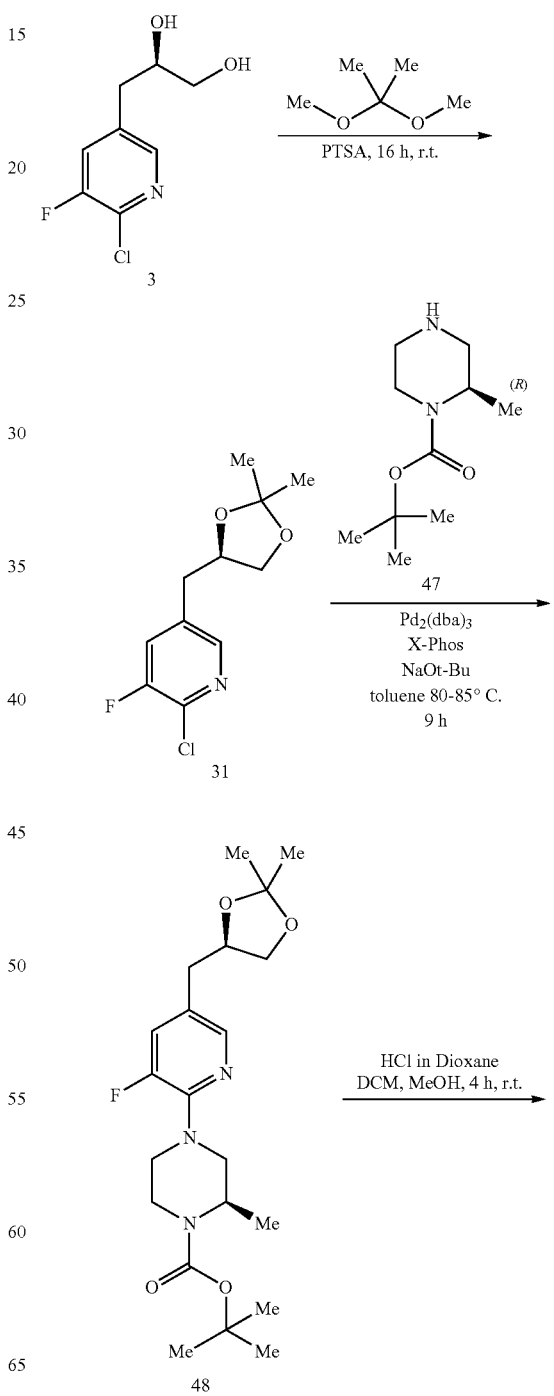

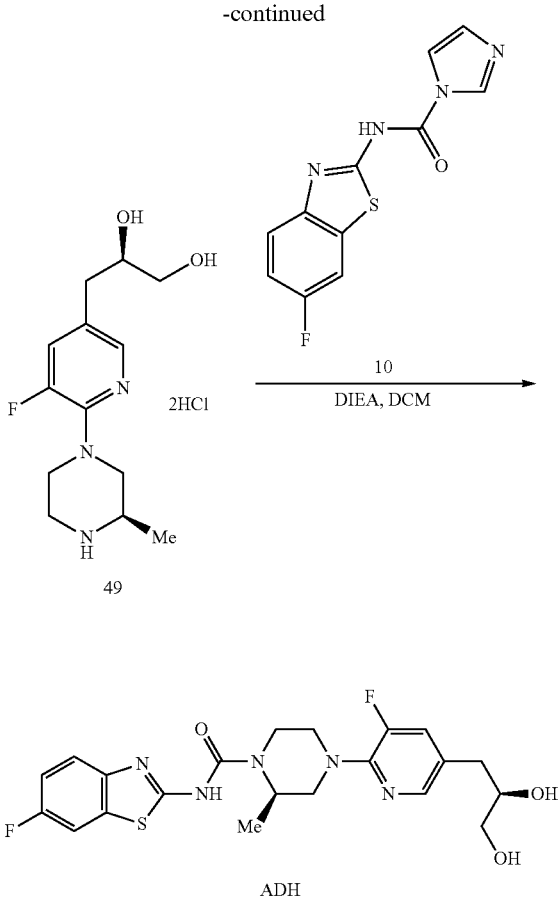

Step 1. Preparation of (R)-2-chloro-5-[(2,2-dimethyl-1,3-dioxolan-4-yl)methyl]-3-fluoropyridine (31)

A suspension of 3 (2.50 g, 12.2 mmol) in dimethoxypropane (25 mL) was cooled with an ice bath and treated with paratoluene sulfonic acid monohydrate (0.23 g, 1.22 mmol). The ice bath was removed and the solution was stirred at room temperature for 16 hrs, cooled to 5° C. and treated with aqueous sat. NaHCO₃ and extracted with ethyl acetate. The organic layer was separated, washed with brine, dried over sodium sulfate and concentrated to afford 2.90 g of 31 (97%) as an oil. ¹HNMR (CDCl₃) δ 1.34 (3 H, s), 1.42 (3 H, s), 2.87 (2 H, d, J=6.0 Hz), 3.62 (1 H, t, J=7.0 Hz), 4.08 (1 H, t, J=6.0 Hz), 4.30 (1 H, q, J=6.0 Hz), 7.46 (1 H, d, J=9.0 Hz), 8.12 (1 H, s). LC/MS (M+1) 247.

Step 2. Preparation of (R)-tert-butyl 4-(5-{[(R)-2,2-dimethyl-1,3-dioxolan-4-yl)methyl]-3-fluoropyridin-2-yl}-2-methylpiperazine-1-carboxylate (48)

To a solution of 31 (2.90 g, 11.79 mmol) in toluene (36 mL) under argon was added 47 (2.36 g, 11.79 mmol), sodium t-butoxide (1.25 g, 12.97 mmol) and 2-dicyclohexylphosphino-2',4',6'-triisopropylbiphenyl (X-Phos) (0.84 g, 1.77 mmol). The mixture was degassed with argon and then tris (dibenzylideneacetone) dipalladium (1.08 g, 1.18 mmol) was added and the mixture was stirred at an oil bath temperature of 80-85° C. for 9 hrs. The reaction mixture was cooled to room temperature, poured into cold water and extracted with ethyl acetate. The organic layer was separated, washed with brine, and concentrated to an oil which was chromatographed by silica gel chromatography column eluted with (0-20%) EtOAc/hexanes to afford 2.52 g (52%) of 48 as a solid. ¹HNMR (CDCl₃) δ 1.26 (3 H, d, J=7.0 Hz), 1.34 (3 H, s), 1.42 (3 H, s), 1.48 (9 H, s), 2.80 (3 H, m), 3.05 (1 H, d, J=9.0 Hz), 3.23 (1 H, t, J=9.0 Hz), 3.62 (1 H, t, J=8.0 Hz), 3.76 (1 H, d, J=12.0 Hz), 3.92 (2 H, d, J=10.0 Hz), 4.02 (1 H, t, J=6.0 Hz), 4.24 (1 H, m), 4.27 (1 H, brs), 7.17 (1 H, d, J=12.0 Hz), 7.84 (1 H, s); LC/MS (M+1) 411.

Step 3. Preparation of (R)-3-(5-fluoro-6-[(R)-3-methylpiperazin-1-yl)pyridin-3-yl]propane-1,2-diol (49)

A solution of 48 (2.50 g, 6.10 mmol) in dichloromethane (13.6 mL) was treated at 0° C. with 4 mol/L HCl in 1,4-dioxane (9.2 mL, 36.6 mmol) followed by methanol (2.0 mL). The flask was sealed with a rubber septa and the mixture was then stirred at room temperature for 4 hrs. The reaction mixture was diluted with ether and the precipitate was washed several times with ether and dried under reduced pressure to afford 1.8 g (86%) of 49 which was confirmed by LC/MS and was used directly for the next step.

Step 4. Preparation of (R)-4-(5-[(R)-2,3-dihydroxypropyl)-3-fluoropyridin-2-yl)-N-(6-fluorobenzo[d]thiazol-2-yl]-2-methylpiperazine-1-carboxamide (ADH)

A suspension of 49 (250 mg, 0.731 mmol) and 10 (192 mg, 0.731 mmol) in dichloromethane (7.2 mL) was cooled with an ice bath and treated with DIEA (1.1 mL). The nonhomogeneous mixture was stirred at room temperature for 16 hrs. The mixture was concentrated, the solid re-dissolved in 20% methanol in dichloromethane and absorbed onto silica to make a plug which was chromatographed by silica gel chromatography column eluted ethyl acetate and 1% methanol in ethyl acetate afford 67 mg (20%) of ADH as a solid. ¹HNMR (DMSO-d₆) δ 1.24 (3 H, d, J=7.0 Hz), 2.46 (2 H, m), 2.72 (1 H d, J=14.0 Hz), 2.83 (1 H, t, J=14.0 Hz), 3.01 (1 H, d, J=14.0 Hz), 3.28 (2 H, m), 3.59 (1 H, m), 3.73 (1 H, d, J=12.0 Hz), 3.89 (1 H, d, J=12.0 Hz), 4.19 (1 H, d, J=14.0 Hz), 4.62 (3 H m), 7.21 (1 H, t, J=10.0 Hz), 7.41 (1 H, d, J=14.0 Hz), 7.54 (1 H, m), 7.77 (1 H, d, J=9.0 Hz), 7.87 (1 H, s); LC/MS (M+1) 465.

Example 33

Preparation of (R)-{5-[(R)-2,3-dihydroxypropyl)-3-methylpyridin-2-yl]-N-(6-fluorobenzo[d]thiazol-2-yl}-2-methylpiperazine-1-carboxamide (ADI)

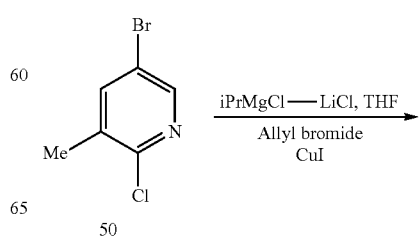

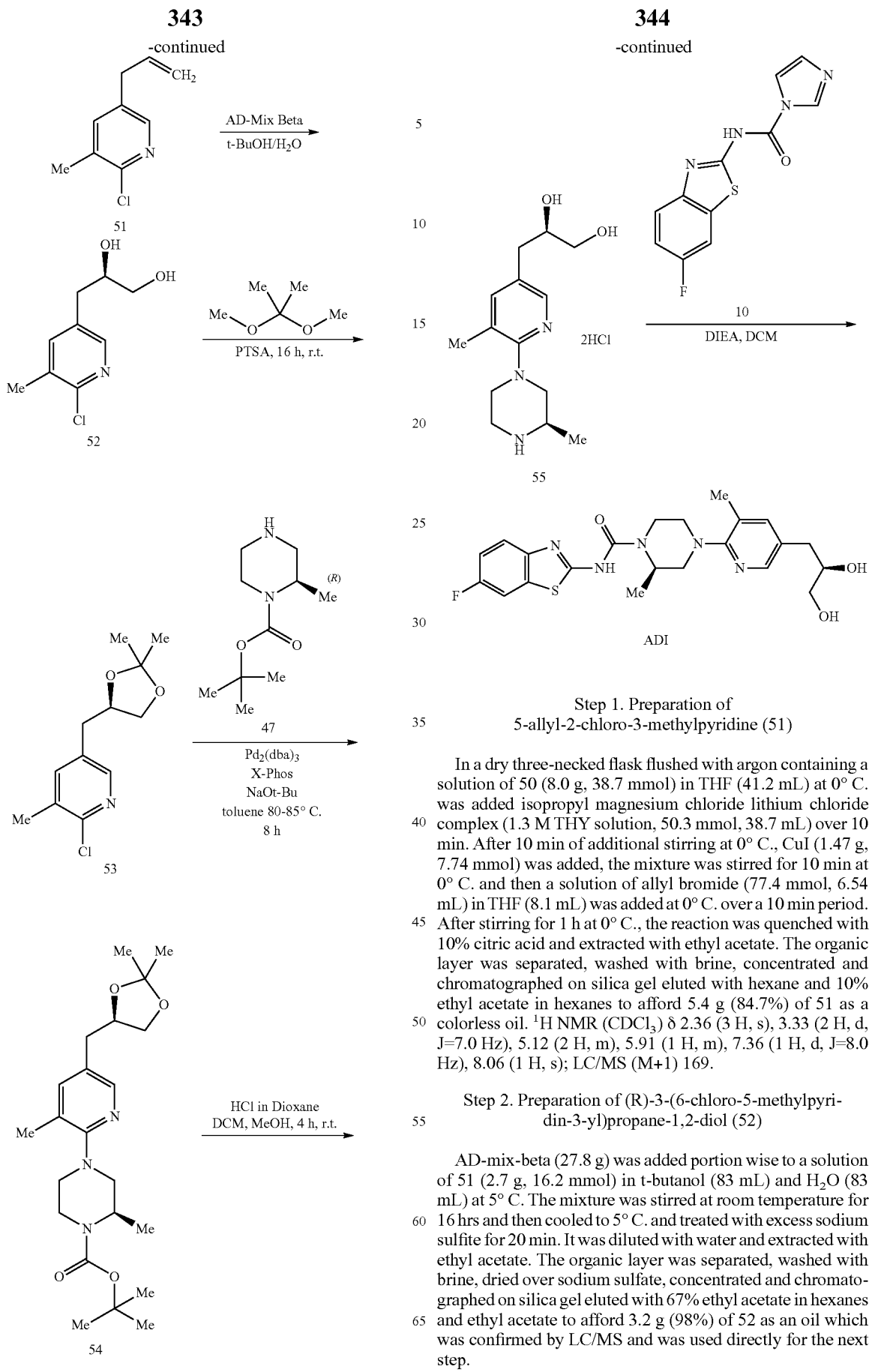

Step 1. Preparation of 5-allyl-2-chloro-3-methylpyridine (51)

In a dry three-necked flask flushed with argon containing a solution of 50 (8.0 g, 38.7 mmol) in THF (41.2 mL) at 0° C. was added isopropyl magnesium chloride lithium chloride complex (1.3 M THY solution, 50.3 mmol, 38.7 mL) over 10 min. After 10 min of additional stirring at 0° C., CuI (1.47 g, 7.74 mmol) was added, the mixture was stirred for 10 min at 0° C. and then a solution of allyl bromide (77.4 mmol, 6.54 mL) in THF (8.1 mL) was added at 0° C. over a 10 min period. After stirring for 1 h at 0° C., the reaction was quenched with 10% citric acid and extracted with ethyl acetate. The organic layer was separated, washed with brine, concentrated and chromatographed on silica gel eluted with hexane and 10% ethyl acetate in hexanes to afford 5.4 g (84.7%) of 51 as a colorless oil. $^1$H NMR (CDCl$_3$) δ 2.36 (3 H, s), 3.33 (2 H, d, J=7.0 Hz), 5.12 (2 H, m), 5.91 (1 H, m), 7.36 (1 H, d, J=8.0 Hz), 8.06 (1 H, s); LC/MS (M+1) 169.

Step 2. Preparation of (R)-3-(6-chloro-5-methylpyridin-3-yl)propane-1,2-diol (52)

AD-mix-beta (27.8 g) was added portion wise to a solution of 51 (2.7 g, 16.2 mmol) in t-butanol (83 mL) and H$_2$O (83 mL) at 5° C. The mixture was stirred at room temperature for 16 hrs and then cooled to 5° C. and treated with excess sodium sulfite for 20 min. It was diluted with water and extracted with ethyl acetate. The organic layer was separated, washed with brine, dried over sodium sulfate, concentrated and chromatographed on silica gel eluted with 67% ethyl acetate in hexanes and ethyl acetate to afford 3.2 g (98%) of 52 as an oil which was confirmed by LC/MS and was used directly for the next step.

Step 3. Preparation of (R)-2-chloro-5-[(2,2-dimethyl-1,3-dioxolan-4-yl)methyl]-3-methylpyridine (53)

A suspension of 52 (3.2 g, 16.2 mmol) in dimethoxypropane (33 mL) was cooled with an ice bath and treated with paratoluene sulfonic acid monohydrate (0.31 g, 1.62 mmol). The ice bath was removed and the solution was stirred at room temperature for 16 hrs, cooled to 5° C. and treated with saturated aqueous sodium bicarbonate and extracted with ethyl acetate. The organic layer was separated, washed with brine, dried over sodium sulfate and concentrated to afford 3.80 g (97%) of 53 as an oil. $^1$HNMR (CDCl$_3$) δ 1.34 (3 H, s), 1.41 (3 H, s), 2.37 (3 H, s), 2.81 (2 H, m), 3.61 (1 H, t, J=7.0 Hz), 4.03 (1 H, m, J=6.0 Hz), 4.27 (1 H, m, J=6.0 Hz), 7.44 (1 H, s), 8.10 (1 H, s). LC/MS (M+1) 258.

Step 4. Preparation of (R)-tert-butyl 4-(5-{[(R)-2,2-dimethyl-1,3-dioxolan-4-yl)methyl]-3-methylpyridin-2-yl}-2-methylpiperazine-1-carboxylate (54)

To a solution of 53 (3.61 g, 15.0 mmol) in toluene (46 mL) under argon was added 47 (3.0 g, 15.0 mmol), sodium t-butoxide (1.58 g, 16.5 mmol) and 2-dicyclohexylphosphino-2',4',6'-triisopropylbiphenyl (X-Phos) (1.07 g, 2.25 mmol). The mixture was degassed with argon and then tris(dibenzylideneacetone) dipalladium (1.37 g, 1.50 mmol) was added and the mixture was stirred at an oil bath temperature of 80-85° C. for 8 hrs. The reaction mixture was cooled to room temperature, poured onto cold water and extracted with ethyl acetate. The organic layer was separated, washed with brine, and concentrated to an oil which was chromatographed on silica gel eluted with hexanes to 20% ethyl acetate in hexanes to afford 2.10 g (35%) of 54 as a solid. $^1$HNMR (CDCl$_3$) δ 1.34 (6 H, m), 1.43 (3 H, s), 1.48 (9 H, s), 2.29 (3 H, s), 2.80 (1 H, m), 2.84 (2 H, m), 2.95 (1 H, m), 3.27 (3 H, m), 3.62 (1 H, t, J=6.0 Hz), 3.98 (1 H, d, J=10.0 Hz), 4.02 (1 FI, t, J=6.0 Hz), 4.25 (1 H, m), 4.27 (1 H, brs), 7.30 (1 H, s), 8.00 (1 H, s); LC/MS (M+1) 407.

Step 5. Preparation of (R)-3-{5-methyl-6-[(R)-3-methylpiperazin-1-yl)pyridin-3-yl]propane}-1,2-diol (55)

A solution of 54 (2.00 g, 4.94 mmol) in dichloromethane (11.0 mL) and methanol (1.6 mL) was treated with 4 mol/L HCl in 1,4-dioxane (7.4 mL, 29.6 mmol) at 5° C. The flask was sealed with rubber septa and the mixture was then stirred at room temperature for 4 hrs. The reaction was diluted with ether and the precipitate was washed several times with ether and dried under reduced pressure to afford 1.2 g (72%) of 55 as a tan solid which was confirmed by LC/MS and was used directly for the next step.

Step 6. Preparation of (R)-4-{5-[(R)-2,3-dihydroxypropyl)-3-methylpyridin-2-yl]-N-(6-fluorobenzo[d]thiazol-2-yl}-2-methylpiperazine-1-carboxamide (ADI)

A suspension of 55 (245 mg, 0.725 mmol) and 10 (171 mg, 0.652 mmol) in dichloromethane (7.2 mL) was cooled with an ice bath and treated with DIEA (3.0 mL). The nonhomogeneous mixture was stirred at room temperature for 3 days. The precipitate was collected by filtration and washed several times with dichloromethane followed by hexanes to afford 165 mg of ADI (50%) as a white solid. $^1$HNMR (DMSO-d$_6$) δ 1.31 (3 H, d, J=6.0 Hz), 2.24 (3 H, s), 2.42-2.33 (2 H, m), 2.80-2.60 (3 H, m), 3.32-3.17 (4 H, m), 3.53 (1 H, m), 4.11 (1 H, m), 4.53 (3 H, m), 7.16 (1 H, t, J=9.0 Hz), 7.35 (1 H, s), 7.57 (1 H, brs), 7.74 (1 H, m), 7.90 (1 H, s); LC/MS (M+1) 461.

Example 34

Preparation of (R)-N-(6-chlorobenzo[d]thiazol-2-yl)-4-{5-[(R)-2,3-dihydroxypropyl]-3-methylpyridin-2-yl}-2-methylpiperazine-1-carboxamide (ADJ)

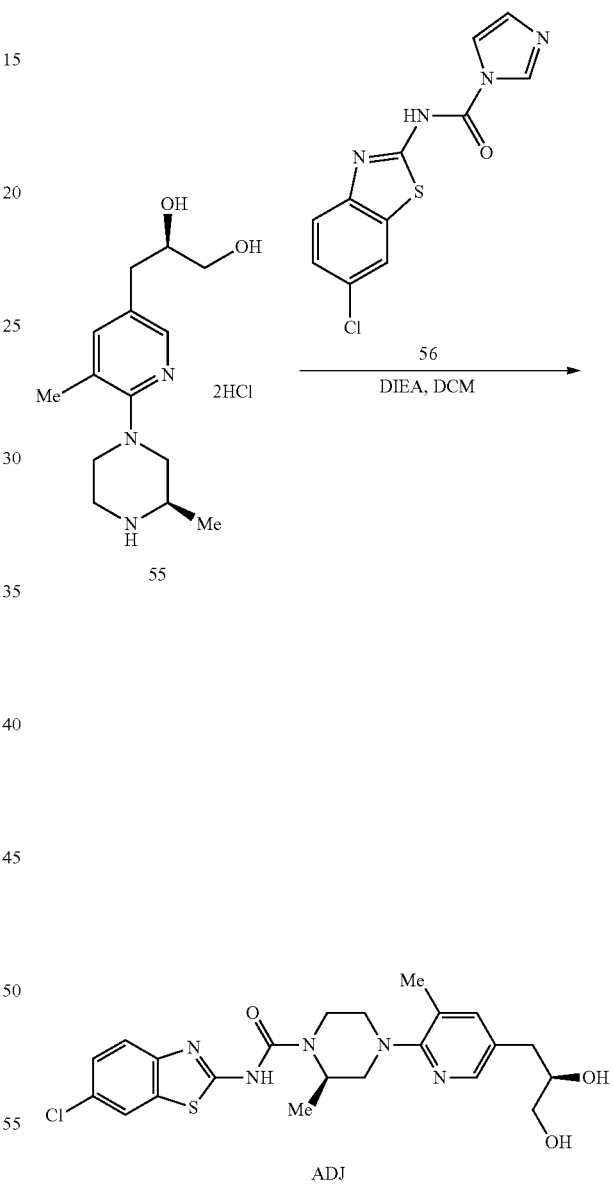

A suspension of 55 (250 mg, 0.739 mmol) and 56 (185 mg, 0.665 mmol) in dichloromethane (7.2 mL) was cooled with an ice bath and treated with DIEA (3.0 mL). The nonhomogeneous mixture was stirred at room temperature for 16 hours. The precipitate was filtered and washed several times with dichloromethane and hexanes to afford 194 mg (55%) of ADJ as a solid. $^1$HNMR (DMSO-d$_6$) δ 1.35 (3 H, d, J=7.0 Hz) 2.28 (3 H, s), 2.38-2.48 (2 H, m), 2.65-2.85 (3 H, m), 3.21-3.35 (4

H, m), 3.57 (1 H, m), 4.19 (1 H, d, J=13.0 Hz), 4.58 (3 H, m), 7.38 (2 H, d, J=8.0 Hz), 7.53 (1 H, brs), 7.96 (2 H, d, J=15.0 Hz); LC/MS (M+1) 476.

Example 35

Preparation of (R)-N-(6-chlorobenzo[d]thiazol-2-yl)-4-{5-[(R)-2,3-dihydroxypropyl]-3-fluoropyridin-2-yl}-2-methylpiperazine-1-carboxamide (ADK)

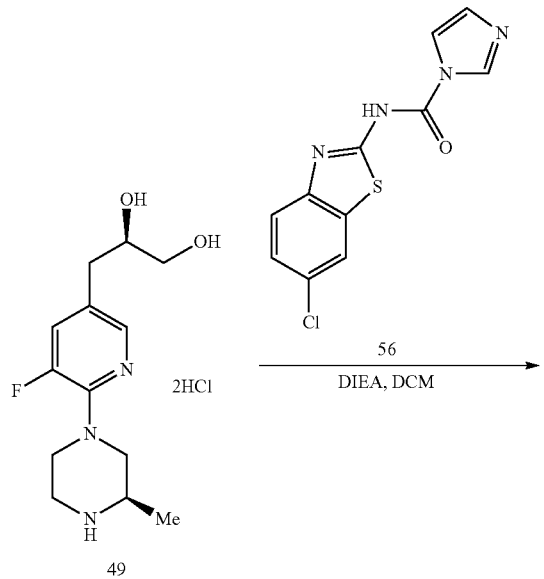

A suspension of 49 (200 mg, 0.580 mmol) and 56 (147 mg, 0.526 mmol) in dichloromethane (5.6 mL) was cooled with an ice bath and treated with DIEA (2.5 mL). The nonhomogeneous mixture was stirred at room temperature for 16 hrs. The precipitate was filtered and washed several times with dichloromethane and hexanes to afford 172 mg (61%) of ADK as a solid. $^1$HNMR (DMSO-$d_6$) δ 1.24 (3 H, d, J=7.0 Hz), 2.41-2.49 (2 H, m), 2.73 (1 H, d, J=13.0 Hz), 2.84 (1 H, t, J=13.0 Hz), 3.01 (1 H, d, J=13.0 Hz), 3.21-3.31 (2 H, m), 3.58 (1 H, m), 3.73 (1 H, d, J=13.0 Hz), 3.89 (1 H, d, J=13.0 Hz), 4.20 (1 H, d, J=13.0 Hz), 4.58-4.66 (3 H, m), 7.37-7.43 (2 H, m), 7.52 (1 H, m), 7.87 (1 H, s), 7.98 (1 H, s); LC/MS (M+1) 480.

Example 36

Preparation of 4-(3-chloro-5-(2,3-dihydroxypropyl)pyridin-2-yl)-N-(5-(trifluoromethyl)pyridin-2-yl)-5,6-dihydropyridine-1(2H)-carboxamide (AAA)

Step 1 Preparation of 5-allyl-2,3-dichloropyridine (58)

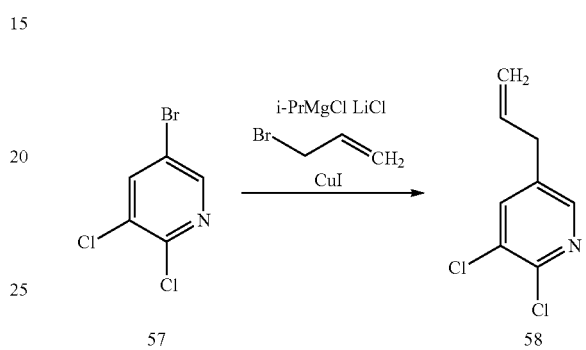

To a solution of 5-bromo-2,3-dichloropyridine 57 (2.095 g, 9.23 mmol) in THF was added i-PrMgCl LiCl complex (9.23 ml, 12.00 mmol) at 0° C. under N$_2$ over 10 min. Control of the halogen-metal exchange was monitored by TLC. CuI (0.352 g, 1.847 mmol) was added. The resulting mixture was stirred at 0° C. for 10 min. Allyl bromide (1.598 ml, 18.47 mmol) was added over 20 min. The resulting mixture was stirred at 0° C. for 30 min. The reaction mixture was diluted with sat NH$_4$Cl, then extracted with EtOAc (2×50 mL). The organic layers were combined and washed with sat NaCl. The organic layer was dried over MgSO$_4$, filtered and concentrated.

The crude product was added to a silica gel chromatography column and was eluted with Hex/EtOAc 4:1. Collected fractions were evaporated to afford 58 (1.632 g 8.68 mmol 94%) as a colorless oil.

$^1$H-NMR (CDCl$_3$) δ: 8.14 (1H, d, J=3.0 Hz), 7.60 (1H, d, J=3.0 Hz), 5.90 (1H, ddt, J=15.0, 9.0, 6.0 Hz), 5.19 (1H, dd, J=9.0, 3.0 Hz), 5.13 (1H, dd, J=15.0, 3.0 Hz), 3.38 (2H, d, J=6.0 Hz).

Step 2 Preparation of 3-(5,6-dichloropyridin-3-yl)propane-1,2-diol (59)

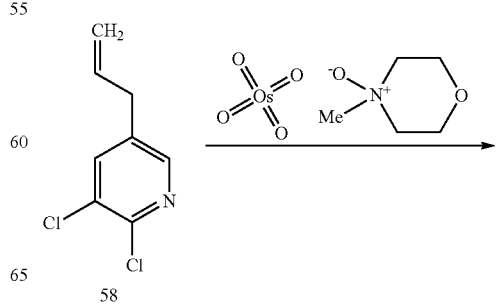

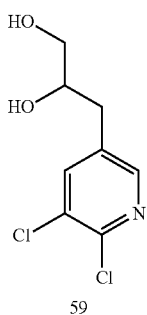

59

To a solution of 5-allyl-2,3-dichloropyridine 58 in THF (2 ml) and H₂O (1 ml) was added NMO (280 mg, 2.393 mmol) and osmium tetraoxide (THF solution) (0.487 ml, 0.080 mmol) at 0° C. The mixture was stirred at room temperature for 1 hr. The reaction mixture was diluted with H₂O, then extracted with EtOAc (3×10 mL). The organic layers were combined and washed with sat NaCl. The organic layer was dried over MgSO4, filtered and concentrated. The crude product was added to a silica gel chromatography column and was eluted with Hex/EtOAc 2:8. Collected fractions were evaporated to afford 59 (255 mg 1.148 mmol 72.0%) as a colorless oil.

¹H-NMR (CDCl₃) δ: 8.17 (1H, d, J=3.0 Hz), 7.74 (1H, d, J=3.0 Hz), 3.93 (1H, m), 3.75 (1H, m), 3.53 (1H, m), 2.74 (2H, m), 2.48 (1H, d, J=3.0 Hz), 2.01 (1H, t, J=3.0 Hz).

Step 3 tert-butyl-4-(3-chloro-5-(2,3-dihydroxypropyl)pyridin-2-yl)-5,6-dihydropyridine-1(2H)-carboxylate (60)

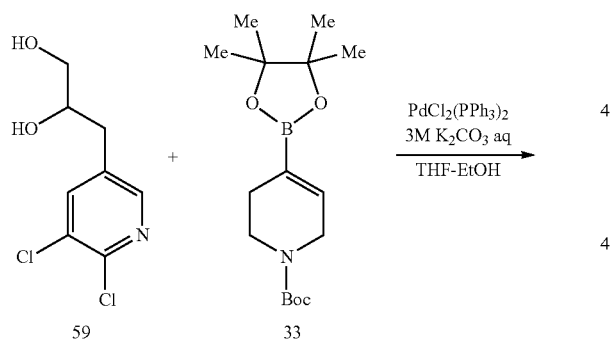

To a solution of 3-(5,6-dichloropyridin-3-yl)propane-1,2-diol 59 (255 mg, 1.148 mmol) in THF (1.8 ml)-EtOH (0.7 ml)-3M K₂CO₃ aq. (0.842 ml, 2.53 mmol) was added tert-butyl 4-(4,4,5,5-tetramethyl-1,3,2-dioxaborolan-2-yl)-5,6-dihydropyridine-1(2 H)-carboxylate 33 (391 mg, 1.263 mmol) and PdCl₂(PPh₃)₂ (24.18 mg, 0.034 mmol) at room temperature under N₂. The mixture was stirred at 85° C. for 1.5 hr. The reaction mixture was diluted with H₂O, then extracted with EtOAc (3×10 mL). The organic layers were combined and washed with brine. The organic layer was dried over MgSO₄, filtered and concentrated. The crude product was added to a silica gel chromatography column and was eluted with CHCl₃/MeOH (10:1) Collected fractions were evaporated to afford 60 (404 mg 1.095 mmol 95%) as a yellow oil.

¹H-NMR (CDCl₃) δ: 8.32 (1 H, s), 7.63 (1 H, s), 6.10 (1 H, br), 4.10 (2 H, m), 3.82 (1 H, br), 3.75-3.48 (4 H, m), 2.77 (2 H, m), 2.63-2.48 (3 H, m), 2.16 (1 H, m), 1.50 (9 H, s).

Step 4 Preparation of 4-(3-chloro-5-(2,3-dihydroxypropyl)pyridin-2-yl)-N-(5-(trifluoromethyl)pyridin-2-yl)-5,6-dihydropyridine-1(2H)-carboxamide (AAA)

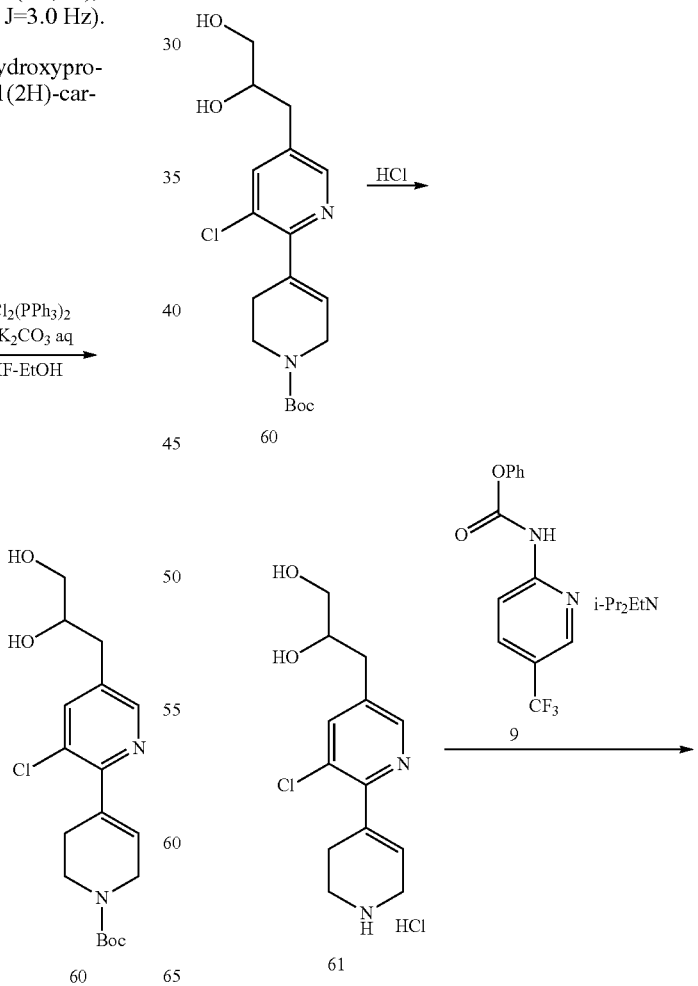

351

-continued

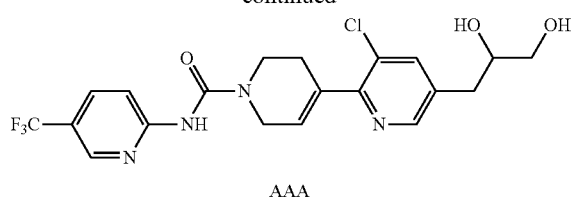

AAA

To a solution of 60 (404 mg, 1.095 mmol) in CH$_2$Cl$_2$ (4 ml) was added 4 mol/L HCl in dioxane (0.821 ml, 3.29 mmol) at room temperature. The mixture was stirred at room temperature for 4 hr. The yellow solid was precipitated. The solid was filtered and rinsed with AcOEt to afford 61 (5.336 g 20.41 mmol 60%) as a white solid. The HCl salt was used directly for next reaction.

To a suspension of 61 (86 mg, 0.282 mmol) in CH$_2$Cl$_2$ (2 ml) was added i-Pr$_2$EtN (0.172 ml, 0.986 mmol) at room temperature under N$_2$. The mixture was stirred at room temperature for 30 min. phenyl 5-(trifluoromethyl)pyridin-2-ylcarbamate 9 (80 mg, 0.282 mmol) was added at 0° C. The resulting mixture was stirred at room temperature for 18 hr. The reaction mixture was diluted with K$_2$CO$_3$ aq, then extracted with CHCl$_3$ (3×10 mL). The organic layers were combined and washed with sat NaCl, The organic layer was dried over MgSO$_4$, filtered and concentrated. The crude product was added to a silica gel chromatography column and was eluted with CHCl$_3$/MeOH 10:1. Collected fractions were evaporated to afford AAA (61 mg 0.134 mmol 47.4%) as a white solid.

$^1$H-NMR (CDCl$_3$) δ: 8.46 (1H, s), 8.30 (1H, d, J=3.0 Hz), 8.21 (1H, d, J=9.0 Hz), 7.88 (1H, dd, J=9.0, 3.0 Hz), 7.66 (1H, d, J=3.0 Hz), 7.51 (1H, s), 6.17 (1H, m), 4.26 (2H, m), 3.97 (1H, m), 3.81-3.72 (3H, m), 3.56 (1H, m), 2.80-2.70 (4H, m), 2.53 (1H, m), 2.13 (1H, m). LC/MS=(100%, t$_r$=2.38 min), m/z=457.05 [M+H]$^+$ (Calc: 456.85).

Example 37

Preparation of (R)-4-(3-Chloro-5-(2,3-dihydroxypropyl)pyridin-2-yl)-N-(5-(trifluoromethyl)pyridin-2-yl)-5,6-dihydropyridine-1(2H)-carboxamide (AAJ)

Step 1 Preparation of (S)-(5,6-Dichloropyridin-3-yl)(2,2-dimethyl-1,3-dioxolan-4-yl)methanone

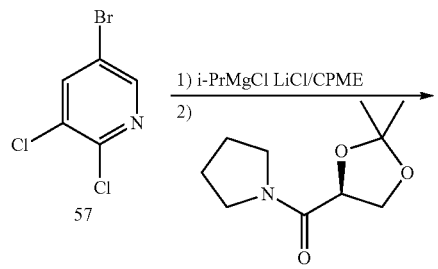

352

-continued

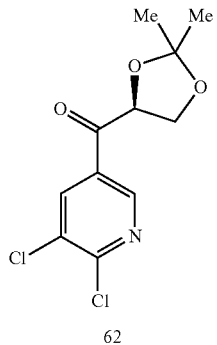

Under nitrogen atmosphere, to a 99 mL cyclopentyl methyl ether solution of 5-bromo-2,3-dichloropyridine (57, 14.18 g, 62.5 mmol) at −10° C. was dropwise added i-PrMgCl LiCl complex (1.3 M in tetrahydrofuran) (52.9 mL, 68.7 mmol) while maintaining the mixture below −5° C. After finishing the addition, the mixture was stirred at −10° C. for 15 min and 43 mL of a cyclopentyl methyl ether solution of (S)-(2,2-dimethyl-1,3-dioxolan-4-yl)(pyrrolidin-1-yl)methanone (13.21 g, 94 mmol) was added over 20 min. The resulting mixture was stirred at −0° C. for 2.5 hrs and slowly warmed up to room temperature. Saturated NH$_4$Cl was added to the reaction flask and the mixture was extracted with ethyl acetate (300 mL×2). The resulting organic layer was washed with H$_2$O, brine, dried over anhydrous sodium sulfate, and concentrated under reduced pressure. The crude product was chromatographed on silica gel eluting with a gradient of ethyl acetate (3-25%)/hexanes to afford 8.00 g of the product 62 as a white solid (77%). $^1$H-NMR (CDCl$_3$) δ: 8.97 (1H, d, J=2.0 Hz), 8.40 (1H, d, J=2.0 Hz), 5.04 (1H, dd, J=7.2, 4.8 Hz), 4.42 (1 H, dd, J=8.7, 4.8 Hz), 4.28 (1H, dd, J=8.7, 7.2 Hz), 1.46 (3H, s), 1.36 (3H, s).

Step 2 Preparation of (5,6-Dichloropyridin-3-yl)((S)-2,2-dimethyl-1,3-dioxolan-4-yl)methanol

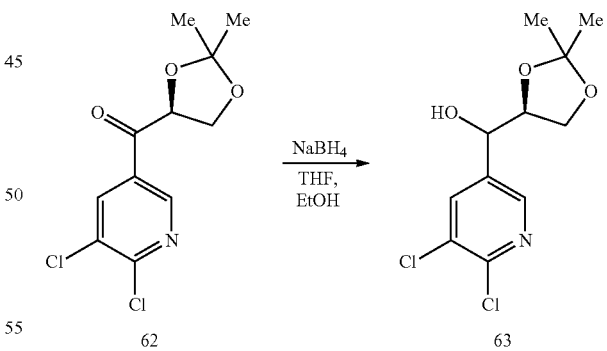

To a solution of (S)-(5,6-dichloropyridin-3-yl)(2,2-dimethyl-1,3-dioxolan-4-yl)methanone (62, 8.00 g, 29.0 mmol) in tetrahydrofuran (40 mL) and ethanol (40 mL) was added sodium tetrahydroborate (0.55 g, 14.49 mmol) at 0° C. under nitrogen atmosphere. The resulting mixture was stirred at −0° C. for 30 min. AcOH was added to the reaction flask and the mixture was extracted with ethyl acetate (150 mL×2). The resulting organic layer was washed with H$_2$O, brine, dried over anhydrous sodium sulfate, and concentrated under reduced pressure. The crude product was chromatographed on silica gel eluted with a gradient of ethyl acetate (20-50%)/hexanes to afford 7.52 g of the product 63 as a colorless oil (93%). $^1$H-NMR (CDCl$_3$) δ: 8.30 (0.2 H, d, J=2.0 Hz), 8.28 (0.8 H, d, J=2.0 Hz), 7.86 (0.8 H, d, J=2.0 Hz), 7.85 (0.2H, d, J=2.0 Hz), 4.86 (0.2H, d, J=5.0 Hz), 4.64 (0.8H, d, J=5.0 Hz), 4.28-4.07 (1H, m), 3.99-3.80 (2H, m), 1.49 (2.4H, s), 1.47 (0.6H, s), 1.37 (2.4H, s), 1.36 (0.6H, s).

Step 3 Preparation of O-(5,6-Dichloropyridin-3-yl)((S)-2,2-dimethyl-1,3-dioxolan-4-yl)methyl O-phenyl carbonothioate

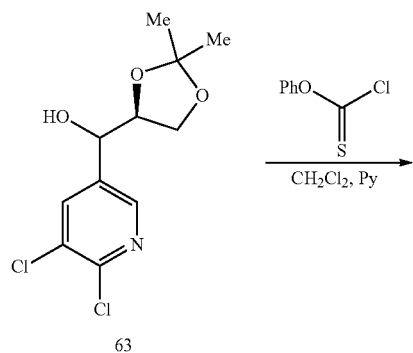

To a solution of O-(5,6-dichloropyridin-3-yl)((S)-2,2-dimethyl-1,3-dioxolan-4-yl)methyl O-phenyl carbonothioate (63, 7.50 g, 27.0 mmol) in dichloromethane (53 mL) and pyridine (53 mL) was added phenyl chlorothionoformate (6.98 g, 40.4 mmol) at 0° C. under nitrogen atmosphere. The resulting mixture was stirred at room temperature for 2 hrs. Saturated NaHCO$_3$ was added to the reaction flask and the mixture was extracted with ethyl acetate (150 mL×2). The resulting organic layer was washed with H$_2$O, brine, dried over anhydrous sodium sulfate, and concentrated under reduced pressure. The crude product was chromatographed on silica gel eluted with a gradient of ethyl acetate (5-20%)/hexanes to afford 11.69 g of the product 64 as a pale yellow oil (quant.). $^1$H-NMR (CDCl$_3$) δ: 8.37 (0.8H, d, J=2.0 Hz), 8.36 (0.2H, d, J=2.0 Hz), 7.87 (0.8H, d, J=2.0 Hz), 7.86 (0.2H, d, J=2.0 Hz), 7.48-7.37 (2H, m), 7.34-7.20 (1H, m), 7.09-7.06 (2H, m), 6.26 (0.8H, d, J=5.3 Hz), 6.08 (0.2H, d, J=5.3 Hz), 4.80-4.58 (1H, m), 4.03-3.82 (2 H, m), 1.44 (2.4H, s), 1.42 (0.6H, s), 1.38 (2.4H, s), 1.35 (0.6H, s).

Step 4 Preparation of (R)-2,3-Dichloro-5-((2,2-dimethyl-1,3-dioxolan-4-yl)methyl)pyridine

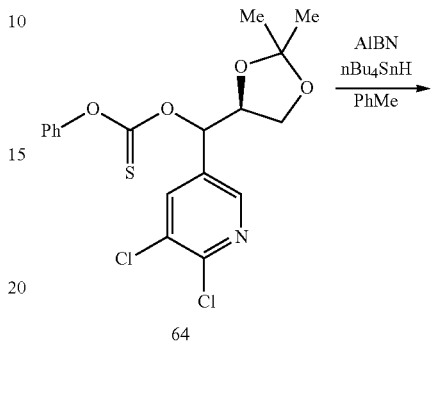

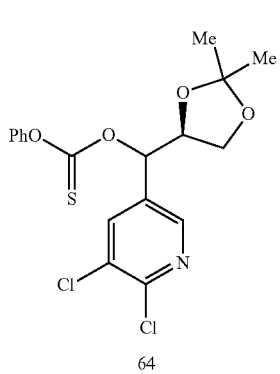

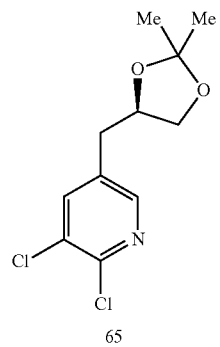

Under nitrogen atmosphere, to a 112 mL toluene solution of O-(5,6-dichloropyridin-3-yl)((S)-2,2-dimethyl-1,3-dioxolan-4-yl)methyl O-phenyl carbonothioate (64, 11.19 g, 27.0 mmol) was added AIBN (0.576 g, 3.51 mmol) and tributylstannane (11.70 g, 40.2 mmol) at room temperature. The mixture was stirred at 80° C. for 4.5 hrs.

The reaction mixture was diluted with 20% KF aq. (100 mL) and stirred for 30 min. then extracted with ethyl acetate (150 mL×2). The resulting organic layer was washed with H$_2$O, brine, dried over anhydrous sodium sulfate, and concentrated under reduced pressure. The crude product was chromatographed on silica gel eluting with a gradient of ethyl acetate (8-25%)/hexanes to afford 4.83 g of the product 65 as a pale yellow oil (68%). $^1$H-NMR (CDCl$_3$) δ: 8.17 (1H, d, J=2.2 Hz), 7.71 (1H, d, J=2.2 Hz), 4.33-4.25 (1H, m), 4.07 (1H, dd, J=8.2, 6.1 Hz), 3.61 (1H, dd, J=8.2, 6.1 Hz), 2.84 (2H, d, J=6.1 Hz), 1.42 (3H, s), 1.34 (3H, s).

Step 5 Preparation of (R)-tert-Butyl-4-(3-chloro-5-((2,2-dimethyl-1,3-dioxolan-4-yl)methyl)pyridin-2-yl)-5,6-dihydropyridine-1(2H)-carboxylate

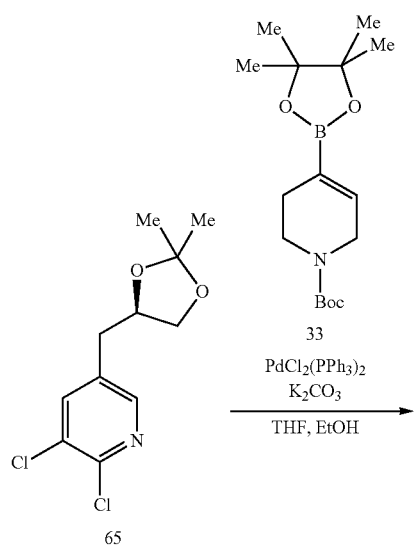

The compound 66 was obtained in the same manner as Reference Example 1, Step 3. Yield 97%. ¹H-NMR (CDCl₃) δ: 8.33 (1H, d, J=1.8 Hz), 7.61 (1H, d, J=1.8 Hz), 6.10 (1H, br), 4.31 (1H, q, J=6.0 Hz), 4.13-4.07 (3H, m), 3.66-3.61 (3H, m), 2.88-2.81 (2H, m), 2.57 (2H, br), 1.49 (9H, s), 1.43 (3H, s), 1.35 (3H, s).

Step 6 Preparation of (R)-3-(5-Chloro-6-(1,2,3,6-tetrahydropyridin-4-yl)pyridin-3-yl)propane-1,2-diol hydrochloride

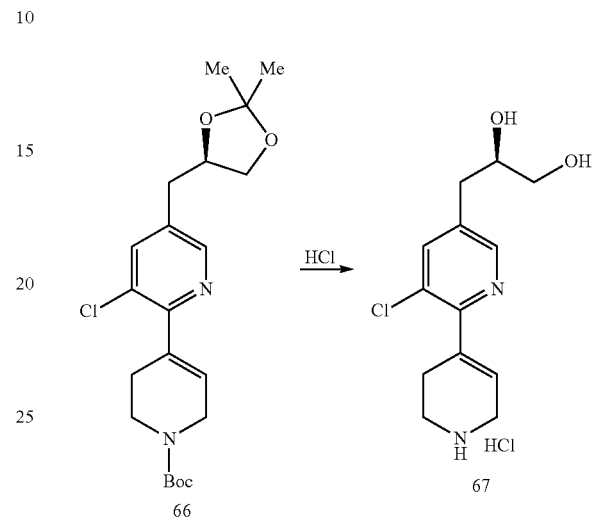

The compound 67 was obtained in the same manner as Reference Example 1, Step 4. Yield 88%. ¹H-NMR (DMSO-d₆) δ: 8.37 (1H, d, J=1.8 Hz), 7.81 (1H, d, J=1.8 Hz), 6.20 (1H, s), 4.11-3.71 (4H, m), 3.70-3.20 (3H, m), 2.86-2.44 (4H, m).

Step 7 Preparation of (R)-4-(3-Chloro-5-(2,3-dihydroxypropyl)pyridin-2-yl)-N-(5-(trifluoromethyl)pyridin-2-yl)-5,6-dihydropyridine-1(2H)-carboxamide (AAJ)

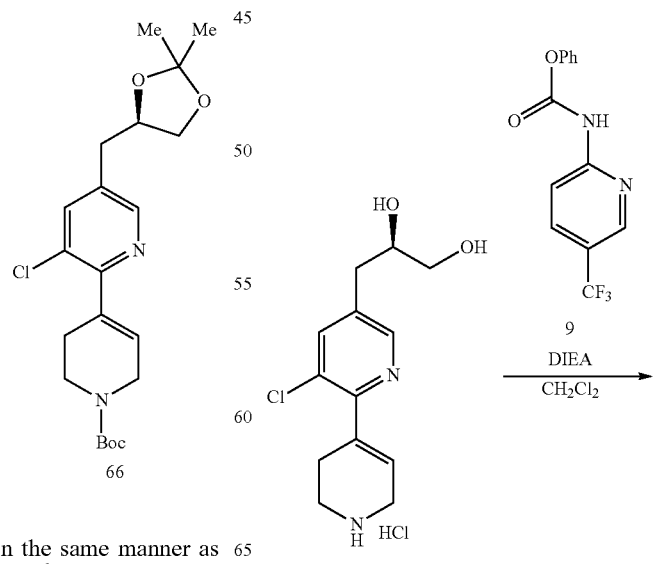

357

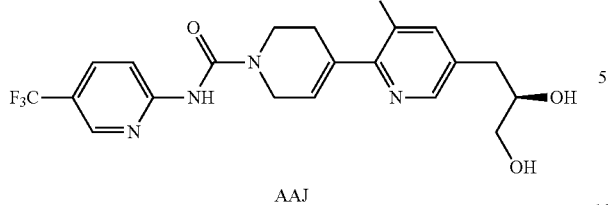

AAJ

The compound AAJ was obtained in the same manner as Example 1. Yield 62%. ¹H-NMR (CDCl₃) δ: 8.46 (1H, s), 8.35 (1H, d, J=1.8 Hz), 8.20 (1H, d, J=8.8 Hz), 7.86 (1H, dd, J=8.8, 1.8 Hz), 7.65 (1H, d, J=1.8 Hz), 7.43 (1H, s), 6.19-6.17 (1H, m), 4.25 (2H, q, J=2.7 Hz), 3.98-3.93 (1H, m), 3.78-3.73 (3H, m), 3.55 (1H, ddd, J=11.6, 6.1, 4.9 Hz), 2.84-2.71 (4H, m), 2.34-2.31 (1H, m), 1.92-1.91 (1H, m).

Example 38

Preparation of (R)-N-(3-Chloro-4-(trifluoromethyl)phenyl)-4-(3-chloro-5-(2,3-dihydroxypropyl)pyridin-2-yl)-5,6-dihydropyridine-1(2H)-carboxamide (AAK)

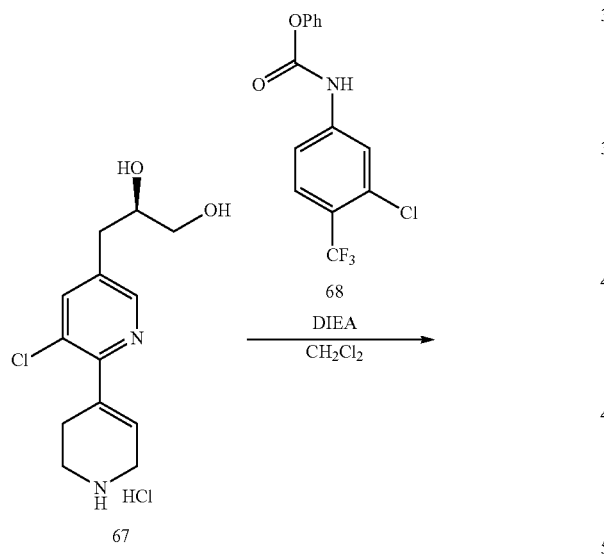

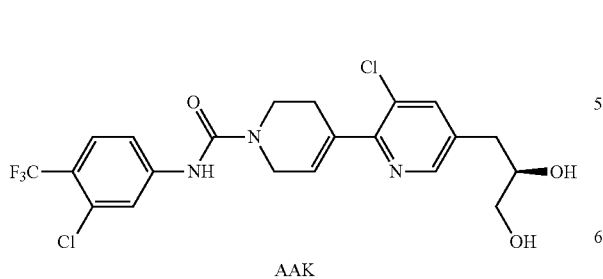

AAK

The compound AAK was obtained in the same manner as Example 1. Yield 39%. ¹H-NMR (CDCl₃) δ: 8.34 (1H, d, J=2.0 Hz), 7.66 (2H, m), 7.58 (1H, d, J=8.5 Hz), 7.36 (1H, dd, J=8.5, 1.9 Hz), 6.66 (1H, s), 6.15-6.14 (1H, m), 4.21 (2H, q,

358

J=2.7 Hz), 3.94-3.92 (1H, m), 3.76-3.72 (3H, m), 3.59-3.51 (1H, m), 2.82-2.62 (5H, m), 1.98 (1H, t, J=5.3 Hz).

Example 39

Preparation of (R)-4-(3-Chloro-5-(2,3-dihydroxypropyl)pyridin-2-yl)-N-(6-fluorobenzo[d]thiazol-2-yl)-5,6-dihydropyridine-1(2H)-carboxamide (AAL)

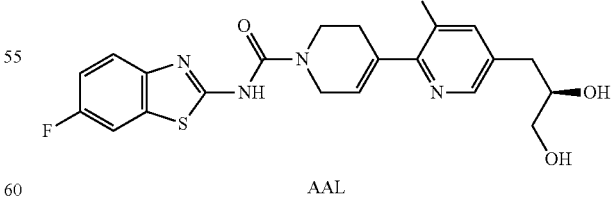

AAL

The compound AAL was obtained in the same manner of Example 10. Yield 71%. ¹H-NMR (DMSO-d₆) δ: 8.35 (1H, d, J=1.7 Hz), 7.77 (1H, d, J=1.7 Hz), 7.68 (1H, d, J=8.4 Hz), 7.48-7.46 (1H, m), 7.13 (1H, t, J=8.4 Hz), 6.18-6.17 (1H, m), 4.73-4.66 (2H, m), 4.25-4.24 (2H, m), 3.77-3.64 (3H, m), 3.38-3.31 (2H, m), 2.85-2.49 (4H, m).

(3H, m), 3.55 (1H, ddd, J=11.6, 6.4, 4.3 Hz), 2.83-2.70 (4H, m), 2.43 (1H, d, J=4.3 Hz), 1.91 (1H, t, J=5.5 Hz).

Example 40

Preparation of (R)-4-(3-Chloro-5-(2,3-dihydroxypropyl)pyridin-2-yl)-N-(3-methoxy-4-(trifluoromethyl)phenyl)-5,6-dihydropyridine-1(2H)-carboxamide (AAM)

Example 41

Preparation of (R)-N-(3-Chloro-4-(trifluoromethoxy)phenyl)-4-(3-chloro-5-(2,3-dihydroxypropyl) pyridin-2-yl)-5,6-dihydropyridine-1(2H)-carboxamide (AAN)

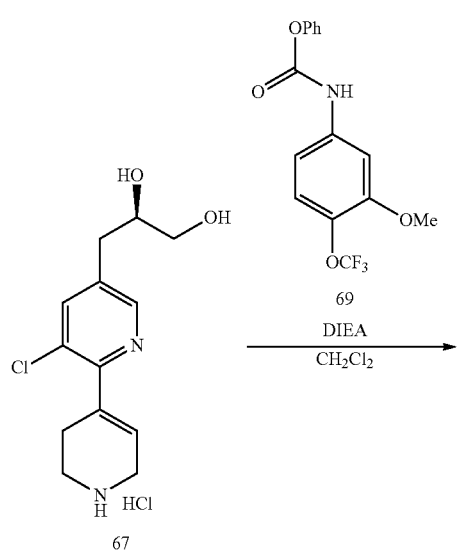

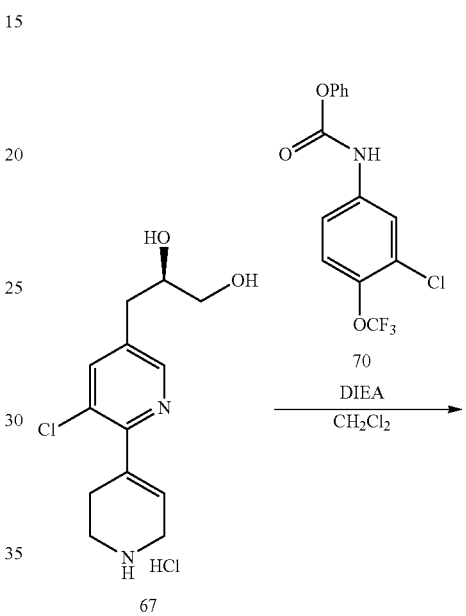

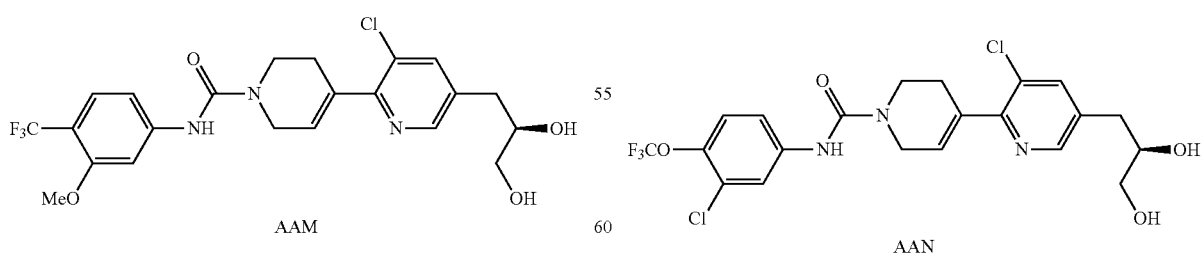

The compound AAM was obtained in the same manner as Example 1. Yield 88%. $^1$H-NMR (CDCl$_3$) δ: 8.35 (1H, d, J=1.7 Hz), 7.64 (1H, d, J=1.7 Hz), 7.54 (1H, s), 7.43 (1H, d, J=8.4 Hz), 6.72 (1H, d, J=8.4 Hz), 6.57 (1H, s), 6.17-6.17 (1H, m), 4.23-4.22 (2H, m), 3.98-3.91 (4H, m), 3.79-3.70

The compound AAN was obtained in the same manner as Example 1. Yield 80%.

$^1$H-NMR (DMSO-d$_6$) δ: 8.92 (1H, s), 8.36 (1H, d, J=1.5 Hz), 7.88 (1H, d, J=2.5 Hz), 7.78 (1H, d, J=1.5 Hz), 7.55 (1H, dd, J=9.0, 2.5 Hz), 7.45 (1H, d, J=9.0 Hz), 6.20-6.17 (1H, m), 4.18-4.17 (2H, m), 3.68-3.62 (3H, m), 3.48-3.24 (2H, m), 2.86-2.50 (4H, m).

Example 42

Preparation of (R)-4-(3-Chloro-5-(2,3-dihydroxypropyl)pyridin-2-yl)-N-(3-methyl-4-(trifluoromethoxy)phenyl)-5,6-dihydropyridine-1(2H)-carboxamide (AAS)

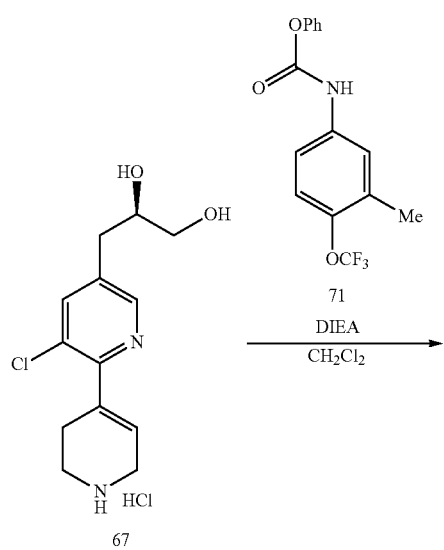

1.2 Hz), 6.19-6.16 (1H, m), 4.74 (1H, br), 4.16-4.16 (2H, m), 3.68-3.60 (3H, m), 3.27-3.04 (2H, m), 2.83-2.56 (4H, m), 2.23 (3H, s).

Example 43

Preparation of (R)-4-(3-Chloro-5-(2,3-dihydroxypropyl)pyridin-2-yl)-N-(3-methyl-4-(trifluoromethyl)phenyl)-5,6-dihydropyridine-1(2H)-carboxamide (AAW)

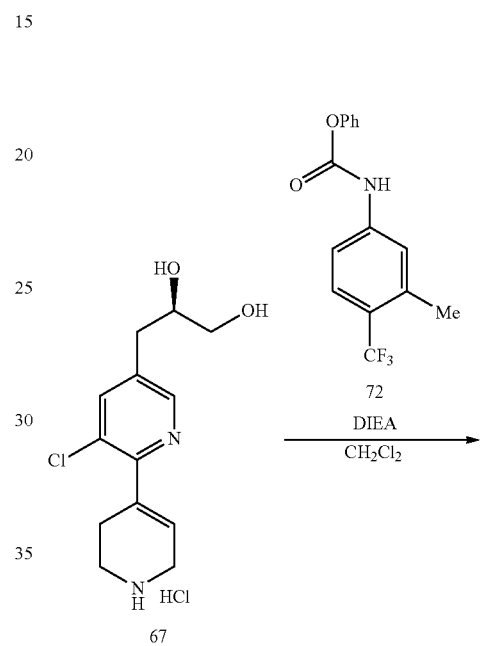

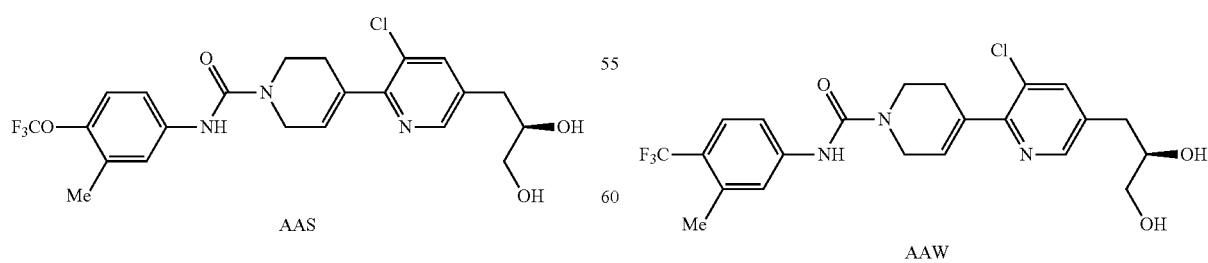

The compound AAS was obtained in the same manner as Example 1. Yield 67%. $^1$H-NMR (DMSO-d$_6$) δ: 8.68 (1H, s), 8.35 (1H, d, J=1.7 Hz), 7.77 (1H, d, J=1.7 Hz), 7.48 (1H, d, J=2.4 Hz), 7.40 (1H, dd, J=8.9, 2.4 Hz), 7.18 (1H, dd, J=8.9, The compound AAW was obtained in the same manner as Example 1. Yield 60%. $^1$H-NMR (DMSO-d$_6$) δ: 8.86 (1H, s), 8.35 (1H, d, J=1.7 Hz), 7.77 (1H, d, J=1.7 Hz), 7.54-7.52 (3H, m), 6.20-6.16 (1H, m), 4.18-4.18 (2H, m), 3.68-3.62 (3H, m), 3.33-3.23 (2H, m), 2.85-2.53 (4H, m), 2.38 (3H, s).

Example 44

Preparation of (S)-4-(3-Chloro-5-(2,3-dihydroxypropyl)pyridin-2-yl)-N-(3-methyl-4-(trifluoromethyl)phenyl)-5,6-dihydropyridine-1(2H)-carboxamide (ACG)

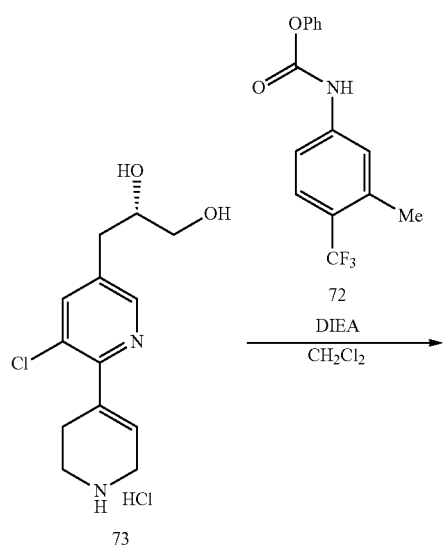

Example 45

Preparation of (S)-4-(3-Chloro-5-(2,3-dihydroxypropyl)pyridin-2-yl)-N-(3-methyl-4-(trifluoromethoxy)phenyl)-5,6-dihydropyridine-1(2H)-carboxamide (ACH)

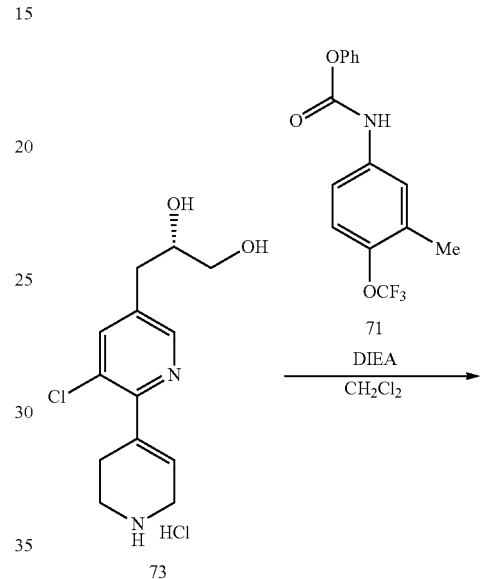

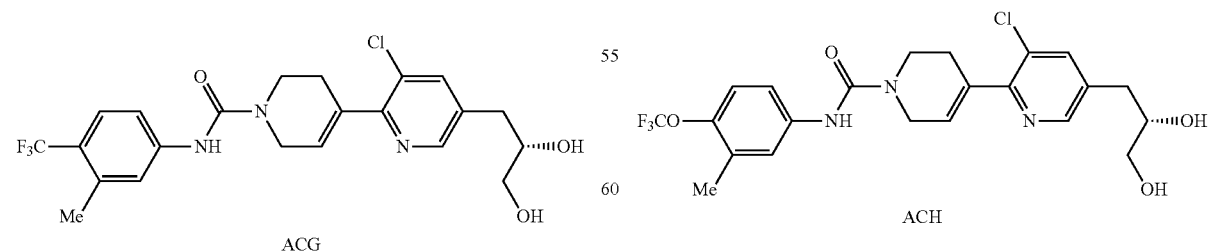

The compound ACG was obtained in the same manner as Example 1. Yield 65%. $^1$H-NMR (DMSO-$d_6$) δ: 8.86 (1H, s), 8.35 (1H, d, J=1.7 Hz), 7.77 (1H, d, J=1.7 Hz), 7.54-7.52 (3H, The compound ACH was obtained in the same manner as Example 1. Yield 55%. $^1$H-NMR (DMSO-$d_6$) δ: 8.68 (1H, s), 8.35 (1H, d, J=1.7 Hz), 7.77 (1H, d, J=1.7 Hz), 7.48 (1H, d, J=2.4 Hz), 7.40 (1H, dd, J=8.9, 2.4 Hz), 7.18 (1H, dd, J=8.9, 1.2 Hz), 6.19-6.16 (1H, m), 4.74 (1H, br), 4.16-4.16 (2H, m), 3.68-3.60 (3H, m), 3.27-3.04 (2H, m), 2.83-2.56 (4H, m), 2.23 (3H, s).

Example 46

Preparation of (S)-N-(3-Chloro-4-(trifluoromethyl)phenyl)-4-(3-chloro-5-(2,3-dihydroxypropyl)pyridin-2-yl)-5,6-dihydropyridine-1(2H)-carboxamide (AAF)

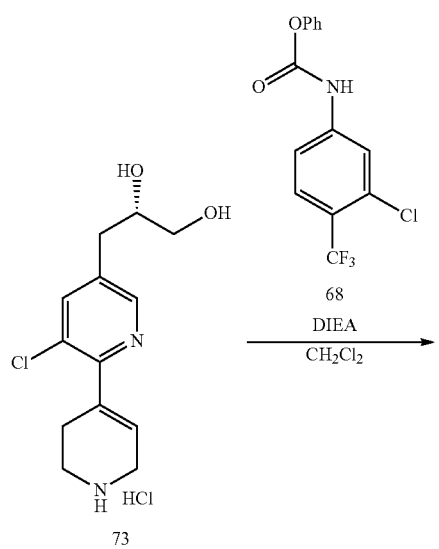

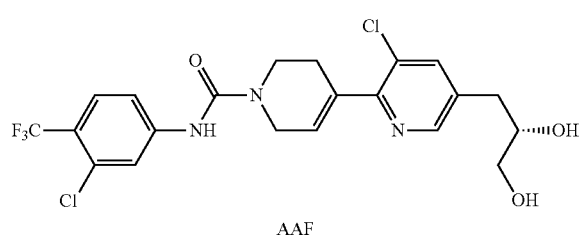

The compound AAF was obtained in the same manner as Example 1. Yield 78%. ¹H-NMR (CDCl₃) δ: 8.34 (1H, d, J=2.0 Hz), 7.66 (2H, m), 7.58 (1H, d, J=8.5 Hz), 7.36 (1H, dd, J=8.5, 1.9 Hz), 6.66 (1H, s), 6.15-6.14 (1H, m), 4.21 (2H, q, J=2.7 Hz), 3.94-3.92 (1H, m), 3.76-3.72 (3H, m), 3.59-3.51 (1H, m), 2.82-2.62 (5H, m), 1.98 (1H, t, J=5.3 Hz).

Example 47

Preparation of (R)-4-(5-(2,3-Dihydroxypropyl)-3-methylpyridin-2-yl)-N-(5-(trifluoromethyl)pyridin-2-yl)-5,6-dihydropyridine-1(2H)-carboxamide (AAT)

Step 1 Preparation of (S)-(6-bromo-5-methylpyridin-3-yl)(2,2-dimethyl-1,3-dioxolan-4-yl)methanone

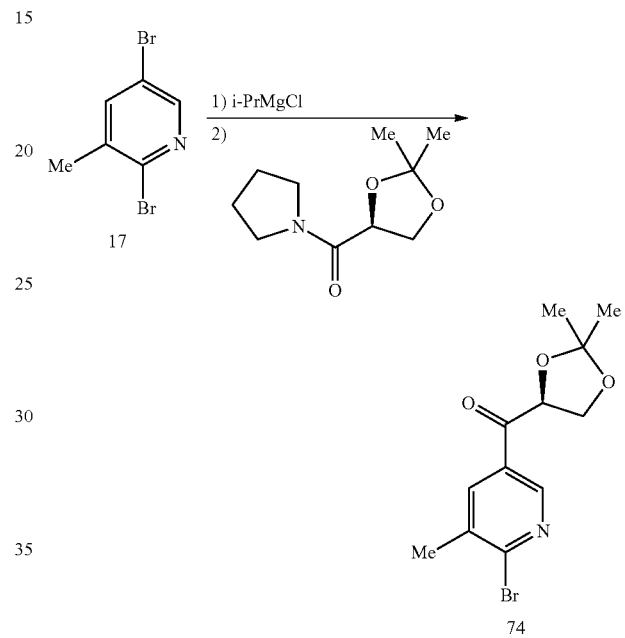

The compound 74 was obtained in the same manner as Example 37, Step 1. Yield 65%.

¹H-NMR (CDCl₃) δ: 8.85 (1H, d, J=2.3 Hz), 8.10 (1H, d, J=2.3 Hz), 5.10 (1H, dd, J=7.2, 5.2 Hz), 4.38 (1H, dd, J=8.7, 5.2 Hz), 4.28 (1H, dd, J=8.6, 7.2 Hz), 2.47 (4H, s), 1.46 (4H, s), 1.38 (4H, s).

Step 2. Preparation of (6-chloro-5-methylpyridin-3-yl)((S)-2,2-dimethyl-1,3-dioxolan-4-yl)methanol The crude compound 75 was obtained in the same manner as Example 37, Step 2. This compound was used directly for next step. (100%)

Step 3. Preparation of O-(6-chloro-5-methylpyridin-3-yl)((S)-2,2-dimethyl-1,3-dioxolan-4-yl)methyl O-phenyl carbonothioate

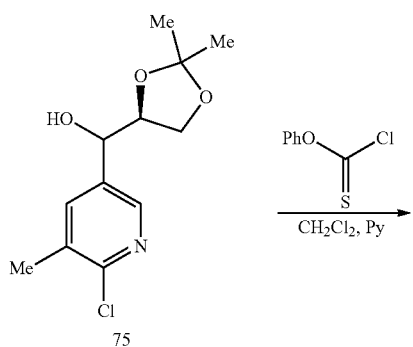

The compound 76 was obtained in the same manner as Example 37, Step 3. Yield 79%

¹H-NMR (CDCl₃) δ: 8.28-8.27 (1H, m), 7.59-7.58 (1H, m), 7.41-7.38 (2H, m), 7.30-7.28 (1H, m), 7.07-7.04 (2H, m), 6.21 (0.9H, d, J=6.6 Hz), 6.09 (0.1H, d, J=6.6 Hz), 4.60-4.53 (1H, m), 4.01-3.74 (2H, m), 2.43 (3H, s), 1.55-1.35 (6H, m).

Step 4. Preparation of (R)-2-chloro-5-((2,2-dimethyl-1,3-dioxolan-4-yl)methyl)-3-methylpyridine The compound 77 was obtained in the same manner as Example 37, Step 4. Yield 76%

¹H-NMR (CDCl₃) δ: 8.06 (1H, d, J=2.4 Hz), 7.40 (1H, d, J=2.4 Hz), 4.32-4.24 (1H, m), 4.02 (1H, dd, J=8.2, 6.0 Hz), 3.60 (1H, dd, J=8.2, 6.0 Hz), 2.83-2.76 (2H, m), 2.37 (3H, s), 1.41 (3H, s), 1.34 (3H, s).

Step 5. Preparation of (R)-tert-butyl 4-(5-((2,2-dimethyl-1,3-dioxolan-4-yl)methyl)-3-methylpyridin-2-yl)-5,6-dihydropyridine-1(2H)-carboxylate The compound 78 was obtained in the same manner as Reference Example 1, Step 3. Yield 78%

¹H-NMR (CDCl₃) δ: 8.26 (1H, d, J=1.8 Hz), 7.36 (1H, d, J=1.8 Hz), 5.75 (1H, br), 4.35-4.27 (1H, m), 4.06 (3H, dq, J=21.9, 5.4 Hz), 3.65-3.62 (3H, m), 2.89-2.77 (2H, m), 2.51-2.50 (2H, br), 2.32 (3H, s), 1.49 (9H, s), 1.43 (3H, s), 1.35 (3H, s).

Step 6. Preparation of (R)-3-(5-methyl-6-(1,2,3,6-tetrahydropyridin-4-yl)pyridin-3-yl)propane-1,2-diol hydrochloride

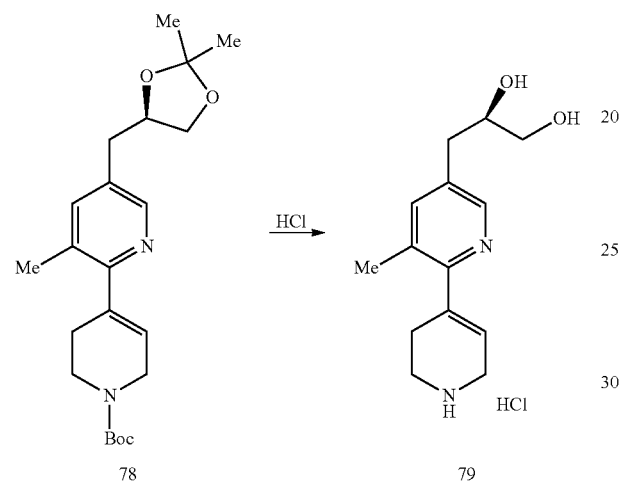

The compound 79 was obtained in the same manner as Reference Example 1, Step 4. Yield 89%

¹H-NMR (DMSO-d₆) δ: 8.48 (1H, s), 8.17 (1H, s), 6.12 (1H, s), 3.79-3.25 (7H, m), 2.94-2.67 (4H, m), 2.43 (3H, s).

Step 7. Preparation of (R)-4-(5-(2,3-Dihydroxypropyl)-3-methylpyridin-2-yl)-N-(5-(trifluoromethyl)pyridin-2-yl)-5,6-dihydropyridine-1(2H)-carboxamide (AAT)

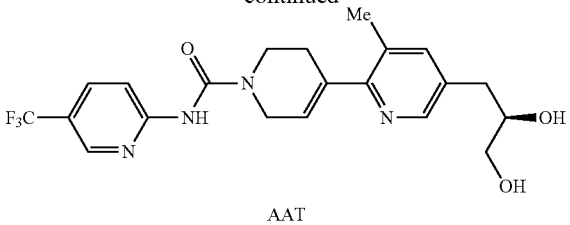

AAT

The compound AAT was obtained in the same manner as Example 1. Yield 98%. ¹H-NMR (CDCl₃) δ: 8.45 (1H, d, J=1.8 Hz), 8.28 (1H, d, J=1.8 Hz), 8.20 (1H, d, J=8.8 Hz), 7.86 (1H, dd, J=8.8, 2.4 Hz), 7.52 (1H, s), 7.41 (1H, d, J=2.4 Hz), 5.83-5.80 (1H, m), 4.22-4.21 (2H, m), 3.98-3.91 (1H, m), 3.80-3.70 (3H, m), 3.54 (1H, dd, J=11.0, 6.9 Hz), 2.76-2.68 (4H, m), 2.50 (1H, br s), 2.33 (3H, s), 2.18 (1H, br s).

Example 48

Preparation of (R)-N-(3-Chloro-4-(trifluoromethyl)phenyl)-4-(5-(2,3-dihydroxypropyl)-3-methylpyridin-2-yl)-5,6-dihydropyridine-1(2H)-carboxamide (AAU)

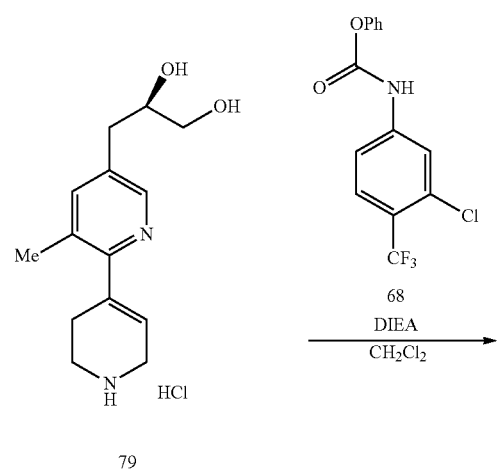

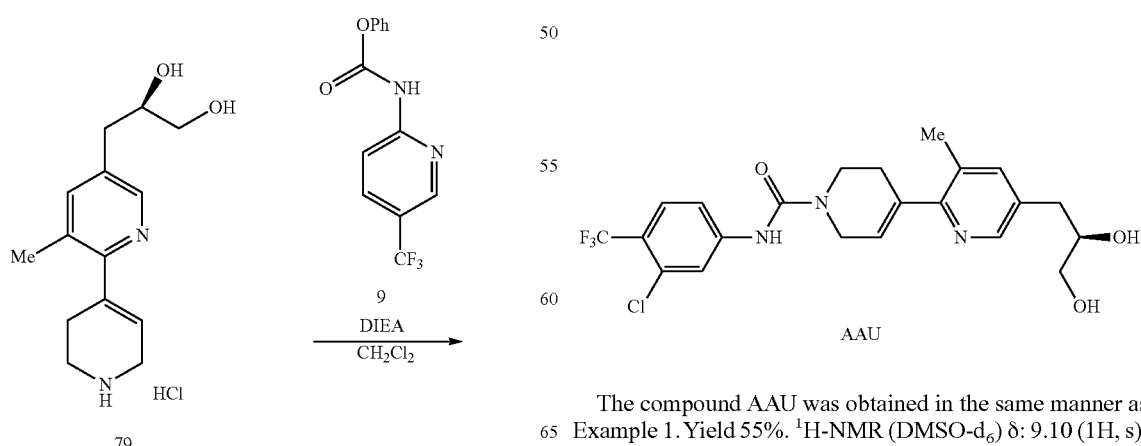

AAU

The compound AAU was obtained in the same manner as Example 1. Yield 55%. ¹H-NMR (DMSO-d₆) δ: 9.10 (1H, s), 8.21 (1H, d, J=1.8 Hz), 7.93 (1H, d, J=1.8 Hz), 7.71 (1H, d, J=8.8 Hz), 7.64 (1H, dd, J=8.8, 1.8 Hz), 7.47 (1H, d, J=1.8

Hz), 5.88-5.84 (1H, m), 4.66-4.65 (2H, m), 4.17-4.16 (2H, m), 3.68-3.60 (3H, m), 3.25-3.10 (2H, m), 2.79-2.44 (4H, m), 2.32 (3H, s).

Example 49

Preparation of (R)-4-(5-(2,3-Dihydroxypropyl)-3-methylpyridin-2-yl)-N-(3-methoxy-4-(trifluoromethyl)phenyl)-5,6-dihydropyridine-1(2H)-carboxamide (AAV)

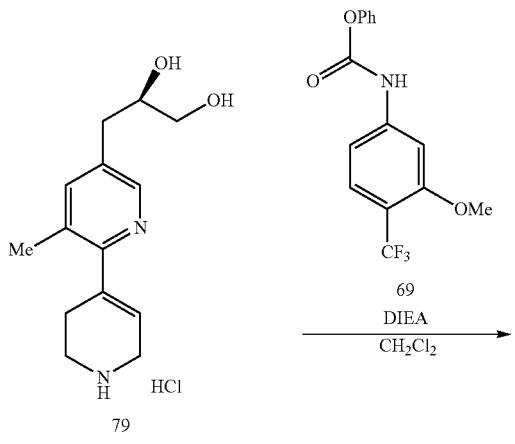

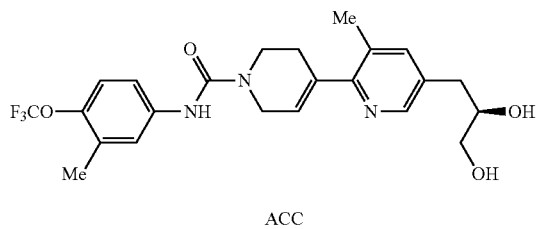 [SMILES: Cc1cc(NC(=O)N2CC=C(c3ncc(C[C@@H](O)CO)cc3C)CC2)ccc1OC(F)(F)F]

The compound AAV was obtained in the same manner as Example 1. Yield 51%. $^1$H-NMR (DMSO-d$_6$) δ: 8.90 (1H, s), 8.21 (1H, s), 7.47-7.44 (3H, m), 7.25 (1H, d, J=8.7 Hz), 5.88-5.85 (1H, m), 4.65 (1H, br), 4.16-4.16 (2H, m), 3.83 (3H, s), 3.68-3.65 (3H, m), 3.29-3.26 (2H, m), 2.79-2.45 (4H, m), 2.32 (3H, s).

Example 50

(R)-4-(5-(2,3-dihydroxypropyl)-3-methylpyridin-2-yl)-N-(3-methyl-4-(trifluoromethoxy)phenyl)-5,6-dihydropyridine-1(2H)-carboxamide (ACC)

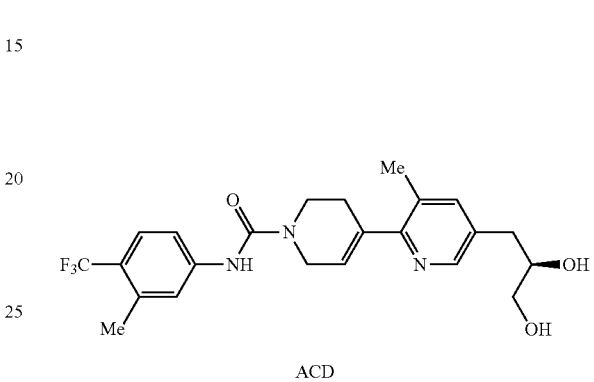

The compound ACC was obtained in the same manner as Example 1. $^1$H-NMR (DMSO-d$_6$): 2.23 (3H, s), 2.32 (3H, s), 3.49 (1H, m), 2.72 (1H, m), 3.49-3.40 (2H, m), 3.67 (1H, m), 4.14 (1H, d, J=2.5 Hz), 4.64 (1H, m), 5.86 (1H, s), 7.18 (1H, d, J=8.7 Hz), 7.42 (1H, dd, J=2.6, 8.7 Hz), 7.47 (1H, d, J=1.5 Hz), 7.48 (1H, d, J=2.6 Hz), 8.21 (1H, d, J=1.5 Hz), 8.66 (1H, s).

MS: 466 [M+H]$^+$

Example 51

(R)-4-(5-(2,3-dihydroxypropyl)-3-methylpyridin-2-yl)-N-(3-methyl-4-(trifluoromethyl)phenyl)-5,6-dihydropyridine-1(2H)-carboxamide (ACD)

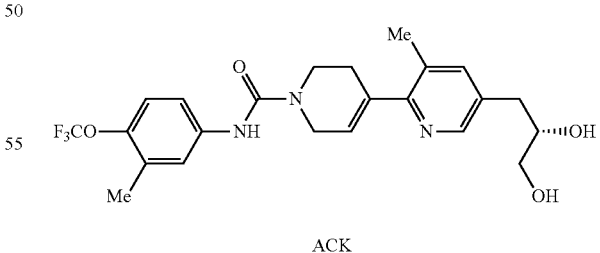

The compound ACD was obtained in the same manner as Example 1. $^1$H-NMR (DMSO-d$_6$): 2.23 (3H, s), 2.32 (3H, s), 2.38 (1H, m), 2.79 (1H, m), 3.67 (3H, m), 4.15 (1H, m), 4.65 (1H, m), 5.86 (1H, brs), 7.47 (1H, s), 7.53 (1H, s), 7.56 (1H, s), 8.21 (1H, s), 8.85 (1H, s).

MS: 450 [M+H]$^+$

Example 52

(S)-4-(5-(2,3-dihydroxypropyl)-3-methylpyridin-2-yl)-N-(3-methyl-4-(trifluoromethoxy)phenyl)-5,6-dihydropyridine-1(2H)-carboxamide (ACK)

The compound ACK was obtained in the same manner as Example 1. $^1$H-NMR (DMSO-d$_6$): 2.23 (3H, s), 2.32 (3H, s), 2.48 (1H, m), 2.75 (1H, m), 3.67 (3H, m), 4.14 (1H, m), 4.65 (1H, m), 5.86 (1H, brs), 7.18 (1H, m), 7.42 (1H, m), 7.48 (1H, m), 8.21 (1H, s), 8.85 (1H, s).

MS: 466 [M+H]$^+$

Example 53

(S)-4-(5-(2,3-dihydroxypropyl)-3-methylpyridin-2-yl)-N-(3-methyl-4-(trifluoromethyl)phenyl)-5,6-dihydropyridine-1(2H)-carboxamide (ACL)

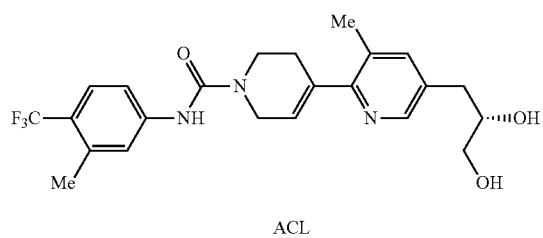 [SMILES: Cc1cc(NC(=O)N2CC=C(c3ncc(C[C@H](O)CO)cc3C)CC2)ccc1C(F)(F)F]

ACL

The compound ACL was obtained in the same manner as Example 1. $^1$H-NMR (DMSO-$d_6$): 2.32 (3H, s), 2.38 (3H, s), 2.48 (1H, m), 2.75 (1H, m), 3.67 (3H, m), 4.16 (1H, m), 4.65 (1H, m), 5.86 (1H, brs), 7.47 (1H, m), 7.53 (1H, m), 7.56 (1H, m), 8.58 (1H, s), 8.91 (1H, s).

MS: 450 [M+H]$^+$

Example 54

Preparation of (R)-4-(3-Chloro-5-(2,3-dihydroxypropyl)pyridin-2-yl)-4-fluoro-N-(3-methyl-4-(trifluoromethyl)phenyl)piperidine-1-carboxamide (ACI)

Step 1 Preparation of tert-butyl 4-(5-allyl-3-chloropyridin-2-yl)-4-fluoropiperidine-1-carboxylate

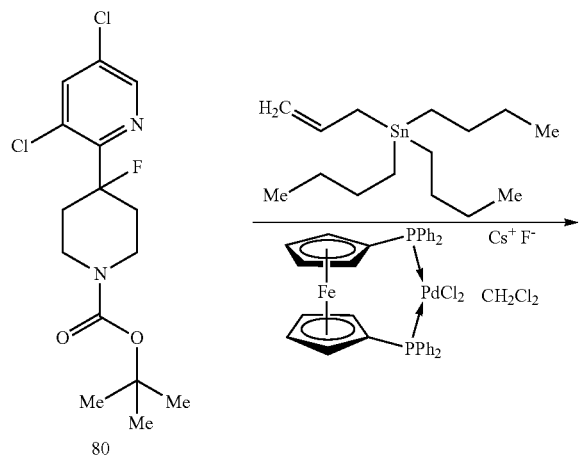

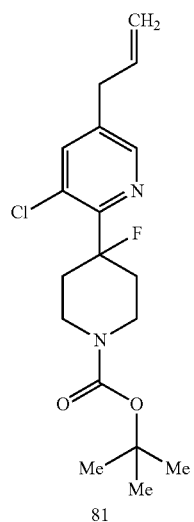

81

To a solution of tert-butyl 4-(3,5-dichloropyridin-2-yl)-4-fluoropiperidine-1-carboxylate 80 (reported in WO2008/132600)(3.49 g, 10 mmol) in THF (40 ml) was added allyltributylstannane (3.31 g, 10.00 mmol) and CsF (4.56 g, 30.0 mmol) at room temperature under N$_2$. A PdCl$_2$(dppf) CH$_2$Cl$_2$ (0.408 g, 0.500 mmol) was added. The resulting mixture was stirred at room temperature for 10 min, and then heated at reflux for 8 hr. The reaction mixture was diluted with 10% citric acid, and then extracted with EtOAc (×2). The organic layers were combined and washed with H$_2$O and brine. The organic layer was dried over MgSO$_4$, filtered and evaporated. The crude product was chromatographed on silica gel eluting with a gradient of ethyl acetate/hexanes to afford 1.37 g of the compound 81 as a yellow oil (39%). $^1$H-NMR (CDCl$_3$) δ: 8.31 (1H, d, J=1.7 Hz), 7.59 (1H, d, J=1.7 Hz), 6.02-5.89 (1H, m), 5.24-5.14 (2H, m), 4.09 (2H, br s), 3.42 (2H, d, J=6.5 Hz), 3.30 (2H, br s), 2.38-2.22 (4H, br m), 1.52 (9H, s).

Step 2 Preparation of (R)-tert-butyl 4-(3-chloro-5-(2,3-dihydroxypropyl)pyridin-2-yl)-4-fluoropiperidine-1-carboxylate

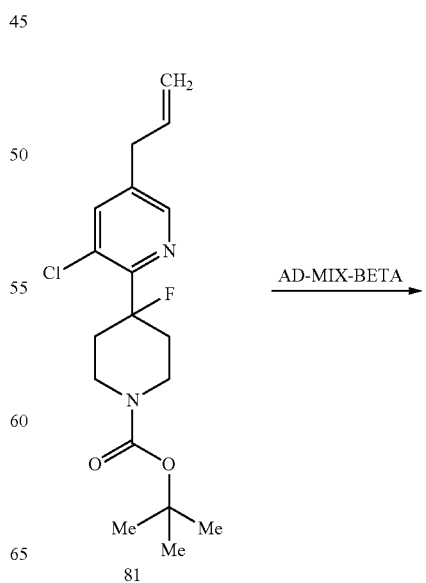

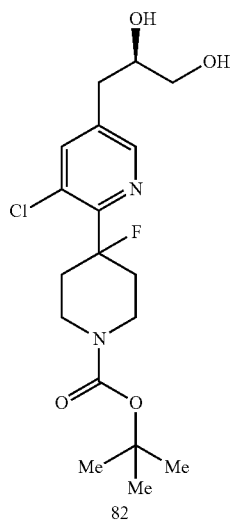

To a solution of tert-butyl 4-(5-allyl-3-chloropyridin-2-yl)-4-fluoropiperidine-1-carboxylate 81 (1.36 g, 3.83 mmol) in t-BuOH (40 ml) and H₂O (40.0 ml) was added AD-MIX-BETA (4 g, 3.83 mmol) at room temperature. A methanesulfonamide (0.365 g, 3.83 mmol) was added. The resulting mixture was stirred at room temperature for 8 hr. AD-MIX-BETA (4 g, 3.83 mmol) was added more. The resulting mixture was stirred at room temperature for more 8 hr. The reaction mixture was filtered through celite. The reaction mixture was diluted with H₂O, then extracted with EtOAc (×2). The organic layers were combined and washed with H₂O and sat NaCl. The organic layer was dried over MgSO₄, filtered and evaporated. The crude product was chromatographed on silica gel eluting with a gradient of ethyl acetate/hexanes to afford 1.26 g of the compound 82 as a colorless foam (85%).

¹H-NMR (CDCl₃) δ: 8.32 (1H, d, J=1.6 Hz), 7.66 (1H, d, J=1.9 Hz), 4.10-3.90 (3H, br m), 3.73 (1H, dd, J=10.7, 3.0 Hz), 3.54 (1H, dd, J=10.9, 6.7 Hz), 3.26 (2H, br s), 2.79-2.74 (2H, m), 2.35-2.20 (4H, m), 1.48 (9H, s).

Step 3. Preparation of (R)-3-(5-chloro-6-(4-fluoropiperidin-4-yl)pyridin-3-yl)propane-1,2-diol

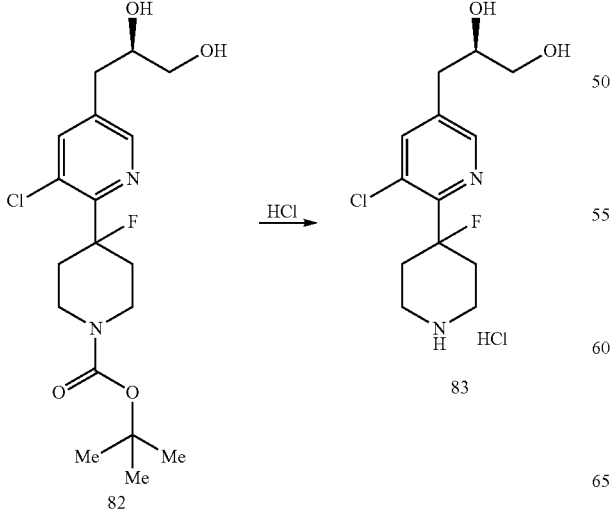

The compound 83 was obtained in the same manner as Example 1, Step 4. Yield 95%

¹H-NMR (DMSO-d₆) δ: 8.40 (1H, d, J=1.7 Hz), 7.85 (1H, d, J=1.7 Hz), 4.30-4.02 (2H, m), 3.67-3.61 (1H, m), 3.38-3.06 (6H, m), 2.88-2.83 (1H, m), 2.61-2.42 (3H, m).

Step 4. Preparation of (R)-4-(3-Chloro-5-(2,3-dihydroxypropyl)pyridin-2-yl)-4-fluoro-N-(3-methyl-4-(trifluoromethyl)phenyl)piperidine-1-carboxamide (ACI)

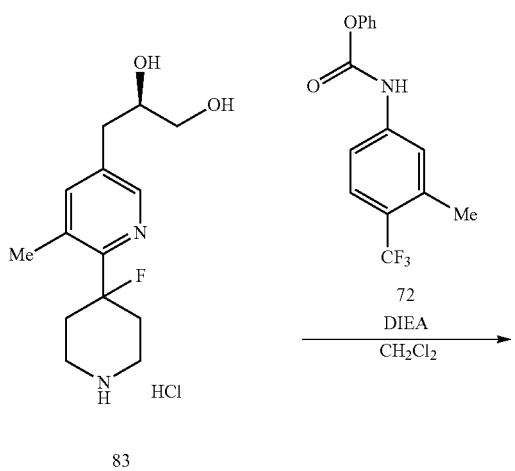

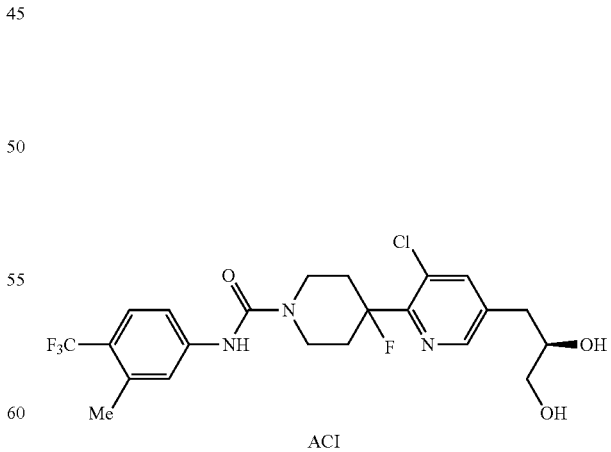

The compound ACI was obtained in the same manner as Example 1. Yield 85%. ¹H-NMR (CDCl₃) δ: 8.31 (1H, d, J=2.0 Hz), 7.67 (1H, d, J=2.0 Hz), 7.51 (1H, d, J=8.7 Hz), 7.35 (1H, s), 7.28-7.24 (1H, m), 6.49 (1H, s), 4.03-3.96 (3H, m), 3.74 (1H, ddd, J=10.9, 5.5, 3.3 Hz), 3.55-3.45 (3H, m), 2.80-2.74 (2H, m), 2.45-2.21 (8H, m), 1.83 (1H, t, J=5.5 Hz), 1.55 (3H, s).

Example 55

Preparation of (R)-4-(3-Chloro-5-(2,3-dihydroxypropyl)pyridin-2-yl)-4-fluoro-N-(3-methyl-4-(trifluoromethoxy)phenyl)piperidine-1-carboxamide (ACJ)

The compound ACJ was obtained in the same manner as Example 1. Yield 72%. $^1$H-NMR (CDCl$_3$) δ: 8.31 (1H, d, J=1.8 Hz), 7.66 (1H, d, J=1.8 Hz), 7.31 (1H, d, J=1.8 Hz), 7.15-7.11 (2H, m), 6.39 (1H, s), 4.04-3.90 (3H, m), 3.73 (1H, ddd, J=10.9, 5.3, 3.4 Hz), 3.57-3.40 (3H, m), 2.81-2.74 (2H, m), 2.38-2.31 (8H, m), 1.88 (1H, t, J=5.3 Hz).

Example 56

Preparation of (S)-4-(3-Chloro-5-(2,3-dihydroxypropyl)pyridin-2-yl)-4-fluoro-N-(3-methyl-4-(trifluoromethyl)phenyl)piperidine-1-carboxamide (ACS)

Step 1. Preparation of (S)-tert-butyl 4-(3-chloro-5-(2,3-dihydroxypropyl)pyridin-2-yl)-4-fluoropiperidine-1-carboxylate

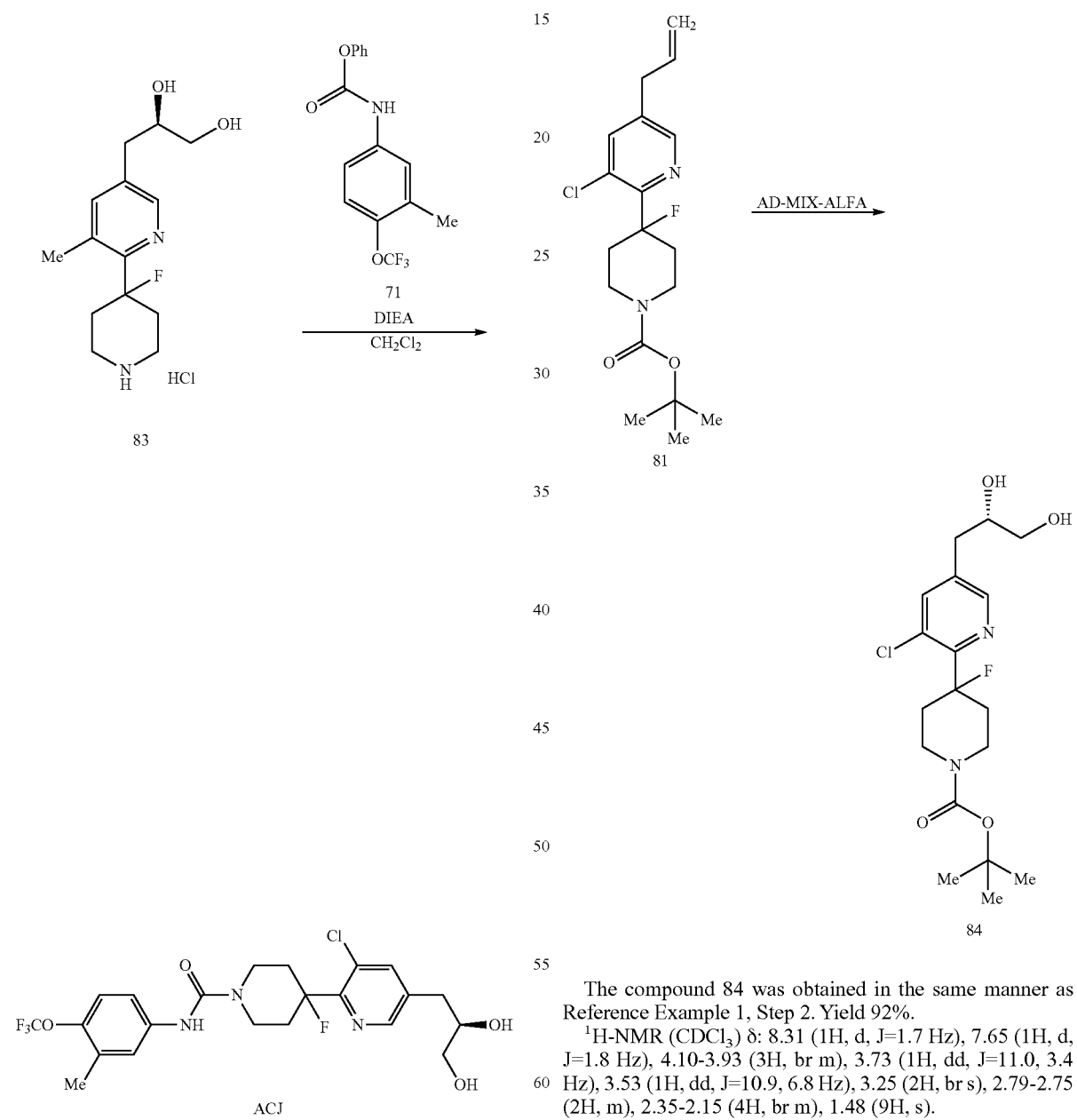

The compound 84 was obtained in the same manner as Reference Example 1, Step 2. Yield 92%.
$^1$H-NMR (CDCl$_3$) δ: 8.31 (1H, d, J=1.7 Hz), 7.65 (1H, d, J=1.8 Hz), 4.10-3.93 (3H, br m), 3.73 (1H, dd, J=11.0, 3.4 Hz), 3.53 (1H, dd, J=10.9, 6.8 Hz), 3.25 (2H, br s), 2.79-2.75 (2H, m), 2.35-2.15 (4H, br m), 1.48 (9H, s).

Step 2. Preparation of (S)-3-(5-chloro-6-(4-fluoropiperidin-4-yl)pyridin-3-yl)propane-1,2-diol (R)-3-(5-chloro-6-(4-fluoropiperidin-4-yl)pyridin-3-yl)propane-1,2-diol

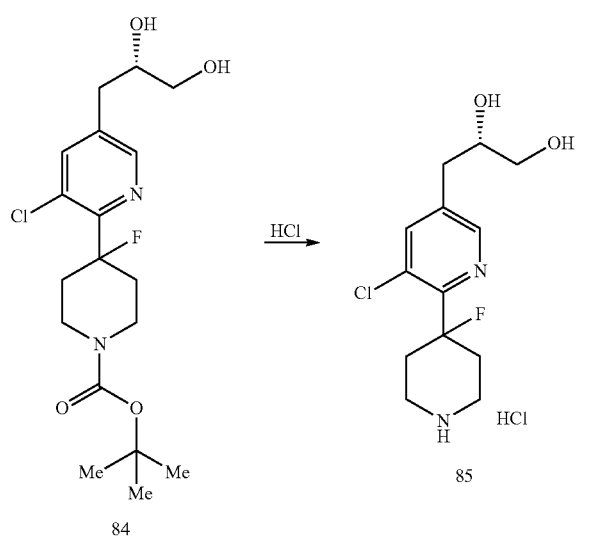 [SMILES: CC(C)(C)OC(=O)N1CCC(F)(c2ncc(C[C@H](O)CO)cc2Cl)CC1 ; Cl ; OC[C@@H](O)Cc1cnc(C2(F)CCNCC2)c(Cl)c1 ; Cl]

The compound 85 was obtained in the same manner as Example 1, Step 4. Yield 95%

¹H-NMR (DMSO-d₆) δ: 8.40 (1H, d, J=1.7 Hz), 7.85 (1H, d, J=1.7 Hz), 4.30-4.02 (2H, m), 3.67-3.61 (1H, m), 3.38-3.06 (6H, m), 2.88-2.83 (1H, m), 2.61-2.42 (3H, m).

Step 3. Preparation of (S)-4-(3-Chloro-5-(2,3-dihydroxypropyl)pyridin-2-yl)-4-fluoro-N-(3-methyl-4-(trifluoromethyl)phenyl) piperidine-1-carboxamide (ACS)

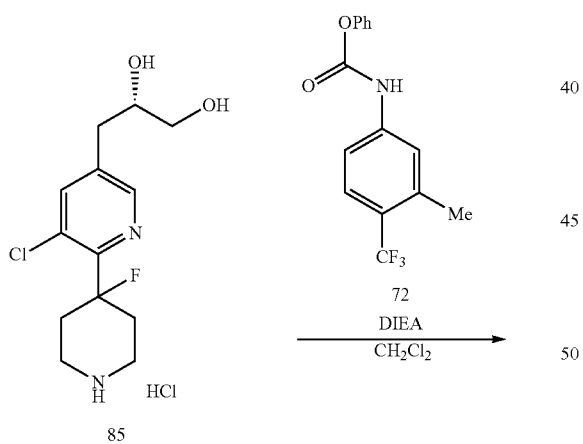

m), 3.74 (1H, ddd, J=10.9, 5.5, 3.3 Hz), 3.55-3.45 (3H, m), 2.80-2.74 (2H, m), 2.45-2.21 (8H, m), 1.83 (1H, t, J=5.5 Hz), 1.55 (3H, s).

Example 57

Preparation of (S)-4-(3-Chloro-5-(2,3-dihydroxypropyl)pyridin-2-yl)-4-fluoro-N-(3-methyl-4-(trifluoromethoxy)phenyl)piperidine-1-carboxamide (ACT)

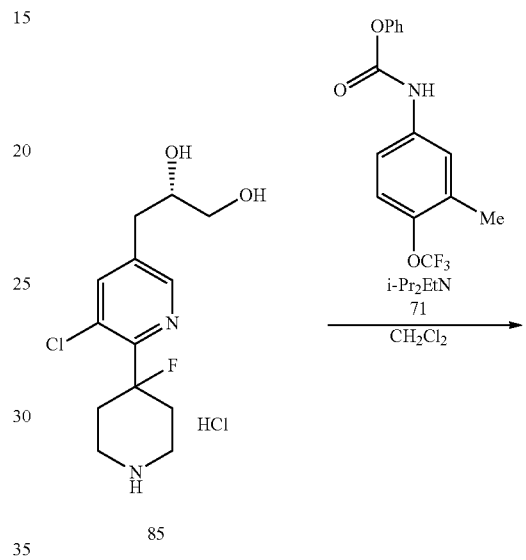

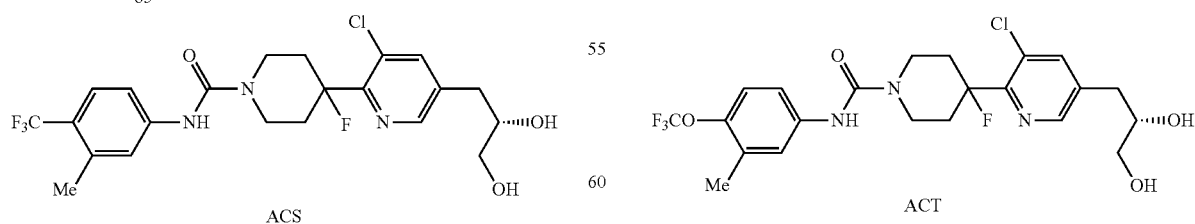

The compound ACS was obtained in the same manner as Example 1. Yield 71%. ¹H-NMR (CDCl₃) δ: 8.31 (1H, d, J=2.0 Hz), 7.67 (1H, d, J=2.0 Hz), 7.51 (1H, d, J=8.7 Hz), 7.35 (1H, s), 7.28-7.24 (1H, m), 6.49 (1H, s), 4.03-3.96 (3H, The compound ACT was obtained in the same manner as Example 1. Yield 83%. ¹H-NMR (CDCl₃) δ: 8.31 (1H, d, J=1.8 Hz), 7.66 (1H, d, J=1.8 Hz), 7.31 (1H, d, J=1.8 Hz), 7.15-7.11 (2H, m), 6.39 (1H, s), 4.04-3.90 (3H, m), 3.73 (1H, ddd, J=10.9, 5.3, 3.4 Hz), 3.57-3.40 (3H, m), 2.81-2.74 (2H, m), 2.38-2.31 (8H, m), 1.88 (1H, t, J=5.3 Hz).

Example 58

Preparation of (R)-4-(5-(2,3-dihydroxypropyl)-3-methylpyridin-2-yl)-4-fluoro-N-(3-methyl-4-(trifluoromethoxy)phenyl)piperidine-1-carboxamide (ACF)

Step 1 Preparation of tert-butyl 4-(5-bromo-3-methylpyridin-2-yl)-4-hydroxypiperidine-1-carboxylate

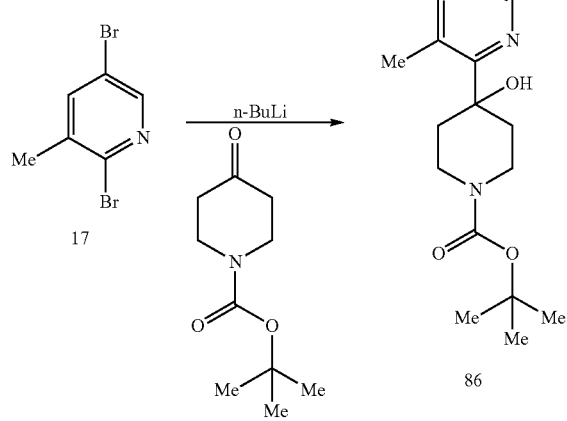

To a solution of 2,5-dibromo-3-methylpyridine 17 (15.06 g, 60 mmol) in Toluene (450 ml) was added n-BuLi (24.18 ml, 66.0 mmol) at –60° C. under N₂. The mixture was stirred at –60° C. for 15 min. A tert-butyl 4-oxopiperidine-1-carboxylate (13.15 g, 66.0 mmol) in toluene was added. The resulting mixture was stirred at –60° C. for 1 hr. The mixture was allowed to warm up to 0° C. for 0.5 hr. The reaction mixture was diluted with 10% citric acid, then extracted with EtOAc (×2). The organic layers were combined and washed with H₂O and brine. The organic layer was dried over MgSO₄, filtered and evaporated. The crude product was chromatographed on silica gel eluting with a gradient of ethyl acetate/hexanes to afford 11.0 g of the compound 86 as a colorless foam (49%). ¹H-NMR (CDCl₃) δ: 8.42 (1H, d, J=2.3 Hz), 7.64 (1H, d, J=2.1 Hz), 5.85 (1H, s), 4.08 (2H, br s), 3.36-3.25 (2H, br m), 2.49 (3H, s), 2.25 (2H, td, J=12.9, 5.0 Hz), 1.46-1.42 (2H, m), 1.46 (9H, s).

Step 2 Preparation of tert-butyl 4-(5-bromo-3-methylpyridin-2-yl)-4-fluoropiperidine-1-carboxylate

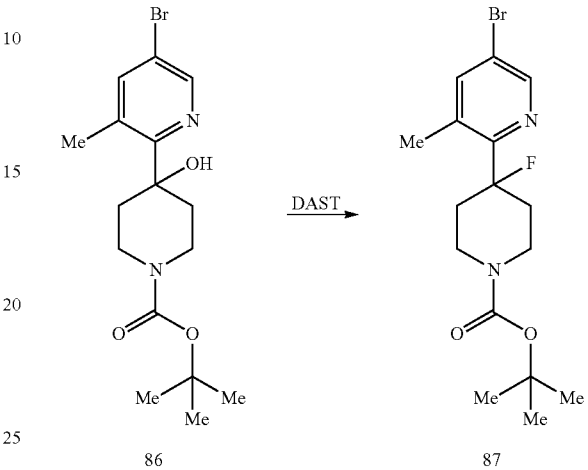

To a solution of tert-butyl 4-(5-bromo-3-methylpyridin-2-yl)-4-hydroxypiperidine-1-carboxylate 86 (11 g, 29.6 mmol) in Toluene (120 ml) was added DAST (5.09 ml, 38.5 mmol) at –60° C. under N₂. The mixture was stirred at –60° C. for 30 min then allowed to warm up to 0° C., further stirred for 2 hr. The reaction mixture was diluted with 10% citric acid, then extracted with EtOAc (×2). The organic layers were combined and washed with H₂O and [brine. The organic layer was dried over MgSO₄, filtered and evaporated. The crude product was chromatographed on silica gel eluting with a gradient of ethyl acetate/hexanes to afford 6.96 g of the compound 87 as a pale yellow solid (63%). ¹H-NMR (CDCl₃) δ: 8.39 (1H, s), 7.62 (1H, d, J=1.8 Hz), 4.07 (2H, br s), 3.20 (2H, t, J=12.1 Hz), 2.49 (3H, d, J=5.3 Hz), 2.36-2.16 (2H, br m), 2.06-1.97 (2H, br m), 1.49 (9H, s).

Step 3. Preparation of tert-butyl 4-(5-allyl-3-methylpyridin-2-yl)-4-fluoropiperidine-1-carboxylate

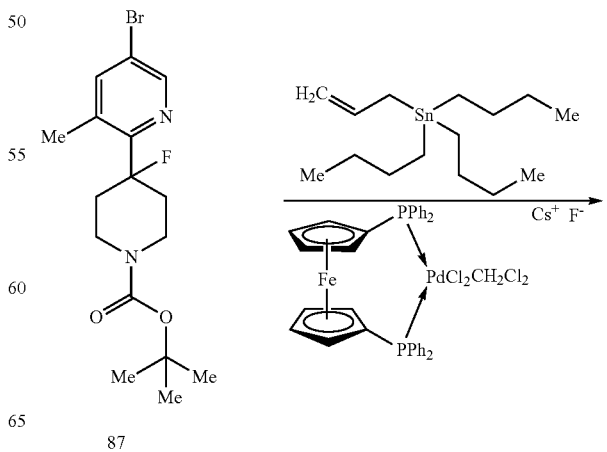

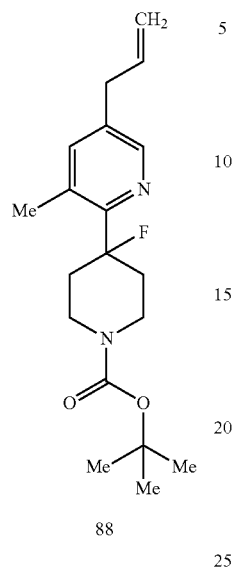

88

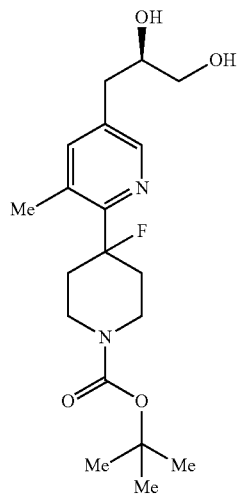

89

The compound 88 was obtained in the same manner as Example 54, Step 1.

¹H-NMR (CDCl₃) δ: 8.18 (1H, s), 7.28 (1H, s), 5.99-5.86 (1H, m), 5.13-5.06 (2H, m), 4.12-4.10 (2H, m), 3.34 (2H, d, J=6.9 Hz), 3.21 (2H, t, J=12.3 Hz), 2.47 (3H, d, J=5.7 Hz), 2.34-2.24 (2H, m), 2.05-2.02 (2H, m), 1.48 (9H, s).

The compound 89 was obtained in the same manner as Example 54, Step 2.

Step 5. Preparation of (R)-3-(6-(4-fluoropiperidin-4-yl)-5-methylpyridin-3-yl)propane-1,2-diol Step 4. Preparation of (R)-tert-butyl 4-(5-(2,3-dihydroxypropyl)-3-methylpyridin-2-yl)-4-fluoropiperidine-1-carboxylate

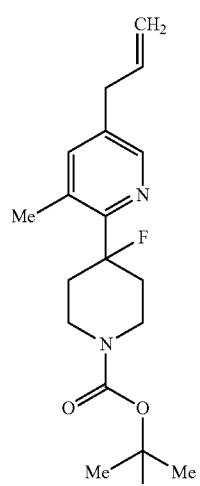

88

AD—MIX—BETA →

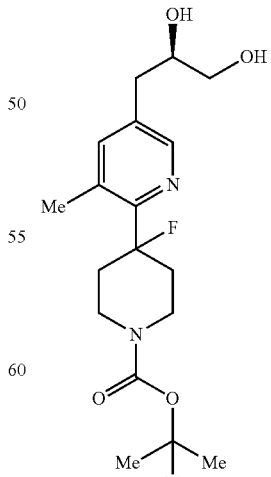

89

HCl →

385
-continued

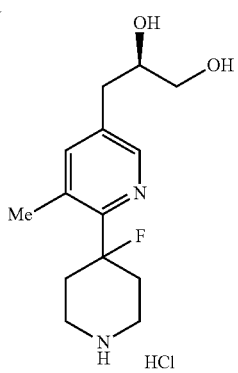

90

The compound 90 was obtained in the same manner as Example 54, Step 3.

Step 6. Preparation of (R)-4-(5-(2,3-dihydroxypropyl)-3-methylpyridin-2-yl)-4-fluoro-N-(3-methyl-4-(trifluoromethoxy)phenyl)piperidine-1-carboxamide (ACF)

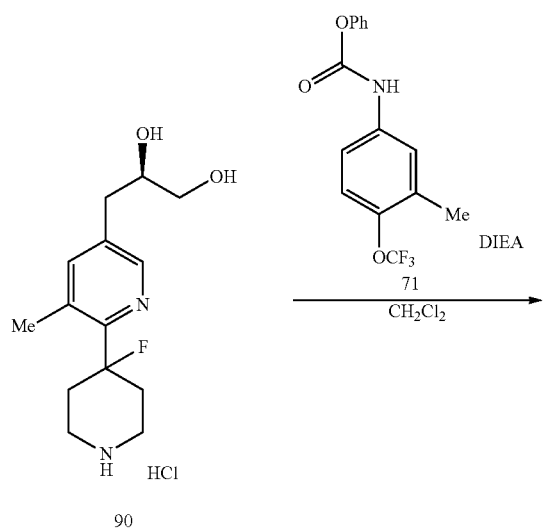

The compound ACF was obtained in the same manner as Example 1.

$^1$H-NMR (CDCl$_3$): 1.97 (1H, brs), 2.13 (2H, m), 2.29 (3H, s), 2.34-2.45 (3H, m), 2.50 (3H, s), 2.72-2.75 (2H, m), 3.41 (2H, m), 3.53 (1H, m), 3.72 (1H, m), 3.94 (1H, brs), 4.02 (2H, m), 6.43 (1H, s), 7.10-7.18 (2H, m), 7.37 (1H, s), 7.52 (1H, s), 8.44 (1H, s).

MS: 486 [M+H]$^+$

386

Example 59

Preparation of (R)-4-(5-(2,3-dihydroxypropyl)-3-methylpyridin-2-yl)-4-fluoro-N-(3-methyl-4-(trifluoromethyl)phenyl)piperidine-1-carboxamide (ACE)

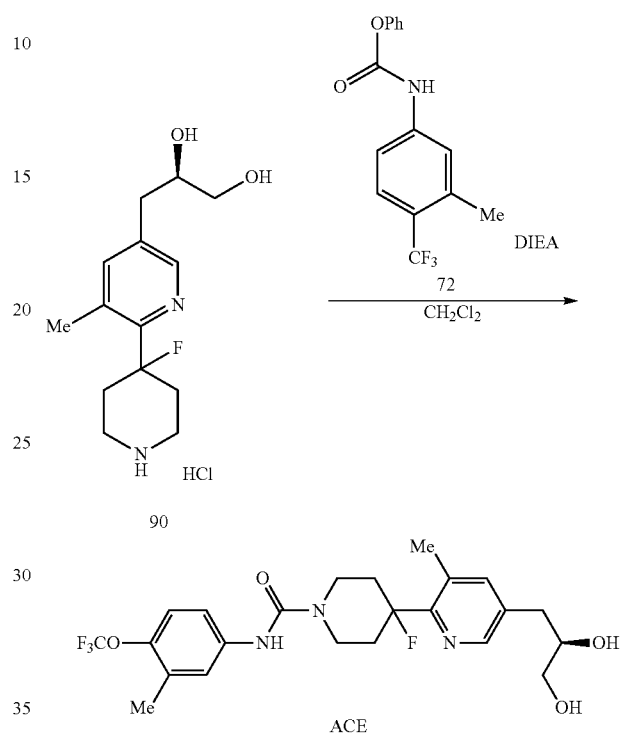

The compound ACE was obtained in the same manner as Example 1.

$^1$H-NMR (DMSO-d$_6$): 2.07-2.38 (4H, m), 2.38 (3H, s), 2.45 (3H, d, J=5.5 Hz), 2.76 (1H, m), 3.62 (1H, m), 4.12 (2H, m), 4.77 (1H, brs), 7.33-7.40 (4H, m), 8.20 (1H, s), 8.93 (1H, s).

MS: 470 [M+H]$^+$

Example 60

Preparation of (S)-4-(5-(2,3-dihydroxypropyl)-3-methylpyridin-2-yl)-4-fluoro-N-(3-methyl-4-(trifluoromethoxy)phenyl)piperidine-1-carboxamide (ACM)

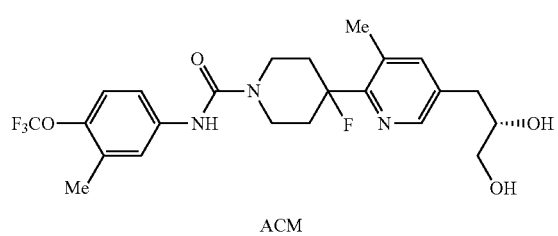 [SMILES: Cc1cc(NC(=O)N2CCC(F)(c3ncc(C[C@H](O)CO)cc3C)CC2)ccc1OC(F)(F)F]

The compound ACM was obtained in the same manner as Example 1.

¹H-NMR (DMSO-d₆): 2.06 (2H, m), 2.23 (5H, m), 2.45 (3H, d, J=5.6 Hz), 2.75 (1H, m), 3.62 (1H, brs), 4.10 (2H, d, J=13.2 Hz), 4.66 (2H, brs), 7.17 (1H, m), 7.39 (1H, m), 7.48 (1H, s), 8.20 (1H, s), 8.83 (1H, s).

MS: 486 [M+H]⁺

Example 61

Preparation of (S)-4-(5-(2,3-dihydroxypropyl)-3-methylpyridin-2-yl)-4-fluoro-N-(3-methyl-4-(trifluoromethyl)phenyl)piperidine-1-carboxamide (ACN)

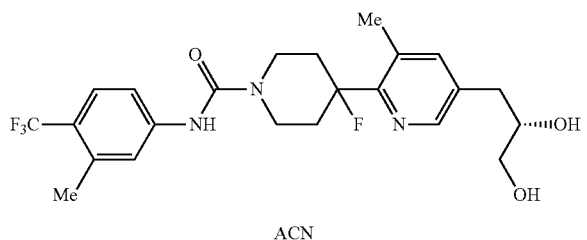 [SMILES: Cc1cc(NC(=O)N2CCC(F)(c3ncc(C[C@H](O)CO)cc3C)CC2)ccc1C(F)(F)F ; "ACN"]

ACN

The compound ACN was obtained in the same manner as Example 1.

¹H-NMR (DMSO-d₆): 2.07-2.38 (4H, m), 2.38 (3H, s), 2.45 (3H, d, J=5.5 Hz), 2.76 (1H, m), 3.62 (1H, m), 4.13 (2H, m), 4.66 (1H, m), 7.47-7.67 (4H, m), 8.20 (1H, s), 8.93 (1H, s).

MS: 470 [M+H]⁺

Example 62

Preparation of 4-(3-Methyl-5-((1S,2S)-1,2,3-trihydroxypropyl)pyridin-2-yl)-N-(5-(trifluoromethyl)pyridin-2-yl)-5,6-dihydropyridine-1(2H)-carboxamide (ABV)

Step 1 Preparation of (S)-(6-Bromo-5-methylpyridin-3-yl)(2,2-dimethyl-1,3-dioxolan-4-yl)methanone

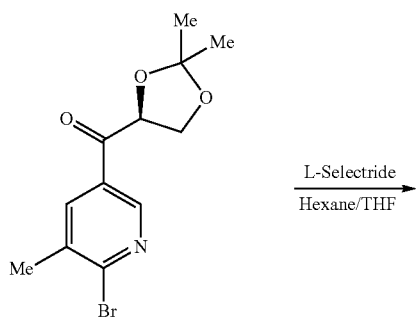

74

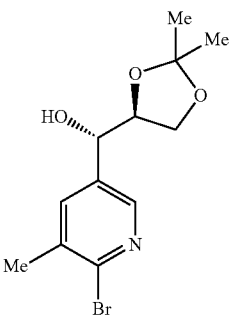

91

To a solution of (S)-(6-bromo-5-methylpyridin-3-yl)(2,2-dimethyl-1,3-dioxolan-4-yl)methanone (74, 2.00 g, 6.66 mmol) in tetrahydrofuran (15 mL) and hexane (45 mL) was added L-Selectride (1.0M in tetrahydrofuran) (13.33 mL, 13.33 mmol) at −78° C. under nitrogen atmosphere. The resulting mixture was stirred for 0.5 hrs. Water and Acetic acid was added to the reaction flask and the mixture was extracted with ethyl acetate (80 mL×2). The resulting organic layer was washed with H₂O, brine, dried over anhydrous sodium sulfate, and concentrated under reduced pressure. The crude product was chromatographed on silica gel eluting with a gradient of ethyl acetate (30-50%)/hexanes to afford 2.08 g of the product 91 as a colorless oil (quant.). ¹H-NMR (CDCl₃) δ: 8.17 (1H, d, J=2.3 Hz), 7.57 (1H, d, J=2.3 Hz), 4.57 (1H, d, J=6.6 Hz), 4.19 (1H, q, J=6.6 Hz), 3.90 (1H, dd, J=8.8, 6.6 Hz), 3.77 (1H, dd, J=8.8, 6.6 Hz), 2.83 (1H, s), 1.49 (3H, s), 1.37 (3H, s).

Step 2 Preparation of tert-Butyl 4-(5-((S)-((S)-2,2-Dimethyl-1,3-dioxolan-4-yl)(hydroxy)methyl)-3-methylpyridin-2-yl)-5,6-dihydropyridine-1(2H)-carboxylate

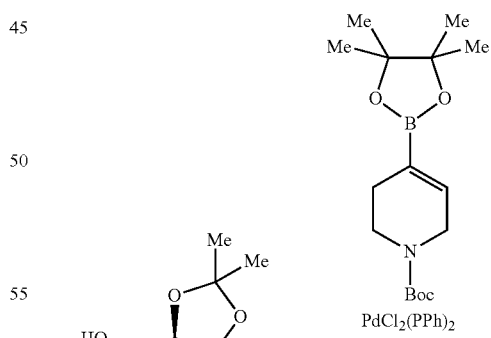

91

-continued

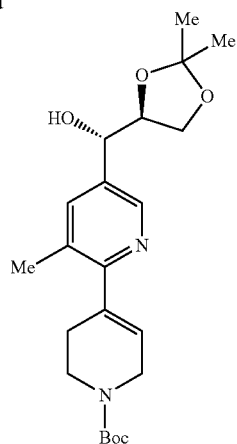

92

The compound 92 was obtained in the same manner as Reference Example 1, Step 3. (quant.).

¹H-NMR (CDCl₃) δ: 8.38 (1H, d, J=2.2 Hz), 7.55 (1H, d, J=2.2 Hz), 5.78 (1H, s), 4.58 (1H, dd, J=6.5, 3.0 Hz), 4.26-4.22 (1H, m), 4.10-4.07 (2H, m), 3.89 (1H, dd, J=8.7, 6.5 Hz), 3.77 (1H, dd, J=8.7, 6.5 Hz), 3.66-3.64 (2H, m), 2.51-2.50 (2H, m), 2.35 (3H, s), 1.51 (3H, s), 1.50 (9H, s), 1.39 (3H, s).

Step 3 Preparation of (1S,2S)-1-(5-Methyl-6-(1,2,3,6-tetrahydropyridin-4-yl)pyridin-3-yl)propane-1,2,3-triol hydrochloride

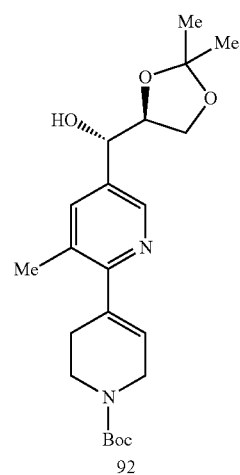
92

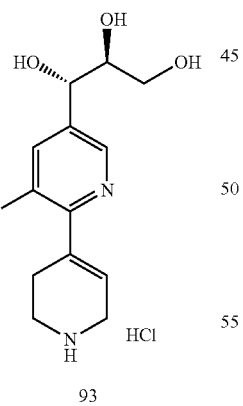
93

The compound 93 was obtained in the same manner as Reference Example 1, Step 4. Yield 74%.

¹H-NMR (DMSO-d₆) δ: 9.49 (2H, br), 8.50 (1H, s), 8.21 (1H, s), 6.13 (1H, s), 4.83 (1H, d, J=3.0 Hz), 3.81-3.77 (2H, m), 3.58-3.53 (2H, m), 3.31-3.28 (3H, m), 2.73-2.70 (2H, m), 2.45 (3H, s).

Step 4 Preparation of 4-(3-Methyl-5-((1S,2S)-1,2,3-trihydroxypropyl)pyridin-2-yl)-N-(5-(trifluoromethyl)pyridin-2-0)-5,6-dihydropyridine-1(2H)-carboxamide

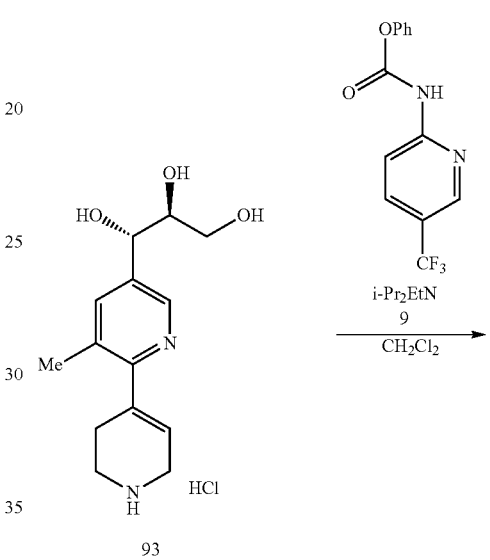

93

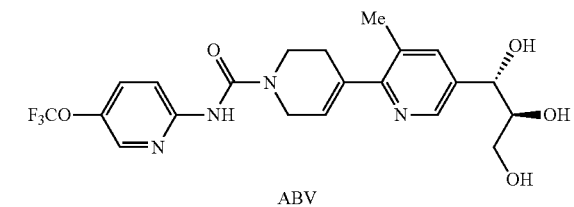

ABV

The compound ABV was obtained in the same manner as Example 1. Yield 45%. ¹H-NMR (DMSO-d₆) δ: 9.77 (1H, s), 8.61 (1H, s), 8.30 (1H, s), 8.05-7.99 (2H, m), 7.54 (1H, d, J=1.5 Hz), 5.86-5.83 (1H, m), 5.17 (1H, d, J=5.2 Hz), 4.64-

4.58 (2H, m), 4.50 (1H, t, J=5.2 Hz), 4.19 (2H, d, J=2.3 Hz), 3.71 (2H, t, J=5.2 Hz), 3.56-3.17 (3H, m), 2.33 (3H, s).

Example 63

Preparation of N-(3-Chloro-4-(trifluoromethyl)phenyl)-4-(3-methyl-5-((1S,2S)-1,2,3-trihydroxypropyl)pyridin-2-yl)-5,6-dihydropyridine-1(2H)-carboxamide (ABW)

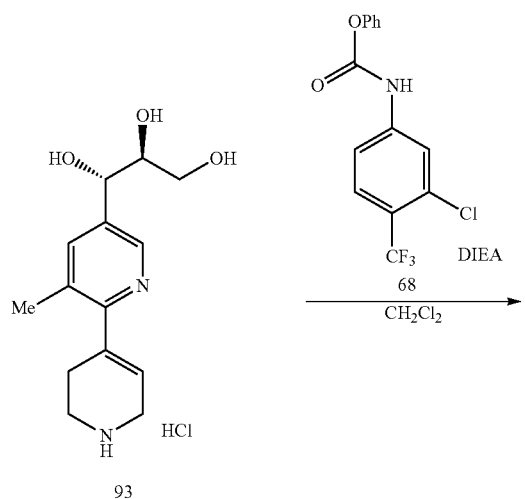

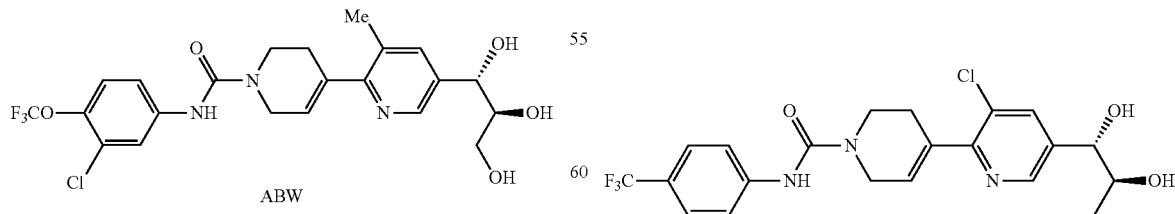

The compound ABW was obtained in the same manner as Example 1. Yield 26%. ¹H-NMR (DMSO-d$_6$) δ: 9.11 (1H, s), 8.30 (1H, s), 7.92 (1H, s), 7.71 (1H, d, J=8.8 Hz), 7.64 (1H, d, J=8.8 Hz), 7.55 (1H, s), 5.89-5.85 (1H, m), 5.20 (1H, d, J=5.3 Hz), 4.63-4.57 (3H, m), 4.17 (2H, d, J=2.3 Hz), 3.70 (2H, t, J=5.3 Hz), 3.59-3.13 (3H, m), 2.34 (3H, s).

Example 64

Preparation of N-(3-Methoxy-4-(trifluoromethyl)phenyl)-4-(3-methyl-5-((1S,2S)-1,2,3-trihydroxypropyl)pyridin-2-yl)-5,6-dihydropyridine-1(2H)-carboxamide (ABX)

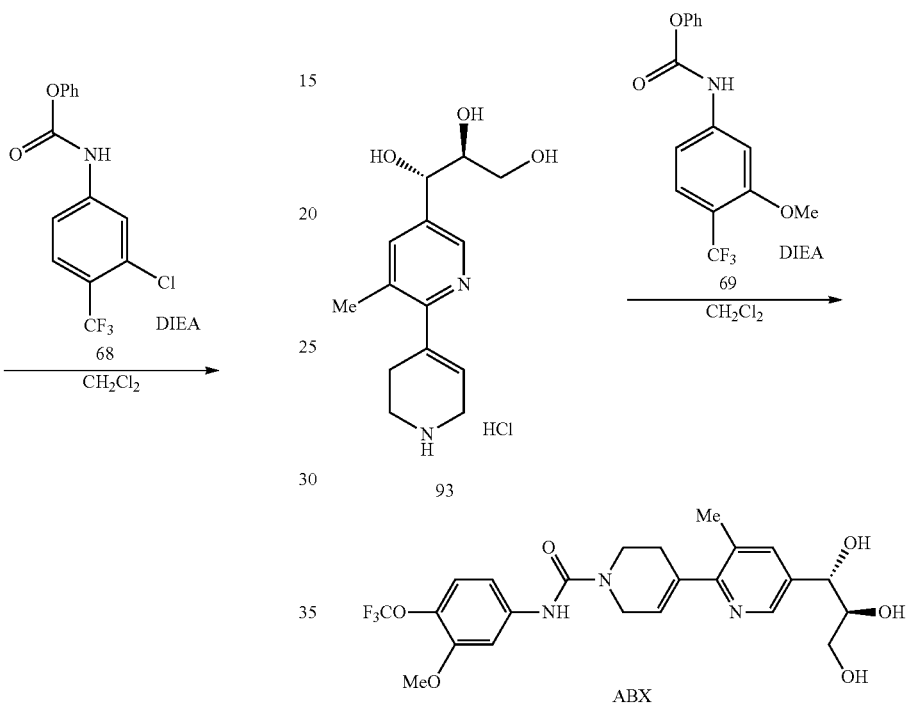

The compound ABX was obtained in the same manner as Example 1. Yield 78%. ¹H-NMR (DMSO-d$_6$) δ: 8.90 (1H, s), 8.31 (1H, d, J=1.7 Hz), 7.53-7.45 (3H, m), 7.26 (1H, d, J=8.7 Hz), 5.89-5.86 (1H, m), 5.17 (1H, d, J=5.3 Hz), 4.65-4.59 (2H, m), 4.50 (1H, t, J=5.3 Hz), 4.17 (2H, d, J=2.6 Hz), 3.83 (3H, s), 3.70 (2H, t, J=5.3 Hz), 3.56-3.17 (3H, m), 2.34 (3H, s).

Example 65

N-(3-chloro-4-(trifluoromethyl)phenyl)-4-(3-chloro-5-((1S,2S)-1,2,3-trihydroxypropyl)pyridin-2-yl)-5,6-dihydropyridine-1(2H)-carboxamide (ABR)

The compound ABR was obtained in the same manner as Example 62. ¹H-NMR (DMSO-d$_6$): 2.58 (2H, brs), 3.25 (1H, m), 3.47 (2H, m), 3.71 (2H, t, J=5.5 Hz), 4.20 (1H, d, J=2.6 Hz), 4.59 (1H, m), 4.71 (1H, m), 4.76 (1H, d, J=5.8 Hz), 5.41 (1H, d, J=5.6 Hz), 6.21 (1H, s), 7.64 (1H, d, J=8.8 Hz), 7.73 (1H, d, J=8.8 Hz), 7.83 (1H, d, J=6.0 Hz), 7.94 (1H, d, J=1.5 Hz), 8.45 (1H, d, J=1.5 Hz), 9.15 (1H, s).

MS: 506 [M+H]$^+$

Example 66

4-(3-chloro-5-((1S,2S)-1,2,3-trihydroxypropyl)pyridin-2-yl)-N-(5-(trifluoromethyl)pyridin-2-yl)-5,6-dihydropyridine-1(2H)-carboxamide (ABS)

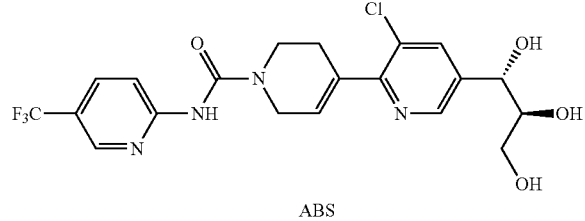 [SMILES: O=C(Nc1ccc(C(F)(F)F)cn1)N1CC=C(c2ncc([C@H](O)[C@@H](O)CO)cc2Cl)CC1 ; "ABS"]

ABS

The compound ABS was obtained in the same manner as Example 62. $^1$H-NMR (DMSO-d$_6$): 2.57 (2H, brs), 3.26 (1H, m), 3.47 (2H, m), 3.71 (2H, t, J=5.4 Hz), 4.22 (1H, d, J=2.0 Hz), 4.59 (1H, m), 4.70 (1H, m), 4.76 (1H, d, J=5.8 Hz), 5.40 (1H, d, J=5.3 Hz), 6.19 (1H, s), 7.84 (1H, s), 7.99 (1H, d, J=8.9 Hz), 8.07 (1H, d, J=8.9 Hz), 8.45 (1H, s), 8.67 (1H, s), 9.84 (1H, s).

MS: 473 [M+H]$^+$

Example 67

4-(3-chloro-5-((1S,2S)-1,2,3-trihydroxypropyl)pyridin-2-yl)-N-(3-methyl-4-(trifluoromethyl)phenyl)-5,6-dihydropyridine-1(2H)-carboxamide (ADF)

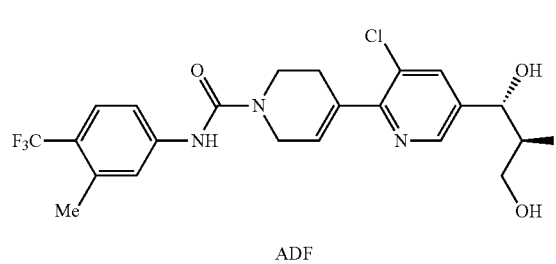

ADF

The compound ADF was obtained in the same manner as Example 62. $^1$H-NMR (DMSO-d$_6$): 2.39 (3H, s), 2.57 (2H, brs), 3.26 (1H, m), 3.47-3.55 (2H, m), 3.69 (2H, m), 4.20 (1H, brs), 4.57 (1H, m), 4.72 (2H, m), 5.37 (1H, m), 6.20 (1H, brs), 7.53-7.56 (3H, m), 7.82 (1H, s), 8.45 (1H, s), 8.88 (1H, s).

MS: 486 [M+H]$^+$

Example 68

4-(3-chloro-5-((1S,2S)-1,2,3-trihydroxypropyl)pyridin-2-yl)-N-(3-methyl-4-(trifluoromethoxy)phenyl)-5,6-dihydropyridine-1(2H)-carboxamide (ADG)

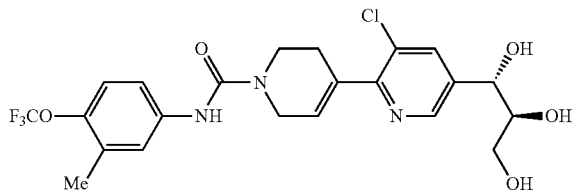

ADG

The compound ADG was obtained in the same manner as Example 62. $^1$H-NMR (DMSO-d$_6$): 2.23 (3H, s), 2.56 (2H, brs), 3.26 (1H, m), 3.47-3.54 (2H, m), 3.67 (2H, m), 4.17 (1H, s), 4.55 (1H, m), 4.69-4.74 (2H, m), 5.37 (1H, d, J=5.6 Hz), 6.20 (1H, brs), 7.18 (1H, d, J=7.9 Hz), 7.42 (1H, dd, J=2.6, 8.9 Hz), 7.50 (1H, d, J=2.6 Hz), 7.83 (1H, s), 8.45 (1H, s), 8.68 (1H, s).

MS: 502 [M+H]$^+$

Reference Example 7

Preparation of (E)-tert-butyl 4-(3-chloro-5-(3-hydroxyprop-1-enyl)pyridin-2-yl)-4-fluoropiperidine-1-carboxylate

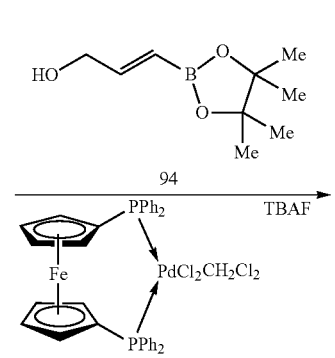

-continued

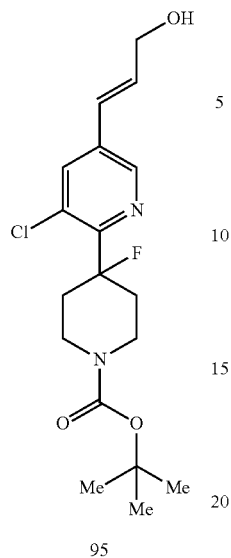

95

To a solution of tert-butyl 4-(3,5-dichloropyridin-2-yl)-4-fluoropiperidine-1-carboxylate 80 (2.095 g, 6 mmol) in THF (10 ml) was added (E)-3-(4,4,5,5-tetramethyl-1,3,2-dioxaborolan-2-yl)prop-2-en-1-ol 94 (1.215 g, 6.60 mmol) and TBAF (14.40 ml, 14.40 mmol) at room temperature under $N_2$. Then $PdCl_2(dppf) CH_2Cl_2$ (0.147 g, 0.180 mmol) was added. The resulting mixture was stirred at room temperature for 10 min, and then heated at reflux for 1 hr. The reaction mixture was diluted with 10% citric acid, and then extracted with EtOAc (×2). The organic layers were combined and washed with $H_2O$ and brine. The organic layer was dried over $MgSO_4$, filtered and evaporated. The crude product was chromatographed on silica gel eluting with a gradient of ethyl acetate/hexanes to afford 1.42 g of the compound 95 as yellow oil (63%). $^1$H-NMR(CDCl$_3$) δ: 8.41 (1H, d, J=2.0 Hz), 7.72 (1H, d, J=2.0 Hz), 6.60 (1H, d, J=16.0 Hz), 6.46 (1H, dt, J=16.0, 4.8 Hz), 4.38 (2H, d, J=4.0 Hz), 4.08 (2H, br s), 3.26 (2H, br s), 2.31-2.28 (4H, br m), 1.48 (9H, s).

Reference Example 8

Preparation of (E)-tert-butyl 4-fluoro-4-(5-(3-hydroxyprop-1-enyl)-3-methylpyridin-2-yl)piperidine-1-carboxylate

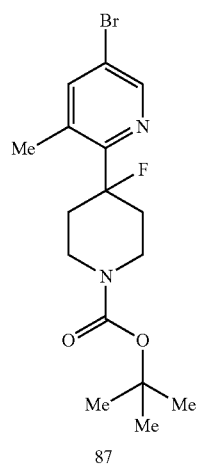

87

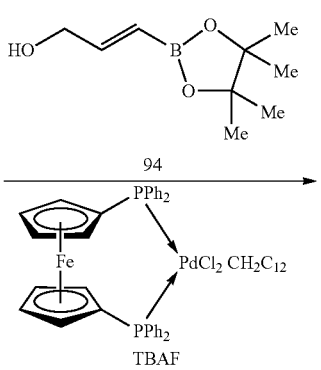

94

-continued

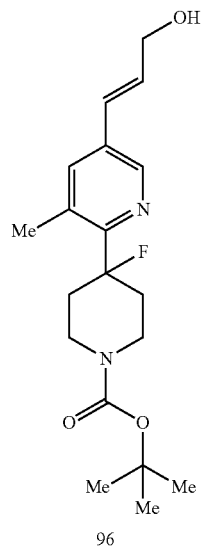

96

The compound 96 was obtained in the same manner as Reference Example 7. Yield 75%.

$^1$H-NMR (CDCl$_3$) δ: 8.34 (1H, s), 7.47 (1H, d, J=1.6 Hz), 6.59 (1H, d, J=15.9 Hz), 6.42 (1H, td, J=10.6, 5.3 Hz), 4.35 (2H, d, J=4.9 Hz), 4.09 (2H, br s), 3.27-3.15 (2H, br m), 2.49 (3H, d, J=5.8 Hz), 2.10-1.93 (4H, br m), 1.48 (9H, s).

Reference Example 9

Preparation of tert-butyl 4-(3-chloro-5-((1S,2S)-1,2,3-trihydroxypropyl)pyridin-2-yl)-4-fluoropiperidine-1-carboxylate

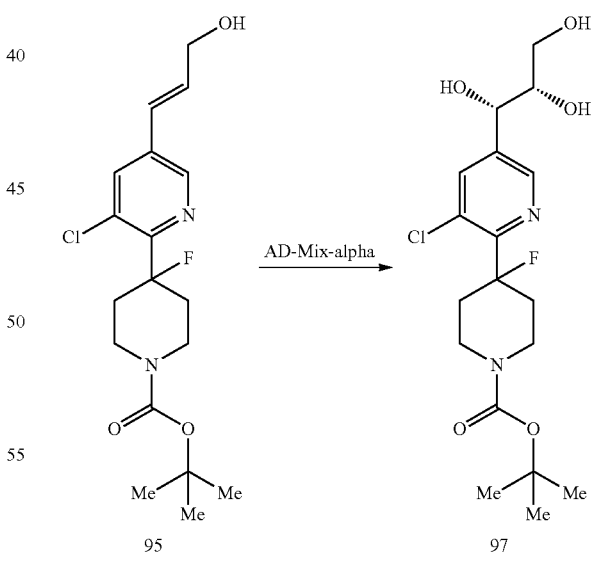

To a solution of (E)-tert-butyl 4-(3-chloro-5-(3-hydroxyprop-1-enyl)pyridin-2-yl)-4-fluoropiperidine-1-carboxylate 95 (1.40 g, 3.78 mmol) in t-BuOH (30 ml) and $H_2O$ (30 ml) was added AD-MIX-ALPHA (7 g, 3.78 mmol) at room temperature. The mixture was stirred at room temperature overnight. The reaction mixture was diluted with $H_2O$, then extracted with EtOAc (×2). The organic layers were combined and washed with H₂O and brine. The organic layer was dried over Na₂SO₄, and then filtered and evaporated. The organic layer was dried over MgSO₄, filtered and evaporated. The crude product was chromatographed on silica gel eluting with a gradient of ethyl acetate/hexanes to afford 0.82 g of the compound 97 as colorless foam (54%). ¹H-NMR (CDCl₃) δ: 8.44 (1H, d, J=1.7 Hz), 7.82 (1H, d, J=2.0 Hz), 4.85 (1H, d, J=5.0 Hz), 4.05 (2H, d, J=12.4 Hz), 3.81-3.75 (2H, m), 3.66 (1H, dd, J=12.3, 5.6 Hz), 3.25 (2H, s), 2.26 (4H, d, J=14.8 Hz), 1.48 (9H, s).

Reference Example 10

Preparation of tert-butyl 4-fluoro-4-(3-methyl-5-((1S,2S)-1,2,3-trihydroxypropyl)pyridin-2-yl)-piperidine-1-carboxylate

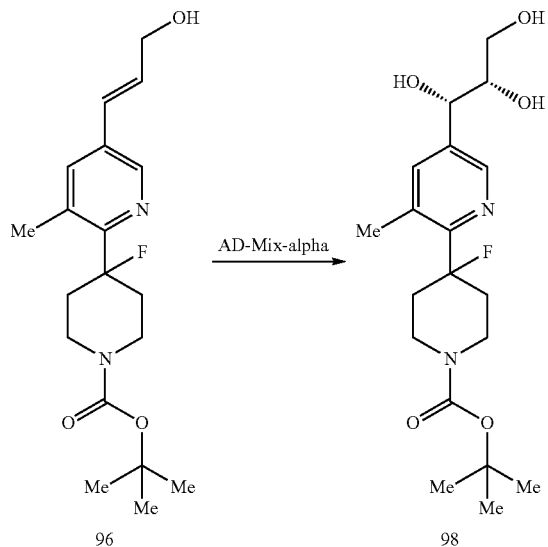 [SMILES: Cc1cc(/C=C/CO)cnc1C1(F)CCN(C(=O)OC(C)(C)C)CC1 ; Cc1cc([C@H](O)[C@@H](O)CO)cnc1C1(F)CCN(C(=O)OC(C)(C)C)CC1]

The compound 98 was obtained in the same manner as Reference Example 9. Yield 41%.

¹H-NMR (CDCl₃) δ: 8.34 (1H, s), 7.53 (1H, d, J=2.0 Hz), 4.78 (1H, d, J=5.9 Hz), 4.15-4.05 (2H, br m), 3.81-3.70 (2H, m), 3.61 (1H, dd, J=11.3, 4.9 Hz), 3.27-3.15 (2H, br m), 2.52 (3H, d, J=5.8 Hz), 2.10-1.96 (4H, br m), 1.49 (9H, s).

Reference Example 11

Preparation of (1S,2S)-1-(5-chloro-6-(4-fluoropiperidin-4-yl)pyridin-3-yl)propane-1,2,3-triol hydrochloride

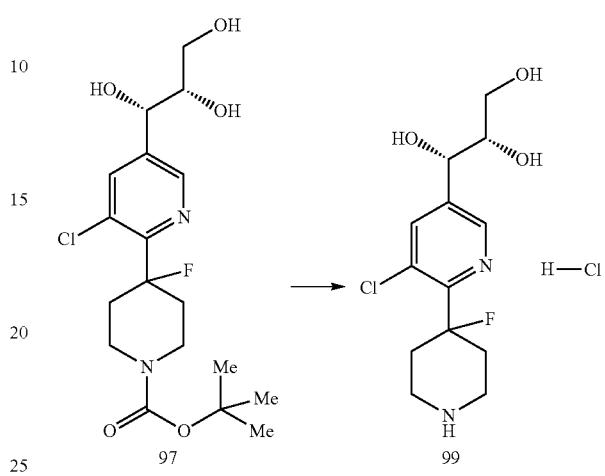

To a solution of tert-butyl 4-(3-chloro-5-((1S,2S)-1,2,3-trihydroxypropyl)pyridin-2-yl)-4-fluoropiperidine-1-carboxylate 97 (0.90 g, 2.223 mmol) in CH₂Cl₂ (20 ml) was added HCl in dioxane (2.223 ml, 8.89 mmol) at room temperature. The mixture was stirred at room temperature for 4 hr. The solvent was concentrated then EtOAc was added to the mixture. The residue was triturated with EtOAc. The resulting solid was filtered through a Buchner Funnel, rinsed with EtOAc, and collected to afford 718 mg of the compound 99 as a white solid (86%).

¹H-NMR (DMSO-d₆) δ: 9.05 (2H, br s), 8.47 (1H, d, J=1.7 Hz), 7.89 (1H, d, J=1.7 Hz), 4.74 (1H, d, J=2.9 Hz), 3.58-3.45 (2H, m), 3.37 (2H, br d), 3.28-3.10 (3H, m), 2.44-2.41 (4H, br m).

Reference Example 12

(1S,2S)-1-(6-(4-fluoropiperidin-4-yl)-5-methylpyridin-3-yl)propane-1,2,3-triol dihydrochloride

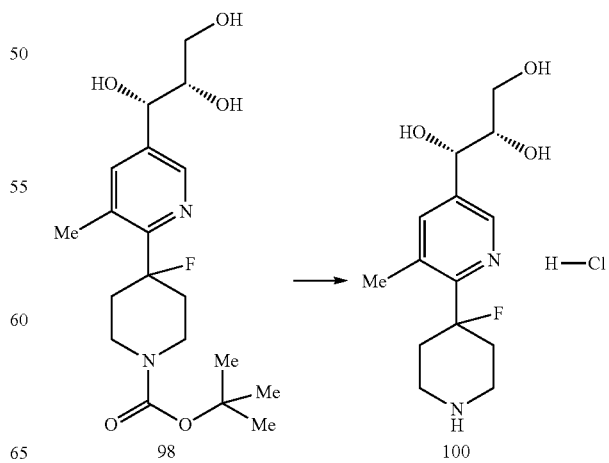

The compound 100 was obtained in the same manner as Reference Example 11. Yield 75%.

$^1$H-NMR (DMSO-d$_6$) δ: 9.26 (2H, br s), 8.34 (1H, s), 7.66 (1H, s), 4.67 (1H, d, J=3.4 Hz), 3.57-3.41 (2H, m), 3.36-3.28 (2H, br m), 3.25-3.07 (3H, m), 2.46 (3H, d, J=4.7 Hz), 2.29-2.20 (2H, br m).

Example 69

Preparation of 4-(3-Chloro-5-((1S,2S)-1,2,3-trihydroxypropyl)pyridin-2-yl)-4-fluoro-N-(6-fluorobenzo[d]thiazol-2-yl)piperidine-1-carboxamide (ABD)

Example 70

Preparation of 4-(3-Chloro-5-((1S,2S)-1,2,3-trihydroxypropyl)pyridin-2-yl)-4-fluoro-N-(5-(trifluoromethyl)pyridin-2-yl)piperidine-1-carboxamide (ABE)

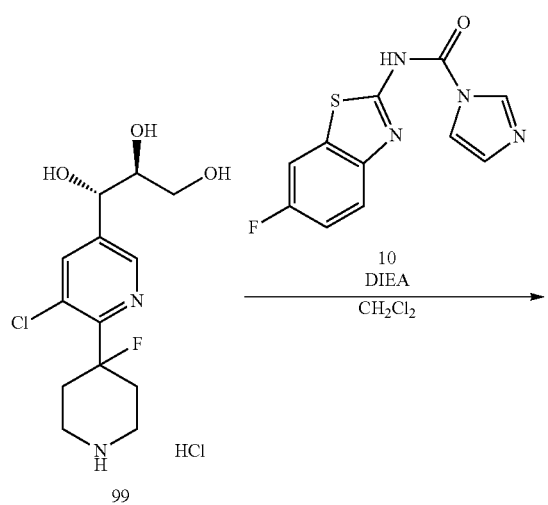

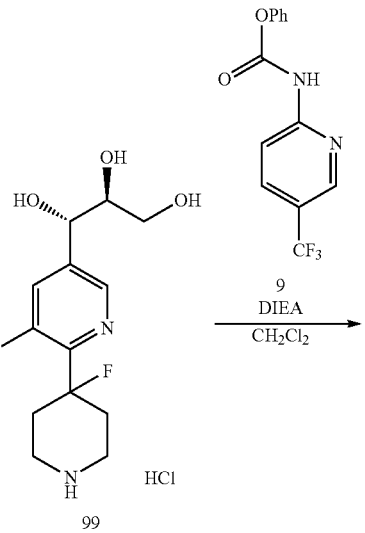

The compound ABD was obtained in the same manner as Example 10. Yield 58%. $^1$H-NMR (DMSO-d$_6$) δ: 8.46 (1H, s), 7.88 (1H, s), 7.79-7.61 (2H, m), 7.23-7.19 (1H, m), 5.41 (1H, d, J=5.5 Hz), 4.74-4.72 (2H, m), 4.56-4.55 (1H, m), 4.23-4.20 (2H, m), 3.52-3.31 (5H, m), 2.30-2.26 (4H, m).

The compound ABE was obtained in the same manner as Example 1. Yield 74%. $^1$H-NMR (DMSO-d$_6$) δ: 9.87 (1H, s), 8.60 (1H, s), 8.45 (1H, d, J=1.5 Hz), 8.04 (1H, dd, J=8.9, 2.5 Hz), 7.96 (1H, d, J=8.9 Hz), 7.87 (1H, d, J=1.5 Hz), 5.41 (1H, d, J=5.6 Hz), 4.74-4.72 (2H, m), 4.56 (1H, t, J=5.6 Hz), 4.16-4.12 (2H, m), 3.51-3.29 (5H, m), 2.27-2.22 (4H, m).

Example 71

Preparation of N-(3-Chloro-4-(trifluoromethyl)phenyl)-4-(3-chloro-5-((1S,2S)-1,2,3-trihydroxypropyl)pyridin-2-yl)-4-fluoropiperidine-1-carboxamide (ABG)

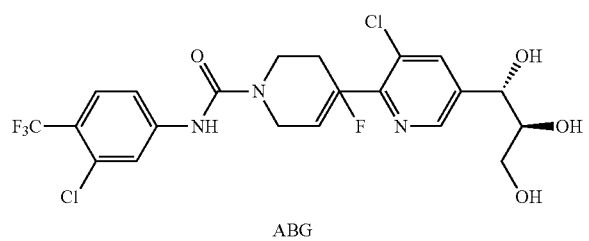

ABG

The compound ABG was obtained in the same manner as Example 1. Yield 68%. $^1$H-NMR (DMSO-d$_6$) δ: 9.18 (1H, s), 8.46 (1H, d, J=1.4 Hz), 7.91-7.88 (2H, m), 7.71 (1H, d, J=8.7 Hz), 7.61 (1H, dd, J=8.7, 1.4 Hz), 5.41 (1H, d, J=5.7 Hz), 4.73-4.68 (2H, m), 4.56 (1H, t, J=5.7 Hz), 4.11-4.05 (2H, m), 3.59-3.16 (5H, m), 2.31-2.15 (4H, m).

Example 72

Preparation of 4-Fluoro-N-(6-fluorobenzo[d]thiazol-2-yl)-4-(3-methyl-5-((1S,2S)-1,2,3-trihydroxypropyl)pyridin-2-yl)piperidine-1-carboxamide (ABF)

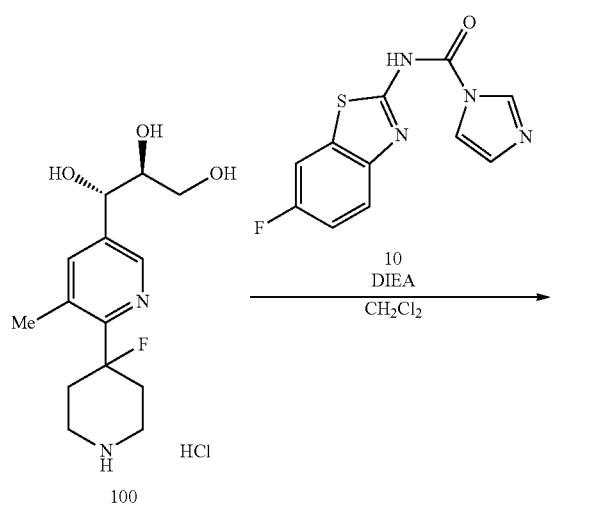

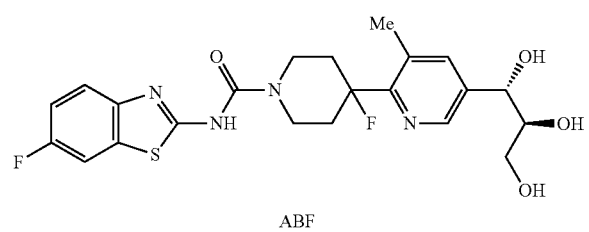

ABF

The compound ABF was obtained in the same manner as Example 10. Yield 63%. $^1$H-NMR (DMSO-d$_6$) δ: 8.29 (1H, s), 7.73-7.61 (3H, m), 7.20 (1H, td, J=9.0, 2.6 Hz), 5.20 (1H, d, J=5.3 Hz), 4.64-4.61 (2H, m), 4.50 (1H, t, J=5.3 Hz), 4.25-4.21 (2H, m), 3.47-3.24 (5H, m), 2.51-2.46 (3H, m), 2.34-2.04 (4H, m).

Example 73

Preparation of N-(3-Chloro-4-(trifluoromethyl)phenyl)-4-fluoro-4-(3-methyl-5-((1S,2S)-1,2,3-trihydroxypropyl)pyridin-2-yl)piperidine-1-carboxamide (ABH)

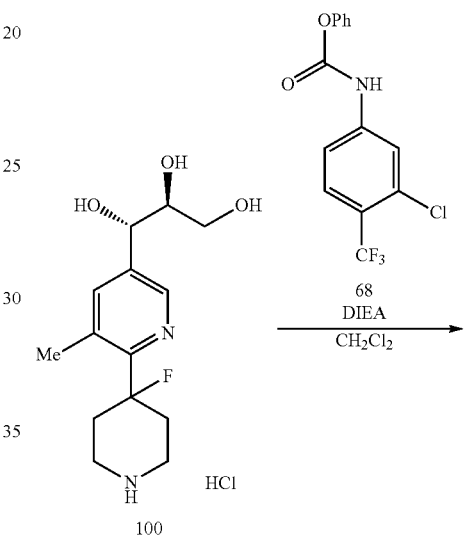

ABH

The compound ABH was obtained in the same manner as Example 1. Yield 44%. $^1$H-NMR (DMSO-d$_6$) δ: 9.17 (1H, s), 8.30 (1H, s), 7.92 (1H, s), 7.71 (1H, d, J=8.7 Hz), 7.62 (1H, d, J=8.7 Hz), 7.56 (1H, s), 5.21 (1H, d, J=5.4 Hz), 4.64-4.62

(2H, m), 4.51 (1H, t, J=5.4 Hz), 4.15-4.11 (2H, m), 3.56-3.16 (5H, m), 2.51-2.46 (3H, m), 2.29-2.11 (4H, m).

Example 74

Preparation of (S)—N-(3-chloro-4-(trifluoromethyl)phenyl)-4-(3-chloro-5-(1,1-difluoro-2,3-dihydroxypropyl)pyridin-2-yl)-5,6-dihydropyridine-1(2H)-carboxamide (ABK)

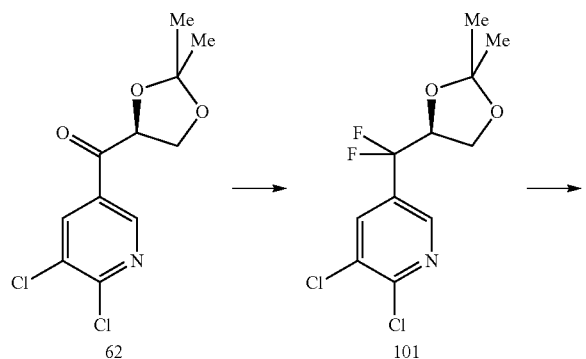

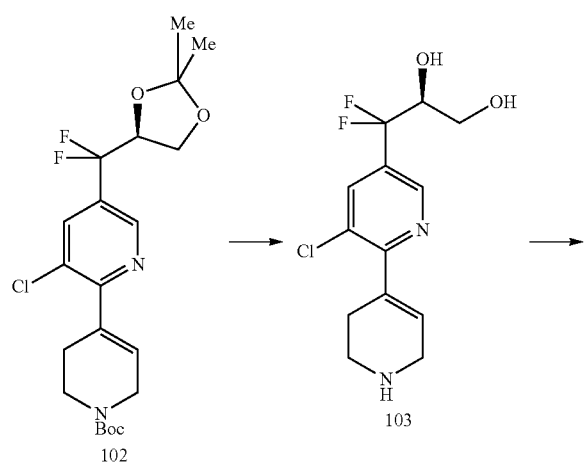

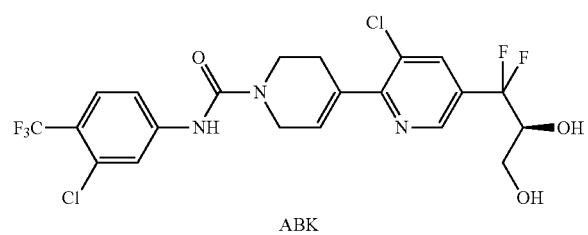

ABK

Step 1 Preparation of compound 97

To a solution of 62 (1.32 g, 4.78 mmol) in 1,2-dichloroethane (15 mL) was added Deoxo-Fluor (2.20 mL, 11.95 mmol) at 0° C. The mixture was allowed to warm to 40° C. and stirred at same temperature for 2.5 hr. After cooled to 0° C., an aqueous solution of NaHCO$_3$ was added to neutralize. The mixture was extracted with CHCl$_3$ (×3). The combined organic layer was dried over MgSO$_4$, filtered and concentrated. The residue was chromatographed on silica gel (n-hexane/EtOAc) to give 101 (1.30 g, 91% yield) as an oil.

Step 2 Preparation of Compound 98

To a solution of 101 (1.30 g, 4.37 mmol) in TIM (9 mL) and EtOH (4.5 mL) was added borate (1.62 g, 5.24 mmol), an aqueous solution of K$_2$CO$_3$ (3 M, 3.2 mL) and PdCl$_2$(PPh$_3$)$_2$ (153 mg, 0.22 mmol). The mixture was stirred at 85° C. for 13 hr, and then cooled to rt. EtOAc and water were added and the aqueous layer was extracted with EtOAc. The combined organic layer was washed with brine, dried over MgSO$_4$, filtered, and concentrated. The residue was chromatographed on silica gel (n-hexane/EtOAc) to give 102 (1.37 g, 70%) as an oil.

Step 3 Preparation of Compound ABK

To a solution of 102 (600 mg, 1.35 mmol) in diethyl ether (3.0 mL) and ethanol (0.2 mL) was added HCl in dioxane (4 N, 1.69 mL) at 0° C. The mixture was warmed to 45° C. and stirred for 3.5 hr. The resulting mixture was cooled to room temperature and EtOAc was added. The solvents was removed by decantation (×4) and the residue was dried under reduced pressure to give a solid containing 103 (500 mg). To a suspension of this solid in dichloromethane (3.0 mL) was added diisopropyl ethylamine (0.31 mL, 1.79 mmol) and phenylcarbamate (125 mg, 0.40 mmol). The mixture was stirred at room temperature over night and diluted with water. The mixture was extracted with CHCl$_3$ (×3). The combined organic layer was dried over MgSO$_4$, filtered and concentrated. The residue was chromatographed on silica gel (dichloromethane/MeOH) and on ODS C18 (reverse phase, water/acetonitrile) to give ABK (70 mg, 34%) as a foam.

$^1$H-NMR (DMSO-d$_6$): 2.60 (2H, brs), 3.61 (1H, m), 3.70 (2H, m), 4.00 (1H, m), 4.40 (1H, m), 4.83 (1H, m), 5.93 (1H, d, J=5.3 Hz), 7.65 (1H, d, J=9.0 Hz), 7.73 (1H, d, J=9.0 Hz), 7.86 (1H, s), 7.94 (1H, s), 8.63 (1H, s), 9.16 (1H, s).

MS: 526 [M+H]$^+$

Example 75

(S)-4-(3-chloro-5-(1,1-difluoro-2,3-dihydroxypropyl)pyridin-2-yl)-N-(5-(trifluoromethyl)pyridin-2-yl)-5,6-dihydropyridine-1(2H)-carboxamide (ABL)

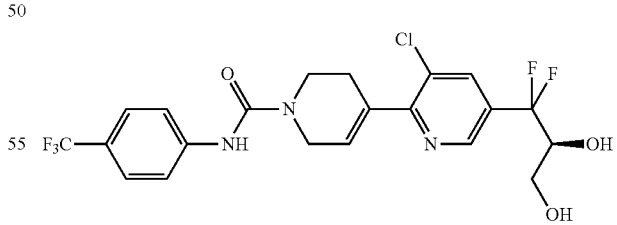

ABL

The compound ABL was obtained in the same manner as Example 74. $^1$H-NMR (CDCl$_3$): 2.03 (1H, brs), 2.73 (2H, m), 3.22 (1H, brs), 3.78-3.98 (4H, m), 4.11 (1H, m), 4.27 (1H, m), 6.28 (1H, m), 7.51 (1H, m), 7.88 (2H, m), 8.21 (1H, d, J=8.8 Hz), 8.47 (1H, s), 8.63 (1H, s)

MS: 493 [M+H]$^+$.

Example 76

(S)—N-(3-chloro-4-(trifluoromethyl)phenyl)-4-(5-(1,1-difluoro-2,3-dihydroxypropyl)-3-fluoropyridin-2-yl)-5,6-dihydropyridine-1(2H)-carboxamide (ABM)

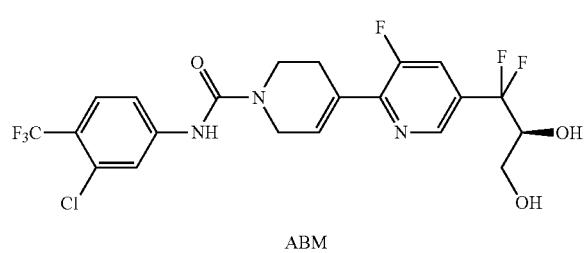 [SMILES: O=C(Nc1ccc(C(F)(F)F)c(Cl)c1)N1CC=C(c2ncc(C(F)(F)[C@@H](O)CO)cc2F)CC1]

ABM

The compound ABM was obtained in the same manner as Example 74. $^1$H-NMR (DMSO-$d_6$): 2.70 (2H, brs), 3.59 (1H, m), 3.71 (2H, m), 4.00 (1H, m), 4.26 (1H, m), 4.82 (1H, t, J=5.8 Hz), 5.91 (1H, d, J=6.2 Hz), 6.69 (1H, brs), 7.65 (1H, dd, J=1.5, 8.9 Hz), 7.73 (1H, d, J=8.9 Hz), 7.85 (1H, d, J=12 Hz), 7.93 (1H, s), 8.54 (1H, s), 9.16 (1H, s).

MS: 510 [M+H]$^+$

Example 77

(S)-4-(3-chloro-5-(1,1-difluoro-2,3-dihydroxypropyl)pyridin-2-yl)-N-(3-methoxy-4-(trifluoromethyl)phenyl)-5,6-dihydropyridine-1(2H)-carboxamide (ABN)

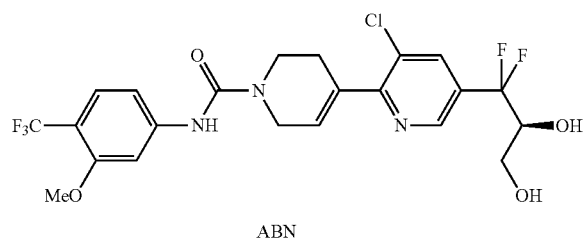 [SMILES: COc1cc(NC(=O)N2CC=C(c3ncc(C(F)(F)[C@@H](O)CO)cc3Cl)CC2)ccc1C(F)(F)F]

ABN

The compound ABN was obtained in the same manner as Example 74. $^1$H-NMR (CDCl$_3$): 1.95 (1H, brs), 2.73 (2H, m), 3.10 (1H, brs), 3.73-3.92 (7H, m), 4.11 (1H, m), 4.26 (1H, m), 6.28 (1H, m), 6.58 (1H, s), 6.73 (1H, d, J=8.5 Hz), 7.44 (1H, d, J=8.5 Hz), 7.53 (1H, s), 7.89 (1H, d, J=1.7 Hz), 8.62 (1H, d, J=1.7 Hz).

MS: 522 [M+H]$^+$

Example 78

(S)-4-(3-chloro-5-(1,1-difluoro-2,3-dihydroxypropyl)pyridin-2-yl)-N-(6-fluorobenzo[d]thiazol-2-yl)-5,6-dihydropyridine-1(2H)-carboxamide (ABP)

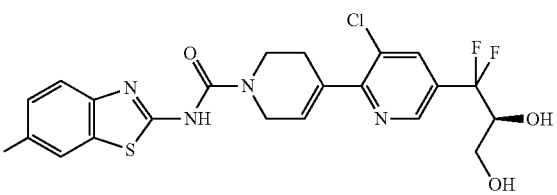

ABP

The compound ABP was obtained in the same manner as Example 74. $^1$H-NMR (DMSO-$d_6$): 2.59 (2H, brs), 3.59 (1H, m), 3.79 (2H, m), 4.00 (1H, m), 4.29 (2H, brs), 4.84 (1H, t, J=5.8 Hz), 5.93 (1H, d, J=6.2 Hz), 6.32 (1H, s), 7.23 (1H, m), 7.60 (1H, brs), 7.79 (1H, d, brs), 8.03 (1H, d, J=1.7 Hz), 8.63 (1H, d, J=1.7 Hz), 11.4 (1H, brs).

MS: 499 [M+H]$^+$

Example 79

(S)-4-(3-chloro-5-(1,1-difluoro-2,3-dihydroxypropyl)pyridin-2-yl)-N-(3-methyl-4-(trifluoromethyl)phenyl)-5,6-dihydropyridine-1(2H)-carboxamide (ADC)

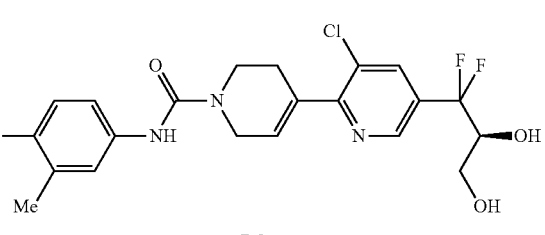

ADC

The compound ADC was obtained in the same manner as Example 74. $^1$H-NMR (DMSO-$d_6$): 2.38 (3H, s), 2.59 (2H, brs), 3.58 (1H, m), 3.70 (2H, m), 4.02 (1H, m), 4.21 (1H, m), 4.83 (1H, m), 5.93 (1H, d, J=5.0 Hz), 6.31 (1H, s), 7.48-7.55 (1H, m), 8.03 (1H, d, J=1.8 Hz), 8.63 (1H, s), 8.90 (1H, s).

MS: 506 [M+H]$^+$

Example 80

(R)-4-(3-chloro-5-(2,3-dihydroxypropyl)pyridin-2-yl)-N-(6-fluorobenzo[d]thiazol-2-yl)piperazine-1-carboxamide (ACV)

Step 1 Preparation of (R)-1-(3-chloro-5-((2,2-dimethyl-1,3-dioxolan-4-yl)methyl)pyridin-2-yl)piperazine

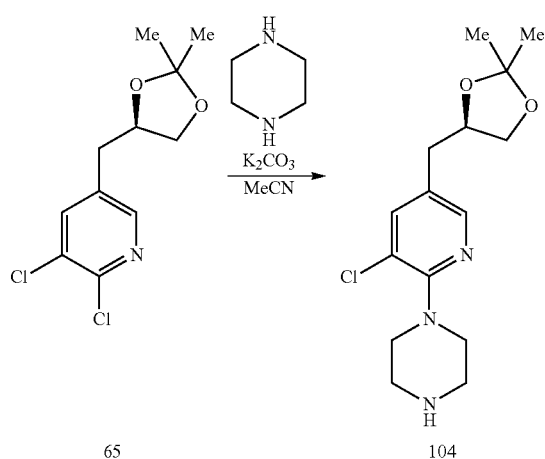

To a 23 mL acetonitrile solution of (R)-2,3-dichloro-5-((2,2-dimethyl-1,3-dioxolan-4-yl)methyl)pyridine (65, 2.31 g, 8.81 mmol) was piperazine (2.66 g, 30.8 mmol) and potassium carbonate (1.22 g, 8.81 mmol) at room temperature. The mixture was stirred at reflux for 26 hrs. The reaction mixture was diluted with H$_2$O (30 mL) and the mixture was extracted with ethyl acetate (30 mL×2). The resulting organic layer was washed with H$_2$O, brine, dried over anhydrous sodium sulfate, and concentrated under reduced pressure. The crude product was chromatographed on silica gel eluting with a gradient of methanol (0-5%)/ethyl acetate. 0.98 g of the product 104 was obtained (36%).

$^1$H-NMR (CDCl$_3$) δ: 8.03 (1H, d, J=2.1 Hz), 7.50 (1H, d, J=2.1 Hz), 4.31-4.22 (1H, m), 4.03 (1H, dd, J=8.1, 5.9 Hz), 3.61 (1H, dd, J=8.1, 5.9 Hz), 3.28-3.27 (4H, m), 3.04-3.02 (4H, m), 2.82-2.72 (2H, m), 1.42 (3H, s), 1.35 (3H, s).

Step 2 Preparation of (R)-3-(5-chloro-6-(piperazin-1-yl)pyridin-3-yl)propane-1,2-diol hydrochloride

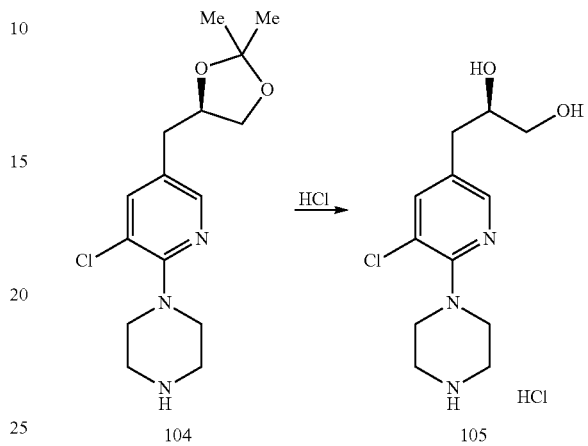

The compound 105 was obtained in the same manner as reference Example 2, step 4. Yield 100% $^1$H-NMR (DMSO-d$_6$) δ: 8.09 (1H, d, J=1.8 Hz), 7.72 (1H, d, J=1.8 Hz), 4.30-4.02 (2H, m), 3.67-3.61 (1H, m), 3.38-3.06 (6H, m), 2.88-2.83 (1H, m), 2.61-2.42 (3H, m).

Step 3. (R)-4-(3-chloro-5-(2,3-dihydroxypropyl)pyridin-2-yl)-N-(6-fluorobenzo[d]thiazol-2-yl)-5,6-dihydropyridine-1(2H)-carboxamide (ACV)

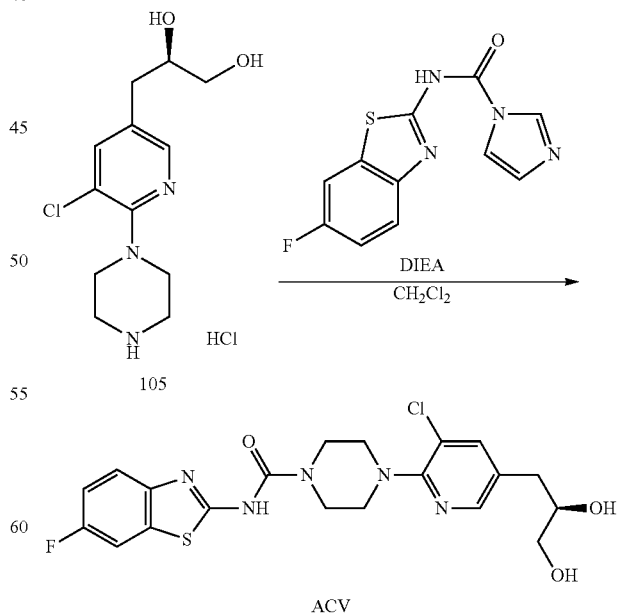

The compound ACV was obtained in the same manner as Example 12. Yield 67%

$^1$H-NMR (DMSO-d$_6$): 2.45 (1H, m), 2.74 (1H, m), 3.23 (4H, s), 3.59 (1H, brs), 3.72 (4H, s), 4.65 (2H, m), 7.22 (1H, m), 7.44 (1H, brs), 7.70 (1H, s), 8.08 (1H, s), 11.5 (1H, brs). MS: 466 [M+11]$^+$

Example 81

(R)-4-(3-chloro-5-((R)-2,3-dihydroxypropyl)pyridin-2-yl)-N-(6-fluorobenzo[d]thiazol-2-yl)-2-methylpiperazine-1-carboxamide (ACU)

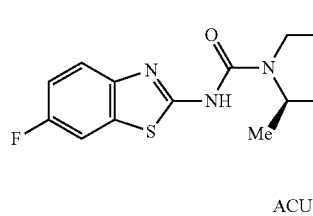

ACU

The compound ACU was obtained in the same manner as Example 12. $^1$H-NMR (DMSO-d$_6$): 1.33 (3H, d, J=6.5 Hz), 2.72-2.89 (3H, m), 3.59 (3H, m), 4.21 (1H, d, J=13.1 Hz), 4.66 (3H, m), 7.18 (1H, m), 7.52 (1H, brs), 7.64 (1H, s), 7.75 (1H, d, J=7.2 Hz), 8.07 (1H, s), 11.5 (1H, brs).

MS: 480 [M+H]$^+$

Reference Example 13

Preparation of (R)-tert-butyl 3-(5,6-dichloropyridin-3-yl)-2-hydroxypropylcarbamate and (S)-tert-butyl 3-(5,6-dichloropyridin-3-yl)-2-hydroxypropylcarbamate

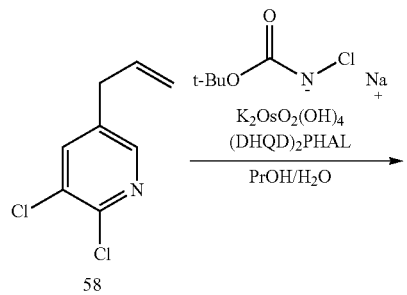

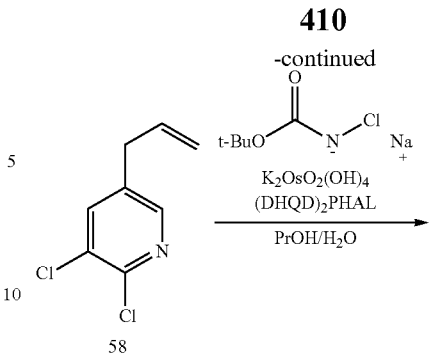

To a solution of tert-butyl carbamate (1.230 g, 10.50 mmol) in PrOH (4 mL), NaOH (g, 10.50 mmol) in water (10.5 mL) and tert-butyl hypochlorite (1.140 g, 10.50 mmol) was stirred at ambient temperature for 5 min. Then the reaction mixture was cooled to 0° C. and added (DHQD)$_2$PHAL (0.136 g, 0.175 mmol) or (DHQ)$_2$PHAL (0.136 g, 0.175 mmol) in PrOH (4 mL), a solution of 5-allyl-2,3-dichloropyridine (58, 0.658 g, 3.5 mmol) in PrOH (7 mL) and Potassium osmate dihydrate (0.052 g, 0.140 mmol). After being stirred for 3 hrs, the reaction mixture was quenched with 10% NaHSO$_3$ and diluted with ethyl acetate (20 mL). The resulting organic layer was separated and the aqueous layer was extracted with ethyl acetate (5 mL), the combined organic layers were washed with brine, dried over Na$_2$SO$_4$ and concentrated under reduced pressure. The crude product was chromatographed on silica gel eluting with a gradient of CHCl$_3$/MeOH (0-8%) to afford 1.64 g of the product (200 for (DHQD)$_2$PHAL or 201 for (DHQ)$_2$PHAL) in % yield as a colorless solid. $^1$H-NMR (DMSO-d$_6$) δ: 8.24 (1H, s), 8.00 (1H, s), 6.78 (1H, br), 4.91 (1H, d, J=5.05 Hz), 3.67 (1H, m), 2.94 (2H, d, J=5.05 Hz), 2.78 (1H, dd, J=13.39, 2.78 Hz), 2.55 (1H, dd, J=7.07 Hz), 1.38 (9H, s). LC/MS (M+1): 321.

Example 82

Step 1 Preparation of (R)-1-acetamido-3-(5,6-dichloropyridin-3-yl)propan-2-yl acetate

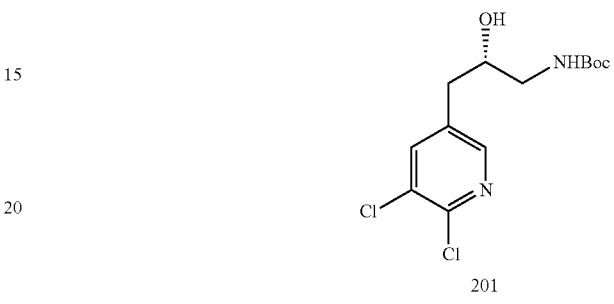

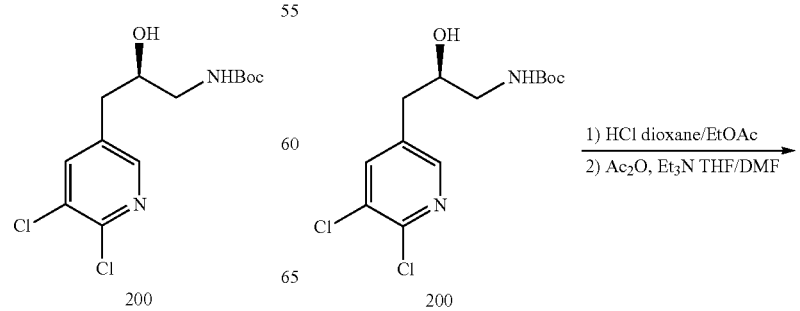

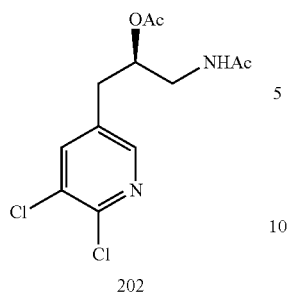

202

To a solution of compound 200 (1.12 g, 3.5 mmol) in ethyl acetate (4 mL) was added excess amount of 4 mol/L HCl in dioxane (4 mL) at room temperature. After being stirred over night, the reaction mixture was concentrated under reduced pressure. The residue was used directly for the next reaction.

To a suspension of crude product in THF (4.00 ml) and DMF (1.2 ml) was added Et$_3$N (2.91 ml, 21.00 mmol) and Ac$_2$O (0.761 ml, 8.05 mmol) at 0° C. under nitrogen. After being stirred over night at room temperature, the reaction mixture was quenched with saturated aqueous NaHCO$_3$ and diluted with ethyl acetate (20 mL). The resulting organic layer was separated and the aqueous layer was extracted with ethyl acetate (5 mL), the combined organic layers were washed with water and brine, dried over Na$_2$SO$_4$ and concentrated under reduced pressure. The crude product waschromatographed on silica gel eluting with a gradient of CHCl$_3$/MeOH (0-10%) to afford 724.4 mg of the compound 202 in 68% yield as a colorless oil. $^1$H-NMR (400 MHz DMSO-d$_6$) δ: 8.26 (1H, s), 8.06 (1H, s), 8.01 (1H, br), 4.98 (1H, br), 3.33 (1H, m), 3.12 (1H, m), 2.93 (1H, dd, J=13.89, 4.29 Hz), 2.79 (1H, dd, J=13.89, 8.08 Hz), 1.94 (3H, s), 1.82 (3H, s).

Step 2 Preparation of (R)-tert-butyl 4-(5-(3-acetamido-2-acetoxypropyl)-3-chloropyridin-2-yl)-5,6-dihydropyridine-1(2H)-carboxylate

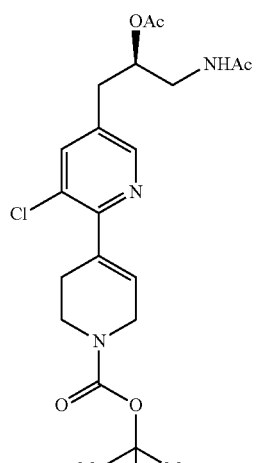

203

The compound 203 was obtained in the same manner as Reference Example 1, Step 3 and used directly for the next reaction.

Step 3 Preparation of (R)-tert-butyl 4-(5-(3-acetamido-2-hydroxypropyl)-3-chloropyridin-2-yl)-5,6-dihydropyridine-1(2H)-carboxylate

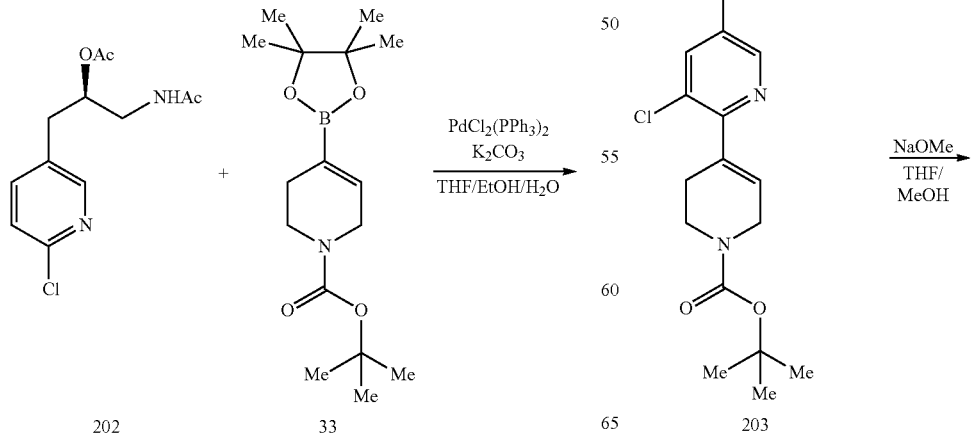

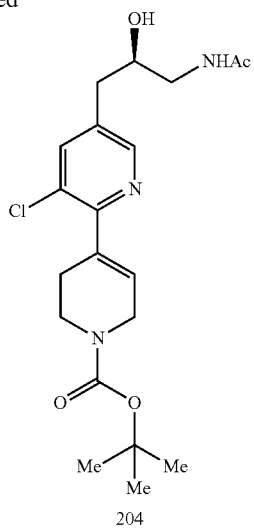

204

To a solution of crude product (203, 1.07 g, 2.37 mmol) in THF (3.5 ml) and MeOH (3.5 ml) was added NaOMe (257 mg, 4.75 mmol) at 0° C. under nitrogen. After being stirred for 2 hrs at room temperature, the reaction mixture was quenched with 10% citric acid (10 mL) and diluted with ethyl acetate (15 mL). The resulting organic layer was separated and the aqueous layer was extracted with ethyl acetate (5 mL), the combined organic layers were washed with water and brine, dried over $Na_2SO_4$ and concentrated under reduced pressure. The crude product was chromatographed on silica gel eluting with a gradient of $CHCl_3$/MeOH (0-10%) to afford 763.3 mg of the product 204 in 78% yield as a yellow amorphous. $^1$H-NMR (DMSO-$d_6$) δ: 8.35 (1H, s), 7.88 (1H, br), 7.79 (1H, s), 6.12 (1H, br), 4.97 (1H, d, J=5.05 Hz), 4.02 (2H, m), 3.70 (1H, m), 3.54 (2H, m), 3.10 (1H, m), 3.03 (1H, m), 2.75 (1H, dd, J=14.1, 3.03 Hz), 2.56 (1H, dd, J=14.1, 7.07 Hz), 2.47 (2H, m), 1.83 (3H, s), 1.44 (9H, s).

Step 4 Preparation of (R)—N-(3-(5-chloro-6-(1,2,3,6-tetrahydropyridin-4-yl)pyridin-3-yl)-2-hydroxypropyl)acetamide hydrochloride

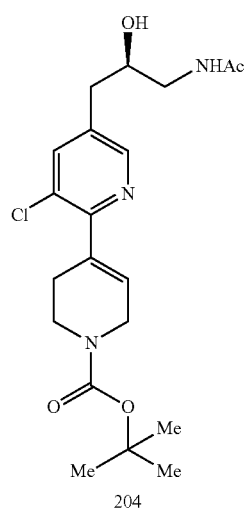

204

4M HCl
CH₂Cl₂/
dioxane

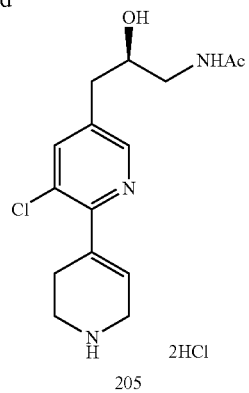

205

The compound 205 was obtained in the same manner as Example 36, Step 4 and used directly for the next reaction.

Step 5 Preparation of 5-((R)-3-Acetylamino-2-hydroxy-propyl)-3-chloro-3',6'-dihydro-2'H-[2,4']bipyridinyl-1'-carboxylic acid (3-chloro-4-trifluoromethyl-phenyl)amide

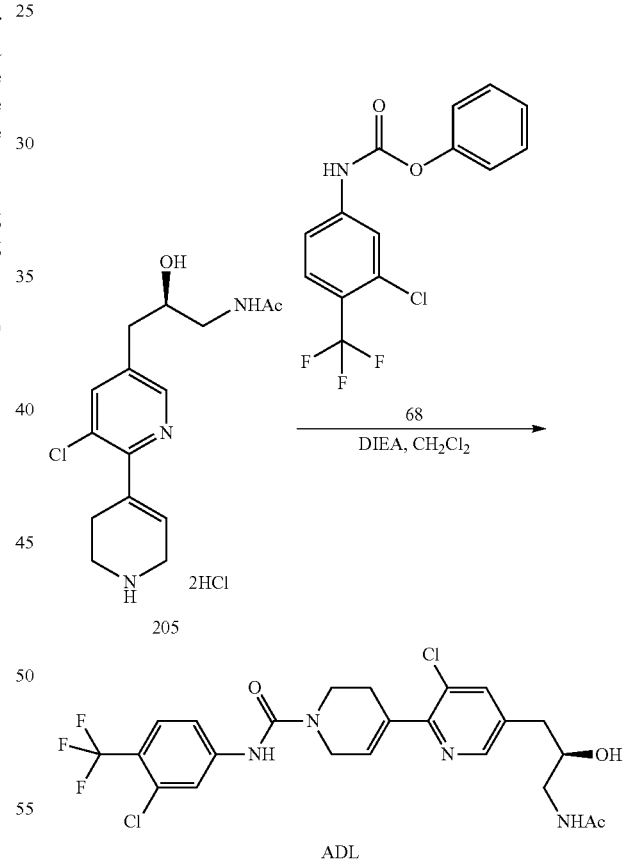

The compound was obtained in the same manner as Example 1 and chromatographed on silica gel with a gradient of methanol (0-10%)/CHCl₃ acetate to afford 110 mg of the compound ADL in 54% yield as a white amorphous. $^1$H-NMR (300 MHz DMSO-$d_6$) δ: 9.13 (1H, s), 8.35 (1H, d, J=1.68 Hz), 7.92 (1H, d, J=1.68 Hz), 7.87 (1H, t, J=5.80 Hz), 7.79 (1H, d, J=1.68 Hz), 7.71 (1H, d, J=8.85 Hz), 7.63 (1H, dd, J=8.85, 1.68 Hz), 6.18 (1H, br), 4.96 (1H, d, J=5.34 Hz), 4.19 (2H, d, J=2.90 Hz), 3.69 (2H, t, J=5.41 Hz), 3.69 (1H, m), 3.10 (1H, m), 3.02 (1H, m), 2.75 (1H, dd, J=13.73, 3.97 Hz), 2.58-2.53 (3H, m), 1.82 (3H, s). LC/MS (M+1): 531.

Example 83

Preparation of 5-((R)-3-Acetylamino-2-hydroxy-propyl)-3-chloro-3',6'-dihydro-2'H-[2,4']bipyridinyl-1'-carboxylic acid (5-trifluoromethyl-pyridin-2-yl)-amide (ADM)

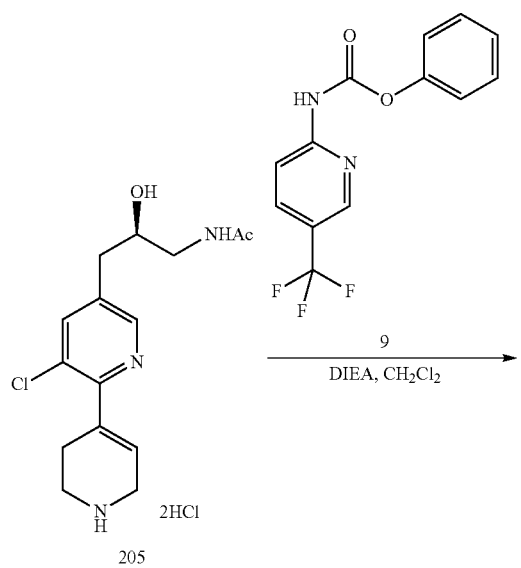

The compound was obtained in the same manner as Example 1 and triturated with ethyl acetate. The resulting solid was filtered through a medium flitted glass funnel, rinsed with ethyl acetate, and collected to afford 70.6 mg of the compound ADM in 45% yield as a white solid.

$^1$H-NMR (DMSO-d$_6$) δ: 9.80 (1H, s), 8.60 (1H, m), 8.35 (1H, d, J=1.83 Hz), 8.05 (1H, dd, J=8.85, 2.86 Hz), 7.97 (1H, d, J=8.85 Hz), 7.87 (1H, t, J=5.80 Hz), 7.78 (1H, d, J=1.83 Hz), 6.16 (1H, br), 4.96 (1H, d, J=5.49 Hz), 4.20 (2H, d, J=2.75 Hz), 3.70 (2H, t, J=5.57 Hz), 3.69 (1H, m), 3.08 (1H, m), 3.02 (1H, m), 2.74 (1H, dd, J=13.88, 4.12 Hz), 2.57-2.53 (3H, m), 1.82 (3H, s). LC/MS (M+1): 498.

Example 84

Preparation of 5-((R)-3-Acetylamino-2-hydroxy-propyl)-3-chloro-3',6'-dihydro-2'H-[2,4']bipyridinyl-1'-carboxylic acid (6-fluoro-benzothiazol-2-yl)-amide (ADP)

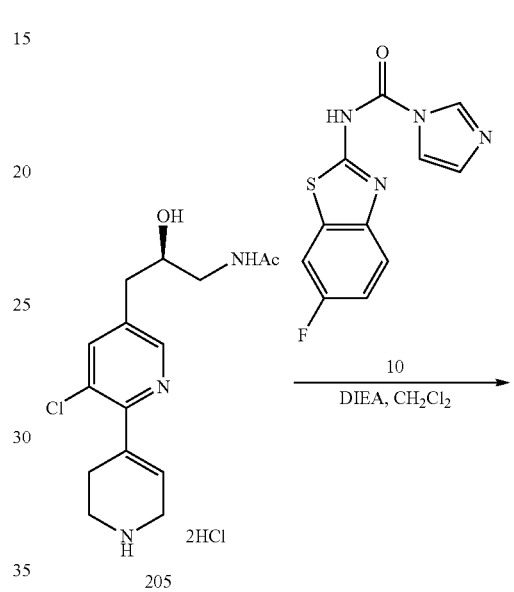

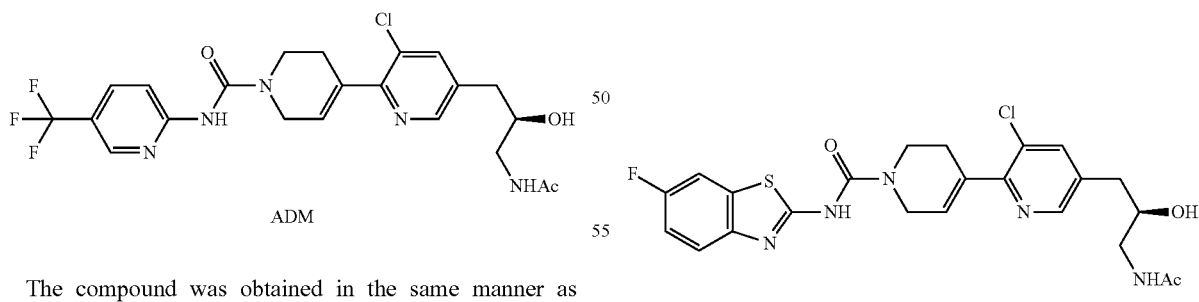

The compound was obtained in the same manner as Example 10 and chromatographed with HPLC-MS column with a gradient of CH$_3$CN/water to afford 96.0 mg of the compound ADP in 61% yield as a white solid. $^1$H-NMR (DMSO-d$_6$) δ: 8.35 (1H, s), 7.86 (1H, t, J=5.41 Hz), 7.78 (1H, s), 7.75 (1H, d, J=9.00 Hz), 7.54 (1H, br), 7.20 (1H, td, J=9.00, 2.34 Hz), 6.18 (1H, br), 4.95 (1H, d, J=5.34 Hz), 4.25

(2H, br), 3.77 (2H, br), 3.69 (1H, br), 3.08 (1H, m), 3.02 (1H, m), 2.74 (1H, dd, J=13.80, 3.74 Hz), 2.57-2.53 (3H, m), 1.82 (3H, s). LC/MS (M+1): 504.

Example 85

Preparation of 5-((S)-3-Acetylamino-2-hydroxypropyl)-3-chloro-3',6'-dihydro-2'H-[2,4']bipyridinyl-1'-carboxylic acid (3-chloro-4-trifluoromethyl-phenyl)-amide (ADN)

m), 3.10 (1H, m), 3.02 (1H, m), 2.75 (1H, dd, J=13.73, 3.97 Hz), 2.58-2.53 (3H, m), 1.82 (3H, s). LC/MS (M+1): 531.

Example 86

Preparation of 5-((S)-3-Acetylamino-2-hydroxypropyl)-3-chloro-3',6'-dihydro-2'H-[2,4']bipyridinyl-1'-carboxylic acid (5-trifluoromethyl-pyridin-2-yl)-amide (ADO)

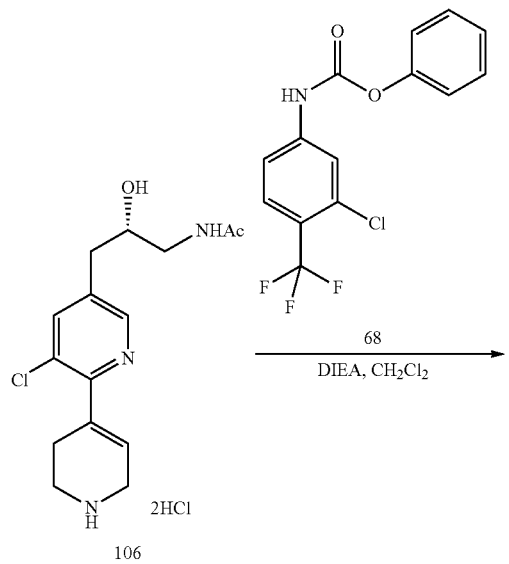

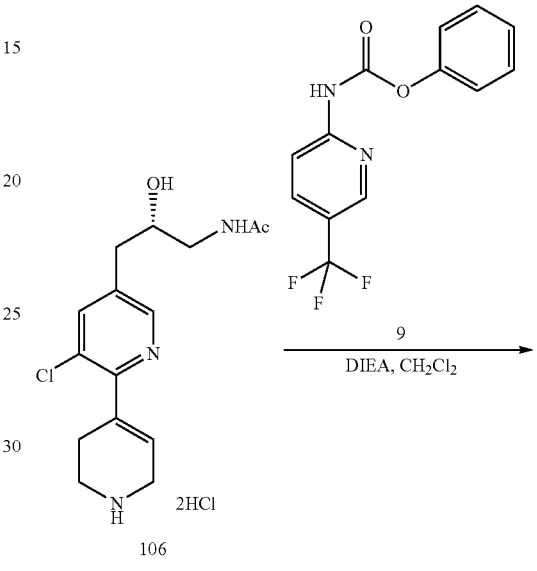

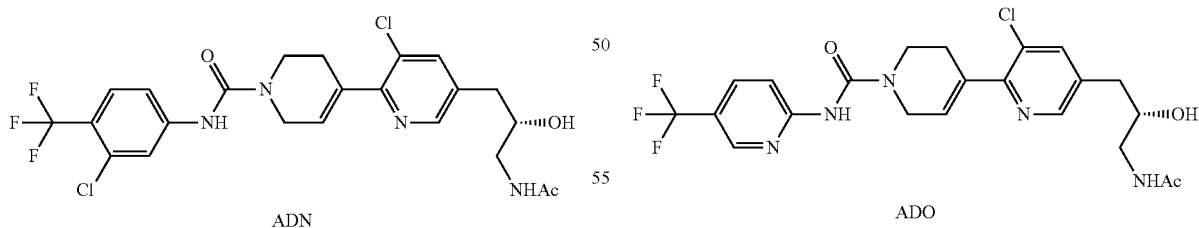

The compound was obtained in the same manner as Example 1 and chromatographed on silica gel with a gradient of methanol (0-10%)/CHCl$_3$ acetate to afford 76.7 mg of the compound ADN in 41% yield as a white amorphous. $^1$H-NMR (300 MHz DMSO-d$_6$) δ: 9.13 (1H, s), 8.35 (1H, d, J=1.68 Hz), 7.92 (1H, d, J=1.68 Hz), 7.87 (1H, t, J=5.80 Hz), 7.79 (1H, d, J=1.68 Hz), 7.71 (1H, d, J=8.85 Hz), 7.63 (1H, dd, J=8.85, 1.68 Hz), 6.18 (1H, br), 4.96 (1H, d, J=5.34 Hz), 4.19 (2H, d, J=2.90 Hz), 3.69 (2H, t, J=5.41 Hz), 3.69 (1H, The compound was obtained in the same manner as Example 1 and triturated with ethyl acetate. The resulting solid was filtered through a medium fitted glass funnel, rinsed with ethyl acetate, and collected to afford 69 mg of the compound ADO in 33% yield as a white solid. $^1$H-NMR (DMSO-d$_6$) δ: 9.80 (1H, s), 8.60 (1H, m), 8.35 (1H, d, J=1.83 Hz), 8.05 (1H, dd, J=8.85, 2.86 Hz), 7.97 (1H, d, J=8.85 Hz), 7.87 (1H, t, J=5.80 Hz), 7.78 (1H, d, J=1.83 Hz), 6.16 (1H, br), 4.96 (1H, d, J=5.49 Hz), 4.20 (2H, d, J=2.75 Hz), 3.70 (2H, t, J=5.57 Hz), 3.69 (1H, m), 3.08 (1H, m), 3.02 (1H, m), 2.74 (1H, dd, J=13.88, 4.12 Hz), 2.57-2.53 (3H, m), 1.82 (3H, s). LC/MS (M+1): 498.

Example 87

Preparation of -((S)-3-Acetylamino-2-hydroxy-propyl)-3-chloro-3',6'-dihydro-2'H-[2,4']bipyridinyl-1'-carboxylic acid (6-fluoro-benzothiazol-2-yl)-amide (ADQ)

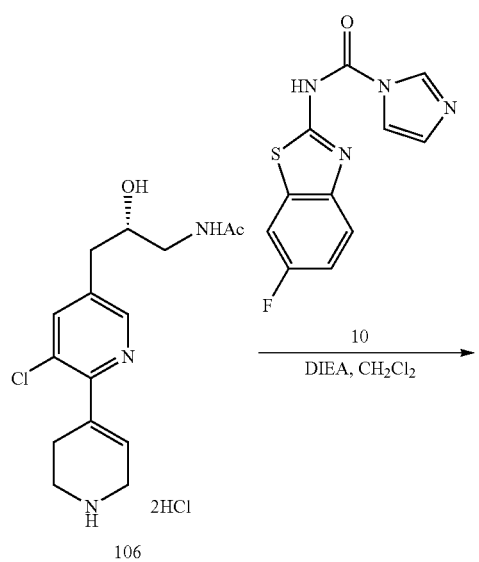

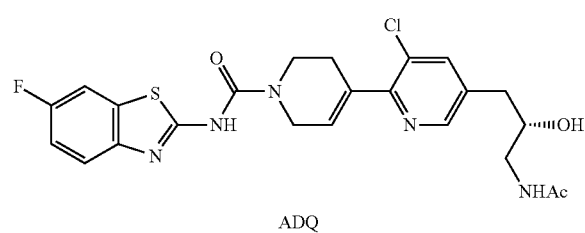

The compound was obtained in the same manner as Example 10 and chromatographed with HPLC-MS column with a gradient of CH$_3$CN/water to afford 53.4 mg of the compound ADQ in 34% yield as a white solid. $^1$H-NMR (DMSO-d$_6$) δ: 8.35 (1H, s), 7.86 (1H, t, J=5.41 Hz), 7.78 (1H, s), 7.75 (1H, d, J=9.00 Hz), 7.54 (1H, br), 7.20 (1H, td, J=9.00, 2.34 Hz), 6.18 (1H, br), 4.95 (1H, d, J=5.34 Hz), 4.25 (2H, br), 3.77 (2H, br), 3.69 (1H, br), 3.08 (1H, m), 3.02 (1H, m), 2.74 (1H, dd, J=13.80, 3.74 Hz), 2.57-2.53 (3H, m), 1.82 (3H, s). LC/MS (M+1): 504.

Example 88

Preparation of (R)-4-(3-chloro-5-(2,3-dihydroxypropyl)pyridin-2-yl)-4-fluoro-N-(6-fluorobenzo[d]thiazol-2-yl)piperidine-1-carboxamide (AEF)

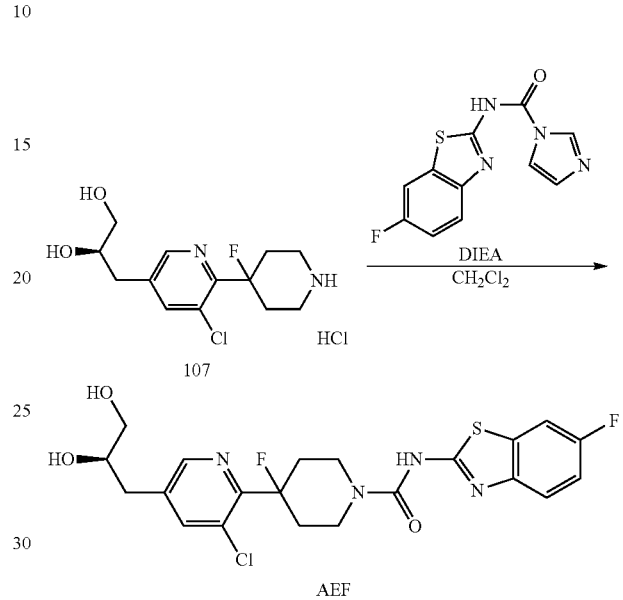

The compound AEF was obtained in the same manner as Example 10. (yield 65%)
1H-NMR (DMSO-d$_6$) δ: 8.37 (1H, d, J=1.7 Hz), 7.82 (1H, d, J=1.7 Hz), 7.77 (1H, dd, J=8.6, 2.4 Hz), 7.56-7.53 (1H, br m), 7.20 (1H, dt, J=8.6, 2.4 Hz), 4.74 (1H, d, J=5.5 Hz), 4.68 (1H, t, J=5.5 Hz), 4.26-4.22 (2H, m), 3.66-3.62 (1H, m), 3.41-2.10 (11H, m).

Example 89

Compound ADR $^1$H NMR (DMSO-d$_6$) δ 2.47 (1 H, dd, J=8.33, 14.03 Hz), 2.74 (1 H, dd, J=3.95, 14.03 Hz), 3.24 (5 H, m), 3.32 (1 H, m), 3.59 (1 H, m), 3.72 (4 H, m), 7.22 (1 H, dt, J=2.63, 9.21 Hz), 7.58 (1 H, m), 7.71 (1 H, d, J=1.97 Hz), 7.78 (1 H, dd, J=2.41, 8.55 Hz), 8.08 (1 H, d, J=1.97 Hz); LC/MS (M+1) 466.

Example 90

Compound ADS $^1$H NMR (DMSO-d$_6$) δ 2.47 (1 H, dd, J=8.11, 14.03 Hz), 2.74 (1 H, dd, J=3.95, 13.81 Hz), 3.24 (5 H, m), 3.32 (1 H, m), 3.59 (1 H, m), 3.73 (4 H, m), 7.21 (1 H, t, J=7.45 Hz), 7.36 (1 H, t, J=7.45 Hz), 7.52 (1 H, br s), 7.70 (1 H, d, J=1.75 Hz), 7.83 (1 H, br s), 8.08 (1 H, d, J=1.97 Hz); LC/MS (M+1) 448.

Example 91

Compound ADW $^1$H NMR (DMSO-d$_6$) δ 2.46 (1 H, m), 2.75 (1 H, dd, J=2.85, 13.37 Hz), 3.24 (5 H, m), 3.32 (1 H, m), 3.59 (1 H, m), 3.72 (4 H, m), 7.39 (1 H, m), 7.56 (1H, br s), 7.70 (1H, m), 8.00 (1H, br s), 8.08 (1 H, m), 11.37 (1 H, br s); LC/MS (M+1) 482.

Example 92

Compound ADX $^1$H NMR (DMSO-d$_6$) δ 2.37 (3 H, s), 2.47 (1 H, dd, J=8.11, 13.81 Hz), 2.74 (1H, dd, J=3.95, 14.03 Hz), 3.22-3.31 (6 H, m), 3.59 (1 H, m), 3.71 (4 H, m), 4.66 (2 H, m), 7.17 (1 H, d, J=7.87 Hz), 7.25-7.63 (2 H, m), 7.70 (1 H, d, J=1.97 Hz), 8.08 (1H, d, J=1.97 Hz), 11.21 (1 H, br s); LC/MS (M+1) 462.

Example 93

Compound AEB $^1$H NMR (DMSO-d$_6$) δ 1.16 (3 H, d, J=6.80 Hz), 2.29 (1 H, m), 2.64 (3 H, m), 3.12 (3 H, m), 3.42 (3 H, m), 4.00 (1 H, m), 4.41 (1 H, m), 7.04 (1 H, t, J=8.76 Hz), 7.47 (1 H, br s), 7.52 (1 H, d, J=7.45 Hz), 7.62 (1 H, d, J=1.75 Hz), 7.90 (1 H, d, J=1.75 Hz), 11.09 (1 H, br s); LC/MS (M+1) 480.

Example 94

Compound AEC $^1$H NMR (DMSO-d$_6$) δ 1.33 (1 H, d, J=6.58 Hz), 2.37 (3 H, s), 2.47 (1 H, dd, J=8.33, 13.81 Hz), 2.74 (1 H, dd, J=3.73, 13.81 Hz), 2.79-2.87 (2 H, m), 3.28 (3 H, m), 3.61 (3 H, m), 4.21 (1 H, m), 4.61 (1 H, m), 7.17 (1 H, d, J=7.67 Hz), 7.26-7.60 (2 H, m), 7.69 (1 H, d, J=1.54 Hz), 8.07 (1 H, d, J=1.75 Hz), 11.18 (1 H, br s); LC/MS (M+1) 476.

Example 95

Compound AED $^1$H NMR (DMSO-d$_6$) δ 1.34 (3 H, d, J=6.58 Hz), 2.48 (1 H, dd, J=8.33, 14.03 Hz), 2.74 (1 H, dd, J=2.84, 12.94 Hz), 2.80-2.87 (2 H, m), 3.28 (3 H, m), 3.59 (3 H, m), 4.21 (1 H, m), 4.61 (1 H, m), 7.20 (1 H, t, J=7.02 Hz), 7.36 (1 H, t, J=7.02 Hz), 7.58 (1 H, br s), 7.69 (1 H, d, J=1.97 Hz), 7.82 (1 H, br s), 8.08 (1 H, d, J=1.97 Hz); LC/MS (M+1) 462.

Example 96

Compound AEG $^1$H NMR (DMSO-d$_6$) δ 1.27 (3 H, d, J=6.79 Hz), 2.40 (1 H, dd, J=8.55, 14.47 Hz), 2.68 (1 H, dd, J=3.73, 14.03 Hz), 2.74 (1 H, dt, J=3.51, 12.50 Hz), 2.82 (1 H, dd, J=3.51, 12.50 Hz), 3.23 (3 H, m), 3.54 (3 H, m), 4.15 (1 H, d, J=10.74 Hz), 4.56 (1 H, t, J=5.48 Hz), 4.60 (1 H, d, J=5.48 Hz), 7.32 (1 H, dd, J=2.19, 8.55 Hz), 7.45 (1H, m), 7.62 (1 H, d, J=1.97 Hz), 7.92 (1 H, m), 8.01 (1 H, d, J=1.97 Hz), 11.68 (1 H, br s); LC/MS (M+1) 496.

Example 97

Compound ADT $^1$H NMR (DMSO-d$_6$) δ 2.47 (3 H, m), 2.74 (1 H, dd, J=3.88, 14.09 Hz), 3.24 (4 H, m), 3.59 (1 H, m), 3.72 (4 H, m), 4.65 (2 H, m), 7.39 (1 H, d, J=8.56 Hz), 7.55 (1 H, br s), 7.70 (1 H, s), 8.00 (1 H, s), 8.08 (1 H, s), 11.46 (1 H, br s); LC/MS (M+1) 483.

Example 98

Compound ADU $^1$H NMR (DMSO-d$_6$) δ 2.37 (3 H, s), 2.47 (3 H, m), 2.75 (1 H, dd, J=3.71, 17.72 Hz), 3.30 (4 H, m), 3.59 (1 H, m), 3.72 (4 H, m), 4.65 (2 H, m), 7.17 (1 H, d, J=9.25 Hz), 7.40 (1 H, d, J=8.10 Hz), 7.62 (1 H, s), 7.70 (1 H, s), 8.08 (1 H, s), 11.46 (1 H, br s); LC/MS (M+1) 463.

Example 99

Compound ADV $^1$H NMR (DMSO-d$_6$) δ 2.52 (3 H, m), 2.78 (1 H, dd, J=3.78, 14.24 Hz), 3.30 (4 H, m), 3.63 (1 H, m), 3.77 (4 H, m), 4.68 (2 H, m), 7.24 (1 H, t, J=6.97 Hz), 7.40 (1 H, t, J=6.97 Hz), 7.55 (1 H, br s), 7.74 (1 H, s), 7.86 (1 H, d, J=7.28 Hz), 8.11 (1 H, s), 11.46 (1 H, br s); LC/MS (M+1) 449.

Example 100

Compound ADY $^1$H NMR (DMSO-d$_6$) δ 1.33 (3 H, d, J=6.76 Hz), 2.49 (2 H, m), 2.81 (3 H, m), 3.74 (2 H, m), 3.60 (3 H, m), 4.21 (1 H, d, J=12.29 Hz), 4.64 (3 H, m), 7.21 (1H, t, J=9.65 Hz), 7.54 (1H, br s), 7.70 (1 H, s), 7.78 (1 H, d, J=7.25 Hz), 8.08 (1 H, s), 11.46 (1 H, br s); LC/MS (M+1) 481.

Example 101

Compound ADZ $^1$H NMR (DMSO-d$_6$) δ 1.34 (3 H, d, J=6.60 Hz), 2.37 (3 H, s), 2.47 (2 H, m), 2.80 (3 H, m), 3.28 (2 H, m), 3.60 (3 H, m), 4.22 (1 H, m), 4.64 (3 H, m), 7.18 (1 H, d, J=8.29 Hz), 7.40 (1 H, br s), 7.61 (1 H, br s), 7.70 (1 H, s), 8.08 (1 H, s), 11.46 (1 H, br s); LC/MS (M+1) 477.

Example 102

Compound AEA $^1$H NMR (DMSO-d$_6$) 1.35 (3 H, d, J=6.60 Hz), 2.47 (2 H, m), 2.75 (1 H, dd, J=3.72, 14.26 Hz), 2.84 (2 H, m), 3.28 (2 H, m), 3.60 (3 H, m), 4.21 (1 H, m), 4.64 (3 H, m), 7.21 (1 H, m), 7.36 (1 H, t, J=7.52 Hz), 7.61 (2 H, br s), 7.85 (1 H, br s), 11.49 (1 H, br s) 8.08 (1 H, s); LC/MS (M+1) 463

Example 103

Compound AEE $^1$H NMR (DMSO-d$_6$) δ 1.35 (3 H, d, J=6.78 Hz), 2.48 (1 H, m), 2.81 (3 H, m), 3.27 (3 H, m), 3.60 (3 H, m), 4.22 (1 H, d, J=13.32 Hz), 4.64 (3 H, m), 7.39 (1 H, dd, J=1.70, 8.30 Hz), 7.53 (1 H, br s), 7.70 (1 H, s), 7.98 (1 H, br s), 8.08 (1 H, s), 11.53 (1 H, br s); LC/MS (M+1) 497.

Example 104

Compound AEH $^1$H NMR (DMSO-d$_6$) δ 2.28 (6 H, s), 2.47 (1 H, m), 2.75 (1 H, dd, J=4.17, 13.81 Hz), 3.23 (5 H, m), 3.32 (1 H, m), 3.59

(1 H, m), 3.72 (4 H, m), 7.29 (1 H, m), 7.56 (1 H, s), 7.70 (1 H, d, J=1.97 Hz), 8.08 (1 H, d, J=1.97 Hz); LC/MS (M+1) 476.

Example 105

Compound AEI $^1$H NMR (DMSO-d$_6$) δ 2.48 (1 H, dd, J=7.89, 14.03 Hz), 2.71 (1 H, dd, J=4.39, 14.03 Hz), 3.32 (6 H, m), 3.59 (1 H, m), 3.72 (4 H, m), 4.64 (2 H, br s), 7.20 (1 H, t, J=7.89 Hz), 7.36 (1 H, t, J=7.89 Hz), 7.44 (1 H, dd, J=1.75, 14.03 Hz), 7.51 (1 H, br s), 7.81 (1 H, d, J=7.89 Hz), 7.89 (1 H, s); LC/MS (M+1) 432.

Example 106

Compound AEP $^1$H NMR (DMSO-d$_6$) δ 1.23 (3 H, d, J=7.02 Hz), 2.40 (4 H, m), 2.73 (1 H, dd, J=3.51, 14.03 Hz), 2.82 (1 H, t, J=12.28 Hz), 3.03 (1 H, d, J=10.52 Hz), 3.29 (4 H, m), 3.57 (1 H, m), 3.75 (1 H, d, J=12.28 Hz), 3.90 (1 H, d, J=11.40 Hz), 4.18 (1 H, br s), 4.67 (2 H, m), 7.18 (1 H, d, J=7.89 Hz), 7.40 (1 H, d, J=14.91 Hz), 7.63 (2 H, m), 7.87 (1 H, s), 11.19 (1 H, br s); LC/MS (M+1) 460.

Example 107

Compound AEQ $^1$H NMR (DMSO-d$_6$) δ 1.24 (3 H, d, J=7.20 Hz), 2.46 (1 H, m), 2.79 (2 H, m), 3.00 (1 H, d, J=11.40 Hz), 3.27 (3 H, m), 3.57 (1 H, m), 3.74 (1 H, d, J=13.13 Hz), 3.89 (1 H, d, J=12.17 Hz), 4.12-4.66 (4 H, m), 7.21 (1 H, m), 7.36 (1 H, t, J=7.02 Hz), 7.43 (1H, dd, J=1.75, 14.03 Hz), 7.64 (2 H, m), 7.87 (1 H, s), 11.28 (1 H, br s); LC/MS (M+1) 446.

Example 108

Compound AER $^1$H NMR (DMSO-d$_6$) δ 2.45 (1 H, dd, J=8.77, 14.03 Hz), 2.72 (1 H, dd, J=4.39, 14.03 Hz), 3.30 (6 H, m), 3.59 (1 H, m), 3.71 (4 H, m), 7.07 (1 H, m), 7.36 (1 H, d, J=4.65 Hz), 7.45 (1 H, d, J=14.03 Hz), 7.89 (2 H, m); LC/MS (M+1) 450.

Example 109

Compound AES $^1$H NMR (DMSO-d$_6$) δ 2.45 (1 H, dd, J=8.77, 14.03 Hz), 2.72 (1 H, dd, J=4.39, 14.03 Hz), 3.30 (6 H, m), 3.59 (1 H, m), 3.71 (4 H, m), 7.07 (1 H, m), 7.36 (1 H, d, J=4.65 Hz), 7.45 (1 H, d, J=14.03 Hz), 7.89 (2 H, m); LC/MS (M+1) 450.

Example 110

Compound AEU $^1$H NMR (DMSO-d$_6$) δ 1.25 (3 H, d, J=6.80 Hz), 2.28 (6 H, m), 2.43 (1 H, m), 2.77 (2 H, m), 2.98 (1 H, m), 3.26 (3 H, m), 3.57 (1 H, m), 3.74 (1 H, d, J=13.06 Hz), 3.87 (1 H, d, J=11.40 Hz), 4.21 (1H, m), 4.62 (3H, m), 7.60 (2H, m), 7.42 (1H, dd, J=1.75, 14.25 Hz), 7.86 (1H, s); LC/MS (M+1) 474.

Example 111

Compound AEV $^1$H NMR (DMSO-d$_6$) δ 1.25 (3 H, d, J=6.58 Hz), 2.45 (1 H, dd, J=7.89, 14.03 Hz), 2.73 (1 H, dd, J=4.60, 14.03 Hz), 2.84 (1 H, m), 3.02 (1 H, d, J=10.74 Hz), 3.28 (3 H, m), 3.59 (1 H, m), 3.73 (1 H, d, J=12.28 Hz), 3.98 (1 H, d, J=12.28 Hz), 4.00-4.61 (4 H, m), 7.08 (1 H, m), 7.40 (1 H, dd, J=1.75, 14.25 Hz), 7.45 (1 H, m), 7.87 (2 H, m), 11.35 (1 H, br s); LC/MS (M+1) 464.

Example 112

Compound AEW $^1$H NMR (DMSO-d$_6$) δ 1.25 (3 H, d, J=6.58 Hz), 2.45 (1 H, dd, J=7.89, 14.03 Hz), 2.73 (1 H, dd, J=4.60, 14.03 Hz), 2.84 (1 H, m), 3.02 (1 H, d, J=10.74 Hz), 3.28 (3 H, m), 3.59 (1 H, m), 3.73 (1 H, d, J=12.28 Hz), 3.98 (1 H, d, J=12.28 Hz), 4.00-4.61 (4 H, m), 7.08 (1 H, m), 7.40 (1 H, dd, J=1.75, 14.25 Hz), 7.45 (1 H, m), 7.87 (2 H, m), 11.35 (1 H, s); LC/MS (M+1) 464.

Example 113

Compound AEX $^1$H NMR (DMSO-d$_6$) δ 2.48 (1 H, dd, J=7.89, 14.03 Hz), 2.71 (1 H, dd, J=4.39, 14.03 Hz), 3.32 (6 H, m), 3.59 (1 H, m), 3.72 (4 H, m), 4.64 (2 H, br s), 7.20 (1 H, t, J=7.89 Hz), 7.36 (1 H, t, J=7.89 Hz), 7.44 (1 H, dd, J=1.75, 14.03 Hz), 7.51 (1H, br s), 7.81 (1 H, d, J=7.89 Hz), 7.89 (1 H, s); LC/MS (M+1) 432.

Example 114

Compound AEY $^1$H NMR (DMSO-d$_6$) δ 1.25 (3 H, d, J=6.80 Hz), 2.47 (1 H, dd, J=8.11, 13.81 Hz), 2.73 (1 H, dd, J=3.95, 14.03 Hz), 2.91 (1 H, m), 3.09 (1 H, dd, J=3.71, 13.15 Hz), 3.28 (3 H, m), 3.58 (1 H, m), 3.74 (1 H, d, J=12.72 Hz), 3.90 (1 H, d, J=12.28 Hz), 4.17 (1 H, d, J=13.15 Hz), 4.58 (1 H, m), 7.50 (1 H, dd, J=1.54, 14.03 Hz), 7.63 (1 H, m), 7.87 (1 H, s), 8.04 (1 H, dd, J=8.11, 10.30 Hz); LC/MS (M+1) 482.

Example 115

Compound AEZ $^1$H NMR (DMSO-d$_6$) δ 1.25 (3 H, d, J=6.80 Hz), 2.47 (1 H, dd, J=8.11, 13.81 Hz), 2.73 (1 H, dd, J=3.95, 14.03 Hz), 2.91 (1 H, m), 3.09 (1 H, dd, J=3.71, 13.15 Hz), 3.28 (3 H, m), 3.58 (1 H, m), 3.74 (1 H, d, J=12.72 Hz), 3.90 (1 H, d, J=12.28 Hz), 4.17 (1 H, d, J=13.15 Hz), 4.58 (1 H, m), 7.50 (1 H, dd, J=1.54, 14.03 Hz), 7.63 (1 H, m), 7.87 (1 H, s), 8.04 (1 H, dd, J=8.11, 10.30 Hz); LC/MS (M+1) 482.

Example 116

Compound AFA $^1$H NMR (DMSO-d$_6$) δ 2.48 (1 H, dd, J=8.11, 14.03 Hz), 2.74 (1 H, dd, J=3.95, 14.03 Hz), 3.25 (1 H, dd, J=5.70, 10.74 Hz), 3.33 (1 H, dd, J=5.26, 10.52 Hz), 3.41 (4 H, m), 3.59 (1 H, m), 3.71 (4 H, m), 7.50 (1 H, dd, J=1.54, 14.03 Hz), 7.65

(1 H, dd, J=7.45, 11.40 Hz), 7.88 (1 H, s), 8.04 (1 H, dd, J=8.11, 10.30 Hz); LC/MS (M+1) 468.

Example 117

Compound AFB

¹H NMR (DMSO-d₆) δ 2.48 (1 H, dd, J=8.11, 14.03 Hz), 2.74 (1 H, dd, J=3.95, 14.03 Hz), 3.25 (1 H, dd, J=5.70, 10.74 Hz), 3.33 (1 H, dd, J=5.26, 10.52 Hz), 3.41 (4 H, m), 3.59 (1 H, m), 3.71 (4 H, m), 7.50 (1 H, dd, J=1.54, 14.03 Hz), 7.65 (1 H, dd, J=7.45, 11.40 Hz), 7.88 (1 H, s), 8.04 (1 H, dd, J=8.11, 10.30 Hz); LC/MS (M+1) 468.

Example 118

Preparation of Compound AFV

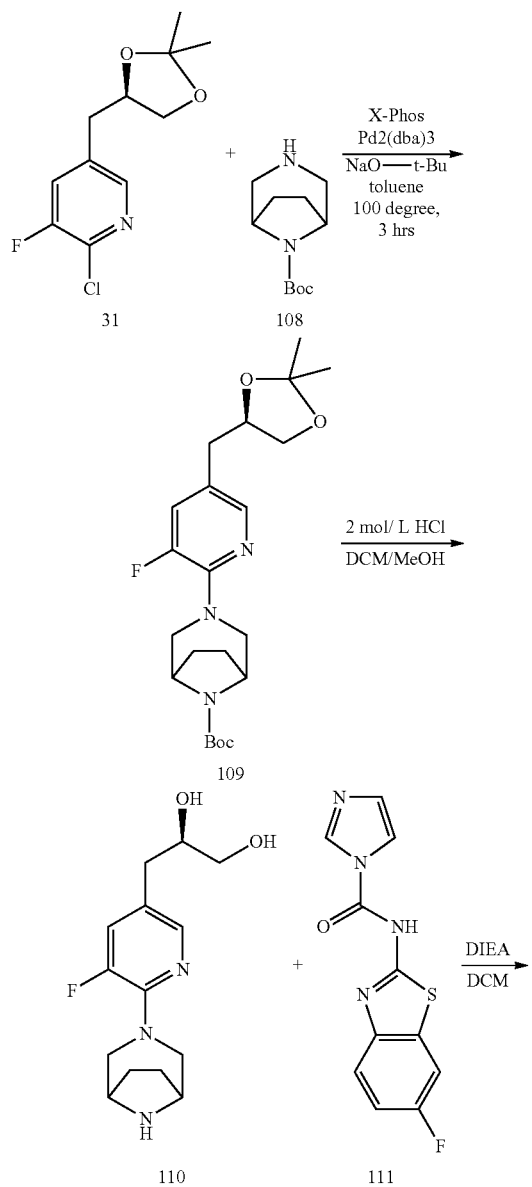

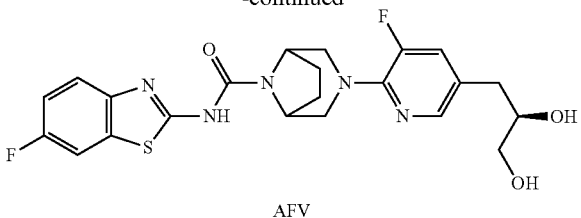

AFV

Step 1. Preparation of tert-butyl 3-{5-[((R)-2,2-dimethyl-1,3-dioxolan-4-yl)methyl]-3-fluoropyridin-2-yl}-3,8-diazabicyclo[3.2.1]octane-8-carboxylate (109)

To a solution of 31 (0.70 g, 2.83 mmol) in toluene (8.7 mL) under argon was added 108 (0.69 g, 2.83 mmol), sodium t-butoxide (0.30 g, 3.11 mmol) and 2-dicyclohexylphosphino-2',4',6'-triisopropylbiphenyl (X-Phos) (0.20 g, 0.42 mmol). The mixture was degassed with argon and then tris(dibenzylideneacetone) dipalladium (0.26 g, 0.283 mmol) was added. The resulting mixture was stirred at 80-85° C. for 1.5 hrs. Then it was cooled to room temperature, poured onto cold water and extracted with ethyl acetate. The organic layer was separated, washed with brine, and concentrated to an oil which was purified on silica gel with 10% ethyl acetate in hexanes and 20% ethyl acetate in hexanes to afford 0.70 g (59%) of 3 as an amber solid. ¹H NMR (CDCl₃) δ 1.34 (3 H, s), 1.43 (3 H, s), 1.48 (9 H, s), 1.91 (4 H, m), 2.72 (1 H, m), 2.81 (1 H, m), 3.14 (2 H, d, J=12.04 Hz), 3.61 (1 H, m), 3.71 (2 H, br s), 4.02 (1 H, m), 4.25 (2 H, m), 4.34 (1 H, br s), 7.16 (1 H, d, J=13.98 Hz), 7.83 (1 H, s); LC/MS (M+1) 422.

Step 2. Preparation of (R)-3-{6-[3,8-diazabicyclo[3.2.1]octan-3-yl]-5-fluoropyridin-3-yl}propane-1,2-diol dihydrochloride (110)

A solution of 109 (0.70 g, 1.67 mmol) in dichloromethane (4.0 mL) and methanol (1.0 mL) was treated at room temperature with 4 mol/L HCl in dioxane (2.5 mL) in a closed vessel for 16 hrs. The resulting suspension was stirred with ether (10 mL). The solid precipitate was collected on filter paper and washed several times with ether to afford a tan solid 110 (95% yield) which was confirmed by LC/MS and used directly for the next step.

Step 3. Preparation of Compound AFV

A suspension of 110 (0.160 g, 0.50 mmol) and 111 (0.132 g, 0.50 mmol) in dichloromethane (5 mL) was cooled with an ice bath and treated with diisopropylethylamine (1.0 mL). The resulting mixture was stirred at room temperature overnight. The precipitate was collected by filtration and washed several times with ethyl ether. The obtained solid was suspend in 2 mol/L HCl aq. solution which was stirred at room temperature 12 hrs, then 1 mol/L NaOH was added to neutralize to a pH of about 6. The collected solid by filtration was dried by oven to afford 0.13 g (yield 55%) AFV as a pale yellow solid. ¹H NMR (CD₃OD) δ 2.05 (4 H, m), 2.58 (1 H, dd, J=8.33, 14.25 Hz), 2.81 (1 H, dd, J=4.16, 14.03 Hz), 3.18 (2 H, m), 3.49 (2 H, m), 3.77 (3 H, m), 4.65 (2 H, m), 7.15 (1 H, m), 7.36 (1 H, dd, J=1.75, 14.25 Hz), 7.56 (1 H, dd, J=2.41, 8.33 Hz), 7.60 (1 H, br s), 7.83 (1 H, s); LC/MS (M+1) 476.

Example 119

Compound AFW $^1$H NMR (DMSO-d$_6$) δ 1.08 (3 H, d, J=6.58 Hz), 2.47 (1 H, dd, J=8.11, 14.25 Hz), 2.73 (1 H, dd, J=4.17, 14.03 Hz), 3.28 (4 H, m), 3.41 (1 H, d, J=12.06 Hz), 3.59 (2 H, m), 4.01 (1 H, d, J=12.71 Hz), 4.18 (2 H, m), 7.09 (1 H, m), 7.38 (1 H, d, J=9.21 Hz), 7.49 (1 H, dd, J=1.54, 14.25 Hz), 7.89 (2 H, m); LC/MS (M+1) 464.

Example 120

Compound AGI $^1$H NMR (DMSO-d$_6$) δ 1.08 (3 H, d, J=6.58 Hz), 2.47 (1 H, dd, J=8.11, 14.25 Hz), 2.73 (1H, dd, J=4.17, 14.03 Hz), 3.28 (4 H, m), 3.41 (1 H, d, J=12.06 Hz), 3.59 (2 H, m), 4.01 (1 H, d, J=12.71 Hz), 4.18 (2 H, m), 7.09 (1 H, m), 7.38 (1 H, d, J=9.21 Hz), 7.49 (1 H, dd, J=1.54, 14.25 Hz), 7.89 (2 H, m); LC/MS (M+1) 464.

Example 121

Compound AGJ $^1$H NMR (DMSO-d$_6$) δ 1.08 (3 H, d, J=6.36 Hz), 2.46 (1 H, dd, J=8.33, 14.25 Hz), 2.72 (1H, dd, J=4.17, 14.23 Hz), 3.28 (4 H, m), 4.43 (1 H, d, J=11.18 Hz), 3.59 (2 H, m), 3.99 (1 H, d, J=12.49 Hz), 4.16 (2 H, m), 7.32 (1 H, m), 7.44 (1 H, d, J=14.25 Hz), 7.73 (1 H, dd, J=1.75, 8.33 Hz), 7.89 (1 H, s), 11.60 (1 H, br s); LC/MS (M+1) 482.

Example 122

Compound AGK $^1$H NMR (DMSO-d$_6$) δ 1.07 (3 H, d, J=6.58 Hz), 2.46 (1 H, dd, J=7.89, 13.81 Hz), 2.72 (1 H, dd, J=4.17, 14.25 Hz), 3.28 (5 H, m), 3.41 (1 H, d, J=12.49 Hz), 3.58 (2 H, m), 4.01 (1 H, d, J=12.94 Hz), 4.16 (2 H, m), 7.39 (1 H, dd, J=2.19, 8.77 Hz), 7.43 (1 H, dd, J=1.75, 14.25 Hz), 7.55 (1 H, br s), 7.89 (1 H, s), 8.00 (1 H, s); LC/MS (M+1) 480.

Example 123

Compound AGL $^1$H NMR (DMSO-d$_6$) δ 1.08 (3 H, d, J=6.58 Hz), 2.47 (1 H, dd, J=8.11, 14.03 Hz), 2.73 (1H, dd, J=3.95, 14.03 Hz), 3.28 (5 H, m), 3.41 (1 H, d, J=11.84 Hz), 3.59 (2 H, m), 3.99 (1 H, d, J=11.84 Hz), 4.17 (2 H, m), 7.46 (1 H, d, J=14.25 Hz), 7.65 (1 H, m), 7.89 (1 H, s), 8.07 (1 H, dd, J=8.11, 10.30 Hz); LC/MS (M+1) 482.

Example 124

Compound AGU $^1$H NMR (DMSO-d$_6$) δ 1.28 (3 H, d, J=6.58 Hz), 2.57 (1 H, dd, J=8.11, 13.81 Hz), 2.85 (1 H, dd, J=3.50, 13.81 Hz), 2.89 (1 H, m), 3.08 (1 H, m), 3.15-3.37 (5 H, m), 3.62 (1 H, m), 4.14 (1 H, m), 4.58 (1 H, m), 4.69 (1 H, t, J=5.70 Hz), 4.73 (1 H, d, J=5.48 Hz), 7.22 (1 H, m), 7.65 (1 H, br s), 7.81 (1 H, br s), 7.97 (1 H, d, J=2.19 Hz), 8.43 (1 H, d, J=1.75 Hz), 11.29 (1 H, br s); LC/MS (M+1) 514.

Example 125

Compound AGV $^1$H NMR (CD$_3$OD) δ 1.28 (3 H, d, J=6.80 Hz), 2.58 (1 H, m), 2.83 (1 H, m), 3.06-3.41 (6 H, m), 3.67 (1 H, m), 4.16 (1 H, d, J=13.15 Hz), 4.61 (1 H, br s), 7.10 (1 H, m), 7.24 (1 H, m), 7.34 (1 H, d, J=8.11 Hz), 7.56 (1 H, d, J=7.67 Hz), 7.88 (1 H, d, J=2.19 Hz), 8.31 (1 H, d, J=1.97 Hz); LC/MS (M+1) 496.

Example 126

Compound AGW $^1$H NMR (DMSO-d$_6$) δ 1.28 (3 H, d, J=6.58 Hz), 2.57 (1 H, dd, J=8.11, 13.81 Hz), 2.85 (1H, dd, J=3.50, 13.81 Hz), 2.89 (1 H, m), 3.08 (1 H, m), 3.15-3.37 (5 H, m), 3.62 (1 H, m), 4.14 (1 H, m), 4.58 (1 H, m), 4.69 (1 H, t, J=5.70 Hz), 4.73 (1 H, d, J=5.48 Hz), 7.22 (1 H, m), 7.65 (1 H, br s), 7.81 (1 H, br s), 7.97 (1 H, d, J=2.19 Hz), 8.43 (1 H, d, J=1.75 Hz), 11.29 (1 H, br s); LC/MS (M+1) 514.

Example 127

Compound AGY $^1$H NMR (CD$_3$OD) δ 1.28 (3 H, d, J=6.80 Hz), 2.58 (1 H, m), 2.83 (1 H, m), 3.06-3.41 (6 H, m), 3.67 (1 H, m), 4.16 (1 H, d, J=13.15 Hz), 4.61 (1 H, br s), 7.10 (1 H, m), 7.24 (1 H, m), 7.34 (1 H, d, J=8.11 Hz), 7.56 (1 H, d, J=7.67 Hz), 7.88 (1 H, d, J=2.19 Hz), 8.31 (1 H, d, J=1.97 Hz); LC/MS (M+1) 496.

Example 128

Compound AGZ $^1$H NMR (DMSO-d$_6$) δ 1.25 (3 H, d, J=6.58 Hz), 2.45 (1 H, dd, J=8.11, 14.03 Hz), 2.72 (1H, dd, J=3.73, 14.03 Hz), 2.84 (1 H, m), 3.02 (1 H, m), 3.29 (3 H, m), 3.58 (1 H, m), 3.73 (1 H, d, J=12.72 Hz), 3.88 (1 H, d, J=12.06 Hz), 4.11-4.56 (4 H, m), 7.22 (1 H, m), 7.43 (1 H, dd, J=1.54, 14.03 Hz), 7.65 (1 H, br s), 7.82 (1 H, br s), 7.87 (1 H, s), 11.29 (1 H, br s); LC/MS (M+1) 464.

Example 129

Compound AHA

Compound AHA was obtained in the same manner as Example for AFV: $^1$H NMR (CD$_3$OD) δ 2.05 (4 H, m), 2.59 (1 H, dd, J=8.11, 14.25 Hz), 2.80 (1 H, dd, J=4.38, 14.25 Hz), 3.19 (2 H, m), 3.77 (3 H, m), 4.66 (2 H, m), 7.24 (1 H, m), 7.38 (1 H, m), 7.58 (1 H, br s), 7.75 (1 H, d, J=7.45 Hz), 7.87 (1 H, s); LC/MS (M+1) 458.

Example 130

Compound AHB

Compound AHB was obtained in the same manner as Example for AFV: $^1$H NMR (CD$_3$OD) δ 2.05 (4 H, m), 2.58 (1 H, dd, J=8.33, 14.25 Hz), 2.81 (1 H, dd, J=4.16, 14.03 Hz), 3.18 (2 H, m), 3.49 (2 H, m), 3.77 (3 H, m), 4.65 (2 H, m), 7.15

(1 H, m), 7.36 (1 H, dd, J=1.75, 14.25 Hz), 7.56 (1 H, dd, J=2.41, 8.33 Hz), 7.60 (1 H, br s), 7.83 (1 H, s); LC/MS (M+1) 476.

Example 131

Compound AFT $^1$H NMR (DMSO-d$_6$) δ 1.48 (6 H, s), 2.48-2.40 (1 H, m), 2.70 (1 H, dd, J=3.95, 14.03 Hz), 3.32-3.21 (2 H, m), 3.48 (2 H, s), 3.63-3.53 (3 H, m), 3.81 (2 H, br s), 4.66-4.59 (2 H, m), 7.21 (1 H, t, J=8.6 Hz), 7.37 (1 H, d, J=15.1 Hz), 7.61 (1 H, br s), 7.77 (1 H, br s), 7.83 (1 H, s), 11.30 (1 H, br s); LC/MS (M+1) 478.

Example 132

Compound AFU $^1$H NMR (DMSO-d$_6$) δ 1.33 (6 H, d, J=6.6 Hz), 2.48-2.43 (1 H, m), 2.74 (1 H, dd, J=3.73, 13.81 Hz), 2.98-2.90 (2 H, m), 3.33-3.22 (2 H, m), 3.63-3.55 (3 H, m), 3.79 (2 H, d, J=12.1 Hz), 4.52 (2 H, br s), 4.68-4.61 (2 H, m), 7.21 (1 H, t, J=7.9 Hz), 7.44 (1 H, d, J=14.0 Hz), 7.62 (1 H, br s), 7.77 (1 H, br s), 7.88 (1 H, s), 11.23 (1 H, br s); LC/MS (M+1) 478.

Example 133

Compound AGD $^1$H NMR (DMSO-d$_6$) δ 1.27 (3 H, d, J=6.4 Hz), 2.48-2.41 (1 H, m), 2.73 (1 H, d, J=13.6 Hz), 2.85 (1 H, t, J=11.6 Hz), 3.03 (1 H, d, J=12.9 Hz), 3.33-3.20 (3 H, m), 3.64-3.54 (1 H, m), 3.73 (1 H, d, J=13.2 Hz), 3.89 (1 H, d, J=11.8 Hz), 4.19 (1 H, d, J=12.1 Hz), 4.70-4.55 (3 H, m), 7.23 (1 H, t, J=7.9 Hz), 7.50-7.39 (2 H, m), 7.91-7.84 (2 H, m), 11.59 (1 H, br s); LC/MS (M+1) 480.

Example 134

Compound AGE $^1$H NMR (DMSO-d$_6$) δ 1.26 (3 H, d, J=6.6 Hz), 2.49-2.42 (1 H, m), 2.54 (3 H, s), 2.73 (1 H, dd, J=3.95, 13.81 Hz), 2.83 (1 H, t, J=11.8 Hz), 3.01 (1 H, d, J=12.5 Hz), 3.33-3.21 (3 H, m), 3.63-3.55 (1 H, m), 3.73 (1 H, d, J=12.7 Hz), 3.89 (1 H, d, J=12.5 Hz), 4.19 (1 H, br s), 4.68-4.60 (3 H, m), 7.14-7.08 (1 H, m), 7.20-7.15 (1 H, m), 7.42 (1 H, d, J=14.0 Hz), 7.66 (1 H, br s), 7.87 (1 H, s), 11.24 (1 H, br s); LC/MS (M+1) 460.

Example 135

Compound AGF $^1$H NMR (DMSO-d$_6$) δ 1.26 (3 H, d, J=6.8 Hz), 2.48-2.42 (1 H, m), 2.73 (1 H, dd, J=3.95, 13.81 Hz), 2.85 (1 H, dt, J=3.29, 12.28 Hz), 3.03 (1 H, dd, J=3.07, 13.15 Hz), 3.33-3.21 (3 H, m), 3.63-3.54 (1 H, m), 3.73 (1 H, d, J=12.5 Hz), 3.89 (1 H, d, J=11.8 Hz), 4.16 (1 H, d, J=13.2 Hz), 4.57 (1 H, br s), 4.68-4.61 (2 H, m), 7.31 (1 H, dt, J=2.19, 10.52 Hz), 7.42 (1 H, d, J=14.3 Hz), 7.72 (1 H, dd, J=1.32, 8.11 Hz), 7.87 (1 H, s), 11.56 (1 H, br s); LC/MS (M+1) 482.

Example 136

Compound AGG $^1$H NMR (DMSO-d$_6$) δ 1.27 (3 H, d, J=6.6 Hz), 2.48-2.41 (1 H, m), 2.73 (1 H, d, J=14.0 Hz), 2.86 (1 H, d, J=10.7 Hz), 3.04 (1 H, d, J=12.5 Hz), 3.32-3.21 (3 H, m), 3.63-3.53 (1 H, m), 3.75 (1 H, d, J=12.1 Hz), 3.90 (1 H, d, J=11.6 Hz), 4.23 (1 H, d, J=11.6 Hz), 4.69-4.58 (3 H, m), 7.43 (1 H, d, J=14.0 Hz), 7.91-7.81 (2 H, m), 8.03 (1 H, d, J=8.6 Hz), 8.81 (1 H, s), 12.21 (1 H, br s); LC/MS (M+1) 578.

Example 137

Compound AGH $^1$H NMR (DMSO-d$_6$) δ 1.23 (3 H, d, J=6.8 Hz), 2.46-2.40 (1 H, m), 2.71 (1 H, dd, J=3.51, 14.25 Hz), 2.83 (1 H, dt, J=3.07, 12.72 Hz), 3.01 (1 H, dd, J=3.07, 12.28 Hz), 3.31-3.18 (3 H, m), 3.60-3.52 (1 H, m), 3.72 (1 H, d, J=12.5 Hz), 3.87 (1 H, d, J=12.5 Hz), 4.19 (1 H, d, J=12.7 Hz), 4.66-4.55 (3 H, m), 7.40 (1 H, d, J=13.8 Hz), 7.52 (1 H, d, J=8.3 Hz), 7.88-7.75 (2 H, m), 8.10 (1 H, br s), 11.61 (1 H, br s); LC/MS (M+1) 514.

Example 138

Compound AGP $^1$H NMR (DMSO-d$_6$) δ 1.25 (3 H, d, J=6.8 Hz), 2.48-2.41 (1 H, m), 2.72 (1 H, dd, J=3.29, 14.25 Hz), 2.83 (1 H, dt, J=3.07, 12.28 Hz), 3.02 (1 H, dd, J=2.85, 12.94 Hz), 3.32-3.21 (3 H, m), 3.63-3.54 (1 H, m), 3.73 (1 H, d, J=12.5 Hz), 3.89 (1 H, d, J=12.1 Hz), 4.19 (1 H, d, J=11.4 Hz), 4.69-4.56 (3 H, m), 7.26 (1 H, dd, J=1.75, 8.11 Hz), 7.42 (1 H, d, J=14.0 Hz), 7.58 (1 H, br s), 7.94-7.84 (2 H, m), 11.56 (1 H, br s); LC/MS (M+1) 480.

Example 139

Compound AGQ $^1$H NMR (DMSO-d$_6$) δ 1.29-1.20 (3 H, m), 2.38 (3 H, s), 2.48-2.41 (1 H, m), 2.72 (1 H, dd, J=3.73, 13.81 Hz), 2.88-2.76 (1 H, m), 3.00 (1 H, d, J=11.4 Hz), 3.32-3.20 (3 H, m), 3.63-3.53 (1 H, m), 3.73 (1 H, d, J=12.3 Hz), 3.88 (1 H, d, J=11.8 Hz), 4.18 (1 H, br s), 4.70-4.51 (3 H, m), 7.03 (1 H, s), 7.32-7.22 (0.5 H, m), 7.42 (1 H, d, J=14.0 Hz), 7.80-7.46 (1.5 H, m), 7.87 (1 H, s), 11.24 (0.5 H, br s), 12.52 (0.5 H, br s); LC/MS (M+1) 460.

Example 140

Compound AGR $^1$H NMR (DMSO-d$_6$) δ 1.26 (3 H, d, J=6.6 Hz), 2.48-2.42 (1 H, m), 2.73 (1 H, dd, J=3.51, 14.03 Hz), 2.84 (1 H, t, J=11.0 Hz), 3.03 (1 H, d, J=12.1 Hz), 3.32-3.21 (3 H, m), 3.63-3.54 (1 H, m), 3.74 (1 H, d, J=13.2 Hz), 3.89 (1 H, d, J=11.8 Hz), 4.21 (1 H, s), 4.70-4.57 (3 H, m), 7.42 (1 H, d, J=14.0 Hz), 7.64 (1 H, br s), 7.67 (1 H, d, J=7.2 Hz), 7.87 (1 H, s), 8.31 (1 H, br s), 11.63 (1 H, br s); LC/MS (M+1) 546.

Example 141

Compound AGS $^1$H NMR (DMSO-d$_6$) δ 1.25 (3 H, d, J=6.6 Hz), 2.48-2.43 (1 H, m), 2.73 (1 H, dd, J=3.95, 13.59 Hz), 2.84 (1 H, dt, J=3.07, 12.72 Hz), 3.02 (1 H, dd, J=3.51, 12.94 Hz), 3.33-3.21 (3 H, m), 3.63-3.54 (1 H, m), 3.73 (1 H, d, J=12.5 Hz), 3.88 (1 H, d, J=12.5 Hz), 4.16 (1 H, d, J=12.5 Hz), 4.57 (1 H, br s), 4.67-4.61 (2 H, m), 7.42 (1 H, dd, J=1.32, 14.25 Hz), 7.68 (1 H, br s), 7.87 (1 H, s), 8.01 (1 H, s), 11.37 (1 H, br s); LC/MS (M+1) 526.

Example 142

Compound AGT $^1$H NMR (DMSO-d$_6$) δ 1.26 (3 H, d, J=6.6 Hz), 2.48-2.43 (1 H, m), 2.73 (1 H, dd, J=4.17, 14.25 Hz), 2.85 (1 H, dt, J=3.29, 12.50 Hz), 3.04 (1 H, dd, J=3.07, 13.15 Hz), 3.33-3.21 (3 H, m), 3.63-3.54 (1 H, m), 3.73 (1 H, d, J=12.3 Hz), 3.89 (1 H, d, J=12.3 Hz), 4.17 (1 H, d, J=13.2 Hz), 4.58 (1 H, br s), 4.68-4.61 (2 H, m), 7.35-7.27 (1 H, m), 7.42 (1 H, dd, J=1.54, 14.03 Hz), 7.77-7.72 (1 H, m), 7.88 (1 H, s), 11.65 (1 H, br s); LC/MS (M+1) 482.

Example 143

Compound AFX $^1$H NMR (CD$_3$OD) δ 0.98 (3 H, t, J=7.55 Hz), 1.85 (2 H, m), 2.49-2.95 (4 H, m), 3.10-3.40 (3 H, m), 3.60-3.80 (3 H, m), 4.21-4.45 (2 H, m), 7.06 (1 H, m), 7.30-7.50 (3 H, m), 7.86 (1 H, s); LC/MS (M+1) 478.

Example 144

Compound AFZ $^1$H NMR (CD$_3$OD) δ 1.57 (6 H, s), 2.59-2.85 (2 H, m), 3.50-3.90 (9 H, m), 7.16 (1 H, m), 7.50 (1 H, m), 7.65 (2 H, m), 7.86 (1 H, s); LC/MS (M+1) 478.

Example 145

Compound AGA $^1$H NMR (CD$_3$OD) δ 2.57-2.80 (2 H, m), 2.91-3.15 (2 H, m), 3.20-4.80 (10 H, m), 7.16 (1 H, m), 7.45-7.65 (3 H, m), 7.89 (1 H, s); LC/MS (M+1) 480.

Example 146

Compound AGB $^1$H NMR (CD$_3$OD) δ 1.25 (3 H, m); 2.49-2.95 (4 H, m), 3.15-3.95 (6 H, m), 4.15 (1 H, m), 4.65 (1 H, m), 7.16 (1 H, t, J=7.95 Hz), 7.25-7.55 (2 H, m), 7.75 (1 H, m), 7.79 (1 H, s); LC/MS (M+1) 480.

Example 147

Compound AGC $^1$H NMR (CD$_3$OD) δ 1.25 (3 H, m); 2.25-2.95 (7 H, m), 3.19-3.55 (3 H, m), 3.65-3.85 (3 H, m), 4.05 (1 H, m), 4.75 (1 H, m), 7.05 (2 H, m), 7.25 (1 H, d, J=14.02 Hz), 7.55 (1 H, s), 7.79 (1 H, s); LC/MS (M+1) 460.

Example 148

Compound AGM $^1$H NMR (CD$_3$OD) δ 1.25 (3 H, m); 2.25-2.99 (7 H, m), 3.19-3.40 (3 H, m), 3.55-3.75 (3 H, m), 4.15 (1 H, m), 4.75 (1 H, m), 6.95 (1 H, m), 7.15-7.55 (3 H, m), 7.90 (1 H, s); LC/MS (M+1) 460.

Example 149

Compound AGN $^1$H NMR (CD$_3$OD) δ 1.25 (3 H, m); 2.50-3.15 (4 H, m), 3.19-4.10 (6 H, m), 4.15 (1 H, m), 4.75 (1 H, m), 6.95 (1 H, m), 7.35 (1 H, d, J=11.20 Hz), 7.50 (1 H, d, J=8.70 Hz), 7.80-7.95 (3 H, m); LC/MS (M+1) 514.

Example 150

Compound AGO $^1$H NMR (CD$_3$OD) δ 1.24 (3 H, m), 2.49-2.95 (4 H, m), 3.20-3.45 (3 H, m), 3.50-3.83 (3 H, m), 4.21 (1 H, m), 4.69 (1 H, m), 7.21 (1 H, m), 7.30 (2 H, m), 7.70 (1 H, d, J=7.95 Hz), 7.86 (1 H, s); LC/MS (M+1) 480.

Example 151

Compound AEJ $^1$H NMR (DMSO-d$_6$) δ 1.24 (3 H, d, J=7.06 Hz), 2.47 (1 H, m), 2.75 (1 H, d, J=13.26 Hz), 2.83 (1 H, t, J=12.39 Hz), 3.03 (1 H, d, J=12.11 Hz), 3.28 (3 H, m), 3.58 (1 H, m), 3.75 (1 H, d, J=12.04 Hz), 3.87 (1 H, d, J=12.42 Hz), 4.18 (1 H, d, J=12.28 Hz), 4.62 (3 H, m), 7.21 (1 H, t, J=9.76 Hz), 7.43 (1 H, d, J=13.92 Hz), 7.50 (1 H, s), 7.78 (1 H, d, J=7.91 Hz), 7.87 (1 H, s), 11.46 (1 H, br s); LC/MS (M+1) 464.

Example 152

Compound AEK $^1$H NMR (DMSO-d$_6$) δ 1.26 (3 H, d, J=7.05 Hz), 2.47 (1 H, m), 2.74 (1 H, dd, J=5.01, 18.42 Hz), 2.83 (1 H, t, J=10.29 Hz), 3.03 (1 H, d, J=8.94 Hz), 3.28 (3 H, m), 3.58 (1 H, m), 3.72 (1 H, d, J=12.40 Hz), 3.90 (1 H, d, J=12.32 Hz), 4.18 (1 H, m), 4.62 (3 H, m), 7.40 (2 H, m), 7.54 (1 H, br s), 7.87 (1 H, s), 7.99 (1 H, s), 11.46 (1 H, br s); LC/MS (M+1) 480.

Example 153

Compound AEL $^1$H NMR (DMSO-d$_6$) δ 1.24 (3 H, d, J=7.05 Hz), 2.47 (1 H, m), 2.75 (1 H, d, J=18.04 Hz), 2.83 (1 H, t, J=10.16 Hz), 3.03 (1 H, d, J=9.03 Hz), 3.28 (3 H, m), 3.58 (1 H, m), 3.75 (1 H, d, J=12.26 Hz), 3.87 (1 H, d, J=12.17 Hz), 4.18 (1 H, d, J=13.24 Hz), 4.62 (3 H, m), 7.21 (1 H, t, J=8.62 Hz), 7.43 (1 H, d, J=14.06 Hz), 7.50 (1 H, s), 7.78 (1 H, d, J=8.14 Hz), 7.87 (1 H, s), 11.46 (1 H, br s); LC/MS (M+1) 464.

Example 154

Compound AEM $^1$H NMR (DMSO-d$_6$) δ 1.24 (3 H, d, J=7.04 Hz), 2.37 (3H, s), 2.47 (1 H, m), 2.74 (1 H, dd, J=4.98, 17.16 Hz), 2.83 (1 H, t, J=10.04 Hz), 3.03 (1 H, d, J=9.17 Hz), 3.28 (3 H, m), 3.58 (1 H, m), 3.73 (1 H, d, J=12.31 Hz), 3.87 (1 H, d, J=12.08 Hz), 4.22 (1 H, d, J=13.28 Hz), 4.62 (3 H, m), 7.16 (1 H, d, J=8.45 Hz) 7.39 (1 H, br s), 7.39 (1 H, d, J=14.16 Hz), 7.61 (1 H, br s), 7.87 (1 H, s), 11.46 (1 H, br s); LC/MS (M+1) 460.

Example 155

Compound AEN

¹H NMR (DMSO-d₆) δ 1.24 (3 H, d, J=7.0 Hz), 2.47 (1 H, m), 2.71 (1 H, dd, J=4.89, 16.88 Hz), 2.83 (1 H, t, J=9.89 Hz), 3.03 (1 H, d, J=9.38 Hz), 3.28 (3 H, m), 3.58 (1 H, m), 3.72 (1 H, d, J=12.22 Hz), 3.87 (1 H, d, J=12.23 Hz), 4.20 (1 H, d, J=13.19 Hz), 4.62 (3 H, m), 7.40 (2 H, m), 7.52 (1 H, br s), 7.87 (1 H, s), 7.98 (1 H, s), 11.46 (1 H, br s); LC/MS (M+1) 480.

Example 156

Compound AEO

¹H NMR (DMSO-d₆) δ 1.24 (3 H, d, J=7.02 Hz), 2.47 (1 H, m), 2.71 (1 H, dd, J=5.12, 17.20 Hz), 2.83 (1 H, m), 3.03 (1 H, d, J=9.42 Hz), 3.28 (3 H, m), 3.58 (1 H, m), 3.72 (1 H, d, J=11.97 Hz), 3.91 (1 H, d, J=12.07 Hz), 4.20 (1 H, m), 4.62 (3 H, m), 7.21 (1 H, m), 7.36 (1 H, m), 7.41 (1 H, d, J=14.02 Hz), 7.67 (1 H, br s), 7.87 (1 H, s), 11.46 (1 H, br s); LC/MS (M+1) 446.

Example 157

Compound AET

¹H NMR (DMSO-d₆) δ 1.24 (3 H, d, J=7.00 Hz), 2.27 (6 H, d, J=6.17 Hz), 2.47 (1 H, m), 2.71 (1 H, dd, J=4.97, 16.92 Hz), 2.81 (1 H, t, J=9.81 Hz), 2.99 (1 H, d, J=9.36 Hz), 3.28 (3 H, m), 3.58 (1 H, m), 3.73 (1 H, d, J=12.06 Hz), 3.88 (1 H, d, J=12.09 Hz), 4.20 (1 H, m), 4.64 (3 H, m), 7.35 (1 H, br s), 7.42 (1 H, d, J=14.0 Hz), 7.55 (1 H, br s), 7.87 (1 H, s); LC/MS (M+1) 474

Example 158

Compound AFR

¹H NMR (DMSO-d₆) δ 1.08 (3 H, d, J=7.03 Hz), 2.45 (1 H, m), 2.72 (1 H, dd, J=4.06, 15.89 Hz), 3.28 (4 H, m), 3.41 (1 H, d, J=13.61 Hz), 3.58 (2 H, m), 4.00 (1 H, d, J=13.23 Hz), 4.16 (2 H, m), 4.64 (2 H, m), 7.41 (2 H, m), 7.55 (1 H, br s), 7.87 (1 H, s); 7.99 (1 H, s); LC/MS (M+1) 480.

Example 159

Compound AFS

¹H NMR (DMSO-d₆) δ 1.08 (3 H, d, J=6.98 Hz), 2.45 (1 H, m), 2.72 (1 H, dd, J=4.01, 17.21 Hz), 3.28 (4 H, m), 3.42 (1 H, d, J=13.52 Hz), 3.58 (2 H, m), 3.99 (1 H, d, J=13.68 Hz), 4.16 (2 H, m), 4.64 (2 H, m), 7.42 (1 H, d, J=14.47 Hz), 7.66 (1 H, m), 7.89 (1 H, s), 8.05 (1 H, m), 11.46 (1 H, br s); LC/MS (M+1) 482.

Example 160

Compound AFY

¹H NMR (DMSO-d₆) δ 1.08 (3 H, d, J=7.04 Hz), 2.45 (1 H, m), 2.72 (1 H, dd, J=4.21, 18.05 Hz), 3.28 (4 H, m), 3.42 (1 H, d, J=13.41 Hz), 3.58 (2 H, m), 3.99 (1 H, d, J=13.73 Hz), 4.16 (2 H, m), 4.64 (2 H, m), 7.31 (1 H, t, J=8.29 Hz), 7.42 (1 H, d, J=14.28 Hz), 7.72 (1 H, d, J=6.52 Hz), 7.89 (1 H, s), 11.61 (1 H, br s); LC/MS (M+1) 482.

Example 161

Preparation of (S)-4-(5-((S)-2,3-dihydroxypropyl)-3-fluoropyridin-2-yl)-N-(6-fluorobenzo[d]thiazol-2-yl)-3-methylpiperazine-1-carboxamide (AFM)

The compound AFM was obtained in the same manner as Example 10. (yield 90%)

1H-NMR (DMSO-d₆) δ: 7.87 (1H, s), 7.49 (1H, br), 7.38 (1H, d, J=14.4 Hz), 7.29 (1H, br), 7.00 (1H, br), 4.63-4.61 (2H, m), 4.22-4.00 (3H, m), 3.44-3.26 (7H, m), 2.71 (1H, dd, J=14.2, 4.1 Hz), 2.56-2.42 (1H, m), 1.05 (3H, d, J=6.4 Hz).

Example 162

Preparation of (S)—N-(benzo[d]thiazol-2-yl)-4-(5-((S)-2,3-dihydroxypropyl)-3-fluoropyridin-2-yl)-3-methylpiperazine-1-carboxamide (AFN)

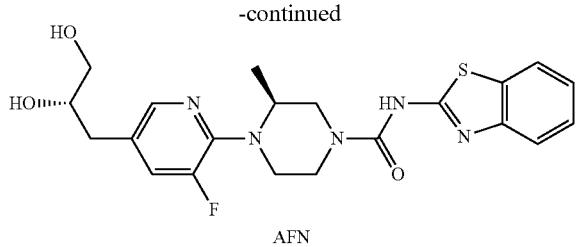

AFN

The compound AFN was obtained in the same manner as Example 10. (yield 79%)

1H-NMR (DMSO-$d_6$) δ: 7.88 (1H, s), 7.78 (1H, d, J=7.7 Hz), 7.49-7.30 (3H, m), 7.16 (1H, t, J=7.5 Hz), 4.65-4.62 (2H, m), 4.18-4.03 (3H, m), 3.58-3.22 (7H, m), 2.72 (1H, dd, J=13.8, 3.8 Hz), 2.56-2.43 (1H, m), 1.06 (3H, d, J=6.4 Hz).

Example 163

Preparation of (S)-4-(5-((R)-2,3-dihydroxypropyl)-3-fluoropyridin-2-yl)-N-(6-fluorobenzo[d]thiazol-2-yl)-3-methylpiperazine-1-carboxamide (AFK)

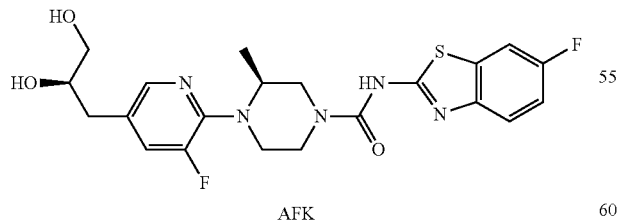

AFK

The compound AFK was obtained in the same manner as Example 10. (quant.)

1H-NMR (DMSO-$d_6$) δ: 7.90-7.87 (1H, m), 7.75 (1H, dd, J=8.7, 2.7 Hz), 7.53 (1H, dd, J=8.6, 4.8 Hz), 7.40 (1H, dd, J=14.3, 1.8 Hz), 7.19 (1H, td, J=9.1, 2.7 Hz), 4.65-4.62 (2H, m), 4.13-4.02 (3H, m), 3.58-3.18 (7H, m), 2.72 (1H, dd, J=13.9, 4.0 Hz), 2.50-2.47 (1H, m), 1.09 (3H, t, J=10.0 Hz).

Example 164

Preparation of (S)—N-(benzo[d]thiazol-2-yl)-4-(5-((R)-2,3-dihydroxypropyl)-3-fluoropyridin-2-yl)-3-methylpiperazine-1-carboxamide (AFL)

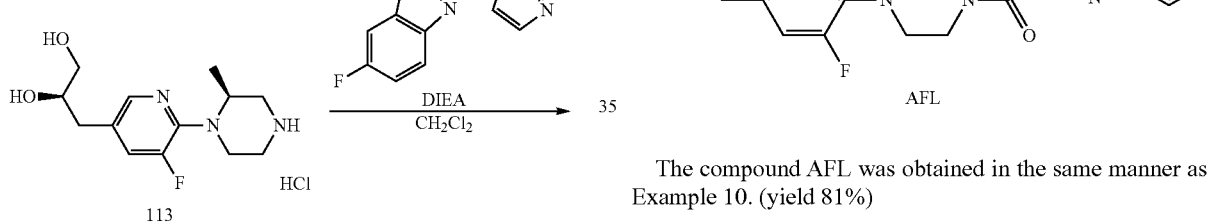

AFL

The compound AFL was obtained in the same manner as Example 10. (yield 81%)

1H-NMR (DMSO-$d_6$) δ: 7.88 (1H, s), 7.81 (1H, d, J=7.6 Hz), 7.51 (1H, d, J=7.6 Hz), 7.41-7.35 (2H, m), 7.20 (1H, t, J=7.6 Hz), 4.63-4.59 (2H, m), 4.15-4.01 (3H, m), 3.51-3.25 (7H, m), 2.72 (1H, dd, J=13.6, 3.7 Hz), 2.52-2.46 (1H, m), 1.07 (3H, d, J=6.5 Hz)

Example 165

Preparation of (S)-4-(5-((R)-2,3-dihydroxypropyl)-3-fluoropyridin-2-yl)-3-methyl-N-(6-methylbenzo[d]thiazol-2-yl)piperazine-1-carboxamide (AFO)

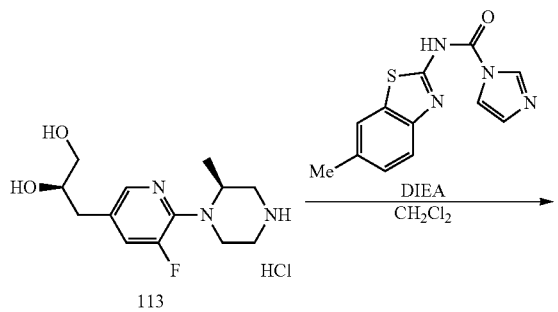

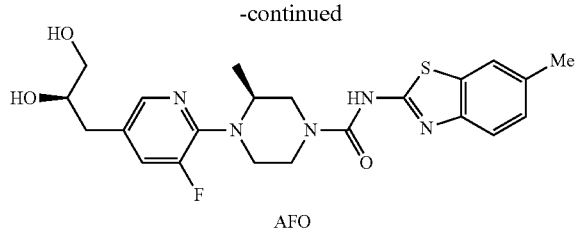

AFO

The compound AFO was obtained in the same manner as Example 10. (yield 79%)

1H-NMR (DMSO-$d_6$) δ: 7.87 (1H, s), 7.36 (1H, dd, J=14.3, 1.7 Hz), 7.24 (1H, s), 7.04 (1H, d, J=8.1 Hz), 6.82 (1H, dd, J=8.1, 1.7 Hz), 4.68 (2H, br), 4.25-4.02 (3H, m), 3.63-2.98 (7H, m), 2.71 (1H, dd, J=13.9, 4.0 Hz), 2.57-2.41 (1H, m), 2.27 (3H, s), 1.03 (3H, d, J=6.4 Hz).

Example 166

Preparation of (S)-4-(5-((S)-2,3-dihydroxypropyl)-3-fluoropyridin-2-yl)-3-methyl-N-(6-methylbenzo[d]thiazol-2-yl)piperazine-1-carboxamide (AFP)

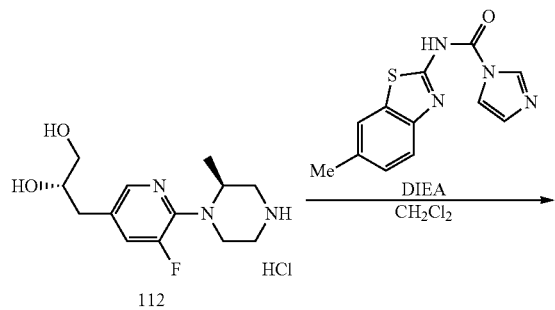

AFP

The compound AFP was obtained in the same manner as Example 10. (yield 79%)

1H-NMR (DMSO-$d_6$) δ: 7.88 (1H, s), 7.74 (1H, dd, J=8.6, 2.6 Hz), 7.52 (1H, dd, J=8.6, 4.6 Hz), 7.40 (1H, dd, J=14.3, 1.5 Hz), 7.18 (1H, dt, J=8.6, 2.6 Hz), 4.63 (2H, br), 4.13-4.02 (3H, m), 3.58-3.17 (7H, m), 2.72 (1H, dd, J=14.0, 4.1 Hz), 2.49-2.44 (1H, m), 1.06 (3H, d, J=6.4 Hz).

Example 167

Preparation of Compound AIH

Step 1 Preparation of 1-(6-chloro-5-fluoropyridin-3-yl)-2-((S)-2,2-dimethyl-1,3-dioxolan-4-yl)ethanol

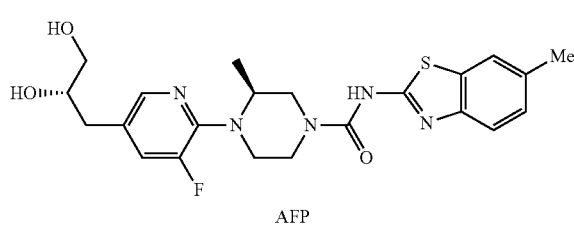

The compound 114 was obtained in the same manner as Example 37, Step 1. (yield 79%)

1H-NMR (CDCl$_3$) δ: 8.18-8.18 (1H, m), 7.58 (1H, dt, J=8.8, 2.0 Hz), 5.09-5.03 (1H, m), 4.34-4.27 (1H, m), 4.16-4.10 (2H, m), 3.66-3.60 (1H, m), 1.92-1.86 (1H, m), 1.47-1.38 (6H, m).

Step 2 Preparation of O-1-(6-chloro-5-fluoropyridin-3-yl)-2-((S)-2,2-dimethyl-1,3-dioxolan-4-yl)ethyl O-phenyl carbonothioate

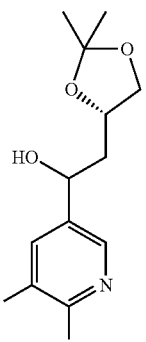 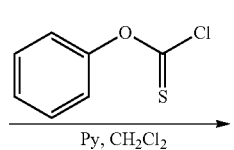

114

-continued

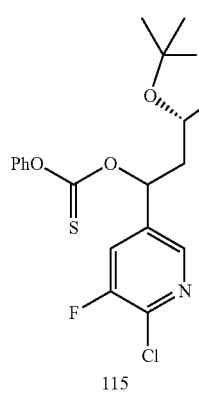

115

The compound 115 was obtained in the same manner as Example 37, Step 3. (yield 82%)

1H-NMR (CDCl₃) δ: 8.31 (0.6H, d, J=1.7 Hz), 8.29 (0.4H, d, J=1.7 Hz), 7.59-7.04 (5H, m), 6.41-6.35 (1H, m), 4.31-4.30 (0.4H, m), 4.16-4.01 (2H, m), 3.92-3.89 (0.6H, m), 3.66-3.63 (1H, m), 2.53-2.44 (0.6H, m), 2.36-2.30 (0.4H, m), 2.14-2.10 (1H, m), 1.46 (1.8H, s), 1.41 (1.2H, s), 1.37 (1.2H, s), 1.32 (1.8H, s).

Step 3 Preparation of (S)-2-chloro-5-(2-(2,2-dimethyl-1,3-dioxolan-4-yl)ethyl)-3-fluoropyridine

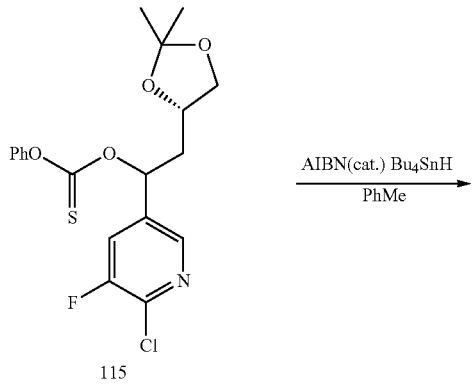

The compound 116 was obtained in the same manner as Example 37, Step 4. (quant.)

1H-NMR (CDCl₃) δ: 8.07 (1H, d, J=2.0 Hz), 7.33 (1H, dd, J=8.8, 2.0 Hz), 4.13-4.01 (2H, m), 3.62-3.57 (1H, m), 2.87-2.66 (2H, m), 1.92-1.77 (2H, m), 1.43 (3H, s), 1.36 (3H, s).

Step 4 Preparation of (S)-tert-butyl 4-(5-(2-(2,2-dimethyl-1,3-dioxolan-4-yl)ethyl)-3-fluoropyridin-2-yl)piperazine-1-carboxylate

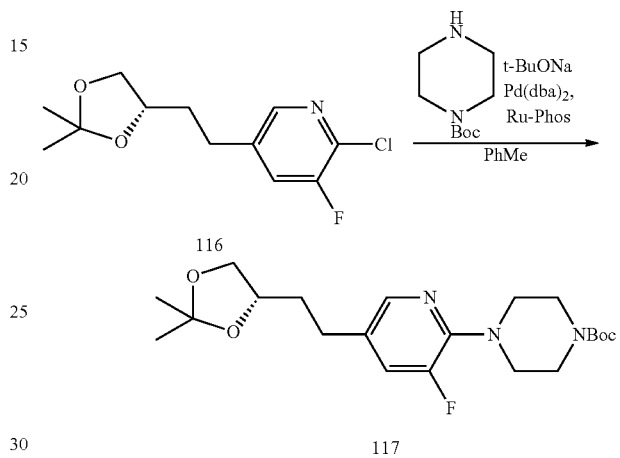

The compound 117 was obtained in the same manner as Example 32, Step 2. (yield 67%)

1H-NMR (CDCl₃) δ: 7.85 (1H, s), 7.12 (1H, dd, J=13.5, 1.9 Hz), 4.12-4.04 (2H, m), 3.57-3.51 (5H, m), 3.38-3.36 (4H, m), 2.75-2.53 (2H, m), 1.94-1.69 (2H, m), 1.48 (9H, s), 1.43 (3H, s), 1.36 (3H, s).

Step 5 Preparation of (S)-4-(5-fluoro-6-(piperazin-1-yl)pyridin-3-yl)butane-1,2-diol hydrochloride

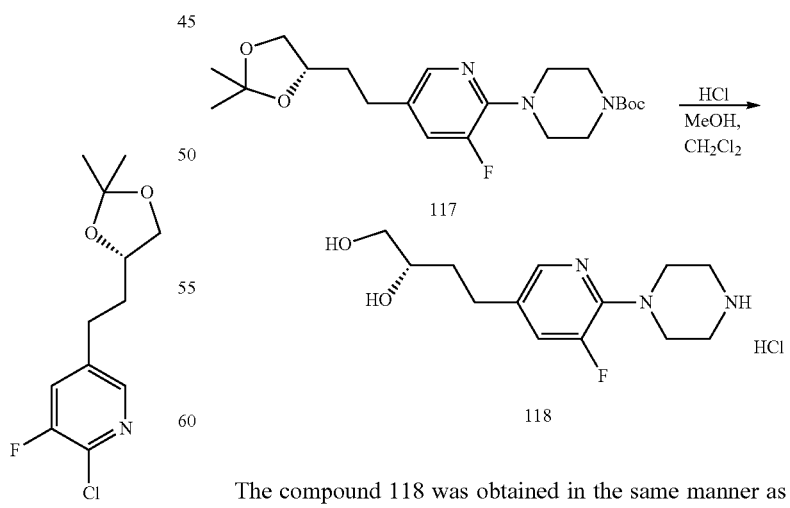

The compound 118 was obtained in the same manner as Example 32, Step 3. (yield 98%)

1H-NMR (DMSO-d₆) δ: 9.44 (1H, br), 7.95 (1H, s), 7.50 (1H, dd, J=14.0, 1.8 Hz), 3.58-3.56 (4H, m), 3.41-3.18 (8H, m), 2.72-2.55 (3H, m), 1.76-1.43 (2H, m).

Step 6 Preparation of (S)-4-(5-(3,4-dihydroxybutyl)-3-fluoropyridin-2-yl)-N-(6-fluorobenzo[d]thiazol-2-yl)piperazine-1-carboxamide (AIH)
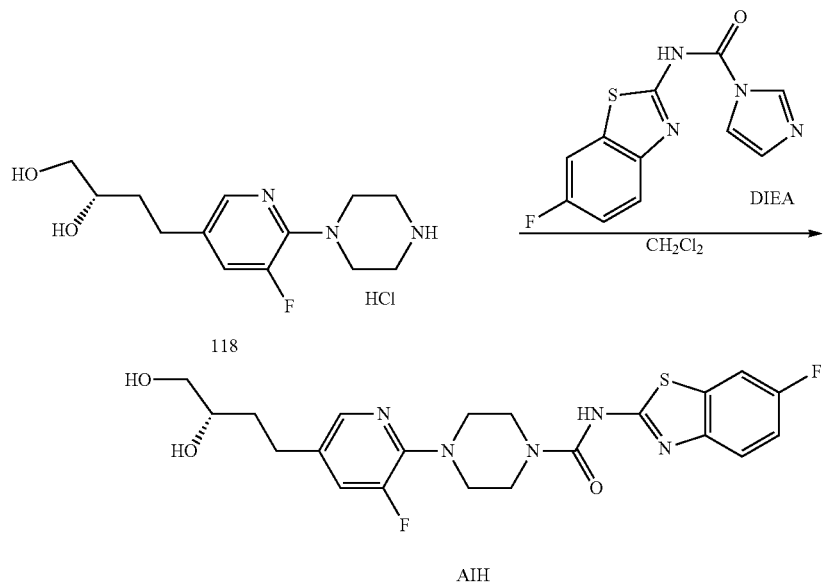
The compound AIH was obtained in the same manner as Example 10. (yield 53%)
1H-NMR (DMSO-$d_6$) δ: 7.89 (1H, s), 7.78 (1H, d, J=8.9 Hz), 7.60 (1H, s), 7.43 (1H, d, J=14.1 Hz), 7.21 (1H, td, J=8.9, 2.5 Hz), 4.53 (1H, d, J=4.9 Hz), 4.47 (1H, t, J=5.5 Hz), 3.71-3.68 (4H, m), 3.39-3.16 (7H, m), 2.71-2.49 (2H, m), 1.75-1.65 (1H, m), 1.54-1.42 (1H, m).
Example 168
Preparation of (S)—N-(benzo[d]thiazol-2-yl)-4-(5-(3,4-dihydroxybutyl)-3-fluoropyridin-2-yl)piperazine-1-carboxamide (AII)
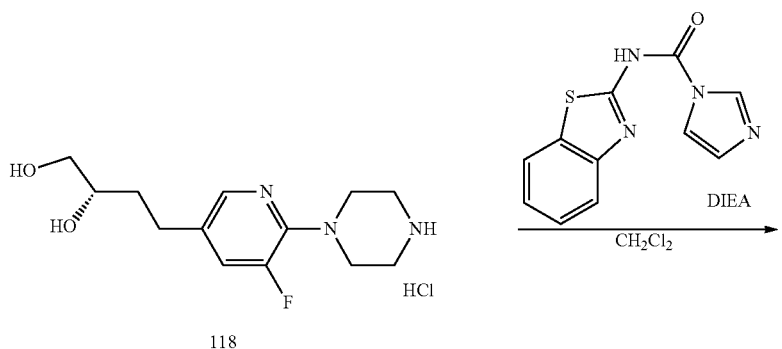
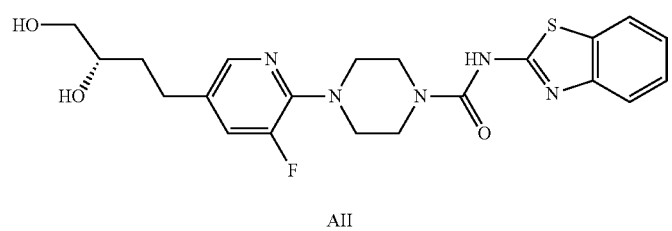

The compound AII was obtained in the same manner as Example 10. (yield 86%)

1H-NMR (DMSO-d$_6$) δ: 7.89 (1H, s), 7.71 (1H, d, J=7.7 Hz), 7.44-7.41 (2H, m), 7.26 (1H, t, J=7.7 Hz), 7.08 (1H, t, J=7.7 Hz), 4.54 (1H, br), 3.69-3.68 (4H, m), 3.38-3.21 (7H, m), 2.68-2.56 (4H, m), 1.75-1.68 (1H, m), 1.51-1.46 (1H, m).

Example 169

Preparation of Compound AHI

Step 1 Preparation of O-1-(5,6-dichloropyridin-3-yl)-2-((S)-2,2-dimethyl-1,3-dioxolan-4-yl)ethyl O-phenyl carbonothioate

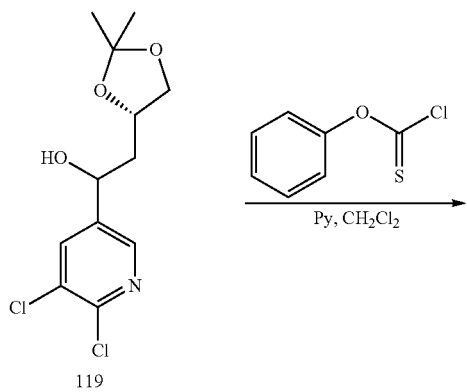

The compound 120 was obtained in the same manner as Example 37, Step 3. (yield 48%)

1H-NMR (CDCl$_3$) δ: 8.40-8.37 (1H, m), 7.87-7.83 (1H, m), 7.44-7.05 (5H, m), 6.39-6.34 (1H, m), 4.34-4.03 (3H, m), 3.69-3.61 (1H, m), 2.49-2.31 (1H, m), 2.16-2.12 (1H, m), 1.47 (1.5H, s), 1.42 (1.5H, s), 1.38 (1.5H, s), 1.33 (1.5H, s).

Step 2 Preparation of (S)-2,3-dichloro-5-(2-(2,2-dimethyl-1,3-dioxolan-4-yl)ethyl)pyridine

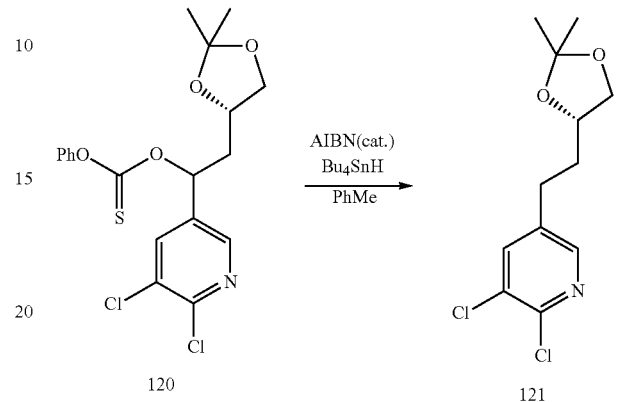

The compound 121 was obtained in the same manner as Example 37, Step 4. (yield 74%)

1H-NMR (CDCl$_3$) δ: 8.15 (1H, d, J=2.2 Hz), 7.63 (1H, d, J=2.2 Hz), 4.09-4.05 (2H, m), 3.60-3.52 (1H, m), 2.84-2.63 (2H, m), 1.92-1.76 (2H, m), 1.43 (3H, s), 1.36 (3H, s).

Step 3 Preparation of (S)-tert-butyl 4-(3-chloro-5-(2-(2,2-dimethyl-1,3-dioxolan-4-yl)ethyl)pyridin-2-yl)piperazine-1-carboxylate

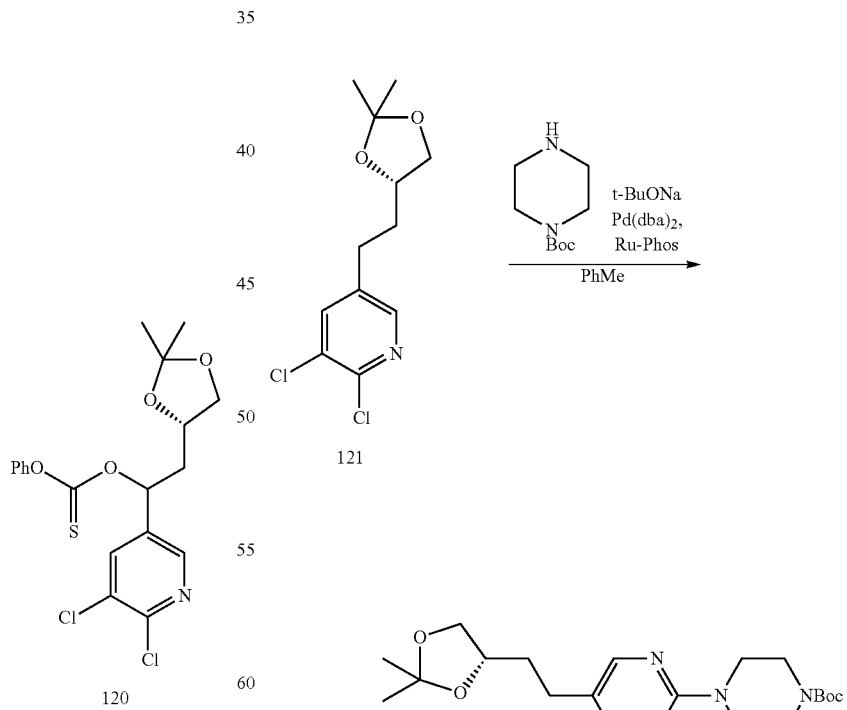

The compound 122 was obtained in the same manner as Example 32, Step 2. (yield 15%)

1H-NMR (CDCl₃) δ: 8.01 (1H, d, J=2.1 Hz), 7.46 (1H, d, J=2.1 Hz), 4.15-4.00 (2H, m), 3.59-3.51 (5H, m), 3.25-3.24 (4H, m), 2.75-2.54 (2H, m), 1.93-1.69 (2H, m), 1.48 (9H, s), 1.43 (3H, s), 1.36 (3H, s).

Step 4 Preparation of (S)-4-(5-chloro-6-(piperazin-1-yl)pyridin-3-yl)butane-1,2-diol hydrochloride

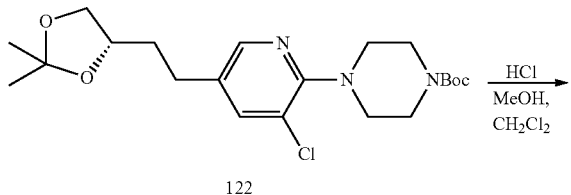

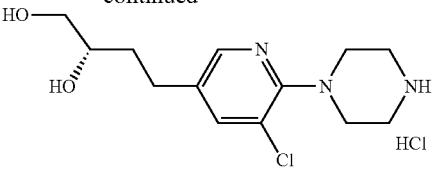

The compound 123 was obtained in the same manner as Example 32, Step 3. (quant.)

1H-NMR (DMSO-d₆) δ: 9.20 (1H, br s), 8.11 (1H, d, J=2.2 Hz), 7.73 (1H, d, J=2.2 Hz), 4.60-4.57 (4H, m), 3.43-3.17 (8H, m), 2.68-2.54 (3H, m), 1.76-1.65 (1H, m), 1.51-1.47 (1H, m).

Step 5 Preparation of (S)-4-(3-chloro-5-(3,4-dihydroxybutyl)pyridin-2-yl)-N-(6-fluorobenzo[d]thiazol-2-yl)piperazine-1-carboxamide (AHI)

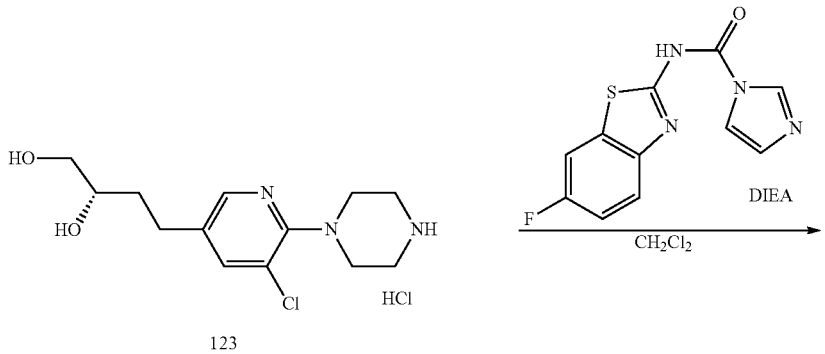

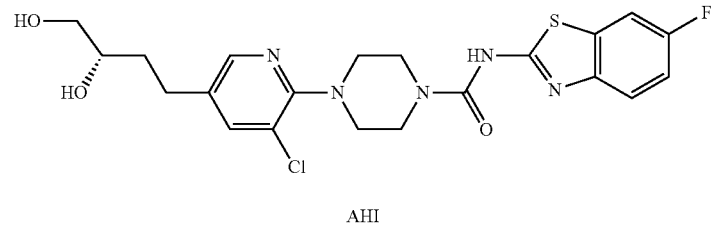

The compound AIR was obtained in the same manner as Example 10. (quant.)

1H-NMR (DMSO-d₆) δ: 8.08 (1H, s), 7.69 (1H, s), 7.56 (1H, d, J=7.6 Hz), 7.38-7.35 (1H, m), 7.04 (1H, t, J=7.6 Hz), 3.50-3.38 (27H, m), 2.63-2.55 (2H, m), 1.71-1.68 (1H, m), 1.52-1.49 (1H, m).

Example 170

Preparation of Compound AIJ (S)—N-(5,6-difluorobenzo[d]thiazol-2-yl)-4-(5-(3,4-dihydroxybutyl)-3-fluoropyridin-2-yl)piperazine-1-carboxamide (AIJ)

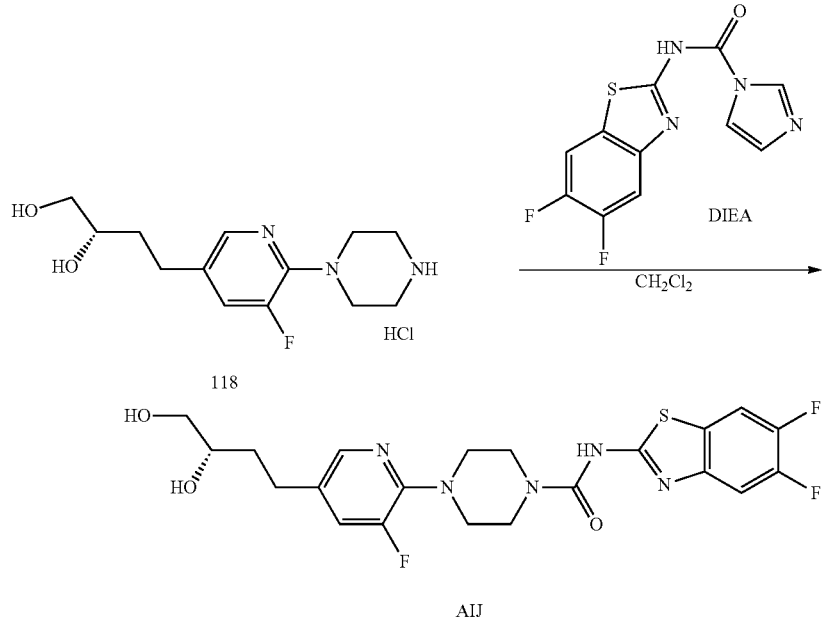

The compound AIJ was obtained in the same manner as Example 10. (yield 32%)

1H-NMR (DMSO-$d_6$) δ: 8.04 (1H, t, J=9.3 Hz), 7.89 (1H, s), 7.66 (1H, br), 7.43 (1H, dd, J=14.1, 1.8 Hz), 4.54 (1H, d, J=4.9 Hz), 4.47 (1H, t, J=5.6 Hz), 3.72-3.66 (4H, m), 3.37-3.19 (7H, m), 2.71-2.49 (2H, m), 1.71-1.45 (2H, m).

Example 171

Preparation of Compound AHC

Step 1 Preparation of O-1-(5,6-dichloropyridin-3-yl)-2-((R)-2,2-dimethyl-1,3-dioxolan-4-yl)ethyl O-phenyl carbonothioate

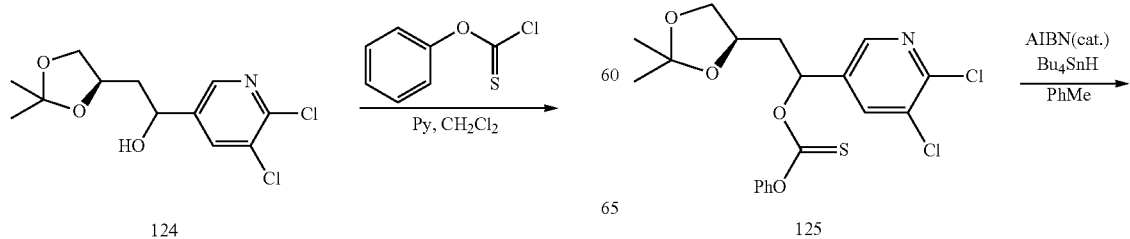

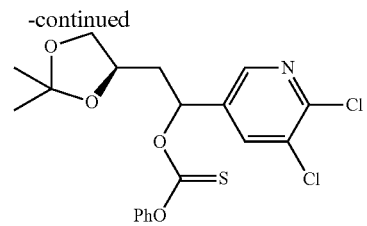

The compound 125 was obtained in the same manner as Example 37, Step 3. (yield 82%)

1H-NMR (CDCl$_3$) δ: 8.40-8.37 (1H, m), 7.87-7.83 (1H, m), 7.44-7.05 (5H, m), 6.39-6.34 (1H, m), 4.34-4.03 (3H, m), 3.69-3.61 (1H, m), 2.49-2.31 (1H, m), 2.16-2.12 (1H, m), 1.47 (1.5H, s), 1.42 (1.5H, s), 1.38 (1.5H, s), 1.33 (1.5H, s).

Step 2 Preparation of (R)-2,3-dichloro-5-(2-(2,2-dimethyl-1,3-dioxolan-4-yl)ethyl)pyridine

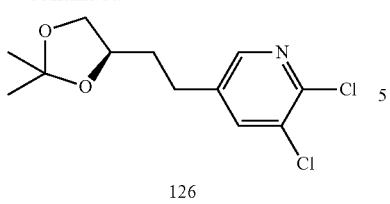

126

The compound 126 was obtained in the same manner as Example 37, Step 4. (yield 73%)

1H-NMR (CDCl$_3$) δ: 8.15 (1H, d, J=2.2 Hz), 7.63 (1H, d, J=2.2 Hz), 4.09-4.05 (2H, m), 3.60-3.52 (1H, m), 2.84-2.63 (2H, m), 1.92-1.76 (2H, m), 1.43 (3H, s), 1.36 (3H, s).

Step 3 Preparation of (R)-tert-butyl 4-(3-chloro-5-(2-(2,2-dimethyl-1,3-dioxolan-4-yl)ethyl)pyridin-2-yl)-5,6-dihydropyridine-1(2H)-carboxylate

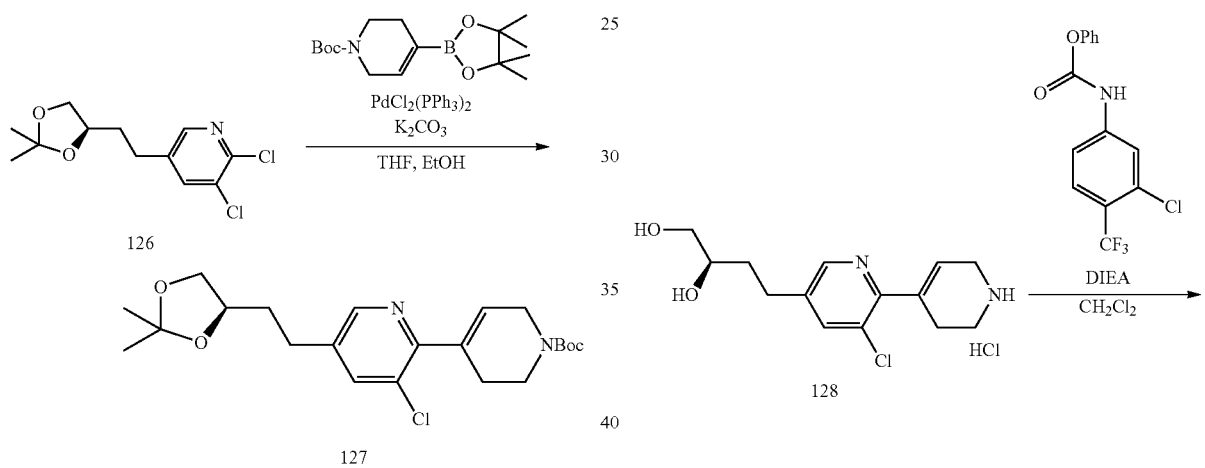

The compound 127 was obtained in the same manner as Reference Example 3, Step 3. (quant.)

1H-NMR (CDCl$_3$) δ: 8.31 (1H, d, J=2.0 Hz), 7.54 (1H, d, J=2.0 Hz), 6.07 (1H, s), 4.11-4.06 (4H, m), 3.66-3.53 (3H, m), 2.83-2.57 (4H, m), 1.92-1.78 (2H, m), 1.49 (9H, s), 1.45 (3H, s), 1.37 (3H, s).

Step 4 Preparation of (R)-4-(5-chloro-6-(1,2,3,6-tetrahydropyridin-4-yl)pyridin-3-yl)butane-1,2-diol hydrochloride

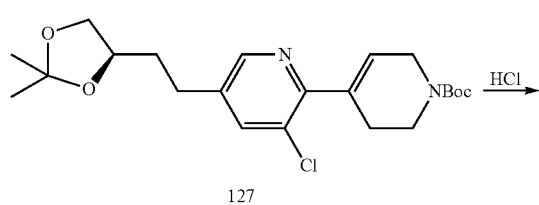

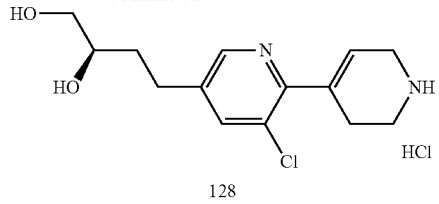

128

The compound 128 was obtained in the same manner as Example 32, Step 3. (yield 91%.)

1H-NMR (DMSO-d$_6$) δ: 8.39 (1H, d, J=1.8 Hz), 7.82 (1H, d, J=1.8 Hz), 6.22-6.18 (1H, m), 3.62-3.41 (7H, m), 2.73-2.69 (4H, m), 1.76-1.48 (2H, m).

Step 5 Preparation of (R)—N-(3-chloro-4-(trifluoromethyl)phenyl)-4-(3-chloro-5-(3,4-dihydroxybutyl)pyridin-2-yl)-5,6-dihydropyridine-1(2H)-carboxamide (AHC)

The compound AHC was obtained in the same manner as Example 1. (yield 48%.)

1H-NMR (CDCl$_3$) δ: 8.34 (1H, d, J=1.8 Hz), 7.69 (1H, d, J=1.8 Hz), 7.59-7.58 (2H, m), 7.37 (1H, d, J=7.9 Hz), 6.53

(1H, s), 6.18-6.17 (1H, m), 4.23-4.22 (2H, m), 3.78-3.46 (5H, m), 2.82-2.73 (4H, m), 2.20 (1H, d, J=4.2 Hz), 1.79-1.74 (3H, m).

Example 172

Preparation of (R)-4-(3-chloro-5-(3,4-dihydroxybutyl)pyridin-2-yl)-N-(5-(trifluoromethyl)pyridin-2-yl)-5,6-dihydropyridine-1(2H)-carboxamide (AHD)

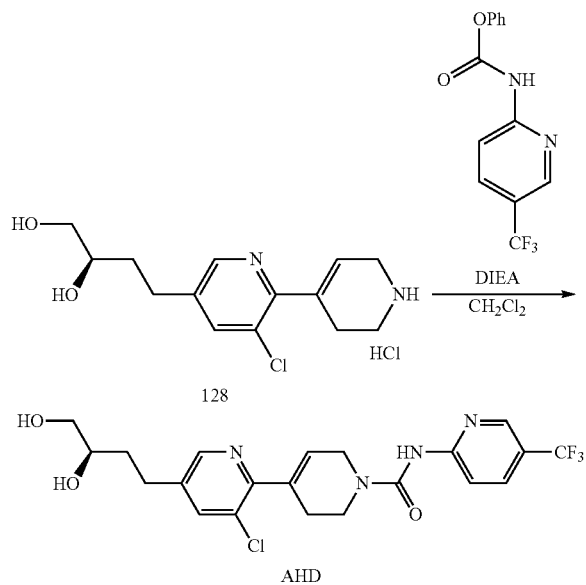

The compound AHD was obtained in the same manner as Example 1. (yield 59%.)

1H-NMR (CDCl$_3$) δ: 8.46 (1H, s), 8.34 (1H, d, J=1.8 Hz), 8.21 (1H, d, J=8.9 Hz), 7.87 (1H, dd, J=8.9, 2.4 Hz), 7.58 (1H, d, J=1.8 Hz), 7.43 (1H, s), 6.18-6.17 (1H, m), 4.27-4.25 (2H, m), 3.81-3.46 (5H, m), 2.85-2.67 (4H, m), 2.22 (1H, d, J=4.2 Hz), 1.81-1.72 (3H, m).

Example 173

Preparation of (R)-4-(3-chloro-5-(3,4-dihydroxybutyl)pyridin-2-yl)-N-(6-fluorobenzo[d]thiazol-2-yl)-5,6-dihydropyridine-1(2H)-carboxamide (AHE)

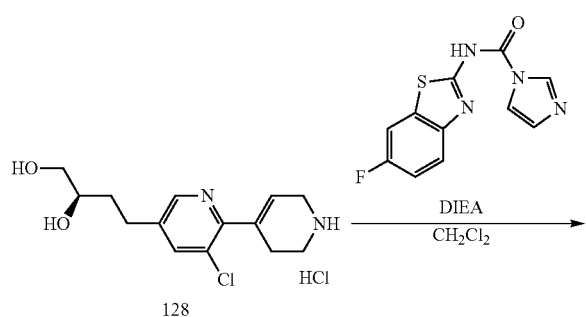

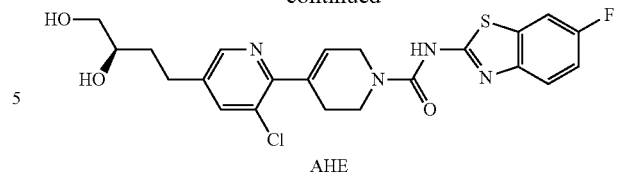

AHE

The compound AHE was obtained in the same manner as Example 10. (yield 71%.)

1H-NMR (DMSO-d$_6$) δ: 8.37 (1H, d, J=1.7 Hz), 7.79 (2H, d, J=1.7 Hz), 7.58 (1H, br), 7.21 (1H, dt, J=9.0, 2.6 Hz), 6.20-6.19 (1H, m), 4.58 (1H, d, J=4.9 Hz), 4.49 (1H, t, J=5.8 Hz), 4.25 (2H, br), 3.77 (2H, br), 3.39-3.21 (3H, m), 2.74-2.61 (4H, m), 1.77-1.50 (2H, m).

Example 174

Preparation of Compound AHF

Step 1 Preparation of (S)-tert-butyl 4-(3-chloro-5-(2-(2,2-dimethyl-1,3-dioxolan-4-yl)ethyl)pyridin-2-yl)-5,6-dihydropyridine-1(2H)-carboxylate

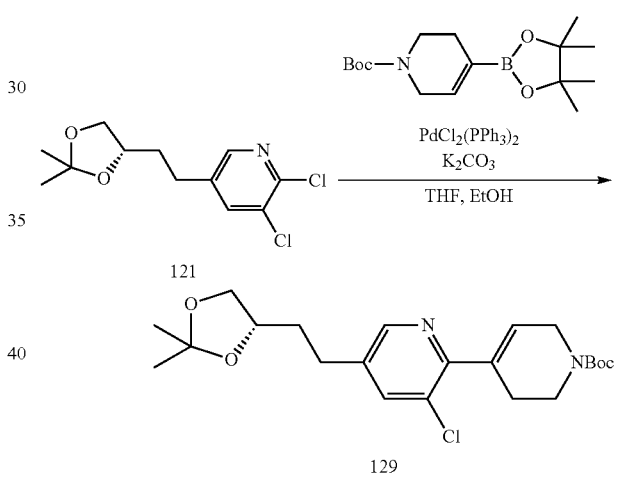

The compound 129 was obtained in the same manner as Reference Example 3, Step 3. (yield 85%.)

1H-NMR (CDCl$_3$) δ: 8.31 (1H, d, J=2.0 Hz), 7.54 (1H, d, J=2.0 Hz), 6.07 (1H, s), 4.11-4.06 (4H, m), 3.66-3.53 (3H, m), 2.83-2.57 (4H, m), 1.92-1.78 (2H, m), 1.49 (9H, s), 1.45 (3H, s), 1.37 (3H, s).

Step 2 Preparation of (S)-4-(5-chloro-6-(1,2,3,6-tetrahydropyridin-4-yl)pyridin-3-yl)butane-1,2-diol hydrochloride -continued

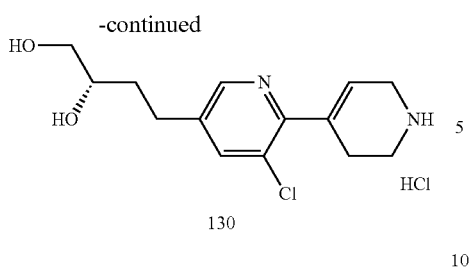

130

The compound 130 was obtained in the same manner as Example 32, Step 3. (yield 90%.)

1H-NMR (DMSO-d₆) δ: 8.39 (1H, d, J=1.8 Hz), 7.82 (1H, d, J=1.8 Hz), 6.22-6.18 (1H, m), 3.62-3.41 (7H, m), 2.73-2.69 (4H, m), 1.76-1.48 (2H, m).

Step 3 Preparation of (S)—N-(3-chloro-4-(trifluoromethyl)phenyl)-4-(3-chloro-5-(3,4-dihydroxybutyl)pyridin-2-yl)-5,6-dihydropyridine-1(2H)-carboxamide (AHF)

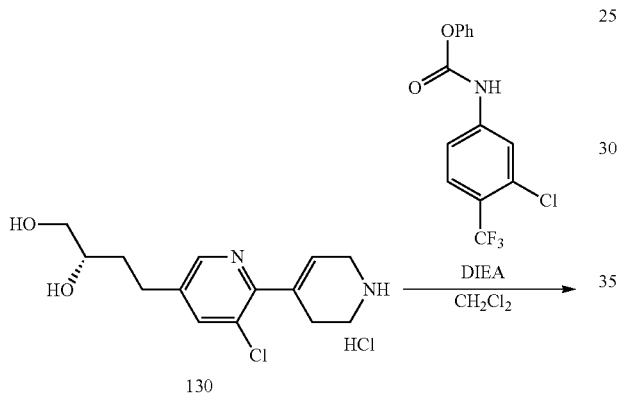

AHF

The compound AHF was obtained in the same manner as Example 1. (yield 70%.)

1H-NMR (CDCl₃) δ: 8.34 (1H, d, J=1.8 Hz), 7.69 (1H, d, J=1.8 Hz), 7.59-7.58 (2H, m), 7.37 (1H, d, J=7.9 Hz), 6.53 (1H, s), 6.18-6.17 (1H, m), 4.23-4.22 (2H, m), 3.78-3.46 (5H, m), 2.82-2.73 (4H, m), 2.20 (1H, d, J=4.2 Hz), 1.79-1.74 (3H, m).

Example 175

Preparation of (S)-4-(3-chloro-5-(3,4-dihydroxybutyl)pyridin-2-yl)-N-(5-(trifluoromethyl)pyridin-2-yl)-5,6-dihydropyridine-1(2H)-carboxamide (AHG)

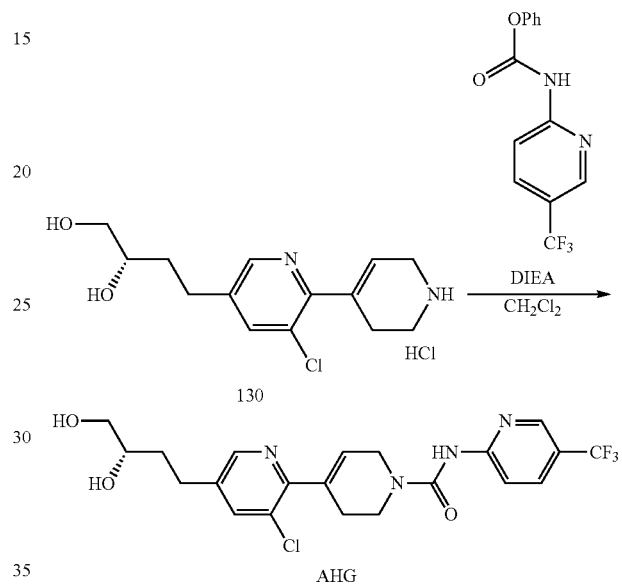

AHG

The compound AHG was obtained in the same manner as Example 1. (yield 70%.)

1H-NMR (CDCl₃) δ: 8.46 (1H, s), 8.34 (1H, d, J=1.8 Hz), 8.21 (1H, d, J=8.9 Hz), 7.87 (1H, dd, J=8.9, 2.4 Hz), 7.58 (1H, d, J=1.8 Hz), 7.43 (1H, s), 6.18-6.17 (1H, m), 4.27-4.25 (2H, m), 3.81-3.46 (5H, m), 2.85-2.67 (4H, m), 2.22 (1H, d, J=4.2 Hz), 1.81-1.72 (3H, m).

Example 176

Preparation of (S)-4-(3-chloro-5-(3,4-dihydroxybutyl)pyridin-2-yl)-N-(6-fluorobenzo[d]thiazol-2-yl)-5,6-dihydropyridine-1(2H)-carboxamide (AHH)

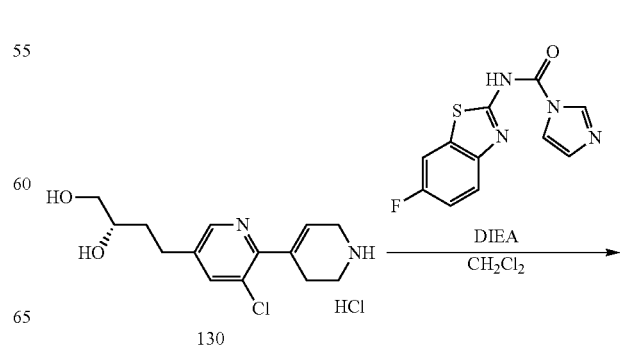

130

-continued

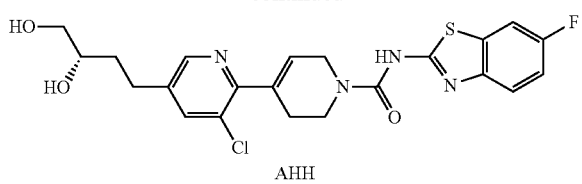

AHH

The compound AHH was obtained in the same manner as Example 10. (yield 72%.)

1H-NMR (DMSO-$d_6$) δ: 8.37 (1H, d, J=1.7 Hz), 7.79 (2H, d, J=1.7 Hz), 7.58 (1H, br), 7.21 (1H, dt, J=9.0, 2.6 Hz), 6.20-6.19 (1H, m), 4.58 (1H, d, J=4.9 Hz), 4.49 (1H, t, J=5.8 Hz), 4.25 (2H, br), 3.77 (2H, br), 3.39-3.21 (3H, m), 2.74-2.61 (4H, m), 1.77-1.50 (2H, m).

Example 177

Preparation of Compound AHO

Step 1 Preparation of Compound 132

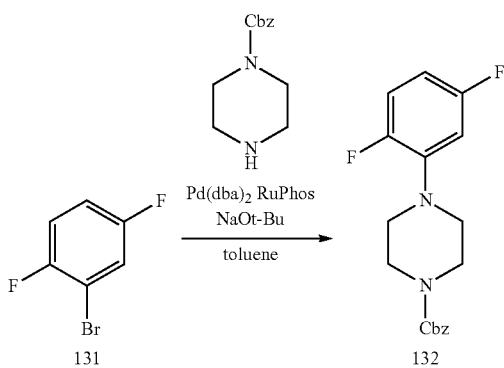 [SMILES: Fc1ccc(F)c(Br)c1 ; O=C(OCc1ccccc1)N1CCNCC1 ; O=C(OCc1ccccc1)N1CCN(c2cc(F)ccc2F)CC1]

To a suspension of NaOt-Bu (3.73 g, 38.9 mmol), Pd(dba)2 (0.298 g, 0.518 mmol), RuPhos (0.484 g, 1.036 mmol) and 2-bromo-1,4-difluorobenzene (5 g, 25.9 mmol) in Toluene (50 ml) was added benzyl piperazine-1-carboxylate (6.00 ml, 31.1 mmol) at r.t. under $N_2$. The mixture was stirred at 100° C. under $N_2$ for 1 hr. The reaction mixture was diluted with $H_2O$ and AcOEt at r.t., then the resulting solid was filtered, rinsed with AcOEt and $H_2O$. The filtrate was extracted with AcOEt×2. The organic layers were combined and washed with brine. The organic layer was dried over $MgSO_4$, flit and conc. The crude product was added to a silica gel column and was eluted with AcOEt-Hexane. Collected fractions were evaporated. The residual oil was triturated with $CH_2Cl_2$-Hexane, then filtered, rinsed with Hexane to afford compound 132 (3.7 g, 43.0%) as a white solid.

1H-NMR (CDCl$_3$) δ: 7.40-7.29 (5H, m), 7.01-6.89 (1H, m), 6.66-6.56 (2H, m), 5.16 (2H, s), 3.67 (4H, t, J=5.1 Hz), 3.11-2.97 (4H, m).

Step 2 Preparation of Compound 133

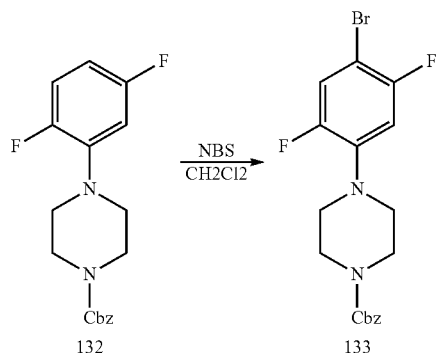

To a solution of compound 132 (4.45 g, 13.39 mmol) in $CH_2Cl_2$ (150 ml) was added NBS (2.502 g, 14.06 mmol) at 0° C. The mixture was stirred at r.t. for 90 min. $H_2O$ (70 ml) and $K_2CO_3$ (9.25 g, 66.9 mmol) were added to the reaction mixture. The mixture was extracted with $CH_2Cl_2$×2. The organic layers were combined and washed with $H_2O$. The organic layer was dried over $MgSO_4$, felt and conc. The resulting solid was filtered, rinsed with Hexane to afford compound 133 (4.73 g, 85.9%) as a white solid.

1H-NMR (CDCl$_3$) δ: 7.43-7.27 (5H, m), 7.20 (1H, dd, J=11.3, 6.4 Hz), 6.67 (1H, dd, J=9.9, 7.5 Hz), 5.15 (2H, s), 3.66 (4H, t, J=5.0 Hz), 3.11-2.95 (4H, m).

Step 3 Preparation of Compound 134

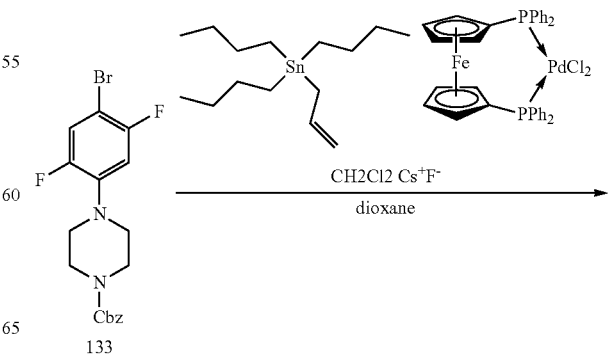

-continued

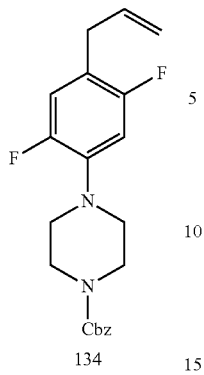

134

To a suspension of compound 133 (3.68 g, 8.95 mmol), cesium fluoride (4.08 g, 26.8 mmol) and PdCl₂(dppf) CH₂Cl₂ (0.365 g, 0.447 mmol) in Dioxane (37 ml) was added allyltributylstannane (3.32 ml, 10.74 mmol) at r.t. under N₂. The mixture was stirred at reflux under N₂ for 6 hr. The mixture was diluted with AcOEt and H₂O. The resulting solid was filtered, rinsed with AcOEt and H₂O. The filtrate was extracted with AcOEt×2. The organic layers were combined and washed with brine. The organic layer was dried over MgSO₄, felt and conc. The crude was added to a silica gel column and was eluted with AcOEt-Hexane. Collected fractions were evaporated to afford compound 134 (2.69 g, 80.7%) as a white solid.

1H-NMR (CDCl₃) δ: 7.39-7.29 (5H, m), 6.85 (1H, dd, J=12.6, 6.9 Hz), 6.59 (1H, dd, J=11.0, 7.2 Hz), 5.96-5.81 (1H, m), 5.15 (2H, s), 5.12-5.02 (2H, m), 3.70-3.63 (4H, m), 3.33-3.28 (2H, m), 3.08-2.93 (4H, m).

Step 4 Preparation of Compound 135

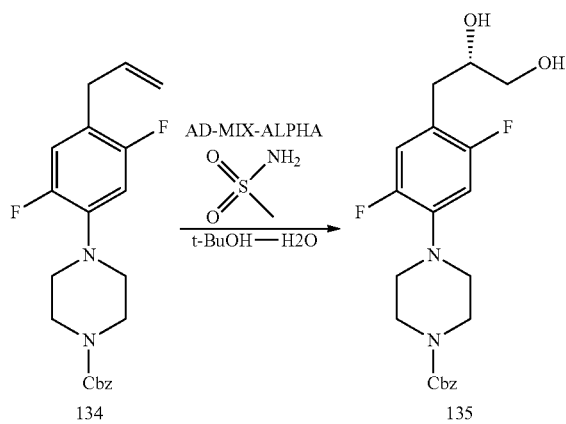

To a solution of compound 134 (1.345 g, 3.61 mmol) in t-BuOH (39 ml)-H₂O (26 ml) were added METHANESULFONAMIDE (344 mg, 3.61 mmol) and AD-MIX-ALPHA (3.6 g, 3.61 mmol) at r.t. The mixture was stirred at r.t. for overnight. AD-MIX-ALPHA (3.6 g, 3.61 mmol) was further added at r.t. The resulting mixture was stirred at r.t. for overnight. The reaction mixture was diluted with H₂O at r.t., then extracted with AcOEt×2. The organic layers were combined and washed with H₂O and brine. The organic layer was dried over MgSO₄, filt and conc. The crude was added to a silica gel column and was eluted with AcOEt-Hexane. Collected fractions were evaporated to afford compound 135 (928.5 mg, 63.3%) as a white solid.

1H-NMR (CDCl₃) δ: 7.41-7.28 (5H, m), 6.93 (1H, dd, J=12.5, 7.0 Hz), 6.60 (1H, dd, J=11.1, 7.2 Hz), 5.16 (2H, s), 3.99-3.87 (1H, m), 3.74-3.62 (5H, m), 3.55-3.44 (1H, m), 3.06-2.95 (4H, m), 2.82-2.64 (2H, m), 2.23 (1H, d, J=4.4 Hz), 2.00 (1H, t, J=5.6 Hz).

Step 5 Preparation of Compound 136

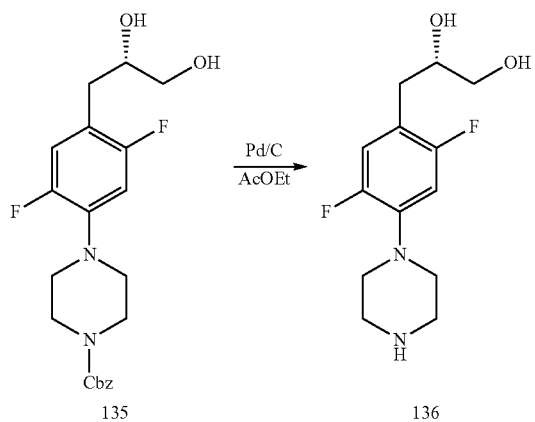 [SMILES: "AcOEt" ; O=C(OCc1ccccc1)N1CCN(c2cc(F)c(C[C@H](O)CO)cc2F)CC1 ; OC[C@@H](O)Cc1cc(F)c(N2CCNCC2)cc1F]

To a solution of compound 135 (925 mg, 2.276 mmol) in AcOEt (10 ml) was added 10% Pd/C (100 mg, 0.940 mmol) at r.t. The mixture was stirred at r.t. under H₂ for 2 hr. MeOH was added to the mixture. Pd/C was filtered, rinsed with MeOH. The filtrate was evaporated. The residual oil was triturated with AcOEt-Hexane, then filtered, rinsed with Hexane to afford compound 136 (521.3 mg, 84.1%) as a white solid.

1H-NMR (DMSO-d₆) δ: 7.04 (1H, dd, J=13.3, 7.1 Hz), 6.74 (1H, dd, J=11.7, 7.5 Hz), 4.68-4.54 (2H, m), 3.65-3.52 (1H, m), 2.94-2.77 (8H, m), 2.72 (1H, dd, J=13.5, 4.2 Hz), 2.42 (1H, dd, J=13.8, 8.3 Hz).

Step 6 Preparation of Compound AHO

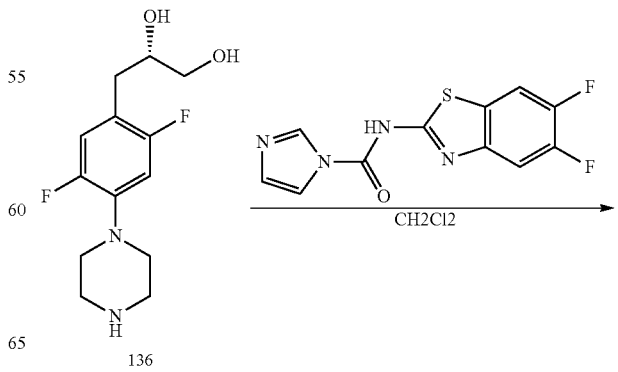

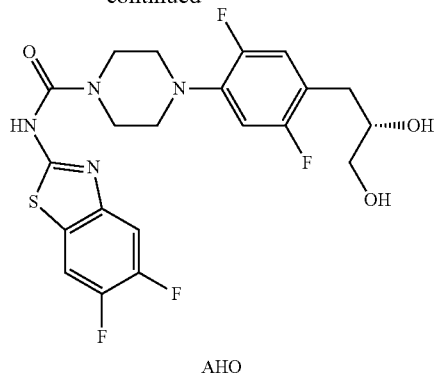

AHO

To a suspension of compound 136 (150 mg, 0.551 mmol) in CH₂Cl₂ (2 ml) was added N-(5,6-difluorobenzo[d]thiazol-2-yl)-1H-imidazole-1-carboxamide (139 mg, 0.496 mmol) at r.t. The mixture was stirred at r.t. for 7.5 hr. The reaction mixture was diluted with CH₂Cl₂ at r.t., then resulting solid was filtered, rinsed with H₂O and CH₂Cl₂. To a suspension of the solid (214.6 mg) in THF (4 ml) was added compound 6 (60.0 mg, 0.220 mmol) at r.t. The mixture was stirred at r.t. for 30 min. The resulting solid was filtered, rinsed with H₂O to afford compound A110 (161.8 mg 67.3%) as a pale yellow solid.

1H-NMR (DMSO-d$_6$) δ: 11.77-11.29 (1H, br), 8.03 (1H, dd, J=10.3, 8.0 Hz), 7.75-7.52 (1H, m), 7.09 (1H, dd, J=13.0, 6.9 Hz), 6.84 (1H, dd, J=11.4, 7.3 Hz), 4.64 (1H, d, J=5.5 Hz), 4.61 (1H, t, J=5.6 Hz), 3.79-3.64 (4H, m), 3.64-3.53 (1H, m), 3.38-3.21 (2H, m), 3.08-2.94 (4H, m), 2.74 (1H, dd, J=13.2, 4.5 Hz), 2.54-2.37 (1H, m).

Example 178

Compound AHJ

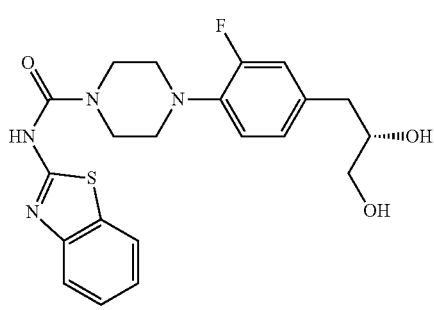

AHJ

1H-NMR (DMSO-d$_6$) δ: 12.20-11.18 (1H, br), 7.81 (1H, d, J=7.8 Hz), 7.56-7.43 (1H, br), 7.35 (1H, t, J=7.6 Hz), 7.19 (1H, t, J=7.6 Hz), 7.05-6.90 (3H, m), 4.64-4.50 (2H, m), 3.73 (4H, m), 3.64-3.51 (1H, m), 3.40-3.18 (2H, m), 3.06-2.90 (4H, m), 2.71 (1H, dd, J=13.8, 4.4 Hz), 2.54-2.40 (1H, m).

Example 179

Compound AHK

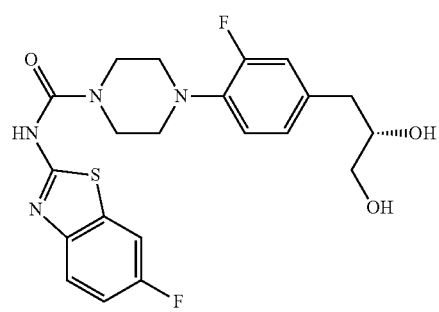

AHK

1H-NMR (DMSO-d$_6$) δ: 7.28 (1H, dd, J=8.9, 2.8 Hz), 7.09 (1H, dd, J=8.6, 5.0 Hz), 7.02-6.88 (3H, m), 6.82 (1H, ddd, J=10.6, 7.7, 1.7 Hz), 3.74-3.52 (5H, m), 3.43-3.19 (2H, m), 2.92-2.83 (4H, m), 2.70 (1H, dd, J=13.8, 4.7 Hz), 2.53-2.39 (1H, m).

Example 180

Compound AHL

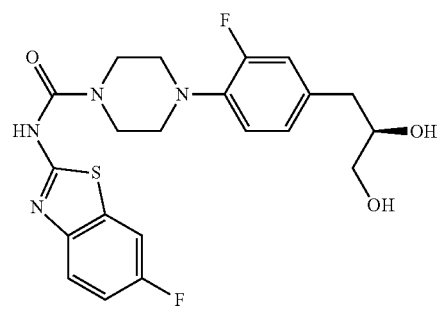

AHL

1H-NMR (DMSO-d$_6$) δ: 11.89-11.29 (1H, br), 7.76 (1H, dd, J=8.7, 2.6 Hz), 7.60-7.48 (1H, m), 7.20 (1H, td, J=9.0, 2.6 Hz), 7.05-6.89 (3H, m), 4.62-4.49 (2H, m), 3.81-3.64 (4H, m), 3.64-3.52 (1H, m), 3.41-3.16 (2H, m), 3.07-2.91 (4H, m), 2.71 (1H, dd, J=13.9, 4.4 Hz), 2.55-2.40 (1H, m).

Example 181

Compound AHM

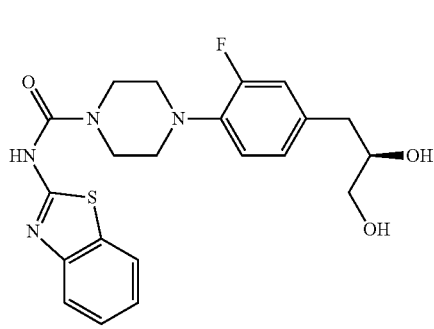

AHM

1H-NMR (DMSO-d$_6$) δ: 7.79 (1.0H, d, J=7.6 Hz), 7.48 (1H, d, J=7.9 Hz), 7.33 (1H, t, J=7.5 Hz), 7.17 (1H, t, J=7.6 Hz), 7.05-6.89 (3H, m), 4.89-4.31 (2H, br), 3.82-3.64 (4H, m), 3.64-3.52 (1H, m), 3.33-3.18 (2H, m), 3.05-2.90 (4H, m), 2.70 (1H, dd, J=13.7, 4.4 Hz), 2.53-2.39 (1H, m).

Example 182

Compound AHN

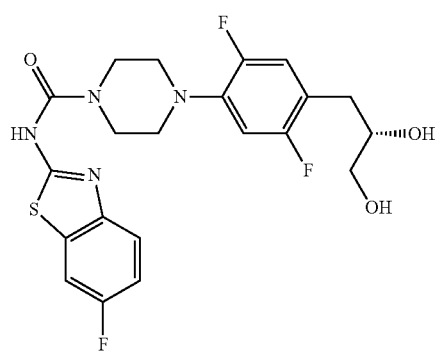

AHN

1H-NMR (DMSO-d$_6$) δ: 11.92-11.28 (1H, br), 7.77 (1H, dd, J=8.5, 2.6 Hz), 7.62-7.45 (1H, m), 7.20 (1H, td, J=9.0, 2.6 Hz), 7.09 (1H, dd, J=13.3, 7.0 Hz), 6.84 (1H, dd, J=11.4, 7.4 Hz), 4.64 (1H, d, J=5.3 Hz), 4.61 (1H, t, J=5.6 Hz), 3.80-3.65 (4H, m), 3.65-3.52 (1H, m), 3.36-3.20 (2H, m), 3.08-2.95 (4H, m), 2.74 (1H, dd, J=13.3, 4.4 Hz), 2.55-2.37 (1H, m).

Example 183

Compound AHP

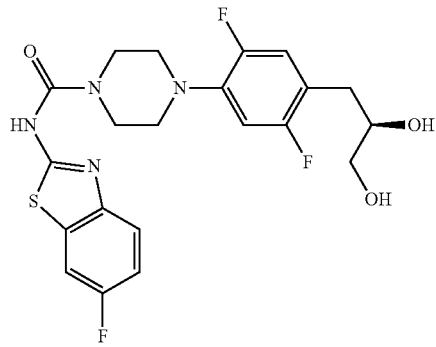

AHP

1H-NMR (DMSO-d$_6$) δ: 11.91-11.24 (1H, br), 7.77 (1H, dd, J=8.9, 2.3 Hz), 7.60-7.47 (1H, m), 7.20 (1H, td, J=9.1, 2.5 Hz), 7.09 (1H, dd, J=13.0, 7.1 Hz), 6.84 (1H, dd, J=11.5, 7.6 Hz), 4.64 (1H, d, J=5.5 Hz), 4.60 (1H, t, J=5.6 Hz), 3.80-3.65 (4H, m), 3.65-3.54 (1H, m), 3.38-3.20 (2H, m), 3.08-2.94 (4H, m), 2.74 (1H, dd, J=13.6, 4.3 Hz), 2.55-2.37 (1H, m).

Example 184

Compound AHQ

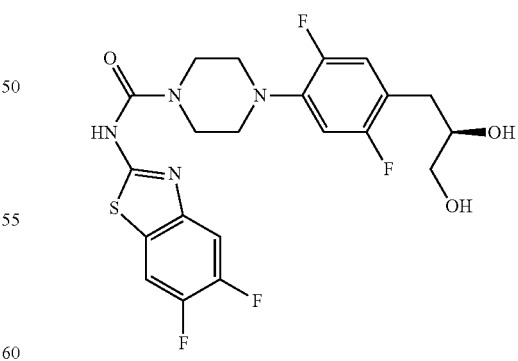

AHQ

1H-NMR (DMSO-d$_6$) δ: 11.67-11.28 (1H, br), 8.03 (1H, dd, J=10.3, 8.0 Hz), 7.63 (1H, dd, J=11.1, 7.2 Hz), 7.09 (1H, dd, J=13.2, 6.9 Hz), 6.83 (1H, dd, J=11.4, 7.5 Hz), 4.64 (1H, d, J=5.3 Hz), 4.60 (1H, t, J=5.6 Hz), 3.76-3.64 (4H, m), 3.64-3.53 (1H, m), 3.37-3.21 (2H, m), 3.06-2.93 (4H, m), 2.73 (1H, dd, J=13.4, 4.3 Hz), 2.43 (1H, dd, J=14.0, 8.1 Hz).

Example 185

Compound AHR

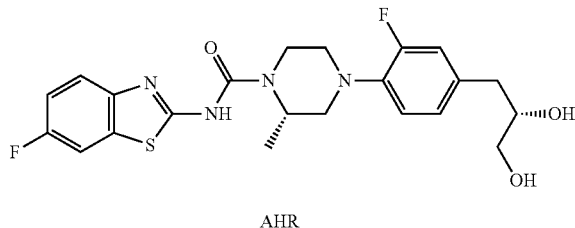 [SMILES: C[C@H]1CN(c2ccc(C[C@H](O)CO)cc2F)CCN1C(=O)Nc1nc2ccc(F)cc2s1 ; "AHR"]

AHR

1H-NMR (DMSO-d$_6$) δ: 11.87-11.06 (1H, m), 7.76 (1H, d, J=8.7 Hz), 7.63-7.44 (1H, m), 7.20 (1H, td, J=9.1, 2.5 Hz), 7.04-6.88 (3H, m), 4.66-4.51 (3H, m), 4.25-4.10 (1H, m), 3.65-3.51 (1H, m), 3.47-3.15 (5H, m), 2.85-2.60 (3H, m), 2.56-2.41 (1H, m), 1.33 (3H, d, J=6.7 Hz).

Example 186

Compound AHS

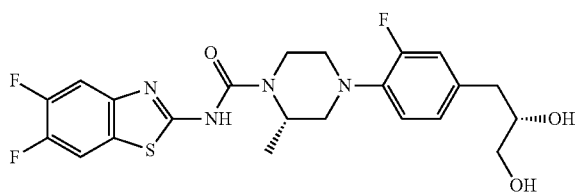

AHS

1H-NMR (DMSO-d$_6$) δ: 11.83-11.15 (1H, br), 8.03 (1H, dd, J=10.1, 8.3 Hz), 7.72-7.54 (1H, m), 7.06-6.88 (3H, m), 4.65-4.48 (3H, m), 4.16 (1H, d, J=13.7 Hz), 3.65-3.51 (1H, m), 3.46-3.13 (1H, m), 2.86-2.59 (5H, m), 2.54-2.39 (3H, m), 1.33 (1H, d, J=6.7 Hz).

Example 187

Compound AHT

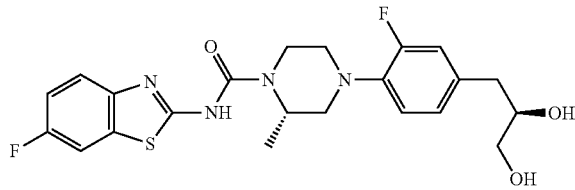

AHT

1H-NMR (DMSO-d$_6$) δ: 11.84-11.02 (1H, br), 7.76 (1H, d, J=7.2 Hz), 7.63-7.42 (1H, m), 7.20 (1H, td, J=9.1, 2.5 Hz), 7.07-6.87 (3H, m), 4.69-4.46 (3H, m), 4.18 (1H, d, J=11.7

Hz), 3.64-3.47 (1H, m), 3.42-3.14 (5H, m), 2.86-2.59 (3H, m), 2.57-2.37 (1H, m), 1.33 (3H, d, J=6.6 Hz).

Example 188

Compound AHU

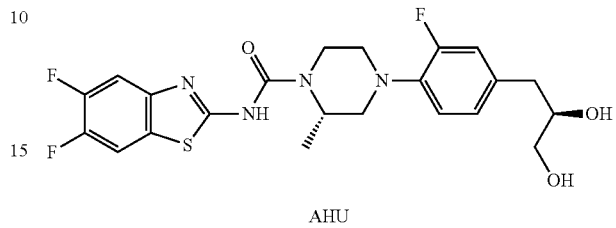

AHU

1H-NMR (DMSO-d$_6$) δ: 11.87-11.16 (1H, br), 8.03 (1H, dd, J=10.2, 8.1 Hz), 7.63 (1H, dd, J=10.7, 6.9 Hz), 7.06-6.86 (3H, m), 4.63-4.49 (3H, m), 4.16 (1H, d, J=12.8 Hz), 3.65-3.51 (1H, m), 3.41-3.13 (5H, m), 2.86-2.61 (3H, m), 2.55-2.38 (1H, m), 1.33 (3H, d, J=6.6 Hz).

Example 189

Compound AHV

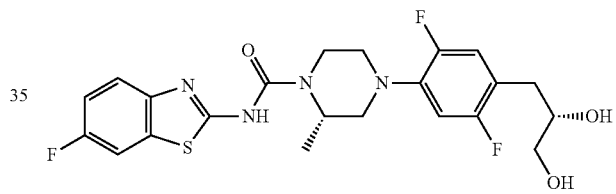

AHV

1H-NMR (DMSO-d$_6$) δ: 11.52-11.14 (1H, br), 7.92-7.44 (2H, m), 7.21 (1H, td, J=9.0, 2.5 Hz), 7.09 (1H, dd, J=13.0, 7.0 Hz), 6.82 (1H, dd, J=11.4, 7.6 Hz), 4.70-4.46 (3H, m), 4.31-4.06 (1H, m), 3.68-3.52 (1H, m), 3.37-3.20 (5H, m), 2.91-2.61 (3H, m), 2.54-2.37 (1H, m), 1.31 (3H, d, J=6.6 Hz).

Example 190

Compound AHW

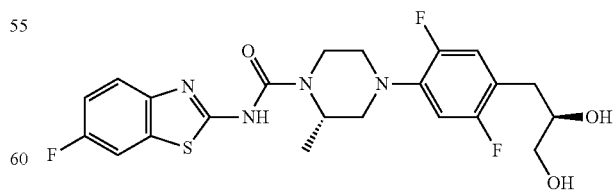

AHW

1H-NMR (DMSO-d$_6$) δ: 11.50-11.14 (1H, br), 7.90-7.41 (2H, m), 7.21 (1H, td, J=9.0, 2.5 Hz), 7.09 (1H, dd, J=13.1, 7.1 Hz), 6.82 (1H, dd, J=11.4, 7.6 Hz), 4.68-4.49 (3H, m), 4.26-4.06 (1H, m), 3.67-3.54 (1H, m), 3.40-3.18 (5H, m), 2.88-2.61 (3H, m), 2.55-2.37 (1H, m), 1.32 (3H, d, J=6.6 Hz).

Example 191

Compound AHX

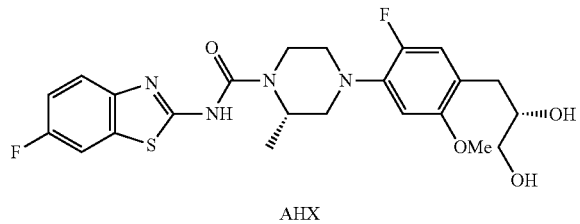

AHX

1H-NMR (DMSO-d$_6$) δ: 11.94-11.28 (1H, br), 7.77 (1H, dd, J=8.6, 2.4 Hz), 7.62-7.47 (1H, m), 7.21 (1H, td, J=9.1, 2.6 Hz), 6.95 (1H, d, J=13.1 Hz), 6.57 (1H, d, J=7.6 Hz), 4.67-4.52 (1H, m), 4.51-4.40 (2H, m), 4.18 (1H, d, J=13.0 Hz), 3.76 (3H, s), 3.67-3.54 (1H, m), 3.38-3.18 (5H, m), 2.91-2.61 (3H, m), 2.40 (1H, dd, J=14.0, 7.5 Hz), 1.33 (3H, d, J=6.6 Hz).

Example 192

Compound AHY

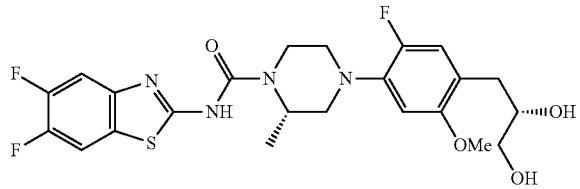

AHY

1H-NMR (DMSO-d$_6$) δ: 11.77-11.25 (1H, br), 8.04 (1H, dd, J=10.3, 8.1 Hz), 7.72-7.57 (1H, m), 6.95 (1H, d, J=13.3 Hz), 6.57 (1H, d, J=7.6 Hz), 4.63-4.51 (1H, m), 4.51-4.40 (2H, m), 4.16 (1H, d, J=13.3 Hz), 3.76 (3H, s), 3.67-3.55 (1H, m), 3.39-3.18 (5H, m), 2.93-2.61 (3H, m), 2.40 (1H, dd, J=14.0, 7.4 Hz), 1.33 (3H, d, J=6.7 Hz).

Example 193

Compound AHZ

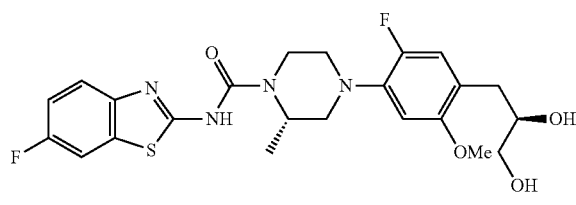

AHZ

1H-NMR (DMSO-d$_6$) δ: 11.50-11.14 (1H, br), 7.89-7.46 (2H, m), 7.21 (1H, td, J=9.1, 2.5 Hz), 6.95 (1H, d, J=13.1 Hz), 6.57 (1H, d, J=7.7 Hz), 4.70-4.42 (3H, m), 4.28-4.07 (1H, m), 3.76 (3H, s), 3.68-3.55 (1H, m), 3.42-3.20 (5H, m), 2.92-2.60 (3H, m), 2.38 (1H, dd, J=13.8, 7.6 Hz), 1.33 (3H, d, J=6.6 Hz).

Example 194

Compound AIA

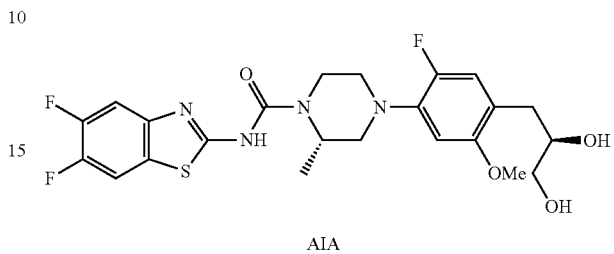

AIA

1H-NMR (DMSO-d$_6$) δ: 11.65-11.25 (1H, br), 8.04 (1H, t, J=9.0 Hz), 7.77-7.55 (1H, br), 6.95 (1H, d, J=13.1 Hz), 6.57 (1H, d, J=7.6 Hz), 4.63-4.40 (3H, m), 4.15 (1H, d, J=12.1 Hz), 3.76 (3H, s), 3.67-3.54 (1H, m), 3.38-3.18 (5H, m), 2.92-2.60 (3H, m), 2.38 (1H, dd, J=13.9, 7.6 Hz), 1.33 (3H, d, J=6.6 Hz).

Example 195

Compound AIB

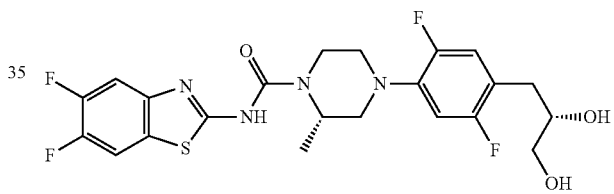

AIB

1H-NMR (DMSO-d$_6$) δ: 11.75-11.28 (1H, br), 8.04 (1H, t, J=9.2 Hz), 7.78-7.51 (1H, br), 7.10 (1H, dd, J=13.2, 7.0 Hz), 6.82 (1H, dd, J=11.3, 7.5 Hz), 4.69-4.49 (3H, m), 4.16 (1H, d, J=12.1 Hz), 3.68-3.52 (1H, m), 3.37-3.20 (5H, m), 2.88-2.61 (3H, m), 2.50-2.39 (1H, m), 1.32 (3H, d, J=6.6 Hz).

Example 196

Compound AIC

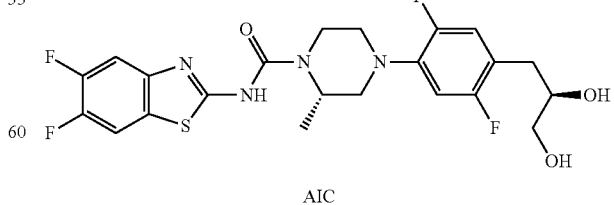

AIC

1H-NMR (DMSO-d$_6$) δ: 11.86-11.26 (1H, br), 8.03 (1H, dd, J=10.2, 8.2 Hz), 7.72-7.52 (1H, br), 7.09 (1H, dd, J=13.0, 7.0 Hz), 6.82 (1H, dd, J=11.5, 7.5 Hz), 4.68-4.49 (3H, m), 4.16 (1H, d, J=13.1 Hz), 3.66-3.52 (1H, m), 3.42-3.17 (5H, m), 2.87-2.65 (3H, m), 2.55-2.38 (1H, m), 1.32 (3H, d, J=6.7 Hz).

Example 197

Compound AID

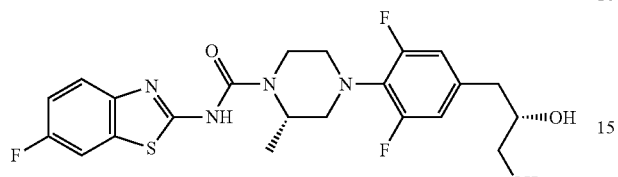

AID

1H-NMR (DMSO-d$_6$) δ: 11.85-11.04 (1H, br), 7.77 (1H, d, J=7.4 Hz), 7.66-7.41 (1H, br), 7.20 (1H, td, J=9.1, 2.6 Hz), 6.90 (1H, d, J=10.2 Hz), 4.70-4.43 (3H, m), 4.12 (1H, d, J=11.9 Hz), 3.68-3.53 (1H, m), 3.41-3.04 (6H, m), 2.97 (1H, d, J=11.4 Hz), 2.73 (1H, dd, J=13.8, 4.0 Hz), 2.55-2.41 (1H, m), 1.34 (3H, d, J=6.6 Hz).

Example 198

Compound AIE

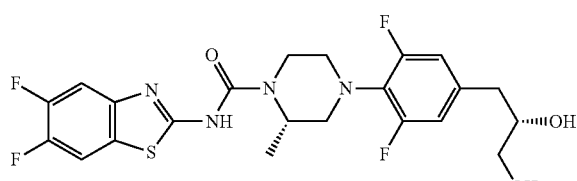

AIE

1H-NMR (DMSO-d$_6$) δ: 11.37 (1H, s), 8.05 (1H, t, J=8.6 Hz), 7.76-7.64 (1H, m), 6.90 (2H, d, J=10.4 Hz), 4.74-4.41 (3H, m), 4.07 (1H, d, J=11.6 Hz), 3.66-3.53 (1H, m), 3.41-3.03 (6H, m), 2.97 (1H, d, J=11.9 Hz), 2.73 (1H, dd, J=13.9, 4.1 Hz), 2.55-2.41 (1H, m), 1.34 (3H, d, J=6.7 Hz).

Example 199

Compound AIF

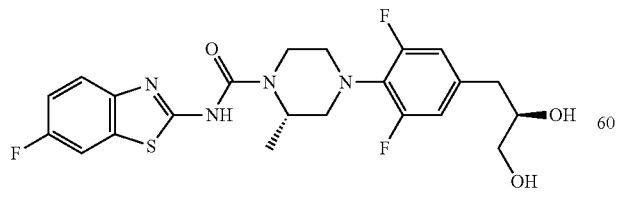

AIF

1H-NMR (DMSO-d$_6$) δ: 11.87-11.14 (1H, br), 7.77 (1H, dd, J=8.6, 2.3 Hz), 7.62-7.45 (1H, br), 7.21 (1H, td, J=9.1, 2.6 Hz), 6.90 (2H, d, J=10.4 Hz), 4.67-4.46 (3H, m), 4.13 (1H, d, J=13.1 Hz), 3.68-3.53 (1H, m), 3.45-3.03 (6H, m), 2.97 (1H, d, J=11.6 Hz), 2.73 (1H, dd, J=13.9, 4.1 Hz), 2.56-2.42 (1H, m), 1.34 (3H, d, J=6.6 Hz).

Example 200

Compound AIG

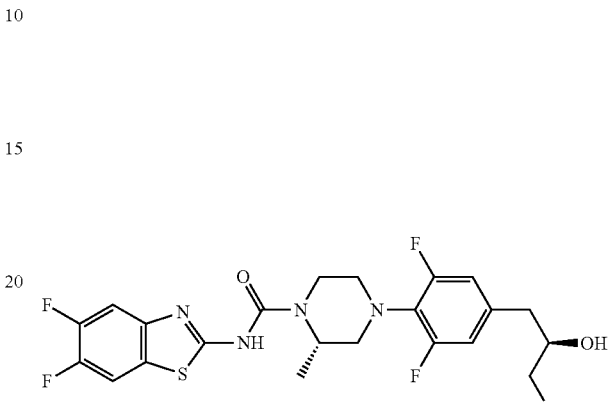

AIG

1H-NMR (DMSO-d$_6$) δ: 11.62-11.19 (1H, br), 8.04 (1H, t, J=9.1 Hz), 7.78-7.51 (1H, br), 6.90 (2H, d, J=10.4 Hz), 4.67-4.42 (3H, m), 4.09 (1H, d, J=11.9 Hz), 3.67-3.53 (1H, m), 3.40-3.03 (6H, m), 2.98 (1H, d, J=11.6 Hz), 2.73 (1H, dd, J=13.9, 4.1 Hz), 2.55-2.40 (1H, m), 1.34 (3H, d, J=6.7 Hz).

Example 201

Compound AFQ

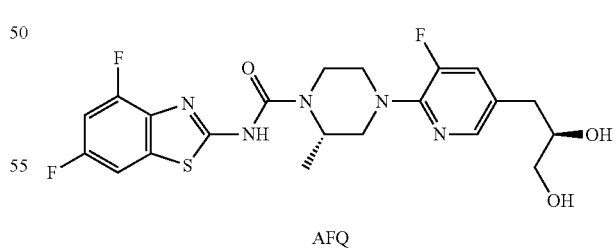

AFQ

1H-NMR (DMSO-d$_6$) δ: 11.53 (1H, s), 7.87 (1H, s), 7.75-7.67 (1H, m), 7.41 (1.0H, dd, J=14.1, 1.7 Hz), 7.29 (1H, ddd, J=11.5, 9.1, 1.8 Hz), 4.67-4.51 (3H, m), 4.15 (1H, d, J=13.1 Hz), 3.89 (1H, d, J=12.1 Hz), 3.73 (1H, d, J=12.8 Hz), 3.58 (1H, ddd, J=14.1, 9.2, 4.6 Hz), 3.40-3.18 (3H, m), 3.03 (1H, dd, J=12.7, 3.4 Hz), 2.85 (1H, td, J=12.3, 2.9 Hz), 2.72 (1H, dd, J=13.9, 4.0 Hz), 2.53-2.42 (1H, m), 1.26 (3H, d, J=6.7 Hz).
Example 202
Compound AFE
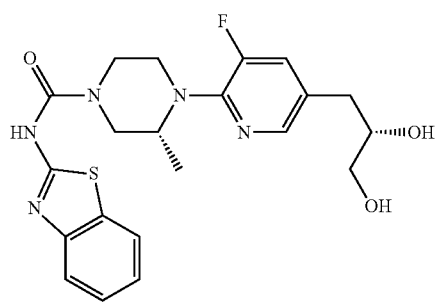
AFE
1H-NMR (DMSO-d6) δ: 12.07-11.24 (1H, br), 7.87 (1H, s), 7.80 (1H, d, J=7.0 Hz), 7.60-7.28 (3H, m), 7.19 (1H, t, J=7.6 Hz), 4.76-4.54 (2H, m), 4.31-3.88 (3H, m), 3.69-3.48 (2H, m), 3.47-3.10 (5H, m), 2.72 (1H, dd, J=14.1, 3.9 Hz), 2.56-2.39 (1H, m), 1.06 (3H, d, J=6.6 Hz).
Example 203
Compound AFF
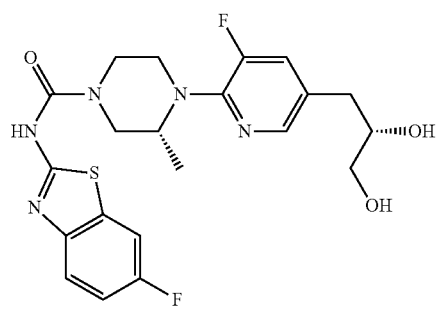
AFF
1H-NMR (DMSO-d6) δ: 7.87 (1H, s), 7.58 (1H, dd, J=8.8, 2.5 Hz), 7.43-7.33 (2H, m), 7.05 (1H, td, J=9.1, 2.6 Hz), 4.76-4.52 (2H, br), 4.24-3.95 (3H, m), 3.65-3.45 (2H, m),
3.40-3.07 (5H, m), 2.71 (1H, dd, J=14.0, 4.0 Hz), 2.54-2.39 (1H, m), 1.05 (3H, d, J=6.4 Hz).
Example 204
Compound AFG
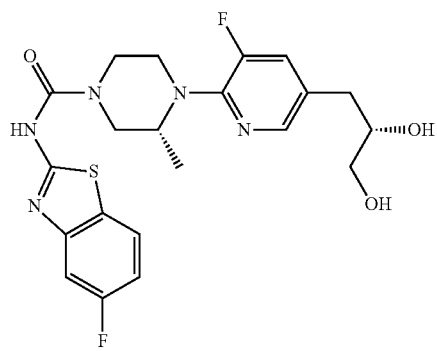
AFG
1H-NMR (DMSO-d6) δ: 11.75-11.27 (1H, br), 7.96-7.80 (2H, m), 7.47-7.28 (2H, m), 7.08 (1H, dt, J=12.7, 4.7 Hz), 4.68-4.57 (2H, m), 4.23-4.08 (2H, m), 3.99 (1H, d, J=13.4 Hz), 3.65-3.49 (2H, m), 3.48-3.15 (5H, m), 2.72 (1H, dd, J=13.7, 4.3 Hz), 2.55-2.40 (1H, m), 1.06 (3H, d, J=6.4 Hz).
Example 205
Compound AFC
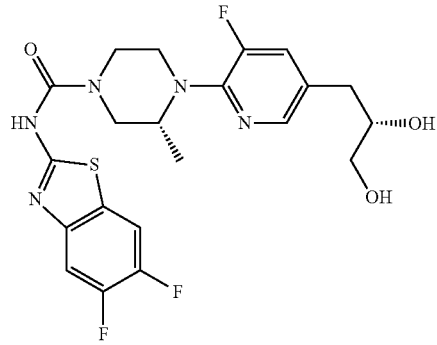
AFC
1H-NMR (DMSO-d6) δ: 7.86 (1H, s), 7.46 (1H, dd, J=10.4, 8.4 Hz), 7.40-7.32 (1H, m), 7.00 (1H, dd, J=12.1, 7.4

Hz), 4.40-3.93 (3H, m), 3.65-2.95 (7H, m), 2.70 (1H, dd, J=13.9, 4.0 Hz), 2.55-2.38 (1H, m), 1.02 (3H, d, J=6.4 Hz).
Example 206
Compound AFH
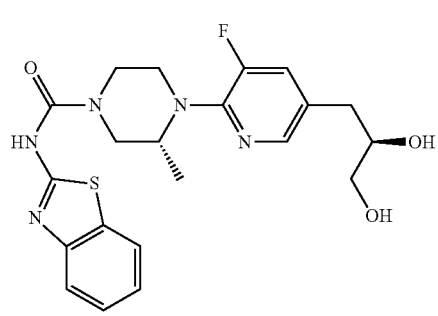
AFH
1H-NMR (DMSO-d$_6$) δ: 11.53-11.09 (1H, br), 7.97-7.28 (5H, m), 7.25-7.13 (1H, m), 4.70-4.56 (2H, m), 4.31-3.88 (3H, m), 3.66-3.48 (2H, m), 3.47-3.04 (5H, m), 2.72 (1H, dd, J=13.9, 4.1 Hz), 2.55-2.37 (1H, m), 1.06 (3H, d, J=6.4 Hz).
Example 207
Compound AFI
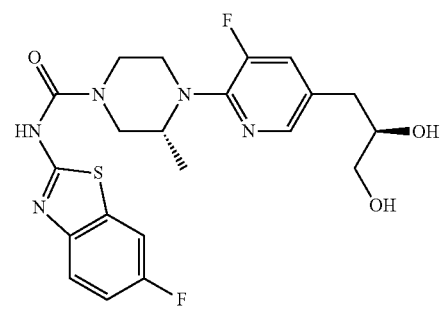
AFI
1H-NMR (DMSO-d$_6$) δ: 11.53-11.18 (1H, br), 7.90-7.83 (1H, m), 7.83-7.72 (1H, m), 7.67-7.48 (1H, br), 7.40 (1H, dd, J=14.3, 1.8 Hz), 7.21 (1H, td, J=9.1, 2.7 Hz), 4.69-4.57 (2H, m), 4.23-4.07 (2H, m), 4.05-3.91 (1H, m), 3.61-3.50 (2H, m),
3.45-3.15 (5H, m), 2.72 (1H, dd, J=13.9, 4.1 Hz), 2.55-2.40 (1H, m), 1.06 (3H, d, J=6.4 Hz).
Example 208
Compound AFJ
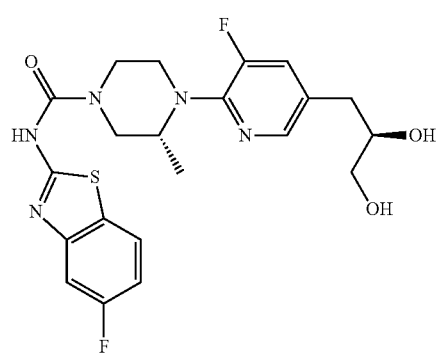 [SMILES: C[C@@H]1CN(C(=O)Nc2nc3ccccc3s2)CCN1c1ncc(C[C@@H](O)CO)cc1F ; "AFH"]
AFJ
1H-NMR (DMSO-d$_6$) δ: 11.80-11.31 (1H, br), 7.96-7.81 (2H, m), 7.48-7.25 (2H, m), 7.08 (1H, td, J=9.0, 2.4 Hz), 4.70-4.57 (2H, m), 4.24-4.08 (2H, m), 3.99 (1H, d, J=11.7 Hz), 3.64-3.48 (2H, m), 3.47-3.14 (5H, m), 2.72 (1H, dd, J=13.7, 4.0 Hz), 2.55-2.41 (1H, m), 1.07 (3H, d, J=6.4 Hz).
Example 209
Compound AFD
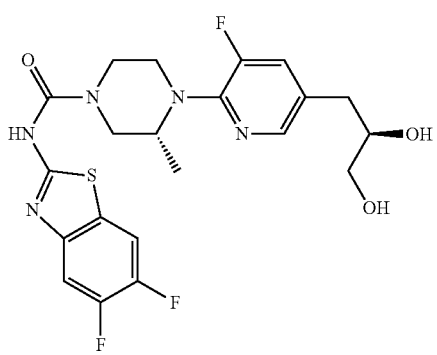
AFD
1H-NMR (DMSO-d$_6$) δ: 7.86 (1H, s), 7.75 (1H, t, J=9.5 Hz), 7.43-7.27 (2H, m), 4.69-4.55 (2H, m), 4.26-3.92 (3H, m), 3.64-3.04 (7H, m), 2.70 (1H, dd, J=13.9, 4.1 Hz), 2.55-2.38 (1H, m), 1.04 (3H, d, J=6.6 Hz).

Example 210

Compound AGX

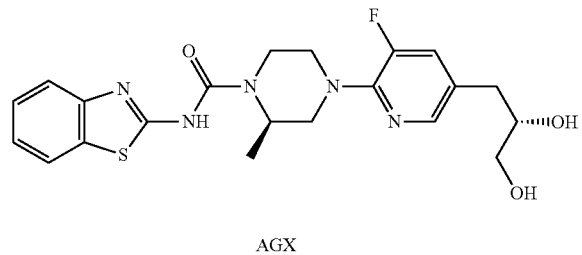 [SMILES: C[C@@H]1CN(c2ncc(C[C@H](O)CO)cc2F)CCN1C(=O)Nc1nc2ccccc2s1]

AGX

1H NMR (CH₃OD) δ 1.37 (3 H, d, J=6.80 Hz), 2.62 (1 H, dd, J=8.11, 14.03 Hz), 2.81 (1 H, dd, J=4.60, 14.25 Hz), 2.93 (1 H, dt, J=3.51, 12.50 Hz), 3.09 (1 H, dd, J=3.51, 12.72 Hz), 3.42 (1 H, m), 3.51 (2 H, m), 3.80 (2 H, m), 3.96 (1 H, d, J=11.18 Hz), 4.32 (1 H, br s), 4.72 (1 H, br s), 7.22 (1 H, t, J=7.89 Hz), 7.37 (3 H, m), 7.69 (1 H, d, J=6.36 Hz), 7.90 (1 H, s); LC/MS (M+1) 446.

Example 211

Compound AAB

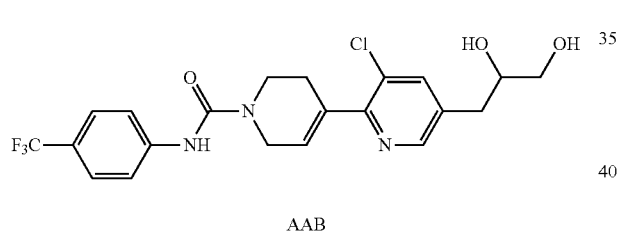

AAB

¹H NMR: δH (300 MHz, CDCl₃): 8.35 (1H, s), 7.65 (1H, s), 7.54 (4H, m), 6.70 (1H, s), 6.15 (1H, s), 4.23 (2H, m), 3.92 (1H, m), 3.78-3.70 (3H, m), 3.55 (1H, m), 2.80-2.69 (4H, m), 1.63 (1H, m), 1.48 (1H, m).

Example 212

Compound AAC

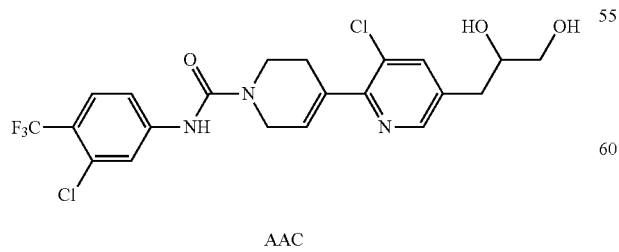

AAC

¹H NMR: δH (300 MHz, CDCl₃): 8.34 (1H, s), 7.69 (1H, s), 7.64 (1H, s), 7.58 (1H, d, J=9.0 Hz), 7.39 (1H, d, J=9.0 Hz), 6.85 (1H, s), 6.13 (1H, s), 4.22 (2H, m), 3.93 (1H, m), 3.75 (3H, m), 3.55 (1H, m), 2.77-2.69 (4H, m), 1.33 (2H, m).

Example 213

Compound AAD

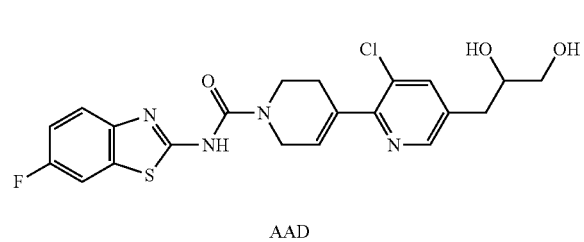 [SMILES: O=C(Nc1nc2ccc(F)cc2s1)N1CC=C(c2ncc(CC(O)CO)cc2Cl)CC1 ; "AAD"]

AAD

¹H NMR: OH (300 MHz, DMSO): 11.40 (1H, br), 8.34 (1H, s), 7.77 (2H, m), 7.52 (1H, m), 7.20 (1H, m), 6.17 (1H, s), 4.76 (1H, d, J=3.0 Hz), 4.70 (1H, t, J=3.0 Hz), 4.24 (2H, m), 3.76 (2H, m), 3.52 (1H, m), 3.26 (2H, m), 2.77 (1H, m), 2.53 (3H, m).

Example 214

Compound AAE

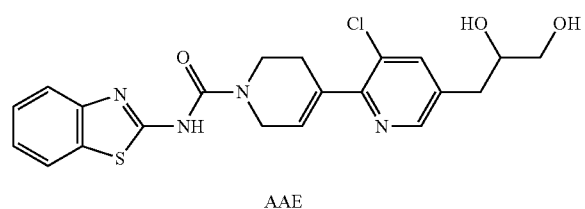 [SMILES: O=C(Nc1nc2ccccc2s1)N1CC=C(c2ncc(CC(O)CO)cc2Cl)CC1]

AAE

¹H NMR: δH (300 MHz, DMSO): 11.50 (1H, br), 8.36 (1H, s), 7.81 (1H, m), 7.79 (1H, s), 7.50 (1H, m), 7.37 (1H, t, J=6.0 Hz), 7.21 (1H, t, J=6.0 Hz), 6.20 (1H, s), 4.77 (1H, d, J=6.0 Hz), 4.70 (1H, d, J=6.0 Hz), 4.27 (2H, m), 3.79 (2H, m), 3.36 (1H, m), 2.82 (1H, m), 2.55 (3H, m).

Example 215

Compound AAG

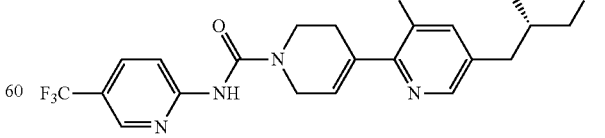

AAG

1H-NMR (CDCl₃) δ: 8.46 (1H, s), 8.30 (1H, d, J=3.0 Hz), 8.21 (1H, d, J=9.0 Hz), 7.88 (1H, dd, J=9.0, 3.0 Hz), 7.66 (1H, d, J=3.0 Hz), 7.51 (1H, s), 6.17 (1H, m), 4.26 (2H, m), 3.97 (1H, m), 3.81-3.72 (3H, m), 3.56 (1H, m), 2.80-2.70 (4H, m), 2.53 (1H, m), 2.13 (1H, m)

Example 216

Compound AAH

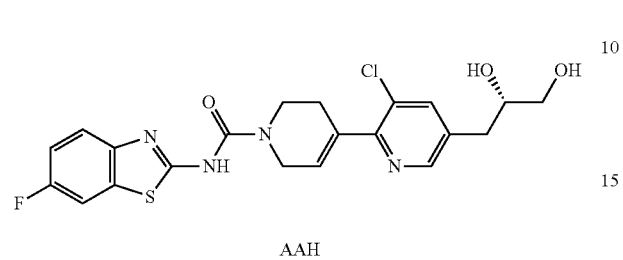

AAH $^1$H NMR: δH (300 MHz, DMSO): 11.40 (1H, br), 8.34 (1H, s), 7.77 (2H, m), 7.52 (1H, m), 7.20 (1H, m), 6.17 (1H, s), 4.76 (1H, d, J=3.0 Hz), 4.70 (1H, t, J=3.0 Hz), 4.24 (2H, m), 3.76 (2H, m), 3.52 (1H, m), 3.26 (2H, m), 2.77 (1H, m), 2.53 (3H, m).

Example 217

Compound AAI

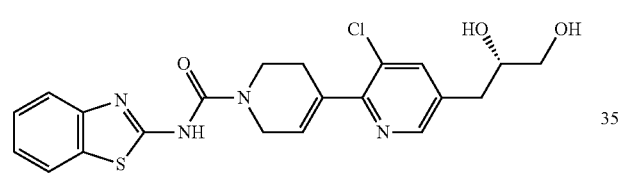

AAI $^1$H NMR: δH (300 MHz, DMSO): 11.50 (1H, br), 8.36 (1H, s), 7.81 (1H, m), 7.79 (1H, s), 7.50 (1H, m), 7.37 (1H, t, J=6.0 Hz), 7.21 (1H, t, J=6.0 Hz), 6.20 (1H, s), 4.77 (1H, d, J=6.0 Hz), 4.70 (1H, d, J=6.0 Hz), 4.27 (2H, m), 3.79 (2H, m), 3.36 (1H, m), 2.82 (1H, m), 2.55 (3H, m).

Example 218

Compound AAX $^1$H NMR (CD$_3$OD) δ 2.65 (1 H, dd, J=8.8, 14.0 Hz), 2.88 (1 H, dd, J=4.0, 14.0 Hz), 3.01 (2 H, t, J=6.4 Hz), 3.42 (2 H, dd, J=1.5, 5.5 Hz), 3.73 (1 H, m), 3.81 (3 H, s), 4.09 (2 H, t, J=6.6 Hz), 6.67 (1 H, s), 7.04 (1 H, dd, J=1.5, 8.6 Hz), 7.40 (1 H, d, J=8.8 Hz), 7.48 (1 H, s), 7.53 (1 H, dd, J=1.5, 12.7 Hz), 8.34 (1 H, s); LC/MS (M+1) 484.

Chemical structures were listed in Table 1 described below as to the product of the following examples;

TABLE 1

| No. of Example | No. of Compound | No. of Example | No. of Compound |
|---|---|---|---|
| 218 | AAX | 117 | AFB |
| 90 | ADS | 159 | AFS |
| 89 | ADR | 158 | AFR |
| 97 | ADT | 131 | AFT |

TABLE 1-continued

| No. of Example | No. of Compound | No. of Example | No. of Compound |
|---|---|---|---|
| 98 | ADU | 132 | AFU |
| 91 | ADW | 143 | AFX |
| 99 | ADV | 119 | AFW |
| 92 | ADX | 160 | AFY |
| 100 | ADY | 144 | AFZ |
| 102 | AEA | 146 | AGB |
| 101 | ADZ | 145 | AGA |
| 93 | AEB | 147 | AGC |
| 94 | AEC | 133 | AGD |
| 103 | AEE | 135 | AGF |
| 95 | AED | 134 | AGE |
| 96 | AEG | 136 | AGG |
| 104 | AEH | 137 | AGH |
| 151 | AEJ | 121 | AGJ |
| 105 | AEI | 120 | AGI |
| 152 | AEK | 122 | AGK |
| 153 | AEL | 123 | AGL |
| 155 | AEN | 149 | AGN |
| 154 | AEM | 148 | AGM |
| 156 | AEO | 150 | AGO |
| 106 | AEP | 138 | AGP |
| 108 | AER | 140 | AGR |
| 107 | AEQ | 139 | AGQ |
| 109 | AES | 141 | AGS |
| 157 | AET | 142 | AGT |
| 111 | AEV | 125 | AGV |
| 110 | AEU | 124 | AGU |
| 112 | AEW | 126 | AGW |
| 113 | AEX | 127 | AGY |
| 115 | AEZ | 129 | AHA |
| 114 | AEY | 128 | AGZ |
| 116 | AFA | 130 | AHB |

TABLE 2

| No. | STRUCTURE |
|---|---|
| AAX | 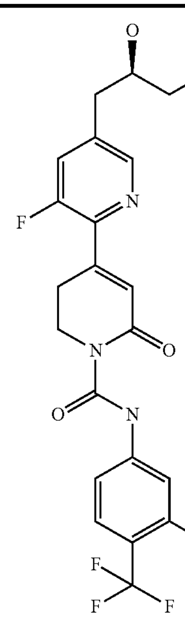 |

TABLE 2-continued
| No. | STRUCTURE |
|---|---|
| ADR | 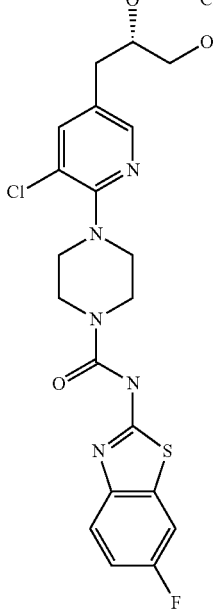 |
| ADS | 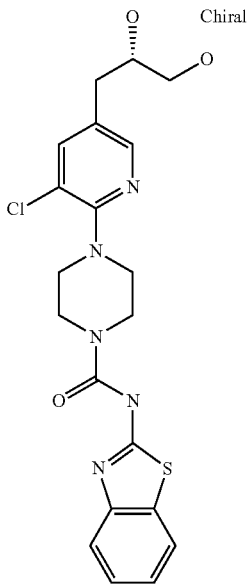 [SMILES: O=C(Nc1nc2ccccc2s1)N1CCN(c2ncc(C[C@H](O)CO)cc2Cl)CC1] |
TABLE 2-continued
| No. | STRUCTURE |
|---|---|
| ADT | 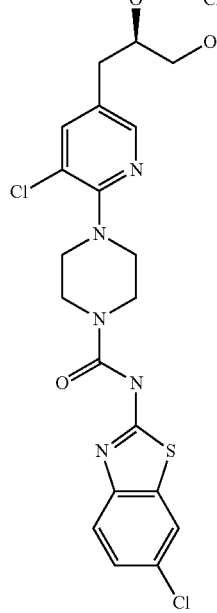 |
| ADU | 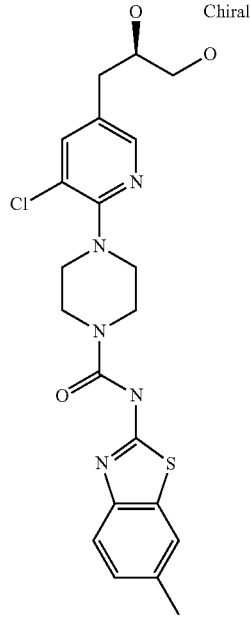 [SMILES: Cc1ccc2nc(NC(=O)N3CCN(c4ncc(C[C@@H](O)CO)cc4Cl)CC3)sc2c1] |

TABLE 2-continued

| No. | STRUCTURE |
|---|---|
| ADV | (structure) |
| ADW | (structure) |
| ADX | (structure) |
| ADY | (structure) |

TABLE 2-continued
| No. | STRUCTURE |
|---|---|
| ADZ | 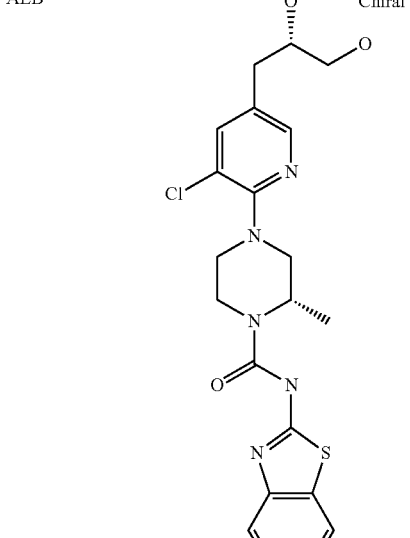 |
| AEA | 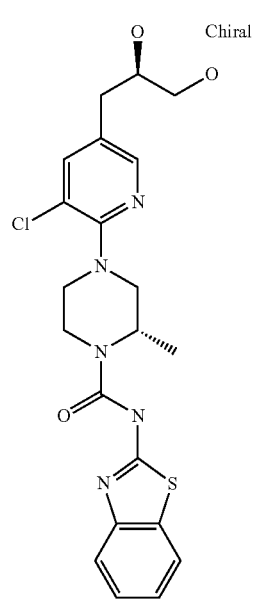 [SMILES: C[C@H]1CN(c2ncc(C[C@@H](O)CO)cc2Cl)CCN1C(=O)Nc1nc2ccccc2s1] |
TABLE 2-continued
| No. | STRUCTURE |
|---|---|
| AEB | (structure with 6-fluorobenzothiazole) |
| AEC | 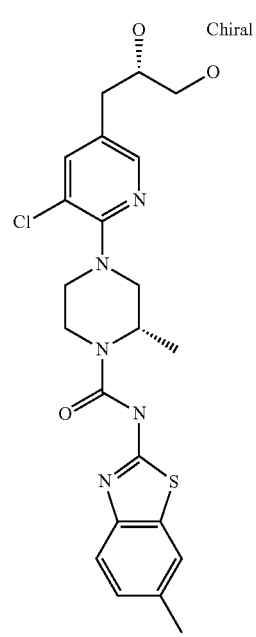 [SMILES: Cc1ccc2nc(NC(=O)N3CCN(c4ncc(C[C@H](O)CO)cc4Cl)C[C@@H]3C)sc2c1] |

TABLE 2-continued
| No. | STRUCTURE |
|---|---|
| AED | 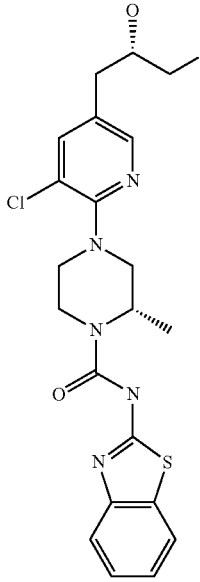 |
| AEE | 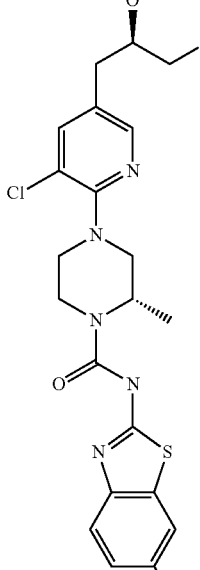 |
| AEG | 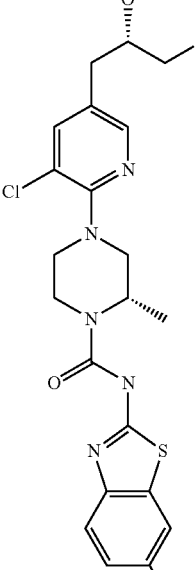 |
| AEH | 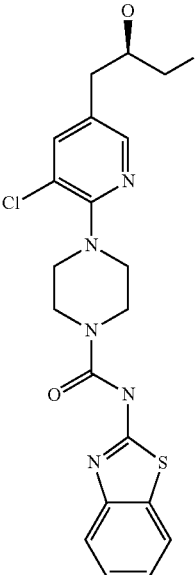 |

TABLE 2-continued
| No. | STRUCTURE |
|---|---|
| AEI | 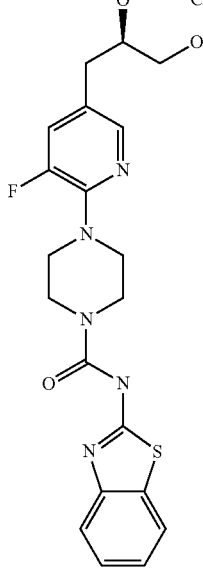 |
| AEJ | 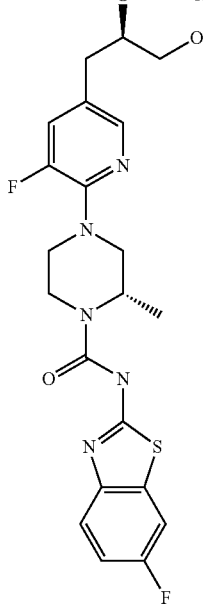 |
TABLE 2-continued
| No. | STRUCTURE |
|---|---|
| AEK | 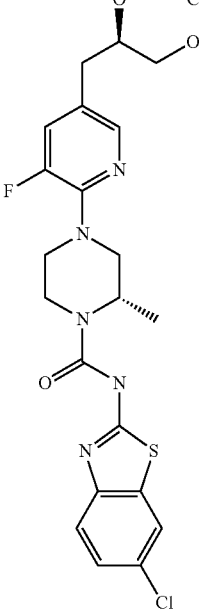 |
| AEL | 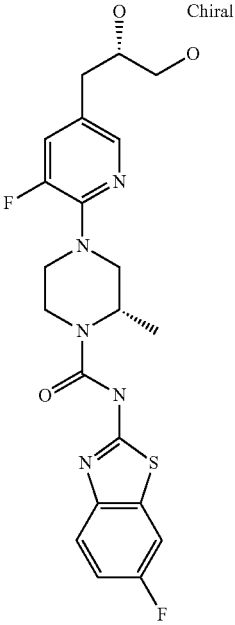 |

TABLE 2-continued
| No. | STRUCTURE |
|---|---|
| AEM | 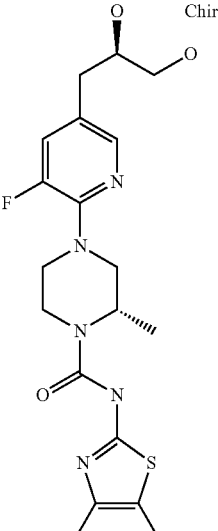 |
| AEN | 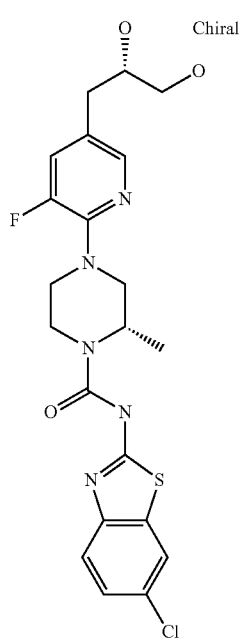 [SMILES: C[C@H]1CN(c2ncc(C[C@H](O)CO)cc2F)CCN1C(=O)Nc1nc2ccc(Cl)cc2s1] |
| AEO | |
| AEP | |

TABLE 2-continued
| No. | STRUCTURE |
|---|---|
| AEQ | 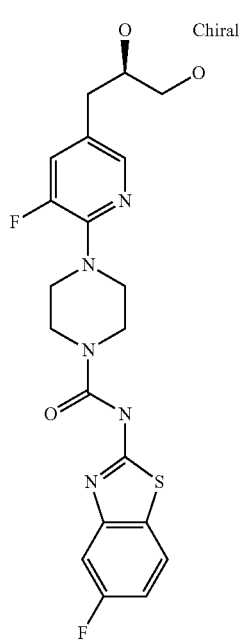 [SMILES: O=C(Nc1nc2cc(F)ccc2s1)N1CCN(c2ncc(C[C@@H](O)CO)cc2F)CC1] |
| AER | |
| No. | STRUCTURE |
|---|---|
| AES | 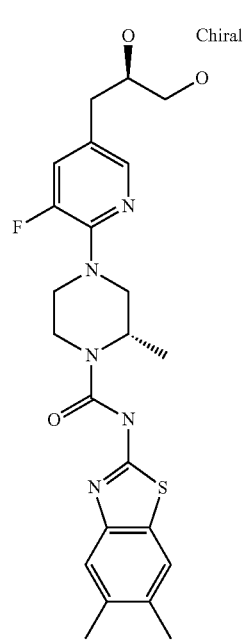 [SMILES: Cc1cc2nc(NC(=O)N3CCN(c4ncc(C[C@@H](O)CO)cc4F)C[C@@H]3C)sc2cc1C] |
| AET | |

TABLE 2-continued
| No. | STRUCTURE |
|---|---|
| AEU | 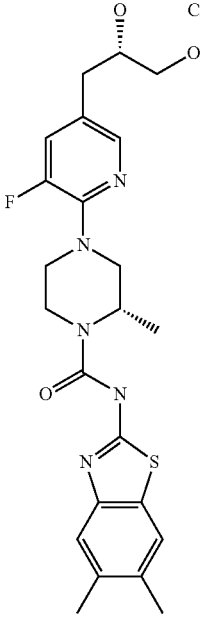 |
| AEV | 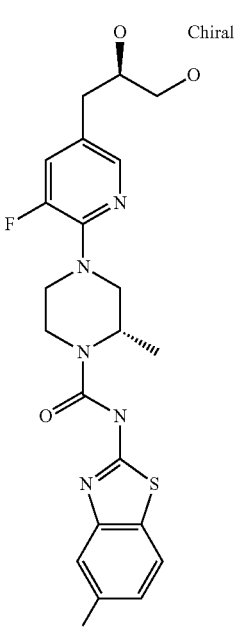 |
TABLE 2-continued
| No. | STRUCTURE |
|---|---|
| AEW | 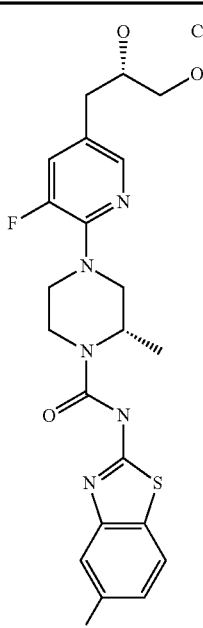 |
| AEX | 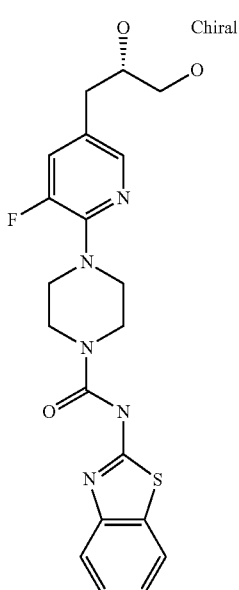 |

TABLE 2-continued
| No. | STRUCTURE |
|---|---|
| AEY | 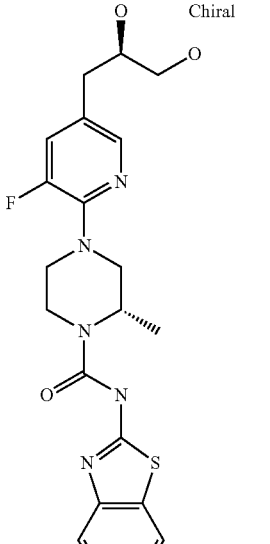 |
| AEZ | 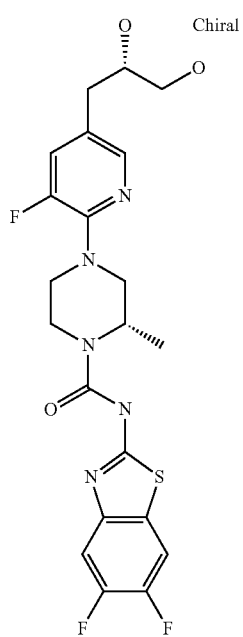 |
| AFA | |
| AFB | 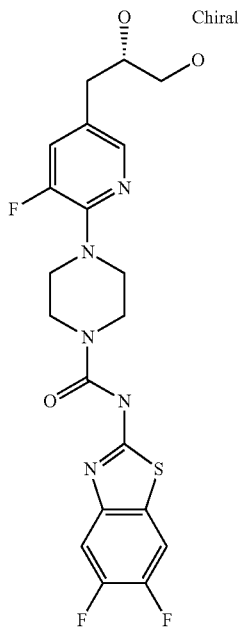 [SMILES: O=C(Nc1nc2cc(F)c(F)cc2s1)N1CCN(c2ncc(C[C@H](O)CO)cc2F)CC1] |

TABLE 2-continued
| No. | STRUCTURE |
|---|---|
| AFR | 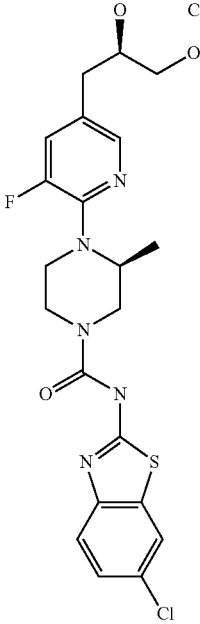 |
| AFS | 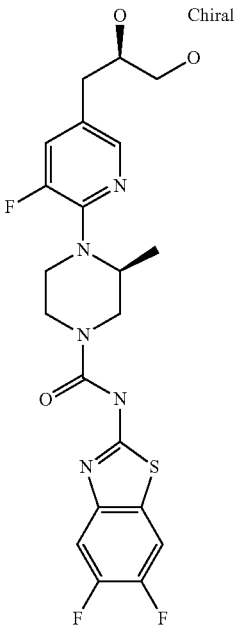 [SMILES: C[C@H]1CN(C(=O)Nc2nc3cc(F)c(F)cc3s2)CCN1c1ncc(C[C@@H](O)CO)cc1F] |
TABLE 2-continued
| No. | STRUCTURE |
|---|---|
| AFT | 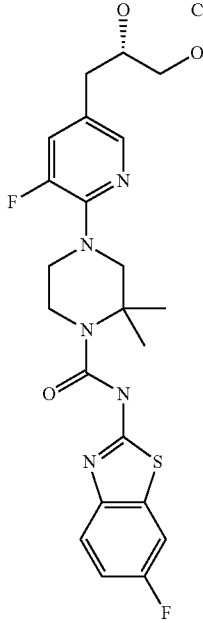 |
| AFU | 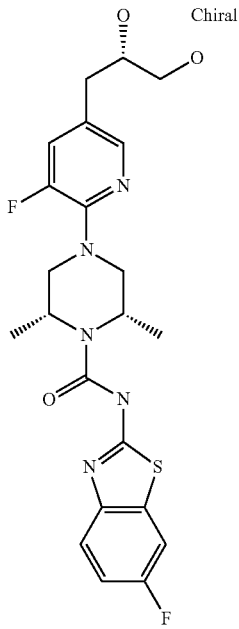 |

TABLE 2-continued
| No. | STRUCTURE |
|---|---|
| AFW | 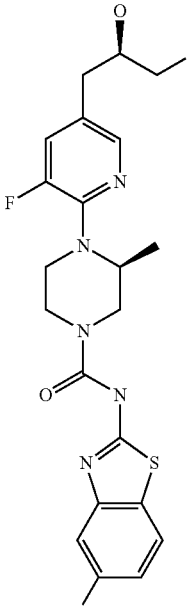 |
| AFX | 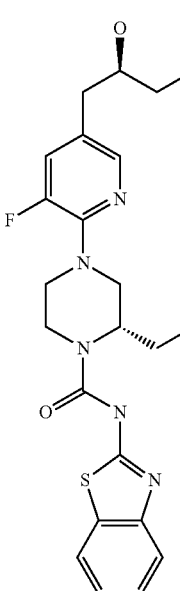 |
TABLE 2-continued
| No. | STRUCTURE |
|---|---|
| AFY | 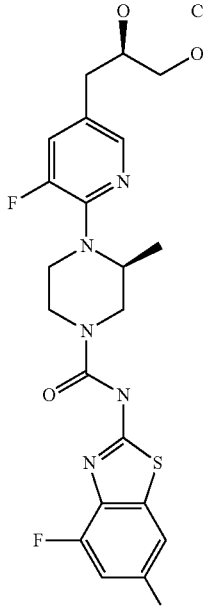 |
| AFZ | 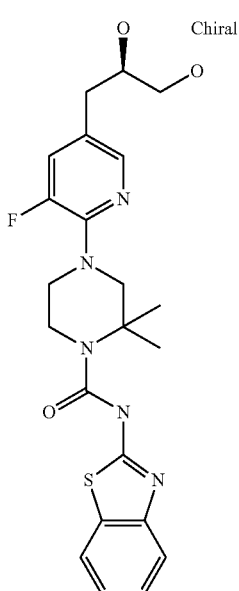 |

TABLE 2-continued
| No. | STRUCTURE |
|---|---|
| AGA | 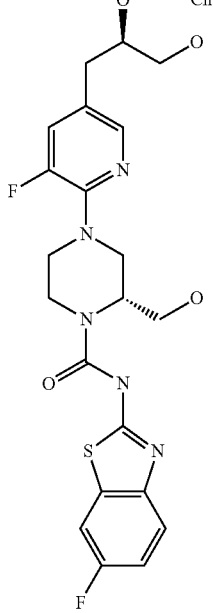 |
| AGB | 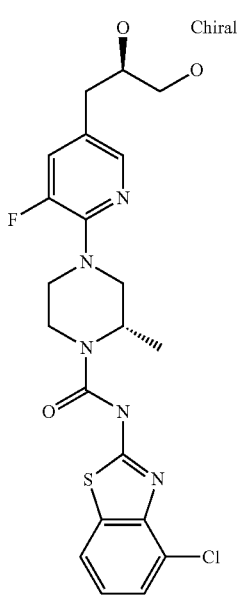 [SMILES: C[C@H]1CN(c2ncc(C[C@@H](O)CO)cc2F)CCN1C(=O)Nc1nc2c(Cl)cccc2s1] |
TABLE 2-continued
| No. | STRUCTURE |
|---|---|
| AGC | 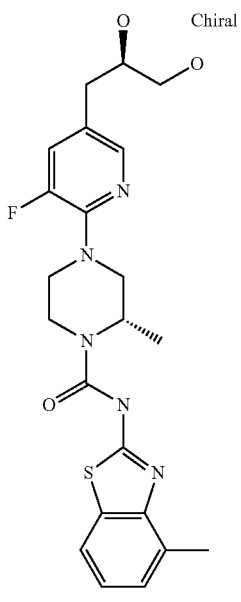 [SMILES: Cc1cccc2sc(NC(=O)N3CCN(c4ncc(C[C@@H](O)CO)cc4F)C[C@@H]3C)nc12] |
| AGD | 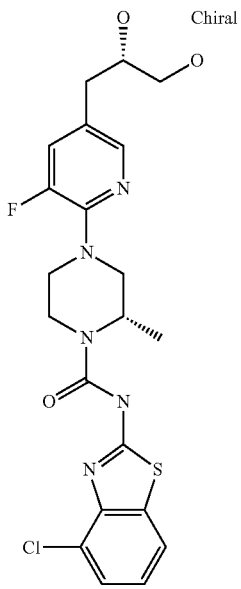 [SMILES: C[C@H]1CN(c2ncc(C[C@H](O)CO)cc2F)CCN1C(=O)Nc1nc2c(Cl)cccc2s1] |

TABLE 2-continued
| No. | STRUCTURE |
|---|---|
| AGE | 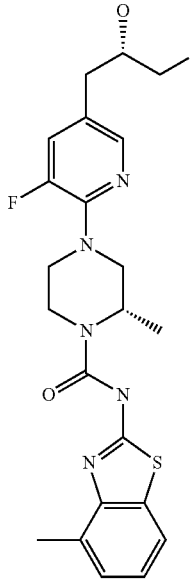 |
| AGF | 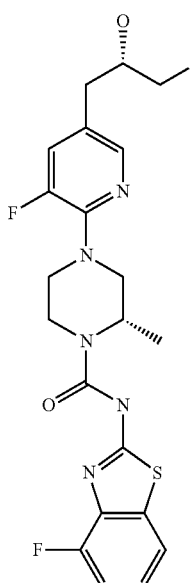 |
TABLE 2-continued
| No. | STRUCTURE |
|---|---|
| AGG | 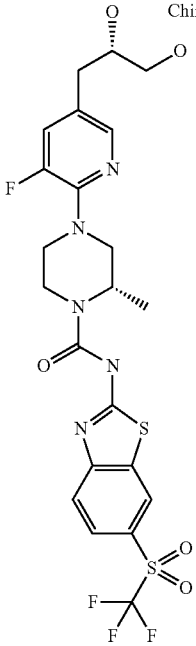 |
| AGH | 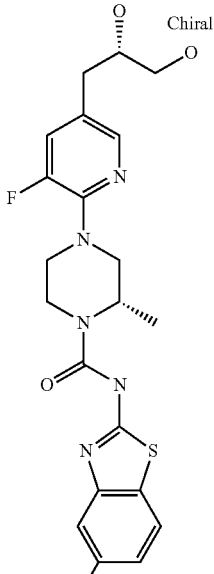 |

TABLE 2-continued
| No. | STRUCTURE |
|---|---|
| AGI | 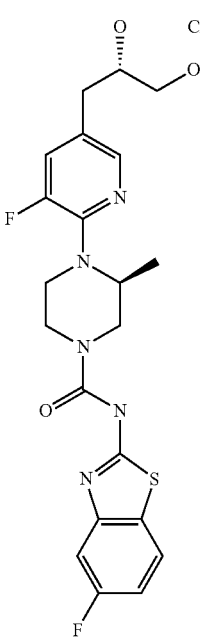 |
| AGJ | 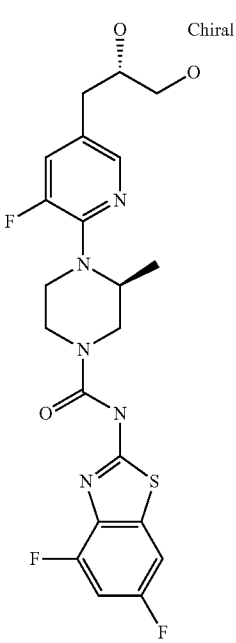 [SMILES: C[C@H]1CN(C(=O)Nc2nc3c(F)cc(F)cc3s2)CCN1c1ncc(C[C@H](O)CO)cc1F] |
TABLE 2-continued
| No. | STRUCTURE |
|---|---|
| AGK | 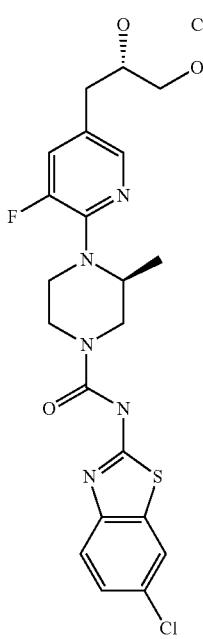 |
| AGL | 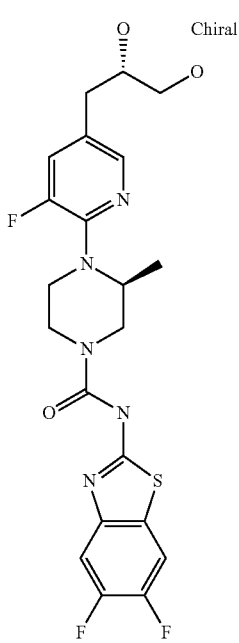 [SMILES: C[C@H]1CN(C(=O)Nc2nc3cc(F)c(F)cc3s2)CCN1c1ncc(C[C@H](O)CO)cc1F] |

TABLE 2-continued
| No. | STRUCTURE |
|---|---|
| AGM | 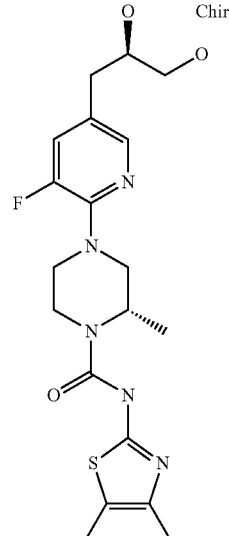 |
| AGN | 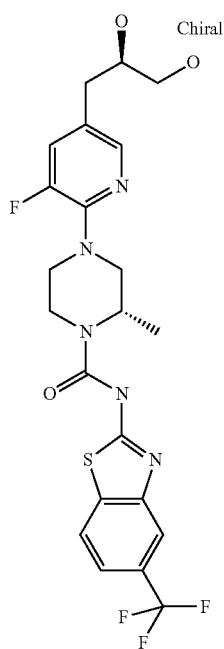 [SMILES: C[C@H]1CN(c2ncc(C[C@@H](O)CO)cc2F)CCN1C(=O)Nc1nc2cc(C(F)(F)F)ccc2s1] |
| AGO | 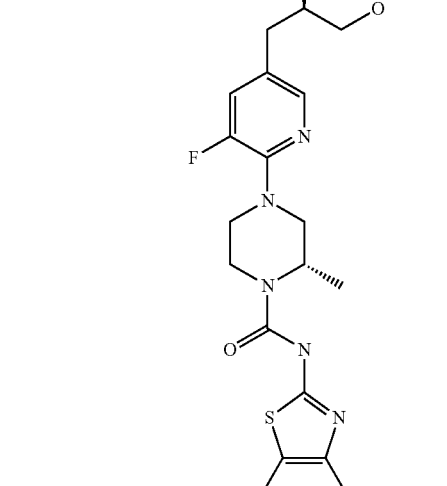 |
| AGP | 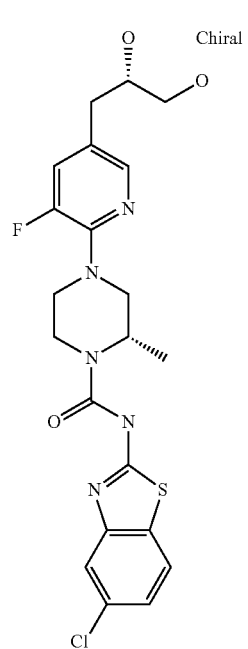 [SMILES: C[C@H]1CN(c2ncc(C[C@H](O)CO)cc2F)CCN1C(=O)Nc1nc2cc(Cl)ccc2s1] |

TABLE 2-continued
| No. | STRUCTURE |
|---|---|
| AGQ | 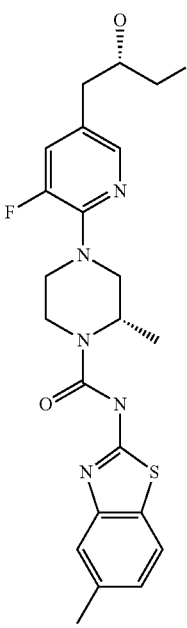 |
| AGR | 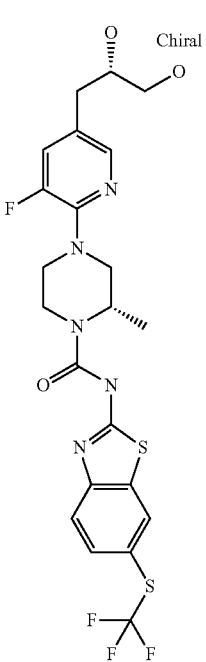 [SMILES: C[C@H]1CN(c2ncc(C[C@H](O)CO)cc2F)CCN1C(=O)Nc1nc2ccc(SC(F)(F)F)cc2s1] |
| AGS | 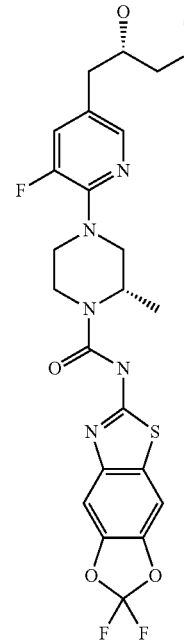 |
| AGT | 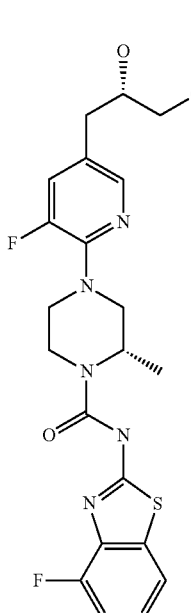 |

TABLE 2-continued

| No. | STRUCTURE |
|---|---|
| AGU | (chemical structure) |
| AGV | (chemical structure) |
| AGW | (chemical structure) |
| AGY | (chemical structure) |

TABLE 2-continued
| No. | STRUCTURE |
|---|---|
| AGZ | 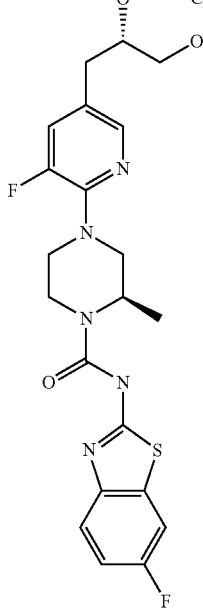 |
| AHA | 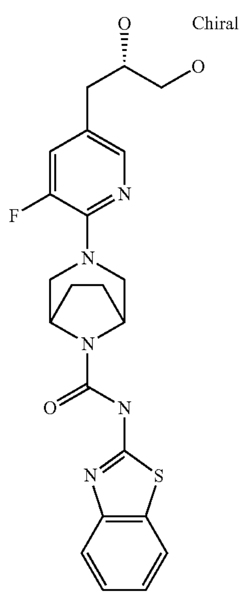 [SMILES: O=C(Nc1nc2ccccc2s1)N1C2CCC1CN(c1ncc(C[C@H](O)CO)cc1F)C2] |
TABLE 2-continued
| No. | STRUCTURE |
|---|---|
| AHB | 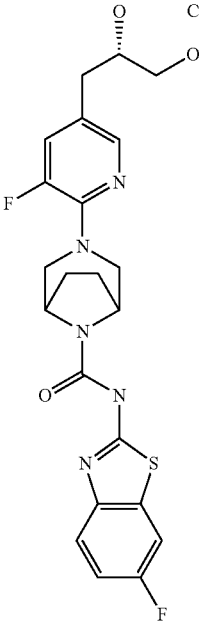 |
In the above tables,
means
means
and
means
.

Example 219

In Vivo Assays for Prevention or Treatment of Pain

Test Animals: Each experiment uses rats weighing between 200-260 g at the start of the experiment. The rats are group-housed and have free access to food and water at all times, except prior to oral administration of a compound of Formula I when food is removed for 16 hours before dosing. A control group acts as a comparison to rats treated with a compound of Formula I. The control group is administered the carrier for the compound of Formula I. The volume of carrier administered to the control group is the same as the volume of carrier and compound of Formula I administered to the test group.

Acute Pain: To assess the actions of the compounds of Formula I on the treatment or prevention of acute pain the rat tail flick test can be used. Rats are gently restrained by hand and the tail exposed to a focused beam of radiant heat at a point 5 cm from the tip using a tail flick unit (Model 7360, commercially available from Ugo Basile of Italy). Tail flick latencies are as defined as the interval between the onset of the thermal stimulus and the flick of the tail. Animals not responding within 20 seconds are removed from the tail flick unit and assigned a withdrawal latency of 20 seconds. Tail flick latencies are measured immediately before (pre-treatment) and 1, 3, and 5 hours following administration of a compound of Formula I. Data are expressed as tail flick latency(s) and the percentage of the maximal possible effect (% MPE), i.e., 20 seconds, is calculated as follows:

$$\% \, MPE = \frac{[(\text{post administration latency}) - (\text{pre-administration latency})]}{(20 \text{ s pre-administration latency})} \times 100$$

The rat tail flick test is described in F. E. D'Amour et al., "A Method for Determining Loss of Pain Sensation," *J. Pharmacol. Exp. Ther.* 72:74-79 (1941).

Acute pain can also be assessed by measuring the animal's response to noxious mechanical stimuli by determining the paw withdrawal threshold ("PWT"), as described below.

Inflammatory Pain: To assess the actions of the compounds of Formula I on the treatment or prevention of inflammatory pain the Freund's complete adjuvant ("FCA") model of inflammatory pain is used. FCA-induced inflammation of the rat hind paw is associated with the development of persistent inflammatory mechanical and thermal hyperalgesia and provides reliable prediction of the anti-hyperalgesic action of clinically useful analgesic drugs (L. Bartho et al., "Involvement of Capsaicin-sensitive Neurones in Hyperalgesia and Enhanced Opioid Antinociception in Inflammation," *Naunyn-Schmiedeberg's Archives of Pharmacol.* 342:666-670 (1990)). The left hind paw of each animal is administered a 50 µL intraplantar injection of 50% FCA. 24 hour post injection, the animal is assessed for response to noxious mechanical stimuli by determining the PWT, or to noxious thermal stimuli by determining the PWL, as described below. Rats are then administered a single injection of 1, 3, 10 or 30 mg/Kg of either a compound of Formula I; 30 mg/Kg of a control selected from Celebrex, indomethacin or naproxen; or carrier. Responses to noxious mechanical or thermal stimuli are then determined 1, 3, 5 and 24 hours post administration. Percentage reversal of hyperalgesia for each animal is defined as:

$$\% \, \text{Reversal} = \frac{\left[\begin{array}{c}(\text{post administration } PWT \text{ or } PWL) - \\ (\text{pre-administration } PWT \text{ or } PWL)\end{array}\right]}{\left[\begin{array}{c}(\text{baseline } PWT \text{ or } PWL) - \\ (\text{pre-administration } PWT \text{ or } PWL)\end{array}\right]} \times 100$$

The results of the FCA-induced inflammation assay are shown below.

TABLE 3

Percentage reversal of hyperalgesia

| Compound | % Reversal (3 mg/Kg, 3 hours post administration) |
|---|---|
| AGU | 71 |
| AEM | 59.7 |
| ACQ | 41.7 |

Neuropathic Pain: To assess the actions of the compounds of Formula I for the treatment or prevention of neuropathic pain either the Seltzer model or the Chung model can be used.

In the Seltzer model, the partial sciatic nerve ligation model of neuropathic pain is used to produce neuropathic hyperalgesia in rats (Z. Seltzer et al., "A Novel Behavioral Model of Neuropathic Pain Disorders Produced in Rats by Partial Sciatic Nerve Injury," *Pain* 43:205-218 (1990)). Partial ligation of the left sciatic nerve is performed under isoflurane/$O_2$ inhalation anaesthesia. Following induction of anaesthesia, the left thigh of the rat is shaved and the sciatic nerve exposed at high thigh level through a small incision and is carefully cleared of surrounding connective tissues at a site near the trocanther just distal to the point at which the posterior biceps semitendinosus nerve branches off of the common sciatic nerve. A 7-0 silk suture is inserted into the nerve with a ⅜ curved, reversed-cutting mini-needle and tightly ligated so that the dorsal ⅓ to ½ of the nerve thickness is held within the ligature. The wound is closed with a single muscle suture (4-0 nylon (Vicryl)) and vetbond tissue glue. Following surgery, the wound area is dusted with antibiotic powder. Sham-treated rats undergo an identical surgical procedure except that the sciatic nerve is not manipulated. Following surgery, animals are weighed and placed on a warm pad until they recover from anaesthesia. Animals are then returned to their home cages until behavioral testing begins. The animal is assessed for response to noxious mechanical stimuli by determining PWT, as described below, prior to surgery (baseline), then immediately prior to and 1, 3, and 5 hours after drug administration for rear paw of the animal. Percentage reversal of neuropathic hyperalgesia is defined as:

$$\% \, \text{Reversal} = \frac{[(\text{post administration } PWT) - (\text{pre-administration } PWT)]}{[(\text{baseline } PWT) - (\text{pre-administration } PWT)]} \times 100$$

In the Chung model, the spinal nerve ligation model of neuropathic pain is used to produce mechanical hyperalgesia, thermal hyperalgesia and tactile allodynia in rats. Surgery is performed under isoflurane/$O_2$ inhalation anaesthesia. Following induction of anaesthesia a 3 cm incision is made and the left paraspinal muscles are separated from the spinous process at the $L_4$-$S_2$ levels. The $L_6$ transverse process is carefully removed with a pair of small rongeurs to identify visually the $L_4$-$L_6$ spinal nerves. The left $L_5$ (or $L_5$ and $L_6$) spinal nerve(s) is isolated and tightly ligated with silk thread. A complete hemostasis is confirmed and the wound is sutured using non-absorbable sutures, such as nylon sutures or stainless steel staples. Sham-treated rats undergo an identical surgical procedure except that the spinal nerve(s) is not manipulated. Following surgery animals are weighed, administered a subcutaneous (s.c.) injection of saline or ringers lactate, the wound area is dusted with antibiotic powder and they are kept on a warm pad until they recover from the anaesthesia. Animals are then be returned to their home cages until behavioral testing begins. The animals are assessed for response to noxious mechanical stimuli by determining PWT, as described below, prior to surgery (baseline), then immediately prior to and 1, 3, and 5 hours after being administered a compound of Formula I for the left rear paw of the animal. The animal can also be assessed for response to noxious thermal stimuli or for tactile allodynia, as described below. The Chung model for neuropathic pain is described in S. H. Kim, "An Experimental Model for Peripheral Neuropathy Produced by Segmental Spinal Nerve Ligation in the Rat," *Pain* 50(3):355-363 (1992).

Response to Mechanical Stimuli as an Assessment of Mechanical Hyperalgesia: The paw pressure assay can be used to assess mechanical hyperalgesia. For this assay, hind paw withdrawal thresholds (PWT) to a noxious mechanical stimulus are determined using an analgesymeter (Model 7200, commercially available from Ugo Basile of Italy) as described in C. Stein, "Unilateral Inflammation of the Hindpaw in Rats as a Model of Prolonged Noxious Stimulation: Alterations in Behavior and Nociceptive Thresholds," *Pharmacol. Biochem. and Behavior* 31:451-455 (1988). The maximum weight that can be applied to the hind paw is set at 250 g and the end point is taken as complete withdrawal of the paw. PWT is determined once for each rat at each time point and only the affected (ipsilateral) paw is tested.

Response to Thermal Stimuli as an Assessment of Thermal Hyperalgesia: The plantar test can be used to assess thermal hyperalgesia. For this test, hind paw withdrawal latencies (PWL) to a noxious thermal stimulus are determined using a plantar test apparatus (commercially available from Ugo Basile of Italy) following the technique described by K. Hargreaves et al., "A New and Sensitive Method for Measuring Thermal Nociception in Cutaneous Hyperalgesia," *Pain* 32(1):77-88 (1988). The maximum exposure time is set at 32 seconds to avoid tissue damage and any directed paw withdrawal from the heat source is taken as the end point. Three latencies are determined at each time point and averaged. Only the affected (ipsilateral) paw is tested.

Assessment of Tactile Allodynia: To assess tactile allodynia, rats are placed in clear, Plexiglas compartments with a wire mesh floor and allowed to habituate for a period of at least 15 minutes. After habituation, a series of von Frey monofilaments are presented to the plantar surface of the left (operated) foot of each rat. The series of von Frey monofilaments consists of six monofilaments of increasing diameter, with the smallest diameter fiber presented first. Five trials are conducted with each filament with each trial separated by approximately 2 minutes. Each presentation lasts for a period of 4-8 seconds or until a nociceptive withdrawal behavior is observed. Flinching, paw withdrawal or licking of the paw are considered nociceptive behavioral responses.

Capsaicin-Induced Eye Wipe Test: To assess the effect of compounds of Formula I on TRPV1 receptor-mediated pain, the capsaicin-induced eye wipe test is used (N. R. Gavva et al., "AMG 9810 [(E)-3-(4-t-Butylphenyl)-N-(2,3-dihydrobenzo[b][1,4]dioxin-6-yl)acrylamide], a Novel Vanilloid Receptor 1 (TRPV1) Antagonist with Antihyperalgesic Properties", *J. Pharmacol. Exp. Ther.* M3:474-484 (2005)). The eye wipe test is a reliable high-throughput test of the effect of TRPV1 antagonists. Rats are given a single injection of 1, 3, 10 or 30 mg/kg of either a compound of Formula I; 30 mg/kg of a control selected from Celebrex, indomethacin or naproxen; or carrier. At 1, 3 or 5 hours after drug administration, 3 μL of a 100 μM capsaicin solution (in 10% EtOH/PBS) is instilled in one eye of each animal with a pipette. The number of forelimb movements (touching or wiping of the capsaicin-treated eye) are counted during a 2 minute period following instillation of capsaicin into the eye.

Example 220

Binding of Compounds of Formula I to TRPV1

Methods for assaying compounds capable of inhibiting TRPV1 are known in the art, for example, those methods disclosed in U.S. Pat. No. 6,239,267 to Duckworth et al.; U.S. Pat. No. 6,406,908 to Mc Intyre et al.; or U.S. Pat. No. 6,335,180 to Julius et al. The results of these assays will demonstrate that compounds of Formula I bind to and modulate the activity of TRPV1.

Protocol 1

Human TRPV1 Cloning:

Human spinal cord RNA (commercially available from Clontech, Palo Alto, Calif.) is used. Reverse transcription is conducted on 1.0 μg total RNA using Thermoscript Reverse Transcriptase (commercially available from Invitrogen, Carlsbad, Calif.) and oligo dT primers as detailed in its product description. Reverse transcription reactions are incubated at 55° C. for 1 h, heat-inactivated at 85° C. for 5 min, and RNase H-treated at 37° C. for 20 min.

Human TRPV1 cDNA sequence is obtained by comparison of the human genomic sequence, prior to annotation, to the published rat sequence. Intron sequences are removed and flanking exonic sequences are joined to generate the hypothetical human cDNA. Primers flanking the coding region of human TRPV1 are designed as follows: forward primer, GAAGATCTTCGCTGGTTGCACACTGGGCCACA (SEQ ID No: 1); and reverse primer, GAAGATCTTCGGGGA-CAGTGACGGTTGGATGT (SEQ ID No: 2).

Using these primers, PCR of TRPV1 is performed on one tenth of the Reverse transcription reaction mixture using Expand Long Template Polymerase and Expand Buffer 2 in a final volume of 50 μL according to the manufacturer's instructions (Roche Applied Sciences, Indianapolis, Ind.). After denaturation at 94° C. for 2 min PCR amplification is performed for 25 cycles at 94° C. for 15 sec, 58° C. for 30 sec, and 68° C. for 3 min followed by a final incubation at 72° C. for 7 min to complete the amplification. The PCR product of about 2.8 kb is gel-isolated using a 1.0% agarose, Tris-Acetate gel containing 1.6 μg/mL of crystal violet and purified with a S.N.A.P. UV-Free Gel Purification Kit (commercially available from Invitrogen). The TRPV1 PCR product is cloned into the pIND/V5-His-TOPO vector (commercially available from Invitrogen) according to the manufacturer's instructions to result in the TRPV1-pIND construct. DNA preparations, restriction enzyme digestions, and preliminary DNA sequencing are performed according to standard protocols. Full-length sequencing confirms the identity of the human TRPV1.

Generation of Inducible Cell Lines:

Unless noted otherwise, cell culture reagents are purchased from Life Technologies of Rockville, Md. HEK293-EcR cells expressing the ecdysone receptor (commercially available from Invitrogen) are cultured in Growth Medium (Dulbecco's Modified Eagles Medium containing 10% fetal bovine serum (commercially available from HYCLONE, Logan, Utah), 1× penicillin/streptomycin, 1× glutamine, 1 mM sodium pyruvate and 400 µg/mL Zeocin (commercially available from Invitrogen)). The TRPV1-pIND constructs are transfected into the HEK293-EcR cell line using Fugene transfection reagent (commercially available from Roche Applied Sciences, Basel, Switzerland). After 48 h, cells are transferred to Selection Medium (Growth Medium containing 300 µg/mL G418 (commercially available from Invitrogen)). Approximately 3 weeks later individual Zeocin/G418 resistant colonies are isolated and expanded. To identify functional clones, multiple colonies are plated into 96-well plates and expression is induced for 48 h using Selection Medium supplemented with 5 µM ponasterone A ("PonA") (commercially available from Invitrogen). On the day of assay, cells are loaded with Fluo-4 (a calcium-sensitive dye that is commercially available from Molecular Probes, Eugene, Oreg.) and CAP-mediated calcium influx is measured using a Fluorescence Imaging Plate Reader ("FLIPR") as described below. Functional clones are re-assayed, expanded, and cryopreserved.

pH-Based Assay:

Two days prior to performing this assay, cells are seeded on poly-D-lysine-coated 96-well clear-bottom black plates (commercially available from Becton-Dickinson) at 75,000 cells/well in growth media containing 5 µM PonA (commercially available from Invitrogen) to induce expression of TRPV1. On the day of the assay, the plates are washed with 0.2 mL 1× Hank's Balanced Salt Solution (commercially available from Life Technologies) containing 1.6 mM $CaCl_2$ and 20 mM HEPES, pH 7.4 ("wash buffer"), and loaded using 0.1 mL of wash buffer containing Fluo-4 (3 µM final concentration, commercially available from Molecular Probes). After 1 h, the cells are washed twice with 0.2 mL wash buffer and resuspended in 0.05 mL 1× Hank's Balanced Salt Solution (commercially available from Life Technologies) containing 3.5 mM $CaCl_2$ and 10 mM Citrate, pH 7.4 ("assay buffer"). Plates are then transferred to a FLIPR for assay. The test compound is diluted in assay buffer, and 50 µL of the resultant solution is added to the cell plates and the solution is monitored for two minutes. The final concentration of the test compound is adjusted to range from about 50 picoM to about 3 µM. Agonist buffer (wash buffer titrated with 1N HCl to provide a solution having a pH of 5.5 when mixed 1:1 with assay buffer) (0.1 mL) is then added to each well, and the plates are incubated for 1 additional minute. Data are collected over the entire time course and analyzed using Excel and Graph Pad Prism to determine the $IC_{50}$.

Capsaicin-Based Assay:

Two days prior to performing this assay, cells are seeded in poly-D-lysine-coated 96-well clear-bottom black plates (50,000 cells/well) in growth media containing 5 µM PonA (commercially available from Invitrogen) to induce expression of TRPV1. On the day of the assay, the plates are washed with 0.2 mL 1× Hank's Balanced Salt Solution (commercially available from Life Technologies) containing 1 mM $CaCl_2$ and 20 mM HEPES, pH 7.4, and cells are loaded using 0.1 mL of wash buffer containing Fluo-4 (3µM final). After one hour, the cells are washed twice with 0.2 mL of wash buffer and resuspended in 0.1 mL of wash buffer. The plates are transferred to a FLIPR for assay. 50 µL of test compound diluted with assay buffer (1× Hank's Balanced Salt Solution containing 1 mM $CaCl_2$ and 20 mM HEPES, pH 7.4) are added to the cell plates and incubated for 2 min. The final concentration of the compound is adjusted to range from about 50 picoM to about 3 µM. Human TRPV1 is activated by the addition of 50 µL of capsaicin (400 nM), and the plates are incubated for an additional 3 min. Data is collected over the entire time course and analyzed using Excel and GraphPad Prism to determine the $IC_{50}$.

Protocol 2

For Protocol 2, a Chinese Hamster Ovary cell line (CHO) that has been engineered to constitutively express human recombinant TRPV1 was used (TRPV1/CHO cells). The TRPV1/CHO cell line was generated as described below.

Human TRPV1 Cloning:

A cDNA for the human TRPV1 receptor (hTRPV1) was amplified by PCR (KOD-Plus DNA polymerase, ToYoBo, Japan) from a human brain cDNA library (BioChain) using primers designed surrounding the complete hTRPV1 open reading frame (forward 5'-GGATCCAGCAAGGATGAAGAAATGG (SEQ ID NO:3), and reverse 5'-TGTCTGCGTGACGTCCTCACTTCT (SEQ ID NO:4)). The resulting PCR products were purified from agarose gels using Gel Band Purification Kit (GE Healthcare Bioscience) and were subcloned into pCR-Blunt vector (Invitrogen). The cloned cDNA was fully sequenced using a fluorescent dye-terminator reagent (BigDye Terminator ver3.1 Cycle Sequencing Kit, Applied Biosystems) and ABI Prism 3100 genetic analyzer (Applied Biosystems). The pCR-Blunt vector containing the hTRPV1 cDNA was subjected to restriction digestion with EcoR1. The restriction fragment was subcloned into expression vector pcDNA3.1(−) (Invitrogen) and named pcDNA3.1(−)-hVR1 plasmid. The sequence of the cDNA encoding TRPV1 is available at GenBank accession number AJ277028.

Generation of the TRPV1/CHO Cell Line:

CHO-K1 cells were maintained in growth medium consisting of α-MEM, 10% FBS (Hyclone), and 100 IU/mL of penicillin 100 µg/mL of streptomycin mixed solution (Nacalai Tesque, Japan) at 37° C. in an environment of humidified 95% air and 5% $CO_2$. The cells were transfected with the pcDNA3.1(−)-hVR1 plasmid using FuGENE6 (Roche) according to the manufacturer's protocol. 24 hr after transfection, neomycin-resistant cells were selected using 1 mg/mL G418 (Nacalai Tesque). After 2 weeks, individual colonies were picked, expanded, and screened for the expression of hTRPV1 in the capsaicin-induced $Ca^{2+}$ influx assay (see below) with a FLIPR (Molecular Devices). A clone with the largest $Ca^{2+}$ response to capsaicin was selected and re-cloned by the same procedure. The cells expressing hTRPV1 were cultured in the growth medium supplemented with 1 mg/mL G418. Approximately 1 month later, stable expression of functional TRPV1 receptors in the selected cell line was confirmed by validating $Ca^{2+}$ responses with or without capsazepine (Sigma, at 1 nM-10 µM) in capsaicin assay.

Capsaicin-Induced $Ca^{2+}$ Influx Assay for Cell Selection:

The following assay was performed to identify cells with hTRPV1 expression. CHO-K1 cells transfected with pcDNA3.1(−)-hVR1 plasmid were seeded in 384-well black-wall clear-bottom plates (Corning) and cultivated in growth medium (see above) for 1 day. On the day of experiment, culture medium was exchanged to assay buffer (20 mM HEPES, 137 mM NaCl, 2.7 mM KCl, 0.9 mM $MgCl_2$, 5.0 mM $CaCl_2$, 5.6 mM D-glucose, 2.5 mM probenecid, pH 7.4) containing 4 µM Fluo-3-AM (Dojin, Japan). After the incubation at 37° C. for 1 hr, each well was washed 3 times with assay buffer using an EMBLA 384 plate washer (Molecular Devices) and refilled with assay buffer. The plates were incubated at a temperature of about 25° C. for 10 min. Subsequently, the plates were inserted into a FLIPR, and 1.5 µM capsaicin (Sigma) solution prepared in assay buffer was added to each well (final concentration was 500 nM). Cellular responses were monitored for 5 min.

Cell Culture:
1. Cell Culture Media
1. Alpha-MEM (Gibco, CAT: 12561-056, LOT: 1285752): 450 mL.
2. Fetal Bovine Serum (FBS), heat inactivated (Gibco, CAT: 16140-071, LOT: 1276457): 50 mL.
3. HEPES Buffer Solution, 1M stock (Gibco, CAT: 15630-080): 10 mL (final 20 mM).
4. Geneticin, 50 mg/mL stock (Gibco, CAT: 10135-035): 10 mL (final 1 mg/mL).
5. Antimicotic Antibiotic Mixed Solution, 100× stock (Nacalai Tesque, Japan, CAT: 02892-54): 5 mL.

Components 1-5 above were combined at the indicated amounts and stored at 4° C. The cell culture media were brought to about 37° C. before use. Optionally, component 5 can be replaced by penicillin-streptomycin solution (for example, Gibco 15140-122 or Sigma P-0781).

2. Thawing the Cells

TRPV1/CHO cells were frozen in Cellbanker™ (Juji-Field INC, Japan, CAT: BLC-1) and stored at −80° C. Optimized cryopreservation solution containing dimethyl sulphoxide and FBS was used.

Vials containing the TRPV1/CHO cells were stored at 80° C. After removal from 80° C., the vial was immediately transferred to a 37° C. water bath to thaw for ca. 1-2 minutes. Once completely thawed, the contents of the vial (1 mL/vial) was transferred to a sterile 15 mL test tube and 9 mL warm culture media were slowly added. The test tube was subsequently centrifuged at 1000 rpm for 4 min at a temperature of about 25° C. The supernatant was removed and the pellet resuspended in 10 mL of culture media. The cell suspension was transferred to a sterile 75 cm² plastic flask and incubated at humidified 5% $CO_2$/95% air at 37° C. To monitor viability, the cells were visually inspected and/or counted, beginning at approximately 1 hr after incubation.

3. Passaging the Cells

The cells in a flask were close to confluence at the time of passaging. Cell culture media were removed from the culture flask and 10 mL of sterile PBS(−) added and the flask gently shaken. The PBS was removed from the flask and 2 mL of trypsin/EDTA solution (0.05% trypsin with EDTA-4Na; Gibco, CAT: 25300-054) was added and the flask gently shaken. The flask was incubated at 37° C. for about 2 min. 8 mL cell culture media were subsequently added to the flask and the flask shaken to ensure that all cells were in solution. The cell suspension was then transferred to a sterile 15 mL or 50 mL plastic tube, centrifuged at 1,000 rpm for 4 min at a temperature of about 25° C. The supernatant was removed and the pellet resuspended in ca. 5 mL of culture media. The cell count was measured using the Burker-Turk hemocytometer.

The cells were seeded into a sterile 75 cm² plastic flask in ca. $0.8 \times 10^5$ cells/mL for 72 hr and incubated in humidified 5% $CO_2$/95% air at 37° C.

4. Freezing the Cells

The procedure up to the measurement of the cell count was the same as in the section Passaging the Cells above. Subsequently, the cell suspension was centrifuged at 1,000 rpm for 4 min at a temperature of about 25° C. The supernatant was removed and the pellet resuspended in Cellbanker™ solution to get a final concentration of from $5 \times 10^5$ to $5 \times 10^6$ cells/mL. The cell suspension was transferred into appropriately labeled 1 mL cryovials and then placed into the 80° C. freezer.

pH-Based Assay:

The following assay was conducted to determine the concentration of sulfuric acid that would give rise to a pH that induces a $Ca^{2+}$ response optimal to test compounds for their effect on TRPV1.

1. Cells

TRPV1/CHO cells were seeded in the 96-well clear-bottom black-wall plate (Nunc) at densities of $1-2 \times 10^4$ cells/well and grown in 100 µL of culture medium (alpha-MEM supplemented with 10% FBS, 20 mM HEPES, 1 mg/mL geneticin and 1% antibiotic-antimycotic mixed stock solution) for 1-2 days before the experiment.

2. Determination of pH Sensitivity and Agonist Dose 2.1. Agonist Solution

Different agonist solutions with sulfuric acid concentrations of from 15 mM to 18 mM (see FIG. 1) were prepared by diluting 1M sulfuric acid with measuring buffer. The different sulfuric acid concentrations in the agonist solutions were selected such that a 1:4 dilution would result in a final sulfuric acid concentration of between 3.0 mM to 3.6 mM, respectively, as indicated in FIG. 1.

2.2. Assay pH dependent $Ca^{2+}$ responses in TRPV1/CHO cells cultured in a 96-well plate are shown in FIG. 2. In particular, $Ca^{2+}$ influx into TRPV1/CHO cells in response to low pH as measured by Fura-2 AM fluorescence is indicated in FIG. 2. The cells were stimulated using 3.0 mM (well number B1-6), 3.1 mM (C1-6), 3.2 mM (D1-6), 3.3 mM (E1-6), 3.4 mM (F1-6), 3.5 mM (G1-6), or 3.6 mM (H1-6) $H_2SO_4$ or pH 7.2 measuring buffer without $H_2SO_4$ (A1-6) (FIG. 2).

(1) Culture medium was removed using an 8-channel-pipette (Rainin, USA) from the 96-well plate and the wells were refilled with 100 µL of loading buffer (20 mM HEPES, 115 mM NaCl, 5.4 mM KCl, 0.8 mM $MgCl_2$, 1.8 mM $CaCl_2$, 13.8 mM D-glucose, 2.5 mM probenecid, pH 7.4) containing 5 µM Fura-2 AM (Dojin, Japan).

(2) The 96-well plate was incubated at 37° C. for 45 min.

(3) The loading buffer was removed from each well. The cells were subsequently washed twice with 150 µL of measuring buffer (20 mM HEPES, 115 mM NaCl, 5.4 mM KCl, 0.8 mM $MgCl_2$, 5.0 mM $CaCl_2$, 13.8 mM D-glucose, 0.1% BSA, pH 7.4) (no probenecid). The wells were then refilled with 80 µL of measuring buffer.

(4) After an incubation at 4° C. for 15 min, the 96-well plate was transferred to FDSS-3000 (Hamamatsu Photonics, Japan).

(5) The Fura-2 fluorescent intensity was monitored at a wavelength of 340 nm and at 380 nm, respectively, at a rate of 0.5 Hz for a total of 240 seconds. After 16 time points (32 sec) of baseline detection, 20 µL of agonist solution was added to each well. The final volume was 100 µL/well.

(6) Fluorescence intensity ratio refers to the fluorescence intensity at 340 nm over the fluorescence intensity at 380 nm at a particular time point. The baseline was set as the average of the fluorescent intensity ratios for the first 16 time points before the addition of agonist solution. The maximum response was the highest fluorescent intensity ratio during the 60 time points following addition of agonist solution.

(7) Maximal signal ratios from each well were calculated as output data using the FDSS-3000 analysis program. Data were analyzed using Excel (Microsoft) and XLfit (idbs) software.

2.3. pH Determination

After the observation of $Ca^{2+}$ responses, the buffer of each lane (50 µL/well, 8-20 wells/plate) was collected well by well and the pH values were measured using a portable pH meter (Shindengen, Japan).

As shown in FIG. 2, the $Ca^{2+}$ responses in lanes D and E were intermediate and therefore optimal for testing the effects of compounds on the TRPV1 calcium channel. The final sulfuric acid concentrations in the wells of these lanes were 3.2 mM and 3.3 mM, respectively. These final sulfuric acid concentrations were obtained using agonist solutions with 16.0 mM and 16.5 mM sulfuric acid concentrations, respectively (lanes D and E in FIG. 1). The pH obtained using these sulfuric acid concentrations was ca. 5.0-5.1.

Thus, agonist solutions with 16.0 mM and 16.5 mM sulfuric acid concentrations, respectively, (lanes D and E in FIG. 1) were selected for the experiments described below in section 3.

3. pH Assay
3.1. Agonist

Two different agonist solutions with different $H_2SO_4$ concentrations were used for the pH assay (FIG. 3A). For one half of a 96-well plate one agonist solution was used, for the other half the other agonist solution. The agonist solutions were obtained by diluting sulfuric acid ($H_2SO_4$, 1M) with measuring buffer. The concentrations for the two agonist solutions were determined as described above in Section 2 of Protocol 2.

The sulfuric acid concentrations between the two agonist solutions differed by 0.5 mM. In the experiment described in Section 2 of Protocol 2, the sulfuric acid concentrations in the agonist solutions were determined to be 16 mM and 16.5 mM, respectively. After 1:4 dilution of the agonist solutions, the final sulfuric acid concentration was 3.2 mM and 3.3 mM, respectively. The resulting pH value for the pH assay was 5.0 to 5.1.

3.2. Test Compounds

Test compounds were dissolved in DMSO to yield 1 mM stock solutions. The stock solutions were further diluted using DMSO in 1:3 serial dilution steps with 6 points (1000 μM, 250 μM, 62.5 μM, 15.625 μM, 3.9062 μM and 0.977 μM). The thereby-obtained solutions were further diluted in measuring buffer (1:100) as 10× stock serial dilutions with a DMSO concentration of 1%. 10 μL of a 10× stock was added into each well at step 3.3.(4) of Protocol 2. Thus, the final concentrations of antagonists ranged from 1000-0.977 nM containing 0.1% DMSO (FIG. 3B).

3.3. Assay

Steps (1) and (2) of this Assay were the same as steps 2.2.(1) and 2.2.(2) of Protocol 2, respectively.

(3) The cells were washed twice with 150 μL of measuring buffer (mentioned in 2.2.(3) of Protocol 2, no probenecid). The wells were subsequently refilled with 70 μL of measuring buffer.

(4) Either 10 μl of measuring buffer or 10 μL of 10× stock serial dilution of test compound (described in 3.2. above) were applied to each well. Usually, only one test compound was tested per 96-well plate. The number of replicates per 96-well plate for a particular antagonist at a particular concentration was 7×2 since two different sulfuric acid concentrations were used per 96-well plate (N=7×2) (FIG. 3).

Step (5) was the same as 2.2.(4) above.

(6) Fura-2 fluorescent intensity was monitored as described in 2.2.(5) above. After 16 time points of baseline detection, 20 μL of agonist solution (measuring buffer titrated with $H_2SO_4$ to yield pH 5.0-5.1 when mixed 1:4 with the measuring buffer containing test compound) was added to each well (final volume 100 μL/well).

Steps (7) and (8) were as described in 2.2.(6) and 2.2.(7) above, respectively.

3.4. pH Check (1) The pH values of the buffer in the wells of A1→H1 and A7→H7 (longitudinally; FIG. 3) were measured one by one using a portable pH meter.

(2) When a well was confirmed as pH 5.0 or 5.1, the next five wells to its right were checked one after another.

(3) For $IC_{50}$ calculation, only the data from wells with pH values of 5.0-5.1 were used.

The number of wells tested for their pH varied among plates (about 16-60 wells/plate). The number depended on the results of 3.4.(1) above and the $Ca^{2+}$ responses.

Capsaicin-Based Assay:

One day prior to assay, TRPV1/CHO cells were seeded in 96-well clear-bottom black plates (20,000 cells/well) in growth media. On the day of the experiment, the cells were washed with 0.2 mL 1× Hank's Balanced Salt Solution (Life Technologies) containing 1.6 mM $CaCl_2$ and 20 mM HEPES, pH 7.4 ("wash buffer"). Subsequently, the cells were loaded by incubation in 0.1 mL of wash buffer containing Fluo-4 at 3 μM final concentration. After 1 hour, the cells were washed twice with 0.2 mL wash buffer and resuspended in 0.1 mL wash buffer. The plates were then transferred to a Fluorescence Imaging Plate Reader (Molecular Devices). Fluorescence intensity was monitored for 15 seconds to establish a baseline. Subsequently, test compounds diluted in assay buffer (1× Hank's Balanced Salt Solution containing 1 mM $CaCl_2$ and 20 mM HEPES, pH 7.4) containing 1% DMSO were added to the cell plate and fluorescence was monitored for 2 minutes. The final concentration of the compound was adjusted to range from 100 μM to 1.5625 μM. If the test compound was an especially potent antagonist, the final concentration of the compound was adjusted to range from 10 μM to 1.5625 nM. Human TRPV1 was then activated by the addition of 50 μL capsaicin (100 nM final concentration) and plates incubated for an additional 3 min. Data were collected over the entire time course and analyzed using Excel and the curve-fitting formula GraphPad Prism.

In order to confirm structural advantage of the alkyl group with $Z_1$-$Z_5$ substituents, a comparative compound of the similar structure without such alkyl group was prepared and assayed. When preparing the comparative compounds, description in WO2004/058754 [compound (3)] and that of WO2005/009988 [compounds (8) and (10)] were referred to.

The results of the assays of Protocol 2 are shown below.

TABLE 4

TRPV1 $IC_{50}$ Potency (pH-Based Assay)

| Compound | $IC_{50}$ (nM) | Comparative compound | $IC_{50}$ (nM) |
|---|---|---|---|
| AAN | 17 | (1) | 139 |

TABLE 4-continued
TRPV1 IC$_{50}$ Potency (pH-Based Assay)
| Compound | IC$_{50}$ (nM) | Comparative compound | IC$_{50}$ (nM) |
|---|---|---|---|
| 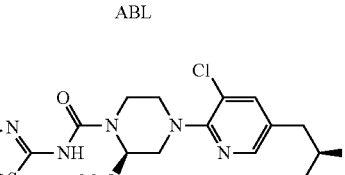 ABL | 46 | 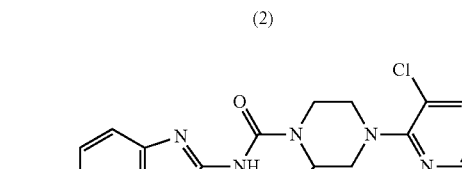 (2) | 185 |
| 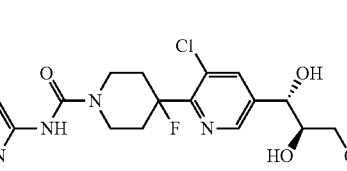 ACU | 1 | 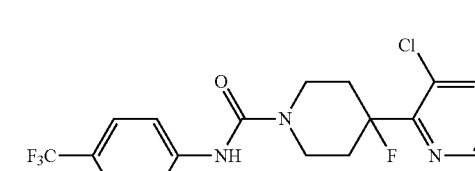 (3) | 24 |
| 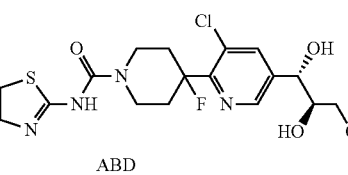 ABE | 143 | 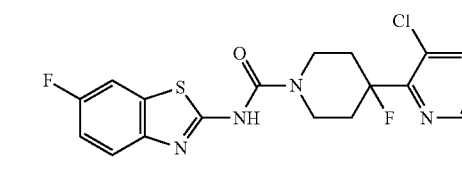 (5) | 154 |
| 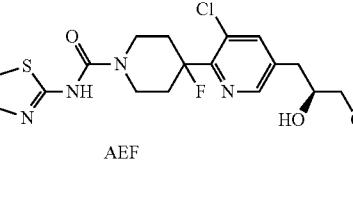 ABD | 171 |  (6) | 1463 |
| 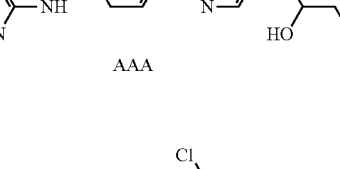 AEF | 614 | | |
|  AAA | 38 | 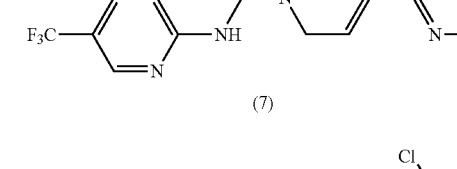 (7) | 185 |
|  AAB | 12 | 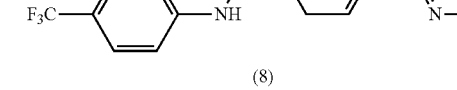 (8) | 32 |

TABLE 4-continued

TRPV1 IC$_{50}$ Potency (pH-Based Assay)

| Compound | IC$_{50}$ (nM) | Comparative compound | IC$_{50}$ (nM) |
|---|---|---|---|
| 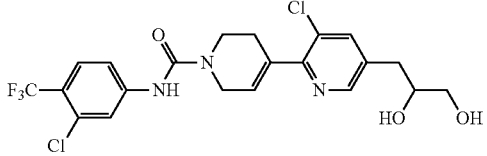<br>AAC | 10 | 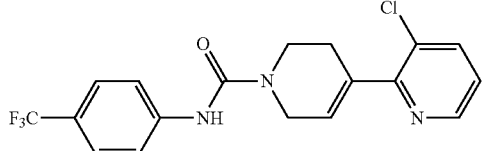<br>(9) | 77 |
| 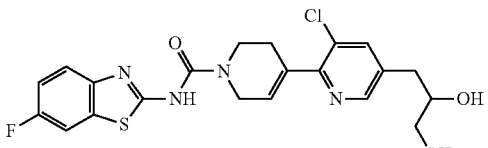<br>AAD | 5 | 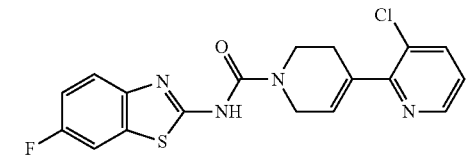<br>(10) | 943 |

The following compounds had an IC$_{50}$ value of 50 nM or less by the pH-Based Assay:

Compounds AAF, AAH, AAJ, AAK, AAL, AAM, AAS, AAW, AAY, AAZ, ABG, ABH, ABY, ABZ, ACA, ACB, ACE, ACF, ACG, ACI, ACJ, ACM, ACN, ACO, ACP, ACQ, ACR, ACS, ACT, ACV, ACW, ACX, ACY, ACZ, ADA, ADB, ADC, ADD, ADE, ADH, ADI, ADJ, ADK, ADR, ADS, ADT, ADU, ADV, ADW, ADY, ADZ, AEA, AEB, AEC, AED, AEE, AEH, AEJ, AEK, AEL, AEM, AEN, AEP, AET, AEU, AEY, AEZ, AFA, AFB, AFM, AFO, AFP, AFR, AFS, AFT, AFU, AFV, AFZ, AGK, AGL, AGR, AGU, AGV, AGW, AGX, AGY, AGZ and AHB.

TABLE 5

TRPV1 IC$_{50}$ Potency (Capsaicin-Based Assay)

| Compound | IC$_{50}$ (nM) | Comparative compound | IC$_{50}$ (nM) |
|---|---|---|---|
| 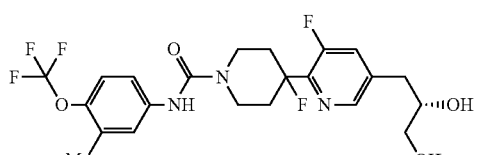<br>ACR | 46 | 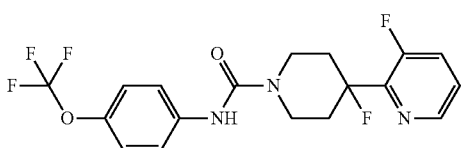<br>(11) | 100 |
| 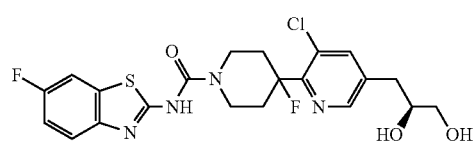<br>AEF | 116 | 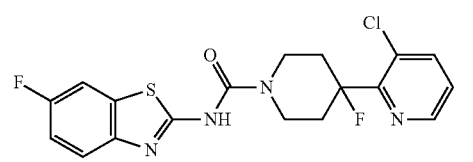<br>(6) | 508 |
| 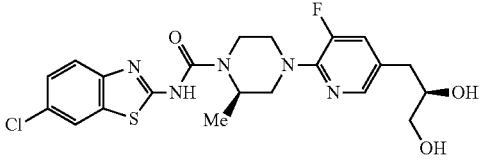<br>ADK | 8 | | |

TABLE 5-continued

TRPV1 IC$_{50}$ Potency (Capsaicin-Based Assay)

| Compound | IC$_{50}$ (nM) | Comparative compound | IC$_{50}$ (nM) |
|---|---|---|---|
| AAW | 40 | | |

The following compounds had an IC$_{50}$ value of 50 nM or less by the Capsaicin-Based Assay:

Compounds AAS, ABY, ACB, ACE, ACF, ACI, ACJ, ACM, ACN, ACO, ACP, ACQ, ACS, ACT, ACU, ACV, ACW, ACX, ACY, ADA, ADB, ADE, ADH, ADI, ADJ, ADR, ADT, ADU, ADW, ADX, ADY, ADZ, AEA, AEB, AEC, AED, AEE, AEG, AEH, AEK, AEN, AEP, AEY, AFB, AFR, AFS, AFT, AFV, AFZ, AGK, AGU, AGW, AGY and AGZ.

Example 221

Measurement of Body Temperature Increase

Test Animals: Selection of rats (Crl/SD rats, 7 weeks, male) for this study was based on rectal body temperature measured during the morning of the day of dosing. In addition, animals selected for this study were acclimated to both the rectal measurement procedure and to being handled and dosed to minimize spontaneous, stress-induced, increases in body temperature. The study was conducted in the animal care laboratories where the room temperature and humidity were kept. The rats were free to move and food and water during the study. Each rat was numbered with color line on the tail, housed in each cage and permitted the normal range of movement. Immediately before each body temperature was measured, they transferred to a single cage at each measurement. To reduce stress which affected the body temperature, the rats were covered with towels at the measurement. The thermistor probe was then carefully inserted into the rectum of each rat and left in place until the value on the digital display had stabilized.

Assays: On the day before dosing, rectal body temperatures were measured at 9:00, 10:00, 11:00, 12:30, 13:30, 14:30 and 15:30 to familiarize the animals with the measurement procedure prior to administration of the test or control treatments. The rats were also dosed by oral gavage without vehicle at 12:30 to acclimate and familiarized the animals with the handling and dosing procedure.

On the day of dosing, only rats whose rectal body temperatures were within the range of 37.0° C. to 37.7° C. were selected for this study. Rectal body temperatures were measured at 9:00, 10:00 and 11:00. Rats whose rectal body temperatures were over 37.9° C. at 10:00, and were outside the range of 37.0° C. to 37.7° C. at 11:00 were excluded from the study. The selected rats were divided to several groups based on their rectal body temperatures at 11:00. Rectal body temperatures of the selected rats were measured again at 12:30, and any rats whose rectal body temperature was 38.0° C. or greater were excluded from the study.

Following the group assignment, test compounds or vehicle was administrated to the rats. Each test compound was dissolved in 0.5% methylcellurose and the final concentration of the compound was adjusted to 1 mg/mL. Test compound was orally administrated in a volume 10 mL/kg once. 10 mL/kg of vehicle (0.5% methylcellurose) was administered to the vehicle group. The rectal body temperatures were measured 0.5, 1 and 2 hrs after the administration. The study was conducted in the animal care laboratories where the room temperature and humidity were kept.

Body temperature increase (ΔTb) was calculated from the difference from an average of the vehicle group at each time point.

TABLE 6

| Body temperature increase | |
|---|---|
| Compound | ΔTb (° C.) |
| ABZ | 0.03 |
| ACP | 0.16 |
| ACZ | 0.24 |

The body temperature increases of Compounds ABY, ACA, ACB, ACQ, ADE, ADT, AAF, AAK, AAM, AAW, ACD, ACK, ACL, ACV, ACW, ACX, ACY, ADD, ADK, ADR, ADU, ADV, ADW, ADX, AEF, AEG and the like were less than 0.5° C.

The invention is not to be limited in scope by the specific embodiments disclosed in the examples which are intended as illustrations of a few aspects of the invention and any embodiments that are functionally equivalent are within the scope of this invention. Indeed, various modifications of the invention in addition to those shown and described herein will become apparent to those skilled in the art and are intended to fall within the scope of the appended claims.

A number of references have been cited, the entire disclosures of which are incorporated herein by reference.

The invention claimed is:

1. A compound of Formula I:

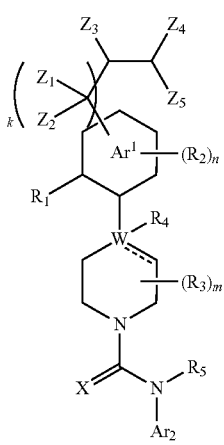

(I)

or a pharmaceutically acceptable salt thereof, wherein

X is O, S, N—CN, or N—OR$_7$;

W is N;

the dashed line denotes the absence of a bond, and

R$_4$ is absent;

R$_1$ is —H, -halo, —NO$_2$, —CN, —OR$_7$, —N(R$_7$)$_2$, (C$_1$-C$_4$)alkyl, —C(halo)$_3$, —CH(halo)$_2$, —CH$_2$(halo), —OC(halo)$_3$, —OCH(halo)$_2$, or —OCH$_2$(halo);

each R$_2$ is independently -halo, —OR$_7$, —CN, —NO$_2$, —N(R$_7$)$_2$, —(C$_1$-C$_{10}$)alkyl, —(C$_2$-C$_{10}$)alkenyl, (C$_2$-C$_{10}$)alkynyl, or -phenyl, each R$_3$ is independently:

(a) —(C$_1$-C$_6$)alkyl, —(C$_1$-C$_6$)alkyl-OR$_{13}$, —C(O)R$_{13}$, —C(O)OR$_{13}$, —N(R$_{13}$)C(O)R$_{13}$, or —C(O)N(R$_{13}$)$_2$;

R$_5$ is —H, —(C$_1$-C$_6$)alkyl, —(C$_3$-C$_8$)cycloalkyl, —(C$_1$-C$_6$)alkyl-OC(O)R$_7$, —C(O)R$_7$, or —C(O)N(R$_8$)$_2$;

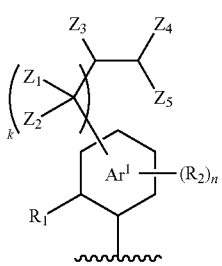

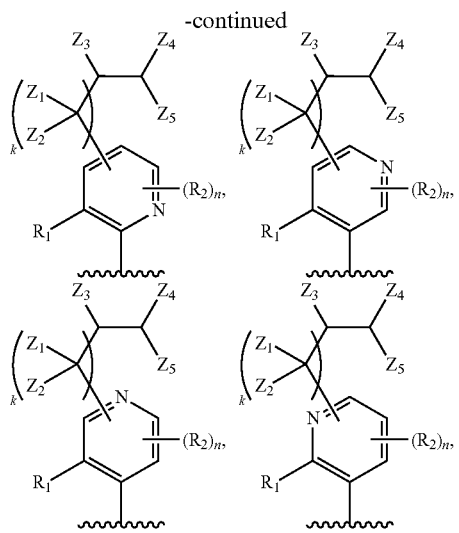

$Z_1$ and $Z_2$ are each independently —H, —($C_1$-$C_6$)alkyl, —($C_2$-$C_6$)alkenyl, —($C_2$-$C_6$)alkynyl, -phenyl, —$OR_{12}$, —$N(R_{12})_2$, -halo, —($C_3$-$C_8$)cycloalkyl, —C(O)$OR_{13}$, —C(O)$R_{13}$, or —CH=N—$OR_{13}$, or $Z_1$ and $Z_2$ groups together form =O or =N—$OR_{13}$;

$Z_3$ and $Z_4$ are each independently —$OR_{12}$ or —$N(R_{12})_2$;

$Z_5$ is —H, —($C_1$-$C_6$)alkyl, —($C_2$-$C_6$)alkenyl, —($C_2$-$C_6$)alkynyl, or -phenyl;

$Ar_2$ is

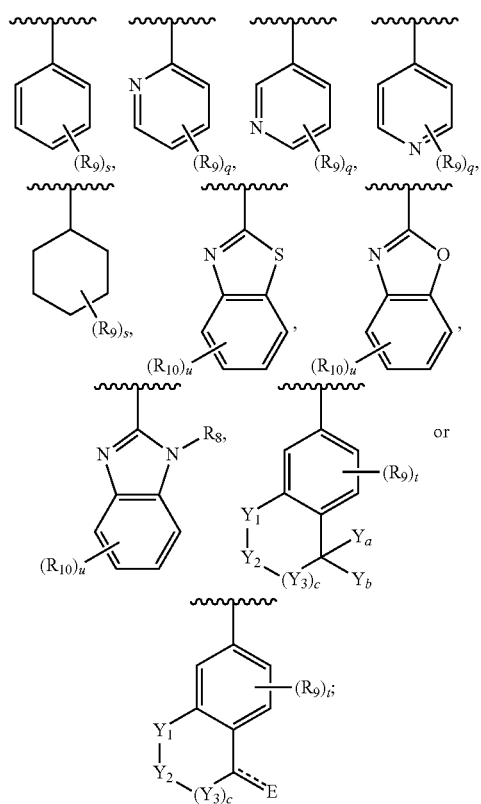

each $R_9$ is independently —($C_1$-$C_6$)alkyl, —($C_2$-$C_6$)alkenyl, —($C_2$-$C_6$)alkynyl, —($C_3$-$C_8$)cycloalkyl, —($C_5$-$C_8$)cycloalkenyl, -phenyl, -(3- to 7-membered)heterocycle, —($C_1$-$C_6$)haloalkyl, —($C_2$-$C_6$)haloalkenyl, —($C_2$-$C_6$)haloalkynyl, —($C_1$-$C_6$)hydroxyalkyl, —($C_2$-$C_6$)hydroxyalkenyl, —($C_2$-$C_6$)hydroxyalkynyl, —($C_1$-$C_6$)alkoxy($C_1$-$C_6$)alkyl, —($C_1$-$C_6$)alkoxy($C_2$-$C_6$)alkenyl, —($C_1$-$C_6$)alkoxy($C_2$-$C_6$)alkynyl, —CN, -halo, —$N_3$, —$NO_2$, —CH=$NR_{13}$, —$N(R_{13})_2$, —$NR_{13}OR_{13}$, —$OR_{13}$, —$SR_{13}$, —$O(CH_2)_bOR_{13}$, —$O(CH_2)_bSR_{13}$, —$O(CH_2)_bN(R_{13})_2$, —$N(R_{13})(CH_2)_bOR_{13}$, —$N(R_{13})(CH_2)_bSR_{13}$, —$N(R_{13})(CH_2)_bN(R_{13})_2$, —$N(R_{13})C(O)R_{13}$, —C(O)$R_{13}$, —C(O)$OR_{13}$, —OC(O)$R_{13}$, —OC(O)$OR_{13}$, —S(O)$R_{13}$, —S(O)$_2R_{13}$, —S(O)$_2N(R_{13})_2$, —S(O)$_2$-(3- to 7-membered)heterocycle, —C(O)N($R_{13}$)$_2$, —($C_1$-$C_6$)alkyl-C=N—$OR_{13}$, —($C_1$-$C_6$)alkyl-C(O)N($R_{13}$)$_2$, —($C_1$-$C_6$)alkyl-NHS(O)$_2$N($R_{13}$)$_2$, or —($C_1$-$C_6$)alkyl-C(=NH)—N($R_{13}$)$_2$, each of which -phenyl, -(3- to 7-membered)heterocycle, or —($C_3$-$C_8$)cycloalkyl is unsubstituted or substituted with 1, 2 or 3 independently selected $R_{13}$ groups;

each $R_{10}$ is independently:

(a) —($C_1$-$C_6$)alkyl, —($C_2$-$C_6$)alkenyl, —($C_2$-$C_6$)alkynyl, —($C_3$-$C_8$)cycloalkyl, —($C_5$-$C_8$)cycloalkenyl, or -phenyl, each of which is unsubstituted or substituted with 1 or 2-OH groups;

(b) —$CH_2CH_2$(halo), —$CH_2CH$(halo)$_2$, —$CH_2C$(halo)$_3$, —C(halo)$_3$, —CH(halo)$_2$, —$CH_2$(halo), —CN, -halo, —$N_3$, —$NO_2$, —CH=$NR_{13}$, —N($R_{13}$)$_2$, —$NR_{13}OR_{13}$, —$OR_{13}$, —C(O)$R_{13}$, —C(O)$OR_{13}$, —OC(O)$R_{13}$, —OC(O)$OR_{13}$, —$SR_{13}$, —S(O)$R_{13}$, or —S(O)$_2R_{13}$; or (c) two $R_{10}$ groups on adjacent carbon atoms together form a ($C_1$-$C_2$)alkylenedioxy bridge, which is unsubstituted or substituted 1, 2 or 3 independently selected $R_{13}$ groups;

$Y_1$, $Y_2$, $Y_3$ are each independently C, N, or O;

wherein no more than one of $Y_1$, $Y_2$, or $Y_3$ can be O, no more than two of $Y_1$, $Y_2$, or $Y_3$ can be N and for each $Y_1$, $Y_2$, and $Y_3$ that is N, the N is bonded to one $R_{14}$ group, and for each $Y_1$, $Y_2$, and $Y_3$ that is C, the C is bonded to two $R_5$ groups, provided that there are no more than a total of two ($C_1$-$C_6$)alkyl groups substituted on all of $Y_1$, $Y_2$, and $Y_3$;

$Y_a$ and $Y_b$ are each independently —H, -halo, or —($C_1$-$C_6$)alkyl, or $Y_a$ and $Y_b$, together with the carbon to which they are attached, form a 3-8 member carbocyclic ring;

E is =O, =S, =C($R_7$)$_2$, =CH($C_2$-$C_6$)alkenyl, =N($R_7$)$_2$, or =N—$OR_5$;

each $R_7$ is independently —H or —($C_1$-$C_6$)alkyl;

each $R_8$ is independently —H, —($C_1$-$C_6$)alkyl, —($C_2$-$C_6$)alkenyl, —($C_2$-$C_6$)alkynyl, —($C_3$-$C_8$)cycloalkyl, or phenyl;

each $R_{12}$ is independently —H, —($C_1$-$C_6$)alkyl, —($C_3$-$C_8$)cycloalkyl, —C(O)$R_{15}$, —C(O)$OR_{13}$, or —C(O)N($R_{13}$)$_2$;

each $R_{13}$ is independently —H, —($C_1$-$C_6$)alkyl, —($C_2$-$C_6$)alkenyl, —($C_2$-$C_6$)alkynyl, —($C_3$-$C_8$)cycloalkyl, —($C_5$-$C_8$)cycloalkenyl, -phenyl, -benzyl, —($C_1$-$C_6$)haloalkyl, —($C_1$-$C_6$)hydroxyalkyl, —($C_1$-$C_6$)alkoxy($C_1$-$C_6$)alkyl, —($C_1$-$C_6$)alkyl-N($R_8$)$_2$, or —C(O)N($R_8$)$_2$;

each $R_{14}$ is independently —H, —($C_1$-$C_6$)alkyl, —C(O)$R_{13}$, —S(O)$R_{13}$, —S(O)$_2R_{13}$,

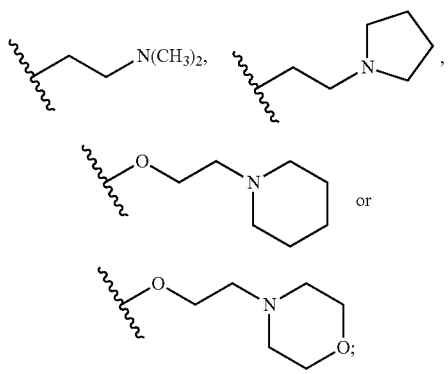

$R_{15}$ is H, —$(C_1-C_6)$alkyl, —$(C_2-C_6)$alkenyl, —$(C_2-C_6)$alkynyl, —$(C_1-C_6)$halo alkyl, —$(C_1-C_6)$hydroxyalkyl, —$(C_1-C_6)$alkoxy$(C_1-C_6)$alkyl, —$(C_1-C_6)$alkyl-$N(R_8)_2$, —$(C_3-C_8)$cyclo alkyl, —$(C_5-C_8)$cycloalkenyl, -phenyl, -benzyl, or -(3- to 7-membered)heterocycle;

each halo is independently —F, —Cl, —Br, or —I;

n is the integer 0, 1, or 2;

m is the integer 0, 1, or 2;

k is the integer 1 or 2;

q is the integer 0, 1, 2, 3, or 4;

s is the integer 0, 1, 2, 3, 4, or 5;

t is the integer 0, 1, 2, or 3;

u is the integer 0, 1, 2 or 3;

each b is independently 1 or 2; and c is the integer 0, 1, or 2.

2. The compound according to claim 1 or a pharmaceutically acceptable salt thereof, wherein

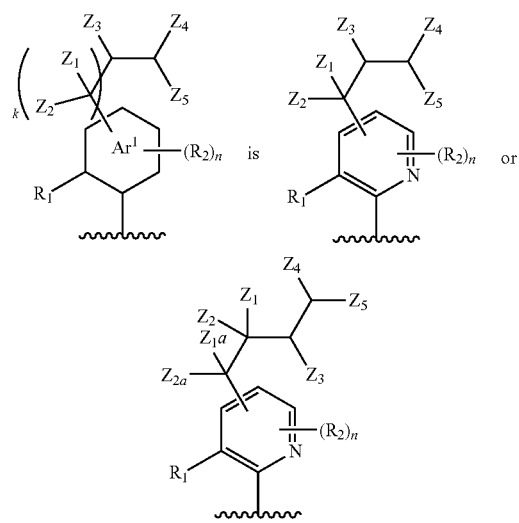

and $Z_{1a}$ and $Z_{2a}$ are each independently —H, —$(C_1-C_6)$alkyl, —$(C_2-C_6)$alkenyl, —$(C_2-C_6)$alkynyl, -phenyl, -halo or —$(C_3-C_8)$cycloalkyl.

3. The compound according to claim 1 or a pharmaceutically acceptable salt thereof, wherein

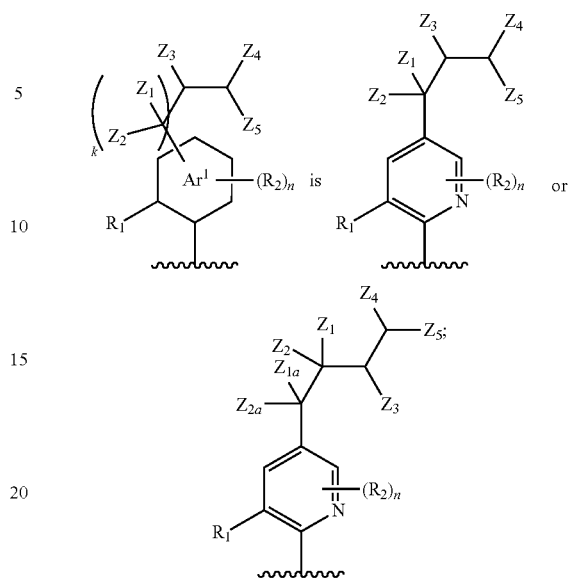

and $Z_{1a}$ and $Z_{2a}$ are each independently —H, —$(C_1-C_6)$alkyl, —$(C_2-C_6)$alkenyl, —$(C_2-C_6)$alkynyl, -phenyl, -halo or —$(C_3-C_8)$cycloalkyl.

4. The compound according to claim 1 or a pharmaceutically acceptable salt thereof, wherein $Z_1$ is —H, —$OR_{12}$, or -halo, $Z_2$, $Z_{1a}$ and $Z_{2a}$ are each independently —H or -halo, $Z_3$ and $Z_4$ are each independently —$OR_{12}$, and $Z_5$ is —H or —$(C_1-C_4)$alkyl.

5. The compound according to claim 1 or a pharmaceutically acceptable salt thereof, wherein $Z_1$ is —H, —OH, or -halo, $Z_2$, $Z_{1a}$ and $Z_{2a}$ are each independently —H or -halo, $Z_3$ and $Z_4$ are —OH, and $Z_5$ is —H or —$CH_3$.

6. The compound according to claim 1 or a pharmaceutically acceptable salt thereof, wherein:

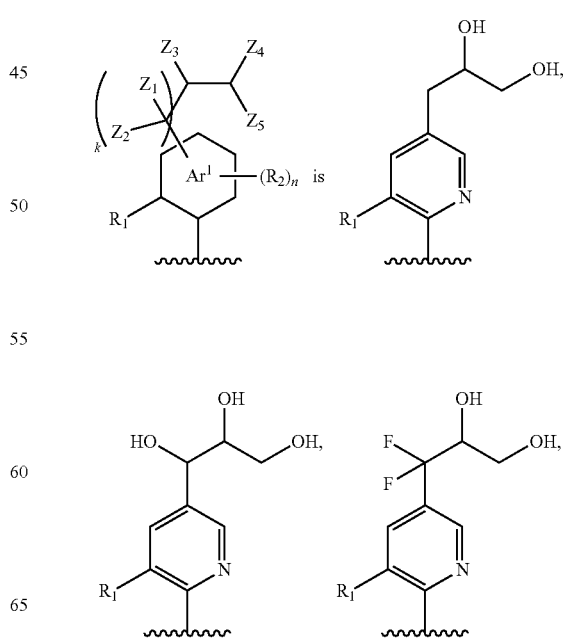

-continued

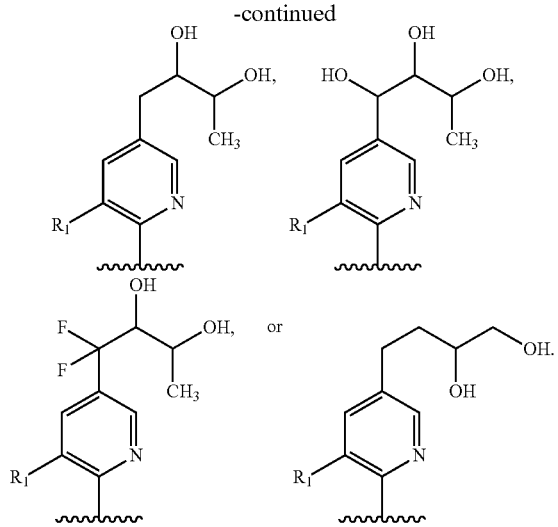

7. The compound according to claim 1 or a pharmaceutically acceptable salt thereof, wherein:

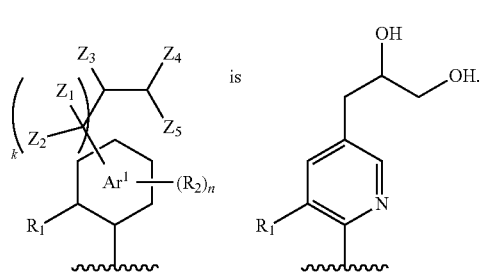

8. The compound according to claim 1 or a pharmaceutically acceptable salt thereof, wherein:

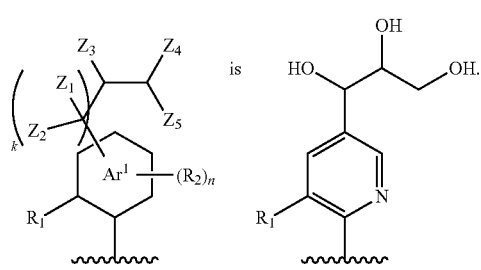

9. The compound according to claim 1 or a pharmaceutically acceptable salt thereof, wherein:

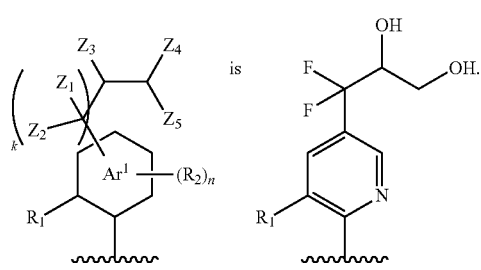

10. The compound according to claim 1 or a pharmaceutically acceptable salt thereof, wherein

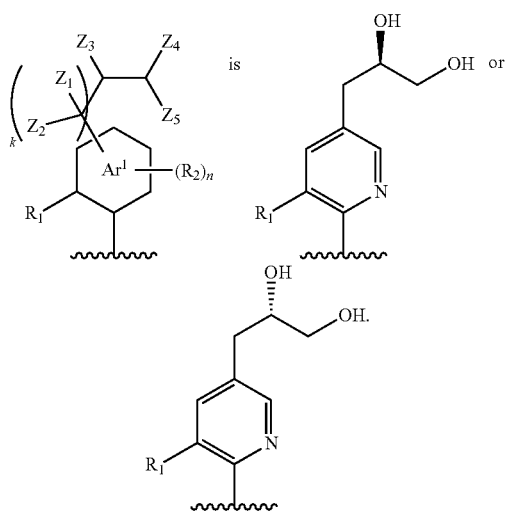

11. The compound according to claim 1 or a pharmaceutically acceptable salt thereof, wherein $R_1$ is —$CH_3$, -halo or —C(halo)$_3$.

12. The compound according to claim 1 for a pharmaceutically acceptable salt thereof, wherein X is O.

13. The compound according to claim 1 or a pharmaceutically acceptable salt thereof, wherein $Ar_2$ is

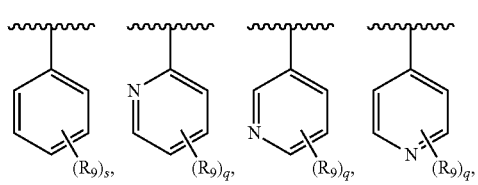

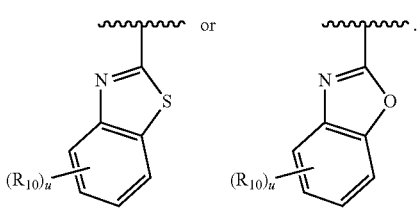

14. The compound according to claim 1 or a pharmaceutically acceptable salt thereof, wherein $Ar_2$ is

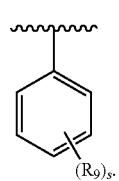

15. The compound according to claim 1 or a pharmaceutically acceptable salt thereof, wherein $Ar_2$ is

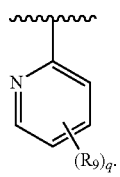

16. The compound according to claim 1 or a pharmaceutically acceptable salt thereof, wherein $Ar_2$ is

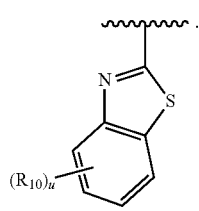

17. The compound according to claim 1 or a pharmaceutically acceptable salt thereof, wherein s, q or u is 1 or 2.
18. The compound according to claim 1 or a pharmaceutically acceptable salt thereof, wherein each $R_9$ is independently selected from -halo, —C(halo)$_3$, —(C$_1$-C$_6$)alkyl, —(C$_1$-C$_6$)alkoxy, —OC(halo)$_3$, and —S(O)$_2$C(halo)$_3$.
19. The compound according to claim 1 or a pharmaceutically acceptable salt thereof, wherein each $R_9$ is independently selected from —CH$_3$, -halo, —C(halo)$_3$, —OCH$_3$, and —OC(halo)$_3$.
20. The compound according to claim 1 or a pharmaceutically acceptable salt thereof, wherein u is the integer 0, 1 or 2 and each $R_{10}$ is independently selected from -halo, —(C$_1$-C$_6$)alkyl, —C(halo)$_3$, —SC(halo)$_3$ and —S(O)$_2$C(halo)$_3$, or two $R_{10}$ groups on adjacent carbon atoms together form a —O—C(halo)$_2$-O-bridge.
21. The compound according to claim 1 or a pharmaceutically acceptable salt thereof, wherein $Ar_2$ is

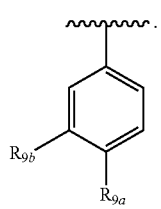

22. The compound according to claim 1 or a pharmaceutically acceptable salt thereof, wherein $Ar_2$ is

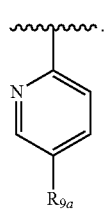

23. The compound according to claim 1 or a pharmaceutically acceptable salt thereof, wherein $Ar_2$ is

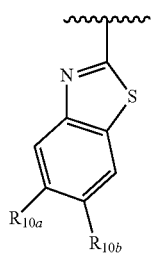

$R_{9a}$ is —C(halo)$_3$ or —OC(halo)$_3$, $R_{9b}$ is —H, -halo, —CH$_3$, or —OCH$_3$ and $R_{10a}$ and $R_{10b}$ are independently selected from —H, -halo, and —CH$_3$.
24. The compound according to claim 1 or a pharmaceutically acceptable salt thereof, wherein n=0.
25. The compound according to claim 1 or a pharmaceutically acceptable salt thereof, wherein m=0, 1 or 2 and $R_3$ is —(C$_1$-C$_6$)alkyl.
26. The compound according to claim 1 or a pharmaceutically acceptable salt thereof, wherein

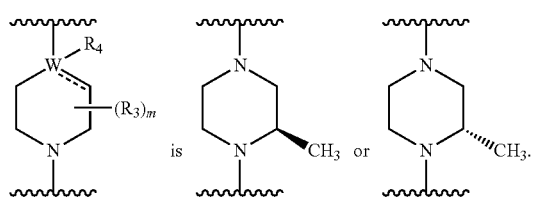

27. The compound according to claim 1 or a pharmaceutically acceptable salt thereof, wherein k is 1.
28. The compound according to claim 1 or a pharmaceutically acceptable salt thereof, wherein s or q is 1 or 2.
29. The compound according to claim 1 or a pharmaceutically acceptable salt thereof, wherein u is 1.
30. A compound of formula III:

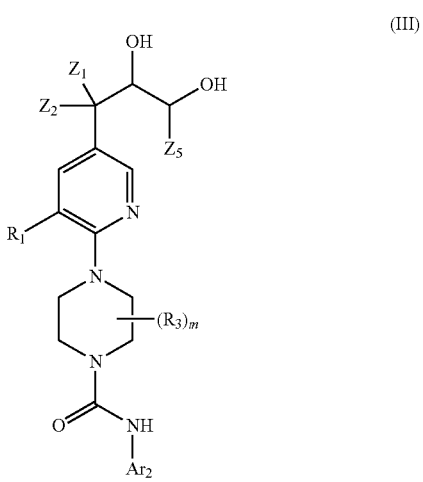

(III)

or a pharmaceutically acceptable salt thereof, wherein
$R_1$ is -halo, (C$_1$-C$_4$)alkyl, —C(halo)$_3$, —CH(halo)$_2$, or —CH$_2$(halo);

each $R_3$ is independently —$(C_1$-$C_6)$alkyl, —$CH_2OR_{13}$, —$C(O)OR_{13}$, or —$C(O)N(R_{13})_2$;
$Z_1$ is —H, —OH, or -halo;
$Z_2$ is —H or -halo;
or $Z_1$ and $Z_2$ groups together form =O or =N—$OR_{13}$;
$Z_5$ is —H, —$CH_3$, or —$CH_2CH_3$;
$Ar_2$ is

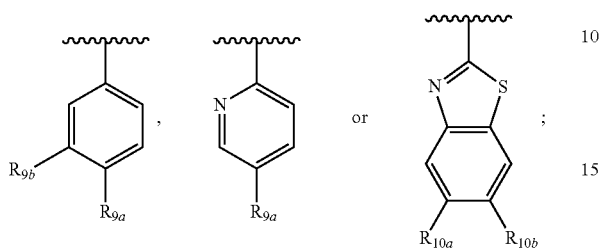

each $R_8$ is independently —H, —$(C_1$-$C_6)$alkyl, —$(C_2$-$C_6)$alkenyl, —$(C_2$-$C_6)$alkynyl, —$(C_3$-$C_8)$cycloalkyl, or phenyl;
$R_{9a}$ is —$(C_1$-$C_6)$haloalkyl, or —$(C_1$-$C_6)$haloalkoxy;
$R_{9b}$ is —H, -halo, —$(C_1$-$C_6)$alkyl, or —$(C_1$-$C_6)$alkoxy;
$R_{10a}$ and $R_{10b}$ are independently selected from —H, -halo, —$(C_1$-$C_6)$alkyl, and —$(C_1$-$C_6)$alkoxy;
each $R_{13}$ is independently —H, —$(C_1$-$C_6)$alkyl, —$(C_2$-$C_6)$alkenyl, —$(C_2$-$C_6)$alkynyl, —$(C_3$-$C_8)$cycloalkyl, —$(C_5$-$C_8)$cycloalkenyl, -phenyl, -benzyl, —$(C_1$-$C_6)$haloalkyl, —$(C_1$-$C_6)$hydroxyalkyl, —$(C_1$-$C_6)$alkoxy$(C_1$-$C_6)$alkyl, —$(C_1$-$C_6)$alkyl-$N(R_8)_2$, or —$C(O)N(R_8)_2$;
each halo is independently —F, —Cl, —Br, or —I; and
m is the integer 0, 1, or 2.

31. A compound of formula IX:

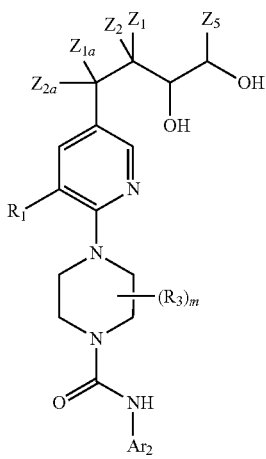

(IX)

or a pharmaceutically acceptable salt thereof, wherein $R_1$ is -halo, $(C_1$-$C_4)$alkyl, —$C(halo)_3$, —$CH(halo)_2$, or —$CH_2(halo)$;
each $R_3$ is independently —$(C_1$-$C_6)$alkyl, —$CH_2OR_{13}$, —$C(O)OR_{13}$, or —$C(O)N(R_{13})_2$;
$Z_1$ is —H, —OH, or -halo;
$Z_2$, $Z_{1a}$ and $Z_{2a}$ are each independently —H or -halo;
or $Z_1$ and $Z_2$ groups together form =O or =N—$OR_{13}$;
$Z_5$ is —H, —$CH_3$, or —$CH_2CH_3$;
$Ar_2$ is

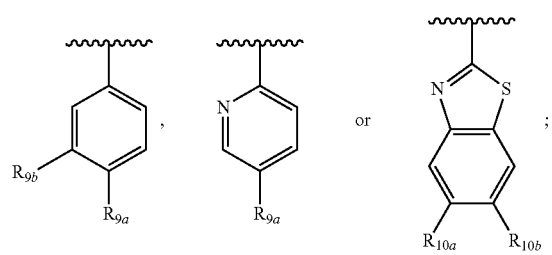

each $R_8$ is independently —H, —$(C_1$-$C_6)$alkyl, —$(C_2$-$C_6)$alkenyl, —$(C_2$-$C_6)$alkynyl, —$(C_3$-$C_8)$cycloalkyl, or phenyl;
$R_{9a}$ is —$(C_1$-$C_6)$haloalkyl, or —$(C_1$-$C_6)$haloalkoxy;
$R_{9b}$ is —H, -halo, —$(C_1$-$C_6)$alkyl, or —$(C_1$-$C_6)$alkoxy;
$R_{10a}$ and $R_{10b}$ are independently selected from —H, -halo, —$(C_1$-$C_6)$alkyl, and —$(C_1$-$C_6)$alkoxy;
each $R_{13}$ is independently —H, —$(C_1$-$C_6)$alkyl, —$(C_2$-$C_6)$alkenyl, —$(C_2$-$C_6)$alkynyl, —$(C_3$-$C_8)$cycloalkyl, —$(C_5$-$C_8)$cycloalkenyl, -phenyl, -benzyl, —$(C_1$-$C_6)$haloalkyl, —$(C_1$-$C_6)$hydroxyalkyl, —$(C_1$-$C_6)$alkoxy$(C_1$-$C_6)$alkyl, —$(C_1$-$C_6)$alkyl-$N(R_8)_2$, or —$C(O)N(R_8)_2$;
each halo is independently —F, —Cl, —Br, or —I; and
m is the integer 0, 1, or 2.

32. A composition comprising the compound of claim 1 or a pharmaceutically acceptable salt thereof and a pharmaceutically acceptable carrier or excipient.

* * * * *

SEQUENCE LISTING

<160> NUMBER OF SEQ ID NOS: 4

<210> SEQ ID NO 1
<211> LENGTH: 32

```
<212> TYPE: DNA
<213> ORGANISM: Artificial Sequence
<220> FEATURE:
<223> OTHER INFORMATION: Synthetic Construct

<400> SEQUENCE: 1
gaagatcttc gctggttgca cactgggcca ca                       32

<210> SEQ ID NO 2
<211> LENGTH: 32
<212> TYPE: DNA
<213> ORGANISM: Artificial Sequence
<220> FEATURE:
<223> OTHER INFORMATION: Synthetic Construct

<400> SEQUENCE: 2
gaagatcttc ggggacagtg acggttggat gt                       32

<210> SEQ ID NO 3
<211> LENGTH: 25
<212> TYPE: DNA
<213> ORGANISM: Artificial Sequence
<220> FEATURE:
<223> OTHER INFORMATION: Synthetic Construct

<400> SEQUENCE: 3
ggatccagca aggatgaaga aatgg                               25

<210> SEQ ID NO 4
<211> LENGTH: 24
<212> TYPE: DNA
<213> ORGANISM: Artificial Sequence
<220> FEATURE:
<223> OTHER INFORMATION: Synthetic Construct

<400> SEQUENCE: 4
tgtctgcgtg acgtcctcac ttct                                24
```